US012435061B2

(12) United States Patent
Wu et al.

(10) Patent No.: US 12,435,061 B2
(45) Date of Patent: *Oct. 7, 2025

(54) COMPOUNDS AND COMPOSITIONS FOR USE IN TREATING SKIN DISORDERS

(71) Applicant: Kamari Pharma Ltd., Ness Ziona (IL)

(72) Inventors: Xinyuan Wu, Newton, MA (US); Bertrand L. Chenard, Waterford, CT (US); Nili Claudia Schutz, Ness Ziona (IL); Dov Terkieltaub, Herzliya (IL)

(73) Assignee: KAMARI PHARMA LTD., Ness Ziona (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/300,234

(22) Filed: Apr. 13, 2023

(65) Prior Publication Data

US 2024/0124413 A1 Apr. 18, 2024

Related U.S. Application Data

(63) Continuation of application No. 17/160,802, filed on Jan. 28, 2021, now Pat. No. 11,807,621.

(60) Provisional application No. 62/967,500, filed on Jan. 29, 2020.

(51) Int. Cl.

| | |
|---|---|
| ***C07D 401/12*** | (2006.01) |
| ***A61P 17/12*** | (2006.01) |
| ***C07D 401/04*** | (2006.01) |
| ***C07D 401/06*** | (2006.01) |
| ***C07D 401/14*** | (2006.01) |
| ***C07D 403/06*** | (2006.01) |
| ***C07D 405/12*** | (2006.01) |
| ***C07D 405/14*** | (2006.01) |
| ***C07D 417/06*** | (2006.01) |
| ***C07D 417/12*** | (2006.01) |
| ***C07D 417/14*** | (2006.01) |

(52) U.S. Cl.

CPC ............ *C07D 401/12* (2013.01); *A61P 17/12* (2018.01); *C07D 401/04* (2013.01); *C07D 401/06* (2013.01); *C07D 401/14* (2013.01); *C07D 403/06* (2013.01); *C07D 405/12* (2013.01); *C07D 405/14* (2013.01); *C07D 417/06* (2013.01); *C07D 417/12* (2013.01); *C07D 417/14* (2013.01)

(58) Field of Classification Search

CPC ..... A61P 17/12; C07D 401/12; C07D 401/04; C07D 401/06; C07D 401/14; C07D 403/06; C07D 405/12; C07D 405/14; C07D 417/06; C07D 417/12; C07D 417/14

See application file for complete search history.

(56) References Cited

U.S. PATENT DOCUMENTS

| | | | |
|---|---|---|---|
| 2,798,053 | A | 7/1957 | Brown |
| 4,183,931 | A | 1/1980 | Wolfe et al. |
| 4,273,927 | A | 6/1981 | White, Jr. et al. |
| 4,461,896 | A | 7/1984 | Portlock |
| 4,509,949 | A | 4/1985 | Huang et al. |
| 4,509,971 | A | 4/1985 | Forster et al. |
| 4,784,682 | A | 11/1988 | Forster et al. |
| 4,833,243 | A | 5/1989 | Forster et al. |
| 5,075,313 | A | 12/1991 | Yu et al. |
| 5,087,445 | A | 2/1992 | Haffey et al. |
| 5,101,034 | A | 3/1992 | Schmidt et al. |
| 5,196,427 | A | 3/1993 | Yu et al. |
| 5,356,864 | A | 10/1994 | Forster et al. |
| 5,442,074 | A | 8/1995 | Forster et al. |
| 5,869,665 | A | 2/1999 | Padia |
| 5,892,114 | A | 4/1999 | Goldmann et al. |
| 5,962,457 | A | 10/1999 | Chenard et al. |
| 5,990,126 | A | 11/1999 | Park et al. |
| 6,060,479 | A | 5/2000 | Chenard et al. |
| 6,136,812 | A | 10/2000 | Chenard et al. |

(Continued)

FOREIGN PATENT DOCUMENTS

| | | | |
|---|---|---|---|
| AU | 2001239694 | B1 | 5/2002 |
| CN | 101287726 | A | 10/2008 |

(Continued)

OTHER PUBLICATIONS

STN Registry Database, Record for RN 1381362-00-0, "6-(3-Pyridinyl)-2-[1-(4-pyridinylcarbonyl)-3-pyrrolidinyl]-4(3H)-pyrimidinone", Entered STN Jul. 4, 2012 (Year: 2012).*

(Continued)

*Primary Examiner* — Daniel R Carcanague
(74) *Attorney, Agent, or Firm* — COOLEY LLP

(57) ABSTRACT

Provided herein is a compound of formula (XXXII) or a pharmaceutically acceptable salt, solvate, hydrate, stereoisomer thereof or a physiologically functional derivative thereof, wherein $R^1$, $R^2$, $R^3$, G, A, E, n, p, and q are defined herein. Also provided herein are compositions comprising a compound of formula (XXXII), and methods of using a compound of formula (XXXII), e.g., in the treatment or prevention of skin disorders.

(XXXII)

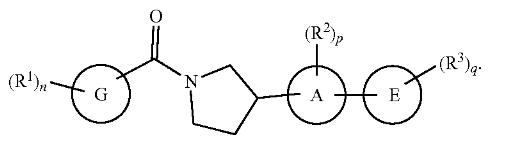

44 Claims, 11 Drawing Sheets

Specification includes a Sequence Listing.

(56) References Cited

U.S. PATENT DOCUMENTS

| | | | | |
|---|---|---|---|---|
| 6,191,157 | B1 | 2/2001 | Goldmann et al. | |
| 6,303,615 | B1 | 10/2001 | Elliott et al. | |
| 6,323,208 | B1 | 11/2001 | Chenard et al. | |
| 6,329,360 | B1 | 12/2001 | Goldmann et al. | |
| 6,380,204 | B1 | 4/2002 | Chenard et al. | |
| 6,403,607 | B1 | 6/2002 | Hidaka et al. | |
| 6,627,755 | B1 | 9/2003 | Chenard et al. | |
| 6,921,764 | B2 | 7/2005 | Chenard et al. | |
| 7,053,216 | B2 | 5/2006 | Sun et al. | |
| 7,501,446 | B2 | 3/2009 | Li et al. | |
| 7,803,790 | B2 | 9/2010 | Chong et al. | |
| 7,893,260 | B2 | 2/2011 | Chong et al. | |
| 7,998,980 | B2 | 8/2011 | Moran et al. | |
| 8,389,546 | B2 | 3/2013 | Moran et al. | |
| 8,552,009 | B2 | 10/2013 | Chong et al. | |
| 8,614,242 | B2 | 12/2013 | Benting et al. | |
| 8,916,550 | B2 | 12/2014 | Chong et al. | |
| 9,181,219 | B2 | 11/2015 | Moran et al. | |
| 9,486,455 | B2 | 11/2016 | Chong et al. | |
| 9,617,214 | B2 | 4/2017 | Wang et al. | |
| 11,807,621 | B2 | 11/2023 | Wu et al. | |
| 2002/0156253 | A1 | 10/2002 | Curtis et al. | |
| 2003/0027164 | A1 | 2/2003 | Gaughan et al. | |
| 2003/0027232 | A1 | 2/2003 | Davis et al. | |
| 2003/0157633 | A1 | 8/2003 | Bevan et al. | |
| 2003/0219806 | A1 | 11/2003 | Glucksmann et al. | |
| 2004/0009537 | A1 | 1/2004 | Roos et al. | |
| 2004/0110777 | A1 | 6/2004 | Annis et al. | |
| 2005/0202539 | A1 | 9/2005 | Chong et al. | |
| 2005/0203159 | A1 | 9/2005 | Zelle et al. | |
| 2006/0052345 | A1 | 3/2006 | Shcherbakova et al. | |
| 2006/0213321 | A1 | 9/2006 | Regenscheit | |
| 2006/0270688 | A1 | 11/2006 | Chong et al. | |
| 2007/0179164 | A1 | 8/2007 | Chong et al. | |
| 2007/0213321 | A1 | 9/2007 | Chong et al. | |
| 2008/0146611 | A1 | 6/2008 | Moran et al. | |
| 2008/0227797 | A1* | 9/2008 | Lisius | A61P 13/00 544/279 |
| 2009/0018147 | A1 | 1/2009 | Chong et al. | |
| 2010/0137260 | A1 | 6/2010 | Hwang et al. | |
| 2010/0152192 | A1 | 6/2010 | Chaudhari et al. | |
| 2010/0152209 | A1 | 6/2010 | Chong et al. | |
| 2010/0273777 | A1 | 10/2010 | Chong et al. | |
| 2011/0144135 | A1 | 6/2011 | Chong et al. | |
| 2011/0151559 | A1 | 6/2011 | Chong et al. | |
| 2013/0210798 | A1 | 8/2013 | Tan et al. | |
| 2014/0018435 | A1 | 1/2014 | Hong et al. | |
| 2016/0009688 | A1 | 1/2016 | Connolly et al. | |
| 2016/0272587 | A1 | 9/2016 | Wang et al. | |
| 2017/0312252 | A1 | 11/2017 | Lai et al. | |
| 2018/0194768 | A1 | 7/2018 | Maianti et al. | |
| 2022/0332697 | A1 | 10/2022 | Wu et al. | |

FOREIGN PATENT DOCUMENTS

| | | | |
|---|---|---|---|
| CN | 102307853 | A | 1/2012 |
| DE | 3018075 | A1 | 11/1981 |
| DE | 3038599 | A1 | 5/1982 |
| DE | 3038652 | A1 | 5/1982 |
| EP | 0572893 | A1 | 12/1993 |
| EP | 0573882 | A1 | 12/1993 |
| EP | 0807633 | A2 | 11/1997 |
| EP | 0934934 | A2 | 8/1999 |
| JP | S56158702 | A | 12/1981 |
| JP | 2007515468 | A | 6/2007 |
| JP | 2009514882 | A | 4/2009 |
| JP | 2016518383 | A | 6/2016 |
| JP | 2017530984 | A | 10/2017 |
| JP | 2019519534 | A | 7/2019 |
| WO | WO-9501334 | A1 | 1/1995 |
| WO | WO-9743276 | A1 | 11/1997 |
| WO | WO-9838173 | A1 | 9/1998 |
| WO | WO-9838187 | A1 | 9/1998 |
| WO | WO-0119800 | A2 | 3/2001 |
| WO | WO-02101045 | A2 | 12/2002 |
| WO | WO-03043961 | A2 | 5/2003 |
| WO | WO-03106435 | A1 | 12/2003 |
| WO | WO-2004041755 | A2 | 5/2004 |
| WO | WO-2005009966 | A1 | 2/2005 |
| WO | WO-2005023242 | A1 | 3/2005 |
| WO | WO-2005044221 | A2 | 5/2005 |
| WO | WO-2005049613 | A1 | 6/2005 |
| WO | WO-2005100341 | A1 | 10/2005 |
| WO | WO-2005120511 | A1 | 12/2005 |
| WO | WO-2006047516 | A2 | 5/2006 |
| WO | WO-2006120481 | A2 | 11/2006 |
| WO | WO-2006122156 | A2 | 11/2006 |
| WO | WO-2006122200 | A1 | 11/2006 |
| WO | WO-2008033564 | A1 | 3/2008 |
| WO | WO-2009152205 | A1 | 12/2009 |
| WO | WO-2010070452 | A1 | 6/2010 |
| WO | WO-2013118817 | A1 | 8/2013 |
| WO | WO-2015152253 | A1 | 10/2015 |
| WO | WO-2023214375 | A1 * | 11/2023 |

OTHER PUBLICATIONS

STN Registry Database, Record for RN 2096217-63-7, "[3-(5-Methyl-2-phenyl-1H-imidazol-1-yl)-1-pyrrolidinyl](5-methyl-2-pyrazinyl)methanone", Entered STN May 19, 2017 (Year: 2017).*

Giuliano; J. Phys. Chem. A 2010, 114, 48, 12725-12730. https://doi.org/10.1021/jp106883s (Year: 2010).*

Tang, "Diagnosis and management of children with atopic dermatitis," Chinese Journal of Practical Pediatrics, 01, 8 pages includes English translation (Jan. 6, 2015).

Badr, et al., "Studies on the synthesis of 2,3-disubstituted 4(3H)quinazolinone," Egyptian Journal of Chemistry, 19(2):341-346 (1976).

Banker et al., "Modern Pharmaceutics, 3rd Ed.," Marcel Dekker, New York, pp. 451 and 596 (1995).

Broad et al., "TRPV3 in Drug Development," Pharmaceuticals 9, 55, pp. 1-17. https://doi.org/10.3390/ph9030055 (Year: 2016).

Burnstock et al., "P2 Purinergic Receptors: Modulation of Cell Function and Therapeutic Potential," The Journal of Pharmacology and Experimental Therapeutics, 295(3):862-869 (2000).

Burnstock, "Pathophysiology and Therapeutic Potential of Purinergic Signaling," Pharmacological Reviews, 58(1):58-86 (2006).

Caterina et al., "The capsaicin receptor: a heat-activated ion channel in the pain pathway," 1997, Nature 389: 816-824.

Chenard et al., "Quinazolin-4-one α-Amino-3-hydroxy-5-methyl-4-isoxazolepropionic Acid (AMPA) Receptor Antagonists: Structure-Activity Relationship of the C-2 Side Chain Tether," J. Med. Chem. 44: 1710-1717 (2001).

Chung et al., "Biphasic Currents Evoked by Chemical or Thermal Activation of the Heat-gated Ion Channel, TRPV3," J. of Biological Chemistry 280(16):15928-15941(2005).

Clapham, David E., "Hot and Cold TRP Ion Channels," Science 295:2228-2229 (2002).

Clapham, David E., "TRP channels as cellular sensors," Nature, 426:517-524 (2003).

Clapham et al., 2003, "International Union of Pharmacology. XLIII. Compendium of Voltage-Gated Ion Channels: Transient Receptor Potential Channels," Pharmacol Rev 55: 591-596.

Clapham et al., "The TRP Ion Channel Family," Nature Reviews, 2:387-396(2001).

Daidone et al., "Synthesis and Pharmacological Activities of Novel 3-(Isoxazol-3-yl)-quinazolin-4(3H)-one Derivatives," Arch. Pharm. Pharm. Med. Chem., 332:50-54 (1999).

Database Chemicals [Online], Chemical Abstracts Service, Columbus, Ohio, US; AKos Screening Library, Order Nos. AKL-P-1811372, AKL-P-0790097, Feb. 7, 2006, 2 pages.

Database Chemicals [Online], Chemical Abstracts Service, Columbus, Ohio, US; Aurora Screening Library, Order Nos. kuk-232311, ken-123216, ken-116846, Sep. 6, 2007, 3 pages.

Dorwald, F.Z., "Side Reactions in Organic Synthesis: A Guide to Successful Synthesis Design," Weinheim: Wiley-VCH Verlag GmbH & Co. KGaA, Preface (2005).

(56) References Cited

OTHER PUBLICATIONS

Dotto, "Signal transduction pathways controlling the switch between keratinocyte growth and differentiation," 1999 Crit Rev Oral Biol Med 10(4):442-457.
Felder et al., "Synthesis of 4(3H)-pteridinones." J. Med. Chem. 15(2):210-211(1972).
Foresta et al., "Extracellular ATP is a Trigger for the Acrosome Reaction in Human Spermatozoa," J. Biol. Chem., 267(27):19443-19447 (1992).
Gopinath et al., "Increased capsaicin receptor TRPV1 in skin nerve fibres and related vanilloid receptors TRPV3 and TRPV4 in keratinocytes in human breast pain," BMC Women's Health, 5(2):1-9 (2005).
Hackam et al. "Translation of research evidence from animals to humans", JAMA, (2006); 296(14):1727-1732.
Hazot, et.al., Topical Oleaginous Minocycline Foam: Efficacious Delivery into Skin Layers in Journal of Analytical and Pharmaceutical Research, 2017, vol. 4(5), pp. 1-4.
Heller, "Electrical wiring of redox enzymes," Acc. Chem. Res. 23(5):128-134 (1990).
Hoenderhop et al., "Function and expression of the epithelial Ca2+ channel family: comparison of mammalian ECaC1 and 2," J Physiology 537(3): 747-761 (2001).
International Search Report and Written Opinion issued by the International Searching Authority for Application No. PCT/US2021/015449, dated Jun. 8, 2021, 10 pages.
Jordan "Tamoxifen: a most unlikely pioneering medicine", Nature Reviews Drug Discovery, (2003); 2(3):205-213.
Krezschmar, E., "Derivatives of 4-oxo-3,4-dihydropyrido[2,3-d)pyrimidine." Pharmazie 35(5-6):253-256 (1980). (Abstract on p. 256).
Kumar et al., "Synthesis and hypotensive activity of trisubstituted quinazolinones." European J. Med. Chem., 20(1):95-96 (1985).
Leszkovszky et al., The pharmacology of quinazolone derivatives. Acta Physiol. Acad. Sci. Hung., 27(1):81-90(1965).
Levine et al., "TRP channels: Targets for the relief of pain," Biochimica et Biophysica Acta, 1772:989-1003 (2007).
Moqrich et al., "Impaired Thermosensation in Mice Lacking TRPV3, a Heat and Camphor Sensor in the Skin," Science, 307(5714):1468-1472 (2005).
Moran et al., "TRP Ion Channels In the Nervous System," Current Opinion in Neurobiology, 14:362-369 (2004).
Naithani et al., "2,3-Disubstituted quinazolinones and their antiparkinsonian activity," Indian Journal of Chemistry Section B, 28B:745-750 (1989).
National Center for Biotechnology Information. PubChem Substance Record for SID 374628203, SCHEMBL20002952, DateAvailable Jun. 23, 2018, 5 pages. Source: SureChEMBL. https://pubchem.ncbi.nlm.nih.gov/substance/374628203 . Accessed Aug. 26, 2022. (Year: 2018).
Nikolova et al., "Characteristics of the analgesic effect of a quinazolone derivative." Farmatsiya (Sofia, Bulgaria), 27(1):53-59(1977). (English abstract provided on p. 59.).
Nikolova et al., "Screening of new synthesized compounds for analgesic effect according to knoll's method." Farmatsiya (Sofia, Bulgaria), 25(4):47-53(1975). (English abstract provided on pp. 52-53.).
Pandey et al., "Quinazolyl-thiazoles as CNS acting agents," Acta Pharm., 46:51-59 (1996).
Park et al., "A novel class of Hsp90 inhibitors isolated by structure-based virtual screening," Bioorganic & Medicinal Chemistry Letters, 17:6345-6349 (2007).
Peier et al., "A Heat-Sensitive TRP Channel Expressed in Keratinocytes," Science 296:2046-2049 (2002).
Pubchem—SID 116084532 Deposit, dated Mar. 29, 2011, 10 pages.
Pubchem—SID 230369822 Deposit, dated Feb. 12, 2015, 2 pages retrieved Jul. 12, 2021 online at https://pubchem.ncbi.nlm.nih.gov/substance/230369822.
Raffa et al., "Synthesis and antileukemic activity of new 3-(1-phenyl-3-methylpyrazol-5-yl)-[2-stvrvlquinazolin-4(3H)-ones," Il Farmaco, 59:215-221 (2004).
Raffa et al., "Synthesis and antileukemic activity of new 3-(5-methylisoxazol-3-yl) and 3-lovrimidin-2-yl)-2-styrylquinazolin-4(3H)-ones," Il Farmaco, 59:451-455 (2004).
Ramana et al., "Mass spectrometer as a probe in the synthesis of 2-substituted-3-phenyl-4(3H)-quinazolinones." Indian J. of Heterocyclic Chem., 9(3): 173-180(2000).
Ramsey et al., "An Introduction to TRP Channels," Annual Rev. Physiology, 68:619-647 (2006).
RD 201017 (Research Disclosure), "Herbicidal Agents," 201:9-17 (1981).
Rush et al., "Electrophysiological properties of two axonal sodium channels, Nav1.2 and Nav1.6, expressed in mouse spinal sensory neurones," 2005, J Physiology 564:808-815.
Saleh et al., "Synthesis and Antiviral Evaluation of Some New Glycosylthioureas Containing a Quinazolinone Nucleus," Nucleosides, Nucleotides & Nucleic Acids, 21(1):93-106 (2002).
Saleh et al., "Synthesis and Biological Activities of Some New 3H-Quinazolin-4-One Derivatives Derived from 3-Phenylamino-2-Thioxo-3H-Quinazolin-4-One," Phosphorus, Sulfur, and Silicon, 179:411-426 (2004).
Shishoo, "Synthesis and pharmacological evaluation of some novel 5-aryl-6-arylamino-1-phenylpyrazolo [3,4- d] pyrimidin-4(5 H )-ones as analgesic and anti-inflammatory agents," Indian Journal of Chemistry Section B, 38B:684-695 (1999).
Smith et al., "TRPV3 is a temperature-sensitive vanilloid receptor-like protein," Nature 418:186-1-90 (2002).
Stefanova, D., "Central depressive effects of M50." Farmatsiya (Sofia, Bulgaria), 24(2):38-43(1974). (English abstract provided on p. 43.).
STN Registry Database, record for RN 107504-08-5, 5-Fiuoro-2-pyridinecarboxylic acid, entered STN Apr. 11, 1987, 1 page.
STN Registry File Records I, RN748783-90-6, dated Sep. 21, 2004, 6 pages.
STN Registry File Records II, RN838100-85-9, dated Feb. 27, 2005, 4 pages.
STN Registry File Records III, RN890595-97-8, dated Jul. 5, 2006, 14 pages.
STN Registry File Records, RN877946-08-0_29 pages, dated 2000-2006.
U.S. Appl. No. 11/920,184, inventor Chong et al., filed Nov. 9, 2007.
Vippagunta, S.R., et al., "Crystalline Solids," Advanced Drug Delivery Reviews, 2001, vol. 48, pp. 3-26.
Wang et al., "Extracellular ATP shows synergistic enhancement of DNA synthesis when combined with agents that are active in wound healing or as neurotransmitters," Biochemical and Biophysical Research Communications, 166(1):251-258 (1990).
Weerapura et al., "A comparison of currents carried by HERG, with and without coexpression of MiRP1, and the native rapid delayed rectifier current. Is MIRP1 the missing link?" 2002, J Physiology 540:(pt1) 15-27.
Welch et al., "Atropisomeric quinazolin-4-one derivatives are potent noncompetitive alpha-amino-3-hydroxy-5-methyl-4-isoxazolepropionic acid (AMPA) receptor antagonists," Bioorganic & Medicinal Chemistry Letters, 11(2):177-181 (2001).
Wolff, Burger's Medicinal Chemistry and Drug Discovery, Fifth Edition, vol. 1: Principles and Practice, New York: John Wiley & Sons, 1995, pp. 975-977.
Xie Zhiqiang, Role of Thermo TRP Channels in Cutaneous Neurogenic Inflammation and Itch, Journal of Zhejiang University (Medical Edition), Vo 38, No. 4, 2009, 6 pages. (English Abstract).
Xu et al., "Oregano, thyme and clove-derived flavors and skin sensitizers activate TRP channels," Nature Neuroscience Advance Online Publication, doi: 10.1038/nn 1692, pp. 1-8 (2006).
Xu et al., "TRPV3 is a calcium-permeable temperature-sensitive cation channel," Nature 418: 181-186 (2002).
Extended European Search Report for European Application No. EP21748179.5 dated Feb. 7, 2024, 8 pages.

(56) References Cited

OTHER PUBLICATIONS

Su et al., "TRPV3: Structure, Diseases and Modulators", Molecules, vol. 28, No. 2, Jan. 12, 2023 (Jan. 12, 2023), p. 774, pp. 1-28, Retrieved from the Internet: URL:https://www.ncbi.nlm.nih.gov/pmc/ivip/ 1420-3049/28/2/774.
Borbiro et al., "Activation of transient receptor potential vanilloid-3 inhibits human hair growth," J Invest Dermatol. 131(8):1605-14 (Aug. 2011).
Chen et al., "ERK2-mediated C-terminal serine phosphorylation of p300 is vital to the regulation of epidermal growth factor-induced keratin 16 gene expression," J Biol Chem 282(37):27215-27228. (Sep. 14, 2007) Epub Jul. 9, 2007.
Cheng et al., "TRP channel regulates EGFR signaling in hair morphogenesis and skin barrier formation," Cell 141:331-43 (Apr. 16, 2010).
Duchatelet et al., "A Olmsted syndrome: clinical, molecular and therapeutic aspects," OrphanetJRareDis. 10:33, pp. 1-10 (2015).
Elsholz et al., "Calcium—a central regulator of keratinocyte differentiation in health and disease," Eur J Dermatol. 24:650-61 (2014).
Maruthappu et al., "Rhomboid family member 2 regulates cytoskeletal stress-associated Keratin 16," Nat Commun. 2017;8:14174, pp. 1-11. (Jan. 27, 2017).
Miyamoto et al., "A TRPV3 regulates nitric oxide synthase-independent nitric oxide synthesis in the skin," Nat Commun 2:369, pp. 1-12 (Jun. 28, 2011).
Proksch et al., "The skin: an indispensable barrier," Exp Dermatol, 2008;17:1063-72 (2008).
Swindle MM (ed.), Swine as Models in Biomedical Research and Toxicology Testing, Veterinary Pathology49(2):344-356 (Mar. 2012).
Wang et al., "Induction of disease-associated keratin 16 gene expression by epidermal growth factor is regulated through cooperation of transcription factors Sp1 and c-Jun," J Biol Chem. 278(46):45848-45857 (Issue of Nov. 14, 2003).
Yadav et al., "TRPV3 mutants causing Olmsted Syndrome induce impaired cell adhesion and nonfunctional lysosomes," Channels (Austin). 11(3):196-208 (May 4, 2017).
Yoshioka et al., "A Spontaneous scratching behaviour in DS-Nh mice as a possible model for pruritus in atopic dermatitis," Immunology. 118(3):293-301 (Jul. 2006).

* cited by examiner

COMPOUNDS AND COMPOSITIONS FOR USE IN TREATING SKIN DISORDERS

CROSS-REFERENCE TO RELATED APPLICATIONS

This application is a continuation of U.S. patent application Ser. No. 17/160,802, filed Jan. 28, 2021, and which claims the benefit of and priority to U.S. Provisional Application No. 62/967,500, filed Jan. 29, 2020, the contents of which are hereby incorporated by reference in their entirety for all purposes.

REFERENCE TO ELECTRONIC SEQUENCE LISTING

This application is a continuation of U.S. patent application Ser. No. 17/160,802, filed Jan. 28, 2021, now U.S. Pat. No. 11,807,621, which claims the benefit of and priority to U.S. Provisional Application No. 62/967,500, filed Jan. 29, 2020, the contents of which are hereby incorporated by reference in their entirety for all purposes.

BACKGROUND

The Transient receptor potential vanilloid 3 (TRPV3) is a non-selective cation channel, displaying relatively high permeability to calcium. In addition to calcium ions, TRPV3 channels are permeable to other cations, for example sodium. Thus, TRPV3 channels modulate membrane potential by modulating the flux of cations such as calcium and sodium ions. Although non-selective cation channels such as TRPV3 modulate, among other things, calcium ion flux, they are mechanistically distinct from voltage-gated calcium channels. Generally, voltage-gated calcium channels respond to membrane depolarization and open to permit an influx of calcium from the extracellular medium that results in an increase in intracellular calcium levels or concentrations. In contrast, TRP channels which are non-selective cation channels are generally signal transduction gated, long lasting, and produce more prolonged changes in ion concentration. These mechanistic differences are accompanied by structural differences among voltage-gated and TRP channels. Thus, although many diverse channels act to regulate ion flux and membrane potential in various cell types and in response to numerous stimuli, it is important to recognize the significant structural, functional, and mechanistic differences among different classes of ion channels.

SUMMARY

The present disclosure relates to compounds that treat or prevent various diseases, conditions, and/or disorders such as various skin disorders (e.g., any compounds of formulae I-XXXXIII) and compositions and methods of use thereof. In some embodiments, the compounds disclosed herein are useful for treating or preventing various diseases, conditions, and/or disorders modulated by TRPV3, such as various skin disorders. In some embodiments, the compounds disclosed herein inhibit TRPV3 activity.

In one aspect, the present disclosure provides a compound having the general formula (XXXII):

(XXXII)

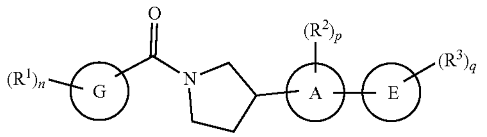

or a pharmaceutically acceptable salt, solvate, hydrate, any stereoisomer thereof or physiologically functional derivative thereof, wherein each of A, E and G, independently of the other, is selected from a monocyclic or polycyclic ring system containing three to twelve atoms;

each $R^1$ is independently cyano, nitro, hydroxy, halo, $C_1$-$C_3$ haloalkyl, $C_1$-$C_3$ haloalkoxy, $C_1$-$C_6$ alkyl, $C_1$-$C_6$ alkoxy, ether, aryl, —$N(R^a)(R^b)$, —$C(O)R^c$, —$CO_2R^c$, —$C(O)N(R^a)(R^b)$, —$SO_2N(R^a)(R^b)$, or —$SOR^c$, or two $R^1$ groups together form a ring system, e.g.,

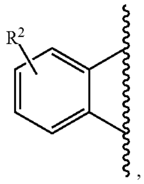

e.g.,

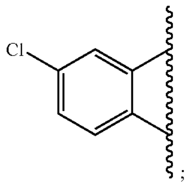

each of $R^2$ and $R^3$ is independently of the other selected from cyano, nitro, hydroxy, halo, $C_1$-$C_3$ haloalkyl, $C_1$-$C_3$ haloalkoxy, $C_1$-$C_6$ alkyl, hydroxyalkyl, $C_3$-$C_8$ cycloalkyl, $C_1$-$C_6$ alkoxy, aryl, —$N(R^a)(R^b)$, —$C(O)R^c$, —$CH_2R^c$, —$CO_2R^c$, —$C(O)N(R^a)(R^b)$, —$SO_2N(R^a)(R^b)$, or —$SOR^c$; each $R^a$ and $R^b$ is independently H, hydroxyl, —$OR^c$, $C_1$-$C_6$ alkyl, —$C(O)R^c$, or —$C(O)OR^c$; $R^c$ is H, $C_1$-$C_6$ alkyl, aryl, —$OR^a$, or —$N(R^a)(R^a)$;

n is 0, 1, or 2; p is 0, 1, or 2; and q is 0, 1, or 2.

In some embodiments, the present disclosure provides a compound having the general formula (XXXIII)

(XXXIII)

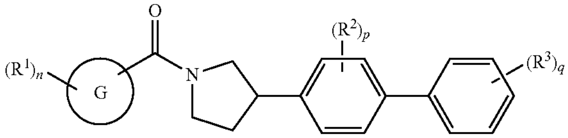

or a pharmaceutically acceptable salt, solvate, hydrate, any stereoisomer thereof or physiologically functional derivative thereof, wherein G is an aryl or a heteroaryl;

$R^1$ is independently cyano, nitro, hydroxy, halo, $C_1$-$C_3$ haloalkyl, $C_1$-$C_3$ haloalkoxy, $C_1$-$C_6$ alkyl, hydroxyalkyl, $C_1$-$C_6$ alkoxy, aryl, —$N(R^a)(R^b)$, —$C(O)R^c$, —$CO_2R^c$, —$C(O)N(R^a)(R^b)$, —$SO_2N(R^a)(R^b)$, or —$SOR^c$, or two R groups together form a ring system, e.g.,

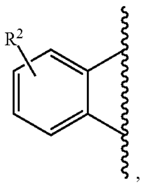

e.g.,

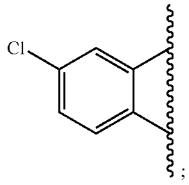

each of $R^2$ and $R^3$ is independently of the other selected from cyano, nitro, hydroxy, halo, $C_1$-$C_3$ haloalkyl, $C_1$-$C_3$ haloalkoxy, $C_1$-$C_6$ alkyl, hydroxyalkyl, $C_3$-$C_8$ cycloalkyl, $C_1$-$C_6$ alkoxy, aryl, —$N(R^a)(R^b)$, —$C(O)R^c$, —$CH_2R^c$, —$CO_2R^c$, —$C(O)N(R^a)(R^b)$, —$SO_2N(R^a)(R^b)$, or —$SOR^c$; each $R^a$ and $R^b$ is independently H, hydroxyl, —$OR^c$, $C_1$-$C_6$ alkyl, —$C(O)R^c$, or —$C(O)OR^c$; $R^c$ is H, $C_1$-$C_6$ alkyl, aryl, —$OR^a$, or —$N(R^a)(R^a)$;

n is 0, 1, or 2; p is 0, 1, or 2; and q is 0, 1, or 2.

In some embodiments, the present disclosure provides a compound having the general formula (XXXXIII)

(XXXXIII)

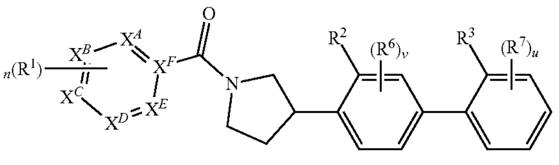

or a pharmaceutically acceptable salt, solvate, hydrate, any stereoisomer thereof or physiologically functional derivative thereof, wherein each one of $X^A$, $X^B$, $X^C$, $X^D$, and $X^E$ is selected from N or CH, $X^F$ is C, $R^1$ is selected from halo, $C_1$-$C_6$ alkyl, $C_1$-$C_6$ alkoxy, hydroxy, $C_1$-$C_3$ haloalkyl, cyano, ether, —$N(R^a)(R^b)$, —$C(O)R^c$, each $R^a$ and $R^b$ is independently H, $C_1$-$C_6$ alkyl, $R^2$ and $R^6$ independently from the other is selected from cyano, nitro, hydroxy, hydroxyalkyl, —$NH_2$, halo, aryl, —$N(R^a)(R^b)$, —$C(O)OH$, —$CH_2R^c$, —$CO_2R$, or —$C(O)N(R^a)(R^b)$;

$R^c$ is H, $C_1$-$C_6$ alkyl, aryl, —$OR^a$, or —$N(R^a)(R^a)$;

$R^3$ and $R^7$ independently from the other is selected from halo, $C_1$-$C_6$ alkyl, $C_1$-$C_6$ alkoxy, or $C_3$-$C_6$ cycloalkyl;

n is 0, 1, or 2; u is 0, 1, or 2; and v is 0, 1, or 2.

In some embodiments, the present disclosure provides methods of using the compounds disclosed herein (e.g., any compounds of formulae I-XXXXIII) in the prevention or treatment of various skin defects/disease/disorders as detailed herein. In some embodiments, the compounds and compositions of the present disclosure are suitable for systemic and/or topical administration.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 2A and 2B, from left to right, G1 naïve, G2 vehicle 1, G3 KM-0001-P1 0.1 mg/kg (mpk), G4 KM-0001-P1 0.01 mpk, G5 vehicle 2, G6 HC-030031 4 mg/mouse.

DETAILED DESCRIPTION OF EMBODIMENTS

Figure 1:
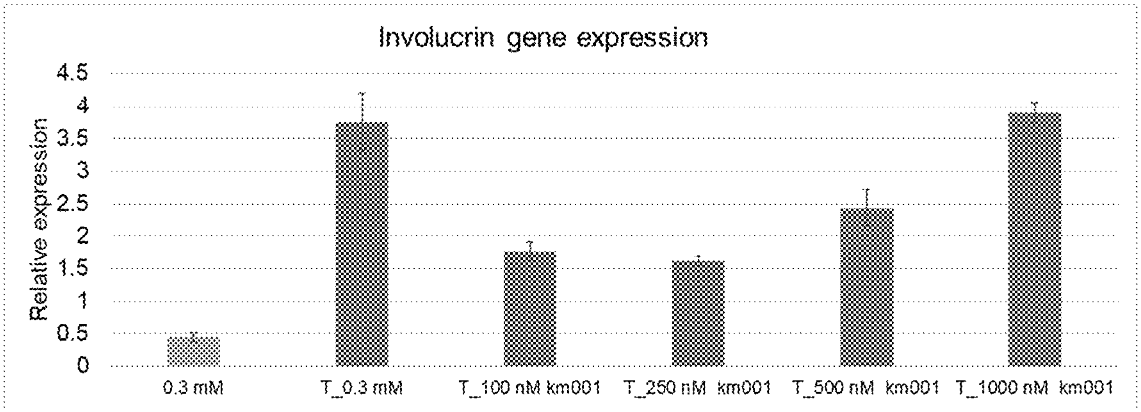
FIG. 1 is a graph showing mRNA levels of Involucrin.

The present disclosure is based on the development of novel compounds including purified preparations thereof that can be used in methods of treating or preventing skin disease. For example, the present disclosure provides compounds or a salt thereof, or a solvate, hydrate, oxidative metabolite or prodrug of the compound or its salt.

In the following text, when referring to at least one compound it is to be understood as also referring to the compositions, methods, and uses disclosed herein. Thus, whenever providing a feature with reference to the at least one compound, it is to be understood as defining the same feature with respect to the compositions, methods, and uses, mutatis mutandis.

Accordingly, in some embodiments, the present disclosure provides compounds of formula (I)

(I)

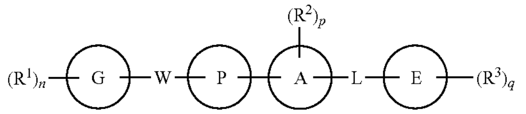

or a pharmaceutically acceptable salt thereof, wherein:

A is bond, aryl, or heteroaryl;

E is aryl, heteroaryl, $C_3$-$C_8$ cycloalkyl, or $C_3$-$C_8$ cycloalkenyl;

G is aryl, heteroaryl, $C_3$-$C_8$ cycloalkyl, or $C_3$-$C_8$ heterocycloalkyl;

L is bond, —$(CR^aR^b)_m$—, —O—, —C(O)—, —C(O)N($R^a$)—, or —CH($OR^c$)—;

P is

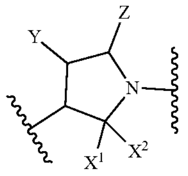

or

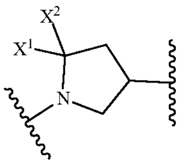

;

W is —O—, —$NR^c$—, —$(CR^aR^b)_m$—, —$(CR^aR^b)_m$—O—, —O—C(O)—, —NH—C(O)—, —$CH_2$—C(O)— or —$(CY^1Y^2)_z$—;

$X^1$ and $X^2$ together are oxo, or each of $X^1$ and $X^2$ is H;

$Y^1$ and $Y^2$ together are oxo, or each of $Y^1$ and $Y^2$ is H;

Y is H or OH;

Z is H, $C_1$-$C_6$ alkyl (e.g., hydroxyalkyl), or $C_1$-$C_6$ alkoxy;

each $R^1$ is independently cyano, nitro, hydroxy, halo, $C_1$-$C_3$ haloalkyl, $C_1$-$C_3$ haloalkoxy, $C_1$-$C_6$ alkyl, $C_1$-$C_6$ alkoxy, aryl, —$N(R^a)(R^b)$, —$C(O)R^c$, —$CO_2R^c$, —$C(O)N(R^a)(R^b)$, —$SO_2N(R^a)(R^b)$, or —$SOR^c$, or two $R^1$ groups together form a ring system, e.g.,

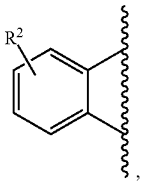

, e.g.,

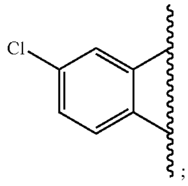

;

each $R^2$ and $R^3$ is independently cyano, nitro, hydroxy, halo, $C_1$-$C_3$ haloalkyl, $C_1$-$C_3$ haloalkoxy, $C_1$-$C_6$ alkyl (e.g., —$CH(OH)CH_2OH$), $C_3$-$C_8$ cycloalkyl, $C_1$-$C_6$ alkoxy, aryl, —$N(R^a)(R^b)$, —$C(O)R^c$, —$CH_2R^c$, —$CO_2R^c$, —$C(O)N(R^a)(R^b)$, —$SO_2N(R^a)(R^b)$, or —$SOR^c$;

each $R^a$ and $R^b$ is independently H, hydroxyl, —$OR^c$, $C_1$-$C_6$ alkyl, —$C(O)R^c$, or —$C(O)OR^c$;

$R^c$ is H, $C_1$-$C_6$ alkyl, aryl, —$OR^a$, or —$N(R^a)(R^a)$;

m is 1, 2, 3, 4, 5, or 6;

z is 1, 2, 3, 4, 5, or 6;

n is 0, 1, or 2;

p is 0, 1, or 2; and q is 0, 1, or 2.

In some embodiments, E is phenyl.

In some embodiments, G is aryl or heteroaryl.

In some embodiments, G is phenyl, 1-naphthyl, 2-naphthyl, and 4-biphenyl, pyridyl, pyrimidinyl, pyrazinyl, pyridazinyl, triazinyl, furyl (furanyl), quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, 1,2,3,-oxadiazoyl, 1,2,4,-oxadiazoyl, 1,2,5,-oxadiazoyl, 1,3,4,-oxadiazoyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. In some embodiments, G is pyridine. In some embodiments, G is one of

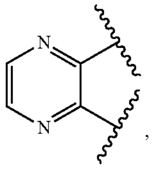

,

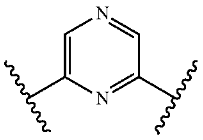

,

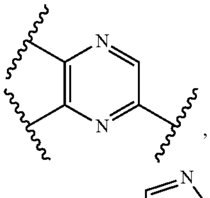

,

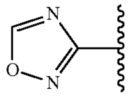

,

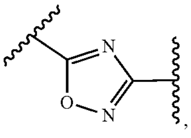

,

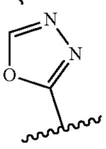

, or

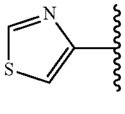

, wherein the wavy line indicates a bond to either W or $R^1$.

In some embodiments, G is absent, such that a compound of Formula (I') is provided (I')

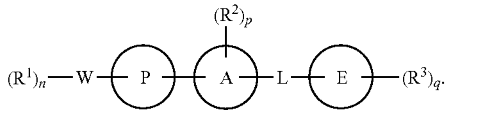

.

In some embodiments, R1 is $C_1$-$C_3$ haloalkyl and n is 1. In some embodiments, W is is —C(O)—.

In some embodiments, the compound of Formula (I') is

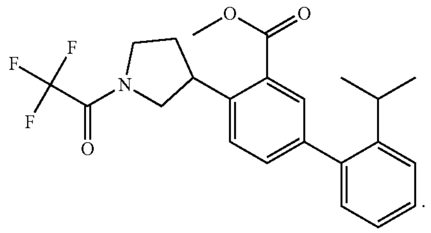 [SMILES: COC(=O)c1cc(-c2ccccc2C(C)C)ccc1C1CCN(C(=O)C(F)(F)F)C1]

In some embodiments, $R^2$ is alkyl or alkoxy.

In some embodiments, $R^2$ is $—CH_2OH$.

In some embodiments, $R^1$ is substituted alkoxy (e.g., $—OCH_2CH_2OH$, $—OCH_2CO_2Et$,

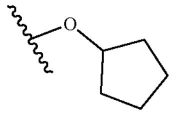
,
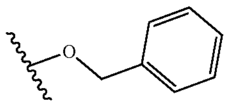
).

In some embodiments, $R^1$ is cyano, halo, $C_1$-$C_3$ haloalkyl, or $C_1$-$C_6$ alkyl.

In some embodiments, $R^1$ is halo or $C_1$-$C_3$ haloalkyl.

In some embodiments, $R^3$ is cyano, halo, $C_1$-$C_3$ haloalkyl, or $C_1$-$C_6$ alkyl.

In some embodiments, $R^3$ is $C_1$-$C_6$ alkyl or $C_3$-$C_8$ cycloalkyl.

In some embodiments, n is 1 and $R^1$ is halo or $C_1$-$C_3$ haloalkyl.

In some embodiments, q is 1 or 2, and $R^3$ is $C_1$-$C_6$ alkyl or $C_3$-$C_8$ cycloalkyl.

In some embodiments, n is 1 and q is 1.

In some embodiments, E is aryl or heteroaryl.

In some embodiments, E is phenyl and L is bond or —O—.

In some embodiments, E is aryl, L is bond or —O—, and $R^2$ is $—CH_2OH$.

In some embodiments, A is phenyl, $R^2$ is $—CH_2OH$, L is bond or —O—, and q is 1 or 2.

In some embodiments, one of X, Y, and Z is absent.

In some embodiments, X and Y are absent.

In some embodiments, X and Z are absent.

In some embodiments, Y and Z are absent.

In some embodiments, X, Y, and Z are absent.

In some embodiments, m is 1, 2, or 3.

In some embodiments, n is 0 or 1.

In some embodiments, q is 1.

In some embodiments, p is 1, and $R^2$ is hydroxy.

In some embodiments, E is aryl, and L is $—(CH_2)_m—$, —O—, or —C(O)—.

In some embodiments, A is phenyl, and L is —O—.

In some embodiments, A and E are phenyl.

In some embodiments, the present disclosure provides compounds of Formula (II):

(II)

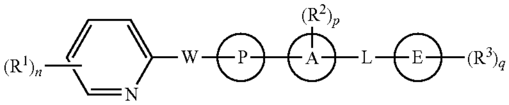

or a pharmaceutically acceptable salt thereof.

In some embodiments, the present disclosure provides compounds of Formula (III):

(III)

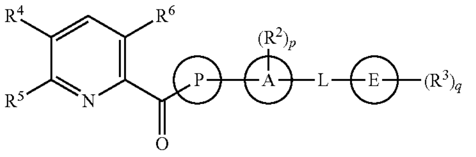

or a pharmaceutically acceptable salt thereof.

In some embodiments, the present disclosure provides compounds of Formula (IV):

(IV)

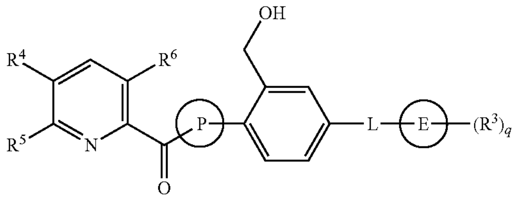

or a pharmaceutically acceptable salt thereof.

In some embodiments, the present disclosure provides compounds of Formula (V):

(V)

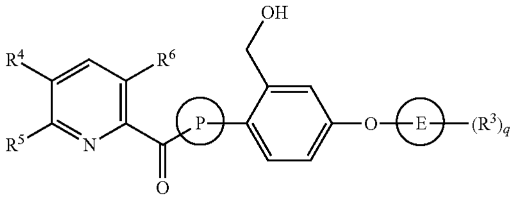

or a pharmaceutically acceptable salt thereof.

In some embodiments, the present disclosure provides compounds of Formula (VI):

(VI)

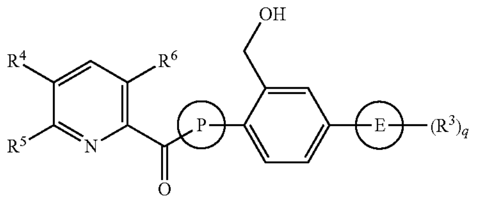

or a pharmaceutically acceptable salt thereof.

In some embodiments, the present disclosure provides compounds of Formula (VII):

(VII)

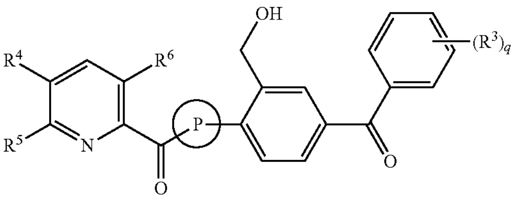

or a pharmaceutically acceptable salt thereof.

In some embodiments, the present disclosure provides compounds of Formula (VIII):

(VIII)

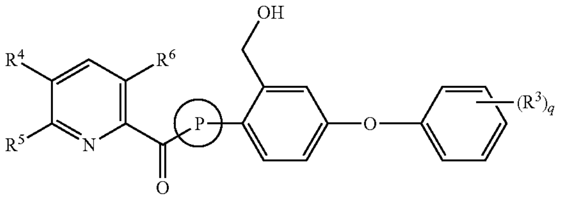

or a pharmaceutically acceptable salt thereof.

In some embodiments, the present disclosure provides compounds of Formula (IX):

(IX)

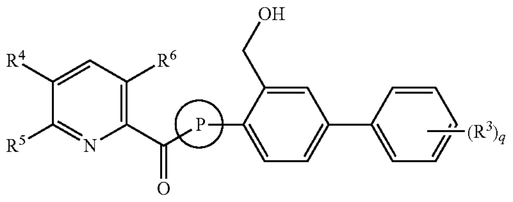

or a pharmaceutically acceptable salt thereof.

In some embodiments, the present disclosure provides compounds of Formula (X):

(X)

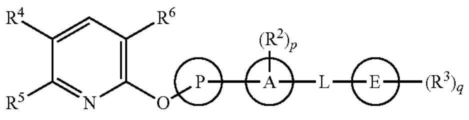

or a pharmaceutically acceptable salt thereof.

In some embodiments, the present disclosure provides compounds of Formula (XI):

(XI)

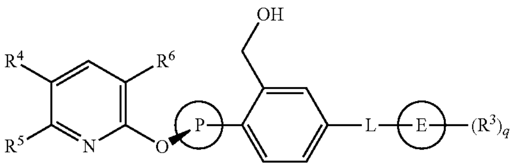

or a pharmaceutically acceptable salt thereof.

In some embodiments, the present disclosure provides compounds of Formula (XII):

(XII)

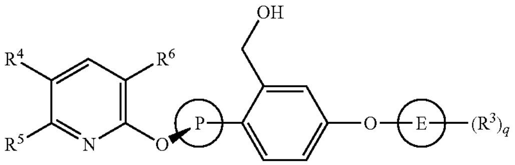

or a pharmaceutically acceptable salt thereof.

In some embodiments, the present disclosure provides compounds of Formula (XIII):

(XIII)

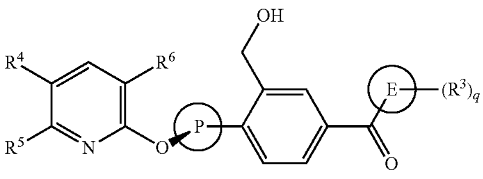

or a pharmaceutically acceptable salt thereof.

In some embodiments, the present disclosure provides compounds of Formula (XIV):

(XIV)

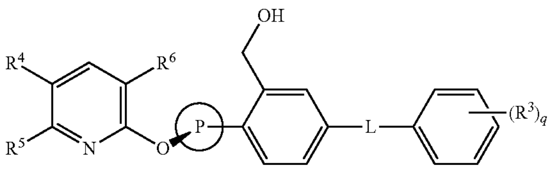

or a pharmaceutically acceptable salt thereof.

In some embodiments, the present disclosure provides compounds of Formula (XV):

(XV)

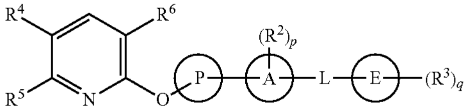

or a pharmaceutically acceptable salt thereof.

In some embodiments, A is selected from the group consisting of phenyl, 1-naphthyl, 2-naphthyl, and 4-biphenyl, pyridyl, pyrimidinyl, pyrazinyl, pyridazinyl, triazinyl, furyl (furanyl), quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, and indolinyl. In some embodiments, A is phenyl.

In some embodiments, W is —C(O)— or —O—, —NH—, —$CH_2$—, —O—$CH_2$—, —N—$CH_2$—, and —NH—C(O)—. In some embodiments, W is —C(O)— or —O—.

In some embodiments, P is

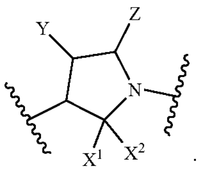

.

In some embodiments, $X^1$, $X^2$, Y and Z are each H.

In some embodiments, P is

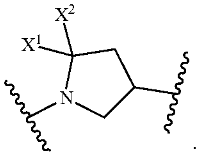

.

In some embodiments, $X^1$ and $X^2$ are each H.

In some embodiments, L is bond, —O—, —C(O)—, or —CH(OH)—.

In some embodiments, E is phenyl.

In some embodiments, $R^2$ is —$CH_2OH$, cyano, nitro, hydroxy, —$NH_2$, halo, aryl, —$N(R^a)(R^b)$, —C(O)OH, —$CH_2R^c$, —$CO_2R^c$, or —$C(O)N(R^a)(R^b)$. In some embodiments, $R^2$ is —$CH_2OH$.

In some embodiments, $R^1$ is halo, $C_1$-$C_6$ alkyl, $C_1$-$C_6$ alkoxy, cyano, or $C_1$-$C_3$ haloalkyl. In some embodiments, $R^1$ is chloro, fluoro, methyl, —OMe, or —$CF_3$.

In some embodiments, $R^3$ is chloro, fluoro, $C_1$-$C_6$ alkyl, $C_1$-$C_6$ alkoxy, or $C_3$-$C_8$ cycloalkyl.

In some embodiments, n is 1 and $R^1$ is halo or $C_1$-$C_3$ haloalkyl.

In some embodiments, q is 1 or 2, and $R^3$ is $C_1$-$C_6$ alkyl or $C_3$-$C_8$ cycloalkyl.

In some embodiments, n is 1 and q is 1.

In some embodiments, E is phenyl and L is bond or —O—.

In some embodiments, E is aryl, L is bond or —O—, and $R^2$ is —$CH_2OH$.

In some embodiments, A is phenyl, $R^2$ is —$CH_2OH$, L is bond or —O—, and q is 1 or 2.

In some embodiments, the compound comprises at least 70% chirally pure enantiomer.

In some embodiments, the compound comprises at least 80% chirally pure enantiomer.

In some embodiments, the compound comprises at least 90% chirally pure enantiomer.

In some embodiments, the compound comprises at least 95% chirally pure enantiomer.

In some embodiments, the compound comprises at least 98% chirally pure enantiomer.

In some embodiments, the compound comprises at least 99% chirally pure enantiomer.

In some embodiments, the present disclosure provides a compound of Formula (XVI):

(XVI)

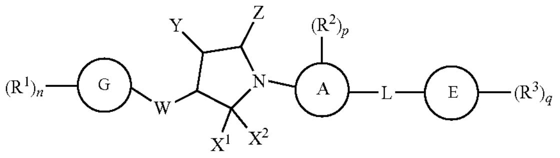

or a pharmaceutically acceptable salt thereof, wherein:

A is bond, aryl, or heteroaryl;

E is aryl, heteroaryl, $C_3$-$C_8$ cycloalkyl, or $C_3$-$C_8$ cycloalkenyl;

G is aryl, heteroaryl, $C_3$-$C_8$ cycloalkyl, or $C_3$-$C_5$ heterocycloalkyl;

L is a bond, —$(CR^aR^b)_m$—, —O—, —C(O)—, —CH($OR^c$)—, or —$C(O)N(R^a)$—;

W is —O—, —$NR^c$—, or —$CR^aR^b$—;

$X^1$ and $X^2$ together are oxo, or each of $X^1$ and $X^2$ is H;

Y is H or OH;

Z is H, $C_1$-$C_6$ alkyl (e.g., hydroxyalkyl), or $C_1$-$C_6$ alkoxy;

each $R^1$ is independently cyano, nitro, hydroxy, halo, $C_1$-$C_3$ haloalkyl, $C_1$-$C_3$ haloalkoxy, $C_1$-$C_6$ alkyl, $C_1$-$C_6$ alkoxy, aryl, —$N(R^a)(R^b)$, —$C(O)R^c$, —$CO_2R^c$, —$C(O)N(R^a)(R^b)$, —$SO_2N(R^a)(R^b)$, or —$SOR^c$, or two $R^1$ groups together form a ring system, e.g.,

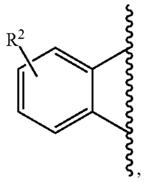

, e.g.,

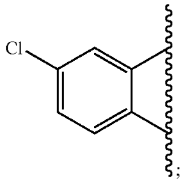

;

each $R^2$ and $R^3$ is independently cyano, nitro, hydroxy, halo, $C_1$-$C_3$ haloalkyl, $C_1$-$C_3$ haloalkoxy, $C_1$-$C_6$ alkyl (e.g., —CH(OH)$CH_2$OH), $C_1$-$C_6$ alkoxy, $C_3$-$C_8$ cycloalkyl, aryl, —$N(R^a)(R^b)$, —$C(O)R^c$, —$CO_2R^c$, —$C(O)N(R^a)(R^b)$, —$SO_2N(R^a)(R^b)$, or —$SOR^c$;

each $R^a$ and $R^b$ is independently H, hydroxyl, —$OR^c$, —$N(R^c)(R^c)$, $C_1$-$C_6$ alkyl, —$C(O)R^c$, or —$C(O)OR^c$;

$R^c$ is H, $C_1$-$C_6$ alkyl, or aryl;

m is 1, 2, 3, 4, 5, or 6;

n is 0, 1, or 2;

p is 0, 1, or 2; and q is 0, 1, or 2.

In some embodiments, $R^1$ is substituted alkoxy (e.g., —$OCH_2CH_2OH$, —$OCH_2CO_2Et$,

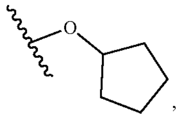
,
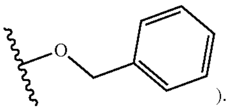
).

In some embodiments, A is aryl.

In some embodiments, L is —$(CH_2)_m$—, —O—, or —CH($OR^c$)—.

In some embodiments, E is aryl or heteroaryl.

In some embodiments, one of X, Y, and Z is absent.

In some embodiments, X and Y are absent.

In some embodiments, X and Z are absent.

In some embodiments, Y and Z are absent.

In some embodiments, X, Y, and Z are absent.

In some embodiments, $R^1$ is cyano, halo, $C_1$-$C_3$ haloalkyl, or $C_1$-$C_6$ alkyl.

In some embodiments, $R^2$ is alkyl or alkoxy.

In some embodiments, m is 1, 2, or 3.

In some embodiments, n is 0 or 1.

In some embodiments, q is 1.

In some embodiments, n is 0 or 1, and $R^1$ is cyano, halo, $C_1$-$C_3$ haloalkyl, or $C_1$-$C_6$ alkyl.

In some embodiments, q is 1, and $R^3$ is cyano, halo, $C_1$-$C_3$ haloalkyl, or $C_1$-$C_6$ alkyl.

In some embodiments, p is 1, and $R^2$ is hydroxy.

In some embodiments, E is aryl, and L is —$(CH_2)_m$—, —O—, or —C(O)—.

In some embodiments, A is phenyl, and L is —O—.

In some embodiments, A and E are phenyl.

In some embodiments, the present disclosure provides a compound of Formula (XVII):

(XVII)

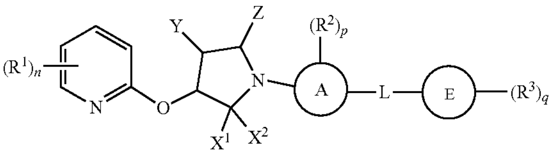

or a pharmaceutically acceptable salt thereof, wherein:

A is bond, aryl, or heteroaryl;

E is aryl, heteroaryl, $C_3$-$C_8$ cycloalkyl, or $C_3$-$C_8$ cycloalkenyl;

L is a bond, —$(CR^aR^b)_m$—, —O—, —C(O)—, or —C(O)N($R^a$)—;

$X^1$ and $X^2$ together are oxo, or each of $X^1$ and $X^2$ is H;

Y is H or OH;

Z is H, $C_1$-$C_6$ alkyl (e.g., hydroxyalkyl), or $C_1$-$C_6$ alkoxy;

each $R^1$ is independently cyano, nitro, hydroxy, halo, $C_1$-$C_3$ haloalkyl, $C_1$-$C_3$ haloalkoxy, $C_1$-$C_6$ alkyl, $C_1$-$C_6$ alkoxy, aryl, —N($R^a$)($R^b$), —C(O)$R^c$, —$CO_2R^c$, —C(O)N($R^a$)($R^b$), —$SO_2$N($R^a$)($R^b$), or —SO$R^c$, or two $R^1$ groups together form a ring system, e.g.,

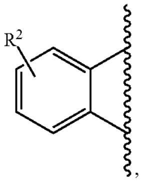
, e.g.,

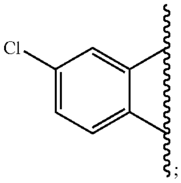
;

each $R^2$ and $R^3$ is independently cyano, nitro, hydroxy, halo, $C_1$-$C_3$ haloalkyl, $C_1$-$C_3$ haloalkoxy, $C_1$-$C_6$ alkyl (e.g., —CH(OH)$CH_2$OH), $C_1$-$C_6$ alkoxy, $C_3$-$C_8$ cycloalkyl, aryl, —N($R^a$)($R^b$), —C(O)$R^c$, —$CO_2R^c$, —C(O)N($R^a$)($R^b$), —$SO_2$N($R^a$)($R^b$), or —SO$R^c$;

each $R^a$ and $R^b$ is independently H, hydroxyl, —O$R^c$, —N($R^c$)($R^c$), $C_1$-$C_6$ alkyl, —C(O)$R^c$, or —C(O)O$R^c$;

$R^c$ is H, $C_1$-$C_6$ alkyl, or aryl;

m is 1, 2, 3, 4, 5, or 6;

n is 0, 1, or 2;

p is 0, 1, or 2; and q is 0, 1, or 2.

In some embodiments, the present disclosure provides a compound of Formula (XVII):

(XVII)

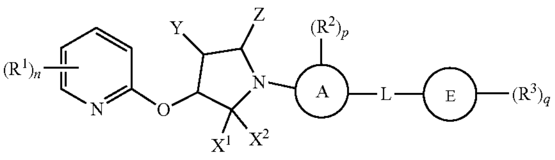

or a pharmaceutically acceptable salt thereof, wherein:

A is bond, aryl, or heteroaryl;

E is aryl, heteroaryl, $C_3$-$C_8$ cycloalkyl, or $C_3$-$C_8$ cycloalkenyl;

L is a bond, —$(CR^aR^b)_m$—, —O—, —C(O)—, or —C(O)N($R^a$)—;

$X^1$ and $X^2$ together are oxo, or each of $X^1$ and $X^2$ is H;

Y is H or OH;

Z is H or $C_1$-$C_6$ alkyl;

each $R^1$ is independently cyano, halo, $C_1$-$C_3$ haloalkyl, $C_1$-$C_6$ alkyl, or —C(O)N($R^a$)($R^b$), or two $R^1$ groups together form a ring system, e.g.,

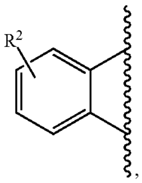
, e.g.,

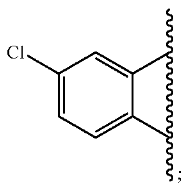

each $R^2$ and $R^3$ is independently cyano, nitro, hydroxy, halo, $C_1$-$C_3$ haloalkyl, $C_1$-$C_3$ haloalkoxy, $C_1$-$C_6$ alkyl, alkoxy, $C_3$-$C_8$ cycloalkyl, aryl, —$N(R^a)(R^b)$, —C(O)$R^c$, —$CO_2R^c$, —C(O)$N(R^a)(R^b)$, —$SO_2N(R^a)(R^b)$, or —$SOR^c$;

each $R^a$ and $R^b$ is independently H, hydroxyl, —$OR^c$, —$N(R^c)(R^c)$, $C_1$-$C_6$ alkyl, —C(O)$R^c$, or —C(O)$OR^c$;

$R^c$ is H, $C_1$-$C_6$ alkyl, or aryl;

m is 1, 2, 3, 4, 5, or 6;

n is 0, 1, or 2;

p is 0, 1, or 2; and q is 0, 1, or 2.

In some embodiments, the present disclosure provides a compound of Formula (XVIII)

(XVIII)

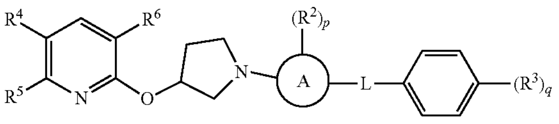

or a pharmaceutically acceptable salt thereof, wherein:

A is bond, aryl, or heteroaryl;

L is a bond, —$(CR^aR^b)_m$—, —O—, —C(O)—, or —C(O)$N(R^a)$—;

each $R^2$ and $R^3$ is independently cyano, nitro, hydroxy, halo, $C_1$-$C_3$ haloalkyl, $C_1$-$C_3$ haloalkoxy, $C_1$-$C_6$ alkyl, alkoxy, $C_3$-$C_8$ cycloalkyl, aryl, —$N(R^a)(R^b)$, —C(O)$R^c$, —$CO_2R^c$, —C(O)$N(R^a)(R^b)$, —$SO_2N(R^a)(R^b)$, or —$SOR^c$;

each $R^4$, $R^5$, and $R^6$ is independently cyano, halo, $C_1$-$C_3$ haloalkyl, $C_1$-$C_6$ alkyl, $C_1$-$C_6$ alkoxyl, or —C(O)$N(R^a)(R^b)$;

each $R^a$ and $R^b$ is independently H, hydroxyl, —$OR^c$, —$N(R^c)(R^c)$, $C_1$-$C_6$ alkyl, —C(O)$R^c$, or —C(O)$OR^c$;

$R^c$ is H, $C_1$-$C_6$ alkyl, or aryl;

m is 1, 2, 3, 4, 5, or 6;

p is 0, 1, or 2; and q is 0, 1, or 2.

In some embodiments, the present disclosure provides a compound of Formula (XIX)

(XIX)

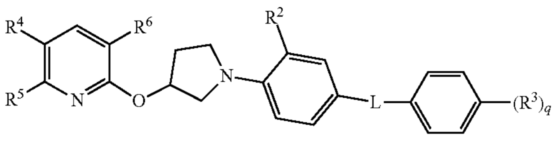

or a pharmaceutically acceptable salt thereof, wherein:

L is bond, —$(CR^aR^b)_m$—, —O—, —C(O)—, or —C(O)$N(R^a)$—;

each $R^2$ and $R^3$ is independently cyano, nitro, hydroxy, halo, $C_1$-$C_3$ haloalkyl, $C_1$-$C_3$ haloalkoxy, $C_1$-$C_6$ alkyl, alkoxy, $C_3$-$C_8$ cycloalkyl, aryl, —$N(R^a)(R^b)$, —C(O)$R^c$, —$CO_2R^c$, —C(O)$N(R^a)(R^b)$, —$SO_2N(R^a)(R^b)$, or —$SOR^c$;

each $R^4$, $R^5$, and $R^6$ is independently cyano, halo, $C_1$-$C_3$ haloalkyl, $C_1$-$C_6$ alkyl, $C_1$-$C_6$ alkoxyl, or —C(O)$N(R^a)(R^b)$;

each $R^a$ and $R^b$ is independently H, hydroxyl, —$OR^c$, —$N(R^c)(R^c)$, $C_1$-$C_6$ alkyl, —C(O)$R^c$, or —C(O)$OR^c$;

$R^c$ is H, $C_1$-$C_6$ alkyl, or aryl;

m is 1, 2, 3, 4, 5, or 6; and q is 0, 1, or 2.

In some embodiments, the present disclosure provides a compound of Formula (XX)

(XX)

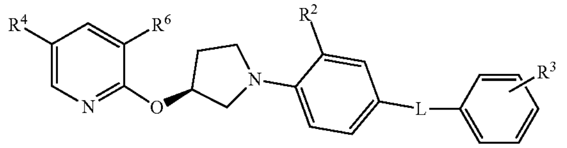

or a pharmaceutically acceptable salt thereof, wherein:

L is bond, —$(CR^aR^b)_m$—, —O—, —C(O)—, or —C(O)$N(R^a)$—;

each $R^2$ and $R^3$ is independently cyano, nitro, hydroxy, halo, $C_1$-$C_3$ haloalkyl, $C_1$-$C_3$ haloalkoxy, $C_1$-$C_6$ alkyl, alkoxy, $C_3$-$C_8$ cycloalkyl, aryl, —$N(R^a)(R^b)$, —C(O)$R^c$, —$CO_2R^c$, —C(O)$N(R^a)(R^b)$, —$SO_2N(R^a)(R^b)$, or —$SOR^c$;

each $R^4$ and $R^6$ is independently cyano, halo, $C_1$-$C_3$ haloalkyl, $C_1$-$C_6$ alkyl, $C_1$-$C_6$ alkoxyl, or —C(O)$N(R^a)(R^b)$;

each $R^a$ and $R^b$ is independently H, hydroxyl, —$OR^c$, —$N(R^c)(R^c)$, $C_1$-$C_6$ alkyl, —C(O)$R^c$, or —C(O)$OR^c$;

$R^c$ is H, $C_1$-$C_6$ alkyl, or aryl; and m is 1, 2, 3, 4, 5, or 6.

In some embodiments, the compound comprises at least 70% chirally pure enantiomer.

In some embodiments, the compound comprises at least 80% chirally pure enantiomer.

In some embodiments, the compound comprises at least 90% chirally pure enantiomer.

In some embodiments, the compound comprises at least 95% chirally pure enantiomer.

In some embodiments, the compound comprises at least 98% chirally pure enantiomer.

In some embodiments, the compound comprises at least 99% chirally pure enantiomer.

In some embodiments, the present disclosure provides a compound of Formula (XXI)

(XXI)

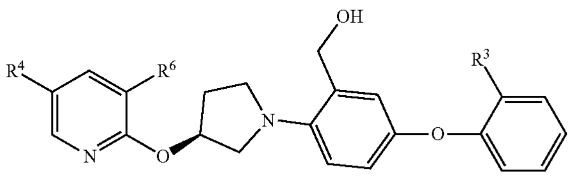

or a pharmaceutically acceptable salt thereof, wherein:

$R^3$ is cyano, nitro, hydroxy, halo, $C_1$-$C_3$ haloalkyl, $C_1$-$C_3$ haloalkoxy, $C_1$-$C_6$ alkyl, alkoxy, aryl, —N($R^a$)($R^b$), —C(O)$R^c$, —$CO_2R^c$, —C(O)N($R^a$)($R^b$), —$SO_2$N($R^a$)($R^b$), or —SO$R^c$;

each $R^4$ and $R^6$ is independently cyano, halo, $C_1$-$C_3$ haloalkyl, $C_1$-$C_6$ alkyl, $C_1$-$C_6$ alkoxyl, or —C(O)N($R^a$)($R^b$);

each $R^a$ and $R^b$ is independently H, $C_1$-$C_6$ alkyl, —O$R^c$, —N($R^c$)($R^c$), —C(O)$R^c$, or —C(O)O$R^c$;

$R^c$ is H, $C_1$-$C_6$ alkyl, or aryl; and m is 1, 2, 3, 4, 5, or 6.

In some embodiments, L is a bond, —$(CH_2)_m$—, —O—, —C(O)—, —C(O)N($R^a$)—, or —CH(O$R^c$)—.

In some embodiments, L is —$(CH_2)_m$—, —O—, or —CH(O$R^c$)—.

In some embodiments, the compound comprises at least 70% chirally pure enantiomer.

In some embodiments, the compound comprises at least 80% chirally pure enantiomer.

In some embodiments, the compound comprises at least 90% chirally pure enantiomer.

In some embodiments, the compound comprises at least 95% chirally pure enantiomer.

In some embodiments, the compound comprises at least 98% chirally pure enantiomer.

In some embodiments, the compound comprises at least 99% chirally pure enantiomer.

In some embodiments, the present disclosure provides a compound of Formula (XXII):

(XXII)

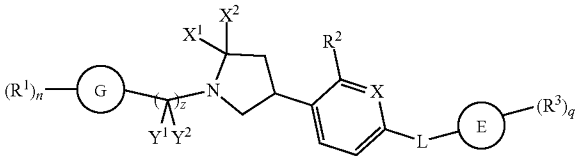

or a pharmaceutically acceptable salt thereof, wherein:

X is —N— or —CH—;

$Y^1$ and $Y^2$ together are oxo, or each of $Y^1$ and $Y^2$ is H;

$X^1$ and $X^2$ together are oxo, or each of $X^1$ and $X^2$ is H;

L is bond, —$(CR^aR^b)_m$—, —O—, —C(O)—, —C(O)N($R^a$)—, or —CH(O$R^c$)—;

E is aryl, heteroaryl, $C_3$-$C_8$ cycloalkyl, or $C_3$-$C_8$ cycloalkenyl;

G is aryl, heteroaryl, $C_3$-$C_8$ cycloalkyl, or $C_3$-$C_8$ heterocycloalkyl;

each $R^1$ is independently cyano, nitro, hydroxy, halo, $C_1$-$C_3$ haloalkyl, $C_1$-$C_3$ haloalkoxy, $C_1$-$C_6$ alkyl, $C_1$-$C_6$ alkoxy, aryl, —N($R^a$)($R^b$), —C(O)$R^c$, —$CO_2R^c$, —C(O)N($R^a$)($R^b$), —$SO_2$N($R^a$)($R^b$), or —SO$R^c$, or two $R^1$ groups together form a ring system, e.g.,

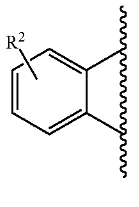

, e.g.,

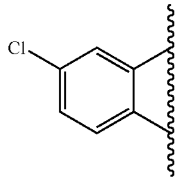

;

each $R^2$ and $R^3$ is independently cyano, nitro, hydroxy, halo, $C_1$-$C_3$ haloalkyl, $C_1$-$C_3$ haloalkoxy, $C_1$-$C_6$ alkyl (e.g., —CH(OH)$CH_2$OH), $C_1$-$C_6$ alkoxy, $C_3$-$C_8$ cycloalkyl, aryl, —N($R^a$)($R^b$), —C(O)$R^c$, —$CO_2R^c$, —C(O)N($R^a$)($R^b$), —$SO_2$N($R^a$)($R^b$), or —SO$R^c$; n is 0, 1, or 2;

q is 0, 1, or 2;

z is 0 or 1;

each $R^a$ and $R^b$ is independently H, hydroxyl, —O$R^c$, —N($R^c$)($R^c$), $C_1$-$C_6$ alkyl, —C(O)$R^c$, or —C(O)O$R^c$; and $R^c$ is H, $C_1$-$C_6$ alkyl, or aryl. The compound of claim 1, wherein X is —CH—.

In some embodiments, $Y^1$ and $Y^2$ together are oxo.

In some embodiments, $X^1$ and $X^2$ are each H.

The compound of claim 96, wherein L is bond or —O—.

In some embodiments, E is phenyl.

In some embodiments, G is aryl or heteroaryl.

In some embodiments, G is pyridine.

In some embodiments, $R^2$ is —$CH_2$OH.

In some embodiments, $R^1$ is halo or $C_1$-$C_3$ haloalkyl.

In some embodiments, $R^3$ is $C_1$-$C_6$ alkyl or $C_3$-$C_8$ cycloalkyl.

In some embodiments, n is 1 and $R^1$ is halo or $C_1$-$C_3$ haloalkyl.

In some embodiments, q is 1 or 2, and $R^3$ is $C_1$-$C_6$ alkyl or $C_3$-$C_8$ cycloalkyl.

In some embodiments, z is 1, and $Y^1$ and $Y^2$ together are oxo.

In some embodiments, X is —CH— and L is bond or —O—.

In some embodiments, n is 1 and q is 1.

In some embodiments, E is phenyl and L is bond or —O—.

In some embodiments, E is aryl, L is bond or —O—, and $R^2$ is —$CH_2$OH.

In some embodiments, X is —CH—, $R^2$ is —$CH_2$OH, L is bond or —O—, and q is 1 or 2.

In some embodiments, the present disclosure provides a compound of Formula (XXIII):

(XXIII)

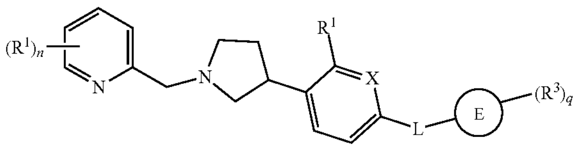

or a pharmaceutically acceptable salt thereof, wherein:

X is —N— or —CH—;

L is bond, —$(CR^aR^b)_m$—, —O—, —C(O)—, —C(O)N($R^a$)—, or —CH(O$R^c$)—;

E is aryl, heteroaryl, $C_3$-$C_8$ cycloalkyl, or $C_3$-$C_8$ cycloalkenyl;

each $R^1$ is independently cyano, nitro, hydroxy, halo, $C_1$-$C_3$ haloalkyl, $C_1$-$C_3$ haloalkoxy, $C_1$-$C_6$ alkyl, $C_1$-$C_6$ alkoxy, aryl, —$N(R^a)(R^b)$, —$C(O)R^c$, —$CO_2R^c$, —$C(O)N(R^a)(R^b)$, —$SO_2N(R^a)(R^b)$, or —$SOR^c$, or two $R^1$ groups together form a ring system, e.g.,

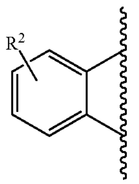

, e.g.,

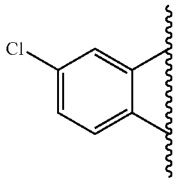

;

each $R^2$ and $R^3$ is independently cyano, nitro, hydroxy, halo, $C_1$-$C_3$ haloalkyl, $C_1$-$C_3$ haloalkoxy, $C_1$-$C_6$ alkyl (e.g., —$CH(OH)CH_2OH$), $C_1$-$C_6$ alkoxy, $C_3$-$C_8$ cycloalkyl, aryl, —$N(R^a)(R^b)$, —$C(O)R^c$, —$CO_2R^c$, —$C(O)N(R^a)(R^b)$, —$SO_2N(R^a)(R^b)$, or —$SOR^c$;

n is 0, 1, or 2;

q is 0, 1, or 2;

each $R^a$ and $R^b$ is independently H, hydroxyl, —$OR^c$, —$N(R^c)(R^c)$, $C_1$-$C_6$ alkyl, —$C(O)R^c$, or —$C(O)OR^c$; and $R^c$ is H, $C_1$-$C_6$ alkyl, or aryl.

In some embodiments, the present disclosure provides a compound of Formula (XXIV):

(XXIV)

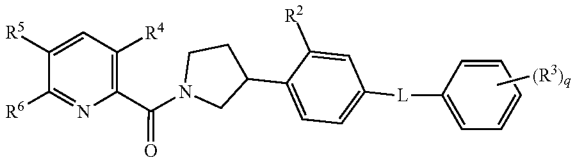

or a pharmaceutically acceptable salt thereof, wherein:

L is bond, —$(CR^aR^b)_m$—, —O—, —C(O)—, —$C(O)N(R^a)$—, or —$CH(OR^c)$—;

each $R^2$ and $R^3$ is independently cyano, nitro, hydroxy, halo, $C_1$-$C_3$ haloalkyl, $C_1$-$C_3$ haloalkoxy, $C_1$-$C_6$ alkyl (e.g., —$CH(OH)CH_2OH$), $C_1$-$C_6$ alkoxy, $C_3$-$C_8$ cycloalkyl, aryl, —$N(R^a)(R^b)$, —$C(O)R^c$, —$CO_2R^c$, —$C(O)N(R^a)(R^b)$, —$SO_2N(R^a)(R^b)$, or —$SOR^c$; each $R^4$, $R^5$, and $R^6$ is independently cyano, $C_1$-$C_6$ alkyl, $C_1$-$C_6$ alkoxyl, halo, $C_1$-$C_3$ haloalkyl, or —$C(O)N(R^a)(R^b)$;

q is 0, 1, or 2;

each $R^a$ and $R^b$ is independently H, hydroxyl, —$OR^c$, —$N(R^c)(R^c)$, $C_1$-$C_6$ alkyl, —$C(O)R^c$, or —$C(O)OR^c$; and $R^c$ is H, $C_1$-$C_6$ alkyl, or aryl.

In some embodiments, the present disclosure provides a compound of Formula (XXV):

(XXV)

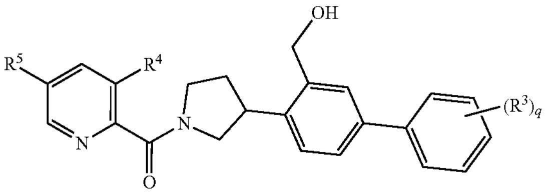

or a pharmaceutically acceptable salt thereof, wherein:

each $R^3$ is independently halo, $C_1$-$C_6$ alkyl, $C_3$-$C_8$ cycloalkyl, or $C_1$-$C_6$ alkoxy;

each $R^4$ and $R^5$ is independently cyano, $C_1$-$C_6$ alkyl, $C_1$-$C_6$ alkoxyl, halo, $C_1$-$C_3$ haloalkyl, or —$C(O)N(R^a)(R^b)$;

q is 0, 1, or 2;

each $R^a$ and $R^b$ is independently H, hydroxyl, —$OR^c$, —$N(R^c)(R^c)$, $C_1$-$C_6$ alkyl, —$C(O)R^c$, or —$C(O)OR^c$; and $R^c$ is H, $C_1$-$C_6$ alkyl, or aryl.

In some embodiments, the present disclosure provides a compound of Formula (XXVI):

(XXVI)

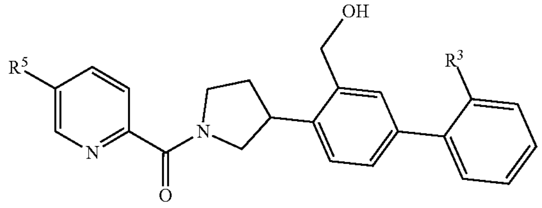

or a pharmaceutically acceptable salt thereof, wherein:

$R^3$ is halo, $C_1$-$C_6$ alkyl, $C_3$-$C_8$ cycloalkyl, or $C_1$-$C_6$ alkoxy;

$R^5$ is cyano, $C_1$-$C_6$ alkyl, $C_1$-$C_6$ alkoxyl, halo, $C_1$-$C_3$ haloalkyl, or —$C(O)N(R^a)(R^b)$;

each $R^a$ and $R^b$ is independently H, hydroxyl, —$OR^c$, —$N(R^c)(R^c)$, $C_1$-$C_6$ alkyl, —$C(O)R^c$, or —$C(O)OR^c$; and $R^c$ is H, $C_1$-$C_6$ alkyl, or aryl.

In some embodiments, the present disclosure provides a compound of Formula (XXVII)

(XXVII)

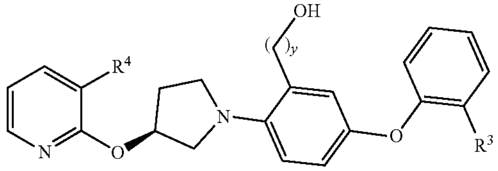

or a pharmaceutically acceptable salt thereof, wherein $R^3$ is —Cl, —F, ethyl, n-propyl, or iso-propyl;

$R^4$ is —Me or —Cl; and y is 1 or 2.

In accordance with some aspects, the present disclosure the provides a compound having the structure of general formula (XXXII):

(XXXII)

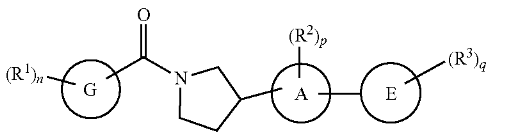

or a pharmaceutically acceptable salt, solvate, hydrate, any stereoisomer thereof or physiologically functional derivative thereof, wherein each of A, E and G, independently of the other, is selected from a ring system containing three to twelve atoms;

$R^1$ is independently selected from cyano, nitro, hydroxy, halo, $C_1$-$C_3$ haloalkyl, $C_1$-$C_3$ haloalkoxy, $C_1$-$C_6$ alkyl, $C_1$-$C_6$ alkoxy, ether, aryl, —N($R^a$)($R^b$), —C(O)$R^c$, —$CO_2R^c$, —C(O)N($R^a$)($R^b$), —$SO_2$N($R^a$)($R^b$), or —SO$R^c$, or two $R^1$ groups together form a ring system, e.g.,

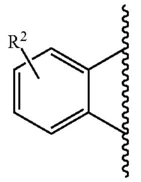

, e.g.,

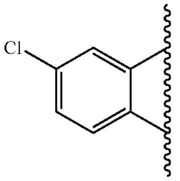

;

each of $R^2$ and $R^3$ is independently of the other selected from cyano, nitro, hydroxy, halo, $C_1$-$C_3$ haloalkyl, $C_1$-$C_3$ haloalkoxy, $C_1$-$C_6$ alkyl (e.g., —CH(OH) $CH_2OH$), $C_3$-$C_8$ cycloalkyl, $C_1$-$C_6$ alkoxy, aryl, —N($R^a$)($R^b$), —C(O)$R^c$, —$CH_2R^c$, —$CO_2R^c$, —C(O) N($R^a$)($R^b$), —$SO_2$N($R^a$)($R^b$), or —SO$R^c$; each $R^a$ and $R^b$ is independently H, hydroxyl, —O$R^c$, $C_1$-$C_6$ alkyl, —C(O)$R^c$, or —C(O)O$R^c$; $R^c$ is H, $C_1$-$C_6$ alkyl, aryl, —O$R^a$, or —N($R^a$)($R^a$)

n is 0, 1, or 2; p is 0, 1, or 2; and q is 0, 1, or 2.

In accordance with some embodiments, in the compounds of the invention, each one of A, E and G, is selected to be a ring system having three to twelve atoms. A ring system as used herein encompasses a monocyclic ring system, or a polycyclic ring system (e.g., a bicyclic ring system). As noted herein, a ring system (for example, a monocyclic ring system or a bicyclic ring system, which can include fused ring systems) may include only carbon atoms or both carbon atoms and heteroatoms. Hence, a ring system having three to twelve atoms encompasses one or more rings having between three to twelve atoms as a total number of atoms. As appreciated, the atoms may include only carbon atoms or alternatively, may include at least one heteroatom, including, inter alia, N, O or S. In accordance with some embodiments, each one of A, E and G is selected to be an aromatic ring system (either monocyclic or bicyclic aromatic ring system).

In accordance with some embodiments, each of A, E and G is independently of the other selected from aryl, heteroaryl, cycloalkyl, heterocycloalkyl, cycloalkenyl or heterocycloalkenyl.

In accordance with some embodiments, each of A, E and G is independently of the other selected from aryl or heteroaryl.

In accordance with some other embodiments, each one of A, E and G is independently of the other selected from cycloalkyl, heterocycloalkyl, cycloalkenyl or heterocycloalkenyl.

In some other embodiments, each of A, E and G is independently of the other is cycloalkyl or heterocycloalkyl.

In some other embodiments, each of A, E and G is independently of the other is cycloalkenyl or heterocycloalkenyl.

In some other embodiments, each of A, E and G in compounds of the invention, such as those, being compounds of the general formula (XXXII), is independently selected from 1-naphthyl, 2-naphthyl, 4-biphenyl, quinolyl, isoquinolyl, phenyl, pyridine, pyrazine, pyrimidine, pyridazine, 1,2,3-triazine, 1,2,4-triazine, 1,3,5-triazine, furan, thipohene, pyrrole, oxazole, thiazole, imidazole, pyrazole, isoxazole, thiazole, benzofurna, indole, benzothiophene, benzoimidazole, indazole, benzoxazole, benzoisoxazole, benzothiazole, isobenzfuran, isoidole or purine.

The number of atoms in a ring system may be in accordance with some embodiments between 3 to 8 atoms. Hence, a ring system having three to eight atoms encompasses one or more rings having between three to eight atoms as a total number of atoms. As appreciated, the atoms may include only carbon atoms or alternatively, may include at least one heteroatom, including, inter alia, N, O or S.

In some embodiments, each of A, E and G is independently of the other is selected in compounds of the invention from aryl, heteroaryl, $C_3$-$C_8$ cycloalkyl, $C_3$-$C_8$ heterocycloalkyl, $C_3$-$C_8$ cycloalkenyl or $C_3$-$C_8$ heterocycloalkenyl.

In some embodiments, each of A, E and G is independently of the other is selected in compounds of the invention from $C_3$-$C_8$ cycloalkyl, $C_3$-$C_5$ heterocycloalkyl, $C_3$-$C_8$ cycloalkenyl or $C_3$-$C_8$ heterocycloalkenyl.

In some embodiments, each of A, E and G is independently of the other is selected from $C_3$-$C_8$ cycloalkyl or $C_3$-$C_8$ heterocycloalkyl.

In some embodiments, each of A, E and G is independently of the other is selected from $C_3$-$C_8$ cycloalkenyl or $C_3$-$C_8$ heterocycloalkenyl.

In some other embodiments, each of A, E and G is independently of the other is selected from aryl, $C_3$-$C_8$ cycloalkyl or $C_3$-$C_8$ cycloalkenyl.

In some other embodiments, each of A, E and G is independently of the other is selected from heteroaryl, $C_3$-$C_8$ heterocycloalkyl or $C_3$-$C_8$ heterocycloalkenyl.

In some embodiments, each one of A, E and G in the compounds of the invention, such as compounds of formula (XXXII) is independently of the other selected from a heteroaryl comprising five atoms or a heteroaryl comprising six atoms.

In some embodiments, each one of A, E and G in the compounds of the invention, such as compounds of formula (XXXII) is independently of the other selected from an aryl comprising five atoms or a aryl comprising six atoms.

In some embodiments, each of A, E and G is independently of the other is a heteroaryl comprising five atoms or six atoms.

In some embodiments, each of A, E and G is independently of the other is a heteroaryl comprising five atoms or six atoms, including carbon atoms and heteroatoms, among which at least one, at least two, at least three heteroatoms or at least four heteroatoms.

In some embodiments, each of A, E and G is independently of the other is selected from 6-membered aryl, 5-membered aryl, 6-membered nitrogen containing heteroaryl or 5-membered nitrogen containing heteroaryl.

In some embodiments, each of A, E and G is independently of the other is selected from 6-membered aryl or 6-membered nitrogen containing heteroaryl.

In some other embodiments, A is a 6-membered or 5-membered nitrogen containing heteroaryl.

In some other embodiments, E is a 6-membered or 5-membered nitrogen containing heteroaryl.

In some other embodiments, G is a 6-membered or 5-membered nitrogen containing heteroaryl.

In some embodiments, each of A, E and G is independently of the other is selected from phenyl, pyridine, pyrazine, pyrimidine, pyridazine, 1,2,3-triazine, 1,2,4-triazine or 1,3,5-triazine.

In some embodiments, E is selected from phenyl, pyridine, pyrazine, pyrimidine, pyridazine, 1,2,3-triazine, 1,2,4-triazine, 1,3,5-triazine.

In some other embodiments, E is phenyl.

In some embodiments, A is selected from an aryl or an heteroaryl, each comprising five atoms or six atoms among which at least one, at least two, at least three heteroatoms or at least four heteroatoms.

In some embodiments, A is selected from phenyl, pyridine, pyrazine, pyrimidine, pyridazine, 1,2,3-triazine, 1,2,4-triazine, 1,3,5-triazine.

In some other embodiments, A is phenyl.

In some embodiments, G is an aryl or, an heteroaryl, each comprising five atoms or six atoms among which at least one, at least two, at least three heteroatoms or at least four heteroatoms.

In some other embodiments, G is a 6-membered nitrogen containing heteroaryl.

In some embodiments, G is selected from phenyl, pyridine, pyrazine, pyrimidine, pyridazine, 1,2,3-triazine, 1,2,4-triazine or 1,3,5-triazine.

In some other embodiments, G is selected from phenyl, pyridine, pyrazine, pyrimidine or pyridazine.

In some embodiments G is selected from the group consisting of:

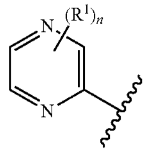,
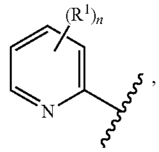,
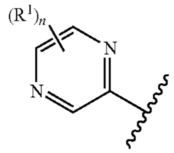,
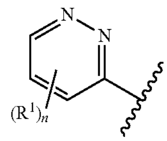, and
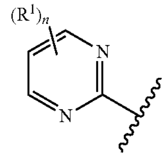.

In some other embodiments, G is pyridine.

In some other embodiments, G is

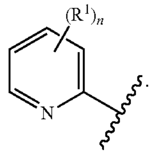.

In some other embodiments, G is pyrazine.

In some other embodiments, G is

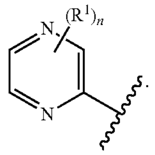.

In some embodiments, G is phenyl.

In some embodiments, in the compounds of the invention, for example, compounds of formula (XXXII), E is phenyl, A is phenyl, and G is selected from phenyl, pyridine, pyrazine, pyrimidine, pyridazine, 1,2,3-triazine, 1,2,4-triazine or 1,3,5-triazine.

In some other embodiments, in the compounds of the invention, for example, compounds of formula (XXXII), E is phenyl, A is phenyl, and G is pyridine.

In some further embodiments, in the compounds of the invention, for example, compounds of formula (XXXII), E is phenyl, A is phenyl, and G is pyrazine.

In some embodiments, $R^1$ is selected from halo, $C_1$-$C_6$ alkyl, $C_1$-$C_6$ alkoxy, hydroxy, $C_1$-$C_3$ haloalkyl, cyano, ether, —$N(R^a)(R^b)$, —$C(O)R^c$, each $R^a$ and $R^b$ is independently H, $C_1$-$C_6$ alkyl and $R^c$ is H or $C_1$-$C_6$ alkyl.

In some other embodiments, $R^1$ is selected from halo, $C_1$-$C_6$ alkyl, $C_1$-$C_6$ alkoxy, hydroxy, $C_1$-$C_3$ haloalkyl, ether, —$N(R^a)(R^b)$, each $R^a$ and $R^b$ is independently H, $C_1$-$C_6$ alkyl.

In some further embodiments, $R^1$ is at least one of fluorine, chlorine, methyl, methoxy, hydroxy, methyl amine, diethyl ether, or $CF_3$.

In some embodiments, $R^1$ is fluorine.

In some other embodiments, $R^1$ is methyl.

In some further embodiments, $R^1$ is methoxy.

In some embodiments, n is 0.

In some embodiments, n is 1 or 2.

In some embodiments, n is 1 or 2 and $R^1$ is selected from fluorine, chlorine, methyl, methoxy, hydroxy, methyl amine or $CF_3$.

In some embodiments, n is 2 and $R^1$ is at least one of fluorine, chlorine, methyl, methoxy, hydroxy, methyl amine or $CF_3$.

In some embodiments, n is 2 and $R^1$ is at least one of methyl and hydroxy.

In some embodiments, n is 1 and $R^1$ is fluorine.

In some embodiments, $R^2$ is selected from —$CH_2OH$, cyano, nitro, hydroxy, hydroxyalkyl, —$NH_2$, halo, aryl, —$N(R^a)(R^b)$, —C(O)OH, —$CH_2R^c$, —$CO_2R^c$, or —C(O)$N(R^a)(R^b)$ In some embodiments, $R^2$ is selected from hydroxyalkyl and halo.

In some embodiments, $R^2$ is hydroxyalkyl.

In some embodiments, $R^2$ is —$CH_2OH$ (Hydroxymethyl).

In some embodiments, p is 0.

In some embodiments, p is 1 or 2.

In some embodiments, p is 1 or 2 and $R^2$ is —$CH_2OH$ (Hydroxymethyl).

In some embodiments, p is 1 or 2 and $R^2$ is at least one of —$CH_2OH$ and fluorine.

In some embodiments, $R^3$ is selected from halo, $C_1$-$C_6$ alkyl, $C_1$-$C_6$ alkoxy, or $C_3$-$C_8$ cycloalkyl.

In some embodiments, $R^3$ is selected from fluorine, cyclopropyl, methyl, ethyl or propyl.

In some embodiments, $R^3$ is selected from methyl, ethyl or propyl.

In some embodiments, $R^3$ is cyclopropyl.

In some embodiments, $R^3$ is methoxy or ethoxy.

In some embodiments, $R^3$ is cyclopropyl and fluorine.

In some embodiments, q is 1 or 2.

In some embodiments, q is 1 or 2 and $R^3$ is at least one of halo, $C_1$-$C_6$ alkyl, $C_1$-$C_6$ alkoxy, or $C_3$-$C_8$ cycloalkyl.

In some embodiments, each one of A and E is independently selected from phenyl or a heteroaryl comprising six atoms. In some other embodiments, each one of A and E is phenyl.

Hence, in accordance with some aspects, which may be considered as embodiments, the present disclosure the provides a compound having the structure of general formula (XXXIII):

(XXXIII)

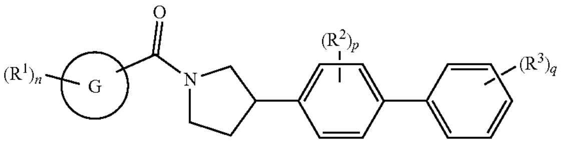

or a pharmaceutically acceptable salt, solvate, hydrate, any stereoisomer thereof or physiologically functional derivative thereof, wherein G, $R^1$, $R^2$, $R^3$, n, p and q are as defined for compounds of formula (XXXII).

In some embodiments, a compound having the structure of general formula (XXII) or (XXXIII) is provided by a compound having the structure of general formulae (XXXIIIa), (XXXIIIb), (XXXIIIc) or (XXXIIId).

(XXXIIIa)

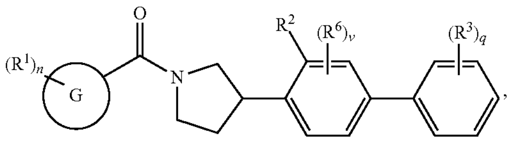

, (XXXIIIb)

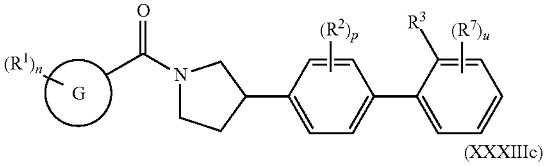

(XXXIIIc)

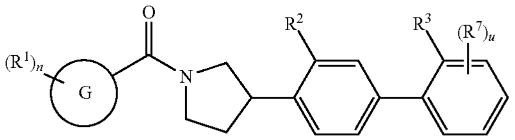

or

-continued (XXXIIId)

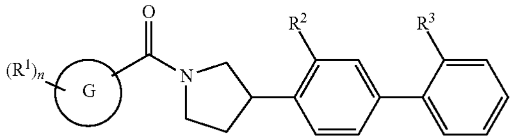

or a pharmaceutically acceptable salt, solvate, hydrate, any stereoisomer thereof or physiologically functional derivative thereof, wherein G, $R^1$, $R^2$, $R^3$ n, p, and q are as defined herein above for compound of formula (XXXIII), each one of $R^6$ and $R^7$ is independently of the other selected from cyano, nitro, hydroxy, halo, $C_1$-$C_3$ haloalkyl, $C_1$-$C_3$ haloalkoxy, $C_1$-$C_6$ alkyl (e.g., —CH(OH) $CH_2OH$), $C_3$-$C_8$ cycloalkyl, $C_1$-$C_6$ alkoxy, aryl, —$N(R^a)(R^b)$, —$C(O)R^c$, —$CH_2R^c$, —$CO_2R^c$, —$C(O)N(R^a)(R^b)$, —$SO_2N(R^a)(R^b)$, or —$SOR^c$; each $R^a$ and $R^b$ is independently H, hydroxyl, —$OR^c$, $C_1$-$C_6$ alkyl, —$C(O)R^c$, or —$C(O)OR^c$; $R^c$ is H, $C_1$-$C_6$ alkyl, aryl, —$OR^a$, or —$N(R^a)(R^a)$; u is 0, 1, or 2; and v is 0, 1, or 2.

In some embodiments, in compounds of the invention, such as those denoted by general formula (XXXII), the compound is a compound provided by general formula (XXXIII), (XXXIIIa), (XXXIIIb), (XXXIIc) or (XXXIId).

In some other embodiments, G is a 6-membered nitrogen containing heteroaryl.

In some embodiments, G is selected from phenyl, pyridine, pyrazine, pyrimidine, pyridazine, 1,2,3-triazine, 1,2,4-triazine, 1,3,5-triazine.

In some other embodiments, G is selected from phenyl, pyridine, pyrazine, pyrimidine or pyridazine.

In some other embodiments, G is selected from pyridine, pyrazine, pyrimidine, pyridazine.

In some embodiments G is selected from the group consisting of:

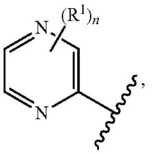

,

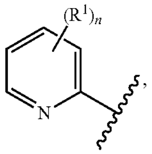

,

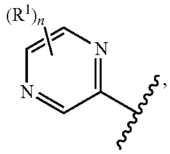

,

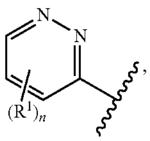

, and

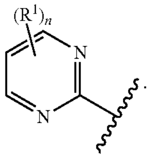

.

In some other embodiments, G is pyridine or pyrazine.

In some other embodiments, G is pyridine.

In some other embodiments, G is

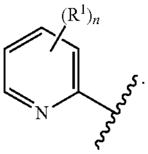

.

In some other embodiments, G is pyrazine.

In some other embodiments, G is

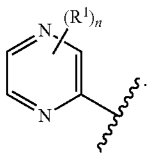

In some embodiments, G is phenyl.

In some embodiments, $R^1$ is selected from halo, $C_1$-$C_6$ alkyl, $C_1$-$C_6$ alkoxy, hydroxy, $C_1$-$C_3$ haloalkyl, cyano, ether, —$N(R^a)(R^b)$, —$C(O)R^c$, each $R^a$ and $R^b$ is independently H, $C_1$-$C_6$ alkyl and $R^c$ is H or $C_1$-$C_6$ alkyl.

In some other embodiments, $R^1$ is selected from halo, $C_1$-$C_6$ alkyl, $C_1$-$C_6$ alkoxy, hydroxy, $C_1$-$C_3$ haloalkyl, ether, —$N(R^a)(R^b)$, each $R^a$ and $R^b$ is independently H, $C_1$-$C_6$ alkyl.

In some further embodiments, $R^1$ is at least one of fluorine, chlorine, methyl, methoxy, hydroxy, methyl amine, diethyl ether, or $CF_3$.

In some embodiments, $R^1$ is fluorine.

In some other embodiments, $R^1$ is methyl.

In some further embodiments, $R^1$ is methoxy.

In some embodiments, n is 0.

In some embodiments, n is 1 or 2.

In some embodiments, n is 1 or 2 and $R^1$ is selected from fluorine, chlorine, methyl, methoxy, hydroxy, methyl amine or $CF_3$.

In some embodiments, n is 2 and $R^1$ is at least one of fluorine, chlorine, methyl, methoxy, hydroxy, methyl amine or $CF_3$.

In some embodiments, n is 2 and $R^1$ is at least one of methyl and hydroxy.

In some embodiments, n is 1 and $R^1$ is fluorine.

In some embodiments, G is selected from pyridine, pyrazine, pyrimidine, pyridazine, n is 1 and $R^1$ is selected from halo, $C_1$-$C_6$ alkyl, $C_1$-$C_6$ alkoxy, hydroxy, $C_1$-$C_3$ haloalkyl, —$N(R^a)(R^b)$, each $R^a$ and $R^b$ is independently H, $C_1$-$C_6$ alkyl.

In some embodiments, G is

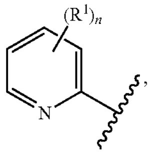

n is 1 and $R^1$ is at least one of fluorine, chlorine, methyl or methoxy.

In some embodiments, G is

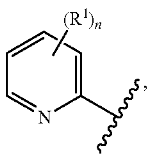

n is 1 and $R^1$ is fluorine or chlorine.

In some embodiments, G is

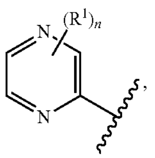

n is 1 and $R^1$ is at least one of fluorine, hydroxy, methyl or methoxy.

In some embodiments, G is

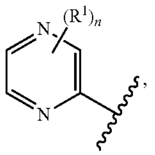

n is 1 and $R^1$ is methyl or methoxy.

In some embodiments, G is

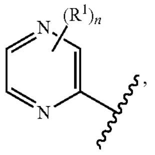

n is 2 and $R^1$ is selected from methyl and hydroxy.

In some embodiments, $R^2$ is at least one of —$CH_2OH$, cyano, nitro, hydroxy, hydroxyalkyl, —$NH_2$, halo, aryl, —$N(R^a)(R^b)$, —C(O)OH, —$CH_2R^c$, —$CO_2R^c$, or —C(O)$N(R^a)(R^b)$.

In some embodiments, $R^2$ is selected from —$CH_2OH$, cyano, nitro, hydroxy, hydroxyalkyl, —$NH_2$, halo, aryl, —$N(R^a)(R^b)$, —C(O)OH, —$CH_2R^c$, —$CO_2R^c$, or —C(O)$N(R^a)(R^b)$ In some embodiments, $R^2$ is selected from hydroxyalkyl and halo.

In some embodiments, $R^2$ is hydroxyalkyl.

In some embodiments, $R^2$ is —$CH_2OH$ (Hydroxymethyl).

In some embodiments, p is 0.

In some embodiments, p is 1 or 2.

In some embodiments, p is 1 or 2 and $R^2$ is —$CH_2OH$ (Hydroxymethyl).

In some embodiments, p is 1 or 2 and $R^2$ is at least one of —$CH_2OH$ and fluorine.

In some embodiments, G is selected from pyridine, pyrazine, pyrimidine, pyridazine, n is 1, $R^1$ is selected from halo, $C_1$-$C_6$ alkyl, $C_1$-$C_6$ alkoxy, hydroxy, $C_1$-$C_3$ haloalkyl, —$N(R^a)(R^b)$, each $R^a$ and $R^b$ is independently H, $C_1$-$C_6$ alkyl, p is 1, $R^2$ is selected from —$CH_2OH$, cyano, nitro, hydroxy, hydroxyalkyl, —$NH_2$, halo, aryl, —$N(R^a)(R^b)$, —C(O)OH, —$CH_2R^c$, —$CO_2R^c$, or —C(O)$N(R^a)(R^b)$.

In some embodiments, G is pyridine or pyrazine, n is 1, $R^1$ is at least one of fluorine, chlorine, methyl or methoxy, p is 1 and $R^2$ is —$CH_2OH$.

In some embodiments, G is pyridine or pyrazine, n is 2, $R^1$ is at least one of fluorine, chlorine, hydroxy, methyl or methoxy, p is 1 and $R^2$ is —$CH_2OH$.

In some embodiments, $R^3$ is selected from halo, $C_1$-$C_6$ alkyl, $C_1$-$C_6$ alkoxy, or $C_3$-$C_8$ cycloalkyl.

In some embodiments, $R^3$ is selected from fluorine, cyclopropyl, methyl, ethyl or propyl.

In some embodiments, $R^3$ is selected from methyl, ethyl or propyl.

In some embodiments, $R^3$ is cyclopropyl.

In some embodiments, $R^3$ is methoxy or ethoxy.

In some embodiments, $R^3$ is cyclopropyl and fluorine.

In some embodiments, q is 1 or 2.

In some embodiments, q is 1 or 2 and $R^3$ is at least one of halo, $C_1$-$C_6$ alkyl, $C_1$-$C_6$ alkoxy, or $C_3$-$C_8$ cycloalkyl.

In some embodiments, q is 1 or 2 and $R^3$ is at least In some embodiments, $R^3$ is selected from halo, $C_1$-$C_6$ alkyl, $C_1$-$C_6$ alkoxy, or $C_3$-$C_8$ cycloalkyl.

In some embodiments, $R^3$ is selected from fluorine, cyclopropyl, methyl, ethyl or propyl.

In some embodiments, $R^3$ is selected from methyl, ethyl or propyl.

In some embodiments, $R^3$ is cyclopropyl.

In some embodiments, $R^3$ is methoxy or ethoxy.

In some embodiments, $R^3$ is cyclopropyl and fluorine.

In some embodiments, q is 1 or 2.

In some embodiments, q is 1 or 2 and $R^3$ is at least one of halo, $C_1$-$C_6$ alkyl, $C_1$-$C_6$ alkoxy, or $C_3$-$C_8$ cycloalkyl.

In some embodiments, u is 1 or 2, $R^7$ is fluorine and $R^3$ is at least one of $C_1$-$C_6$ alkyl, $C_1$-$C_6$ alkoxy, or $C_3$-$C_8$ cycloalkyl.

In some embodiments, G is selected from pyridine, pyrazine, pyrimidine, pyridazine, n is 1 or 2, $R^1$ is selected from halo, $C_1$-$C_6$ alkyl, $C_1$-$C_6$ alkoxy, hydroxy, $C_1$-$C_3$ haloalkyl, —$N(R^a)(R^b)$, each $R^a$ and $R^b$ is independently H, $C_1$-$C_6$ alkyl, p is 1 or 2, $R^2$ is selected from —$CH_2OH$, cyano, nitro, hydroxy, hydroxyalkyl, —$NH_2$, halo, aryl, —$N(R^a)(R^b)$, —C(O)OH, —$CH_2R^c$, —$CO_2R^c$, or —$C(O)N(R^a)(R^b)$, q is 1 or 2, $R^3$ is selected from halo, $C_1$-$C_6$ alkyl, $C_1$-$C_6$ alkoxy, or $C_3$-$C_8$ cycloalkyl.

In some embodiments, G is pyridine or pyrazine, n is 1, $R^1$ is at least one of fluorine, chlorine, methyl, hydroxy, or methoxy, p is 1, $R^2$ is —$CH_2OH$, q is 1 or 2, $R^3$ is at least one of fluorine, cyclopropyl, methyl, ethyl or propyl.

In some embodiments, G is pyridine or pyrazine, n is 1, $R^1$ is at least one of fluorine, chlorine, methyl or methoxy, p is 1, $R^2$ is —$CH_2OH$, q is 2, $R^3$ is selected from fluorine, cyclopropyl, methyl, ethyl or propyl.

In some embodiments, in compounds of the invention, G is selected from pyridine, pyrazine, pyrimidine, pyridazine, n is 1 or 2, $R^1$ is selected from halo, $C_1$-$C_6$ alkyl, $C_1$-$C_6$ alkoxy, hydroxy, $C_1$-$C_3$ haloalkyl, —$N(R^a)(R^b)$, each $R^a$ and $R^b$ is independently H, $C_1$-$C_6$ alkyl, p is 1 or 2, $R^2$ is selected from —$CH_2OH$, cyano, nitro, hydroxy, hydroxyalkyl, —$NH_2$, halo, aryl, —$N(R^a)(R^b)$, —C(O)OH, —$CH_2R^c$, —$CO_2R^c$, or —$C(O)N(R^a)(R^b)$, v is 0, u is 0, q is 1 or 2, $R^3$ is at least one of halo, $C_1$-$C_6$ alkyl, $C_1$-$C_6$ alkoxy, or $C_3$-$C_6$ cycloalkyl.

In some embodiments, in compounds of the invention, G is selected from pyridine, pyrazine, pyrimidine, pyridazine, n is 1 or 2, $R^1$ is selected from halo, $C_1$-$C_6$ alkyl, $C_1$-$C_6$ alkoxy, hydroxy, $C_1$-$C_3$ haloalkyl, —$N(R^a)(R^b)$, each $R^a$ and $R^b$ is independently H, $C_1$-$C_6$ alkyl, p is 1 or 2, $R^2$ is selected from —$CH_2OH$, cyano, nitro, hydroxy, hydroxyalkyl, —$NH_2$, halo, aryl, —$N(R^a)(R^b)$, —C(O)OH, —$CH_2R^c$, —$CO_2R^c$, or —$C(O)N(R^a)(R^b)$, v is 0, u is 1 or 2, $R^3$ is at least one of halo, $C_1$-$C_6$ alkyl, $C_1$-$C_6$ alkoxy, or $C_3$-$C_6$ cycloalkyl and $R^7$ is halo.

In some embodiments, G is pyridine or pyrazine, n is 1 or 2, $R^1$ is selected from halo, $C_1$-$C_6$ alkyl, $C_1$-$C_6$ alkoxy, hydroxy, $C_1$-$C_3$ haloalkyl, —$N(R^a)(R^b)$, each $R^a$ and $R^b$ is independently H, $C_1$-$C_6$ alkyl, p is 1 or 2, $R^2$ is selected from —$CH_2OH$, cyano, nitro, hydroxy, hydroxyalkyl, —$NH_2$, halo, aryl, —$N(R^a)(R^b)$, —C(O)OH, —$CH_2R^c$, —$CO_2R^c$, or —$C(O)N(R^a)(R^b)$, p is 1, $R^2$ is —$CH_2OH$, v is 0, u is 0, q is 1, $R^3$ is selected from cyclopropyl, methyl, ethyl or propyl.

In some embodiments, G is pyridine or pyrazine, n is 1 or 2, $R^1$ is selected from halo, $C_1$-$C_6$ alkyl, $C_1$-$C_6$ alkoxy, hydroxy, $C_1$-$C_3$ haloalkyl, —$N(R^a)(R^b)$, each $R^a$ and $R^b$ is independently H, $C_1$-$C_6$ alkyl, p is 1 or 2, $R^2$ is selected from —$CH_2OH$, cyano, nitro, hydroxy, hydroxyalkyl, —$NH_2$, halo, aryl, —$N(R^a)(R^b)$, —C(O)OH, —$CH_2R^c$, —$CO_2R^c$, or —$C(O)N(R^a)(R^b)$, p is 1, $R^2$ is —$CH_2OH$, v is 0, u is 1 or 2, $R^7$ is fluorine, $R^3$ is selected from cyclopropyl, methyl, ethyl or propyl.

In some embodiments, G is pyridine or pyrazine, n is 1, $R^1$ is halo, $C_1$-$C_6$ alkyl, $C_1$-$C_6$ alkoxy, hydroxy, p is 1, $R^2$ is —$CH_2OH$, v is 0, u is 0, q is 1, $R^3$ is selected from cyclopropyl, methyl, ethyl or propyl.

In some embodiments, G is pyridine or pyrazine, n is 1, $R^1$ is halo, $C_1$-$C_6$ alkyl, $C_1$-$C_6$ alkoxy, hydroxy, p is 1, $R^2$ is —$CH_2OH$, v is 0, u is 1, $R^7$ is halo and $R^3$ is selected from cyclopropyl, methyl, ethyl or propyl.

In some embodiments, G is pyridine or pyrazine, n is 1, $R^1$ is fluorine, chlorine, methyl or methoxy, p is 1, $R^2$ is —$CH_2OH$, v is 0, u is 0, q is 1, $R^3$ is selected from cyclopropyl, methyl, ethyl or propyl.

In some embodiments, G is pyridine or pyrazine, n is 1, $R^1$ is fluorine, chlorine, methyl or methoxy, p is 1, $R^2$ is —$CH_2OH$, v is 0, u is 1, q is 1, $R^7$ is fluorine and $R^3$ is selected from cyclopropyl, methyl, ethyl or propyl.

In accordance with some embodiments, the compound of formula (XXXII), (XXXIII) or any variation thereof has the structure of general formulae (XXVIV), (XXXIV) or (XXVV)

(XXVIV)

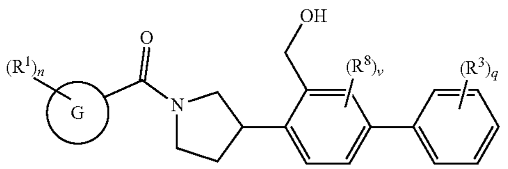

(XXXIV)

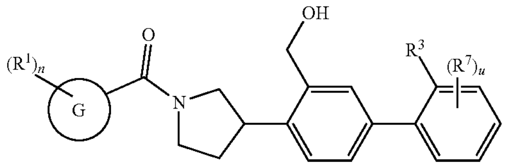

or (XXVV)

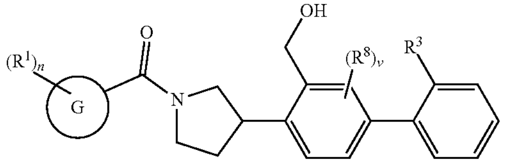

or a pharmaceutically acceptable salt, solvate, hydrate, any stereoisomer thereof or physiologically functional derivative thereof, wherein G, $R^1R^3$, $R^7$, $R^8$, n and u, v are as defined herein above.

In accordance with some aspects, the present disclosure provides a compound having general formula (XXXXIII)

(XXXXIII)

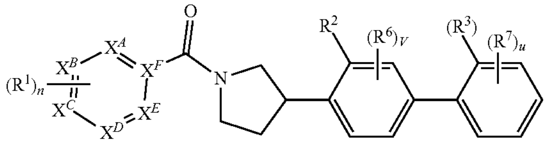

or a pharmaceutically acceptable salt, solvate, hydrate, any stereoisomer thereof or physiologically functional derivative thereof, wherein each of $X^A$, $X^B$, $X^C$, $X^D$, and $X^E$ is selected from N or CH, and XF is C, $R^1$ is selected from halo, $C_1$-$C_6$ alkyl, $C_1$-$C_6$ alkoxy, hydroxy, $C_1$-$C_3$ haloalkyl, —$N(R^a)(R^b)$, each $R^a$ and $R^b$ is independently H, $C_1$-$C_6$ alkyl; $R^2$ and $R^6$ independently from the other is selected from —$CH_2OH$, cyano, nitro, hydroxy, hydroxyalkyl, —$NH_2$, halo, aryl, —$N(R^a)(R^b)$, —C(O)OH, —$CH_2R^c$, —$CO_2R^c$, or —$C(O)N(R^a)(R^b)$;

$R^3$ and $R^7$ independently from the other is selected from halo, $C_1$-$C_6$ alkyl, $C_1$-$C_6$ alkoxy, or $C_3$-$C_6$ cycloalkyl;

n is 0, 1, or 2; u is 0, 1, or 2; and v is 0, 1, or 2.

In some embodiments, $R^1$ is selected from halo, $C_1$-$C_6$ alkyl, $C_1$-$C_6$ alkoxy, hydroxy, $C_1$-$C_3$ haloalkyl, cyano, ether, —$N(R^a)(R^b)$, —$C(O)R^c$, each $R^a$ and $R^b$ is independently H, $C_1$-$C_6$ alkyl and $R^c$ is H or $C_1$-$C_6$ alkyl.

In some other embodiments, $R^1$ is selected from halo, $C_1$-$C_6$ alkyl, $C_1$-$C_6$ alkoxy, hydroxy, $C_1$-$C_3$ haloalkyl, ether, —$N(R^a)(R^b)$, each $R^a$ and $R^b$ is independently H, $C_1$-$C_6$ alkyl.

In some further embodiments, $R^1$ is at least one of fluorine, chlorine, methyl, methoxy, hydroxy, methyl amine, diethyl ether, or $CF_3$.

In some embodiments, $R^1$ is fluorine.

In some other embodiments, $R^1$ is methyl.

In some further embodiments, $R^1$ is methoxy.

In some embodiments, n is 0.

In some embodiments, n is 1 or 2.

In some embodiments, n is 1 or 2 and $R^1$ is selected from fluorine, chlorine, methyl, methoxy, hydroxy, methyl amine or $CF_3$.

In some embodiments, n is 2 and $R^1$ is at least one of fluorine, chlorine, methyl, methoxy, hydroxy, methyl amine or $CF_3$.

In some embodiments, n is 2 and $R^1$ is at least one of methyl and hydroxy.

In some embodiments, n is 1 and $R^1$ is fluorine.

In some embodiments, $R^2$ is selected from —$CH_2OH$, cyano, nitro, hydroxy, hydroxyalkyl, —$NH_2$, halo, aryl, —$N(R^a)(R^b)$, —C(O)OH, —$CH_2R^c$, —$CO_2R^c$, or —$C(O)N(R^a)(R^b)$ In some embodiments, $R^2$ is selected from hydroxyalkyl and halo.

In some embodiments, $R^2$ is hydroxyalkyl.

In some embodiments, $R^2$ is —$CH_2OH$ (Hydroxymethyl).

In some embodiments, p is 0.

In some embodiments, p is 1 or 2.

In some embodiments, p is 1 or 2 and $R^2$ is —$CH_2OH$ (Hydroxymethyl).

In some embodiments, p is 1 or 2 and $R^2$ is at least one of —$CH_2OH$ and fluorine.

In some embodiments, p is 1, v is 1, $R^2$ is hydroxyalkyl and $R^6$ is halo.

In some embodiments, p is 1, v is 1, $R^2$ is —$CH_2OH$ and $R^6$ is fluorine.

In some embodiments, $R^3$ is selected from halo, $C_1$-$C_6$ alkyl, $C_1$-$C_6$ alkoxy, or $C_3$-$C_8$ cycloalkyl.

In some embodiments, $R^3$ is selected from fluorine, cyclopropyl, methyl, ethyl or propyl.

In some embodiments, $R^3$ is selected from methyl, ethyl or propyl.

In some embodiments, $R^3$ is cyclopropyl.

In some embodiments, $R^3$ is methoxy or ethoxy.

In some embodiments, $R^3$ is cyclopropyl and fluorine.

In some embodiments, q is 1 or 2.

In some embodiments, q is 1 or 2 and $R^3$ is at least one of halo, $C_1$-$C_6$ alkyl, $C_1$-$C_6$ alkoxy, or $C_3$-$C_8$ cycloalkyl.

In some embodiments, q is 1, u is 1, $R^3$ is at least one of halo, $C_1$-$C_6$ alkyl, $C_1$-$C_6$ alkoxy, or $C_3$-$C_8$ cycloalkyl and $R^7$ is halo.

In some embodiments, q is 1, u is 1, $R^3$ is at least one of cyclopropyl, methyl, ethyl or propyl and $R^7$ is flourine.

In some embodiments, a) $X^A$, is N; and $X^B$, $X^C$, $X^D$, and $X^E$ are CH, and $X^F$ is C; b) $X^B$, is N; and $X^A$, $X^C$, $X^D$, and $X^E$ are CH, and $X^F$ is C; c) $X^C$, is N; and $X^A$, $X^B$, $X^D$, $X^E$ are CH, and $X^F$ is C; or d) $X^A$, $X^D$ are N; and $X^B$, $X^C$, $X^E$ and CH and $X^F$ is C.

In some embodiments, the compound o formula (XXXXIII) has a general formula (XXXV) or (XXXVI)

(XXXV)

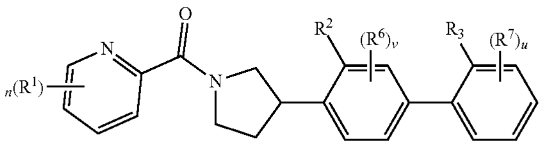

or (XXXVI)

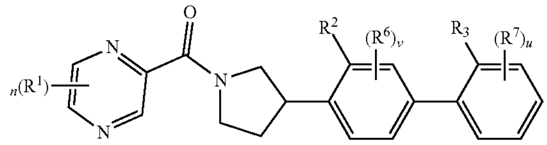

or a pharmaceutically acceptable salt, solvate, hydrate, any stereoisomer thereof or physiologically functional derivative thereof, In some embodiments a compound having the structure of general formula (XXVVI) or (XXXV):

(XXVVI)

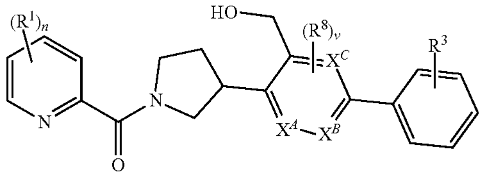

(XXXV)

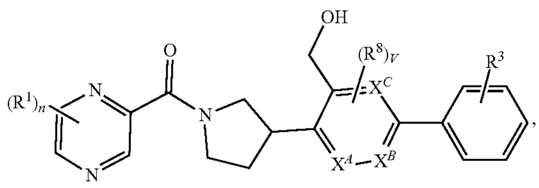

, or a pharmaceutically acceptable salt, solvate, hydrate, any stereoisomer thereof or physiologically functional derivative thereof, In some embodiments, a) $X^A$, is N; and $X^B$ and $X^C$ are both CH; b) $X^B$, is N; and $X^A$ and $X^C$ are both CH; or c) $X^C$, is N; and $X^A$ and $X^B$ are both CH.

In some embodiments, n is 1, and v is 0.

In some embodiments, $R^3$ is halo, $C_1$-$C_6$ alkyl, $C_1$-$C_6$ alkoxy, or $C_3$-$C_6$ cycloalkyl.

In some embodiments, $R^3$ is fluorine, cyclopropyl, methyl, ethyl or propyl.

In some embodiments, $R^3$ is methyl, ethyl or propyl.

In some embodiments, $R^3$ is cyclopropyl.

In some embodiments, $R^3$ is methoxy, ethoxy.

In some embodiments, $R^3$ is $C_1$-$C_6$ alkyl, $C_1$-$C_6$ alkoxy, or $C_3$-$C_8$ cycloalkyl.

In some other embodiments, $R^3$ is cyclopropyl and $R^1$ is F.

In accordance with some embodiments, the compound having the structure of general formulae selected from (XXXVII), (XXXVIII), (XXXIX), (XXXX), (XXXXI), or (XXXXII):

(XXXVII)

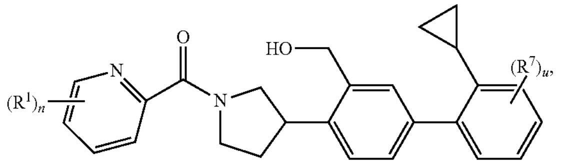

(XXXVIII)

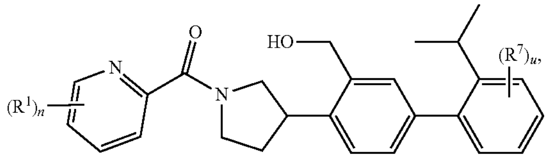

(XXXIX)

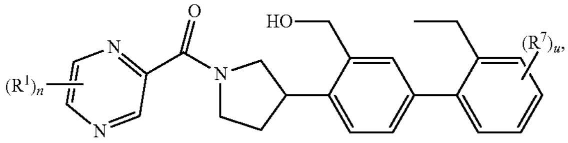

(XXXX)

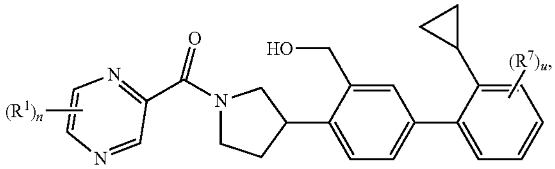

(XXXXI)

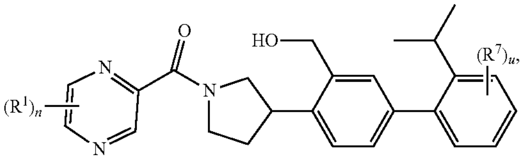

or

-continued (XXXXII)

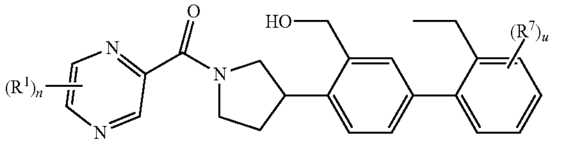

In some embodiments, $R^7$ is halo, $C_1$-$C_6$ alkyl, $C_1$-$C_6$ alkoxy, or $C_3$-$C_6$ cycloalkyl and u is 0, 1 or 2.

In some embodiments, $R^7$ is fluorine, cyclopropyl, methyl, ethyl or propyl.

In some embodiments, u is 1 and $R^7$ is fluorine, cyclopropyl, methyl, ethyl or propyl.

In some embodiments, u is 1 and $R^7$ is fluorine.

In some embodiments, the compound having the structure of general formulae selected from (XXXVIIa), (XXXVIIIa), (XXXIXa), (XXXXa), (XXXXIa), or (XXXXIIa):

(XXXVIIa)

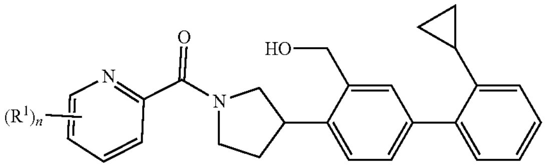

(XXXVIIIa)

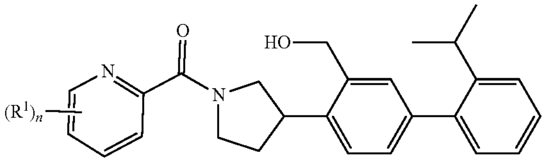

(XXXIXa)

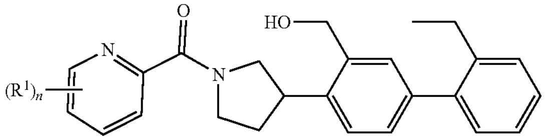

(XXXXa)

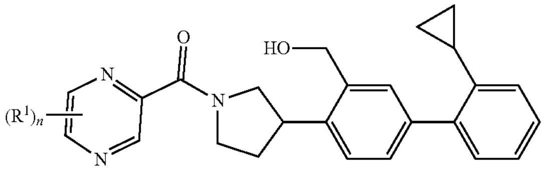

(XXXXIa)

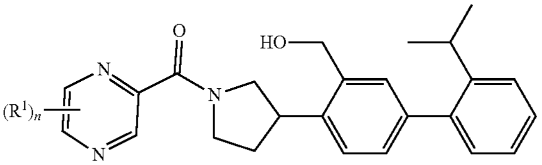

or

-continued (XXXXIIa)

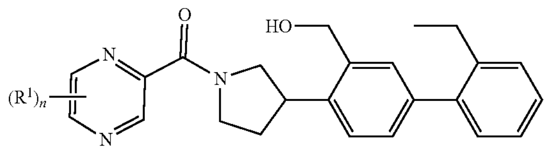

or a pharmaceutically acceptable salt, solvate, hydrate, any stereoisomer thereof or physiologically functional derivative thereof, wherein $R^1$ is as described above. In accordance with some embodiments, the compounds of this invention include mixtures of enantiomers (possibly as a racemic mixture) as well as purified enantiomers or enantiomerically enriched mixtures. The present invention also encompases the individual enantiomer(s) (i.e. R or S) of the compounds being represented by the formulas above as racemic mixtures.

Methods of preparing substantially isomerically pure compounds are known in the art. If, for instance, a particular enantiomer of a compound of the present disclosure is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers. Alternatively, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Techniques for inverting or leaving unchanged a particular stereocenter, and those for resolving mixtures of stereoisomers are well known in the art, and it is well within the ability of one of skill in the art to choose an appropriate method for a particular situation. See, generally, Furniss et al. (eds.), *Vogel's Encyclopedia of Practical Organic Chemistry* 5$^{th}$ *Ed.*, Longman Scientific and Technical Ltd., Essex, 1991, pp. 809-816; and Heller, *Acc. Chem. Res.* 23: 128 (1990).

Unless otherwise indicated, when referring to a compound having a chiral atom, it should be clear to refer to a racemic mixture of the compound. As appreciated, chirality may be indicated by a chemical structure of a compound or by a structure name of the compound.

A racemic mixture also denoted as racemate as used denotes that for a chiral compound, there are equal amounts of left- and right-handed enantiomers. In other words, the compound includes a mixture of 50% left-hand enantiomer and 50% right-hand enantiomer.

The term "stereoisomer" as used herein is meant to encompass an isomer that possess identical constitution as a corresponding stereoisomer, but which differs in the arrangement of its atoms in space from the corresponding stereoisomer.

Certain of the compounds described herein may contain one or more chiral atoms, or may otherwise be capable of existing as two enantiomers or as two or more diastereomers. Accordingly, the compounds of this invention include mixtures of enantiomers as well as purified enantiomers or enantiomerically enriched mixtures. Furthermore, the compounds of this invention include mixtures of diastereomers, as well as purified stereoisomers or diastereomerically enriched mixtures. Also included within the scope of the invention are the individual isomers of the compounds of the invention, as defined above, as well as any wholly or partially mixtures thereof. The present invention also covers the individual isomers of the compounds represented by the formulas above as mixtures with isomers thereof in which one or more chiral centers are inverted.

In some embodiments, a compound of the invention comprises at least 60% chirally pure enantiomer In some embodiments, a compound of the invention comprises at least 70% chirally pure enantiomer.

In some embodiments, the compound of the invention comprises at least 80% chirally pure enantiomer.

In some embodiments, the compound of the invention comprises at least 90% chirally pure enantiomer.

In some embodiments, the compound of the invention comprises at least 95% chirally pure enantiomer.

In some embodiments, the compound of the invention comprises at least 98% chirally pure enantiomer.

In some embodiments, the compound of the invention comprises at least 99% chirally pure enantiomer.

The terms "enantiomerically pure", "enantiomeric purity", "chiral purity" and "chirally pure" are used alternatively to reflect the fact that one enantiomer is found in the composition in greater proportion in relation to its mirror image. The proportion between two enantiomers is expressed by the absolute proportion of one of the enantiomers, which is at least 70%, at least 80%, at least 90%, at least 95%, at least 98%, and at least 99% or more.

The enantiomeric purity can be determined by types of tests known in the art. Typically, the chiral purity of enantiomers according to the present disclosure is determined by analytical chiral HPLC.

In some embodiments, compounds of the invention, such as compounds provided by formulae (I)-(XXXXIII) comprises at least 70% chirally pure enantiomer, at times at least 80% chirally pure enantiomer, at times at least 90% chirally pure enantiomer, at times at least 95% chirally pure enantiomer, at times at least 98% chirally pure enantiomer, at times at least 99% chirally pure enantiomer.

In accordance with some aspects, which may be considered as embodiments of the invention, the present disclosure provides a compound having the general formula selected from:

(XXXIII')

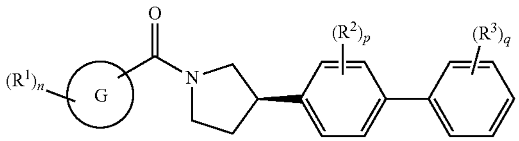

(XXXIIIa')

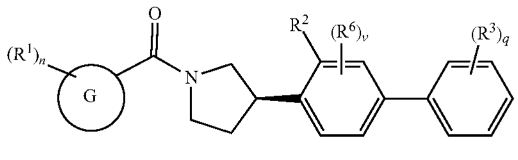

-continued (XXXIIIb')

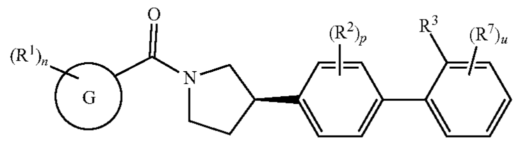

(XXXIIId')

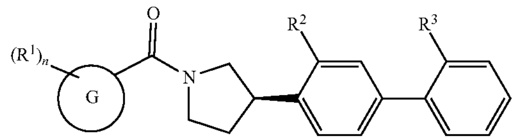

(XXVIV')

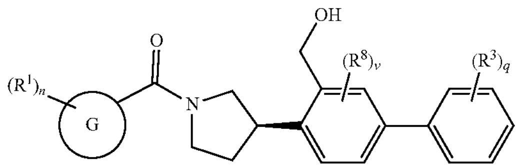

(XXVV')

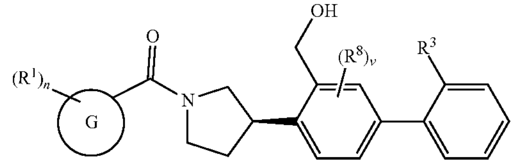

(XXVVI')

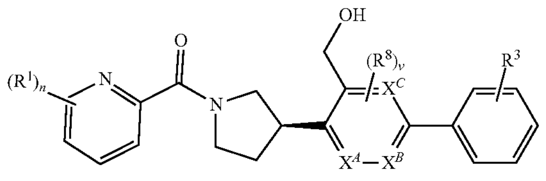

(XXVVIa')

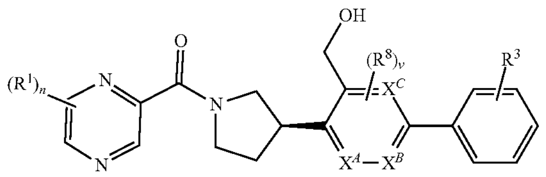

(XXXVII')

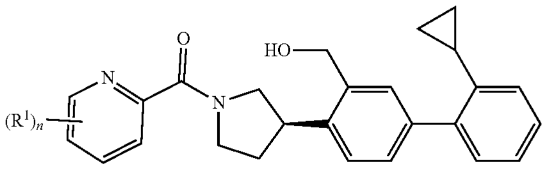

(XXXVIII')

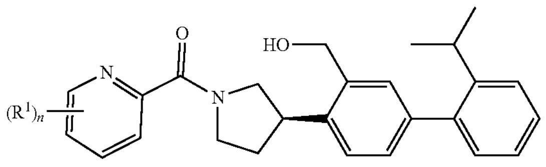

-continued (XXXIXa')

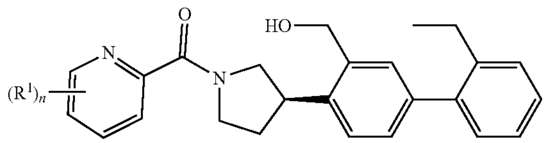

(XXXXa')

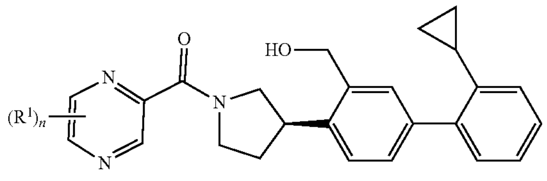

(XXXXIa')

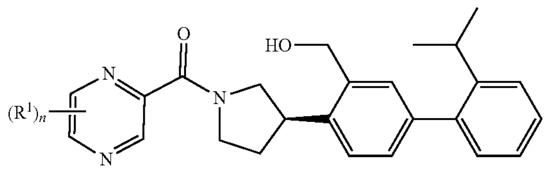

or (XXXXIIa')

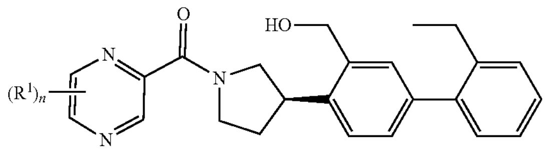

wherein the substitutions are as defined in the parent formula (without ').

In some embodiments, specific examples of compounds or pharmaceutically acceptable salts or hydrates or any stereoisomer thereof of the compounds of Formula I-XXXXIII include, without limitation compounds of Table 2 denoted as 2-29, 2-30, 2-51, 2-53, 2-56, 2-57, 2-67, 2-72 or 2-77. Specifically, compounds of the invention are provided by formulae (XXXII), (XXXIII), (XXVIV), (XXXIV), (XXVV), (XXXV), (XXXVI), (XXVVI), (XXXVII), (XXXVIII), (XXXIX), (XXXX), (XXXXI), (XXXXII) or (XXXIII) as detailed in Table 2 and Table 4.

In accordance with some aspects, the invention provides a compound selected from the following list:

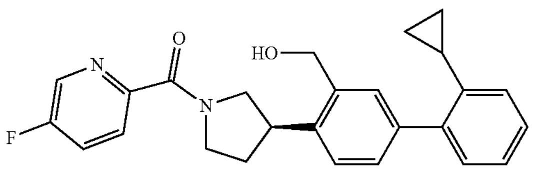

[3-(2'-Cyclopropyl-3-hydroxymethyl-biphenyl-4-yl)-pyrrolidin-1-yl]-(5-fluoro-pyridin-2-yl)-methanone (Denoted Herein: KM-001-E1 or Compound A)

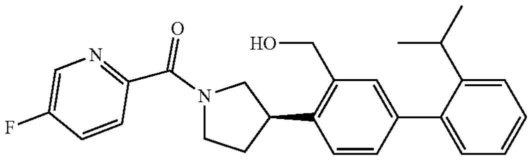 [SMILES: CC(C)c1ccccc1-c1ccc([C@H]2CCN(C(=O)c3ccc(F)cn3)C2)c(CO)c1]

(5-Fluoro-pyridin-2-yl)-[3-(3-hydroxymethyl-2'-isopropyl-biphenyl-4-yl)-pyrrolidin-1-yl]-methanone (Denoted Herein: KM-002-E1 or Compound B)

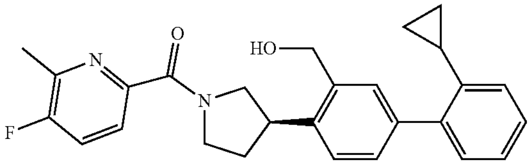

[3-(2'-Cyclopropyl-3-hydroxymethyl-biphenyl-4-yl)-pyrrolidin-1-yl]-(5-hydroxy-6-methyl-pyridin-2-yl)-methanone (Denoted Herein: KM-023-E1 or Compound C)

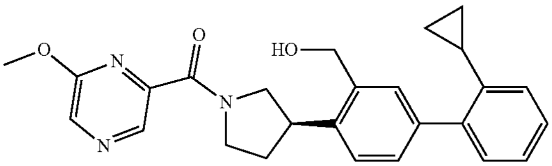 [SMILES: COc1cncc(C(=O)N2CC[C@H](c3ccc(-c4ccccc4C4CC4)cc3CO)C2)n1]

[3-(2'-Cyclopropyl-3-hydroxymethyl-biphenyl-4-yl)-pyrrolidin-1-yl]-(6-methoxy-pyrazin-2-yl)-methanone (Denoted Herein: KM-031-E1 or Compound D)

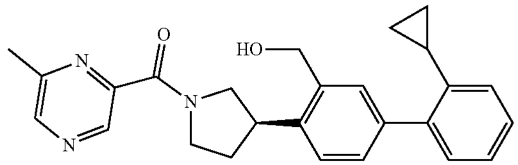 [SMILES: Cc1cncc(C(=O)N2CC[C@H](c3ccc(-c4ccccc4C4CC4)cc3CO)C2)n1]

[3-(2'-Cyclopropyl-3-hydroxymethyl-biphenyl-4-yl)-pyrrolidin-1-yl]-(6-methyl-pyrazin-2-yl)-methanone (Denoted Herein: KM-032-E1 or Compound E)

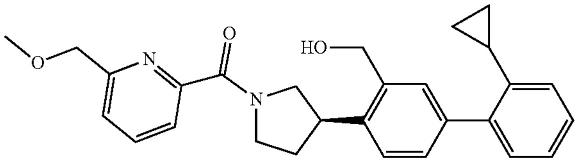 [SMILES: COCc1cccc(C(=O)N2CC[C@H](c3ccc(-c4ccccc4C4CC4)cc3CO)C2)n1]

[3-(2'-Cyclopropyl-3-hydroxymethyl-biphenyl-4-yl)-pyrrolidin-1-yl]-(6-methoxymethyl-pyridin-2-yl)-methanone (Denoted Herein: KM-036-E1 or Compound F)

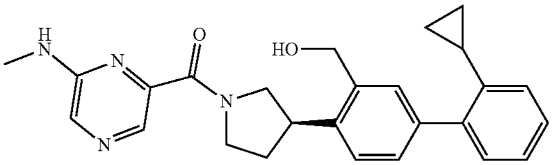 [SMILES: CNc1cncc(C(=O)N2CC[C@H](c3ccc(-c4ccccc4C4CC4)cc3CO)C2)n1]

[3-(2'-Cyclopropyl-3-hydroxymethyl-biphenyl-4-yl)-pyrrolidin-1-yl]-(6-methylamino-pyrazin-2-yl)-methanone (Denoted Herein: KM-054-E1 or Compound G)

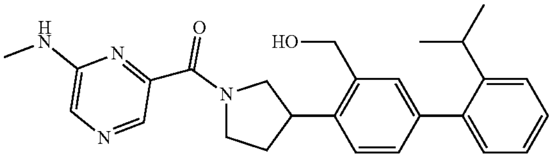 [SMILES: CNc1cncc(C(=O)N2CCC(c3ccc(-c4ccccc4C(C)C)cc3CO)C2)n1]

[3-(3-Hydroxymethyl-2'-isopropyl-biphenyl-4-yl)-pyrrolidin-1-yl]-(6-methylamino-pyrazin-2-yl)-methanone (Denoted Herein: KM-069 or Compound H)

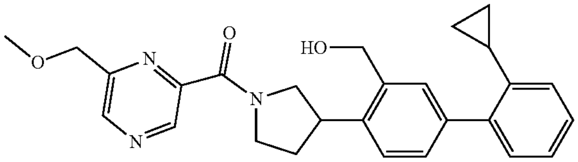 [SMILES: COCc1cncc(C(=O)N2CCC(c3ccc(-c4ccccc4C4CC4)cc3CO)C2)n1]

[3-(2'-Cyclopropyl-3-hydroxymethyl-biphenyl-4-yl)-pyrrolidin-1-yl]-(6-methoxymethyl-pyrazin-2-yl)-methanone (Denoted Herein: KM-070 or Compound I)

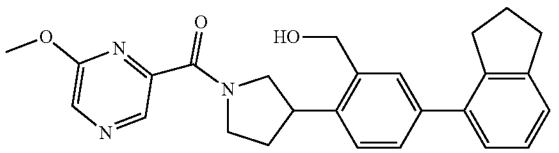 [SMILES: COc1cncc(C(=O)N2CCC(c3ccc(-c4cccc5c4CCC5)cc3CO)C2)n1]

[3-(2-Hydroxymethyl-4-indan-4-yl-phenyl)-pyrrolidin-1-yl]-(6-methoxy-pyrazin-2-yl)-methanone (Denoted Herein: KM-071 or Compound J)

In accordance with some embodiments, the compounds of the invention do not include at least one compound of Table 2 denoted as 2-68 or 2-70.

In accordance with some embodiments, the compounds of the invention do not include at least one compound of Table 2 denoted as 2-41, 2-45, 2-61, 2-63, 2-71, 2-75, 2-78, 2-80, 2-81, 2-82, 2-95, 2-104, 2-110 or 2-111.

For compounds of the disclosure in which a variable appears more than once, each variable can be a different moiety selected from the Markush group defining the variable. For example, where a structure is described having two R groups that are simultaneously present on the same compound; the two R groups can represent different moieties selected from the Markush group defined for R.

It is further appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

As used herein, "acyl" refers to the group ($C_1$-$C_6$ alkyl)-C(O)—.

As used herein, "alkyl," by itself or as part of another substituent, means, unless otherwise stated, a straight or branched chain, and can have a number of carbon atoms optionally designated (i.e., $C_1$-$C_6$ means one to six carbons). Examples of saturated hydrocarbon groups include, but are not limited to, groups such as methyl, ethyl, n-propyl, isopropyl, n-butyl, t-butyl, isobutyl, sec-butyl, n-pentyl, isopentyl, homologs and isomers of, for example, n-pentyl, n-hexyl, and the like. Unless stated otherwise specifically in the specification, an alkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen or alkyl.

As used herein, "alkenyl" can be a straight or branched hydrocarbon chain, containing at least one double bond, and having from two to six carbon atoms (i.e. $C_2$-$C_6$ alkenyl). Examples of alkenyl groups, include, but are not limited to, groups such as ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen or alkyl.

As used herein, "alkoxy" can be a straight chain or branched alkoxy group having from one to six carbon atoms (i.e., $C_1$-$C_6$ alkoxy). Examples of alkoxy groups, include, but are not limited to, groups such as methoxy, ethoxy, propyloxy, isopropyloxy, butyloxy, isobutyloxy, tert-butyloxy, pentyloxy, or hexyloxy, and the like. Unless stated otherwise specifically in the specification, an alkoxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen or alkyl.

As used herein, "alkynyl" can be a straight or branched hydrocarbon chain, containing at least one triple bond, having from two to six carbon atoms (i.e. $C_2$-$C_6$ alkynyl). Examples of alkynyl groups, include, but are not limited to, groups such as ethynyl, propynyl, butynyl, pentynyl, hexynyl, and the like. Unless stated otherwise specifically in the specification, an alkynyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen or alkyl.

As used herein, "amide" or "amido" refers to a chemical moiety with the formula —$C(O)NR^a$— or —$NR^aC(O)$— wherein $R^a$ is H or $C_1$-$C_6$ alkyl.

As used herein, "amino" or "amine" refers to a —$NH_2$ radical group.

As used herein, "alkylamino" refers to a group of formula —NH(alkyl), wherein the alkyl group each has 1 to 6 carbons.

As used herein, the term "dialkylamino" refers to a group of formula —$N(alkyl)_2$, wherein the two alkyl groups each independently has, 1 to 6 carbons.

As used herein, "aryl" refers to a polyunsaturated, aromatic, hydrocarbon moiety which can be a single ring or multiple rings (e.g., 1 to 2 rings) which are fused together or linked covalently, having from six to twelve carbon atoms (i.e. $C_6$-$C_{12}$ aryl). Non-limiting examples of aryl groups include phenyl, 1-naphthyl, 2-naphthyl, and 4-biphenyl. Unless stated otherwise specifically in the specification, an aryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, wherein each R$^a$ is independently hydrogen or alkyl.

As used herein, "arylalkyl" refers to an (aryl)alkyl— radical wherein aryl and alkyl moieties are as disclosed herein.

As used herein, "aryloxy" refers to —O-(aryl), wherein the heteroaryl moiety is as defined herein.

As used herein, "arylalkoxy" refers to —O-(arylalkyl), wherein the heteroaryl moiety is as defined herein.

As used herein, "carboxyl" refers to a —(C═O)OH radical.

As used herein, "cyano" refers to a —CN radical.

As used herein, "cycloalkyl" refers to a monocyclic or polycyclic radical that contains only carbon and hydrogen, and may be saturated, or partially unsaturated. Cycloalkyl groups include groups having from 3 to 12 ring atoms (i.e. $C_3$-$C_{10}$ cycloalkyl). Examples of cycloalkyl groups include, but are not limited to, groups such as cyclopropyl, cyclobutyl, cyclopentyl, cyclopentenyl, cyclohexyl, cyclohexenyl, cycloheptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen or alkyl.

As used herein, "cycloalkenyl" refers to a monocyclic or polycyclic radical that contains only carbon and hydrogen, and is partially unsaturated, e.g., wherein the monocyclic or polycyclic radical contains one or more double bonds. Cycloalkenyl groups include groups having from 3 to 12 ring atoms (i.e. $C_3$-$C_{12}$ cycloalkenyl). Examples of cycloalkenyl groups include, but are not limited to, groups such as cyclopentenyl, cyclohexenyl, cycloheptenyl, and the like. Unless stated otherwise specifically in the specification, a cycloalkenyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O) OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen or alkyl.

As used herein, "$C_3$-$C_7$ cycloalkyloxy" refers to —O—($C_3$-$C_7$ cycloalkyl), wherein the $C_3$-$C_7$cycloalkyl moiety is as defined herein.

As used herein, "halo" or "halogen," independently or as part of another substituent, mean, unless otherwise stated, a fluorine, chlorine, bromine, or iodine atom. The term "halide" by itself or as part of another substituent, refers to a fluoride, chloride, bromide, or iodide atom.

As used herein, "haloalkyl" and "haloalkoxy" can include alkyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine. Unless stated otherwise specifically in the specification, a haloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O) OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen or alkyl.

As used herein, "heteroalkyl" can include an optionally substituted alkyl, which has one or more skeletal chain atoms selected from an atom other than carbon, e.g., oxygen, nitrogen, sulfur, phosphorus or combinations thereof. A numerical range may be given, e.g. $C_1$-$C_6$ heteroalkyl which refers to the number of carbons in the chain, which in this example includes 1 to 6 carbon atoms. For example, a —$CH_2OCH_2CH_3$ radical is referred to as a "$C_3$" heteroalkyl. Connection to the rest of the molecule may be through either a heteroatom or a carbon in the heteroalkyl chain. Unless stated otherwise specifically in the specification, a heteroalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen or alkyl.

As used herein, "heteroaryl" refers to a 3- to 12-membered aromatic radical (e.g., $C_3$-$C_{12}$ heteroaryl) that includes one or more ring heteroatoms selected from nitrogen, oxygen and sulfur, and which may be a monocyclic or bicyclic ring system. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryl groups include without limitation, pyridyl, pyrimidinyl, pyrazinyl, pyridazinyl, triazinyl, furyl (furanyl), quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, =O, =S, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —$N(R^a)C(O)R^a$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, wherein each $R^a$ is independently hydrogen or alkyl.

As used herein, "heteraryloxy" refers to —O-(heteroaryl), wherein the heteroaryl moiety is as defined herein.

As used herein, "heterocycloalkyl" can be a stable 3- to 12-membered non-aromatic ring radical that comprises two to twelve carbon atoms and from one to six heteroatoms selected from nitrogen, oxygen and sulfur. Examples of heterocycloalkyl groups include, but are not limited to, groups such as dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, and the like. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, =O, =S, —$OR^a$, —$SR^a$, —OC(O)—$R^a$, —$N(R^a)_2$, —$C(O)R^a$, —$C(O)OR^a$, —$C(O)N(R^a)_2$, —$N(R^a)C(O)OR^a$, —$N(R^a)C(O)R^a$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, wherein each $R^a$ is independently hydrogen or alkyl.

As used herein, "hydroxy" or "hydroxyl" refers to —OH.

As used herein, "hydroxyalkyl" refers to an alkyl group having 1 to 6 carbon atoms, which is substituted with a hydroxyl group, e.g., hydroxypropyl.

As used herein, "nitro" refers to —$NO_2$.

As used herein, "oxo" refers to =O.

As used herein, "urea" refers to —$NR^a$—C(O)—$NR^a_2$ or —$NR^a$—C(O)$NR^a$—, wherein $R^a$ is H or $C_1$-$C_6$ alkyl.

As used herein, "sulfonylurea" refers to —$S(O)_2$—$NR^a$—C(O)—$NR^a$— or —$NR^a$—C(O)—$NR^a$—$SO_2$—, wherein $R^a$ is H or $C_1$-$C_6$ alkyl, e.g., an $C_1$-$C_6$ alkyl group as described herein.

As used herein, "sulfonamidyl" refers to —$S(O)_2$—$NR^a$— or —$NR^aS(O)_2$—, wherein $R^a$ is H or $C_1$-$C_6$ alkyl, e.g., an $C_1$-$C_6$ alkyl group as described herein.

In the context of the present disclosure and as described herein, reference to the compounds of any one of the compounds of formulae I-XXXXIII, for example, compounds of formulae (XXXII), (XXXIII), (XXVIV), (XXXIV), (XXVV), (XXXV), (XXXVI), (XXVVI), (XXXVII), (XXXVIII), (XXXIX), (XXXX), (XXXXI), (XXXXII) or (XXXIII) encompasses solvates, hydrates, pharmaceutically acceptable prodrugs, pharmaceutically active metabolites, and pharmaceutically acceptable salts of the compounds or any variations detailed herein The term "solvate" refers to an aggregate of a molecule with one or more solvent molecules, such as hydrate, alcoholate (aggregate or adduct with alcohol), and the like.

The term "hydrate" refers to a compound formed by the addition of water. The hydrates may be obtained by any known method in the art by dissolving the compounds in water and recrystallizing them to incorporate water into the crystalline structure.

A "pharmaceutically acceptable prodrug" is a compound that may be converted under physiological conditions to the specified compound or to a pharmaceutically acceptable salt of such compound.

The term "physiologically functional derivative" used herein relates to any physiologically acceptable derivative of a compound as described herein. The physiologically functional derivatives also include prodrugs of the compounds of the invention. Such prodrugs may be metabolized in vivo to a compound of the invention. These pro-drugs may or may not be active themselves and are also an object of the present invention.

The term "pharmaceutically acceptable salt" refers to salts derived from organic and inorganic acids of a compound described herein. Exemplary salts include, but are not limited to, sulfate, citrate, acetate, oxalate, chloride, hydrochloride, bromide, hydrobromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, succinate, fumarate, maleate, malonate, mandelate, malate, phthalate, and pamoate. The term "pharmaceutically acceptable salt" as used herein also refers to a salt of a compound described herein having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like. The term "pharmaceutically acceptable salt" also includes hydrates of a salt of a compound described herein.

In a further aspect, the invention relates to a composition comprising an effective amount of at least one compound having the general formulae (I) to (XXXXIII) or a pharmaceutically acceptable salt or hydrate thereof including any stereoisomer thereof, or any vehicle, matrix, nano- or micro-particle comprising the same.

In more specific embodiments, the composition comprises an effective amount of at least one compound having the formulae (XXXII), (XXXIII), (XXVIV), (XXXIV), (XXVV), (XXXV), (XXXVI), (XXVVI), (XXXVII), (XXXVIII), (XXXIX), (XXXX), (XXXXI), (XXXXII) or (XXXXIII).

In accordance with some embodiments, the composition is a pharmaceutical composition.

In some embodiments, the composition of the invention may optionally further comprise at least one of pharmaceutically acceptable carrier/s, excipient/s, additive/s diluent/s and adjuvant/s. As used herein "pharmaceutically acceptable carrier" includes any and all solvents, dispersion media, coatings and the like. The use of such media and agents for pharmaceutical active substances is well known in the art.

Except as any conventional media or agent is incompatible with the active ingredient, its use in the therapeutic composition is contemplated.

In some other embodiments, the pharmaceutical composition may comprise a vehicle, matrix, nano- or micro-particle.

The compounds or the compositions comprising the compounds of the present invention may be useful for a variety of application.

Specifically, the compounds described herein may be useful in affecting multiple physiological/biological process and are selected for treatment, based on various parameters, including, inter alia, on the disorder to be treated or the severity of the disorder or the route of compound administration. For example, prior to treatment, diagnostics of the disorder and the severity may determine these parameters.

Hence, the compounds of the invention may be for use to treat a disease treatable by the compounds.

Specifically, as shown in the examples below, for example in example 1 providing results of patch clamp experiments, compounds of the present disclosure were shown to inhibit flow of ion and specifically of cations such as calcium ions ($Ca^{+2}$) in an cation channel such as Transient Receptor Potential Cation Channel Subfamily V Member 3 (TRPV3). In other words, compounds of the present disclosure were shown to inhibit TRPV3 activity.

TRPV3 is provided in accordance with some embodiments by a protein accession number Q8NET8.

In yet some further aspects, the invention provides a composition comprising an effective amount of any of the compounds of the invention as described above or any vehicle, matrix, nano- or micro-particle comprising the same, specifically, for example the compounds of any one of the compounds of Formulas I-XXXXIII, e.g., any one of the compounds of Formulas (XXXII), (XXXIII), (XXVIV), (XXXIV), (XXVV), (XXXV), (XXXVI), (XXVVI), (XXXVII), (XXXVIII), (XXXIX), (XXXX), (XXXXI), (XXXXII) or (XXXXIII) as well as the compounds denoted compound A, compound B, compound C, compound D, compound E, compound F, compound G, compound H, compound I or compound J as described herein or any analogs or derivative thereof including any stereoisomer or salt thereof for use in a method of modulating the activity of a cation channel, specifically a $Ca^{+2}$ channel and more specifically TRPV3.

In some embodiments, the compositions of the invention are for use in inhibiting the activity of a cation channel, specifically a $Ca^{+2}$ channel and more specifically TRPV3.

Hence, the present disclosure also provides in accordance with some aspects, at least one compound of Formulas I-XXXXIII as an TRPV3 antagonist.

Specifically, the invention provides compounds, specifically, the compounds a defined in Formulae I-XXXXIII, for use as TRPV3 antagonists. Hence, compounds of any of the above structures may be used to inhibit an activity of TRPV3 in vitro or in vivo, and/or can be used in the manufacture of medicaments to inhibit an activity of TRPV3 in vitro or in vivo.

In some embodiments, compounds of any of the above structures being compounds according to the present disclosure may be considered as TRPV3 inhibitors. In some embodiments, a compound of any of the above structures may be used an antagonist of TRPV3.

The terms "antagonist" and "inhibitor" are used interchangeably to refer to an agent that decreases or suppresses a biological activity, such as to repress an activity of an ion channel, such as TRPV3. Hence, compounds of the present invention that may be TRPV3 inhibitors can be used to inhibit an activity of TRPV3, and/or can be used in the manufacture of medicaments to inhibit an activity of TRPV3 in vitro or in vivo.

In yet some further aspects, the invention provides a composition comprising an effective amount of any of the compounds of the invention as described above or any vehicle, matrix, nano- or micro-particle comprising the same, for example the compounds of any one of the compounds of Formulas I-XXXXIII, e.g., any one of the compounds of Formulas (XXXII), (XXXIII), (XXVIV), (XXXIV), (XXVV), (XXXV), (XXXVI), (XXVVI), (XXXVII), (XXXVIII), (XXXIX), (XXXX), (XXXXI), (XXXXII) or (XXXXIII) as well as the compounds denoted compound A, compound B, compound C, compound D, compound E, compound F, compound G, compound H, compound I or compound J as described herein and any or any analogs or derivative thereof including any stereoisomer or salt thereof for use in a method for treating, preventing, inhibiting, reducing, eliminating, protecting or delaying the onset of a TRPV3 mediated disorders in a subject in need thereof.

As used herein the term TRPV3 mediated disorders relates to a disease/disorder/condition involving activation of TRPV3. TRPV3 function has been implicated in multiple physiological processes, including, inter alia, the reception and transduction of skin defects and pain.

In some embodiments, the TRPV3 mediated disorder is related to at least one mutation in the gene encoding TRVP3. In some other embodiments, the TRPV3 mediated disorder is related to an increased activation of TRVP3.

In some embodiments, TRPV3 mediated disorder is selected from the following group: acute and/or chronic pain, touch sensitivity, burns, inflammation, diabetic neuropathy, psoriasis, eczema, dermatitis, post-herpetic neuralgia (shingles), migraine, incontinence, fever, hot flashes, osteoarthritis, oral mucositis, cancer pain, bladder cystits, pain associated with Crohn's disease and Irritable Bowel Syndrome (IBS), rheumatoid arthritis, Grierson-Gopalan syndrome (better known as burning feet syndrome), burning mouth syndrome (BMS) and cough.

In accordance with some aspects, the present disclosure provides compounds or pharmaceutical composition comprising an effective amount of any of the compounds of the invention as described above or any vehicle, matrix, nano- or micro-particle comprising the same for use in treating, preventing, inhibiting, reducing, eliminating, protecting or delaying the onset of a skin disorder in a subject in need thereof. Specifically, the present disclosure provides a pharmaceutical composition comprising any one of the compounds of Formulas I-XXXXIII, for example, any one of the compounds of Formulas (XXXII), (XXXIII), (XXVIV), (XXXIV), (XXVV), (XXXV), (XXXVI), (XXVVI), (XXXVII), (XXXVIII), (XXXIX), (XXXX), (XXXXI), (XXXXII) or (XXXXIII) as well as the compounds denoted compound A, compound B, compound C, compound D, compound E, compound F, compound G, compound H, compound I or compound J as described herein or any or any analogs or derivative thereof including any stereoisomer or salt thereof for use in a method for treating, preventing, inhibiting, reducing, eliminating, protecting or delaying the onset of a skin disorder in a subject in need thereof.

The compounds of the invention may be administrated in combination with a second active agent.

As described herein, TRPV3 function has been implicated in, among other things, the reception and transduction of skin defects. Specifically, influx of calcium across plasma membrane of skin cells is a critical signaling element involved in cellular differentiation in the skin epidermis (Dotto, 1999 *Crit Rev Oral Biol Med* 10:442-457). Regulating or modulating the calcium entry pathway, and thus a critical control point for skin cell growth, can treat or prevent skin diseases or disorders that are characterized by epidermal hyperplasia, a condition in which skin cells both proliferate too rapidly and differentiate poorly. Such diseases include psoriasis, and basal and squamous cell carcinomas. Psoriasis, estimated to affect up to 7 million Americans, afflicts sufferers with mild to extreme discomfort, enhanced susceptibility to secondary infections, and psychological impact due to disfigurement of the affected areas (Lebwohl and Ali, 2001 *J Am Acad Dermatol* 45:487-498). Basal cell carcinomas (BCC) and squamous cell carcinomas (SCC) of the skin represent at least one-third of all cancers diagnosed in the United States each year. More than 1 million new cases are reported annually and incidence is increasing. Despite being relatively non-aggressive, slow-growing cancers, BCCs are capable of significant local tissue destruction and disfigurement. SCCs are more aggressive and thus present even greater complications. Further, given that 80% of lesions are on the head and neck with another 15% on shoulders, back or chest, BCCs and SCCs of the skin can have a significant impact on the appearance and quality of life of the afflicted patient.

As used herein, a skin condition denotes any disease/disorder/condition that affect the skin. As appreciated, the skin is the layer of usually soft, flexible outer tissue covering the body of a vertebrate animal, with three main functions: protection, regulation, and sensation. Mammalian skin is composed of three primary layers: the epidermis the dermis and the hypodermis. The epidermis is composed of the outermost layers of the skin which forms a protective barrier over the body's surface, responsible for keeping water in the body and preventing pathogens from entering. The epidermis is composed of basal proliferative layer, differentiated suprabasal and spinous layer, Granular terminally differentiated keratinocytes layer and a stratified squamous epithelium. Most of the epidermis (about 95%) is composed of keratinocytes.

A skin disease in accordance with the present disclosure may be characterized by having one of more skin irregularities. Skin irregularity may include at least one symptom of raised bumps, a rash, itchy, scaly (rough skin), peeling skin, ulcers, open sores or lesions, dry, cracked skin, discolored patches of skin, fleshy bumps, warts (or other skin growths), changes in mole color or size, a loss of skin pigment, inflammation or excessive flushing.

The compounds of the present invention may have a variety of clinical, cosmetic in vitro and in vivo uses related to skin defects/disease/disorders or a disease having at least one symptom as detailed herein above.

As shown in the examples below, compounds of the present invention were shown to be effective in normalizing skin structure, skin cells differentiation and barrier function, suggesting that the compounds of the invention can be used as a treatment for skin diseases.

For example, and as shown in Example 12 below, providing results of an engineered CRISPR-Cas9 ABCA12 KO equivalent (3D model), selective inhibition by KM-001 restored skin structure as well as barrier function in a dose dependent manner. In addition, KM-001 normalized Keratin 10 expression in a dose dependent manner.

In addition, as shown in Example 16 below, KM-001 was shown to normalize epidermis differentiation and to reduce inflammation in DS-Nh TRPV3 mutation genetic model.

Further, as shown in Example 17 below, pre-treatment with either dose of oral KM-023 decrease the number of scratches observed 30 minutes post induction.

Hence, the present disclosure encompasses any disease/disorder/condition associated with any part/segment of the skin. The term skin disorders may be interchangeably with the term dermatological disorder.

The skin disease as used herein encompasses an inherent (genetic) skin disease or an acquired skin disease. In some embodiments, the skin disease is a chronic disease. In some embodiments, the skin disorder is one or more of the following: a keratoderma, an ichthyosis, epidermolysis bullosa, pachyonychia congenita, pruritis (itch), dry skin (Xerosis), eczema (including atopic dermatitis) or burns.

In some embodiments, the skin disease relates to improper skin differentiation.

Improper skin differentiation relates to disruption of a differentiation process which tend to affect one or more of the skin epidermal layers; basal, spinous, granular or stratum corneum and may result from various functional mechanisms including $Ca^{+2}$ dysregulation, keratins deformation, inflammation, collagen deconstruction. The improper skin differentiation may result in one or more of hyperkeratosis, acanthosis, inflammation or dysregulation of barrier function.

In some embodiments, skin disease related to improper skin differentiation include keratoderma, ichthyosis or combination thereof.

It is suggested that normalization of skin differentiation may play a key regulator in treatment of such disease as in turn it can lead to reduction of inflammation and barrier re-construction.

In some embodiments, the skin disorder is a keratoderma.

The term keratoderma and specifically palmoplantar keratoderma also known as keratosis palmaris et plantaris refers a disease/disorder characterized by a thickening of the skin and specifically of palms and soles.

In some embodiments, the keratoderma is at least one of a diffuse keratodermata, a focal keratoderma or a punctate keratoderma.

A diffuse keratoderma often affects the palms and soles, focal keratoderma mainly affects pressure areas, whereas punctate keratoderma typically results in tiny bumps on palms and soles.

In some embodiments, the keratoderma is an inherent (hereditary) keratoderma. A hereditary keratoderma may be caused by a gene abnormality resulting, for example, in an abnormal skin protein (keratin).

In some embodiments, a hereditary palmoplantar keratoderma (PPK) is at least one of diffuse hereditary palmoplantar keratoderma, focal hereditary palmoplantar keratoderma, punctate palmoplantar keratoderma.

In some embodiments, a diffuse hereditary palmoplantar keratoderma is at least one of Mutilating Palmoplantar keratoderma with periorificial keratotic plaques (Olmstead Syndrome), Diffuse palmoplantar keratoderma, Diffuse non-epidermolytic palmoplantar keratoderma, Diffuse epidermolytic palmoplantar keratoderma (diffuse EPPK, Vorner disease, PPK cum degenerations granulose, Progressive Palmoplantar Keratoderma (Greither disease, PPK transgrediens et progrediens), Mal de Meleda (Keratosis extremitatum hereditaria transgrediens et progrediens), PPK Mutilans Vohwinkel (mutilating keratoderma, Vohwinkel syndrome, and palmoplantar keratoderma mutilans), Palmoplantar Keratoderma with sclerodactyly (hardening and thickening of the connective tissues of the fingers and toes) (Huriez syndrome), Palmoplantar Keratoderma with peridontitis (inflammation of the gums) (Papillon-Lefevre Syndrome).

Diffuse palmoplantar keratoderma is a type of palmoplantar keratoderma that is characterized by an even, thick, symmetric hyperkeratosis over the whole of the palm and sole, usually evident at birth or in the first few months of life.

Diffuse non-epidermolytic palmoplantar keratoderma is an autosomal dominantly inherited condition traced to K1 and K16 keratins. Onset of clinical features usually presents within the first two years of life. Even, widespread thickened skin (keratosis) over the palms and soles, a red band at the edges of the keratosis, other keratotic lesions, excessive perspiration, nails may be thickened.

Diffuse epidermolytic palmoplantar keratoderma (diffuse EPPK, Vorner disease, PPK cum degenerations granulose) is the most common type of hereditary PPK. It has an autosomal dominant inheritance traced to KRT9 keratin. Onset of clinical features usually takes place within the first year. Similar to diffuse non-epidermolytic PPK but the skin is fragile and may blister.

Progressive PalmoplantarKeratoderma (Greither disease, PPK transgrediens et progrediens) is transmitted through an autosomal dominant inheritance. Onset of clinical features usually appears between ages 8 and 10. The widespread thickened skin spreads from the palms and the soles to the tops of the hands and feet and up the Achilles tendon (back of the heel). Excessive perspiration and variations in signs and symptoms between affected family members are common. Signs and symptoms tend to be worse during childhood, static after puberty, and improve in middle age.

Diffuse Hereditary PPK with associatedfeatures is typically associated with extra palmoplantar skin involvement in several inherited disorders of cornification, Mal de Meleda (Keratosis extremitatum hereditaria transgrediens et progrediens) is a rare disorder seen in approximately 1 in 100,000 people. It was initially observed in inhabitants of the Adriatic island of Meleda (Miljet). It is transmitted through an autosomal recessive inheritance. Clinical features of the disorder usually appear in early infancy. Palmoplantar keratoderma is often the only manifestation. Widespread thickened skin with a prominent red border, which spreads onto the tops of the hands and feet. The widespread hyperkeratosis may resemble gloves or stockings on the hands and feet. Tight constricting bands around the fingers and toes, which result in spontaneous amputation, have been reported. Individuals may have well defined psoriasis-like plaques or lichenoid patches (small firm lesions set very close together) on the knees and elbows. Excessive sweating. Reddened and thickened skin around the eye socket. Nail changes. A ridged tongue, webbed fingers or toes, hair on the palms or soles, a high arched palate (roof of the mouth), and left-handedness are associated features.

PPK Mutilans Vohwinkel (mutilating keratoderma, Vohwinkel syndrome, and palmoplantar keratoderma mutilans) is a rare disorder that can be transmitted through an autosomal dominant inheritance or an autosomal recessive inheritance. The genetic defect has been traced to the GJB2 gene and connexin 26. Clinical features usually appear in infancy. Presents in infants as a honeycomb-like thickening of the skin on the palms and the soles. Later-forming, constricting, fibrous bands on the fingers and toes lead to progressive strangulation and autoamputation. Starfish-shaped thickened skin may occur on the tops of the fingers and knees. Baldness, deafness, spastic impairment of the muscles, nearsightedness, scaly skin, and nail abnormalities are associated.

Mutilating Palmoplantar keratoderma with periorificial keratotic plaques (Olmstead Syndrome) is a rare disorder transmitted through an autosomal dominant inheritance. Clinical features usually appear within the first year of life. Symmetrical, sharply defined palmoplantar keratoderma surrounded by reddened skin and deformities of the joints that lead to constriction and spontaneous amputation. Horny growths around the eyes and mouth. Nail abnormalities. White thickened patches of skin around the anus and in the mouth. Sparse hair.

Palmoplantar Keratoderma with sclerodactyly (hardening and thickening of the connective tissues of the fingers and toes) (Huriez syndrome) is a rare disorder transmitted through an autosomal dominant inheritance. Clinical symptoms are visible in infancy. Sclerodactyly—scleroderma or hardening and thickening of the connective tissues of the fingers and toes. Widespread thickened skin more marked on the soles than on the palms. Nail abnormalities. Decreased sweating. Associated with squamous cell carcinoma.

Palmoplantar Keratoderma with peridontitis (inflammation of the gums) (Papillon-Lefevre Syndrome) is a rare disease transmitted through an autosomal recessive inheritance. The disorder results from mutations in cathepsin C. It occurs equally among males and females. Clinical features usually appear within the first and fifth years of life. Widespread or focal thickened skin on the palms and the soles. Unless treated, periodontitis results in severe gum disease and loss of teeth by age 5. Patients may exhibit an increased susceptibility to infection. Scaly, red lesions over knees, elbows, and knuckles are occasionally observed. Excessive sweating and body odor.

In some embodiments, the keratoderma is an acquired keratoderma. An acquired keratoderma may be due to a health change or an environment change.

In some embodiments, an acquired keratoderma is a focal keratoderma or a diffuse keratoderma.

In some embodiments, the keratoderma is Olmstead Syndrome.

In some embodiments, the skin disorder is an ichthyosis disease.

Ichthyosis refers to a genetic disease characterized by the presence of excessive amounts of dry surface scales persistently dry, thickened, 'fish scale' skin. It is regarded as a disorder of keratinization or cornification, and it is due to abnormal epidermal differentiation or metabolism.

The ichthyosiform dermatoses may be classified according to clinical manifestations, genetic presentation, and histologic findings. Inherited and acquired forms of ichthyosis have been described, and ocular alterations may occur in specific subtypes. There are at least 20 different types of ichthyosis. Some types are inherited at birth and other types are acquired during adulthood.

Inherited types of ichthyosis may be congenital or have delayed onset. Inherited types of ichthyosis may be congenital or have delayed onset. Ichthyosis vulgaris has an autosomal dominant inheritance, meaning an abnormal gene is inherited from a parent. Penetrance is 90%. Onset is delayed until at least three months of age. Recessive X-linked ichthyosis mainly affects males, who have a single X chromosome with the abnormal gene. Females are protected by usually having a normal second X chromosome. Onset may be congenital or delayed by up to 6 months. In autosomal recessive congenital ichthyosis one abnormal gene is inherited from each parent. Congenital ichthyosiform erythroderma (CIE) is a variant of autosomal recessive congenital ichthyosis (ARCI), a rare epidermal disease, characterized by fine, whitish scales on a background of erythematous skin over the whole body. Keratinopathic ichthyoses have recessive and dominant forms and present at birth with a collodion membrane. Harlequin ichthyosis is a rare and severe form of ichthyosis that results in hard, thickened armour-like plates of skin covering the entire body from birth. Harlequin ichthyosis is also called harlequin-type ichthyosis, and harlequin fetus. Lamellar ichthyosis is a rare genetic condition. Infants affected by lamellar ichthyosis are generally born with a shiny, waxy layer of skin (called a collodian membrane) that is typically shed within the first two weeks of life. The skin beneath the collodian membrane is red and scaly. Epidermolytic ichthyosis (EI) is a rare, genetic skin disorder. It becomes apparent at birth, or shortly after birth, with reddening, scaling, and severe blistering of the skin. Hyperkeratosis develops within months and worsens over time. Blister formation decreases but may still occur after skin trauma or during summer months. Skin can be itchy and smelly, and prone to infection. Other features may include reduced sweating; nail abnormalities; and in severe cases, growth failure. Superficial epidermolytic ichthyosis (SEI), formerly know as Ichthyosis bullosa of Siemens (IBS), is a rare keratinization disorder with superficial peeling. Although hyperkeratotic, the skin is unusually fragile and has tendency to shed the outer layers of the epidermis, producing localized denuded areas. Netherton syndrome (*Ichthyosis linearis circumflexa*) is a rare hereditary disorder characterized by scaling skin, hair anomalies, increased susceptibility to atopic eczema (a skin condition that can result in dry, red and flaky skin), elevated IgE levels, and other related symptoms. Netherton syndrome is inherited as an autosomal recessive trait. Pachyonychia congenita (PC) is a rare group of autosomal dominant skin disorders that are caused by a mutation in one of five different keratin genes. Pachyonychia congenita is often associated with thickened toenails, plantar keratoderma, and plantar pain.

There are other types of ichthyosis including but not limited to Chanarin-Dorfman syndrome (neutral lipid storage disease), CHILD syndrome (unilateral hemidysplasia), Conradi-Hunermann syndrome (X-linked dominant chondrodysplasia punctata), Darier disease, epidermal nevi (ichthyosis hystrix, linear epidermal nevus), epidermolytic hyperkeratosis (EHK), erythrokeratodermia variabilis (EKV), Giroux-Barbeau syndrome, Hailey-Hailey disease (benign familial pemphigus), ichthyosis hystrix Curth-Macklin type, keratosis follicularis spinulosa decalvans, KID syndrome (keratitis, ichthyosis, deafness), multiple sulfatase deficiency, peeling skin syndrome, *Pityriasis rubra pilaris* (PRP), Refsum's disease (phytanic acid storage disease), Rud's syndrome, Sjogren-Larsson syndrome, Tay's syndrome (trichothiodystrophy, IBIDS syndrome).

In some embodiments, the skin disorder is Harlequin Ichtyosis.

Ichthyosis can also be due to a new spontaneous mutation.

In some embodiments, the skin disease is itch sensation.

Itch sensation is initiated in the skin by peripheral afferents of primary sensory neurons, with cell bodies located in dorsal root ganglia (DRG) and trigeminal ganglia, then transmitted to the spinal dorsal horn and then further to the brain. Itch used to be regarded as a sub-modality of pain because of their similarities.

TRP channel with major role in itch transmission, TrpA1, is increased in nerve fibers, keratinocytes and tryptase positive mast cells from lesional skin of atopic dermatitis patients. Notably dermal cells in healthy skin have minimal expression of TrpA1. In addition, expression of TrpV3 is also increased in atopic dermatitis lesional skin though its role in itch is not entirely clear. Elevated TrpA1 expression is also detected in postburn pruritus. Levels of TrpA1 and two other channels TrpV3 and TrpV4 are all higher in post-burn patients with pruritus comparing with post-burn patients without pruritus. Unlike TrpV1 and TrpA1, TrpV3 expression is mainly detected in keratinocytes.

Activation of TrpV3 can trigger release of multiple factors including PGE2, ATP, nitric oxide and NGF, contributing to the inflammation processes in dermatitis. TrpV3 Gly573 mutations are detected in DS-Nh mice (Gly573Ser) and WBN/Kob-Ht rats (Gly573Cys), both spontaneous hairless mutant strains. These animals develop spontaneous dermatitis phenotypes including increased keratinocytes and pruritus. Transgenic mice carrying Gly573Ser mutation mimics dermatitis phenotypes from the two spontaneous mutant rodent strains confirming the causal role of this single amino acid mutation. Recent studies also link this TrpV3 missense mutation to Olmsted Syndrome (OS), a rare congenital disorder featuring palmoplantar, periorificial keratoderma and severe itching. OS patients were identified to carry missense mutation in TrpV3 gene (in most cases Gly573Ser or Gly573Cys).

Dry skin (Xerosis), skin dehydration with constant itch is another chronic itch condition commonly modeled in animals. Repeated skin dehydration with acetone and ether can trigger spontaneous scratching and increase trans-epidermal water loss without infiltration of inflammatory cells mimicking symptoms of Xerosis. In animal model of dry skin, both TrpA1 and TrpV3 are required for induction of spontaneous itch.

In some embodiments, the skin condition is pruritis.

Pruritis or itch is defined as an unpleasant sensation of the skin that provokes the urge to scratch. It is a characteristic feature of many skin diseases and an unusual sign of some systemic diseases. Pruritus may be localized or generalized and can occur as an acute or chronic condition. Itching lasting more than 6 weeks is termed chronic pruritus. Itching can be intractable and incapacitating, as well as a diagnostic and therapeutic challenge. Itch can be produced by mechanical (gentle touch, pressure, vibration, and wool), thermal and electrical stimuli such as transcutaneous or direct nerve stimulation. The sensation is received by free nerve endings in the skin and transmitted via unmyelinated C fibers and myelinated Aδ fibers to the central spinothalamic tracts. Microneurography studies have demonstrated that itch and pain are transmitted by separate neural pathways. Histamine is one of the most important mediators of itch, although other chemical substances have also been implicated. Some, such as neuropeptides, act by releasing histamine from mast cells, and itching caused by them responds to antihistamines. Others act independently; therefore, antihistamines are not effective in some forms of pruritus. Opioids have a central pruritic action and also act peripherally by augmenting histamine itch. Patients with tumors and lesions of the central nervous system have been reported to have intractable pruritus. Administration of opioids in epidural anesthesia can also lead to pruritus.

Itching is an important component of some disorders (atopic eczema, dermatitis herpetiformis, lichen simplex chronicus, and nodular prurigo) and these conditions are rarely diagnosed in its absence. Dermatologic Disorders Associated with Chronic Pruritus include but are not limited to the following: autoimmune related: Dermatitis herpetiformis, Dermatomyositis, Pemphigoid, Sjögren's syndrome; genetic related: Darier's disease, Hailey-Hailey disease, Ichthyoses, Sjögren-Larsson syndrome; Infections and Infestations related: Arthropod reactions, Dermatophytosis Folliculitis, Impetigo and other bacterial infections, Insect bites, Pediculosis, Scabies, Viral; Inflammatory related: Asteatosis (dry skin), including aging and senile pruritus, Atopic eczema, Contact dermatitis (irritant, allergic), Drug reactions, "Invisible dermatoses", Lichen planus, Lichen simplex chronicus, Mastocytosis (urticaria pigmentosa), Miliaria, Psoriasis, Scars, Urticaria; Neoplastic related: Cutaneous T-cell lymphoma or mycosis fungoides (especially Sezary syndrome), Cutaneous B-cell lymphoma, Leukemia cutis; Pregnancy related: Pemphigoid gestationis, Polymorphic eruption of pregnancy, Prurigo gestationis. Select Systemic Causes of Chronic Pruritus may include: Endocrine and Metabolic Diseases, such as Chronic renal failure, Diabetes mellitus (questionable; may be localized to scalp), Hyperthyroidism, Hypothyroidism, Liver disease (with or without cholestasis), Malabsorption, Perimenopausal pruritus; Infectious Diseases such as Helminthosis, HIV infection, Parasitosis; Neoplastic and hematological diseases such as Hodgkin's disease, Iron deficiency, Leukemia, Non-Hodgkin's lymphoma, Multiple myeloma, Plasmacytoma, *Polycythemia rubra vera*; Visceral Neoplasms sauch as Carcinoid syndrome and Solid tumors of the cervix, prostate, or colon; Pregnancy related disorders such as Pruritus gravidarum (with or without cholestasis); Induced by drugs, such as, Allopurinol, Amiodarone, Angiotensin-converting enzyme inhibitors, Estrogen, Hydrochlorothiazide, Hydroxyethyl cellulose, Opioids, Simvastatin. Other causes of chronic pruritis may result from Neurologic disease (Abscess, Infarcts, Multiple sclerosis, Notalgia Paresthetica, Tumors) or Psychiatric disease (Anxiety disorders, Depression, Obsessive-compulsive disorder).

In some embodiments, the skin condition is Eczema.

Eczema is the name for a group of conditions that cause the skin to become itchy, inflamed, and red in lighter skin tones or brown, purple, gray or ashen in darker skin tones. Eczema is very common. In fact, more than 31 million Americans have some form of eczema. There are seven different types of eczema: Atopic dermatitis, Contact dermatitis, Neurodermatitis, Dyshidrotic eczema, Nummular eczema, Seborrheic dermatitis, Stasis dermatitis, Atopic dermatitis. Atopic dermatitis (AD) is the most common type of eczema, affecting more than 9.6 million children and about 16.5 million adults in the United States. In people with AD the immune system becomes disordered and overactive. This triggers inflammation that damages the skin barrier, leaving it dry and prone to itching and rashes that may appear purple, brown, or grayish hue in darker skin tones and red in lighter skin tones. Research shows that in some cases of atopic dermatitis, there is a mutation of the gene responsible for creating filaggrin.

In some embodiments, the skin condition is a burn.

A burn is a type of injury to skin, or other tissues, caused by heat, cold, electricity, chemicals, friction, or radiation. Burns are classified either by common causes or by degree of severity. Common causes of burns include:

Friction or mechanical burns are caused by an object rubbing off some of the skin. It is both an abrasion (scrape) and a heat burn. Cold burns are caused by exposure to extreme cold temperatures. Thermal burns are caused by exposure to extreme hot temperatures. Radiation burns are caused by either sun radiation or by other sources of radiation, like X-rays or radiation therapy to treat cancer. Chemical burns are caused by strong acids, solvents, or detergents. Electrical burns are caused by the contact with an electrical current.

Burns that affect only the superficial skin layers are known as superficial or first-degree burns. They appear red without blisters and pain typically lasts around three days. When the injury extends into some of the underlying skin layer, it is a partial-thickness or second-degree burn. Blisters are frequently present, and they are often very painful. Healing can require up to eight weeks and scarring may occur. In a full-thickness or third-degree burn, the injury extends to all layers of the skin. Often there is no pain and the burnt area is stiff Healing typically does not occur on its own. A fourth-degree burn additionally involves injury to deeper tissues, such as muscle, tendons, or bone. The burn is often black and frequently leads to loss of the burned part.

In some embodiments, the skin condition is a scar formation.

Scar formation occurs after an injury and is an area of fibrous tissue that replaces normal skin and is the final condition resulting from a complex repair mechanism of the human body. The various clinical manifestations of scarring are an important topic for physicians in many disciplines. The prevention of excessive scarring is more successful than the treatment afterwards. Pathological scaring is differentiated into two groups: Hypertrophic scars and keloids. Hypertrophic scars generally have cell-rich connective tissue and usually parallel collagen fibers at the surface. There may also be focal nodular areas. In the latter there are numerous alpha-actin-positive myofibroblasts. In keloids, a more cell-poor connective tissue dominates, and the collagen fibers are organized randomly and in larger nodules. The fibers are hypereosinophilic, hyaline, and thicker. In addition—often in the center of the scar—there are cell-poor areas. Alpha-actin-positive myofibroblasts are either absent or found only focally. Between the fibers there are abundant small vessels in both hypertrophic scars as well as in keloid.

The pharmaceutical composition of the invention can be administered and dosed by the methods of the invention, in accordance with good medical practice. Hence, the pharmaceutical compositions or compounds described herein may be adjusted, adapted or configured for administration by a variety of administration routes.

For example, the compositions used in the methods of the invention, described herein below, may be adapted for administration by various modes of administration known in the art including, for example, systemic, parenteral, intraperitoneal, transdermal, oral (including buccal or sublingual), rectal, topical (including buccal or sublingual), vaginal, intranasal and any other appropriate routes. Specific examples include but not limited to, injection (e.g., using a subcutaneous, intramuscular, intravenous, or intradermal injection), intranasal administration and oral administration.

In some embodiments, administration of the compound of the invention is by systemic administration. Hence the compound is adjusted to be suitable for systemic administration. "Systemic administration" and "administered systemically" as used herein mean that the administration of a compound or a composition comprising at least one compound of the invention into the circulatory system so that the entire body is affected.

In accordance with some embodiments, the compounds of the invention or the composition comprising the compounds of the invention are suitable for systemic administration.

In some embodiments, any of the compounds of formulae I-XXXXIII, or a composition comprising any of the compounds of formulae I-XXXXIII, are suitable for systemic administration. In some embodiments, at least the compounds denoted as KM-0023 or a composition the compounds denoted as KM-0023 are suitable for systemic administration.

In some embodiments, the compound is administered enterally.

In some embodiments, the compound is administered orally.

Compositions for oral administration may include powders or granules, suspensions or solutions in water or non-aqueous media, capsules, sachets, lozenges (including liquid-filled), chews, multi- and nano-particulates, gels, solid solution, liposome, films, ovules, sprays or tablets. Thickeners, flavoring agents, diluents, emulsifiers, dispersing aids or binders may be desirable.

It should be understood that in addition to the ingredients particularly mentioned above, the compositions may also include other agents conventional in the art having regard to the type of formulation in question, for example those suitable for oral administration may include flavoring agents.

In some embodiments, the compound is administered parentally.

"Parenteral administration" and "administered parenterally" as used herein includes modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

In some embodiments, the formulation is suitable for intravenous injection. In some embodiments, the formulation is suitable for intravenous infusion.

In some embodiments, administration of the compound of the invention is by local administration.

In some embodiments, the compound is administered topically. Hence the compound is adjusted to be suitable for topical administration. "Topical administration" and "administered topically" as used herein mean that the administration of a compound or a composition comprising at least one compound of the is applied to a particular place on or in the body. Typically, topical administration refers to application to body surfaces such as skin or mucous membranes.

The topically administrable compounds may be formulated into a suitable formulation or composition. The carriers may be selected from powders, oils, creams, foams, ointments, lotions, gels, pastes, mousiness, hydrogels or delivery systems such as liposome, niosome, microsponge, microemulsion, microsphere, SLN, aerosol and others.

The compounds of the invention may be effectively dispersed or suspended or solubilized in a liquid medium to form a solution, a suspension or a dispersion that may be applied topically, sprayed onto the skin or delivered by contact via the use of a sponge, a plaster, a pad or any skin dressing. For some applications, controlled release of the compounds of such delivery systems may be essential.

In accordance with some embodiments, the compounds of the invention or the composition comprising the compounds of the invention are suitable for topical administration.

In some embodiments, any of the compounds of formulae I-XXXXIII, or a composition comprising any of the compounds of formulae I-XXXXIII, are suitable for topical administration. In some embodiments, at least the compounds denoted as KM-001, KM-002, KM-031, KM-032, KM-036, KM-054, KM-069 or the composition comprising KM-001, KM-002, KM-031, KM-032, KM-036, KM-054, KM-069 are suitable for topical administration.

In some embodiments, the unit dosage formulations are those containing a daily dose or sub-dose, as herein above recited, or an appropriate fraction thereof, of an active ingredient.

In accordance with some aspects, the present disclosure provides a method for modulating the activity of a cation channel, for example a $Ca^{+2}$ channel—e.g. TRPV3. In some embodiments, the methods of the invention comprise inhibiting the activity of a cation channel, for example a $Ca^{+2}$ channel—e.g. TRPV3 activity in a cell. In more specific embodiments, the method comprising the step of contacting the cell with an effective amount of at least one compound having the general formula (I)-(XXXXIII) or a pharmaceutically acceptable salt or hydrate thereof including any stereoisomer thereof. In some specific embodiments, the method comprising the step of contacting the cell with an effective amount of at least one compound having the general formula (I)-(XXXXIII), for example, any one of the compounds of Formulas (XXXII), (XXXIII), (XXVIV), (XXXIV), (XXVV), (XXXV), (XXXVI), (XXVVI), (XXXVII), (XXXVIII), (XXXIX), (XXXX), (XXXXI), (XXXXII) or (XXXXIII) as well as the compounds denoted compound A, compound B, compound C, compound D, compound E, compound F, compound G, compound H, compound I or compound J as described herein or a pharmaceutically acceptable salt or hydrate thereof including any stereoisomer thereof. In some embodiments, the methods of the invention comprise contacting the cell with an effective amount of at least one compound of the invention in at least one of in vitro, in vivo, ex vivo or combinations thereof.

In certain embodiments the compound/s used by the method of the invention may be any compound as defined by the invention. In further embodiments, the method of the invention may involve the use of any of the compositions encompassed by the invention, and specifically, any of the compositions as described herein above.

In yet another aspect, the invention provides a method for treating, preventing, inhibiting, reducing, eliminating, protecting or delaying the onset of a TRPV3 mediated disorders in a subject in need thereof. In yet another aspect, the invention provides a method for treating, preventing, inhibiting, reducing, eliminating, protecting or delaying the onset of a skin disorder in a subject in need thereof.

In more specific embodiments the methods comprising administering to such subject a therapeutically effective amount of at least one compound/s including any stereoisomer or salt thereof or of any vehicle, matrix, nano- or micro-particle, or a composition comprising the same.

In more specific embodiments, the compound used by the method/s of the invention may have the general formula (I)-(XXXXIII), for example any one of the compounds of Formulas (XXXII), (XXXIII), (XXVIV), (XXXIV), (XXVV), (XXXV), (XXXVI), (XXVVI), (XXXVII), (XXXVIII), (XXXIX), (XXXX), (XXXXI), (XXXXII) or (XXXXIII) or a pharmaceutically acceptable salt or hydrate thereof including any stereoisomer thereof.

In some embodiments, the compound used by the method/s of the invention may be denoted compound A, compound B, compound C, compound D, compound E, compound F, compound G, compound H, compound I or compound J as described herein.

In some embodiments, the method/s of the invention comprises topically or systemically administering to a subject a therapeutically effective amount of at least one compound (I)-(XXXXIII), specifically any one of the compounds of Formulas (XXXII), (XXXIII), (XXVIV), (XXXIV), (XXVV), (XXXV), (XXXVI), (XXVVI), (XXXVII), (XXXVIII), (XXXIX), (XXXX), (XXXXI), (XXXXII) or (XXXXIII) or a pharmaceutically acceptable salt or hydrate thereof including any stereoisomer thereof.

In some embodiments, the method(s) is for treating, preventing, inhibiting, reducing, eliminating, protecting or delaying the onset of a skin disorder in a subject in need thereof.

In some other embodiments, the skin disorder is at least one keratoderma.

In some other embodiments, the skin disorder is Olmstead Syndrome.

In some embodiments, the skin disorder is an ichthyosis disease.

In some embodiments, the skin condition is pruritis.

In some specific embodiments, the method/s of the invention comprises topically administering to such subject a therapeutically effective amount of at least one of the compounds denoted herein as compound A, compound B, compound C, compound D, compound E, compound F, compound G, compound H, compound I or compound J as described herein.

In some specific embodiments, the method/s of the invention comprises topically administering to such subject a therapeutically effective amount of the compound denoted herein as compound A.

In some embodiments, the method/s of the invention comprises administering to a subject a therapeutically effective amount of the compound 3-(2'-Cyclopropyl-3-hydroxymethyl-biphenyl-4-yl)-pyrrolidin-1-yl]-(5-fluoro-pyridin-2-yl)-methanone having the structure

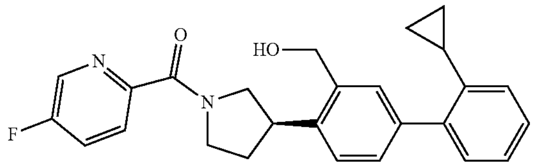 [SMILES: O=C(c1ccc(F)cn1)N1CC[C@H](c2ccc(-c3ccccc3C3CC3)cc2CO)C1]

including any stereoisomer or salt thereof or of any vehicle, matrix, nano- or micro-particle, or a composition comprising the same. In some embodiments, the method/s of the invention comprises topically administering to a subject a therapeutically effective amount of the compound 3-(2'-Cyclopropyl-3-hydroxymethyl-biphenyl-4-yl)-pyrrolidin-1-yl]-(5-fluoro-pyridin-2-yl)-methanone having the structure

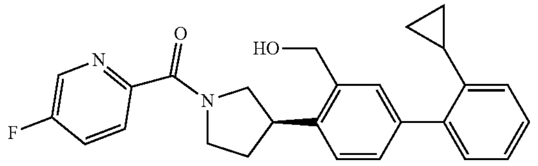 [SMILES: O=C(c1ccc(F)cn1)N1CC[C@H](c2ccc(-c3ccccc3C3CC3)cc2CO)C1]

including any stereoisomer or salt thereof or of any vehicle, matrix, nano- or micro-particle, or a composition comprising the same In some specific embodiments, the method/s of the invention comprises systemically administering to such subject a therapeutically effective amount of at least one of the compounds denoted herein as compound A, compound B, compound C, compound D, compound E, compound F, compound G, compound H, compound I or compound J as described herein.

In some specific embodiments, the method/s of the invention comprises systemically administering to such subject a therapeutically effective amount of the compound denoted herein as compound C.

In some embodiments, the method/s of the invention comprises administering to a subject a therapeutically effective amount of the compound 3-(2'-Cyclopropyl-3-hydroxymethyl-biphenyl-4-yl)-pyrrolidin-1-yl]-(5-hydroxy-6-methyl-pyridin-2-yl)-methanone having the structure including any stereoisomer or salt thereof or of any vehicle, matrix, nano- or micro-particle, or a composition comprising the same. In some embodiments, the methods of the invention comprises systemically administering to a subject a therapeutically effective amount of the compound 3-(2'-Cyclopropyl-3-hydroxymethyl-biphenyl-4-yl)-pyrrolidin-1-yl]-(5-hydroxy-6-methyl-pyridin-2-yl)-methanone including any stereoisomer or salt thereof or of any vehicle, matrix, nano- or micro-particle, or a composition comprising the same.

In yet another aspect, the invention provides a method for treating, preventing, inhibiting, reducing, eliminating, protecting or delaying the onset of a skin disorder in a subject in need thereof, specifically a keratoderma, more specifically Olmstead Syndrome, the method comprises administering, specifically topical administrating to a subject a therapeutically effective amount of the compound 3-(2'-Cyclopropyl-3-hydroxymethyl-biphenyl-4-yl)-pyrrolidin-1-yl]-(5-fluoro-pyridin-2-yl)-methanone having the structure

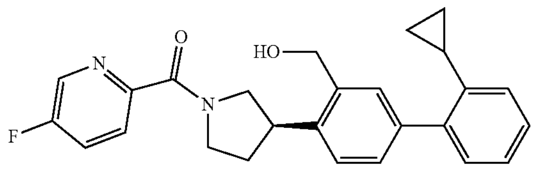 [SMILES: O=C(c1ccc(F)cn1)N1CC[C@H](c2ccc(-c3ccccc3C3CC3)cc2CO)C1]

including any stereoisomer or salt thereof or of any vehicle, matrix, nano- or micro-particle, or a composition comprising the same.

In yet another aspect, the invention provides a method for treating, preventing, inhibiting, reducing, eliminating, protecting or delaying the onset of a skin disorder in a subject in need thereof, specifically ichthyosis, the method comprises administering, specifically topical administrating to a subject a therapeutically effective amount of the compound 3-(2'-Cyclopropyl-3-hydroxymethyl-biphenyl-4-yl)-pyrrolidin-1-yl]-(5-fluoro-pyridin-2-yl)-methanone having the structure

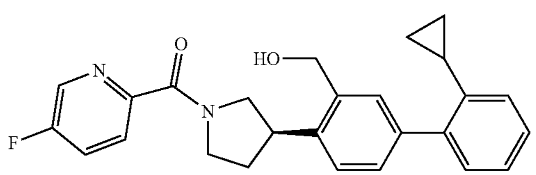 [SMILES: O=C(c1ccc(F)cn1)N1CC[C@H](c2ccc(-c3ccccc3C3CC3)cc2CO)C1]

including any stereoisomer or salt thereof or of any vehicle, matrix, nano- or micro-particle, or a composition comprising the same.

In some embodiments, the method/s of the invention comprises administering to a subject a therapeutically effective amount of the compound 3-(2'-Cyclopropyl-3-hydroxymethyl-biphenyl-4-yl)-pyrrolidin-1-yl]-(5-hydroxy-6-methyl-pyridin-2-yl)-methanone

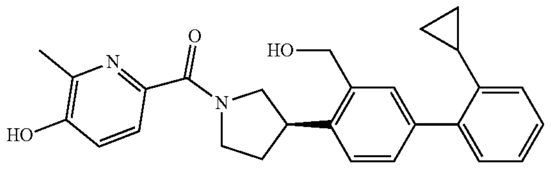 [SMILES: Cc1nc(C(=O)N2CC[C@H](c3ccc(-c4ccccc4C4CC4)cc3CO)C2)ccc1O]

having the structure including any stereoisomer or salt thereof or of any vehicle, matrix, nano- or micro-particle, or a composition comprising the same.

In yet another aspect, the invention provides a method for treating, preventing, inhibiting, reducing, eliminating, protecting or delaying the onset of a skin disorder in a subject in need thereof, specifically a keratoderma, more specifically Olmstead Syndrome, the method comprises administering, specifically systemic administrating to a subject a therapeutically effective amount of the compound 3-(2'-Cyclopropyl-3-hydroxymethyl-biphenyl-4-yl)-pyrrolidin-1-yl]-(5-hydroxy-6-methyl-pyridin-2-yl)-methanone having the structure

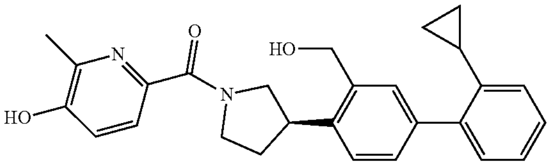 [SMILES: Cc1nc(C(=O)N2CC[C@H](c3ccc(-c4ccccc4C4CC4)cc3CO)C2)ccc1O]

including any stereoisomer or salt thereof or of any vehicle, matrix, nano- or micro-particle, or a composition comprising the same.

In yet another aspect, the invention provides a method for treating, preventing, inhibiting, reducing, eliminating, protecting or delaying the onset of a skin disorder in a subject in need thereof, specifically ichthyosis, the method comprises administering, specifically topical administrating to a subject a therapeutically effective amount of the compound 3-(2'-Cyclopropyl-3-hydroxymethyl-biphenyl-4-yl)-pyrrolidin-1-yl]-(5-hydroxy-6-methyl-pyridin-2-yl)-methanone having the structure

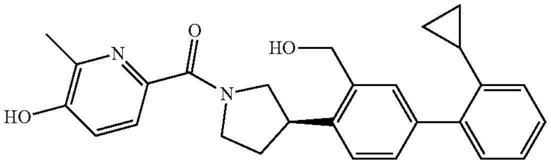 [SMILES: Cc1nc(C(=O)N2CC[C@H](c3ccc(-c4ccccc4C4CC4)cc3CO)C2)ccc1O]

including any stereoisomer or salt thereof or of any vehicle, matrix, nano- or micro-particle, or a composition comprising the same.

The present invention provides methods for treating skin disorder. The term "treatment or prevention" refers to the complete range of therapeutically positive effects of administrating to a subject including inhibition, reduction of, alleviation of, and relief from, skin disorder symptoms or undesired side effects of such skin disorder related disorders. More specifically, treatment or prevention includes the prevention or postponement of development of the disease, prevention or postponement of development of symptoms and/or a reduction in the severity of such symptoms that will or are expected to develop. These further include ameliorating existing symptoms, preventing—additional symptoms and ameliorating or preventing the underlying metabolic causes of symptoms.

As used herein, "disease", "disorder", "condition" and the like, as they relate to a subject's health, are used interchangeably and have meanings ascribed to each and all of such terms.

The present invention relates to the treatment of subjects, or patients, in need thereof. By "patient" or "subject in need" it is meant any organism who may be affected by the above-mentioned conditions, and to whom the treatment methods herein described are desired, including humans, domestic and non-domestic mammals such as canine and feline subjects, bovine, simian, equine and murine subjects, rodents, domestic birds, aquaculture, fish and exotic aquarium fish. It should be appreciated that the treated subject may be also any reptile or zoo animal. More specifically, the methods and compositions of the invention are intended for mammals. By "mammalian subject" is meant any mammal for which the proposed therapy is desired, including human, equine, canine, and feline subjects, most specifically humans. It should be noted that specifically in cases of non-human subjects, the method of the invention may be performed using administration via injection, drinking water, feed, spraying, oral gavage and directly into the digestive tract of subjects in need thereof. It should be further noted that particularly in case of human subject, administering of the compositions of the invention to the patient includes both self-administration and administration to the patient by another person.

The invention provides methods for treating skin disorders, and further relates to disorders associated or related to skin disorders. It is understood that the interchangeably used terms "associated" and "related", when referring to pathologies herein, mean diseases, disorders, conditions, or any pathologies which at least one of: share causalities, co-exist at a higher than coincidental frequency, or where at least one disease, disorder condition or pathology causes the second disease, disorder, condition or pathology.

The invention further provides the use of an effective amount of at least one compound and any combination thereof in the preparation of a composition for treating, preventing, inhibiting, reducing, eliminating, protecting or delaying the onset of a skin disorder in a subject in need thereof.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range. As used herein the term "about" refers to +10%.

The terms "comprises", "comprising", "includes", "including", "having" and their conjugates mean "including but not limited to". This term encompasses the terms "consisting of" and "consisting essentially of". The phrase "consisting essentially of" means that the composition or method may include additional ingredients and/or steps, but only if the additional ingredients and/or steps do not materially alter the basic and novel characteristics of the claimed composition or method. Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

At various places in the present specification, substituents of compounds of the disclosure are disclosed in groups or in ranges. It is specifically intended that the disclosure include each and every individual subcombination of the members of such groups and ranges.

NON-LIMITING EXAMPLES

Example 1: In Vitro Studies

Example 1A: High-Throughput Screening Assay

The assay depends on detection of the rise in intracellular $Ca^{2+}$ concentration ($[Ca^{2+}]_i$) following channel activation in cells inducibly expressing the TRPV3 channel. $Ca^{2+}$ rise is quantified with the use of fluorescent $Ca^{2+}$ indicators that are loaded into cells and thereafter indicated the $[Ca^2]_i$. $Ca^{2+}$ influx follows activation of the TRPV3 channel. Compounds inhibiting this $[Ca^2]_i$ rise are considered hits for further investigation.

The commercially available HEK293/TREx line (Invitrogen) was stably transfected with a TRPV3 construct and screened by immunostaining to find clones with TRPV3 expression following stimulation with 1 μg/ml tetracycline. Clonal TRPV3-expressing cells were maintained in the growth medium recommended by the manufacturer supplemented with 100 μg/ml hygromycin to promote retention of the TRPV3 construct. After growing to near confluency, cells are plated at a density of ~25,000 cells/well in 384 well plates in the presence of 1 μg/ml tetracycline, and allowed to grow for 20-30 hrs. A nearly confluent monolayer results. Cells are then loaded with $Ca^{2+}$ dye: Fura-2/AM or Fluo4/AM are added to the wells to a final concentration of 2 μM or 1 μM, respectively, and incubated for 80 min or 60 min, respectively, at room temperature. Supernatant is then removed from the cells by inverting plates with a sharp flick, and 40 μl Ringer's solution (140 mM NaCl, 4.5 mM KCl, 2 mM $CaCl_2$), 1 mM $MgCl_2$, 10 mM HEPES, 10 mM glucose, pH 7.4) is then added to each well. Following ~1 hour for recovery from loading, cells are assayed using the Hamamatsu FDSS 6000 system, which permits illumination alternately at 340 nM and 380 nM for Fura-2 experiments, or at 485 nM for Fluo4 experiments. Frames were acquired at a rate of 0.2 Hz. During the assay, the plates are continuously vortexed, with pipette mixing of wells following addition of each reagent. For the screening assay, 13 μl of a diluted stock of each compound to be tested (at 50 μM) was added to each well for 2 minutes following the collection of a short (4 frame) baseline. 13 μl 750 μM 2-APB (2-aminoethyldiphenylborinate) was added to each well, achieving a final concentration of 10 μM each compound and 150 μM 2-APB. Data were collected for ~3 minutes following addition of 2-APB, where the fluorescent intensity (for Fluo4) and the F340/F380 ratio (for Fura-2) are proportional to the $[Ca^{2+}]_i$. Negative controls consisted of HEK293/TREx TRPV3 cells exposed to 2-APB, but no test compound. Positive control cells were usually HEK293/TREx ("parental") cells exposed to 2-APB but no test compound, but sometimes normal HEK/293 TREx TRPV3 cells were also used, but not exposed to 2-APB or test compound. These controls defined a screening window, and "hits" were defined as those test compounds inhibiting the fluorescence response by at least 40%.

Example 1B: Patch Clamp Experiments

Whole-cell patch clamp experiments permit the detection of currents through the TRPV3 channel in the cell line described above. A glass electrode is brought into contact with a single cell and the membrane is then ruptured, permitting control of the voltage of the cell membrane and measurement of currents flowing across the membrane using the amplifier attached to the electrode. A perfusion system permits control of the extracellular solution, including the addition of blockers and activators of the current. The current can be activated by heating this solution to 28° C. or warmer or by addition of 20 μM 2-APB to the solution.

TRPV3 cells were induced 20-48 hours, removed from growth plates, and replated at low density (to attain good single-cell physical separation) on glass coverslips for measurement. In some cases, cells were grown in low density overnight on glass coverslips. Patch clamp recordings were made in the whole-cell mode with a holding potential of −40 mV. Every 5 seconds, a voltage ramp was applied from −120 to +100 mV, 400 ms in duration. Currents elicited were quantified at −80 mV and +80 mV. The internal solution consisted of 140 mM cesium aspartate, 10 mM EGTA, 2.27 mM $MgCl_2$, 1.91 mM $CaCl_2$) and 10 mM HEPES, pH to 7.2 with KOH; with 50 nM calculated free $Ca^{21}$. External solution was Ringer's solution described above. Upon addition of 2-APB or upon heating of the extraceullar solution as described above, TRPV3 current was induced only in TRPV3-expressing cells and not in parental HEK293 TREx cells. This current showed a small inward component, reversal near +10 mV and a strong outward rectification, and is referred to as Phase I. Upon continued or repeated readdition of 2-APB or heat as a stimulus, current characteristics change, resulting in a Phase II that is linear through +10 mV. Removal of the stimulus caused most of the current to go away, and inhibitor addition could still inhibit this current. Compounds of interest were tested against TRPV3 at concentrations up to 30 μM, and the resulting data was used to estimate $IC_{50}$ for inhibition of the Phase 1 and Phase 2 TRPV3-mediated currents.

To determine whether compounds are selective for TRPV3 inhibition over inhibition of other ion channel types, the human ERG (hERG), NaV1.2, and TRPV1 (hTRPV1) channels and the rat TRPV6 (rTRPV6) channel can be stably transfected and expressed or induced to express in mammalian cell lines. The methods for measuring currents from these channels are well-established and have been described in numerous publications (See, Weerapura et al., 2002, *J Physiology* 540: 15-27; Rush et al., 2005, *J Physiology* 564: 808-815; Caterina et al., 1997, *Nature* 389: 816-824; Hoenderhop et al., 2001, *J Physiology* 537: 747-761; Clapham et al., 2003, *Pharmacol Rev* 55: 591-596). Compounds of interest can be tested against these channels at concentrations up to 30 μM, and the resulting data can be used to estimate $IC_{50}$ for inhibition of the activity of these other ion channels.

Table 1 provides data obtained in this assay for particular compounds of the disclosure. P1 refers to the Phase 1 current for human (h) TRPV3, and P2 refers to the Phase 2 current for human (h) TRPV3. As shown in Table 1, A refers to an inhibitor of hTRPV3 with an $IC_{50}$ between 0 nM and 10 nM. B refers to an inhibitor of hTRPV3 with an $IC_{50}$ between 10 nM and 100 nM. C refers to an inhibitor of hTRPV3 with an $IC_{50}$ between 100 nM and 1000 nM. D refers to an inhibitor of hTRPV3 with an $IC_{50}$ between >1000 nM. ND refers to data not determined.

TABLE 1

Data from Patch Clamp Experiments of selected compounds

| Compound ID | Structure | hTRPV3 Patch P1 Inwd (nM) | hTRPV3 Patch P2 Inwd (nM) |
|---|---|---|---|
| 1-1. | 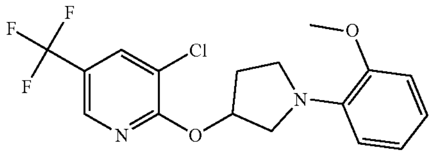 [SMILES: COc1ccccc1N1CCC(Oc2ncc(C(F)(F)F)cc2Cl)C1] | D | D |
| 1-2. | 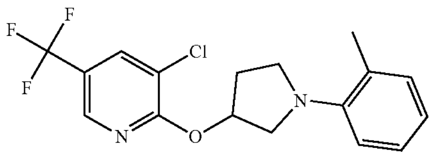 [SMILES: Cc1ccccc1N1CCC(Oc2ncc(C(F)(F)F)cc2Cl)C1] | ND | ND |
| 1-3. | 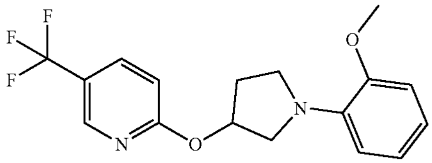 [SMILES: COc1ccccc1N1CCC(Oc2ccc(C(F)(F)F)cn2)C1] | ND | ND |
| 1-4. | 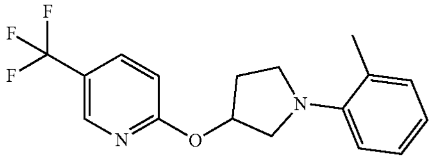 [SMILES: Cc1ccccc1N1CCC(Oc2ccc(C(F)(F)F)cn2)C1] | ND | ND |
| 1-5. | 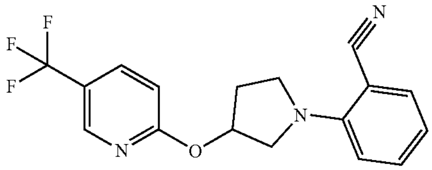 [SMILES: N#Cc1ccccc1N1CCC(Oc2ccc(C(F)(F)F)cn2)C1] | D | D |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-6. | 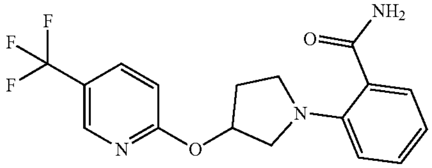 [SMILES: NC(=O)c1ccccc1N1CCC(Oc2ccc(C(F)(F)F)cn2)C1] | ND | ND |
| 1-7. | 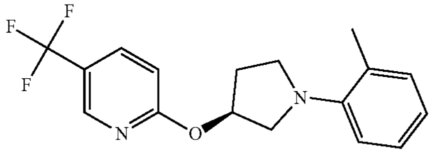 [SMILES: Cc1ccccc1N1CC[C@H](Oc2ccc(C(F)(F)F)cn2)C1] | ND | ND |
| 1-8. | 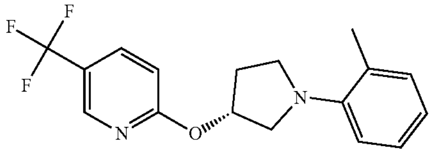 [SMILES: Cc1ccccc1N1CC[C@@H](Oc2ccc(C(F)(F)F)cn2)C1] | ND | ND |
| 1-9. | 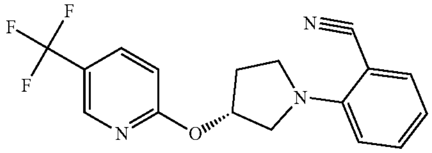 [SMILES: N#Cc1ccccc1N1CC[C@@H](Oc2ccc(C(F)(F)F)cn2)C1] | D | ND |
| 1-10. | 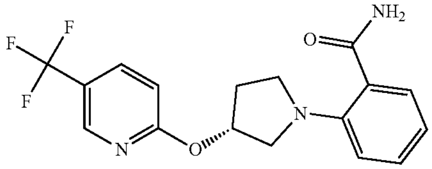 [SMILES: NC(=O)c1ccccc1N1CC[C@@H](Oc2ccc(C(F)(F)F)cn2)C1] | ND | ND |
| 1-11. | 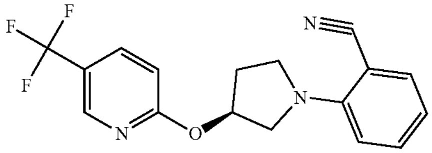 [SMILES: N#Cc1ccccc1N1CC[C@H](Oc2ccc(C(F)(F)F)cn2)C1] | D | ND |
| 1-12. | 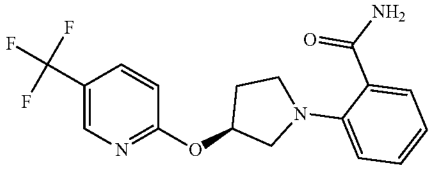 [SMILES: NC(=O)c1ccccc1N1CC[C@H](Oc2ccc(C(F)(F)F)cn2)C1] | ND | ND |
| 1-13. | 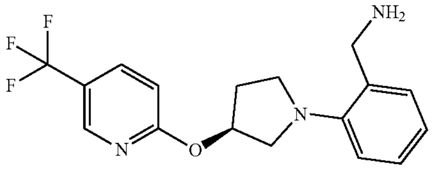 [SMILES: NCc1ccccc1N1CC[C@H](Oc2ccc(C(F)(F)F)cn2)C1] | D | D |

TABLE 1-continued
Data from Patch Clamp Experiments of selected compounds
| Compound ID | Structure | hTRPV3 Patch P1 Inwd (nM) | hTRPV3 Patch P2 Inwd (nM) |
|---|---|---|---|
| 1-14. | 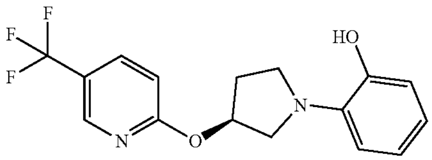 [SMILES: Oc1ccccc1N1CC[C@H](Oc2ccc(C(F)(F)F)cn2)C1] | ND | ND |
| 1-15. | 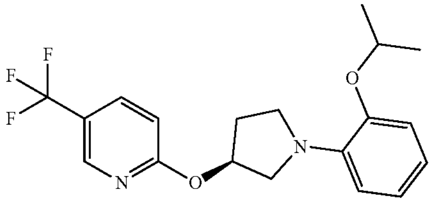 [SMILES: CC(C)Oc1ccccc1N1CC[C@H](Oc2ccc(C(F)(F)F)cn2)C1] | D | D |
| 1-16. | 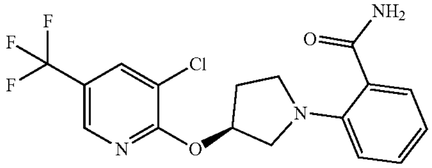 [SMILES: NC(=O)c1ccccc1N1CC[C@H](Oc2ncc(C(F)(F)F)cc2Cl)C1] | ND | ND |
| 1-17. | 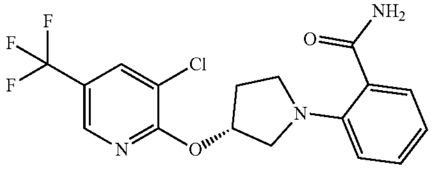 [SMILES: NC(=O)c1ccccc1N1CC[C@@H](Oc2ncc(C(F)(F)F)cc2Cl)C1] | ND | ND |
| 1-18. | 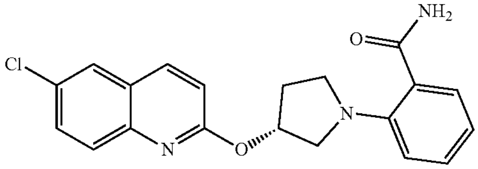 [SMILES: NC(=O)c1ccccc1N1CC[C@@H](Oc2ccc3cc(Cl)ccc3n2)C1] | ND | ND |
| 1-19. | 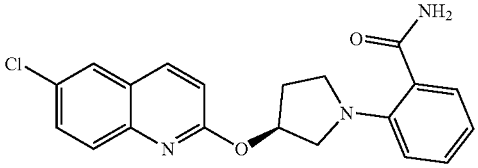 [SMILES: NC(=O)c1ccccc1N1CC[C@H](Oc2ccc3cc(Cl)ccc3n2)C1] | ND | ND |
| 1-20. | 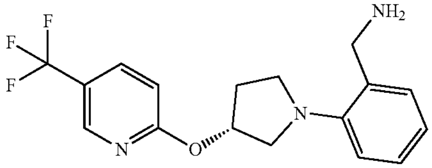 [SMILES: NCc1ccccc1N1CC[C@@H](Oc2ccc(C(F)(F)F)cn2)C1] | D | D |
| 1-21. | 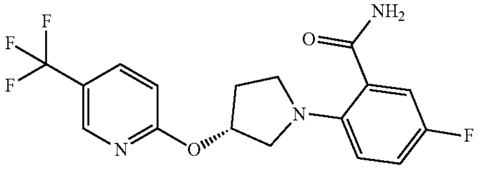 [SMILES: NC(=O)c1cc(F)ccc1N1CC[C@@H](Oc2ccc(C(F)(F)F)cn2)C1] | ND | ND |

TABLE 1-continued
| Compound ID | Structure | hTRPV3 Patch P1 Inwd (nM) | hTRPV3 Patch P2 Inwd (nM) |
|---|---|---|---|
| 1-22. | 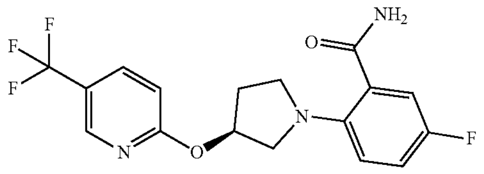 [SMILES: NC(=O)c1cc(F)ccc1N1CC[C@H](Oc2ccc(C(F)(F)F)cn2)C1] | ND | ND |
| 1-23. | 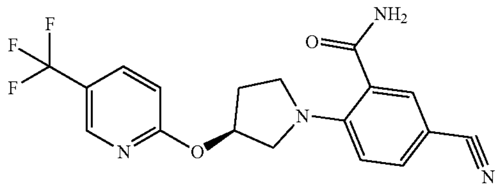 [SMILES: N#Cc1ccc(N2CC[C@H](Oc3ccc(C(F)(F)F)cn3)C2)c(C(N)=O)c1] | D | ND |
| 1-24. | 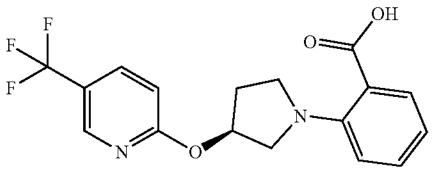 [SMILES: O=C(O)c1ccccc1N1CC[C@H](Oc2ccc(C(F)(F)F)cn2)C1] | D | ND |
| 1-25. | 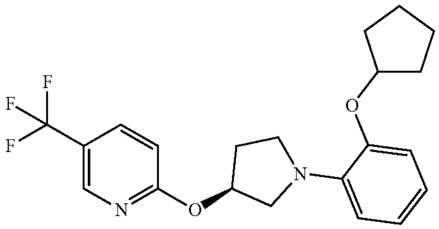 [SMILES: FC(F)(F)c1ccc(O[C@H]2CCN(c3ccccc3OC3CCCC3)C2)nc1] | D | ND |
| 1-26. | 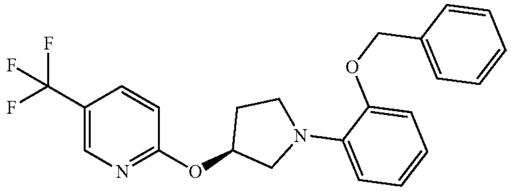 [SMILES: FC(F)(F)c1ccc(O[C@H]2CCN(c3ccccc3OCc3ccccc3)C2)nc1] | D | ND |
| 1-27. | 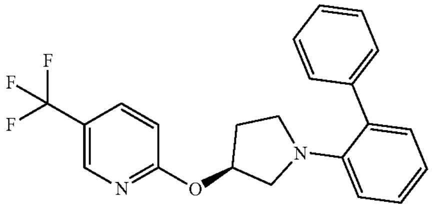 [SMILES: FC(F)(F)c1ccc(O[C@H]2CCN(c3ccccc3-c3ccccc3)C2)nc1] | D | ND |
| 1-28. | 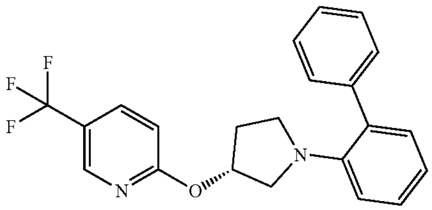 [SMILES: FC(F)(F)c1ccc(O[C@@H]2CCN(c3ccccc3-c3ccccc3)C2)nc1] | D | ND |
Data from Patch Clamp Experiments of selected compounds TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-29. | 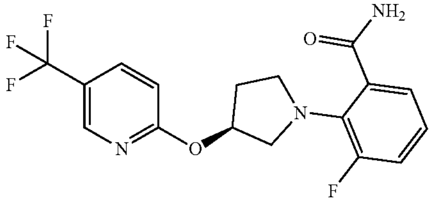 [SMILES: NC(=O)c1cccc(F)c1N1CC[C@H](Oc2ccc(C(F)(F)F)cn2)C1] | ND | ND |
| 1-30. | 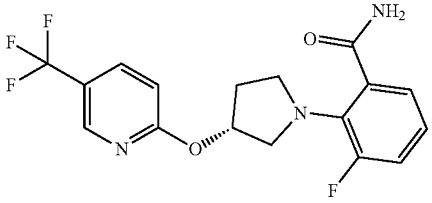 [SMILES: NC(=O)c1cccc(F)c1N1CC[C@@H](Oc2ccc(C(F)(F)F)cn2)C1] | ND | ND |
| 1-31. | 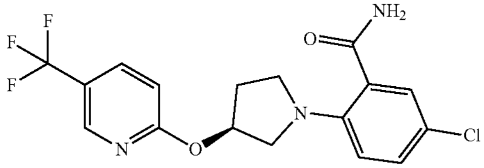 [SMILES: NC(=O)c1cc(Cl)ccc1N1CC[C@H](Oc2ccc(C(F)(F)F)cn2)C1] | C | C |
| 1-32. | 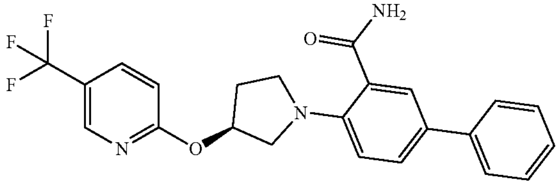 [SMILES: NC(=O)c1cc(-c2ccccc2)ccc1N1CC[C@H](Oc2ccc(C(F)(F)F)cn2)C1] | C | C |
| 1-33. | 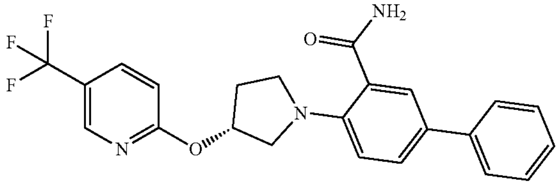 [SMILES: NC(=O)c1cc(-c2ccccc2)ccc1N1CC[C@@H](Oc2ccc(C(F)(F)F)cn2)C1] | C | ND |
| 1-34. | 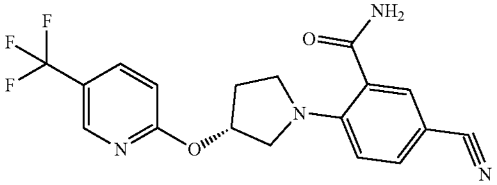 [SMILES: N#Cc1ccc(N2CC[C@@H](Oc3ccc(C(F)(F)F)cn3)C2)c(C(N)=O)c1] | D | ND |
| 1-35. | 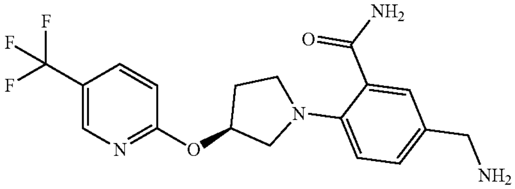 [SMILES: NCc1ccc(N2CC[C@H](Oc3ccc(C(F)(F)F)cn3)C2)c(C(N)=O)c1] | D | ND |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-36. | 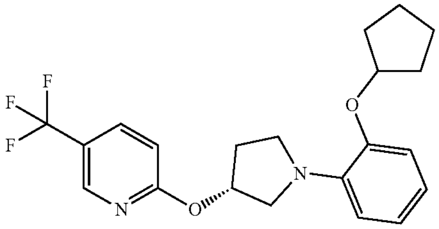 [SMILES: FC(F)(F)c1ccc(O[C@@H]2CCN(c3ccccc3OC3CCCC3)C2)nc1] | D | ND |
| 1-37. | 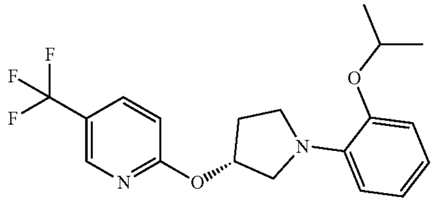 [SMILES: CC(C)Oc1ccccc1N1CC[C@@H](Oc2ccc(C(F)(F)F)cn2)C1] | D | ND |
| 1-38. | 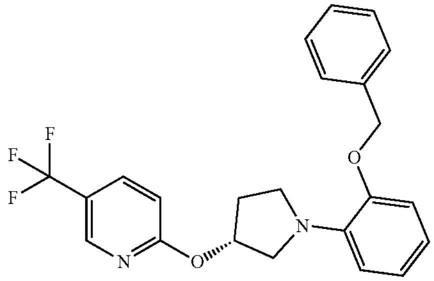 [SMILES: FC(F)(F)c1ccc(O[C@@H]2CCN(c3ccccc3OCc3ccccc3)C2)nc1] | D | ND |
| 1-39. | 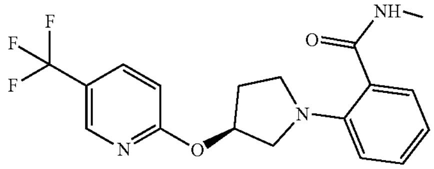 [SMILES: CNC(=O)c1ccccc1N1CC[C@H](Oc2ccc(C(F)(F)F)cn2)C1] | D | ND |
| 1-40. | 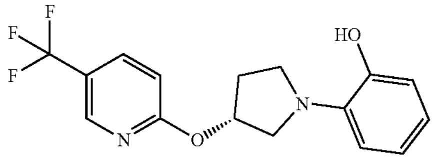 [SMILES: Oc1ccccc1N1CC[C@@H](Oc2ccc(C(F)(F)F)cn2)C1] | ND | ND |
| 1-41. | 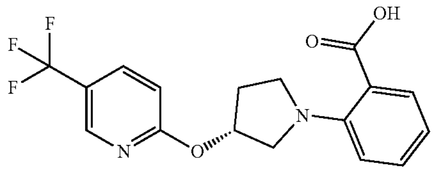 [SMILES: O=C(O)c1ccccc1N1CC[C@@H](Oc2ccc(C(F)(F)F)cn2)C1] | D | D |
| 1-42. | 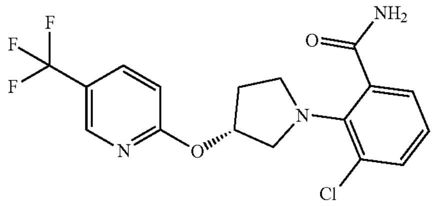 [SMILES: NC(=O)c1cccc(Cl)c1N1CC[C@@H](Oc2ccc(C(F)(F)F)cn2)C1] | ND | ND |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-43. | 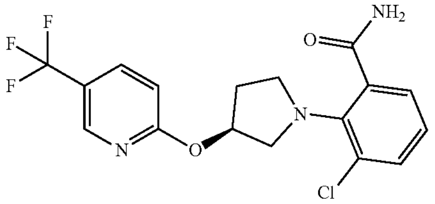 | ND | ND |
| 1-44. | 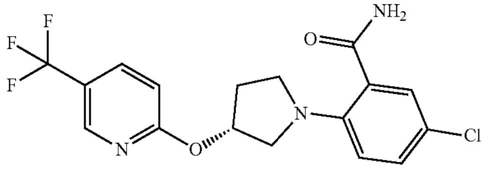 [SMILES: NC(=O)c1cc(Cl)ccc1N1CC[C@@H](Oc2ccc(C(F)(F)F)cn2)C1] | ND | ND |
| 1-45. | 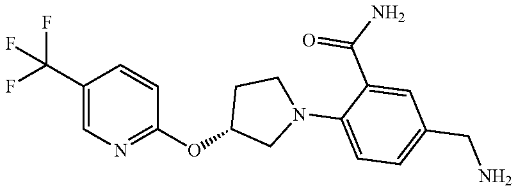 [SMILES: NCc1ccc(N2CC[C@@H](Oc3ccc(C(F)(F)F)cn3)C2)c(C(N)=O)c1] | D | ND |
| 1-46. | 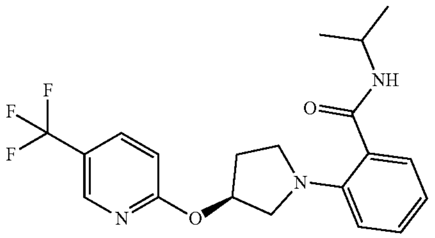 [SMILES: CC(C)NC(=O)c1ccccc1N1CC[C@H](Oc2ccc(C(F)(F)F)cn2)C1] | D | ND |
| 1-47. | 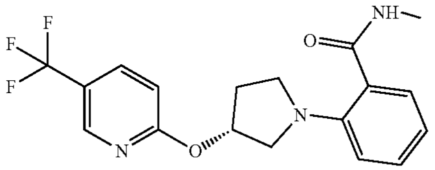 [SMILES: CNC(=O)c1ccccc1N1CC[C@@H](Oc2ccc(C(F)(F)F)cn2)C1] | D | ND |
| 1-48. | 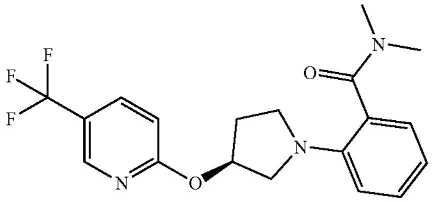 [SMILES: CN(C)C(=O)c1ccccc1N1CC[C@H](Oc2ccc(C(F)(F)F)cn2)C1] | D | ND |
| 1-49. | 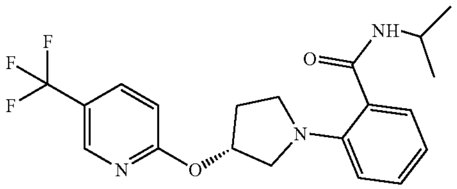 [SMILES: CC(C)NC(=O)c1ccccc1N1CC[C@@H](Oc2ccc(C(F)(F)F)cn2)C1] | D | ND |

TABLE 1-continued
Data from Patch Clamp Experiments of selected compounds
| Compound ID | Structure | hTRPV3 Patch P1 Inwd (nM) | hTRPV3 Patch P2 Inwd (nM) |
|---|---|---|---|
| 1-50. | 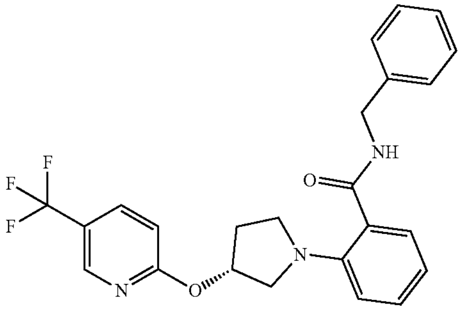 [SMILES: O=C(NCc1ccccc1)c1ccccc1N1CC[C@@H](Oc2ccc(C(F)(F)F)cn2)C1] | D | D |
| 1-51. | 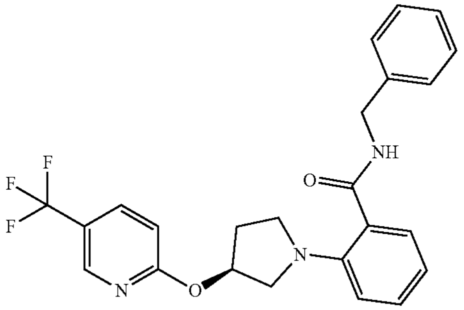 [SMILES: O=C(NCc1ccccc1)c1ccccc1N1CC[C@H](Oc2ccc(C(F)(F)F)cn2)C1] | ND | D |
| 1-52. | 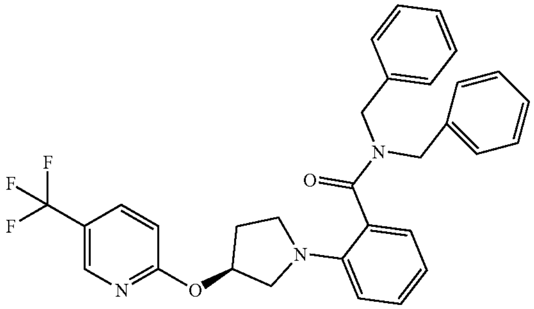 [SMILES: O=C(c1ccccc1N1CC[C@H](Oc2ccc(C(F)(F)F)cn2)C1)N(Cc1ccccc1)Cc1ccccc1] | D | ND |
| 1-53. | 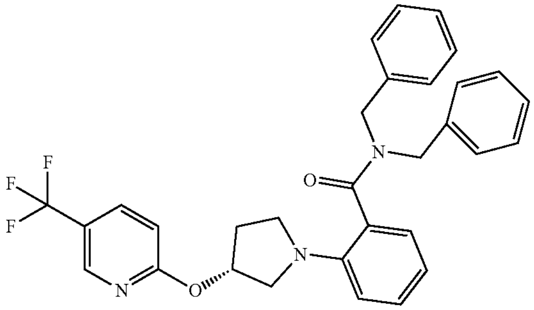 [SMILES: O=C(c1ccccc1N1CC[C@@H](Oc2ccc(C(F)(F)F)cn2)C1)N(Cc1ccccc1)Cc1ccccc1] | D | ND |
| 1-54. | 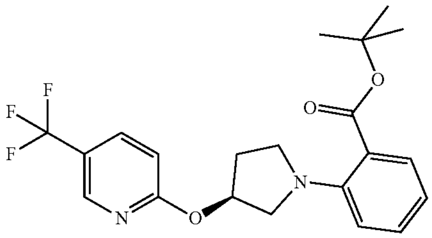 [SMILES: CC(C)(C)OC(=O)c1ccccc1N1CC[C@H](Oc2ccc(C(F)(F)F)cn2)C1] | D | ND |

TABLE 1-continued
Data from Patch Clamp Experiments of selected compounds
| Compound ID | Structure | hTRPV3 Patch P1 Inwd (nM) | hTRPV3 Patch P2 Inwd (nM) |
|---|---|---|---|
| 1-55. | 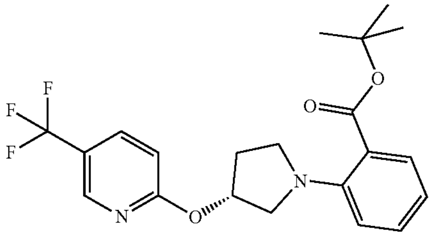 [SMILES: CC(C)(C)OC(=O)c1ccccc1N1CC[C@@H](Oc2ccc(C(F)(F)F)cn2)C1] | D | D |
| 1-56. | 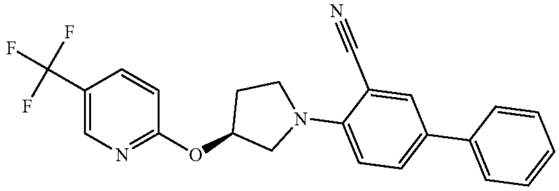 [SMILES: N#Cc1cc(-c2ccccc2)ccc1N1CC[C@H](Oc2ccc(C(F)(F)F)cn2)C1] | ND | C |
| 1-57. | 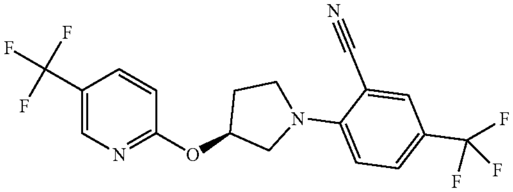 [SMILES: N#Cc1cc(C(F)(F)F)ccc1N1CC[C@H](Oc2ccc(C(F)(F)F)cn2)C1] | C | C |
| 1-58. | 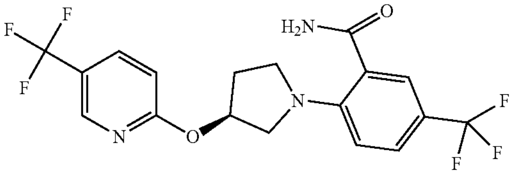 [SMILES: NC(=O)c1cc(C(F)(F)F)ccc1N1CC[C@H](Oc2ccc(C(F)(F)F)cn2)C1] | ND | C |
| 1-59. | 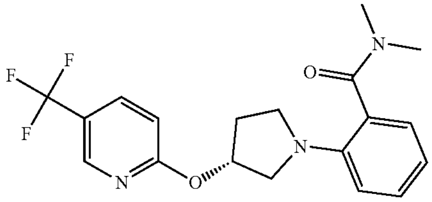 [SMILES: CN(C)C(=O)c1ccccc1N1CC[C@@H](Oc2ccc(C(F)(F)F)cn2)C1] | D | ND |
| 1-60. | 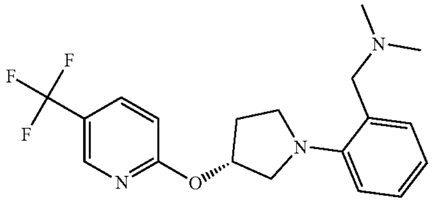 [SMILES: CN(C)Cc1ccccc1N1CC[C@@H](Oc2ccc(C(F)(F)F)cn2)C1] | D | D |
| 1-61. | 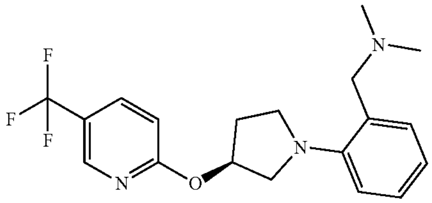 [SMILES: CN(C)Cc1ccccc1N1CC[C@H](Oc2ccc(C(F)(F)F)cn2)C1] | D | ND |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-62. | 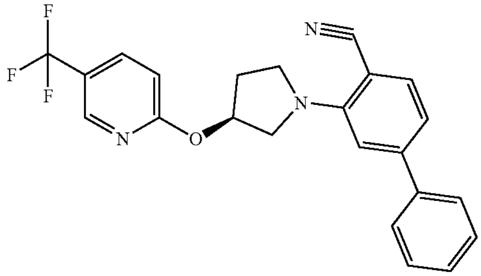 [SMILES: N#Cc1ccc(-c2ccccc2)cc1N1CC[C@H](Oc2ccc(C(F)(F)F)cn2)C1] | D | D |
| 1-63. | 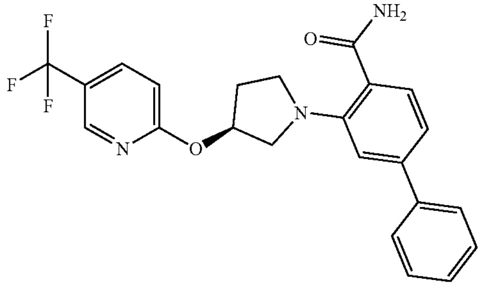 [SMILES: NC(=O)c1ccc(-c2ccccc2)cc1N1CC[C@H](Oc2ccc(C(F)(F)F)cn2)C1] | D | D |
| 1-64. | 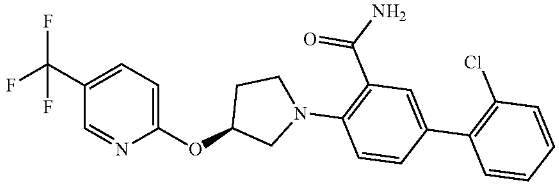 [SMILES: NC(=O)c1cc(-c2ccccc2Cl)ccc1N1CC[C@H](Oc2ccc(C(F)(F)F)cn2)C1] | C | C |
| 1-65. | 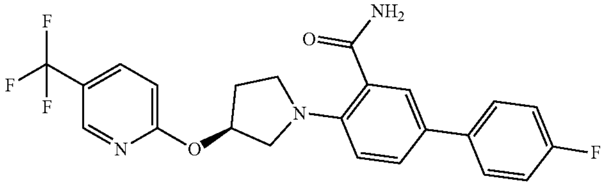 [SMILES: NC(=O)c1cc(-c2ccc(F)cc2)ccc1N1CC[C@H](Oc2ccc(C(F)(F)F)cn2)C1] | C | C |
| 1-66. | 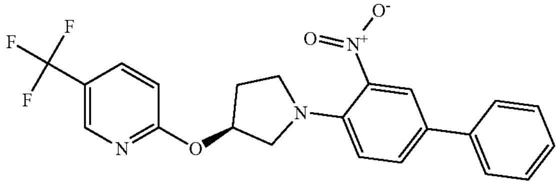 [SMILES: O=[N+]([O-])c1cc(-c2ccccc2)ccc1N1CC[C@H](Oc2ccc(C(F)(F)F)cn2)C1] | ND | ND |
| 1-67. | 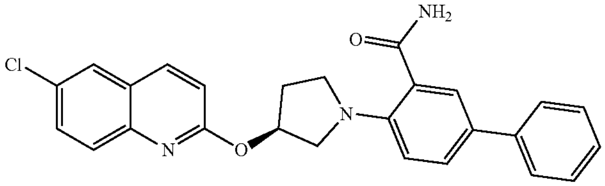 [SMILES: NC(=O)c1cc(-c2ccccc2)ccc1N1CC[C@H](Oc2ccc3cc(Cl)ccc3n2)C1] | D | C |
| 1-68. | 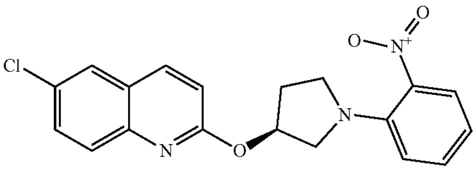 | D | D |

TABLE 1-continued
Data from Patch Clamp Experiments of selected compounds
| Compound ID | Structure | hTRPV3 Patch P1 Inwd (nM) | hTRPV3 Patch P2 Inwd (nM) |
|---|---|---|---|
| 1-69. | 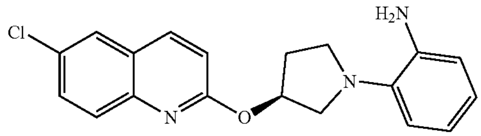 | ND | ND |
| 1-70. | 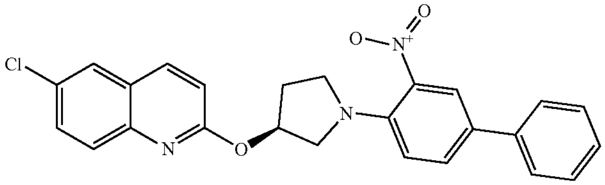 | D | D |
| 1-71. | 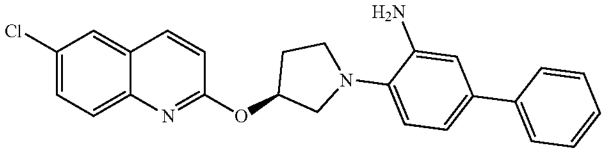 | D | D |
| 1-72. | 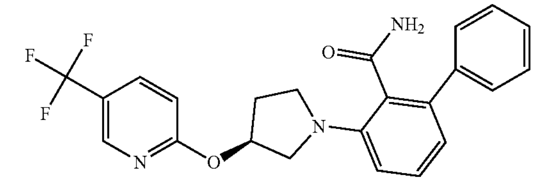 [SMILES: NC(=O)c1c(-c2ccccc2)cccc1N1CC[C@H](Oc2ccc(C(F)(F)F)cn2)C1] | ND | D |
| 1-73. | 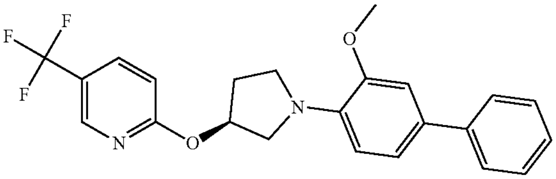 [SMILES: COc1cc(-c2ccccc2)ccc1N1CC[C@H](Oc2ccc(C(F)(F)F)cn2)C1] | B | B |
| 1-74. | 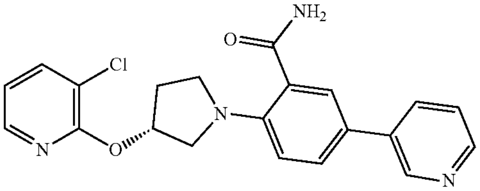 [SMILES: NC(=O)c1cc(-c2cccnc2)ccc1N1CC[C@@H](Oc2ncccc2Cl)C1] | ND | D |
| 1-75. | 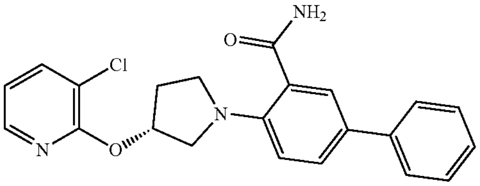 [SMILES: NC(=O)c1cc(-c2ccccc2)ccc1N1CC[C@@H](Oc2ncccc2Cl)C1] | D | C |
| 1-76. | 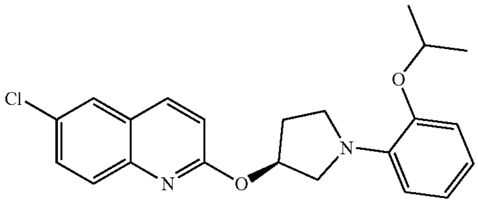 [SMILES: CC(C)Oc1ccccc1N1CC[C@H](Oc2ccc3cc(Cl)ccc3n2)C1] | D | D |

TABLE 1-continued
Data from Patch Clamp Experiments of selected compounds
| Compound ID | Structure | hTRPV3 Patch P1 Inwd (nM) | hTRPV3 Patch P2 Inwd (nM) |
|---|---|---|---|
| 1-77. | 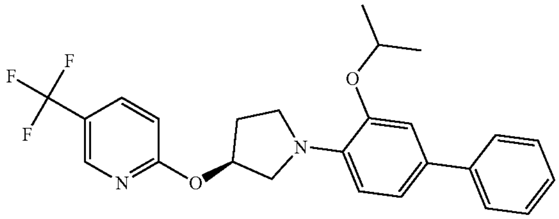 [SMILES: CC(C)Oc1cc(-c2ccccc2)ccc1N1CC[C@H](Oc2ccc(C(F)(F)F)cn2)C1] | D | D |
| 1-78. | 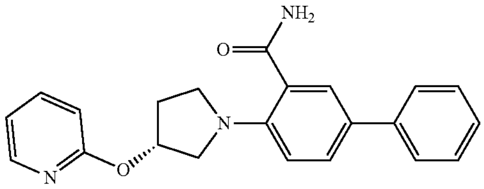 | C | C |
| 1-79. | 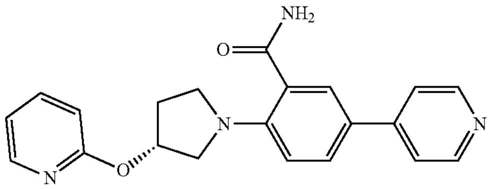 [SMILES: NC(=O)c1cc(-c2ccncc2)ccc1N1CC[C@@H](Oc2ccccn2)C1] | D | D |
| 1-80. | 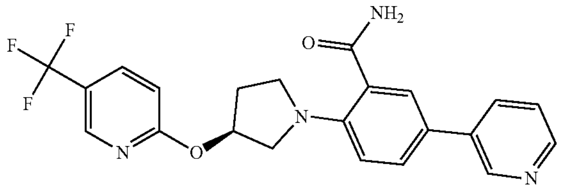 [SMILES: NC(=O)c1cc(-c2cccnc2)ccc1N1CC[C@H](Oc2ccc(C(F)(F)F)cn2)C1] | D | D |
| 1-81. | 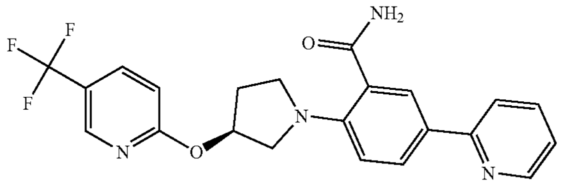 [SMILES: NC(=O)c1cc(-c2ccccn2)ccc1N1CC[C@H](Oc2ccc(C(F)(F)F)cn2)C1] | D | D |
| 1-82. | 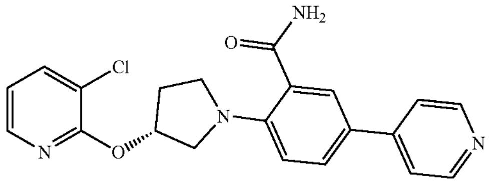 [SMILES: NC(=O)c1cc(-c2ccncc2)ccc1N1CC[C@@H](Oc2ncccc2Cl)C1] | D | D |
| 1-83. | 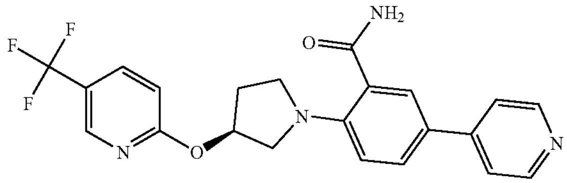 [SMILES: NC(=O)c1cc(-c2ccncc2)ccc1N1CC[C@H](Oc2ccc(C(F)(F)F)cn2)C1] | D | D |

TABLE 1-continued
Data from Patch Clamp Experiments of selected compounds
| Compound ID | Structure | hTRPV3 Patch P1 Inwd (nM) | hTRPV3 Patch P2 Inwd (nM) |
|---|---|---|---|
| 1-84. | 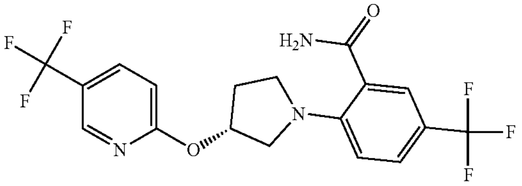 [SMILES: NC(=O)c1cc(C(F)(F)F)ccc1N1CC[C@@H](Oc2ccc(C(F)(F)F)cn2)C1] | C | ND |
| 1-85. | 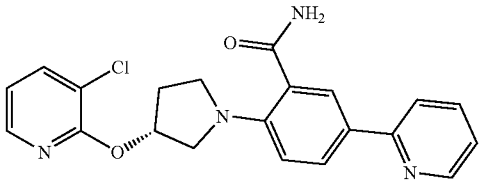 [SMILES: NC(=O)c1cc(-c2ccccn2)ccc1N1CC[C@@H](Oc2ncccc2Cl)C1] | D | ND |
| 1-86. | 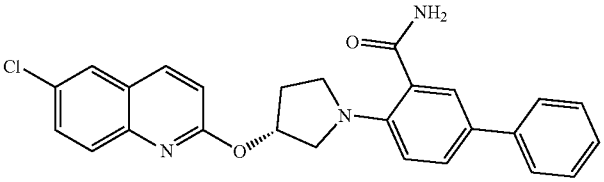 [SMILES: NC(=O)c1cc(-c2ccccc2)ccc1N1CC[C@@H](Oc2ccc3cc(Cl)ccc3n2)C1] | ND | D |
| 1-87. | 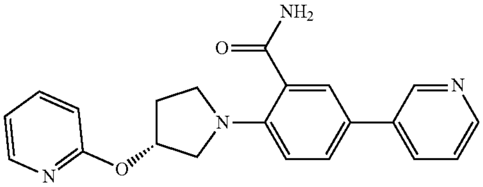 [SMILES: NC(=O)c1cc(-c2cccnc2)ccc1N1CC[C@@H](Oc2ccccn2)C1] | D | ND |
| 1-88. | 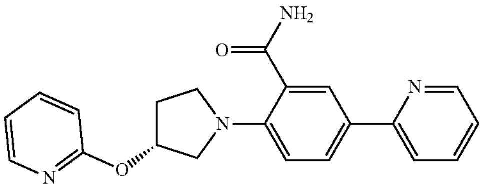 [SMILES: NC(=O)c1cc(-c2ccccn2)ccc1N1CC[C@@H](Oc2ccccn2)C1] | D | D |
| 1-89. | 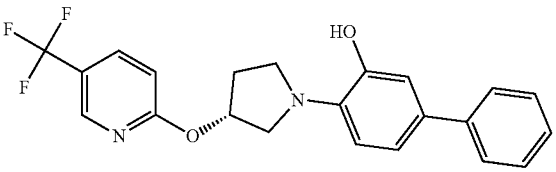 [SMILES: Oc1cc(-c2ccccc2)ccc1N1CC[C@@H](Oc2ccc(C(F)(F)F)cn2)C1] | D | D |
| 1-90. | 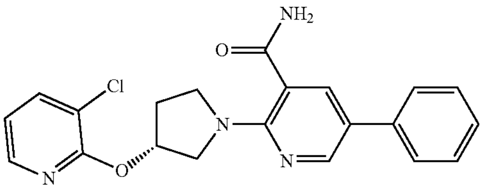 [SMILES: NC(=O)c1cc(-c2ccccc2)cnc1N1CC[C@@H](Oc2ncccc2Cl)C1] | D | D |
| 1-91. | 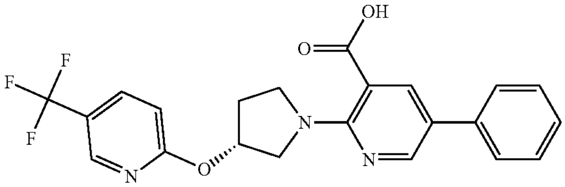 | ND | ND |

TABLE 1-continued
Data from Patch Clamp Experiments of selected compounds
| Compound ID | Structure | hTRPV3 Patch P1 Inwd (nM) | hTRPV3 Patch P2 Inwd (nM) |
|---|---|---|---|
| 1-92. | 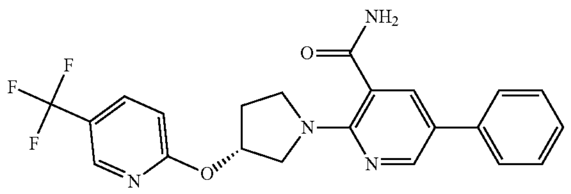 [SMILES: O=C(O)c1cc(-c2ccccc2)cnc1N1CC[C@@H](Oc2ccc(C(F)(F)F)cn2)C1] | ND | ND |
| 1-93. | 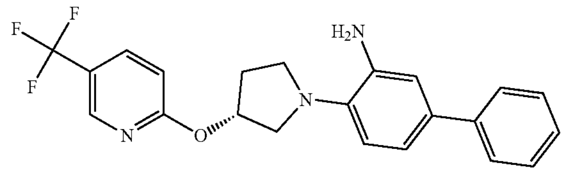 [SMILES: Nc1cc(-c2ccccc2)ccc1N1CC[C@@H](Oc2ccc(C(F)(F)F)cn2)C1] | ND | ND |
| 1-94. | 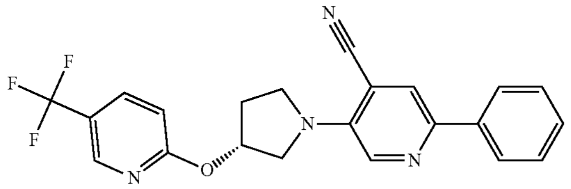 [SMILES: N#Cc1cc(-c2ccccc2)ncc1N1CC[C@@H](Oc2ccc(C(F)(F)F)cn2)C1] | ND | Flag/ND/ND/~117 |
| 1-95. | 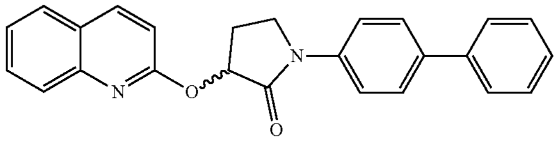 [SMILES: O=C1C(Oc2ccc3ccccc3n2)CCN1c1ccc(-c2ccccc2)cc1] | D | ND |
| 1-96. | 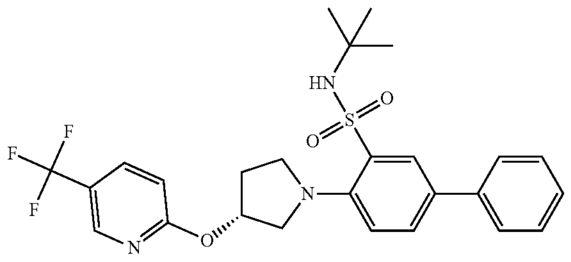 [SMILES: CC(C)(C)NS(=O)(=O)c1cc(-c2ccccc2)ccc1N1CC[C@@H](Oc2ccc(C(F)(F)F)cn2)C1] | D | D |
| 1-97. | 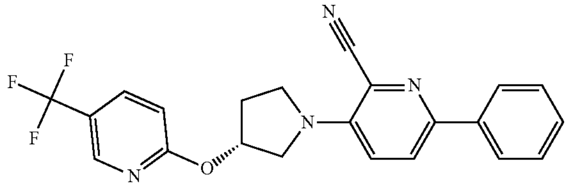 [SMILES: N#Cc1nc(-c2ccccc2)ccc1N1CC[C@@H](Oc2ccc(C(F)(F)F)cn2)C1] | ND | D |
| 1-98. | 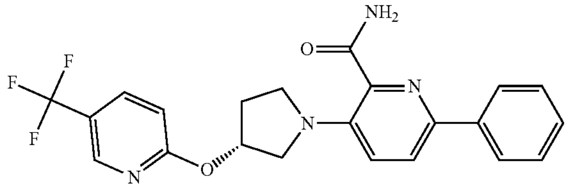 [SMILES: NC(=O)c1nc(-c2ccccc2)ccc1N1CC[C@@H](Oc2ccc(C(F)(F)F)cn2)C1] | C | ND |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-99. | 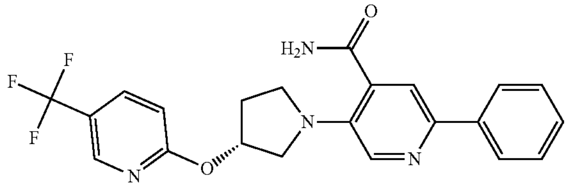 [SMILES: NC(=O)c1cc(-c2ccccc2)ncc1N1CC[C@@H](Oc2ccc(C(F)(F)F)cn2)C1] | C | C |
| 1-100. | 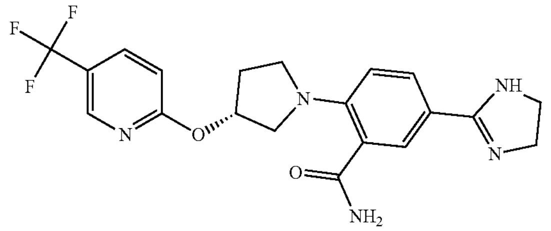 [SMILES: NC(=O)c1cc(C2=NCCN2)ccc1N1CC[C@@H](Oc2ccc(C(F)(F)F)cn2)C1] | D | D |
| 1-101. | 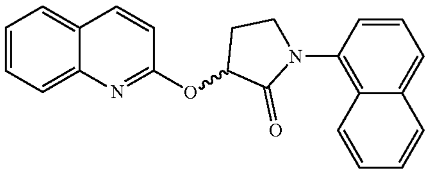 [SMILES: O=C1C(Oc2ccc3ccccc3n2)CCN1c1cccc2ccccc12] | D | D |
| 1-102. | 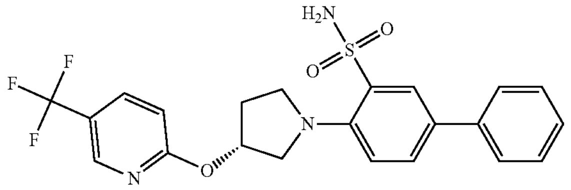 [SMILES: NS(=O)(=O)c1cc(-c2ccccc2)ccc1N1CC[C@@H](Oc2ccc(C(F)(F)F)cn2)C1] | D | D |
| 1-103. | 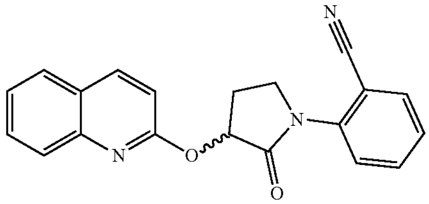 [SMILES: N#Cc1ccccc1N1CCC(Oc2ccc3ccccc3n2)C1=O] | D | ND |
| 1-104. | 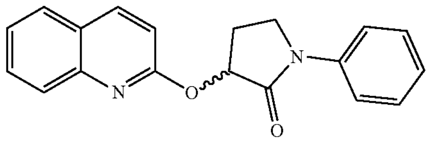 [SMILES: O=C1C(Oc2ccc3ccccc3n2)CCN1c1ccccc1] | D | ND |
| 1-105. | 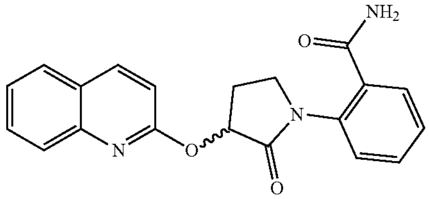 [SMILES: NC(=O)c1ccccc1N1CCC(Oc2ccc3ccccc3n2)C1=O] | D | ND |
| 1-106. | 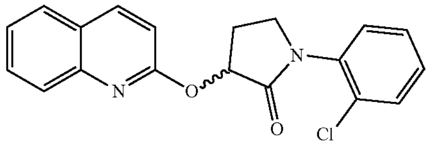 [SMILES: O=C1C(Oc2ccc3ccccc3n2)CCN1c1ccccc1Cl] | D | D |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-107. | 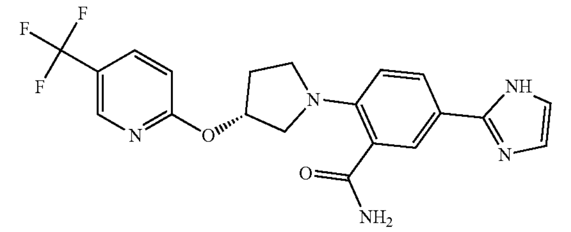 [SMILES: NC(=O)c1cc(-c2ncc[nH]2)ccc1N1CC[C@@H](Oc2ccc(C(F)(F)F)cn2)C1] | D | D |
| 1-108. | 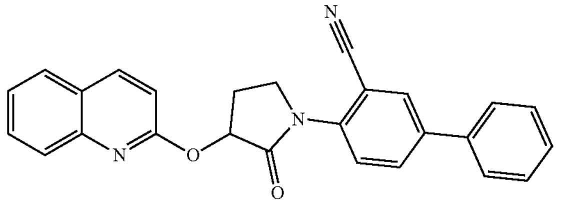 [SMILES: N#Cc1cc(-c2ccccc2)ccc1N1CCC(Oc2ccc3ccccc3n2)C1=O] | ND | D |
| 1-109. | 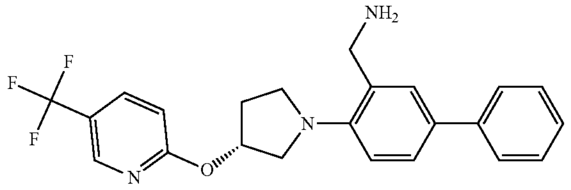 [SMILES: NCc1cc(-c2ccccc2)ccc1N1CC[C@@H](Oc2ccc(C(F)(F)F)cn2)C1] | D | D |
| 1-110. | 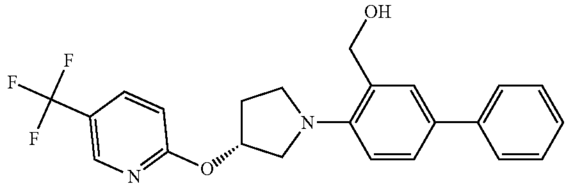 [SMILES: OCc1cc(-c2ccccc2)ccc1N1CC[C@@H](Oc2ccc(C(F)(F)F)cn2)C1] | C | C |
| 1-111. | 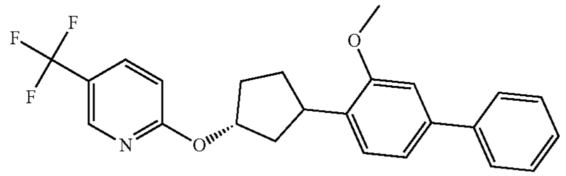 [SMILES: COc1cc(-c2ccccc2)ccc1C1CC[C@@H](Oc2ccc(C(F)(F)F)cn2)C1] | D | ND |
| 1-112. | 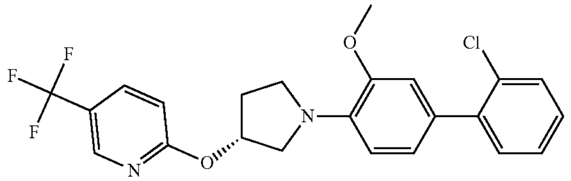 [SMILES: COc1cc(-c2ccccc2Cl)ccc1N1CC[C@@H](Oc2ccc(C(F)(F)F)cn2)C1] | D | ND |
| 1-113. | 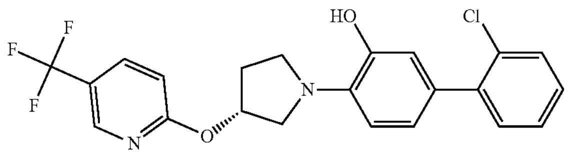 [SMILES: Oc1cc(-c2ccccc2Cl)ccc1N1CC[C@@H](Oc2ccc(C(F)(F)F)cn2)C1] | C | C |

TABLE 1-continued
| Compound ID | Structure | hTRPV3 Patch P1 Inwd (nM) | hTRPV3 Patch P2 Inwd (nM) |
| --- | --- | --- | --- |
| Data from Patch Clamp Experiments of selected compounds | | | |
| 1-114. | 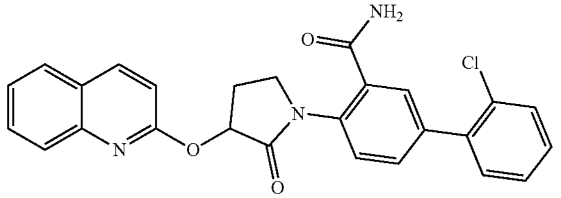 [SMILES: NC(=O)c1cc(-c2ccccc2Cl)ccc1N1CCC(Oc2ccc3ccccc3n2)C1=O] | D | D |
| 1-115. | 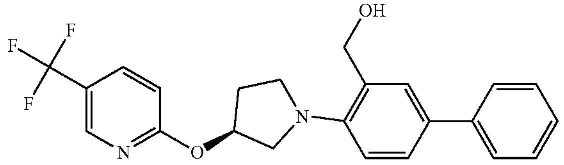 [SMILES: OCc1cc(-c2ccccc2)ccc1N1CC[C@H](Oc2ccc(C(F)(F)F)cn2)C1] | B | B |
| 1-116. | 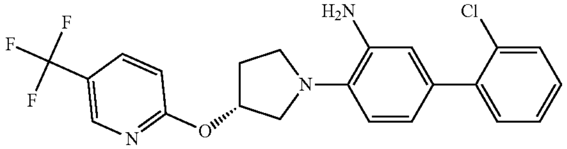 [SMILES: Nc1cc(-c2ccccc2Cl)ccc1N1CC[C@@H](Oc2ccc(C(F)(F)F)cn2)C1] | ND | ND |
| 1-117. | 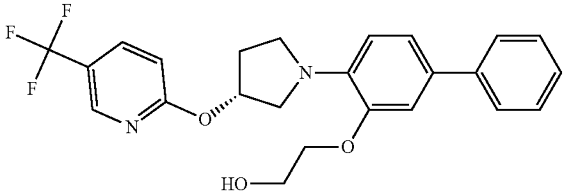 [SMILES: OCCOc1cc(-c2ccccc2)ccc1N1CC[C@@H](Oc2ccc(C(F)(F)F)cn2)C1] | D | C |
| 1-118. | 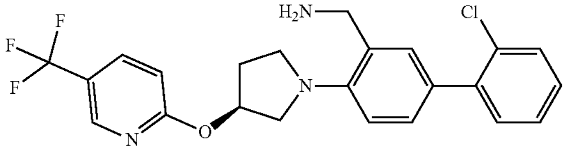 [SMILES: NCc1cc(-c2ccccc2Cl)ccc1N1CC[C@H](Oc2ccc(C(F)(F)F)cn2)C1] | D | D |
| 1-119. | 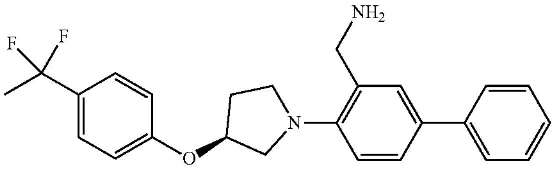 [SMILES: CC(F)(F)c1ccc(O[C@H]2CCN(c3ccc(-c4ccccc4)cc3CN)C2)cc1] | ND | D |
| 1-120. | 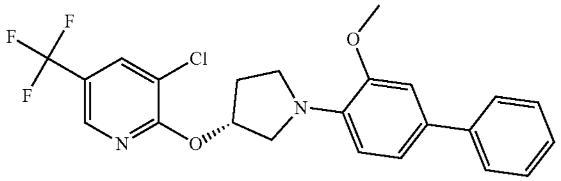 [SMILES: COc1cc(-c2ccccc2)ccc1N1CC[C@@H](Oc2ncc(C(F)(F)F)cc2Cl)C1] | D | D |
| 1-121. | 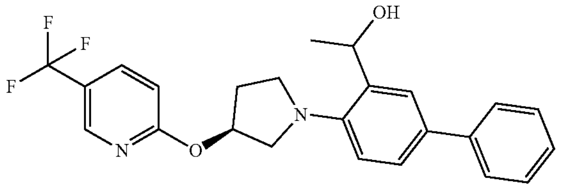 [SMILES: CC(O)c1cc(-c2ccccc2)ccc1N1CC[C@H](Oc2ccc(C(F)(F)F)cn2)C1] | B | ND |

TABLE 1-continued
| Compound ID | Structure | hTRPV3 Patch P1 Inwd (nM) | hTRPV3 Patch P2 Inwd (nM) |
|---|---|---|---|
| Data from Patch Clamp Experiments of selected compounds | | | |
| 1-122. | 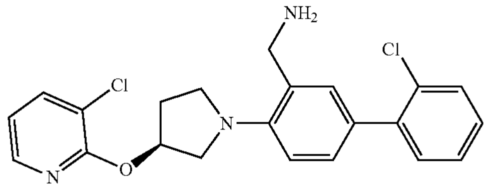 [SMILES: NCc1cc(-c2ccccc2Cl)ccc1N1CC[C@H](Oc2ncccc2Cl)C1] | D | D |
| 1-123. | 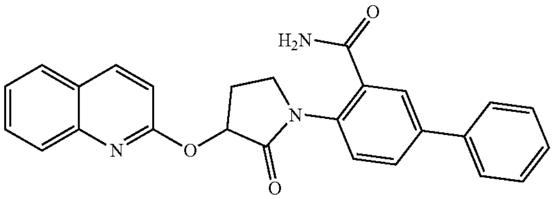 [SMILES: NC(=O)c1cc(-c2ccccc2)ccc1N1CCC(Oc2ccc3ccccc3n2)C1=O] | D | ND |
| 1-124. | 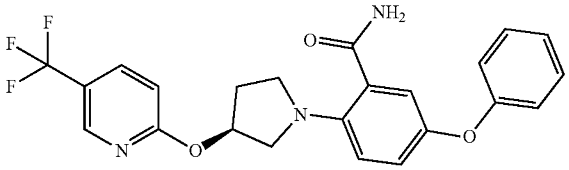 [SMILES: NC(=O)c1cc(Oc2ccccc2)ccc1N1CC[C@H](Oc2ccc(C(F)(F)F)cn2)C1] | C | ND |
| 1-125. | 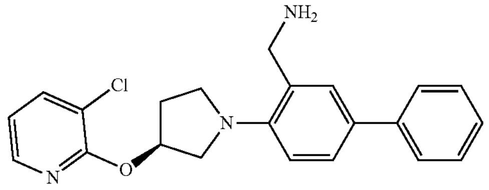 | ND | D |
| 1-126. | 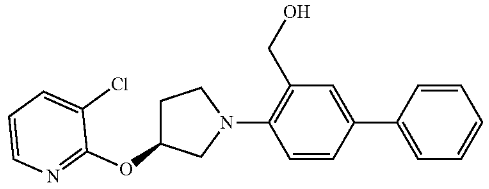 [SMILES: OCc1cc(-c2ccccc2)ccc1N1CC[C@H](Oc2ncccc2Cl)C1] | ND | C |
| 1-127. | 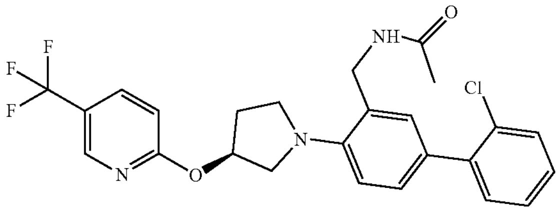 [SMILES: CC(=O)NCc1cc(-c2ccccc2Cl)ccc1N1CC[C@H](Oc2ccc(C(F)(F)F)cn2)C1] | ND | D |
| 1-128. | 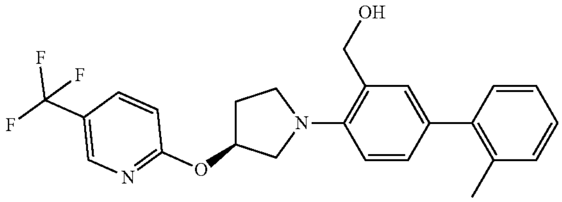 [SMILES: Cc1ccccc1-c1ccc(N2CC[C@H](Oc3ccc(C(F)(F)F)cn3)C2)c(CO)c1] | C | ND |

TABLE 1-continued
Data from Patch Clamp Experiments of selected compounds
| Compound ID | Structure | hTRPV3 Patch P1 Inwd (nM) | hTRPV3 Patch P2 Inwd (nM) |
|---|---|---|---|
| 1-129. | 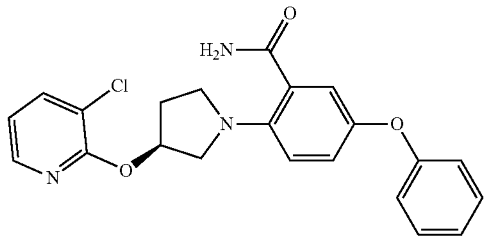 [SMILES: NC(=O)c1cc(Oc2ccccc2)ccc1N1CC[C@H](Oc2ncccc2Cl)C1] | C | ND |
| 1-130. | 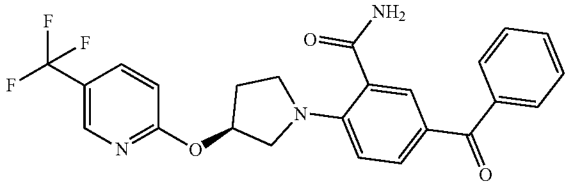 [SMILES: NC(=O)c1cc(C(=O)c2ccccc2)ccc1N1CC[C@H](Oc2ccc(C(F)(F)F)cn2)C1] | D | ND |
| 1-131. | 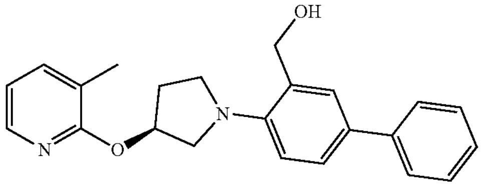 [SMILES: Cc1cccnc1O[C@H]1CCN(c2ccc(-c3ccccc3)cc2CO)C1] | C | ND |
| 1-132. | 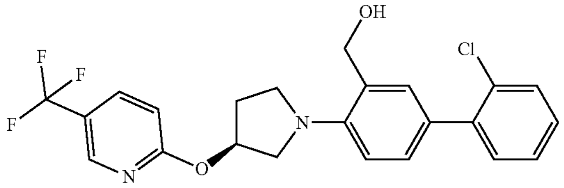 [SMILES: OCc1cc(-c2ccccc2Cl)ccc1N1CC[C@H](Oc2ccc(C(F)(F)F)cn2)C1] | B | ND |
| 1-133. | 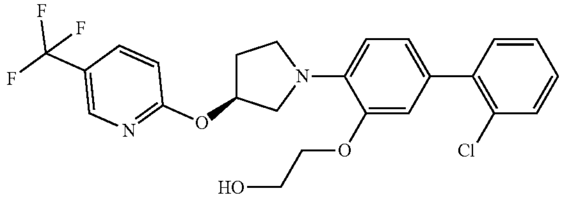 [SMILES: OCCOc1cc(-c2ccccc2Cl)ccc1N1CC[C@H](Oc2ccc(C(F)(F)F)cn2)C1] | D | ND |
| 1-134. | 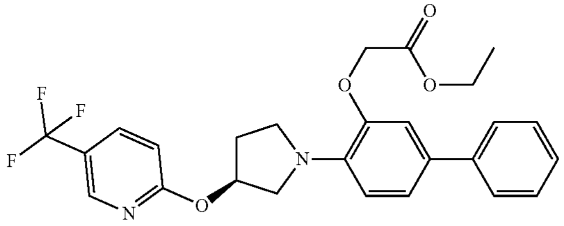 [SMILES: CCOC(=O)COc1cc(-c2ccccc2)ccc1N1CC[C@H](Oc2ccc(C(F)(F)F)cn2)C1] | D | D |
| 1-135. | 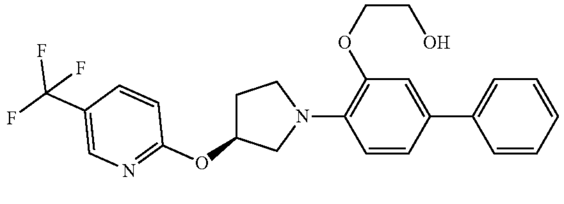 [SMILES: OCCOc1cc(-c2ccccc2)ccc1N1CC[C@H](Oc2ccc(C(F)(F)F)cn2)C1] | C | ND |

TABLE 1-continued
| Compound ID | Structure | hTRPV3 Patch P1 Inwd (nM) | hTRPV3 Patch P2 Inwd (nM) |
|---|---|---|---|
| Data from Patch Clamp Experiments of selected compounds | | | |
| 1-136. | 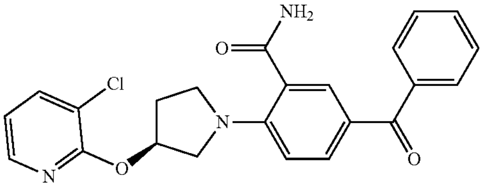 [SMILES: NC(=O)c1cc(C(=O)c2ccccc2)ccc1N1CC[C@H](Oc2ncccc2Cl)C1] | D | D |
| 1-137. | 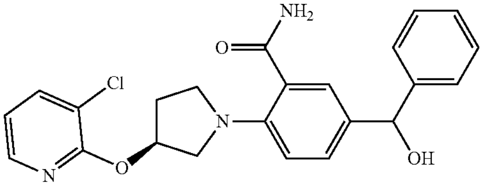 [SMILES: NC(=O)c1cc(C(O)c2ccccc2)ccc1N1CC[C@H](Oc2ncccc2Cl)C1] | D | ND |
| 1-138. | 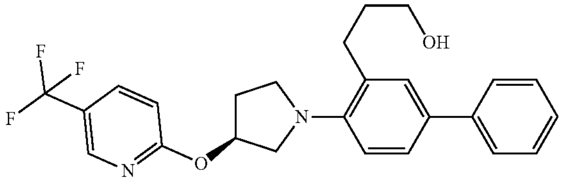 [SMILES: OCCCc1cc(-c2ccccc2)ccc1N1CC[C@H](Oc2ccc(C(F)(F)F)cn2)C1] | C | ND |
| 1-139. | 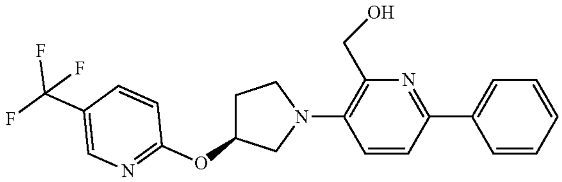 [SMILES: OCc1nc(-c2ccccc2)ccc1N1CC[C@H](Oc2ccc(C(F)(F)F)cn2)C1] | B | ND |
| 1-140. | 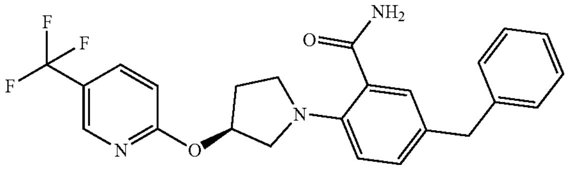 [SMILES: NC(=O)c1cc(Cc2ccccc2)ccc1N1CC[C@H](Oc2ccc(C(F)(F)F)cn2)C1] | C | ND |
| 1-141. | 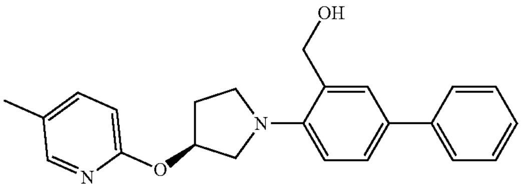 [SMILES: Cc1ccc(O[C@H]2CCN(c3ccc(-c4ccccc4)cc3CO)C2)nc1] | C | ND |
| 1-142. | 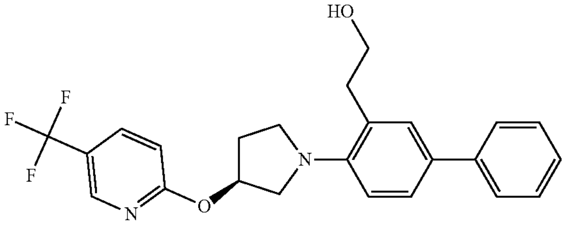 [SMILES: OCCc1cc(-c2ccccc2)ccc1N1CC[C@H](Oc2ccc(C(F)(F)F)cn2)C1] | C | ND |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-143. | 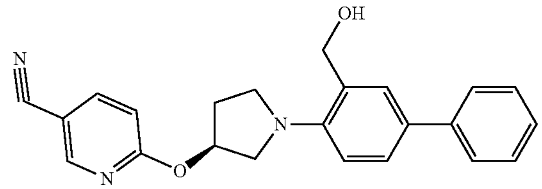 [SMILES: N#Cc1ccc(O[C@H]2CCN(c3ccc(-c4ccccc4)cc3CO)C2)nc1] | C | ND |
| 1-144. | 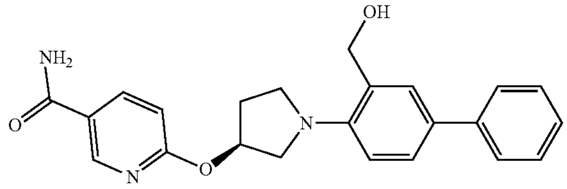 [SMILES: NC(=O)c1ccc(O[C@H]2CCN(c3ccc(-c4ccccc4)cc3CO)C2)nc1] | D | D |
| 1-145. | 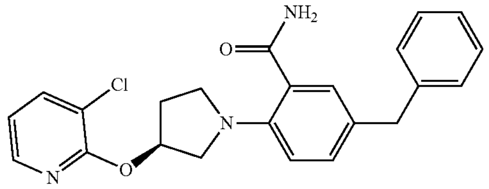 [SMILES: NC(=O)c1cc(Cc2ccccc2)ccc1N1CC[C@H](Oc2ncccc2Cl)C1] | D | C |
| 1-146. | 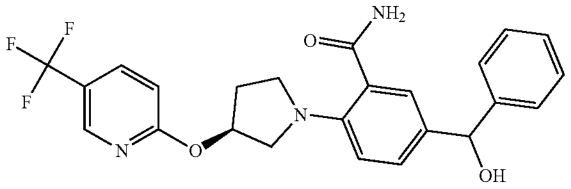 [SMILES: NC(=O)c1cc(C(O)c2ccccc2)ccc1N1CC[C@H](Oc2ccc(C(F)(F)F)cn2)C1] | C | ND |
| 1-147. | 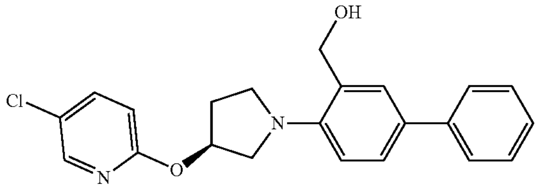 [SMILES: OCc1cc(-c2ccccc2)ccc1N1CC[C@H](Oc2ccc(Cl)cn2)C1] | C | ND |
| 1-148. | 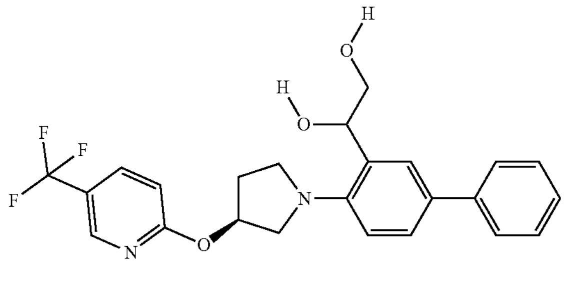 [SMILES: OCC(O)c1cc(-c2ccccc2)ccc1N1CC[C@H](Oc2ccc(C(F)(F)F)cn2)C1] | C | C |
| 1-149. | 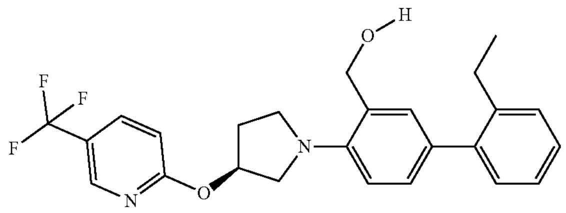 [SMILES: CCc1ccccc1-c1ccc(N2CC[C@H](Oc3ccc(C(F)(F)F)cn3)C2)c(CO)c1] | B | A |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-150. | 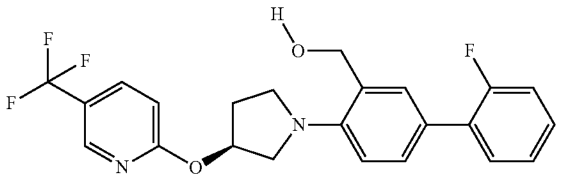 [SMILES: OCc1cc(-c2ccccc2F)ccc1N1CC[C@H](Oc2ccc(C(F)(F)F)cn2)C1] | B | B |
| 1-151. | 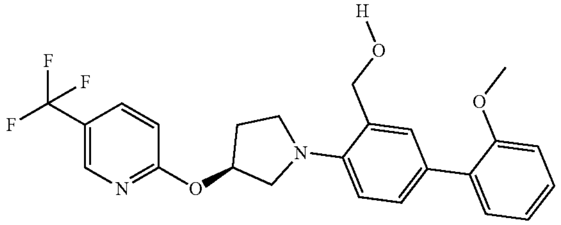 [SMILES: COc1ccccc1-c1ccc(N2CC[C@H](Oc3ccc(C(F)(F)F)cn3)C2)c(CO)c1] | C | ND |
| 1-152. | 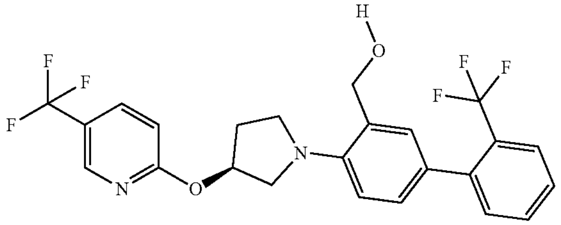 [SMILES: OCc1cc(-c2ccccc2C(F)(F)F)ccc1N1CC[C@H](Oc2ccc(C(F)(F)F)cn2)C1] | B | ND |
| 1-153. | 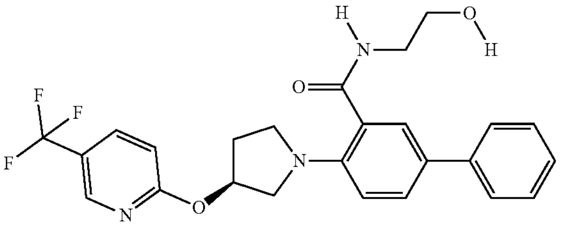 [SMILES: O=C(NCCO)c1cc(-c2ccccc2)ccc1N1CC[C@H](Oc2ccc(C(F)(F)F)cn2)C1] | D | ND |
| 1-154. | 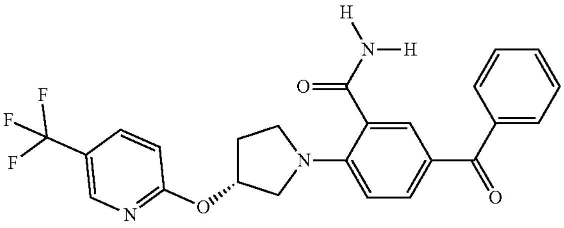 [SMILES: NC(=O)c1cc(C(=O)c2ccccc2)ccc1N1CC[C@@H](Oc2ccc(C(F)(F)F)cn2)C1] | D | ND |
| 1-155. | 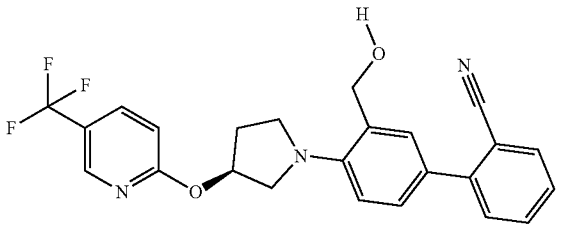 [SMILES: N#Cc1ccccc1-c1ccc(N2CC[C@H](Oc3ccc(C(F)(F)F)cn3)C2)c(CO)c1] | C | ND |

TABLE 1-continued
Data from Patch Clamp Experiments of selected compounds
| Compound ID | Structure | hTRPV3 Patch P1 Inwd (nM) | hTRPV3 Patch P2 Inwd (nM) |
|---|---|---|---|
| 1-156. | 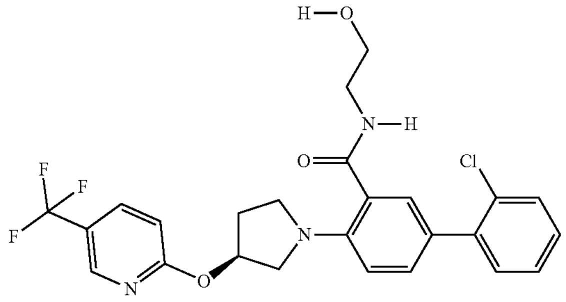 [SMILES: O=C(NCCO)c1cc(-c2ccccc2Cl)ccc1N1CC[C@H](Oc2ccc(C(F)(F)F)cn2)C1] | D | ND |
| 1-157. | 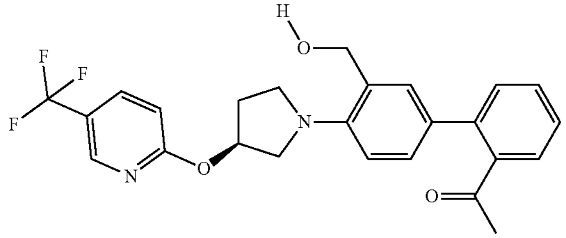 [SMILES: CC(=O)c1ccccc1-c1ccc(N2CC[C@H](Oc3ccc(C(F)(F)F)cn3)C2)c(CO)c1] | C | ND |
| 1-158. | 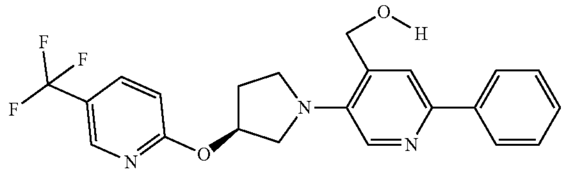 [SMILES: OCc1cc(-c2ccccc2)ncc1N1CC[C@H](Oc2ccc(C(F)(F)F)cn2)C1] | C | C |
| 1-159. | 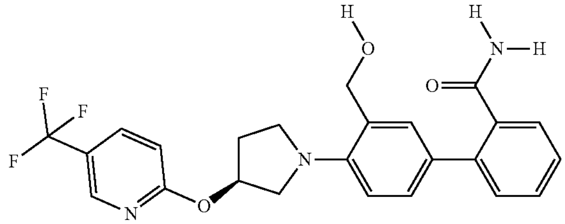 [SMILES: NC(=O)c1ccccc1-c1ccc(N2CC[C@H](Oc3ccc(C(F)(F)F)cn3)C2)c(CO)c1] | D | D |
| 1-160. | 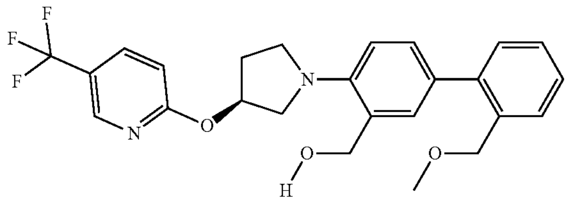 [SMILES: COCc1ccccc1-c1ccc(N2CC[C@H](Oc3ccc(C(F)(F)F)cn3)C2)c(CO)c1] | B | C |
| 1-161. | 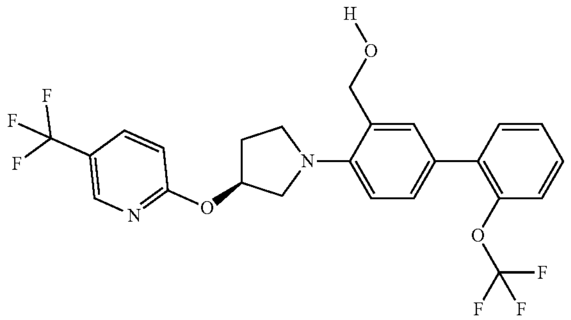 [SMILES: OCc1cc(-c2ccccc2OC(F)(F)F)ccc1N1CC[C@H](Oc2ccc(C(F)(F)F)cn2)C1] | B | ND |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-162. | 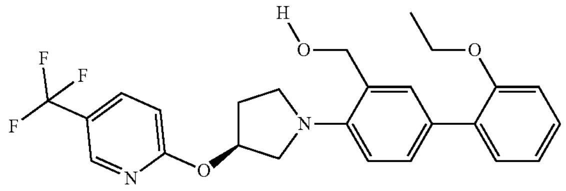 [SMILES: CCOc1ccccc1-c1ccc(N2CC[C@H](Oc3ccc(C(F)(F)F)cn3)C2)c(CO)c1] | B | ND |
| 1-163. | 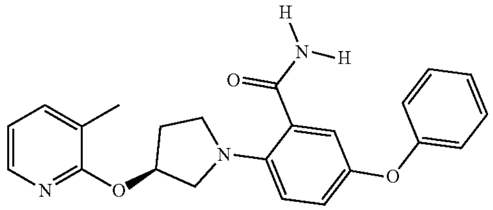 [SMILES: Cc1cccnc1O[C@H]1CCN(c2ccc(Oc3ccccc3)cc2C(N)=O)C1] | D | ND |
| 1-164. | 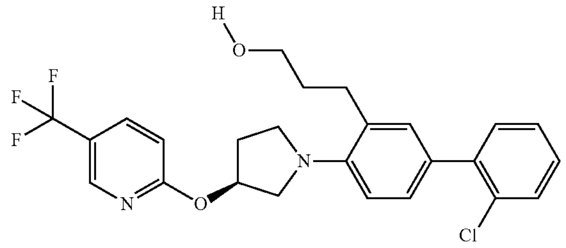 [SMILES: OCCCc1cc(-c2ccccc2Cl)ccc1N1CC[C@H](Oc2ccc(C(F)(F)F)cn2)C1] | C | ND |
| 1-165. | 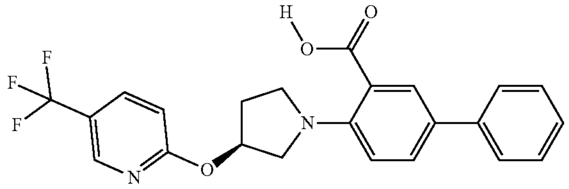 [SMILES: O=C(O)c1cc(-c2ccccc2)ccc1N1CC[C@H](Oc2ccc(C(F)(F)F)cn2)C1] | D | ND |
| 1-166. | 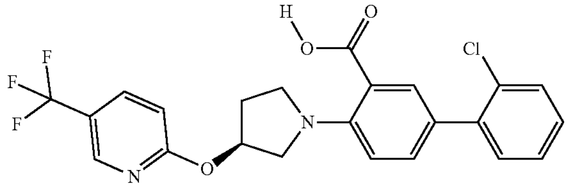 [SMILES: O=C(O)c1cc(-c2ccccc2Cl)ccc1N1CC[C@H](Oc2ccc(C(F)(F)F)cn2)C1] | D | D |
| 1-167. | 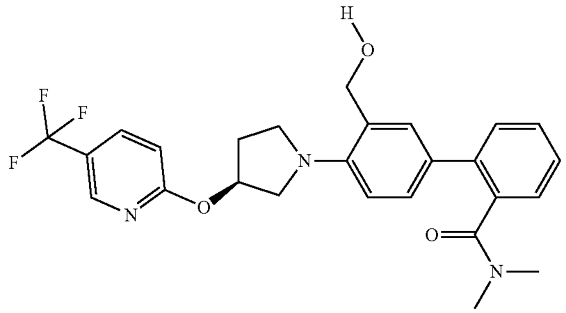 [SMILES: CN(C)C(=O)c1ccccc1-c1ccc(N2CC[C@H](Oc3ccc(C(F)(F)F)cn3)C2)c(CO)c1] | D | D |

TABLE 1-continued
| Compound ID | Structure | hTRPV3 Patch P1 Inwd (nM) | hTRPV3 Patch P2 Inwd (nM) |
|---|---|---|---|
| Data from Patch Clamp Experiments of selected compounds | | | |
| 1-168. | 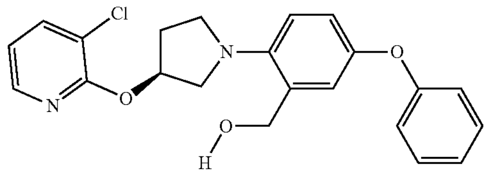 [SMILES: OCc1cc(Oc2ccccc2)ccc1N1CC[C@H](Oc2ncccc2Cl)C1] | B | B |
| 1-169. | 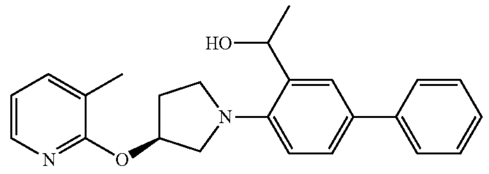 [SMILES: Cc1cccnc1O[C@H]1CCN(c2ccc(-c3ccccc3)cc2C(C)O)C1] | C | C |
| 1-170. | 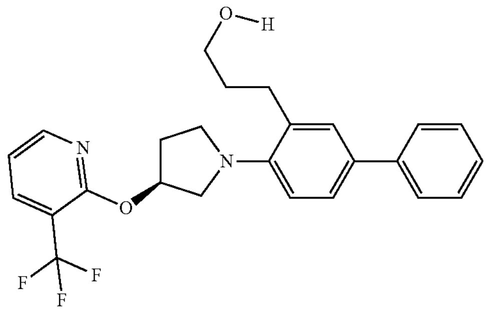 [SMILES: OCCCc1cc(-c2ccccc2)ccc1N1CC[C@H](Oc2ncccc2C(F)(F)F)C1] | ND | C |
| 1-171. | 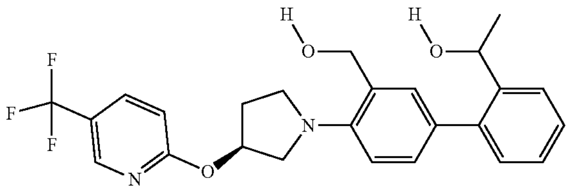 [SMILES: CC(O)c1ccccc1-c1ccc(N2CC[C@H](Oc3ccc(C(F)(F)F)cn3)C2)c(CO)c1] | C | C |
| 1-172. | 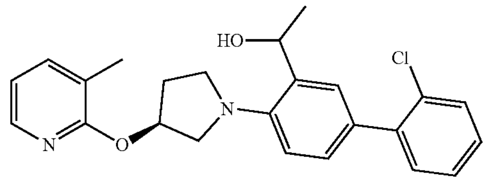 [SMILES: Cc1cccnc1O[C@H]1CCN(c2ccc(-c3ccccc3Cl)cc2C(C)O)C1] | C | ND |
| 1-173. | 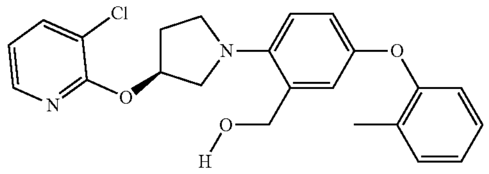 [SMILES: Cc1ccccc1Oc1ccc(N2CC[C@H](Oc3ncccc3Cl)C2)c(CO)c1] | B | B |
| 1-174. | 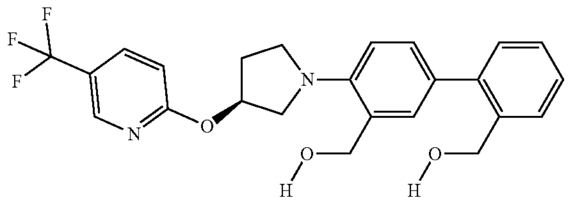 [SMILES: OCc1ccccc1-c1ccc(N2CC[C@H](Oc3ccc(C(F)(F)F)cn3)C2)c(CO)c1] | C | D |

TABLE 1-continued
Data from Patch Clamp Experiments of selected compounds
| Compound ID | Structure | hTRPV3 Patch P1 Inwd (nM) | hTRPV3 Patch P2 Inwd (nM) |
|---|---|---|---|
| 1-175. | 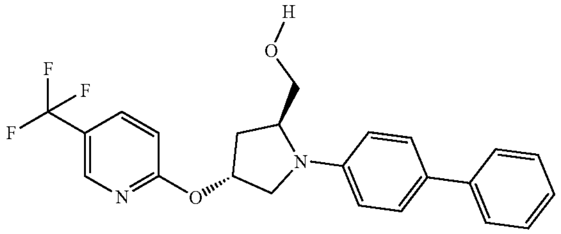 [SMILES: OC[C@@H]1C[C@@H](Oc2ccc(C(F)(F)F)cn2)CN1c1ccc(-c2ccccc2)cc1] | D | D |
| 1-176. | 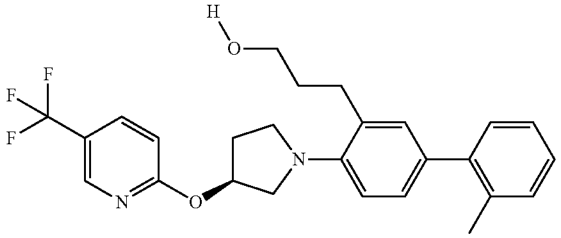 [SMILES: Cc1ccccc1-c1ccc(N2CC[C@H](Oc3ccc(C(F)(F)F)cn3)C2)c(CCCO)c1] | D | D |
| 1-177. | 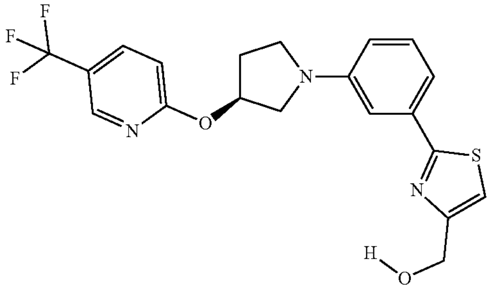 [SMILES: OCc1csc(-c2cccc(N3CC[C@H](Oc4ccc(C(F)(F)F)cn4)C3)c2)n1] | D | ND |
| 1-178. | 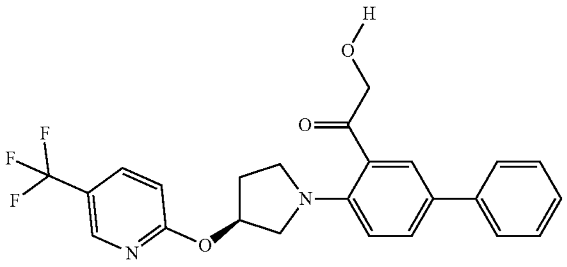 [SMILES: O=C(CO)c1cc(-c2ccccc2)ccc1N1CC[C@H](Oc2ccc(C(F)(F)F)cn2)C1] | ND | C |
| 1-179. | 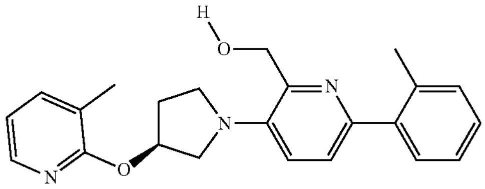 [SMILES: Cc1ccccc1-c1ccc(N2CC[C@H](Oc3ncccc3C)C2)c(CO)n1] | C | C |

TABLE 1-continued
Data from Patch Clamp Experiments of selected compounds
| Compound ID | Structure | hTRPV3 Patch P1 Inwd (nM) | hTRPV3 Patch P2 Inwd (nM) |
|---|---|---|---|
| 1-180. | 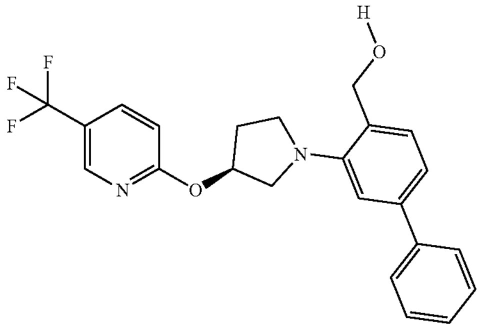 [SMILES: OCc1ccc(-c2ccccc2)cc1N1CC[C@H](Oc2ccc(C(F)(F)F)cn2)C1] | D | D |
| 1-181. | 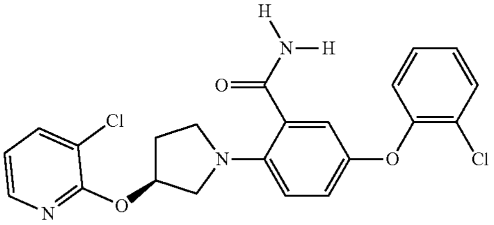 [SMILES: NC(=O)c1cc(Oc2ccccc2Cl)ccc1N1CC[C@H](Oc2ncccc2Cl)C1] | C | C |
| 1-182. | 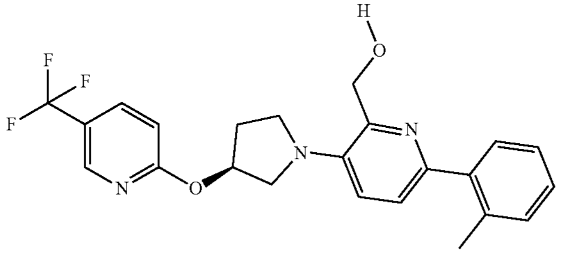 [SMILES: Cc1ccccc1-c1ccc(N2CC[C@H](Oc3ccc(C(F)(F)F)cn3)C2)c(CO)n1] | D | ND |
| 1-183. | 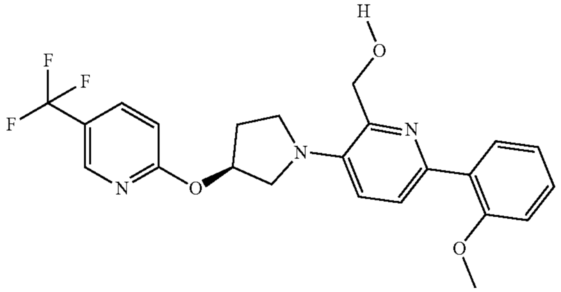 [SMILES: COc1ccccc1-c1ccc(N2CC[C@H](Oc3ccc(C(F)(F)F)cn3)C2)c(CO)n1] | ND | D |
| 1-184. | 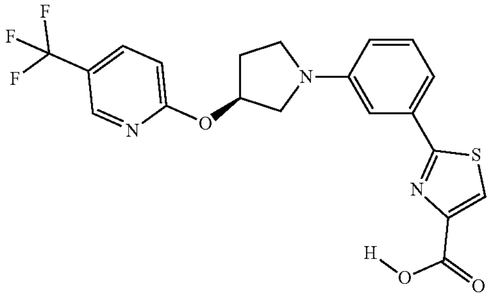 [SMILES: O=C(O)c1csc(-c2cccc(N3CC[C@H](Oc4ccc(C(F)(F)F)cn4)C3)c2)n1] | D | ND |

TABLE 1-continued
Data from Patch Clamp Experiments of selected compounds
| Compound ID | Structure | hTRPV3 Patch P1 Inwd (nM) | hTRPV3 Patch P2 Inwd (nM) |
|---|---|---|---|
| 1-185. | 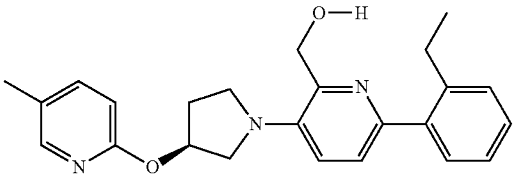 | D | D |
| 1-186. | 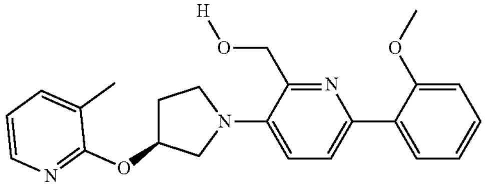 [SMILES: COc1ccccc1-c1ccc(N2CC[C@H](Oc3ncccc3C)C2)c(CO)n1] | D | C |
| 1-187. | 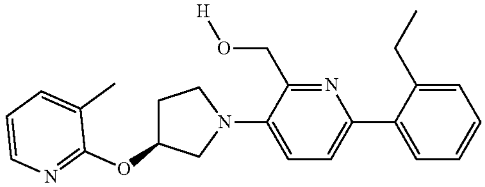 [SMILES: CCc1ccccc1-c1ccc(N2CC[C@H](Oc3ncccc3C)C2)c(CO)n1] | C | D |
| 1-188. | 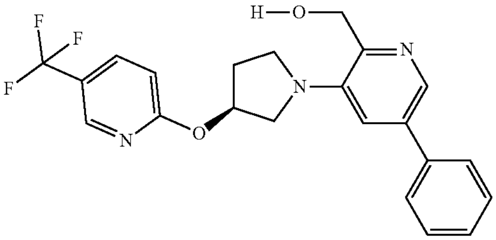 [SMILES: OCc1ncc(-c2ccccc2)cc1N1CC[C@H](Oc2ccc(C(F)(F)F)cn2)C1] | D | ND |
| 1-189. | 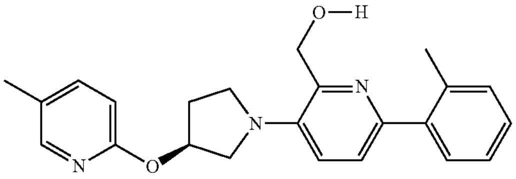 | C | D |
| 1-190. | 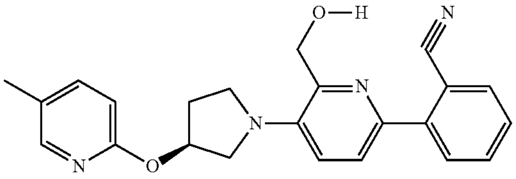 [SMILES: Cc1ccc(O[C@H]2CCN(c3ccc(-c4ccccc4C#N)nc3CO)C2)nc1] | D | D |
| 1-191. | 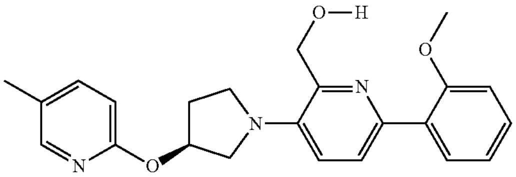 [SMILES: COc1ccccc1-c1ccc(N2CC[C@H](Oc3ccc(C)cn3)C2)c(CO)n1] | D | ND |

TABLE 1-continued
| Compound ID | Structure | hTRPV3 Patch P1 Inwd (nM) | hTRPV3 Patch P2 Inwd (nM) |
|---|---|---|---|
| Data from Patch Clamp Experiments of selected compounds | | | |
| 1-192. | 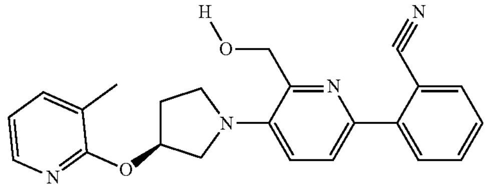 [SMILES: Cc1cccnc1O[C@H]1CCN(c2ccc(-c3ccccc3C#N)nc2CO)C1] | D | D |
| 1-193. | 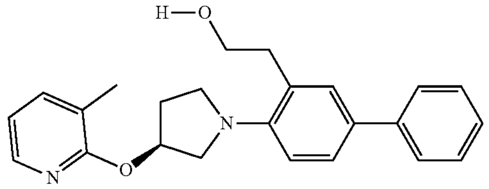 [SMILES: Cc1cccnc1O[C@H]1CCN(c2ccc(-c3ccccc3)cc2CCO)C1] | C | ND |
| 1-194. | 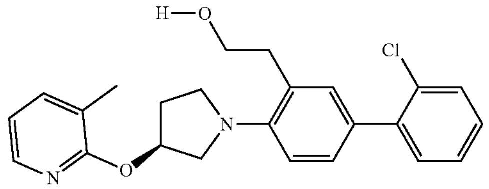 [SMILES: Cc1cccnc1O[C@H]1CCN(c2ccc(-c3ccccc3Cl)cc2CCO)C1] | C | ND |
| 1-195. | 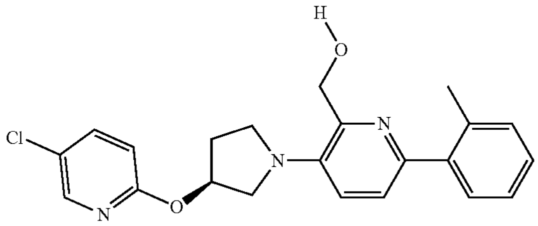 [SMILES: Cc1ccccc1-c1ccc(N2CC[C@H](Oc3ccc(Cl)cn3)C2)c(CO)n1] | C | B |
| 1-196. | 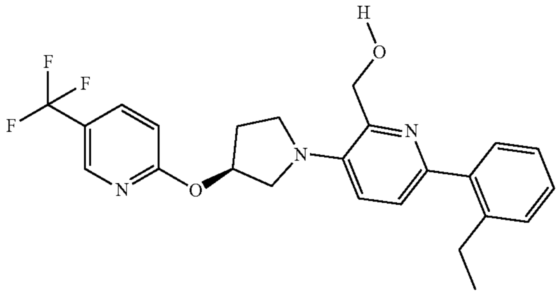 [SMILES: CCc1ccccc1-c1ccc(N2CC[C@H](Oc3ccc(C(F)(F)F)cn3)C2)c(CO)n1] | D | ND |
| 1-197. | 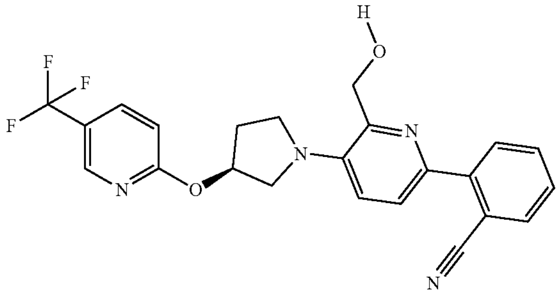 [SMILES: N#Cc1ccccc1-c1ccc(N2CC[C@H](Oc3ccc(C(F)(F)F)cn3)C2)c(CO)n1] | B | ND |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-198. | 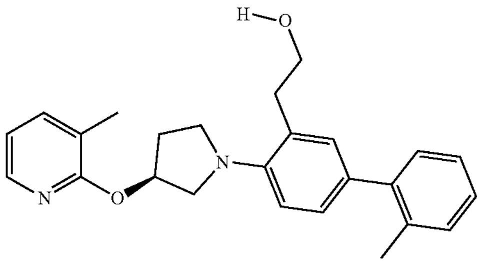 [SMILES: Cc1ccccc1-c1ccc(N2CC[C@H](Oc3ncccc3C)C2)c(CCO)c1] | C | ND |
| 1-199. | 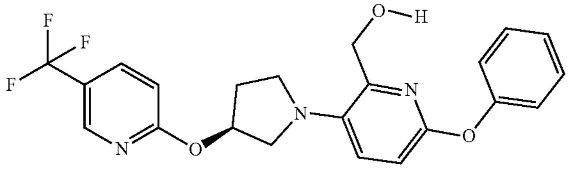 [SMILES: OCc1nc(Oc2ccccc2)ccc1N1CC[C@H](Oc2ccc(C(F)(F)F)cn2)C1] | D | D |
| 1-200. | 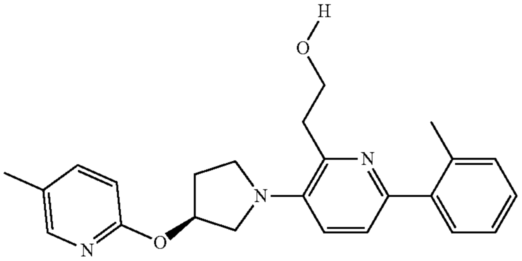 [SMILES: Cc1ccc(O[C@H]2CCN(c3ccc(-c4ccccc4C)nc3CCO)C2)nc1] | C | ND |
| 1-201. | 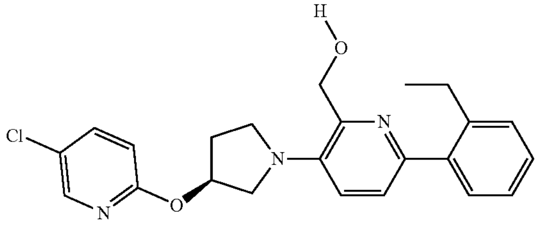 | D | ND |
| 1-202. | 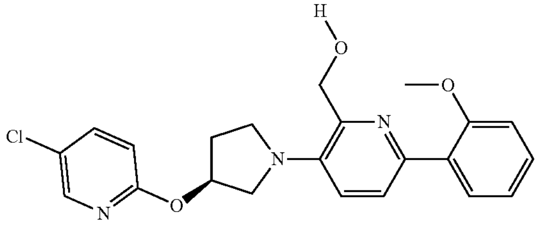 [SMILES: COc1ccccc1-c1ccc(N2CC[C@H](Oc3ccc(Cl)cn3)C2)c(CO)n1] | ND | ND |
| 1-203. | 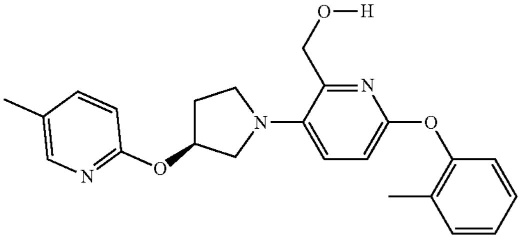 [SMILES: Cc1ccc(O[C@H]2CCN(c3ccc(Oc4ccccc4C)nc3CO)C2)nc1] | D | D |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-204. | 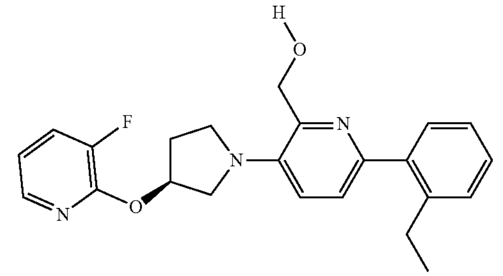 | D | ND |
| 1-205. | 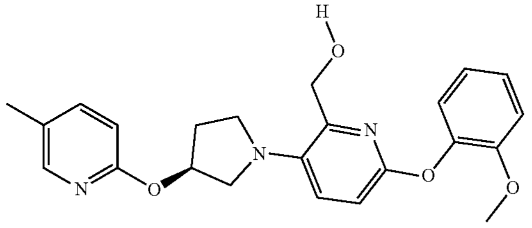 [SMILES: COc1ccccc1Oc1ccc(N2CC[C@H](Oc3ccc(C)cn3)C2)c(CO)n1] | D | D |
| 1-206. | 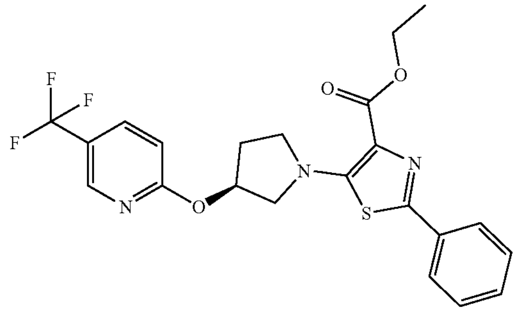 [SMILES: CCOC(=O)c1nc(-c2ccccc2)sc1N1CC[C@H](Oc2ccc(C(F)(F)F)cn2)C1] | D | ND |
| 1-207. | 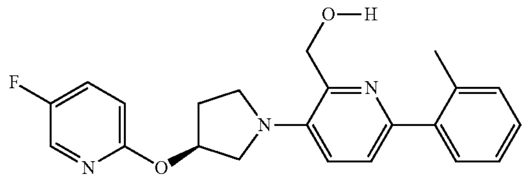 [SMILES: Cc1ccccc1-c1ccc(N2CC[C@H](Oc3ccc(F)cn3)C2)c(CO)n1] | C | ND |
| 1-208. | 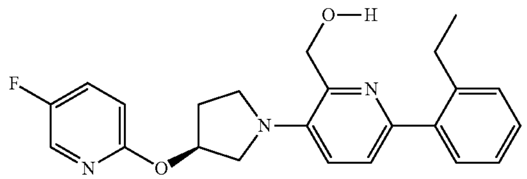 [SMILES: CCc1ccccc1-c1ccc(N2CC[C@H](Oc3ccc(F)cn3)C2)c(CO)n1] | D | C |
| 1-209. | 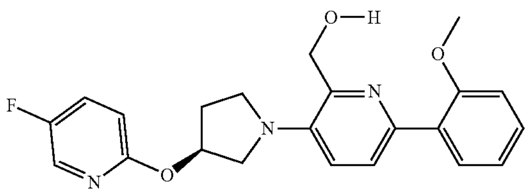 [SMILES: COc1ccccc1-c1ccc(N2CC[C@H](Oc3ccc(F)cn3)C2)c(CO)n1] | D | ND |

TABLE 1-continued
Data from Patch Clamp Experiments of selected compounds
| Compound ID | Structure | hTRPV3 Patch P1 Inwd (nM) | hTRPV3 Patch P2 Inwd (nM) |
|---|---|---|---|
| 1-210. | 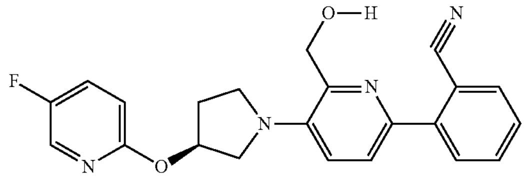 [SMILES: N#Cc1ccccc1-c1ccc(N2CC[C@H](Oc3ccc(F)cn3)C2)c(CO)n1] | C | ND |
| 1-211. | 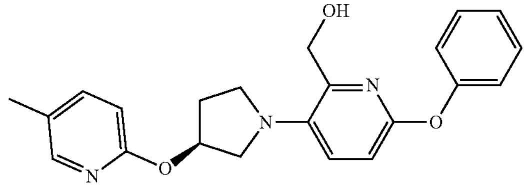 [SMILES: Cc1ccc(O[C@H]2CCN(c3ccc(Oc4ccccc4)nc3CO)C2)nc1] | C | C |
| 1-212. | 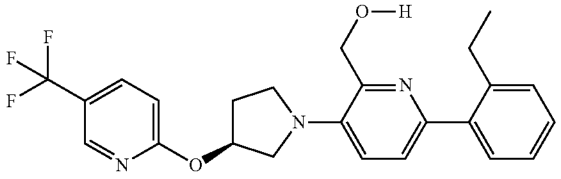 [SMILES: CCc1ccccc1-c1ccc(N2CC[C@H](Oc3ccc(C(F)(F)F)cn3)C2)c(CO)n1] | D | ND |
| 1-213. | 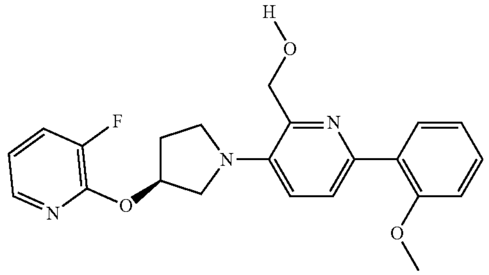 | D | ND |
| 1-214. | 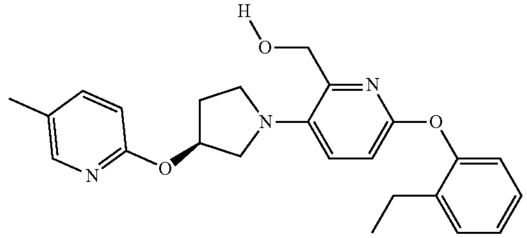 [SMILES: CCc1ccccc1Oc1ccc(N2CC[C@H](Oc3ccc(C)cn3)C2)c(CO)n1] | ND | ND |
| 1-215. | 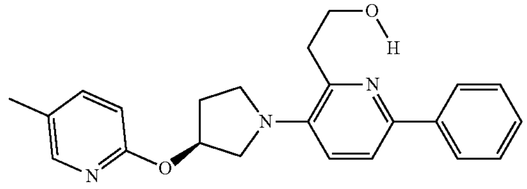 [SMILES: Cc1ccc(O[C@H]2CCN(c3ccc(-c4ccccc4)nc3CCO)C2)nc1] | D | ND |
| 1-216. | 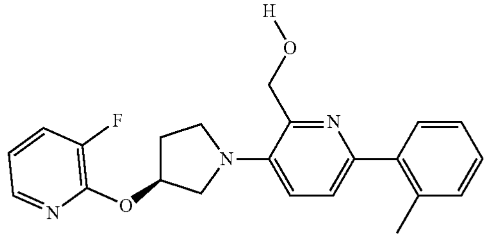 [SMILES: Cc1ccccc1-c1ccc(N2CC[C@H](Oc3ncccc3F)C2)c(CO)n1] | D | ND |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-217. | 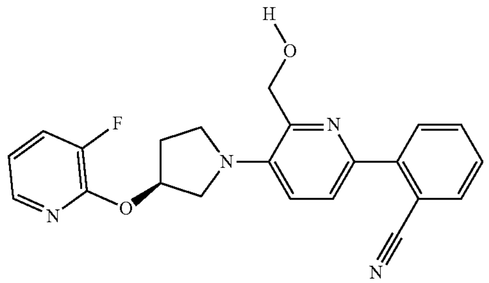 [SMILES: N#Cc1ccccc1-c1ccc(N2CC[C@H](Oc3ncccc3F)C2)c(CO)n1] | D | ND |
| 1-218. | 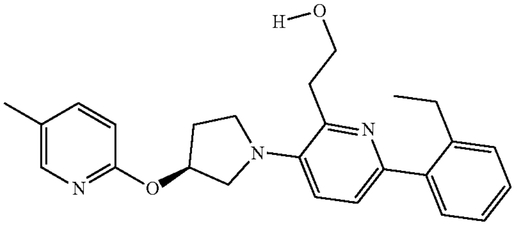 [SMILES: CCc1ccccc1-c1ccc(N2CC[C@H](Oc3ccc(C)cn3)C2)c(CCO)n1] | C | ND |
| 1-219. | 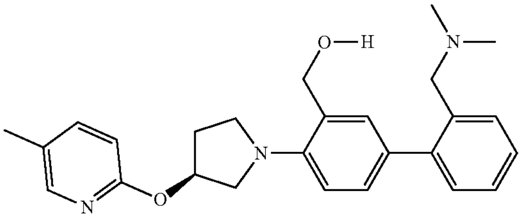 [SMILES: Cc1ccc(O[C@H]2CCN(c3ccc(-c4ccccc4CN(C)C)cc3CO)C2)nc1] | D | ND |
| 1-220. | 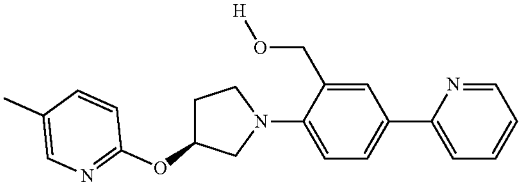 [SMILES: Cc1ccc(O[C@H]2CCN(c3ccc(-c4ccccn4)cc3CO)C2)nc1] | D | ND |
| 1-221. | 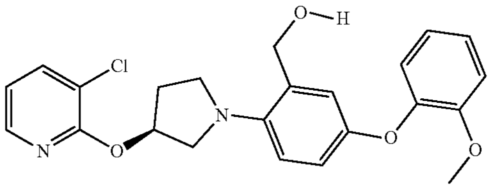 [SMILES: COc1ccccc1Oc1ccc(N2CC[C@H](Oc3ncccc3Cl)C2)c(CO)c1] | C | ND |
| 1-222. | 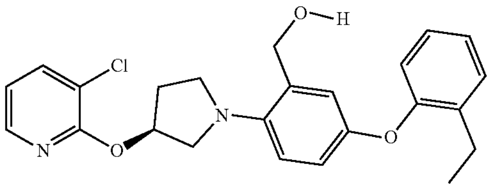 [SMILES: CCc1ccccc1Oc1ccc(N2CC[C@H](Oc3ncccc3Cl)C2)c(CO)c1] | A | ND |
| 1-223. | 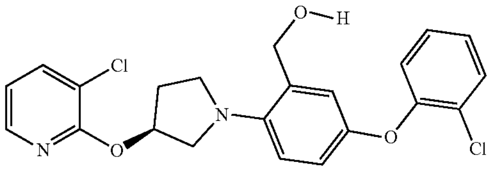 [SMILES: OCc1cc(Oc2ccccc2Cl)ccc1N1CC[C@H](Oc2ncccc2Cl)C1] | B | B |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-224. | 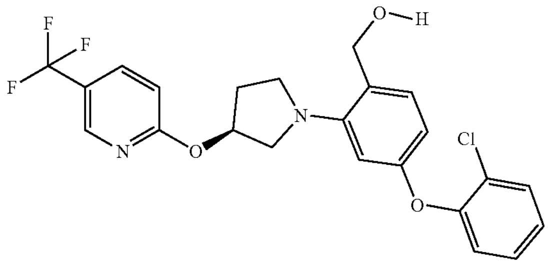 [SMILES: OCc1ccc(Oc2ccccc2Cl)cc1N1CC[C@H](Oc2ccc(C(F)(F)F)cn2)C1] | C | ND |
| 1-225. | 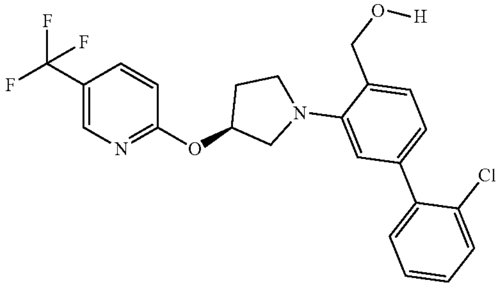 [SMILES: OCc1ccc(-c2ccccc2Cl)cc1N1CC[C@H](Oc2ccc(C(F)(F)F)cn2)C1] | C | ND |
| 1-226. | 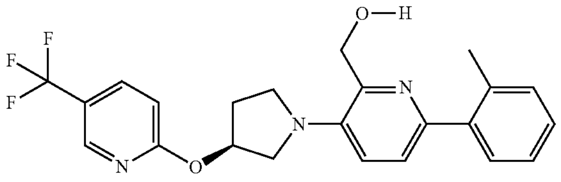 [SMILES: Cc1ccccc1-c1ccc(N2CC[C@H](Oc3ccc(C(F)(F)F)cn3)C2)c(CO)n1] | C | ND |
| 1-227. | 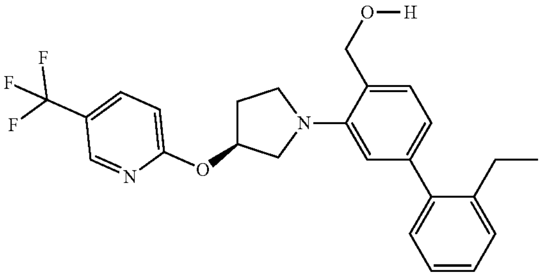 [SMILES: CCc1ccccc1-c1ccc(CO)c(N2CC[C@H](Oc3ccc(C(F)(F)F)cn3)C2)c1] | C | ND |
| 1-228. | 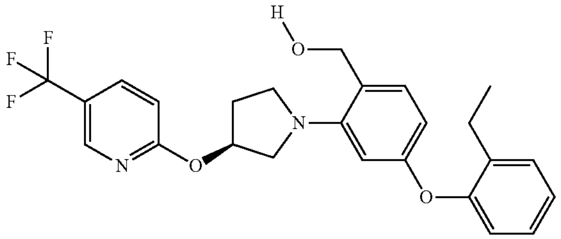 [SMILES: CCc1ccccc1Oc1ccc(CO)c(N2CC[C@H](Oc3ccc(C(F)(F)F)cn3)C2)c1] | B | ND |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-229. | 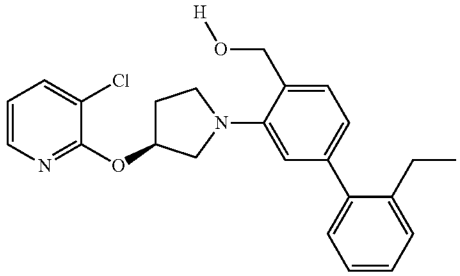 [SMILES: CCc1ccccc1-c1ccc(CO)c(N2CC[C@H](Oc3ncccc3Cl)C2)c1] | B | ND |
| 1-230. | 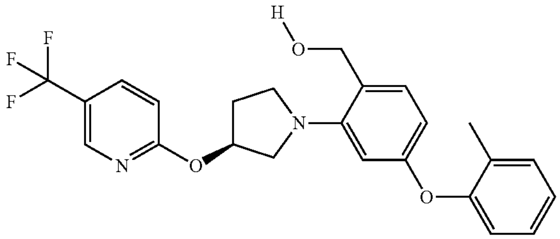 [SMILES: Cc1ccccc1Oc1ccc(CO)c(N2CC[C@H](Oc3ccc(C(F)(F)F)cn3)C2)c1] | C | ND |
| 1-231. | 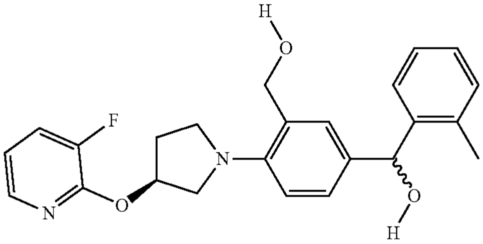 [SMILES: Cc1ccccc1C(O)c1ccc(N2CC[C@H](Oc3ncccc3F)C2)c(CO)c1] | C | ND |
| 1-232. | 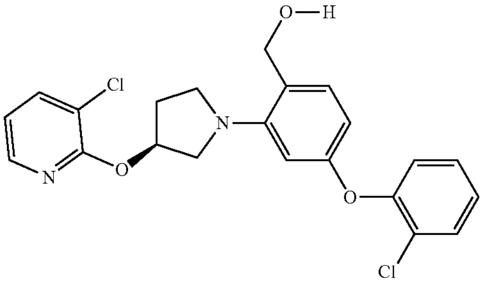 [SMILES: OCc1ccc(Oc2ccccc2Cl)cc1N1CC[C@H](Oc2ncccc2Cl)C1] | B | ND |
| 1-233. | 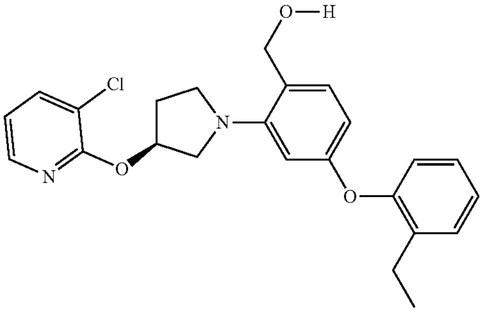 [SMILES: CCc1ccccc1Oc1ccc(CO)c(N2CC[C@H](Oc3ncccc3Cl)C2)c1] | B | ND |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-234. | 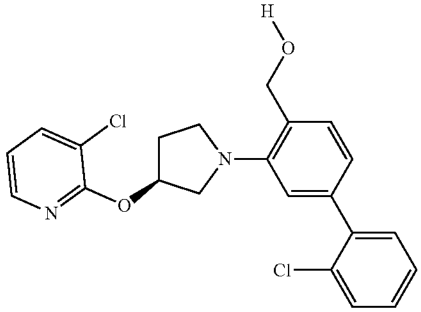 [SMILES: OCc1ccc(-c2ccccc2Cl)cc1N1CC[C@H](Oc2ncccc2Cl)C1] | C | ND |
| 1-235. | 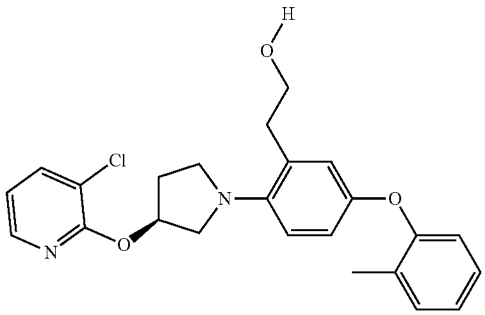 [SMILES: Cc1ccccc1Oc1ccc(N2CC[C@H](Oc3ncccc3Cl)C2)c(CCO)c1] | B | ND |
| 1-236. | 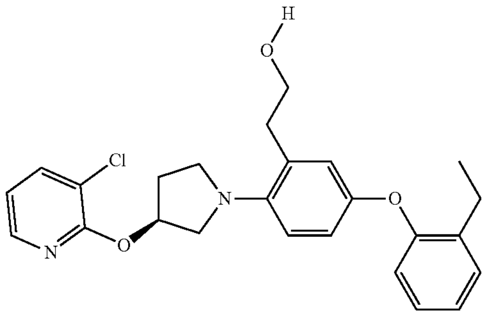 [SMILES: CCc1ccccc1Oc1ccc(N2CC[C@H](Oc3ncccc3Cl)C2)c(CCO)c1] | A | ND |
| 1-237. | 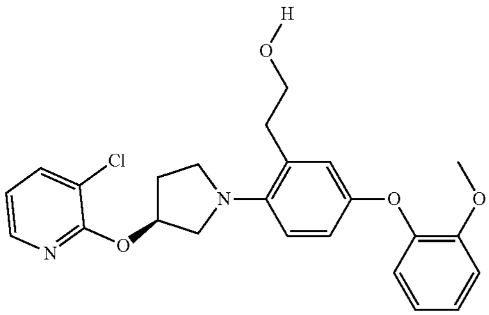 [SMILES: COc1ccccc1Oc1ccc(N2CC[C@H](Oc3ncccc3Cl)C2)c(CCO)c1] | C | ND |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-238. | 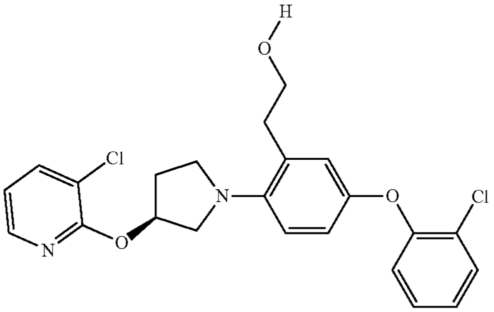 [SMILES: OCCc1cc(Oc2ccccc2Cl)ccc1N1CC[C@H](Oc2ncccc2Cl)C1] | B | ND |
| 1-239. | 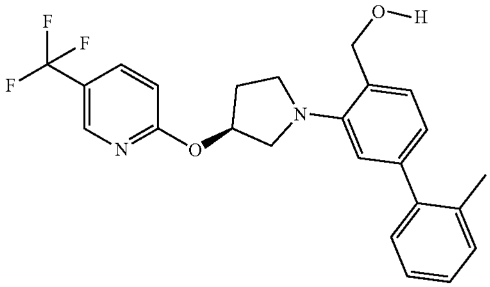 [SMILES: Cc1ccccc1-c1ccc(CO)c(N2CC[C@H](Oc3ccc(C(F)(F)F)cn3)C2)c1] | C | ND |
| 1-240. | 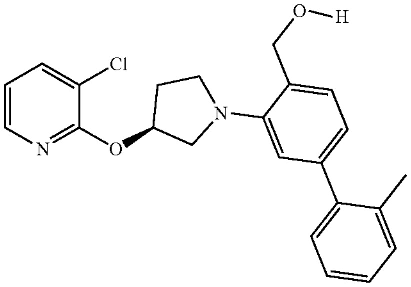 [SMILES: Cc1ccccc1-c1ccc(CO)c(N2CC[C@H](Oc3ncccc3Cl)C2)c1] | C | ND |
| 1-241. | 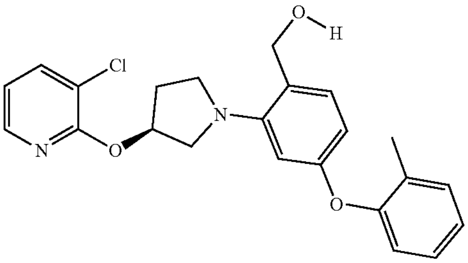 [SMILES: Cc1ccccc1Oc1ccc(CO)c(N2CC[C@H](Oc3ncccc3Cl)C2)c1] | B | ND |
| 1-242. | 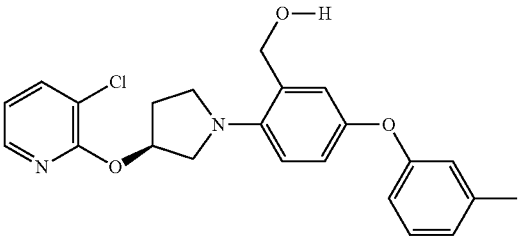 [SMILES: Cc1cccc(Oc2ccc(N3CC[C@H](Oc4ncccc4Cl)C3)c(CO)c2)c1] | B | ND |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-243. | 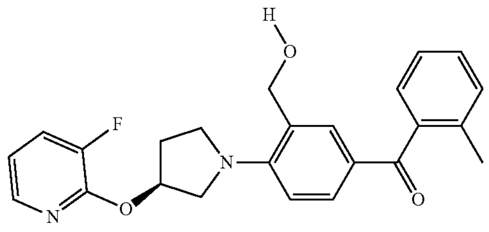 [SMILES: Cc1ccccc1C(=O)c1ccc(N2CC[C@H](Oc3ncccc3F)C2)c(CO)c1] | C | ND |
| 1-244. | 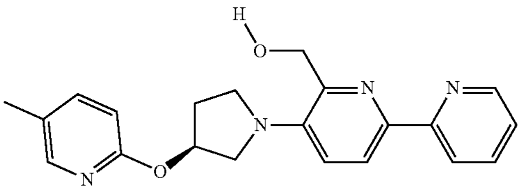 [SMILES: Cc1ccc(O[C@H]2CCN(c3ccc(-c4ccccn4)nc3CO)C2)nc1] | D | ND |
| 1-245. | 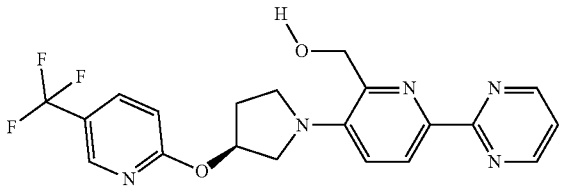 [SMILES: OCc1nc(-c2ncccn2)ccc1N1CC[C@H](Oc2ccc(C(F)(F)F)cn2)C1] | D | ND |
| 1-246. | 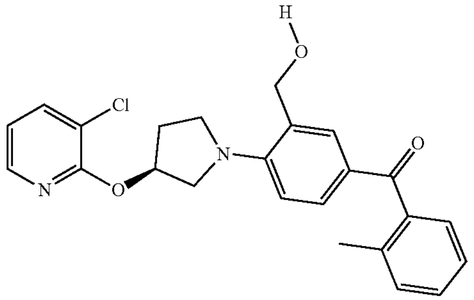 [SMILES: Cc1ccccc1C(=O)c1ccc(N2CC[C@H](Oc3ncccc3Cl)C2)c(CO)c1] | C | C |
| 1-247. | 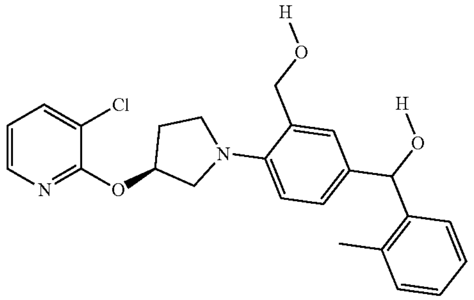 [SMILES: Cc1ccccc1C(O)c1ccc(N2CC[C@H](Oc3ncccc3Cl)C2)c(CO)c1] | C | C |
| 1-248. | 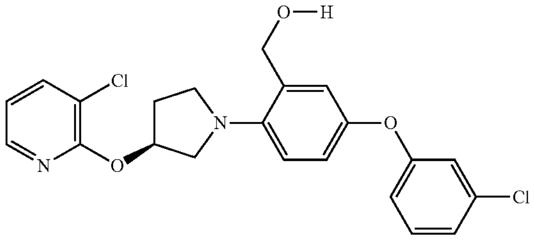 [SMILES: OCc1cc(Oc2cccc(Cl)c2)ccc1N1CC[C@H](Oc2ncccc2Cl)C1] | B | ND |

TABLE 1-continued
Data from Patch Clamp Experiments of selected compounds
| Compound ID | Structure | hTRPV3 Patch P1 Inwd (nM) | hTRPV3 Patch P2 Inwd (nM) |
|---|---|---|---|
| 1-249. | 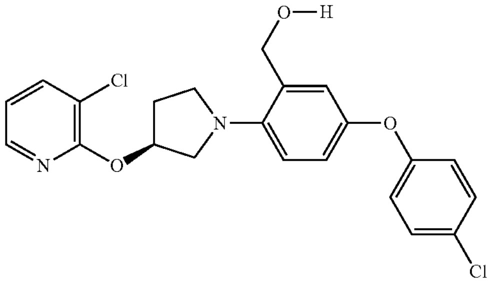 [SMILES: OCc1cc(Oc2ccc(Cl)cc2)ccc1N1CC[C@H](Oc2ncccc2Cl)C1] | B | ND |
| 1-250. | 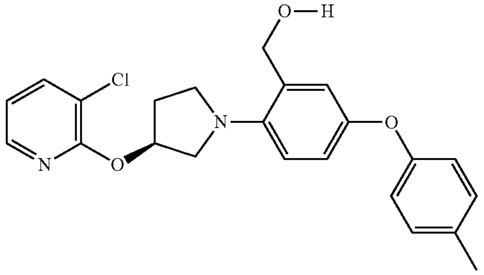 [SMILES: Cc1ccc(Oc2ccc(N3CC[C@H](Oc4ncccc4Cl)C3)c(CO)c2)cc1] | A | ND |
| 1-251. | 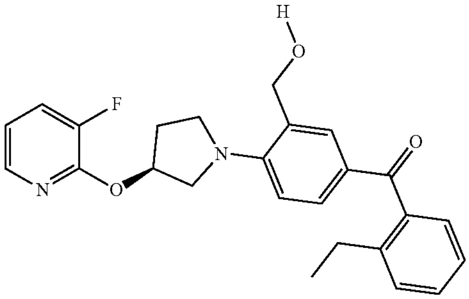 [SMILES: CCc1ccccc1C(=O)c1ccc(N2CC[C@H](Oc3ncccc3F)C2)c(CO)c1] | B | ND |
| 1-252. | 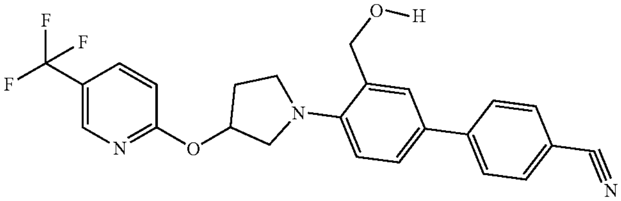 [SMILES: N#Cc1ccc(-c2ccc(N3CCC(Oc4ccc(C(F)(F)F)cn4)C3)c(CO)c2)cc1] | C | ND |
| 1-253. | 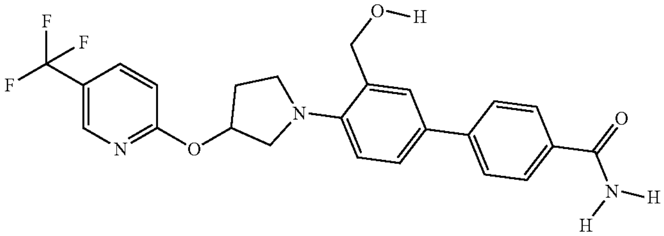 [SMILES: NC(=O)c1ccc(-c2ccc(N3CCC(Oc4ccc(C(F)(F)F)cn4)C3)c(CO)c2)cc1] | D | ND |
| 1-254. | 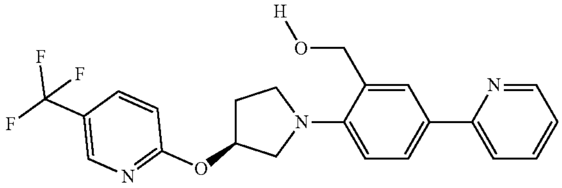 [SMILES: OCc1cc(-c2ccccn2)ccc1N1CC[C@H](Oc2ccc(C(F)(F)F)cn2)C1] | D | ND |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-255. | 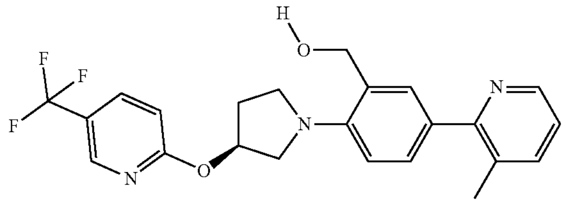 [SMILES: Cc1cccnc1-c1ccc(N2CC[C@H](Oc3ccc(C(F)(F)F)cn3)C2)c(CO)c1] | C | ND |
| 1-256. | 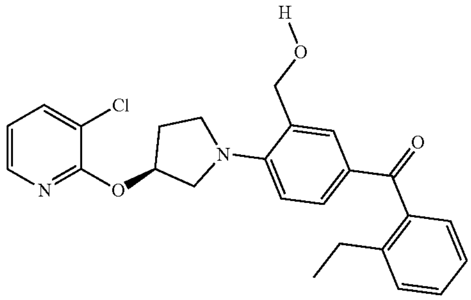 [SMILES: CCc1ccccc1C(=O)c1ccc(N2CC[C@H](Oc3ncccc3Cl)C2)c(CO)c1] | B | ND |
| 1-257. | 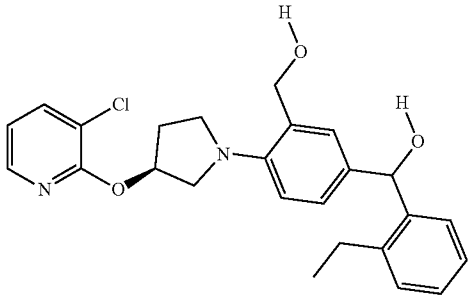 [SMILES: CCc1ccccc1C(O)c1ccc(N2CC[C@H](Oc3ncccc3Cl)C2)c(CO)c1] | C | D |
| 1-258. | 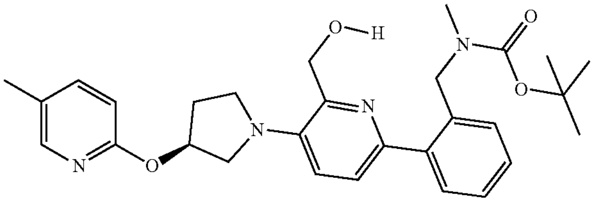 [SMILES: Cc1ccc(O[C@H]2CCN(c3ccc(-c4ccccc4CN(C)C(=O)OC(C)(C)C)nc3CO)C2)nc1] | C | ND |
| 1-259. | 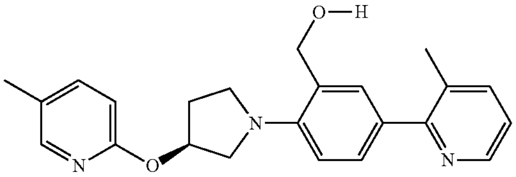 [SMILES: Cc1ccc(O[C@H]2CCN(c3ccc(-c4ncccc4C)cc3CO)C2)nc1] | D | D |
| 1-260. | 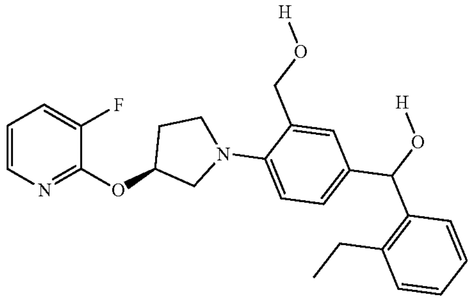 | D | ND |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-261. | 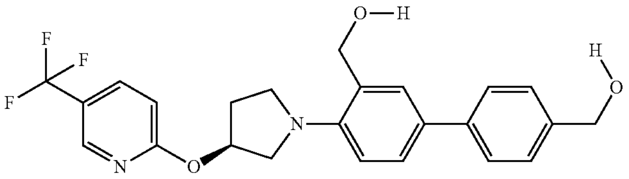 [SMILES: OCc1ccc(-c2ccc(N3CC[C@H](Oc4ccc(C(F)(F)F)cn4)C3)c(CO)c2)cc1] | C | ND |
| 1-262. | 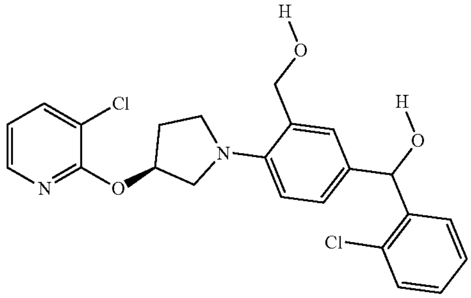 [SMILES: OCc1cc(C(O)c2ccccc2Cl)ccc1N1CC[C@H](Oc2ncccc2Cl)C1] | B | ND |
| 1-263. | 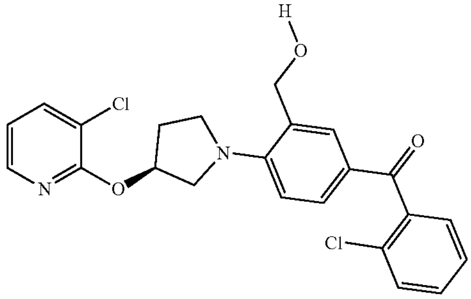 [SMILES: O=C(c1ccc(N2CC[C@H](Oc3ncccc3Cl)C2)c(CO)c1)c1ccccc1Cl] | C | ND |
| 1-264. | 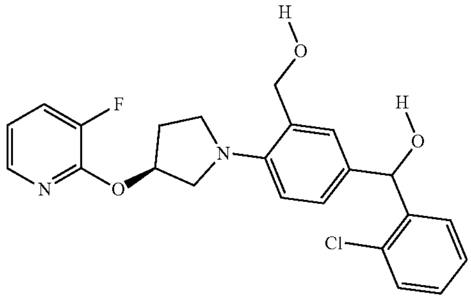 | B | B |
| 1-265. | 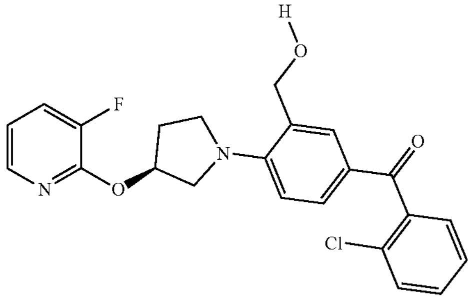 | D | ND |

TABLE 1-continued
Data from Patch Clamp Experiments of selected compounds
| Compound ID | Structure | hTRPV3 Patch P1 Inwd (nM) | hTRPV3 Patch P2 Inwd (nM) |
|---|---|---|---|
| 1-266. | 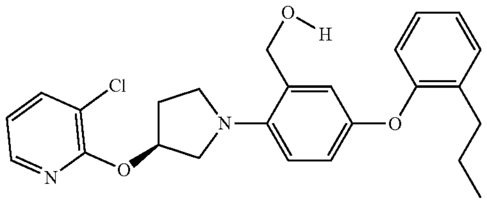 [SMILES: CCCc1ccccc1Oc1ccc(N2CC[C@H](Oc3ncccc3Cl)C2)c(CO)c1] | A | ND |
| 1-267. | 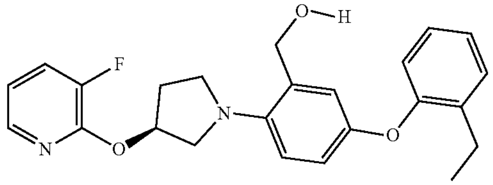 | B | ND |
| 1-268. | 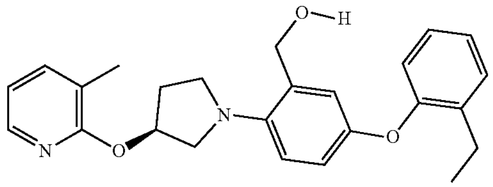 [SMILES: CCc1ccccc1Oc1ccc(N2CC[C@H](Oc3ncccc3C)C2)c(CO)c1] | A | A |
| 1-269. | 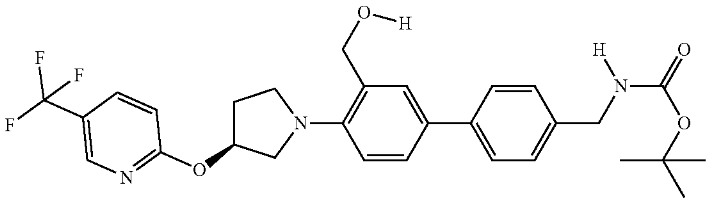 [SMILES: CC(C)(C)OC(=O)NCc1ccc(-c2ccc(N3CC[C@H](Oc4ccc(C(F)(F)F)cn4)C3)c(CO)c2)cc1] | D | ND |
| 1-270. | 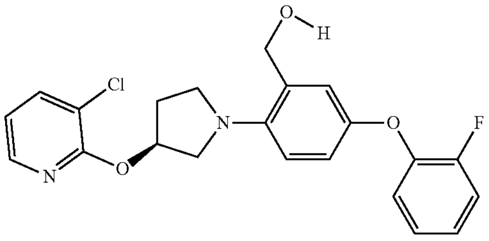 [SMILES: OCc1cc(Oc2ccccc2F)ccc1N1CC[C@H](Oc2ncccc2Cl)C1] | A | A |
| 1-271. | 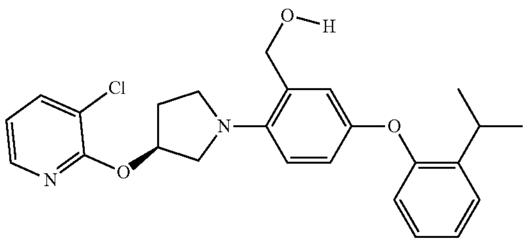 [SMILES: CC(C)c1ccccc1Oc1ccc(N2CC[C@H](Oc3ncccc3Cl)C2)c(CO)c1] | A | ND |

TABLE 1-continued
| Compound ID | Structure | hTRPV3 Patch P1 Inwd (nM) | hTRPV3 Patch P2 Inwd (nM) |
|---|---|---|---|
| Data from Patch Clamp Experiments of selected compounds | | | |
| 1-272. | 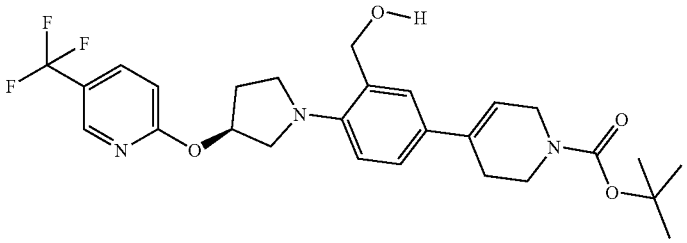 [SMILES: CC(C)(C)OC(=O)N1CC=C(c2ccc(N3CC[C@H](Oc4ccc(C(F)(F)F)cn4)C3)c(CO)c2)CC1] | D | ND |
| 1-273. | 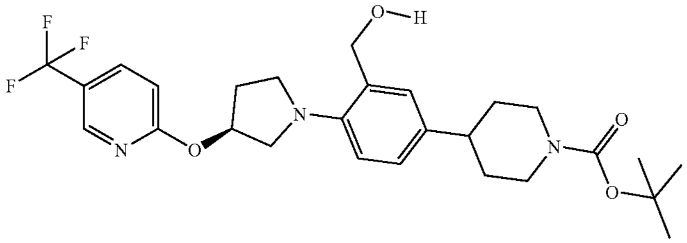 [SMILES: CC(C)(C)OC(=O)N1CCC(c2ccc(N3CC[C@H](Oc4ccc(C(F)(F)F)cn4)C3)c(CO)c2)CC1] | D | ND |
| 1-274. | 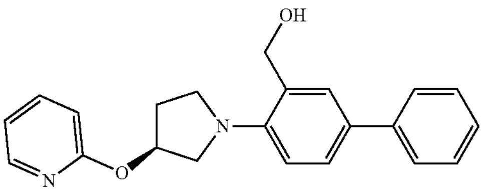 [SMILES: OCc1cc(-c2ccccc2)ccc1N1CC[C@H](Oc2ccccn2)C1] | C | ND |
| 1-275. | 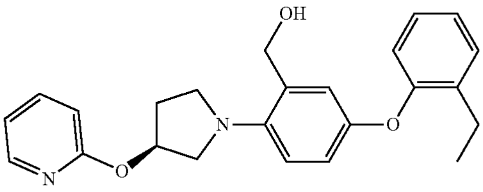 [SMILES: CCc1ccccc1Oc1ccc(N2CC[C@H](Oc3ccccn3)C2)c(CO)c1] | B | ND |
| 1-276. | 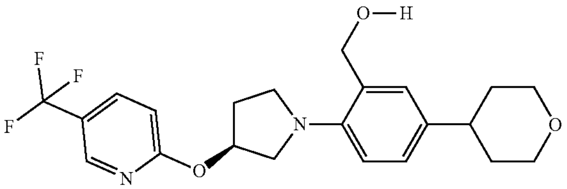 [SMILES: OCc1cc(C2CCOCC2)ccc1N1CC[C@H](Oc2ccc(C(F)(F)F)cn2)C1] | D | ND |
| 1-277. | 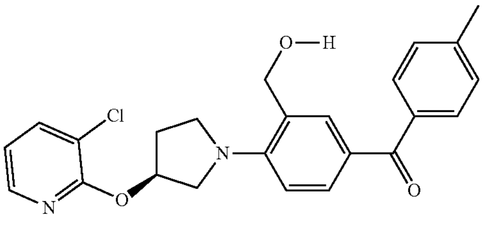 [SMILES: Cc1ccc(C(=O)c2ccc(N3CC[C@H](Oc4ncccc4Cl)C3)c(CO)c2)cc1] | B | ND |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-278. | 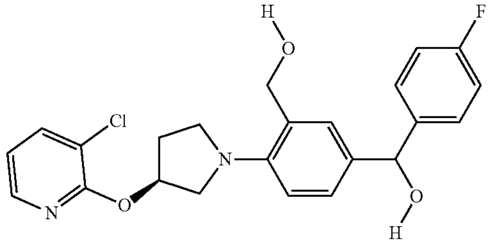 [SMILES: OCc1cc(C(O)c2ccc(F)cc2)ccc1N1CC[C@H](Oc2ncccc2Cl)C1] | C | ND |
| 1-279. | 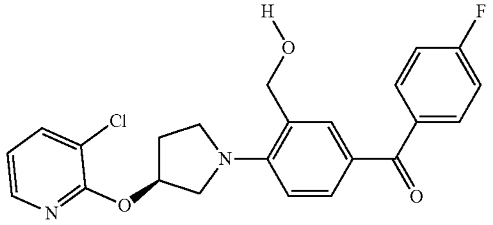 [SMILES: O=C(c1ccc(F)cc1)c1ccc(N2CC[C@H](Oc3ncccc3Cl)C2)c(CO)c1] | B | ND |
| 1-280. | 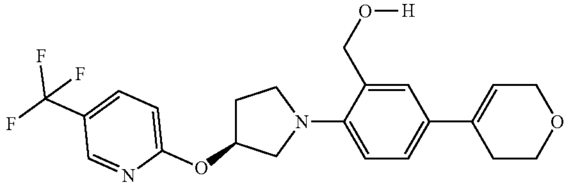 [SMILES: OCc1cc(C2=CCOCC2)ccc1N1CC[C@H](Oc2ccc(C(F)(F)F)cn2)C1] | D | ND |
| 1-281. | 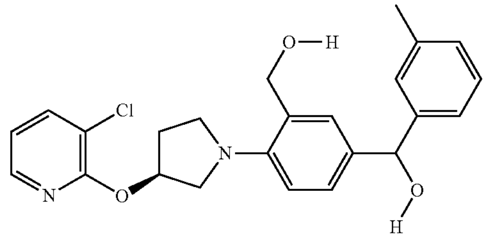 [SMILES: Cc1cccc(C(O)c2ccc(N3CC[C@H](Oc4ncccc4Cl)C3)c(CO)c2)c1] | D | ND |
| 1-282. | 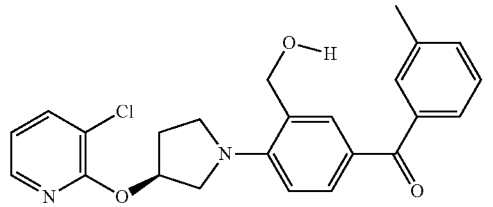 [SMILES: Cc1cccc(C(=O)c2ccc(N3CC[C@H](Oc4ncccc4Cl)C3)c(CO)c2)c1] | B | ND |
| 1-283. | 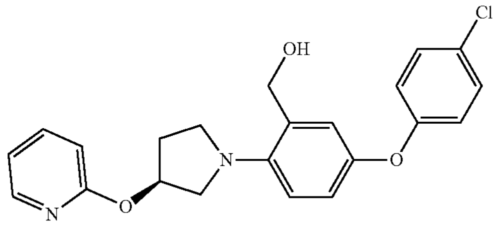 [SMILES: OCc1cc(Oc2ccc(Cl)cc2)ccc1N1CC[C@H](Oc2ccccn2)C1] | C | ND |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-284. | 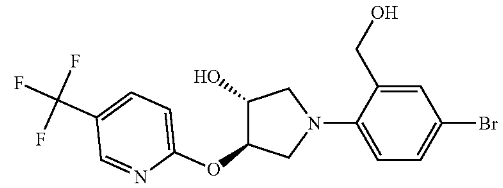 [SMILES: OCc1cc(Br)ccc1N1C[C@@H](O)[C@H](Oc2ccc(C(F)(F)F)cn2)C1] | D | ND |
| 1-285. | 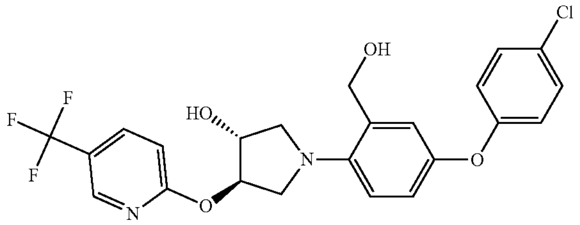 [SMILES: OCc1cc(Oc2ccc(Cl)cc2)ccc1N1C[C@@H](O)[C@H](Oc2ccc(C(F)(F)F)cn2)C1] | D | D |
| 1-286. | 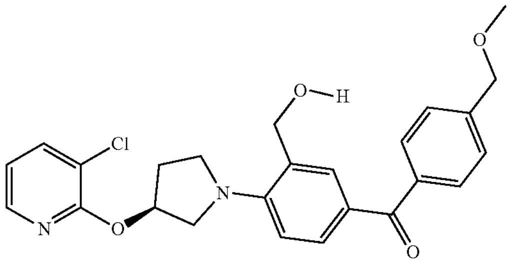 [SMILES: COCc1ccc(C(=O)c2ccc(N3CC[C@H](Oc4ncccc4Cl)C3)c(CO)c2)cc1] | C | ND |
| 1-287. | 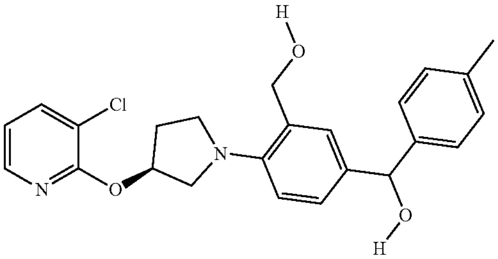 [SMILES: Cc1ccc(C(O)c2ccc(N3CC[C@H](Oc4ncccc4Cl)C3)c(CO)c2)cc1] | C | ND |
| 1-288. | 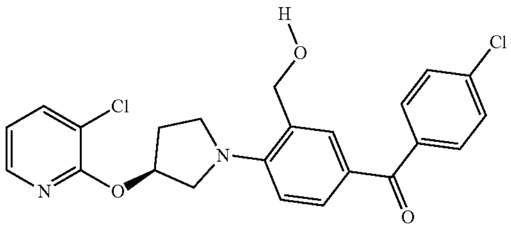 [SMILES: O=C(c1ccc(Cl)cc1)c1ccc(N2CC[C@H](Oc3ncccc3Cl)C2)c(CO)c1] | B | ND |
| 1-289. | 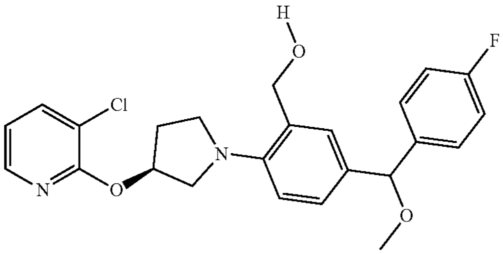 [SMILES: COC(c1ccc(F)cc1)c1ccc(N2CC[C@H](Oc3ncccc3Cl)C2)c(CO)c1] | B | ND |

TABLE 1-continued
Data from Patch Clamp Experiments of selected compounds
| Compound ID | Structure | hTRPV3 Patch P1 Inwd (nM) | hTRPV3 Patch P2 Inwd (nM) |
|---|---|---|---|
| 1-290. | 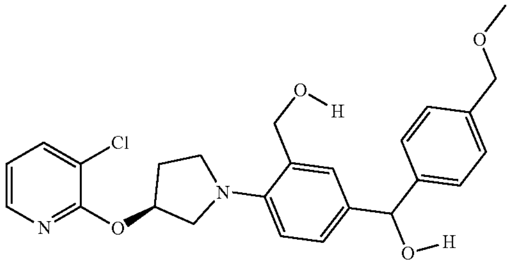 [SMILES: COCc1ccc(C(O)c2ccc(N3CC[C@H](Oc4ncccc4Cl)C3)c(CO)c2)cc1] | D | D |
| 1-291. | 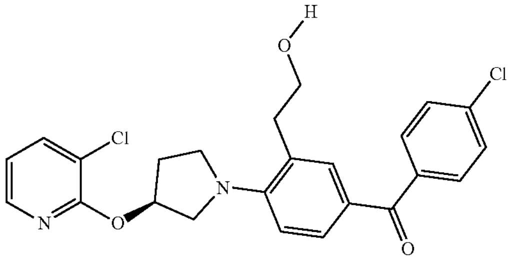 [SMILES: O=C(c1ccc(Cl)cc1)c1ccc(N2CC[C@H](Oc3ncccc3Cl)C2)c(CCO)c1] | C | C |
| 1-292. | 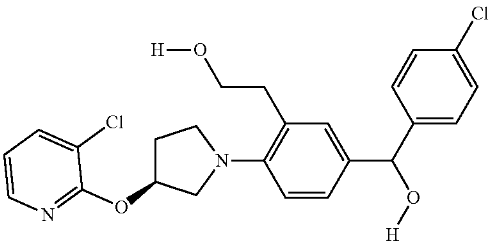 [SMILES: OCCc1cc(C(O)c2ccc(Cl)cc2)ccc1N1CC[C@H](Oc2ncccc2Cl)C1] | D | D |
| 1-293. | 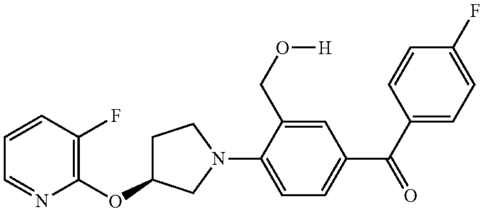 [SMILES: O=C(c1ccc(F)cc1)c1ccc(N2CC[C@H](Oc3ncccc3F)C2)c(CO)c1] | C | C |
| 1-294. | 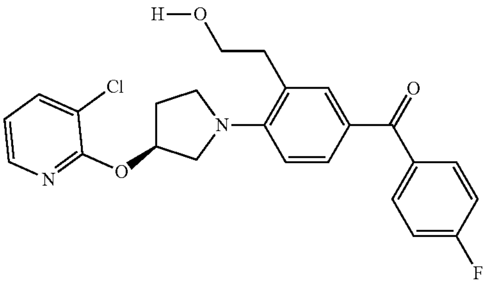 [SMILES: O=C(c1ccc(F)cc1)c1ccc(N2CC[C@H](Oc3ncccc3Cl)C2)c(CCO)c1] | C | C |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-295. | 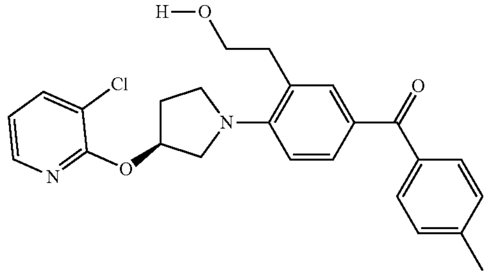 [SMILES: Cc1ccc(C(=O)c2ccc(N3CC[C@H](Oc4ncccc4Cl)C3)c(CCO)c2)cc1] | C | C |
| 1-296. | 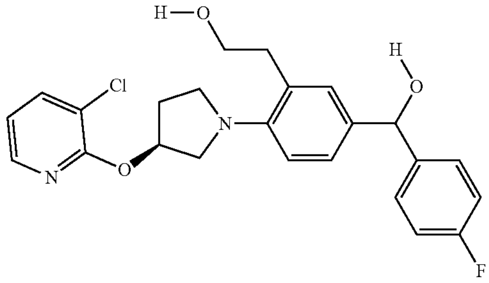 [SMILES: OCCc1cc(C(O)c2ccc(F)cc2)ccc1N1CC[C@H](Oc2ncccc2Cl)C1] | D | D |
| 1-297. | 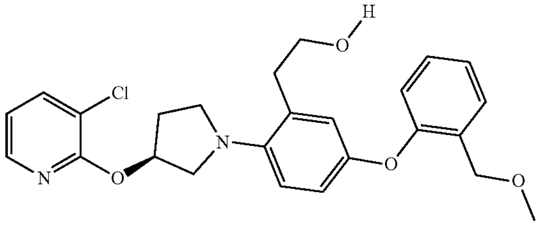 [SMILES: COCc1ccccc1Oc1ccc(N2CC[C@H](Oc3ncccc3Cl)C2)c(CCO)c1] | B | ND |
| 1-298. | 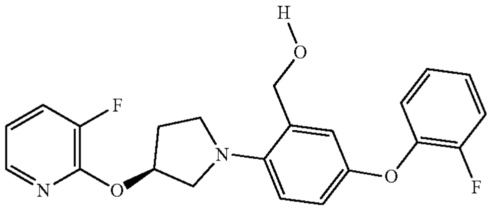 [SMILES: OCc1cc(Oc2ccccc2F)ccc1N1CC[C@H](Oc2ncccc2F)C1] | B | B |
| 1-299. | 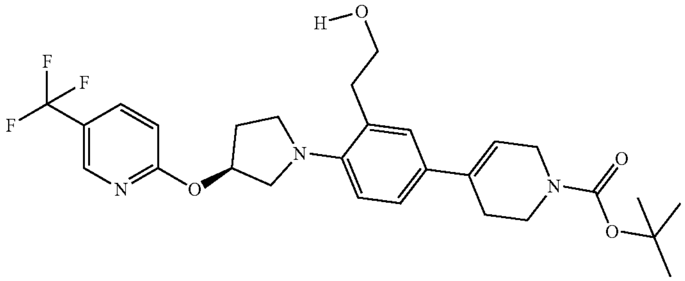 [SMILES: CC(C)(C)OC(=O)N1CC=C(c2ccc(N3CC[C@H](Oc4ccc(C(F)(F)F)cn4)C3)c(CCO)c2)CC1] | D | ND |
| 1-300. | 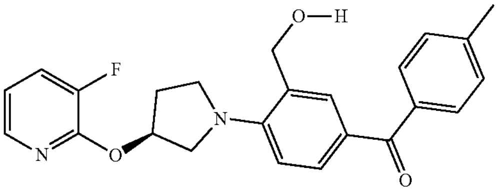 [SMILES: Cc1ccc(C(=O)c2ccc(N3CC[C@H](Oc4ncccc4F)C3)c(CO)c2)cc1] | C | ND |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-301. | 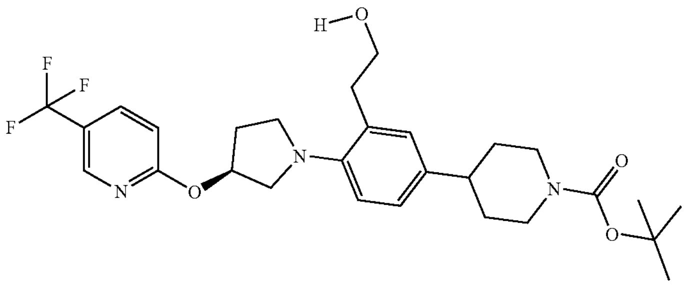 [SMILES: CC(C)(C)OC(=O)N1CCC(c2ccc(N3CC[C@H](Oc4ccc(C(F)(F)F)cn4)C3)c(CCO)c2)CC1] | D | ND |
| 1-302. | 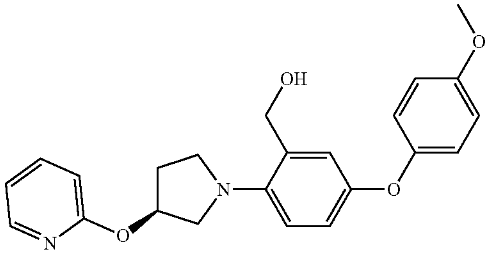 [SMILES: COc1ccc(Oc2ccc(N3CC[C@H](Oc4ccccn4)C3)c(CO)c2)cc1] | C | ND |
| 1-303. | 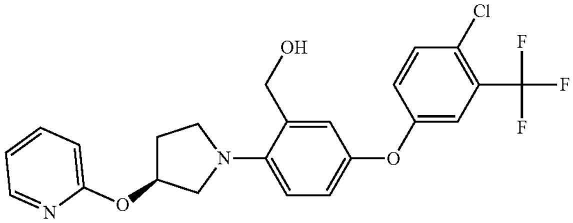 [SMILES: OCc1cc(Oc2ccc(Cl)c(C(F)(F)F)c2)ccc1N1CC[C@H](Oc2ccccn2)C1] | B | ND |
| 1-304. | 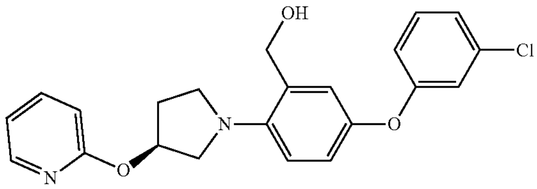 [SMILES: OCc1cc(Oc2cccc(Cl)c2)ccc1N1CC[C@H](Oc2ccccn2)C1] | B | ND |
| 1-305. | 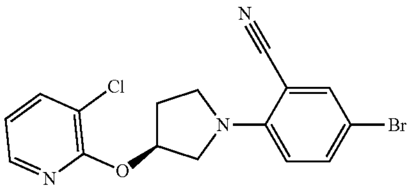 [SMILES: N#Cc1cc(Br)ccc1N1CC[C@H](Oc2ncccc2Cl)C1] | D | ND |
| 1-306. | 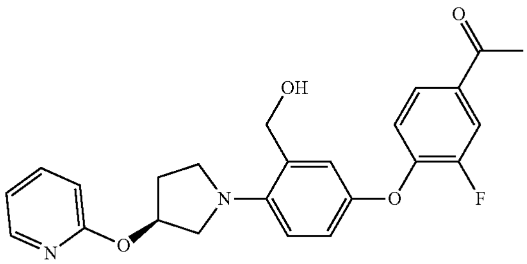 [SMILES: CC(=O)c1ccc(Oc2ccc(N3CC[C@H](Oc4ccccn4)C3)c(CO)c2)c(F)c1] | C | C |

TABLE 1-continued
Data from Patch Clamp Experiments of selected compounds
| Compound ID | Structure | hTRPV3 Patch P1 Inwd (nM) | hTRPV3 Patch P2 Inwd (nM) |
|---|---|---|---|
| 1-307. | 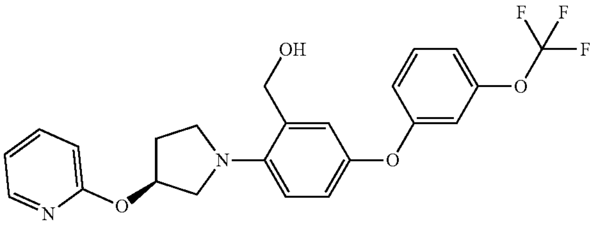 [SMILES: OCc1cc(Oc2cccc(OC(F)(F)F)c2)ccc1N1CC[C@H](Oc2ccccn2)C1] | B | ND |
| 1-308. | 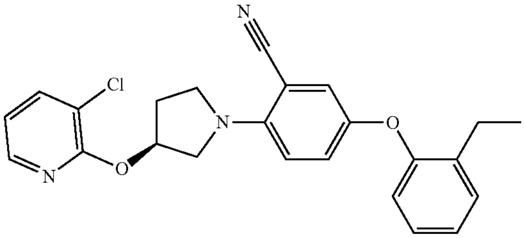 [SMILES: CCc1ccccc1Oc1ccc(N2CC[C@H](Oc3ncccc3Cl)C2)c(C#N)c1] | D | ND |
| 1-309. | 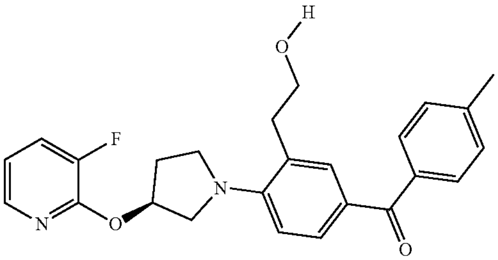 [SMILES: Cc1ccc(C(=O)c2ccc(N3CC[C@H](Oc4ncccc4F)C3)c(CCO)c2)cc1] | D | C |
| 1-310. | 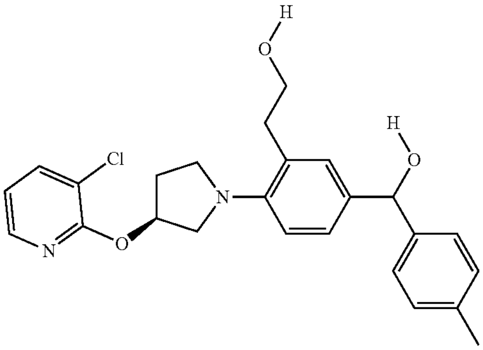 [SMILES: Cc1ccc(C(O)c2ccc(N3CC[C@H](Oc4ncccc4Cl)C3)c(CCO)c2)cc1] | D | ND |
| 1-311. | 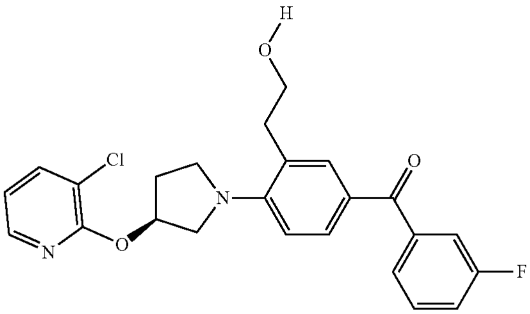 [SMILES: O=C(c1cccc(F)c1)c1ccc(N2CC[C@H](Oc3ncccc3Cl)C2)c(CCO)c1] | C | ND |

TABLE 1-continued
| Compound ID | Structure | hTRPV3 Patch P1 Inwd (nM) | hTRPV3 Patch P2 Inwd (nM) |
|---|---|---|---|
| Data from Patch Clamp Experiments of selected compounds | | | |
| 1-312. | 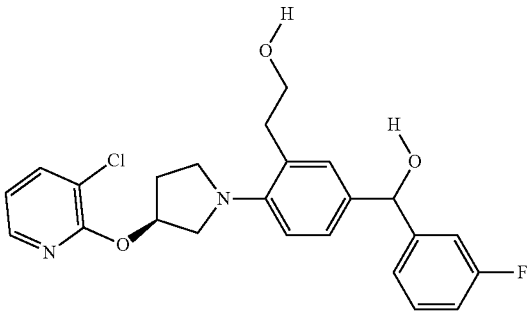 [SMILES: OCCc1cc(C(O)c2cccc(F)c2)ccc1N1CC[C@H](Oc2ncccc2Cl)C1] | D | ND |
| 1-313. | 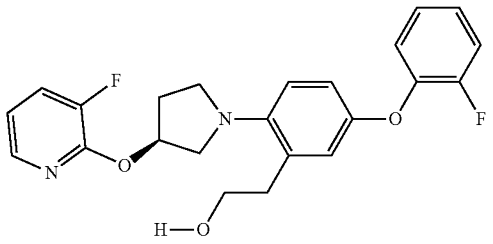 [SMILES: OCCc1cc(Oc2ccccc2F)ccc1N1CC[C@H](Oc2ncccc2F)C1] | B | B |
| 1-314. | 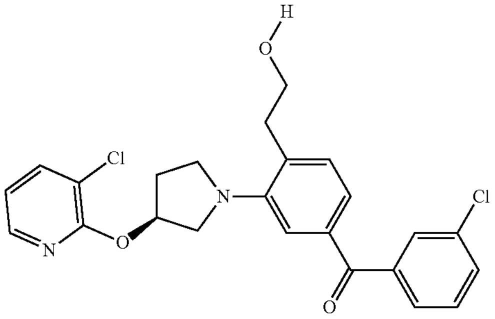 [SMILES: O=C(c1cccc(Cl)c1)c1ccc(CCO)c(N2CC[C@H](Oc3ncccc3Cl)C2)c1] | C | C |
| 1-315. | 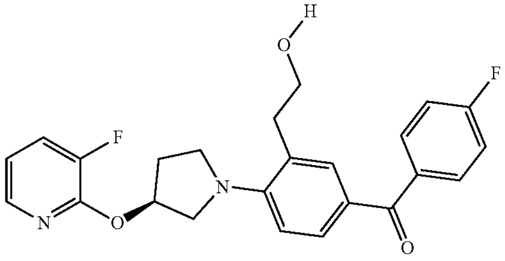 [SMILES: O=C(c1ccc(F)cc1)c1ccc(N2CC[C@H](Oc3ncccc3F)C2)c(CCO)c1] | D | ND |
| 1-316. | 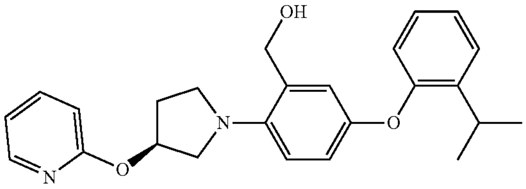 [SMILES: CC(C)c1ccccc1Oc1ccc(N2CC[C@H](Oc3ccccn3)C2)c(CO)c1] | A | ND |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-317. | 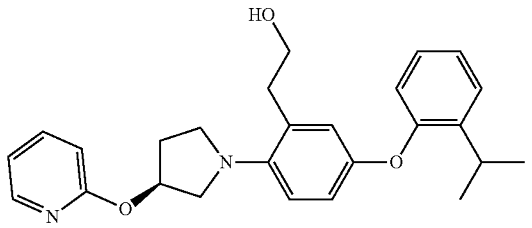 [SMILES: CC(C)c1ccccc1Oc1ccc(N2CC[C@H](Oc3ccccn3)C2)c(CCO)c1] | B | ND |
| 1-318. | 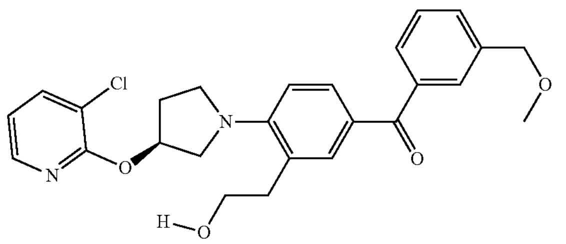 [SMILES: COCc1cccc(C(=O)c2ccc(N3CC[C@H](Oc4ncccc4Cl)C3)c(CCO)c2)c1] | D | ND |
| 1-319. | 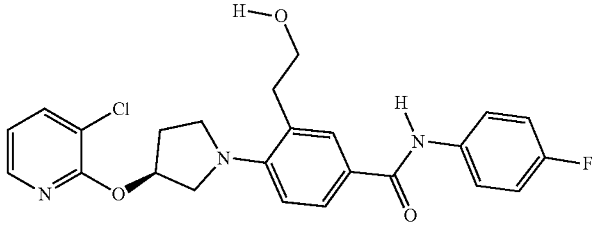 [SMILES: O=C(Nc1ccc(F)cc1)c1ccc(N2CC[C@H](Oc3ncccc3Cl)C2)c(CCO)c1] | D | ND |
| 1-320. | 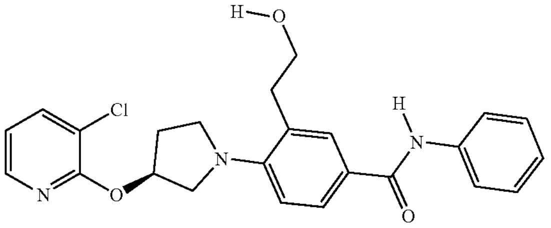 [SMILES: O=C(Nc1ccccc1)c1ccc(N2CC[C@H](Oc3ncccc3Cl)C2)c(CCO)c1] | D | ND |
| 1-321. | 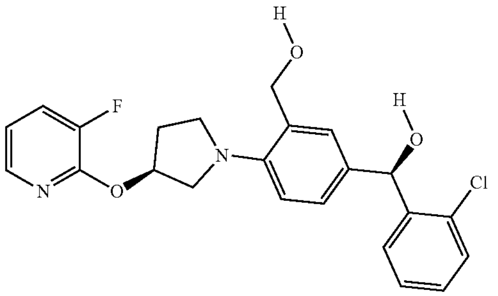 [SMILES: OCc1cc([C@@H](O)c2ccccc2Cl)ccc1N1CC[C@H](Oc2ncccc2F)C1] | B | ND |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-322. | 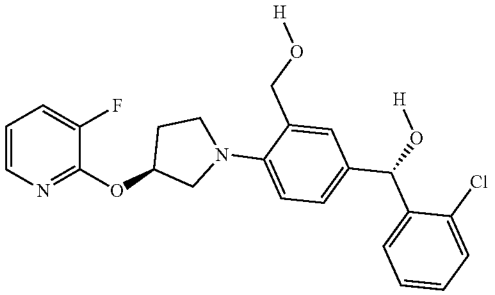 [SMILES: OCc1cc([C@H](O)c2ccccc2Cl)ccc1N1CC[C@H](Oc2ncccc2F)C1] | C | ND |
| 1-323. | 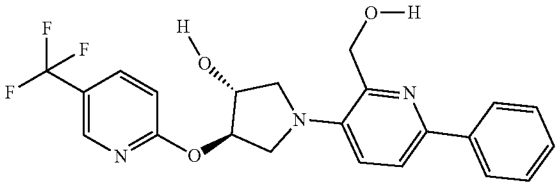 [SMILES: OCc1nc(-c2ccccc2)ccc1N1C[C@@H](O)[C@H](Oc2ccc(C(F)(F)F)cn2)C1] | D | ND |
| 1-324. | 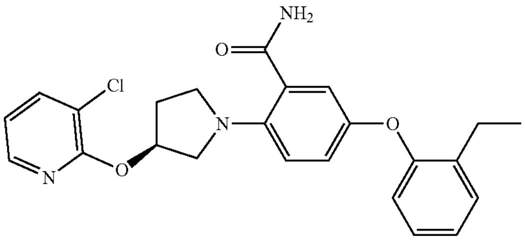 [SMILES: CCc1ccccc1Oc1ccc(N2CC[C@H](Oc3ncccc3Cl)C2)c(C(N)=O)c1] | ND | ND |
| 1-325. | 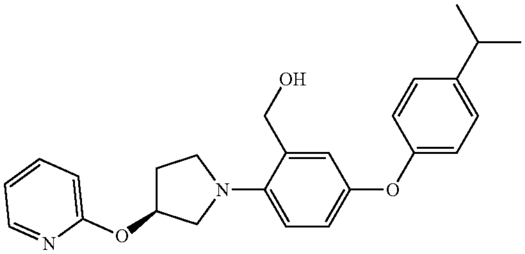 [SMILES: CC(C)c1ccc(Oc2ccc(N3CC[C@H](Oc4ccccn4)C3)c(CO)c2)cc1] | ND | ND |
| 1-326. | 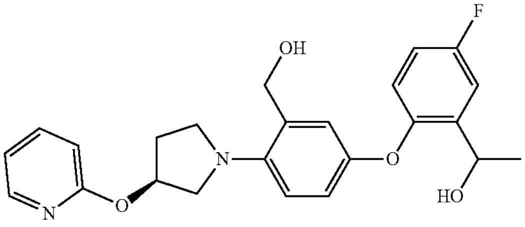 [SMILES: CC(O)c1cc(F)ccc1Oc1ccc(N2CC[C@H](Oc3ccccn3)C2)c(CO)c1] | D | C |
| 1-327. | 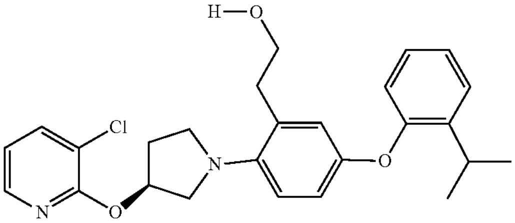 [SMILES: CC(C)c1ccccc1Oc1ccc(N2CC[C@H](Oc3ncccc3Cl)C2)c(CCO)c1] | B | ND |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-328. | 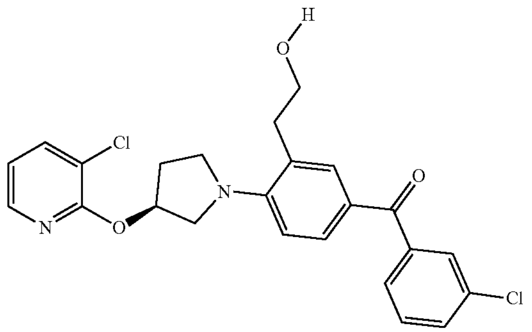 [SMILES: O=C(c1cccc(Cl)c1)c1ccc(N2CC[C@H](Oc3ncccc3Cl)C2)c(CCO)c1] | C | ND |
| 1-329. | 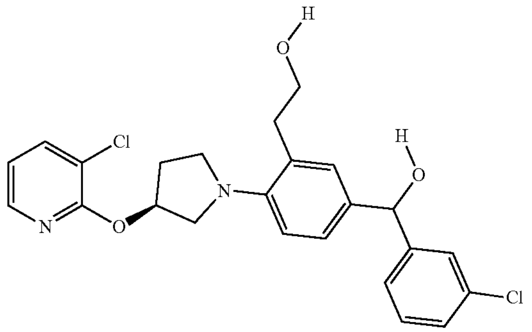 [SMILES: OCCc1cc(C(O)c2cccc(Cl)c2)ccc1N1CC[C@H](Oc2ncccc2Cl)C1] | D | ND |
| 1-330. | 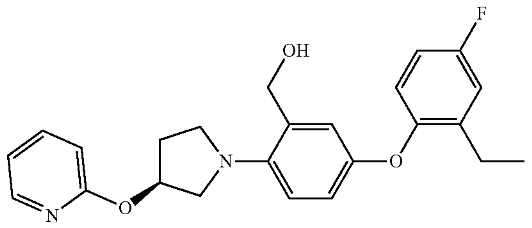 [SMILES: CCc1cc(F)ccc1Oc1ccc(N2CC[C@H](Oc3ccccn3)C2)c(CO)c1] | B | B |
| 1-331. | 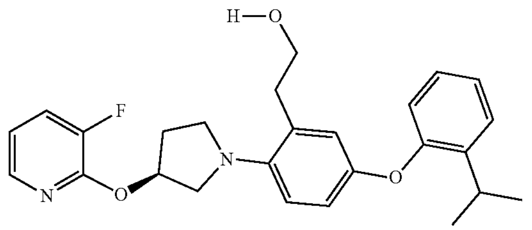 [SMILES: CC(C)c1ccccc1Oc1ccc(N2CC[C@H](Oc3ncccc3F)C2)c(CCO)c1] | B | ND |
| 1-332. | 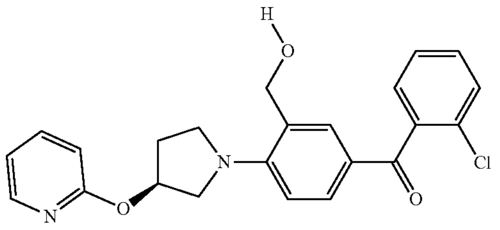 [SMILES: O=C(c1ccc(N2CC[C@H](Oc3ccccn3)C2)c(CO)c1)c1ccccc1Cl] | D | D |

TABLE 1-continued
Data from Patch Clamp Experiments of selected compounds
| Compound ID | Structure | hTRPV3 Patch P1 Inwd (nM) | hTRPV3 Patch P2 Inwd (nM) |
|---|---|---|---|
| 1-333. | 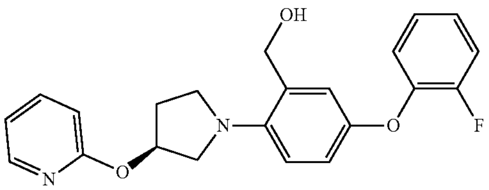 [SMILES: OCc1cc(Oc2ccccc2F)ccc1N1CC[C@H](Oc2ccccn2)C1] | C | C |
| 1-334. | 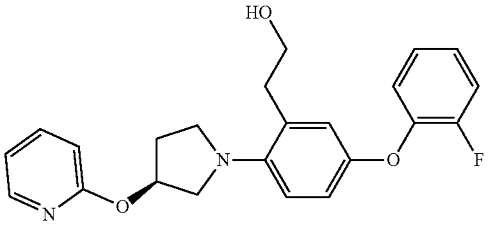 [SMILES: OCCc1cc(Oc2ccccc2F)ccc1N1CC[C@H](Oc2ccccn2)C1] | C | C |
| 1-335. | 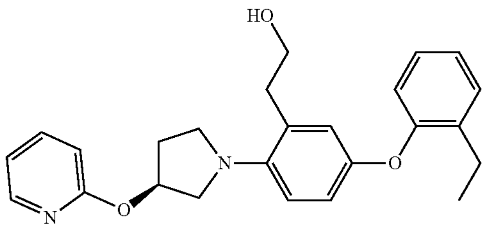 [SMILES: CCc1ccccc1Oc1ccc(N2CC[C@H](Oc3ccccn3)C2)c(CCO)c1] | B | ND |
| 1-336. | 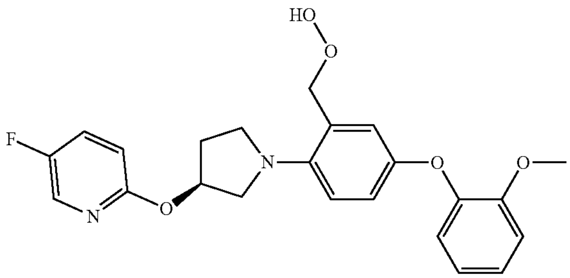 [SMILES: COc1ccccc1Oc1ccc(N2CC[C@H](Oc3ccc(F)cn3)C2)c(COO)c1] | C | C |
| 1-337. | 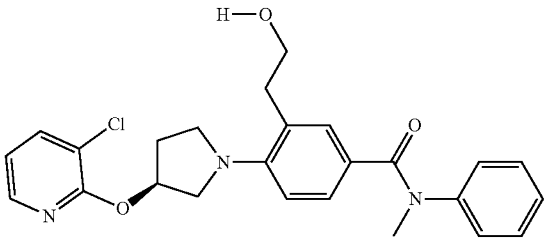 [SMILES: CN(C(=O)c1ccc(N2CC[C@H](Oc3ncccc3Cl)C2)c(CCO)c1)c1ccccc1] | D | ND |
| 1-338. | 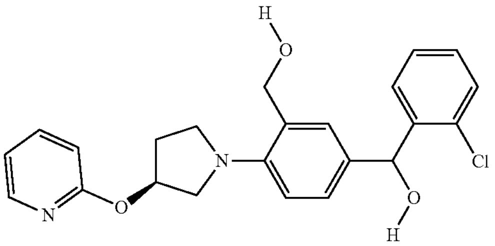 [SMILES: OCc1cc(C(O)c2ccccc2Cl)ccc1N1CC[C@H](Oc2ccccn2)C1] | C | ND |

TABLE 1-continued
Data from Patch Clamp Experiments of selected compounds
| Compound ID | Structure | hTRPV3 Patch P1 Inwd (nM) | hTRPV3 Patch P2 Inwd (nM) |
| --- | --- | --- | --- |
| 1-339. | 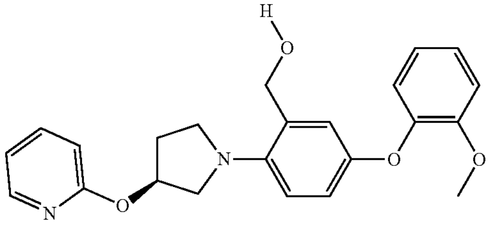 [SMILES: COc1ccccc1Oc1ccc(N2CC[C@H](Oc3ccccn3)C2)c(CO)c1] | C | ND |
| 1-340. | 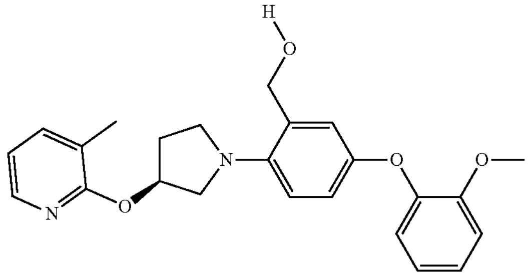 [SMILES: COc1ccccc1Oc1ccc(N2CC[C@H](Oc3ncccc3C)C2)c(CO)c1] | B | B |
| 1-341. | 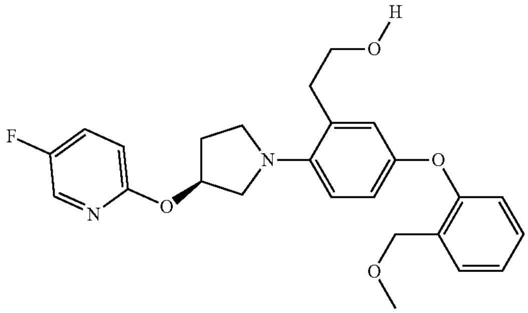 [SMILES: COCc1ccccc1Oc1ccc(N2CC[C@H](Oc3ccc(F)cn3)C2)c(CCO)c1] | C | C |
| 1-342. | 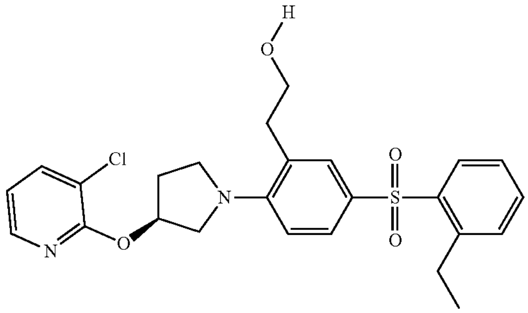 [SMILES: CCc1ccccc1S(=O)(=O)c1ccc(N2CC[C@H](Oc3ncccc3Cl)C2)c(CCO)c1] | ND | D |
| 1-343. | 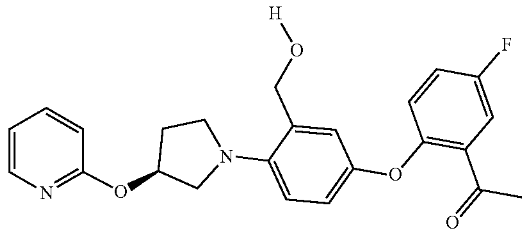 [SMILES: CC(=O)c1cc(F)ccc1Oc1ccc(N2CC[C@H](Oc3ccccn3)C2)c(CO)c1] | C | ND |

TABLE 1-continued
Data from Patch Clamp Experiments of selected compounds
| Compound ID | Structure | hTRPV3 Patch P1 Inwd (nM) | hTRPV3 Patch P2 Inwd (nM) |
|---|---|---|---|
| 1-344. | 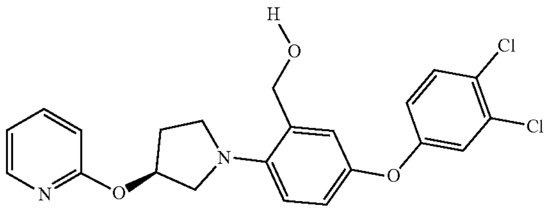 [SMILES: OCc1cc(Oc2ccc(Cl)c(Cl)c2)ccc1N1CC[C@H](Oc2ccccn2)C1] | B | ND |
| 1-345. | 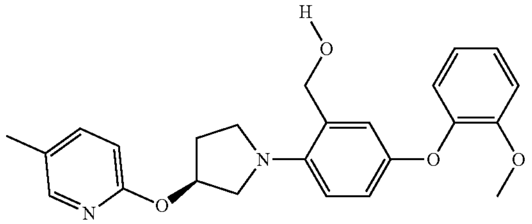 [SMILES: COc1ccccc1Oc1ccc(N2CC[C@H](Oc3ccc(C)cn3)C2)c(CO)c1] | D | ND |
| 1-346. | 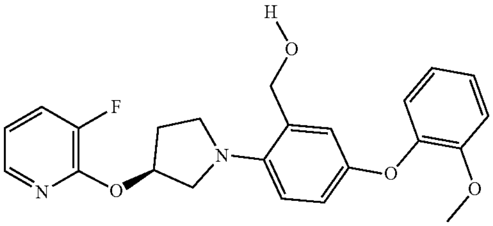 [SMILES: COc1ccccc1Oc1ccc(N2CC[C@H](Oc3ncccc3F)C2)c(CO)c1] | C | ND |
| 1-347. | 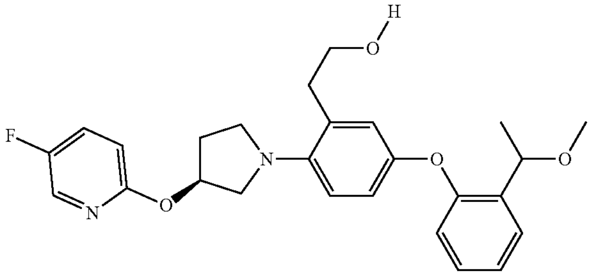 [SMILES: COC(C)c1ccccc1Oc1ccc(N2CC[C@H](Oc3ccc(F)cn3)C2)c(CCO)c1] | C | C |
| 1-348. | 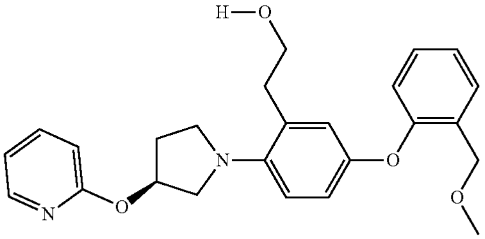 [SMILES: COCc1ccccc1Oc1ccc(N2CC[C@H](Oc3ccccn3)C2)c(CCO)c1] | D | ND |
| 1-349. | 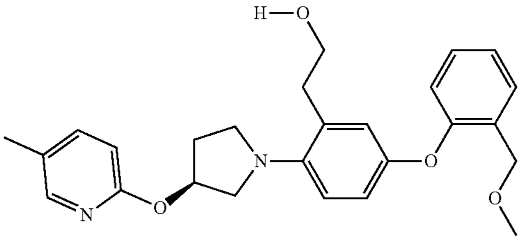 | C | ND |

TABLE 1-continued
| Data from Patent Clamp Experiments of selected compounds | | | |
|---|---|---|---|
| Compound ID | Structure | hTRPV3 Patch P1 Inwd (nM) | hTRPV3 Patch P2 Inwd (nM) |
| 1-350. | 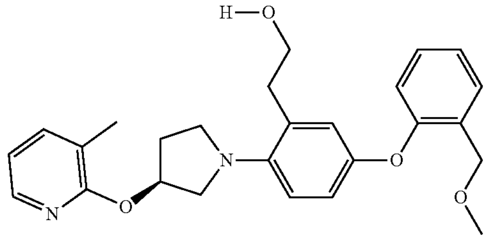 [SMILES: COCc1ccccc1Oc1ccc(N2CC[C@H](Oc3ncccc3C)C2)c(CCO)c1] | C | ND |
| 1-351. | 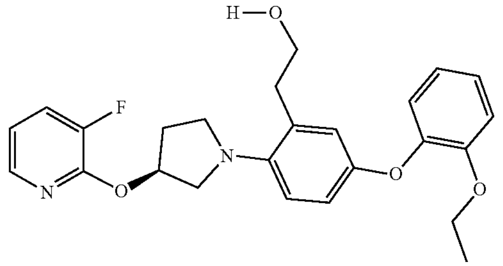 [SMILES: CCOc1ccccc1Oc1ccc(N2CC[C@H](Oc3ncccc3F)C2)c(CCO)c1] | C | ND |
| 1-352. | 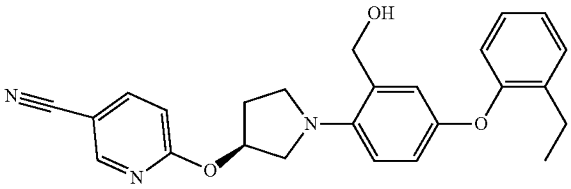 [SMILES: CCc1ccccc1Oc1ccc(N2CC[C@H](Oc3ccc(C#N)cn3)C2)c(CO)c1] | C | ND |
| 1-353. | 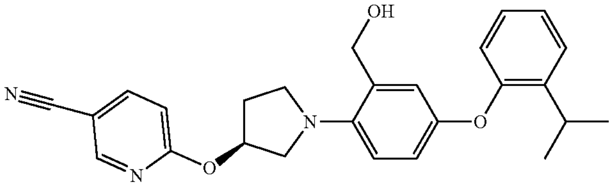 [SMILES: CC(C)c1ccccc1Oc1ccc(N2CC[C@H](Oc3ccc(C#N)cn3)C2)c(CO)c1] | B | ND |
| 1-354. | 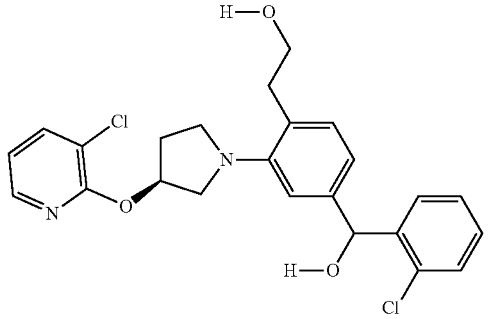 [SMILES: OCCc1ccc(C(O)c2ccccc2Cl)cc1N1CC[C@H](Oc2ncccc2Cl)C1] | D | ND |
| 1-355. | 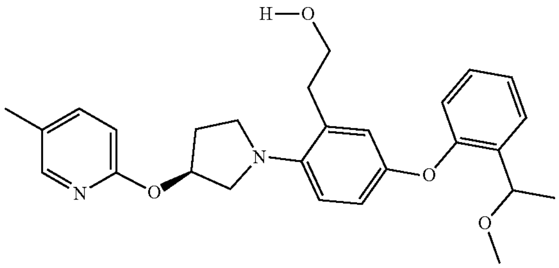 [SMILES: COC(C)c1ccccc1Oc1ccc(N2CC[C@H](Oc3ccc(C)cn3)C2)c(CCO)c1] | C | ND |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-356. | 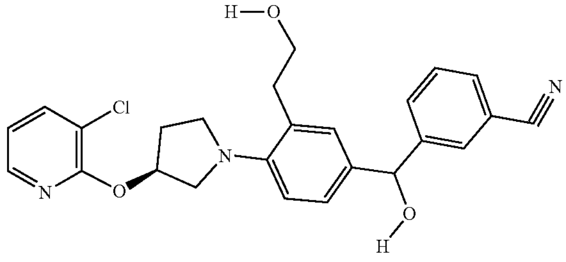 [SMILES: N#Cc1cccc(C(O)c2ccc(N3CC[C@H](Oc4ncccc4Cl)C3)c(CCO)c2)c1] | D | ND |
| 1-357. | 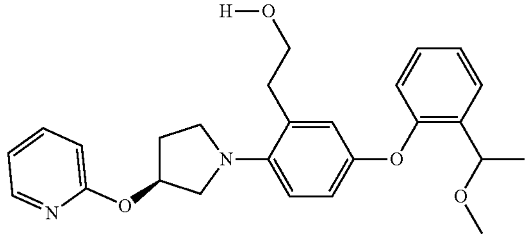 [SMILES: COC(C)c1ccccc1Oc1ccc(N2CC[C@H](Oc3ccccn3)C2)c(CCO)c1] | C | ND |
| 1-358. | 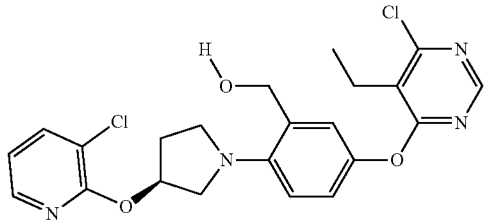 [SMILES: CCc1c(Cl)ncnc1Oc1ccc(N2CC[C@H](Oc3ncccc3Cl)C2)c(CO)c1] | C | ND |
| 1-359. | 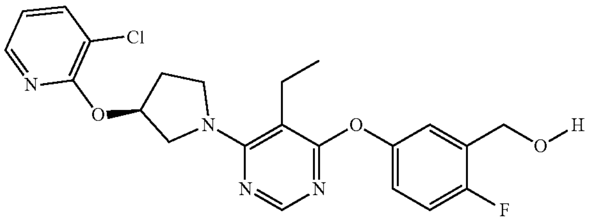 [SMILES: CCc1c(Oc2ccc(F)c(CO)c2)ncnc1N1CC[C@H](Oc2ncccc2Cl)C1] | ND | ND |
| 1-360. | 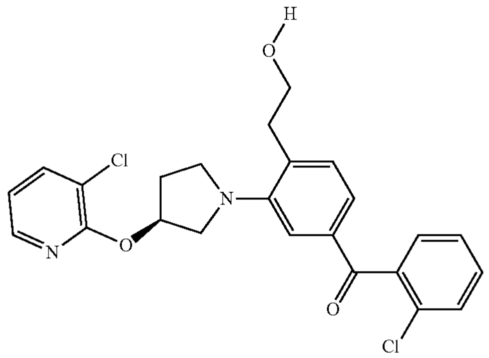 [SMILES: O=C(c1ccc(CCO)c(N2CC[C@H](Oc3ncccc3Cl)C2)c1)c1ccccc1Cl] | C | ND |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-361. | 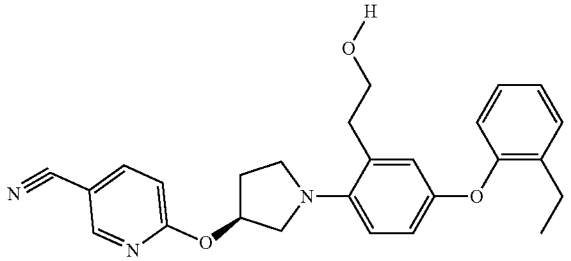 [SMILES: CCc1ccccc1Oc1ccc(N2CC[C@H](Oc3ccc(C#N)cn3)C2)c(CCO)c1] | C | ND |
| 1-362. | 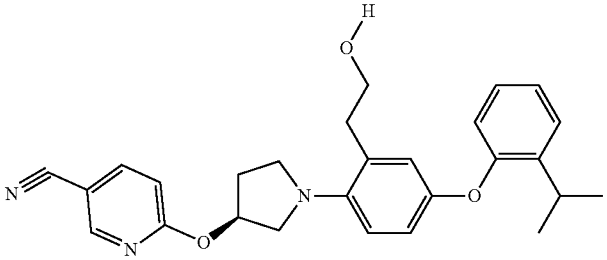 [SMILES: CC(C)c1ccccc1Oc1ccc(N2CC[C@H](Oc3ccc(C#N)cn3)C2)c(CCO)c1] | B | ND |
| 1-363. | 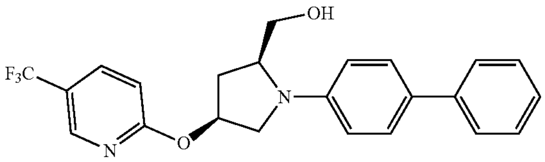 [SMILES: OC[C@@H]1C[C@H](Oc2ccc(C(F)(F)F)cn2)CN1c1ccc(-c2ccccc2)cc1] | ND | ND |
| 1-364. | 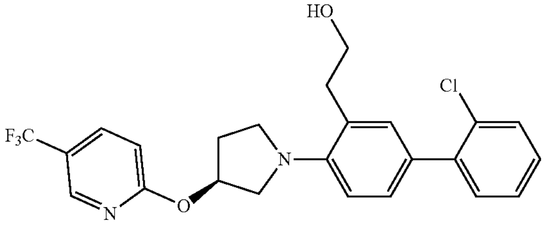 [SMILES: OCCc1cc(-c2ccccc2Cl)ccc1N1CC[C@H](Oc2ccc(C(F)(F)F)cn2)C1] | ND | ND |
| 1-365. | 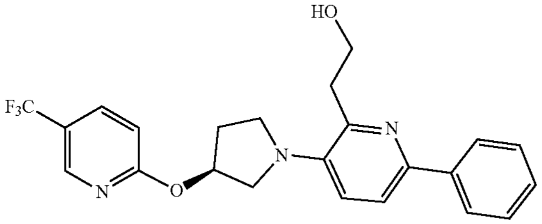 [SMILES: OCCc1nc(-c2ccccc2)ccc1N1CC[C@H](Oc2ccc(C(F)(F)F)cn2)C1] | ND | ND |
| 1-366. | 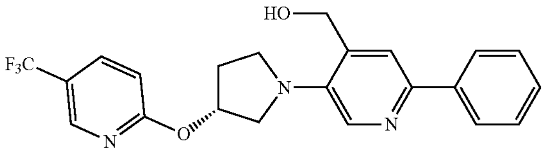 [SMILES: OCc1cc(-c2ccccc2)ncc1N1CC[C@@H](Oc2ccc(C(F)(F)F)cn2)C1] | ND | ND |
| 1-367. | 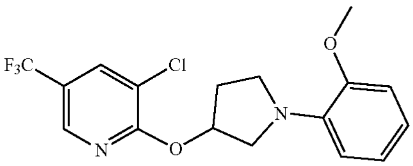 [SMILES: COc1ccccc1N1CCC(Oc2ncc(C(F)(F)F)cc2Cl)C1] | ND | ND |

TABLE 1-continued
Data from Patch Clamp Experiments of selected compounds
| Compound ID | Structure | hTRPV3 Patch P1 Inwd (nM) | hTRPV3 Patch P2 Inwd (nM) |
|---|---|---|---|
| 1-368. | 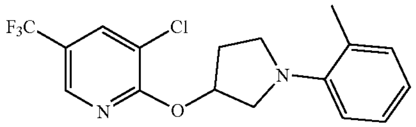 [SMILES: Cc1ccccc1N1CCC(Oc2ncc(C(F)(F)F)cc2Cl)C1] | ND | ND |
| 1-369. | 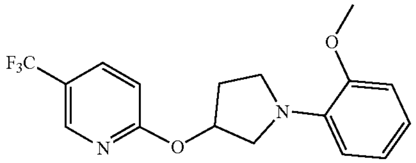 [SMILES: COc1ccccc1N1CCC(Oc2ccc(C(F)(F)F)cn2)C1] | ND | ND |
| 1-370. | 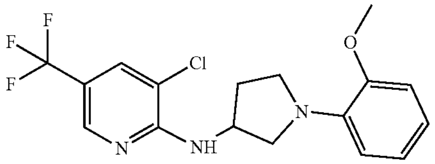 [SMILES: COc1ccccc1N1CCC(Nc2ncc(C(F)(F)F)cc2Cl)C1] | D | ND |
| 1-371. | 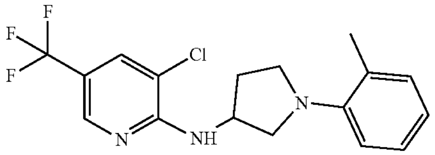 [SMILES: Cc1ccccc1N1CCC(Nc2ncc(C(F)(F)F)cc2Cl)C1] | D | D |
| 1-372. | 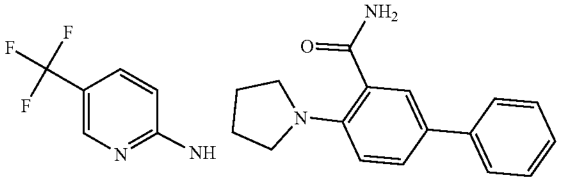 | D | D |
| 1-373. | 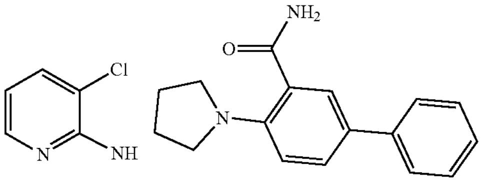 | ND | C |
| 1-374. | 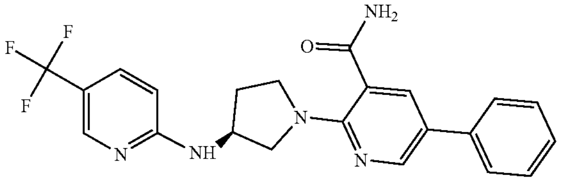 [SMILES: NC(=O)c1cc(-c2ccccc2)cnc1N1CC[C@H](Nc2ccc(C(F)(F)F)cn2)C1] | D | D |
| 1-375. | 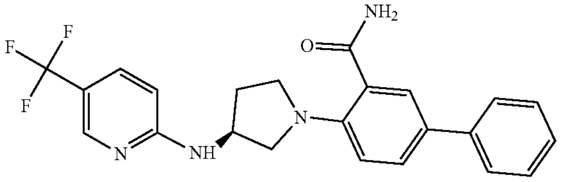 [SMILES: NC(=O)c1cc(-c2ccccc2)ccc1N1CC[C@H](Nc2ccc(C(F)(F)F)cn2)C1] | D | D |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-376. | 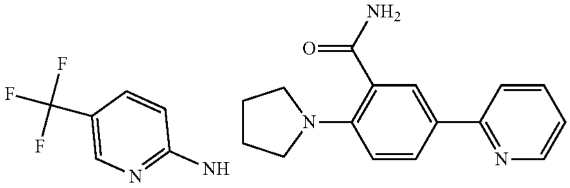 | D | D |
| 1-377. | 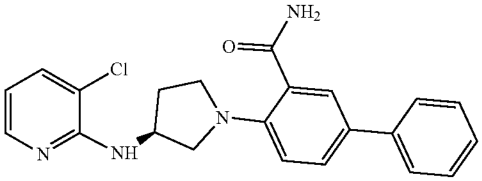 [SMILES: NC(=O)c1cc(-c2ccccc2)ccc1N1CC[C@H](Nc2ncccc2Cl)C1] | C | C |
| 1-378. | 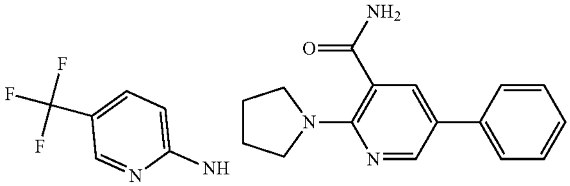 | D | D |
| 1-379. | 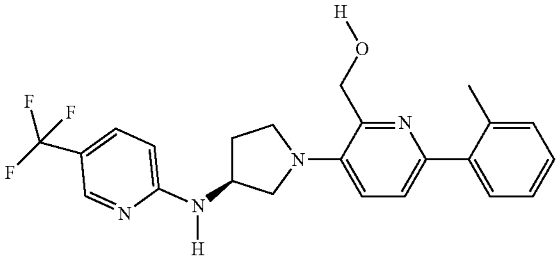 [SMILES: Cc1ccccc1-c1ccc(N2CC[C@H](Nc3ccc(C(F)(F)F)cn3)C2)c(CO)n1] | D | D |
| 1-380. | 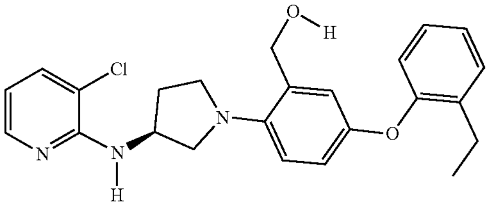 [SMILES: CCc1ccccc1Oc1ccc(N2CC[C@H](Nc3ncccc3Cl)C2)c(CO)c1] | B | ND |
| 1-381. | 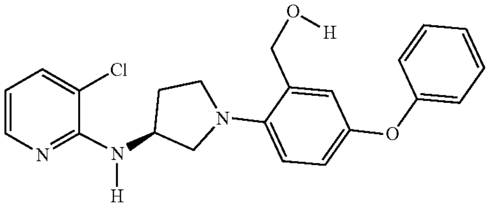 [SMILES: OCc1cc(Oc2ccccc2)ccc1N1CC[C@H](Nc2ncccc2Cl)C1] | B | ND |
| 1-382. | 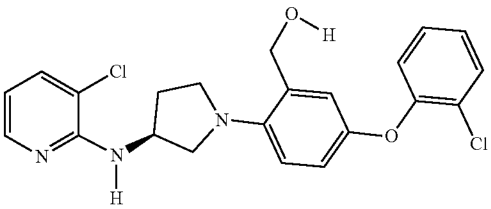 [SMILES: OCc1cc(Oc2ccccc2Cl)ccc1N1CC[C@H](Nc2ncccc2Cl)C1] | B | ND |

TABLE 1-continued
| Compound ID | Structure | hTRPV3 Patch P1 Inwd (nM) | hTRPV3 Patch P2 Inwd (nM) |
|---|---|---|---|
| Data from Patch Clamp Experiments of selected compounds | | | |
| 1-383. | 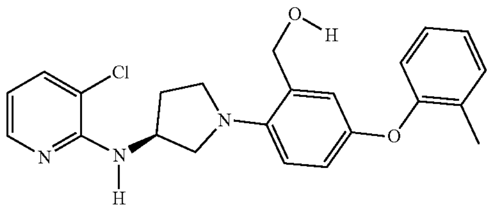 [SMILES: Cc1ccccc1Oc1ccc(N2CC[C@H](Nc3ncccc3Cl)C2)c(CO)c1] | B | ND |
| 1-384. | 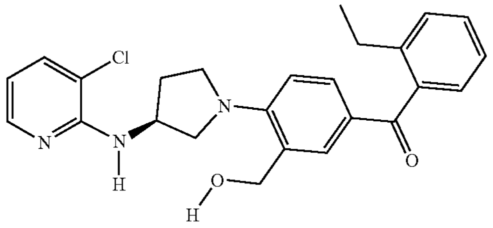 [SMILES: CCc1ccccc1C(=O)c1ccc(N2CC[C@H](Nc3ncccc3Cl)C2)c(CO)c1] | C | ND |
| 1-385. | 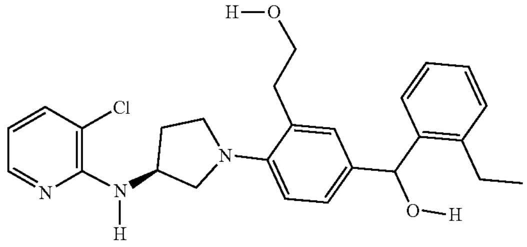 [SMILES: CCc1ccccc1C(O)c1ccc(N2CC[C@H](Nc3ncccc3Cl)C2)c(CCO)c1] | D | ND |
| 1-386. | 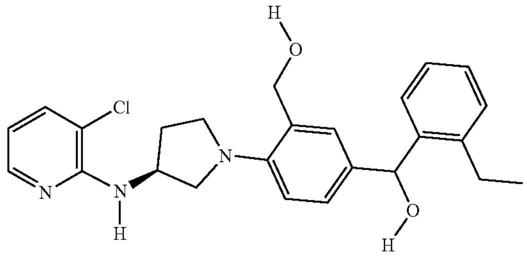 [SMILES: CCc1ccccc1C(O)c1ccc(N2CC[C@H](Nc3ncccc3Cl)C2)c(CO)c1] | D | D |
| 1-387. | 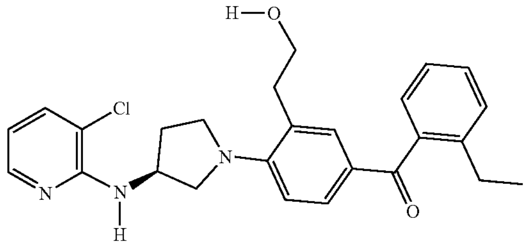 [SMILES: CCc1ccccc1C(=O)c1ccc(N2CC[C@H](Nc3ncccc3Cl)C2)c(CCO)c1] | D | ND |
| 1-388. | 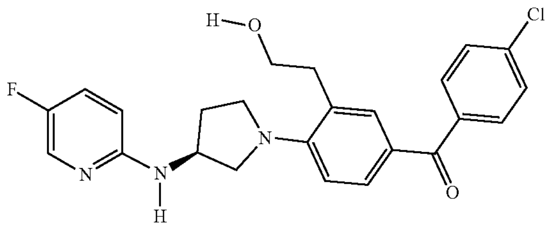 [SMILES: O=C(c1ccc(Cl)cc1)c1ccc(N2CC[C@H](Nc3ccc(F)cn3)C2)c(CCO)c1] | D | ND |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-389. | 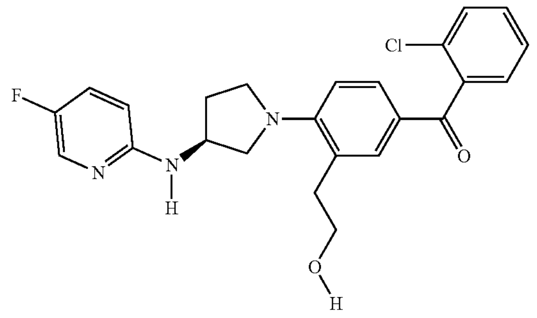 [SMILES: O=C(c1ccc(N2CC[C@H](Nc3ccc(F)cn3)C2)c(CCO)c1)c1ccccc1Cl] | D | ND |
| 1-390. | 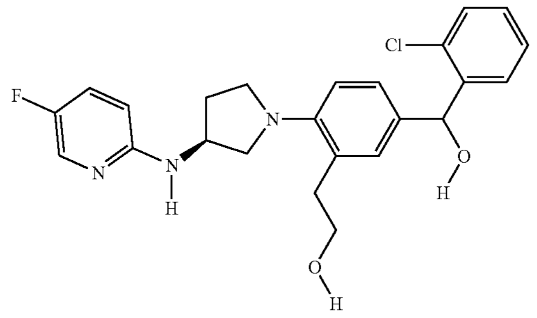 [SMILES: OCCc1cc(C(O)c2ccccc2Cl)ccc1N1CC[C@H](Nc2ccc(F)cn2)C1] | C | ND |
| 1-391. | 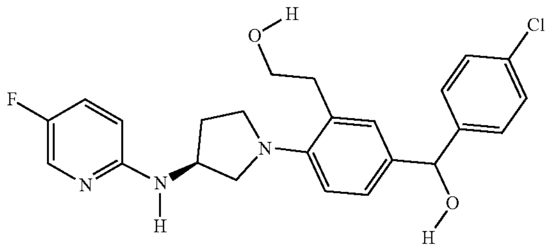 [SMILES: OCCc1cc(C(O)c2ccc(Cl)cc2)ccc1N1CC[C@H](Nc2ccc(F)cn2)C1] | D | ND |
| 1-392. | 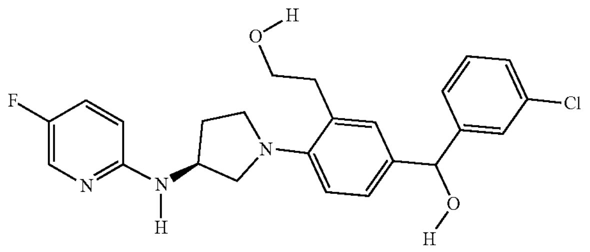 [SMILES: OCCc1cc(C(O)c2cccc(Cl)c2)ccc1N1CC[C@H](Nc2ccc(F)cn2)C1] | D | ND |
| 1-393. | 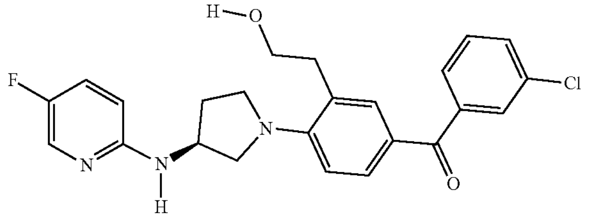 [SMILES: O=C(c1cccc(Cl)c1)c1ccc(N2CC[C@H](Nc3ccc(F)cn3)C2)c(CCO)c1] | D | D |

TABLE 1-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 1-394. | 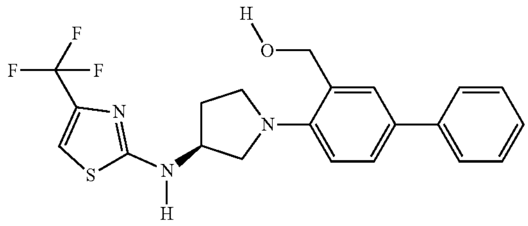 [SMILES: OCc1cc(-c2ccccc2)ccc1N1CC[C@H](Nc2nc(C(F)(F)F)cs2)C1] | C | C |
| 1-395. | 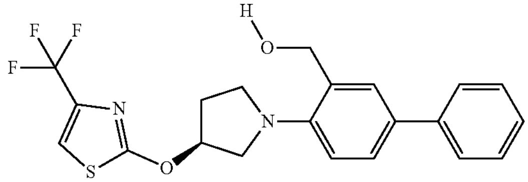 [SMILES: OCc1cc(-c2ccccc2)ccc1N1CC[C@H](Oc2nc(C(F)(F)F)cs2)C1] | D | D |
| 1-396. | 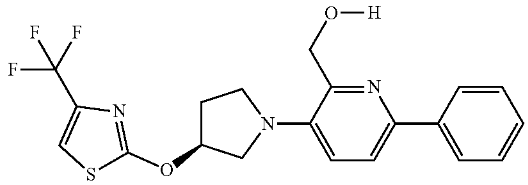 [SMILES: OCc1nc(-c2ccccc2)ccc1N1CC[C@H](Oc2nc(C(F)(F)F)cs2)C1] | D | D |
| 1-397. | 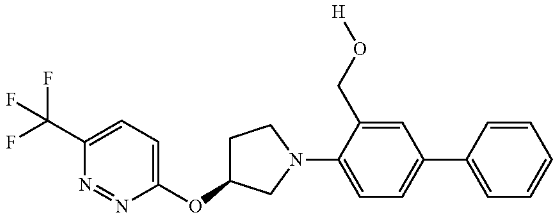 [SMILES: OCc1cc(-c2ccccc2)ccc1N1CC[C@H](Oc2ccc(C(F)(F)F)nn2)C1] | D | D |
TABLE 2
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 2-1. | 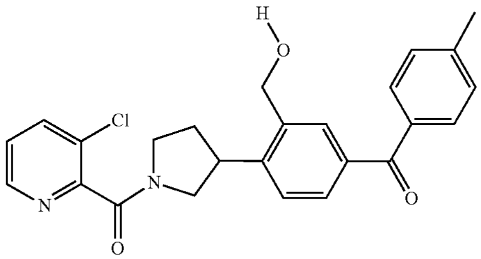 [SMILES: Cc1ccc(C(=O)c2ccc(C3CCN(C(=O)c4ncccc4Cl)C3)c(CO)c2)cc1] | D | ND |

TABLE 2-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 2-2. | 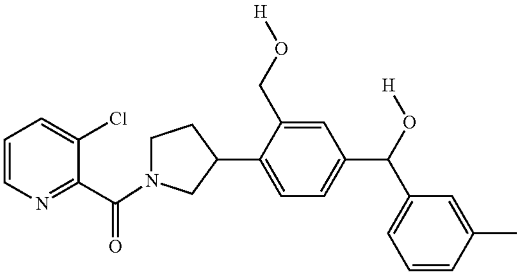 [SMILES: Cc1cccc(C(O)c2ccc(C3CCN(C(=O)c4ncccc4Cl)C3)c(CO)c2)c1] | C | ND |
| 2-3. | 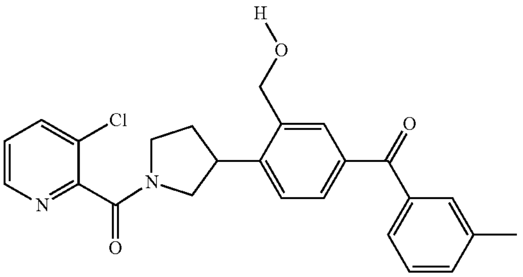 [SMILES: Cc1cccc(C(=O)c2ccc(C3CCN(C(=O)c4ncccc4Cl)C3)c(CO)c2)c1] | B | ND |
| 2-4. | 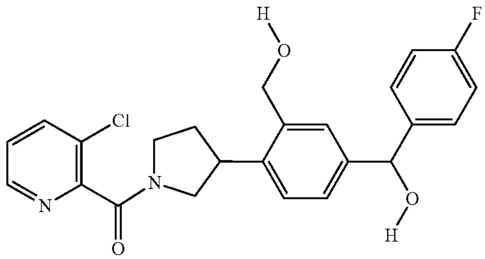 [SMILES: O=C(c1ncccc1Cl)N1CCC(c2ccc(C(O)c3ccc(F)cc3)cc2CO)C1] | D | ND |
| 2-5. | 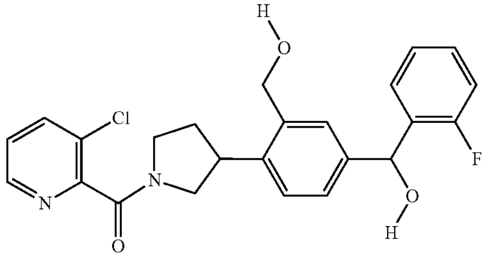 [SMILES: O=C(c1ncccc1Cl)N1CCC(c2ccc(C(O)c3ccccc3F)cc2CO)C1] | D | ND |
| 2-6. | 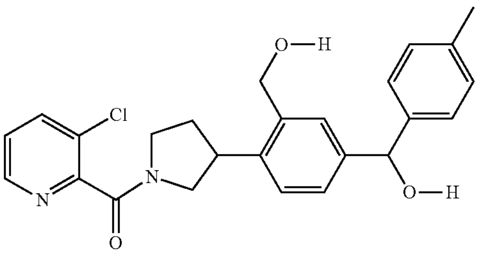 [SMILES: Cc1ccc(C(O)c2ccc(C3CCN(C(=O)c4ncccc4Cl)C3)c(CO)c2)cc1] | D | ND |

TABLE 2-continued
| Compound ID | Structure | hTRPV3 Patch P1 Inwd (nM) | hTRPV3 Patch P2 Inwd (nM) |
|---|---|---|---|
| Data from Patch Clamp Experiments of selected compounds | | | |
| 2-7. | 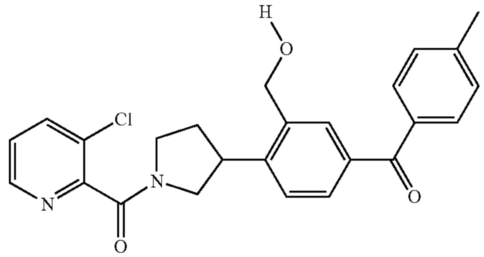 [SMILES: Cc1ccc(C(=O)c2ccc(C3CCN(C(=O)c4ncccc4Cl)C3)c(CO)c2)cc1] | D | ND |
| 2-8. | 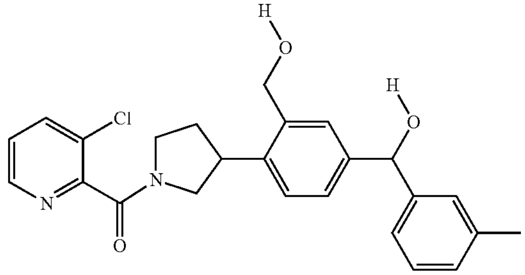 [SMILES: Cc1cccc(C(O)c2ccc(C3CCN(C(=O)c4ncccc4Cl)C3)c(CO)c2)c1] | D | ND |
| 2-9. | 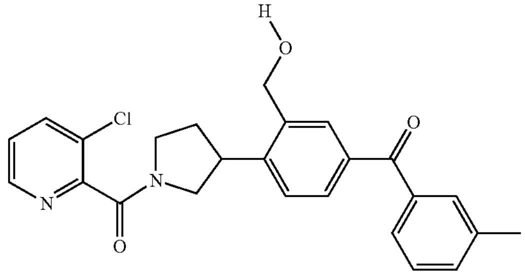 [SMILES: Cc1cccc(C(=O)c2ccc(C3CCN(C(=O)c4ncccc4Cl)C3)c(CO)c2)c1] | D | ND |
| 2-10. | 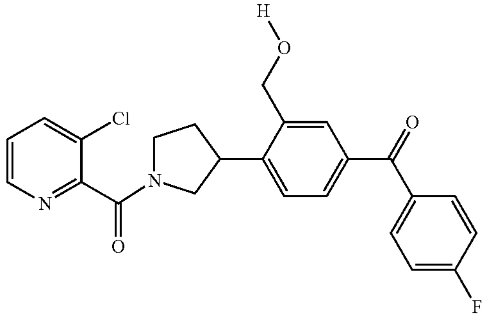 [SMILES: O=C(c1ccc(F)cc1)c1ccc(C2CCN(C(=O)c3ncccc3Cl)C2)c(CO)c1] | D | ND |
| 2-11. | 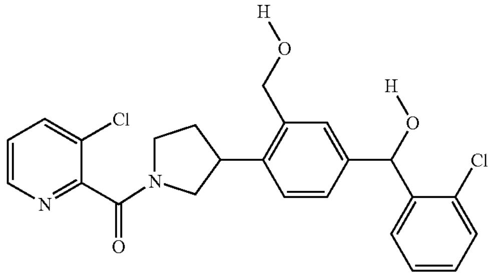 [SMILES: O=C(c1ncccc1Cl)N1CCC(c2ccc(C(O)c3ccccc3Cl)cc2CO)C1] | D | ND |

TABLE 2-continued
| Compound ID | Structure | hTRPV3 Patch P1 Inwd (nM) | hTRPV3 Patch P2 Inwd (nM) |
|---|---|---|---|
| Data from Patch Clamp Experiments of selected compounds | | | |
| 2-12. | 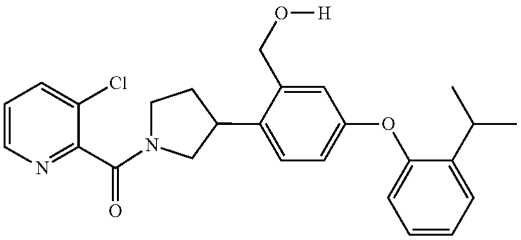 [SMILES: CC(C)c1ccccc1Oc1ccc(C2CCN(C(=O)c3ncccc3Cl)C2)c(CO)c1] | B | ND |
| 2-13. | 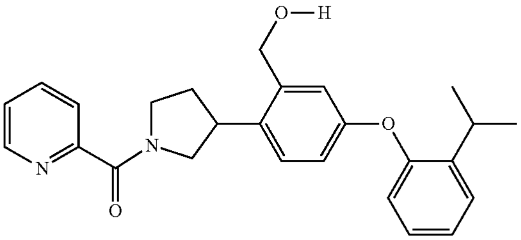 [SMILES: CC(C)c1ccccc1Oc1ccc(C2CCN(C(=O)c3ccccn3)C2)c(CO)c1] | C | ND |
| 2-14. | 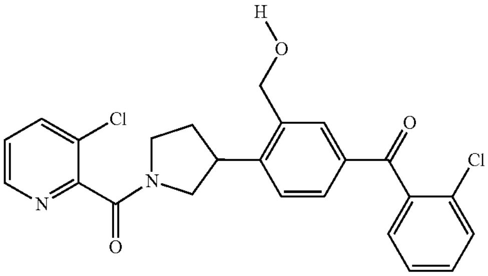 [SMILES: O=C(c1ccc(C2CCN(C(=O)c3ncccc3Cl)C2)c(CO)c1)c1ccccc1Cl] | D | ND |
| 2-15. | 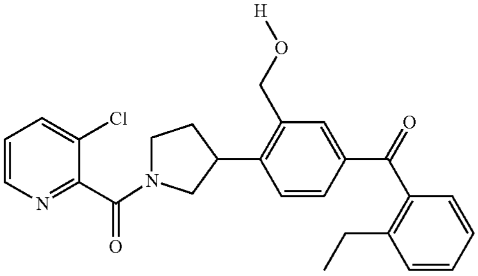 [SMILES: CCc1ccccc1C(=O)c1ccc(C2CCN(C(=O)c3ncccc3Cl)C2)c(CO)c1] | D | ND |
| 2-16. | 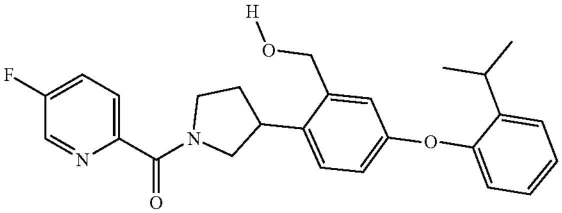 [SMILES: CC(C)c1ccccc1Oc1ccc(C2CCN(C(=O)c3ccc(F)cn3)C2)c(CO)c1] | B | B |
| 2-17. | 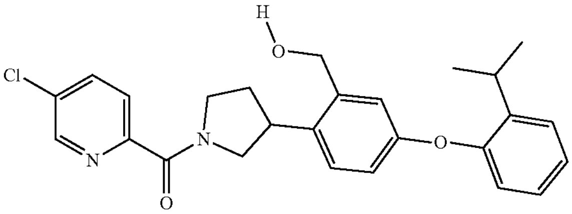 [SMILES: CC(C)c1ccccc1Oc1ccc(C2CCN(C(=O)c3ccc(Cl)cn3)C2)c(CO)c1] | B | ND |

TABLE 2-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 2-18. | 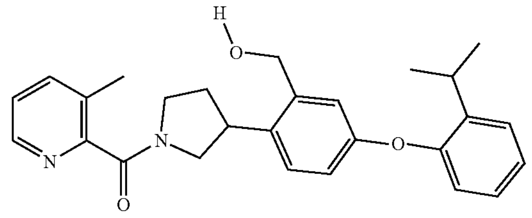 [SMILES: Cc1cccnc1C(=O)N1CCC(c2ccc(Oc3ccccc3C(C)C)cc2CO)C1] | C | ND |
| 2-19. | 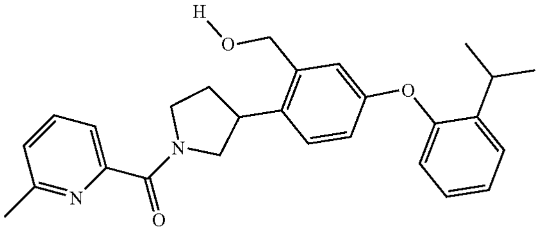 [SMILES: Cc1cccc(C(=O)N2CCC(c3ccc(Oc4ccccc4C(C)C)cc3CO)C2)n1] | B | ND |
| 2-20. | 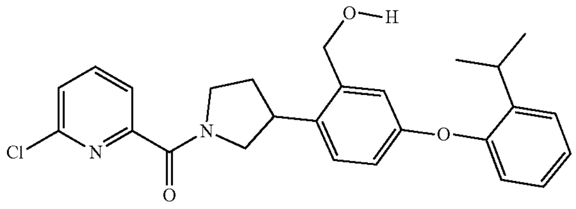 [SMILES: CC(C)c1ccccc1Oc1ccc(C2CCN(C(=O)c3cccc(Cl)n3)C2)c(CO)c1] | B | ND |
| 2-21. | 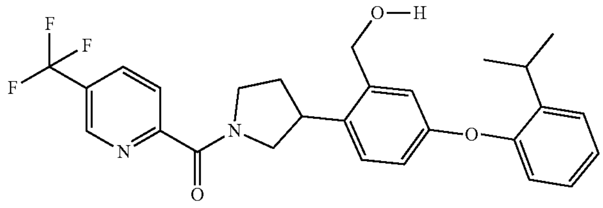 [SMILES: CC(C)c1ccccc1Oc1ccc(C2CCN(C(=O)c3ccc(C(F)(F)F)cn3)C2)c(CO)c1] | B | ND |
| 2-22. | 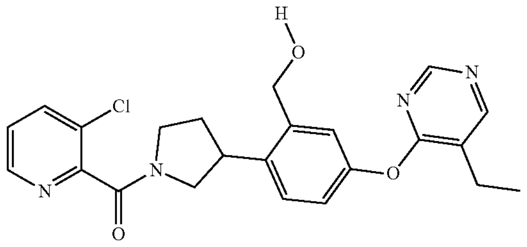 [SMILES: CCc1cncnc1Oc1ccc(C2CCN(C(=O)c3ncccc3Cl)C2)c(CO)c1] | D | ND |
| 2-23. | 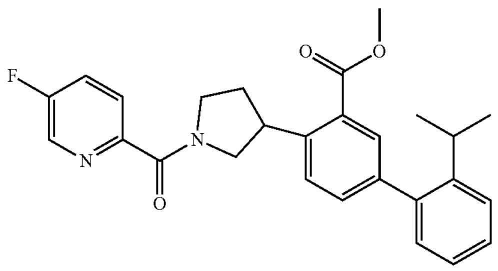 [SMILES: COC(=O)c1cc(-c2ccccc2C(C)C)ccc1C1CCN(C(=O)c2ccc(F)cn2)C1] | C | ND |

TABLE 2-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 2-24. | 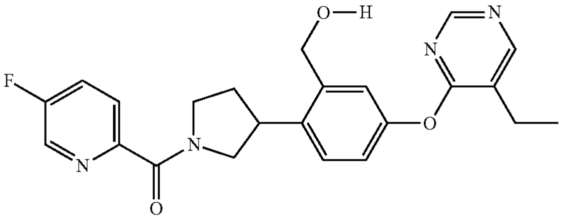 [SMILES: CCc1cncnc1Oc1ccc(C2CCN(C(=O)c3ccc(F)cn3)C2)c(CO)c1] | D | ND |
| 2-25. | 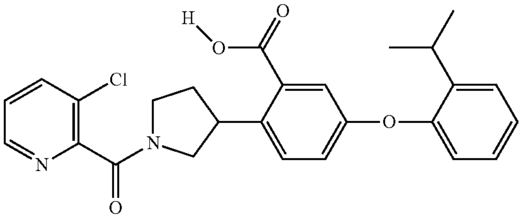 [SMILES: CC(C)c1ccccc1Oc1ccc(C2CCN(C(=O)c3ncccc3Cl)C2)c(C(=O)O)c1] | D | ND |
| 2-26. | 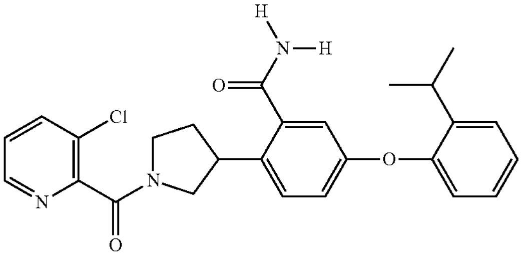 [SMILES: CC(C)c1ccccc1Oc1ccc(C2CCN(C(=O)c3ncccc3Cl)C2)c(C(N)=O)c1] | C | ND |
| 2-27. | 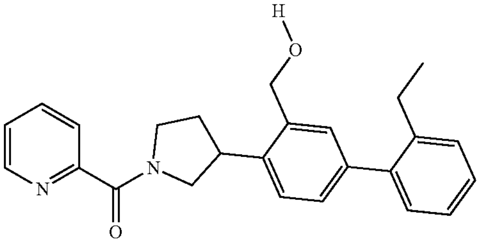 [SMILES: CCc1ccccc1-c1ccc(C2CCN(C(=O)c3ccccn3)C2)c(CO)c1] | B | ND |
| 2-28. | 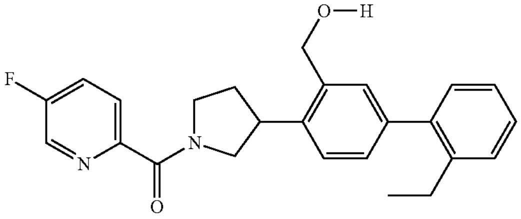 [SMILES: CCc1ccccc1-c1ccc(C2CCN(C(=O)c3ccc(F)cn3)C2)c(CO)c1] | B | ND |
| 2-29. | 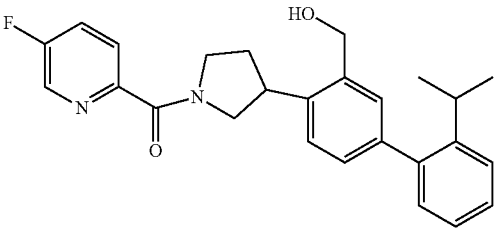 [SMILES: CC(C)c1ccccc1-c1ccc(C2CCN(C(=O)c3ccc(F)cn3)C2)c(CO)c1] | A | ND |

TABLE 2-continued
Data from Patch Clamp Experiments of selected compounds
| Compound ID | Structure | hTRPV3 Patch P1 Inwd (nM) | hTRPV3 Patch P2 Inwd (nM) |
|---|---|---|---|
| 2-30. | 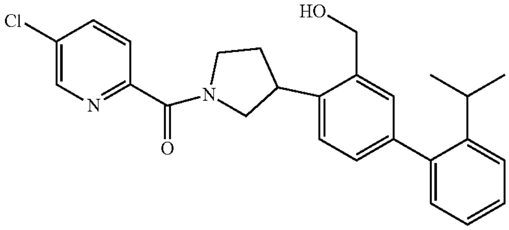 [SMILES: CC(C)c1ccccc1-c1ccc(C2CCN(C(=O)c3ccc(Cl)cn3)C2)c(CO)c1] | A | ND |
| 2-31. | 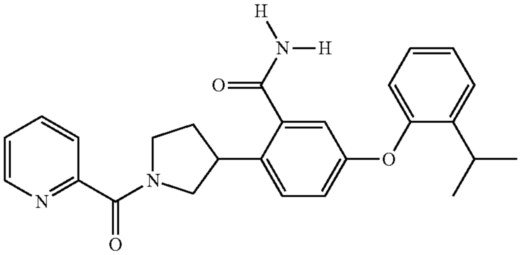 [SMILES: CC(C)c1ccccc1Oc1ccc(C2CCN(C(=O)c3ccccn3)C2)c(C(N)=O)c1] | D | ND |
| 2-32. | 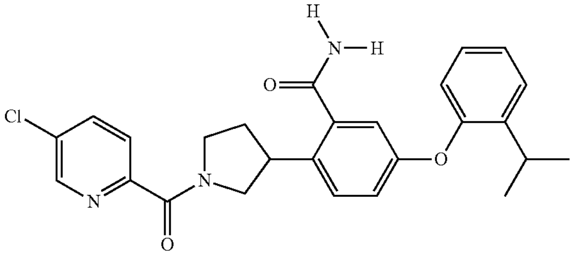 [SMILES: CC(C)c1ccccc1Oc1ccc(C2CCN(C(=O)c3ccc(Cl)cn3)C2)c(C(N)=O)c1] | C | ND |
| 2-33. | 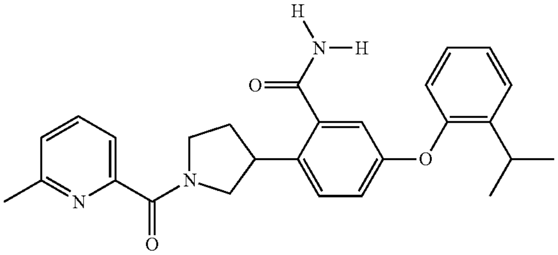 [SMILES: Cc1cccc(C(=O)N2CCC(c3ccc(Oc4ccccc4C(C)C)cc3C(N)=O)C2)n1] | C | ND |
| 2-34. | 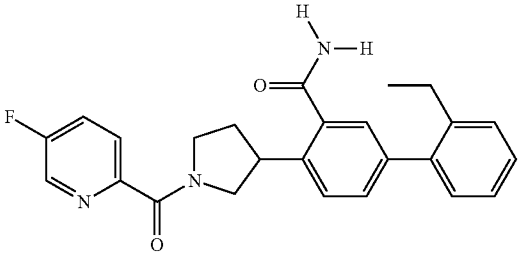 [SMILES: CCc1ccccc1-c1ccc(C2CCN(C(=O)c3ccc(F)cn3)C2)c(C(N)=O)c1] | C | ND |
| 2-35. | 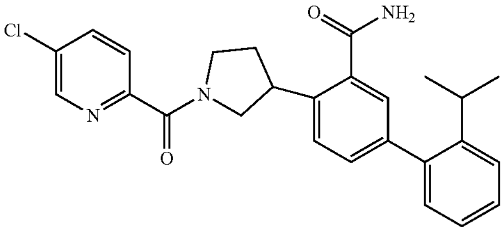 [SMILES: CC(C)c1ccccc1-c1ccc(C2CCN(C(=O)c3ccc(Cl)cn3)C2)c(C(N)=O)c1] | B | B |

TABLE 2-continued
Data from Patch Clamp Experiments of selected compounds
| Compound ID | Structure | hTRPV3 Patch P1 Inwd (nM) | hTRPV3 Patch P2 Inwd (nM) |
|---|---|---|---|
| 2-36. | 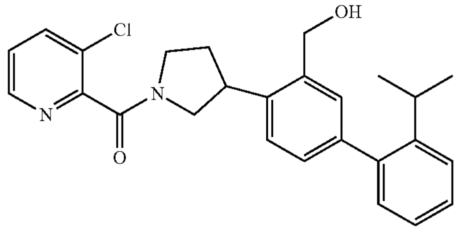 [SMILES: CC(C)c1ccccc1-c1ccc(C2CCN(C(=O)c3ncccc3Cl)C2)c(CO)c1] | B | ND |
| 2-37. | 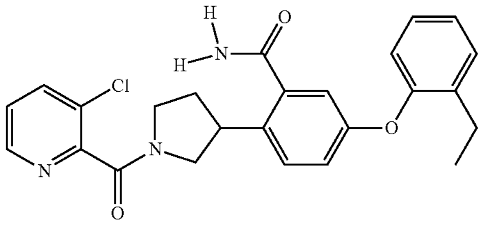 [SMILES: CCc1ccccc1Oc1ccc(C2CCN(C(=O)c3ncccc3Cl)C2)c(C(N)=O)c1] | D | ND |
| 2-38. | 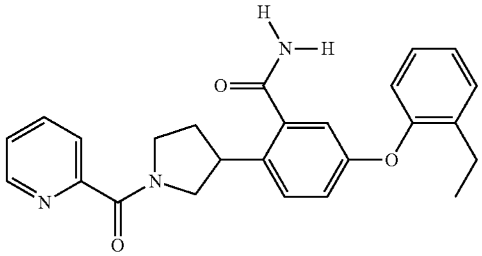 [SMILES: CCc1ccccc1Oc1ccc(C2CCN(C(=O)c3ccccn3)C2)c(C(N)=O)c1] | D | ND |
| 2-39. | 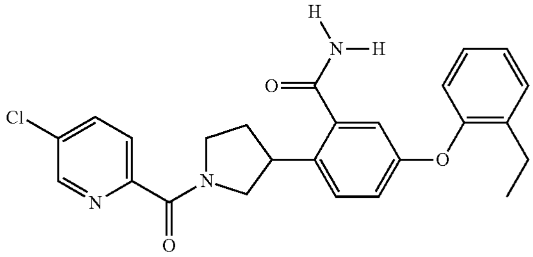 [SMILES: CCc1ccccc1Oc1ccc(C2CCN(C(=O)c3ccc(Cl)cn3)C2)c(C(N)=O)c1] | C | ND |
| 2-40. | 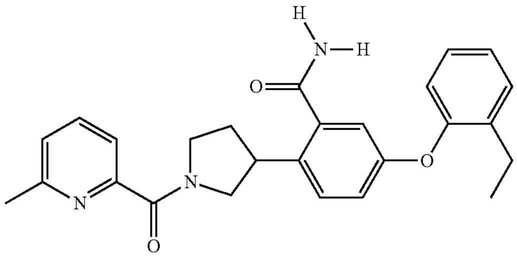 [SMILES: CCc1ccccc1Oc1ccc(C2CCN(C(=O)c3cccc(C)n3)C2)c(C(N)=O)c1] | D | ND |
| 2-41. | 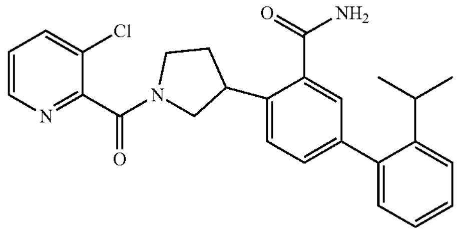 [SMILES: CC(C)c1ccccc1-c1ccc(C2CCN(C(=O)c3ncccc3Cl)C2)c(C(N)=O)c1] | C | ND |

TABLE 2-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 2-42. | 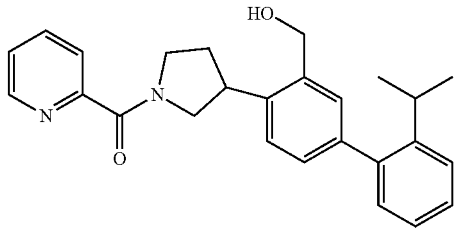 [SMILES: CC(C)c1ccccc1-c1ccc(C2CCN(C(=O)c3ccccn3)C2)c(CO)c1] | B | ND |
| 2-43. | 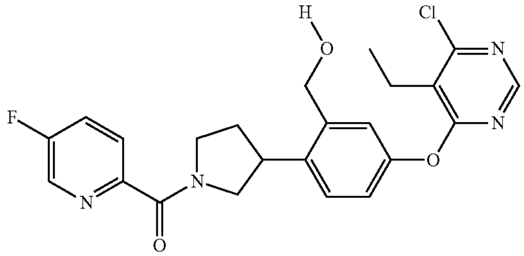 [SMILES: CCc1c(Cl)ncnc1Oc1ccc(C2CCN(C(=O)c3ccc(F)cn3)C2)c(CO)c1] | D | ND |
| 2-44. | 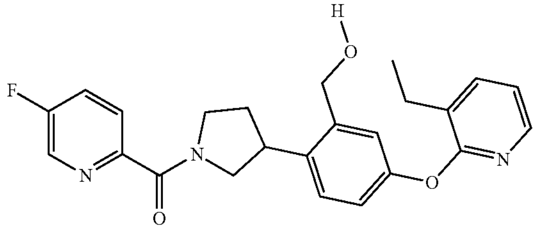 [SMILES: CCc1cccnc1Oc1ccc(C2CCN(C(=O)c3ccc(F)cn3)C2)c(CO)c1] | D | ND |
| 2-45. | 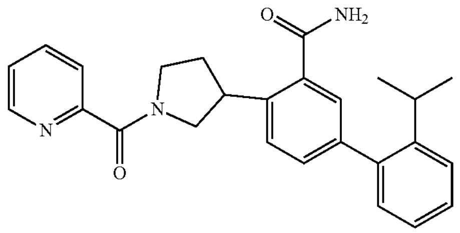 [SMILES: CC(C)c1ccccc1-c1ccc(C2CCN(C(=O)c3ccccn3)C2)c(C(N)=O)c1] | C | ND |
| 2-46. | 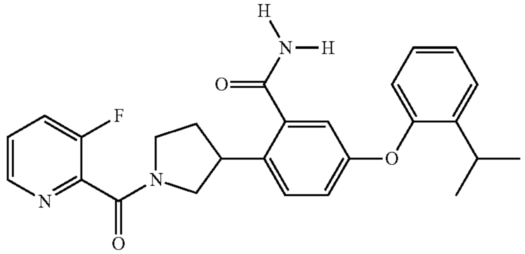 | D | ND |
| 2-47. | 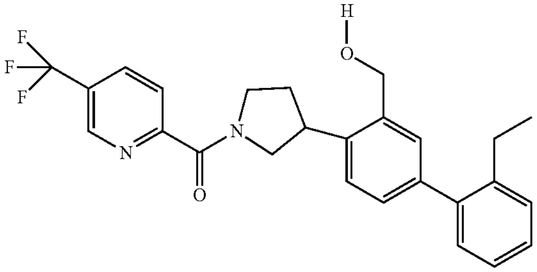 [SMILES: CCc1ccccc1-c1ccc(C2CCN(C(=O)c3ccc(C(F)(F)F)cn3)C2)c(CO)c1] | B | ND |

TABLE 2-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 2-48. | 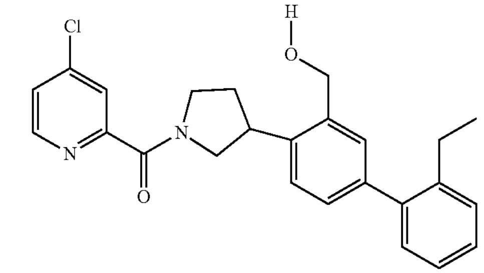 [SMILES: CCc1ccccc1-c1ccc(C2CCN(C(=O)c3cc(Cl)ccn3)C2)c(CO)c1] | B | ND |
| 2-49. | 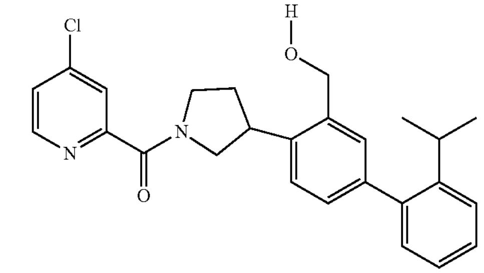 [SMILES: CC(C)c1ccccc1-c1ccc(C2CCN(C(=O)c3cc(Cl)ccn3)C2)c(CO)c1] | B | ND |
| 2-50. | 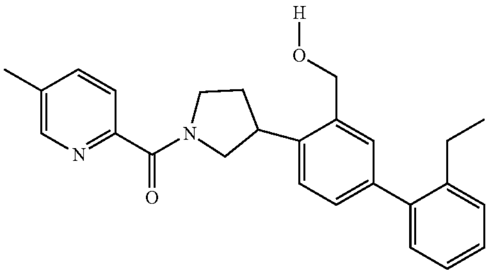 [SMILES: CCc1ccccc1-c1ccc(C2CCN(C(=O)c3ccc(C)cn3)C2)c(CO)c1] | B | ND |
| 2-51. | 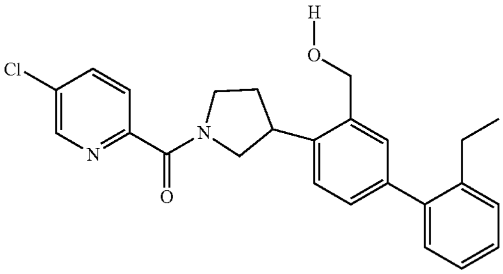 [SMILES: CCc1ccccc1-c1ccc(C2CCN(C(=O)c3ccc(Cl)cn3)C2)c(CO)c1] | A | ND |
| 2-52. | 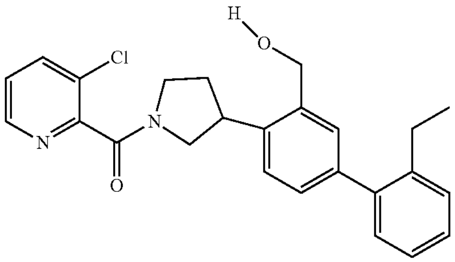 [SMILES: CCc1ccccc1-c1ccc(C2CCN(C(=O)c3ncccc3Cl)C2)c(CO)c1] | B | ND |

TABLE 2-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 2-53. | 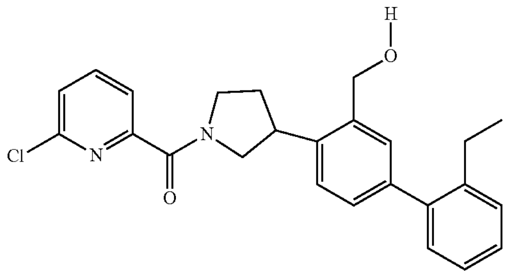 [SMILES: CCc1ccccc1-c1ccc(C2CCN(C(=O)c3cccc(Cl)n3)C2)c(CO)c1] | A | ND |
| 2-54. | 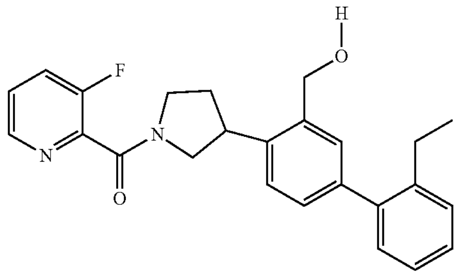 [SMILES: CCc1ccccc1-c1ccc(C2CCN(C(=O)c3ncccc3F)C2)c(CO)c1] | B | ND |
| 2-55. | 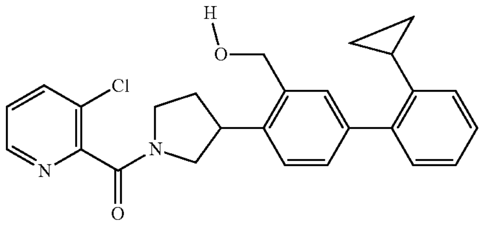 [SMILES: O=C(c1ncccc1Cl)N1CCC(c2ccc(-c3ccccc3C3CC3)cc2CO)C1] | B | ND |
| 2-56. | 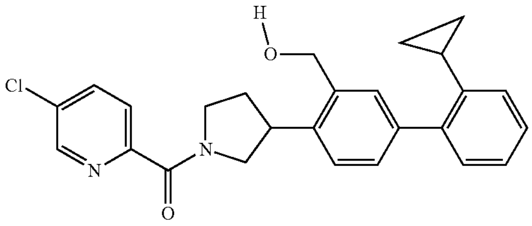 [SMILES: O=C(c1ccc(Cl)cn1)N1CCC(c2ccc(-c3ccccc3C3CC3)cc2CO)C1] | A | ND |
| 2-57. | 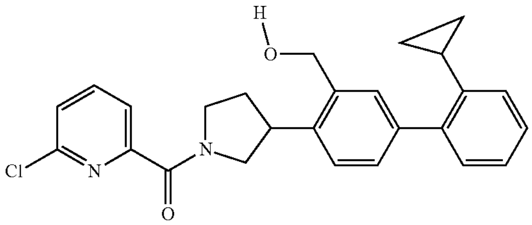 [SMILES: O=C(c1cccc(Cl)n1)N1CCC(c2ccc(-c3ccccc3C3CC3)cc2CO)C1] | A | ND |
| 2-58. | 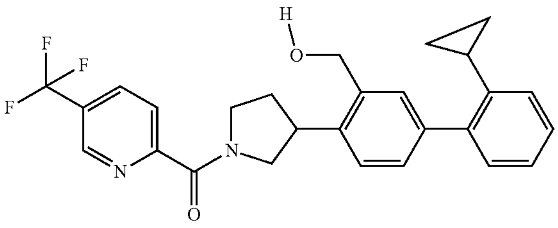 [SMILES: O=C(c1ccc(C(F)(F)F)cn1)N1CCC(c2ccc(-c3ccccc3C3CC3)cc2CO)C1] | B | ND |

TABLE 2-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 2-59. | 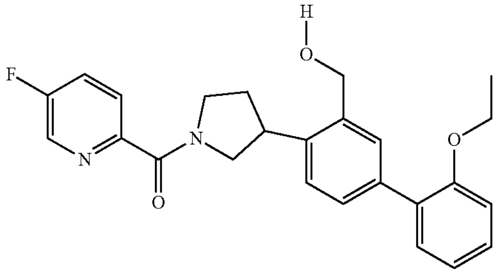 [SMILES: CCOc1ccccc1-c1ccc(C2CCN(C(=O)c3ccc(F)cn3)C2)c(CO)c1] | B | ND |
| 2-60. | 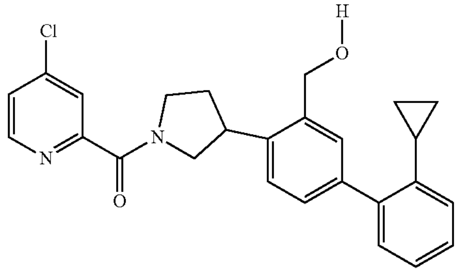 [SMILES: O=C(c1cc(Cl)ccn1)N1CCC(c2ccc(-c3ccccc3C3CC3)cc2CO)C1] | B | ND |
| 2-61. | 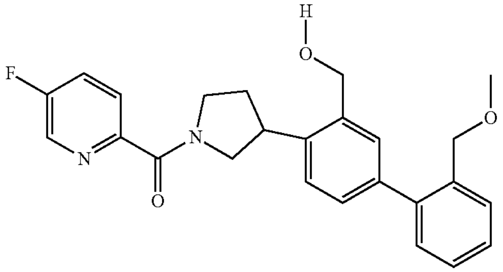 | C | ND |
| 2-62. | 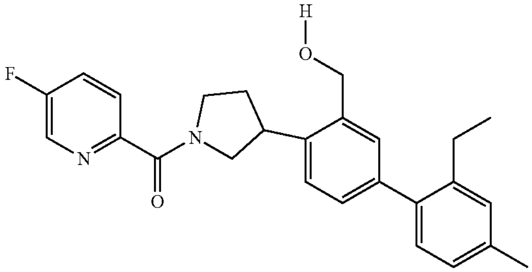 [SMILES: CCc1cc(C)ccc1-c1ccc(C2CCN(C(=O)c3ccc(F)cn3)C2)c(CO)c1] | B | ND |
| 2-63. | 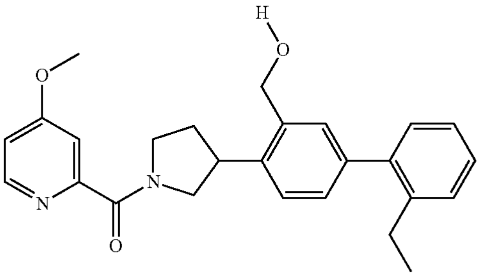 [SMILES: CCc1ccccc1-c1ccc(C2CCN(C(=O)c3cc(OC)ccn3)C2)c(CO)c1] | C | ND |

TABLE 2-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 2-64. | 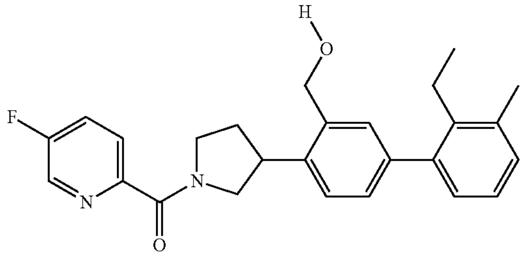 [SMILES: CCc1c(C)cccc1-c1ccc(C2CCN(C(=O)c3ccc(F)cn3)C2)c(CO)c1] | B | ND |
| 2-65. | 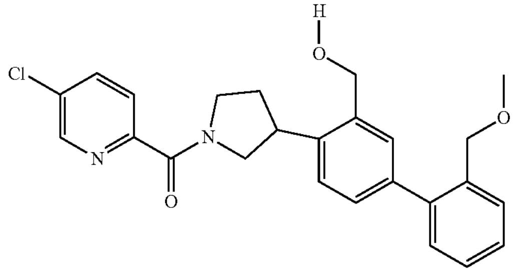 [SMILES: COCc1ccccc1-c1ccc(C2CCN(C(=O)c3ccc(Cl)cn3)C2)c(CO)c1] | B | ND |
| 2-66. | 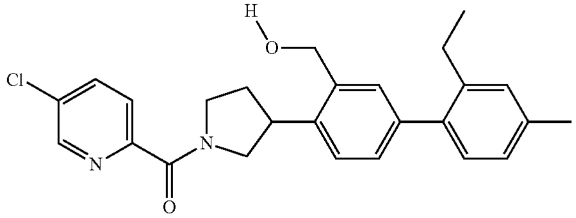 [SMILES: CCc1cc(C)ccc1-c1ccc(C2CCN(C(=O)c3ccc(Cl)cn3)C2)c(CO)c1] | B | ND |
| 2-67. | 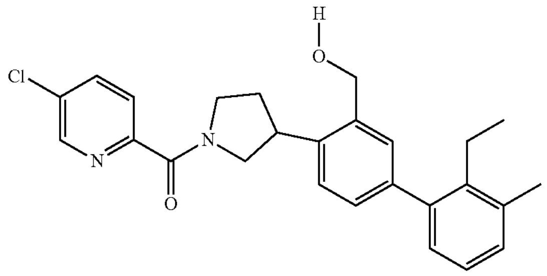 [SMILES: CCc1c(C)cccc1-c1ccc(C2CCN(C(=O)c3ccc(Cl)cn3)C2)c(CO)c1] | A | ND |
| 2-68. | 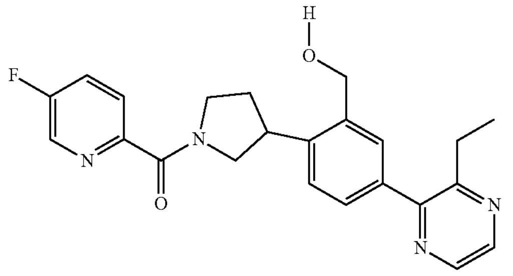 [SMILES: CCc1nccnc1-c1ccc(C2CCN(C(=O)c3ccc(F)cn3)C2)c(CO)c1] | D | ND |

TABLE 2-continued
Data from Patch Clamp Experiments of selected compounds
| Compound ID | Structure | hTRPV3 Patch P1 Inwd (nM) | hTRPV3 Patch P2 Inwd (nM) |
| --- | --- | --- | --- |
| 2-69. | 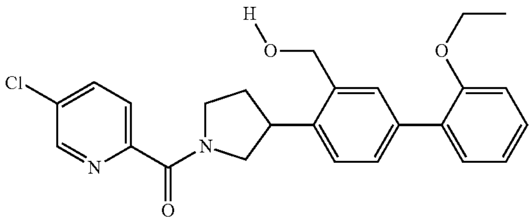 [SMILES: CCOc1ccccc1-c1ccc(C2CCN(C(=O)c3ccc(Cl)cn3)C2)c(CO)c1] | B | ND |
| 2-70. | 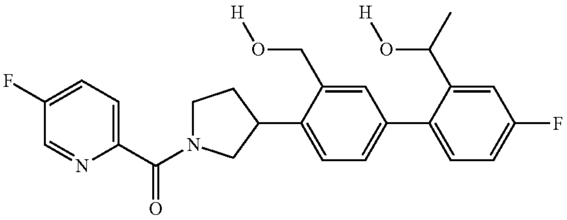 [SMILES: CC(O)c1cc(F)ccc1-c1ccc(C2CCN(C(=O)c3ccc(F)cn3)C2)c(CO)c1] | D | ND |
| 2-71. | 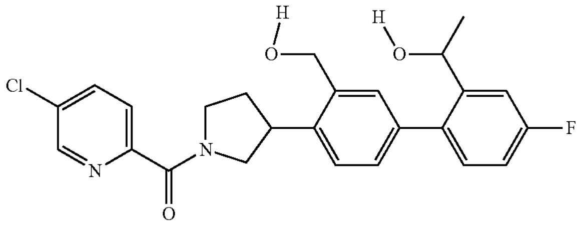 [SMILES: CC(O)c1cc(F)ccc1-c1ccc(C2CCN(C(=O)c3ccc(Cl)cn3)C2)c(CO)c1] | C | C |
| 2-72. | 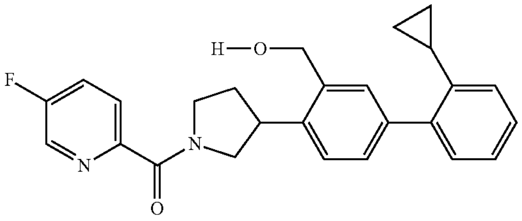 [SMILES: O=C(c1ccc(F)cn1)N1CCC(c2ccc(-c3ccccc3C3CC3)cc2CO)C1] | A | ND |
| 2-73. | 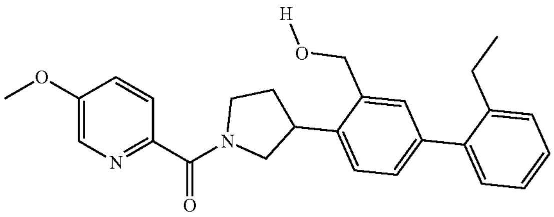 [SMILES: CCc1ccccc1-c1ccc(C2CCN(C(=O)c3ccc(OC)cn3)C2)c(CO)c1] | B | ND |
| 2-74. | 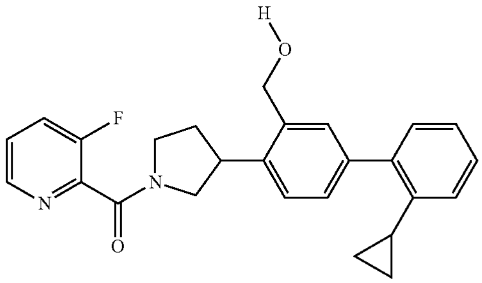 [SMILES: O=C(c1ncccc1F)N1CCC(c2ccc(-c3ccccc3C3CC3)cc2CO)C1] | B | B |

TABLE 2-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 2-75. | 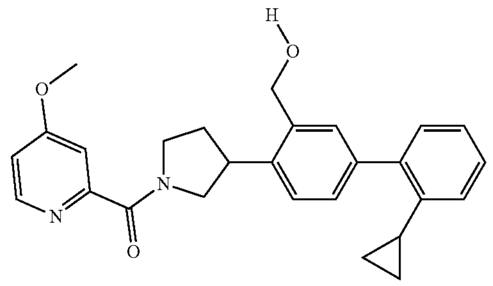 [SMILES: COc1ccnc(C(=O)N2CCC(c3ccc(-c4ccccc4C4CC4)cc3CO)C2)c1] | C | ND |
| 2-76. | 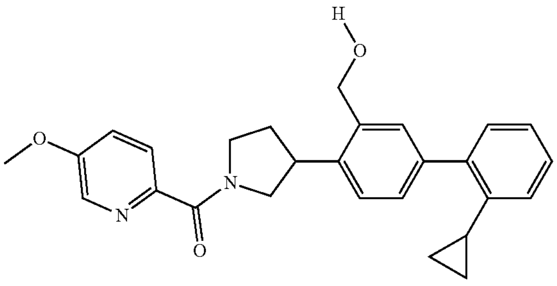 [SMILES: COc1ccc(C(=O)N2CCC(c3ccc(-c4ccccc4C4CC4)cc3CO)C2)nc1] | B | ND |
| 2-77. | 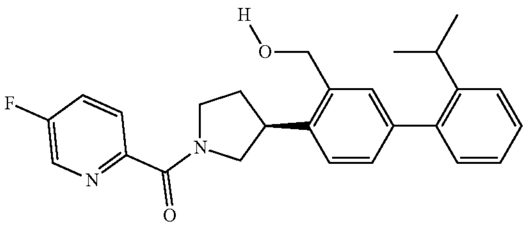 [SMILES: CC(C)c1ccccc1-c1ccc([C@@H]2CCN(C(=O)c3ccc(F)cn3)C2)c(CO)c1] | A | ND |
| 2-78. | 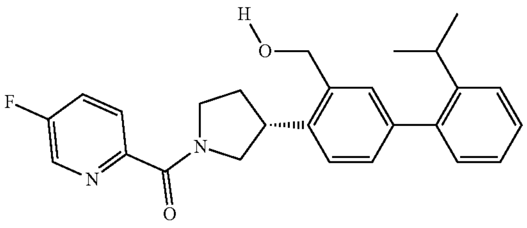 [SMILES: CC(C)c1ccccc1-c1ccc([C@H]2CCN(C(=O)c3ccc(F)cn3)C2)c(CO)c1] | C | ND |
| 2-79. | 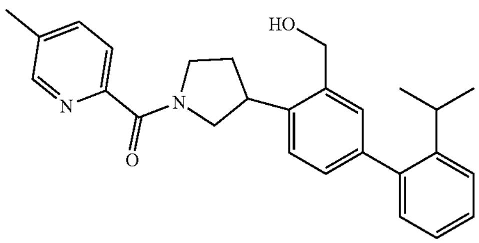 [SMILES: Cc1ccc(C(=O)N2CCC(c3ccc(-c4ccccc4C(C)C)cc3CO)C2)nc1] | B | ND |

TABLE 2-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 2-80. | 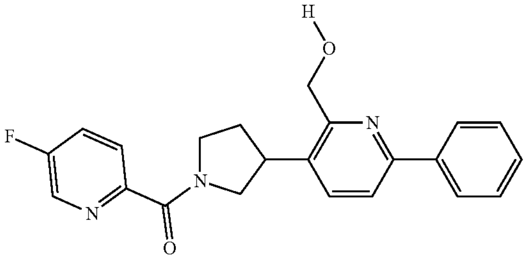 [SMILES: O=C(c1ccc(F)cn1)N1CCC(c2ccc(-c3ccccc3)nc2CO)C1] | C | ND |
| 2-81. | 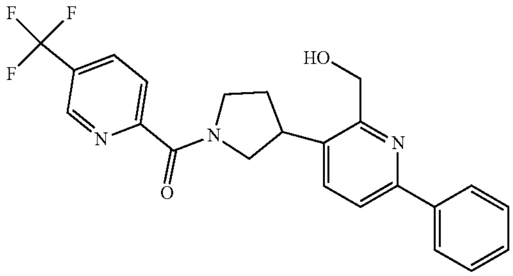 [SMILES: O=C(c1ccc(C(F)(F)F)cn1)N1CCC(c2ccc(-c3ccccc3)nc2CO)C1] | C | C |
| 2-82. | 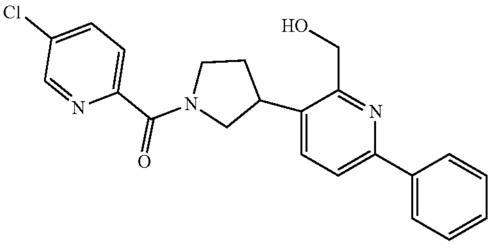 [SMILES: O=C(c1ccc(Cl)cn1)N1CCC(c2ccc(-c3ccccc3)nc2CO)C1] | C | ND |
| 2-83. | 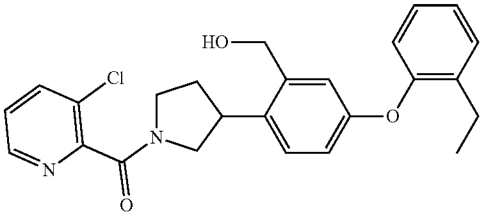 [SMILES: CCc1ccccc1Oc1ccc(C2CCN(C(=O)c3ncccc3Cl)C2)c(CO)c1] | — | — |
| 2-84. | 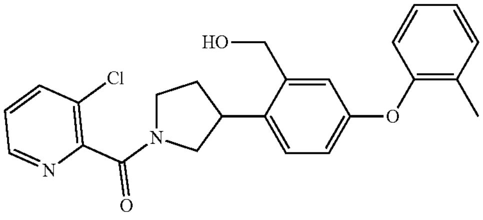 [SMILES: Cc1ccccc1Oc1ccc(C2CCN(C(=O)c3ncccc3Cl)C2)c(CO)c1] | — | — |

TABLE 2-continued
| Compound ID | Structure | hTRPV3 Patch P1 Inwd (nM) | hTRPV3 Patch P2 Inwd (nM) |
|---|---|---|---|
| Data from Patch Clamp Experiments of selected compounds | | | |
| 2-85. | 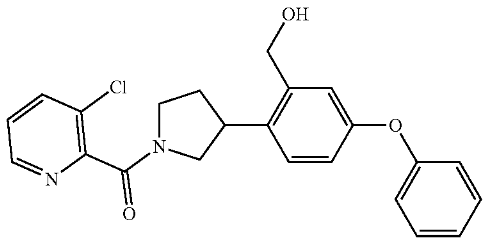 [SMILES: O=C(c1ncccc1Cl)N1CCC(c2ccc(Oc3ccccc3)cc2CO)C1] | — | — |
| 2-86. | 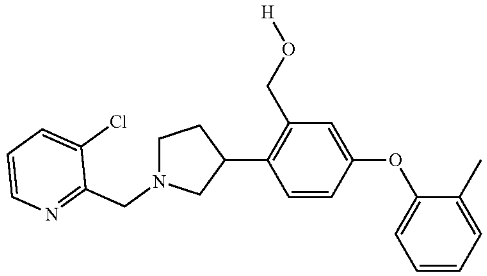 [SMILES: Cc1ccccc1Oc1ccc(C2CCN(Cc3ncccc3Cl)C2)c(CO)c1] | C | ND |
| 2-87. | 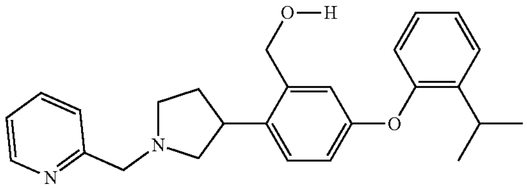 [SMILES: CC(C)c1ccccc1Oc1ccc(C2CCN(Cc3ccccn3)C2)c(CO)c1] | C | ND |
| 2-88. | 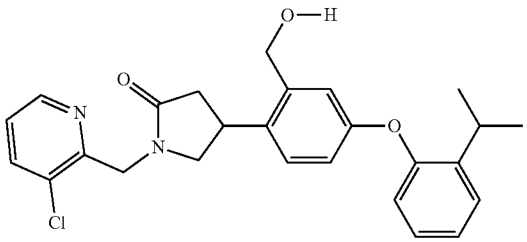 [SMILES: CC(C)c1ccccc1Oc1ccc(C2CC(=O)N(Cc3ncccc3Cl)C2)c(CO)c1] | C | C |
| 2-89. | 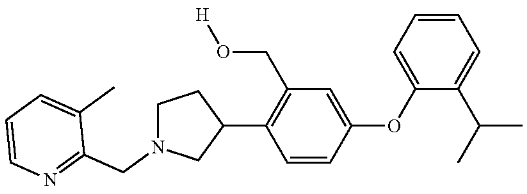 [SMILES: Cc1cccnc1CN1CCC(c2ccc(Oc3ccccc3C(C)C)cc2CO)C1] | D | ND |
| 2-90. | 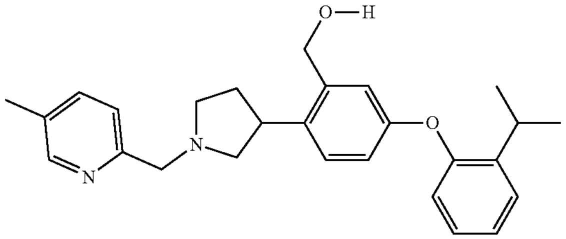 [SMILES: Cc1ccc(CN2CCC(c3ccc(Oc4ccccc4C(C)C)cc3CO)C2)nc1] | C | ND |

TABLE 2-continued
| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 2-91. | 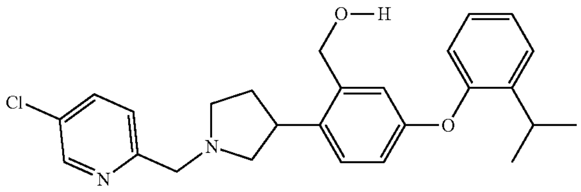 [SMILES: CC(C)c1ccccc1Oc1ccc(C2CCN(Cc3ccc(Cl)cn3)C2)c(CO)c1] | C | ND |
| 2-92. | 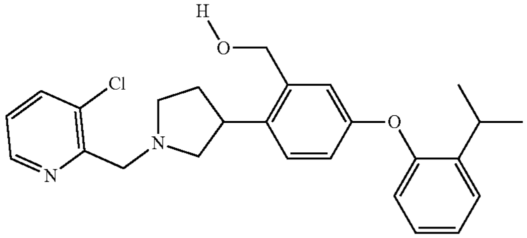 [SMILES: CC(C)c1ccccc1Oc1ccc(C2CCN(Cc3ncccc3Cl)C2)c(CO)c1] | C | ND |
| 2-93. | 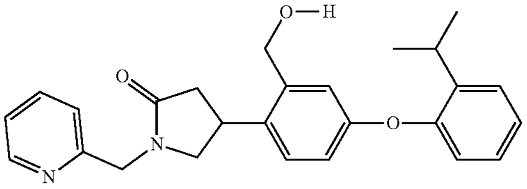 [SMILES: CC(C)c1ccccc1Oc1ccc(C2CC(=O)N(Cc3ccccn3)C2)c(CO)c1] | C | ND |
| 2-94. | 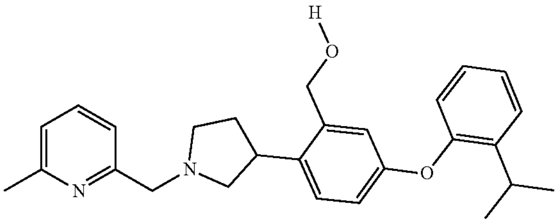 [SMILES: Cc1cccc(CN2CCC(c3ccc(Oc4ccccc4C(C)C)cc3CO)C2)n1] | C | ND |
| 2-95. | 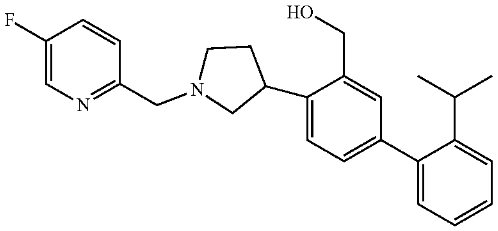 [SMILES: CC(C)c1ccccc1-c1ccc(C2CCN(Cc3ccc(F)cn3)C2)c(CO)c1] | C | ND |
| 2-96. | 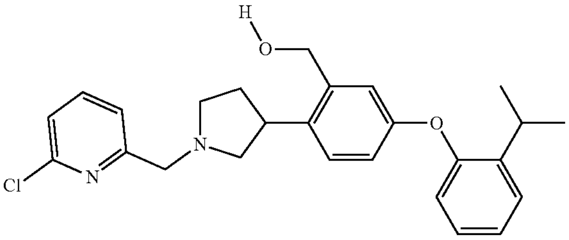 [SMILES: CC(C)c1ccccc1Oc1ccc(C2CCN(Cc3cccc(Cl)n3)C2)c(CO)c1] | C | ND |

TABLE 2-continued
Data from Patch Clamp Experiments of selected compounds
| Compound ID | Structure | hTRPV3 Patch P1 Inwd (nM) | hTRPV3 Patch P2 Inwd (nM) |
|---|---|---|---|
| 2-97. | 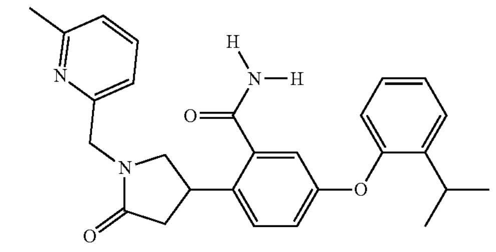 [SMILES: Cc1cccc(CN2CC(c3ccc(Oc4ccccc4C(C)C)cc3C(N)=O)CC2=O)n1] | D | ND |
| 2-98. | 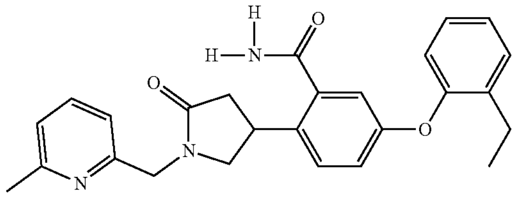 [SMILES: CCc1ccccc1Oc1ccc(C2CC(=O)N(Cc3cccc(C)n3)C2)c(C(N)=O)c1] | D | ND |
| 2-99. | 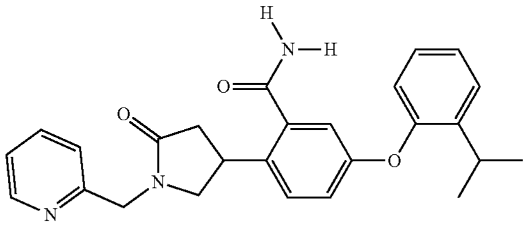 [SMILES: CC(C)c1ccccc1Oc1ccc(C2CC(=O)N(Cc3ccccn3)C2)c(C(N)=O)c1] | D | ND |
| 2-100. | 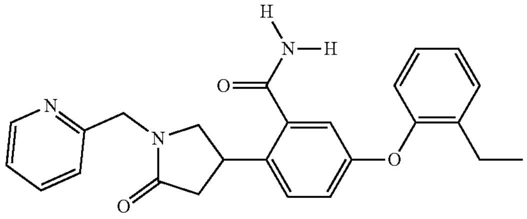 [SMILES: CCc1ccccc1Oc1ccc(C2CC(=O)N(Cc3ccccn3)C2)c(C(N)=O)c1] | D | ND |
| 2-101. | 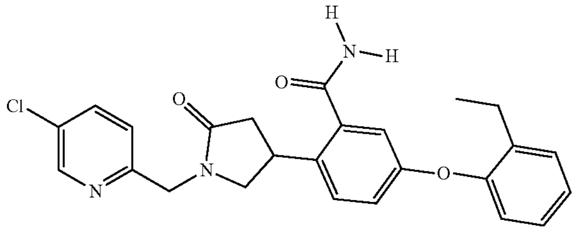 [SMILES: CCc1ccccc1Oc1ccc(C2CC(=O)N(Cc3ccc(Cl)cn3)C2)c(C(N)=O)c1] | D | ND |
| 2-102. | 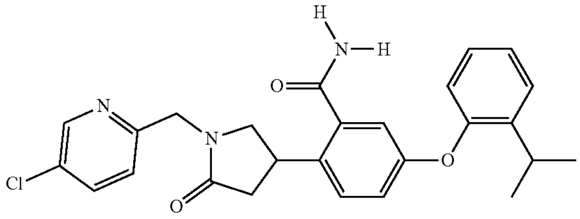 [SMILES: CC(C)c1ccccc1Oc1ccc(C2CC(=O)N(Cc3ccc(Cl)cn3)C2)c(C(N)=O)c1] | D | ND |

TABLE 2-continued
| Compound ID | Structure | hTRPV3 Patch P1 Inwd (nM) | hTRPV3 Patch P2 Inwd (nM) |
|---|---|---|---|
| Data from Patch Clamp Experiments of selected compounds | | | |
| 2-103. | 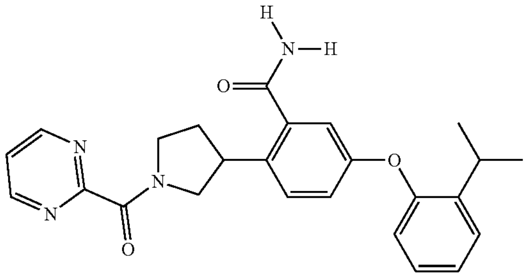 [SMILES: CC(C)c1ccccc1Oc1ccc(C2CCN(C(=O)c3ncccn3)C2)c(C(N)=O)c1] | D | ND |
| 2-104. | 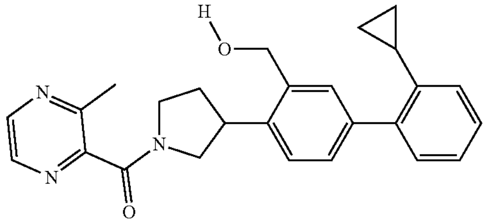 [SMILES: Cc1nccnc1C(=O)N1CCC(c2ccc(-c3ccccc3C3CC3)cc2CO)C1] | C | ND |
| 2-105. | 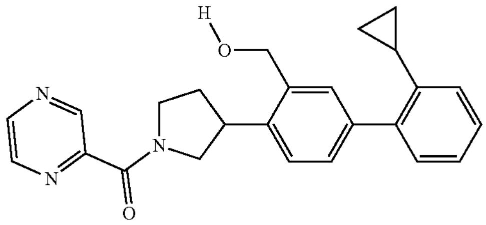 [SMILES: O=C(c1cnccn1)N1CCC(c2ccc(-c3ccccc3C3CC3)cc2CO)C1] | B | ND |
| 2-106. | 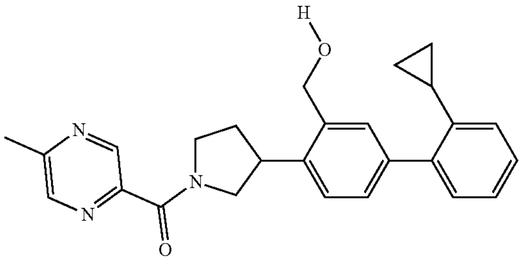 [SMILES: Cc1cnc(C(=O)N2CCC(c3ccc(-c4ccccc4C4CC4)cc3CO)C2)cn1] | B | ND |
| 2-107. | 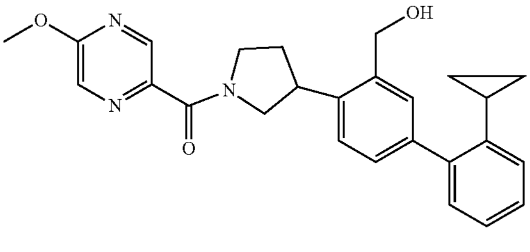 [SMILES: COc1cnc(C(=O)N2CCC(c3ccc(-c4ccccc4C4CC4)cc3CO)C2)cn1] | B | ND |
| 2-108. | 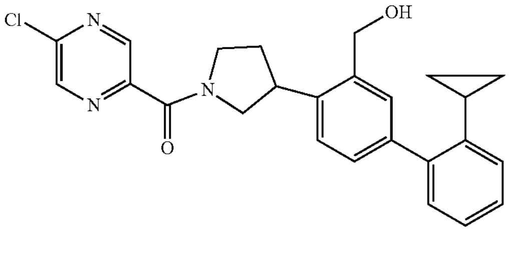 [SMILES: O=C(c1cnc(Cl)cn1)N1CCC(c2ccc(-c3ccccc3C3CC3)cc2CO)C1] | B | ND |

TABLE 2-continued
| Compound ID | Structure | hTRPV3 Patch P1 Inwd (nM) | hTRPV3 Patch P2 Inwd (nM) |
|---|---|---|---|
| Data from Patch Clamp Experiments of selected compounds | | | |
| 2-109. | 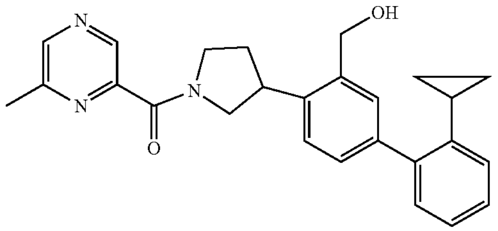 [SMILES: Cc1cncc(C(=O)N2CCC(c3ccc(-c4ccccc4C4CC4)cc3CO)C2)n1] | B | ND |
| 2-110. | 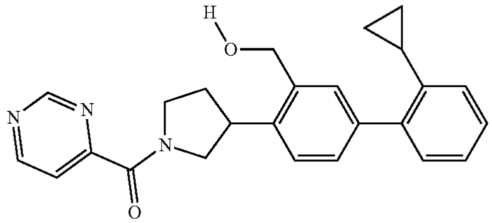 [SMILES: O=C(c1ccncn1)N1CCC(c2ccc(-c3ccccc3C3CC3)cc2CO)C1] | C | ND |
| 2-111. | 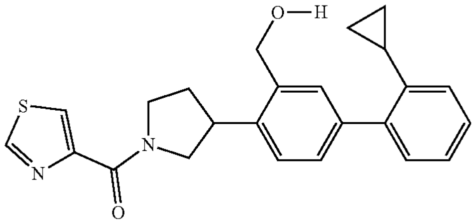 [SMILES: O=C(c1cscn1)N1CCC(c2ccc(-c3ccccc3C3CC3)cc2CO)C1] | C | ND |
| 2-112. | 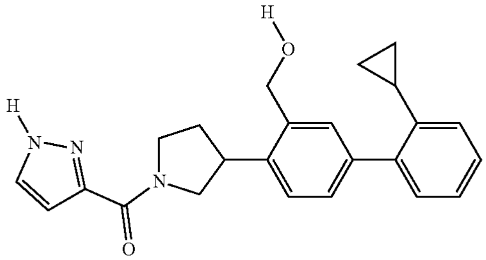 [SMILES: O=C(c1cc[nH]n1)N1CCC(c2ccc(-c3ccccc3C3CC3)cc2CO)C1] | B | ND |
| 2-113. | 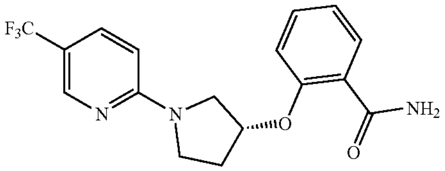 [SMILES: NC(=O)c1ccccc1O[C@@H]1CCN(c2ccc(C(F)(F)F)cn2)C1] | | |
| 2-114. | 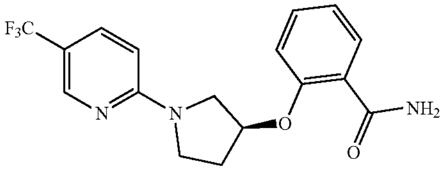 [SMILES: NC(=O)c1ccccc1O[C@H]1CCN(c2ccc(C(F)(F)F)cn2)C1] | | |

TABLE 2-continued

| Data from Patch Clamp Experiments of selected compounds | | | |
|---|---|---|---|
| Compound ID | Structure | hTRPV3 Patch P1 Inwd (nM) | hTRPV3 Patch P2 Inwd (nM) |
| 2-115. | 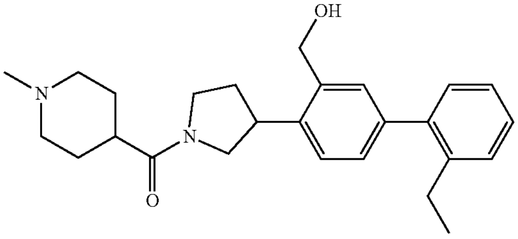 [SMILES: CCc1ccccc1-c1ccc(C2CCN(C(=O)C3CCN(C)CC3)C2)c(CO)c1] | | |

Tables 3 and 4 provide additional data obtained for particular compounds of the disclosure. In Tables 3 and 4, Phase 1 refers to Phase 1 current for human (h) TRPV3 or rat (r) TRPV3, and Phase 2 refers to Phase 2 current for human (h) TRPV3 or rat (r) TRPV3. The hTRPV3 and rTRPV3 assays were performed as described herein. hERG refers to the inhibition the human ERG (hERG) channel. NaV1.5, refers to the pore forming aL-subunit of the voltage-dependent cardiac Na(+) channel and is an integral membrane protein involved in the initiation and conduction of action potentials. hTRPV3 HAMA $IC_{50}$ refers to the $IC_{50}$ of TRPV3 cells stably expressed in TRex-293 cells. Solubility Ringer refers to the compounds' solubility in Ringer's solution. LM $T_{1/2}$ refers to liver microsome half-lives in either rat or human liver microsomes. FLIPR $IC_{50}$ refers to the $IC_{50}$ of the test compounds against recombinant hTRPV3 cells.

hERG assay: Briefly, cells from a stable CHO cell line expressing human hERG channels were plated onto glass coverslips and used in patch clamp assays on the same day. After seal formation and break-in to whole-cell configuration, voltage steps were applied as follows: from the holding potential of −90 mV, a 2 second long step to +40 mV was applied, followed by a 1.5 second step to −50 mV. These steps were applied once every 5 seconds. The hERG current was measured at the peak of the outward tail current at −50 mV. The pipette solution was potassium aspartate based and the external solution was normal Ringer's.

All currents were recorded in whole-cell configuration using an Axopatch 200B controlled by pClamp 10 software (Molecular Devices). In each cell, when the current stabilized, the compound was perfused locally onto the cell. Two to three concentrations of the test compound were applied to each cell. At the end of compound testing, 10 μM verapamil was applied to completely block hERG currents and assess leak current.

Data were analyzed by computing the degree of current block after compound addition compared with the unblocked current amplitude. The unblocked current was predicted from the interpolation between the current amplitude prior to compound addition and after compound washout. The resulting percent block at each concentration was used to make a concentration-response plot and fitted to the Hill equation: percent block=minimum block+(maximum block-minimum block)/(1+10^(Hill slope*(log $IC_{50}$–concentration))). The minimum block was 0% and maximum block was 100% (determined by unblocked and positive control block conditions, respectively) while the Hill slope and the $IC_{50}$ are determined by the curve fitting routine.

hNaV1.5 assay: Human $Na_v1.5$ was stably expressed in HEK-293 cells. Cells were prepared for assay by trypsinization and replating onto glass coverslips on the morning of the assay. Compounds were prepared in Ringer solution at 320 nM, 1, 3.2, 10 or 32 mM by direct dilution from 10 mM DMSO stock. Compound preparation occurred immediately before assaying.

$Na_v1.5$ was activated by a voltage step protocol on a Nanion Pathchliner. A cesium fluoride internal solution was used. Normal ringer solution served as the external solution. Data were analyzed by computing the degree of current block after compound addition compared with the unblocked current amplitude. The unblocked current was predicted from the interpolation between the current amplitude prior to compound addition and after compound washout. The resulting percent block at each concentration was used to make a concentration-response plot and fitted to the Hill equation: percent block=minimum block+(maximum block-minimum block)/(1+10^(Hill slope*(log $IC_{50}$–concentration))). The minimum block was 0% and maximum block was 100% (determined by unblocked and positive control block conditions, respectively) while the Hill slope and the $IC_{50}$ are determined by the curve fitting routine.

hTRPV3 HAMA $IC_{50}$ assay: TRex-293 cells stably expressing TRPV3 were plated into black-sided, clear bottom, 384-well plates, induced with tertacycline and assayed 24-30 hours later on a Hamamatsu FDSS6000. Cells were loaded with the fluorescent calcium indicator Fluo-4AM (1.25 uM) or Fura-2AM (2.5 uM). Calcium ion flux was stimulated by the addition of 2-APB at a final concentration of 200 uM. Test compounds were tested in triplicate at concentrations that typically ranged from 27 nM to 20 uM. A Z' was calculated for each plate and any plates with Z' values less than 0.4 were discarded. IC50s were calculated using CBIS from ChemInnovation (San Diego).

Aqueous solubility assay: Briefly, solubility in Normal Ringer Solution was determined by dissolving a standard range of volumes of stock (e.g. in 10 μM DMSO) of indicated compounds in Normal Ringer Solution at room temperature. Following vortex and incubation for a sufficient time (e.g. 40 minutes at room temperature), solutions were filtered, quenched with acetonitrile, and analyzed by Liquid Chromotography. Solubility Limits were determined by comparison to a standard curve.

Metabolic Stability assay: The metabolic stability was determined by adding compound dissolved in DMSO to human or rat, liver microsomes. Briefly, assays were run with a starting concentration of 1 μM test article. The reaction was started by addition of NADPH regeneration components at 37° C. at which time an aliquot was immediately quenched in ice-cold acetonitrile/MeOH/$H_2O$ solution. Reaction mixture was incubated at 37° C. on a shaker, and additional aliquots were taken at 7, 15, 30 and 60 minutes. Following quench and centrifugation, samples were analyzed on HPLC/MS/MS.

FLIPR Assay: HEK293 cells stably expressing TRPV3 were plated onto 96-well, black walled transparent bottom, 384-well plates in culture media and maintained at 37° C. and 500 $C_2$ overnight. The cells were treated with IBSS and 20 mM HEPES adjusted to pH 7.4 in the presence of the fluorescent calcium indicator e.g. Fluo-4AM (5 uM) and the plates were incubated at 37° C. and 500 $CO_2$ for approximately 1 hour and cooled to room temperature. Test compounds were added at the optimized parameters and calcium ion flux was stimulated by the addition of appropriate agonist e.g. 2-APB (5-6× volume of $EC_{80}$ concentration). Relative Fluorescence Units (RFU) were measured for each response for signal maximum minus minimum during approximately 90 seconds after addition.

TABLE 3

| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-27 | 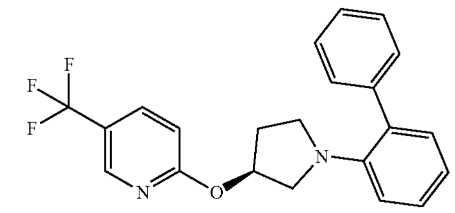 [SMILES: FC(F)(F)c1ccc(O[C@H]2CCN(c3ccccc3-c3ccccc3)C2)nc1] | >3200 (Phase 1) | | | | no fit (5 min) | | |
| 1-28 | 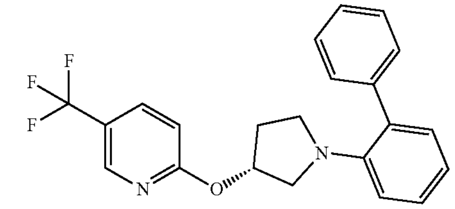 [SMILES: FC(F)(F)c1ccc(O[C@@H]2CCN(c3ccccc3-c3ccccc3)C2)nc1] | >3200 (Phase 1) | | | | no fit (5 min) | | |
| 1-31 | 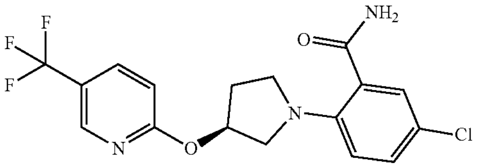 [SMILES: NC(=O)c1cc(Cl)ccc1N1CC[C@H](Oc2ccc(C(F)(F)F)cn2)C1] | ~883 (Phase 1) 546 (Phase 2) | | | | no fit (5 min) | >16800 | 34.3 (rat) |
| 1-32 | 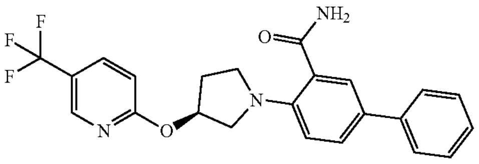 [SMILES: NC(=O)c1cc(-c2ccccc2)ccc1N1CC[C@H](Oc2ccc(C(F)(F)F)cn2)C1] | 285 (Phase 1) !273 (Phase 2) | | | | no fit (5 min) | BLQ | 44.3 (rat) |
| 1-33 | 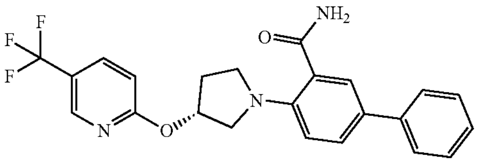 [SMILES: NC(=O)c1cc(-c2ccccc2)ccc1N1CC[C@@H](Oc2ccc(C(F)(F)F)cn2)C1] | 139 (Phase 1) | 283 (Phase 1) 776 (Phase 2) | | | no fit (5 min) | | |
| 1-56 | 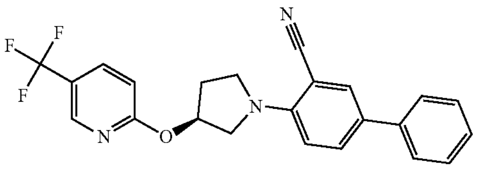 [SMILES: N#Cc1cc(-c2ccccc2)ccc1N1CC[C@H](Oc2ccc(C(F)(F)F)cn2)C1] | ~504 (Phase 2) | | | | R2 fail (5 min) | | |

TABLE 3-continued

| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-57 | 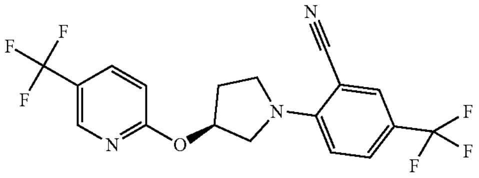 [SMILES: N#Cc1cc(C(F)(F)F)ccc1N1CC[C@H](Oc2ccc(C(F)(F)F)cn2)C1] | !706 (Phase 1) 219 (Phase 2) | | | | no fit (5 min) | BLQ | |
| 1-58 | 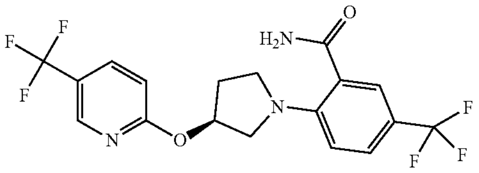 [SMILES: NC(=O)c1cc(C(F)(F)F)ccc1N1CC[C@H](Oc2ccc(C(F)(F)F)cn2)C1] | Flag/ 1250/ 1520/ >3200/ 1040 (Phase 1) 241 (Phase 2) | | | | no fit (5 min) | >11300 | >60 (human) >60 (rat) |
| 1-64 | 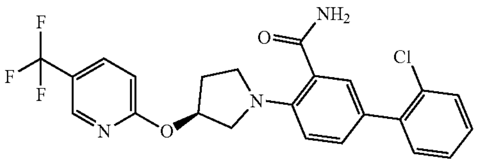 [SMILES: NC(=O)c1cc(-c2ccccc2Cl)ccc1N1CC[C@H](Oc2ccc(C(F)(F)F)cn2)C1] | 145 (Phase 1) 160 (Phase 2) | | | | no fit (5 min) | BLQ | |
| 1-65 | 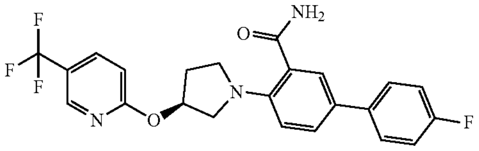 [SMILES: NC(=O)c1cc(-c2ccc(F)cc2)ccc1N1CC[C@H](Oc2ccc(C(F)(F)F)cn2)C1] | !475 (Phasee 1) !417 (Phase 2) | !1140 (Phase 1) !3250 (Phase 2) | | | no fit (5 min) | BLQ | 77.3 (rat) |
| 1-66 | 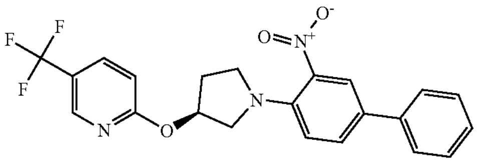 [SMILES: O=[N+]([O-])c1cc(-c2ccccc2)ccc1N1CC[C@H](Oc2ccc(C(F)(F)F)cn2)C1] | Incomplete Block (Phase 1) | | | | no fit (5 min) | BLQ | |
| 1-67 | 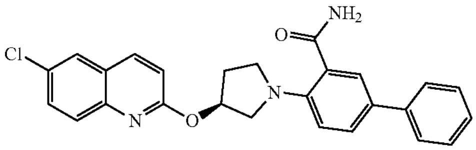 [SMILES: NC(=O)c1cc(-c2ccccc2)ccc1N1CC[C@H](Oc2ccc3cc(Cl)ccc3n2)C1] | !1270 (Phase 1) !585 (Phase 2) | | | | no fit (5 min) | BLQ | |
| 1-68 | 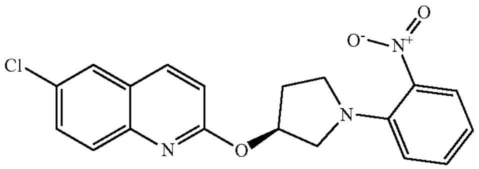 | >3200 (Phase 1) >3200 (Phase 2) | | | | no fit (5 min) | | |
| 1-69 | 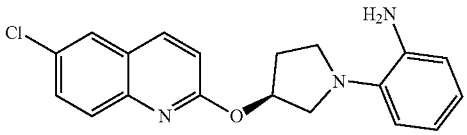 | Agonist (Phase 2) | | | | no fit (5 in) | | |
| 1-70 | 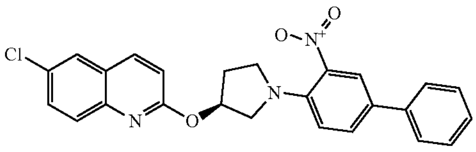 | >3200 (Phase 1) >3200 (Phase 2) | | | | no fit (5 min) | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-71 | 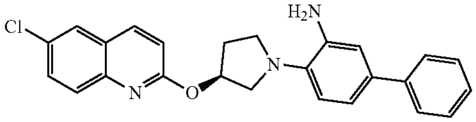 [SMILES: Nc1cc(-c2ccccc2)ccc1N1CC[C@H](Oc2ccc3cc(Cl)ccc3n2)C1] | >3200 (Phase 1) >3200 (Phase 2) | | | | no fit (5 min) | | |
| 1-72 | 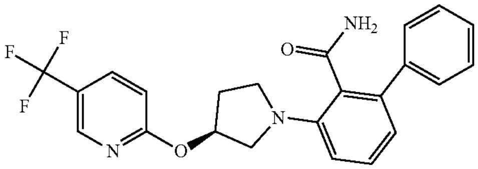 [SMILES: NC(=O)c1c(-c2ccccc2)cccc1N1CC[C@H](Oc2ccc(C(F)(F)F)cn2)C1] | Agonist (Phase 1) >3200 (Phase 2) | | | | no fit (5 min) | | |
| 1-73 | 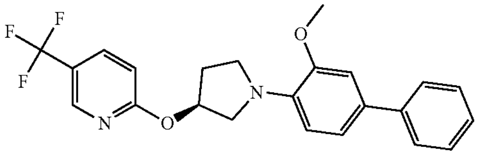 [SMILES: COc1cc(-c2ccccc2)ccc1N1CC[C@H](Oc2ccc(C(F)(F)F)cn2)C1] | ~86.3 (Phase 1) <100 (Phase 2) | | | | no fit (5 min) | BLQ | |
| 1-74 | 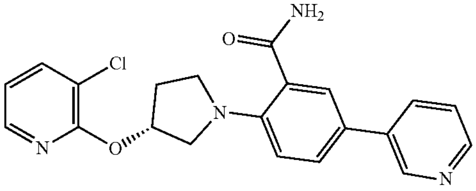 [SMILES: NC(=O)c1cc(-c2cccnc2)ccc1N1CC[C@@H](Oc2ncccc2Cl)C1] | ~5040 (Phase 2) | | | | | >13500 | |
| 1-75 | 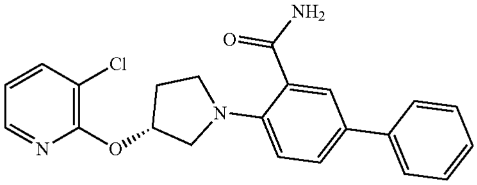 [SMILES: NC(=O)c1cc(-c2ccccc2)ccc1N1CC[C@@H](Oc2ncccc2Cl)C1] | !~2300 (Phase 1) !342 (Phase 2) | | | | | 320 | |
| 1-76 | 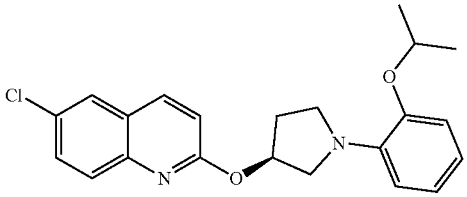 [SMILES: CC(C)Oc1ccccc1N1CC[C@H](Oc2ccc3cc(Cl)ccc3n2)C1] | !>3200 (Phase 1) !~4600 (Phase 2) | | | | | BLQ | |
| 1-77 | 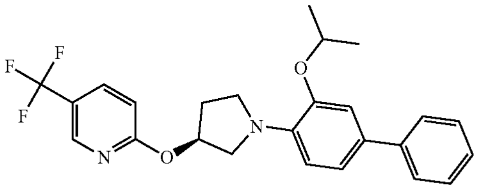 [SMILES: CC(C)Oc1cc(-c2ccccc2)ccc1N1CC[C@H](Oc2ccc(C(F)(F)F)cn2)C1] | >3200 (Phase 1) 1470 (Phase 2) | | | | | | |
| 1-78 | 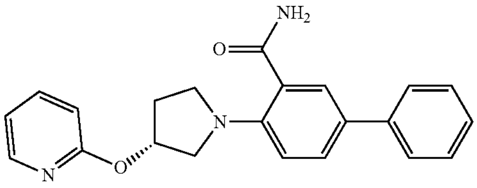 [SMILES: NC(=O)c1cc(-c2ccccc2)ccc1N1CC[C@@H](Oc2ccccn2)C1] | ~835 (Phase 1) 402 (Phase 2) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-79 | 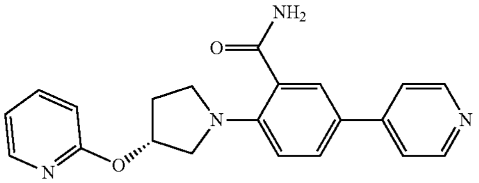 [SMILES: NC(=O)c1cc(-c2ccncc2)ccc1N1CC[C@@H](Oc2ccccn2)C1] | >3200 (Phase 1) >3200 (Phase 2) | | | | | | |
| 1-80 | 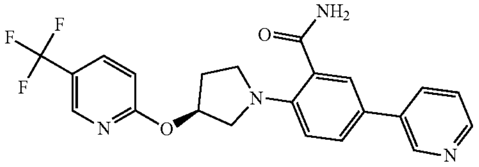 [SMILES: NC(=O)c1cc(-c2cccnc2)ccc1N1CC[C@H](Oc2ccc(C(F)(F)F)cn2)C1] | >3200 (Phase 1) !~5900 (Phase 2) | | | | | >3300 | |
| 1-81 | 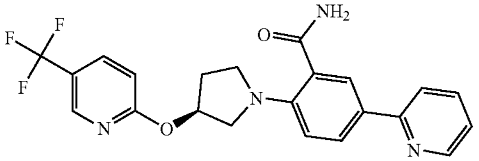 [SMILES: NC(=O)c1cc(-c2ccccn2)ccc1N1CC[C@H](Oc2ccc(C(F)(F)F)cn2)C1] | !>3200 (Phase 1) !2190 (Phase 2) | | | | | ~1400 | |
| 1-82 | 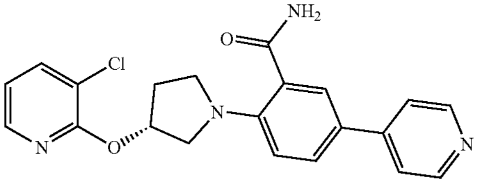 [SMILES: NC(=O)c1cc(-c2ccncc2)ccc1N1CC[C@@H](Oc2ncccc2Cl)C1] | 3600 (Phase 1) 1930 (Phase 2) | | | | | | |
| 1-83 | 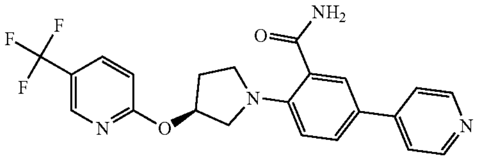 [SMILES: NC(=O)c1cc(-c2ccncc2)ccc1N1CC[C@H](Oc2ccc(C(F)(F)F)cn2)C1] | 2840 (Phase 1) 3350 (Phase 2) | | | | | >3900 | |
| 1-84 | 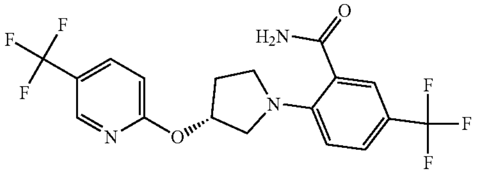 [SMILES: NC(=O)c1cc(C(F)(F)F)ccc1N1CC[C@@H](Oc2ccc(C(F)(F)F)cn2)C1] | 631 (Phase 1) | | | | | | |
| 1-85 | 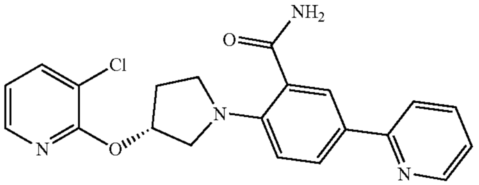 [SMILES: NC(=O)c1cc(-c2ccccn2)ccc1N1CC[C@@H](Oc2ncccc2Cl)C1] | 3480 (Phase 1) | | | | | | |
| 1-86 | 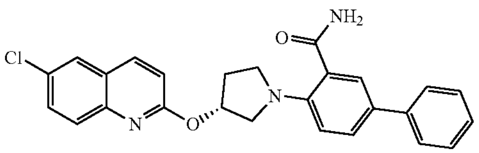 [SMILES: NC(=O)c1cc(-c2ccccc2)ccc1N1CC[C@@H](Oc2ccc3cc(Cl)ccc3n2)C1] | >3200 (Phase 2) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-87 | 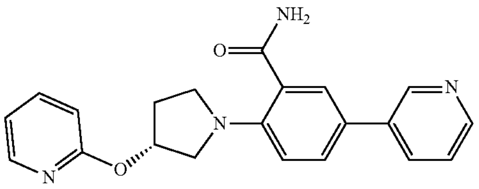 [SMILES: NC(=O)c1cc(-c2cccnc2)ccc1N1CC[C@@H](Oc2ccccn2)C1] | >3200 (Phase 1) | | | | | | |
| 1-88 | 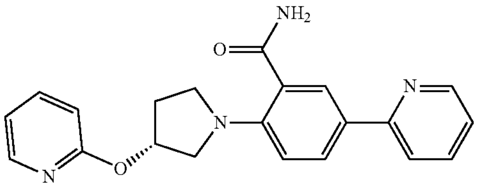 [SMILES: NC(=O)c1cc(-c2ccccn2)ccc1N1CC[C@@H](Oc2ccccn2)C1] | >3200 (Phase 1) >3200 (Phase 2) | | | | | | |
| 1-375 | 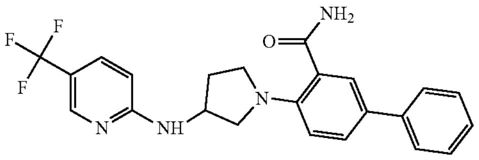 [SMILES: NC(=O)c1cc(-c2ccccc2)ccc1N1CCC(Nc2ccc(C(F)(F)F)cn2)C1] | >1000 (Phase 1) >1000 (Phase 2) | | | | | | |
| 1-89 | 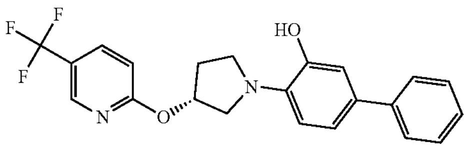 [SMILES: Oc1cc(-c2ccccc2)ccc1N1CC[C@@H](Oc2ccc(C(F)(F)F)cn2)C1] | >3200 (Phase 1) >3200 (Phase 2) | | | | | | |
| 1-90 | 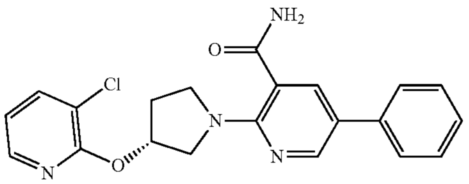 [SMILES: NC(=O)c1cc(-c2ccccc2)cnc1N1CC[C@@H](Oc2ncccc2Cl)C1] | ~3000 (Phase 1) 1600 (Phase 2) | | | | | | |
| 1-91 | 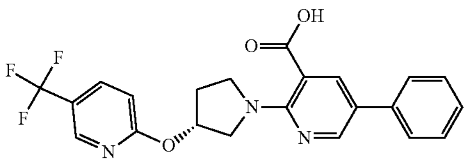 [SMILES: O=C(O)c1cc(-c2ccccc2)cnc1N1CC[C@@H](Oc2ccc(C(F)(F)F)cn2)C1] | Agonist (Phase 1) | | | | | | |
| 1-92 | 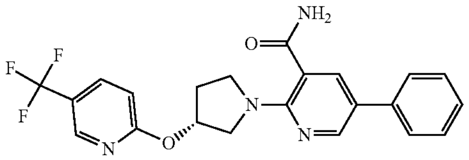 [SMILES: NC(=O)c1cc(-c2ccccc2)cnc1N1CC[C@@H](Oc2ccc(C(F)(F)F)cn2)C1] | Incomplete Block (Phase 1) Incomplete Block (Phase 2) | | | | | | |
| 1-373 | 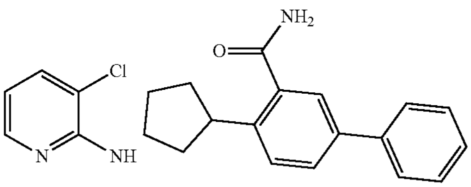 | 669 (Phase 2) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-374 | 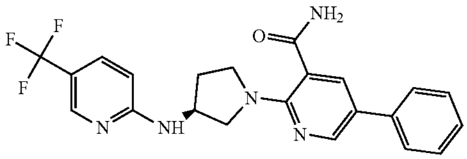 [SMILES: NC(=O)c1cc(-c2ccccc2)cnc1N1CC[C@H](Nc2ccc(C(F)(F)F)cn2)C1] | >3200 (Phase 1) >3200 (Phase 2) | | | | | | |
| 1-93 | 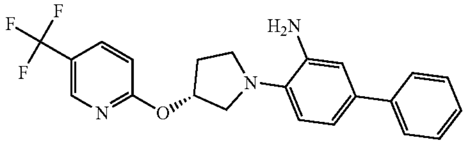 | Flag/ Incomplete Block/ Incomplete Block/494/ <320 (Phase 2) | | | | | | |
| 1-375 | 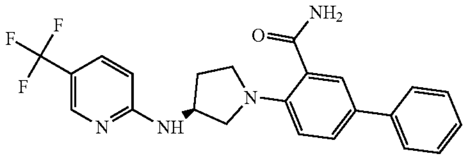 [SMILES: NC(=O)c1cc(-c2ccccc2)ccc1N1CC[C@H](Nc2ccc(C(F)(F)F)cn2)C1] | ~5500 (Phase 1) ~2850 (Phase 2) | | | | | | |
| 1-376 | 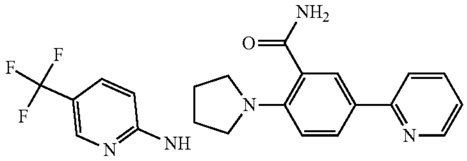 | >3200 (Phase 1) >3200 (Phase 2) | | | | | | |
| 1-94 | 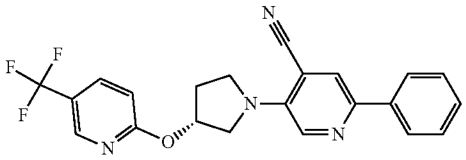 [SMILES: N#Cc1cc(-c2ccccc2)ncc1N1CC[C@@H](Oc2ccc(C(F)(F)F)cn2)C1] | Flag/ Incomplete Block/ Incomplete Block/~117 (Phase 2) | | | | | BLQ | |
| 1-95 | 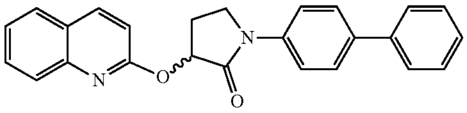 [SMILES: O=C1C(Oc2ccc3ccccc3n2)CCN1c1ccc(-c2ccccc2)cc1] | >3200 (Phase 1) | | | | | | |
| 1-96 | 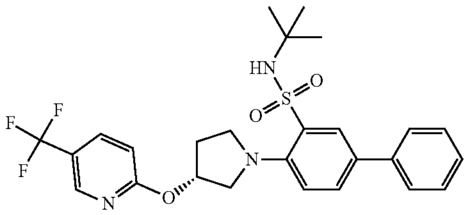 [SMILES: CC(C)(C)NS(=O)(=O)c1cc(-c2ccccc2)ccc1N1CC[C@@H](Oc2ccc(C(F)(F)F)cn2)C1] | >3200 (Phase 1) >3200 (Phase 2) | | | | | | |
| 1-377 | 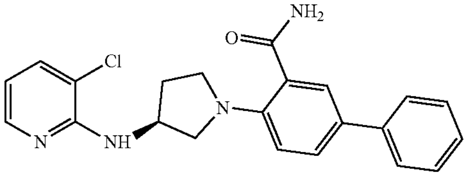 [SMILES: NC(=O)c1cc(-c2ccccc2)ccc1N1CC[C@H](Nc2ncccc2Cl)C1] | 360 (Phase 1) 318 (Phase 2) | | | | | >3200 | 35.6 (rat) |
| 1-97 | 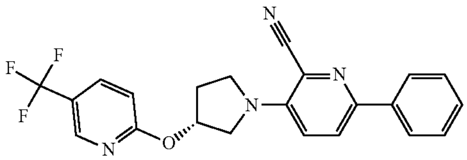 [SMILES: N#Cc1nc(-c2ccccc2)ccc1N1CC[C@@H](Oc2ccc(C(F)(F)F)cn2)C1] | 2930 (Phase 2) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-98 | 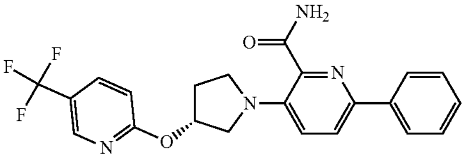 [SMILES: NC(=O)c1nc(-c2ccccc2)ccc1N1CC[C@@H](Oc2ccc(C(F)(F)F)cn2)C1] | 479 (Phase 1) | | | | | | |
| 1-99 | 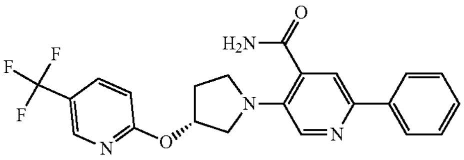 [SMILES: NC(=O)c1cc(-c2ccccc2)ncc1N1CC[C@@H](Oc2ccc(C(F)(F)F)cn2)C1] | ~787 (Phase 1) 349 (Phase 2) | | | | | | |
| 1-100 | 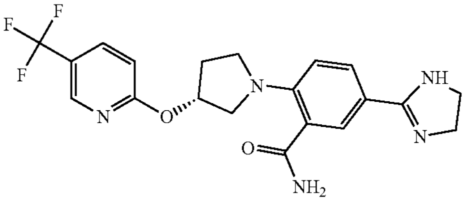 [SMILES: NC(=O)c1cc(C2=NCCN2)ccc1N1CC[C@@H](Oc2ccc(C(F)(F)F)cn2)C1] | >3200 (Phase 1) >3200 (Phase 2) | | | | | | |
| 1-101 | 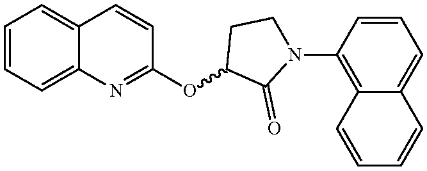 [SMILES: O=C1C(Oc2ccc3ccccc3n2)CCN1c1cccc2ccccc12] | >1000 (Phase 1) >1000 (Phase 2) | | | | | | |
| 1-102 | 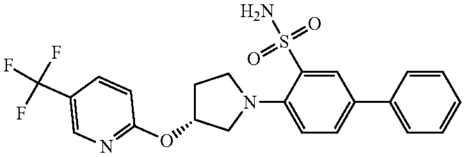 [SMILES: NS(=O)(=O)c1cc(-c2ccccc2)ccc1N1CC[C@@H](Oc2ccc(C(F)(F)F)cn2)C1] | !1660 (Phase 1) !1390 (Phase 2) | | | | | ~230 | |
| 1-378 | 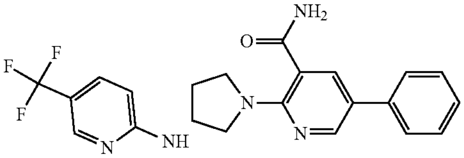 | >3200 (Phase 1) >3200 (Phase 2) | | | | | | |
| 1-103 | 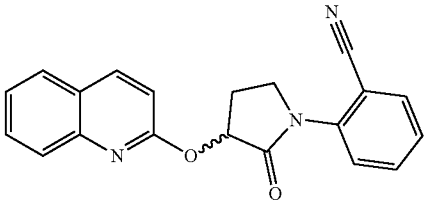 [SMILES: N#Cc1ccccc1N1CCC(Oc2ccc3ccccc3n2)C1=O] | >3200 (Phase 1) | | | | | | |
| 1-104 | 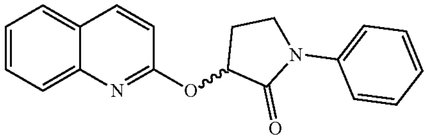 [SMILES: O=C1C(Oc2ccc3ccccc3n2)CCN1c1ccccc1] | >3200 (Phase 1) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-105 | 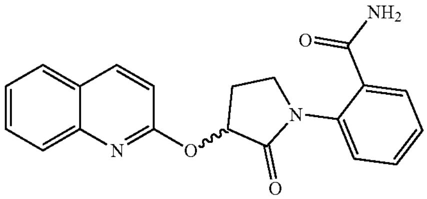 [SMILES: NC(=O)c1ccccc1N1CCC(Oc2ccc3ccccc3n2)C1=O] | >3200 (Phase 1) | | | | | | |
| 1-106 | 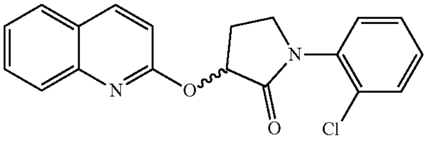 [SMILES: O=C1C(Oc2ccc3ccccc3n2)CCN1c1ccccc1Cl] | >3200 (Phase 1) >3200 (Phase 2) | | | | | | |
| 1-107 | 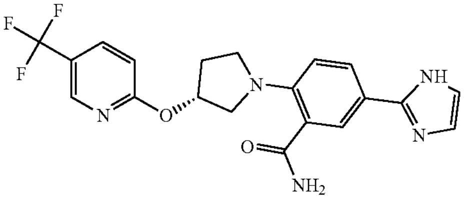 | >1000 (Phase 1) >1000 (Phase 2) | | | | | | |
| 1-108 | 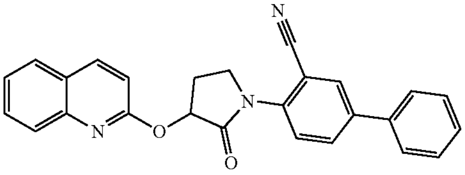 [SMILES: N#Cc1cc(-c2ccccc2)ccc1N1CCC(Oc2ccc3ccccc3n2)C1=O] | >3200 (Phase 2) | | | | | | |
| 1-109 | 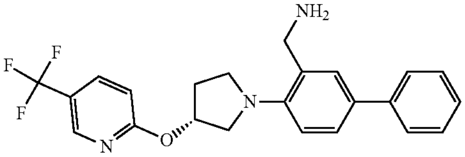 [SMILES: OCc1cc(-c2ccccc2)ccc1N1CC[C@@H](Oc2ccc(C(F)(F)F)cn2)C1] | 1870 (Phase 1) 1930 (Phase 2) | | | | | >2950 | |
| 1-110 | 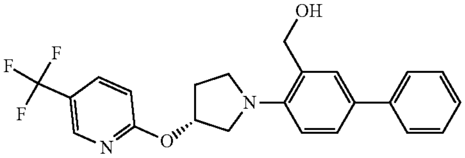 | !710 (Phase 1) !685 (Phase 2) | | | | | BLQ | |
| 1-111 | 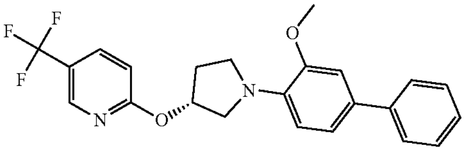 [SMILES: COc1cc(-c2ccccc2)ccc1N1CC[C@@H](Oc2ccc(C(F)(F)F)cn2)C1] | !3280 (Phase 1) | | | | | BLQ | |
| 1-112 | 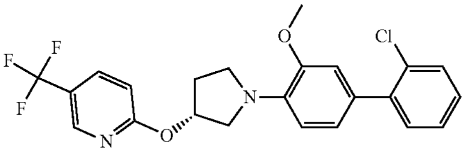 [SMILES: COc1cc(-c2ccccc2Cl)ccc1N1CC[C@@H](Oc2ccc(C(F)(F)F)cn2)C1] | ~2900 (Phase 1) Incomplete Block (Phase 2) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-113 | 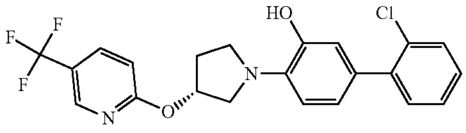 | ~97.5 (Phase 1) 109 (Phase 2) | | | | | BLQ | 33.5 (rat) |
| 1-114 | 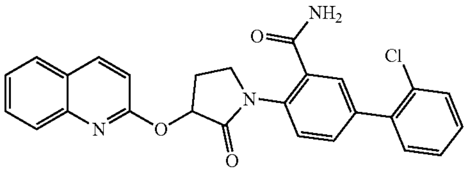 [SMILES: NC(=O)c1cc(-c2ccccc2Cl)ccc1N1CCC(Oc2ccc3ccccc3n2)C1=O] | ~3900 (Phase 1) ~3150 (Phase 2) | | | | | | |
| 1-115 | 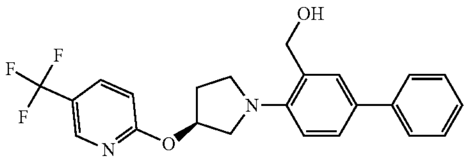 [SMILES: OCc1cc(-c2ccccc2)ccc1N1CC[C@H](Oc2ccc(C(F)(F)F)cn2)C1] | 74.2 (Phase 1) 59 (Phase 2) | | | | Flag/ >20000/ 5860 (5 min) | 370 | 45.8 (rat) |
| 1-116 | 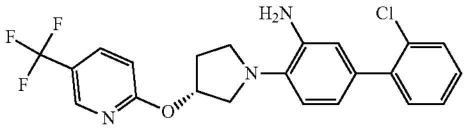 [SMILES: Nc1cc(-c2ccccc2Cl)ccc1N1CC[C@@H](Oc2ccc(C(F)(F)F)cn2)C1] | Agonist/ Antagonist (Phase 1) Agonist/ Antagonist (Phase 2) | | | | | | |
| 1-117 | 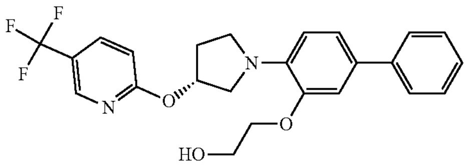 [SMILES: OCCOc1cc(-c2ccccc2)ccc1N1CC[C@@H](Oc2ccc(C(F)(F)F)cn2)C1] | 1920 (Phase 1) 486 (Phase 2) | | | | | ~2000 | 79.8 (rat) |
| 1-118 | 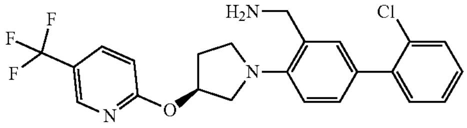 [SMILES: NCc1cc(-c2ccccc2Cl)ccc1N1CC[C@H](Oc2ccc(C(F)(F)F)cn2)C1] | ~1300 (Phase 1) <3200 (Phase 2) | | | | | | |
| 1-119 | 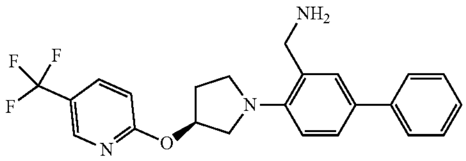 [SMILES: NCc1cc(-c2ccccc2)ccc1N1CC[C@H](Oc2ccc(C(F)(F)F)cn2)C1] | >3200 (Phase 2) | | | | | | |
| 1-120 | 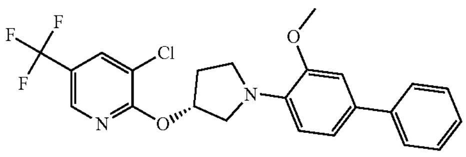 [SMILES: COc1cc(-c2ccccc2)ccc1N1CC[C@@H](Oc2ncc(C(F)(F)F)cc2Cl)C1] | >3200 (Phase 1) >3200 (Phase 2) | | | | | | |
| 1-121 | 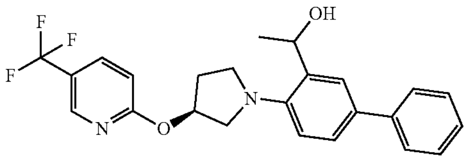 [SMILES: CC(O)c1cc(-c2ccccc2)ccc1N1CC[C@H](Oc2ccc(C(F)(F)F)cn2)C1] | 102 (Phase 1) | | | | no fit (5 min) | BLQ | 33.3 (rat) |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-122 | 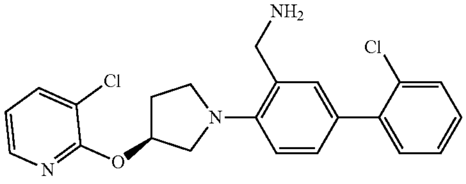 | >3200 (Phase 1) <3200 (Phase 2) | | | | | | |
| 1-123 | 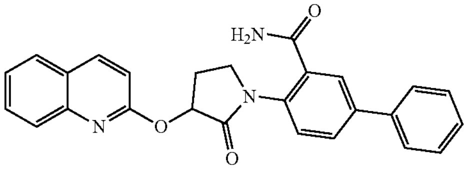 [SMILES: NC(=O)c1cc(-c2ccccc2)ccc1N1CCC(Oc2ccc3ccccc3n2)C1=O] | >3200 (Phase 1) | | | | | | |
| 1-124 | 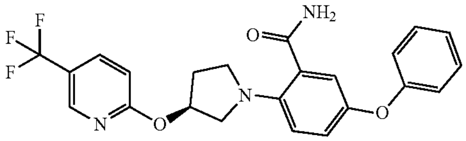 [SMILES: NC(=O)c1cc(Oc2ccccc2)ccc1N1CC[C@H](Oc2ccc(C(F)(F)F)cn2)C1] | !729 (Phase 1) | | | | | BLQ | |
| 1-125 | 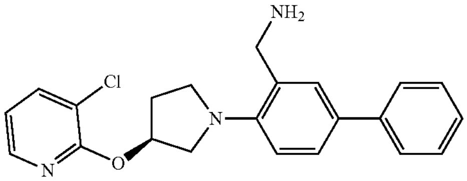 | >3200 (Phase 2) | | | | | | |
| 1-126 | 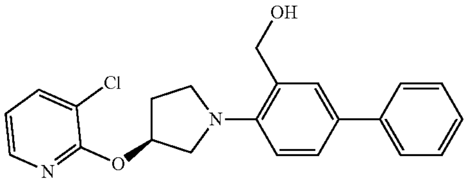 [SMILES: OCc1cc(-c2ccccc2)ccc1N1CC[C@H](Oc2ncccc2Cl)C1] | 369 (Phase 2) | | | | | | |
| 1-127 | 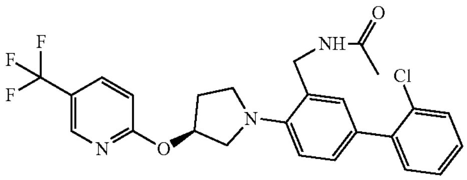 [SMILES: CC(=O)NCc1cc(-c2ccccc2Cl)ccc1N1CC[C@H](Oc2ccc(C(F)(F)F)cn2)C1] | 1140 (Phase 2) | | | | | | |
| 1-128 | 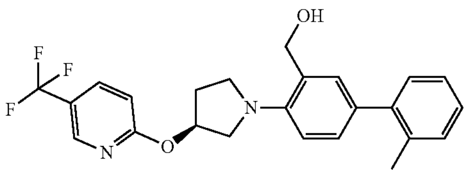 | 114 (Phase 1) | | | | no fit (5 min) | BLQ | |
| 1-129 | 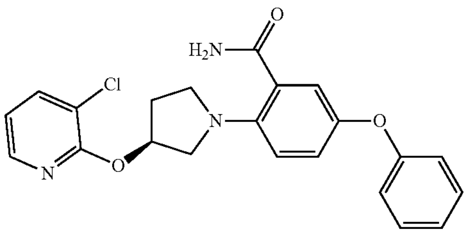 [SMILES: NC(=O)c1cc(Oc2ccccc2)ccc1N1CC[C@H](Oc2ncccc2Cl)C1] | 533 (Phase 1) | | | | no fit (5 min) | ~1600 | 6.42 (rat) |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-130 | 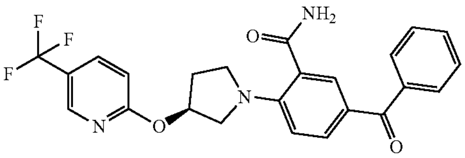 [SMILES: NC(=O)c1cc(C(=O)c2ccccc2)ccc1N1CC[C@H](Oc2ccc(C(F)(F)F)cn2)C1] | 1540 (Phase 1) | | | | no fit (5 min) | ~12200 | 67 (rat) |
| 1-131 | 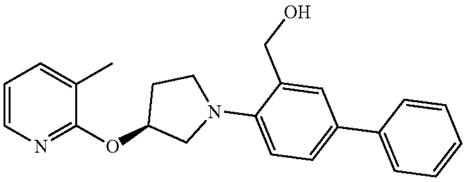 [SMILES: Cc1cccnc1O[C@H]1CCN(c2ccc(-c3ccccc3)cc2CO)C1] | 148 (Phase 1) | | | | no fit (5 min) | ~620 | 23.5 (rat) |
| 1-132 | 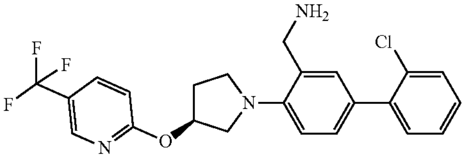 [SMILES: NCc1cc(-c2ccccc2Cl)ccc1N1CC[C@H](Oc2ccc(C(F)(F)F)cn2)C1] | 32 (Phase 1) | | | | no fit (5 min) | BLQ | 54.1 (rat) |
| 1-133 | 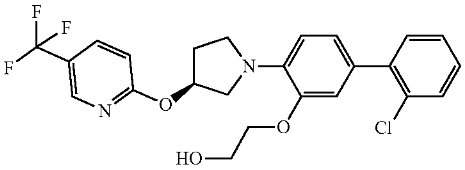 [SMILES: OCCOc1cc(-c2ccccc2Cl)ccc1N1CC[C@H](Oc2ccc(C(F)(F)F)cn2)C1] | !1120 (Phase 1) | | | | | 560 | 55 (rat) |
| 1-134 | 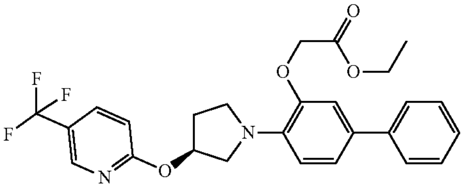 [SMILES: CCOC(=O)COc1cc(-c2ccccc2)ccc1N1CC[C@H](Oc2ccc(C(F)(F)F)cn2)C1] | ~4820 (Phase 1) >3200 (Phase 2) | | | | no fit (5 min) | | |
| 1-135 | 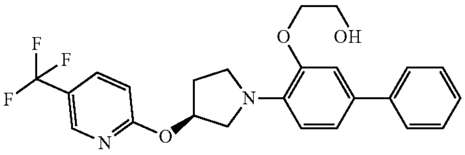 [SMILES: OCCOc1cc(-c2ccccc2)ccc1N1CC[C@H](Oc2ccc(C(F)(F)F)cn2)C1] | !765 (Phase 1) | | | | no fit (5 min) | 190 | 69.7 (rat) |
| 1-136 | 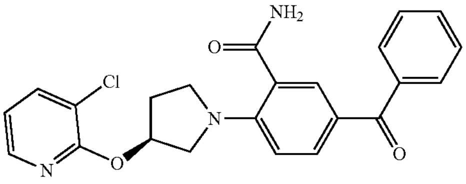 [SMILES: NC(=O)c1cc(C(=O)c2ccccc2)ccc1N1CC[C@H](Oc2ncccc2Cl)C1] | 1620 (Phase 1) 1670 (Phase 2) | | | | | >15000 | 19.7 (rat) |
| 1-137 | 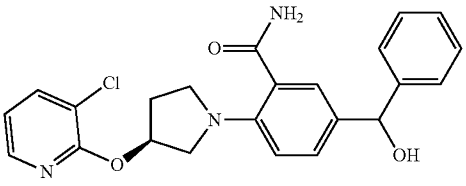 [SMILES: NC(=O)c1cc(C(O)c2ccccc2)ccc1N1CC[C@H](Oc2ncccc2Cl)C1] | 2980 (Phase 1) | | | | no fit (5 min) | >17700 | 8.72 (rat) |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-138 | 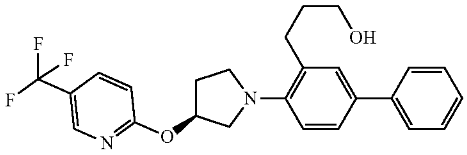 [SMILES: OCCCc1cc(-c2ccccc2)ccc1N1CC[C@H](Oc2ccc(C(F)(F)F)cn2)C1] | 275 (Phase 1) | | | | no fit (5 min) | BLQ | 62.4 (rat) |
| 1-139 | 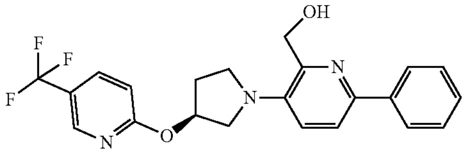 [SMILES: OCc1nc(-c2ccccc2)ccc1N1CC[C@H](Oc2ccc(C(F)(F)F)cn2)C1] | 23.6 (Phase 1) | | | | 5750 (5 min) | ~300 | 30.7 (rat) |
| 1-140 | 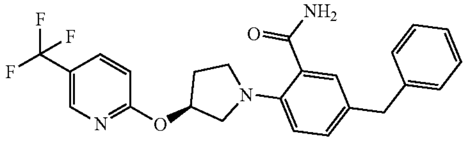 [SMILES: NC(=O)c1cc(Cc2ccccc2)ccc1N1CC[C@H](Oc2ccc(C(F)(F)F)cn2)C1] | !710 (Phase 1) | | | | no fit (5 min) | BLQ | 27.7 (rat) |
| 1-141 | 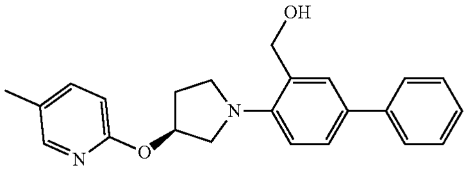 [SMILES: Cc1ccc(O[C@H]2CCN(c3ccc(-c4ccccc4)cc3CO)C2)nc1] | 125 (Phase 1) | | | | | ~970 | 38.4 (rat) |
| 1-142 | 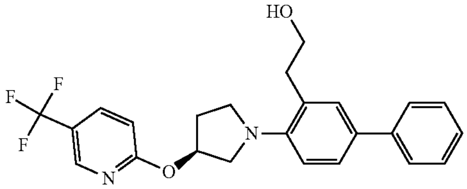 [SMILES: OCCc1cc(-c2ccccc2)ccc1N1CC[C@H](Oc2ccc(C(F)(F)F)cn2)C1] | !275 (Phase 1) | | | | | BLQ | 65.2 (rat) |
| 1-143 | 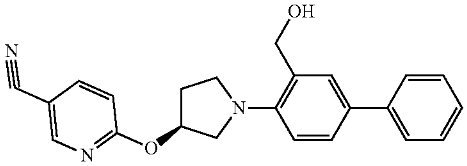 [SMILES: N#Cc1ccc(O[C@H]2CCN(c3ccc(-c4ccccc4)cc3CO)C2)nc1] | 337 (Phase 1) | | | | | 1400 | |
| 1-144 | 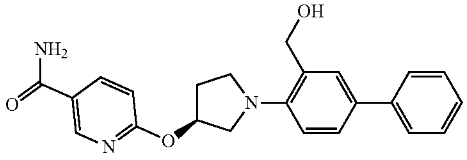 [SMILES: NC(=O)c1ccc(O[C@H]2CCN(c3ccc(-c4ccccc4)cc3CO)C2)nc1] | 1280 (Phase 1)<br>4220 (Phase 2) | | | | | | |
| 1-145 | 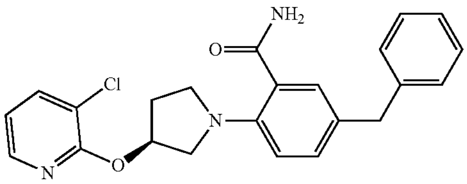 [SMILES: NC(=O)c1cc(Cc2ccccc2)ccc1N1CC[C@H](Oc2ncccc2Cl)C1] | 1950 (Phase 1)<br>749 (Phase 2) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-146 | 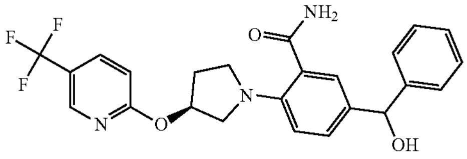 [SMILES: NC(=O)c1cc(C(O)c2ccccc2)ccc1N1CC[C@H](Oc2ccc(C(F)(F)F)cn2)C1] | 686 (Phase 1) | | | | 11800 (5 min) | >13300 | 45.8 (rat) |
| 1-147 | 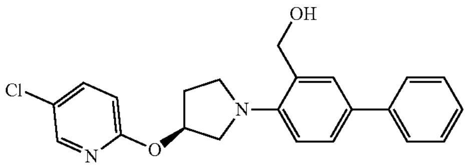 [SMILES: OCc1cc(-c2ccccc2)ccc1N1CC[C@H](Oc2ccc(Cl)cn2)C1] | 171 (Phase 1) | | | | | | |
| 1-148 | 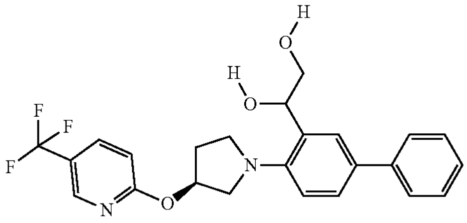 [SMILES: OCC(O)c1cc(-c2ccccc2)ccc1N1CC[C@H](Oc2ccc(C(F)(F)F)cn2)C1] | 550 (Phase 1)<br>699 (Phase 2) | | | | | | |
| 1-149 | 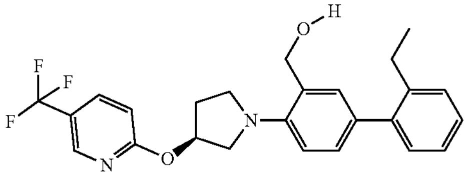 [SMILES: CCc1ccccc1-c1ccc(N2CC[C@H](Oc3ccc(C(F)(F)F)cn3)C2)c(CO)c1] | 34.7 (Phase 1)<br>10.7 (Phase 2) | | | | | | |
| 1-150 | 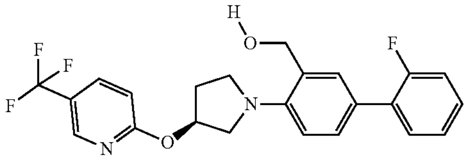 [SMILES: OCc1cc(-c2ccccc2F)ccc1N1CC[C@H](Oc2ccc(C(F)(F)F)cn2)C1] | 71.7 (Phase 1)<br>74.7 (Phase 2) | | | | | | |
| 1-151 | 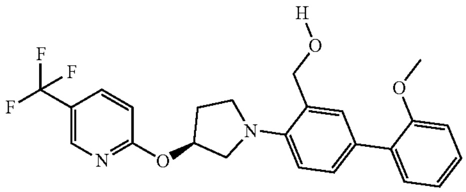 [SMILES: COc1ccccc1-c1ccc(N2CC[C@H](Oc3ccc(C(F)(F)F)cn3)C2)c(CO)c1] | 125 (Phase 1) | | | | | BLQ | 38.9 (rat) |
| 1-152 | 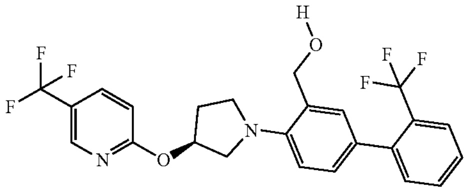 [SMILES: OCc1cc(-c2ccccc2C(F)(F)F)ccc1N1CC[C@H](Oc2ccc(C(F)(F)F)cn2)C1] | 20.4 (Phase 1) | | | | no fit (5 min) | | |
| 1-153 | 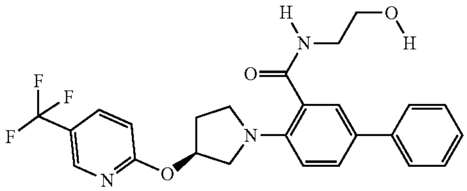 [SMILES: O=C(NCCO)c1cc(-c2ccccc2)ccc1N1CC[C@H](Oc2ccc(C(F)(F)F)cn2)C1] | 4420 (Phase 1) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-154 | 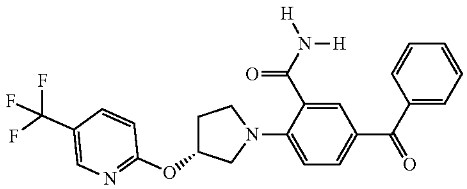 [SMILES: NC(=O)c1cc(C(=O)c2ccccc2)ccc1N1CC[C@@H](Oc2ccc(C(F)(F)F)cn2)C1] | 3040 (Phase 1) | | | | no fit (5 min) | | 54.5 (rat) |
| 1-397 | 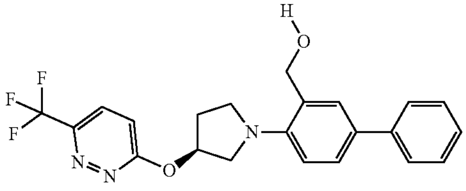 [SMILES: OCc1cc(-c2ccccc2)ccc1N1CC[C@H](Oc2ccc(C(F)(F)F)nn2)C1] | 2740 (Phase 1) 1370 (Phase 2) | | | | | | |
| 1-155 | 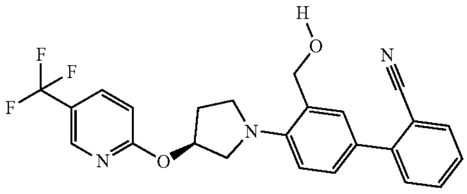 [SMILES: N#Cc1ccccc1-c1ccc(N2CC[C@H](Oc3ccc(C(F)(F)F)cn3)C2)c(CO)c1] | 112 (Phase 1) | | | | | BLQ | |
| 1-156 | 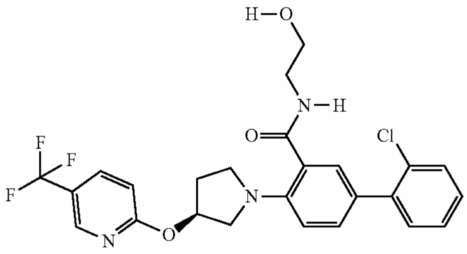 [SMILES: O=C(NCCO)c1cc(-c2ccccc2Cl)ccc1N1CC[C@H](Oc2ccc(C(F)(F)F)cn2)C1] | 3750 (Phase 1) | | | | | | |
| 1-157 | 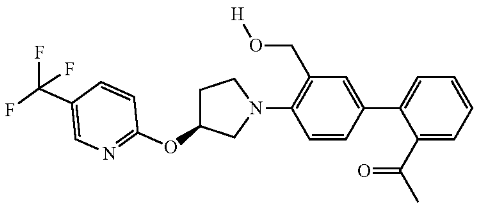 [SMILES: CC(=O)c1ccccc1-c1ccc(N2CC[C@H](Oc3ccc(C(F)(F)F)cn3)C2)c(CO)c1] | 211 (Phase 1) | | | | | ~1800 | 17.5 (rat) |
| 1-158 | 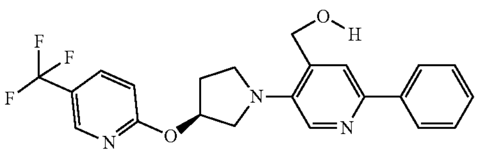 [SMILES: OCc1cc(-c2ccccc2)ncc1N1CC[C@H](Oc2ccc(C(F)(F)F)cn2)C1] | 773 (Phase 1) 747 (Phase 2) | | | | | ~2000 | |
| 1-159 | 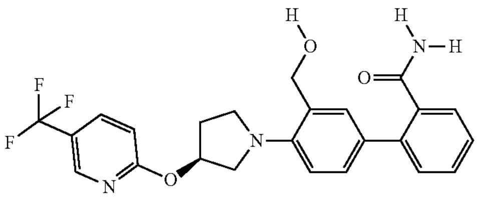 [SMILES: NC(=O)c1ccccc1-c1ccc(N2CC[C@H](Oc3ccc(C(F)(F)F)cn3)C2)c(CO)c1] | >3200 (Phase 1) >3200 (Phase 2) | | | | | >16600 | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-160 | 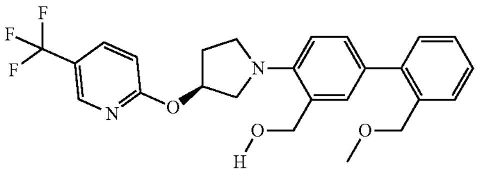 [SMILES: COCc1ccccc1-c1ccc(N2CC[C@H](Oc3ccc(C(F)(F)F)cn3)C2)c(CO)c1] | 71.6 (Phase 1) 106 (Phase 2) | | | | | ~400 | 19.1 (rat) |
| 1-161 | 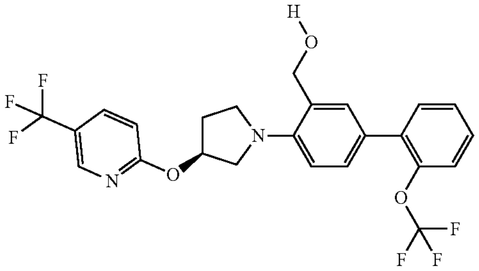 [SMILES: OCc1cc(-c2ccccc2OC(F)(F)F)ccc1N1CC[C@H](Oc2ccc(C(F)(F)F)cn2)C1] | 93.4 (Phase 1) | | | | no fit (5 min) | BLQ | |
| 1-162 | 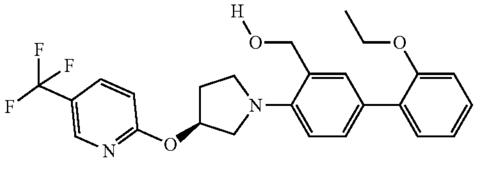 [SMILES: CCOc1ccccc1-c1ccc(N2CC[C@H](Oc3ccc(C(F)(F)F)cn3)C2)c(CO)c1] | 101 (Phase 1) | | | | no fit (5 min) | | 22.8 (rat) |
| 1-163 | 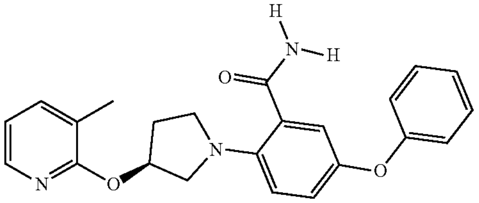 [SMILES: Cc1cccnc1O[C@H]1CCN(c2ccc(Oc3ccccc3)cc2C(N)=O)C1] | 2180 (Phase 1) | | | | | | |
| 1-164 | 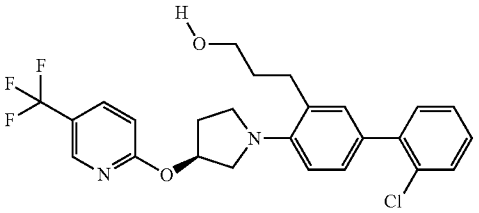 [SMILES: OCCCc1cc(-c2ccccc2Cl)ccc1N1CC[C@H](Oc2ccc(C(F)(F)F)cn2)C1] | 190 (Phase 1) | | | | no fit (5 min) | BLQ | |
| 1-165 | 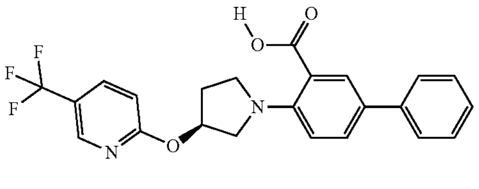 [SMILES: O=C(O)c1cc(-c2ccccc2)ccc1N1CC[C@H](Oc2ccc(C(F)(F)F)cn2)C1] | >3200 (Phase 1) | | | | | | |
| 1-166 | 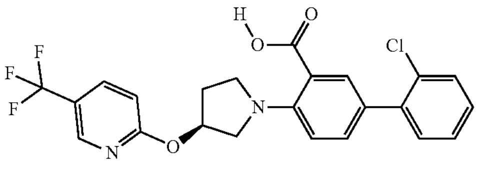 [SMILES: O=C(O)c1cc(-c2ccccc2Cl)ccc1N1CC[C@H](Oc2ccc(C(F)(F)F)cn2)C1] | ~2210 (Phase 1) ~2230 (Phase 2) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-395 | 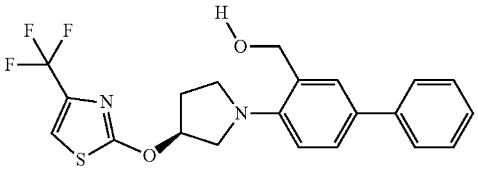 [SMILES: OCc1cc(-c2ccccc2)ccc1N1CC[C@H](Oc2nc(C(F)(F)F)cs2)C1] | !>3200 (Phase 1) ?>3200 (Phase 2) | | | | | BLQ | |
| 1-167 | 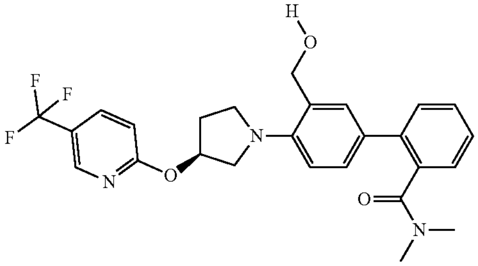 [SMILES: CN(C)C(=O)c1ccccc1-c1ccc(N2CC[C@H](Oc3ccc(C(F)(F)F)cn3)C2)c(CO)c1] | ~1290 (Phase 1) >3200 (Phase 2) | | | | | >12600 | |
| 1-168 | 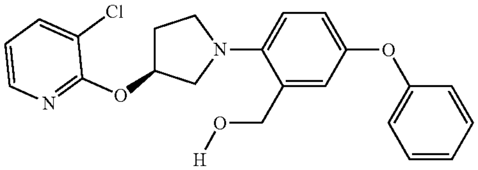 [SMILES: OCc1cc(Oc2ccccc2)ccc1N1CC[C@H](Oc2ncccc2Cl)C1] | 61.2 (Phase 1) 90.5 (Phase 2) | | | | >20000 (5 min) | ~500 | 26.7 (rat) |
| 1-169 | 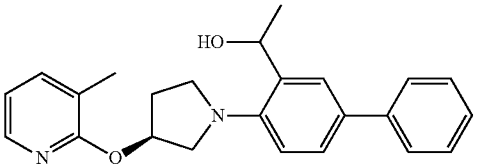 [SMILES: Cc1cccnc1O[C@H]1CCN(c2ccc(-c3ccccc3)cc2C(C)O)C1] | 476 (Phase 1) 655 (Phase 2) | | | | | | |
| 1-170 | 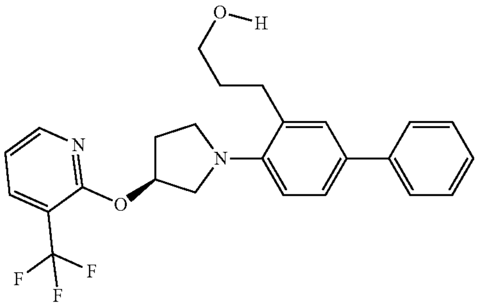 [SMILES: OCCCc1cc(-c2ccccc2)ccc1N1CC[C@H](Oc2ncccc2C(F)(F)F)C1] | 551 (Phase 2) | | | | | | |
| 1-171 | 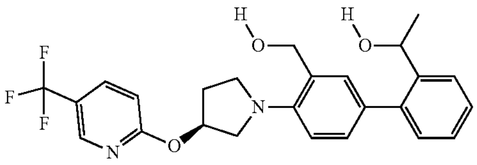 [SMILES: CC(O)c1ccccc1-c1ccc(N2CC[C@H](Oc3ccc(C(F)(F)F)cn3)C2)c(CO)c1] | 740 (Phase 1) 636 (Phase 2) | | | | | >5350 | |
| 1-172 | 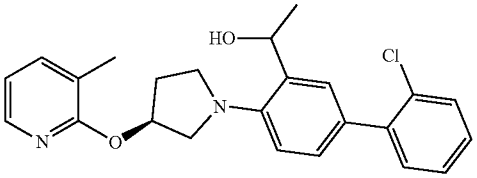 [SMILES: Cc1cccnc1O[C@H]1CCN(c2ccc(-c3ccccc3Cl)cc2C(C)O)C1] | 882 (Phase 1) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-173 | 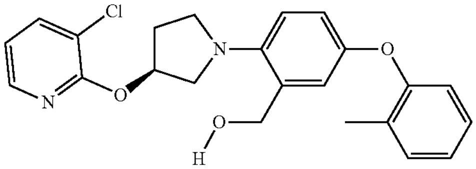 [SMILES: Cc1ccccc1Oc1ccc(N2CC[C@H](Oc3ncccc3Cl)C2)c(CO)c1] | ~29 (Phase 1) 34.7 (Phase 2) | | | | Flag/ >20000/ 12000 (5 min) 1900 (30 in) | BLQ | 27.9 (rat) |
| 1-174 | 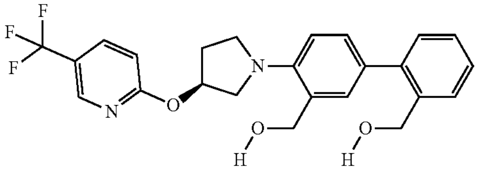 [SMILES: OCc1ccccc1-c1ccc(N2CC[C@H](Oc3ccc(C(F)(F)F)cn3)C2)c(CO)c1] | >320 (Phase 1) !>3200 (Phase 2) | | | | | >670 | |
| 1-175 | 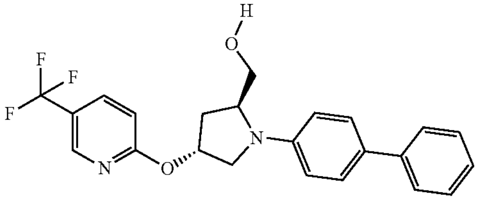 [SMILES: OC[C@@H]1C[C@@H](Oc2ccc(C(F)(F)F)cn2)CN1c1ccc(-c2ccccc2)cc1] | !>3200 (Phase 1) !>3200 (Phase 2) | | | | | ~680 | |
| 1-176 | 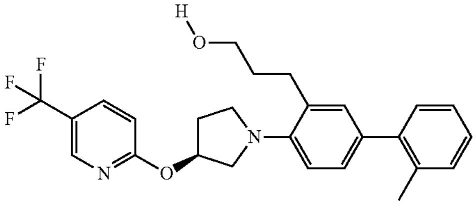 [SMILES: Cc1ccccc1-c1ccc(N2CC[C@H](Oc3ccc(C(F)(F)F)cn3)C2)c(CCCO)c1] | >3200 (Phase 1) 2550 (Phase 2) | | | | | | |
| 1-177 | 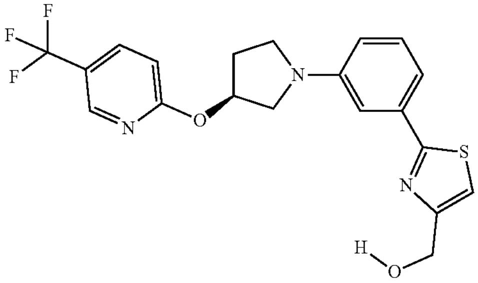 [SMILES: OCc1csc(-c2cccc(N3CC[C@H](Oc4ccc(C(F)(F)F)cn4)C3)c2)n1] | >3200 (Phase 1) | | | | | | |
| 1-178 | 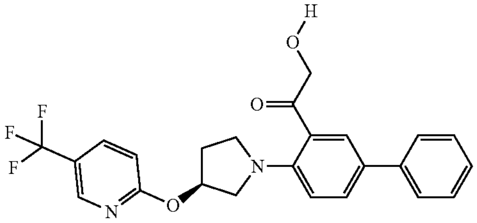 [SMILES: O=C(CO)c1cc(-c2ccccc2)ccc1N1CC[C@H](Oc2ccc(C(F)(F)F)cn2)C1] | 146 (Phase 2) | | | | | ~200 | 66.5 (rat) |
| 1-179 | 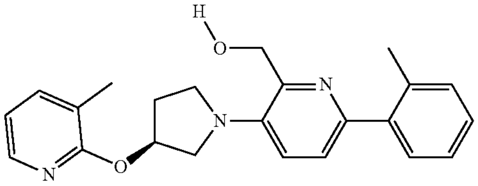 [SMILES: Cc1ccccc1-c1ccc(N2CC[C@H](Oc3ncccc3C)C2)c(CO)n1] | 329 (Phase 1) ~841 (Phase 2) | | | | no fit (5 min) | >730 | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-180 | 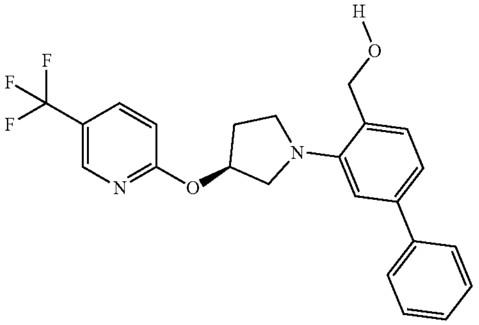 [SMILES: OCc1ccc(-c2ccccc2)cc1N1CC[C@H](Oc2ccc(C(F)(F)F)cn2)C1] | !1550 (Phase 1) !1860 (Phase 2) | | | | no fit (5 min) no fit (30 min) | ~200 | |
| 1-181 | 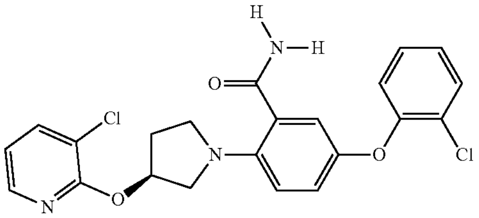 [SMILES: NC(=O)c1cc(Oc2ccccc2Cl)ccc1N1CC[C@H](Oc2ncccc2Cl)C1] | 571 (Phase 1) 834 (Phase 2) | | | | no fit (5 min) | | 8.96 (rat) |
| 1-182 | 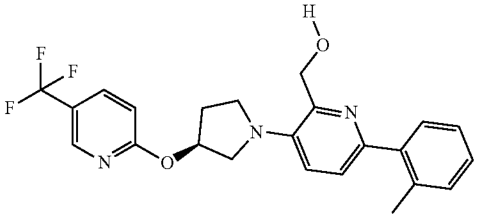 [SMILES: Cc1ccccc1-c1ccc(N2CC[C@H](Oc3ccc(C(F)(F)F)cn3)C2)c(CO)n1] | !>3200 (Phase 1) | | | | 19900 (5 min) 4600 (30 min) | ~800 | |
| 1-183 | 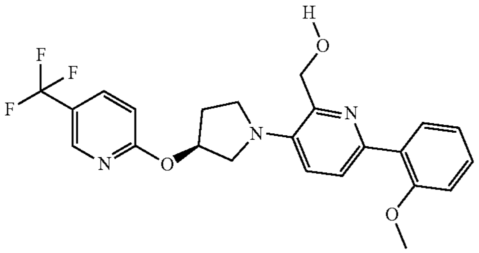 | !>3200 (Phase 2) | | | | no fit (5 min) no fit (30 min) | 840 | |
| 1-184 | 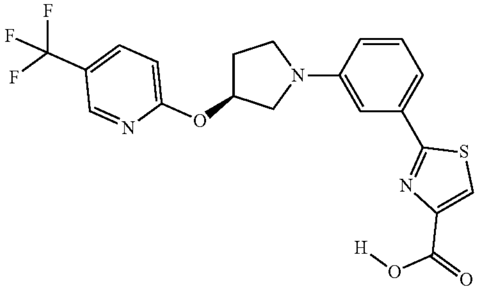 [SMILES: O=C(O)c1csc(-c2cccc(N3CC[C@H](Oc4ccc(C(F)(F)F)cn4)C3)c2)n1] | >3200 (Phase 1) | | | | no fit (5 min) no fit (30 min) | | |
| 1-185 | 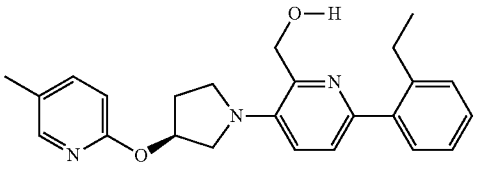 [SMILES: CCc1ccccc1-c1ccc(N2CC[C@H](Oc3ccc(C)cn3)C2)c(CO)n1] | >3200 (Phase 1) 2950 (Phase 2) | | | | no fit (5 min) no fit (30 min) | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-186 | 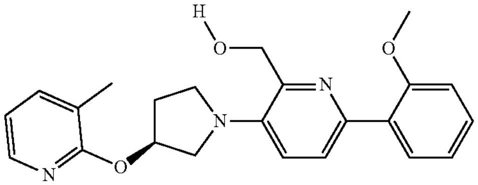 [SMILES: COc1ccccc1-c1ccc(N2CC[C@H](Oc3ncccc3C)C2)c(CO)n1] | 1010 (Phase 1) 980 (Phase 2) | | | | no fit (5 min) no fit (30 min) | | |
| 1-187 | 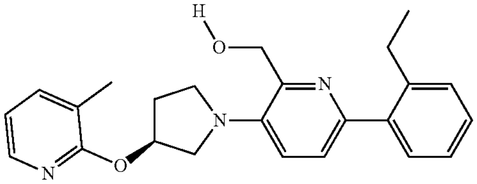 | 720 (Phase 1) ~1000 (Phase 2) | | | | no fit (5 min) no fit (30 min) | | |
| 1-188 | 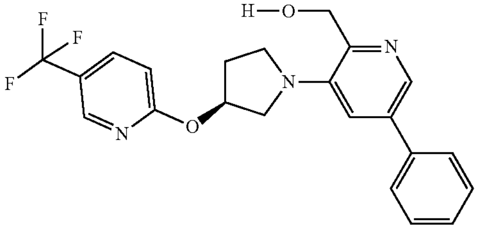 [SMILES: OCc1ncc(-c2ccccc2)cc1N1CC[C@H](Oc2ccc(C(F)(F)F)cn2)C1] | >3200 (Phase 1) | | | | no fit (5 min) no fit (30 min) | | |
| 1-189 | 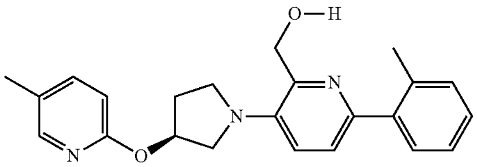 [SMILES: Cc1ccc(O[C@H]2CCN(c3ccc(-c4ccccc4C)nc3CO)C2)nc1] | 636 (Phase 1) 1120 (Phase 2) | | | | | | |
| 1-190 | 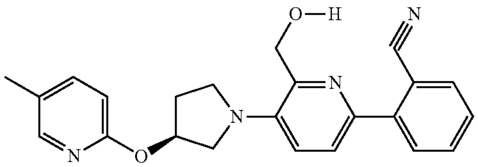 [SMILES: Cc1ccc(O[C@H]2CCN(c3ccc(-c4ccccc4C#N)nc3CO)C2)nc1] | >3200 (Phase 1) >3200 (Phase 2) | | | | | | |
| 1-191 | 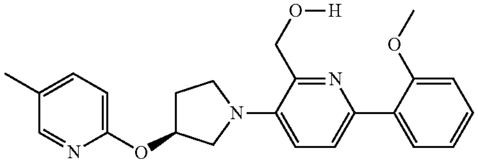 | >3200 (Phase 1) | | | | | | |
| 1-192 | 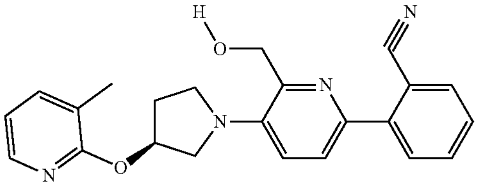 [SMILES: Cc1cccnc1O[C@H]1CCN(c2ccc(-c3ccccc3C#N)nc2CO)C1] | >3200 (Phase 1) ~2750 (Phase 2) | | | | | | |
| 1-193 | 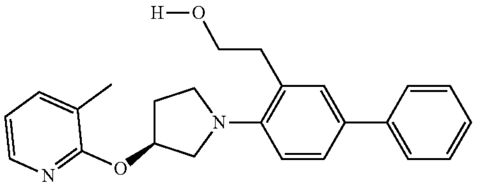 [SMILES: Cc1cccnc1O[C@H]1CCN(c2ccc(-c3ccccc3)cc2CCO)C1] | 260 (Phase 1) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-194 | 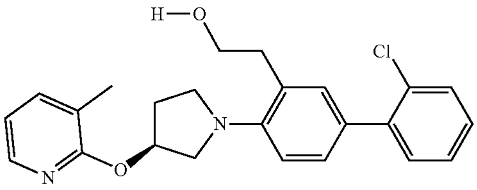 [SMILES: Cc1cccnc1O[C@H]1CCN(c2ccc(-c3ccccc3Cl)cc2CCO)C1] | 327 (Phase 1) | | | | no fit (5 min) | | |
| 1-195 | 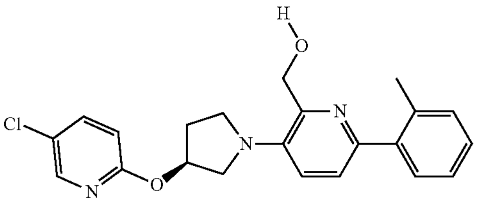 [SMILES: Cc1ccccc1-c1ccc(N2CC[C@H](Oc3ccc(Cl)cn3)C2)c(CO)n1] | 106 (Phase 1) 71.3 (Phase 2) | | | | | | |
| 1-396 | 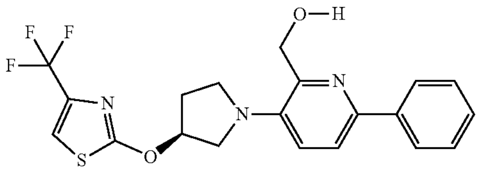 [SMILES: OCc1nc(-c2ccccc2)ccc1N1CC[C@H](Oc2nc(C(F)(F)F)cs2)C1] | 1130 (Phase 1) 2900 (Phase 2) | | | | | | |
| 1-196 | 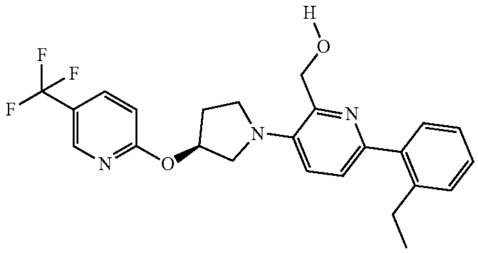 [SMILES: CCc1ccccc1-c1ccc(N2CC[C@H](Oc3ccc(C(F)(F)F)cn3)C2)c(CO)n1] | >3200 (Phase 1) | | | | | | |
| 1-197 | 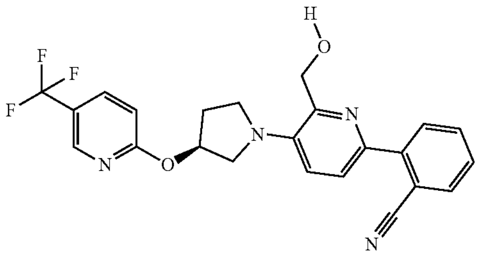 [SMILES: N#Cc1ccccc1-c1ccc(N2CC[C@H](Oc3ccc(C(F)(F)F)cn3)C2)c(CO)n1] | ~38.5 (Phase 1) | | | | | ~400 | |
| 1-198 | 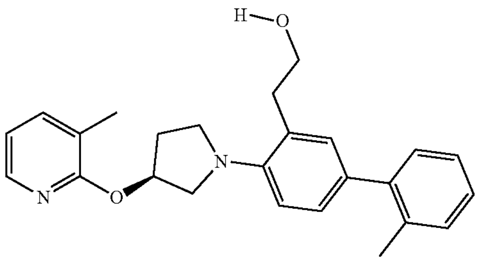 [SMILES: Cc1ccccc1-c1ccc(N2CC[C@H](Oc3ncccc3C)C2)c(CCO)c1] | 184 (Phase 1) | | | | | | |
| 1-199 | 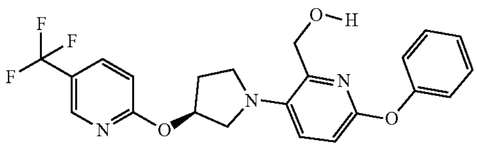 [SMILES: OCc1nc(Oc2ccccc2)ccc1N1CC[C@H](Oc2ccc(C(F)(F)F)cn2)C1] | >3200 (Phase 1) >3200 (Phase 2) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-200 | 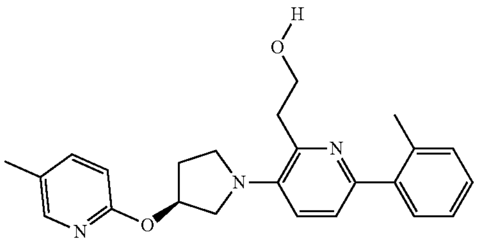 [SMILES: Cc1ccc(O[C@H]2CCN(c3ccc(-c4ccccc4C)nc3CCO)C2)nc1] | 709 (Phase 1) | | | | | | |
| 1-201 | 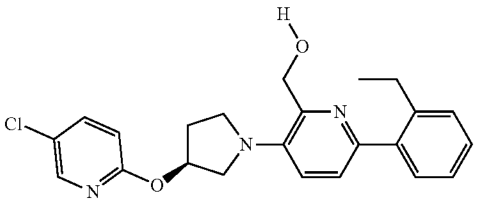 | >3200 (Phase 1) | | | | | | |
| 1-202 | 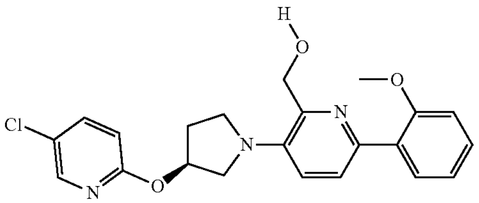 [SMILES: CCc1ccccc1-c1ccc(N2CC[C@H](Oc3ccc(Cl)cn3)C2)c(CO)n1] | Incomplete Block (Phase 1) | | | | | | |
| 1-203 | 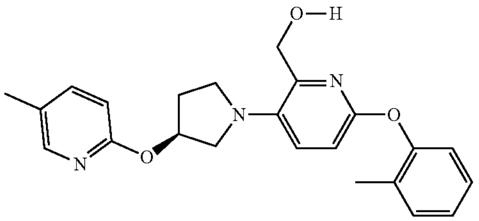 [SMILES: Cc1ccc(O[C@H]2CCN(c3ccc(Oc4ccccc4C)nc3CO)C2)nc1] | !~5050 (Phase 1) !3270 (Phase 2) | | | | | ~1400 | |
| 1-204 | 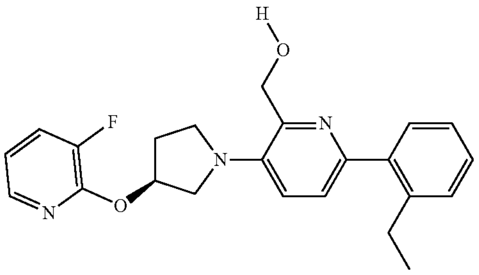 [SMILES: CCc1ccccc1-c1ccc(N2CC[C@H](Oc3ncccc3F)C2)c(CO)n1] | 2670 (Phase 1) | | | | | >1800 | |
| 1-205 | 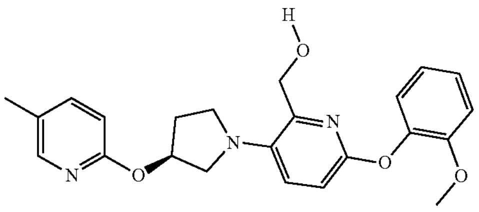 [SMILES: COc1ccccc1Oc1ccc(N2CC[C@H](Oc3ccc(C)cn3)C2)c(CO)n1] | ~3000 (Phase 1) ~6000 (Phase 2) | | | | | >7200 | 16 (rat) |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-206 | 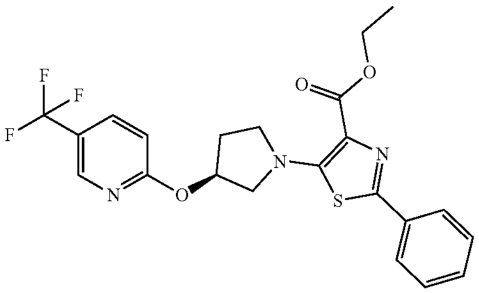 [SMILES: CCOC(=O)c1nc(-c2ccccc2)sc1N1CC[C@H](Oc2ccc(C(F)(F)F)cn2)C1] | 2670 (Phase 1) | | | | | | |
| 1-207 | 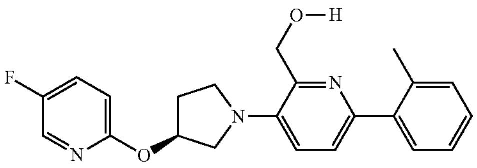 [SMILES: Cc1ccccc1-c1ccc(N2CC[C@H](Oc3ccc(F)cn3)C2)c(CO)n1] | 283 (Phase 1) | | | | | | |
| 1-208 | 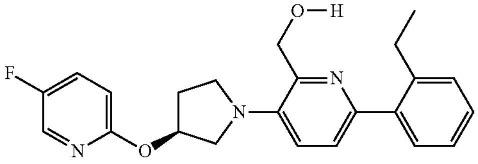 [SMILES: CCc1ccccc1-c1ccc(N2CC[C@H](Oc3ccc(F)cn3)C2)c(CO)n1] | 1220 (Phase 1) 787 (Phase 2) | | | | | | |
| 1-209 | 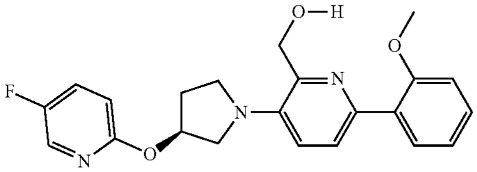 [SMILES: COc1ccccc1-c1ccc(N2CC[C@H](Oc3ccc(F)cn3)C2)c(CO)n1] | ?3470 (Phase 1) | | | | | ~2300 | |
| 1-210 | 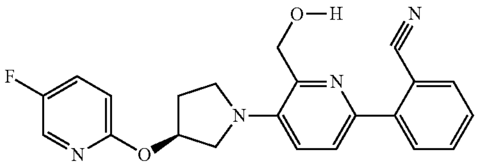 [SMILES: N#Cc1ccccc1-c1ccc(N2CC[C@H](Oc3ccc(F)cn3)C2)c(CO)n1] | 972 (Phase 1) | | | | | | |
| 1-211 | 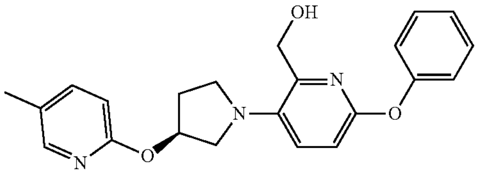 [SMILES: Cc1ccc(O[C@H]2CCN(c3ccc(Oc4ccccc4)nc3CO)C2)nc1] | 931 (Phase 1) 936 (Phase 2) | | | | | | |
| 1-212 | 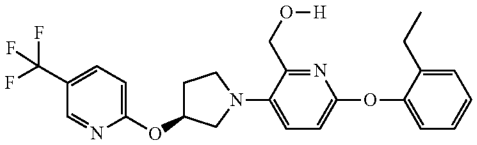 | >3200 (Phase 1) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-213 | 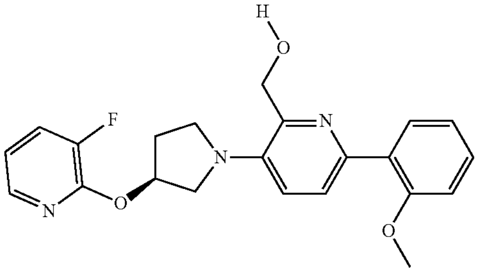 [SMILES: COc1ccccc1-c1ccc(N2CC[C@H](Oc3ncccc3F)C2)c(CO)n1] | 2790 (Phase 1) | | | | | | |
| 1-214 | 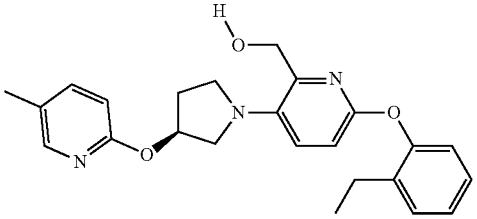 [SMILES: CCc1ccccc1Oc1ccc(N2CC[C@H](Oc3ccc(C)cn3)C2)c(CO)n1] | Incomplete Block (Phase 1) | | | | | | |
| 1-215 | 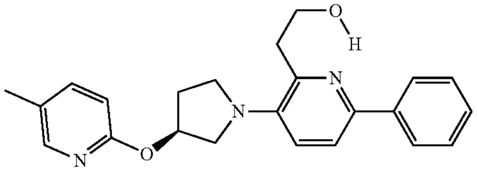 [SMILES: Cc1ccc(O[C@H]2CCN(c3ccc(-c4ccccc4)nc3CCO)C2)nc1] | 1000 (Phase 1) | | | | | | |
| 1-394 | 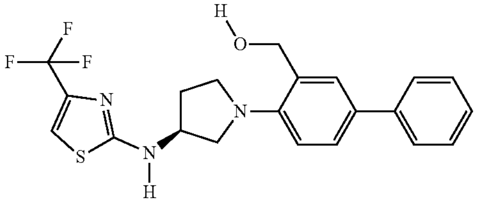 [SMILES: OCc1cc(-c2ccccc2)ccc1N1CC[C@H](Nc2nc(C(F)(F)F)cs2)C1] | 616 (Phase 1) 496 (Phase 2) | | | | | 1870 | |
| 1-216 | 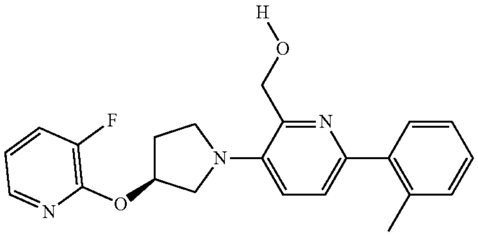 [SMILES: Cc1ccccc1-c1ccc(N2CC[C@H](Oc3ncccc3F)C2)c(CO)n1] | 1160 (Phase 1) | | | | | | |
| 1-379 | 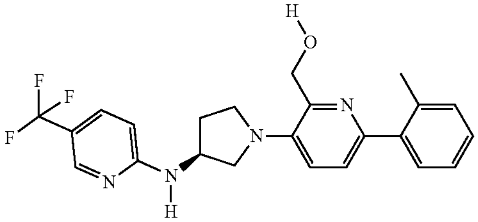 [SMILES: Cc1ccccc1-c1ccc(N2CC[C@H](Nc3ccc(C(F)(F)F)cn3)C2)c(CO)n1] | >3200 (Phase 1) >3200 (Phase 2) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-217 | 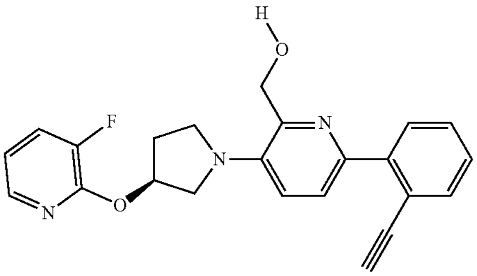 [SMILES: C#Cc1ccccc1-c1ccc(N2CC[C@H](Oc3ncccc3F)C2)c(CO)n1] | 3900 (Phase 1) | | | | | | |
| 1-218 | 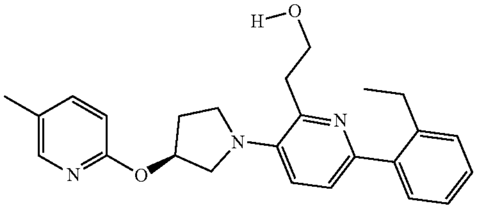 [SMILES: CCc1ccccc1-c1ccc(N2CC[C@H](Oc3ccc(C)cn3)C2)c(CCO)n1] | 614 (Phase 1) | | | | | | |
| 1-219 | 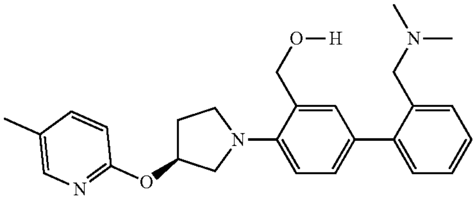 [SMILES: Cc1ccc(O[C@H]2CCN(c3ccc(-c4ccccc4CN(C)C)cc3CO)C2)nc1] | >3200 (Phase 1) | | | | no fit (5 min) no fit (30 min) | >20000 | |
| 1-220 | 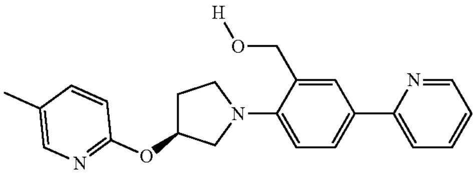 [SMILES: Cc1ccc(O[C@H]2CCN(c3ccc(-c4ccccn4)cc3CO)C2)nc1] | >3200 (Phase 1) | | | | no fit (5 min) no fit (30 min) | | |
| 1-221 | 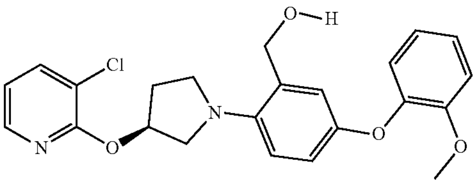 [SMILES: COc1ccccc1Oc1ccc(N2CC[C@H](Oc3ncccc3Cl)C2)c(CO)c1] | 159 (Phase 1) | | | | no fit (5 min) 19400 (30 min) | ~2900 | 12.9 (rat) |
| 1-222 | 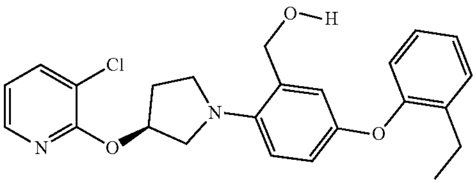 [SMILES: CCc1ccccc1Oc1ccc(N2CC[C@H](Oc3ncccc3Cl)C2)c(CO)c1] | 3.91 (Phase 1) | | | | no fit (5 min) 1790 (30 min) | BLQ | 18.7 (rat) |
| 1-223 | 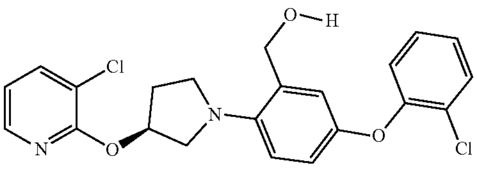 [SMILES: OCc1cc(Oc2ccccc2Cl)ccc1N1CC[C@H](Oc2ncccc2Cl)C1] | 39.3 (Phase 1) 13.3 (Phase 2) | | | | no fit (5 min) 14600 (30 min) | BLQ | 17.2 (rat) |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-224 | 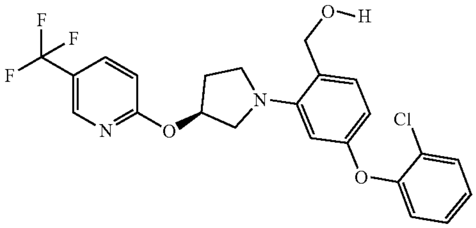 [SMILES: OCc1ccc(Oc2ccccc2Cl)cc1N1CC[C@H](Oc2ccc(C(F)(F)F)cn2)C1] | 161 (Phase 1) | | | | no fit (5 min) no fit (30 min) | | |
| 1-225 | 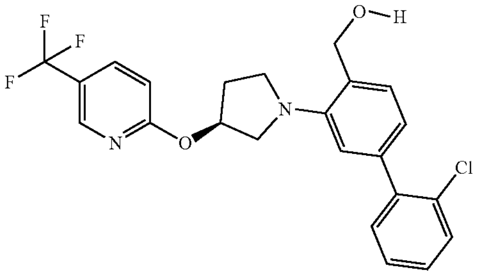 [SMILES: OCc1ccc(-c2ccccc2Cl)cc1N1CC[C@H](Oc2ccc(C(F)(F)F)cn2)C1] | 215 (Phase 1) | | | | no fit (5 min) no fit (30 min) | | |
| 1-226 | 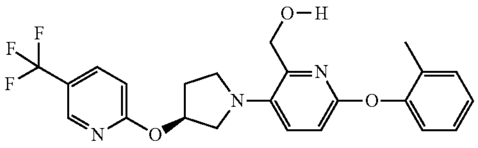 [SMILES: Cc1ccccc1Oc1ccc(N2CC[C@H](Oc3ccc(C(F)(F)F)cn3)C2)c(CO)n1] | ~158 (Phase 1) | | | | no fit (5 min) no fit (30 min) | | |
| 1-227 | 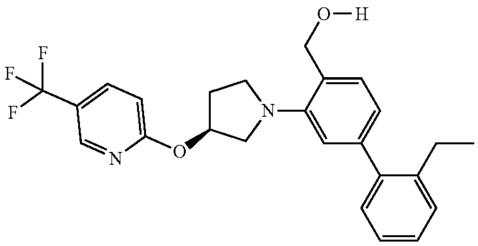 [SMILES: CCc1ccccc1-c1ccc(CO)c(N2CC[C@H](Oc3ccc(C(F)(F)F)cn3)C2)c1] | 200 (Phase 1) | | | | no fit (5 min) no fit (30 min) | | |
| 1-228 | 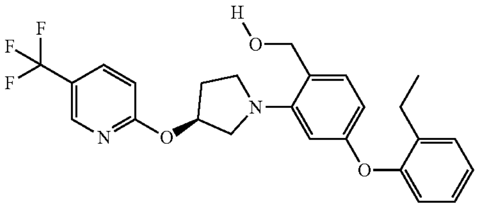 [SMILES: CCc1ccccc1Oc1ccc(CO)c(N2CC[C@H](Oc3ccc(C(F)(F)F)cn3)C2)c1] | 62.1 (Phase 1) | | | | no fit (5 min) no fit (30 min) | | |
| 1-229 | 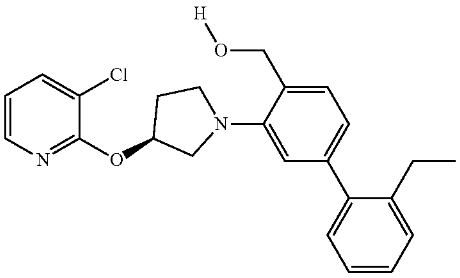 [SMILES: CCc1ccccc1-c1ccc(CO)c(N2CC[C@H](Oc3ncccc3Cl)C2)c1] | 69.2 (Phase 1) | | | | no fit (5 min) no fit (30 min) | 160 | 4.46 (rat) |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-230 | 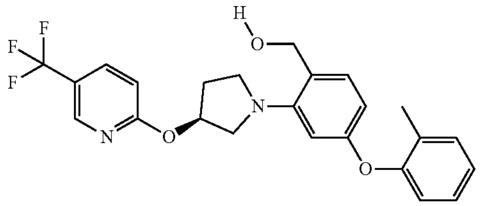 [SMILES: Cc1ccccc1Oc1ccc(CO)c(N2CC[C@H](Oc3ccc(C(F)(F)F)cn3)C2)c1] | 198 (Phase 1) | | | | no fit (5 min) no fit (30 min) | | |
| 1-231 | 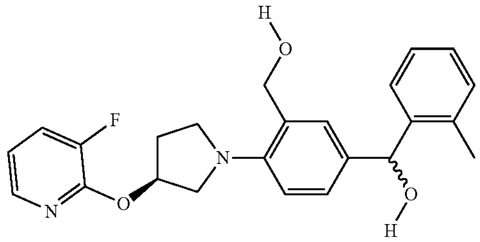 [SMILES: Cc1ccccc1C(O)c1ccc(N2CC[C@H](Oc3ncccc3F)C2)c(CO)c1] | 182 (Phase 1) | | | | no fit (5 min) 1280 (30 min) | >26800 | 16.3 (rat) |
| 1-232 | 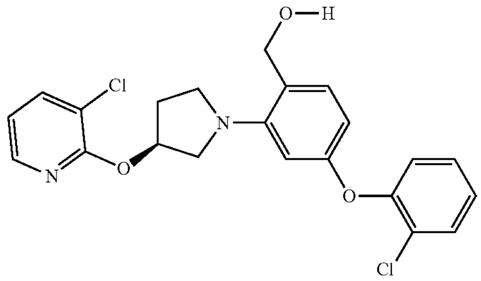 [SMILES: OCc1ccc(Oc2ccccc2Cl)cc1N1CC[C@H](Oc2ncccc2Cl)C1] | ~72.5 (Phase 1) | | | | no fit (5 min) no fit (30 min) | 250 | 5.87 (rat) |
| 1-233 | 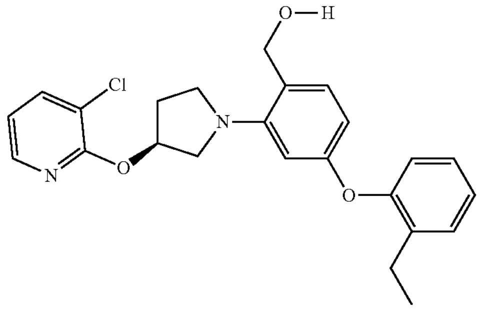 [SMILES: CCc1ccccc1Oc1ccc(CO)c(N2CC[C@H](Oc3ncccc3Cl)C2)c1] | ~21.6 (Phase 1) | | | | no fit (5 min) >20000 (30 min) | BLQ | 10.4 (rat) |
| 1-234 | 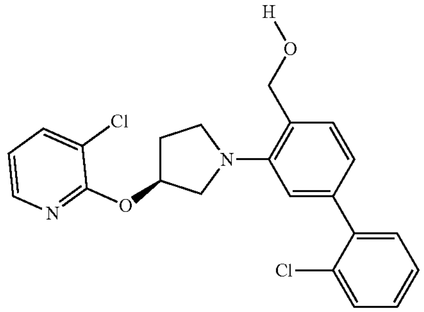 [SMILES: OCc1ccc(-c2ccccc2Cl)cc1N1CC[C@H](Oc2ncccc2Cl)C1] | 737 (Phase 1) | | | | no fit (5 min) no fit (30 min) | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-235 | 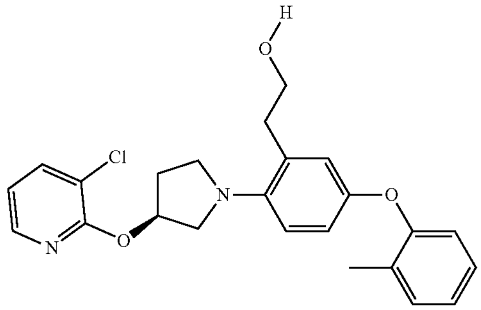 [SMILES: Cc1ccccc1Oc1ccc(N2CC[C@H](Oc3ncccc3Cl)C2)c(CCO)c1] | 19.9 (Phase 1) | | | | >20000 (5 min) 6600 (30 min) | BLQ | 21.9 (rat) |
| 1-236 | 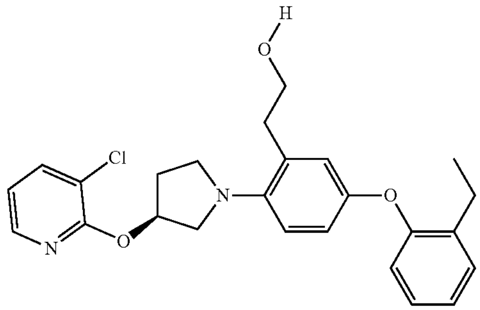 [SMILES: CCc1ccccc1Oc1ccc(N2CC[C@H](Oc3ncccc3Cl)C2)c(CCO)c1] | 8.27 (Phase 1) | | | | no fit (5 min) 5900 (30 min) | BLQ | |
| 1-237 | 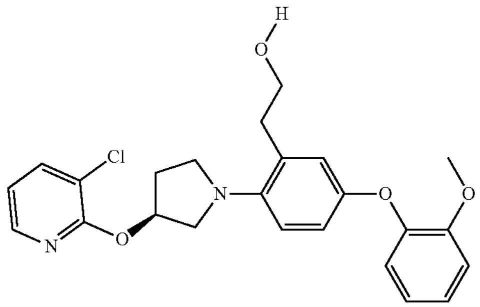 [SMILES: COc1ccccc1Oc1ccc(N2CC[C@H](Oc3ncccc3Cl)C2)c(CCO)c1] | 251 (Phase 1) | | | | >20000 (5 min) 19800 (30 min) | ~1500 | 8.33 (rat) |
| 1-238 | 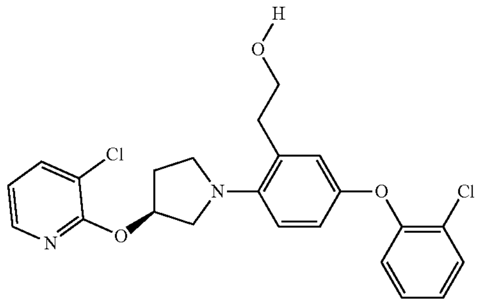 [SMILES: OCCc1cc(Oc2ccccc2Cl)ccc1N1CC[C@H](Oc2ncccc2Cl)C1] | ~51 (Phase 1) | | | | >20000 (5 min) 16700 (30 min) | BLQ | |
| 1-239 | 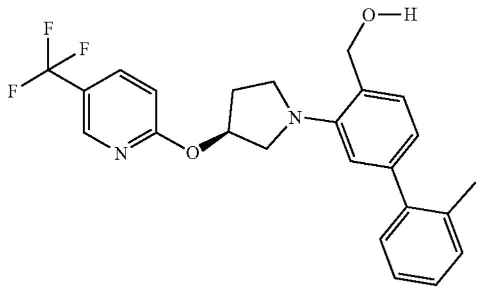 [SMILES: Cc1ccccc1-c1ccc(CO)c(N2CC[C@H](Oc3ccc(C(F)(F)F)cn3)C2)c1] | 607 (Phase 1) | | | | no fit (5 min) no fit (30 min) | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-240 | 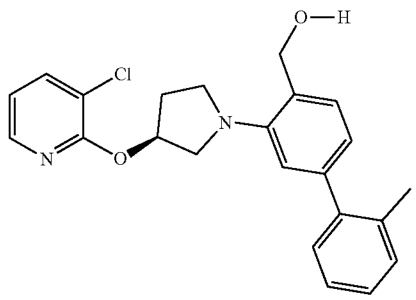 [SMILES: Cc1ccccc1-c1ccc(CO)c(N2CC[C@H](Oc3ncccc3Cl)C2)c1] | 934 (Phase 1) | | | | no fit (5 min) no fit (30 min) | | |
| 1-241 | 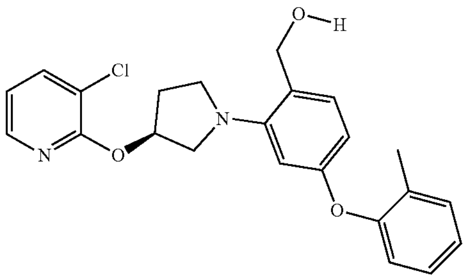 [SMILES: Cc1ccccc1Oc1ccc(CO)c(N2CC[C@H](Oc3ncccc3Cl)C2)c1] | 18.6 (Phase 1) | | | | no fit (5 min) no fit (30 min) | ~370 | 6.19 (rat) |
| 1-242 | 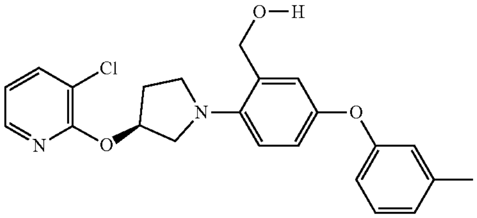 [SMILES: Cc1cccc(Oc2ccc(N3CC[C@H](Oc4ncccc4Cl)C3)c(CO)c2)c1] | 37 (Phase 1) | | | | | | |
| 1-243 | 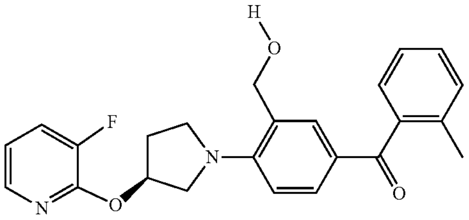 [SMILES: Cc1ccccc1C(=O)c1ccc(N2CC[C@H](Oc3ncccc3F)C2)c(CO)c1] | 296 (Phase 1) | | | | | ~7340 | 6.26 (rat) |
| 1-244 | 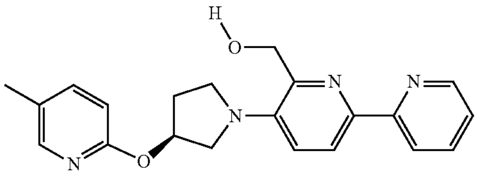 [SMILES: Cc1ccc(O[C@H]2CCN(c3ccc(-c4ccccn4)nc3CO)C2)nc1] | 4650 (Phase 1) | | | | | | |
| 1-245 | 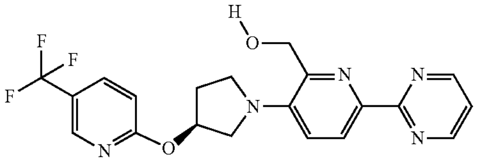 [SMILES: OCc1nc(-c2ncccn2)ccc1N1CC[C@H](Oc2ccc(C(F)(F)F)cn2)C1] | >3200 (Phase 1) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-246 | 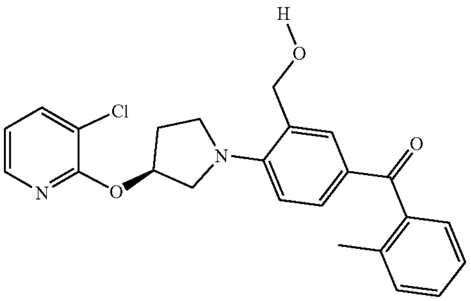 [SMILES: Cc1ccccc1C(=O)c1ccc(N2CC[C@H](Oc3ncccc3Cl)C2)c(CO)c1] | 136 (Phase 1)<br>136 (Phase 2) | | | | | ~1870 | 7.36 (rat) |
| 1-247 | 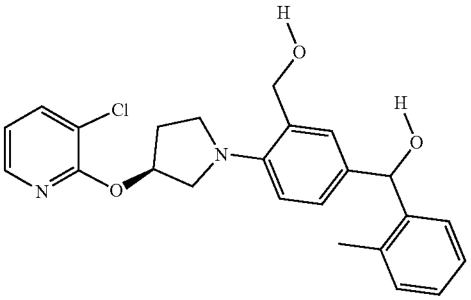 [SMILES: Cc1ccccc1C(O)c1ccc(N2CC[C@H](Oc3ncccc3Cl)C2)c(CO)c1] | 132 (Phase 1)<br>202 (Phase 2) | | | | | >9000 | 13.1 (rat) |
| 1-248 | 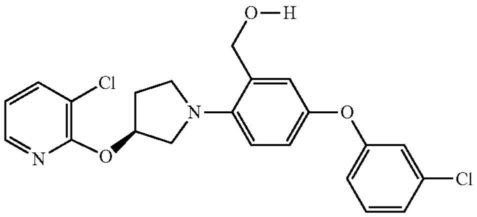 [SMILES: OCc1cc(Oc2cccc(Cl)c2)ccc1N1CC[C@H](Oc2ncccc2Cl)C1] | 12.3 (Phase 1) | | | | | BLQ | |
| 1-249 | 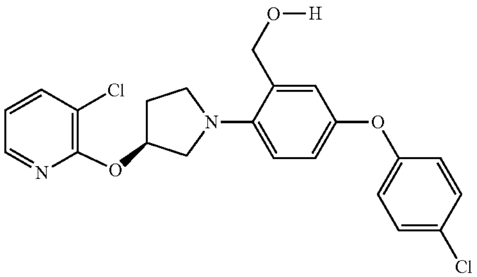 [SMILES: OCc1cc(Oc2ccc(Cl)cc2)ccc1N1CC[C@H](Oc2ncccc2Cl)C1] | 22.1 (Phase 1) | | | | | BLQ | |
| 1-250 | 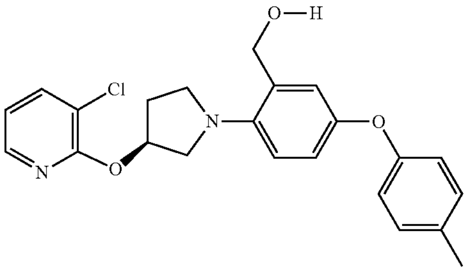 [SMILES: Cc1ccc(Oc2ccc(N3CC[C@H](Oc4ncccc4Cl)C3)c(CO)c2)cc1] | 8.42 (Phase 1) | | | | | ~100 | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-380 | 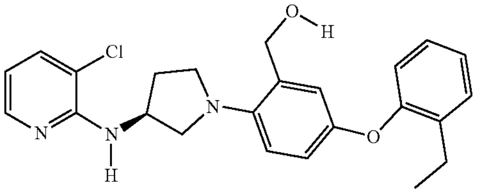 [SMILES: CCc1ccccc1Oc1ccc(N2CC[C@H](Nc3ncccc3Cl)C2)c(CO)c1] | 25.6 (Phase 1) | | | | | BLQ | 20.9 (rat) |
| 1-251 | 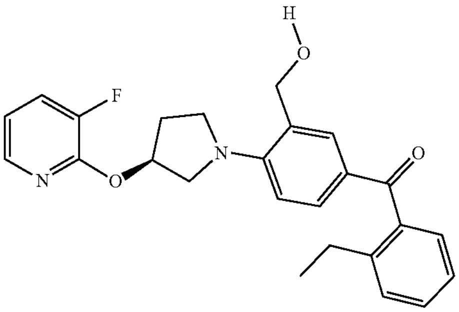 [SMILES: CCc1ccccc1C(=O)c1ccc(N2CC[C@H](Oc3ncccc3F)C2)c(CO)c1] | 102 (Phase 1) | | | | | >3600 | 6.25 (rat) |
| 1-252 | 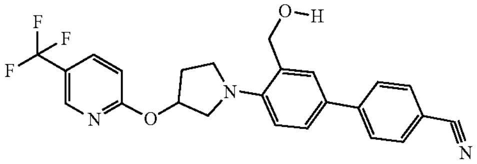 [SMILES: N#Cc1ccc(-c2ccc(N3CCC(Oc4ccc(C(F)(F)F)cn4)C3)c(CO)c2)cc1] | 886 (Phase 1) | | | | | | |
| 1-253 | 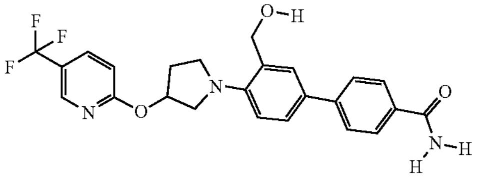 [SMILES: NC(=O)c1ccc(-c2ccc(N3CCC(Oc4ccc(C(F)(F)F)cn4)C3)c(CO)c2)cc1] | >3200 (Phase 1) | | | | | | |
| 1-254 | 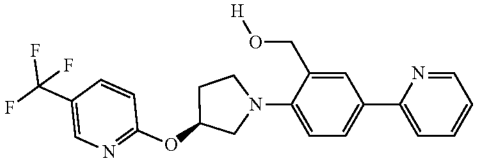 | 1290 (Phase 1) | | | | | | |
| 1-255 | 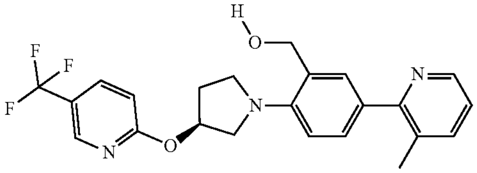 | 806 (Phase 1) | | | | | | |
| 1-256 | 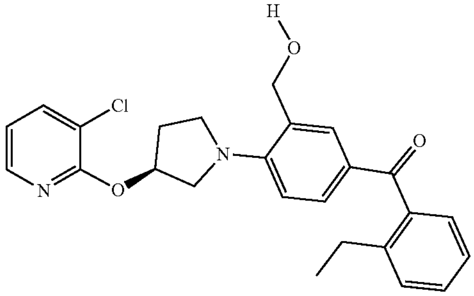 [SMILES: CCc1ccccc1C(=O)c1ccc(N2CC[C@H](Oc3ncccc3Cl)C2)c(CO)c1] | 50.9 (Phase 1) | | | | | ~450 | 6.05 (rat) |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-257 | 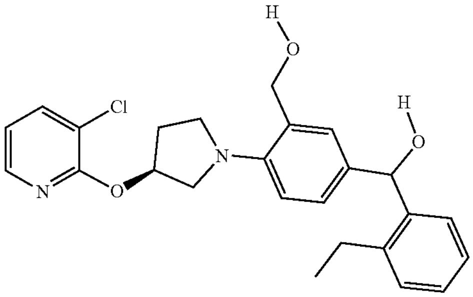 [SMILES: CCc1ccccc1C(O)c1ccc(N2CC[C@H](Oc3ncccc3Cl)C2)c(CO)c1] | 1060 (Phase 1)<br>1110 (Phase 2) | | | | | >6600 | |
| 1-258 | 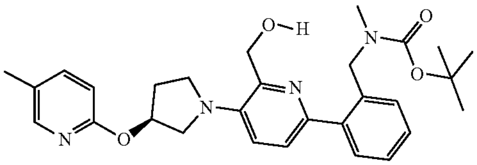 [SMILES: Cc1ccc(O[C@H]2CCN(c3ccc(-c4ccccc4CN(C)C(=O)OC(C)(C)C)nc3CO)C2)nc1] | 276 (Phase 1) | | | | | | |
| 1-381 | 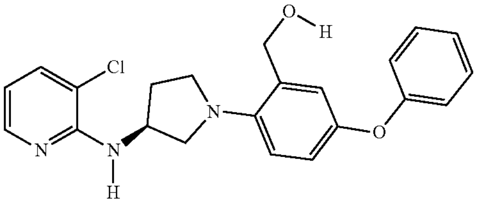 [SMILES: OCc1cc(Oc2ccccc2)ccc1N1CC[C@H](Nc2ncccc2Cl)C1] | 23.3 (Phase 1) | | | | | >1600 | |
| 1-259 | 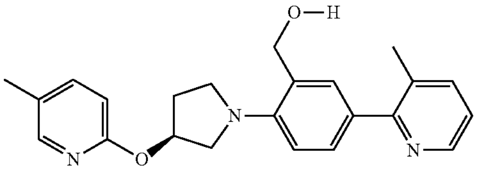 [SMILES: Cc1ccc(O[C@H]2CCN(c3ccc(-c4ncccc4C)cc3CO)C2)nc1] | 3050 (Phase 1)<br>2260 (Phase 2) | | | | | | |
| 1-260 | 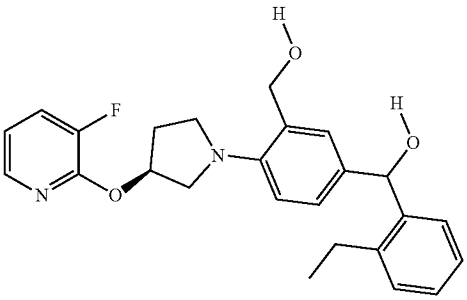 [SMILES: CCc1ccccc1C(O)c1ccc(N2CC[C@H](Oc3ncccc3F)C2)c(CO)c1] | 3150 (Phase 1) | | | | | | |
| 1-261 | 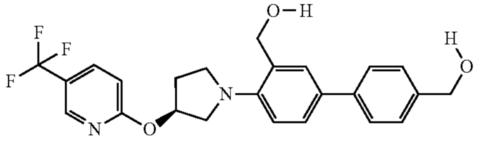 [SMILES: OCc1ccc(-c2ccc(N3CC[C@H](Oc4ccc(C(F)(F)F)cn4)C3)c(CO)c2)cc1] | 604 (Phase 1) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-262 | 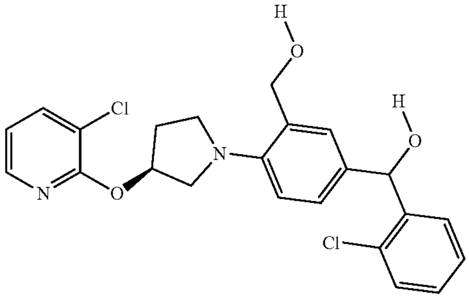 [SMILES: OCc1cc(C(O)c2ccccc2Cl)ccc1N1CC[C@H](Oc2ncccc2Cl)C1] | 23.7 (Phase 1) | ~20 (Phase 1) 21.3 (Phase 2) | | | | ~4700 | 14.6 (rat) |
| 1-263 | 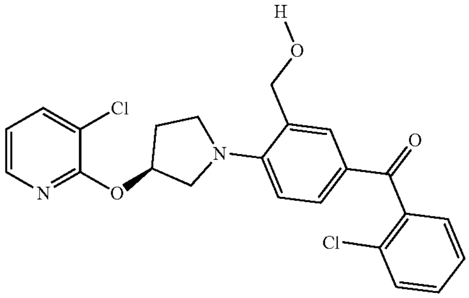 | 444 (Phase 1) | | | | | | |
| 1-264 | 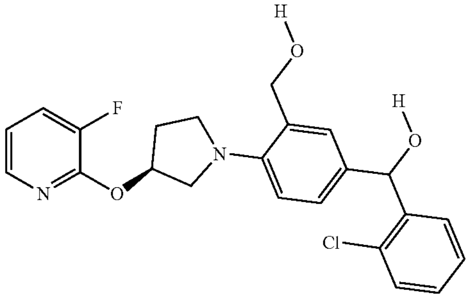 [SMILES: OCc1cc(C(O)c2ccccc2Cl)ccc1N1CC[C@H](Oc2ncccc2F)C1] | 54.1 (Phase 1) 79.3 (Phase 2) | | | | | >13200 | 19.4 (rat) |
| 1-265 | 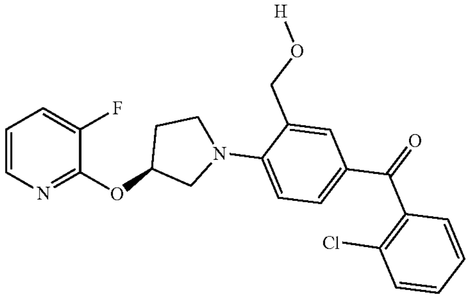 [SMILES: O=C(c1ccc(N2CC[C@H](Oc3ncccc3F)C2)c(CO)c1)c1ccccc1Cl] | 1780 (Phase 1) | | | | | | |
| 1-382 | 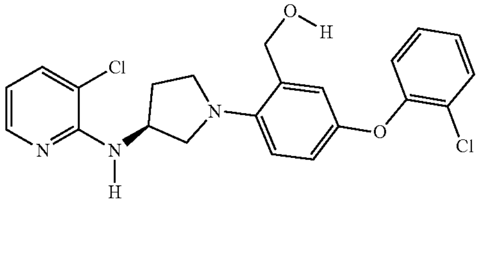 [SMILES: OCc1cc(Oc2ccccc2Cl)ccc1N1CC[C@H](Nc2ncccc2Cl)C1] | 30.9 (Phase 1) | | | | | 500 | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-383 | 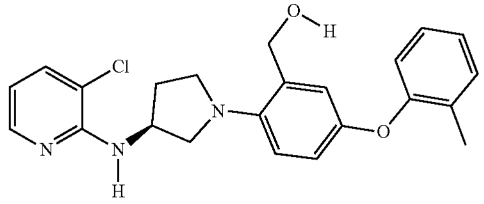 [SMILES: Cc1ccccc1Oc1ccc(N2CC[C@H](Nc3ncccc3Cl)C2)c(CO)c1] | 12.6 (Phase 1) | | | | | ~350 | 31.4 (rat) |
| 1-266 | 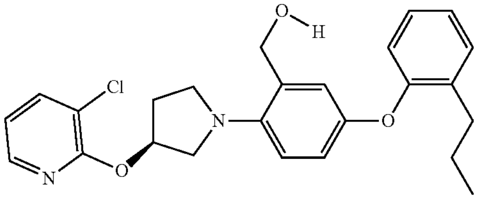 [SMILES: CCCc1ccccc1Oc1ccc(N2CC[C@H](Oc3ncccc3Cl)C2)c(CO)c1] | 2.65 (Phase 1) | | | | | | |
| 1-267 | 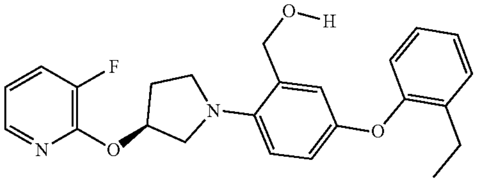 [SMILES: CCc1ccccc1Oc1ccc(N2CC[C@H](Oc3ncccc3F)C2)c(CO)c1] | 19.1 (Phase 1) | | | | | ~380 | 30.6 (rat) |
| 1-268 | 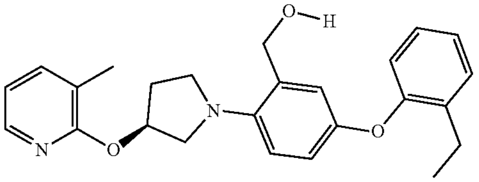 [SMILES: CCc1ccccc1Oc1ccc(N2CC[C@H](Oc3ncccc3C)C2)c(CO)c1] | 2.8 (Phase 1) ~2.54 (Phase 2) | | | | | 250 | 22 (rat) |
| 1-269 | 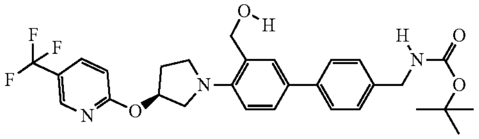 | >3200 (Phase 1) | | | | | | |
| 1-270 | 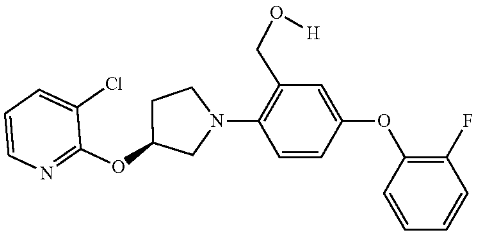 | 9.39 (Phase 1) 7.44 (Phase 2) | | | | | 1000 | 24.3 (rat) |
| 1-271 | 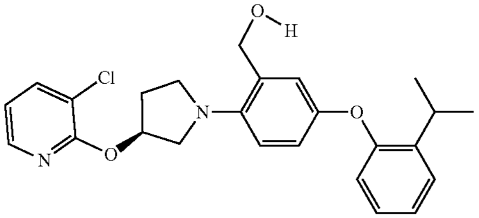 | 2.01 (Phase 1) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-272 | 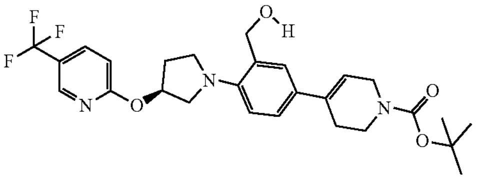 [SMILES: CC(C)(C)OC(=O)N1CC=C(c2ccc(N3CC[C@H](Oc4ccc(C(F)(F)F)cn4)C3)c(CO)c2)CC1] | !>3200 (Phase 1) | | | | | BLQ | |
| 1-273 | 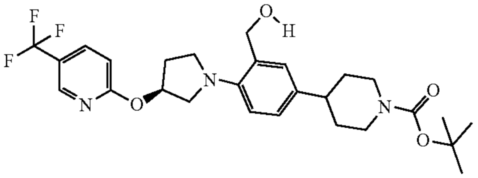 [SMILES: CC(C)(C)OC(=O)N1CCC(c2ccc(N3CC[C@H](Oc4ccc(C(F)(F)F)cn4)C3)c(CO)c2)CC1] | !>3200 (Phase 1) | | | | | BLQ | |
| 1-274 | 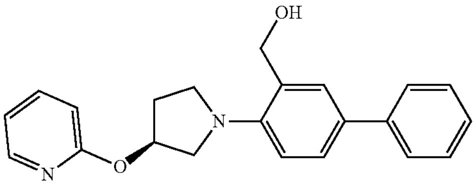 [SMILES: OCc1cc(-c2ccccc2)ccc1N1CC[C@H](Oc2ccccn2)C1] | 241 (Phase 1) | | | | | ~5500 | |
| 1-275 | 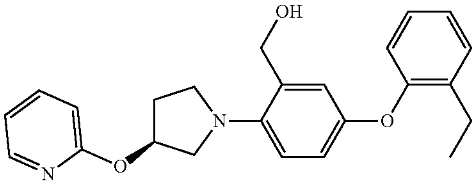 [SMILES: CCc1ccccc1Oc1ccc(N2CC[C@H](Oc3ccccn3)C2)c(CO)c1] | 24.8 (Phase 1) | | | | | ~1000 | 22.8 (rat) |
| 1-276 | 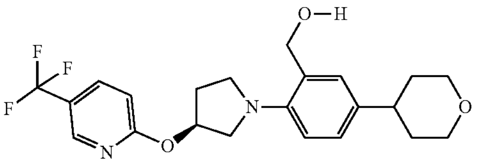 | >3200 (Phase 1) | | | | | | |
| 1-277 | 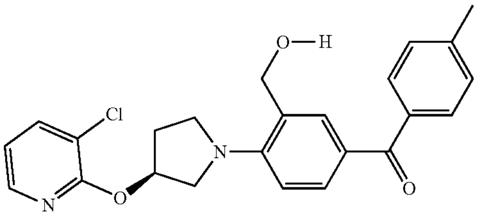 [SMILES: Cc1ccc(C(=O)c2ccc(N3CC[C@H](Oc4ncccc4Cl)C3)c(CO)c2)cc1] | 63 (Phase 1) | | | | | 470 | 15.7 (rat) |
| 1-278 | 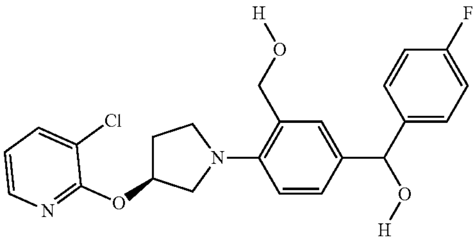 [SMILES: OCc1cc(C(O)c2ccc(F)cc2)ccc1N1CC[C@H](Oc2ncccc2Cl)C1] | 254 (Phase 1) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-279 | 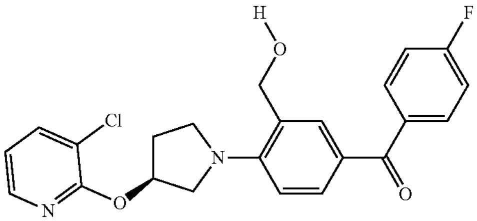 [SMILES: O=C(c1ccc(F)cc1)c1ccc(N2CC[C@H](Oc3ncccc3Cl)C2)c(CO)c1] | 56.9 (Phase 1) | | | | | 1200 | 18.4 (rat) |
| 1-280 | 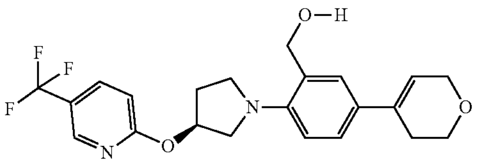 | ~3600 (Phase 1) | | | | | | |
| 1-281 | 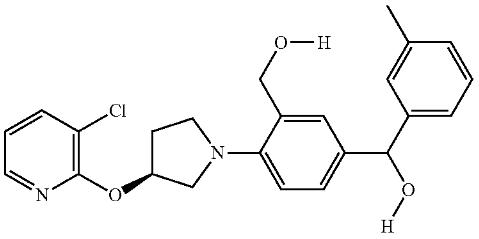 [SMILES: Cc1cccc(C(O)c2ccc(N3CC[C@H](Oc4ncccc4Cl)C3)c(CO)c2)c1] | 1100 (Phase 1) | | | | | | |
| 1-282 | 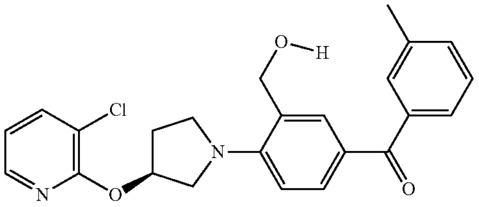 [SMILES: Cc1cccc(C(=O)c2ccc(N3CC[C@H](Oc4ncccc4Cl)C3)c(CO)c2)c1] | 62.3 (Phase 1) | | | | | ~670 | 16.1 (rat) |
| 1-283 | 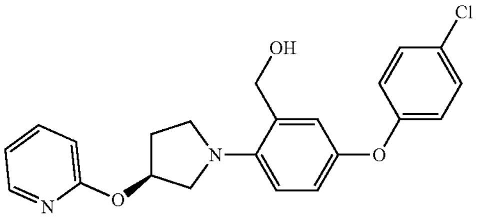 [SMILES: OCc1cc(Oc2ccc(Cl)cc2)ccc1N1CC[C@H](Oc2ccccn2)C1] | 283 (Phase 1) | | | | | | |
| 1-284 | 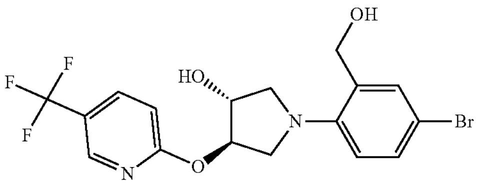 [SMILES: OCc1cc(Br)ccc1N1C[C@@H](O)[C@H](Oc2ccc(C(F)(F)F)cn2)C1] | 1630 (Phase 1) | | | | | | |
| 1-285 | 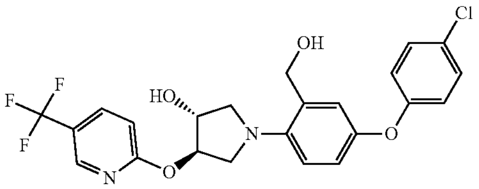 [SMILES: OCc1cc(Oc2ccc(Cl)cc2)ccc1N1C[C@@H](O)[C@H](Oc2ccc(C(F)(F)F)cn2)C1] | >3200 (Phase 1) ~4900 (Phase 2) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-286 | 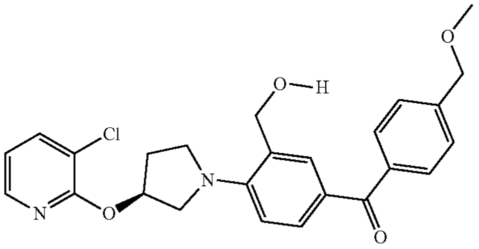 [SMILES: COCc1ccc(C(=O)c2ccc(N3CC[C@H](Oc4ncccc4Cl)C3)c(CO)c2)cc1] | 607 (Phase 1) | | | | | | |
| 1-287 | 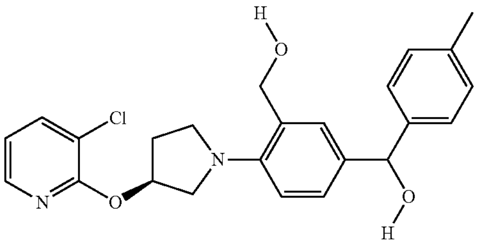 [SMILES: Cc1ccc(C(O)c2ccc(N3CC[C@H](Oc4ncccc4Cl)C3)c(CO)c2)cc1] | 674 (Phase 1) | | | | | | |
| 1-288 | 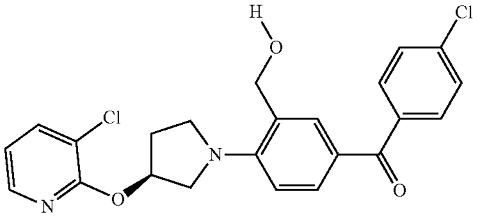 [SMILES: O=C(c1ccc(Cl)cc1)c1ccc(N2CC[C@H](Oc3ncccc3Cl)C2)c(CO)c1] | 74.2 (Phase 1) | | | | | | |
| 1-289 | 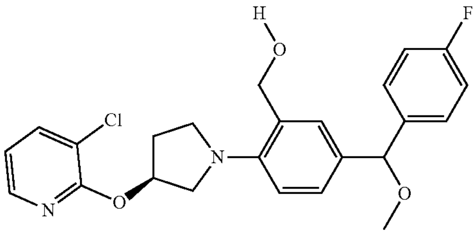 [SMILES: COC(c1ccc(F)cc1)c1ccc(N2CC[C@H](Oc3ncccc3Cl)C2)c(CO)c1] | 66.2 (Phase 1) | | | | | ~1750 | 9.22 (rat) |
| 1-384 | 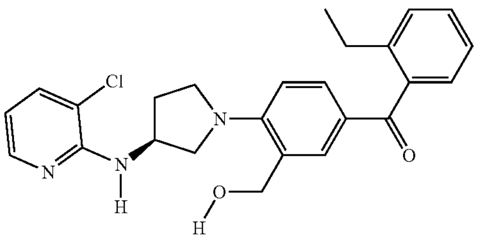 [SMILES: CCc1ccccc1C(=O)c1ccc(N2CC[C@H](Nc3ncccc3Cl)C2)c(CO)c1] | 495 (Phase 1) | | | | | | |
| 1-290 | 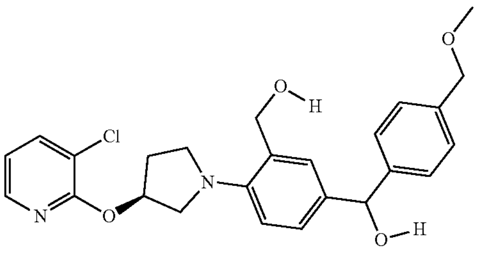 [SMILES: COCc1ccc(C(O)c2ccc(N3CC[C@H](Oc4ncccc4Cl)C3)c(CO)c2)cc1] | >3200 (Phase 1) >3200 (Phase 2) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-385 | 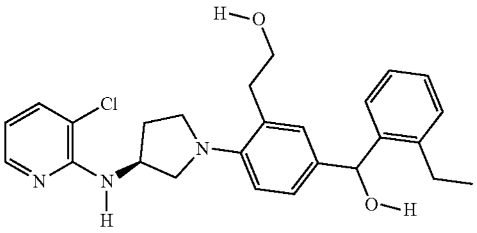 [SMILES: CCc1ccccc1C(O)c1ccc(N2CC[C@H](Nc3ncccc3Cl)C2)c(CCO)c1] | >3200 (Phase 1) | | | | | | |
| 1-291 | 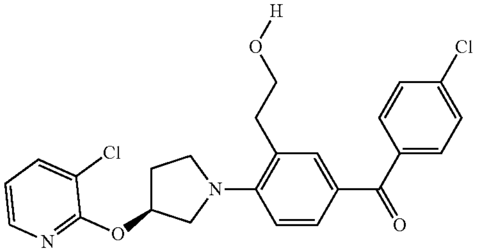 [SMILES: O=C(c1ccc(Cl)cc1)c1ccc(N2CC[C@H](Oc3ncccc3Cl)C2)c(CCO)c1] | ~188 (Phase 1) ~217 (Phase 2) | | | | | | |
| 1-292 | 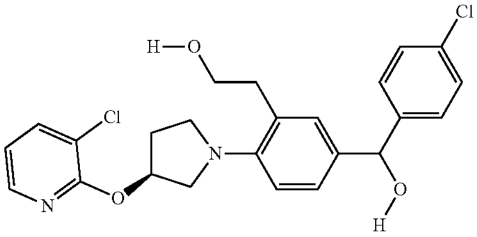 [SMILES: OCCc1cc(C(O)c2ccc(Cl)cc2)ccc1N1CC[C@H](Oc2ncccc2Cl)C1] | ~4900 (Phase 1) ~5100 (Phase 2) | | | | | | |
| 1-386 | 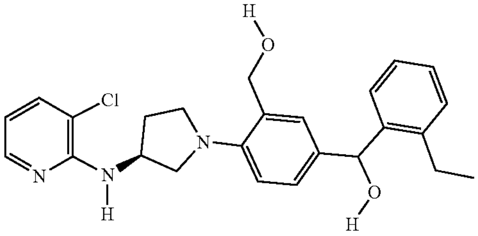 [SMILES: CCc1ccccc1C(O)c1ccc(N2CC[C@H](Nc3ncccc3Cl)C2)c(CO)c1] | ~1260 (Phase 1) ~2150 (Phase 2) | | | | | | |
| 1-387 | 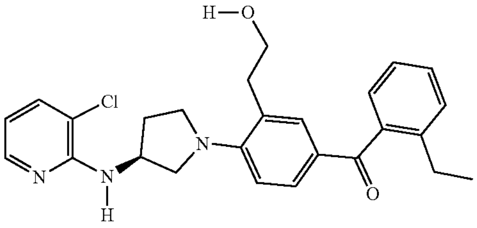 [SMILES: CCc1ccccc1C(=O)c1ccc(N2CC[C@H](Nc3ncccc3Cl)C2)c(CCO)c1] | 1630 (Phase 1) | | | | | | |
| 1-398 | 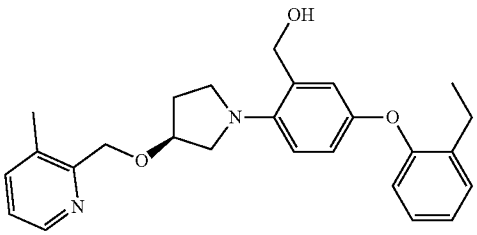 [SMILES: CCc1ccccc1Oc1ccc(N2CC[C@H](OCc3ncccc3C)C2)c(CO)c1] | 187 (Phase 1) 64.8 (Phase 2) | | | | | ~1400 | 5.19 (rat) |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-399 | 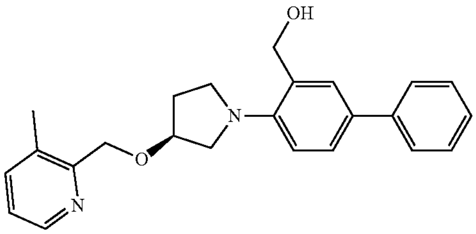 [SMILES: Cc1cccnc1CO[C@H]1CCN(c2ccc(-c3ccccc3)cc2CO)C1] | >3200 (Phase 1) 481 (Phase 2) | | | | | | |
| 1-293 | 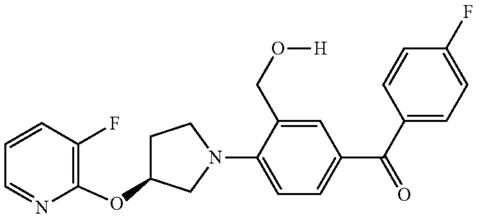 [SMILES: O=C(c1ccc(F)cc1)c1ccc(N2CC[C@H](Oc3ncccc3F)C2)c(CO)c1] | 329 (Phase 1) 322 (Phase 2) | | | | | | |
| 1-294 | 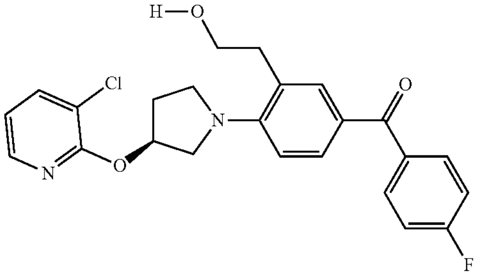 [SMILES: O=C(c1ccc(F)cc1)c1ccc(N2CC[C@H](Oc3ncccc3Cl)C2)c(CCO)c1] | 511 (Phase 1) 502 (Phase 2) | | | | | | |
| 1-295 | 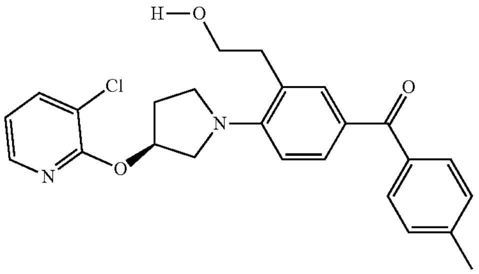 [SMILES: Cc1ccc(C(=O)c2ccc(N3CC[C@H](Oc4ncccc4Cl)C3)c(CCO)c2)cc1] | ~225 (Phase 1) ~178 (Phase 2) | | | | | | |
| 1-296 | 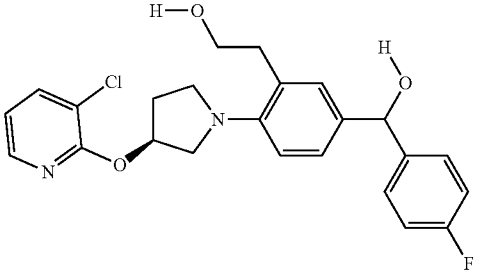 [SMILES: OCCc1cc(C(O)c2ccc(F)cc2)ccc1N1CC[C@H](Oc2ncccc2Cl)C1] | 1070 (Phase 1) 2160 (Phase 2) | | | | | | |
| 1-297 | 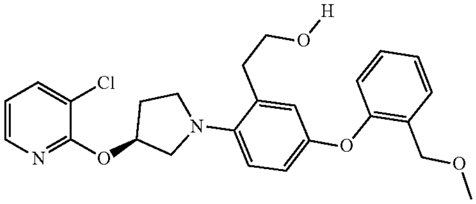 [SMILES: COCc1ccccc1Oc1ccc(N2CC[C@H](Oc3ncccc3Cl)C2)c(CCO)c1] | 56.6 (Phase 1) | | | | | 1400 | 7.44 (rat) |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-298 | 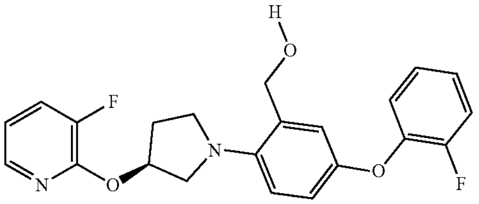 [SMILES: OCc1cc(Oc2ccccc2F)ccc1N1CC[C@H](Oc2ncccc2F)C1] | 65.7 (Phase 1) 52.9 (Phase 2) | | | | | | |
| 1-299 | 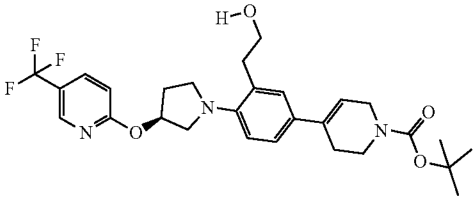 [SMILES: CC(C)(C)OC(=O)N1CC=C(c2ccc(N3CC[C@H](Oc4ccc(C(F)(F)F)cn4)C3)c(CCO)c2)CC1] | >3200 (Phase 1) | | | | | | |
| 1-300 | 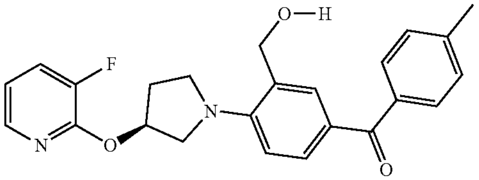 [SMILES: Cc1ccc(C(=O)c2ccc(N3CC[C@H](Oc4ncccc4F)C3)c(CO)c2)cc1] | 860 (Phase 1) | | | | | | |
| 1-301 | 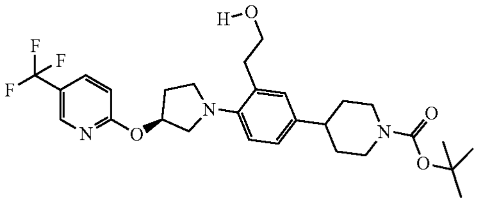 [SMILES: CC(C)(C)OC(=O)N1CCC(c2ccc(N3CC[C@H](Oc4ccc(C(F)(F)F)cn4)C3)c(CCO)c2)CC1] | ~2980 (Phase 1) | | | | | | |
| 1-302 | 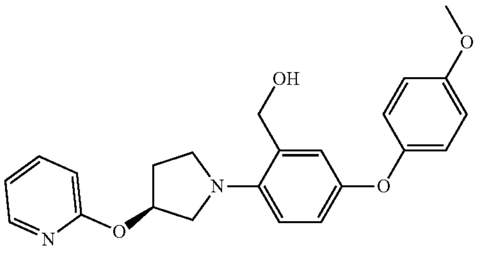 [SMILES: COc1ccc(Oc2ccc(N3CC[C@H](Oc4ccccn4)C3)c(CO)c2)cc1] | 282 (Phase 1) | | | | | | |
| 1-303 | 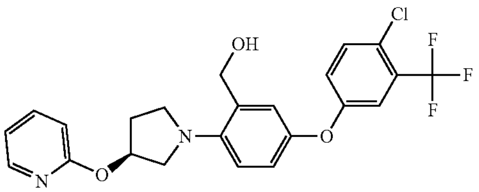 [SMILES: OCc1cc(Oc2ccc(Cl)c(C(F)(F)F)c2)ccc1N1CC[C@H](Oc2ccccn2)C1] | 56.3 (Phase 1) | | | | | | |
| 1-304 | 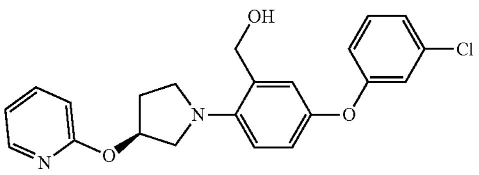 [SMILES: OCc1cc(Oc2cccc(Cl)c2)ccc1N1CC[C@H](Oc2ccccn2)C1] | 55.8 (Phase 1) | | | | | ~1000 | 17.5 (rat) |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-306 | 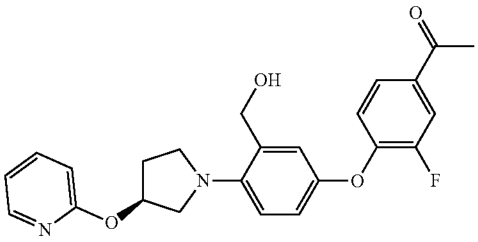 [SMILES: CC(=O)c1ccc(Oc2ccc(N3CC[C@H](Oc4ccccn4)C3)c(CO)c2)c(F)c1] | 982 (Phase 1) 735 (Phase 2) | | | | | | |
| 1-307 | 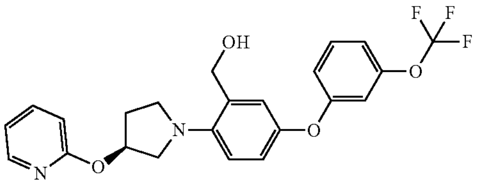 [SMILES: OCc1cc(Oc2cccc(OC(F)(F)F)c2)ccc1N1CC[C@H](Oc2ccccn2)C1] | ~59.5 (Phase 1) | | | | | | |
| 1-308 | 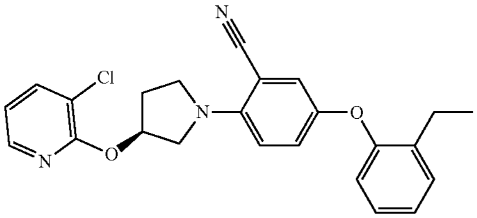 [SMILES: CCc1ccccc1Oc1ccc(N2CC[C@H](Oc3ncccc3Cl)C2)c(C#N)c1] | >3200 (Phase 1) | | | | | | |
| 1-309 | 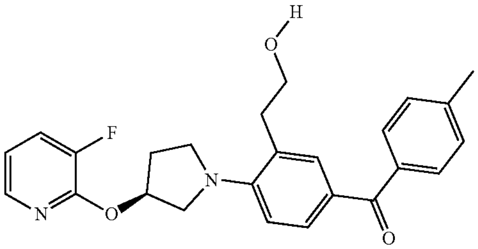 [SMILES: Cc1ccc(C(=O)c2ccc(N3CC[C@H](Oc4ncccc4F)C3)c(CCO)c2)cc1] | ~2080 (Phase 1) 822 (Phase 2) | | | | | | |
| 1-310 | 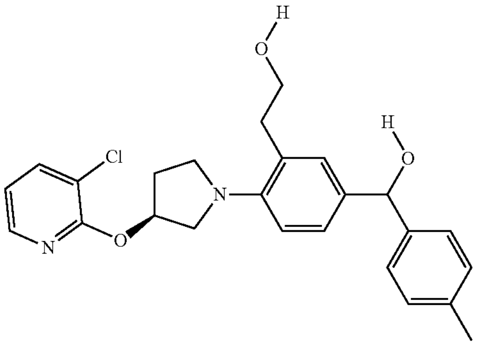 [SMILES: Cc1ccc(C(O)c2ccc(N3CC[C@H](Oc4ncccc4Cl)C3)c(CCO)c2)cc1] | 4200 (Phase 1) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-311 | 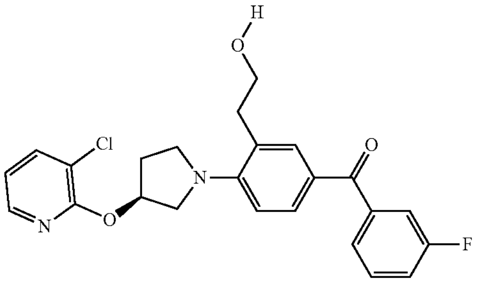 [SMILES: O=C(c1cccc(F)c1)c1ccc(N2CC[C@H](Oc3ncccc3Cl)C2)c(CCO)c1] | 417 (Phase 1) | | | | | | |
| 1-312 | 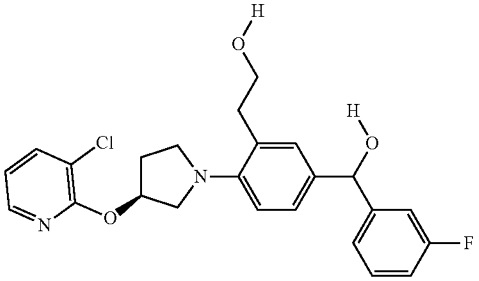 [SMILES: OCCc1cc(C(O)c2cccc(F)c2)ccc1N1CC[C@H](Oc2ncccc2Cl)C1] | ~1920 (Phase 1) | | | | | | |
| 1-313 | 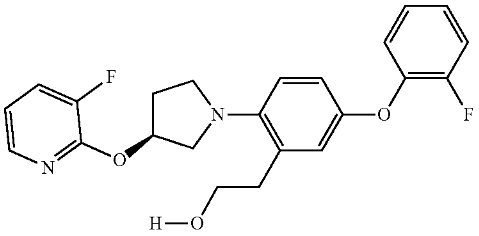 [SMILES: OCCc1cc(Oc2ccccc2F)ccc1N1CC[C@H](Oc2ncccc2F)C1] | 72.5 (Phase 1)<br>71.3 (Phase 2) | | | | | ~2000 | 9.29 (rat) |
| 1-314 | 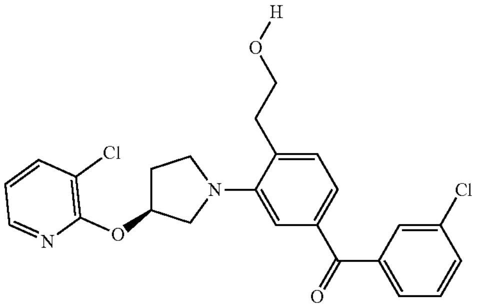 [SMILES: O=C(c1cccc(Cl)c1)c1ccc(CCO)c(N2CC[C@H](Oc3ncccc3Cl)C2)c1] | 229 (Phase 1)<br>307 (Phase 2) | | | | | | |
| 1-315 | 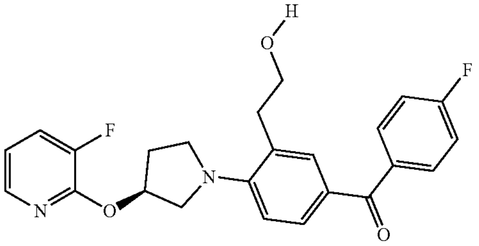 [SMILES: O=C(c1ccc(F)cc1)c1ccc(N2CC[C@H](Oc3ncccc3F)C2)c(CCO)c1] | 1260 (Phase 1) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-316 | 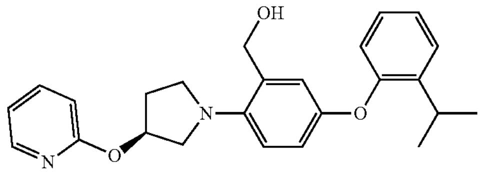 [SMILES: CC(C)c1ccccc1Oc1ccc(N2CC[C@H](Oc3ccccn3)C2)c(CO)c1] | 7.77 (Phase 1) | | | | | >4000 | 18.9 (rat) |
| 1-317 | 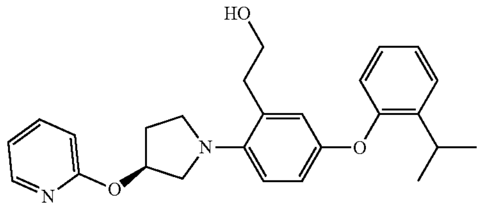 [SMILES: CC(C)c1ccccc1Oc1ccc(N2CC[C@H](Oc3ccccn3)C2)c(CCO)c1] | 20.8 (Phase 1) | | | | | BLQ | 12.1 (rat) |
| 1-318 | 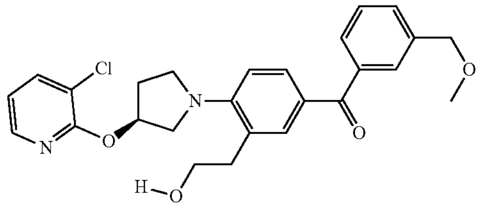 [SMILES: COCc1cccc(C(=O)c2ccc(N3CC[C@H](Oc4ncccc4Cl)C3)c(CCO)c2)c1] | ~3000 (Phase 1) | | | | | | |
| 1-388 | 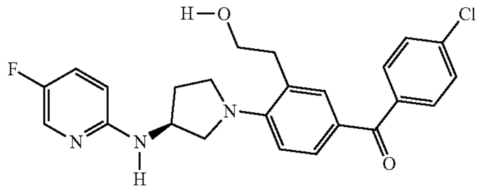 [SMILES: O=C(c1ccc(Cl)cc1)c1ccc(N2CC[C@H](Nc3ccc(F)cn3)C2)c(CCO)c1] | >3200 (Phase 1) | | | | | | |
| 1-319 | 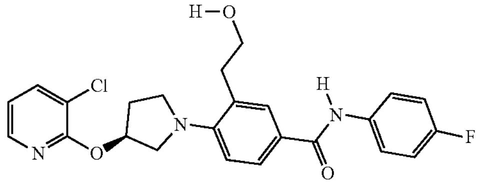 [SMILES: O=C(Nc1ccc(F)cc1)c1ccc(N2CC[C@H](Oc3ncccc3Cl)C2)c(CCO)c1] | 3440 (Phase 1) | | | | | | |
| 1-320 | 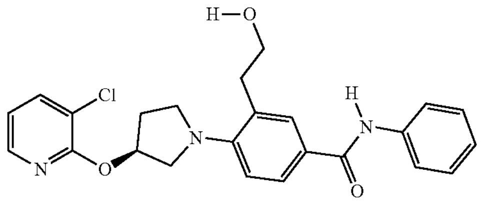 [SMILES: O=C(Nc1ccccc1)c1ccc(N2CC[C@H](Oc3ncccc3Cl)C2)c(CCO)c1] | ~4660 (Phase 1) | | | | | | |
| 1-321 | 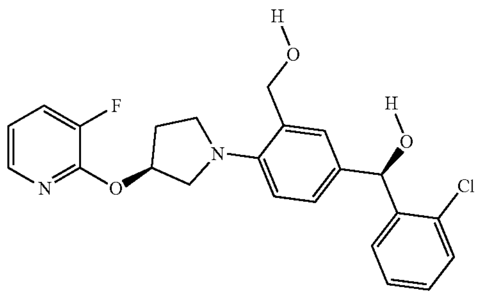 [SMILES: OCc1cc([C@@H](O)c2ccccc2Cl)ccc1N1CC[C@H](Oc2ncccc2F)C1] | 12.2 (Phase 1) Flag/~30/~44/ Incomplete Block (Phase 2) | 5.37 (Phase 1) ~15.7 (Phase 2) | ~3730 (PL) | | | >9800 | 16.9 (rat) |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-322 | 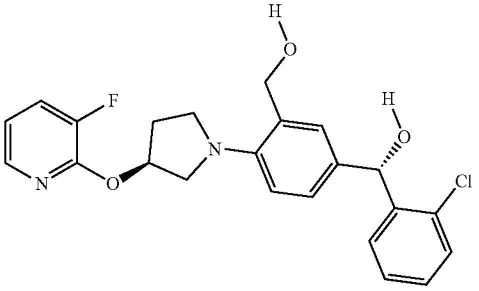 [SMILES: OCc1cc([C@H](O)c2ccccc2Cl)ccc1N1CC[C@H](Oc2ncccc2F)C1] | 794 (Phase 1) | | | | | >9300 | |
| 1-389 | 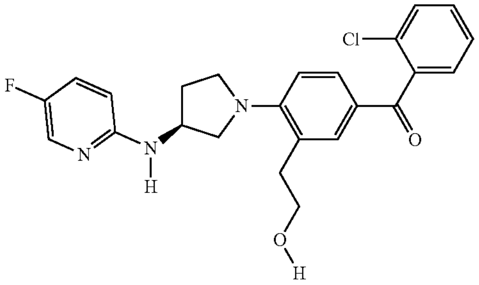 [SMILES: O=C(c1ccc(N2CC[C@H](Nc3ccc(F)cn3)C2)c(CCO)c1)c1ccccc1Cl] | >3200 (Phase 1) | | | | | | |
| 1-390 | 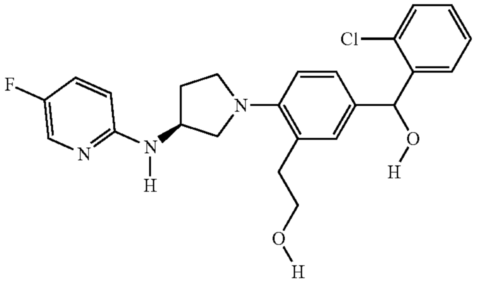 [SMILES: OCCc1cc(C(O)c2ccccc2Cl)ccc1N1CC[C@H](Nc2ccc(F)cn2)C1] | 219 (Phase 1) | | | | | >13600 | 7.23 (rat) |
| 1-323 | 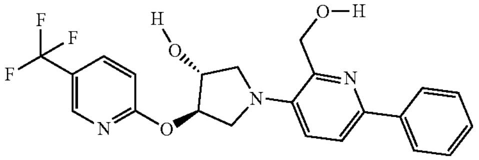 [SMILES: OCc1nc(-c2ccccc2)ccc1N1C[C@@H](O)[C@H](Oc2ccc(C(F)(F)F)cn2)C1] | 3610 (Phase 1) | | | | | | |
| 1-324 | 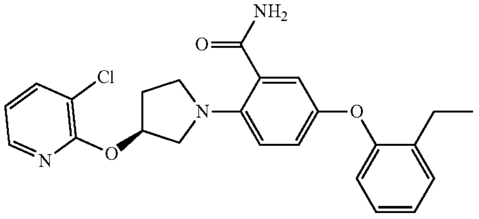 [SMILES: CCc1ccccc1Oc1ccc(N2CC[C@H](Oc3ncccc3Cl)C2)c(C(N)=O)c1] | Incomplete Block (Phase 1) | | | | | | |
| 1-325 | 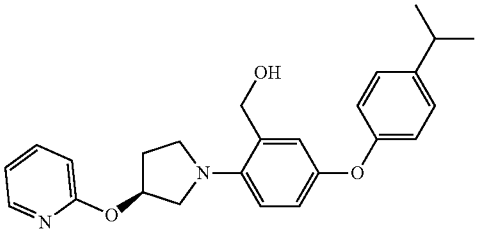 [SMILES: CC(C)c1ccc(Oc2ccc(N3CC[C@H](Oc4ccccn4)C3)c(CO)c2)cc1] | Incomplete Block (Phase 1) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-326 | 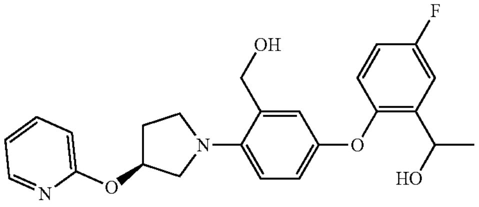 [SMILES: CC(O)c1cc(F)ccc1Oc1ccc(N2CC[C@H](Oc3ccccn3)C2)c(CO)c1] | 1470 (Phase 1) 575 (Phase 2) | | | | | | |
| 1-327 | 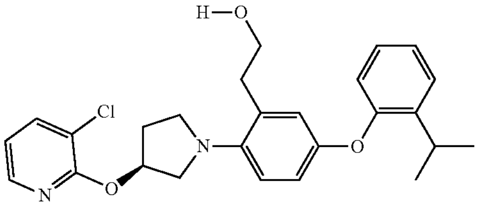 [SMILES: CC(C)c1ccccc1Oc1ccc(N2CC[C@H](Oc3ncccc3Cl)C2)c(CCO)c1] | 15.9 (Phase 1) | | | | | BLQ | 14.6 (rat) |
| 1-328 | 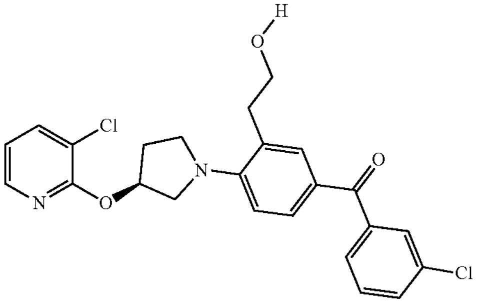 [SMILES: O=C(c1cccc(Cl)c1)c1ccc(N2CC[C@H](Oc3ncccc3Cl)C2)c(CCO)c1] | 615 (Phase 1) | | | | | | |
| 1-329 | 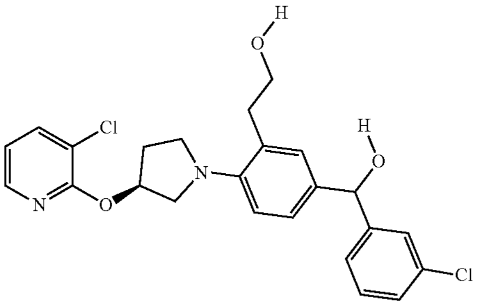 [SMILES: OCCc1cc(C(O)c2cccc(Cl)c2)ccc1N1CC[C@H](Oc2ncccc2Cl)C1] | 3100 (Phase 1) | | | | | | |
| 1-391 | 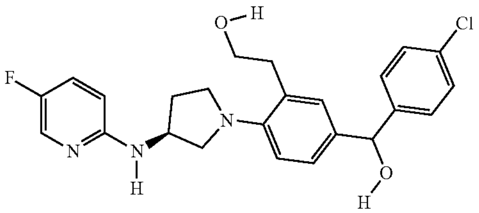 [SMILES: OCCc1cc(C(O)c2ccc(Cl)cc2)ccc1N1CC[C@H](Nc2ccc(F)cn2)C1] | >3200 (Phase 1) | | | | | | |
| 1-392 | 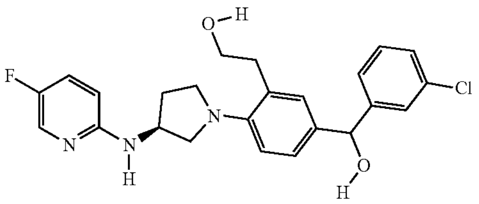 [SMILES: OCCc1cc(C(O)c2cccc(Cl)c2)ccc1N1CC[C@H](Nc2ccc(F)cn2)C1] | >3200 (Phase 1) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-330 | 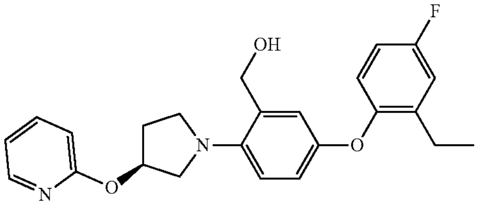 [SMILES: CCc1cc(F)ccc1Oc1ccc(N2CC[C@H](Oc3ccccn3)C2)c(CO)c1] | 49.5 (Phase 1) 56.6 (Phase 2) | | | | | | 24.8 (rat) |
| 1-331 | 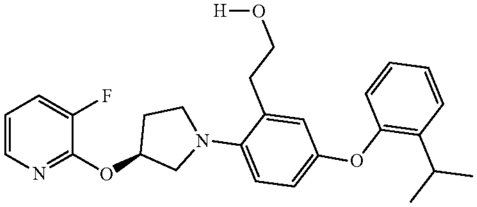 [SMILES: CC(C)c1ccccc1Oc1ccc(N2CC[C@H](Oc3ncccc3F)C2)c(CCO)c1] | 28 (Phase 1) | | | | | | |
| 1-393 | 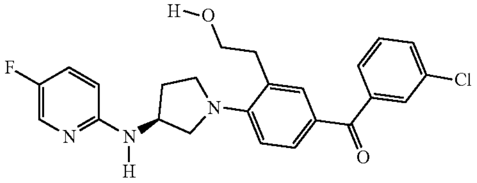 [SMILES: O=C(c1cccc(Cl)c1)c1ccc(N2CC[C@H](Nc3ccc(F)cn3)C2)c(CCO)c1] | ~2950 (Phase 1) >3200 (Phase 2) | | | | | | |
| 1-332 | 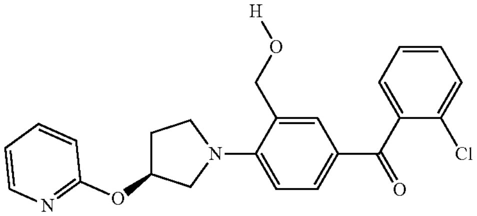 [SMILES: O=C(c1ccc(N2CC[C@H](Oc3ccccn3)C2)c(CO)c1)c1ccccc1Cl] | >3200 (Phase 1) >3200 (Phase 2) | | | | | | |
| 1-333 | 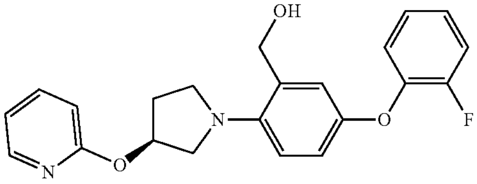 [SMILES: OCc1cc(Oc2ccccc2F)ccc1N1CC[C@H](Oc2ccccn2)C1] | 207 (Phase 1) 111 (Phase 2) | | | | | | |
| 1-334 | 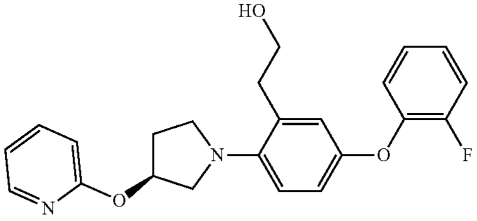 [SMILES: OCCc1cc(Oc2ccccc2F)ccc1N1CC[C@H](Oc2ccccn2)C1] | 289 (Phase 1) ~243 (Phase 2 | | | | | | |
| 1-335 | 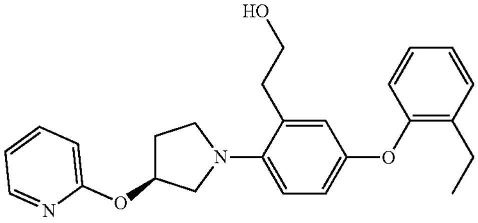 [SMILES: CCc1ccccc1Oc1ccc(N2CC[C@H](Oc3ccccn3)C2)c(CCO)c1] | 66.3 (Phase 1) | | | | x | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-336 | 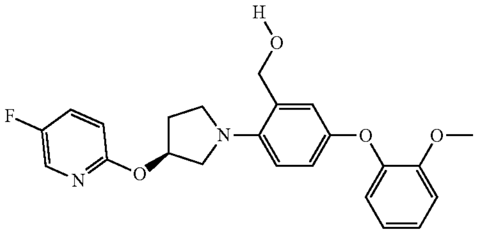 [SMILES: COc1ccccc1Oc1ccc(N2CC[C@H](Oc3ccc(F)cn3)C2)c(CO)c1] | 329 (Phase 1) 384 (Phase 2) | | | | | | |
| 1-337 | 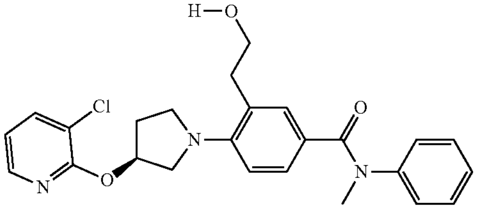 [SMILES: CN(C(=O)c1ccc(N2CC[C@H](Oc3ncccc3Cl)C2)c(CCO)c1)c1ccccc1] | >3200 (Phase 1) | | | | | | |
| 1-338 | 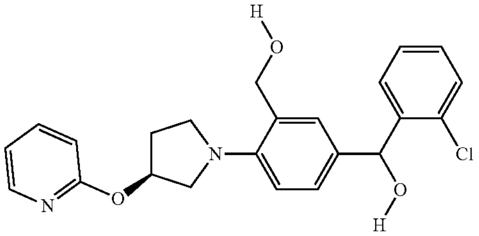 [SMILES: OCc1cc(C(O)c2ccccc2Cl)ccc1N1CC[C@H](Oc2ccccn2)C1] | 196 (Phase 1) | | | | | | |
| 1-339 | 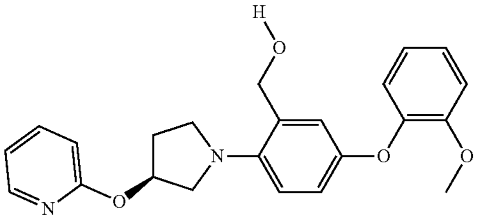 [SMILES: COc1ccccc1Oc1ccc(N2CC[C@H](Oc3ccccn3)C2)c(CO)c1] | 521 (Phase 1) | | | | | | |
| 1-340 | 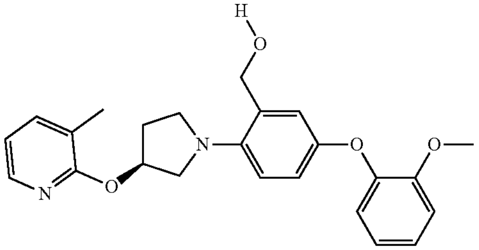 [SMILES: COc1ccccc1Oc1ccc(N2CC[C@H](Oc3ncccc3C)C2)c(CO)c1] | 70.1 (Phase 1) 74.4 (Phase 2) | | | | | ~2400 | |
| 1-341 | 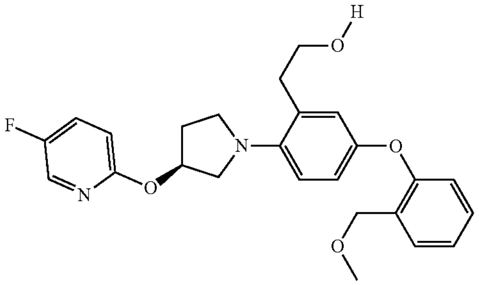 [SMILES: COCc1ccccc1Oc1ccc(N2CC[C@H](Oc3ccc(F)cn3)C2)c(CCO)c1] | 877 (Phase 1) 748 (Phase 2) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-342 | 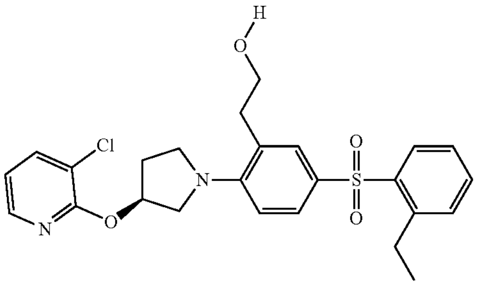 [SMILES: CCc1ccccc1S(=O)(=O)c1ccc(N2CC[C@H](Oc3ncccc3Cl)C2)c(CCO)c1] | >3200 (Phase 2) | | | | | | |
| 1-343 | 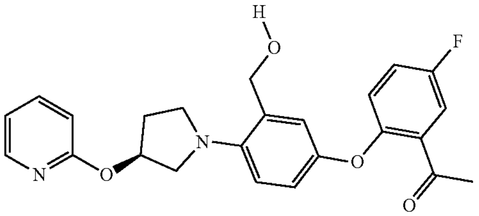 [SMILES: CC(=O)c1cc(F)ccc1Oc1ccc(N2CC[C@H](Oc3ccccn3)C2)c(CO)c1] | 199 (Phase 1) | | | | | | |
| 1-344 | 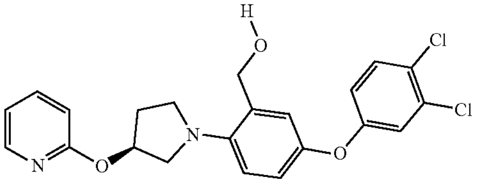 [SMILES: OCc1cc(Oc2ccc(Cl)c(Cl)c2)ccc1N1CC[C@H](Oc2ccccn2)C1] | 65.3 (Phase 1) | | | | | | |
| 1-345 | 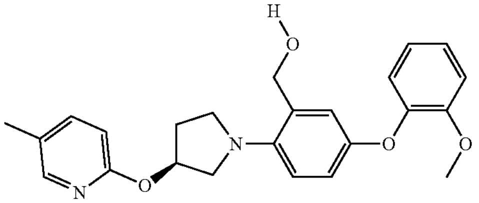 [SMILES: COc1ccccc1Oc1ccc(N2CC[C@H](Oc3ccc(C)cn3)C2)c(CO)c1] | ~2450 (Phase 1) | | | | | | |
| 1-346 | 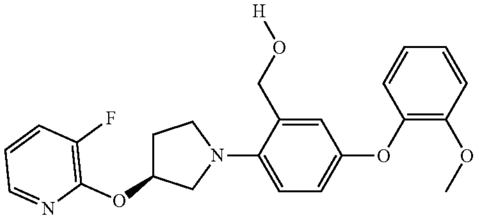 [SMILES: COc1ccccc1Oc1ccc(N2CC[C@H](Oc3ncccc3F)C2)c(CO)c1] | 612 (Phase 1) | | | | | | |
| 1-347 | 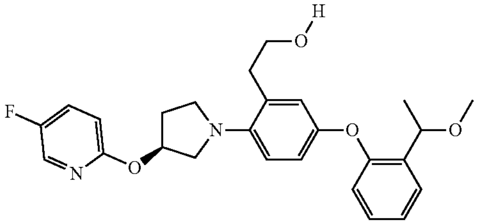 [SMILES: COC(C)c1ccccc1Oc1ccc(N2CC[C@H](Oc3ccc(F)cn3)C2)c(CCO)c1] | 220 (Phase 1)<br>198 (Phase 2) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-348 | 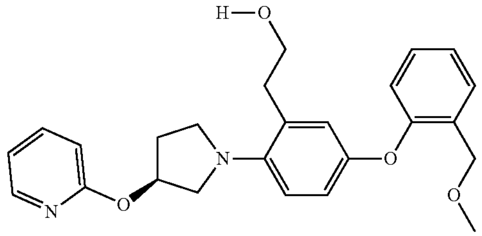 [SMILES: COCc1ccccc1Oc1ccc(N2CC[C@H](Oc3ccccn3)C2)c(CCO)c1] | >3200 (Phase 1) | | | | | | |
| 1-349 | 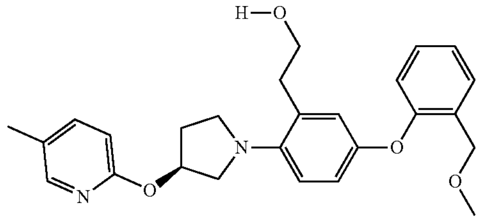 | 908 (Phase 1) | | | | | | |
| 1-350 | 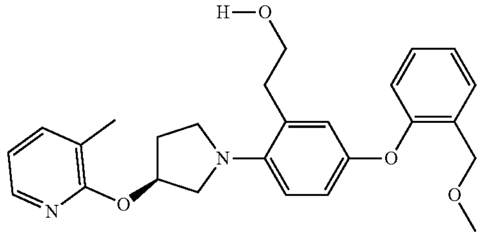 [SMILES: COCc1ccccc1Oc1ccc(N2CC[C@H](Oc3ncccc3C)C2)c(CCO)c1] | 311 (Phase 1) | | | | | | |
| 1-351 | 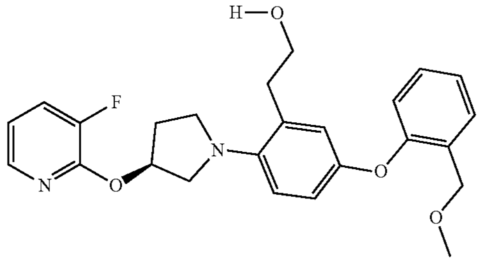 [SMILES: COCc1ccccc1Oc1ccc(N2CC[C@H](Oc3ncccc3F)C2)c(CCO)c1] | 461 (Phase 1) | | | | | | |
| 1-352 | 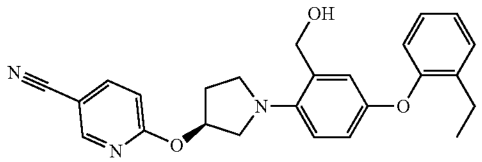 [SMILES: CCc1ccccc1Oc1ccc(N2CC[C@H](Oc3ccc(C#N)cn3)C2)c(CO)c1] | 974 (Phase 1) | | | | | | |
| 1-353 | 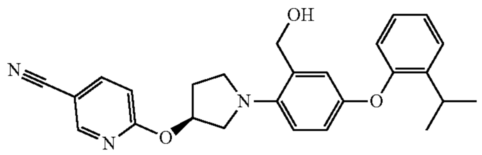 [SMILES: CC(C)c1ccccc1Oc1ccc(N2CC[C@H](Oc3ccc(C#N)cn3)C2)c(CO)c1] | 26.8 (Phase 1) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-354 | 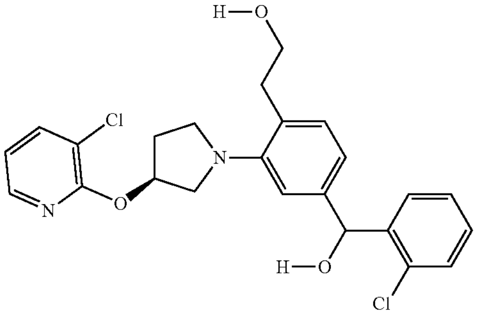 [SMILES: OCCc1ccc(C(O)c2ccccc2Cl)cc1N1CC[C@H](Oc2ncccc2Cl)C1] | 1010 (Phase 1) | | | | | | |
| 1-355 | 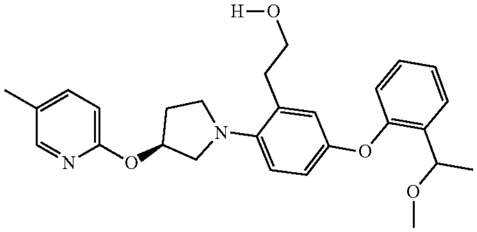 [SMILES: COC(C)c1ccccc1Oc1ccc(N2CC[C@H](Oc3ccc(C)cn3)C2)c(CCO)c1] | 173 (Phase 1) | | | | | | |
| 1-356 | 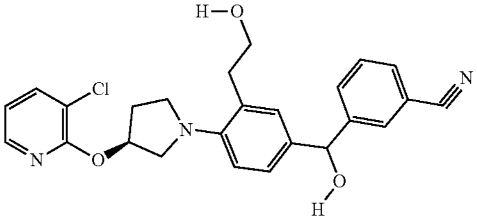 [SMILES: N#Cc1cccc(C(O)c2ccc(N3CC[C@H](Oc4ncccc4Cl)C3)c(CCO)c2)c1] | >3200 (Phase 1) | | | | | | |
| 1-357 | 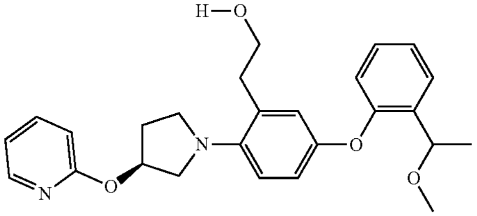 [SMILES: COC(C)c1ccccc1Oc1ccc(N2CC[C@H](Oc3ccccn3)C2)c(CCO)c1] | 312 (Phase 1) | | | | | | |
| 1-358 | 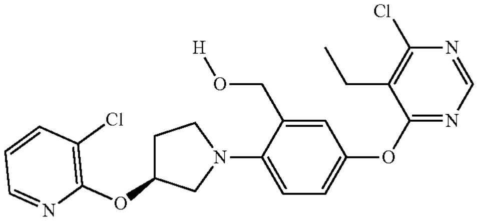 [SMILES: CCc1c(Cl)ncnc1Oc1ccc(N2CC[C@H](Oc3ncccc3Cl)C2)c(CO)c1] | 174 (Phase 1) | | | | | ~2100 | 16.7 (rat) |
| 1-359 | 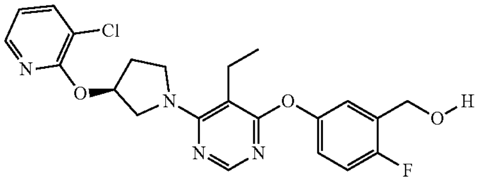 [SMILES: CCc1c(Oc2ccc(F)c(CO)c2)ncnc1N1CC[C@H](Oc2ncccc2Cl)C1] | Agonist (Phase 1) | | | | | | |

TABLE 3-continued
| No. | Structure | hTRPV3 (nM) | rTRPV3 (nM) | hERG (nM) | hNaV1.5 (nM) | hTRPV3 HAMA IC50 (nM) | Solubility Ringer (nM) | LM T1/2 (min) |
|---|---|---|---|---|---|---|---|---|
| 1-360 | 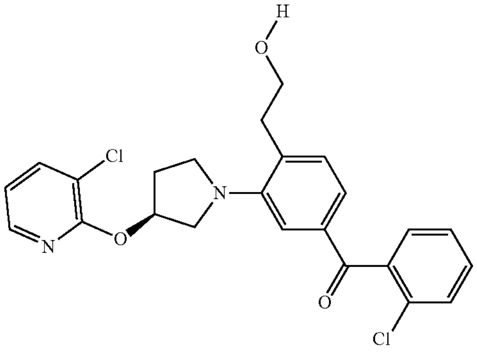 [SMILES: O=C(c1ccc(CCO)c(N2CC[C@H](Oc3ncccc3Cl)C2)c1)c1ccccc1Cl] | 770 (Phase 1) | | | | | | |
| 1-361 | 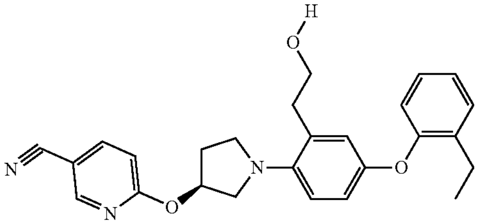 [SMILES: CCc1ccccc1Oc1ccc(N2CC[C@H](Oc3ccc(C#N)cn3)C2)c(CCO)c1] | 117 (Phase 1) | | | | | | |
| 1-362 | 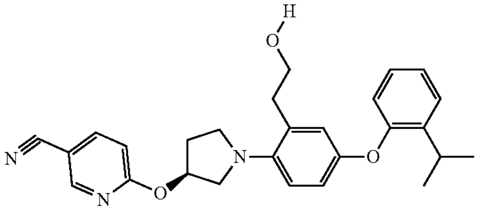 [SMILES: CC(C)c1ccccc1Oc1ccc(N2CC[C@H](Oc3ccc(C#N)cn3)C2)c(CCO)c1] | 61.2 (Phase 1) | | | | | | |

TABLE 4
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-85 | 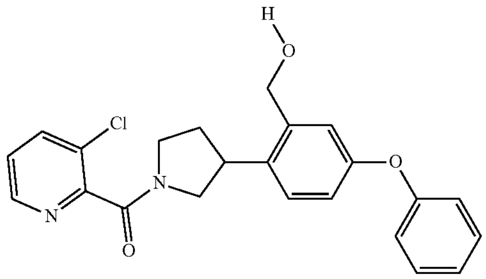 [SMILES: O=C(c1ncccc1Cl)N1CCC(c2ccc(Oc3ccccc3)cc2CO)C1] | 3310 (Phase 1) | | | | | | | |
| 2-84 | 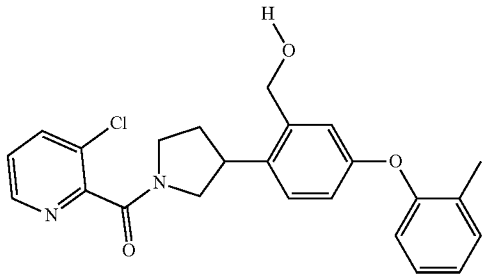 [SMILES: Cc1ccccc1Oc1ccc(C2CCN(C(=O)c3ncccc3Cl)C2)c(CO)c1] | 932 (Phase 1) | | | | | | | |
| 2-83 | 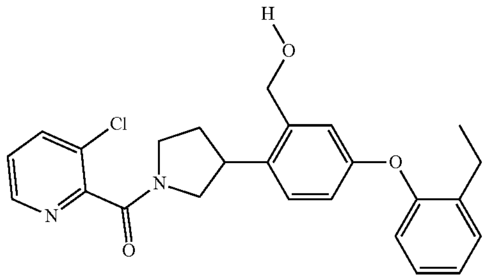 [SMILES: CCc1ccccc1Oc1ccc(C2CCN(C(=O)c3ncccc3Cl)C2)c(CO)c1] | 95.1 (Phase 1) | | !16000 (PL) | | | >11000 | 9.46 (rat) | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-86 | 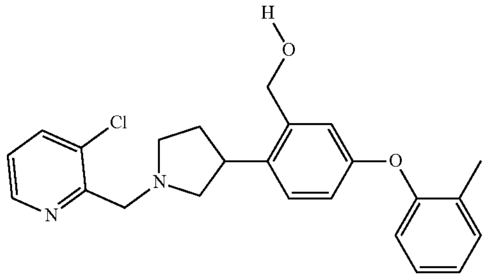 [SMILES: Cc1ccccc1Oc1ccc(C2CCN(Cc3ncccc3Cl)C2)c(CO)c1] | 226 (Phase 1) | | | | | ~2200 | | |
| 2-4 | 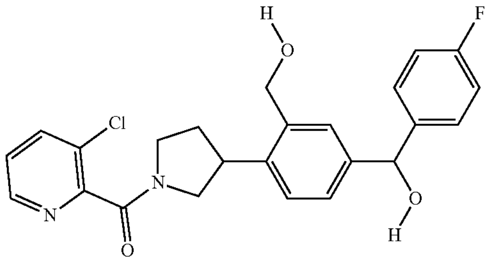 [SMILES: O=C(c1ncccc1Cl)N1CCC(c2ccc(C(O)c3ccc(F)cc3)cc2CO)C1] | >3200 (Phase 1) | | | | | | | |
| 2-5 | 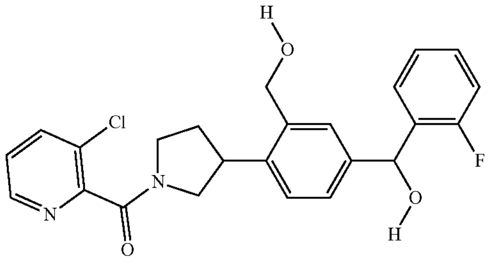 [SMILES: O=C(c1ncccc1Cl)N1CCC(c2ccc(C(O)c3ccccc3F)cc2CO)C1] | >3200 (Phase 1) | | | | | | | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-6 | 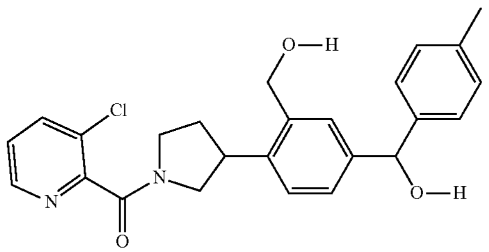 [SMILES: Cc1ccc(C(O)c2ccc(C3CCN(C(=O)c4ncccc4Cl)C3)c(CO)c2)cc1] | >3200 (Phase 1) | | | | | | | |
| 2-7 | 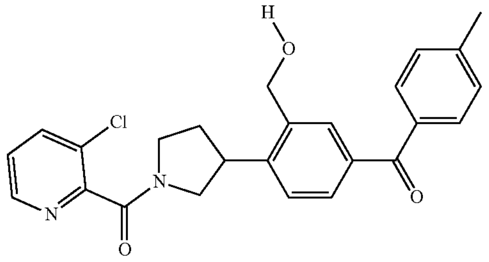 [SMILES: Cc1ccc(C(=O)c2ccc(C3CCN(C(=O)c4ncccc4Cl)C3)c(CO)c2)cc1] | >3200 (Phase 1) | | | | | | | |
| 2-8 | 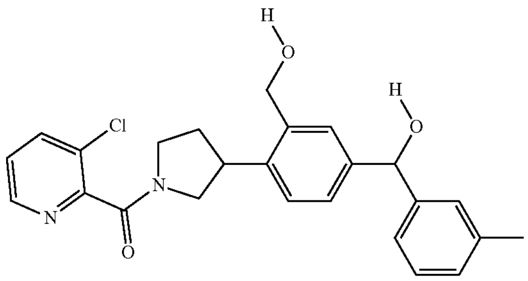 [SMILES: Cc1cccc(C(O)c2ccc(C3CCN(C(=O)c4ncccc4Cl)C3)c(CO)c2)c1] | >3200 (Phase 1) | | | | | | | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-9 | 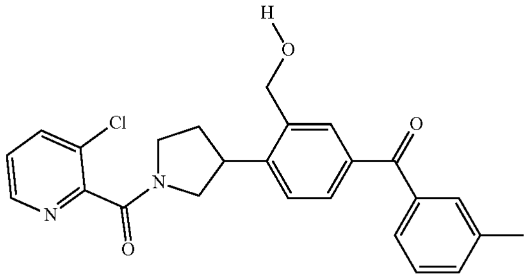 [SMILES: Cc1cccc(C(=O)c2ccc(C3CCN(C(=O)c4ncccc4Cl)C3)c(CO)c2)c1] | >3200 (Phase 1) | | | | | | | |
| 2-10 | 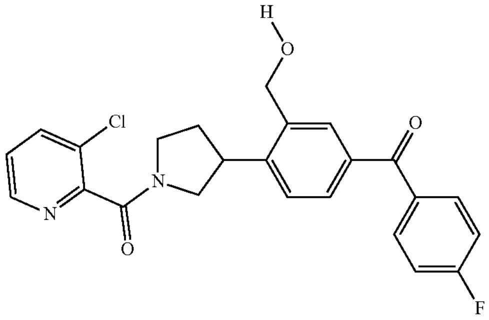 [SMILES: O=C(c1ccc(F)cc1)c1ccc(C2CCN(C(=O)c3ncccc3Cl)C2)c(CO)c1] | >3200 (Phase 1) | | | | | | | |
| 2-11 | 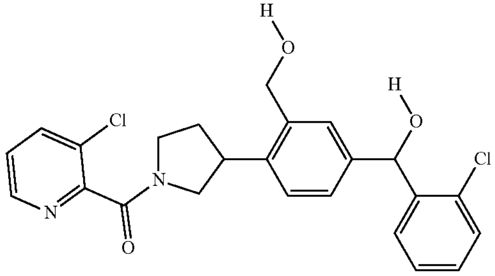 [SMILES: O=C(c1ncccc1Cl)N1CCC(c2ccc(C(O)c3ccccc3Cl)cc2CO)C1] | >3200 (Phase 1) | | | | | | | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-12 | 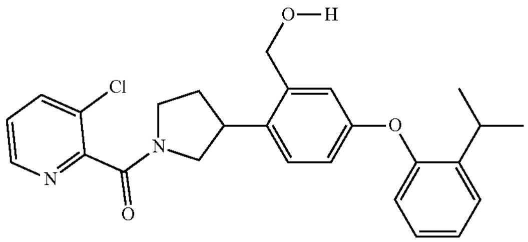 [SMILES: CC(C)c1ccccc1Oc1ccc(C2CCN(C(=O)c3ncccc3Cl)C2)c(CO)c1] | 101 (Phase 1) | | !12600 (PL) | | | >8000 | 7.55 (rat) | |
| 2-13 | 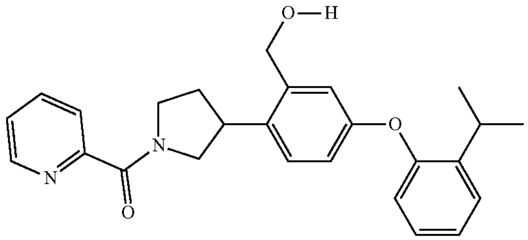 [SMILES: CC(C)c1ccccc1Oc1ccc(C2CCN(C(=O)c3ccccn3)C2)c(CO)c1] | 193 (Phase 1) | | | | | | | |
| 2-87 | 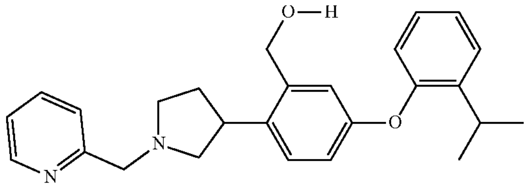 [SMILES: CC(C)c1ccccc1Oc1ccc(C2CCN(Cc3ccccn3)C2)c(CO)c1] | 699 (Phase 1) | | 260 (PL) | | | | 2.46 (rat) | |
| 2-14 | 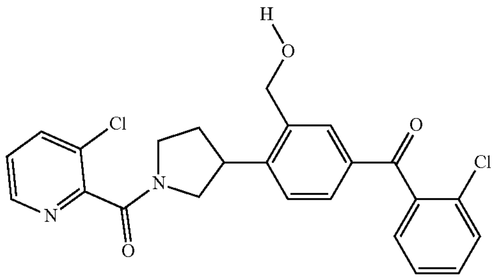 [SMILES: O=C(c1ccc(C2CCN(C(=O)c3ncccc3Cl)C2)c(CO)c1)c1ccccc1Cl] | >3200 (Phase 1) | | | | | | | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-15 | 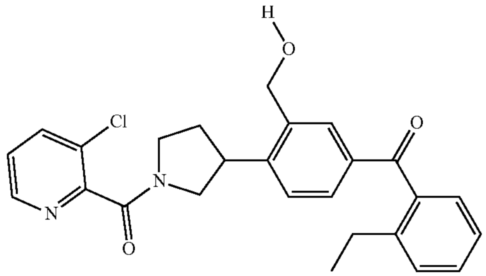 [SMILES: CCc1ccccc1C(=O)c1ccc(C2CCN(C(=O)c3ncccc3Cl)C2)c(CO)c1] | >3200 (Phase 1) | | | | | | | |
| 2-16 | 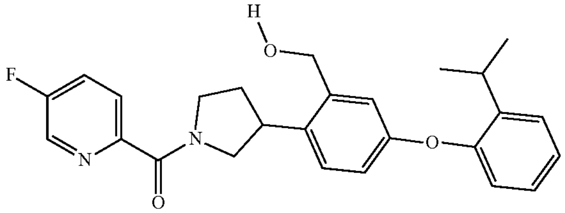 [SMILES: CC(C)c1ccccc1Oc1ccc(C2CCN(C(=O)c3ccc(F)cn3)C2)c(CO)c1] | 29.7 (Phase 1) 25.7 (Phase 2) | | !9650 (PL) | | | ~4700 | 5.3 (rat) | |
| 2-17 | 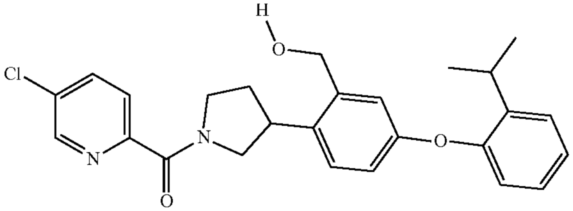 [SMILES: CC(C)c1ccccc1Oc1ccc(C2CCN(C(=O)c3ccc(Cl)cn3)C2)c(CO)c1] | 57.4 (Phase 1) | | | | | | 7.93 (rat) | |
| 2-18 | 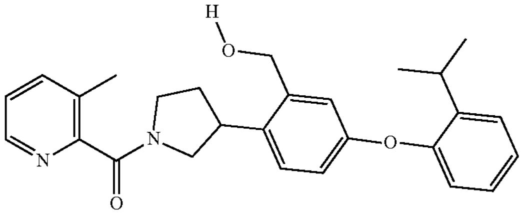 [SMILES: Cc1cccnc1C(=O)N1CCC(c2ccc(Oc3ccccc3C(C)C)cc2CO)C1] | 314 (Phase 1) | | | | | | 7.81 (rat) | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-116 | 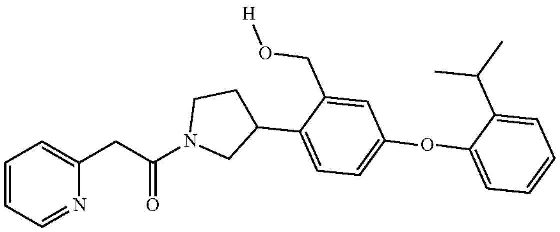 [SMILES: CC(C)c1ccccc1Oc1ccc(C2CCN(C(=O)Cc3ccccn3)C2)c(CO)c1] | ~3500 (Phase 1) 2600 (Phase 2) | | | | | | 3.62 (rat) | |
| 2-117 | 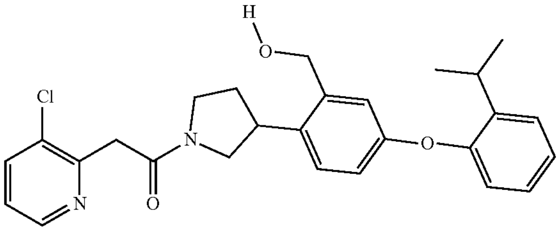 [SMILES: CC(C)c1ccccc1Oc1ccc(C2CCN(C(=O)Cc3ncccc3Cl)C2)c(CO)c1] | ~3500 (Phase 1) 2620 (Phase 2) | | | | | | | |
| 2-88 | 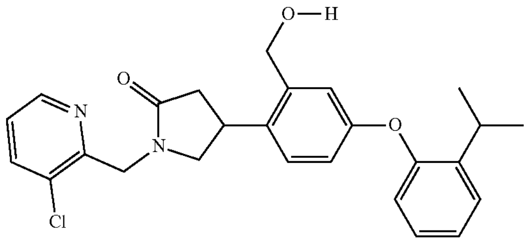 [SMILES: CC(C)c1ccccc1Oc1ccc(C2CC(=O)N(Cc3ncccc3Cl)C2)c(CO)c1] | 169 (Phase 1) 184 (Phase 2) | | | | | | | |
| 2-19 | 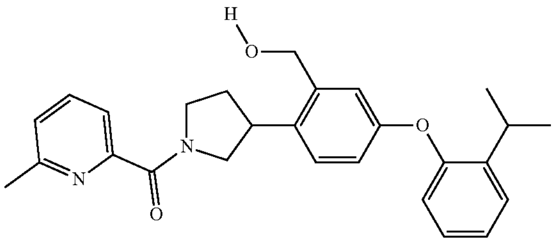 [SMILES: Cc1cccc(C(=O)N2CCC(c3ccc(Oc4ccccc4C(C)C)cc3CO)C2)n1] | 191 (Phase 1) | | | | | | | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-89 | 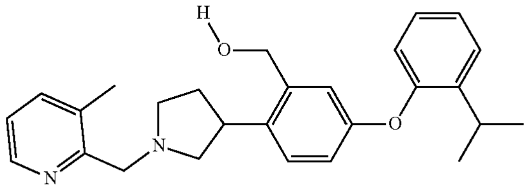 [SMILES: Cc1cccnc1CN1CCC(c2ccc(Oc3ccccc3C(C)C)cc2CO)C1] | 1230 (Phase 1) | | | | | | | |
| 2-90 | 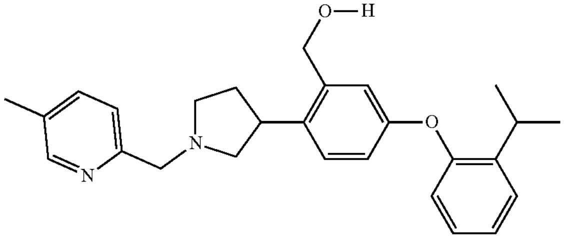 [SMILES: Cc1ccc(CN2CCC(c3ccc(Oc4ccccc4C(C)C)cc3CO)C2)nc1] | 812 (Phase 1) | | | | | | | |
| 2-119 | 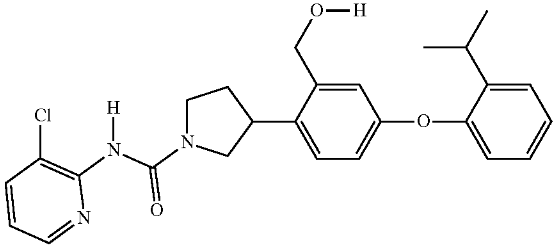 [SMILES: CC(C)c1ccccc1Oc1ccc(C2CCN(C(=O)Nc3ncccc3Cl)C2)c(CO)c1] | 549 (Phase 1) | | | | | | | |
| 2-91 | 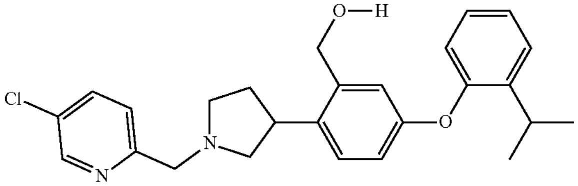 [SMILES: CC(C)c1ccccc1Oc1ccc(C2CCN(Cc3ccc(Cl)cn3)C2)c(CO)c1] | 325 (Phase 1) | | | | | | | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-92 | 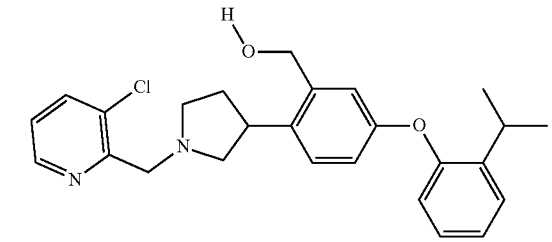 [SMILES: CC(C)c1ccccc1Oc1ccc(C2CCN(Cc3ncccc3Cl)C2)c(CO)c1] | 592 (Phase 1) | | | | | | | |
| 2-93 | 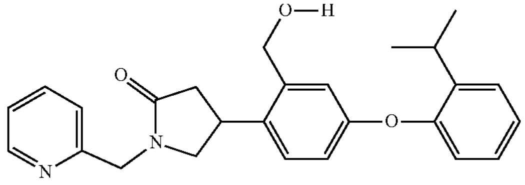 [SMILES: CC(C)c1ccccc1Oc1ccc(C2CC(=O)N(Cc3ccccn3)C2)c(CO)c1] | 205 (Phase 1) | | !~10800 (M) !~5970 (PL) | | | ~4200 | 5.05 (rat) | |
| 2-20 | 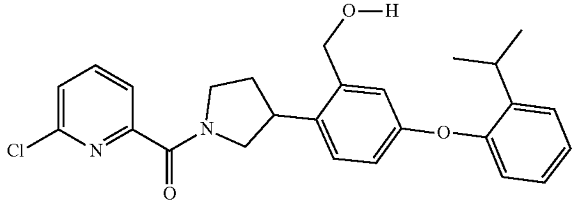 [SMILES: CC(C)c1ccccc1Oc1ccc(C2CCN(C(=O)c3cccc(Cl)n3)C2)c(CO)c1] | 62 (Phase 1) | | !3910 (M) !~5330 (PL) | | | ~1600 | 8.33 (rat) | |
| 2-21 | 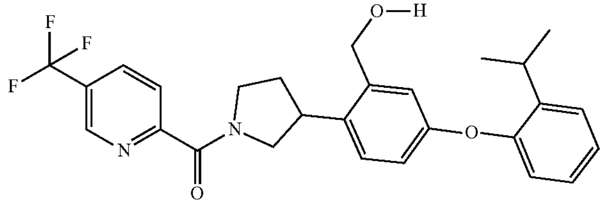 [SMILES: CC(C)c1ccccc1Oc1ccc(C2CCN(C(=O)c3ccc(C(F)(F)F)cn3)C2)c(CO)c1] | 97.1 (Phase 1) | | | | | | | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-22 | 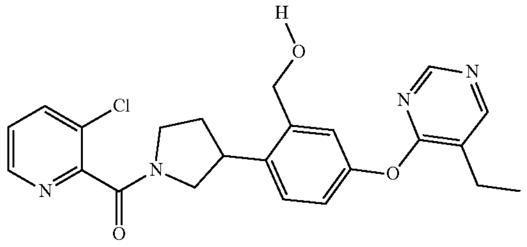 [SMILES: CCc1cncnc1Oc1ccc(C2CCN(C(=O)c3ncccc3Cl)C2)c(CO)c1] | >3200 (Phase 1) | | >32000 (PL) | | | >20300 | 31.8 (rat) | |
| 2-23 | 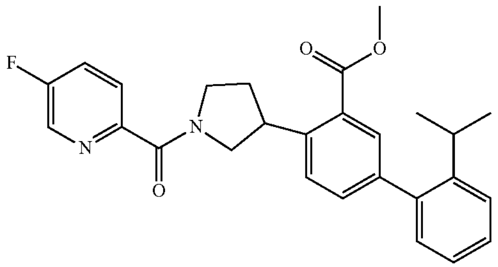 [SMILES: COC(=O)c1cc(-c2ccccc2C(C)C)ccc1C1CCN(C(=O)c2ccc(F)cn2)C1] | 886 (Phase 1) | | | | | | | |
| 2-24 | 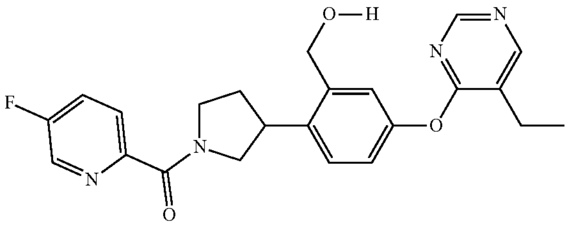 [SMILES: CCc1cncnc1Oc1ccc(C2CCN(C(=O)c3ccc(F)cn3)C2)c(CO)c1] | >3200 (Phase 1) | | | | | | | |
| 2-25 | 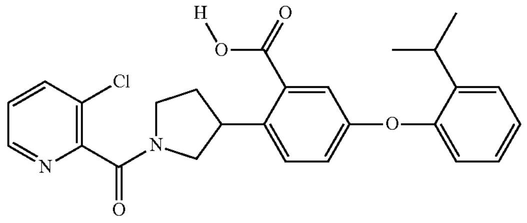 [SMILES: CC(C)c1ccccc1Oc1ccc(C2CCN(C(=O)c3ncccc3Cl)C2)c(C(=O)O)c1] | >3200 (Phase 1) | | | | | | | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-26 | 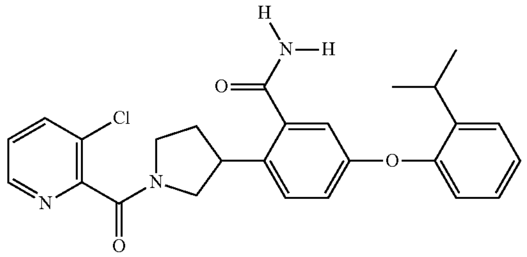 [SMILES: CC(C)c1ccccc1Oc1ccc(C2CCN(C(=O)c3ncccc3Cl)C2)c(C(N)=O)c1] | 217 (Phase 1) | | 10400 (PL) | | | >19200 | 19.7 (rat) | |
| 2-27 | 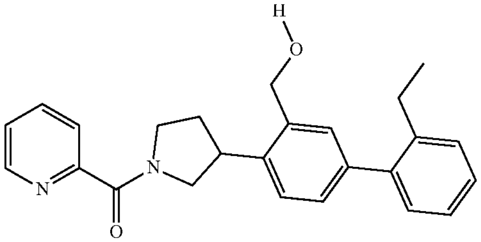 [SMILES: CCc1ccccc1-c1ccc(C2CCN(C(=O)c3ccccn3)C2)c(CO)c1] | 73 (Phase 1) | | | | | | 12.9 (rat) | |
| 2-94 | 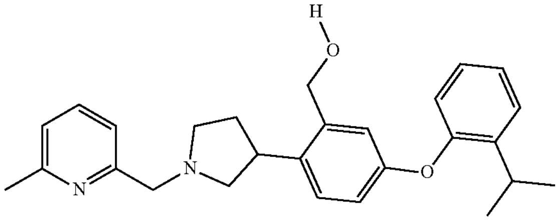 [SMILES: Cc1cccc(CN2CCC(c3ccc(Oc4ccccc4C(C)C)cc3CO)C2)n1] | 339 (Phase 1) | | | | | | | |
| 2-28 | 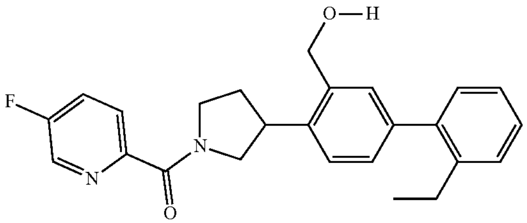 [SMILES: CCc1ccccc1-c1ccc(C2CCN(C(=O)c3ccc(F)cn3)C2)c(CO)c1] | 19.6 (Phase 1) | | 13700 (PL) | | | >15000 | 18.4 (rat) | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-95 | 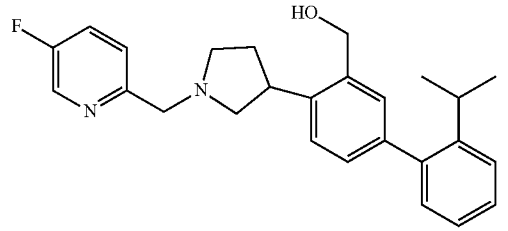 [SMILES: CC(C)c1ccccc1-c1ccc(C2CCN(Cc3ccc(F)cn3)C2)c(CO)c1] | 582 (Phase 1) | | <1000 (PL) | | | | | |
| 2-29 | 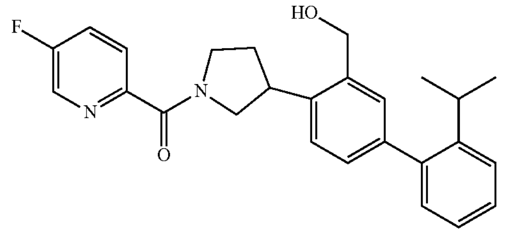 [SMILES: CC(C)c1ccccc1-c1ccc(C2CCN(C(=O)c3ccc(F)cn3)C2)c(CO)c1] | 6.03 (Phase 1) | 5.56 (Phase 1) | 7380 (M) 7480 (PL) | | | >16600 | 8.8 (human) 16.8 (rat) | |
| 2-30 | 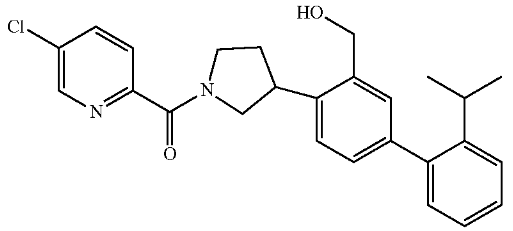 [SMILES: CC(C)c1ccccc1-c1ccc(C2CCN(C(=O)c3ccc(Cl)cn3)C2)c(CO)c1] | 2.68 (Phase 1) | | | | | ~3700 | 13.9 (rat) | |
| 2-96 | 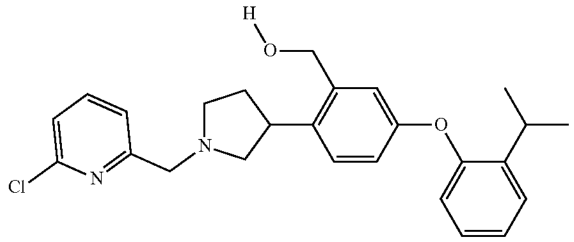 [SMILES: CC(C)c1ccccc1Oc1ccc(C2CCN(Cc3cccc(Cl)n3)C2)c(CO)c1] | 246 (Phase 1) | | | | | | | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-31 | 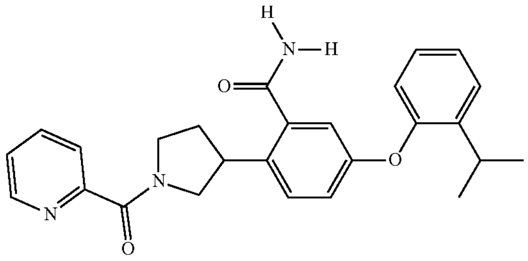 [SMILES: CC(C)c1ccccc1Oc1ccc(C2CCN(C(=O)c3ccccn3)C2)c(C(N)=O)c1] | 1370 (Phase 1) | | | | | | | |
| 2-32 | 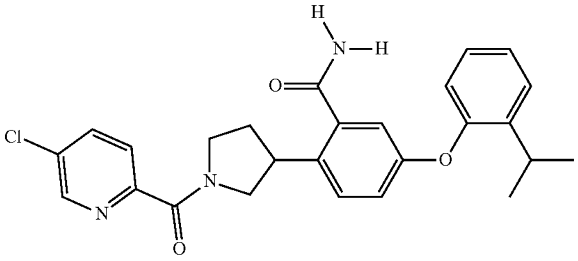 [SMILES: CC(C)c1ccccc1Oc1ccc(C2CCN(C(=O)c3ccc(Cl)cn3)C2)c(C(N)=O)c1] | 677 (Phase 1) | | | | | | 6.86 (rat) | |
| 2-33 | 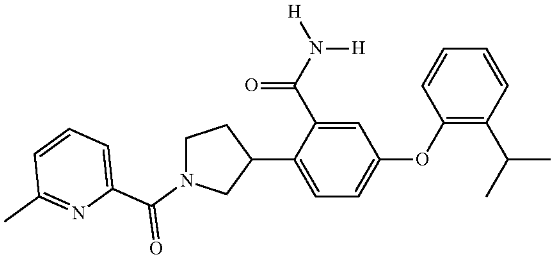 [SMILES: Cc1cccc(C(=O)N2CCC(c3ccc(Oc4ccccc4C(C)C)cc3C(N)=O)C2)n1] | 645 (Phase 1) | | | | | | 11 (rat) | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-34 | 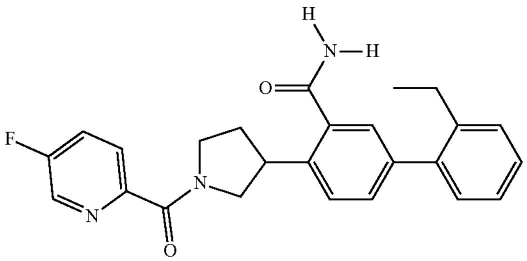 [SMILES: CCc1ccccc1-c1ccc(C2CCN(C(=O)c3ccc(F)cn3)C2)c(C(N)=O)c1] | 337 (Phase 1) | | | | | | 26.4 (rat) | |
| 2-35 | 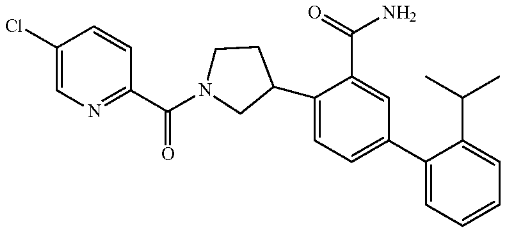 [SMILES: CC(C)c1ccccc1-c1ccc(C2CCN(C(=O)c3ccc(Cl)cn3)C2)c(C(N)=O)c1] | 61.7 (Phase 1) 64.3 (Phase 2) | | | | | ~3300 | 7.16 (rat) | |
| 2-36 | 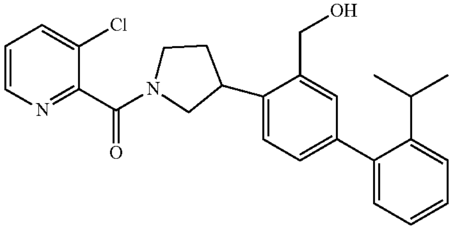 [SMILES: CC(C)c1ccccc1-c1ccc(C2CCN(C(=O)c3ncccc3Cl)C2)c(CO)c1] | 39.3 (Phase 1) | | | | | | 11.2 (rat) | |
| 2-97 | 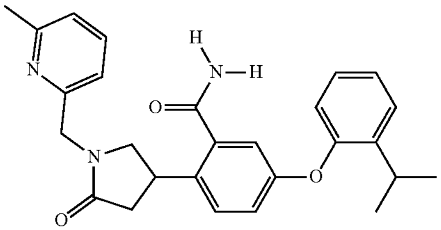 [SMILES: Cc1cccc(CN2CC(c3ccc(Oc4ccccc4C(C)C)cc3C(N)=O)CC2=O)n1] | >3200 (Phase 1) | | | | | | | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-37 | 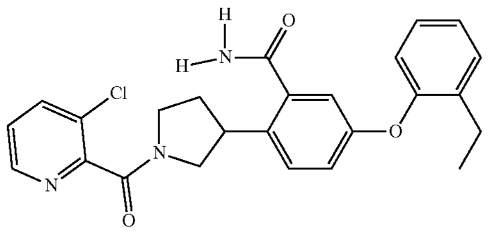 [SMILES: CCc1ccccc1Oc1ccc(C2CCN(C(=O)c3ncccc3Cl)C2)c(C(N)=O)c1] | ~2190 Phase 1) | | | | | | | |
| 2-98 | 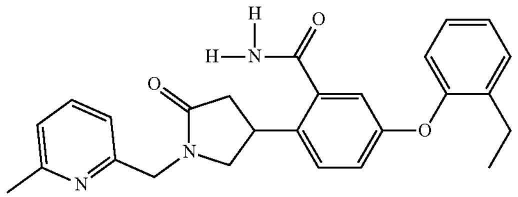 [SMILES: CCc1ccccc1Oc1ccc(C2CC(=O)N(Cc3cccc(C)n3)C2)c(C(N)=O)c1] | >3200 (Phase 1) | | | | | | | |
| 2-38 | 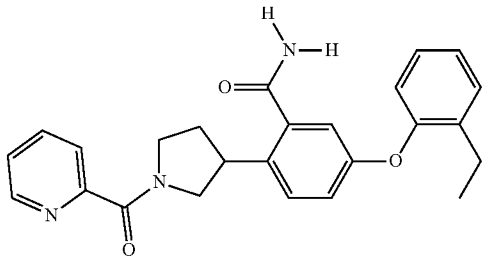 [SMILES: CCc1ccccc1Oc1ccc(C2CCN(C(=O)c3ccccn3)C2)c(C(N)=O)c1] | 2820 (Phase 1) | | | | | | | |
| 2-39 | 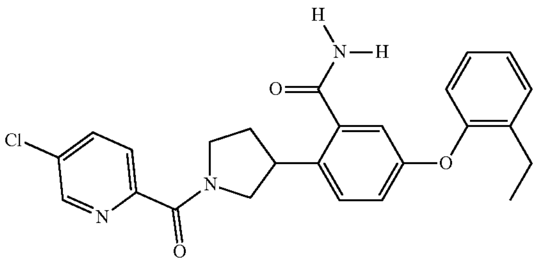 [SMILES: CCc1ccccc1Oc1ccc(C2CCN(C(=O)c3ccc(Cl)cn3)C2)c(C(N)=O)c1] | 681 (Phase 1) | | | | | | | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-99 | 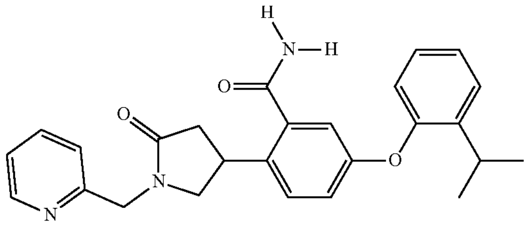 [SMILES: CC(C)c1ccccc1Oc1ccc(C2CC(=O)N(Cc3ccccn3)C2)c(C(N)=O)c1] | >3200 (Phase 1) | | | | | | | |
| 2-40 | 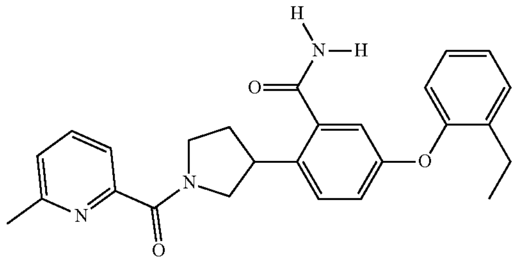 [SMILES: CCc1ccccc1Oc1ccc(C2CCN(C(=O)c3cccc(C)n3)C2)c(C(N)=O)c1] | 4900 (Phase 1) | | | | | | | |
| 2-41 | 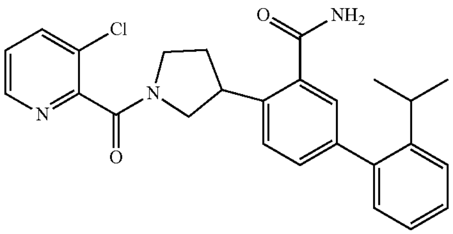 [SMILES: CC(C)c1ccccc1-c1ccc(C2CCN(C(=O)c3ncccc3Cl)C2)c(C(N)=O)c1] | 575 (Phase 1) | | | | | | | |
| 2-42 | 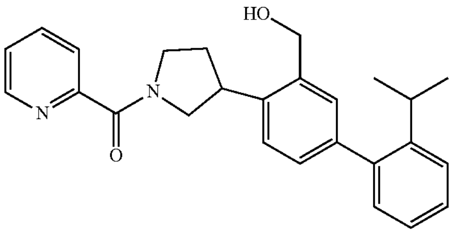 [SMILES: CC(C)c1ccccc1-c1ccc(C2CCN(C(=O)c3ccccn3)C2)c(CO)c1] | 22.7 (Phase 1) | | 18300 (PL) | | | >19700 | 11.7 (rat) | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-100 | 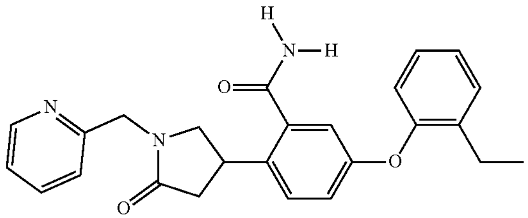 [SMILES: CCc1ccccc1Oc1ccc(C2CC(=O)N(Cc3ccccn3)C2)c(C(N)=O)c1] | >3200 (Phase 1) | | | | | | | |
| 2-43 | 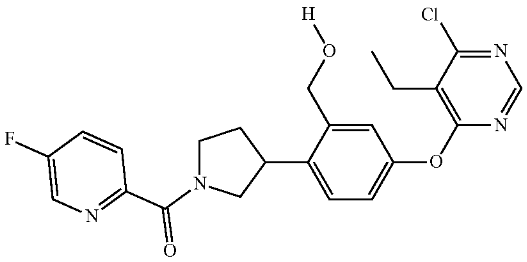 [SMILES: CCc1c(Cl)ncnc1Oc1ccc(C2CCN(C(=O)c3ccc(F)cn3)C2)c(CO)c1] | >3200 (Phase 1) | | | | | | | |
| 2-44 | 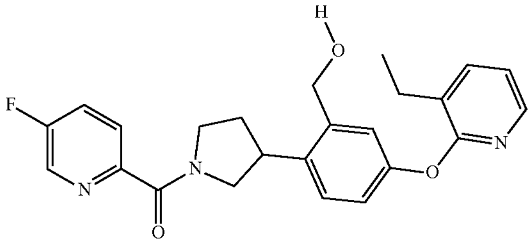 [SMILES: CCc1cccnc1Oc1ccc(C2CCN(C(=O)c3ccc(F)cn3)C2)c(CO)c1] | >3200 (Phase 1) | | | | | | | |
| 2-101 | 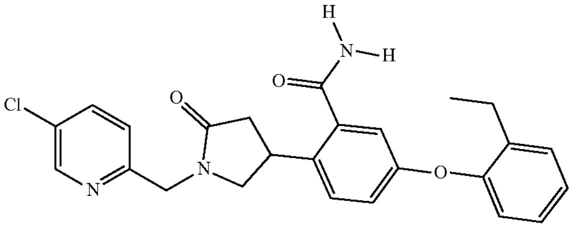 [SMILES: CCc1ccccc1Oc1ccc(C2CC(=O)N(Cc3ccc(Cl)cn3)C2)c(C(N)=O)c1] | >3200 (Phase 1) | | | | | | | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-45 | 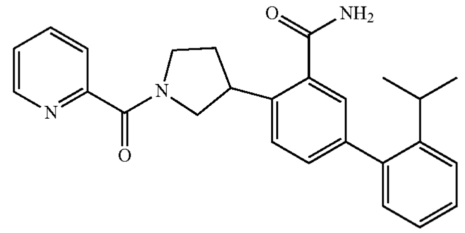 [SMILES: CC(C)c1ccccc1-c1ccc(C2CCN(C(=O)c3ccccn3)C2)c(C(N)=O)c1] | 929 (Phase 1) | | | | | | | |
| 2-102 | 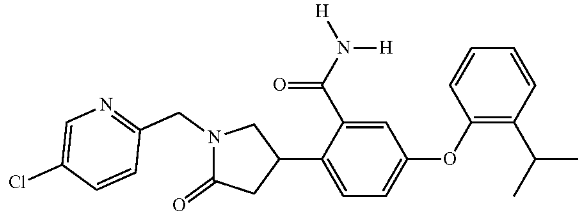 [SMILES: CC(C)c1ccccc1Oc1ccc(C2CC(=O)N(Cc3ccc(Cl)cn3)C2)c(C(N)=O)c1] | ~2150 (Phase 1) | | | | | | | |
| 2-119 | 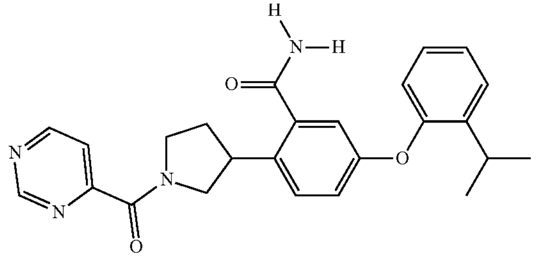 [SMILES: CC(C)c1ccccc1Oc1ccc(C2CCN(C(=O)c3ccncn3)C2)c(C(N)=O)c1] | >3200 (Phase 1) | | | | | | | |
| 2-46 | 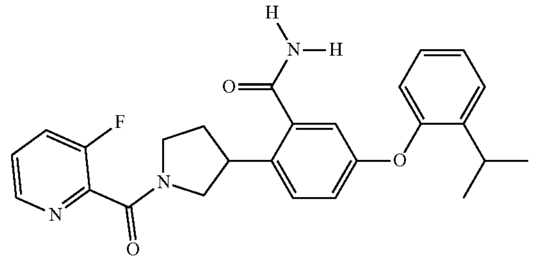 | ~2250 (Phase 1) | | | | | | | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-103 | 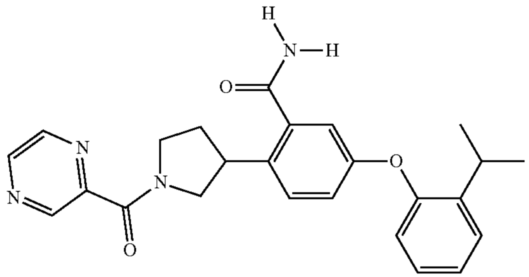 [SMILES: CC(C)c1ccccc1Oc1ccc(C2CCN(C(=O)c3cnccn3)C2)c(C(N)=O)c1] | ~5250 (Phase 1) | | | | | | | |
| 2-47 | 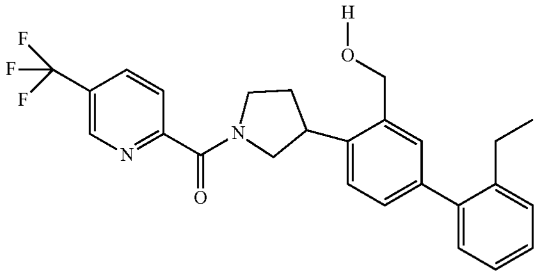 [SMILES: CCc1ccccc1-c1ccc(C2CCN(C(=O)c3ccc(C(F)(F)F)cn3)C2)c(CO)c1] | 18.4 (Phase 1) | | !17200 (PL) | | | ~5600 | 28.1 (rat) | |
| 2-48 | 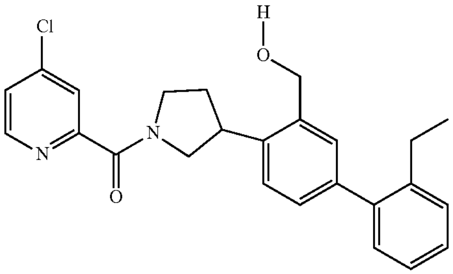 [SMILES: CCc1ccccc1-c1ccc(C2CCN(C(=O)c3cc(Cl)ccn3)C2)c(CO)c1] | 69.3 (Phase 1) | | !13400 (PL) | | | >8000 | 7.54 (rat) | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-49 | 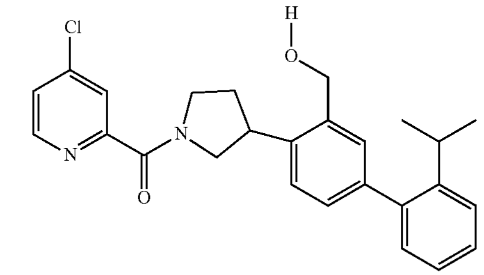 [SMILES: CC(C)c1ccccc1-c1ccc(C2CCN(C(=O)c3cc(Cl)ccn3)C2)c(CO)c1] | 25.7 (Phase 1) | | 6970 (PL) | | | >12800 | 12.2 (human) 20.6 (rat) | |
| 2-50 | 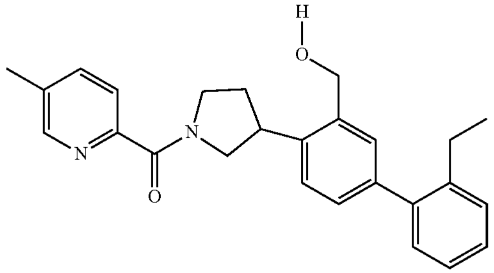 [SMILES: CCc1ccccc1-c1ccc(C2CCN(C(=O)c3ccc(C)cn3)C2)c(CO)c1] | 89.8 (Phase 1) | | | | | ~3900 | 8.67 (rat) | |
| 2-51 | 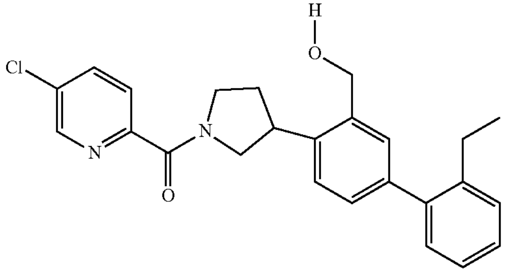 [SMILES: CCc1ccccc1-c1ccc(C2CCN(C(=O)c3ccc(Cl)cn3)C2)c(CO)c1] | 7.37 (Phase 1) | | | | | ~5300 | 14.4 (rat) | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-120 | 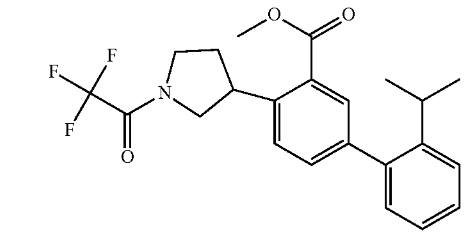 [SMILES: COC(=O)c1cc(-c2ccccc2C(C)C)ccc1C1CCN(C(=O)C(F)(F)F)C1] | >3200 (Phase 1) | | | | | | | |
| 2-52 | 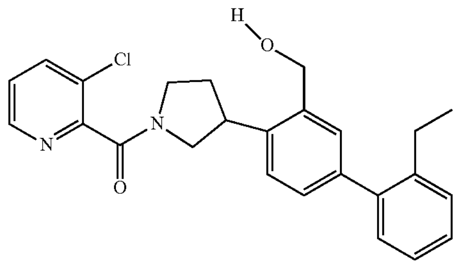 [SMILES: CCc1ccccc1-c1ccc(C2CCN(C(=O)c3ncccc3Cl)C2)c(CO)c1] | 67.3 (Phase 1) | | | | | >17800 | 14.4 (human) 9.2 (rat) | |
| 2-53 | 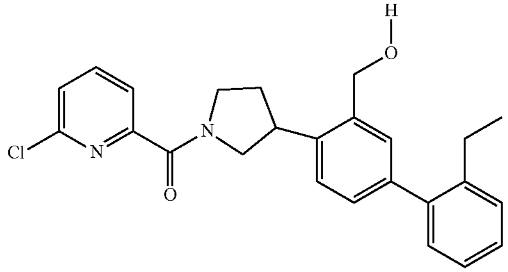 [SMILES: CCc1ccccc1-c1ccc(C2CCN(C(=O)c3cccc(Cl)n3)C2)c(CO)c1] | 8.39 (Phase 1) | | | | | ~7700 | 24.9 (human) 12.3 (rat) | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-54 | 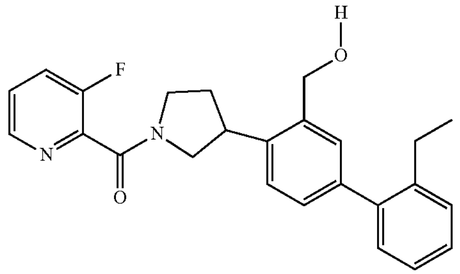 [SMILES: CCc1ccccc1-c1ccc(C2CCN(C(=O)c3ncccc3F)C2)c(CO)c1] | 91.3 (Phase 1) | | | | | | | |
| 2-55 | 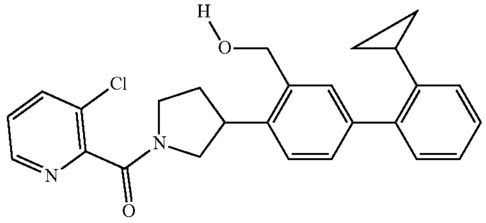 [SMILES: O=C(c1ncccc1Cl)N1CCC(c2ccc(-c3ccccc3C3CC3)cc2CO)C1] | 88.4 (Phase 1) | | | | | | | |
| 2-56 | 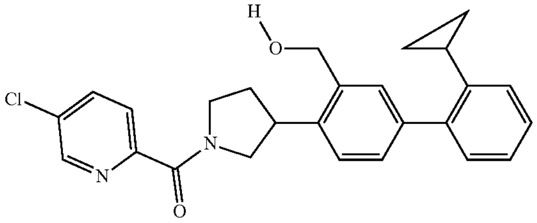 [SMILES: O=C(c1ccc(Cl)cn1)N1CCC(c2ccc(-c3ccccc3C3CC3)cc2CO)C1] | 2.04 (Phase 1) | | !7290 (PL) | | | ~5100 | 24.6 (human) | |
| 2-57 | 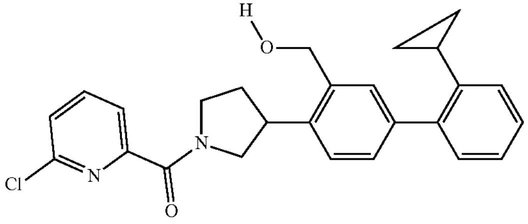 [SMILES: O=C(c1cccc(Cl)n1)N1CCC(c2ccc(-c3ccccc3C3CC3)cc2CO)C1] | 7.34 (Phase 1) | | | | | | 32.3 (rat) | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-58 | 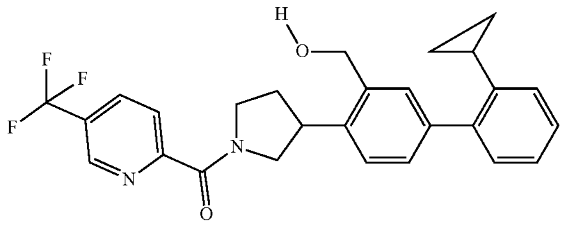 [SMILES: O=C(c1ccc(C(F)(F)F)cn1)N1CCC(c2ccc(-c3ccccc3C3CC3)cc2CO)C1] | 27.3 (Phase 1) | | !15000 (PL) | | | ~5200 | 54.6 (human) 47.9 (rat) | |
| 2-59 | 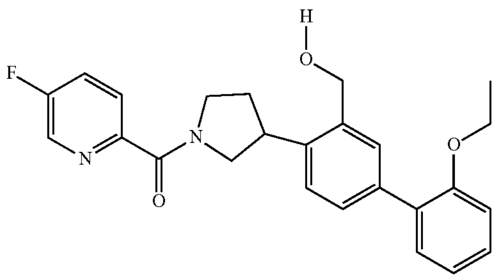 [SMILES: CCOc1ccccc1-c1ccc(C2CCN(C(=O)c3ccc(F)cn3)C2)c(CO)c1] | 62.1 (Phase 1) | | | | | | | |
| 2-60 | 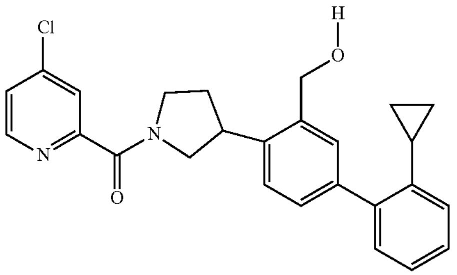 [SMILES: O=C(c1cc(Cl)ccn1)N1CCC(c2ccc(-c3ccccc3C3CC3)cc2CO)C1] | 26.5 (Phase 1) | | | | | | | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-61 | 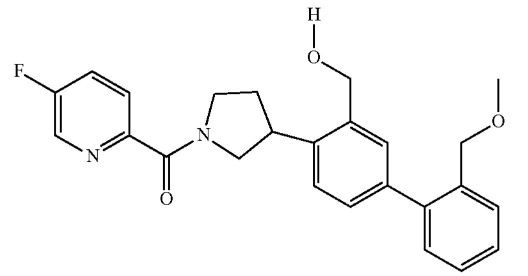 [SMILES: COCc1ccccc1-c1ccc(C2CCN(C(=O)c3ccc(F)cn3)C2)c(CO)c1] | 153 (Phase 1) | | | | | | | |
| 2-62 | 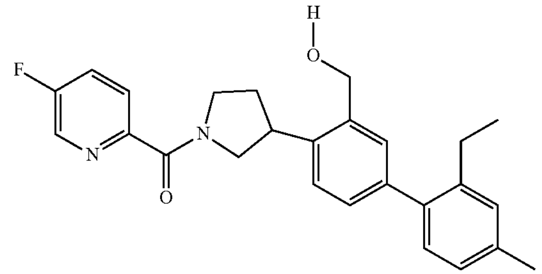 [SMILES: CCc1cc(C)ccc1-c1ccc(C2CCN(C(=O)c3ccc(F)cn3)C2)c(CO)c1] | 64.9 (Phase 1) | | 17700 (PL) | | | >12100 | 14.9 (human) 14 (rat) | |
| 2-115 | 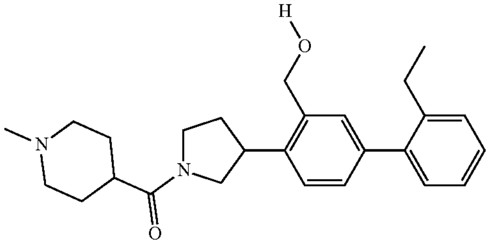 [SMILES: CCc1ccccc1-c1ccc(C2CCN(C(=O)C3CCN(C)CC3)C2)c(CO)c1] | >3200 (Phase 1) | | | | | | | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-63 | 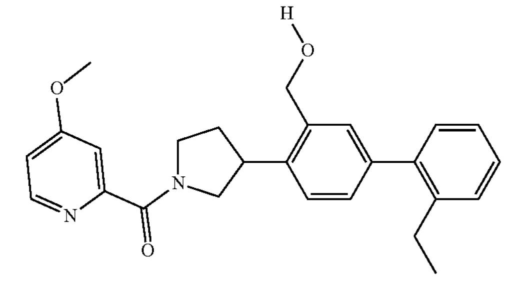 [SMILES: CCc1ccccc1-c1ccc(C2CCN(C(=O)c3cc(OC)ccn3)C2)c(CO)c1] | 235 (Phase 1) | | | | | | | |
| 2-64 | 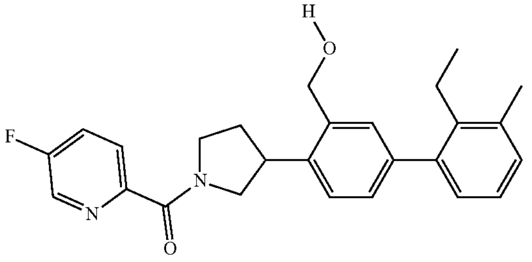 [SMILES: CCc1c(C)cccc1-c1ccc(C2CCN(C(=O)c3ccc(F)cn3)C2)c(CO)c1] | 18 (Phase 1) | | 10100 (PL) | | | >15700 | 6.38 (rat) | |
| 2-65 | 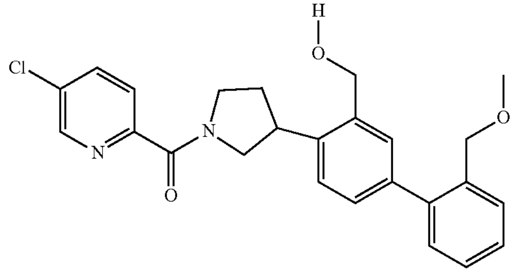 [SMILES: COCc1ccccc1-c1ccc(C2CCN(C(=O)c3ccc(Cl)cn3)C2)c(CO)c1] | 97.7 (Phase 1) | | | | | | | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-66 | 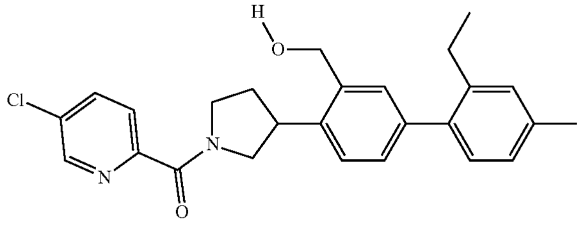 | 16.5 (Phase 1) | | | | | ~1900 | 24.9 (rat) | |
| 2-67 | 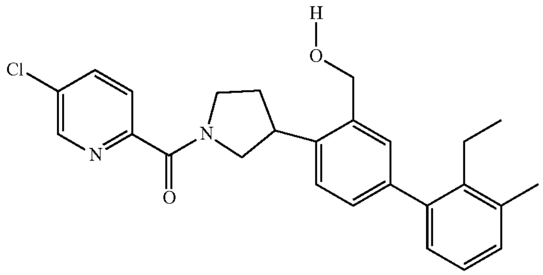 [SMILES: CCc1c(C)cccc1-c1ccc(C2CCN(C(=O)c3ccc(Cl)cn3)C2)c(CO)c1] | 0.698 (Phase 1) | | | | | ~3600 | 8.47 (rat) | |
| 2-68 | 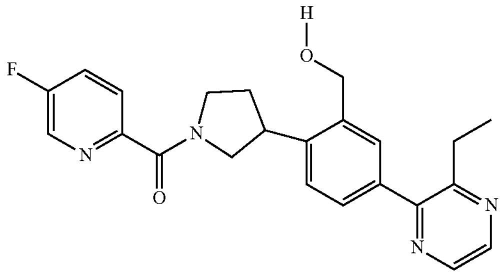 [SMILES: CCc1nccnc1-c1ccc(C2CCN(C(=O)c3ccc(F)cn3)C2)c(CO)c1] | >3200 (Phase 1) | | | | | | | |
| 2-69 | 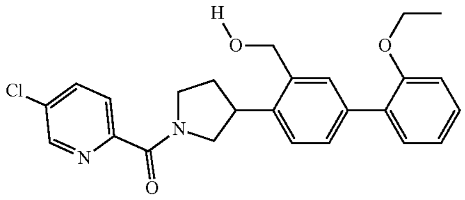 [SMILES: CCOc1ccccc1-c1ccc(C2CCN(C(=O)c3ccc(Cl)cn3)C2)c(CO)c1] | 25.3 (Phase 1) | | 12300 (PL) | | | >16000 | 12.6 (rat) | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-70 | 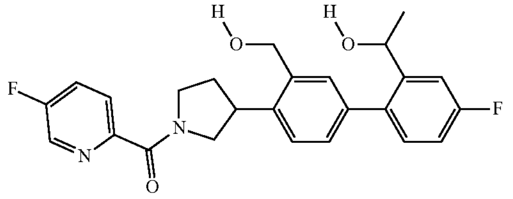 [SMILES: CC(O)c1cc(F)ccc1-c1ccc(C2CCN(C(=O)c3ccc(F)cn3)C2)c(CO)c1] | 2330 (Phase 1) | | | | | | | |
| 2-71 | 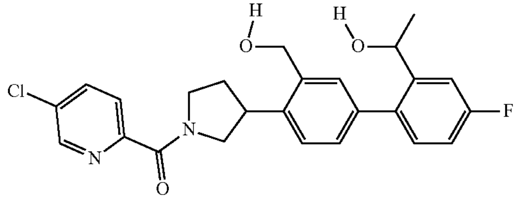 [SMILES: CC(O)c1cc(F)ccc1-c1ccc(C2CCN(C(=O)c3ccc(Cl)cn3)C2)c(CO)c1] | 860 (Phase 1) 572 (Phase 2) | | | | | | | |
| 2-72 | 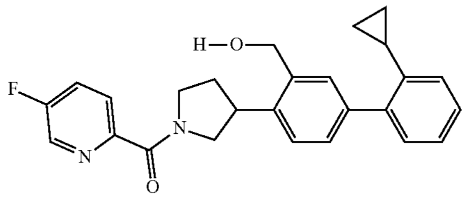 [SMILES: O=C(c1ccc(F)cn1)N1CCC(c2ccc(-c3ccccc3C3CC3)cc2CO)C1] | 4.87 (Phase 1) | 3.99 (Phase 1) 2.25 (Phase 2) | 9240 (M) 8460 (PL) | | | ~25500 | 17.5 (human) 31.3 (rat) | |
| 2-73 | 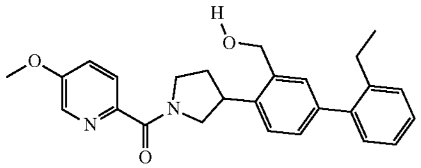 [SMILES: CCc1ccccc1-c1ccc(C2CCN(C(=O)c3ccc(OC)cn3)C2)c(CO)c1] | 20.5 (Phase 1) | | | | | >26200 | 9.84 (rat) | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-74 | 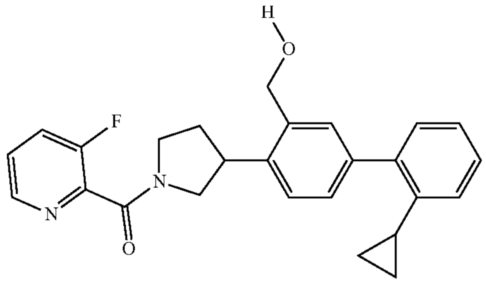 [SMILES: O=C(c1ncccc1F)N1CCC(c2ccc(-c3ccccc3C3CC3)cc2CO)C1] | 90.5 (Phase 1) 54.6 (Phase 2) | | | | | | | |
| 2-75 | 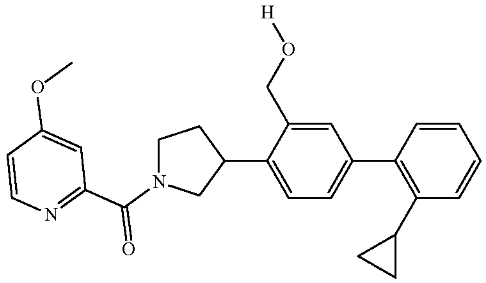 [SMILES: COc1ccnc(C(=O)N2CCC(c3ccc(-c4ccccc4C4CC4)cc3CO)C2)c1] | 215 (Phase 1) | | | | | | | |
| 2-76 | 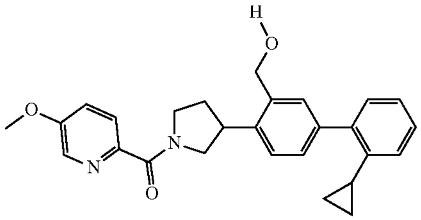 [SMILES: COc1ccc(C(=O)N2CCC(c3ccc(-c4ccccc4C4CC4)cc3CO)C2)nc1] | 71 (Phase 1) | | | | | | | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-111 | 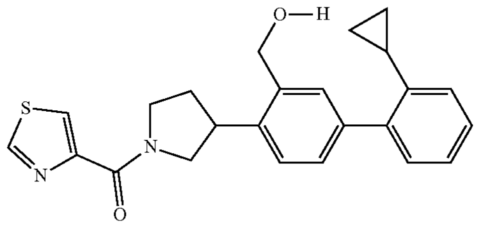 [SMILES: O=C(c1cscn1)N1CCC(c2ccc(-c3ccccc3C3CC3)cc2CO)C1] | 194 (Phase 1) | | | | | | | |
| 2-77 | 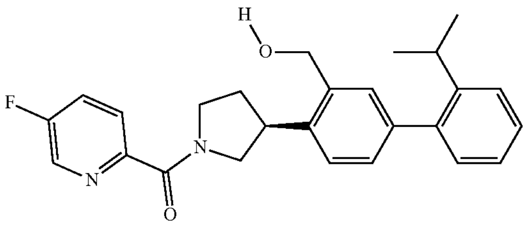 | 2.27 (Phase 1) | | | | | >15500 | 9.14 (rat) | |
| 2-78 | 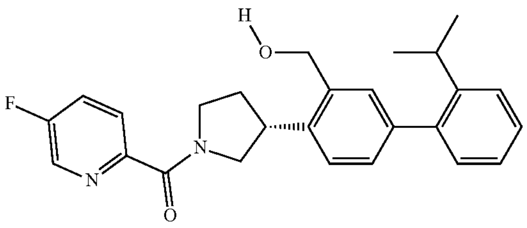 [SMILES: CC(C)c1ccccc1-c1ccc([C@H]2CCN(C(=O)c3ccc(F)cn3)C2)c(CO)c1] | 234 (Phase 1) | | | | | >15400 | 12.1 (rat) | |
| 2-104 | 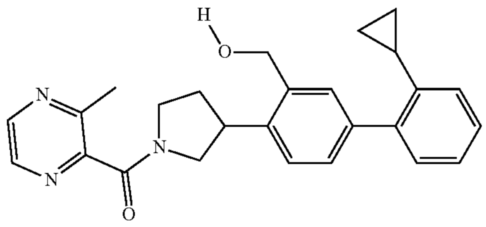 [SMILES: Cc1nccnc1C(=O)N1CCC(c2ccc(-c3ccccc3C3CC3)cc2CO)C1] | 756 (Phase 1) | | | | | | | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-105 | 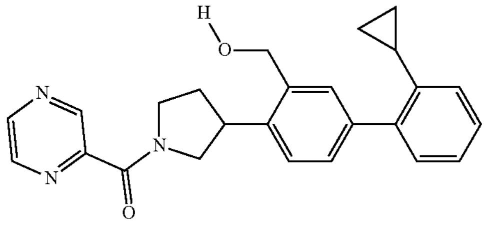 | 61.2 (Phase 1) | | 11700 (PL) | | | >21000 | 12.9 (rat) | |
| 2-110 | 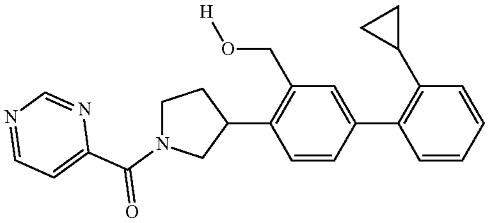 [SMILES: O=C(c1ccncn1)N1CCC(c2ccc(-c3ccccc3C3CC3)cc2CO)C1] | 197 (Phase 1) | | | | | | | |
| 2-79 | 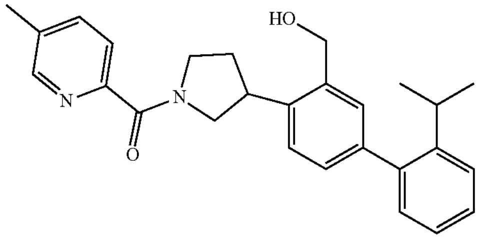 [SMILES: Cc1ccc(C(=O)N2CCC(c3ccc(-c4ccccc4C(C)C)cc3CO)C2)nc1] | 19.8 (Phase 1) | | | | | 7380 | | |
| 2-112 | 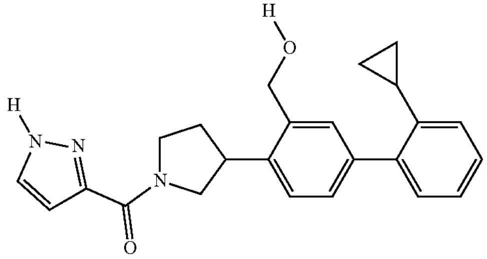 [SMILES: O=C(c1cc[nH]n1)N1CCC(c2ccc(-c3ccccc3C3CC3)cc2CO)C1] | 98 (Phase 1) | | | | | | | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-121 | 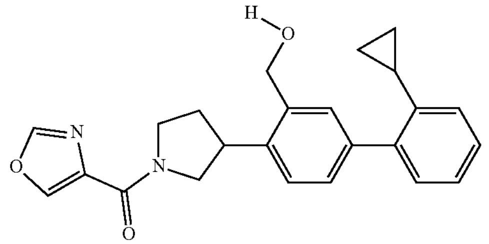 [SMILES: O=C(c1cocn1)N1CCC(c2ccc(-c3ccccc3C3CC3)cc2CO)C1] | 61.2 (Phase 1) | | | | | | | |
| 2-106 | 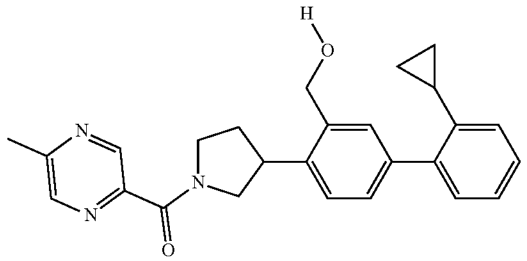 [SMILES: Cc1cnc(C(=O)N2CCC(c3ccc(-c4ccccc4C4CC4)cc3CO)C2)cn1] | 67 (Phase 1) | | | | | | | |
| 2-122 | 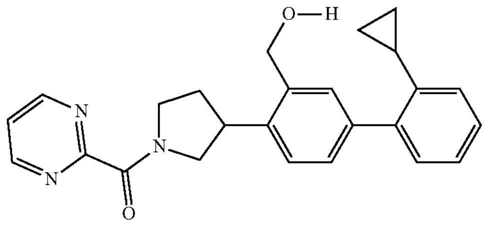 [SMILES: O=C(c1ncccn1)N1CCC(c2ccc(-c3ccccc3C3CC3)cc2CO)C1] | 202 (Phase 1) | | | | | | | |
| 2-123 | 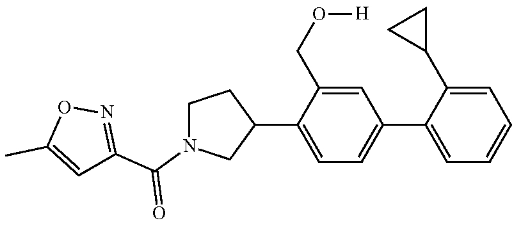 [SMILES: Cc1cc(C(=O)N2CCC(c3ccc(-c4ccccc4C4CC4)cc3CO)C2)no1] | 62.9 (Phase 1) | | | | | | | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-124 | 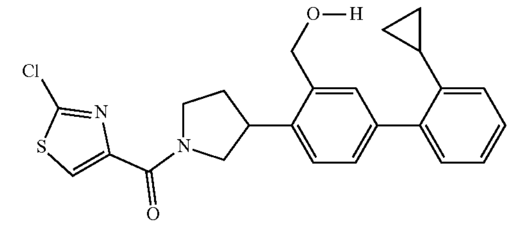 [SMILES: O=C(c1csc(Cl)n1)N1CCC(c2ccc(-c3ccccc3C3CC3)cc2CO)C1] | 20.7 (Phase 1) | | | | | | | |
| 2-107 | 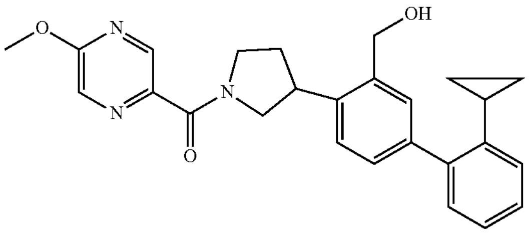 [SMILES: COc1cnc(C(=O)N2CCC(c3ccc(-c4ccccc4C4CC4)cc3CO)C2)cn1] | 31.5 (Phase 1) | | | | | 9250 | 25.7 (rat) | |
| 2-108 | 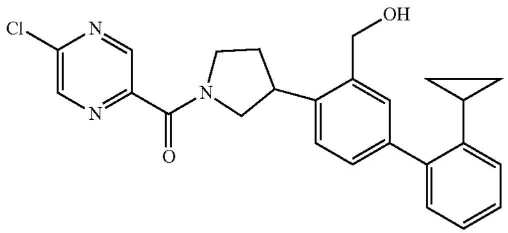 [SMILES: O=C(c1cnc(Cl)cn1)N1CCC(c2ccc(-c3ccccc3C3CC3)cc2CO)C1] | 12.9 (Phase 1) | | | | | | | |
| 2-80 | 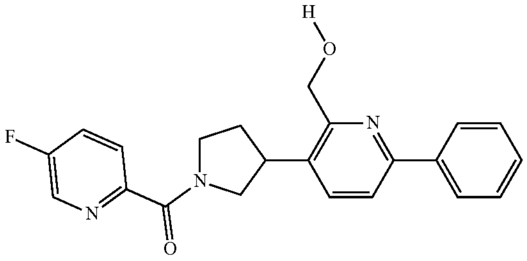 [SMILES: O=C(c1ccc(F)cn1)N1CCC(c2ccc(-c3ccccc3)nc2CO)C1] | 163 (Phase 1) | | 5520 (PL) | | | | | |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-81 | 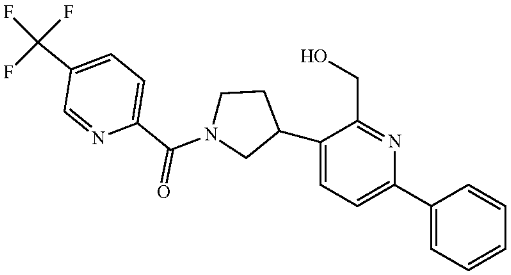 [SMILES: O=C(c1ccc(C(F)(F)F)cn1)N1CCC(c2ccc(-c3ccccc3)nc2CO)C1] | 268 (Phase 1) 298 (Phase 2) | | | | | | | |
| 2-109 | 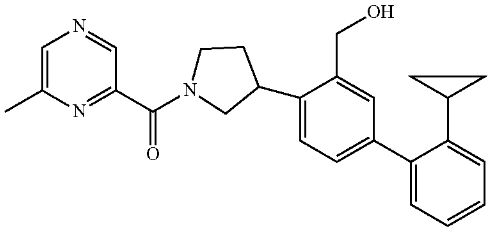 [SMILES: Cc1cncc(C(=O)N2CCC(c3ccc(-c4ccccc4C4CC4)cc3CO)C2)n1] | 18.2 (Phase 1) | | | | | | | |
| 2-82 | 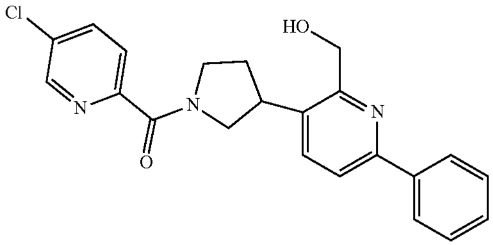 [SMILES: O=C(c1ccc(Cl)cn1)N1CCC(c2ccc(-c3ccccc3)nc2CO)C1] | 836 (Phase 1) | | | | | | | |
| 2-125 | 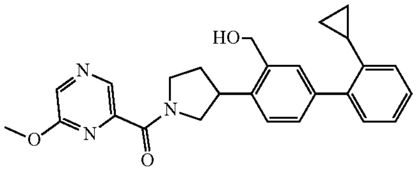 [SMILES: COc1cncc(C(=O)N2CCC(c3ccc(-c4ccccc4C4CC4)cc3CO)C2)n1] | | | | | 99.57 | | | 1.79 |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-126 | 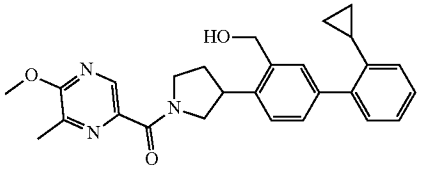 [SMILES: COc1ncc(C(=O)N2CCC(c3ccc(-c4ccccc4C4CC4)cc3CO)C2)nc1C] | | | | | 83.99 | | | 1.18 |
| 2-127 | 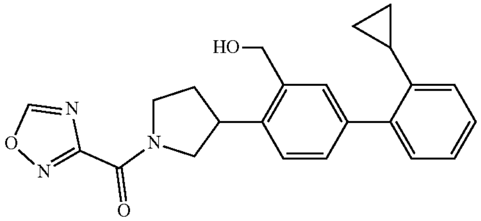 [SMILES: O=C(c1ncon1)N1CCC(c2ccc(-c3ccccc3C3CC3)cc2CO)C1] | | | | | 129.8 | | | 1.9 |
| 2-128 | 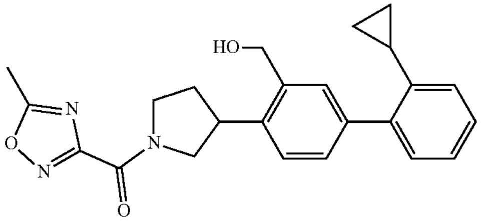 | | | | | 478.7 | | | 1.85 |
| 2-129 | 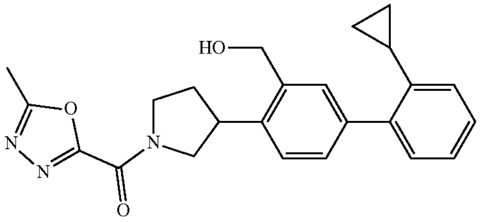 [SMILES: Cc1nnc(C(=O)N2CCC(c3ccc(-c4ccccc4C4CC4)cc3CO)C2)o1] | | | | | | | | >10 |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-130 | 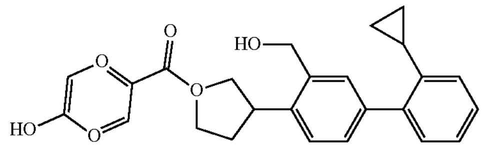 | | | | | | | | 4.8 |
| 2-131 | 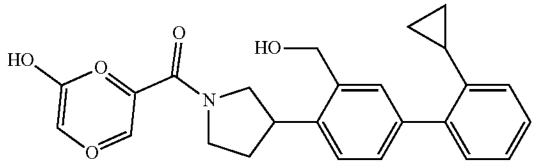 | | | | | | | | >10 |
| 2-132 | 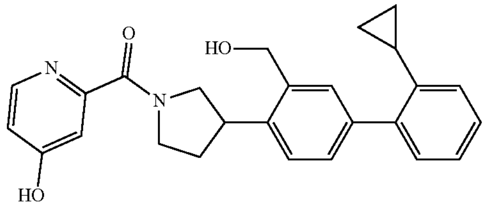 [SMILES: O=C(c1cc(O)ccn1)N1CCC(c2ccc(-c3ccccc3C3CC3)cc2CO)C1] | | | | | | | | >10 |
| 2-133 | 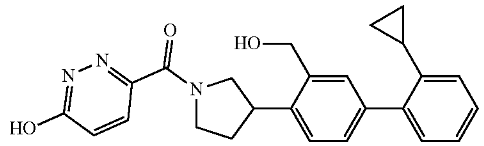 | | | | | | | | >10 |
| 2-134 | 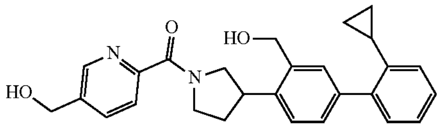 | | | | | | | | 9.5 |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-135 | 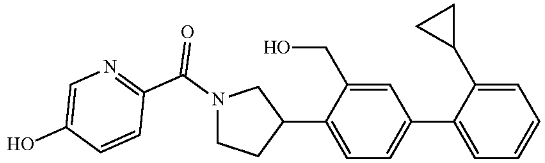 | | | | | | | | 3.09 |
| 2-136 | 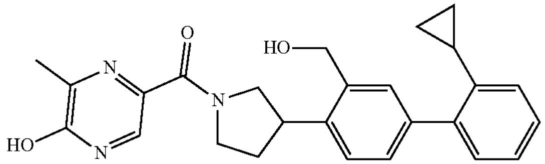 | | | | | | | | 5.17 |
| 2-137 | 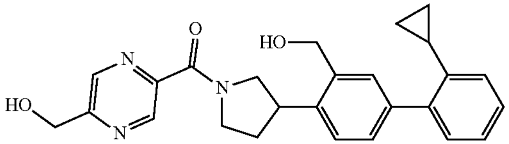 [SMILES: O=C(c1cnc(CO)cn1)N1CCC(c2ccc(-c3ccccc3C3CC3)cc2CO)C1] | | | | | | | | >10 |
| 2-138 | 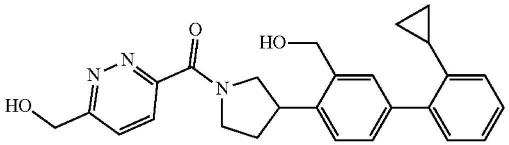 | | | | | | | | >10 |
| 2-139 | 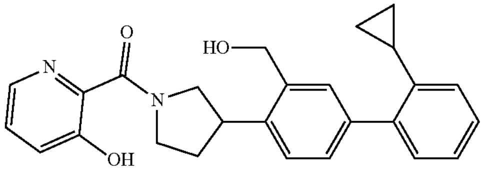 [SMILES: O=C(c1ncccc1O)N1CCC(c2ccc(-c3ccccc3C3CC3)cc2CO)C1] | | | | | | | | 7.68 |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-140 | 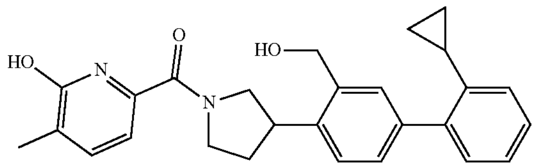 [SMILES: Cc1ccc(C(=O)N2CCC(c3ccc(-c4ccccc4C4CC4)cc3CO)C2)nc1O] | | | | | | | | 5.57 |
| 2-141 | 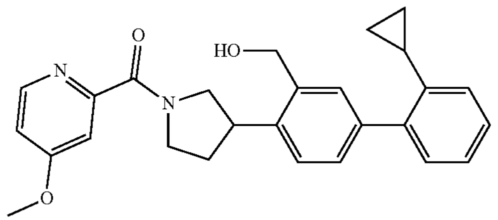 [SMILES: COc1ccnc(C(=O)N2CCC(c3ccc(-c4ccccc4C4CC4)cc3CO)C2)c1] | | | | | | | | 4.49 |
| 2-142 | 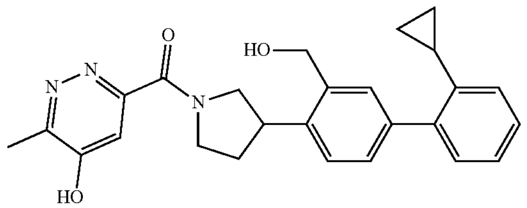 [SMILES: Cc1nnc(C(=O)N2CCC(c3ccc(-c4ccccc4C4CC4)cc3CO)C2)cc1O] | | | | | | | | >10 |
| 2-143 | 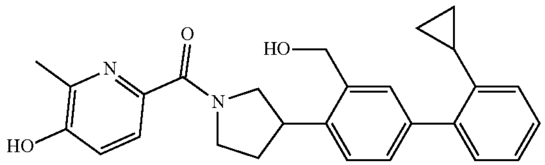 | | | | | 10.3 | 18.29 | | 0.86 |
| 2-144 | 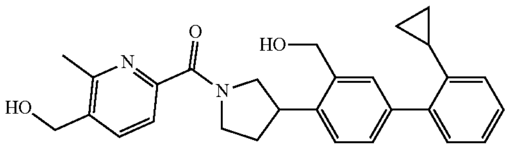 [SMILES: Cc1nc(C(=O)N2CCC(c3ccc(-c4ccccc4C4CC4)cc3CO)C2)ccc1CO] | | | | | | | | 3.27 |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2.145 | 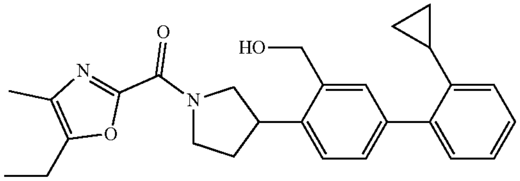 [SMILES: CCc1oc(C(=O)N2CCC(c3ccc(-c4ccccc4C4CC4)cc3CO)C2)nc1C] | | | | | | | | 4.43 |
| 2.146 | 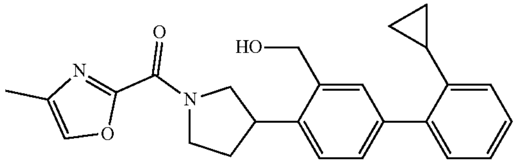 [SMILES: Cc1coc(C(=O)N2CCC(c3ccc(-c4ccccc4C4CC4)cc3CO)C2)n1] | | | | | | | | 5.95 |
| 2.147 | 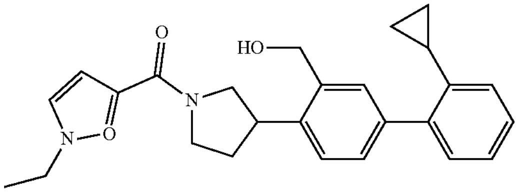 | | | | | | | | 5.74 |
| 2.148 | 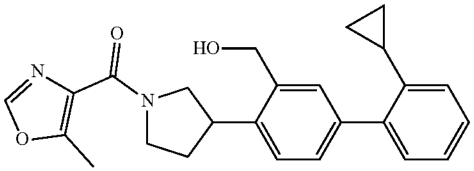 [SMILES: Cc1ocnc1C(=O)N1CCC(c2ccc(-c3ccccc3C3CC3)cc2CO)C1] | | | | | | | | 2.93 |
| 2.149 | 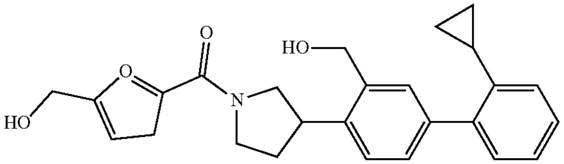 | | | | | | | | >10 |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2.150 | 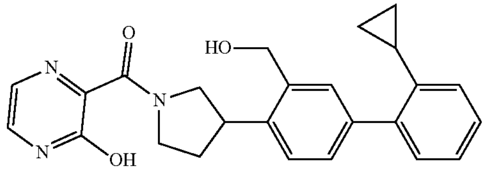 | | | | | | | | >10 |
| 2.151 | 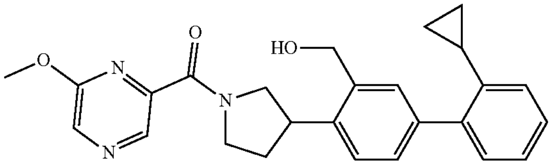 [SMILES: COc1cncc(C(=O)N2CCC(c3ccc(-c4ccccc4C4CC4)cc3CO)C2)n1] | | | | | | | | 0.78 |
| 2.152 | 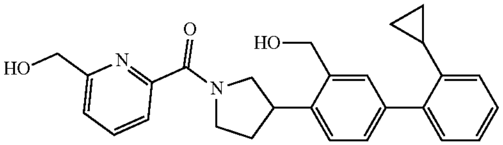 [SMILES: O=C(c1cccc(CO)n1)N1CCC(c2ccc(-c3ccccc3C3CC3)cc2CO)C1] | | | | | | | | 4.56 |
| 2.153 | 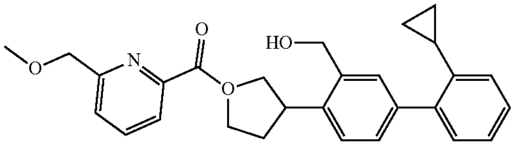 | | | | | | | | 0.66 |
| 2.154 | 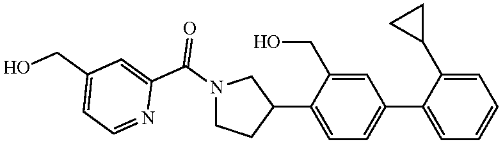 | | | | | | | | 4.21 |
| 2.155 | 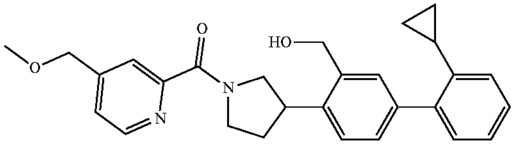 | | | | | | | | 9.25 |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2.156 | 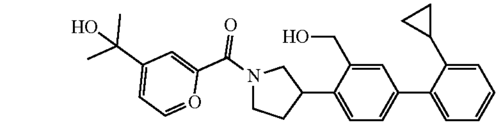 | | | | | | | | >10 |
| 2.157 | 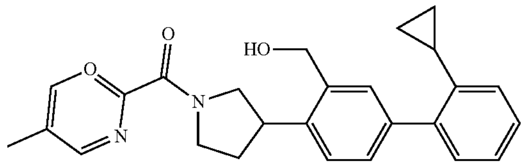 | | | | | | | | 4.6 |
| 2.158 | 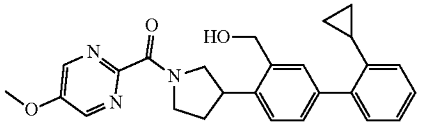 [SMILES: COc1cnc(C(=O)N2CCC(c3ccc(-c4ccccc4C4CC4)cc3CO)C2)nc1] | | | | | | | | 6.12 |
| 2-159 | 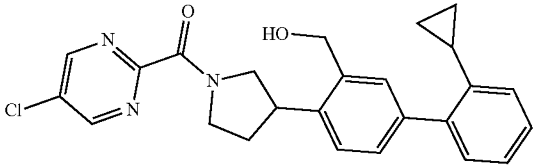 [SMILES: O=C(c1ncc(Cl)cn1)N1CCC(c2ccc(-c3ccccc3C3CC3)cc2CO)C1] | | | | | | | | 5.18 |
| 2-160 | 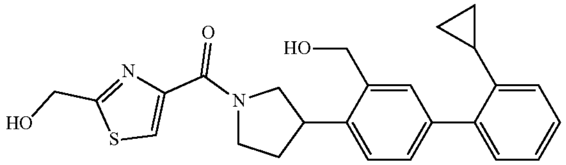 [SMILES: O=C(c1csc(CO)n1)N1CCC(c2ccc(-c3ccccc3C3CC3)cc2CO)C1] | | | | | | | | >10 |
| 2-161 | 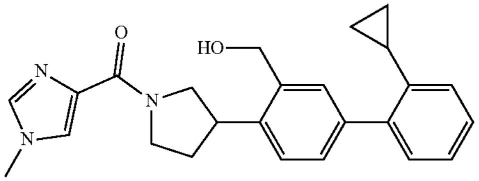 [SMILES: Cn1cnc(C(=O)N2CCC(c3ccc(-c4ccccc4C4CC4)cc3CO)C2)c1] | | | | | | | | 9.52 |

TABLE 4-continued
| Cmpd No. | Structure | hTRPV3 (nM) | rTRPV3 (nM) | hERG (nM) | hNaV 1.5 (nM) | hTRPV3 HAMA IC50 (nM) | Solubility Ringer (nM) | LM T1/2 (min) | FLIPR IC50 (uM) |
|---|---|---|---|---|---|---|---|---|---|
| 2-162 | 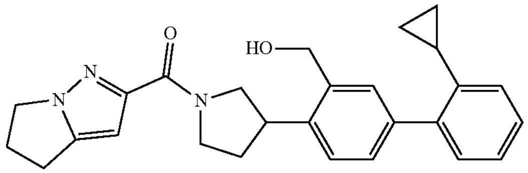 [SMILES: O=C(c1cc2n(n1)CCC2)N1CCC(c2ccc(-c3ccccc3C3CC3)cc2CO)C1] | | | | | | | | 5.19 |
| 2-163 | 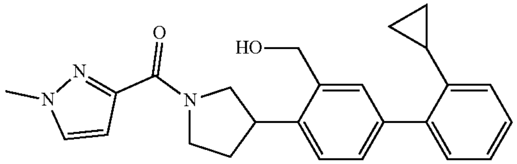 [SMILES: Cn1ccc(C(=O)N2CCC(c3ccc(-c4ccccc4C4CC4)cc3CO)C2)n1] | | | | | | | | >10 |
| 2-164 | 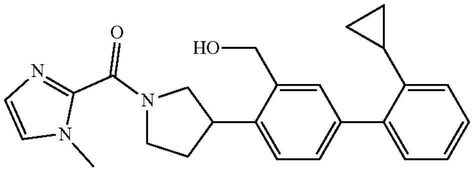 [SMILES: Cn1ccnc1C(=O)N1CCC(c2ccc(-c3ccccc3C3CC3)cc2CO)C1] | | | | | | | | >10 |
| 2-165 | 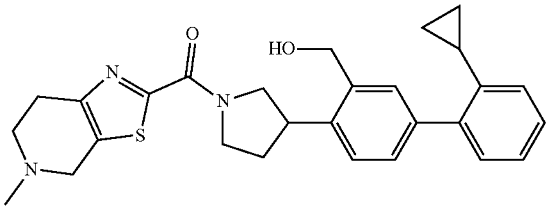 [SMILES: CN1CCc2nc(C(=O)N3CCC(c4ccc(-c5ccccc5C5CC5)cc4CO)C3)sc2C1] | | | | | | | | >10 |

Example 1C. Other Screening Assays

Although the exemplary TRPV3 inhibitors provided herein were identified using the assays described in Examples 1A and 1B, other cell-based assays can be used to identify and/or characterize TRPV3 inhibitors. One such assay is described in US application Ser. No. 11,078,188, filed Mar. 11, 2005, the contents of which are hereby incorporated by reference in their entirety. TRPV3 protein can be expressed in the prokaryotic cell system described in application Ser. No. 11,078,188, and this system can be used to screen for compounds that modulate an activity of the TRPV3 protein. Alternatively, an ion channel other than TRPV3 can be expressed in the prokaryotic cell system, and the system can be used to evaluate the activity profile of an identified TRPV3 inhibitors with respect to other ion channels.

Any assays performed to identify and/or characterize compounds that inhibit an activity of TRPV3 can be performed in a high-throughput fashion, or can be performed on a smaller scale examining individual compounds or small numbers of compounds. Additionally, any of these assays can be performed (i) as a primary assay to identify compounds that inhibit a function of TRPV3; (ii) as a secondary assay to assess the specificity of a compound with respect to its activity against other ion channels; (iii) as an assay used in a medicinal chemistry program to optimize subject compounds.

Example 1D. Semi-Auto Patch Clamp Recording

Materials and Methods:

Compounds were tested at room temperature using the whole-cell patch clamp technique with a HEKA EPC 10 usb patch-clamp amplifier (HEKA Elektronik, Germany). Output signals from the amplifier were digitized and recorded with PatchMaster (v2x90.5 HEKA Elektronik, Germany). For quality control, the minimum seal resistance was set at 100 MΩ, and the outward current was stabilized with at least 1 nA of rectifying current at +80 mV while the inward current was stabilized with at least 300 pA of rectifying current at −80 mV.

NPC-1 Chips

NPC-1 Chips (Nanion, Germany) were used to trap a single cell. For both WT or transfected cells, chips of the categories 2-3 MOhm and 3-5 MOhm were used. Chips are disposable and each recording required a new chip. 5 μl of internal solution was applied in the inner pore of the chip, then it was screwed on top of the inner electrode. The upper unit of the patch lamp device was assembled over the chip, and 15 μl external buffer were added between the chip pore and the external electrode. Recording of the current between the electrodes and the chip's pore was used to confirm that chip was properly placed and treated.

Cell Preparation for Patch Clamp:

Basal nHEK cells at Passage 2 or 3 and at the density of 70-90% confluency were used for patch clamp or transfection. For patch-clamp, cells were suspended in TrypLE enzyme for 5 min in 37° C., and then harvested using KBM-Gold media. Cells were then centrifuged for 5 min at 110 g RT. Supernatant was then removed, and cells were re-suspended in the KBM-Gold media and maintained at RT until patch-clamp. After patch clamp system was initialized, and once cell was capture on the chip, media was washed together with free cells, and replaced by external buffer. For TRPV3-mu transfected cells, cells were maintained in KBM-Gold media containing 3 uM of the tested antagonist.

Transfection of nHEK Cells.

nHEK cells were transfected according to SOP KP-Lab-001.For patch clamp, cells were seeded in 12 well plate and harvested 24 hours after transfection according to the SOP section 2.8.2 "Cell preparation for patch clamp".

Recording from a Whole Cell:

For WT nHEK cells, the "intermediate protocol" in the semi-automatic Port-a-Patch device software was selected based on the parameters: initial sealing, measured by resistance, and its ability to maintain sealing along with assay.

The procedure was started with the "Startup procedure" protocol that validates chip contact and adjusts offset, then after the system was ready, 5 μl of cells suspended in extracellular buffer was added and the intermediate protocol was automatically launched.

When a cell was trapped by vacuum, the value "v-membrane" was raised by 100%, then 15 μl of sealing solution was added. The procedure continued automatically through all its steps until the final step "maintain the whole-cell". At this step, the sealing solution was washed using three 20 μl washes with an external buffer, and the values C-fast and C-slow were adjusted twice using the "Auto E" buttons.

The sensitivity of reading was adjusted by changing the gain from 2.0 to 0.5.

To initiate recording, the "Ramp" protocol was initiated, and currents were recorded for several minutes until the signal remained stable for both inward and outward currents.

For TRPV3-mu transfected nHEK cells, a similar procedure was used, but with "Fragile protocol", and the addition of the antagonist at the step of sealing. For all cells, if low sealing was observed, additional steps of sealing or whole-cell maintenance were added until sealing reached the minimal value of 100 MO.

Voltage Command Protocol & Compounds Addition:

Nanion's system automatically maintained cells in the holding potential of −40 mV. Then the voltage was ramped from 80 mV to +80 mV for 160 ms. Finally, the voltage was stepped back to the holding potential (−40 mV). This voltage command protocol was repeated in cycles of 400 ms (FIG. 1). This command protocol was performed continuously during the test, with vehicle control perfusion first, For WT cells this protocol was followed by 100 μM of HC-081790 and the test compound dissolved in HC solution.

For TRPV3-mu transfected cells, 1500 nM of tested compound was added, and currents were measured, The antagonist was washed in steps, by diluting the solution by 50% for each wash, using external buffer without antagonist.

Compound Application:

For TRPV3-WT nHEKs, when both inward and outward currents were stable, 100 uM of the agonist HC-081790 were added in three washes of 20 μl, currents were measured for several minutes until were stable, and then the reading was paused for labeling and buffer change. At this step, an increasing concentration of the tested compound dissolved in the presence of 100 uM HC-081790 was manually added (one pulse of 10 μl into final volume of 20 ul). The solution was then gently mixed and current recording resumed. The next concentration of tested compound was added only after currents were stable; this procedure continued until a complete response was observed.

For TRPV3-mu nHEKs, an initial concentration of 1500 uM of the tested antagonist was added (one pulse of 10 μl into final volume of 20 ul), and then, in 15 wash steps was gradually removed from tested environment using external buffer.

Data Analysis

Data analysis was carried out using PatchMaster (v2x90.5 HEKA Elektronik, Germany), Excel (Microsoft Excel for Microsoft 365 MS016.0.12827.20236 64 bit), IC50 toolkit (http://www.ic50.tk/) and GraphPad Prism 8.4.2.

Within each cellular recording, the percent of control values were calculated for each test compound concentration-current response based on peak current in the presence of the agonist and full response. The fraction of current remaining after compound addition ($I_{test}$), subtract the 100% block level ($I_{blocked}$), and divide that by the 0% block current ($I_{unblocked}$) to get the fraction of current remaining:

$$\text{Fraction current remaining} = (I\text{test} - I\text{blocked})/(I\text{unblocked} - I\text{blocked})$$

Results:

As shown in Table 5 below, A refers to an inhibitor of hTRPV3 with an $IC_{50}$ between 0 nM and 10 nM. B refers to an inhibitor of hTRPV3 with an $IC_{50}$ between 10 nM and 100 nM. C refers to an inhibitor of hTRPV3 with an $IC_{50}$ between 100 nM and 1000 nM. D refers to an inhibitor of hTRPV3 with an $IC_{50}$ between >1000 nM. ND refers to data not determined.

TABLE 5

Results from Patch Clamp experiments

| Compound ID | Structure | IC50 human TRPV3 (nM) |
|---|---|---|
| KM-001 | 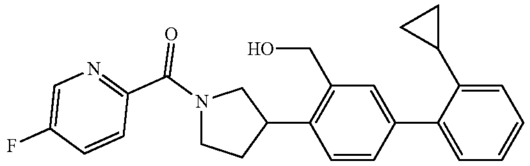 | B |
| KM-001-E1 | 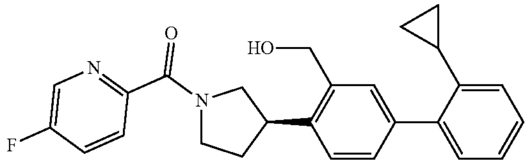 [SMILES: O=C(c1ccc(F)cn1)N1CCC(c2ccc(-c3ccccc3C3CC3)cc2CO)C1] | A |
| KM-001-E2 | 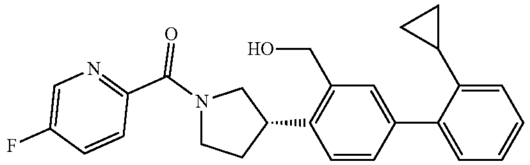 [SMILES: O=C(c1ccc(F)cn1)N1CC[C@@H](c2ccc(-c3ccccc3C3CC3)cc2CO)C1] | C |
| KM-002 | 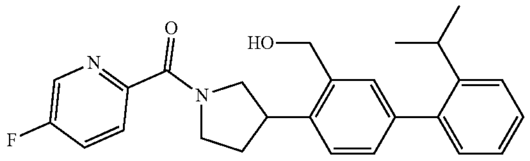 | A |
| KM-002-E1 | 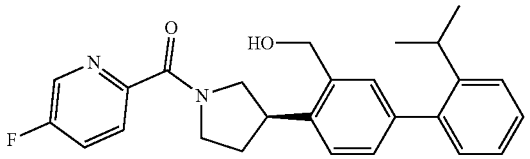 [SMILES: CC(C)c1ccccc1-c1ccc([C@H]2CCN(C(=O)c3ccc(F)cn3)C2)c(CO)c1] | A |
| KM-002-E2 | 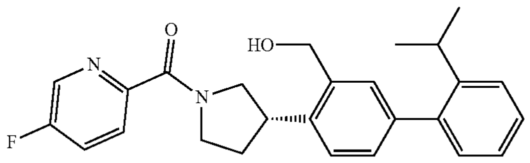 [SMILES: CC(C)c1ccccc1-c1ccc([C@@H]2CCN(C(=O)c3ccc(F)cn3)C2)c(CO)c1] | B |

TABLE 5-continued
| Results from Patch Clamp experiments | | |
|---|---|---|
| Compound ID | Structure | IC50 human TRPV3 (nM) |
| KM-023-E1 | 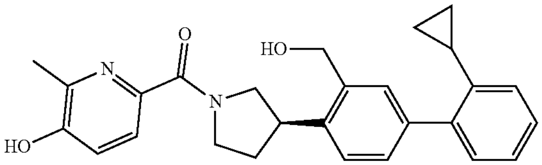 [SMILES: Cc1nc(C(=O)N2CC[C@H](c3ccc(-c4ccccc4C4CC4)cc3CO)C2)ccc1O] | A |
| KM-031-E1 | 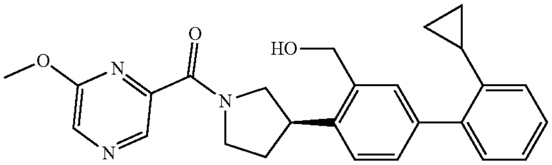 [SMILES: COc1cncc(C(=O)N2CC[C@H](c3ccc(-c4ccccc4C4CC4)cc3CO)C2)n1] | B |
| KM-032 | 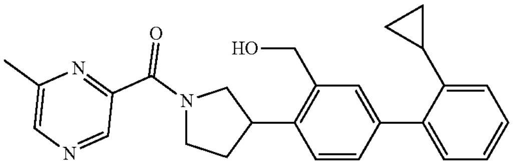 [SMILES: Cc1cncc(C(=O)N2CCC(c3ccc(-c4ccccc4C4CC4)cc3CO)C2)n1] | B |
| KM-032-E1 | 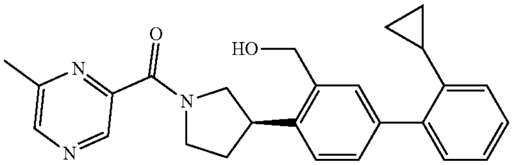 [SMILES: Cc1cncc(C(=O)N2CC[C@H](c3ccc(-c4ccccc4C4CC4)cc3CO)C2)n1] | B |
| KM-036 | 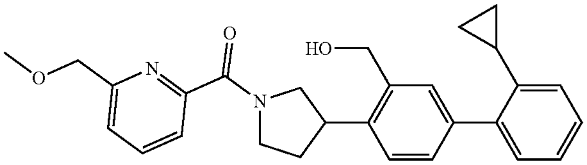 [SMILES: COCc1cccc(C(=O)N2CCC(c3ccc(-c4ccccc4C4CC4)cc3CO)C2)n1] | B |
| KM-036-E1 | 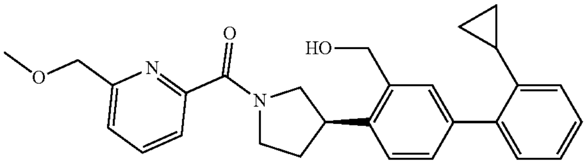 [SMILES: COCc1cccc(C(=O)N2CC[C@H](c3ccc(-c4ccccc4C4CC4)cc3CO)C2)n1] | B |
| KM-054-E1 | 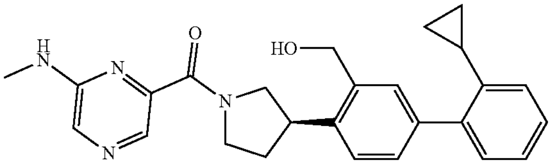 | A |
| KM-069 | 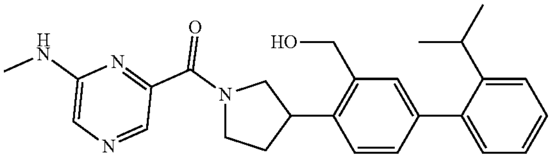 [SMILES: CNc1cncc(C(=O)N2CCC(c3ccc(-c4ccccc4C(C)C)cc3CO)C2)n1] | B |

TABLE 5-continued

Results from Patch Clamp experiments

| Compound ID | Structure | IC50 human TRPV3 (nM) |
| --- | --- | --- |
| KM-070 | 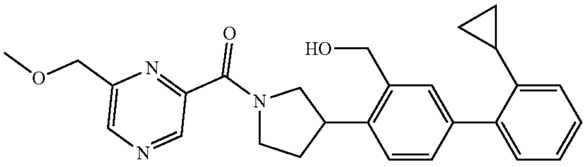 | B |
| KM-071 | 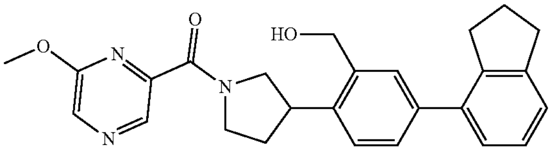 [SMILES: COc1cncc(C(=O)N2CCC(c3ccc(-c4cccc5c4CCC5)cc3CO)C2)n1] | B |
| KM-084 | 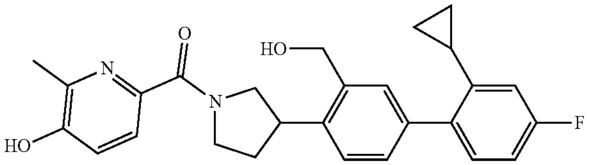 [SMILES: Cc1nc(C(=O)N2CCC(c3ccc(-c4ccc(F)cc4C4CC4)cc3CO)C2)ccc1O] | B |
| KM-085 | 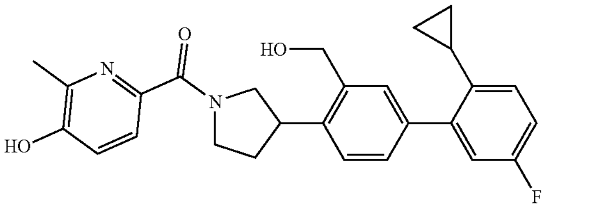 [SMILES: Cc1nc(C(=O)N2CCC(c3ccc(-c4cc(F)ccc4C4CC4)cc3CO)C2)ccc1O] | A |

Example 2 Synthesis of Compounds of the Disclosure

General Procedure A:

Abbreviations used: Chromatography=silica gel chromatography; EA=ethyl acetate; DMF=N,N-dimethylformamide; Dess-Martin periodinane=1,1-dihydro-1,1,1-triacetoxy-1,2-benzoiodooxol-3 (1H)-one; DCM=Dichloromethane; THF=Tetrahydrofuran; LAH=Lithium aluminium hydride; DME=1, 2-Dimethoxyethane; TEA=Triethylamine; EIPEA=Ethyldiisopropylamine; DEAD=Diethyl azodicarboxylate; DIAD=Diisopropyl azodicarboxylate; HATU=2-(7-Aza-1H-benzotriazole-1-yl)-1,1,3,3-tetramethyluronium hexafluorophosphate; EDCI=N-(3-dimethylaminopropyl)-N'-ethylcarbodiimide hydrochloride; HOBt=1-Hydroxybenzotriazole; DIBAL-H=Diisobutylaluminium hydride; Bn=Benzyl; DMSO=Dimethyl sulfoxide; RT=room temperature; DBU=1,8-Diazabicyclo[5.4.0]undec-7-ene; NCS=N-Chlorosuccinimide; LiHMDS=Lithium bis(trimethylsilyl)amide; DMAP=4-Dimethylaminopyridine; n-BuLi=n-Butyllithium.

General Procedures:

All reagents were purchased from commercial suppliers (Sigma-Aldrich, Alfa, Across etc.) and used without further purification unless otherwise stated. THE was continuously refluxed and freshly distilled from sodium and benzophenone under nitrogen, DCM was continuously refluxed and freshly distilled from $H_2Ca$ under nitrogen. Reactions were monitored via TLC on silica gel 60 HSGF254 percolated plates (0.15-0.2 mm $SiO_2$) and visualized using UV light and/or staining with a solution of DNP (12 g 2,4-dinitrofenylhydrazin, 60 mL H2SO4con., 80 ml H2O, 200 mL EtOH) and subsequent heating or monitored via LCMS (Chromolith SpeedROD, RP-18e, 50×4.6 mm, mobile phase: Solvent A: $CH_3CN/H_2O/HCOOH$=10/90/0.05, Solvent B: $CH_3CN/H_2O/HCOOH$=90/10/0.05, 0.8 min@ 10% B, 2.7 min gradient (10-95% B), then 0.8 min@95% B, Flow rate: 3 mL/min, temperature: 40° C.); and HPLC (Chromolith SpeedROD, RP-18e, 50×4.6 mm, mobile phase: Solvent A: $CH_3CN/H_2O/HCOOH$=10/90/0.05, Solvent B: $CH_3CN/H_2O/HCOOH$=90/10/0.05, 0.8 min@ 10% B, 2.7 min gradient (10-95% B), then 0.8 min@95% B, Flow rate: 3 mL/min, temperature: 40° C.). $^1H$ spectra were recorded on Bruker Avance II 400 MHz, Chemical shifts (δ) are reported in ppm relative to tetramethylsilane (δ=0.000 ppm) and the spectra were calibrated to the residual solvent signal of chloroform (δ=7.26 for 1H). Data for 1H NMR spectra are reported as follows: chemical shift (multiplicity, number of hydrogens). Abbreviations are as follows: s (singlet), d (doublet), t (triplet), q (quartet), quant (quintet), m (multiple), br (broad).

Supporting Information S2

HPLC purifications were performed either on an SHIMADZU LC-8A (Column: YMC Pack ODS-A (150*30 mm, 10 m)) or LC-6AD (Column: Shim=Pack PREP-ODS-H (250*20 mm, 10 μm)) with UV detection which were controlled by LC solution Chemstation software. H2O (0.1% HCOOH) and MeOH (MeCN) as mobile phase at the indicated flow rate. And SFC (column type: OD-H 3*25 cm column, mobile phase: H/E/M=80/15/5 (v/v/v), flow rate: 20 mL/min) was employed for separation of racemic compound

Section A: Synthesis of the Intermediates

Intermediate 1: 3-chloro-2-(pyrrolidin-3-yloxy)-5-(trifluoromethyl) pyridine trifluoroacetate salt

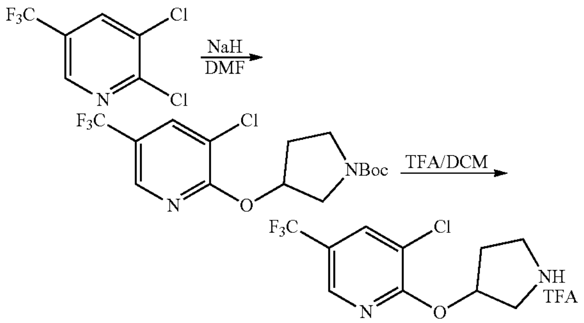

Step 1: tert-butyl 3-(3-chloro-5-(trifluoromethyl) pyridin-2-yloxy)pyrrolidine-1-carboxylate

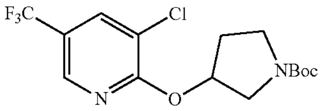 [SMILES: CC(C)(C)OC(=O)N1CCC(Oc2ncc(C(F)(F)F)cc2Cl)C1]

To a solution of tert-butyl 3-hydroxypyrrolidine-1-carboxylate (1 g, 5.3 mmol) in DMF (10 mL) at 0° C. was added NaH (1.2 g, 31 mmol, 60% dispersion in mineral oil), the resulting mixture was stirred at this temperature for 20 min; before 2,3-dichloro-5-(trifluoromethyl)pyridine (1.38 g, 6.4 mmol) was added, the reaction mixture was stirred at rt. for 1.5 h. The reaction was quenched by ice-water at 0° C., diluted with EA (50 mL), washed with LiCl solution and brine, and dried over $Na_2SO_4$. Concentrate to dryness, the residue was purified by silica gel to give tert-butyl 3-(3-chloro-5-(trifluoromethyl)pyridin-2-yloxy)pyrrolidine-1-carboxylate (1.7 g, 86.7% yield), Mass spec: 367 (M+H)

Step 2: 3-chloro-2-(pyrrolidin-3-yloxy)-5-(trifluoromethyl) pyridine trifluoroacetate salt

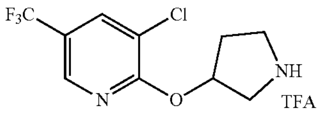 [SMILES: FC(F)(F)c1cnc(OC2CCNC2)c(Cl)c1]

To a solution of tert-butyl 3-(3-chloro-5-(trifluoromethyl) pyridin-2-yloxy)pyrrolidine-1-carboxylate (1.7 g, 4.6 mmol) in DCM (10 mL) at 0° C. was added TFA (5 mL), the resulting mixture was stirred at rt for 2 h; the mixture was concentrated to leave 3-chloro-2-(pyrrolidin-3-yloxy)-5-(trifluoromethyl) pyridine as its TFA salt (1.76 g, quant.), Mass spec: 267 (M+H).

Intermediate 2: 2-(pyrrolidin-3-yloxy)-5-(trifluoromethyl)pyridine trifluoroacetate salt (XJ-000098-129)

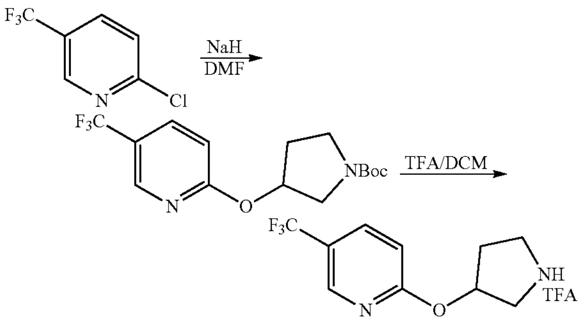

Step 1: tert-butyl 3-(5-(trifluoromethyl)pyridin-2-yloxy)pyrrolidine-1-carboxylate (XJ-000098-128)

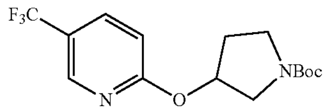 [SMILES: CC(C)(C)OC(=O)N1CCC(Oc2ccc(C(F)(F)F)cn2)C1]

The title compound was prepared following procedures described in step 1 of Intermediate 1 to give tert-butyl 3-(5-(trifluoromethyl)pyridin-2-yloxy)pyrrolidine-1-carboxylate (1.7 g, 92.8% yield), Mass spec: 333 (M+H)

Step 2: 2-(pyrrolidin-3-yloxy)-5-(trifluoromethyl)pyridine trifluoroacetate salt

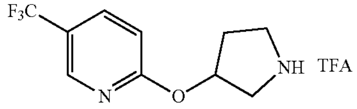 [SMILES: FC(F)(F)c1ccc(OC2CCNC2)nc1]

The title compound was prepared following procedures described in Intermediate 2 step 2 to give 2-(pyrrolidin-3-yloxy)-5-(trifluoromethyl)pyridine trifluoroacetate salt (1.76 g, quant.), Mass spec: 233 (M+H)

Intermediate 3: (S)-3-chloro-2-(pyrrolidin-3-yloxy)-5-(trifluoromethyl)pyridine hydrochloride

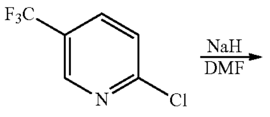

-continued

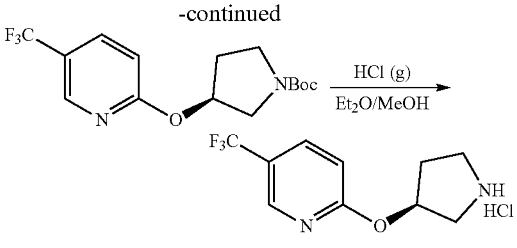

Step 1: (S)-tert-butyl 3-(5-(trifluoromethyl)pyridin-2-yloxy)pyrrolidine-1-carboxylate (LHH-000206-094)

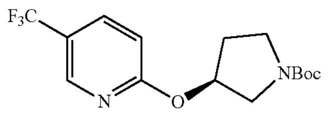 [SMILES: CC(C)(C)OC(=O)N1CC[C@H](Oc2ccc(C(F)(F)F)cn2)C1]

The title compound was prepared following procedures described in step 1 of Intermediate 1 to give (S)-tert-butyl 3-(5-(trifluoromethyl)pyridin-2-yloxy)pyrrolidine-1-carboxylate (34 g, 97% yield), Mass spec: 333 (M+H)

Step 2: (S)-3-chloro-2-(pyrrolidin-3-yloxy)-5-(trifluoromethyl)pyridine hydrochloride

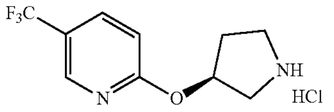 [SMILES: FC(F)(F)c1ccc(O[C@H]2CCNC2)nc1 ; Cl]

HCl gas was bubbled through a solution of (S)-tert-butyl 3-(5-(trifluoromethyl)pyridin-2-yloxy)pyrrolidine-1-carboxylate (LHH-000206-094) (5 g, 15 mmol) in Et2O/MeOH (20 mL, 5:1) at 0° C. for 3 h, filtered, the (S)-3-chloro-2-(pyrrolidin-3-yloxy)-5-(trifluoromethyl)pyridine hydrochloride was obtained as white solid (3.8 g, 94%), Mass spec: 233 (M+H)

Intermediate 4: (S)-3-chloro-2-(pyrrolidin-3-yloxy)-5-(trifluoromethyl)pyridine hydrochloride

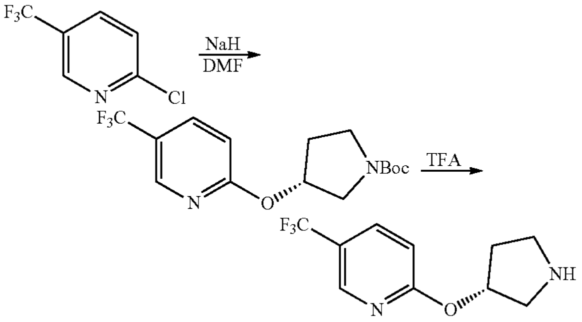

Step 1: (R)-tert-butyl 3-(5-(trifluoromethyl)pyridin-2-yloxy)pyrrolidine-1-carboxylate

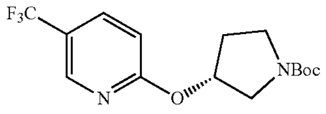 [SMILES: CC(C)(C)OC(=O)N1CC[C@@H](Oc2ccc(C(F)(F)F)cn2)C1]

The title compound was prepared following procedures described in step 1 of Intermediate 1 to give crude (R)-tert-butyl 3-(5-(trifluoromethyl)pyridin-2-yloxy)pyrrolidine-1-carboxylate (8.6 g, 126% yield), Mass spec: 333 (M+H)

Step 2: (R)-3-chloro-2-(pyrrolidin-3-yloxy)-5-(trifluoromethyl)pyridine

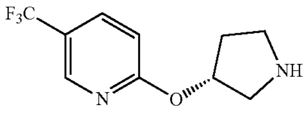 [SMILES: FC(F)(F)c1ccc(O[C@@H]2CCNC2)nc1]

To a solution of (R)-tert-butyl 3-(5-(trifluoromethyl)pyridin-2-yloxy)pyrrolidine-1-carboxylate (8.6 g, 25.9 mmol) in DCM (60 mL) was added TFA (30 mL) at 0° C., and the mixture was stirred at this temperature for 2 h. removal the solvent in vacuum to left dark liquid which was diluted with EA, the organic layer was washed with NaHCO3 solution, brine, dried over Na2SO4, concentrated to give (R)-3-chloro-2-(pyrrolidin-3-yloxy)-5-(trifluoromethyl)pyridine (6 g, quant.), Mass spec: 233 (M+H).

Intermediate 5: 3-(2-(1,3-dioxan-2-yl)-4-methoxyphenyl)pyrrolidine

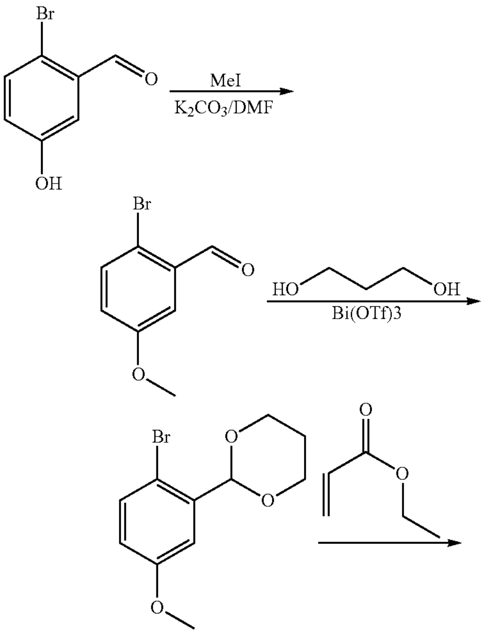

-continued

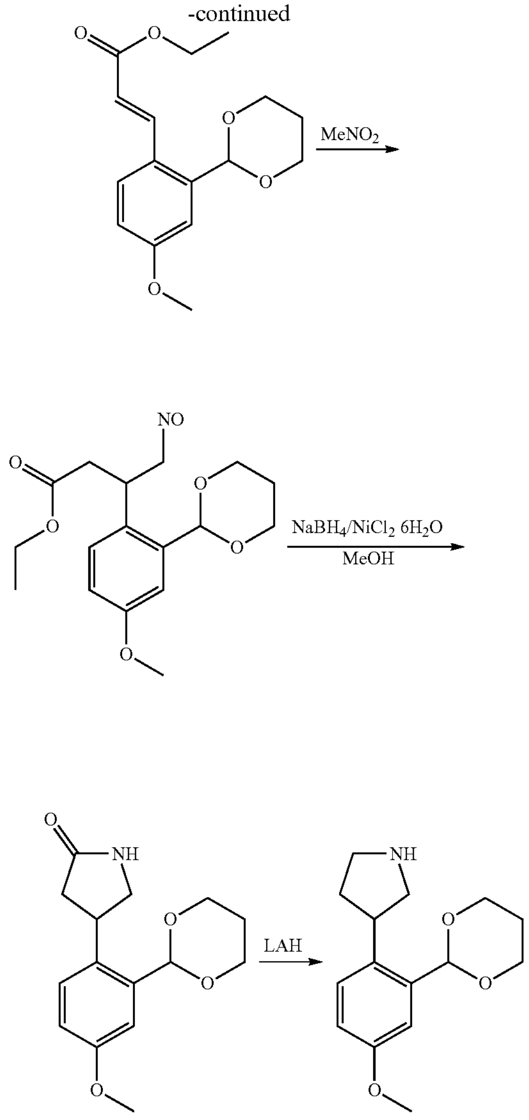

Step 1: 2-bromo-5-methoxybenzaldehyde

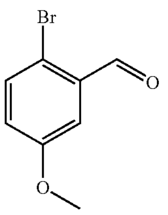

To a solution of 2-bromo-5-hydroxybenzaldehyde (10.0 g, 50.0 mmol) in DMF was added iodomethane (3.7 ml, 60.0 mmol), and $K_2CO_3$ (20.7 g, 150.0 mmol) at rt. Then the mixture was stirred at 44° C. for 8 h. the mixture was evaporated to obtain a residue, which was dissolved in EA, washed with 5% LiCl solution (3×100 ml), the organic layer was dried, evaporated, and purified by silica gel to give 2-bromo-5-methoxybenzaldehyde (9.0 g, 85% yield), Mass spec: 215 (M+1)

Step 2: 2-(2-bromo-5-methoxyphenyl)-1,3-dioxane

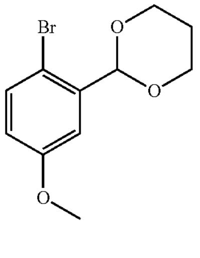

A homogeneous mixture of 2-bromo-5-methoxybenzaldehyde (428 mg, 2.0 mmol), propane-1,3-diol (270 mg, 3.6 mmol) and triethyl orthoformate (296 mg, 2.0 mmol) was stirred at r.t. as $Bi(OTf)_3$ (6.5 mg, 1% mmol yield) was added. After 1.5 h, the mixture was completed, 20% NaOH solution (10 ml) was added, extracted with EA, dried ($Na_2SO_4$) and evaporated, purified by silica gel to give 2-(2-bromo-5-methoxyphenyl)-1,3-dioxane (400 mg, 73% yield), Mass spec: 273 (M+1).

Step 3: (E)-ethyl 3-(2-(1,3-dioxan-2-yl)-4-methoxyphenyl)acrylate

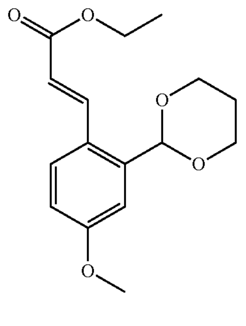 [SMILES: CCOC(=O)/C=C/c1ccc(OC)cc1C1OCCCO1]

To a solution of 2-(2-bromo-5-methoxyphenyl)-1,3-dioxane (272 mg, 1.0 mmol) in 4 ml CH3CN was added ethyl acrylate (86.09 mg, 1.0 mmol), $Pd(OAc)_2$ (11.2 mg, 0.05 mmol), DIPEA (0.5 ml, 3.0 mmol), tri(p-toly)phosphine (30 mg, 0.1 mmol). the mixture was degassed for 5 min, then reflux at 100° C. for overnight. After cooling to r.t., the mixture was evaporated, and purified by silica gel to give (E)-ethyl 3-(2-(1,3-dioxan-2-yl)-4-methoxyphen-yl)acrylate (60 mg, 20.5% yield), Mass spec: 293 (M+1). $^1$H-NMR (400 Hz, DMSO) δ=8.173-8.134 (d, 1H), 7.817-7.796 (d, 1H), 7.097-7.069 (d, 1H), 6.976-6.948 (d, 1H), 6.418-6.378 (d, 1H), 5.705 (s, 1H), 4.208-4.155 (m, 4H), 3.999-3.938 (m, 2H), 3.799 (s, 3H), 2.084-2.007 (m, 1H), 1.509-1.476 (m, 1H), 1.288-1.252 (m, 1H).

Step 4: ethyl 3-(2-(1,3-dioxan-2-yl)-4-methoxyphenyl)-4-nitrobutanoate

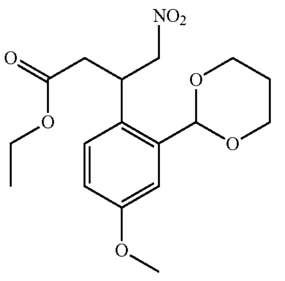 [SMILES: CCOC(=O)CC(C[N+](=O)[O-])c1ccc(OC)cc1C1OCCCO1]

To a solution of (E)-ethyl 3-(2-(1,3-dioxan-2-yl)-4-methoxyphenyl)acrylate (146 mg, 0.5 mmol), in $MeNO_2$ (152.5 mg, 2.5 mmol) was added dropwise DBU (76 mg, 0.5 mmol) at 0° C., and the mixture was stirred at r.t. for 3 h. the mixture was diluted with water and extracted with EA (3×5 ml), dried ($Na_2SO_4$), evaporated and purified by silica gel to give ethyl 3-(2-(1,3-dioxan-2-yl)-4-methoxyphenyl)-4-nitrobutanoate (80 mg, 45%) as white solid, Mass spec: 354 (M+1).

Step 5: 4-(2-(1,3-dioxan-2-yl)-4-methoxyphenyl) pyrrolidin-2-one

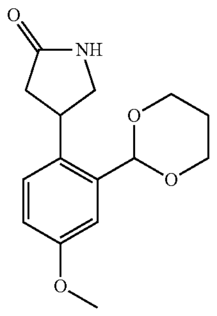 [SMILES: COc1ccc(C2CNC(=O)C2)c(C2OCCCO2)c1]

$NiCl_2 \cdot 6H_2O$ (730 mg, 5.66 mmol) was added to a solution of ethyl 3-(2-(1,3-dioxan-2-yl)-4-methoxyphenyl)-4-nitrobutanoate (1.0 g, 2.83 mmol) in 10 ml MeOH at r.t. After 5 min, $NaBH_4$ (1.07 g, 28.3 mmol) was added in five portions. Then the mixture was stirred at rt for 30 min, stirred at 70° C. for overnight. The mixture was cooled to r.t. Then filter-ed, the filtrate was evaporated, purified by silica gel to give 4-(2-(1,3-dioxan-2-yl)-4-methoxyphenyl)pyrrolidin-2-one (670 mg, 85.9% yield) as white solid, Mass spec: 278 (M+1), $^1$H-NMR (400 Hz, DMSO) δ=7.645 (s, 1H), 7.342-7.291 (d, 1H), 6.986-6.980 (d, 1H), 6.900-6.893 (d, 1H), 6.878-6.871 (d, 1H), 5.637 (s, 1H), 4.140-4.084 (m, 2H), 3.971-3.897 (m, 3H), 3.701 (s, 3H), 3.507-3.463 (m, 1H), 3.118-3.077 (m, 1H), 2.483-2.382 (m, 1H), 2.237-2.174 (m, 1H), 2.017-2.002 (m, 1H), 1.434-1.402 (m, 1H).

Step 6: 3-(2-(1,3-dioxan-2-yl)-4-methoxyphenyl) pyrrolidine

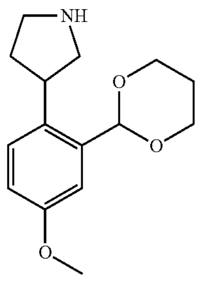 [SMILES: COc1ccc(C2CCNC2)c(C2OCCCO2)c1]

To a solution of 4-(2-(1,3-dioxan-2-yl)-4-methoxyphenyl) pyrrolidin-2-one (670 mg, 2.41 mmol) in 10 ml THE was added LAH (184 mg, 4.82 mmol) at 0° C. and then stirred at r.t. for 5 min, then stirred at 70° C. for overnight. The mixture was quenched with 0.18 ml $H_2O$, 0.18 ml 15% NaOH solution, 0.55 ml $H_2O$ by follow, then stirred at r.t. for 15 min, filtered to get the filtrate, evaporated to give the product 3-(2-(1,3-dioxan-2-yl)-4-methoxyphenyl)pyrrolidine as white solid (500 mg, 80% yield), Mass spec: 264 (M+1).

Intermediate 6: 3-(4-(2-isopropylphenoxy)-2-((tetrahydro-2H-pyran-2-yloxy)methyl)phenyl)pyrr-olidine

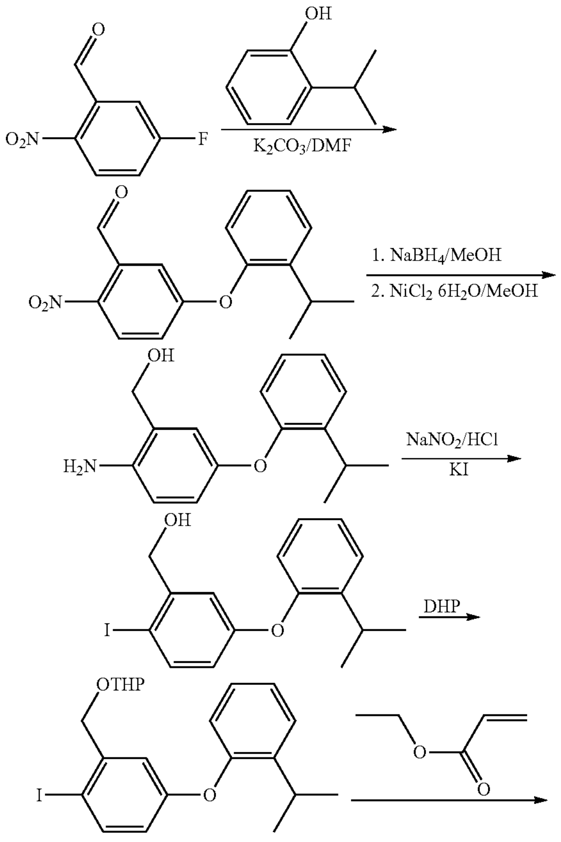

-continued

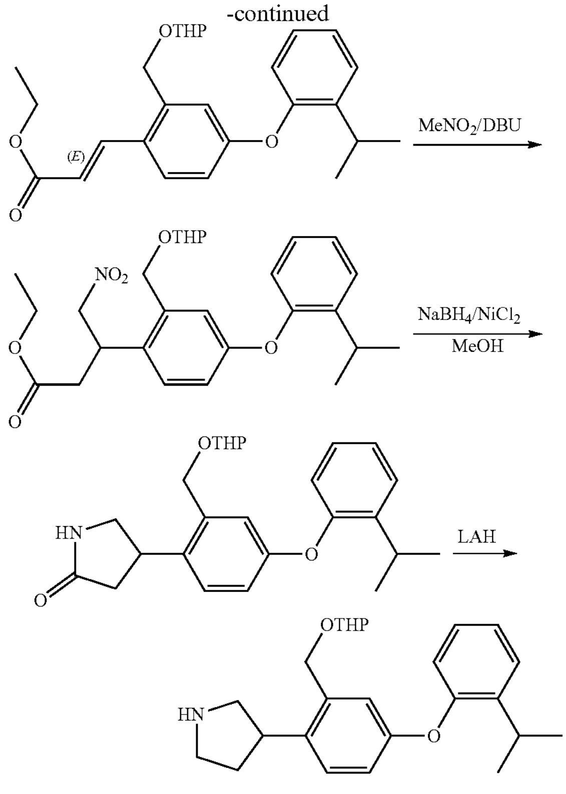

Step 1: 5-(2-isopropylphenoxy)-2-nitrobenzaldehyde

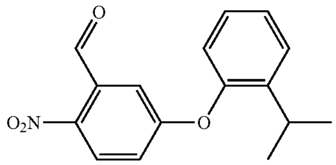 [SMILES: CC(C)c1ccccc1Oc1ccc([N+](=O)[O-])c(C=O)c1]

To a solution of 5-fluoro-2-nitrobenzaldehyde (20.0 g, 118.0 mmol) in 100 ml DMF was added $K_2CO_3$ (32.7 g, 237 mmol) and 2-isopropylphenol (19.25 g, 141.6 mmol), then stirred at 120° C. for 1 h. the reaction was almost completed, the mixture was evaporated to give a residue, which dissolved in EA, washed with LiCl solution (3×100 ml), dried (Na2SO4), and concentrated, purified by silica gel to give 5-(2-isopropylphenoxy)-2-nitrobenzaldehyde (30 g, 91% yield) as yellow oil, Mass spec: 286 (M+1).

Step 2: (2-amino-5-(2-isopropylphenoxy)phenyl)methanol

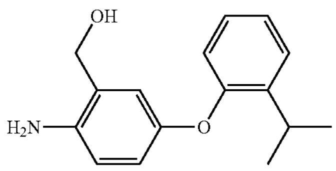 [SMILES: CC(C)c1ccccc1Oc1ccc(N)c(CO)c1]

To a solution of 5-(2-isopropylphenoxy)-2-nitrobenzaldehyde (15.0 g, 52.6 mmol) in MeOH (100 ml) was added $NaBH_4$ (4.0 g, 105.25 mmol) at 0° C., then stirred at rt for 30 min, cooled to 0° C. again, $NiCl_2$ $6H_2O$ (2.5 g, 105.2 mmol) was added slowly. Then added another $NaBH_4$ (4.0 g, 105.25 mmol) slowly at 0° C., stirred at r.t. for 30 min. the mixture was evaporated, added diluted HCl solution to dissolve the inorganic residue, then adjust pH=8 by $NH_3H_2O$, extracted with EA (3×50 ml), the EA layer was washed with brine (2×100 ml), dried, filtered, and evaporated to give (2-amino-5-(2-isopropylphenoxy)phenyl)methanol (6.0 g, 44% yield), Mass spec: 258 (M+1).

Step 3: (2-iodo-5-(2-isopropylphenoxy)phenyl)methanol

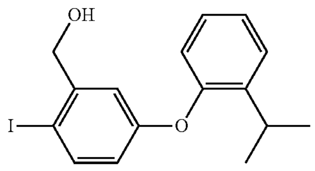 [SMILES: CC(C)c1ccccc1Oc1ccc(I)c(CO)c1]

A cold solution of Sodium nitrite (1.6 g, 23.0 mmol) in 5 ml water was added dropwise to a stirred cooled suspension of (2-amino-5-(2-isopropylphenoxy)phenyl)methanol (5.0 g, 19.0 mmmol) in water (15 ml) and hydrochloric acid (15 ml), when diazotization was completed, a solution of potassium iodine in water (5 ml) was added. After 1 h at r.t., the mixture was quenched by NaHSO3, extracted with EA (3×20 ml), dried over Na2SO4, evaporated and purified by silica gel to give 2-iodo-5-(2-isopropylphenoxy)phenyl)methanol (2.4 g, 34% yield), Mass spec: 369 (M+1).

Step 4: 2-(2-iodo-5-(2-isopropylphenoxy)benzyloxy)tetrahydro-2H-pyran

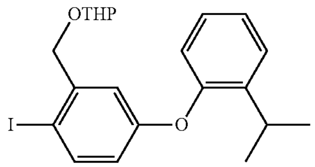

To a solution of 2-iodo-5-(2-isopropylphenoxy)phenyl)methanol (1.0 g, 2.7 mmol) in DCM (8 ml) was added DHP (75 mg, 8.96 mmol) and PPTS (1.0 g, 4.05 mmol) at 0° C. then stirred at r.t. for overnight. The mixture was diluted with DCM (20 ml), washed with H2O (3×20 ml), the DCM layer was dried, evaporated to give crude 2-(2-iodo-5-(2-isopropylphenoxy)benzyloxy)tetrahydro-2H-pyran (2.4 g, 200% yield), Mass spec: 453 (M+1).

Step 5: (E)-ethyl 3-(4-(2-isopropylphenoxy)-2-((tetrahydro-2H-pyran-2-yloxy)methyl)phenyl)acrylate

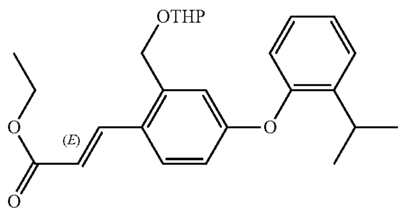

The title compound was prepared following procedures described in Intermediate 5 step 3 to give (E)-ethyl 3-(4-(2-isopropylphenoxy)-2-((tetrahydro-2H-pyran-2-yloxy)methyl)phenyl)acrylate (1.6 g, 88% yield), Mass spec: 425 (M+1).

Step 6: ethyl 3-(4-(2-isopropylphenoxy)-2-((tetrahydro-2H-pyran-2-yloxy)methyl)phenyl)-4-nitrobutanoate

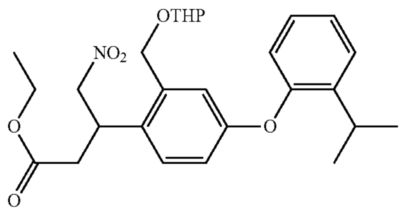

The title compound was prepared following procedures described in Intermediate 5 step 4 to give ethyl 3-(4-(2-isopropylphenoxy)-2-((tetrahydro-2H-pyran-2-yloxy)methyl)phenyl)-4-nitrobutanoate (1.5 g, 83.0% yield), Mass spec: 486 (M+1).

Step 7: 4-(4-(2-isopropylphenoxy)-2-((tetrahydro-2H-pyran-2-yloxy)methyl)phenyl)pyrrolidin-2-one

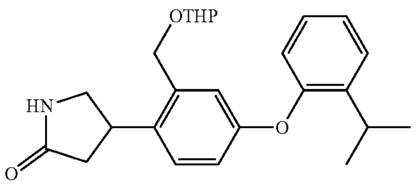

The title compound was prepared following procedures described in Intermediate 5 step 5 to give 4-(4-(2-isopropylphenoxy)-2-((tetrahydro-2H-pyran-2-yloxy)methyl)phenyl)pyrrolidin-2-one (730 mg, 60.8% yield), Mass spec: 410 (M+1).

Step 8: 3-(4-(2-isopropylphenoxy)-2-((tetrahydro-2H-pyran-2-yloxy)methyl)phenyl)pyrrolidine

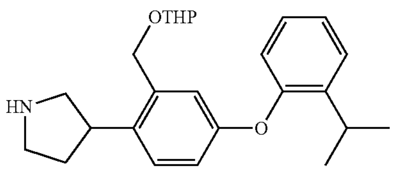

The title compound was prepared following procedures described in Intermediate 5 step 6 to give 3-(4-(2-isopropylphenoxy)-2-((tetrahydro-2H-pyran-2-yloxy)methyl)phenyl)pyrrolidine (530 mg, 69.2% yield), Mass spec: 396 (M+1).

Intermediate 7: (S)-5-fluoro-N-(pyrrolidin-3-yl)pyridin-2-amine

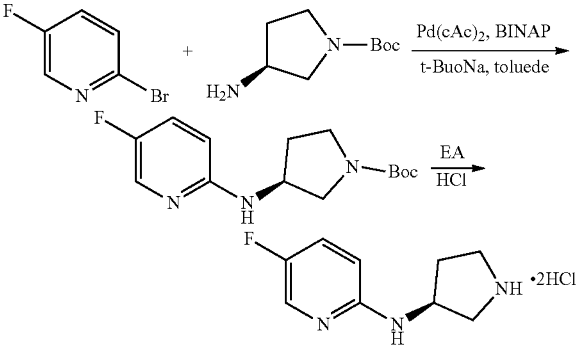

Step 1: (S)-tert-butyl 3-(5-fluoropyridin-2-ylamino)pyrrolidine-1-carboxylate

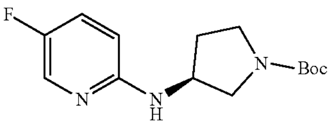 [SMILES: CC(C)(C)OC(=O)N1CC[C@H](Nc2ccc(F)cn2)C1]

To a solution of 2-bromo-5-fluoropyridine (4.772 g, 27.11 mmol) in toluene (55 mL) was added Pd(cAc)2 (607.3 mg, 2.711 mmol), BINAP (1.686 g, 2.711 mmol), t-BuoNa (7.81 g, 81.33 mmol) under N2, the reaction mixture was stirred at 80° C. for 4 h. The reaction was diluted with EA (50 mL), washed with brine, and dried over $Na_2SO_4$. Concentrate to dryness, the residue was purified by silica gel to give tert-butyl (S)-tert-butyl 3-(5-fluoropyridin-2-ylamino)pyrrolidine-1-carboxylate (600 mg, 15% yield), Mass spec: 282 (M+H)

Step 2: (S)-5-fluoro-N-(pyrrolidin-3-yl)pyridin-2-amine

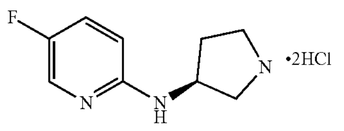 [SMILES: Fc1ccc(N[C@H]2CCNC2)nc1]

To a solution of 5-fluoro-N-(pyrrolidin-3-yl)pyridin-2-amine (600 mg, 2.135 mmol) in EA (10 mL) was added EA/HCl (10 mL), the resulting mixture was stirred at rt for 1 h; the mixture was concentrated to give (S)-5-fluoro-N-(pyrrolidin-3-yl)pyridin-2-amine (2.5 g, 80%. yield), Mass spec: 189 (M+H)

Intermediate 8: 4-(2-chlorobenzoyl)-2-fluorobenzaldehyde

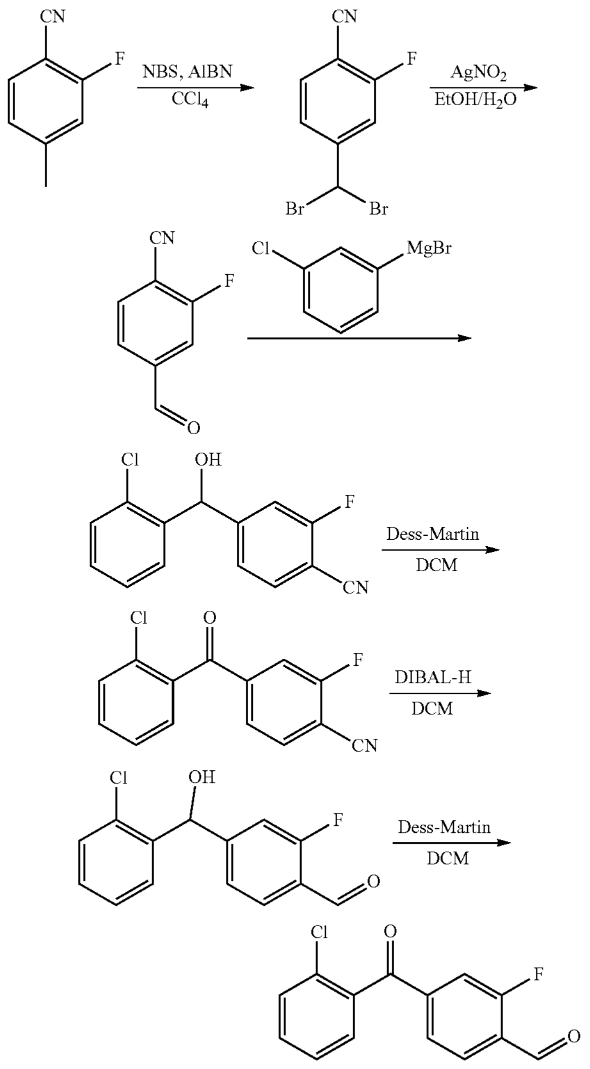

Step 1: 4-(dibromomethyl)-2-fluorobenzonitrile

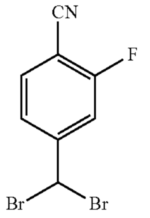

To a solution of 2-fluoro-4-methylbenzonitrile (5.4 g, 40 mmol) in CCl4 (40 mL) was added NBS (15.7 g, 88 mmol), AIBN (657 mg, 4 mmol), the resulting mixture was stirred at 90° C. for 24 h under N2; the mixture was concentrated to leave 4-(dibromomethyl)-2-fluorobenzonitrile (8.8 g, 80% yield), Mass spec: 292 (M+H)

Step 2: 2-fluoro-4-formylbenzonitrile

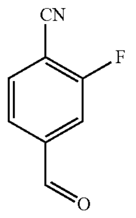 [SMILES: N#Cc1ccc(C=O)cc1F]

To a solution of 4-(dibromomethyl)-2-fluorobenzonitrile (8.8 g, 30 mmol) in 90 mL EtOH/H2O was added AgNO3 (10.2 g, 60 mmol), the resulting mixture was refluxed for 3 h; The reaction was diluted with DCM (100 mL), washed with brine, and dried over $Na_2SO_4$. Concentrate to dryness, the residue was purified by silica gel to give 2-fluoro-4-formylbenzonitrile (2 g, 44.4% yield), Mass spec: 150 (M+H).

Step 3: 4-((2-chlorophenyl)(hydroxy)methyl)-2-fluorobenzonitrile

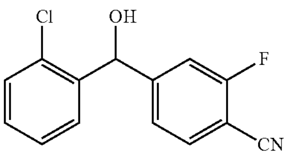 [SMILES: N#Cc1ccc(C(O)c2ccccc2Cl)cc1F]

To a solution of Mg (300 mg, 12.5 mmol), LiCl (265 mg, 6.25 mmol) in THF (20 mL) was added DIBAL-H (0.05 ml) to rt. for 5 min, The reaction was cooled to −30° C. and 1-bromo-3-chlorobenzene (958 mg, 5 mmol) dropwise to −20° C. for 30 min and warmed at rt. for 1 h, after that, the above solution was added into 2-fluoro-4-formylbenzonitrile (410 mg, 2.75 mmol) in THF (5 ml) to 0° C., the reaction mixture was stirred at 0° C. for 15 min and NH4Cl was added for quenching. The layer was separated, dried over $Na_2SO_4$ and concentrate to give 4-((2-chlorophenyl)(hydroxy)methyl)-2-fluorobenzonitrile (750 mg, 40% yield) Mass spec: 244 (M−17)

Step 4: 4-(2-chlorobenzoyl)-2-fluorobenzonitrile

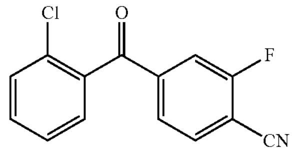 [SMILES: N#Cc1ccc(C(=O)c2ccccc2Cl)cc1F]

To a solution of 4-((2-chlorophenyl)(hydroxy)methyl)-2-fluorobenzonitrile (740 mg, 2.75 mmol) in DCM (15 mL) was added Dess-Martin (1.4 g, 3.3 mmol) with stirring to rt. for 1.5 h. The reaction was concentrated to dryness, the residue was purified by Prep-TLC to give 4-(2-chlorobenzoyl)-2-fluorobenzonitrile (530 mg, 80% yield), Mass spec: NO Step 5: 4-((2-chlorophenyl)(hydroxy)methyl)-2-fluorobenzaldehyde

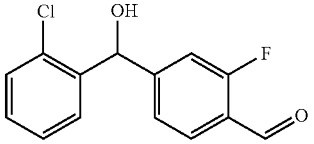 [SMILES: O=Cc1ccc(C(O)c2ccccc2Cl)cc1F]

To a solution of 4-(2-chlorobenzoyl)-2-fluorobenzonitrile (520 mg, 2 mmol) in DCM (15 mL) was added Et3N (203 mg, 2 mmol) and DIBAL-H in hexane (1.5M) (1.4 g, 3.3 mmol) to −78° C. for 45 min. The reaction was poured into icewater, extracted, separated, dried over $Na_2SO_4$ and concentrate to give 4-((2-chlorophenyl)(hydroxy)methyl)-2-fluorobenzaldehyd (470 mg, 70%) Mass spec: 265 (M+H)

Step 6: 4-(2-chlorobenzoyl)-2-fluorobenzaldehyde

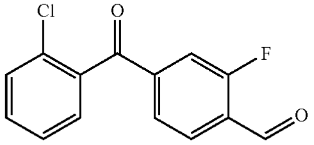 [SMILES: O=Cc1ccc(C(=O)c2ccccc2Cl)cc1F]

The title compound was prepared following procedures described in step 4 to give 4-(2-chlorobenzoyl)-2-fluorobenzaldehyde (580 mg, quant), Mass spec: NO, $^1$H-NMR (400 Hz, DMSO) δ=10.220 (s, 1H), 8.098-8.116 (m, 2H), 7.566-7.657 (m, 5H).

Intermediate 9: (2'-ethyl-4-(pyrrolidin-3-yl)biphenyl-3-yl)methanol

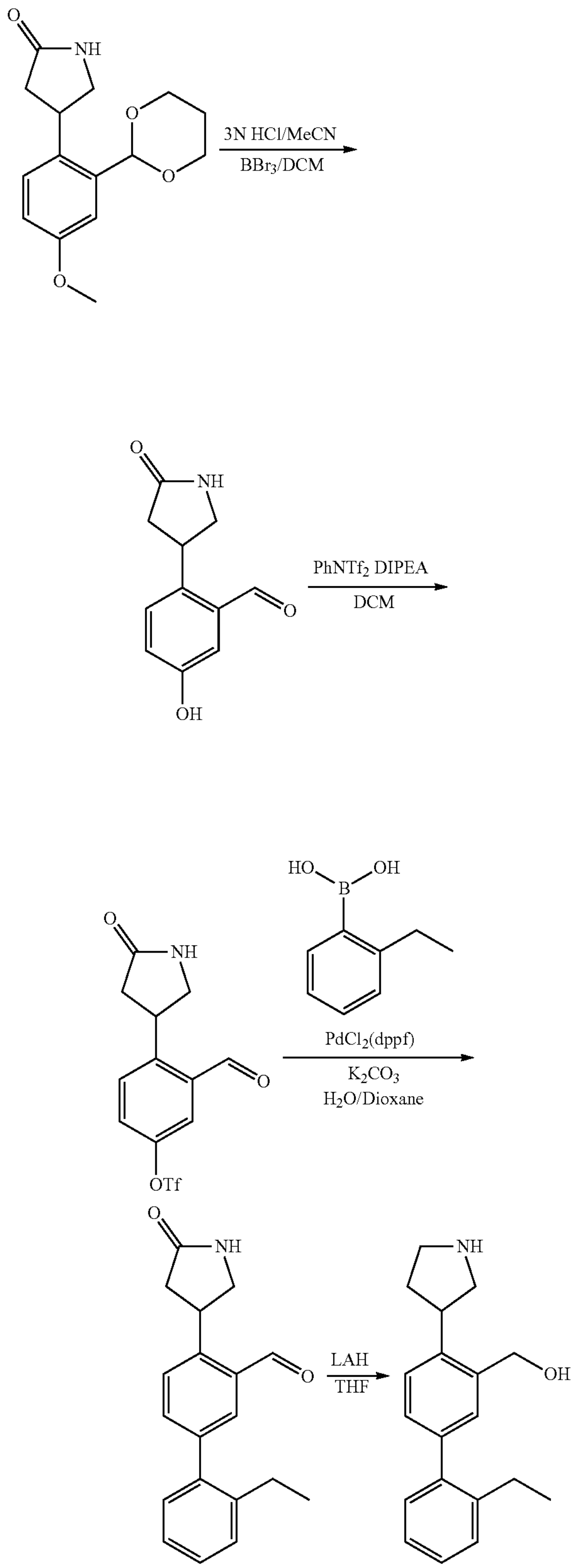

Step 1: 5-hydroxy-2-(5-oxopyrrolidin-3-yl)benzaldehyde

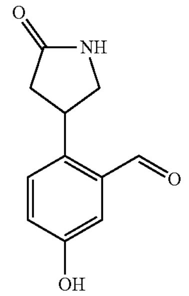 [SMILES: O=Cc1cc(O)ccc1C1CNC(=O)C1]

To a solution of 4-(2-(1,3-dioxan-2-yl)-4-methoxyphenyl) pyrrolidin-2-one (1 g, 3.6 mmol) (intermediate 5 step 5) in 4 mL MeCN at 0° C. was added 3N HCl (4 mL) slowly, the mixture stirred at rt for 30 min, water was added, extracted with EA, washed by brine, dried over $Na_2SO_4$, removal the solvent to left the crude product which was dissolved in 10 mL DCM, to this solution was stirred at 0° C. was added $BBr_3$ (0.6 mL, 7.2 mmol) drop-wised, and stirred at rt for 1 h, the mixture was poured into ice water, extracted with EA/THF (v:v=3/1), combined organic phase washed with brine, dried over $Na_2SO_4$, removal the solvent to left the crude product which was purified by silica gel to give 5-hydroxy-2-(pyrrolidin-3-yl)benzaldehyde (400 mg, 54.0% yield), Mass spec: 206 (M+1).

Step 2: 3-formyl-4-(5-oxopyrrolidin-3-yl)phenyl trifluoromethanesulfonate

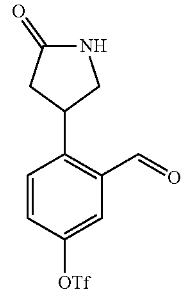 [SMILES: O=Cc1cc(OS(=O)(=O)C(F)(F)F)ccc1C1CNC(=O)C1]

To a solution of 5-hydroxy-2-(5-oxopyrrolidin-3-yl) benzaldehyde (100 mg, 0.49 mmol) in 2 mL DCM was added $PhNTf_2$ (208 mg, 0.58 mmol) and DIPEA (0.24 mL, 1.5 mmol), The mixture was stirred at rt for 2 h, water was added, extracted with DCM, the organic phase was washed with water, brine, dried over Na2SO4, removal the solvent to left the crude product which was purified by silica gel to give 3-formyl-4-(5-oxopyrrolidin-3-yl) phenyl trifluoromethanesulfonate (160 mg, 94.0% yield), Mass spec: 338 (M+1).

Step 3: 2'-ethyl-4-(5-oxopyrrolidin-3-yl) biphenyl-3-carbaldehyde

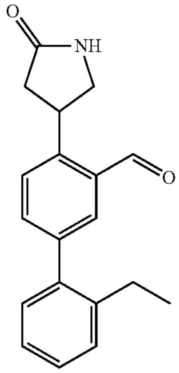 [SMILES: CCc1ccccc1-c1ccc(C2CNC(=O)C2)c(C=O)c1]

To a solution of 3-formyl-4-(pyrrolidin-3-yl)phenyl trifluoromethanesulfonate (300 mg, 0.89 mmol), 2-ethylphenylboronic acid (160 mg, 1.07 mmol) in 10 mL dioxane/water (v:v 4/1) was added $PdCl_2$(dppf) (72 mg, 0.09 mmol) and $K_3PO_4$ (566 mg, 2.67 mmol), The mixture was stirred at 90° C. for 2 h under $N_2$, the mixture was diluted with water, extracted with EA, the organic phase was washed with water, brine, dried over $Na_2SO_4$, removal the solvent to give crude product which was purified by silica gel to give 2'-ethyl-4-(5-oxopyrrolidin-3-yl)biphenyl-3-carbaldehyde (210 mg, 80.1% yield), Mass spec: 294 (M+1).

Step 4: (2'-ethyl-4-(pyrrolidin-3-yl)biphenyl-3-yl) methanol

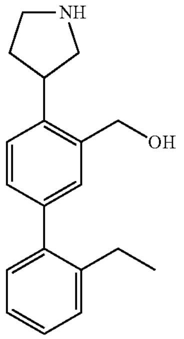 [SMILES: CCc1ccccc1-c1ccc(C2CCNC2)c(CO)c1]

To a suspension of LAH (0.6225 g, 16.3 mmol) in 10 mL THE at 0° C. was added another solution of 2'-ethyl-4-(5-oxopyrrolidin-3-yl) biphenyl-3-carbaldehyde (1.6 g, 5.4 mmol) in 10 mL THE drop-wised. the mixture was refluxed for 2 h under $N_2$, quenched with water (0.6 mL), NaOH (15%) (0.6 mL), and water (1.8 mL), filtered, the filtrate was concentrated to left crude product which was purified by silica gel to give the product (2'-ethyl-4-(pyrrolidin-3-yl) biphenyl-3-yl) methanol (800 mg, 48.1% yield), Mass spec: 282 (M+1).

Intermediate 10: (2'-cyclopropyl-4-(pyrrolidin-3-yl)biphenyl-3-yl)methanol

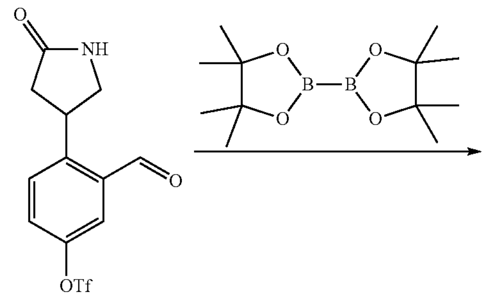

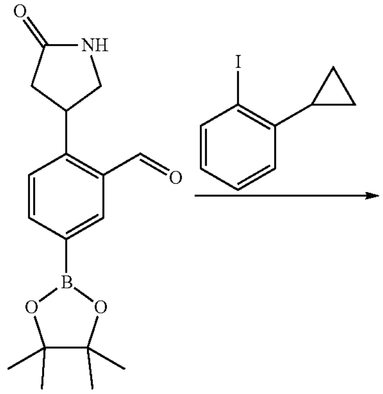

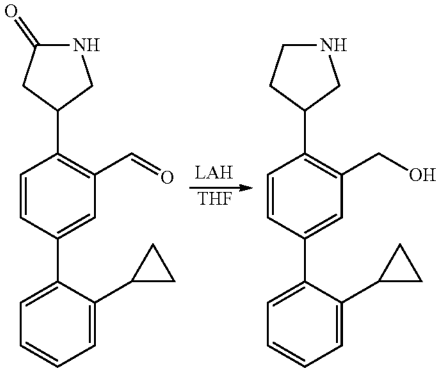

Step 1: 2-(5-oxopyrrolidin-3-yl)-5-(4,4,5,5-tetramethyl-1,3,2-dioxaborolan-2-yl)benzaldehyde

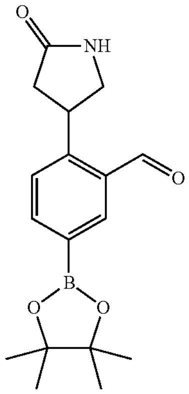 [SMILES: CC1(C)OB(c2ccc(C3CNC(=O)C3)c(C=O)c2)OC1(C)C]

To a solution of 3-formyl-4-(5-oxopyrrolidin-3-yl) phenyl trifluoromethanesulfonate (3 g, 8.9 mmol) (Intermediate 9 (step 2)) in 8 mL dioxane was added 4, 4, 4', 4', 5, 5, 5', 5'-octamethyl-2, 2'-bi(1,3,2-dioxaborolane) (3.3 g, 13.3 mmol), AcOK (1.7 g, 17.8 mmol) and Pd(dppf)$Cl_2$ (400 mg, 0.89 mmol), the mixture was stirred at 100° C. for 2 h under $N_2$. After reaction finished, diluted with water, extracted with EA, the organic layer was washed by water, brine, dried over Na2SO4, removal the solvent to give crude product (2.8 g, quant.) which can be used directly, Mass spec: 316 (M+H).

Step 2: 2'-cyclopropyl-4-(5-oxopyrrolidin-3-yl)biphenyl-3-carbaldehyde

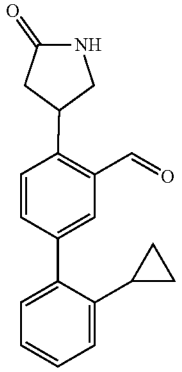 [SMILES: O=Cc1cc(-c2ccccc2C2CC2)ccc1C1CNC(=O)C1]

To a solution of 2-(5-oxopyrrolidin-3-yl)-5-(4,4,5,5-tetramethyl-1,3,2-dioxaborolan-2-yl) benzaldehyde (2.2 g, 7 mmol) in dioxane/$H_2O$ (16 mL/1 mL) was added 1-cyclopropyl-2-iodobenzene (2 g, 8.4 mmol), $K_2CO_3$ (1.98 g, 14 mmol) and Pd(dppf)$Cl_2$ (200 mg, 0.7 mmol), the mixture was stirred at 100° C. for 5 h under $N_2$, diluted with EA, the mixture was washed by water, brine, dried over $Na_2SO_4$, removal the solvent to left crude product which was purified by silica gel to give the product 2'-cyclopropyl-4-(5-oxopyrrolidin-3-yl)biphenyl-3-carbaldehyde (500 mg, 23.9% yield), Mass spec: 321 (M+H).

Step 3: (2'-cyclopropyl-4-(pyrrolidin-3-yl)biphenyl-3-yl)methanol

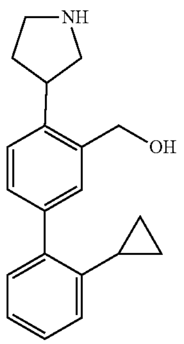 [SMILES: OCc1cc(-c2ccccc2C2CC2)ccc1C1CCNC1]

The title compound was prepared following procedures described in intermediate 9 step 4 to give (2'-cyclopropyl-4-(pyrrolidin-3-yl)biphenyl-3-yl)methanol (200 mg, 50% yield), Mass spec: 294 (M+H).

Section B: Synthesis of the Example

Example 4: 2-(1-o-tolylpyrrolidin-3-yloxy)-5-(trifluoromethyl)pyridine (Compound 1-1)

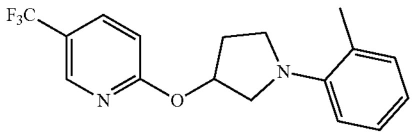 [SMILES: Cc1ccccc1N1CCC(Oc2ccc(C(F)(F)F)cn2)C1]

The title compound was prepared following procedures described in example 1 using Intermediate 2 and 1-bromo-2-methylbenzene to give 2-(1-o-tolylpyrrolidin-3-yloxy)-5-(trifluoromethyl)pyridine (60 mg, 17.8% yield), Mass spec: 323 (M+H), $t_R$=3.098 min, $^1$H-NMR (400 Hz, CDCl3) δ=8.454 (s, 1H), 7.773-7.801 (q, 1H), 7.141-7.176 (m, 2H), 6.829-6.957 (m, 3H), 5.658-5.688 (m, 1H), 3.706-3.747 (m, 1H), 3.475-3.534 (m, 1H), 3.304-3.336 (m, 1H), 3.201-3.254 (m, 1H), 3.416-3.465 (m, 1H), 2.359 (s, 3H), 2.189-2.227 (m, 1H).

Example 5: 2-(3-(5-(trifluoromethyl)pyridin-2-yloxy)pyrrolidin-1-yl)benzonitrile (Compound 1-2)

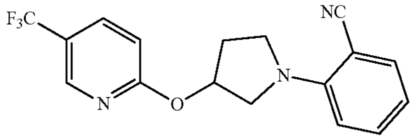 [SMILES: N#Cc1ccccc1N1CCC(Oc2ccc(C(F)(F)F)cn2)C1]

To a solution of 2-(pyrrolidin-3-yloxy)-5-(trifluoromethyl)pyridine (1.2 g, 5.2 mmol) in DMF (15 mL) was added 2-fluorobenzonitrile (814 mg, 6.7 mmol), K2CO3 (2.2 g, 15.6 mmol) at rt, the mixture was stirred at 100° C. for overnight, diluted with EA, washed with water and brine, and dried over Na2SO4, removal of the solvent, and purified by silica gel to give 2-(3-(5-(trifluoromethyl)pyridin-2-yloxy)pyrrolidin-1-yl)benzonitrile as liquid (400 mg, 23% yield), Mass spec: 334 (M+H), $t_R$=1.724 min, $^1$H-NMR (400 Hz, CDCl3) δ=6.469 (s, 1H), 7.790-7.817 (m, 1H), 7.475-7.498 (m, 1H), 7.354-7.398 (m, 1H), 6.816-6.838 (d, 1H), 6.678-6.843 (m, 2H), 5.776-5.787 (m, 1H), 4.105-4.146 (m, 1H), 3.882-3.947 (m, 1H), 3.743-3.793 (m, 2H), 2.330-2.383 (m, 2H).

Example 6: 2-(3-(5-(trifluoromethyl)pyridin-2-yloxy)pyrrolidin-1-yl)benzamide (Compound 1-3)

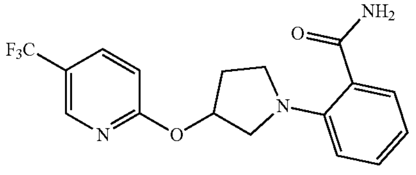 [SMILES: NC(=O)c1ccccc1N1CCC(Oc2ccc(C(F)(F)F)cn2)C1]

To a solution of 2-(3-(5-(trifluoromethyl)pyridin-2-yloxy) pyrrolidin-1-yl)benzonitrile (Example 5) (100 mg, 0.3 mmol) in NaOH solution (6 mmol/mL, 0.3 mL) and MeOH (5 mL) was added $H_2O_2$ (30%, 3 mL), the mixture was heated to 50° C. for 2 h, it was quenched by addition of HCl solution (1N) to pH=3, extracted with EA, removal the solvent to left crude product which was purified by silica gel to give 2-(3-(5-(trifluoromethyl)pyridin-2-yloxy)pyrrolidin-1-yl)benzamide (30 mg, 28% yield) as white solid. Mass spec: 352 (M+H), $t_R$=1.350 min, $^1$H-NMR (400 Hz, CDCl3) δ=8.444 (s, 1H), 7.783-7.877 (m, 3H), 7.398-7.440 (m, 1H), 7.031-7.085 (m, 2H), 6.802-6.823 (d, 1H), 5.817 (br, 1H), 5.683-5.716 (m, 1H), 3.661-3.702 (m, 1H), 3.532-3.591 (m, 1H), 3.394-3.423 (d, 1H), 3.237-3.294 (m, 1H), 2.435-2.489 (m, 1H), 2.225-2.260 (m, 1H)

Example 7: (S)-2-(1-o-tolylpyrrolidin-3-yloxy)-5-(trifluoromethyl)pyridine (Compound 1-7)

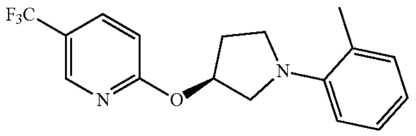 [SMILES: Cc1ccccc1N1CC[C@H](Oc2ccc(C(F)(F)F)cn2)C1]

The title compound was prepared following procedures described in example 1 with t-BuOK to give (S)-2-(1-o-tolylpyrrolidin-3-yloxy)-5-(trifluoromethyl)pyridine (40 mg, 31% yield), Mass spec: 323 (M+H), $t_R$=3.228 min, $^1$H-NMR (400 Hz, CDCl3) δ=8.450 (s, 1H), 7.771-7.80 (m, 1H), 7.146-7.17 (m, 2H), 6.829-6.956 (m, 3H), 5.663-5.679 (m, 1H), 3.705-3.746 (m, 1H), 3.493-3.515 (m, 1H), 3.302-3.335 (m, 1H), 3.219-3.342 (m, 1H), 2.414-2.464 (m, 1H), 2.358 (s, 3H), 2.2 (m, 1H).

Example 8: (R)-2-(1-o-tolylpyrrolidin-3-yloxy)-5-(trifluoromethyl)pyridine (Compound 1-8)

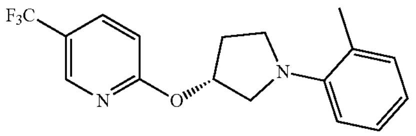 [SMILES: Cc1ccccc1N1CC[C@@H](Oc2ccc(C(F)(F)F)cn2)C1]

The title compound was prepared following procedures described in example 1 with t-BuOK to give (R)-2-(1-o-tolylpyrrolidin-3-yloxy)-5-(trifluoromethyl)pyridine (30 mg, 5% yield), Mass spec: 323 (M+H), $t_R$=3.241 min, $^1$H-NMR (400 Hz, CDCl3) δ=8.450 (s, 1H), 7.771-7.80 (m, 1H), 7.146-7.17 (m, 2H), 6.829-6.956 (m, 3H), 5.656-5.687 (m, 1H), 3.705-3.746 (m, 1H), 3.493-3.515 (m, 1H), 3.302-3.335 (m, 1H), 3.219-3.342 (m, 1H), 2.414-2.464 (m, 1H), 2.358 (s, 3H), 2.187-2.227 (m, 1H).

Example 9: (R)-2-(3-(5-(trifluoromethyl)pyridin-2-yloxy)pyrrolidin-1-yl)benzonitrile (Compound 1-9)

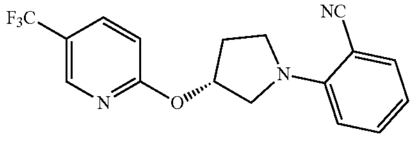 [SMILES: N#Cc1ccccc1N1CC[C@@H](Oc2ccc(C(F)(F)F)cn2)C1]

The title compound was prepared following procedures described in example 5 using (R)-2-(pyrrolidin-3-yloxy)-5-(trifluoromethyl)pyridine and 2-fluorobenzonitrile to give (R)-2-(3-(5-(trifluoromethyl)pyridin-2-yloxy)pyrrolidin-1-yl)benzonitrile (1.9 g, 29% yield), Mass spec: 334 (M+H), $t_R$=2.909 min, $^1$H-NMR (400 Hz, CDCl3) δ=8.47 (s, 1H), 7.798-7.826 (m, 1H), 7.482-7.505 (m, 1H), 7.362-7.406 (m, 1H), 6.825-6.846 (d, 1H), 6.686-6.752 (m, 2H), 5.78-5.795 (m, 1H), 4.113-4.154 (m, 1H), 3.890-3.913 (m, 1H), 3.759-3.801 (m, 2H), 2.338-2.391 (m, 2H).

Example 10: (R)-2-(3-(5-(trifluoromethyl)pyridin-2-yloxy)pyrrolidin-1-yl)benzamide (Compound 1-10)

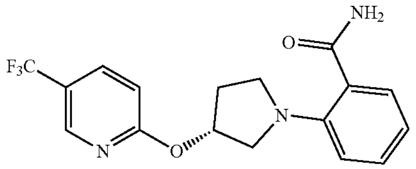 [SMILES: NC(=O)c1ccccc1N1CC[C@@H](Oc2ccc(C(F)(F)F)cn2)C1]

The title compound was prepared following procedures described in example 6 using (R)-2-(3-(5-(trifluoromethyl)pyridin-2-yloxy)pyrrolidin-1-yl)benzonitrile to give (R)-2-(3-(5-(trifluoromethyl)pyridin-2-yloxy)pyrrolidin-1-yl)benzamide (515 mg, 39.5% yield), Mass spec: 352 (M+H), $t_R$=2.324 min, $^1$H-NMR (400 Hz, CDCl3) δ=8.456 (s, 1H), 7.792-7.884 (m, 3H), 7.406-7.448 (m, 1H), 7.039-7.093 (m, 2H), 6.810-6.832 (d, 1H), 5.826 (br, 1H), 5.691-5.720 (m, 1H), 3.669-3.709 (m, 1H), 3.539-3.581 (m, 1H), 3.404-3.432 (d, 1H), 3.258-3.302 (m, 1H), 2.444-2.480 (m, 1H), 2.249-2.267 (m, 1H).

Example 11: (S)-2-(3-(5-(trifluoromethyl)pyridin-2-yloxy)pyrrolidin-1-yl)benzonitrile (Compound 1-11)

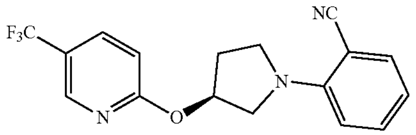 [SMILES: N#Cc1ccccc1N1CC[C@H](Oc2ccc(C(F)(F)F)cn2)C1]

The title compound was prepared following procedures described in example 5 using (R)-2-(pyrrolidin-3-yloxy)-5-(trifluoromethyl)pyridine hydrochloride and 2-fluorobenzonitrile to give (S)-2-(3-(5-(trifluoromethyl)pyridin-2-yloxy)pyrrolidin-1-yl)benzonitrile (1.3 g, 60% yield), Mass spec: 334 (M+H), $t_R$=2.907 min, $^1$H-NMR (400 Hz, CDCl3) δ=8.47 (s, 1H), 7.798-7.826 (m, 1H), 7.482-7.505 (m, 1H), 7.362-7.406 (m, 1H), 6.825-6.846 (d, 1H), 6.686-6.752 (m, 2H), 5.773-5.5.806 (m, 1H), 4.113-4.178 (m, 1H), 3.890-3.954 (m, 1H), 3.750-3.800 (m, 2H), 2.349-2.411 (m, 2H).

Example 12: (S)-2-(3-(5-(trifluoromethyl)pyridin-2-yloxy)pyrrolidin-1-yl)benzamide (Compound 1-12)

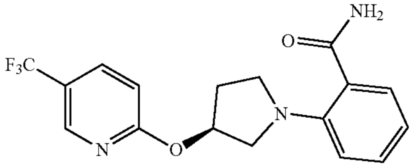 [SMILES: NC(=O)c1ccccc1N1CC[C@H](Oc2ccc(C(F)(F)F)cn2)C1]

The title compound was prepared following procedures described in example 6 using (S)-2-(3-(5-(trifluoromethyl)pyridin-2-yloxy)pyrrolidin-1-yl)benzonitrile to give (S)-2-(3-(5-(trifluoromethyl)pyridin-2-yloxy)pyrrolidin-1-yl)benzamide (510 mg, 39.3% yield), Mass spec: 352 (M+H), $t_R$=2.335 min, $^1$H-NMR (400 Hz, CDCl3) δ=8.455 (s, 1H), 7.797-7.822 (m, 3H), 7.409-7.447 (m, 1H), 7.043-7.095 (m, 1H), 6.813-6.835 (m, 1H), 5.881 (br, 1H), 5.708 (br, 1H), 3.674-3.713 (m, 1H), 3.544-3.600 (m, 1H), 3.405-3.431 (m, 1H), 3.251-3.403 (m, 1H), 2.462-2.499 (m, 1H), 2.253-2.399 (m, 1H).

Example 13: (S)-(2-(3-(5-(trifluoromethyl)pyridin-2-yloxy)pyrrolidin-1-yl)phenyl)methanamine HCl salt (Compound 1-13)

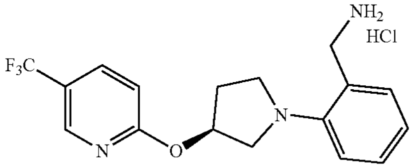 [SMILES: NCc1ccccc1N1CC[C@H](Oc2ccc(C(F)(F)F)cn2)C1 ; Cl]

To a solution of (S)-2-(3-(5-(trifluoromethyl)pyridin-2-yloxy)pyrrolidin-1-yl)benzamide (example 12) (130 mg, 0.54 mmol) in dry THE at 0° C. was added LAH (30 mg, 0.8 mmol), the mixture was heated to 50° C. for 3 h, quenched with NH4Cl solution, diluted by EA, the organic layer was washed by brine, dried over Na2SO4, removal the solvent to left the crude product which was purified by stirring in HC/EA for 30 min, filtered, washed with ether (10 ml×2) to give (S)-(2-(3-(5-(trifluoromethyl)pyridin-2-yloxy)pyrrolidin-1-yl)phenyl)methanamine HCl salt (30 mg, 15% yield) as white solid. Mass spec: 338 (M+H), $t_R$=1.793 min, $^1$H-NMR (400 Hz, DMSO) δ=8.6 (br, 4H), 8.078-8.107 (dd, 1H), 7.509-7.526 (d, 1H), 7.312-7.350 (m, 1H), 7.207-7.228 (m, 1H), 7.071-7.110 (m, 2H), 5.653-5.681 (m, 1H), 4.092-4.120 (m, 2H), 3.650-3.690 (m, 1H), 3.393-3.415 (m, 1H), 3.215-3.292 (m, 2H), 2.432-2.483 (m, 1H), 2.112-2.145 (m, 1H).

Example 14: (S)-2-(3-(5-(trifluoromethyl)pyridin-2-yloxy)pyrrolidin-1-yl)phenol (Compound 1-14)

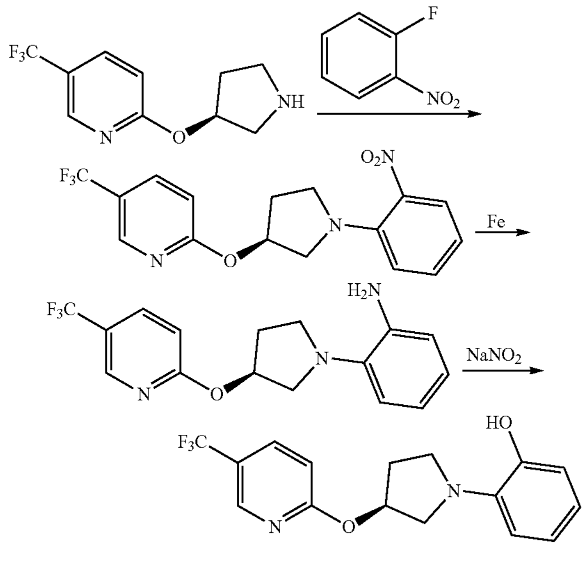

Step 1: (S)-2-(1-(2-nitrophenyl)pyrrolidin-3-yloxy)-5-(trifluoromethyl)pyridine

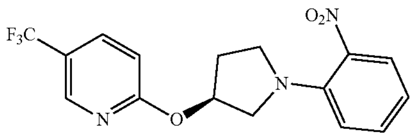

The title compound was prepared following procedures described in example using (S)-2-(pyrrolidin-3-yloxy)-5-(trifluoromethyl)pyridine hydrochloride (Intermediate 3) and 1-fluoro-2-nitrobenzene to give (S)-2-(1-(2-nitrophenyl) pyrrolidin-3-yloxy)-5-(trifluoromethyl)pyridine (2.8 g, 80% yield), Mass spec: 354 (M+H).

Step 2: (S)-2-(3-(5-(trifluoromethyl)pyridin-2-yloxy)pyrrolidin-1-yl)aniline

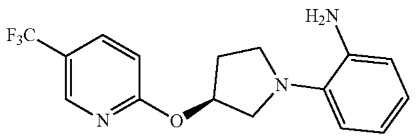 [SMILES: O=[N+]([O-])c1ccccc1N1CC[C@H](Oc2ccc(C(F)(F)F)cn2)C1]

To a solution of (S)-2-(1-(2-nitrophenyl)pyrrolidin-3-yloxy)-5-(trifluoromethyl)pyridine (2.8 g, 8 mmol) in MeOH/H2O (50 mL/50 mL) was added Fe powder and NH4Cl, stirred at 80° C. for 2 h, the mixture was filtered, the filtrate was concentrated and purified by silica gel to give (S)-2-(3-(5-(trifluoromethyl) pyridin-2-yloxy) pyrrolidin-1-yl)aniline (1.2 g, 46 yield) as brown oil, Mass spec: 324 (M+H).

Step 3: (S)-2-(3-(5-(trifluoromethyl)pyridin-2-yloxy)pyrrolidin-1-yl)phenol

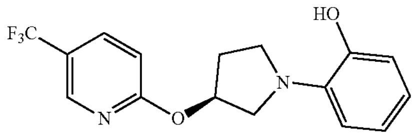

To a solution of (S)-2-(3-(5-(trifluoromethyl)pyridin-2-yloxy)pyrrolidin-1-yl)aniline (1.2 g, 3.7 mmol) in H2O/H2SO4con. (4 mL/4 mL) at 0° C. was added NaNO2 (384 mg, 5.5 mmol) in H2O (2 mL), and stirred at 80° C. for 2 h, the mixture was cooled down to rt, poured into ice-water, adjust the pH with NaHCO3 solution to 7, extracted with EA, dried over Na2SO4, removal the solvent to left the crude product which was purified by silica gel to give (S)-2-(3-(5-(trifluoromethyl)pyridin-2-yloxy)pyrrolidin-1-yl)phenol (290 mg, 20% yield) as clarity oil. Mass spec: 325 (M+H), $t_R$=2.298 min, $^1$H-NMR (400 Hz, DMSO) δ=9.073 (s, 1H), 8.615 (s, 1H), 8.055-8.083 (dd, 1H), 7.012-7.034 (d, 1H), 6.613-6.735 (m, 4H), 5.588-5.617 (m, 1H), 3.731-3.774 (m, 1H), 3.402-3.501 (m, 2H), 3.158-3.212 (m, 1H), 2.309-2.359 (m, 1H), 2.055-2.089 (m, 1H)

Example 15a: (S)-2-(1-(2-isopropoxyphenyl)pyrrolidin-3-yloxy)-5-(trifluoromethyl)pyridine (Compound 1-15)

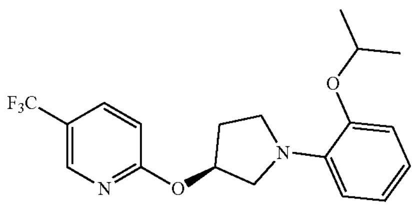 [SMILES: CC(C)Oc1ccccc1N1CC[C@H](Oc2ccc(C(F)(F)F)cn2)C1]

To a solution of (S)-2-(3-(5-(trifluoromethyl)pyridin-2-yloxy)pyrrolidin-1-yl)phenol (64 mg, 0.2 mmol) (example 14) in dry DMF (2 mL) at 0° C. was added NaH (44 mg, 0.22 mmol, 60% dispersion in mineral oil), and stirred for 30 min at rt before 2-iodopropane (81 mg, 0.48 mmol) was added, the mixture was stirred for 24 h, the mixture was diluted with EA, washed with LiCl solution, brine, dried over Na2SO4, removal the solvent to left the crude product which was purified by silica gel to give the (S)-2-(1-(2-isopropoxyphenyl) yrrolidin-3-yloxy)-5-(trifluoromethyl)pyridine (30 mg, 95% yield) as clarity oil. Mass spec: 367 (M+H), $t_R$=3.402 min, $^1$H-NMR (400 Hz, DMSO) δ=8.616 (s, 1H), 8.055-8.083 (dd, 1H), 7.011-7.034 (d, 1H), 6.698-6.890 (m, 4H), 6.599-6.527 (m, 1H), 4.500-4.545 (m, 1H), 3.682-3.724 (m, 1H), 3.455-3.509 (m, 2H), 3.192-3.247 (m, 1H), 2.307-2.356 (m, 1H), 2.083-2.118 (m, 1H), 1.191-1.236 (m, 6H).

Example 15b: (S)-2-(1-(2-(benzyloxy)phenyl)pyrrolidin-3-yloxy)-5-(trifluoromethyl)pyridine (Compound 1-26)

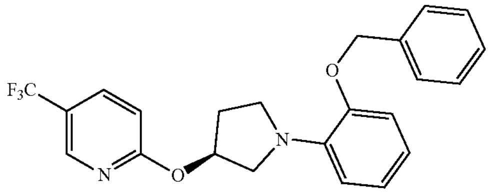 [SMILES: FC(F)(F)c1ccc(O[C@H]2CCN(c3ccccc3OCc3ccccc3)C2)nc1]

The title compound was prepared following procedures described in example 15a using (S)-2-(3-(5-(trifluoromethyl)pyridin-2-yloxy)pyrrolidin-1-yl)phenol to give (S)-2-(1-(2-(benzyloxy)phenyl)pyrrolidin-3-yloxy)-5-(trifluoromethyl)pyridine (25 mg, 30% yield), Mass spec: 415 (M+H), $t_R$=3.623 min, $^1$H-NMR (400 Hz, DMSO) δ=8.583 (s, 1H), 8.048-8.076 (dd, 1H), 7.387-7.425 (m, 2H), 7.283-7.344 (m, 3H), 6.982-7.017 (m, 2H), 6.738-6.875 (m, 3H), 5.600 (br, 1H), 5.050 (s, 2H), 3.673-3.716 (m, 1H), 3.466-3.529 (m, 2H), 3.213-3.255 (m, 1H), 2.307-2.341 (m, 1H), 2.103 (m, 1H).

Example 15c: (S)-2-(1-(2-(cyclopentyloxy)phenyl)pyrrolidin-3-yloxy)-5-(trifluoromethyl)pyridine (Compound 1-25)

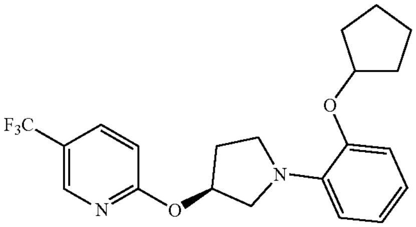 [SMILES: FC(F)(F)c1ccc(O[C@H]2CCN(c3ccccc3OC3CCCC3)C2)nc1]

The title compound was prepared following procedures described in example 15a using (S)-2-(3-(5-(trifluoromethyl)pyridin-2-yloxy)pyrrolidin-1-yl)phenol to give (S)-2-(1-(2-(cyclopentyloxy)phenyl)pyrrolidin-3-yloxy)-5-(trifluoromethyl)pyridine (41.5 mg, 52.6% yield), Mass spec: 393 (M+H), $t_R$=3.691 min, $^1$H-NMR (400 Hz, DMSO) δ=8.607 (s, 1H), 8.061-8.090 (dd, 1H), 7.013-7.034 (d, 1H), 6.688-6.851 (m, 4H), 5.608 (br, 1H), 4.750-4.778 (m, 1H), 3.535-3.627 (m, 2H), 3.400-3.430 (m, 1H), 3.159-3.214 (m, 1H), 2.314-2.363 (m, 1H), 2.092-2.123 (m, 1H), 2.168-2.184 (m, 2H), 1.497-1.631 (m, 6H).

Example 16: (R)-2-(3-(5-(trifluoromethyl)pyridin-2-yloxy)pyrrolidin-1-yl)benzamide (Compound 1-17)

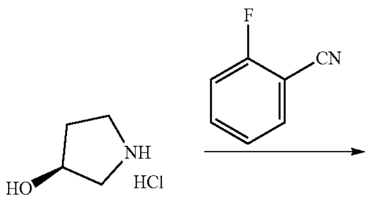

-continued

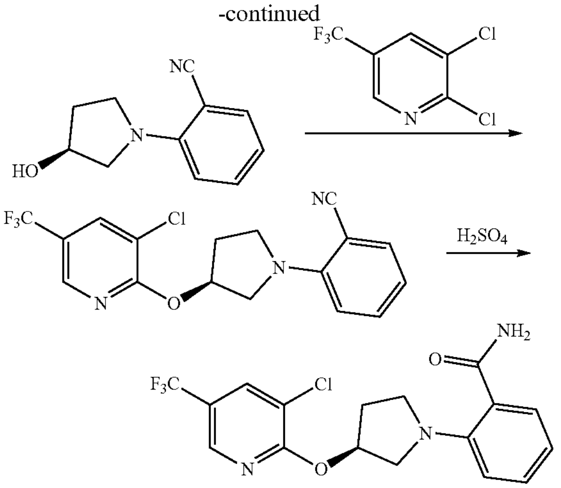

Step 1: (R)-2-(3-hydroxypyrrolidin-1-yl)benzonitrile

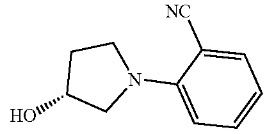 [SMILES: N#Cc1ccccc1N1CC[C@@H](O)C1]

To a solution of (S)-pyrrolidin-3-ol hydrochloride (1 g, 8.1 mmol) and 2-fluorobenzonitrile (1.27 g, 10.5 mmol) in DMF (20 mL) was added K2CO3 (3.35 g, 24.3 mmol), it was stirred at 100° C. overnight. Quenched with water, extracted with EA, washed with LiCl solution, brine, dried over Na2SO4, removal the solvent to left crude (R)-2-(3-hydroxypyrrolidin-1-yl)benzonitrile (1.7 g, 111% yield) which was used the next step directly without further purification. Mass spec: 189 (M+H)

Step 2: (R)-2-(3-(3-chloro-5-(trifluoromethyl)pyridin-2-yloxy)pyrrolidin-1-yl)benzonitrile

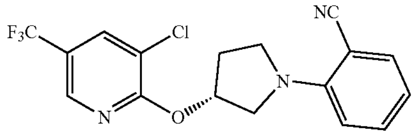 [SMILES: N#Cc1ccccc1N1CC[C@@H](Oc2ncc(C(F)(F)F)cc2Cl)C1]

To a solution of (R)-2-(3-hydroxypyrrolidin-1-yl)benzonitrile (244 mg, 1.3 mmol) in dry DMF (2 mL) at 0° C. was add NaH (120 mg, 4 mmol, 60% dispersion in mineral oil), and stirred for 30 min at this temperature before 2,3-dichloro-5-(trifluoromethyl)pyridine (216 mg, 1 mmol) in 1 mL DMF was added, the mixture was stirred for 1 h at same temperature, the reaction mixture was poured into ice-water, extracted with EA, and organic layer was washed by LiCl solution, brine, dried over Na2SO4, removal the solvent to left brown oil which was purified by silica gel to give (R)-2-(3-(3-chloro-5-(trifluoromethyl)pyridin-2-yloxy)pyrrolidin-1-yl)benzonitrile (220 mg, 59.9% yield) as light yellow oil, Mass spec: 368 (M+H)

Step 3: (R)-2-(3-(3-chloro-5-(trifluoromethyl)pyridin-2-yloxy)pyrrolidin-1-yl)benzamide

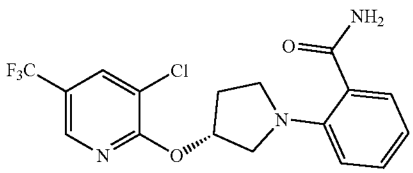 [SMILES: NC(=O)c1ccccc1N1CC[C@@H](Oc2ncc(C(F)(F)F)cc2Cl)C1]

(R)-2-(3-(3-chloro-5-(trifluoromethyl)pyridin-2-yloxy) pyrrolidin-1-yl)benzonitrile (100 mg, 0.27 mmol) was added to H2SO4$_{(con.)}$ at 0° C., the mixture was stirred overnight at rt. the reaction mixture was poured in ice-water, and adjust the ph with NaHCO3 solution to 7, extracted with EA, washed with brine, dried over Na2SO4, removal the solvent to left the crude product which was purified by silica gel to give (R)-2-(3-(3-chloro-5-(trifluoromethyl)pyridin-2-yloxy) pyrrolidin-1-yl)benzamide (45 mg, 45% yield). Mass spec: 386 (M+H), $t_R$=2.665 min, $^1$H-NMR (400 Hz, DMSO) δ=8.606 (s, 1H), 8.407-8.412 (d, 1H), 7.817 (br, 2H), 7.249-7.324 (m, 3H), 6.740-6.835 (m, 2H), 5.735 (br, 1H), 3.859-3.90 (m, 1H), 3.308-3.401 (m, 3H), 2.346 (m, 1H), 2.236-2.344 (m, 1H)

Example 17: (S)-2-(3-(5-(trifluoromethyl)pyridin-2-yloxy)pyrrolidin-1-yl)benzamide (Compound 1-16)

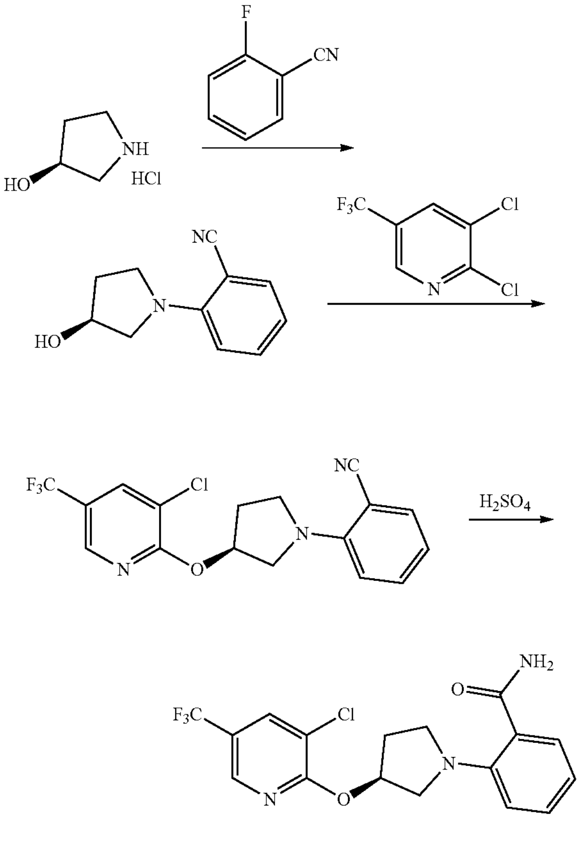

Step 1: (S)-2-(3-hydroxypyrrolidin-1-yl)benzonitrile

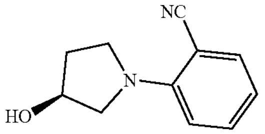 [SMILES: N#Cc1ccccc1N1CC[C@H](O)C1]

The title compound was prepared following procedures described in example 16 (step 1) using (S)-pyrrolidin-3-ol hydrochloride to give (S)-2-(3-hydroxypyrrolidin-1-yl)benzonitrile (750 mg, 82% yield), Mass spec: 189 (M+H).

Step 2: (S)-2-(3-(3-chloro-5-(trifluoromethyl)pyridin-2-yloxy)pyrrolidin-1-yl)benzonitrile

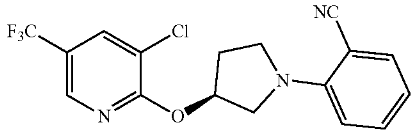 [SMILES: N#Cc1ccccc1N1CC[C@H](Oc2ncc(C(F)(F)F)cc2Cl)C1]

The title compound was prepared following procedures described in example 16 (step 2) using (S)-2-(3-hydroxypyrrolidin-1-yl)benzonitrile to give (S)-2-(3-(3-chloro-5-(trifluoromethyl)pyridin-2-yloxy)pyrrolidin-1-yl)benzonitrile (160 mg, 53% yield), Mass spec: 368 (M+H).

Step 3: (S)-2-(3-(3-chloro-5-(trifluoromethyl)pyridin-2-yloxy)pyrrolidin-1-yl)benzamide

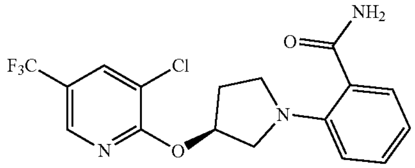 [SMILES: NC(=O)c1ccccc1N1CC[C@H](Oc2ncc(C(F)(F)F)cc2Cl)C1]

The title compound was prepared following procedures described in example 16 (step 3) using (S)-2-(3-(3-chloro-5-(trifluoromethyl)pyridin-2-yloxy)pyrrolidin-1-yl)benzonitrile at 90° C. for 1.5 h to give (S)-2-(3-(3-chloro-5-(trifluoromethyl)pyridin-2-yloxy)pyrrolidin-1-yl)benzamide (110 mg, 66.7% yield), Mass spec: 386 (M+H), $t_R$=2.736 min, $^1$H-NMR (400 Hz, DMSO) δ=8.602 (s, 1H), 8.401 (s, 1H), 7.772 (s, 1H), 7.241-7.272 (m, 3H), 6.698-6.902 (m, 2H), 5.732 (s, 1H), 3.848-3.889 (m, 1H), 3.508-3.526 (m, 1H), 3.289-3.351 (m, 2H), 2.511 (m, 1H), 2.236-2.335 (m, 1H).

Example 18: (S)-2-(3-(6-chloroquinolin-2-yloxy) pyrrolidin-1-yl)benzamide (Compound 1-19)

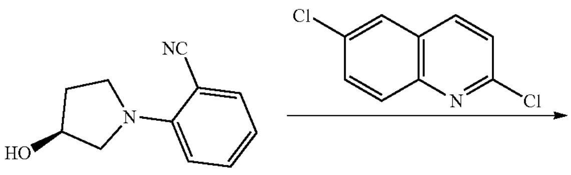

-continued

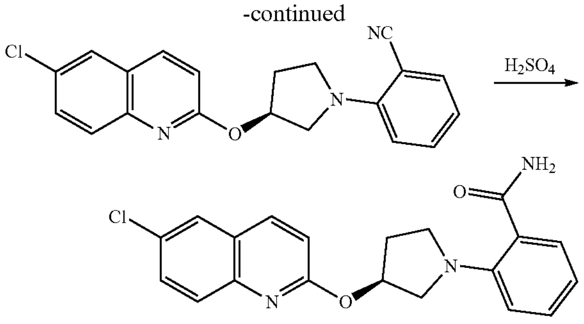

Step 1: (S)-2-(3-(6-chloroquinolin-2-yloxy)pyrrolidin-1-yl)benzonitrile

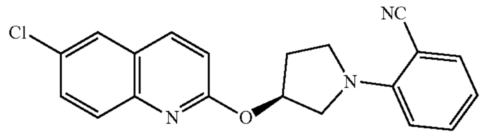 [SMILES: N#Cc1ccccc1N1CC[C@H](Oc2ccc3cc(Cl)ccc3n2)C1]

The title compound was prepared following procedures described in example 16 (step 2) using (S)-2-(3-hydroxy-pyrrolidin-1-yl)benzonitrile and 2,6-dichloroquinoline to give (S)-2-(3-(6-chloroquinolin-2-yloxy)pyrrolidin-1-yl) benzonitrile (210 mg, 60% yield), Mass spec: 350 (M+H).

Step 2: (S)-2-(3-(6-chloroquinolin-2-yloxy)pyrrolidin-1-yl)benzamide

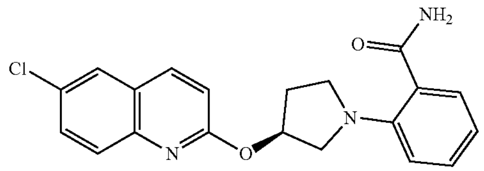 [SMILES: NC(=O)c1ccccc1N1CC[C@H](Oc2ccc3cc(Cl)ccc3n2)C1]

The title compound was prepared following procedures described in example 16 (step 3) using (S)-2-(3-(6-chloro-quinolin-2-yloxy)pyrrolidin-1-yl)benzonitrile at 90° C. for 1.5 h to give (S)-2-(3-(6-chloroquinolin-2-yloxy)pyrrolidin-1-yl)benzamide (60 mg, 51.9% yield), Mass spec: 368 (M+H), $t_R$=2.774 min, $^1$H-NMR (400 Hz, DMSO) δ=8.217-8.239 (d, 1H), 8.022 (s, 1H), 7.670-7.805 (m, 3H), 7.219-7.281 (m, 3H), 7.048-7.071 (d, 2H), 5.796 (br, 1H), 3.851-3.893 (m, 1H), 3.515-3.533 (m, 1H), 3.318-3.359 (m, 2H), 2.336-2.370 (m, 1H), 2.237-2.246 (m, 1H).

Example 19: (R)-2-(3-(6-chloroquinolin-2-yloxy) pyrrolidin-1-yl)benzamide (Compound 1-18)

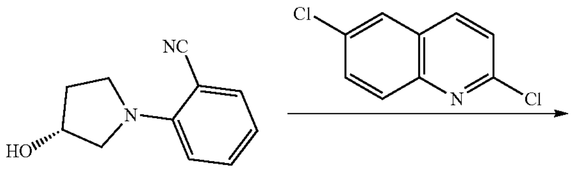

-continued

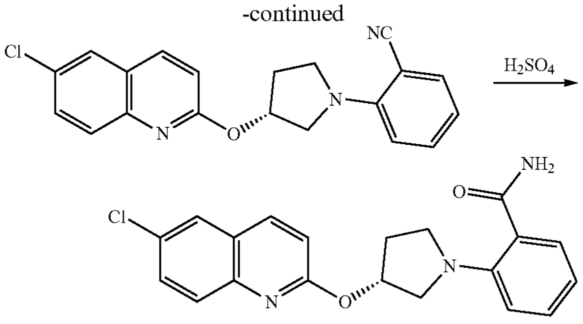

Step 1: (R)-2-(3-(6-chloroquinolin-2-yloxy)pyrrolidin-1-yl)benzonitrile

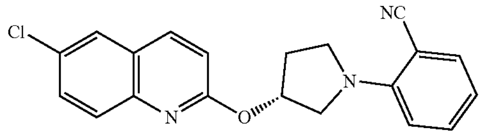 [SMILES: N#Cc1ccccc1N1CC[C@@H](Oc2ccc3cc(Cl)ccc3n2)C1]

The title compound was prepared following procedures described in example 16 (step 2) using (R)-2-(3-hydroxy-pyrrolidin-1-yl)benzonitrile and 2,6-dichloroquinoline to give (R)-2-(3-(6-chloroquinolin-2-yloxy)pyrrolidin-1-yl) benzonitrile (250 mg, 71% yield), Mass spec: 350 (M+H).

Step 2: (R)-2-(3-(6-chloroquinolin-2-yloxy)pyrrolidin-1-yl)benzamide

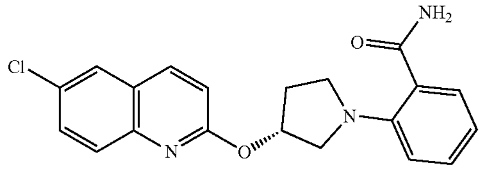 [SMILES: NC(=O)c1ccccc1N1CC[C@@H](Oc2ccc3cc(Cl)ccc3n2)C1]

The title compound was prepared following procedures described in example 16 (step 3) using (R)-2-(3-(6-chloro-quinolin-2-yloxy)pyrrolidin-1-yl)benzonitrile at 90° C. for 1.5 h to give (R)-2-(3-(6-chloroquinolin-2-yloxy)pyrrolidin-1-yl)benzamide (55 mg, 48% yield), Mass spec: 368 (M+H), $t_R$=2.813 min, $^1$H-NMR (400 Hz, DMSO) δ=8.230 (s, 1H), 8.034 (s, 1H), 7.784-7.837 (m, 2H), 7.697 (m, 1H), 7.270-7.360 (m, 3H), 7.061-7.080 (d, 2H), 6.748-6.860 (m, 2H), 5.804 (br, 1H), 3.886-3.899 (m, 1H), 3.390 (m, 3H), 2.380 (m, 1H), 2.252 (m, 1H).

Example 20: (R)-(2-(3-(5-(trifluoromethyl)pyridin-2-yloxy)pyrrolidin-1-yl)phenyl)methanamine (Compound 1-20)

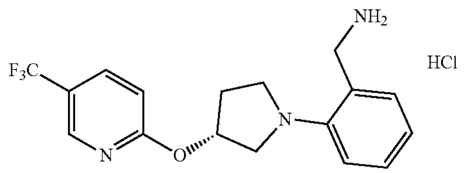 [SMILES: NCc1ccccc1N1CC[C@@H](Oc2ccc(C(F)(F)F)cn2)C1 ; Cl]

To a solution of (R)-2-(3-(5-(trifluoromethyl)pyridin-2-yloxy)pyrrolidin-1-yl)benzamide (example 10) (33 mg, 0.1 mmol) in EtOH (2 mL) was added Rany-Nikel (100 mg wet), the mixture was stirred at 60° C. for 1 h under H2 atmosphere, filtered, removal the solvent, the residue was purified by silica gel to give the product, which was stirred in HCl/EA to obtain (R)-(2-(3-(5-(trifluoromethyl)pyridin-2-yloxy) pyrrolidin-1-yl)phenyl)methanamine HCl salt (20 mg, 53.6%). Mass spec: 338 (M+H), $t_R$=1.758 min, $^1$H-NMR (400 Hz, DMSO) δ=8.61 (s, 1H), 8.406 (br, 3H), 8.084-8.150 (m, 1H), 7.452-7.471 (d, 1H), 7.307-7.345 (t, 1H), 7.181-7.201 (d, 1H), 7.057-70.94 (m, 2H), 5.648-5.676 (m, 1H), 4.064-4.125 (m, 1H), 3.602-3.642 (m, 2H), 3.343-3.401 (m, 1H), 3.343-3.401 (m, 1H), 3.144-3.237 (m, 2H), 2.421-2.472 (m, 1H), 2.091-2.141 (m, 1H).

Example 21: (R)-(2-(3-(5-(trifluoromethyl)pyridin-2-yloxy)pyrrolidin-1-yl)phenyl)methanamine (Compound 1-23)

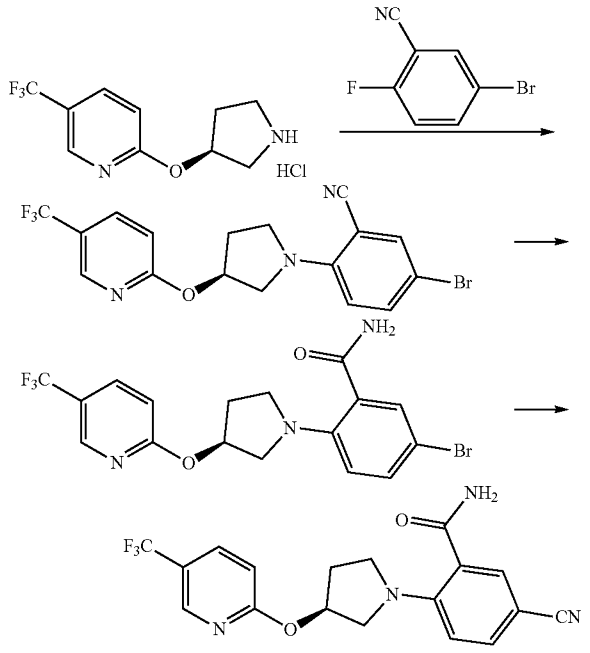

Step 1: (S)-5-bromo-2-(3-(5-(trifluoromethyl)pyridin-2-yloxy)pyrrolidin-1-yl)benzonitrile

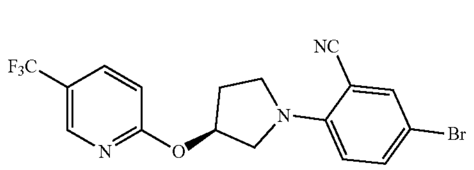 [SMILES: N#Cc1cc(Br)ccc1N1CC[C@H](Oc2ccc(C(F)(F)F)cn2)C1]

The title compound was prepared following procedures described in example 5 using (S)-2-(pyrrolidin-3-yloxy)-5-(trifluoromethyl)pyridine hydrochloride (Intermediate 3) and 5-bromo-2-fluorobenzonitrile to give (S)-5-bromo-2-(3-(5-(trifluoromethyl)pyridin-2-yloxy)pyrrolidin-1-yl)benzonitrile (3.3 g, 81% yield), Mass spec: 412 (M+H)

Step 2: (S)-5-bromo-2-(3-(5-(trifluoromethyl)pyridin-2-yloxy)pyrrolidin-1-yl)benzamide

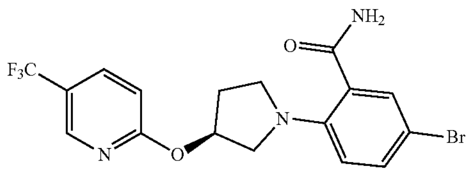 [SMILES: NC(=O)c1cc(Br)ccc1N1CC[C@H](Oc2ccc(C(F)(F)F)cn2)C1]

The title compound was prepared following procedures described in example 16 (step 3) using (S)-5-bromo-2-(3-(5-(trifluoromethyl)pyridin-2-yloxy)pyrrolidin-1-yl)benzonitrile at 90° C. for 1 h to give (S)-5-bromo-2-(3-(5-(trifluoromethyl)pyridin-2-yloxy)pyrrolidin-1-yl)benzamide (1.8 g, 82% yield), Mass spec: 430 (M+H).

Step 3: (S)-5-cyano-2-(3-(5-(trifluoromethyl)pyridin-2-yloxy)pyrrolidin-1-yl)benzamide

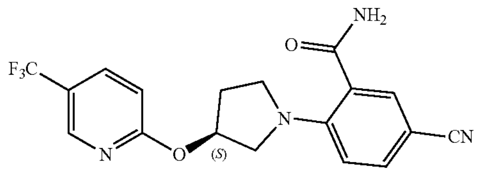

To a solution of (S)-5-bromo-2-(3-(5-(trifluoromethyl) pyridin-2-yloxy)pyrrolidin-1-yl)benzamide (42.9 mg, 0.1 mmol), Pd2(dba)3 (2.25 mg, 0.1 mmol) and dppf (5.78 mg, 0.1 mmol) in DMF (3 ml) was added Zn(Cn)2 (11.2 mg, 1 mmol), the mixture was stirred at 80° C. for 10 min with microwave, filtered, the filtrate was diluted by water, extracted with EA, washed by LiCl solution, brine, dried over Na2SO4, removal the solvent to left the crude product which was purified by silica gel to give (S)-5-cyano-2-(3-(5-(trifluoromethyl)pyridin-2-yloxy)pyrrolidin-1-yl)benzamide (9 mg, 23% yield), Mass spec: 377 (M+H), $t_R$=2.386 min, $^1$H-NMR (400 Hz, DMSO) δ=8.623 (s, 1H), 8.064-8.093 (m, 1H), 7.950 (s, 1H), 7.486-7.605 (m, 3H), 7.007-7.029 (d, 1H), 6.807-6.829 (d, 1H), 5.707 (br, 1H), 3.876-3.918 (m, 1H), 3.587-3.612 (m, 1H), 3.477-3.497 (m, 1H), 3.314 (m, 1H), 2.252-2.308 (m, 2H).

Example 22: (S)-4-(3-(5-(trifluoromethyl)pyridin-2-yloxy)pyrrolidin-1-yl)biphenyl-3-carboxamide (Compound 1-32)

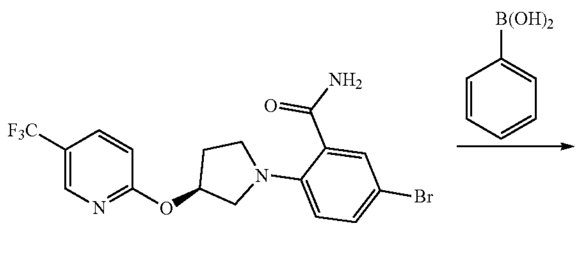

-continued

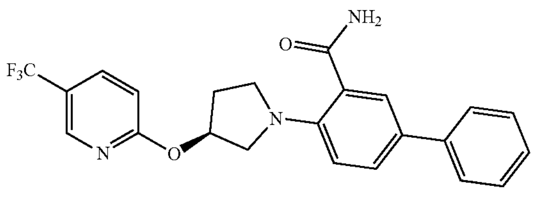

To a solution of (S)-5-bromo-2-(3-(5-(trifluoromethyl)pyridin-2-yloxy)pyrrolidin-1-yl)benzamide (42.9 mg, 0.1 mmol) (example 22 (step 2)) and phenylboronic acid (134 mg, 0.11 mmol) in MeCN/H2O (1 mL/1 mL) was added K2CO3 (27.6 mg, 0.2 mmol) and PdCl2 (dppf) (4 mg, 10% Wt), the mixture was stirred at 80° C. for 10 min with microwave, filtered, the filtrate was diluted by water, extracted with EA, washed by LiCl solution, brine, dried over Na2SO4, removal the solvent to left the crude product which was purified by silica gel to give (S)-4-(3-(5-(trifluoromethyl)pyridin-2-yloxy)pyrrolidin-1-yl)biphenyl-3-carboxamide (20 mg, 46% yield), Mass spec: 428 (M+H), $t_R$=2.911 min, $^1$H-NMR (400 Hz, DMSO) δ=8.631 (s, 1H), 8.059-8.087 (dd, 1H), 7.881 (s, 1H), 7.532-7.612 (m, 4H), 7.026-7.527 (m, 4H), 7.004-7.026 (d, 1H), 6.846-6.859 (d, 1H), 5.683 (m, 1H), 3.599-3.901 (m, 1H), 3.555-3.599 (m, 1H), 3.262-3.325 (m, 2H), 2.198-2.357 (m, 2H)

Example 23: (S)-2'-chloro-4-(3-(5-(trifluoromethyl)pyridin-2-yloxy)pyrrolidin-1-yl)biphenyl-3-carboxamide (Compound 1-64)

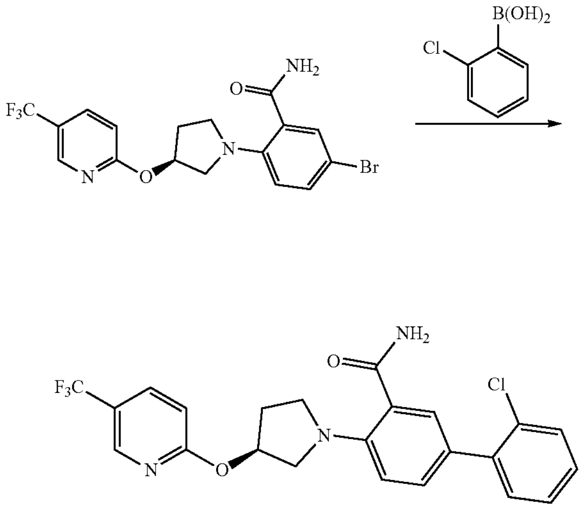

The title compound was prepared following procedures described in example 22 using Dioxane/H2O as solvent to give (S)-2'-chloro-4-(3-(5-(trifluoromethyl)pyridin-2-yloxy)pyrrolidin-1-yl)biphenyl-3-carboxamide (30 mg, 20% yield), Mass spec: 462 (M+H), $t_R$=3.147 min, $^1$H-NMR (400 Hz, DMSO) δ=8.633 (s, 1H), 8.064-8.092 (dd, 1H), 7.813 (s, 1H), 7.522-7.542 (d, 1H), 7.313-7.408 (m, 1H), 7.016-7.037 (d, 1H), 6.832-6.853 (d, 1H), 5.704 (m, 1H), 3.874-3.915 (m, 1H), 3.570-3.587 (m, 1H) 3.410-3.446 (m, 1H), 3.415-3.360 (m, 1H) 2.243-2.349 (m, 2H).

Example 24: (S)-4'-fluoro-4-(3-(5-(trifluoromethyl)pyridin-2-yloxy)pyrrolidin-1-yl)biphenyl-3-carboxamide (Compound 1-65)

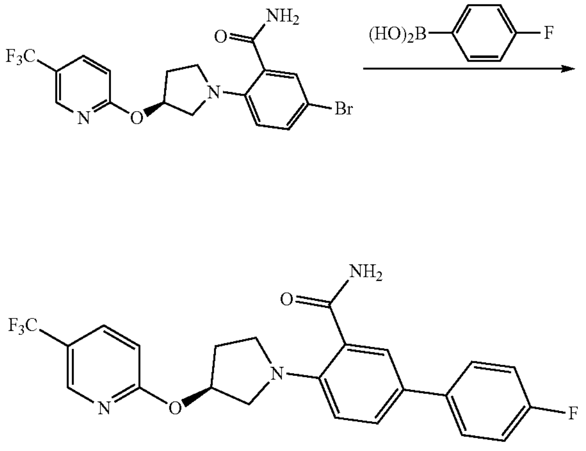 [SMILES: NC(=O)c1cc(Br)ccc1N1CC[C@H](Oc2ccc(C(F)(F)F)cn2)C1 ; OB(O)c1ccc(F)cc1 ; NC(=O)c1cc(-c2ccc(F)cc2)ccc1N1CC[C@H](Oc2ccc(C(F)(F)F)cn2)C1]

The title compound was prepared following procedures described in example 22 using Dioxane/H2O as solvent to give (S)-4'-fluoro-4-(3-(5-(trifluoromethyl)pyridin-2-yloxy)pyrrolidin-1-yl)biphenyl-3-carboxamide (23 mg, 20% yield), Mass spec: 446 (M+H), $t_R$=3.082 min, $^1$H-NMR (400 Hz, DMSO) δ=8.630 (s, 1H), 8.059-8.087 (m, 1H), 7.868 (s, 1H), 7.506-7.649 (m, 4H), 7.350 (s, 1H), 7.220-7.264 (m, 2H), 7.003-7.025 (d, 1H), 6.834-6.856 (d, 1H), 5.692 (br, 1H), 3.858-3.898 (m, 1H), 3.532-3.574 (m, 1H), 3.391-3.428 (m, 1H), 3.316-3.327 (m, 1H), 2.194-2.353 (m, 2H).

Example 25: (S)-5-(pyridin-3-yl)-2-(3-(5-(trifluoromethyl)pyridin-2-yloxy)pyrrolidin-1-yl)benzamide (Compound 1-80)

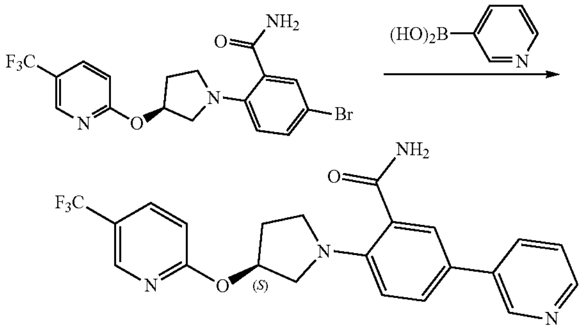

The title compound was prepared following procedures described in example 22 using DMF as solvent to give (S)-5-(pyridin-3-yl)-2-(3-(5-(trifluoromethyl)pyridin-2-yloxy)pyrrolidin-1-yl)benzamide (30 mg, 7% yield), Mass spec: 429 (M+H), $t_R$=1.876 min, $^1$H-NMR (400 Hz, DMSO) δ=8.847 (1 s, 1H, 8.632 (s, 1H), 8.462-8.476 (m, 1H), 7.885-8.087 (m, 3H), 7.578-7.650 (m, 2H), 7.374-7.433 (m, 2H), 7.008-7.027 (d, 1H), 6.865-6.887 (d, 1H), 5.698 (Br, 1H), 3.873-3.914 (m, 1H), 3.338-3.615 (m, 3H), 2.199-2.355 (m, 2H).

Example 26: (S)-5-(pyridin-4-yl)-2-(3-(5-(trifluoromethyl)pyridin-2-yloxy)pyrrolidin-1-yl)benzamide (Compound 1-83)

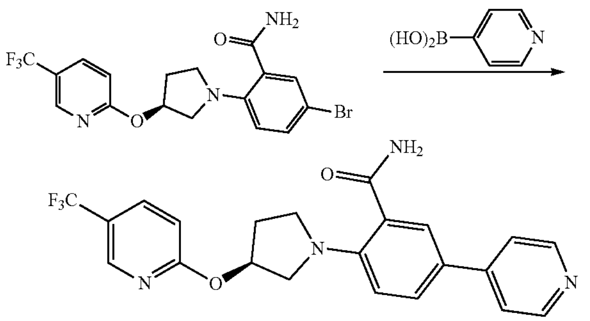

The title compound was prepared following procedures described in example 22 using DMF as solvent to give (S)-5-(pyridin-4-yl)-2-(3-(5-(trifluoromethyl)pyridin-2-yloxy)pyrrolidin-1-yl)benzamide (35 mg, 8.1% yield), Mass spec: 429 (M+H), $t_R$=1.712 min, $^{1}$H-NMR (400 Hz, DMSO) δ=8.631 (s, 1H), 8.530-8.545 (d, 1H), 8.057-8.086 (m, 1H), 7.905 (s, 1H), 7.638-7.745 (m, 4H), 7.398 (s, 1H), 7.002-7.024 (d, 1H), 6.857-6.879 (d, 1H), 5.704 (br, 1H), 3.884-3.926 (m, 1H), 3.567-3.615 (m, 2H), 3.415-3.417 (m, 1H), 2.245-3.343 (m, 2H).

Example 27: (S)-5-(pyridin-2-yl)-2-(3-(5-(trifluoromethyl)pyridin-2-yloxy)pyrrolidin-1-yl) (Compound 1-81)

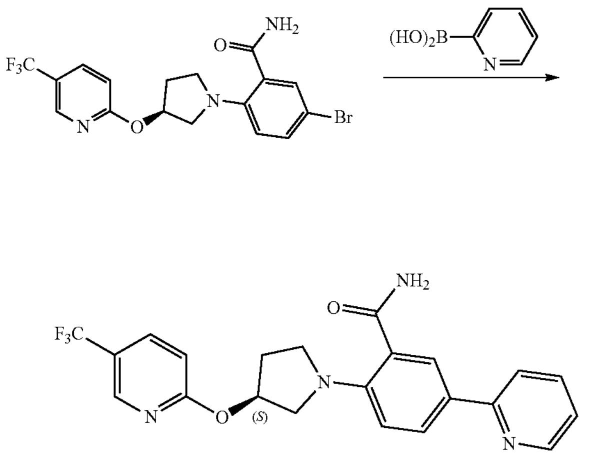

The title compound was prepared following procedures described in example 22 using DMF as solvent to give (S)-5-(pyridin-2-yl)-2-(3-(5-(trifluoromethyl)pyridin-2-yloxy)pyrrolidin-1-yl)benzamide (36 mg, 8.2% yield), Mass spec: 429 (M+H), $t_R$=1.720 min, $^{1}$H-NMR (400 Hz, DMSO) δ=8.595 (s, 1H), 8.538-8.549 (d, 1H), 8.028-8.048 (m, 1H), 7.932-7.974 (m, 2H), 7.741-7.850 (m, 3H), 7.314 (br, 1H), 7.174-7.202 (m, 1H), 6.976-6.997 (d, 1H), 6.798-6.821 (d, 1H), 5.677 (br, 1H), 3.855-3.895 (m, 1H), 3.539-3.604 (m, 2H), 3.274 (m, 1H), 2.186-2.292 (m, 2H).

Example 28: (S)-4-(3-(5-(trifluoromethyl)pyridin-2-yloxy)pyrrolidin-1-yl)biphenyl-3-carboxamide (Compound 1-35)

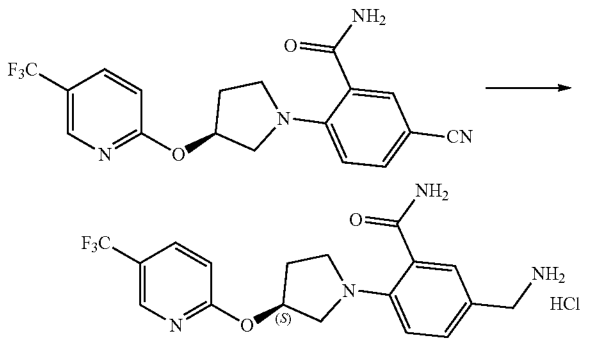

To a solution of (S)-5-cyano-2-(3-(5-(trifluoromethyl)pyridin-2-yloxy)pyrrolidin-1-yl)benzamide (37.6 mg, 0.1 mmol) (example 21) in MeOH/AcOH (2 ml/1 ml) was added Pd/C (10%), the mixture was stirred at rt for 12 h under H2 atmosphere, filtered, removal the solvent to left the crude product which was purified by silica gel, the product was stirred in HCl/EA for 30 min, filtered, the solid was washed by Et2O to give (S)-4-(3-(5-(trifluoromethyl)pyridin-2-yloxy)pyrrolidin-1-yl)biphenyl-3-carboxamide HCl salt (20 mg, 48% yield), Mass spec: 381 (M+H), $t_R$=1.604 min, $^{1}$H-NMR (400 Hz, CD3OD) δ=8.539 (s, 1H), 7.992-8.041 (m, 2H), 7.699-7.805 (dd, 2H), 7.058-7.079 (d, 1H), 5.921-5.936 (m, 1H), 4.149-4.208 (m, 3H), 3.964-4.031 (m, 1H), 3.755-3.862 (m, 2H), 2.535-2.734 (m, 1H), 2.489-2.518 (m, 1H).

Example 29: (S)-4-(3-(5-(trifluoromethyl)pyridin-2-yloxy)pyrrolidin-1-yl)biphenyl-3-carbonitrile (Compound 1-56)

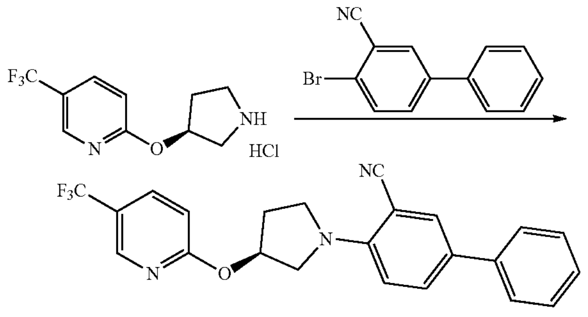

The title compound was prepared following procedures described in example 5 using Intermediate 3 and DBU as base to give (S)-4-(3-(5-(trifluoromethyl)pyridin-2-yloxy)pyrrolidin-1-yl)biphenyl-3-carbonitrile (20 mg, 50% yield), Mass spec: 410 (M+H), $t_R$=3.528 min, $^{1}$H-NMR (400 Hz, DMSO) δ=8.644 (s, 1H), 8.077-8.105 (dd, 1H), 7.770-7.832 (m, 2H), 7.406-7.445 (m, 2H), 7.228-7.325 (m, 3H), 6.917-7.071 (dd, 2H), 5.769 (br, 1H), 4.077-4.117 (m, 1H), 3.606-6.794 (m, 3H), 2.283-2.399 (m, 2H).

Example 30: (R)-5-fluoro-2-(3-(5-(trifluoromethyl)pyridin-2-yloxy)pyrrolidin-1-yl)benzamide (Compound 1-21)

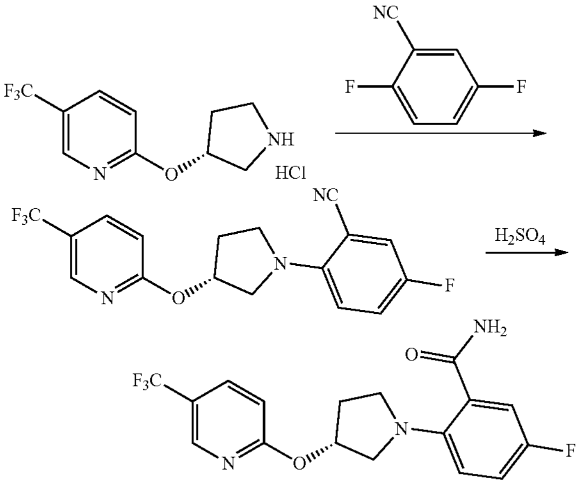

Step 1: (R)-5-fluoro-2-(3-(5-(trifluoromethyl)pyridin-2-yloxy)pyrrolidin-1-yl)benzonitrile

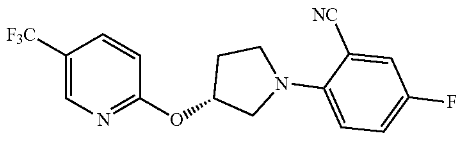 [SMILES: N#Cc1cc(F)ccc1N1CC[C@@H](Oc2ccc(C(F)(F)F)cn2)C1]

The title compound was prepared following procedures described in example 5 using Intermediate 4 and 2,5-difluorobenzonitrile to give (R)-5-fluoro-2-(3-(5-(trifluoromethyl)pyridin-2-yloxy)pyrrolidin-1-yl)benzonitrile (230 mg, 50.7% yield), Mass spec: 352 (M+H).

Step 2: (R)-5-fluoro-2-(3-(5-(trifluoromethyl)pyridin-2-yloxy)pyrrolidin-1-yl)benzamide

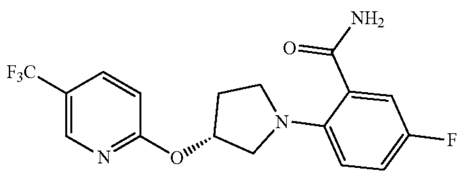 [SMILES: NC(=O)c1cc(F)ccc1N1CC[C@@H](Oc2ccc(C(F)(F)F)cn2)C1]

The title compound was prepared following procedures described in Example 17 (step 3) to give (R)-5-fluoro-2-(3-(5-(trifluoromethyl)pyridin-2-yloxy)pyrrolidin-1-yl)benzamide (30 mg, 11% yield), Mass spec: 370 (M+H). $t_R$=2.578 min, $^1$H-NMR (400 Hz, DMSO) δ=8.616 (s, 1H), 8.059-8.087 (dd, 1H), 7.943 (s, 1H), 7.442 (s, 1H), 7.001-7.152 (m, 3H), 6.803-6.837 (m, 1H), 5.653 (br, 1H), 3.741-3.782 (m, 1H), 3.432-3.494 (m, 1H), 3.228-3.312 (m, 2H), 2.30-2.335 (m, 1H), 2.175-2.192 (m, 1H).

Example 31: (S)-5-fluoro-2-(3-(5-(trifluoromethyl)pyridin-2-yloxy)pyrrolidin-1-yl)benzamide (Compound 1-31)

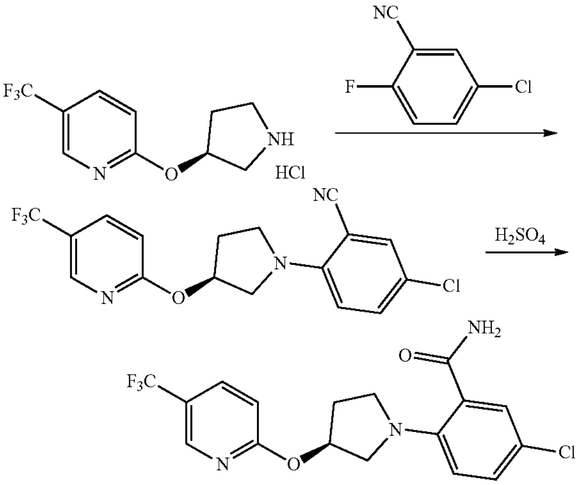

Step 1: (S)-5-chloro-2-(3-(5-(trifluoromethyl)pyridin-2-yloxy)pyrrolidin-1-yl)benzonitrile

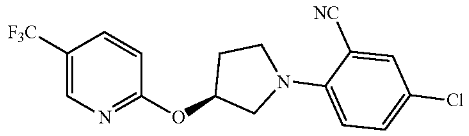 [SMILES: N#Cc1cc(Cl)ccc1N1CC[C@H](Oc2ccc(C(F)(F)F)cn2)C1]

The title compound was prepared following procedures described in example 5 using Intermediate 3 and 5-chloro-2-fluorobenzonitrile to give (S)-5-chloro-2-(3-(5-(trifluoromethyl)pyridin-2-yloxy)pyrrolidin-1-yl)benzonitrile (196 mg, 53% yield), Mass spec: 368 (M+H).

Step 2: (S)-5-chloro-2-(3-(5-(trifluoromethyl)pyridin-2-yloxy)pyrrolidin-1-yl)benzamide

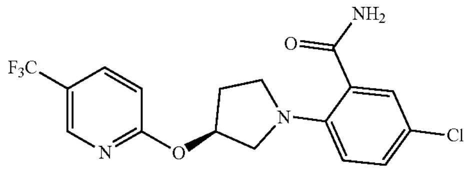 [SMILES: NC(=O)c1cc(Cl)ccc1N1CC[C@H](Oc2ccc(C(F)(F)F)cn2)C1]

The title compound was prepared following procedures described in Example 17 (step 3) to give (S)-5-chloro-2-(3-(5-(trifluoromethyl)pyridin-2-yloxy)pyrrolidin-1-yl)benzamide (80 mg, 38.4% yield), Mass spec: 386 (M+H). $t_R$=2.694 min, $^1$H-NMR (400 Hz, DMSO) δ=8.616 (s, 1H), 8.055-8.083 dd, 1H), 7.877 (s, 1H), 7.403 (s, 1H), 7.195-7.271 (m, 2H), 6.995-7.016 (d, 1H), 6.750-6.773 (d, 1H), 5.668 (br, 1H), 3.80-3.817 (m, 1H), 3.390-3.398 (m, 1H), 3.288-3.354 (m, 2H), 2.168-2.316 (m, 2H).

Example 32: (R)-5-fluoro-2-(3-(5-(trifluoromethyl)pyridin-2-yloxy)pyrrolidin-1-yl)benzamide (Compound 1-44)

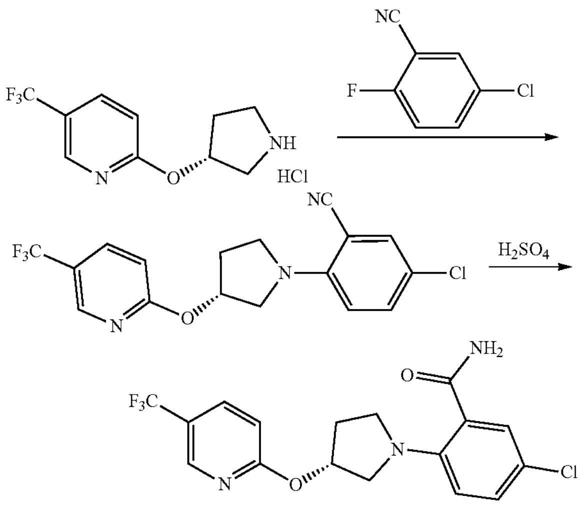

Step 1: (R)-5-chloro-2-(3-(5-(trifluoromethyl)pyridin-2-yloxy)pyrrolidin-1-yl)benzonitrile

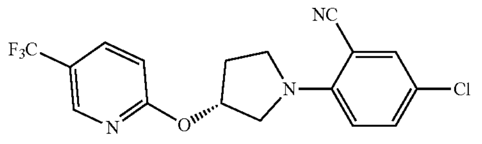 [SMILES: N#Cc1cc(Cl)ccc1N1CC[C@@H](Oc2ccc(C(F)(F)F)cn2)C1]

The title compound was prepared following procedures described in example 5 using Intermediate 3 and 5-chloro-2-fluorobenzonitrile to give (R)-5-chloro-2-(3-(5-(trifluoromethyl)pyridin-2-yloxy)pyrrolidin-1-yl)benzonitrile (200 mg, 54% yield), Mass spec: 368 (M+H).

Step 2: (R)-5-chloro-2-(3-(5-(trifluoromethyl)pyridin-2-yloxy)pyrrolidin-1-yl)benzamide

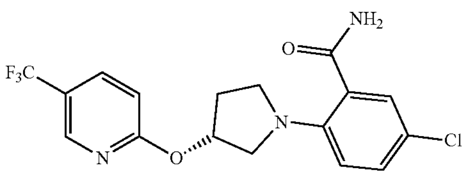

The title compound was prepared following procedures described in Example 17 (step 3) to give (R)-5-chloro-2-(3-(5-(trifluoromethyl)pyridin-2-yloxy)pyrrolidin-1-yl)benzamide (80 mg, 38.4% yield), Mass spec: 386 (M+H). $t_R$=2.666 min, $^1$H-NMR (400 Hz, DMSO) δ=8.616 (s, 1H), 8.056-8.084 (dd, 1H), 7.880 (s, 1H), 7.403 (s, 1H), 7.201-7.271 (m, 2H), 6.996-7.018 (d, 1H), 6.750-6.773 (d, 1H), 5.669 (br, 1H), 3.80-3.829 (m, 1H), 3.468-3.509 (m, 1H), 3.259-3.378 (m, 2H), 2.205-2.316 (m, 2H).

Example 33: (S)-3-fluoro-2-(3-(5-(trifluoromethyl)pyridin-2-yloxy)pyrrolidin-1-yl)benzamide (Compound 1-29)

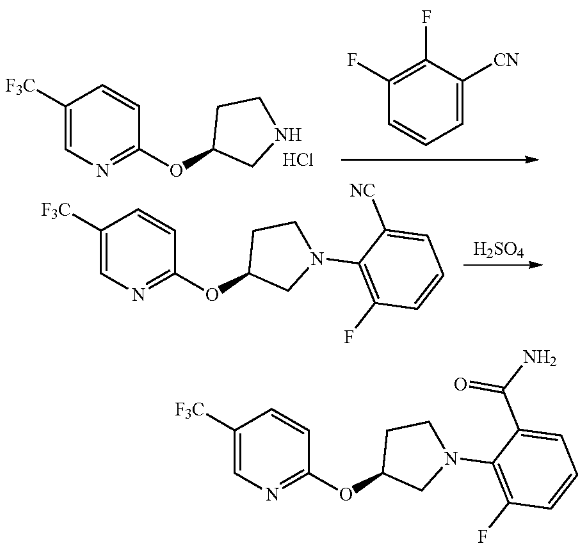

Step 1: (S)-3-fluoro-2-(3-(5-(trifluoromethyl)pyridin-2-yloxy)pyrrolidin-1-yl)benzonitrile

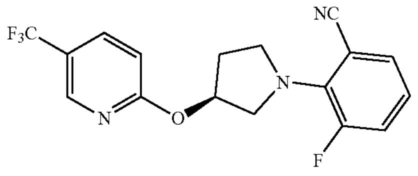 [SMILES: N#Cc1cccc(F)c1N1CC[C@H](Oc2ccc(C(F)(F)F)cn2)C1]

The title compound was prepared following procedures described in example 5 using Intermediate 3 and 2,3-difluorobenzonitrile to give (S)-3-fluoro-2-(3-(5-(trifluoromethyl)pyridin-2-yloxy)pyrrolidin-1-yl)benzonitrile (413 mg, 73% yield), Mass spec: 352 (M+H).

Step 2: (S)-3-fluoro-2-(3-(5-(trifluoromethyl)pyridin-2-yloxy)pyrrolidin-1-yl)benzamide

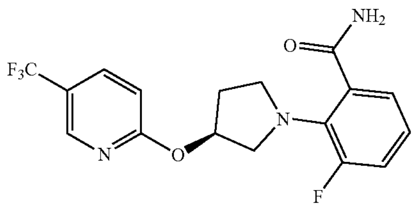 [SMILES: NC(=O)c1cccc(F)c1N1CC[C@H](Oc2ccc(C(F)(F)F)cn2)C1]

The title compound was prepared following procedures described in Example 17 (step 3) to give (S)-3-fluoro-2-(3-(5-(trifluoromethyl)pyridin-2-yloxy)pyrrolidin-1-yl)benzamide (189 m, 43% yield), Mass spec: 370 (M+H). $t_R$=2.757 min, $^1$H-NMR (400 Hz, CDCl3) δ=10.267 (s, 1H), 8.453 (s, 1H), 8.113-8.133 (dd, 1H), 7.812-7.839 (m, 1H), 7.225-

7.326 (m, 2H), 6.824-6.846 (d, 1H), 5.769 (br, 1H), 3.693-3.731 (m, 1H), 3.506-3.546 (m, 1H), 3.349-3.430 (m, 2H), 2.520-2.558 (m, 1H), 2.278-2.295 (m, 1H).

Example 34: (R)-3-fluoro-2-(3-(5-(trifluoromethyl) pyridin-2-yloxy)pyrrolidin-1-yl)benzamide (Compound 1-30)

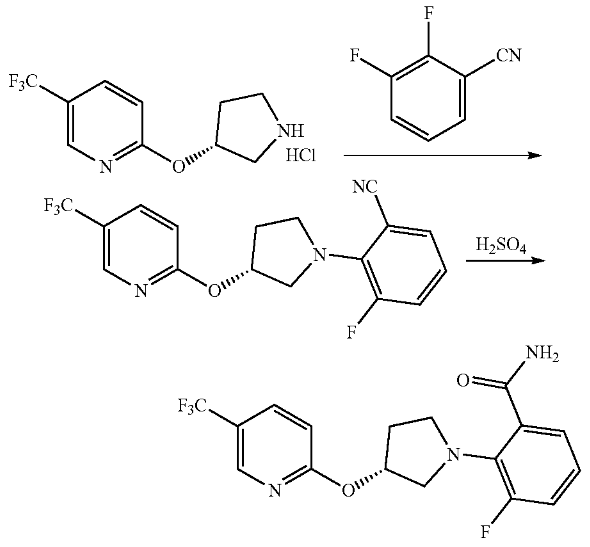

Step 1: (R)-3-fluoro-2-(3-(5-(trifluoromethyl)pyridin-2-yloxy)pyrrolidin-1-yl)benzonitrile

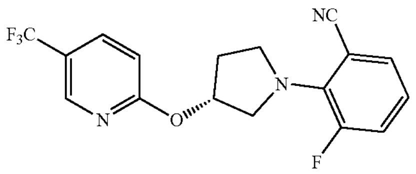 [SMILES: N#Cc1cccc(F)c1N1CC[C@@H](Oc2ccc(C(F)(F)F)cn2)C1]

The title compound was prepared following procedures described in example 5 using Intermediate 3 and 2,3-difluorobenzonitrile to give (R)-3-fluoro-2-(3-(5-(trifluoromethyl)pyridin-2-yloxy)pyrrolidin-1-yl)benzonitrile (327 mg, 77.6% yield), Mass spec: 352 (M+H).

Step 2: (R)-3-fluoro-2-(3-(5-(trifluoromethyl)pyridin-2-yloxy)pyrrolidin-1-yl)benzamide

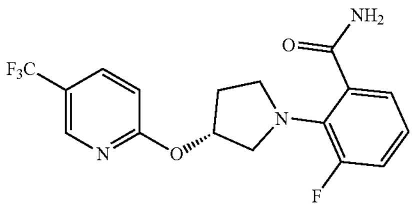 [SMILES: NC(=O)c1cccc(F)c1N1CC[C@@H](Oc2ccc(C(F)(F)F)cn2)C1]

The title compound was prepared following procedures described in Example 17 (step 3) to give (R)-3-fluoro-2-(3-(5-(trifluoromethyl)pyridin-2-yloxy)pyrrolidin-1-yl)benzamide (34 mg, 30.8% yield), Mass spec: 370 (M+H). $t_R$=2.742 min, $^1$H-NMR (400 Hz, CDCl3) δ=10.269 (br, 1H), 8.455 (s, 1H), 8.116-8.133 (d, 1H), 7.812-7.840 (d, 2 h), 7.246-7.327 (m, 2H), 6.823-6.845 (d, 1H), 5.776 (br, 1H), 3.689-3.731 (m, 1H), 3.508-3.547 (m, 1H), 3.350-3.429 (m, 2H), 2.520-2.558 (m, 1H), 2.279-2.296 (m, 1H).

Example 35: (R)-(2-(3-(5-(trifluoromethyl)pyridin-2-yloxy)pyrrolidin-1-yl)phenyl)methanamine (Compound 1-34)

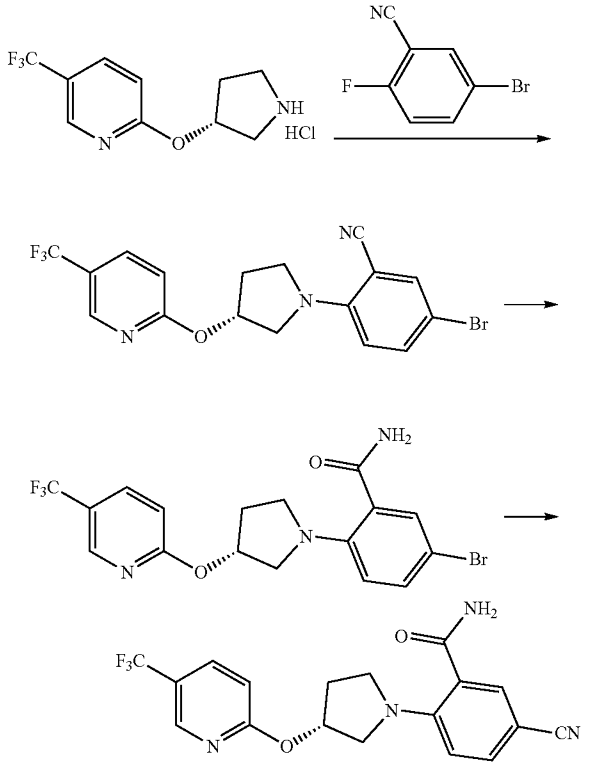

Step 1: (R)-5-bromo-2-(3-(5-(trifluoromethyl)pyridin-2-yloxy)pyrrolidin-1-yl)benzonitrile

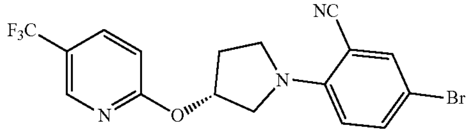 [SMILES: N#Cc1cc(Br)ccc1N1CC[C@@H](Oc2ccc(C(F)(F)F)cn2)C1]

The title compound was prepared following procedures described in example using (R)-2-(pyrrolidin-3-yloxy)-5-(trifluoromethyl)pyridine hydrochloride (Intermediate 4) and 5-bromo-2-fluorobenzonitrile to give (R)-5-bromo-2-(3-(5-(trifluoromethyl)pyridin-2-yloxy)pyrrolidin-1-yl)benzonitrile (900 mg, 51% yield), Mass spec: 412 (M+H)

Step 2: (R)-5-bromo-2-(3-(5-(trifluoromethyl)pyridin-2-yloxy)pyrrolidin-1-yl)benzamide

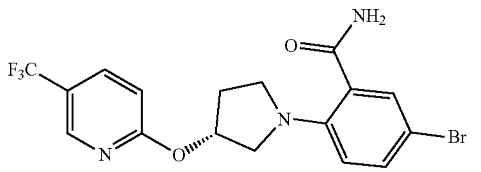 [SMILES: NC(=O)c1cc(Br)ccc1N1CC[C@@H](Oc2ccc(C(F)(F)F)cn2)C1]

The title compound was prepared following procedures described in example 16 (step 3) using (R)-5-bromo-2-(3-(5-(trifluoromethyl)pyridin-2-yloxy)pyrrolidin-1-yl)benzonitrile at 90° C. for 1 h to give (R)-5-bromo-2-(3-(5-(trifluoromethyl)pyridin-2-yloxy)pyrrolidin-1-yl)benzamide (780 mg, 83% yield), Mass spec: 430 (M+H).

Step 3: (R)-5-cyano-2-(3-(5-(trifluoromethyl)pyridin-2-yloxy)pyrrolidin-1-yl)benzamide

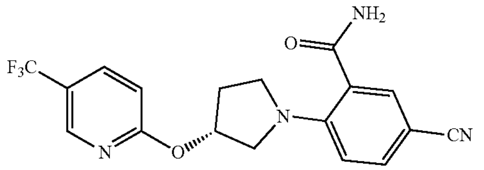 [SMILES: N#Cc1ccc(N2CC[C@@H](Oc3ccc(C(F)(F)F)cn3)C2)c(C(N)=O)c1]

The title compound was prepared following procedures described in example 16 (step 3) using (R)-5-bromo-2-(3-(5-(trifluoromethyl)pyridin-2-yloxy)pyrrolidin-1-yl)benzamide to give (R)-5-cyano-2-(3-(5-(trifluoromethyl)pyridin-2-yloxy)pyrrolidin-1-yl)benzamide (150 mg, 31% yield), Mass spec: 377 (M+H), $t_R$=2.350 min, $^1$H-NMR (400 Hz, DMSO) δ=8.620 (s, 1H), 8.059-8.087 (dd, 1H), 7.943 (s, 1H), 7.483-7.603 (m, 3H), 7.003-7.025 (d, 1H), 6.807-6.829 (d, 1H), 5.707 (br, 1H), 3.877-3.919 (m, 1H), 3.588-3.613 (m, 1H), 3.478-3.497 (m, 1H), 3.420-3.458 (m, 1H), 2.254-2.308 (m, 2H).

Example 36: (R)-4-(3-(5-(trifluoromethyl)pyridin-2-yloxy)pyrrolidin-1-yl)biphenyl-3-carboxamide (Compound 1-33)

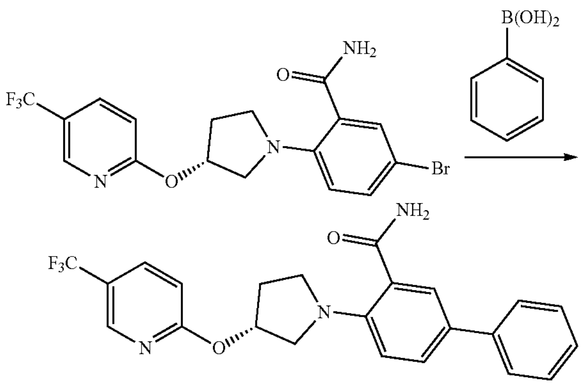

The title compound was prepared following procedures described in example 22 to give (R)-4-(3-(5-(trifluoromethyl)pyridin-2-yloxy)pyrrolidin-1-yl)biphenyl-3-carboxamide (11 mg, 25% yield), Mass spec: 428 (M+H), $t_R$=2.909 min, $^1$H-NMR (400 Hz, DMSO) δ=8.630 (s, 1H), 8.060-8.089 (dd, 1H), 7.891 (s, 1H), 7.532-7.612 (m, 4H), 7.251-7.437 (m, 4H), 7.005-7.027 (d, 1H), 6.844-6.865 (d, 1H), 5.693 (m, 1H), 3.860-3.901 (m, 1H), 3.555-3.560 (m, 1H), 3.297-3.356 (m, 2H), 2.227-2.342 (m, 2H)

Example 37: (R)-4-(3-(5-(trifluoromethyl)pyridin-2-yloxy)pyrrolidin-1-yl)biphenyl-3-carboxamide (Compound 1-45)

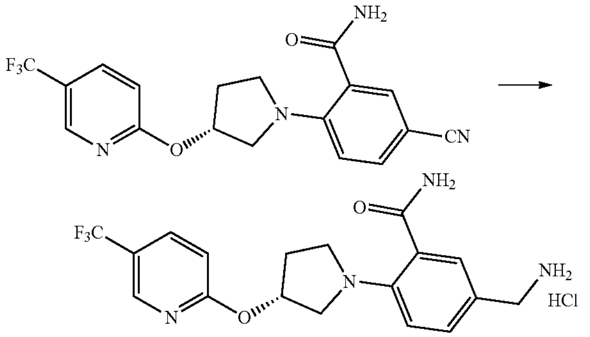

The title compound was prepared following procedures described in example 28 to give (R)-4-(3-(5-(trifluoromethyl)pyridin-2-yloxy)pyrrolidin-1-yl)biphenyl-3-carboxamide (25 mg, 44% yield), Mass spec: 381 (M+H), $t_R$=1.621 min, $^1$H-NMR (400 Hz, CD3OD) δ=8.524 (s, 1H), 8.150 (s, 1H), 8.009-8.037 (m, 1H), 7.872-7.932 (m, 2H), 7.081-7.103 (d, 1H), 5.954 (br, 1H), 4.198-4.240 (m, 3H), 3.968-4.081 (m, 2H), 3.853-3.893 (m, 1H), 2.789-2.824 (m, 1H), 2.528-2.548 (m, 1H).

Example 38: (S)-2-(3-(5-(trifluoromethyl)pyridin-2-yloxy)pyrrolidin-1-yl)benzoic acid (Compound 1-24)

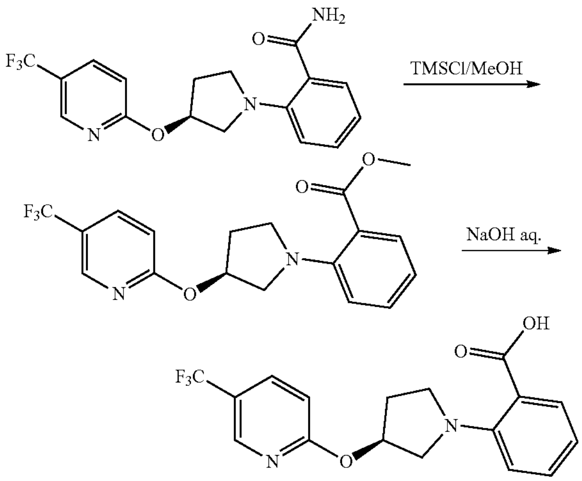

Step 1: (S)-methyl 2-(3-(5-(trifluoromethyl)pyridin-2-yloxy)pyrrolidin-1-yl)benzoate

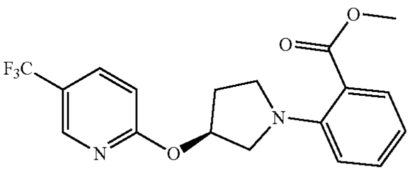 [SMILES: COC(=O)c1ccccc1N1CC[C@H](Oc2ccc(C(F)(F)F)cn2)C1]

To a solution of (S)-2-(3-(5-(trifluoromethyl)pyridin-2-yloxy)pyrrolidin-1-yl)benzamide (example 12) (1.5 g/4.2 mmol) in MeOH (10 mL) was added TMSCl (10 mL), the mixture was heated to reflux for overnight, then quenched with water, extracted by EA, dried over Na2SO4, removal the solvent to left the crude which was purified by silica gel to give (S)-methyl 2-(3-(5-(trifluoromethyl)pyridin-2-yloxy)pyrrolidin-1-yl)benzoate (350 mg, 22.7% yield), Mass spec: 367 (M+H).

Step 2: (S)-2-(3-(5-(trifluoromethyl)pyridin-2-yloxy)pyrrolidin-1-yl)benzoic acid

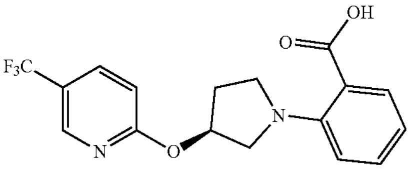 [SMILES: O=C(O)c1ccccc1N1CC[C@H](Oc2ccc(C(F)(F)F)cn2)C1]

To a solution of (S)-methyl 2-(3-(5-(trifluoromethyl)pyridin-2-yloxy)pyrrolidin-1-yl)benzoate (300 mg, 0.81 mmol) in THE was added NaOH solution (2 mL, 30%), the mixture was stirred at 60° C. for overnight, diluted with EA, adjust the pH with HCl (1N) to 3, the organic layer was washed by water, brine, dried over Na2SO4, removal the solvent to left the crude product which was purified by silica gel to give (S)-2-(3-(5-(trifluoromethyl)pyridin-2-yloxy)pyrrolidin-1-yl)benzoic acid (120 mg, 41.5% yield), Mass spec: 353 (M+H), $t_R$=2.240 min, $^1$H-NMR (400 Hz, DMSO) δ=8.606 (s, 1H), 8.053-8.047 (m, 1H), 7.265-7.245 (m, 1H), 7.016-7.250 (br, 1H), 6.994-7.016 (d, 1H), 6.798-6.994 (br, 1H), 6.673-6.694 (br, 1H), 5.664 (br, 1H), 3.685-3.872 (m, 1H), 3.590-3.676 (m, 1H), 3.117-3.237 (m, 2H), 2.290-2.329 (m, 1H), 2.167-2.274 (m, 1H).

Example 39: (S)—N-methyl-2-(3-(5-(trifluoromethyl)pyridin-2-yloxy)pyrrolidin-1-yl)benzamide (Compound 1-39)

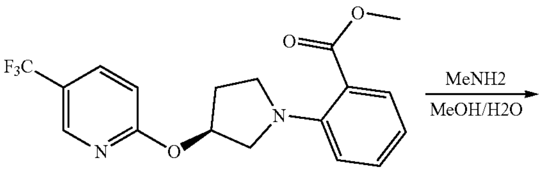

-continued

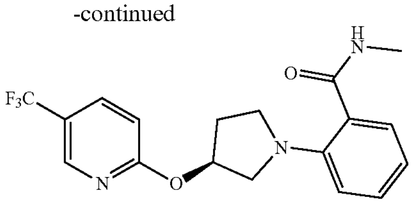

To a solution (S)-methyl 2-(3-(5-(trifluoromethyl)pyridin-2-yloxy)pyrrolidin-1-yl)benzoate (40 mg, 0.11 mmol) in MeOH/MeNH2 aq. (1 mL/1 mL) was heated to 90° C. in a sealed tube for overnight. H2O (6 mL) was added, filtered, washed by water, dried under vacuum to give (S)—N-methyl-2-(3-(5-(trifluoromethyl)pyridin-2-yloxy)pyrrolidin-1-yl)benzamide (20 mg, 49.8% yield), Mass spec: 366 (M+H), $t_R$=2.500 min, $^1$H-NMR (400 Hz, DMSO) δ=8.615 (s, 1H), 8.056-8.200 (m, 2H), 7.162-7.2545 (m, 2H), 6.994-7.016 (d, 1H), 6.676-6.764 (m, 2H), 5.653 (br, 1H), 3.714-3.755 (m, 1H), 3.427-3.492 (m, 1H), 3.251-3.325 (m, 2H), 2.704-2.751 (d, 3H), 2.249-2.317 (m, 1H), 2.151-2.199 (m, 1H).

Example 40: (S)—N,N-dimethyl-2-(3-(5-(trifluoromethyl)pyridin-2-yloxy)pyrrolidin-1-yl)benzamide (Compound 1-48)

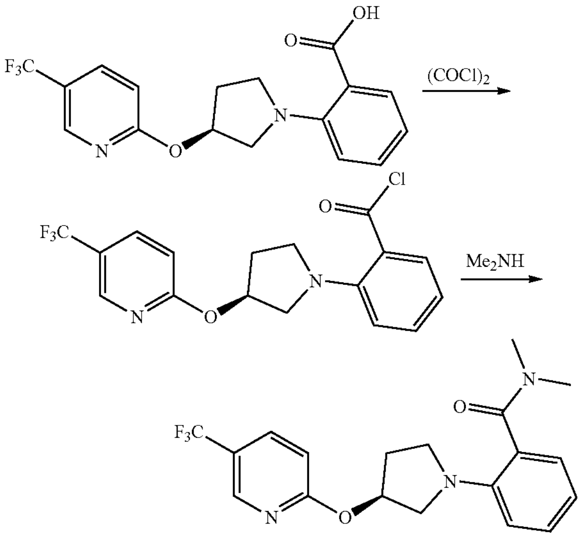

Step 1: (S)-2-(3-(5-(trifluoromethyl)pyridin-2-yloxy)pyrrolidin-1-yl)benzoyl chloride

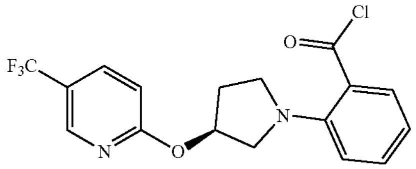 [SMILES: O=C(Cl)c1ccccc1N1CC[C@H](Oc2ccc(C(F)(F)F)cn2)C1]

To a solution of (S)-2-(3-(5-(trifluoromethyl)pyridin-2-yloxy)pyrrolidin-1-yl)benzoic acid (120 mg, 0.34 mmol) in DCM was added (COCl)2 (64.28 mL, 0.51 mmol) and one drop DMF, the mixture was stirred at rt for 30 min, removal the solvent to give (S)-2-(3-(5-(trifluoromethyl)pyridin-2-yloxy)pyrrolidin-1-yl)benzoyl chloride (130 mg, quant.) which can be used to next step directly.

Step 2: (S)—N,N-dimethyl-2-(3-(5-(trifluoromethyl) pyridin-2-yloxy)pyrrolidin-1-yl)benzamide

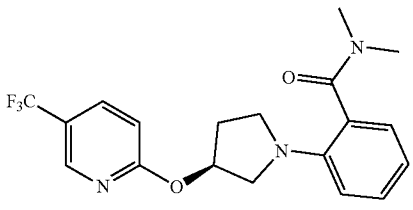 [SMILES: CN(C)C(=O)c1ccccc1N1CC[C@H](Oc2ccc(C(F)(F)F)cn2)C1]

To a solution of (S)-2-(3-(5-(trifluoromethyl)pyridin-2-yloxy)pyrrolidin-1-yl)benzoyl chloride (50 mg, 0.13 mmol) in DCM (3 mL) was added dimethylamine hydrochloride (21 mg, 0.26 mmol) and TEA (52 mg, 0.52 mmol), the mixture was stirred at rt, after finished, diluted with DCM (10 mL), washed by water, brine, dried over Na2SO4, removal the solvent to give the crude product which was purified by silica gel to give (S)—N,N-dimethyl-2-(3-(5-(trifluoromethyl)pyridin-2-yloxy)pyrrolidin-1-yl)benzamide (20 mg, 40.5% yield), Mass spec: 380 (M+H), $t_R$=2.087 min, $^1$H-NMR (400 Hz, CDCl3) δ=8.451 (s, 1H), 7.770-7.792 (d, 1H), 7.241-7.285 (m, 2H), 7.194-7.213 (d, 1H), 7.100-7.117 (d, 1H), 6.706-6.819 (m, 2H), 5.673-5.715 (m, 1H), 3.827-3.855 (m, 0.5H), 3.592-3.647 (m, 2.5H), 3.258-3.354 (m, 1H), 3.105-3.134 (d, 3H), 2.875-2.942 (d, 3H), 2.269-2.304 (m, 2H).

Example 41: (S)—N-benzyl-2-(3-(5-(trifluoromethyl)pyridin-2-yloxy)pyrrolidin-1-yl)benzamide (Compound 1-51)

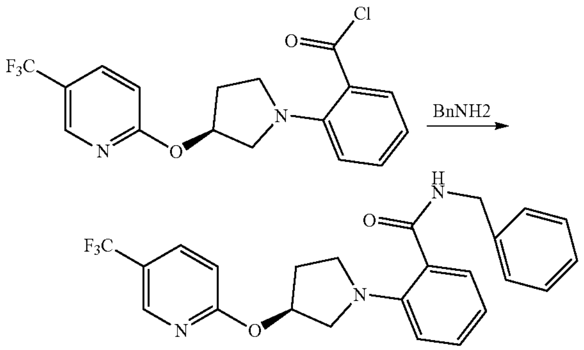

The title compound was prepared following procedures described in example 40 (step 2) to give (S)—N-benzyl-2-(3-(5-(trifluoromethyl)pyridin-2-yloxy)pyrrolidin-1-yl)benzamide (30 mg, 42% yield), Mass spec: 442 (M+H), $t_R$=3.080 min, $^1$H-NMR (400 Hz, DMSO) δ=8.838-8.869 (t, 1H), 8.593 (s, 1H), 8.055-8.083 (dd, 1H), 7.214-7.340 (m, 7H), 6.970-6.992 (d, 1H), 6.701-6.780 (d, 2H), 5.594 (br, 1H), 4.376-4.419 (dd, 2H), 3.670-3.715 (m, 1H), 3.408-3.432 (m, 1H), 3.200-3.270 (m, 2H), 2.506-2.519 (m, 1H), 2.232-2.254 (m, 1H).

Example 42: (S)—N-isopropyl-2-(3-(5-(trifluoromethyl)pyridin-2-yloxy)pyrrolidin-1-yl)benzamide (Compound 1-46)

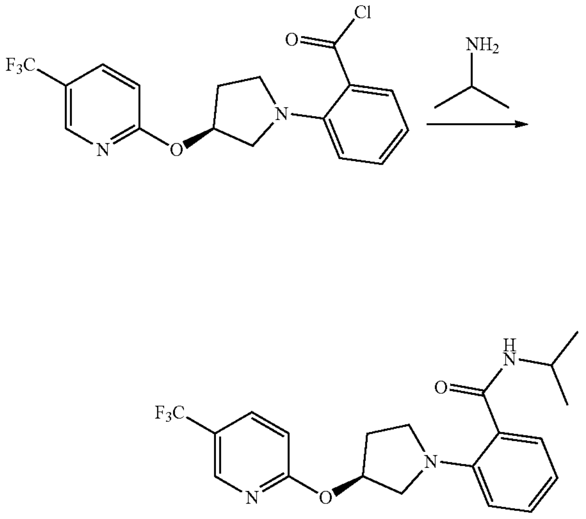

The title compound was prepared following procedures described in example 40 (step 2) to give (S)—N-isopropyl-2-(3-(5-(trifluoromethyl)pyridin-2-yloxy)pyrrolidin-1-yl) benzamide (30 mg, 47.7% yield), Mass spec: 394 (M+H), $t_R$=2.896 min, $^1$H-NMR (400 Hz, DMSO) δ=8.574 (s, 1H), 8.056-8.194 (dd, 2H), 7.207-7.246 (m, 1H), 7.115-7.248 (m, 1H), 6.985-7.007 (d, 1H), 6.671-6.759 (m, 2H), 5.639 (br, 1H), 3.959-4.012 (m, 1H), 3.769-3.810 (m, 1H), 3.452-3.492 (m, 1H), 3.264-3.333 (m, 2H), 2.220-2.323 (m, 1H), 2.205-2.212 (m, 1H), 1.070-1.103 (m, 6H).

Example 43: (S)—N,N-dibenzyl-2-(3-(5-(trifluoromethyl)pyridin-2-yloxy)pyrrolidin-1-yl)benzamide (Compound 1-52)

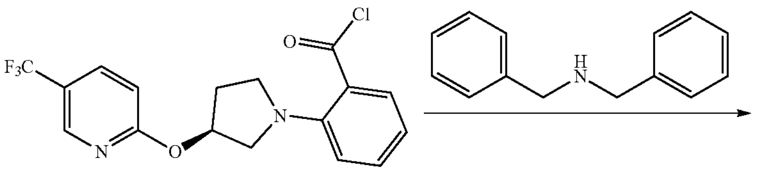

-continued

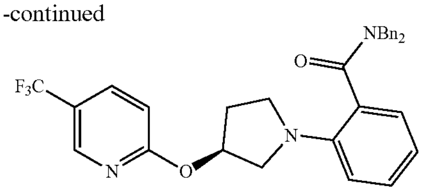

The title compound was prepared following procedures described in example (step 2) to give (S)—N,N-dibenzyl-2-(3-(5-(trifluoromethyl)pyridin-2-yloxy)pyrrolidin-1-yl) benzamide (27 mg, 34% yield), Mass spec: 532 (M+H), $t_R$=3.616 min, $^1$H-NMR (400 Hz, DMSO) δ=8.395-8.461 (d, 1H), 7.775-7.797 (m, 1H), 7.236-7.396 (m, 10H), 7.115-7.157 (m, 2H), 6.733-6.842 (m, 3H), 5.512-5.601 (d, 1H), 4.975-5.176 (dd, 1H), 4.401-4.536 (m, 1.5H), 4.130-4.272 (m, 1.5H), 3.550-3.562 (m, 0.5H), 3.338-3.506 (m, 2H), 3.257-3.327 (m, 1.5H), 2.125-2.195 (m, 2H).

Example 44: (S)-tert-butyl 2-(3-(5-(trifluoromethyl) pyridin-2-yloxy)pyrrolidin-1-yl)benzoate (Compound 1-54)

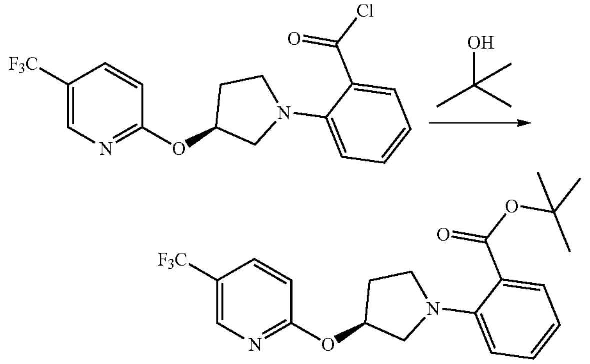

The title compound was prepared following procedures described in example 40 (step 2) to give (S)-tert-butyl 2-(3-(5-(trifluoromethyl)pyridin-2-yloxy)pyrrolidin-1-yl) benzoate (32 mg, 49% yield), Mass spec: 409 (M+H), $t_R$=3.544 min, $^1$H-NMR (400 Hz, CDC13) δ=8.429 (s, 1H), 7.754-7.781 (m, 1H), 7.536-7.559 (m, 1H), 7.288-7.348 (m, 1H), 6.737-6.829 (m, 3H), 5.690 (br, 1H), 3.896-3.937 (m, 1H), 3.635-3.654 (m, 1H), 3.257-3.601 (m, 1H), 3.22-3.250 (m, 1H), 2.310-2.343 (m, 2H), 1.586 (s, 9H).

Example 45: (S)—N,N-dimethyl-1-(2-(3-(5-(trifluoromethyl)pyridin-2-yloxy)pyrrolidin-1-yl)phenyl) methanamine hydrochloride (Compound 1-61)

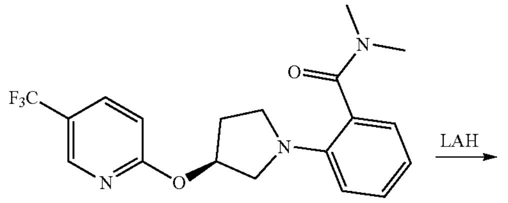

-continued

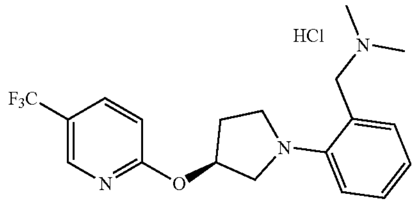

The title compound was prepared following procedures described in example 13 to give (S)—N,N-dimethyl-1-(2-(3-(5-(trifluoromethyl)pyridin-2-yloxy)pyrrolidin-1-yl)phenyl) methanamine hydrochloride (21 mg, 33.7% yield), Mass spec: 366 (M+H), $t_R$=2.637 min, $^1$H-NMR (400 Hz, DMSO) δ=9.980 (br, 1H), 8.611 (s, 1H), 8.082-8.110 (m, 1H), 7.432-7.556 (m, 1H), 7.290-7.404 (m, 1H), 7.270-7.384 (m, 1H), 7.044-7.270 (m, 2H), 5.660 (br, 1H), 4.362-4.374 (d, 2H), 3.626-3.702 (m, 1H), 3.327-3.628 (m, 1H), 3.156-3.221 (m, 2H), 2.671-2.739 (dd, 6H), 2.140-2.479 (m, 1H), 2.118-2.139 (m, 1H).

Example 46: (R)-2-(3-(5-(trifluoromethyl)pyridin-2-yloxy)pyrrolidin-1-yl)benzoic acid (Compound 1-41)

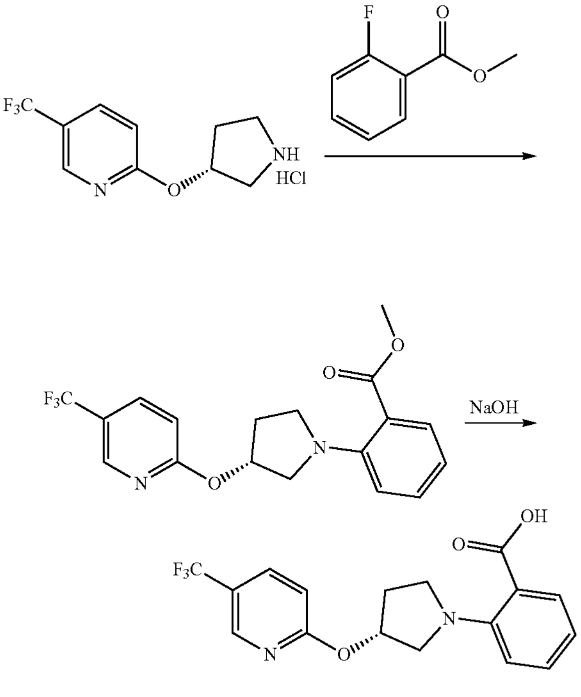

Step 1: (R)-methyl 2-(3-(5-(trifluoromethyl)pyridin-2-yloxy)pyrrolidin-1-yl)benzoate

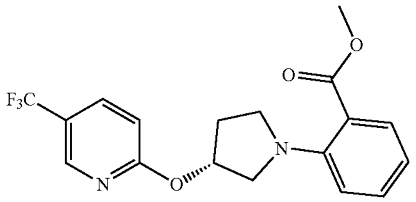 [SMILES: COC(=O)c1ccccc1N1CC[C@@H](Oc2ccc(C(F)(F)F)cn2)C1]

To a solution of (R)-2-(pyrrolidin-3-yloxy)-5-(trifluoromethyl)pyridine hydrochloride (Intermediate 4) (1.2 g, 5.2 mmol) and methyl 2-fluorobenzoate (1.2 g, 7.8 mmol) in DMSO (8 mL) was added DBU (1.58 g, 10.4 mmol) at rt, the mixture was heated to 100° C. for overnight, water was added, extracted by EA, washed by water, brine, dried over Na2SO4, removal the solvent to left the crude product which purified by silica gel to give (R)-methyl 2-(3-(5-(trifluoromethyl)pyridin-2-yloxy)pyrrolidin-1-yl)benzoate (550 mg, 28%), Mass spec: 367 (M+H).

Step 2: (R)-2-(3-(5-(trifluoromethyl)pyridin-2-yloxy)pyrrolidin-1-yl)benzoic acid

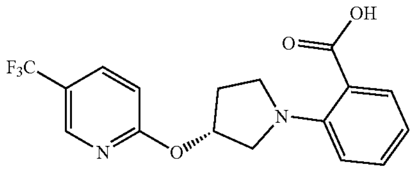 [SMILES: O=C(O)c1ccccc1N1CC[C@@H](Oc2ccc(C(F)(F)F)cn2)C1]

The title compound was prepared following procedures described in example 38 (step 2) to give (R)-2-(3-(5-(trifluoromethyl)pyridin-2-yloxy)pyrrolidin-1-yl)benzoic acid (20 mg, 40.6% yield), Mass spec: 353 (M+H), $t_R$=2.180 min, $^1$H-NMR (400 Hz, CDCl3) δ=8.440 (s, 1H), 8.310-8.334 (d, 1H), 7.836-7.864 (d, 1H), 7.620-7.658 (m, 1H), 7.413-7.453 (m, 2H), 6.950-6.971 (d, 1H), 5.794-5.821 (m, 1H), 3.656 (m, 1H), 3.519-3.544 (m, 1H), 3.411-3.440 (m, 1H), 3.309-3.331 (m, 1H), 2.579-2.616 (m, 1H), 2.400-2.419 (m, 1H). 0

Example 47: (R)—N-methyl-2-(3-(5-(trifluoromethyl)pyridin-2-yloxy)pyrrolidin-1-yl)benzamide (Compound 1-47)

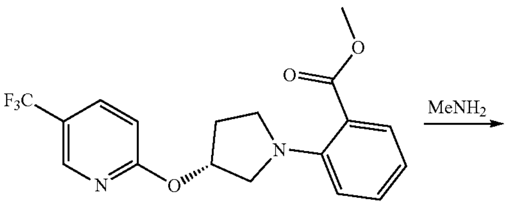

-continued

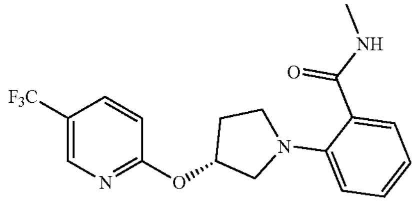

The title compound was prepared following procedures described in example 39 to give (R)—N-methyl-2-(3-(5-(trifluoromethyl)pyridin-2-yloxy)pyrrolidin-1-yl)benzamide (25 mg, 50% yield), Mass spec: 366 (M+H), $t_R$=2.571 min, $^1$H-NMR (400 Hz, DMSO) δ=8.611 (s, 1H), 8.190-8.199 (d, 1H), 8.057-8.078 (d, 1H), 7.214-7.252 (m, 1H), 7.142-7.161 (m, 1H), 6.993-7.015 (m, 1H), 6.678-6.766 (m, 2H), 5.650 (br, 1H), 3.713-3.753 (m, 1H), 3.250-3.304 (m, 3H), 2.705-2.715 (d, 3H), 2.272-2.304 (m, 1H), 2.171-2.197 (m, 1H).

Example 48: (R)-tert-butyl 2-(3-(5-(trifluoromethyl)pyridin-2-yloxy)pyrrolidin-1-yl)benzoate (Compound 1-55)

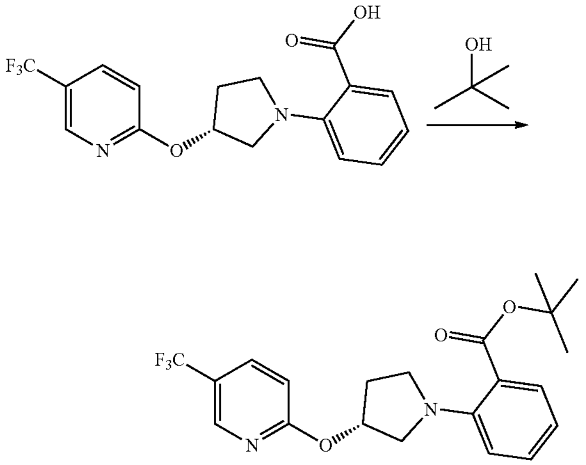

To a solution of (R)-2-(3-(5-(trifluoromethyl)pyridin-2-yloxy)pyrrolidin-1-yl)benzoic acid (Example 46) (45 mg, 0.13 mmol) in DCM (1 mL) was added (COCl)2 (36.6 mg, 0.288 mmol) and one drop DMF, the mixture was stirred at rt, after finished, the solvent was removed to give (R)-2-(3-(5-(trifluoromethyl) pyridin-2-yloxy)pyrrolidin-1-yl)benzoyl chloride (quant.); to the benzoyl chloride in DCM (1 mL) was added 2-methylpropan-2-ol (13.5 mg, 0.153 mmol) and TEA (3 drops), the mixture was stirred at rt, after finished, quenched by water, extracted with EA, washed by water, brine, dried by Na2SO4, removal the solvent to left the crude product which was purified by silica gel to give (R)-tert-butyl 2-(3-(5-(trifluoromethyl)pyridin-2-yloxy)pyrrolidin-1-yl)benzoate (10 mg, 19% yield), Mass spec: 409 (M+H), $t_R$=3.504 min, $^1$H-NMR (400 Hz, CDCl3) δ=8.403 (s, 1H), 7.728-7.757 (m, 1H), 7.516-7.539 (m, 1H), 7.259-7.305 (m, 1H), 6.720-6.822 (m, 3H), 5.669 (br, 1H), 3.878-3.919 (m, 1H), 3.615-3.633 (m, 3H), 3.244-2.249 (m, 1H), 2.204-3.232 (d, 1H), 2.307-2.315 (m, 2H).

Example 49: (R)—N-benzyl-2-(3-(5-(trifluoromethyl)pyridin-2-yloxy)pyrrolidin-1-yl)benzamide (Compound 1-50)

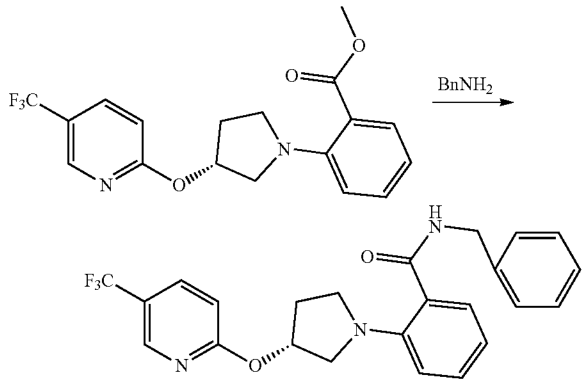

To a solution of (R)-methyl 2-(3-(5-(trifluoromethyl)pyridin-2-yloxy)pyrrolidin-1-yl)benzoate (50 mg, 0.137 mmol) (example 46, step 1) and BnNH2 (45 mg, 0.41 mmol) in Toluene was added Al(Me)3 (2M in toluene, 0.41 mmol) at 110° C. for overnight, quenched with NH4Cl solution, extracted by DCM, washed with water, brine, dried over Na2SO4, removal the solvent to left crude product which was purified by silica gel to give (R)—N-benzyl-2-(3-(5-(trifluoromethyl)pyridin-2-yloxy)pyrrolidin-1-yl)benzamide (40 mg, 66% yield) as white solid. Mass spec: 442 (M+H), $t_R$=3.090 min, $^1$H-NMR (400 Hz, DMSO) δ=8.594-8.860 (t, 1H), 8.594 (s, 1H), 8.054-8.081 (dd, 1H), 7.216-7.342 (m, 7H), 6.969-6.991 (d, 1H), 6.705-6.783 (d, 2H), 5.595 (br, 1H), 4.379-4.422 (dd, 2H), 3.433-3.713 (m, 1H), 3.392-3.433 (m, 1H), 3.204-3.294 (m, 2H), 2.506-2.514 (m, 1H), 2.114-2.123 (m, 1H).

Example 50: (R)—N,N-dibenzyl-2-(3-(5-(trifluoromethyl)pyridin-2-yloxy)pyrrolidin-1-yl)benzamide (Compound 1-53)

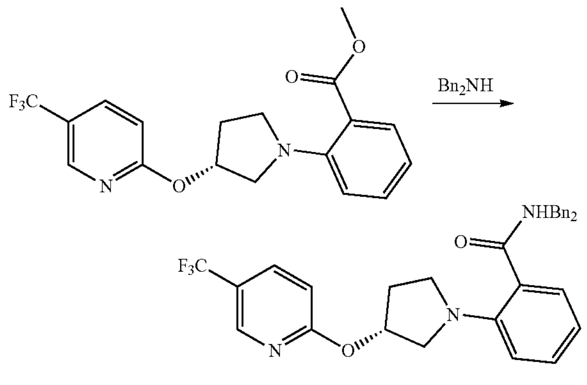

The title compound was prepared following procedures described in example 49 to give (R)—N,N-dibenzyl-2-(3-(5-(trifluoromethyl)pyridin-2-yloxy)pyrrolidin-1-yl)benzamide (35 mg, 48% yield), Mass spec: 532 (M+H), $t_R$=3.618 min, $^1$H-NMR (400 Hz, DMSO) δ=8.562-8.619 (d, 1H), 8.072-8.111 (m, 1H), 7.215-7.331 (m, 9H), 7.098-7.157 (m, 3H), 6.981-7.002 (m, 1H), 6.684-6.775 (m, 2H), 5.466-5.578 (d, 1H), 4.446-4.958 (dd, 1H), 4.147-4.407 (m, 3H), 3.645-3.6866 (m, 1H), 3.161-3.267 (m, 2H), 2.107-2.219 (m, 1H), 1.984-1.995 (m, 1H).

Example 51: (R)—N-isopropyl-2-(3-(5-(trifluoromethyl)pyridin-2-yloxy)pyrrolidin-1-yl)benzamide (Compound 1-49)

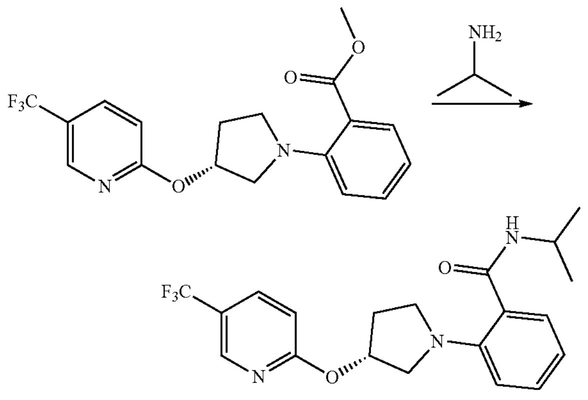

The title compound was prepared following procedures described in example 49 to give (R)—N-isopropyl-2-(3-(5-(trifluoromethyl)pyridin-2-yloxy)pyrrolidin-1-yl)benzamide (25 mg, 46% yield), Mass spec: 394 (M+H), $t_R$=2.909 min, $^1$H-NMR (400 Hz, DMSO) δ=8.573 (s, 1H), 8.170-8.190 (d, 1H), 8.052-8.081 (d, 1H), 7.210-7.248 (m, 1H), 7.118-7.140 (m, 1H), 6.984-7.006 (d, 1H), 6.710-6.760 (m, 1H), 6.673-6.691 (t, 1H), 5.639 (br, 1H), 3.960-4.012 (m, 1H), 3.768-3.809 (m, 1H), 3.474-3.492 (m, 1H), 3.295-3.345 (m, 2H), 2.291-2.325 (m, 1H), 2.203-2.210 (m, 1H), 1.070-1.103 (m, 6H.)

Example 52: (R)—N,N-dimethyl-2-(3-(5-(trifluoromethyl)pyridin-2-yloxy)pyrrolidin-1-yl)benzamide (Compound 1-59)

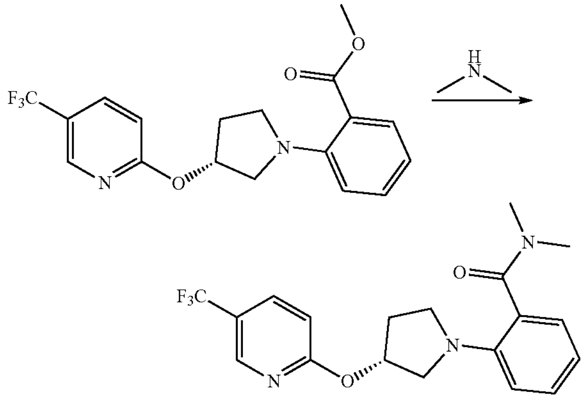

The title compound was prepared following procedures described in example 49 to give (R)—N,N-dimethyl-2-(3-(5-(trifluoromethyl)pyridin-2-yloxy)pyrrolidin-1-yl)benzamide (110 mg, 71% yield), Mass spec: 380 (M+H), $t_R$=2.799 min, $^1$H-NMR (400 Hz, CDCl3) δ=8.451 (s, 1H), 7.770-7.792 (d, 1H), 7.214-7.285 (m, 2H), 7.100-7.119 (m, 3H), 5.671-5.713 (m, 1H), 3.829-3.856 (m, 1H), 3.592-3.662 (m, 2H), 3.466-3.504 (m, 1H), 3.134-3.257 (d, 3H), 2.873-2.942 (d, 3H), 2.268-2.304 (m, 2H).

Example 53: (R)—N,N-dimethyl-1-(2-(3-(5-(trifluoromethyl)pyridin-2-yloxy)pyrrolidin-1-yl)phenyl) methanamine hydrochloride (Compound 1-60)

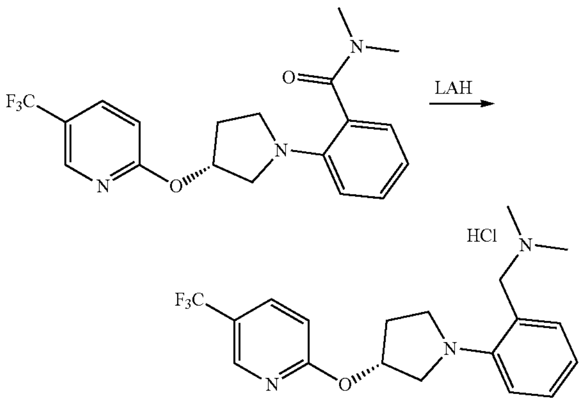

The title compound was prepared following procedures described in example 13 to give (R)—N,N-dimethyl-1-(2-(3-(5-(trifluoromethyl)pyridin-2-yloxy)pyrrolidin-1-yl)phenyl) methanamine hydrochloride (25 mg, 52% yield), Mass spec: 366 (M+H), $t_R$=1.988 min, $^1$H-NMR (400 Hz, DMSO) δ=10.151 (br, 1H), 8.609 (s, 1H), 8.081-8.609 (m, 1H), 7.569-7.588 (m, 1H), 7.382-7.420 (m, 1H), 7.268-7.288 (m, 1H), 7.048-7.129 (m, 2H), 5.645-5.673 (m, 1H), 4.364-4.376 (m, 1H), 3.635-3.676 (m, 1H), 3.330-3.390 (m, 1H), 3.148-3.220 (m, 1H), 2.664-2.728 (dd, 6H), 2.430-2.513 (m, 1H), 2.094-2.112 (m, 1H).

Example 54: (R)-2-(3-(5-(trifluoromethyl)pyridin-2-yloxy)pyrrolidin-1-yl)phenol (Compound 1-40)

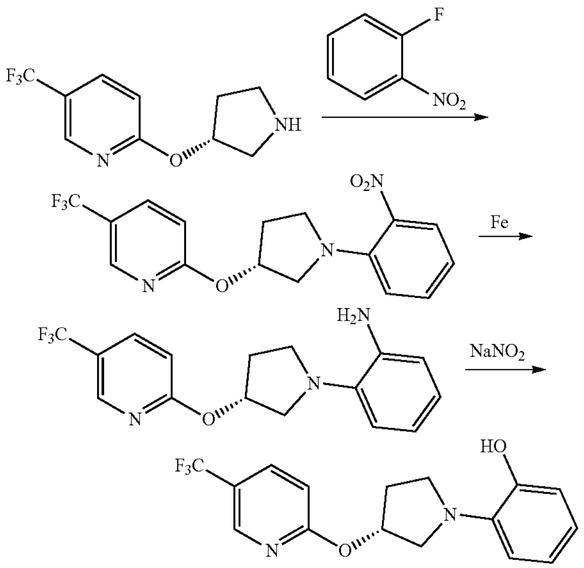

Step 1: (R)-2-(1-(2-nitrophenyl)pyrrolidin-3-yloxy)-5-(trifluoromethyl)pyridine

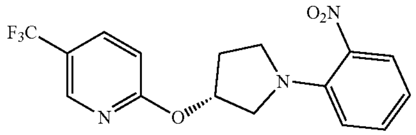 [SMILES: O=[N+]([O-])c1ccccc1N1CC[C@@H](Oc2ccc(C(F)(F)F)cn2)C1]

The title compound was prepared following procedures described in example 5 to give (R)-2-(1-(2-nitrophenyl) pyrrolidin-3-yloxy)-5-(trifluoromethyl)pyridin (900 mg, 80% yield), Mass spec: 354 (M+H).

Step 2: (R)-2-(3-(5-(trifluoromethyl)pyridin-2-yloxy)pyrrolidin-1-yl)aniline

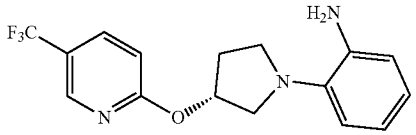 [SMILES: Nc1ccccc1N1CC[C@@H](Oc2ccc(C(F)(F)F)cn2)C1]

The title compound was prepared following procedures described in example 14 (step 2) to give (R)-2-(3-(5-(trifluoromethyl)pyridin-2-yloxy)pyrrolidin-1-yl)aniline (800 mg, quant.), Mass spec: 324 (M+H).

Step 3: (R)-2-(3-(5-(trifluoromethyl)pyridin-2-yloxy)pyrrolidin-1-yl)phenol

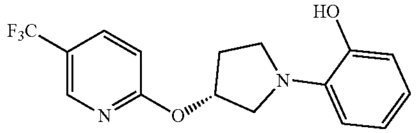 [SMILES: Oc1ccccc1N1CC[C@@H](Oc2ccc(C(F)(F)F)cn2)C1]

The title compound was prepared following procedures described in example 14 (step 2) to give (R)-2-(3-(5-(trifluoromethyl)pyridin-2-yloxy)pyrrolidin-1-yl)phenol (290 mg, 20% yield) as clarity oil. Mass spec: 325 (M+H), $t_R$=1.380 min, $^1$H-NMR (400 Hz, CD3OD) δ=8.492 (s, 1H), 7.926-7.955 (dd, 1H), 6.953-6.975 (d, 1H), 6.858-6.877 (m, 1H), 6.744-6.810 (m, 3H), 5.659-5.698 (m, 1H), 4.622-4.651 (m, 1H), 3.734-3.777 (m, 1H), 3.401-3.511 (m, 2H), 3.208-3.321 (m, 1H), 2.202-2.501 (m, 1H), 2.146-2.184 (m. 1H).

Example 55: (R)-2-(1-(2-(benzyloxy)phenyl)pyrrolidin-3-yloxy)-5-(trifluoromethyl)pyridine (Compound 1-38)

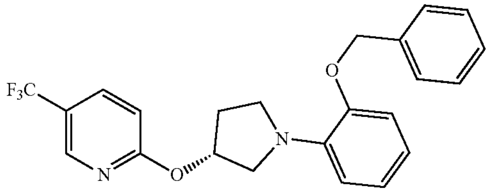 [SMILES: FC(F)(F)c1ccc(O[C@@H]2CCN(c3ccccc3OCc3ccccc3)C2)nc1]

The title compound was prepared following procedures described in example 15a using (R)-2-(3-(5-(trifluoromethyl)pyridin-2-yloxy)pyrrolidin-1-yl)phenol and (bromomethyl)benzene to give (R)-2-(1-(2-(benzyloxy)phenyl)pyrrolidin-3-yloxy)-5-(trifluoromethyl)pyridine (8 mg, 76 yield), Mass spec: 415 (M+H), $t_R$=3.566 min, $^1$H-NMR (400 Hz, CD3OD) δ=8.42 (s, 1H), 7.907-7.943 (dd, 1H), 7.331-7.447 (m, 2H), 7.254-7.323 (m, 3H), 7.002-7.026 (m, 1H), 6.837-6.928 (m, 4H), 5.617 (br, 1H), 5.067 (s, 2H), 3.615-3.693 (m, 2H), 3.501-3.543 (m, 1H), 3.251-3.321 (m, 1H), 2.201-2.451 (m, 1H), 2.167-2.188 (m, 1H).

Example 56: (R)-2-(1-(2-(cyclopentyloxy)phenyl) pyrrolidin-3-yloxy)-5-(trifluoromethyl)pyridine (Compound 1-36)

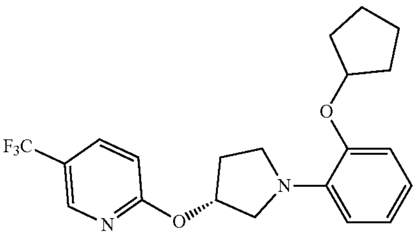 [SMILES: FC(F)(F)c1ccc(O[C@@H]2CCN(c3ccccc3OC3CCCC3)C2)nc1]

The title compound was prepared following procedures described in example 15a using (R)-2-(3-(5-(trifluoromethyl)pyridin-2-yloxy)pyrrolidin-1-yl)phenol and iodocyclopentane to give (R)-2-(1-(2-(cyclopentyloxy)phenyl)pyrrolidin-3-yloxy)-5-(trifluoromethyl)pyridine (11 mg, 85% yield), Mass spec: 393 (M+H), $t_R$=3.517 min, $^1$H-NMR (400 Hz, CD3OD) δ=8.488 (s, 1H), 7.928-7.956 (dd, 1H), 6.826-6.965 (m, 5H), 5.644 (br, 1H), 4.809-4.837 (m, 1H), 3.568-3.640 (m, 3H), 3.216-3.236 (m, 1H), 2.399-2.449 (m, 1H), 2.178-2.231 (m, 1H), 1.779-1.884 (m, 5H), 1.616-1.665 (m, 3H).

Example 57: (R)-2-(1-(2-isopropoxyphenyl)pyrrolidin-3-yloxy)-5-(trifluoromethyl)pyridine (Compound 1-37)

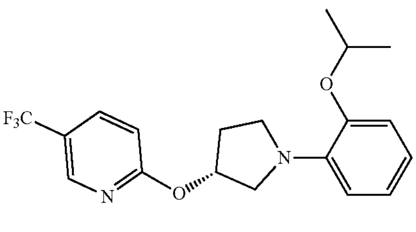 [SMILES: CC(C)Oc1ccccc1N1CC[C@@H](Oc2ccc(C(F)(F)F)cn2)C1]

The title compound was prepared following procedures described in example 15a using (R)-2-(3-(5-(trifluoromethyl)pyridin-2-yloxy)pyrrolidin-1-yl)phenol and 2-bromopropane to give (R)-2-(1-(2-isopropoxyphenyl)pyrrolidin-3-yloxy)-5-(trifluoromethyl)pyridine (8.5 mg, 78 yield), Mass spec: 393 (M+H), $t_R$=3.213 min, $^1$H-NMR (400 Hz, CD3OD) δ=8.499 (s, 1H), 7.928-7.956 (dd, 1H), 6.808-6.965 (m, 5H), 5.678 (br, 1H), 4.559-4.635 (m, 1H), 3.691-3.734 (m, 1H), 3.321-3.580 (m, 2H), 3.250-3.285 (m, 1H), 2.193-2.443 (m, 1H), 2.168-2.190 (m, 1H), 1.278-1.293 (m, 6H).

Example 58: (S)-2-(1-(biphenyl-2-yl)pyrrolidin-3-yloxy)-5-(trifluoromethyl)pyridine (Compound 1-27)

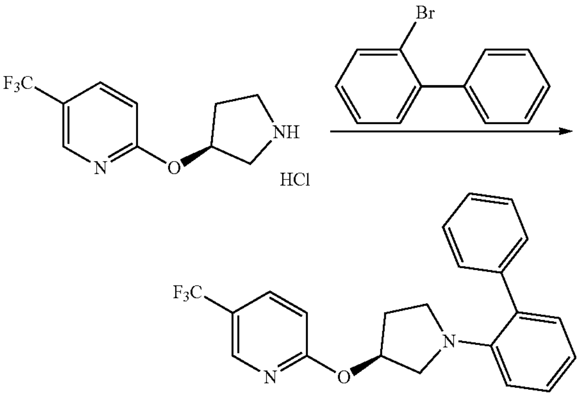

To a solution of (S)-2-(pyrrolidin-3-yloxy)-5-(trifluoromethyl)pyridine hydrochloride (200 mg, 0.86 mmol) (Intermediate 3), 2-bromobiphenyl (0.18 ml, 1.04 mmol), Pd2 (dba)3 (157 mg, 0.17 mmol), BINAP (107 mg, 0.17 mmol) in Toluene was added t-BuONa (165 mg, 1.72 mmol), the mixture was degassed with N2, then heated to 120° C. under microwave for 30 min, removal the solvent to left the crude product which was purified by silica gel to give 70 mg (22% yield), Mass spec: 385 (M+H), $t_R$=3.719 min, $^1$H-NMR (400 Hz, DMSO) δ=8.497 (s, 1H), 8.020-8.047 (dd, 1H), 7.314-7.403 (m, 4H), 7.182-7.246 (m, 2H), 7.083-7.101 (m, 1H), 6.871-6.969 (m, 3H), 5.418 (br, 1H), 3.116-3.327 (m, 2H), 2.981-3.011 (m, 1H), 2.877-2.904 (m, 1H), 2.183-2.217 (m, 1H), 1.988-2.005 (m, 1H).

Example 59: (R)-2-(1-(biphenyl-2-yl)pyrrolidin-3-yloxy)-5-(trifluoromethyl)pyridine (Compound 1-28)

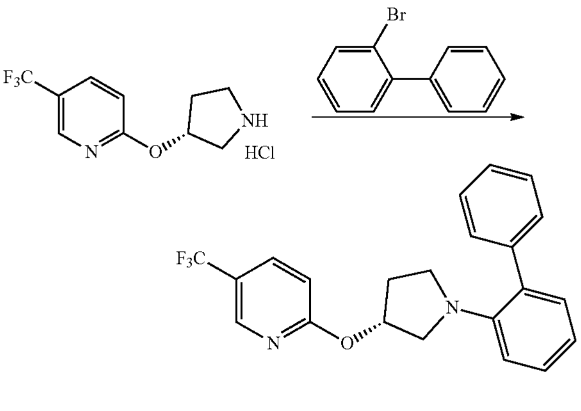

To a solution of (R)-2-(pyrrolidin-3-yloxy)-5-(trifluoromethyl)pyridine hydrochloride (200 mg, 0.86 mmol) (Intermediate 3), 2-bromobiphenyl (0.18 ml, 1.04 mmol), Pd2 (dba)3 (157 mg, 0.17 mmol), BINAP (107 mg, 0.17 mmol) in Toluene was added t-BuONa (165 mg, 1.72 mmol), the mixture was degassed with N2, then heated to 120° C. under microwave for 30 min, removal the solvent to left the crude product which was purified by silica gel to give 56 mg (17% yield), Mass spec: 385 (M+H), $t_R$=3.710 min, $^1$H-NMR (400 Hz, DMSO) δ=8.497 (s, 1H), 8.022-8.049 (dd, 1H), 7.315-7.404 (m, 4H), 7.183-7.247 (m, 2H), 7.085-7.103 (m, 1H), 6.892-6.972 (m, 3H), 5.420 (br, 1H), 3.118-3.316 (m, 2H), 2.982-3.013 (m, 1H), 2.877-3.004 (m, 1H), 2.188-2.222 (m, 1H), 1.991-2.008 (m, 1H).

Example 60: (S)-3-chloro-2-(3-(5-(trifluoromethyl)pyridin-2-yloxy)pyrrolidin-1-yl)benzamide (Compound 43)

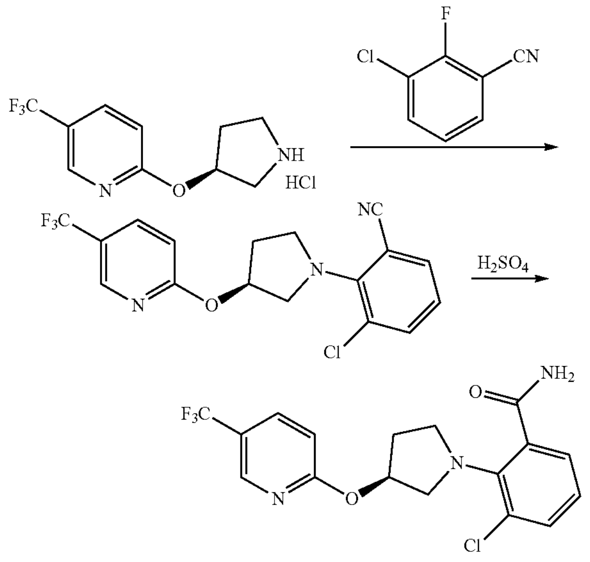

Step 1: (S)-3-chloro-2-(3-(5-(trifluoromethyl)pyridin-2-yloxy)pyrrolidin-1-yl)benzonitrile

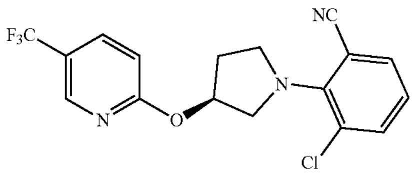 [SMILES: N#Cc1cccc(Cl)c1N1CC[C@H](Oc2ccc(C(F)(F)F)cn2)C1]

The title compound was prepared following procedures described in example 5 to give 340 mg (72% yield), Mass spec: 367 (M+H).

Step 2: (S)-3-chloro-2-(3-(5-(trifluoromethyl)pyridin-2-yloxy)pyrrolidin-1-yl)benzamide

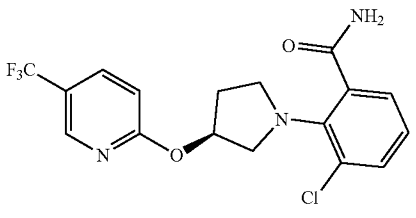 [SMILES: NC(=O)c1cccc(Cl)c1N1CC[C@H](Oc2ccc(C(F)(F)F)cn2)C1]

The title compound was prepared following procedures described in example 16 (step 3) at 90° C. for 30 min to give (S)-3-chloro-2-(3-(5-(trifluoromethyl)pyridin-2-yloxy)pyrrolidin-1-yl)benzamide (70 mg, 20% yield), Mass spec: 386 (M+H), $t_R$=2.867 min, $^1$H-NMR (400 Hz, DMSO) δ=8.590 (s, 1H), 8.398 (br, 1H), 8.064-8.091 (dd, 1H), 7.602 (br, 1H), 7.473-7.522 (m, 2H), 7.174-7.212 (m, 1H), 7.046-7.068 (m, 1H), 5.645 (br, 1H), 3.758-3.796 (m, 1H), 3.455-3.503 (m, 1H), 3.292-3.353 (m, 2H), 2.375-2.410 (m, 1H), 2.098-2.106 (m, 1H).

Example 61: (R)-3-chloro-2-(3-(5-(trifluoromethyl)pyridin-2-yloxy)pyrrolidin-1-yl)benzamide (Compound 1-42)

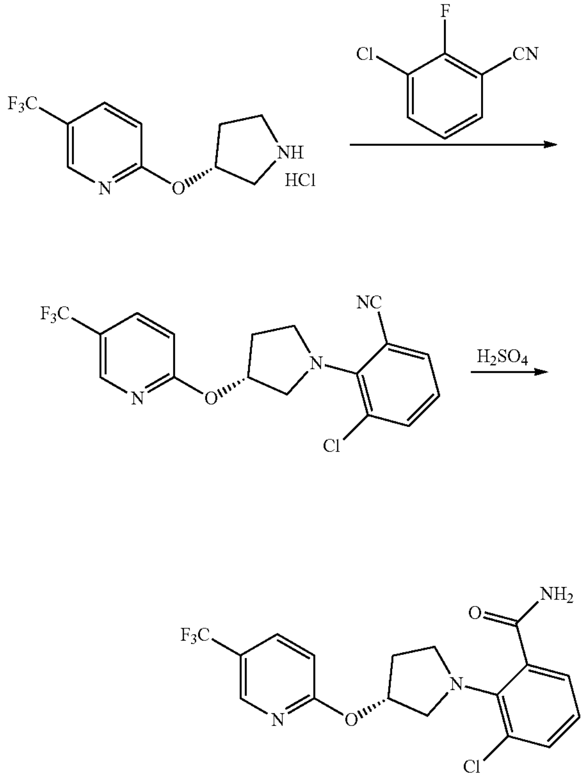

Step 1: (R)-3-chloro-2-(3-(5-(trifluoromethyl)pyridin-2-yloxy)pyrrolidin-1-yl)benzonitrile

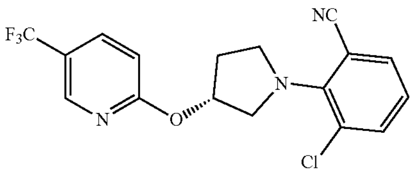 [SMILES: N#Cc1cccc(Cl)c1N1CC[C@@H](Oc2ccc(C(F)(F)F)cn2)C1]

The title compound was prepared following procedures described in example to give (R)-3-chloro-2-(3-(5-(trifluoromethyl)pyridin-2-yloxy)pyrrolidin-1-yl)benzonitrile (300 mg, 63% yield), Mass spec: 367 (M+H).

Step 2: (R)-3-chloro-2-(3-(5-(trifluoromethyl)pyridin-2-yloxy)pyrrolidin-1-yl)benzamide

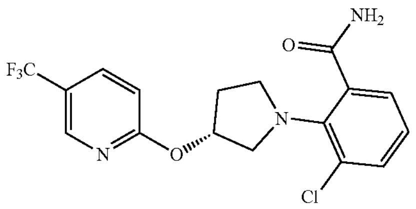 [SMILES: NC(=O)c1cccc(Cl)c1N1CC[C@@H](Oc2ccc(C(F)(F)F)cn2)C1]

The title compound was prepared following procedures described in example 16 (step 3) at 90° C. for 30 min to give (R)-3-chloro-2-(3-(5-(trifluoromethyl)pyridin-2-yloxy)pyrrolidin-1-yl)benzamide (90 mg, 28.8% yield), Mass spec: 386 (M+H), $t_R$=2.868 min, $^1$H-NMR (400 Hz, DMSO) δ=8.601 (s, 1H), 8.406 (br, 1H), 8.074-8.103 (dd, 1H), 7.613 (br, 1H), 7.487-7.532 (m, 2H), 7.184-7.223 (m, 1H), 7.056-7.077 (m, 1H), 5.656 (br, 1H), 3.769-3.807 (m, 1H), 3.474-3.514 (m, 1H), 3.302-3.364 (m, 2H), 2.510-2.513 (m, 1H), 2.402-2.420 (m, 1H).

Example 62: (S)-5-(trifluoromethyl)-2-(3-(5-(trifluoromethyl)pyridin-2-yloxy)pyrrolidin-1-yl)benzamide (Compound 1-58)

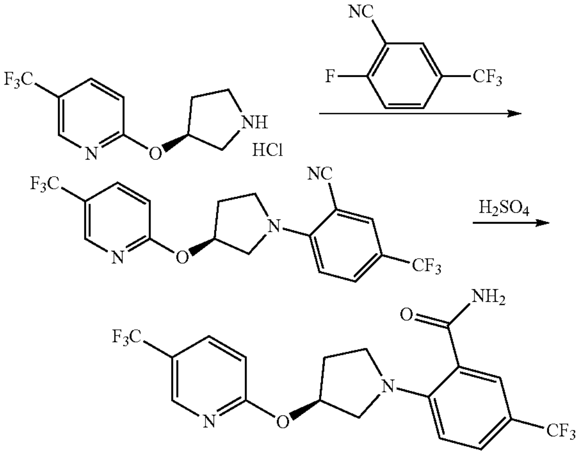

Step 1: (S)-5-(trifluoromethyl)-2-(3-(5-(trifluoromethyl)pyridin-2-yloxy)pyrrolidin-1-yl)benzonitrile

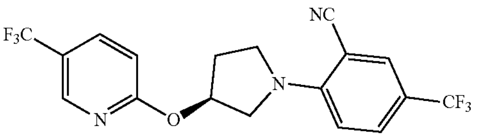 [SMILES: N#Cc1cc(C(F)(F)F)ccc1N1CC[C@H](Oc2ccc(C(F)(F)F)cn2)C1]

The title compound was prepared following procedures described in example 5 to give (S)-5-(trifluoromethyl)-2-(3-(5-(trifluoromethyl)pyridin-2-yloxy)pyrrolidin-1-yl)benzonitrile (120 mg, 59.8% yield), Mass spec: 402 (M+H), $t_R$=3.348 min, $^1$H-NMR (400 Hz, DMSO) δ=8.474 (s, 1H), 7.804-7.832 (dd, 1H), 7.733 (s, 1H), 7.533-7.562 (d, 1H), 6.825-6.847 (d, 1H), 6.719-6.741 (d, 1H), 5.813 (br, 1H), 4.136-4.177 (m, 1H), 3.958-3.989 (m, 1H), 3.851-3.881 (m, 2H), 2.361-2.436 (m, 2H).

Step 2: (S)-5-(trifluoromethyl)-2-(3-(5-(trifluoromethyl)pyridin-2-yloxy)pyrrolidin-1-yl)benzamide

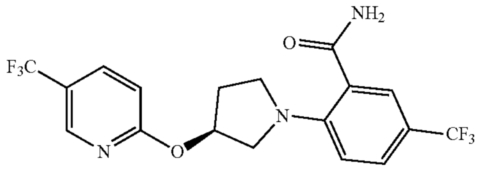 [SMILES: NC(=O)c1cc(C(F)(F)F)ccc1N1CC[C@H](Oc2ccc(C(F)(F)F)cn2)C1]

The title compound was prepared following procedures described in example 6 with EtOH to give (S)-5-(trifluoromethyl)-2-(3-(5-(trifluoromethyl)pyridin-2-yloxy)pyrrolidin-1-yl)benzamide (45 mg, 42.9% yield), Mass spec: 420 (M+H), $t_R$=3.646 min, $^1$H-NMR (400 Hz, DMSO) δ=8.627 (s, 1H), 8.062-8.089 (m, 1H), 7.949 (m, 1H), 7.504-7.528 (m, 1H), 7.452 (s, 1H), 7.002-7.024 (d, 1H), 6.850-6.873 (m, 1H), 5.707 (br, 1H), 3.874-3.914 (m, 1H), 3.584-3.601 (m, 1H), 3.394-3.461 (m, 2H), 2.257-2.267 (m, 2H).

Example 65: (S)-3-(3-(5-(trifluoromethyl)pyridin-2-yloxy)pyrrolidin-1-yl)biphenyl-4-carbonitrile (Compound 1-62)

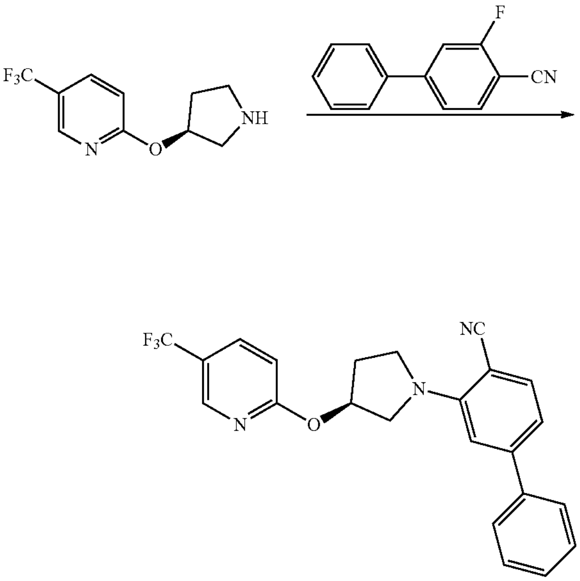

The title compound was prepared following procedures described in example to give (S)-3-(3-(5-(trifluoromethyl) pyridin-2-yloxy)pyrrolidin-1-yl)biphenyl-4-carbonitrile (90 mg, 17% yield), Mass spec: 410 (M+H), $t_R$=3.483 min, $^1$H-NMR (400 Hz, CDCl3) δ=8.478 (s, 1H), 7.795-7.8 (d, 1H), 7.544-7.592 (m, 3H), 7.420-7.494 (m, 3H), 6.940-6.960 (d, 1H), 6.825-6.848 (m, 2H), 5.809 (br, 1H), 3.988 (m, 1H), 3.823-3.852 (m, 2H), 2.385-2.399 (m, 2H).

Example 66: (S)-3-(3-(5-(trifluoromethyl)pyridin-2-yloxy)pyrrolidin-1-yl)biphenyl-4-carboxamide (Compound 1-63)

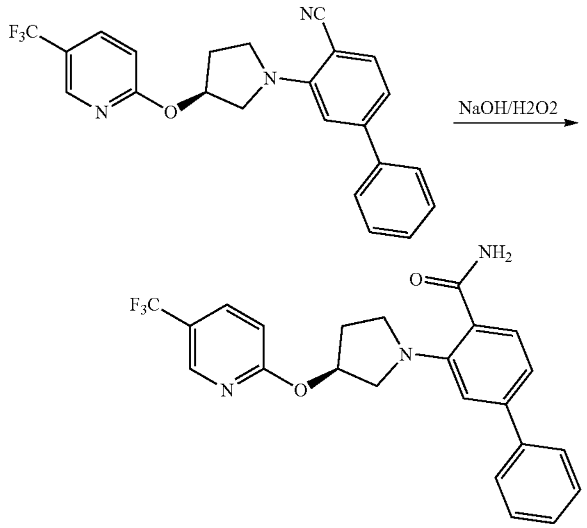

The title compound was prepared following procedures described in example 63 (step 3) to give (S)-3-(3-(5-(trifluoromethyl)pyridin-2-yloxy)pyrrolidin-1-yl)biphenyl-4-carboxamide (32 mg, 44% yield), Mass spec: 428 (M+H), $t_R$=3.678 min, $^1$H-NMR (400 Hz, DMSO) δ=8.624 (s, 1H), 8.059-8.087 (m, 1H), 7.813 (s, 1H), 7.662-7.683 (m, 2H), 7.447-7.484 (m, 2H), 7.319-7.394 (m, 3H), 6.954-7.026 (m, 3H), 5.697 (br, 1H), 3.874-3.915 (m, 1H), 3.601-3.618 (m, 1H), 3.421-3.473 (m, 2H), 2.328-2.350 (m, 1H), 2.222-2.240 (m, 1H).

Example 67: (S)-2-(1-(3-nitrobiphenyl-4-yl)pyrrolidin-3-yloxy)-5-(trifluoromethyl)pyridine (Compound 1-66)

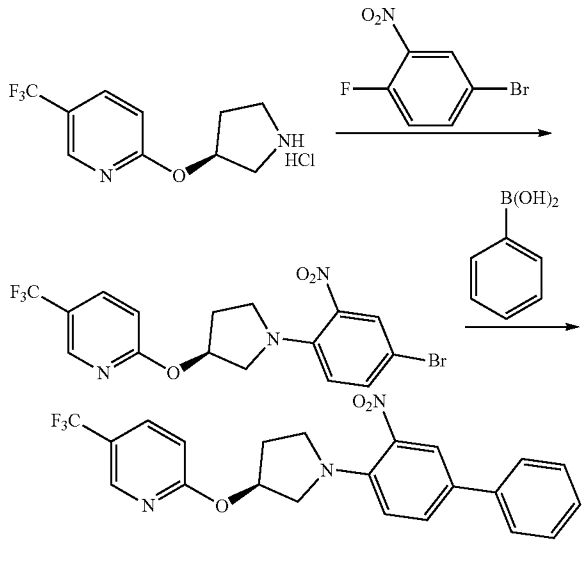

Step 1: (S)-2-(1-(4-bromo-2-nitrophenyl)pyrrolidin-3-yloxy)-5-(trifluoromethyl)pyridine

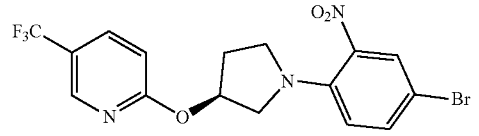 [SMILES: O=[N+]([O-])c1cc(Br)ccc1N1CC[C@H](Oc2ccc(C(F)(F)F)cn2)C1]

The title compound was prepared following procedures described in example to give (S)-2-(1-(4-bromo-2-nitrophenyl)pyrrolidin-3-yloxy)-5-(trifluoromethyl)pyridine (3.7 g, 85% yield), Mass spec: 432 (M+H).

Step 2: (S)-2-(1-(3-nitrobiphenyl-4-yl)pyrrolidin-3-yloxy)-5-(trifluoromethyl)pyridine

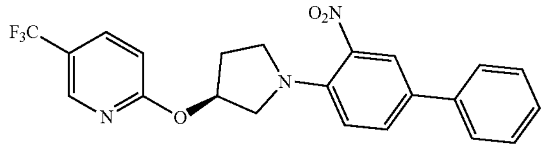 [SMILES: O=[N+]([O-])c1cc(-c2ccccc2)ccc1N1CC[C@H](Oc2ccc(C(F)(F)F)cn2)C1]

To a solution of (S)-2-(1-(4-bromo-2-nitrophenyl)pyrrolidin-3-yloxy)-5-(trifluoromethyl)pyridine (2.2 g, 5 mmol) and phenylboronic acid (732 mg, 6 mmol) in Dioxane/H2O (5 mL/1 mL) was added Pd(dppf)Cl2 (400 mg, 0.5 mmol) and K2CO3 (2 g, 15 mmol), the mixture was degassed by N2, and stirred at 90° C. for 2 h, diluted with EA, washed with water, brine, dried over Na2SO4, removal the solvent to left the residue which was purified by silica gel to give (S)-2-(1-(3-nitrobiphenyl-4-yl)pyrrolidin-3-yloxy)-5-(trifluoromethyl)pyridine (2.3 g, 94% yield), Mass spec: 430 (M+H), $t_R$=3.601 min, $^1$H-NMR (400 Hz, DMSO) δ=8.625 (s, 1H), 8.022-8.091 (m, 2H), 7.830-8.016 (d, 1H), 7.660-7.681 (d, 2H), 7.351-7.369 (m, 2H), 7.314-7.338 (m, 1H), 7.188-7.210 (d, 1H), 7.027-7.050 (d, 1H), 5.744 (br, 1H), 3.613-3.815 (m, 1H), 3.595-3.613 (m, 1H), 3.332-3.345 (m, 1H), 3.180-3.322 (m, 1H), 2.293-2.351 (m, 2H).

Example 68: (S)-2-(1-(3-methoxybiphenyl-4-yl)pyrrolidin-3-yloxy)-5-(trifluoromethyl)pyridine (Compound 1-73)

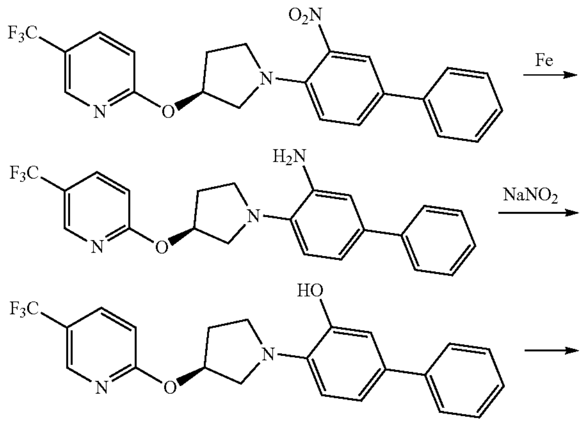

-continued

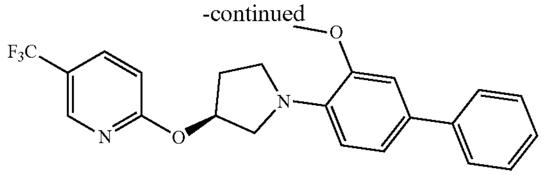

Step 1: (S)-4-(3-(5-(trifluoromethyl)pyridin-2-yloxy)pyrrolidin-1-yl)biphenyl-3-amine

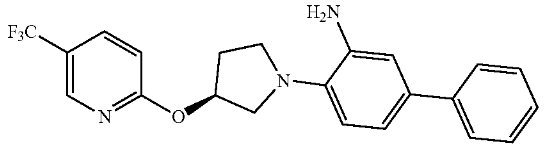

The title compound was prepared following procedures described in example 14 (step 2) to give (S)-4-(3-(5-(trifluoromethyl)pyridin-2-yloxy)pyrrolidin-1-yl)biphenyl-3-amine (830 mg, 59.5% yield), Mass spec: 400 (M+H).

Step 2: (S)-4-(3-(5-(trifluoromethyl)pyridin-2-yloxy)pyrrolidin-1-yl)biphenyl-3-ol

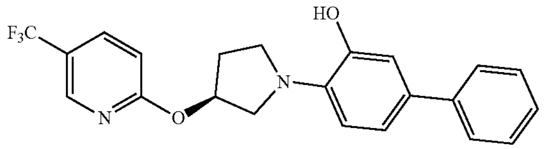 [SMILES: Oc1cc(-c2ccccc2)ccc1N1CC[C@H](Oc2ccc(C(F)(F)F)cn2)C1]

The title compound was prepared following procedures described in example 14 (step 3) to give (S)-4-(3-(5-(trifluoromethyl)pyridin-2-yloxy)pyrrolidin-1-yl)biphenyl-3-ol (105 mg, 21% yield), Mass spec: 401 (M+H).

Step 3: (S)-2-(1-(3-methoxybiphenyl-4-yl)pyrrolidin-3-yloxy)-5-(trifluoromethyl)pyridine

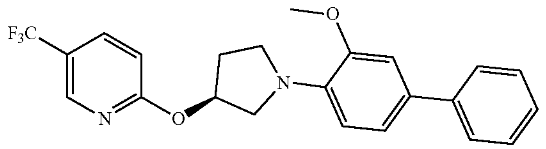 [SMILES: COc1cc(-c2ccccc2)ccc1N1CC[C@H](Oc2ccc(C(F)(F)F)cn2)C1]

The title compound was prepared following procedures described in example 15a to give (S)-2-(1-(3-methoxybiphenyl-4-yl)pyrrolidin-3-yloxy)-5-(trifluoromethyl)pyridine (22 mg, 54% yield), Mass spec: 415 (M+H). $t_R$=2.249 min, $^1$H-NMR (400 Hz, DMSO) δ=8.628 (s, 1H), 8.059-8.088 (dd, 1H), 7.619-7.637 (d, 2H), 7.393-7.431 (m, 2H), 7.255-7.292 (m, 1H), 7.144-7.178 (m, 2H), 7.021-7.043 (d, 1H), 6.767-6.788 (d, 1H), 5.656 (br, 1H), 3.846-3.882 (m, 4H), 3.557-3.575 (m, 1H), 3.407-3.437 (1H), 3.283-3.316 (m, 1H), 2.331-2.352 (m, 1H), 2.150 (m, 1H).

Example 69: (S)-2-(1-(3-isopropoxybiphenyl-4-yl)pyrrolidin-3-yloxy)-5-(trifluoromethyl)pyridine (Compound 1-77)

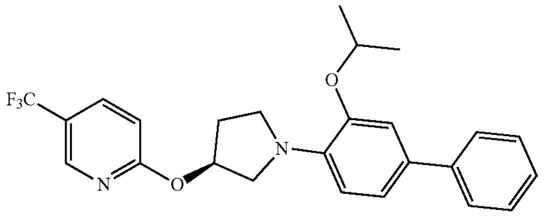 [SMILES: CC(C)Oc1cc(-c2ccccc2)ccc1N1CC[C@H](Oc2ccc(C(F)(F)F)cn2)C1]

The title compound was prepared following procedures described in example 15a using (S)-4-(3-(5-(trifluoromethyl)pyridin-2-yloxy)pyrrolidin-1-yl)biphenyl-3-ol and 2-iodopropane to give (S)-2-(1-(3-isopropoxybiphenyl-4-yl)pyrrolidin-3-yloxy)-5-(trifluoromethyl)pyridine (18 mg, 40% yield), Mass spec: 443 (M+H). $t_R$=3.874 min, $^1$H-NMR (400 Hz, CDCl3) δ=8.468 (s, 1H), 7.771-7.798 (m, 1H), 7.559-7.580 (m, 2H), 7.409-7.447 (m, 2H), 7.285-7.332 (m, 1H), 7.113-7.163 (m, 2H), 6.823-6.858 (m, 2H), 5.715 (br, 1H), 4.650-4.682 (m, 1H), 3.935-3.977 (m, 1H), 3.595-3.652 (m, 2H), 3.425-3.445 (m, 1H), 2.396-2.415 (m, 1H), 2.246-2.272 (m, 1H), 1.386-1.414 (m, 6H).

Example 70: (S)-3-(3-(5-(trifluoromethyl)pyridin-2-yloxy)pyrrolidin-1-yl)biphenyl-2-carboxamide (Compound 1-72)

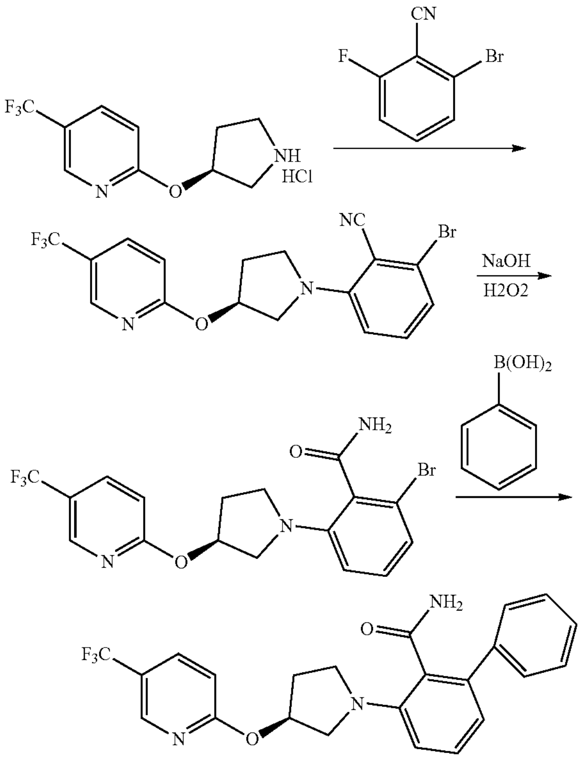

Step 1: (S)-2-bromo-6-(3-(5-(trifluoromethyl)pyridin-2-yloxy)pyrrolidin-1-yl)benzonitrile (YJ-000233-081)

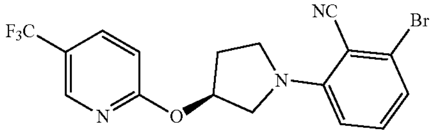 [SMILES: N#Cc1c(Br)cccc1N1CC[C@H](Oc2ccc(C(F)(F)F)cn2)C1]

The title compound was prepared following procedures described in example to give (S)-2-bromo-6-(3-(5-(trifluoromethyl)pyridin-2-yloxy)pyrrolidin-1-yl)benzonitrile (350 mg, 57% yield), Mass spec: 412 (M+H).

Step 2: (S)-2-bromo-6-(3-(5-(trifluoromethyl)pyridin-2-yloxy)pyrrolidin-1-yl)benzamide

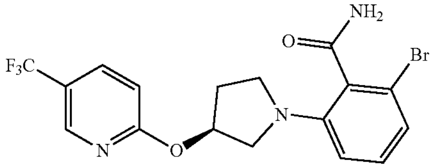 [SMILES: NC(=O)c1c(Br)cccc1N1CC[C@H](Oc2ccc(C(F)(F)F)cn2)C1]

The title compound was prepared following procedures described in example 17 (step 3) to give (S)-2-bromo-6-(3-(5-(trifluoromethyl)pyridin-2-yloxy)pyrrolidin-1-yl)benzamide (300 mg, 82% yield), Mass spec: 430 (M+H).

Step 3: (S)-3-(3-(5-(trifluoromethyl)pyridin-2-yloxy)pyrrolidin-1-yl)biphenyl-2-carboxamide

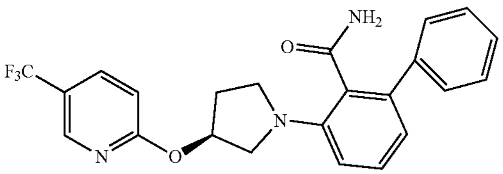 [SMILES: NC(=O)c1c(-c2ccccc2)cccc1N1CC[C@H](Oc2ccc(C(F)(F)F)cn2)C1]

The title compound was prepared following procedures described in example 67 (step 2) to give (S)-3-(3-(5-(trifluoromethyl)pyridin-2-yloxy)pyrrolidin-1-yl)biphenyl-2-carboxamide (45 mg, 35% yield), Mass spec: 428 (M+H), $t_R$=2.906 min, $^1$H-NMR (400 Hz, DMSO) δ=8.610 (s, 1H), 8.062-8.091 (m, 1H), 7.515 (s, 1H), 7.289-7.358 (m, 5H), 7.171-7.238 (m, 2H), 7.006-7.027 (d, 1H), 6.760-6.781 (d, 1H), 6.544-6.562 (d, 1H), 5.684 (br, 1H), 3.893-3.935 (m, 1H), 3.471-3.612 (m, 3H), 2.290-2.314 (m, 1H), 2.193-2.200 (m, 1H).

Example 71: (S)-6-chloro-2-(1-(2-nitrophenyl)pyrrolidin-3-yloxy)quinoline (Compound 1-68)

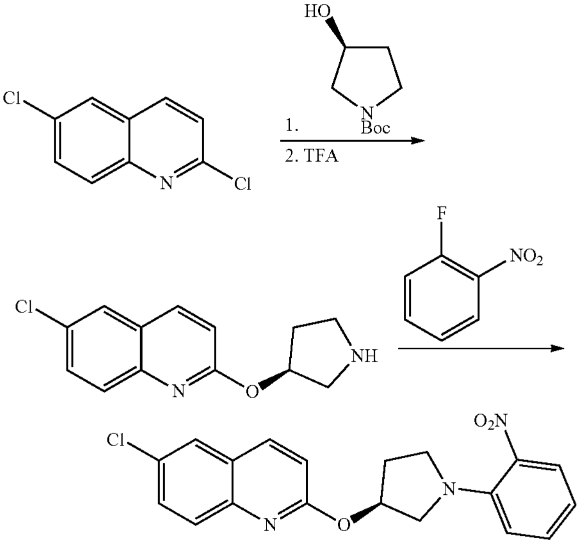

Step 1: (S)-6-chloro-2-(pyrrolidin-3-yloxy)quinoline

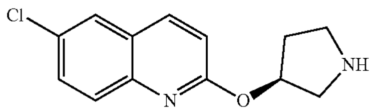 [SMILES: Clc1ccc2nc(O[C@H]3CCNC3)ccc2c1]

The title compound was prepared following procedures described Intermediate 4 to give crude (S)-6-chloro-2-(pyrrolidin-3-yloxy)quinoline (1.7 g, 89% yield), Mass spec: 249 (M+H)

Step 2: (S)-6-chloro-2-(1-(2-nitrophenyl)pyrrolidin-3-yloxy)quinoline

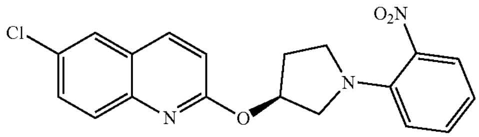 [SMILES: O=[N+]([O-])c1ccccc1N1CC[C@H](Oc2ccc3cc(Cl)ccc3n2)C1]

The title compound was prepared following procedures described in example 5 to give (S)-6-chloro-2-(1-(2-nitrophenyl)pyrrolidin-3-yloxy)quinoline (1.1 g, 67.5% yield), Mass spec: 370 (M+H), $t_R$=3.495 min, $^1$H-NMR (400 Hz, DMSO) δ=8.221-8.243 (d, 1H), 8.020-8.027 (d, 1H), 7.667-7.798 (m, 3H), 7.468-7.511 (m, 1H), 7.065-7.121 (m, 2H), 6.790-6.828 (m, 1H), 5.848 (br, 1H), 3.767-3.808 (m, 1H), 3.551-3.582 (m, 1H), 3.258-3.277 (m, 1H), 3.132-3.161 (m, 1H), 2.373-2.396 (m, 1H), 2.311-2.327 (m, 1H).

Example 72: (S)-2-(3-(6-chloroquinolin-2-yloxy) pyrrolidin-1-yl)aniline (Compound 1-69)

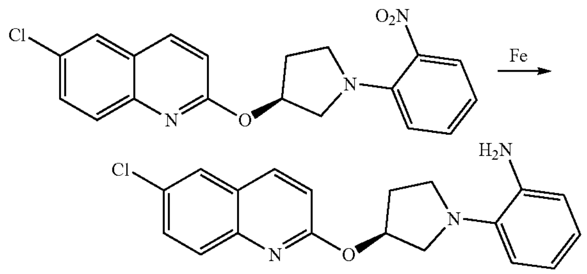

The title compound was prepared following procedures described in example 14 (step 2) to give (S)-2-(3-(6-chloroquinolin-2-yloxy)pyrrolidin-1-yl)aniline (420 mg, 54% yield), Mass spec: 340 (M+H), $t_R$=3.081 min, $^1$H-NMR (400 Hz, DMSO) δ=8.230-8.243 (d, 1H), 8.023-8.029 (d, 1H), 7.657-7.787 (dd, 2H), 7.096-7.119 (d, 1H), 6.896-6.918 (m, 1H), 6.747-6.787 (m, 1H), 6.654-6.676 (m, 1H), 6.517-6.558 (m, 1H), 5.710 (br, 1H), 4.687 (br, 2H), 3.524-3.566 (m, 1H), 3.195-3.234 (m, 1H), 3.112-3.147 (m, 1H), 3.026-3.143 (m, 1H), 2.469-2.486 (m, 1H), 2.041-2.077 (m, 1H).

Example 73: (S)-6-chloro-2-(1-(2-isopropoxyphenyl)pyrrolidin-3-yloxy)quinoline (Compound 1-76)

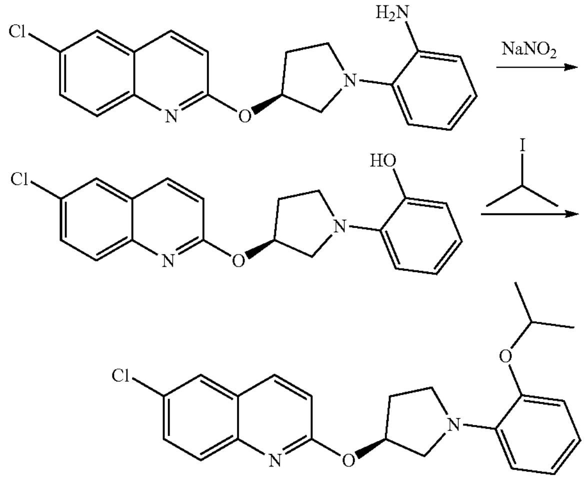

Step 1: (S)-2-(3-(6-chloroquinolin-2-yloxy)pyrrolidin-1-yl)phenol

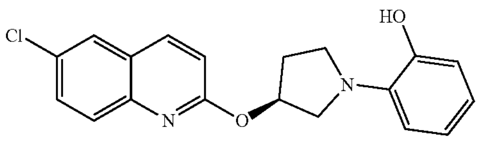 [SMILES: Oc1ccccc1N1CC[C@H](Oc2ccc3cc(Cl)ccc3n2)C1]

The title compounds was prepared following procedures described in example 14 (step 3) to give (S)-2-(3-(6-chloroquinolin-2-yloxy)pyrrolidin-1-yl)phenol (69 mg, 25% yield), Mass spec: 341 (M+H).

Step 2: (S)-6-chloro-2-(1-(2-isopropoxyphenyl)pyrrolidin-3-yloxy)quinoline

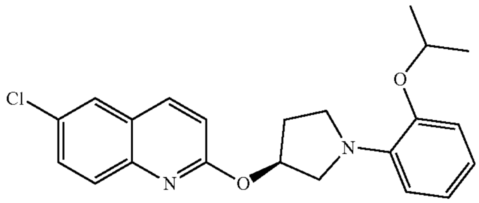 [SMILES: CC(C)Oc1ccccc1N1CC[C@H](Oc2ccc3cc(Cl)ccc3n2)C1]

The title compound was prepared following procedures described in example 15a to give (S)-6-chloro-2-(1-(2-isopropoxyphenyl)pyrrolidin-3-yloxy)quinoline (33 mg, 43% yield), Mass spec: 383 (M+H). $t_R$=4.596 min, $^1$H-NMR (400 Hz, DMSO) δ=8.223-8.246 (d, 1H), 8.027 (d, 1H), 7.669-7.795 (dd, 2H), 7.707-7.092 (d, 1H), 6.863-6.883 (d, 1H), 6.713-6.810 (m, 3H), 5.715 (br, 1H), 4.515-4.545 (m, 1H), 3.801-3.844 (m, 1H), 3.426-3.530 (m, 2H), 3.252-3.264 (m, 1H), 2.372-2.391 (m, 1H), 2.148 (m, 1H), 1.177-1.226 (m, 6H).

Example 74: (S)-6-chloro-2-(1-(3-nitrobiphenyl-4-yl)pyrrolidin-3-yloxy)quinoline (Compound 1-70)

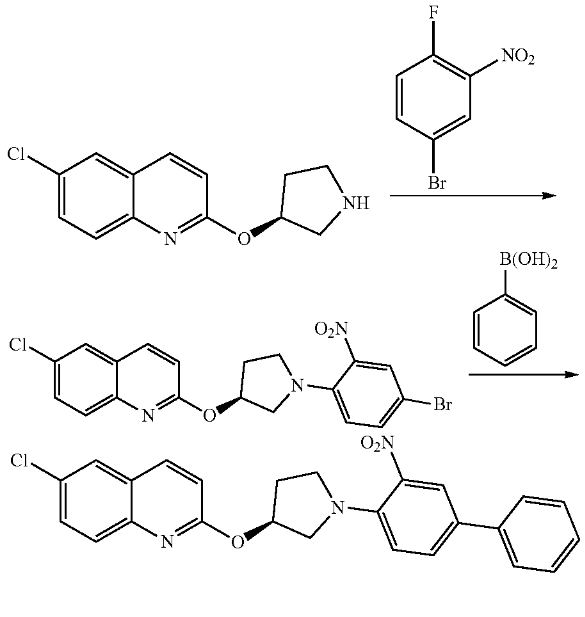

Step 1: (S)-2-(1-(4-bromo-2-nitrophenyl)pyrrolidin-3-yloxy)-6-chloroquinoline

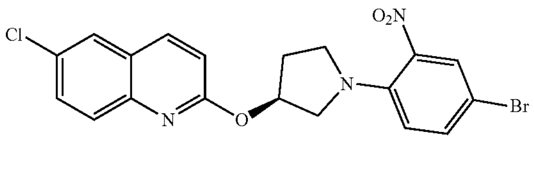 [SMILES: O=[N+]([O-])c1cc(Br)ccc1N1CC[C@H](Oc2ccc3cc(Cl)ccc3n2)C1]

The title compound was prepared following procedures described in example 5 to give (S)-2-(1-(4-bromo-2-nitrophenyl)pyrrolidin-3-yloxy)-6-chloroquinoline (824 mg, 65.6% yield), Mass spec: 448 (M+H).

Step 2: (S)-6-chloro-2-(1-(3-nitrobiphenyl-4-yl)pyrrolidin-3-yloxy)quinoline

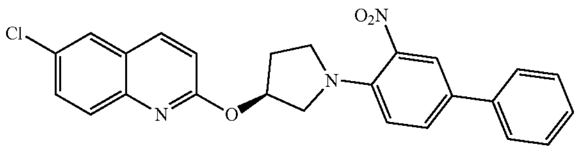 [SMILES: O=[N+]([O-])c1cc(-c2ccccc2)ccc1N1CC[C@H](Oc2ccc3cc(Cl)ccc3n2)C1]

The title compound was prepared following procedures described in example 67 (step 2) to give (S)-6-chloro-2-(1-(3-nitrobiphenyl-4-yl)pyrrolidin-3-yloxy)quinoline (673 mg, 82% yield), Mass spec: 446 (M+H), $t_R$=4.551 min, $^1$H-NMR (400 Hz, CDCl3) δ=8.037 (s, 1H), 7.911-7.933 (d, 1H), 7.770-7.792 (d, 1H), 7.683-7.7.716 (m, 2H), 7.562-7.602 (m, 3H), 7.350-7.471 (m, 2H), 7.285-7.346 (m, 1H), 7.059-7.081 (d, 1H), 6.885-6.907 (d, 1H), 5.949 (br, 1H), 3.924-3.965 (m, 1H), 3.749-3.772 (m, 1H), 3.452-3.459 (m, 1H), 3.257-3.287 (m, 1H), 2.431-2.461 (m, 2H).

Example 75: (S)-4-(3-(6-chloroquinolin-2-yloxy)pyrrolidin-1-yl)biphenyl-3-amine (Compound 1-71)

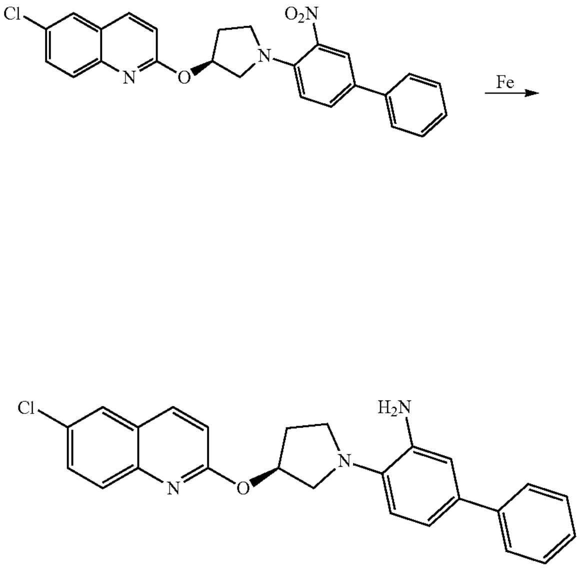

The title compound was prepared following procedures described in example 14 (step 2) to give (S)-4-(3-(6-chloroquinolin-2-yloxy)pyrrolidin-1-yl)biphenyl-3-amine (287 mg, 68.9% yield), Mass spec: 416 (M+H), $t_R$=3.658 min, $^1$H-NMR (400 Hz, CDCl3) δ=7.921-7.943 (d, 1H), 7.764-7.786 (d, 1H), 7.714-7.720 (d, 1H), 7.559-7.586 (m, 3H), 7.401-7.439 (m, 2H), 7.297-7.334 (m, 1H), 7.109-7.131 (m, 1H), 6.959-7.026 (m, 3H), 5.841 (br, 1H), 4.021 (br, 2H), 3.595-3.622 (m, 1H), 3.402-3.434 (m, 2H), 3.190-3.208 (m, 1H), 2.565-2.616 (m, 1H), 2.227-2.250 (m, 2H).

Example 76: (S)-4-(3-(6-chloroquinolin-2-yloxy)pyrrolidin-1-yl)biphenyl-3-carboxamide (Compound 1-67)

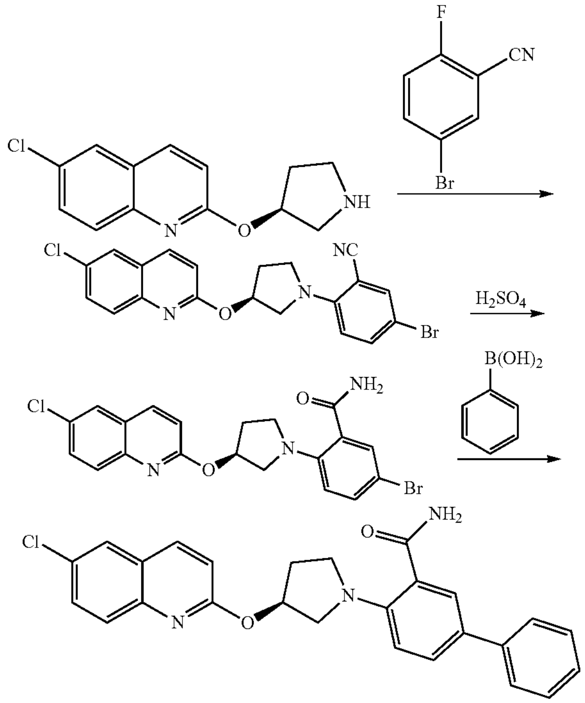

Step 1: (S)-5-bromo-2-(3-(6-chloroquinolin-2-yloxy)pyrrolidin-1-yl)benzonitrile

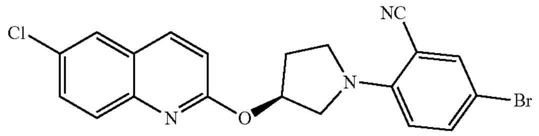 [SMILES: N#Cc1cc(Br)ccc1N1CC[C@H](Oc2ccc3cc(Cl)ccc3n2)C1]

The title compound was prepared following procedures described in example 5 to give (S)-5-bromo-2-(3-(6-chloroquinolin-2-yloxy)pyrrolidin-1-yl)benzonitrile (270 mg, 63% yield), Mass spec: 428 (M+H).

Step 2: (S)-5-bromo-2-(3-(6-chloroquinolin-2-yloxy)pyrrolidin-1-yl)benzamide

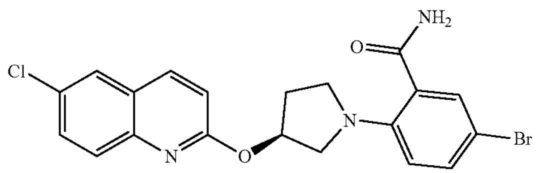 [SMILES: NC(=O)c1cc(Br)ccc1N1CC[C@H](Oc2ccc3cc(Cl)ccc3n2)C1]

The title compound was prepared following procedures described in example 64 (step 2) to give (S)-5-bromo-2-(3-

(6-chloroquinolin-2-yloxy)pyrrolidin-1-yl)benzamide (300 mg, 106% yield), Mass spec: 446 (M+H).

Step 3: (S)-4-(3-(6-chloroquinolin-2-yloxy)pyrrolidin-1-yl)biphenyl-3-carboxamide

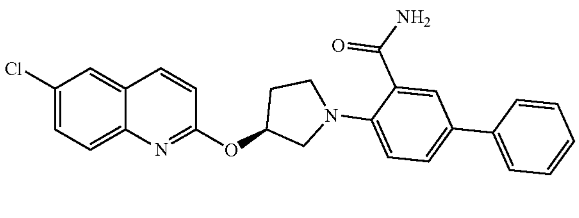 [SMILES: NC(=O)c1cc(-c2ccccc2)ccc1N1CC[C@H](Oc2ccc3cc(Cl)ccc3n2)C1]

The title compound was prepared following procedures described in example 67 (step 2) to give (S)-4-(3-(6-chloroquinolin-2-yloxy)pyrrolidin-1-yl)biphenyl-3-carboxamide (80 mg, 36% yield), Mass spec: 444 (M+H), $t_R$=4.144 min, $^1$H-NMR (400 Hz, DMSO) δ=8.229-8.252 (d, 1H), 8.032-8.037 (d, 1H), 7.799-7.873 (m, 2H), 7.683-7.711 (m, 1H), 7.533-7.611 (m, 4H), 7.341-7.435 (m, 2H), 7.287 (s, 1H), 7.268 (m, 1H), 7.062-7.064 (d, 1H), 6.858-6.880 (d, 1H), 5.825 (br, 1H), 3.912-3.954 (m, 1H), 3.582-3.601 (m, 1H), 3.430-3.453 (m, 2H), 2.372 (m, 1H), 2.283 (m, 1H).

Example 77: (R)-2-(3-(3-chloropyridin-2-yloxy)pyrrolidin-1-yl)-5-(pyridin-3-yl)benzamide hydrochloride (Compound 1-74)

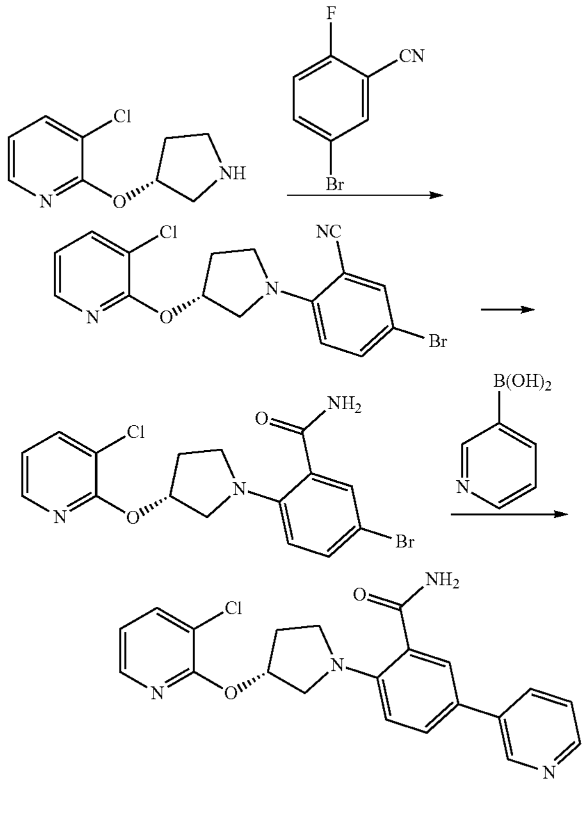

Step 1: (R)-5-bromo-2-(3-(3-chloropyridin-2-yloxy)pyrrolidin-1-yl)benzonitrile

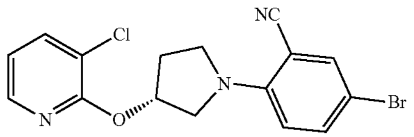 [SMILES: N#Cc1cc(Br)ccc1N1CC[C@@H](Oc2ncccc2Cl)C1]

The title compound was prepared following procedures described in example 5 using (R)-3-chloro-2-(pyrrolidin-3-yloxy)pyridine (prepared as intermediate 4) to give (R)-5-bromo-2-(3-(3-chloropyridin-2-yloxy)pyrrolidin-1-yl)benzonitrile (2.3 g, 80% yield), Mass spec: 378 (M+H).

Step 2: (R)-5-bromo-2-(3-(3-chloropyridin-2-yloxy)pyrrolidin-1-yl)benzamide

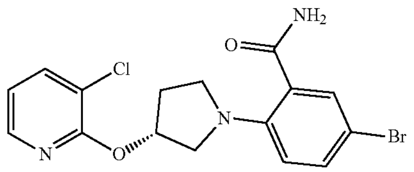 [SMILES: NC(=O)c1cc(Br)ccc1N1CC[C@@H](Oc2ncccc2Cl)C1]

The title compound was prepared following procedures described in example 64 (step 2) to give (R)-5-bromo-2-(3-(3-chloropyridin-2-yloxy)pyrrolidin-1-yl)benzamide (1.5 g, 82% yield), Mass spec: 396 (M+H).

Step 3: (R)-2-(3-(3-chloropyridin-2-yloxy)pyrrolidin-1-yl)-5-(pyridin-3-yl)benzamide hydrochloride

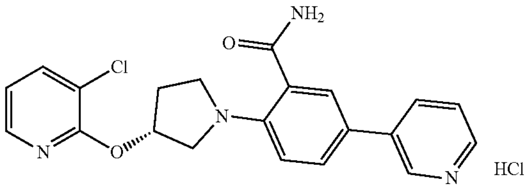 [SMILES: NC(=O)c1cc(-c2cccnc2)ccc1N1CC[C@@H](Oc2ncccc2Cl)C1 ; Cl]

The title compound was prepared following procedures described in example 67 (step 2) to give (R)-2-(3-(3-chloropyridin-2-yloxy)pyrrolidin-1-yl)-5-(pyridin-3-yl)benzamide hydrochloride (23.6 mg, 10.5% yield), Mass spec: 395 (M+H), $t_R$=1.525 min, $^1$H-NMR (400 Hz, DMSO) δ=9.159-9.162 (d, 1H), 8.705-8.799 (m, 2H), 8.130-8.146 (m, 1H), 8.003-8.036 (m, 1H), 7.865-7.886 (m, 2H), 7.747-7.862 (m, 2H), 7.429 (s, 1H), 7.013-7.044 (m, 1H), 6.892-6.915 (d, 1H), 5.661 (br, 1H), 3.901-3.942 (m, 2H), 3.252-3.360 (m, 2H), 2.215-2.326 (m, 2H).

Example 78: (R)-4-(3-(3-chloropyridin-2-yloxy)pyrrolidin-1-yl)biphenyl-3-carboxamide (Compound 1-75)

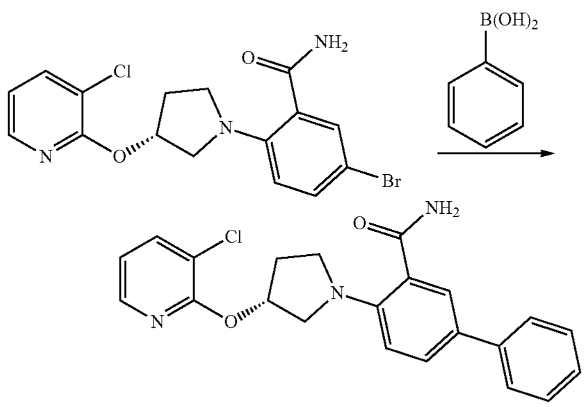

The title compound was prepared following procedures described in example 67 (step 2) to give (R)-4-(3-(3-chloropyridin-2-yloxy)pyrrolidin-1-yl)biphenyl-3-carboxamide (49.8 mg, 24.9% yield), Mass spec: 394 (M+H), $t_R$=2.741 min, $^1$H-NMR (400 Hz, DMSO) δ=8.126-8.143 (m, 1H), 7.849-7.878 (m, 2H), 7.499-7.582 (m, 4H), 7.299-7.407 (m, 2H), 7.223-7.259 (m, 2H), 7.003-7.036 (m, 1H), 6.630-6.851 (m, 1H), 5.642 (br, 1H), 3.856-3.898 (m, 1H), 3.509-3.549 (m, 1H), 3.381-3.403 (m, 1H), 3.266-3.284 (m, 1H), 2.283-2.318 (m, 1H), 2.171-2.202 (m, 1H).

Example 79: (R)-2-(3-(3-chloropyridin-2-yloxy)pyrrolidin-1-yl)-5-(pyridin-4-yl)benzamide hydrochloride (Compound 1-82)

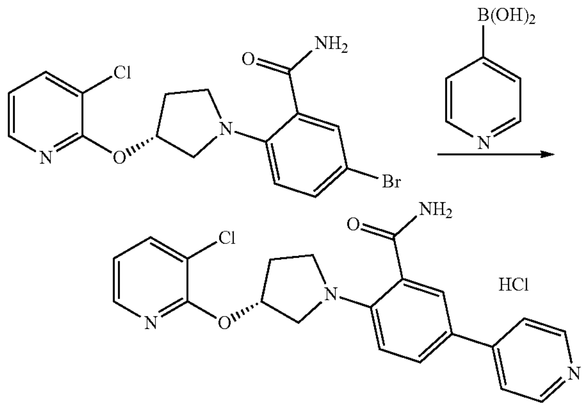

The title compound was prepared following procedures described in example 67 (step 2) to give (R)-2-(3-(3-chloropyridin-2-yloxy)pyrrolidin-1-yl)-5-(pyridin-4-yl)benzamide hydrochloride (90 mg, 45% yield), Mass spec: 395 (M+H), $t_R$=1.161 min, $^1$H-NMR (400 Hz, DMSO) δ=8.671-8.693 (m, 1H), 8.130-8.147 (m, 1H), 8.018 (m, 2H), 7.930 (m, 1H), 7.862-7.885 (m, 2H), 7.514-7.821 (m, 1H), 7.014-7.045 (m, 1H), 6.878-6.901 (m, 1H), 5.665 (br, 1H), 3.916-3.956 (m, 1H), 3.585-3.650 (m, 1H), 3.507-3.528 (m, 2H), 2.283-2.328 (m, 1H), 2.195-2.235 (m, 1H).

Example 80: (R)-2-(3-(3-chloropyridin-2-yloxy)pyrrolidin-1-yl)-5-(pyridin-2-yl)benzamide (Compound 1-85)

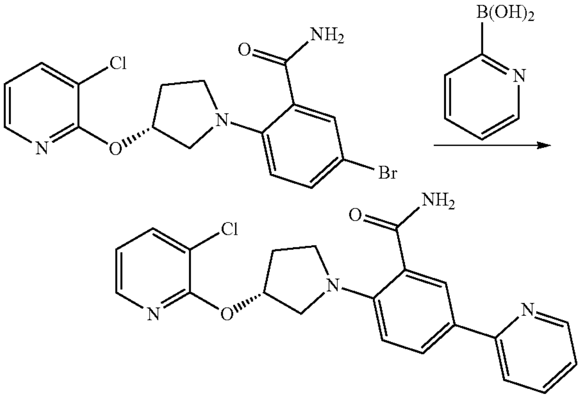

The title compound was prepared following procedures described in example 67 (step 2) to give (R)-2-(3-(3-chloropyridin-2-yloxy)pyrrolidin-1-yl)-5-(pyridin-2-yl)benzamide (21.5 mg, 53% yield), Mass spec: 395 (M+H), $t_R$=1.540 min, $^1$H-NMR (400 Hz, DMSO) δ=8.571-8.582 (d, 1H), 8.158-8.174 (m, 1H), 7.964-8.002 (m, 2H), 7.770-7.913 (m, 4H), 7.351 (m, 1H), 7.204-7.234 (m, 1H), 7.036-7.068 (m, 1H), 6.841-6.863 (m, 1H), 5.682 (br, 1H), 3.908-3.948 (m, 1H), 3.570-3.610 (m, 2H), 2.291-2.345 (m, 1H), 2.234-2.244 (m, 1H).

Example 81: (R)-4-(3-(pyridin-2-yloxy)pyrrolidin-1-yl)biphenyl-3-carboxamide (Compound 1-78)

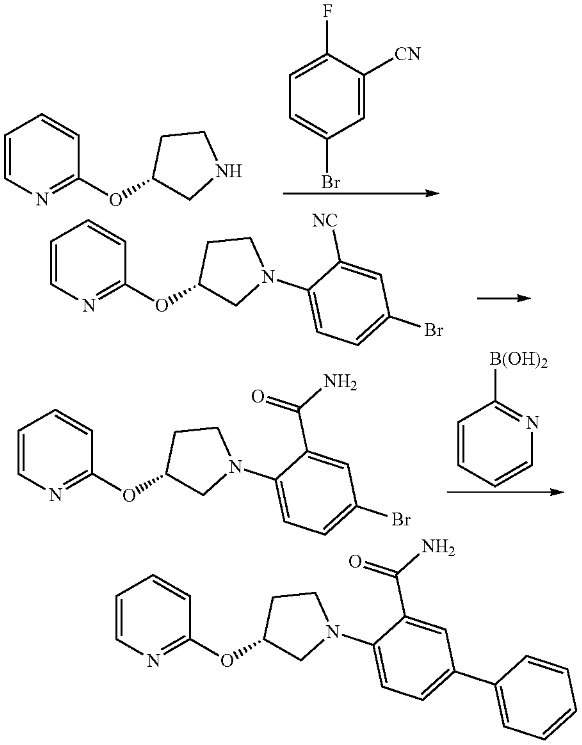

Step 1: (R)-5-bromo-2-(3-(pyridin-2-yloxy)pyrrolidin-1-yl)benzonitrile

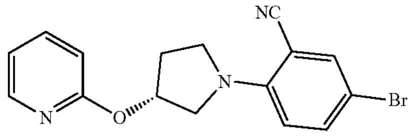 [SMILES: N#Cc1cc(Br)ccc1N1CC[C@@H](Oc2ccccn2)C1]

The title compound was prepared following procedures described in example 5 using (R)-2-(pyrrolidin-3-yloxy) pyridine (prepared as intermediate 4) to give (R)-5-bromo-2-(3-(pyridin-2-yloxy)pyrrolidin-1-yl)benzonitrile (700 mg, 60% yield), Mass spec: 344 (M+H).

Step 2: (R)-5-bromo-2-(3-(pyridin-2-yloxy)pyrrolidin-1-yl)benzamide

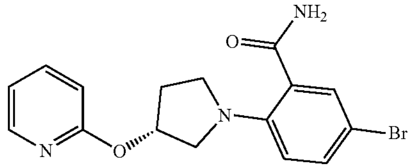 [SMILES: NC(=O)c1cc(Br)ccc1N1CC[C@@H](Oc2ccccn2)C1]

The title compound was prepared following procedures described in example 64 (step 2) to give (R)-5-bromo-2-(3-(pyridin-2-yloxy)pyrrolidin-1-yl)benzamide (450 mg, 55% yield), Mass spec: 362 (M+H).

Step 3: (R)-4-(3-(pyridin-2-yloxy)pyrrolidin-1-yl) biphenyl-3-carboxamide

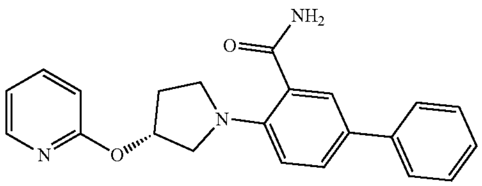 [SMILES: NC(=O)c1cc(-c2ccccc2)ccc1N1CC[C@@H](Oc2ccccn2)C1]

The title compound was prepared following procedures described in example 67 (step 2) to give (R)-4-(3-(pyridin-2-yloxy)pyrrolidin-1-yl)biphenyl-3-carboxamide (40 mg, 40% yield), Mass spec: 360 (M+H), $t_R$=2.491 min, $^1$H-NMR (400 Hz, DMSO) δ=8.195 (m, 1H), 7.897 (m, 1H), 7.527-7.703 (m, 5H), 7.269-7.416 (m, 4H), 6.989 (m, 1H), 6.784-6.860 (dd, 2H), 5.606 (br, 1H), 3.837-3.862 (m, 1H), 3.519-3.563 (m, 1H), 3.331-3.365 (m, 2H), 2.286 (m, 1H), 2.189 (m, 1H).

Example 82: (R)-2-(3-(pyridin-2-yloxy)pyrrolidin-1-yl)-5-(pyridin-4-yl)benzamide (Compound 1-79)

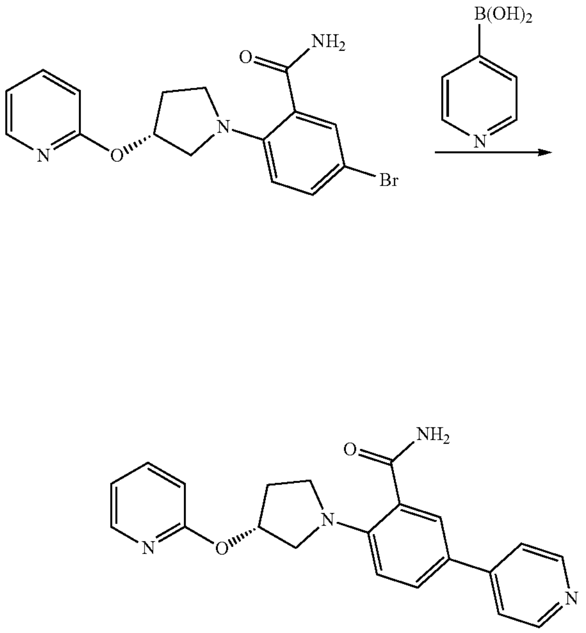 [SMILES: NC(=O)c1cc(Br)ccc1N1CC[C@@H](Oc2ccccn2)C1 ; OB(O)c1ccncc1 ; NC(=O)c1cc(-c2ccncc2)ccc1N1CC[C@@H](Oc2ccccn2)C1]

The title compound was prepared following procedures described in example 67 (step 2) to give (R)-2-(3-(pyridin-2-yloxy)pyrrolidin-1-yl)-5-(pyridin-4-yl)benzamide (30 mg, 46% yield), Mass spec: 361 (M+H), $t_R$=0.700 min, $^1$H-NMR (400 Hz, DMSO) δ=8.522-8.537 (d, 2H), 8.180-8.193 (d, 1H), 7.903 (s, 1H), 7.627-7.671 (m, 5H), 7.386 (s, 1H), 6.775-6.991 (m, 3H), 5.609 (br, 1H), 3.863-3.893 (m, 1H), 3.567-3.591 (m, 1H), 3.312-3.381 (m, 2H), 2.288 (m, 1H), 2.199 (m, 1H).

Example 83: (R)-2-(3-(3-chloropyridin-2-yloxy) pyrrolidin-1-yl)-5-(pyridin-3-yl)benzamide hydrochloride (Compound 1-87)

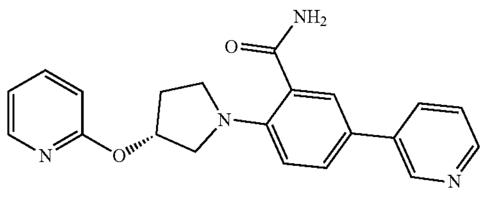 [SMILES: NC(=O)c1cc(-c2cccnc2)ccc1N1CC[C@@H](Oc2ccccn2)C1]

The title compound was prepared following procedures described in example 67 (step 2) to give (R)-2-(3-(3-chloropyridin-2-yloxy)pyrrolidin-1-yl)-5-(pyridin-3-yl)benzamide hydrochloride (20 mg, 20.5% yield), Mass spec: 361 (M+H), $t_R$=2.116 min, $^1$H-NMR (400 Hz, DMSO) δ=8.843 (s, 1H), 8.461-8.473 (d, 1H), 8.186-8.197 (d, 1H), 7.787-7.992 (m, 2H), 7.579-7.701 (m, 3H), 7.360 (m, 2H), 6.784-6.991 (m, 3H), 5.610 (br, 1H), 3.856 (m, 1H), 3.556-3.566 (m, 1H), 3.420 (m, 1H), 3.297-3.337 (m, 1H), 2.209-2.308 (m, 2H).

Example 84: (R)-5-(pyridin-2-yl)-2-(3-(pyridin-2-yloxy)pyrrolidin-1-yl)benzamide (Compound 1-88)

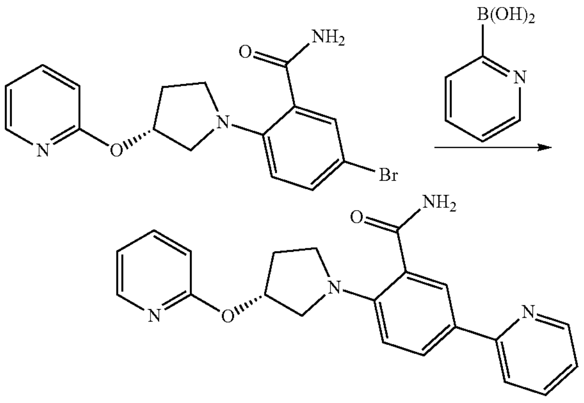

The title compound was prepared following procedures described in example 67 (step 2) to give (R)-5-(pyridin-2-yl)-2-(3-(pyridin-2-yloxy)pyrrolidin-1-yl)benzamide (100 mg, 61% yield), Mass spec: 361 (M+H), $t_R$=1.474 min, $^1$H-NMR (400 Hz, DMSO) δ=8.664-8.676 (m, 1H), 8.179-8.197 (m, 1H), 7.957-7.977 (m, 1H), 7.871-7.875 (m, 2H), 7.694-7.697 (d, 1H), 7.479 (s, 1H), 7.329-7.376 (m, 4H), 6.969-6.999 (m, 1H), 6.781-6.802 (d, 1H), 5.609 (br, 1H), 3.868-3.884 (m, 1H), 3.593-3.610 (m, 1H), 3.435-3.440 (m, 1H), 3.297-3.312 (m, 1H), 2.285-2.331 (m, 1H), 2.186-2.198 (m, 1H).

Example 85: (R)-4-(3-(5-(trifluoromethyl)pyridin-2-yloxy)pyrrolidin-1-yl)biphenyl-3-amine (Compound 1-93)

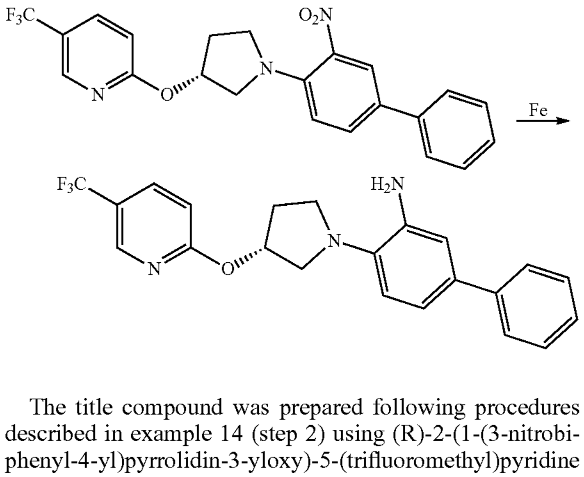

The title compound was prepared following procedures described in example 14 (step 2) using (R)-2-(1-(3-nitrobiphenyl-4-yl)pyrrolidin-3-yloxy)-5-(trifluoromethyl)pyridine (prepared as example 67) to give (R)-4-(3-(5-(trifluoromethyl)pyridin-2-yloxy)pyrrolidin-1-yl)biphenyl-3-amine (360 mg, 39% yield), Mass spec: 400 (M+H). $t_R$=3.387 min, $^1$H-NMR (400 Hz, DMSO) δ=8.599-8.606 (m, 1H), 8.056-8.084 (dd, 1H), 7.520-7.541 (M, 2 h), 7.382-7.420 (M, 2H), 7.253-7.292 (m, 1H), 7.034-7.057 (d, 1H), 6.944-6.984 (m, 2H), 6.825-6.851 (m, 1H), 5.615 (br, 1H), 4.762 (s, 1H), 3.544-3.583 (m, 1H), 3.266-3.299 (m, 1H), 3.118-3.153 (m, 1H), 3.014-3.069 (m, 1H), 2.422-2.509 (m, 1H), 2.030-2.051 (m, 1H).

Example 86: (R)-4-(3-(5-(trifluoromethyl)pyridin-2-yloxy)pyrrolidin-1-yl)biphenyl-3-ol (Compound 1-89)

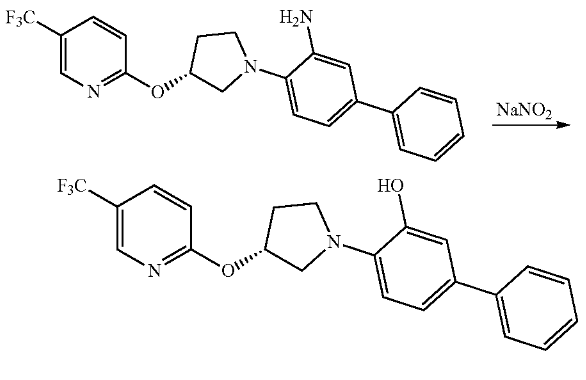

The title compound was prepared following procedures described in example 14 (step 3) to give (R)-4-(3-(5-(trifluoromethyl)pyridin-2-yloxy)pyrrolidin-1-yl)biphenyl-3-ol (50 mg, 12% yield), Mass spec: 401 (M+H), $t_R$=3.186 min, $^1$H-NMR (400 Hz, DMSO) δ=9.285 (s, 1H), 8.621-8.623 (d, 1H), 8.060-8.088 (m, 1H), 7.381-7.552 (m, 4H), 7.238-7.275 (m, 1H), 7.002-7.042 (m, 3H), 6.718-6.738 (d, 1H), 5.629 (br, 1H), 3.807-3.850 (m, 1H), 3.483-3.572 (m, 2H), 3.259-3.328 (m, 1H), 2.312-2.365 (m, 1H), 2.078-2.128 (m, 1H).

Example 87: (R)-2-(1-(3-methoxybiphenyl-4-yl)pyrrolidin-3-yloxy)-5-(trifluoromethyl)pyridine (Compound 1-111)

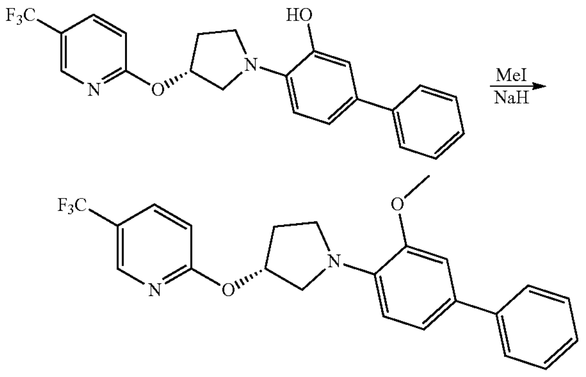

The title compound was prepared following procedures described in example 68 (step 3) to give (R)-2-(1-(3-methoxybiphenyl-4-yl)pyrrolidin-3-yloxy)-5-(trifluoromethyl)pyridine (50 mg, 50% yield), Mass spec: 415 (M+H), $t_R$=3.631 min, $^1$H-NMR (400 Hz, DMSO) δ=8.629 (s, 1H), 8.059-8.087 (q, 1H), 7.619-7.639 (d, 2H), 7.393-7.431 (m, 2H), 7.274-7.293 (m, 1H), 7.145-7.184 (m, 2H), 7.022-7.044 (d, 1H), 6.767-6.788 (d, 1H), 5.656 (br, 1H), 3.848-3.833 (m, 4H), 3.557-3.677 (m, 1H), 3.410-30440 (m, 1H), 3.297-3.318 (m, 1H), 2.505-2.514 (m, 1H), 2.331-2.337 (m, 1H).

Example 88: (R)-2-(4-(3-(5-(trifluoromethyl)pyridin-2-yloxy)pyrrolidin-1-yl)biphenyl-3-yloxy)ethanol (Compound 1-117)

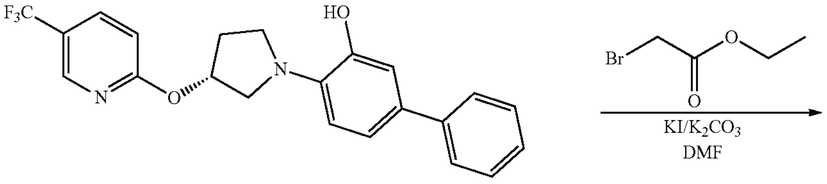

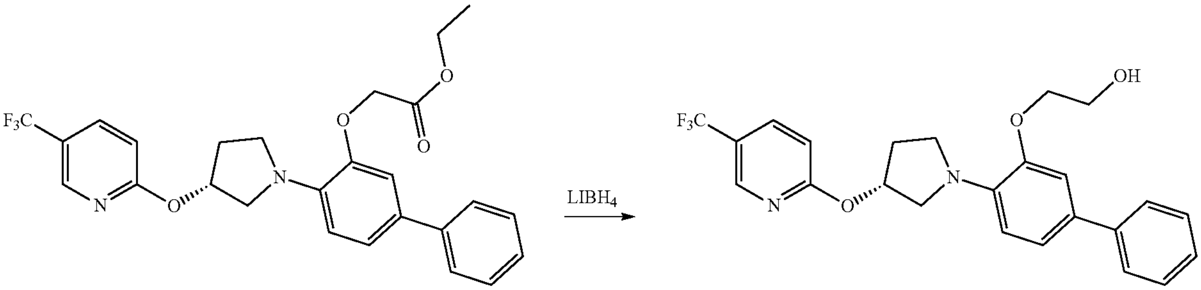

Step 1: (R)-ethyl 2-(4-(3-(5-(trifluoromethyl)pyridin-2-yloxy)pyrrolidin-1-yl)biphenyl-3-yloxy)acetate

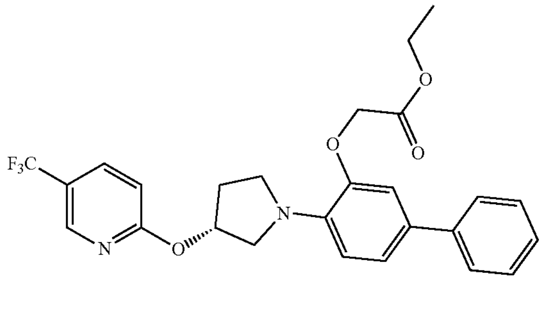 [SMILES: CCOC(=O)COc1cc(-c2ccccc2)ccc1N1CC[C@@H](Oc2ccc(C(F)(F)F)cn2)C1]

To a solution of (R)-4-(3-(5-(trifluoromethyl)pyridin-2-yloxy)pyrrolidin-1-yl)biphenyl-3-ol (60 mg, 0.15 mmol) in DMF was added ethyl 2-bromoacetate (49.5 mg, 0.3 mmol), K2CO3 (50 mg, 0.3 mmol), and KI ( ), the mixture was stirred at 45° C. for 1 h, diluted with DCM, washed by NaHCO3 solution, LiCl solution, and brine, dried over Na2SO4, removal the solvent to left the residue which was purified by silica gel to give (R)-ethyl 2-(4-(3-(5-(trifluoromethyl)pyridin-2-yloxy)pyrrolidin-1-yl)biphenyl-3-yloxy)acetate (70 mg, 90% yield), Mass spec: 487 (M+H).

Step 2: (R)-2-(4-(3-(5-(trifluoromethyl)pyridin-2-yloxy)pyrrolidin-1-yl)biphenyl-3-yloxy)ethanol

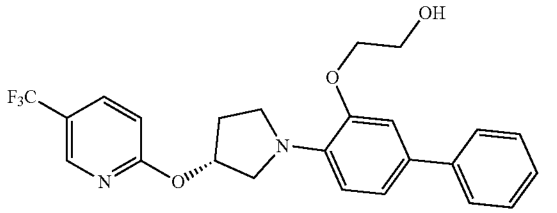 [SMILES: OCCOc1cc(-c2ccccc2)ccc1N1CC[C@@H](Oc2ccc(C(F)(F)F)cn2)C1]

To a solution of (R)-ethyl 2-(4-(3-(5-(trifluoromethyl) pyridin-2-yloxy)pyrrolidin-1-yl)biphenyl-3-yloxy) acetate (40 mg, 0.08 mmol) in DME (1 mL) at 0° C. was added LiBH4 (3 mg, 0.16 mmol), the mixture was stirred at rt for 2 h, cooled to 0° C., extracted with DCM, washed with NH4Cl, dried over Na2SO4, removal the solvent to left the residue which was purified by silica gel to give (R)-2-(4-(3-(5-(trifluoromethyl) pyri din-2-yloxy)pyrrolidin-1-yl)biphenyl-3-yloxy)ethanol (17 mg, 35%), Mass spec: 445 (M+H), $t_R$=3.087 min, $^1$H-NMR (400 Hz, CDCl3) δ=8.462-8.467 (q, 1H), 7.777-7.806 (d, 1H), 7.556-7.579 (d, 2H), 7.417-7.455 (m, 2H), 7.196-7.342 (m, 3H), 6.929-6.949 (d, 1H), 6.856-6.877 (d, 1H), 5.719 (br, 1H), 4.221-4.242 ( ) m, 2H), 3.816-3.887 (m, 3H), 3.559-3.703 (m, 2H), 3.345-3.358 (m, 1H), 2.428-2.462 (m, 1H), 2.264-2.281 (m, 1H).

Example 89: (S)-ethyl 2-(4-(3-(5-(trifluoromethyl)pyridin-2-yloxy)pyrrolidin-1-yl)biphenyl-3-yloxy)acetate (Compound 134)

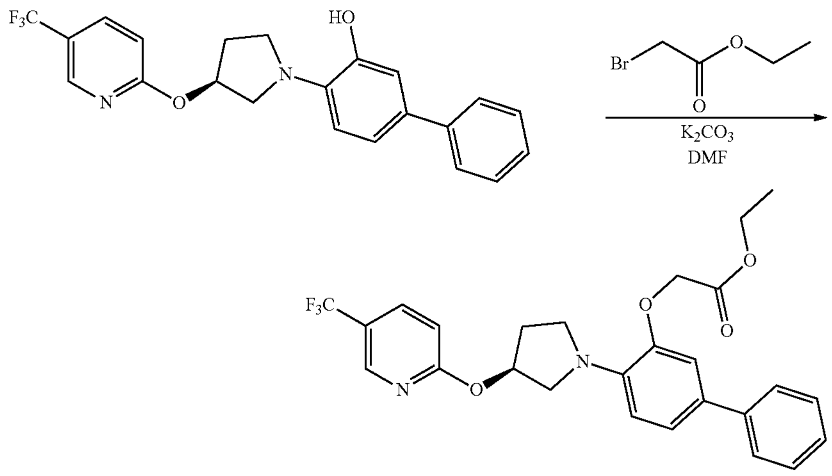

The title compound was prepared following procedures described in example 88 (step 1) to give (S)-ethyl 2-(4-(3-(5-(trifluoromethyl)pyridin-2-yloxy)pyrrolidin-1-yl)biphenyl-3-yloxy)acetate (190 mg, 90% yield), Mass spec: 487 (M+H), $t_R$=3.400 min, $^1$H-NMR (400 Hz, DMSO) δ=8.617-8.620 (d, 1H), 8.061-8.089 (m, 1H), 7.603-7.624 (m, 2H), 7.388-7.426 (2H), 7.139-7.288 (m, 3H), 7.022-7.043 (d, 1H), 6.784-6.805 (d, 1H), 5.671 (br, 1H), 4.863 (s, 2H), 4.135-4.188 (q, 2H), 3.904-3.948 (m, 1H), 3.549-3.637 (m, 2H), 3.343-3.347 (m, 1H), 2.327-2.360 (m, 1H), 2.162-2.165 (m, 1H).

Example 90: (S)-2-(4-(3-(5-(trifluoromethyl)pyridin-2-yloxy)pyrrolidin-1-yl)biphenyl-3-yloxy)ethanol (Compound 135)

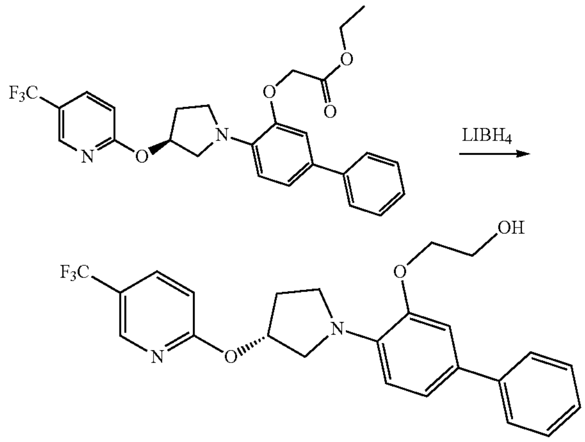

The title compound was prepared following procedures described in example 88 (step 2) to give (S)-2-(4-(3-(5-(trifluoromethyl)pyridin-2-yloxy)pyrrolidin-1-yl)biphenyl-3-yloxy)ethanol (90 mg, 75% yield), Mass spec: 445 (M+H), $t_R$=2.922 min, $^1$H-NMR (400 Hz, DMSO) δ=8.618-8.624 (s, 1H), 8.057-8.086 (m, 1H), 7.605-7.627 (m, 2H), 7.385-7.424 (m, 2H), 7.247-7.284 (m, 1H), 7.142-7.187 (m, 2H), 7.018-7.040 (d, 1H), 6.750-6.771 (d, 1H), 5.672 (br, 1H), 4.840-4.868 (t, 1H), 4.043-4.082 (m, 2H), 3.892-3.935 (m, 1H), 3.737-3.767 (m, 2H), 3.593-3.624 (m, 1H), 3.469-3.499 (m, 1H), 3.332-3.335 (m, 1H), 2.319-2.325 (m, 1H), 2.116-2.119 (m, 1H).

Example 91: (R)-5-(4,5-dihydro-1H-imidazol-2-yl)-2-(3-(5-(trifluoromethyl)pyridin-2-yloxy)pyrrolidin-1-yl)benzamide (Compound 100)

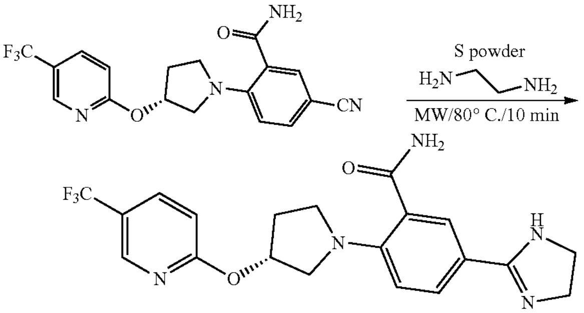

To a solution of (R)-5-cyano-2-(3-(5-(trifluoromethyl)pyridin-2-yloxy)pyrrolidin-1-yl)benzamide (example 35) (100 mg, 0.26 mmol) in ethane-1,2-diamine was added sulfur (33 mg, 0.13 mmol). The mixture was heated to 80° C. under microwave for 10 min, then poured into ice water, which caused the product to precipitates as a solid, the product was purified by vacuum filtration and dried to give (R)-5-(4,5-dihydro-1H-imidazol-2-yl)-2-(3-(5-(trifluoromethyl)pyridin-2-yloxy)pyrrolidin-1-yl)benzamide (21 mg, 17% yield), Mass spec: 420 (M+H), $t_R$=0.429 min, $^1$H-NMR (400 Hz, DMSO) δ=8.625 (s, 1H), 8.335 (br, 1H), 8.060-8.089 (dd, 1H), 7.865 (s, 1H), 7.146-7.406 (m, 4H), 7.001-7.022 (d, 1H), 5.701 (br, 1H), 3.813-3.877 (m, 2H), 3.728 (s, 4H), 3.293-3.387 (m, 2H), 2.250-2.330 (m, 1H), 2.234-2.244 (m, 1H).

Example 92: (R)-5-(1H-imidazol-2-yl)-2-(3-(5-(trifluoromethyl)pyridin-2-yloxy)pyrrolidin-1-yl)benzamide (Compound 1-107)

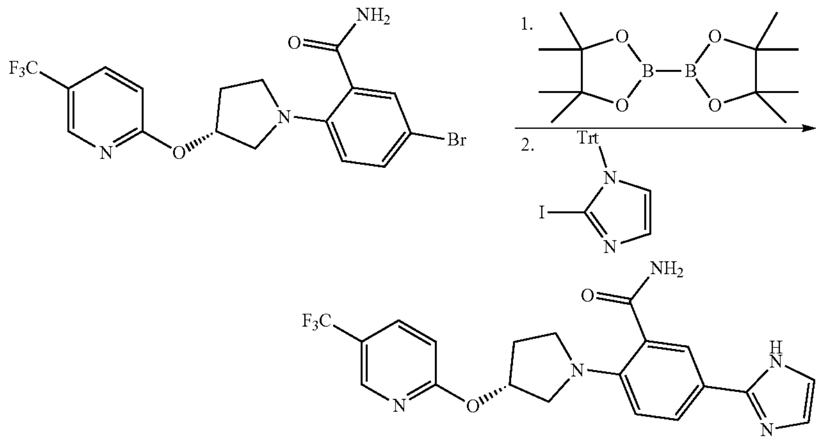

To a solution of (R)-5-bromo-2-(3-(5-(trifluoromethyl)pyridin-2-yloxy)pyrrolidin-1-yl)benzamide (example 35, step 2) (214 mg, 0.5 mmol), 4,4,4',4',5,5,5',5'-octamethyl-2,2'-bi(1,3,2-dioxaborolane) (254 mg, 1 mmol) in dioxane (2 mL) was added AcOK (147 mg, 1.5 mmol), Pd(dppf)Cl2 (21 mg, 10% wt), the mixture was degassed with N2, then heated to 80° C. for 3 h, EA was added, filtered, the organic layer was washed by water, brine, dried over Na2SO4, removal the solvent to get the crude product which could be used directly. The crude product (48 mg, 0.1 mmol) in Dioxane/H2O (5 mL/1 mL) was added 2-iodo-1-trityl-1H-imidazole (38 mg, 2 mmol) (prepared according to PCT 2008096360), Pd(dppf)Cl2 (5 mg, 10% wt) and K2CO3, the mixture was stirred at 100° C. for 1 h, diluted with EA, washed with water, brine, dried over Na2SO4, removal the solvent to left crude product which was purified by silica gel to give (R)-5-(1H-imidazol-2-yl)-2-(3-(5-(trifluoromethyl)pyridin-2-yloxy)pyrrolidin-1-yl)benzamide (10 mg, 24% yield), Mass spec: 418 (M+H), $t_R$=2.622 min, $^1$H-NMR (400 Hz, DMSO) δ=12.565 (s, 1H), 8.624 (s, 1H), 8.052-8.080 (dd, 1H), 7.792 (s, 1H), 7.248-7.345 (m, 5H), 7.005-7.026 (m, 2H), 5.694 (br, 1H), 3.848-3.888 (m, 1H), 3.492-3.630 (m, 3H), 2.331-2.352 (m, 1H), 2.210-2.246 (m, 1H).

Example 93: (R)-5-(trifluoromethyl)-2-(3-(5-(trifluoromethyl)pyridin-2-yloxy)pyrrolidin-1-yl)benzamide (Compound 1-84)

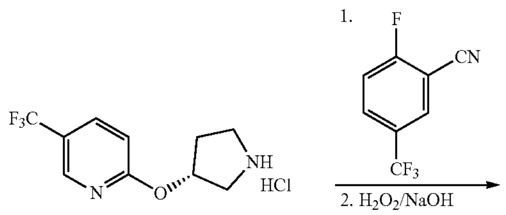

-continued

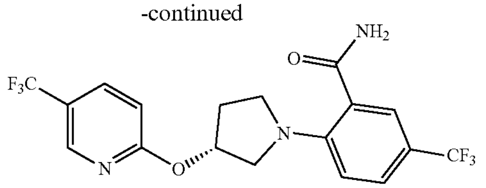

To a solution of (R)-2-(pyrrolidin-3-yloxy)-5-(trifluoromethyl)pyridine hydrochloride (250 mg, 1.07 mmol) (intermediate 4), 2-fluoro-5-(trifluoromethyl)benzonitrile (189 mg, 1.0 mmol) and K2CO3 (414 mg, 3 mmol) in 5 mL DMF was stirred at 100° C. for 2 h, the mixture was washed with LiCl solution, extracted with EA, dried over Na2SO4, evaporated to give the intermediate product as brown oil, which, dissolved in 12 mL EtOH, was added $H_2O_2$ (6 mL, 30%) and NaOH solution (12 mL, 6M), stirred at 60° C. for overnight, the mixture was poured into ice-water, the precipitate was filtered, washed by Et2O, and dried to give (R)-5-(trifluoromethyl)-2-(3-(5-(trifluoromethyl)pyridin-2-yloxy)pyrrolidin-1-yl)benzamide (200 mg, 47.6% yield), Mass spec: 420 (M+H), $t_R$=2.855 min, $^1$H-NMR (400 Hz, DMSO) δ=8.613-8.617 (d, 1H), 8.050-8.077 (dd, 1H), 7.933 (s, 1H), 7.494-7.521 (m, 1H), 7.437-1.441 (d, 1H), 6.991-7.013 (d, 1H), 6.840-6.862 (d, 1H), 5.699 (br, 1H), 3.864-3.906 (m, 1H), 3.550-3.593 (m, 1H), 3.400-3.471 (m, 1H), 3.313-3.336 (m, 1H), 2.297-2.329 (m, 1H), 2.224-2.256 (m, 1H).

Example 94: (S)-5-phenoxy-2-(3-(5-(trifluoromethyl)pyridin-2-yloxy)pyrrolidin-1-yl)benzamide (Compound 1-124)

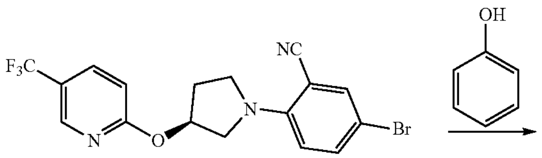

-continued

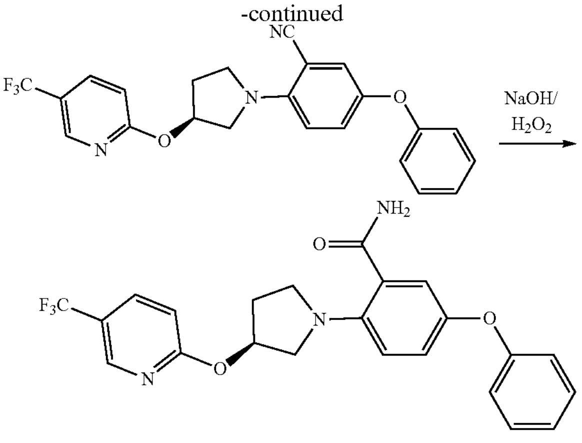

Step 1: (S)-5-phenoxy-2-(3-(5-(trifluoromethyl)pyridin-2-yloxy)pyrrolidin-1-yl)benzonitrile

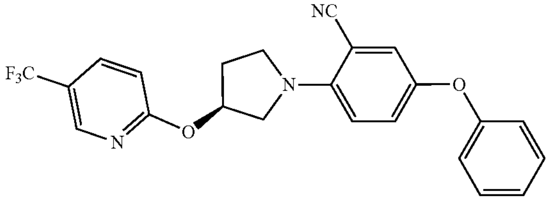 [SMILES: N#Cc1cc(Oc2ccccc2)ccc1N1CC[C@H](Oc2ccc(C(F)(F)F)cn2)C1]

The mixture of (S)-5-bromo-2-(3-(5-(trifluoromethyl)pyridin-2-yloxy)pyrrolidin-1-yl)benzonitrile (205 mg, 0.5 mmol) (example 27, step 2), phenol (94 mg, 1 mmol), CuI (47 mg, 0.25 mmol), Cs2CO3 (326 mg, 1 mmol) and 2-(dimethylamino)acetic acid hydrochloride (35 mg, 0.25 mmol) in Dioxane/DMF (1.5 mL/0.5 mL) was stirred at 160° C. under microwave for 1 h, diluted with EA, washed with water, brine, dried over Na2SO4, removal the solvent to left the crude (S)-5-phenoxy-2-(3-(5-(trifluoromethyl)pyridin-2-yloxy)pyrrolidin-1-yl)benzonitrile (220 mg) which can be used directly, Mass spec: 426 (M+H).

Step 2: (S)-5-phenoxy-2-(3-(5-(trifluoromethyl)pyridin-2-yloxy)pyrrolidin-1-yl)benzamide

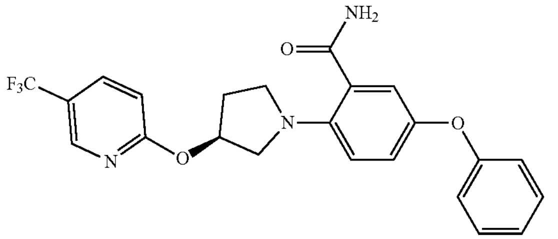 [SMILES: NC(=O)c1cc(Oc2ccccc2)ccc1N1CC[C@H](Oc2ccc(C(F)(F)F)cn2)C1]

The title compound was prepared following procedures described in example 63 (step 3) to give (S)-5-phenoxy-2-(3-(5-(trifluoromethyl)pyridin-2-yloxy)pyrrolidin-1-yl)benzamide (30 mg, 22% yield), Mass spec: 444 (M+H), $t_R$=3.098 min, $^1$H-NMR (400 Hz, DMSO) δ=8.617 (s, 1H), 8.064-8.093 (q, 1H), 7.941 (s, 1H), 7.328-7.374 (m, 3H), 6.861-7.088 (m, 7H), 5.665 (br, 1H), 3.762-3.791 (m, 1H), 3.473-3.494 (m, 1H), 3.257-3.338 (m, 2H), 2.330-2.351 (m, 1H), 2.188-2.190 (m, 1H).

Example 95: (S)-(4-(3-(3-chloropyridin-2-yloxy)pyrrolidin-1-yl)biphenyl-3-yl)methanamine hydrochloride (Compound 1-125)

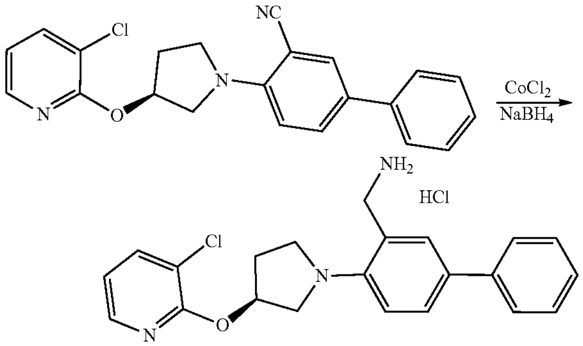

To a solution of (S)-4-(3-(3-chloropyridin-2-yloxy)pyrrolidin-1-yl)biphenyl-3-carbonitrile (300 mg, 0.8 mmol) in 5 mL MeOH was added CoCl2 (206 mg, 1.6 mmol) and NaBH4 (304 mg, 8 mmol) at 0° C., the mixture was stirred at rt, for 12 h, the reaction mixture was filtered, the filtrate was quenched with NH3·H2O, extracted with DCM, dried over Na2SO4, removal the solvent to left the residue which was purified by silica gel, then Prep-HPLC, freezing dryness with HCl to give (S)-(4-(3-(3-chloropyridin-2-yloxy)pyrrolidin-1-yl)biphenyl-3-yl)methanamine hydrochloride (9 mg, 3%), Mass spec: 380 (M+H), $t_R$=2.177 min, $^1$H-NMR (400 Hz, DMSO) δ=8.479 (br, 3H), 8.153-8.168 (q, 1H), 7.851-7.937 (m, 2H), 7.622-7.604 (m, 3H), 7.444-7.483 (m, 2H), 7.318-7.335 (m, 1H), 7.234-7.255 (d, 1H), 7.043-7.234 (m, 1H), 5.668 (br, 1H), 4.163-4.194 (m, 2H), 3.694-3.734 (m, 1H), 3.418-3.477 (m, 1H), 3.239-3.282 (m, 2H), 2.421-2.471 (m, 1H), 2.128-2.161 (m, 1H).

Example 96: (S)-(4-(3-(3-chloropyridin-2-yloxy)pyrrolidin-1-yl)biphenyl-3-yl)methanol (Compound 1-126)

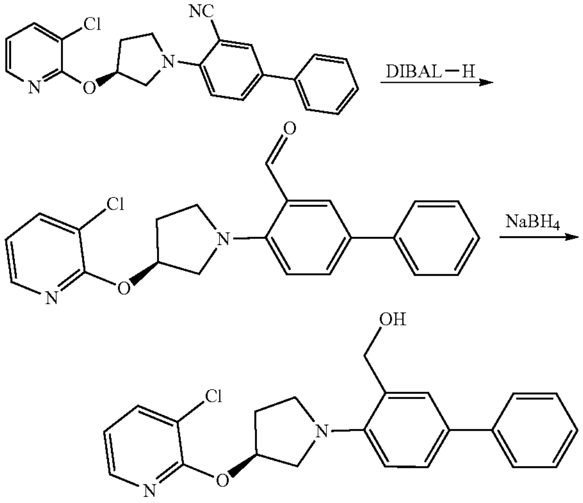

Step 1: (S)-4-(3-(3-chloropyridin-2-yloxy)pyrrolidin-1-yl)biphenyl-3-carbaldehyde

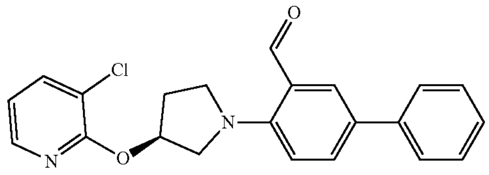 [SMILES: O=Cc1cc(-c2ccccc2)ccc1N1CC[C@H](Oc2ncccc2Cl)C1]

To a solution of (S)-4-(3-(3-chloropyridin-2-yloxy)pyrrolidin-1-yl)biphenyl-3-carbonitrile (600 mg, 1.6 mmol) in DCM/THF (4 mL/3 mL) at −78° C. was added DIBAL-H (10 ml, 1.5M in Tol.), the mixture was stirred at this temperature for 3 h, quenched by ice water, extracted with DCM, dried over Na2SO4, removal the solvent to left the residue which was purified by silica gel to give (S)-4-(3-(3-chloropyridin-2-yloxy)pyrrolidin-1-yl)biphenyl-3-carbaldehyde (90 mg, 15%), Mass spec: 379 (M+H).

Step 2: (S)-(4-(3-(3-chloropyridin-2-yloxy)pyrrolidin-1-yl)biphenyl-3-yl)methanol

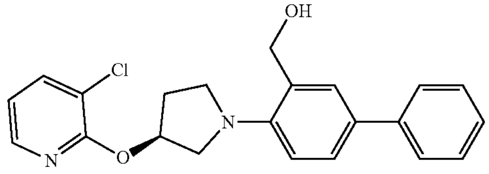 [SMILES: OCc1cc(-c2ccccc2)ccc1N1CC[C@H](Oc2ncccc2Cl)C1]

To a solution of (S)-4-(3-(3-chloropyridin-2-yloxy)pyrrolidin-1-yl)biphenyl-3-carbaldehyde (90 mg, 0.25 mmol) in MeOH was added NaBh4 (23 mg, 0.72 mmol) at 0° C., the mixture was stirred at rt for 10 min, quenched by NH4Cl solution, extracted with EA, washed by brine, dried over Na2SO4, removal the solvent to left the residue which was purified by silica gel to give (S)-(4-(3-(3-chloropyridin-2-yloxy)pyrrolidin-1-yl)biphenyl-3-yl)methanol (61 mg, 64%), Mass spec: 381 (M+H), $t_R$=3.035 min, $^1$H-NMR (400 Hz, DMSO) δ=8.157-8.166 (d, 1H), 7.901-7.925 (q, 1H), 7.681-7.686 (d, 1H), 7.591-7.610 (m, 2H), 7.408-7.474 (m, 3H), 7.285-7.303 (m, 1H), 7.044 (m, 1H), 6.951-7.044 (m, 1H), 5.641 (br, 1H), 5.136-5.164 (m, 1H), 4.579 (m, 2H), 3.722-3.749 (m, 1H), 3.470-3.491 (m, 1H), 3.266-3.322 (m, 2H), 2.376-2.379 (m, 1H), 2.141-2.149 (m, 1H).

Example 97: (R)-4-(3-(5-(trifluoromethyl)pyridin-2-yloxy)pyrrolidin-1-yl)biphenyl-3-amine (Compound 1-116)

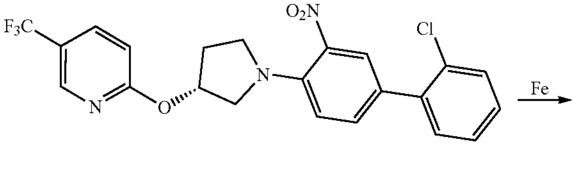

-continued

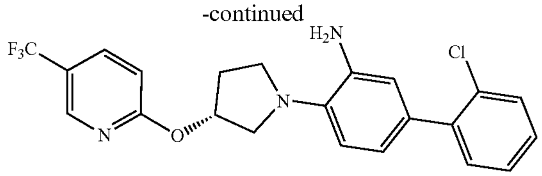

To a solution of (R)-2-(1-(2'-chloro-3-nitrobiphenyl-4-yl)pyrrolidin-3-yloxy)-5-(trifluoromethyl)pyridine (500 mg, 1.08 mmol) (prepared as example 67) in DMF/H2O (21 ml/7 mL) was added Zn (1.4 g, 21.6 mmol) and FeCL3 (175 mg, 1.08 mmol), the mixture was stirred at rt for 3 h, diluted with DCM, filtered and the filtrate was extracted with DCM, washed LiCl solution, dried over na2SO4, removal the solvent to left the residue which was purified by silica gel to give (R)-4-(3-(5-(trifluoromethyl)pyridin-2-yloxy)pyrrolidin-1-yl)biphenyl-3-amine (100 mg, 20% yield), Mass spec: 434 (M+H), $t_R$=3.472 min, $^1$H-NMR (400 Hz, DMSO) δ=8.620 (s, 1H), 8.071-8.099 (q, 1H), 7.495-7.515 (m, 1H), 7.313-7.382 (m, 3H), 7.048-7.070 (m, 1H), 6.938-6.958 (m, 1H), 6.745-6.750 (m, 1H), 6.586-6.610 (m, 1H), 5.618 (br, 1H), 4.778 (m, 2H), 3.561-3.602 (m, 1H), 3.277-3.317 (m, 1H), 3.060-3.163 (m, 2H), 2.430-2.506 (m, 1H), 2.045-2.079 (m, 1H).

Example 98: (R)-2'-chloro-4-(3-(5-(trifluoromethyl)pyridin-2-yloxy)pyrrolidin-1-yl)biphenyl-3-ol (Compound 1-113)

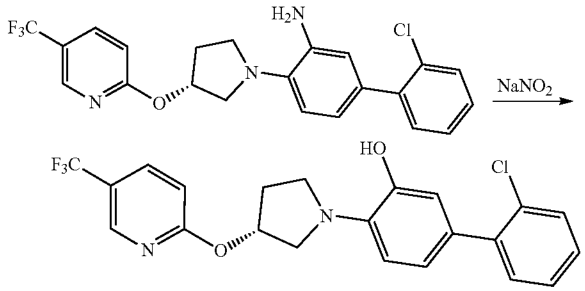

The title compound was prepared following procedures described in example 14 (step 3) to give (R)-2'-chloro-4-(3-(5-(trifluoromethyl)pyridin-2-yloxy)pyrrolidin-1-yl)biphenyl-3-ol (310 mg, 50% yield), Mass spec: 435 (M+H), $t_R$=3.242 min, $^1$H-NMR (400 Hz, CDCl3) δ=8.427-8.433 (q, 1H), 7.775-7.803 (m, 1H), 7.432-7.455 (m, 1H), 7.172-7.131 (m, 3H), 7.035-7.039 (m, 1H), 6.944-6.968 (m, 1H), 6.846-6.868 (d, 1H), 5.574-5.706 (m, 1H), 3.624-3.666 (m, 1H), 3.335-3.426 (m, 2H), 3.210-3.238 (m, 1H), 2.505-2.557 (m, 1H), 2.224-2.244 (m, 1H).

Example 99: (R)-2-(1-(2'-chloro-3-methoxybiphenyl-4-yl)pyrrolidin-3-yloxy)-5-(trifluoromethyl)pyridine (Compound 1-112)

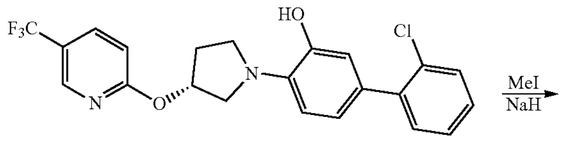

-continued

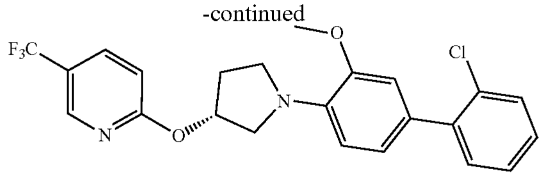

The title compound was prepared following procedures described in example 15a to give (R)-2-(1-(2'-chloro-3-methoxybiphenyl-4-yl)pyrrolidin-3-yloxy)-5-(trifluoromethyl)pyridine (43 mg, 40% yield), Mass spec: 449 (M+H). $t_R$=3.676 min, $^1$H-NMR (400 Hz, CDCl3) δ=8.464-8.470 (q, 1H), 7.767-7.795 (d, 1H), 7.461-7.485 (d, 1H), 7.289-7.385 (m, 3H), 6.997-7.019 (m, 2H), 6.822-6.842 (d, 1H), 5.693-5.733 (m, 1H), 3.969-4.012 (m, 1H), 3.878 (s, 3H), 3.627-3.688 (m, 1H), 3.446-3.568 (m, 1H), 3.413-3.437 (m, 1H), 2.400-2.420 (m, 1H), 2.260-2.269 (m, 1H).

Example 100: (S)-2-(2'-chloro-4-(3-(5-(trifluoromethyl)pyridin-2-yloxy)pyrrolidin-1-yl)biphenyl-3-yloxy)ethanol (Compound 1-133)

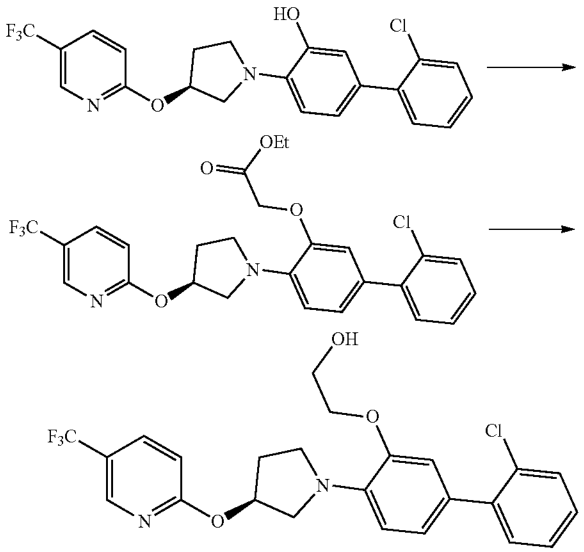

Step 1: (S)-ethyl 2-(2'-chloro-4-(3-(5-(trifluoromethyl)pyridin-2-yloxy)pyrrolidin-1-yl)biphenyl-3-yloxy)acetate

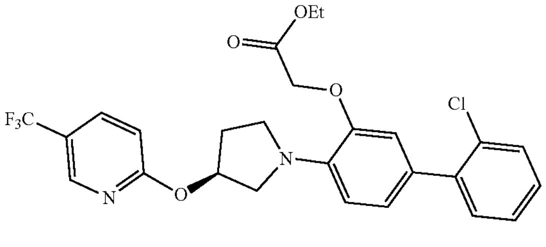 [SMILES: CCOC(=O)COc1cc(-c2ccccc2Cl)ccc1N1CC[C@H](Oc2ccc(C(F)(F)F)cn2)C1]

The title compound was prepared following procedures described in example 89 to give (S)-ethyl 2-(2'-chloro-4-(3-(5-(trifluoromethyl)pyridin-2-yloxy)pyrrolidin-1-yl)biphenyl-3-yloxy)acetate (143 mg, 90% yield), Mass spec: 521 (M+H).

Step 2: (S)-2-(2'-chloro-4-(3-(5-(trifluoromethyl)pyridin-2-yloxy)pyrrolidin-1-yl)biphenyl-3-yloxy)ethanol

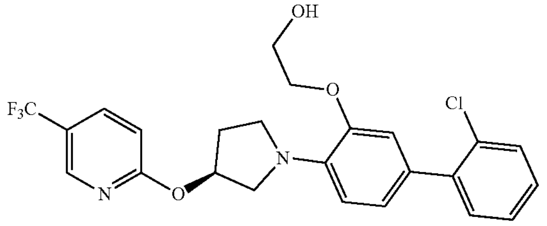 [SMILES: OCCOc1cc(-c2ccccc2Cl)ccc1N1CC[C@H](Oc2ccc(C(F)(F)F)cn2)C1]

The title compound was prepared following procedures described in example 90 to give (S)-2-(2'-chloro-4-(3-(5-(trifluoromethyl)pyridin-2-yloxy)pyrrolidin-1-yl)biphenyl-3-yloxy)ethanol (130 mg, quant.), Mass spec: 479 (M+H), $t_R$=3.003 min, $^1$H-NMR (400 Hz, DMSO) δ=8.622 (s, 1H), 8.060-8.089 (q, 1H), 7.509-7.530 (m, 1H), 7.313-7.414 (m, 3H), 6.910-7.044 (m, 3H), 6.739-6.759 (d, 1H), 5.666 (br, 1H), 4.817-4.843 (t, 1H), 3.916-4.018 (m, 3H), 3.701-3.741 (m, 2H), 3.603-3.620 (m, 1H), 3.518-3.581 (m, 1H), 3.336-3.345 (m, 1H), 2.169-2.353 (m, 1H), 2.145-2.154 (m, 1H).

Example 101: (R)-4-(3-(6-chloroquinolin-2-yloxy)pyrrolidin-1-yl)biphenyl-3-carboxamide (Compound 1-86)

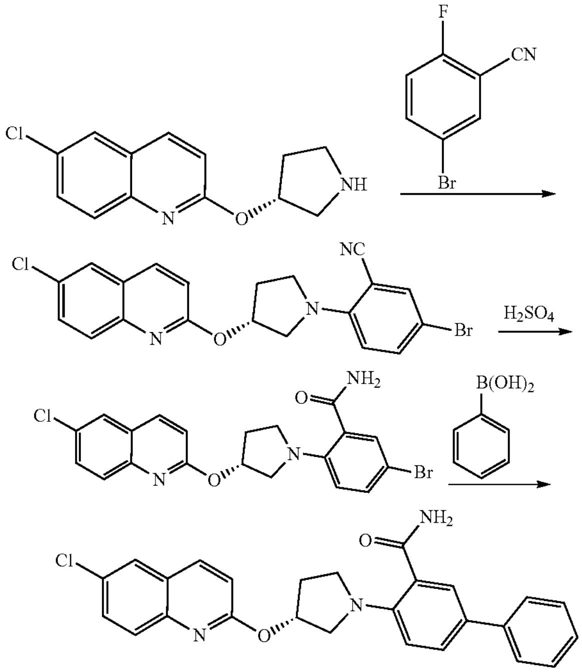

Step 1: (R)-5-bromo-2-(3-(6-chloroquinolin-2-yloxy)pyrrolidin-1-yl)benzonitrile

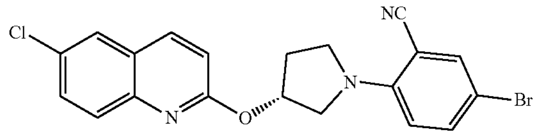 [SMILES: N#Cc1cc(Br)ccc1N1CC[C@@H](Oc2ccc3cc(Cl)ccc3n2)C1]

The title compound was prepared following procedures described in example 5 to give (R)-5-bromo-2-(3-(6-chloroquinolin-2-yloxy)pyrrolidin-1-yl)benzonitrile (410 mg, 47% yield), Mass spec: 428 (M+H).

Step 2: (R)-5-bromo-2-(3-(6-chloroquinolin-2-yloxy)pyrrolidin-1-yl)benzamide

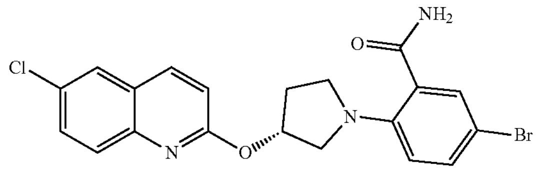 [SMILES: NC(=O)c1cc(Br)ccc1N1CC[C@@H](Oc2ccc3cc(Cl)ccc3n2)C1]

The title compound was prepared following procedures described in example 64 (step 2) to give (R)-5-bromo-2-(3-(6-chloroquinolin-2-yloxy)pyrrolidin-1-yl)benzamide (370 mg, 86% yield), Mass spec: 446 (M+H).

Step 3: (R)-4-(3-(6-chloroquinolin-2-yloxy)pyrrolidin-1-yl)biphenyl-3-carboxamide

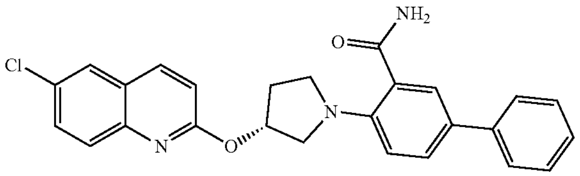 [SMILES: NC(=O)c1cc(-c2ccccc2)ccc1N1CC[C@@H](Oc2ccc3cc(Cl)ccc3n2)C1]

The title compound was prepared following procedures described in example 67 (step 2) to give (R)-4-(3-(6-chloroquinolin-2-yloxy)pyrrolidin-1-yl)biphenyl-3-carboxamide (80 mg, 36% yield), Mass spec: 444 (M+H), $t_R$=3.20 min, $^1$H-NMR (400 Hz, DMSO) δ=8.226-8.249 (d, 1H), 8.030-8.036 (d, 1H), 7.796-7.875 (m, 2H), 7.687-7.709 (m, 1H), 7.530-7.611 (m, 4H), 7.343-7.434 (m, 2H), 7.285 (s, 1H), 7.248-7.267 (m, 1H), 7.060-7.248 (d, 1H), 6.855-6.878 (d, 1H), 5.826 (br, 1H), 3.912-3.954 (m, 1H), 3.581-3.599 (m, 1H), 3.401-3.438 (m, 1H), 3.335 (m, 1H), 2.372 (m, 1H), 2.275-2.281 (m, 1H).

Example 102: (S)—N-tert-butyl-4-(3-(5-(trifluoromethyl)pyridin-2-yloxy)pyrrolidin-1-yl)biphenyl-3-sulfonamide (Compound 1-96)

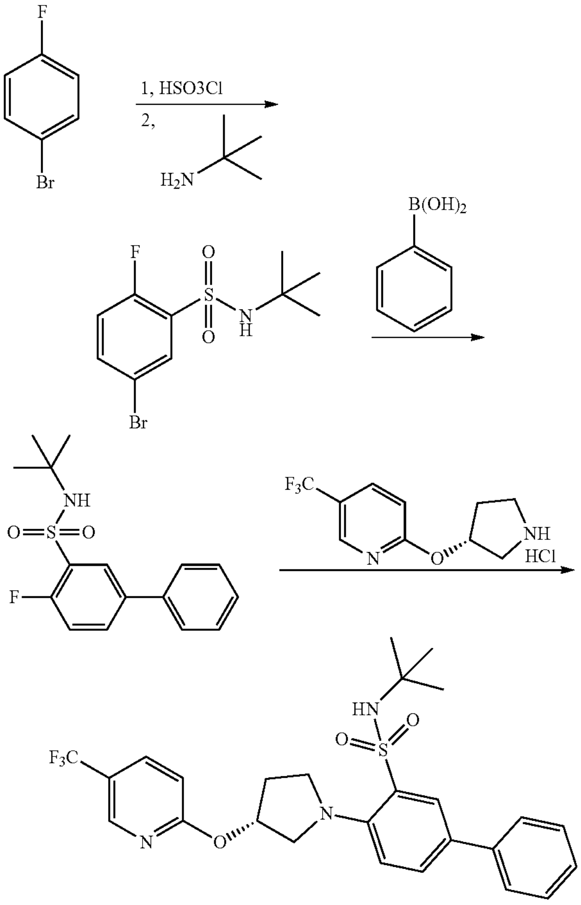

Step 1: 5-bromo-N-tert-butyl-2-fluorobenzenesulfonamide

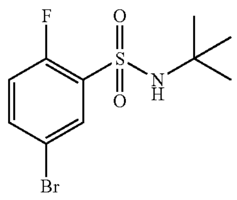 [SMILES: CC(C)(C)NS(=O)(=O)c1cc(Br)ccc1F]

The solution of 1-bromo-4-fluorobenzene (2.0 mL, 17.2 mmol) in HSO3Cl (10 mL) was heated to 100° C. for 2.5 h, the reaction was drop-wised to ice water, and filtered, the solid was dried under vacuum to give 5-bromo-2-fluorobenzene-1-sulfonyl chloride (3.5 g, 76%). To a solution of 2-methylpropan-2-amine (1.36 g, 18.5 mmol) in 5 mL THF at 0° C. was added 5-bromo-2-fluorobenzene-1-sulfonyl chloride (1 g, 3.7 mmol), the mixture was stirred at rt for 2 h, diluted with EA, washed by water, brine, dried over Na2SO4, removal the solvent to left the residue which was purified by silica gel to give 5-bromo-N-tert-butyl-2-fluorobenzenesulfonamide (1 g, 87% yield), Mass spec: 310 (M+H).

Step 2: N-tert-butyl-4-fluorobiphenyl-3-sulfonamide

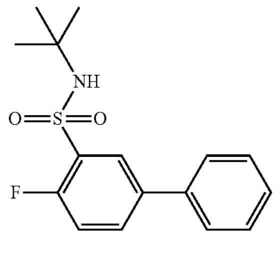 [SMILES: CC(C)(C)NS(=O)(=O)c1cc(-c2ccccc2)ccc1F]

The title compound was prepared following procedures described in example 67 (step 2) to give N-tert-butyl-4-fluorobiphenyl-3-sulfonamide (250 mg, 80.6% yield), Mass spec: 308 (M+H).

Step 3: (S)—N-tert-butyl-4-(3-(5-(trifluoromethyl)pyridin-2-yloxy)pyrrolidin-1-yl)biphenyl-3-sulfonamide

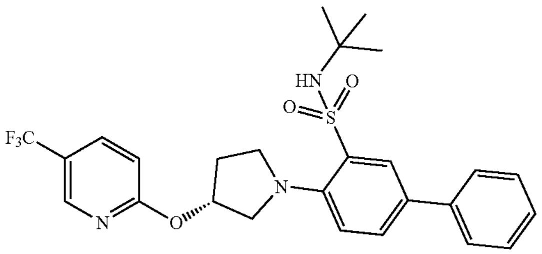 [SMILES: CC(C)(C)NS(=O)(=O)c1cc(-c2ccccc2)ccc1N1CC[C@@H](Oc2ccc(C(F)(F)F)cn2)C1]

To a solution of (R)-2-(pyrrolidin-3-yloxy)-5-(trifluoromethyl)pyridine hydrochloride (153 mg, 0.5 mmol) and N-tert-butyl-4-fluorobiphenyl-3-sulfonamide (174 mg, 0.75 mmol) in 3 mL Dioxane was added DBU (300 mg, 2 mmol), the mixture was stirred at 130° C. for overnight, cooled down to rt, water was added, extracted with EA, dried over Na2SO4, removal the solvent to left the residue which was purified by silica gel to give (S)—N-tert-butyl-4-(3-(5-(trifluoromethyl)pyridin-2-yloxy)pyrrolidin-1-yl)biphenyl-3-sulfonamide (40 mg, 15% yield), Mass spec: 520 (M+H), $t_R$=3.639 min, $^1$H-NMR (400 Hz, DMSO) δ=8.623 (s, 1H), 8.809-8.125 (m, 2H), 7.841-7.675 (m, 1H), 7.656-7.675 (m, 2H), 7.471-7.508 (m, 3H), 7.360-7.396 (m, 1H), 7.028-7.046 (m, 2H), 5.697 (br, 1H), 3.797-3.838 (m, 1H), 3.573-3.613 (m, 1H), 3.499-3.527 (m, 1H), 3.301-3.314 (m, 1H), 2.456-2.473 (m, 1H), 2.111-2.144 (m, 1H), 1.158 (s, 9H).

Example 103: 1-(biphenyl-4-yl)-3-(quinolin-2-yloxy)pyrrolidin-2-one (Compound 1-102)

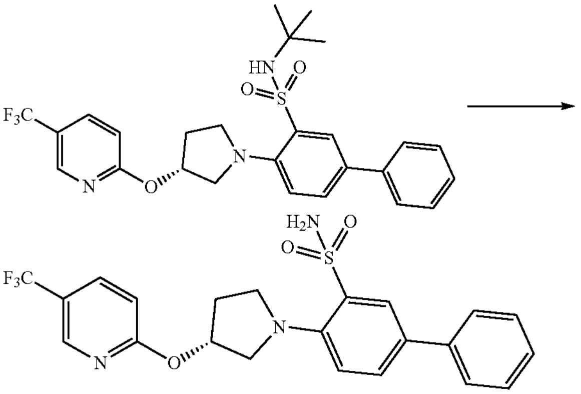

A solution of (S)—N-tert-butyl-4-(3-(5-(trifluoromethyl)pyridin-2-yloxy)pyrrolidin-1-yl)biphenyl-3-sulfonamide (35 mg, 0.06 mmol) in 2 mL CF3COOH was heated to 40° C. for 5 h, the mixture was treated with $NaHCO_3$ solution to pH to 7, extracted with DCM, dried over Na2SO4, removal the solvent to left residue which was purified by silica gel to give 1-(biphenyl-4-yl)-3-(quinolin-2-yloxy)pyrrolidin-2-one (15 mg, 50% yield), as white solid, Mass spec: 464 (M+H), $t_R$=3.183 min, $^1$H-NMR (400 Hz, DMSO) δ=8.622 (s, 1H), 8.801-8.148 (m, 2H), 7.790-7.816 (m, 1H), 7.650-7.696 (m, 2H), 7.462-7.500 (m, 3H), 7.322-7.382 (m, 4H), 7.019-7.040 (m, 1H), 5.694 (br, 1H), 3.905-3.945 (m, 1H), 3.515-3.605 (m, 2H), 3.386-3.436 (m, 1H), 2.414-2.434 (m, 1H), 2.165-2.175 (m, 1H).

Example 104: 1-(biphenyl-4-yl)-3-(quinolin-2-yloxy)pyrrolidin-2-one (Compound 1-95)

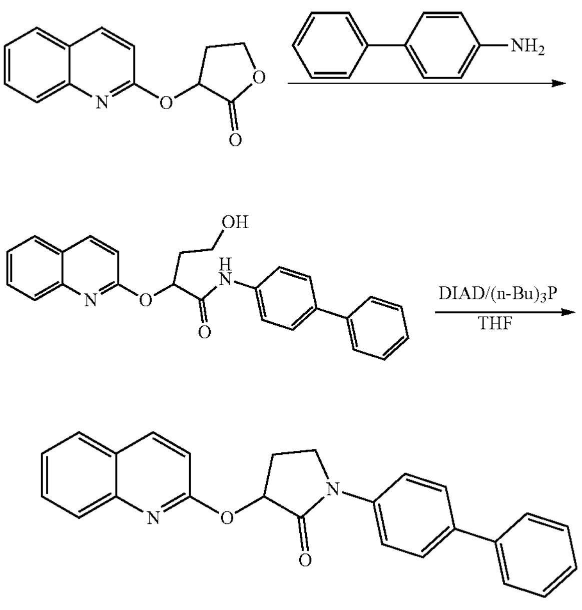

Step 1: N-(biphenyl-4-yl)-4-hydroxy-2-(quinolin-2-yloxy)butanamide

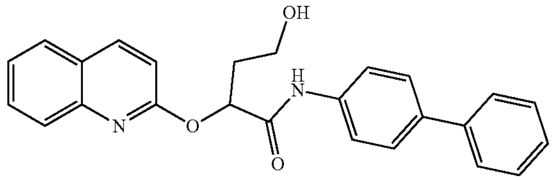 [SMILES: O=C(Nc1ccc(-c2ccccc2)cc1)C(CCO)Oc1ccc2ccccc2n1]

To a solution of biphenyl-4-amine (34 mg, 0.2 mmol) in 2 mL DCM at 0° C. was added AlMe3 (0.5 mL, 2M in Tol), the mixture was stirred at rt for 1 h before 3-(quinolin-2-yloxy)dihydrofuran-2 (3H)-one (45.8 mg, 0.2 mmol) was added, the mixture was stirred at rt for overnight, quenched by water, extracted with DCM, the organic layer was washed by water, brine, dried over Na2SO4, removal the solvent to left residue which was purified by silica gel to give N-(biphenyl-4-yl)-4-hydroxy-2-(quinolin-2-yloxy)butanamide (40 mg, 50% yield), Mass spec: 399 (M+H).

Step 2: N-(biphenyl-4-yl)-4-hydroxy-2-(quinolin-2-yloxy)butanamide

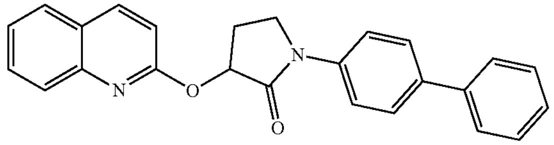 [SMILES: O=C1C(Oc2ccc3ccccc3n2)CCN1c1ccc(-c2ccccc2)cc1]

To a solution of DIAD (60 mg, 0.3 mmol) and (n-Bu)3P (60 mg, 0.3 mmol) in 2 mL THE was stirred at 0° C. for 30 min, before N-(biphenyl-4-yl)-4-hydroxy-2-(quinolin-2-yloxy)butanamide (40 mg, 0.1 mmol) was added, the mixture was stirred at rt for 2 h, quenched by water, extracted with EA, dried over Na2SO4, removal the solvent to left the residue which was purified by re-crystallized form Et2O and hexane to give N-(biphenyl-4-yl)-4-hydroxy-2-(quinolin-2-yloxy)butanamide (21 mg, 55% yield) as white solid, Mass spec: 381 (M+H), $t_R$=3.197 min, $^1$H-NMR (400 Hz, DMSO) δ=8.321-8.344 (d, 1H), 7.684-7.947 (m, 9H), 7.348-7.498 (m, 4H), 7.134-7.155 (m, 1H), 6.063-6.106 (t, 1H), 3.988-4.022 (m, 2H), 2.839-2.891 (m, 1H), 2.183-2.237 (m, 1H).

Example 105: 2-(2-oxo-3-(quinolin-2-yloxy)pyrrolidin-1-yl)benzonitrile (Compound 1-103)

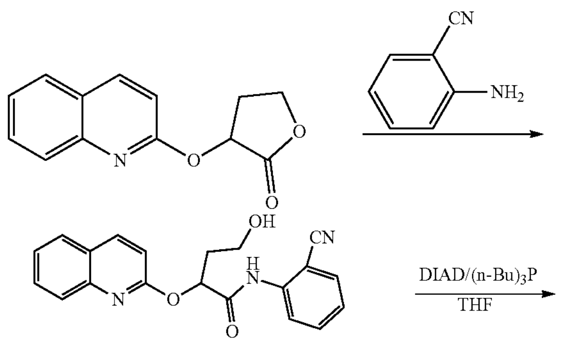

-continued

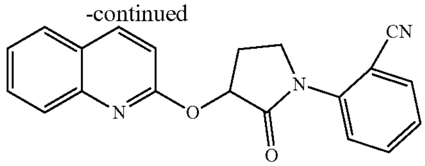

Step 1: N-(2-cyanophenyl)-4-hydroxy-2-(quinolin-2-yloxy)butanamide

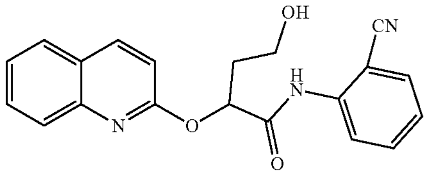 [SMILES: N#Cc1ccccc1NC(=O)C(CCO)Oc1ccc2ccccc2n1]

The title compound was prepared following procedures described in example 104 (step 1) to give N-(2-cyanophenyl)-4-hydroxy-2-(quinolin-2-yloxy)butanamide (160 mg, 70.3% yield), Mass spec: 348 (M+H).

Step 2: 2-(2-oxo-3-(quinolin-2-yloxy)pyrrolidin-1-yl)benzonitrile

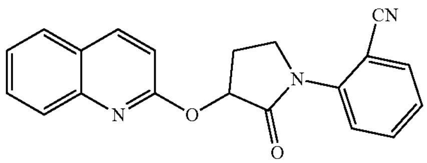 [SMILES: N#Cc1ccccc1N1CCC(Oc2ccc3ccccc3n2)C1=O]

The title compound was prepared following procedures described in example 104 (step 2) to give 2-(2-oxo-3-(quinolin-2-yloxy)pyrrolidin-1-yl)benzonitrile (90 mg, 59% yield), Mass spec: 330 (M+H), $t_R$=2.566 min, $^1$H-NMR (400 Hz, CD3OD) δ=8.168-8.172 (d, 1H), 7.769-7.864 (m, 4H), 7.614-7.671 (m, 2H), 7.517-7.558 (m, 1H), 7.409-7.449 (m, 1H), 7.053-7.075 (d, 1H), 6.093-6.135 (t, 1H), 4.019-4.093 (m, 2H), 3.019-3.023 (m, 1H), 2.359-2.413 (m, 1H).

Example 106: 2-(2-oxo-3-(quinolin-2-yloxy)pyrrolidin-1-yl)benzamide (Compound 1-105)

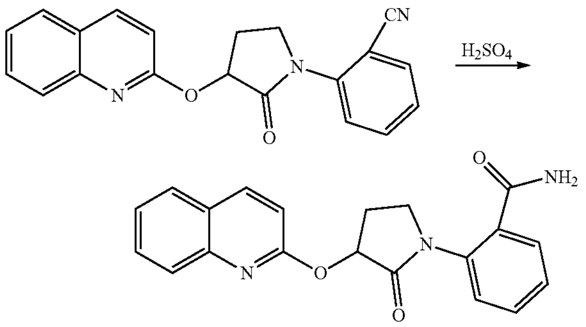

The title compound was prepared following procedures described in example 64 (step 2) to give 2-(2-oxo-3-(quinolin-2-yloxy)pyrrolidin-1-yl)benzamide (25 mg, 50% yield), Mass spec: 348 (M+H), $t_R$=1.968 min, $^1$H-NMR (400 Hz, CD3OD) δ=8.308-8.330 (d, 1H), 7.918-7.941 (m, 1H), 7.710-7.808 (m, 3H), 7.365-7.588 (m, 6H), 7.113-7.135 (d, 1H), 5.931-5.795 (t, 1H), 3.841-3.864 (m, 2H), 2.826-2.857 (m, 1H), 2.144-2.198 (m, 1H).

Example 107: 1-phenyl-3-(quinolin-2-yloxy)pyrrolidin-2-one (Compound 1-104)

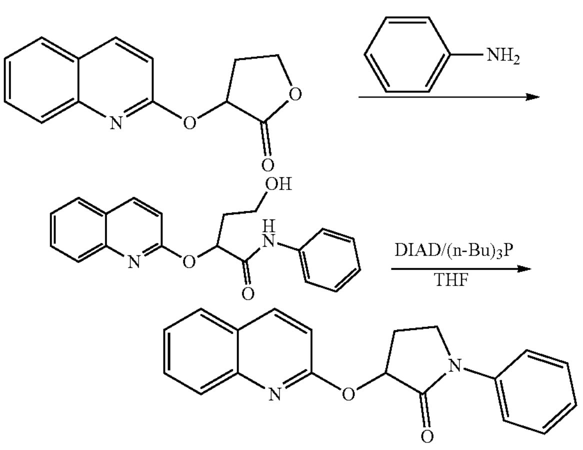

Step 1: 4-hydroxy-N-phenyl-2-(quinolin-2-yloxy)butanamide

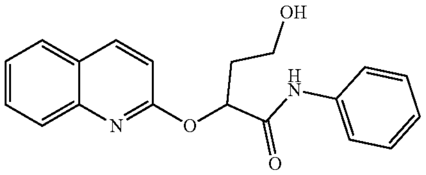 [SMILES: O=C(Nc1ccccc1)C(CCO)Oc1ccc2ccccc2n1]

The title compound was prepared following procedures described in example 104 (step 1) to give 4-hydroxy-N-phenyl-2-(quinolin-2-yloxy)butanamide (130 mg, 91% yield), Mass spec: 323 (M+H).

Step 2: 1-phenyl-3-(quinolin-2-yloxy)pyrrolidin-2-one

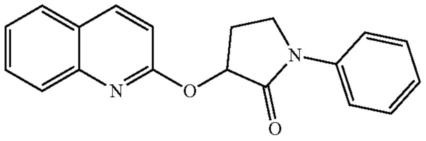 [SMILES: O=C1C(Oc2ccc3ccccc3n2)CCN1c1ccccc1]

The title compound was prepared following procedures described in example 104 (step 2) to give 1-phenyl-3-(quinolin-2-yloxy)pyrrolidin-2-one (45 mg, 47% yield), Mass spec: 305 (M+H), $t_R$=2.785 min, $^1$H-NMR (400 Hz, DMSO) δ=8.304-8.326 (d, 1H), 7.913-7.933 (m, 1H), 7.686-

7.743 (m, 4H), 7.407-7.468 (m, 3H), 7.194-7.210 (m, 1H), 7.111-7.133 (d, 1H), 6.025-6.068 (t, 1H), 3.930-3.956 (m, 2H), 2.802-2.855 (m, 1H), 2.138-2.220 (m, 1H).

Example 108: 1-(2-chlorophenyl)-3-(quinolin-2-yloxy)pyrrolidin-2-one (Compound 1-106)

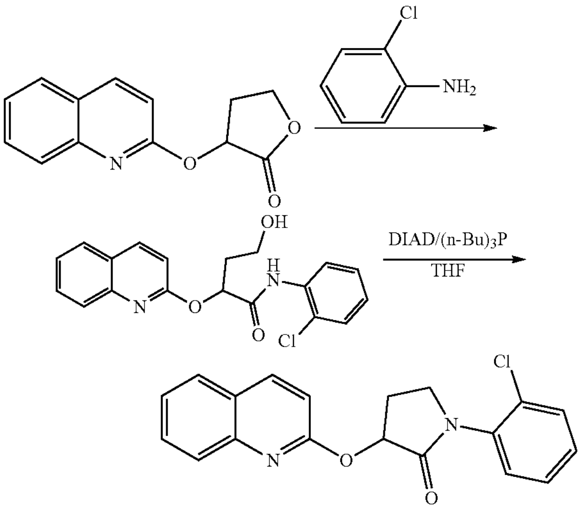

Step 1: N-(2-chlorophenyl)-4-hydroxy-2-(quinolin-2-yloxy)butanamide

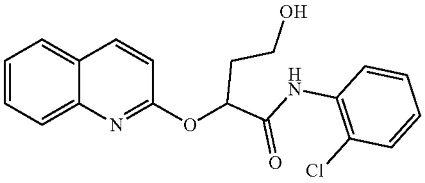 [SMILES: O=C(Nc1ccccc1Cl)C(CCO)Oc1ccc2ccccc2n1]

The title compound was prepared following procedures described in example 104 (step 1) to give N-(2-chlorophenyl)-4-hydroxy-2-(quinolin-2-yloxy)butanamide (120 mg, 51.8% yield), Mass spec: 357 (M+H).

Step 2: 1-(2-chlorophenyl)-3-(quinolin-2-yloxy) pyrrolidin-2-one

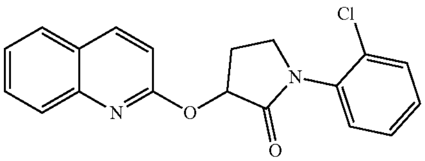 [SMILES: O=C1C(Oc2ccc3ccccc3n2)CCN1c1ccccc1Cl]

The title compound was prepared following procedures described in example 104 (step 2) to give 1-(2-chlorophenyl)-3-(quinolin-2-yloxy)pyrrolidin-2-one (20 mg, 21% yield), Mass spec: 339 (M+H), $t_R$=2.747 min, $^1$H-NMR (400 Hz, DMSO) δ=8.304-8.326 (d, 1H), 7.913-7.918 (m, 1H), 7.791-7.802 (m, 1H), 7.518-7.522 (m, 1H), 7.441-7.478 (m, 5H), 7.111-7.133 (d, 1H), 6.062-6.066 (t, 1H), 3.768-3.853 (m, 2H), 2.849-2.855 (m, 1H), 2.215-2.229 (m, 1H).

Example 109: 4-(2-oxo-3-(quinolin-2-yloxy)pyrrolidin-1-yl)biphenyl-3-carbonitrile (Compound 1-108)

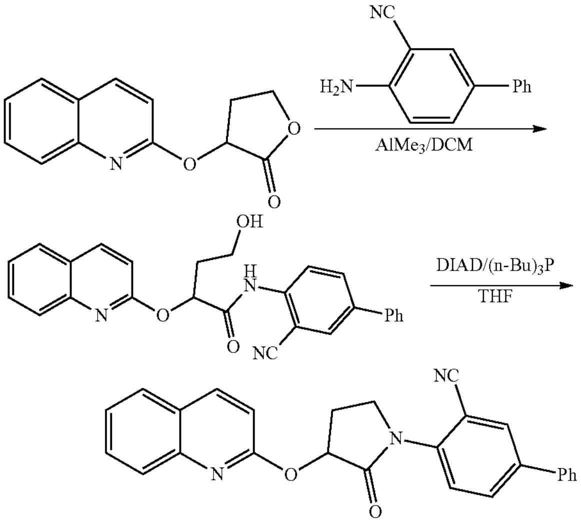

Step 1: N-(3-cyanobiphenyl-4-yl)-4-hydroxy-2-(quinolin-2-yloxy)butanamide

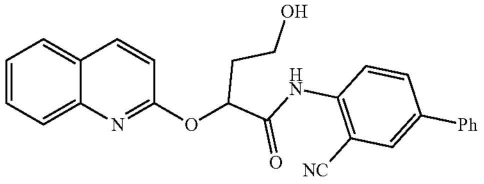 [SMILES: N#Cc1cc(-c2ccccc2)ccc1NC(=O)C(CCO)Oc1ccc2ccccc2n1]

The title compound was prepared following procedures described in example 104 (step 1) to give N-(3-cyanobiphenyl-4-yl)-4-hydroxy-2-(quinolin-2-yloxy)butanamide (400 mg, 38% yield), Mass spec: 424 (M+H).

Step 2: 4-(2-oxo-3-(quinolin-2-yloxy)pyrrolidin-1-yl)biphenyl-3-carbonitrile

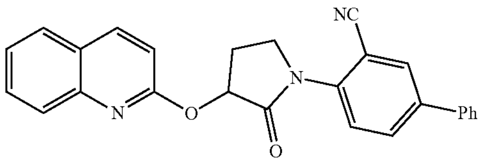 [SMILES: N#Cc1cc(-c2ccccc2)ccc1N1CCC(Oc2ccc3ccccc3n2)C1=O]

The title compound was prepared following procedures described in example 104 (step 2) to give 4-(2-oxo-3-(quinolin-2-yloxy)pyrrolidin-1-yl)biphenyl-3-carbonitrile (300 mg, 75% yield), Mass spec: 406 (M+H), $t_R$=3.005 min, $^1$H-NMR (400 Hz, DMSO) δ=8.327-8.349 (d, 1H), 8.252-8.257 (d, 1H), 8.120-8.141 (d, 1H), 7.929-7.950 (d, 1H), 7.714-7.826 (m, 5H), 7.451-7.539 (m, 4H), 7.149-7.171 (d, 1H), 6.104-6.148 (t, 1H), 4.053-4.097 (m, 1H), 3.961-4.001 (m, 1H), 2.907-2.942 (m, 1H), 2.263-2.317 (m, 1H).

Example 113: 2'-chloro-4-(2-oxo-3-(quinolin-2-yloxy)pyrrolidin-1-yl)biphenyl-3-carboxamide (Compound 1-114)

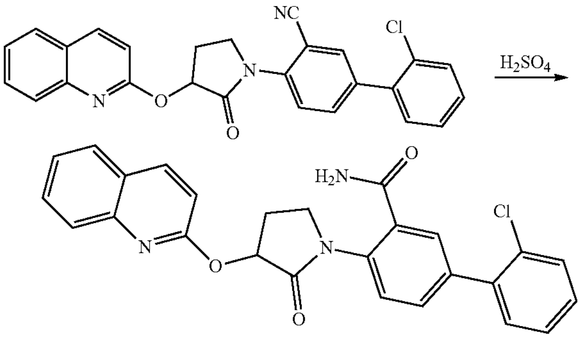

The title compound was prepared following procedures described in example 64 (step 2) to give 2'-chloro-4-(2-oxo-3-(quinolin-2-yloxy)pyrrolidin-1-yl)biphenyl-3-carboxamide (18 mg, 39% yield), Mass spec: 458 (M+H), $t_R$=2.629 min, $^1$H-NMR (400 Hz, DMSO) δ=8.316-8.338 (d, 1H), 7.926-7.946 (m, 1H), 7.822-7.861 (m, 2H), 7.655-7.738 (m, 4H), 7.413-7.631 (m, 6H), 7.129-7.151 (d, 1H), 5.959-6.004 (t, 1H), 3.901-3.938 (m, 2H), 2.858-2.890 (m, 1H), 2.177-2.232 (m, 1H).

Example 114: 4-(2-oxo-3-(quinolin-2-yloxy)pyrrolidin-1-yl)biphenyl-3-carboxamide (Compound 1-123)

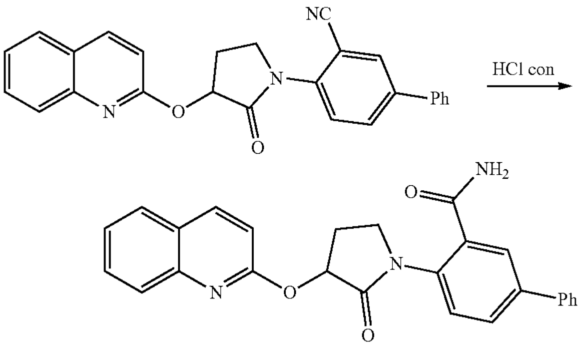

The compound 4-(2-oxo-3-(quinolin-2-yloxy)pyrrolidin-1-yl)biphenyl-3-carbonitrile (70 mg, 0.17 mmol) in concentrate HCl was heated to 50° C. for 7 h, water was added, filtered and got the crude as light yellow solid, washed with ether, to give the pure 4-(2-oxo-3-(quinolin-2-yloxy)pyrrolidin-1-yl)biphenyl-3-carboxamide (40 mg, 60%), Mass spec: 424 (M+H), $t_R$=2.685 min, $^1$H-NMR (400 Hz, DMSO) δ=8.314-8.336 (d, 1H), 7.924-7.968 (m, 2H), 7.820-7.924 (m, 3H), 7.698-7.750 (m, 3H), 7.498-7.552 (m, 4H), 7.421-7.484 (m, 2H), 7.124-7.146 (d, 1H), 5.951-5.995 (t, 1H), 3.897-3.902 (m, 2H), 2.891-2.896 (m, 1H), 2.197-2.204 (m, 1H).

Example 117: (R)-(4-(3-(5-(trifluoromethyl)pyridin-2-yloxy)pyrrolidin-1-yl)biphenyl-3-yl)methanamine hydrochloride (Compound 1-109)

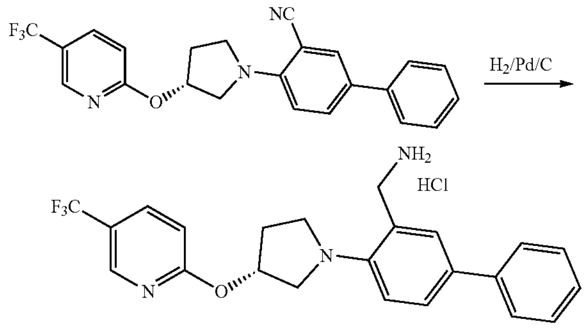

To a solution of (R)-4-(3-(5-(trifluoromethyl)pyridin-2-yloxy)pyrrolidin-1-yl)biphenyl-3-carbonitrile (50 mg, 0.12 mmol) (prepared as example 67) in 15 mL MeOH and 1.5 mL DCM was added Pd/C (20 mg), and stirred at rt under H2 atmosphere for 2 d, filtered, removal the solvent to left the residue which was purified by Prep-HPLC to give (R)-(4-(3-(5-(trifluoromethyl)pyridin-2-yloxy)pyrrolidin-1-yl)biphenyl-3-yl)methanamine hydrochloride (20 mg, 37% yield), Mass spec: 414 (M+H), $t_R$=2.291 min, $^1$H-NMR (400 Hz, DMSO) δ=8.622 (s, 1H), 8.441-8.483 (br, 3H), 8.087-8.115 (m, 1H), 7.830-7.835 (m, 1H), 7.620-7.699 (m, 3H), 7.444-7.483 (m, 2H), 7.318-7.354 (m, 1H), 7.211-7.2322 (m, 1H), 7.057-7.079 (m, 1H), 5.690-5.697 (m, 1H), 4.131-4.220 (m, 2H), 3.670-3.709 (m, 1H), 3.411-3.470 (m, 1H), 3.199-3.295 (m, 2H), 2.164-2.478 (m, 1H, 2.126-2.152 (m, 1H).

Example 118: (R)-(4-(3-(5-(trifluoromethyl)pyridin-2-yloxy)pyrrolidin-1-yl)biphenyl-3-yl)methanol (Compound 1-110)

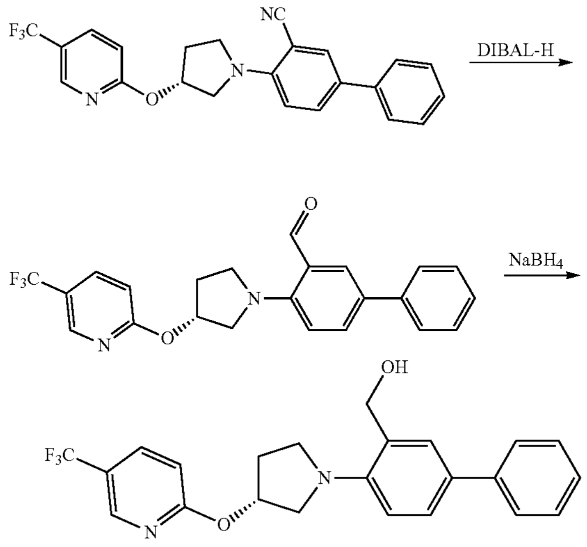

Step 1: (R)-4-(3-(5-(trifluoromethyl)pyridin-2-yloxy)pyrrolidin-1-yl)biphenyl-3-carbaldehyde

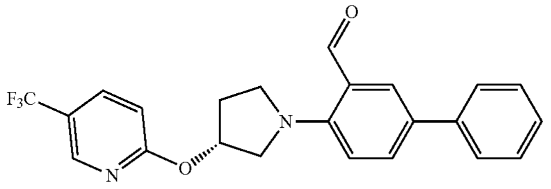 [SMILES: O=Cc1cc(-c2ccccc2)ccc1N1CC[C@@H](Oc2ccc(C(F)(F)F)cn2)C1]

The title compound was prepared following procedures described in example 96 (step 1) to give (R)-4-(3-(5-(trifluoromethyl)pyridin-2-yloxy)pyrrolidin-1-yl)biphenyl-3-carbaldehyde (30 mg, 29% yield), Mass spec: 413 (M+H).

Step 2: (R)-(4-(3-(5-(trifluoromethyl)pyridin-2-yloxy)pyrrolidin-1-yl)biphenyl-3-yl)methanol

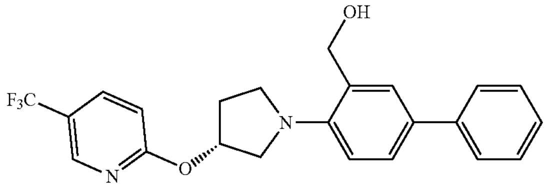 [SMILES: OCc1cc(-c2ccccc2)ccc1N1CC[C@@H](Oc2ccc(C(F)(F)F)cn2)C1]

The title compound was prepared following procedures described in example 96 (step 2) to give (R)-(4-(3-(5-(trifluoromethyl)pyridin-2-yloxy)pyrrolidin-1-yl)biphenyl-3-yl)methanol (18 mg, 62% yield), Mass spec: 415 (M+H), $t_R$=3.269 min, $^1$H-NMR (400 Hz, DMSO) δ=8.622-8.625 (d, 1H), 8.069-8.098 (q, 1H), 7.591-7.682 (m, 3H), 7.286-7.472 (m, 4H), 7.037-7.059 (d, 1H), 6.939-6.961 (d, 1H), 5.667 (br, 1H), 5.127-5.155 (t, 1H), 4.561-4.588 (m, 2H), 3.721-3.749 (m, 1H), 3.366-3.472 (m, 2H), 3.261-3.263 (m, 1H), 2.379-2.406 (m, 1H), 2.134-2.172 (m, 1H).

Example 119: (S)-(4-(3-(5-(trifluoromethyl)pyridin-2-yloxy)pyrrolidin-1-yl)biphenyl-3-yl)methanol (Compound 1-115)

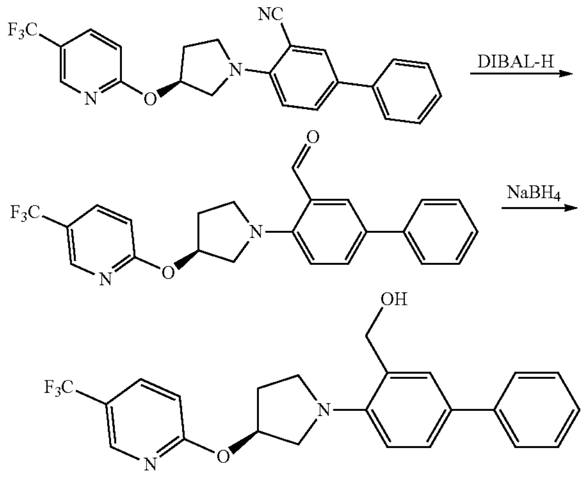

Step 1: (S)-4-(3-(5-(trifluoromethyl)pyridin-2-yloxy)pyrrolidin-1-yl)biphenyl-3-carbaldehyde

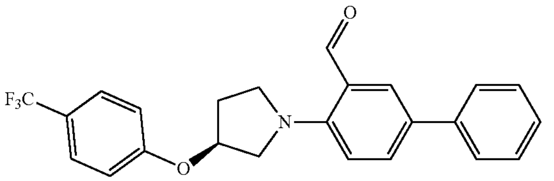 [SMILES: O=Cc1cc(-c2ccccc2)ccc1N1CC[C@H](Oc2ccc(C(F)(F)F)cc2)C1]

The title compound was prepared following procedures described in example 96 (step 1) using example 29 to give (S)-4-(3-(5-(trifluoromethyl)pyridin-2-yloxy)pyrrolidin-1-yl)biphenyl-3-carbaldehyde (57 mg, 28% yield), Mass spec: 413 (M+H).

Step 2: (S)-(4-(3-(5-(trifluoromethyl)pyridin-2-yloxy)pyrrolidin-1-yl)biphenyl-3-yl)methanol

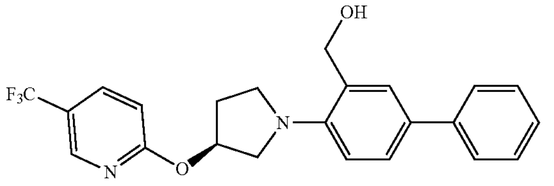 [SMILES: OCc1cc(-c2ccccc2)ccc1N1CC[C@H](Oc2ccc(C(F)(F)F)cn2)C1]

The title compound was prepared following procedures described in example 96 (step 2) to give (S)-(4-(3-(5-(trifluoromethyl)pyridin-2-yloxy)pyrrolidin-1-yl)biphenyl-3-yl)methanol (31 mg, 53% yield), Mass spec: 415 (M+H), $t_R$=3.141 min, $^{1}$H-NMR (400 Hz, DMSO) δ=8.622 (s, 1H), 8.067-8.095 (q, 1H), 7.590-7.681 (m, 3H), 7.408-7.471 (m, 3H), 7.266-7.303 (m, 1H), 7.035-7.057 (d, 1H), 6.939-6.951 (d, 1H), 5.660-5.667 (m, 1H), 5.132-5.159 (t, 1H), 4.561-4.589 (m, 2H), 3.720-3.761 (m, 1H), 3.377-3.494 (m, 2H), 3.262-3.229 (m, 1H), 2.510-2.514 (m, 1H), 2.386-2.405 (m, 1H).

Example 120: 1-(4-((S)-3-(5-(trifluoromethyl)pyridin-2-yloxy)pyrrolidin-1-yl)biphenyl-3-yl)ethanol 121)

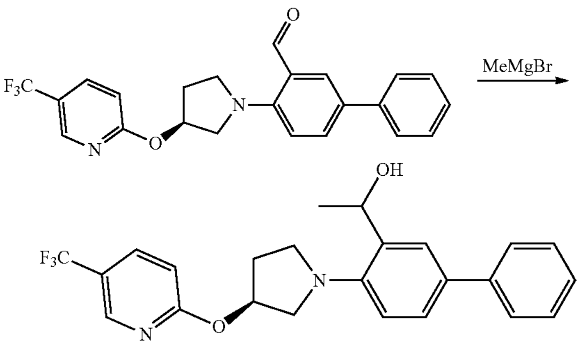

To a solution of (S)-4-(3-(5-(trifluoromethyl)pyridin-2-yloxy)pyrrolidin-1-yl)biphenyl-3-carbaldehyde (70 mg, 0.17 mmol) in 3 mL THF was added MeMgbr (0.15 mL, 3M in THF) at 0° C., the mixture was stirred at rt for overnight, quenched by water, extracted by DCM, dried over Na2SO4, removal the solvent to left the residue which was purified by Prep-HPLC to give 1-(4-((S)-3-(5-(trifluoromethyl)pyridin-2-yloxy)pyrrolidin-1-yl)biphenyl-3-yl)ethanol (40 mg, 54% yield), Mass spec: 429 (M+H), $t_R$=2.837 min. $^{1}$H-NMR (400 Hz, DMSO) δ=8.614 (s, 1H), 8.073-8.091 (d, 1H), 7.768-7.774 (m, 1H), 7.595-7.616 (m, 2H), 7.438-7.459 (m, 3H), 7.308-7.328 (m, 1H), 7.056-7.105 (m, 2H), 5.641 (br, 1H), 5.121-5.137 (m, 2H), 2.594-3.672 (m, 2H), 3.151-3.217 (m, 2H), 2.409-2.436 (m, 1H), 2.096-2.118 (m, 1H), 1.337-1.426 (m, 3H).

Example 121: (S)-(4-(3-(5-(trifluoromethyl)pyridin-2-yloxy)pyrrolidin-1-yl)biphenyl-3-yl)methanamine (Compound 1-119)

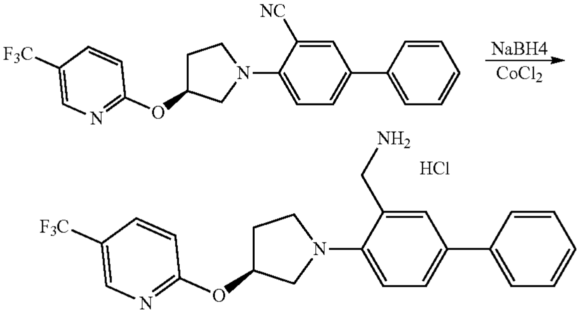

The title compound was prepared following procedures described in example 95 to give (S)-(4-(3-(5-(trifluoromethyl)pyridin-2-yloxy)pyrrolidin-1-yl)biphenyl-3-yl)methanamine (19 mg, 17% yield), Mass spec: 414 (M+H), $t_R$=2.409 min, $^{1}$H-NMR (400 Hz, DMSO) δ=8.622 (s, 1H), 8.290-8.352 (br, 3H), 8.095-8.110 (d, 1H), 7.794 (s, 1H), 7.616-7.686 (m, 3H), 7.448-7.486 (m, 2H), 7.321-7.358 (m, 1H), 7.210-7.231 (d, 1H), 8.050-7.071 (d, 1H), 5.675-5.696 (m, 1H), 4.158-4.214 (m, 2H), 3.655-3.711 (m, 1H), 3.196-3.283 (m, 2H), 2.425-2.474 (m, 1H), 2.130-2.162 (m, 1H).

Example 122: (S)-(2'-chloro-4-(3-(5-(trifluoromethyl)pyridin-2-yloxy)pyrrolidin-1-yl)biphenyl-3-yl)methanamine (Compound 1-118)

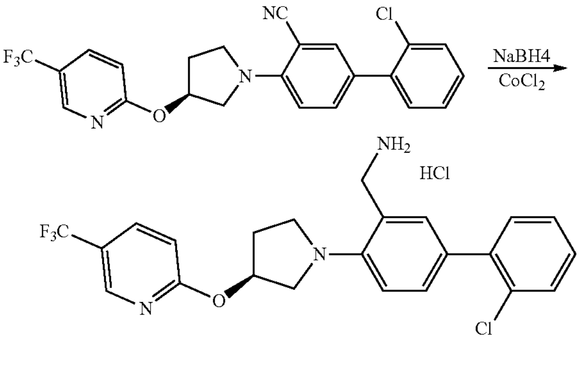

The title compound was prepared following procedures described in example 95 to give (S)-(2'-chloro-4-(3-(5-(trifluoromethyl)pyridin-2-yloxy)pyrrolidin-1-yl)biphenyl- 3-yl)methanamine (30 mg, 20% yield), Mass spec: 448 (M+H), $t_R$=2.300 min, $^1$H-NMR (400 Hz, DMSO) δ=8.609 (s, 1H), 8.346 (br, 3H), 8.077-8.105 (d, 1H), 7.512-7.567 (m, 2H), 7.382-7.425 (m, 3H), 7.192-7.213 (d, 1H), 7.048-7.070 (d, 1H), 5.687 (br, 1H), 4.135-4.164 (m, 1H), 3.444-3.466 (m, 2H), 3.280-3.304 (m, 1H), 2.418 (m, 1H), 2.088-2.207 (m, 1H).

Example 123: (S)—N-((2'-chloro-4-(3-(5-(trifluoromethyl)pyridin-2-yloxy)pyrrolidin-1-yl)biphenyl-3-yl)methyl)acetamide (Compound 1-127)

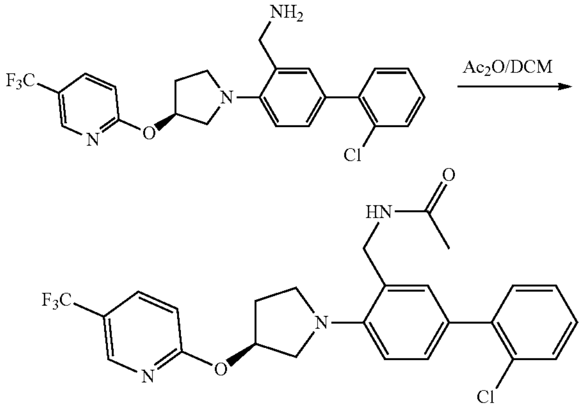

To a solution of (S)-(2'-chloro-4-(3-(5-(trifluoromethyl)pyridin-2-yloxy)pyrrolidin-1-yl)biphenyl-3-yl)methanamine (50 mg, 0.11 mmol) (Example 122) in 1 mL DCM was added Ac2O (7 drops), the mixture was stirred rt for 2 h, quenched by water, extracted with DCM, dried over Na2SO4, removal the solvent to left the residue which was purified by Prep-HPLC to give (S)—N-((2'-chloro-4-(3-(5-(trifluoromethyl)pyridin-2-yloxy)pyrrolidin-1-yl)biphenyl-3-yl)methyl)acetamide (20 mg, 37% yield) Mass spec: 490 (M+H), $t_R$=3.196 min, $^1$H-NMR (400 Hz, DMSO) δ=8.621-8.623 (d, 1H), 8.253-8.281 (m, 1H), 8.073-8.101 (m, 1H), 7.526-7.547 (m, 1H), 7.351-7.408 (m, 3H), 7.258-7.257 (m, 2H), 7.031-7.064 (m, 2H), 5.649-5.677 (m, 1H), 4.314-4.346 (m, 2H), 3.711-3.752 (m, 1H), 3.453-3.494 (m, 1H), 3.289-3.318 (m, 1H), 3.207-3.249 (m, 1H), 2.442-2.519 (m, 1H), 2.128-2.392 (m, 1H), 2.186 (s, 3H).

Example 124: (S)-(2'-chloro-4-(3-(5-(trifluoromethyl)pyridin-2-yloxy)pyrrolidin-1-yl)biphenyl-3-yl)methanol (Compound 1-132)

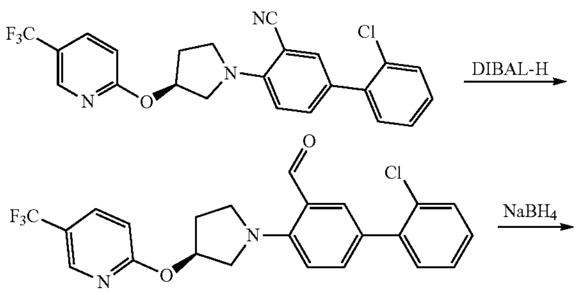

-continued

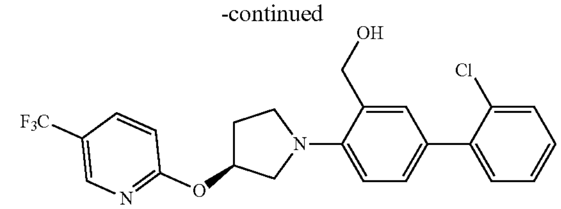

Step 1: (S)-2'-chloro-4-(3-(5-(trifluoromethyl)pyridin-2-yloxy)pyrrolidin-1-yl)biphenyl-3-carbaldehyde

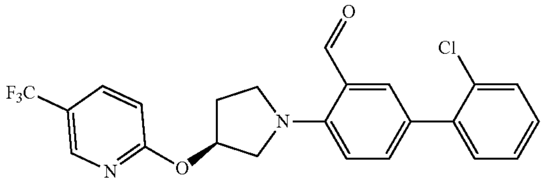 [SMILES: O=Cc1cc(-c2ccccc2Cl)ccc1N1CC[C@H](Oc2ccc(C(F)(F)F)cn2)C1]

The title compound was prepared following procedures described in example 96 (step 1) using example 29 to give (S)-2'-chloro-4-(3-(5-(trifluoromethyl)pyridin-2-yloxy)pyrrolidin-1-yl)biphenyl-3-carbaldehyde (60 mg, 11% yield), Mass spec: 447 (M+H).

Step 2: (S)-(2'-chloro-4-(3-(5-(trifluoromethyl)pyridin-2-yloxy)pyrrolidin-1-yl)biphenyl-3-yl)methanol

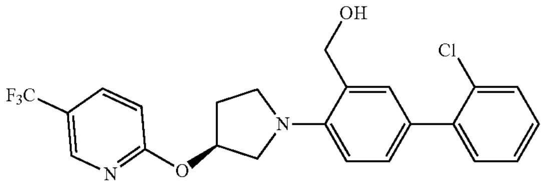 [SMILES: OCc1cc(-c2ccccc2Cl)ccc1N1CC[C@H](Oc2ccc(C(F)(F)F)cn2)C1]

The title compound was prepared following procedures described in example 96 (step 2) to give (S)-(2'-chloro-4-(3-(5-(trifluoromethyl)pyridin-2-yloxy)pyrrolidin-1-yl)biphenyl-3-yl)methanol (40 mg, 66% yield), Mass spec: 449 (M+H), $t_R$=3.039 min, $^1$H-NMR (400 Hz, DMSO) δ=8.625-8.628 (d, 1H), 8.071-8.099 (d, 1H), 7.521-7.524 (d, 1H) m 7.362-7.450 (m, 4H), 7.276-7.279 (m, 1H), 7.039-7.061 (d, 1H), 6.920-6.942 (d, 1H), 5.665 (br, 1H), 5.142 (t, 1H), 4.558 (m, 2H), 3.765-3.804 (m, 1H), 3.471-3.519 (m, 1H), 3.402-3.416 (m, 1H), 3.280-3.295 (m, 1H), 2.391-2.403 (m, 1H), 2.122-2.146 (m, 1H).

Example 125: (S)-(2'-chloro-4-(3-(3-chloropyridin-2-yloxy)pyrrolidin-1-yl)biphenyl-3-yl)methanamine hydrochloride (Compound 1-122)

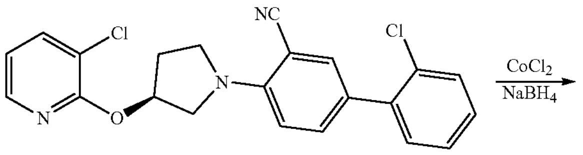

-continued

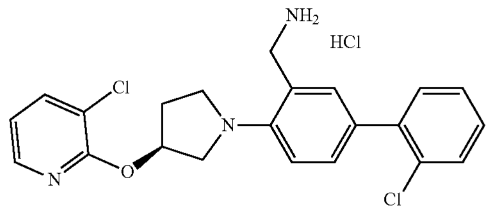

To a solution of (S)-2'-chloro-4-(3-(3-chloropyridin-2-yloxy)pyrrolidin-1-yl)biphenyl-3-carbonitrile (328 mg, 0.8 mmol) (prepared as example 29) in 5 mL MeOH was added CoCl2 (206 mg, 1.6 mmol) and NaBH4 (304 mg, 8 mmol) at 0° C., the mixture was stirred at rt for 12 h, the reaction mixture was filtered, the filtrate was quenched with NH3·H2O, extracted with DCM, dried over Na2SO4, removal the solvent to left the residue which was purified by silica gel, then Prep-HPLC, freezing dryness with HCl to give (S)-(2'-chloro-4-(3-(3-chloropyridin-2-yloxy)pyrrolidin-1-yl)biphenyl-3-yl)methanamine hydrochloride (12 mg, 3%), Mass spec: 414 (M+H), $t_R$=1.667 min, $^1$H-NMR (400 Hz, CDCl3) δ=8.952 (br, 3H), 7.971-8.019 (m, 2H), 7.875-7.894 (m, 1H), 7.787-7.807 (m, 1H), 7.659-7.676 (m, 2H), 7.278-7.297 (m, 1H), 7.217-7.257 (m, 1H), 7.104-7.171 (m, 1H), 6.895-6.922 (m, 1H), 5.822 (br, 1H), 4.980-4.994 (m, 1H), 4.692-4.806 (m, 2H), 4.487-4.493 (m, 1H), 3.574-3.605 (m, 2H), 2.702 (m, 1H), 2.403-2.434 (m, 1H).

Example 126: (R)-3-chloro-2-(1-(3-methoxybiphenyl-4-yl)pyrrolidin-3-yloxy)-5-(trifluoromethyl)pyridine (Compound 1-120)

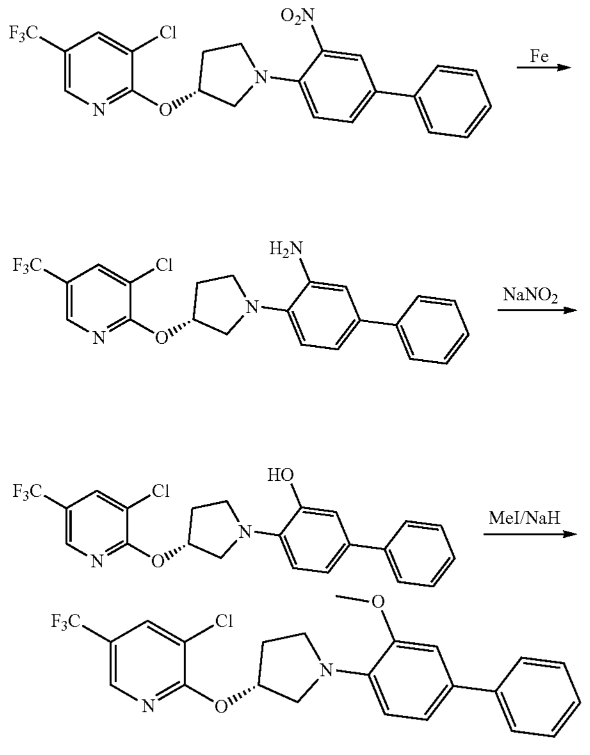

Step 1: (R)-4-(3-(3-chloro-5-(trifluoromethyl)pyridin-2-yloxy)pyrrolidin-1-yl)biphenyl-3-amine

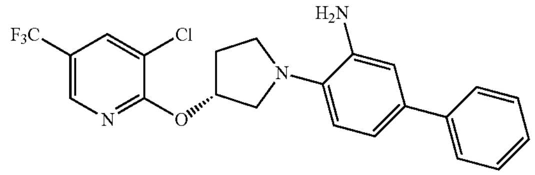 [SMILES: Nc1cc(-c2ccccc2)ccc1N1CC[C@@H](Oc2ncc(C(F)(F)F)cc2Cl)C1]

The title compound was prepared following procedures described in example 14 (step 2) using (R)-3-chloro-2-(1-(3-nitrobiphenyl-4-yl)pyrrolidin-3-yloxy)-5-(trifluoromethyl)pyridine (prepared as example 67) to give (R)-4-(3-(3-chloro-5-(trifluoromethyl)pyridin-2-yloxy)pyrrolidin-1-yl)biphenyl-3-amine (291 mg, 78% yield), Mass spec: 464 (M+H).

Step 2: (R)-4-(3-(3-chloro-5-(trifluoromethyl)pyridin-2-yloxy)pyrrolidin-1-yl)biphenyl-3-ol

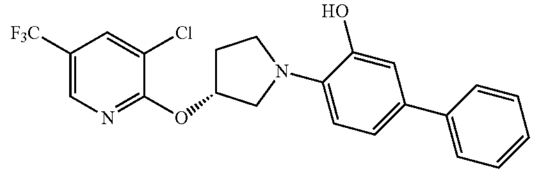 [SMILES: Oc1cc(-c2ccccc2)ccc1N1CC[C@@H](Oc2ncc(C(F)(F)F)cc2Cl)C1]

The title compound was prepared following procedures described in example 14 (step 3) to give (R)-4-(3-(3-chloro-5-(trifluoromethyl)pyridin-2-yloxy)pyrrolidin-1-yl)biphenyl-3-ol (48 mg, 16% yield), Mass spec: 435 (M+H).

Step 3: (R)-3-chloro-2-(1-(3-methoxybiphenyl-4-yl)pyrrolidin-3-yloxy)-5-(trifluoromethyl)pyridine

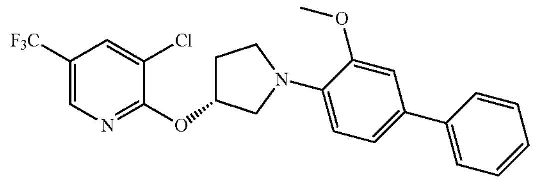 [SMILES: COc1cc(-c2ccccc2)ccc1N1CC[C@@H](Oc2ncc(C(F)(F)F)cc2Cl)C1]

The title compound was prepared following procedures described in example 68 (step 3) to give (R)-3-chloro-2-(1-(3-methoxybiphenyl-4-yl)pyrrolidin-3-yloxy)-5-(trifluoromethyl)pyridine (8.6 mg, 17% yield), Mass spec: 449 (M+H), $t_R$=3.737 min, $^1$H-NMR (400 Hz, DMSO) δ=8.580-8.582 (d, 1H), 8.368-8.373 (d, 1H), 7.592-7.610 (d, 2H), 7.366-7.405 (m, 2H), 7.230-7.267 (m, 1H), 7.123-7.160 (m, 2H), 6.754-6.774 (d, 1H), 5.685 (br, 1H), 3.824-3.912 (m, 1H), 3.744 (s, 3H), 3.511-3.550 (m, 1H), 3.395-3.425 (m, 1H), 3.211-3.271 (m, 1H), 2.297-2.367 (m, 1H), 2.131-2.163 (m, 1H).

Example 127: (S)-(2'-methyl-4-(3-(5-(trifluoromethyl)pyridin-2-yloxy)pyrrolidin-1-yl)biphenyl-3-yl)methanol (Compound 1-128)

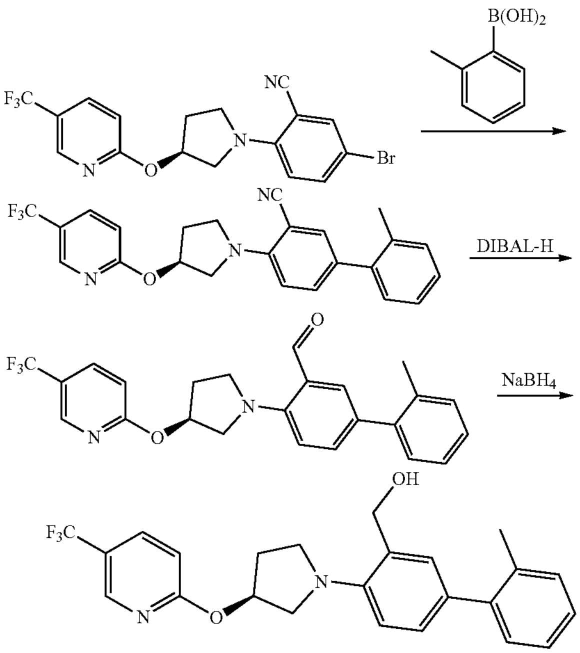

Step 1: (S)-2'-methyl-4-(3-(5-(trifluoromethyl)pyridin-2-yloxy)pyrrolidin-1-yl)biphenyl-3-carbonitrile

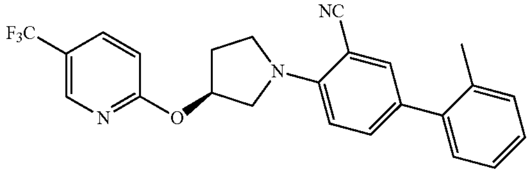 [SMILES: Cc1ccccc1-c1ccc(N2CC[C@H](Oc3ccc(C(F)(F)F)cn3)C2)c(C#N)c1]

The title compound was prepared following procedures described in example 67 (step 2) to give (S)-2'-methyl-4-(3-(5-(trifluoromethyl)pyridin-2-yloxy)pyrrolidin-1-yl)biphenyl-3-carbonitrile (433 mg, 70% yield), Mass spec: 424 (M+H).

Step 2: (S)-2'-methyl-4-(3-(5-(trifluoromethyl)pyridin-2-yloxy)pyrrolidin-1-yl)biphenyl-3-carbaldehyde

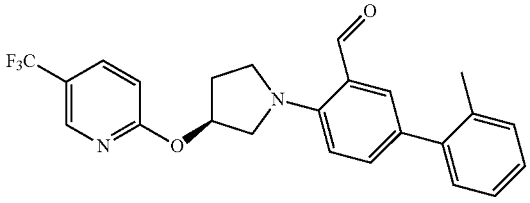 [SMILES: Cc1ccccc1-c1ccc(N2CC[C@H](Oc3ccc(C(F)(F)F)cn3)C2)c(C=O)c1]

The title compound was prepared following procedures described in example 96 (step 1) to give (S)-2'-methyl-4-(3-(5-(trifluoromethyl)pyridin-2-yloxy)pyrrolidin-1-yl)biphenyl-3-carbaldehyde (150 mg, 74% yield), Mass spec: 427 (M+H).

Step 3: (S)-(2'-methyl-4-(3-(5-(trifluoromethyl)pyridin-2-yloxy)pyrrolidin-1-yl)biphenyl-3-yl)methanol

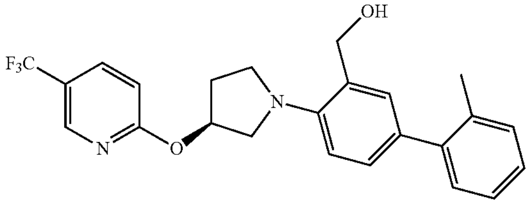 [SMILES: Cc1ccccc1-c1ccc(N2CC[C@H](Oc3ccc(C(F)(F)F)cn3)C2)c(CO)c1]

The title compound was prepared following procedures described in example 96 (step 2) to give (S)-(2'-methyl-4-(3-(5-(trifluoromethyl)pyridin-2-yloxy)pyrrolidin-1-yl)biphenyl-3-yl)methanol (70 mg, 46% yield), Mass spec: 429 (M+H), $t_R$=3.337 min, $^1$H-NMR (400 Hz, DMSO) δ=8.625 (s, 1H), 8.073-8.101 (d, 1H), 7.347 (s, 1H), 7.181-7.260 (m, 3H), 7.119-7.144 (m, 2H), 7.042-7.065 (d, 1H), 6.922-6.943 (d, 1H), 5.659-5.666 (m, 1H), 5.093-5.122 (t, 1H), 4.544-4.570 (m, 2H), 3.709-3.751 (m, 1H), 3.462-3.483 (m, 1H), 3.377-3.379 (m, 1H), 3.247-3.259 (m, 1H), 2.410-2.413 (m, 1H), 2.256 (s, 1H), 2.184-2.190 (m, 1H).

Example 128: (S)-(4-(3-(3-methylpyridin-2-yloxy)pyrrolidin-1-yl)biphenyl-3-yl)methanol (Compound 1-131)

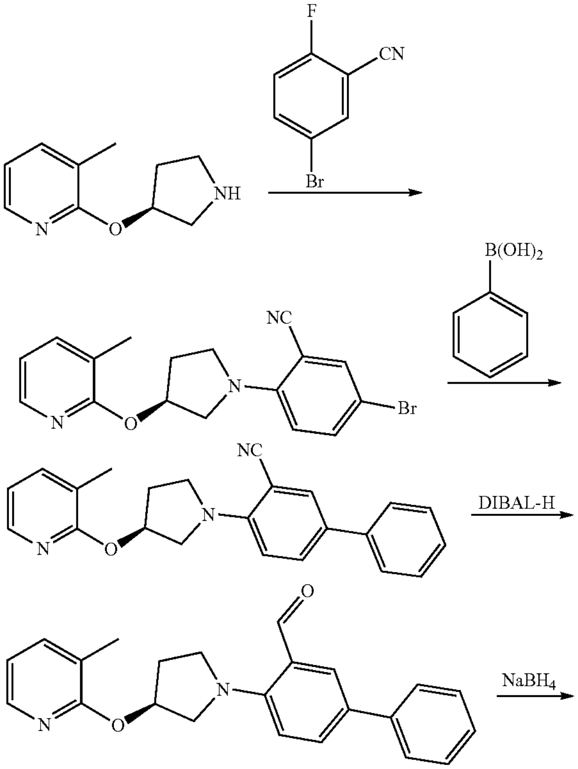

-continued

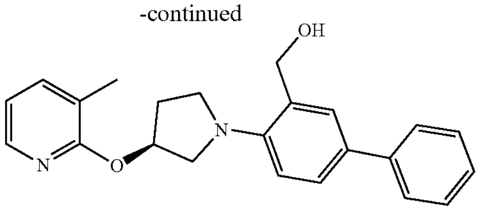

Step 1: (S)-5-bromo-2-(3-(3-methylpyridin-2-yloxy) pyrrolidin-1-yl)benzonitrile

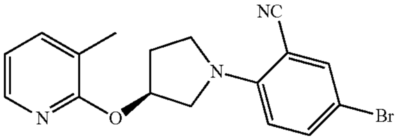 [SMILES: Cc1cccnc1O[C@H]1CCN(c2ccc(Br)cc2C#N)C1]

The title compound was prepared following procedures described in example 5 using (S)-3-methyl-2-(pyrrolidin-3-yloxy)pyridine (prepared as Intermediate 3) and 5-bromo-2-fluorobenzonitrile to give (S)-5-bromo-2-(3-(3-methylpyridin-2-yloxy)pyrrolidin-1-yl)benzonitrile (2.3 g, 82% yield), Mass spec: 358 (M+H)

Step 2: (S)-4-(3-(3-methylpyridin-2-yloxy)pyrrolidin-1-yl)biphenyl-3-carbonitrile

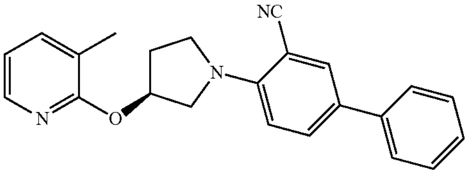 [SMILES: Cc1cccnc1O[C@H]1CCN(c2ccc(-c3ccccc3)cc2C#N)C1]

The title compound was prepared following procedures described in example 67 (step 2) to give (S)-4-(3-(3-methylpyridin-2-yloxy)pyrrolidin-1-yl)biphenyl-3-carbonitrile (750 mg, 75% yield), Mass spec: 356 (M+H).

Step 3: (S)-4-(3-(3-methylpyridin-2-yloxy)pyrrolidin-1-yl)biphenyl-3-carbaldehyde

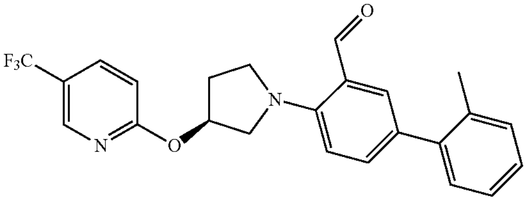 [SMILES: Cc1ccccc1-c1ccc(N2CC[C@H](Oc3ccc(C(F)(F)F)cn3)C2)c(C=O)c1]

The title compound was prepared following procedures described in example 96 (step 1) to give (S)-4-(3-(3-methylpyridin-2-yloxy)pyrrolidin-1-yl)biphenyl-3-carbaldehyde (150 mg, 42% yield), Mass spec: 356 (M+H).

Step 4: (S)-(4-(3-(3-methylpyridin-2-yloxy)pyrrolidin-1-yl)biphenyl-3-yl)methanol (CF-000270-026)

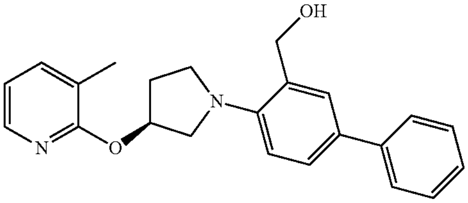 [SMILES: Cc1cccnc1O[C@H]1CCN(c2ccc(-c3ccccc3)cc2CO)C1]

The title compound was prepared following procedures described in example 96 (step 2) to give (S)-(4-(3-(3-methylpyridin-2-yloxy)pyrrolidin-1-yl)biphenyl-3-yl) methanol (75 mg, 69% yield), Mass spec: 361 (M+H), $t_R$=2.687 min, $^1$H-NMR (400 Hz, DMSO) δ=8.001-8.018 (m, 1H), 7.678-7.683 (m, 1H), 7.536-7.606 (m, 3H), 7.406-7.467 (m, 3H), 7.282-7.300 (m, 1H), 6.882-6.963 (m, 2H), 5.598 (br, 1H), 5.135-5.163 (t, 1H), 4.562-4.593 (m, 2H), 3.701-3.726 (m, 1H), 3.474-3.478 (m, 1H), 3.294-3.321 (m, 2H), 2.505-2.514 (m, 1H), 2.128-2.131 (m, 4H).

Example 129: (S)-(4-(3-(3-methylpyridin-2-yloxy) pyrrolidin-1-yl)biphenyl-3-yl)methanol (Compound 1-129)

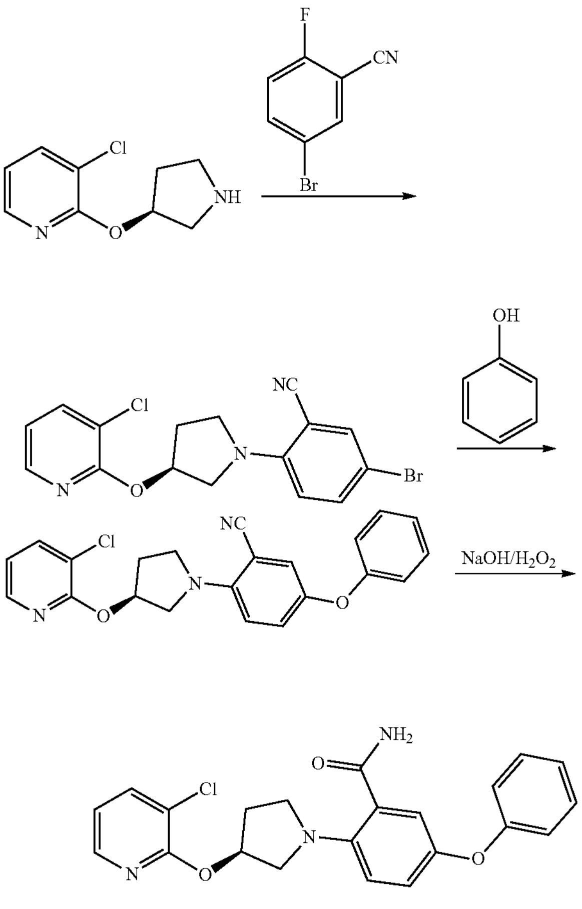

Step 1: (S)-5-bromo-2-(3-(3-chloropyridin-2-yloxy)pyrrolidin-1-yl)benzonitrile

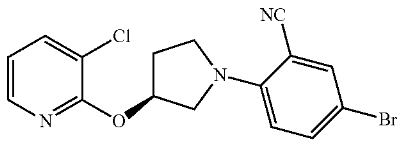 [SMILES: N#Cc1cc(Br)ccc1N1CC[C@H](Oc2ncccc2Cl)C1]

The title compound was prepared following procedures described in example 5 using (S)-3-chloro-2-(pyrrolidin-3-yloxy)pyridine (prepared as Intermediate 3) and 5-bromo-2-fluorobenzonitrile to give (S)-5-bromo-2-(3-(3-chloropyridin-2-yloxy)pyrrolidin-1-yl)benzonitrile (5.4 g, 90% yield), Mass spec: 378 (M+H)

Step 2: (S)-2-(3-(3-chloropyridin-2-yloxy)pyrrolidin-1-yl)-5-phenoxybenzonitrile

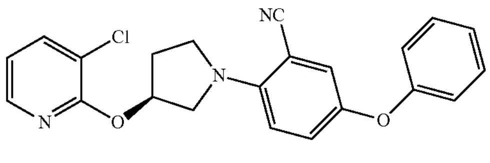 [SMILES: N#Cc1cc(Oc2ccccc2)ccc1N1CC[C@H](Oc2ncccc2Cl)C1]

The title compound was prepared following procedures described in example 94 (step 1) to give (S)-2-(3-(3-chloropyridin-2-yloxy)pyrrolidin-1-yl)-5-phenoxybenzonitrile (129 mg, 50% yield), Mass spec: 392 (M+H)

Step 2: (S)-2-(3-(3-chloropyridin-2-yloxy)pyrrolidin-1-yl)-5-phenoxybenzonitrile

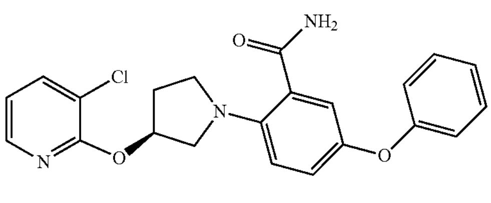 [SMILES: NC(=O)c1cc(Oc2ccccc2)ccc1N1CC[C@H](Oc2ncccc2Cl)C1]

The title compound was prepared following procedures described in example 94 (step 2) to give (S)-2-(3-(3-chloropyridin-2-yloxy)pyrrolidin-1-yl)-5-phenoxybenzonitrile (11 mg, 8% yield), Mass spec: 410 (M+H), $t_R$=2.642 min, $^1$H-NMR (400 Hz, DMSO) δ=8.151 (s, 1H), 7.949 (br, 1H), 7.896-7.919 (m, 1H), 7.329-7.378 (m, 3H), 6.877-7.090 (7H), 5.630-5.653 (m, 1H), 3.800-3.846 (m, 1H), 3.480-3.484 (m, 1H), 3.268-3.331 (m, 2H), 2.319-2.352 (m, 1H), 2.171-2.175 (m, 1H).

Example 184: (S)-4-(3-(3-chloropyridin-2-yloxy)pyrrolidin-1-yl)-3-(2-hydroxyethyl)-N-phenylbenzamide (Compound 1-320)

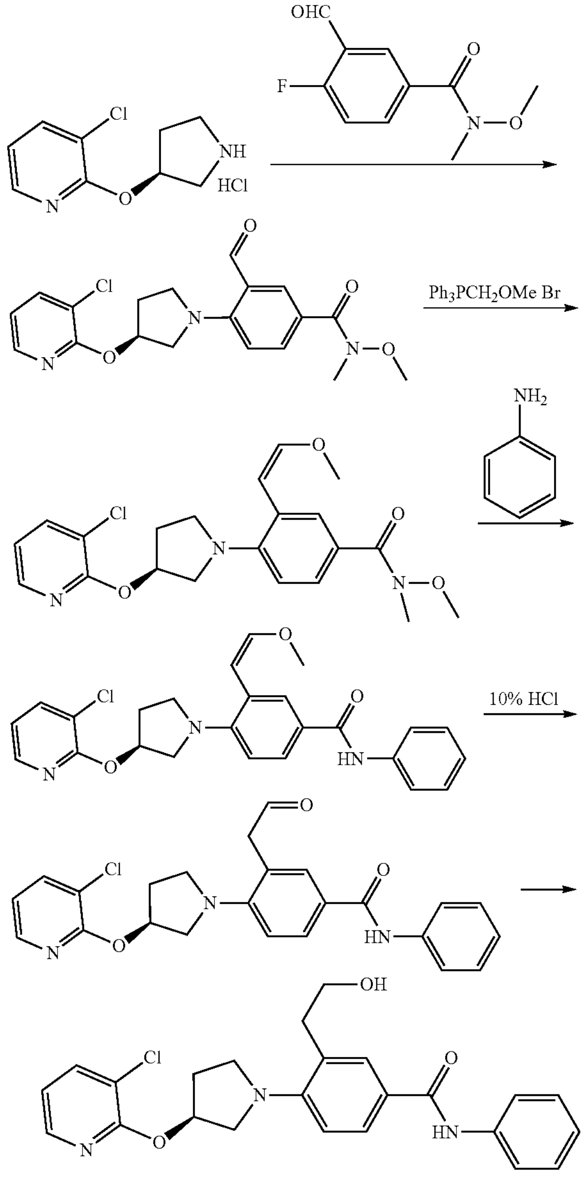

Step 1: (S)-4-(3-(3-chloropyridin-2-yloxy)pyrrolidin-1-yl)-3-formyl-N-methoxy-N-methylbenzamide

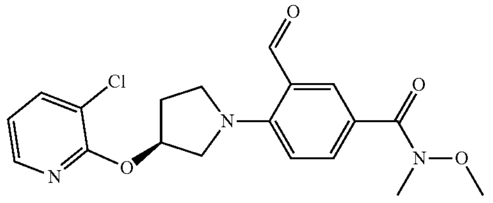 [SMILES: CON(C)C(=O)c1ccc(N2CC[C@H](Oc3ncccc3Cl)C2)c(C=O)c1]

The title compound was prepared following procedures described in Step 2 of Example 178 to give (S)-4-(3-(3-chloropyridin-2-yloxy)pyrrolidin-1-yl)-3-formyl-N-methoxy-N-methylbenzamide (2.2 g, 56% yield), Mass spec: 390 (M+H).

Step 2: (S)-4-(3-(3-chloropyridin-2-yloxy)pyrrolidin-1-yl)-N-methoxy-3-(2-methoxyvinyl)-N-methylbenzamide

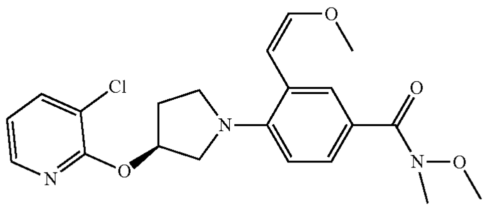 [SMILES: CO/C=C\c1cc(C(=O)N(C)OC)ccc1N1CC[C@H](Oc2ncccc2Cl)C1]

The title compound was prepared following procedures described in Step 2 of Example 168 to give (S)-4-(3-(3-chloropyridin-2-yloxy)pyrrolidin-1-yl)-N-methoxy-3-(2-methoxyvinyl)-N-methylbenzamide (2.4 g, 85% yield), Mass spec: 418 (M+H).

Step 3: (S)-4-(3-(3-chloropyridin-2-yloxy)pyrrolidin-1-yl)-3-(2-methoxyvinyl)-N-phenylbenzamide

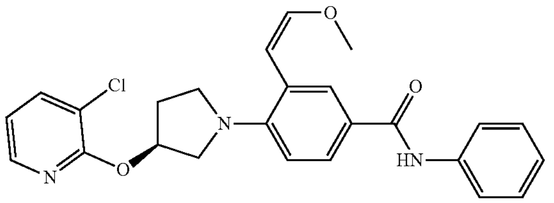 [SMILES: CO/C=C\c1cc(C(=O)Nc2ccccc2)ccc1N1CC[C@H](Oc2ncccc2Cl)C1]

To a solution of aniline (46 mg, 0.5 mmol) was added n-BuLi (0.24 ml, 2.5 M in hexane) at ice water bath, the mixture was stirred for 30 min at this temperature, before (S)-4-(3-(3-chloropyridin-2-yloxy)pyrrolidin-1-yl)-N-methoxy-3-(2-methoxyvinyl)-N-methylbenzamide (104 mg, 0.25 mmol) was added, then return to rt slowly, quenched by NH4Cl solution, EA was added, washed by brine, removal the solvent to left the crude (S)-4-(3-(3-chloropyridin-2-yloxy)pyrrolidin-1-yl)-3-(2-methoxyvinyl)-N-phenylbenzamide (50 mg, 44% yield), Mass spec: 418 (M+H).

Step 4: (S)-4-(3-(3-chloropyridin-2-yloxy)pyrrolidin-1-yl)-3-(2-oxoethyl)-N-phenylbenzamide

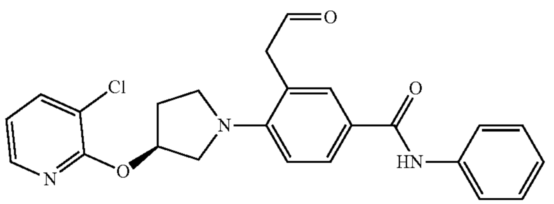 [SMILES: O=CCc1cc(C(=O)Nc2ccccc2)ccc1N1CC[C@H](Oc2ncccc2Cl)C1]

The title compound was prepared following procedures described in Step 3 of Example 168 to give (S)—(S)-4-(3-(3-chloropyridin-2-yloxy)pyrrolidin-1-yl)-3-(2-oxoethyl)-N-phenylbenzamide (30 mg, 62% yield), Mass spec: 436 (M+H).

Step 5: (S)-4-(3-(3-chloropyridin-2-yloxy)pyrrolidin-1-yl)-3-(2-hydroxyethyl)-N-phenylbenzamide

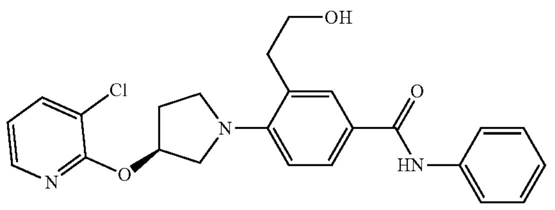

The title compound was prepared following procedures described in Step 4 of Example 168 to give (S)-4-(3-(3-chloropyridin-2-yloxy)pyrrolidin-1-yl)-3-(2-hydroxyethyl)-N-phenylbenzamide (10 mg, 48.9% yield), Mass spec: 438 (M+H), $t_R$=2.479 min, $^1$H-NMR (400 Hz, DMSO) δ=9.335 (s, 1H), 8.159-8.172 (m, 1H), 7.905-7.925 (m, 1H), 7.737-7.901 (m, 4H), 7.310-7.350 (m, 2H), 7.036-7.083 (m, 2H), 6.931-6.953 (m, 1H), 5.661-5.686 (br, 1H), 4.675-4.901 (t, 1H), 3.828-3.869 (m, 1H), 3.588-3.701 (m, 3H), 3.309-3.363 (m, 2H), 2.514-2.938 (m, 2H), 2.191-2.496 (m, 2H).

Example 185: (S)-4-(3-(3-chloropyridin-2-yloxy)pyrrolidin-1-yl)-3-(2-hydroxyethyl)-N-methyl-N-phenylbenzamide (Compound 1-337)

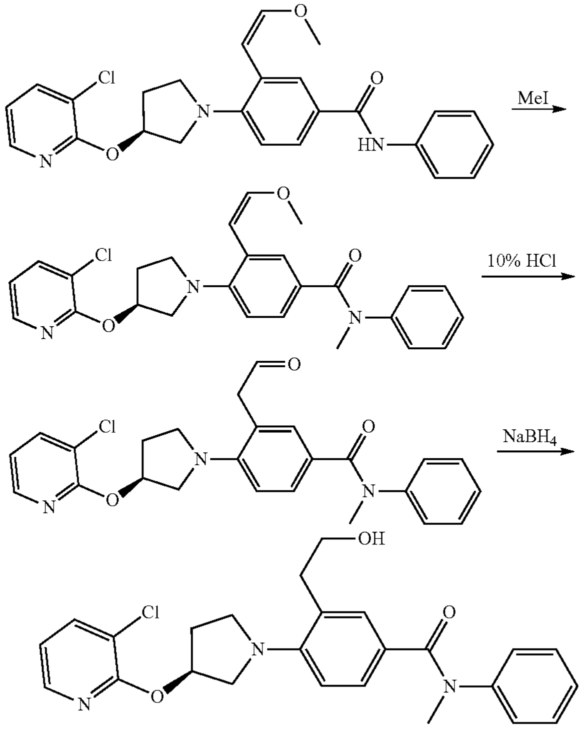

Step 1: (S,Z)-4-(3-(3-chloropyridin-2-yloxy)pyrrolidin-1-yl)-3-(2-methoxyvinyl)-N-methyl-N-phenylbenzamide

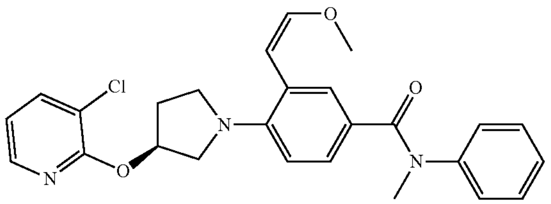 [SMILES: CO/C=C\c1cc(C(=O)N(C)c2ccccc2)ccc1N1CC[C@H](Oc2ncccc2Cl)C1]

To a solution of (S)-4-(3-(3-chloropyridin-2-yloxy)pyrrolidin-1-yl)-3-(2-methoxyvinyl)-N-phenylbenzamide (100 mg, 0.22 mmol) (example 184 step 3) in 4 mL THE was added NaH (17.6 mg, 0.44 mmol) at 0° C., the mixture was stirred for 20 min at rt, then MeI (62 mg, 0.44 mmol) was added, stirred for another 30 min, quenched by water, extracted with EA, washed by water, brine, dried over Na2SO4, removal the solvent to give crude (S,Z)-4-(3-(3-chloropyridin-2-yloxy)pyrrolidin-1-yl)-3-(2-methoxyvinyl)-N-methyl-N-phenylbenzamide (80 mg, 78%) which can be used directly, Mass spec: 464 (M+H).

Step 2: (S)-4-(3-(3-chloropyridin-2-yloxy)pyrrolidin-1-yl)-N-methyl-3-(2-oxoethyl)-N-phenylbenzamide

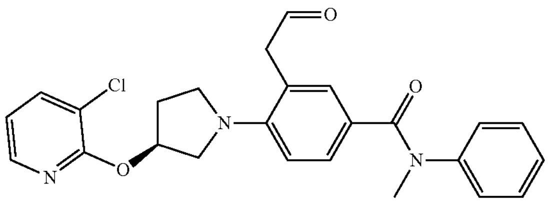 [SMILES: CN(C(=O)c1ccc(N2CC[C@H](Oc3ncccc3Cl)C2)c(CC=O)c1)c1ccccc1]

The title compound was prepared following procedures described in Example 184 (step 4) to give (S)-4-(3-(3-chloropyridin-2-yloxy)pyrrolidin-1-yl)-N-methyl-3-(2-oxoethyl)-N-phenylbenzamide (70 mg, 85% yield), Mass spec: 450 (M+H).

Step 2: (S)-4-(3-(3-chloropyridin-2-yloxy)pyrrolidin-1-yl)-3-(2-hydroxyethyl)-N-methyl-N-phenylbenzamide

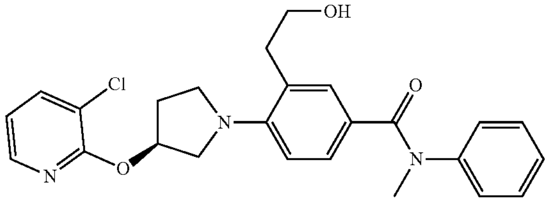

The title compound was prepared following procedures described in Example 184 (step 5) to give (S)-4-(3-(3-chloropyridin-2-yloxy)pyrrolidin-1-yl)-3-(2-hydroxyethyl)-N-methyl-N-phenylbenzamide (20 mg, 85% yield), Mass spec: 452 (M+H), $t_R$=2.559 min, $^1$H-NMR (400 Hz, DMSO) δ=8.123-8.140 (m, 1H), 7.883-7.906 (m, 1H), 7.270-7.308 (m, 2H), 7.123-7.187 (m, 3H), 6.997-7.048 (m, 3H), 6.658-6.679 (d, 1H), 5.581-5.592 (br, 1H), 4.569-4.595 (t, 1H), 3.671-3.712 (m, 1H), 3.414-3.475 (m, 3H), 3.346 (s, 3H), 3.155-3.213 (m, 2H), 2.593-2.652 (m, 2H), 2.277-2.325 (m, 1H), 2.087-2.101 (m, 1H).

Example 186: (S)-4-(3-(3-chloropyridin-2-yloxy)pyrrolidin-1-yl)-N-(4-fluorophenyl)-3-(2-hydroxyethyl)benzamide (Compound 1-319)

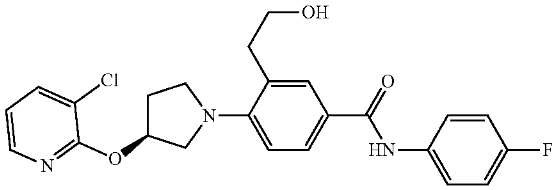 [SMILES: O=C(Nc1ccc(F)cc1)c1ccc(N2CC[C@H](Oc3ncccc3Cl)C2)c(CCO)c1]

The title compound was prepared following procedures described in Example 184 to give (S)-4-(3-(3-chloropyridin-2-yloxy)pyrrolidin-1-yl)-N-(4-fluorophenyl)-3-(2-hydroxyethyl)benzamide (15 mg, 48.9% yield), Mass spec: 456 (M+H), $t_R$=2.618 min, $^1$H-NMR (400 Hz, DMSO) δ=10.001 (s, 1H), 8.160-8.172 (m, 1H), 7.903-7.926 (m, 1H), 7.728-7.904 (m, 4H), 7.152-7.197 (m, 2H), 7.037-7.069 (m, 1H), 6.929-6.950 (m, 1H), 5.661-5.686 (br, 1H), 4.683-4.709 (t, 1H), 3.829-3.870 (m, 1H), 3.590-3.709 (m, 3H), 3.309-3.347 (m, 2H), 2.864-2.937 (m, 2H), 2.176-2.509 (m, 2H).

Example 189: 2-(5-((3-chlorophenyl)(hydroxy)methyl)-2-((S)-3-(3-chloropyridin-2-yloxy)pyrrolidin-1-yl)phenyl)ethanol (Compound 1-329)

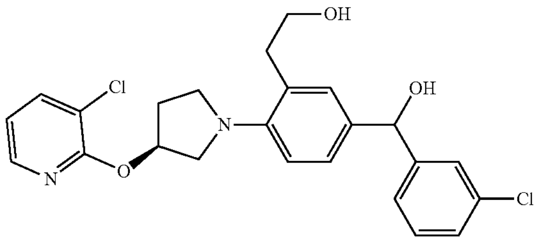 [SMILES: OCCc1cc(C(O)c2cccc(Cl)c2)ccc1N1CC[C@H](Oc2ncccc2Cl)C1]

The title compound was prepared following procedures described in example 168 to give 2-(5-((3-chlorophenyl)(hydroxy)methyl)-2-((S)-3-(3-chloropyridin-2-yloxy)pyrrolidin-1-yl)phenyl)ethanol (32 mg, 34% yield), Mass spec: 459 (M+H), $t_R$=2.523 min $^1$H-NMR (400 Hz, DMSO) δ=8.126-8.130 (m, 1H), 7.883-7.907 (m, 1H), 7.401 (s, 1H), 7.165-7.321 (m, 4H), 6.930-7.093 (m, 3H), 5.864-5.874 (d, 1H), 5.569-5.620 (m, 2H), 4.623-4.650 (t, 1H), 3.576-3.638 (m, 3H), 3.328-3.352 (m, 1H), 3.074-3.157 (m, 2H), 2.765-2.801 (m, 2H), 2.339-2.449 (m, 1H), 2.065-2.081 (m, 1H).

Example 190: (S)-(3-chlorophenyl)(4-(3-(3-chloropyridin-2-yloxy)pyrrolidin-1-yl)-3-(2-hydroxyethyl)phenyl)methanone (Compound 1-328)

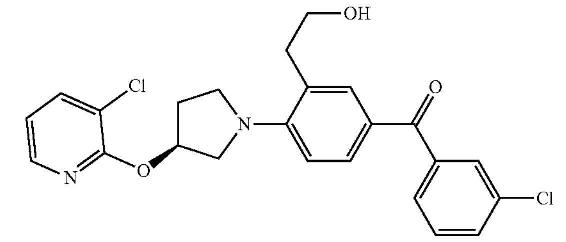 [SMILES: O=C(c1cccc(Cl)c1)c1ccc(N2CC[C@H](Oc3ncccc3Cl)C2)c(CCO)c1]

The title compound was prepared following procedures described in example 169 to give (S)-(3-chlorophenyl)(4-(3-(3-chloropyridin-2-yloxy)pyrrolidin-1-yl)-3-(2-hydroxyethyl)phenyl)methanone (26 mg, 34% yield), Mass spec: 457 (M+H), $t_R$=3.025 min $^1$H-NMR (400 Hz, DMSO) δ=8.156-8.160 (m, 1H), 7.901-7.924 (m, 1H), 7.488-7.700 (m, 6H), 7.040-7.071 (m, 1H), 6.878-6.900 (d, 1H), 5.069-5.701 (br, 1H), 4.660-4.686 (t, 1H), 3.934-3.974 (m, 3H), 3.554-3.703 (m, 3H), 3.448-3.490 (m, 2H), 2.840-2.971 (m, 2H), 2.325-2.360 (m, 1H), 2.196-2.009 (m, 1H).

Example 191: (S)-(2-chlorophenyl)(3-(hydroxymethyl)-4-(3-(pyridin-2-yloxy)pyrrolidin-1-yl)phenyl)methanone (Compound 1-332)

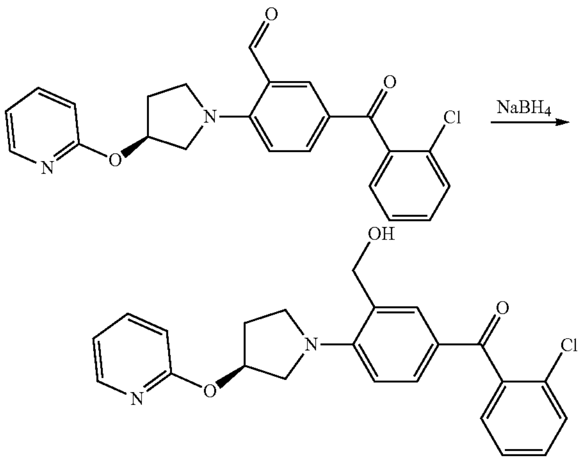

To a solution of (S)-5-(2-chlorobenzoyl)-2-(3-(pyridin-2-yloxy)pyrrolidin-1-yl)benzaldehyde (100 mg, 0.25 mmol) (prepared as 168 step 1 (WLX-000371-012)) in 2 mL MeOH was added NaBH4 (29 mg, 0.75 mmol) with stirring for 20 min at 0° C., after finished, quenched by water, extracted with EA, washed by brine, dried over Na2SO4, filtered and removal the solvent to give crude product which was purified by Prep-HPLC to give (S)-(2-chlorophenyl)(3-(hydroxymethyl)-4-(3-(pyridin-2-yloxy)pyrrolidin-1-yl)phenyl) methanone (15 mg, 14% yield), Mass spec: 409 (M+H), $t_R$=2.604 min, $^1$H-NMR (400 Hz, DMSO) δ=8.179-8.195 (m, 1H), 7.692-7.725 (m, 2H), 7.449-7.583 (m, 3H), 7.369-7.396 (m, 2H), 6.989-7.006 (m, 1H), 6.799-6.821 (d, 1H), 6.722-6.744 (d, 1H), 5.622-5.633 (br, 1H), 5.221-5.249 (t, 1H), 4.470-4.598 (m, 2H), 3.979-4.020 (m, 1H), 3.616-3.709 (m, 3H), 2.197-2.272 (m, 1H), 2.182-2.190 (m, 1H).

Example 192: (2-chlorophenyl)(3-(hydroxymethyl)-4-((S)-3-(pyridin-2-yloxy)pyrrolidin-1-yl)phenyl) methanol (Compound 1-338)

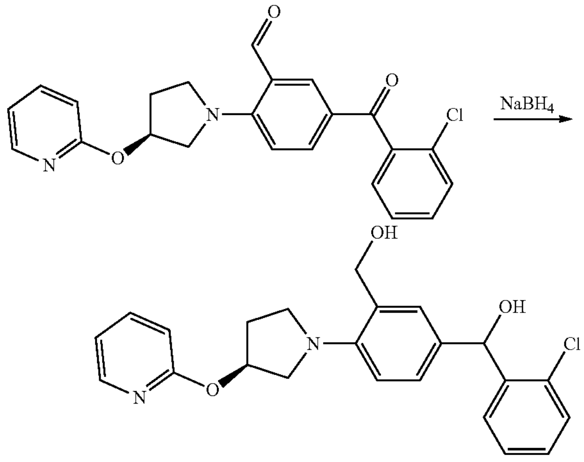

The title compound was prepared following procedures described in example 191 at 0° C. for 1 h to give (2-chlorophenyl)(3-(hydroxymethyl)-4-((S)-3-(pyridin-2-yloxy) pyrrolidin-1-yl)phenyl)methanol (10 mg, 48% yield), Mass spec: 411 (M+H), $t_R$=1.325 min, $^1$H-NMR (400 Hz, DMSO) δ=8.153-8.171 (m, 1H), 7.672-7.716 (m, 2H), 7.351-7.392 (m, 3H), 7.235-7.277 (m, 1H), 7.039-7.076 (m, 1H), 6.821-6.925 (m, 1H), 6.723-6.821 (m, 2H), 5.850-5.927 (m, 2H), 5.507-5.537 (m, 1H), 5.041-5.067 (m, 1H), 4.437-4.464 (m, 1H), 3.558-3.599 (m, 1H), 3.304-3.321 (m, 1H), 3.089-3.198 (m, 2H), 2.293-2.343 (m, 1H), 2.010-2.044 (m, 1H).

Example 193: (2-chlorophenyl)(4-((S)-3-(3-fluoropyridin-2-yloxy)pyrrolidin-1-yl)-3-(hydroxymethyl) phenyl)methanol (Compound 1-264)

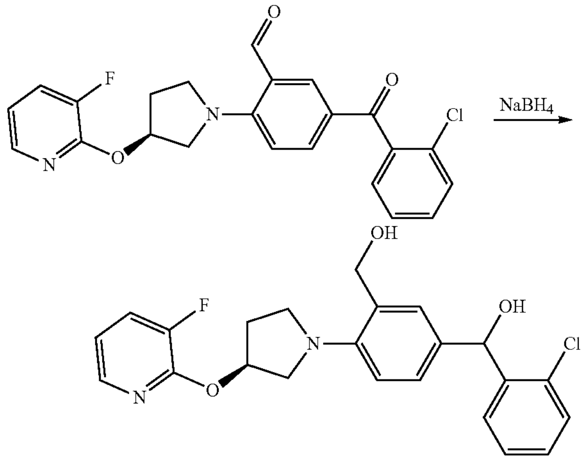

To a solution of (S)-5-(2-chlorobenzoyl)-2-(3-(3-fluoropyridin-2-yloxy)pyrrolidin-1-yl)benzaldehyde (170 mg, 0.4 mmol)(prepared as 168 step 1 (XXL-000382-079)) in 4 mL MeOH was added NaBH4 (46 mg, 1.2 mmol) with stirring for 20 min at 0° C., after finished, quenched by water, extracted with EA, washed by brine, dried over Na2SO4, filtered and removal the solvent to give crude product which was purified by Prep-HPLC to give (2-chlorophenyl)(4-((S)-3-(3-fluoropyridin-2-yloxy)pyrrolidin-1-yl)-3-(hydroxymethyl)phenyl)methanol (53 mg, 31% yield), Mass spec: 429 (M+H), $t_R$=2.477 min, $^1$H-NMR (400 Hz, DMSO) δ=7.977-7.987 (m, 1H), 7.654-7.713 (m, 1H), 7.352-7.390 (m, 3H), 7.238-7.276 (m, 1H), 7.004-7.085 (m, 2H), 6.810-6.836 (d, 1H), 5.882-5.927 (m, 2H), 5.579 (br, 1H), 5.074-5.099 (t, 1H), 4.445-4.470 (m, 2H), 3.578-3.619 (m, 1H), 3.337-3.369 (m, 1H), 3.221-3.248 (m, 1H), 3.115-3.138 (m, 1H), 2.330-2.380 (m, 1H), 2.057-2.089 (m, 1H).

Example 194: (S)-(2-chlorophenyl)(4-(3-(3-fluoropyridin-2-yloxy)pyrrolidin-1-yl)-3-(hydroxymethyl)phenyl)methanone (Compound 1-265)

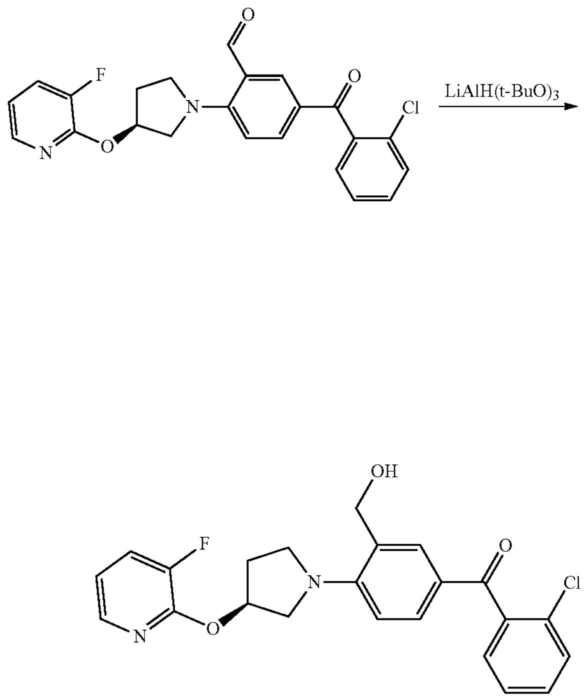

To a solution of (S)-5-(2-chlorobenzoyl)-2-(3-(3-fluoropyridin-2-yloxy)pyrrolidin-1-yl)benzaldehyde (170 mg, 0.4 mmol)(prepared as 168 step 1 (XXL-000382-079)) in 4 mL THE was added LiAlH(t-BuO)3 (203 mg, 0.8 mmol) with stirring for 2 h at 30° C., after finished, quenched by water, extracted with EA, washed by brine, dried over Na2SO4, filtered and removal the solvent to give crude product which was purified by Prep-HPLC to give (2-chlorophenyl)(4-((S)-3-(3-fluoropyridin-2-yloxy)pyrrolidin-1-yl)-3-(hydroxymethyl)phenyl)methanol (41 mg, 24% yield), Mass spec: 427 (M+H), $t_R$=2.742 min, $^1$H-NMR (400 Hz, DMSO) δ=8.001-8.011 (m, 1H), 7.665-7.711 (m, 2H), 7.449-7.585 (m, 3H), 7.387-7.403 (m, 2H), 7.044-7.051 (m, 1H), 6.736-6.758 (d, 1H), 5.706 (br, 1H), 5.243 (t, 1H), 4.475-4.602 (m, 2H), 4.016-4.052 (m, 1H), 3.631-3.742 (m, 3H), 2.312-2.331 (m, 1H), 2.234-2.236 (m, 1H).

Example 195: (2-chlorophenyl)(4-((S)-3-(3-fluoropyridin-2-yloxy)pyrrolidin-1-yl)-3-(hydroxymethyl)phenyl)methanol (Compound 1-321 & 322)

Peak 1

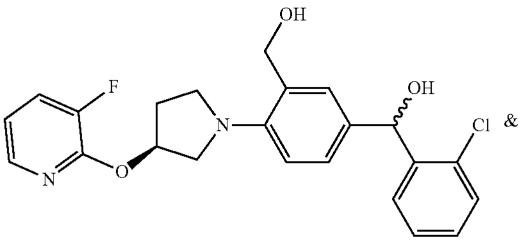

&

Peak 2

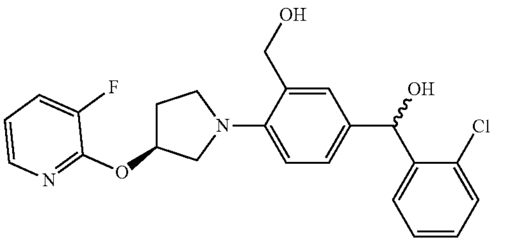

The title compound was prepared following procedures described in example 193 and separated by SFC to give peak1 and peak2, Mass spec: 429 (M+H), $t_R$=2.450 min (peak1) and $t_R$=2.188 min (peak2), $^1$H-NMR (400 Hz, DMSO)

Peak 1: δ=7.977-7.987 (m, 1H), 7.652-7.714 (m, 2H), 7.352-7.393 (m, 3H), 7.257-7.277 (m, 1H), 7.013-7.074 (m, 2H), 6.814-6.835 (d, 1H), 5.858-5.931 (m, 2H), 5.599 (br, 1H), 5.060 (t, 1H), 4.456-4.460 (m, 2H), 3.577-3.618 (m, 1H), 3.345-3.377 (m, 1H), 3.224-3.251 (m, 1H), 3.117-3.130 (m, 1H), 2.346-2.350 (m, 1H), 2.079-2.082 (m, 1H).

Peak 2: δ=7.974-7.990 (m, 1H), 7.680-7.708 (m, 2H), 7.354-7.392 (m, 3H), 7.256-7.272 (m, 1H), 7.025-7.068 (m, 2H), 6.818-6.839 (d, 1H), 5.857-5.936 (m, 2H), 5.606 (br, 1H), 5.057 (t, 1H), 4.442-4.468 (m, 2H), 3.590-3.592 (m, 1H), 3.341-3.360 (m, 1H), 3.222-3.244 (m, 1H), 3.108-3.131 (m, 1H), 2.331-2.381 (m, 1H), 2.057-2.097 (m, 1H).

Example 196: (2-chlorophenyl)(4-((S)-3-(3-chloropyridin-2-yloxy)pyrrolidin-1-yl)-3-(hydroxymethyl)phenyl)methanol (Compound 1-262)

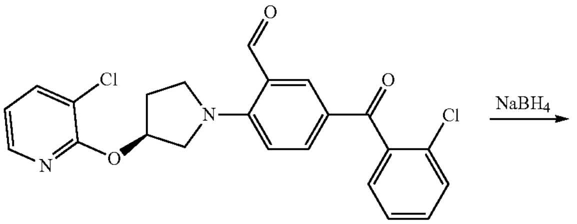

-continued

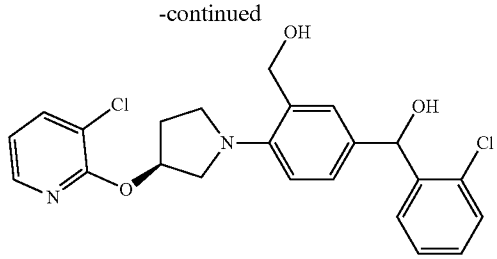

The title compound was prepared following procedures described in example 193 to give (2-chlorophenyl)(4-((S)-3-(3-chloropyridin-2-yloxy)pyrrolidin-1-yl)-3-(hydroxymethyl)phenyl)methanol (56.7 mg, 28% yield), Mass spec: 445 (M+H), $t_R$=2.627 min, $^1$H-NMR (400 Hz, DMSO) δ=8.125-8.142 (m, 1H), 7.882-7.905 (m, 1H), 7.694-7.712 (m, 1H), 7.350-7.396 (m, 3H), 7.251-7.275 (m, 1H), 7.009-7.068 (m, 2H), 6.816-6.840 (d, 1H), 5.890-5.933 (m, 2H), 5.570-5.584 (br, 1H), 5.081-5.111 (t, 1H), 4.443-4.472 (m, 2H), 3.574-3.615 (m, 1H), 3.336-3.372 (m, 1H), 3.197-3.224 (m, 1H), 3.116-3.129 (m, 1H), 2.321-2.372 (m, 1H), 2.037-2.070 (m, 1H).

Example 197: (S)-(2-chlorophenyl)(4-(3-(3-chloropyridin-2-yloxy)pyrrolidin-1-yl)-3-(hydroxymethyl)phenyl)methanone (Compound 1-263)

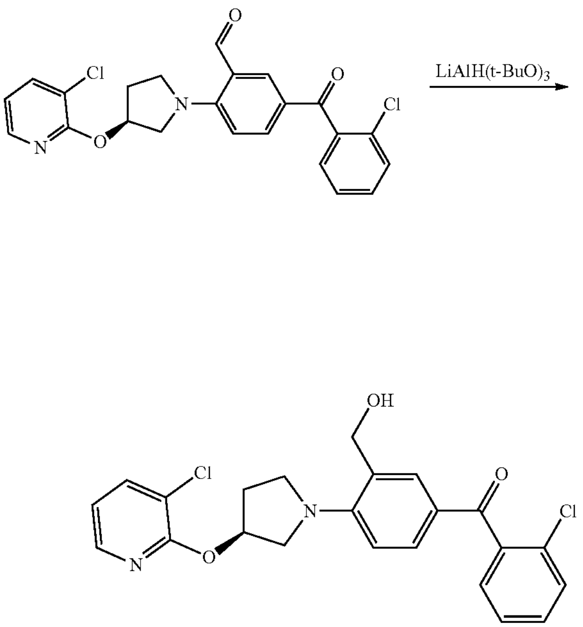

The title compound was prepared following procedures described in example 194 to give (S)-(2-chlorophenyl)(4-(3-(3-chloropyridin-2-yloxy)pyrrolidin-1-yl)-3-(hydroxymethyl)phenyl)methanone (37 mg, 20.9% yield), Mass spec: 443 (M+H), $t_R$=2.864 min, $^1$H-NMR (400 Hz, DMSO) δ=8.152-8.164 (m, 1H), 7.894-7.913 (m, 1H), 7.717 (s, 1H), 7.466-7.584 (m, 3H), 7.371-7.388 (m, 2H), 7.035-7.065 (m, 1H), 6.743-6.764 (d, 1H), 5.690 (br, 1H), 5.230-5.256 (t, 1H), 4.473-4.601 (m, 2H), 4.014-4.054 (m, 1H), 3.610-3.716 (m, 3H), 2.304-2.326 (m, 1H), 2.210-2.214 (m, 1H).

Example 198: (4-((S)-3-(3-chloropyridin-2-yloxy)pyrrolidin-1-yl)-3-(hydroxymethyl)phenyl)(2-ethylphenyl)methanol (Compound 1-260)

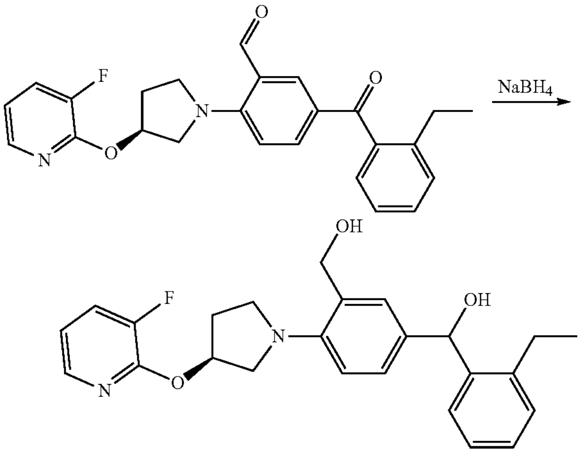

The title compound was prepared following procedures described in example 193 to give (4-((S)-3-(3-chloropyridin-2-yloxy)pyrrolidin-1-yl)-3-(hydroxymethyl)phenyl)(2-ethylphenyl)methanol (20 mg, 30% yield), Mass spec: 439 (M+H), $t_R$=2.606 min, $^1$H-NMR (400 Hz, DMSO) δ=7.975-7.987 (m, 1H), 7.655-7.702 (m, 1H), 7.462-7.475 (m, 1H), 7.337-7.343 (m, 1H), 7.136-7.185 (m, 3H), 7.002-7.035 (m, 2H), 6.812-6.832 (m, 1H), 5.818-5.828 (m, 1H), 5.594 (br, 2H), 5.046-5.059 (t, 1H), 4.440-4.465 (m, 2H), 3.567-3.608 (m, 1H), 3.212-3.238 (m, 1H), 3.106-3.119 (m, 1H), 2.618-2.654 (m, 1H), 2.507-2.553 (m, 2H), 2.334-2.368 (m, 1H), 2.070-2.087 (m, 1H), 1.056-1.094 (t, 3H).

Example 199: (S)-(4-(3-(3-chloropyridin-2-yloxy)pyrrolidin-1-yl)-3-(hydroxymethyl)phenyl)(2-ethylphenyl)methanone (Compound 1-251)

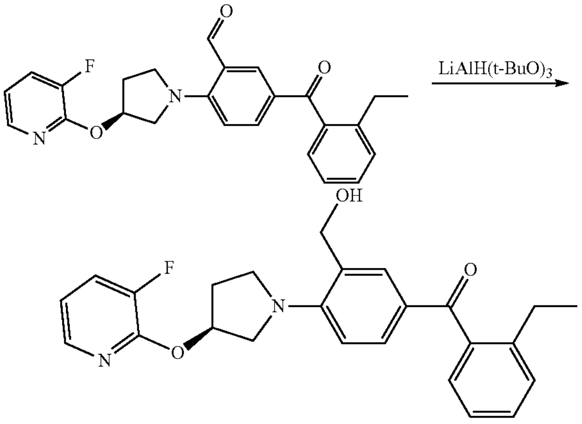

The title compound was prepared following procedures described in example 194 to give (S)-(4-(3-(3-chloropyridin-2-yloxy)pyrrolidin-1-yl)-3-(hydroxymethyl)phenyl)(2-ethylphenyl)methanone (30 mg, 36% yield), Mass spec: 437 (M+H), $t_R$=2.923 min, $^1$H-NMR (400 Hz, DMSO) δ=8.001-8.013 (m, 1H), 7.670-7.733 (m, 2H), 7.264-7.448 (m, 4H), 7.164-7.183 (m, 1H), 7.028-7.069 (m, 1H), 6.733-6.755 (m, 1H), 5.701 (br, 1H), 5.223-5.250 (t, 1H), 4.465-4.592 (m, 2H), 3.995-4.035 (m, 1H), 3.604-3.717 (m, 3H), 2.506-2.550 (m, 2H), 2.298-2.331 (m, 1H), 2.223-2.230 (m, 1H), 1.035-1.073 (t, 3H).

Example 200: (S)-(4-(3-(3-chloropyridin-2-yloxy)pyrrolidin-1-yl)-3-(hydroxymethyl)phenyl)(o-tolyl)methanone & (4-((S)-3-(3-chloropyridin-2-yloxy)pyrrolidin-1-yl)-3-(hydroxymethyl)phenyl)(o-tolyl)methanol (Compound 1-246 & 247)

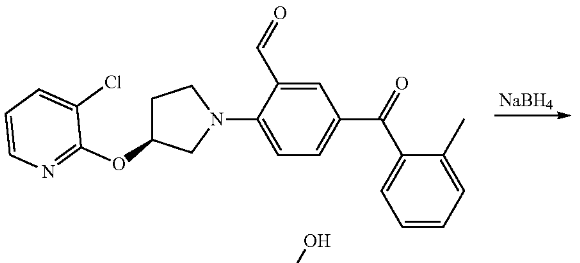

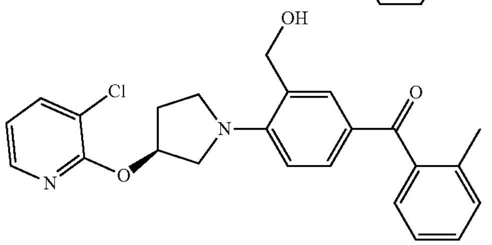

&

XXL-000328-069A

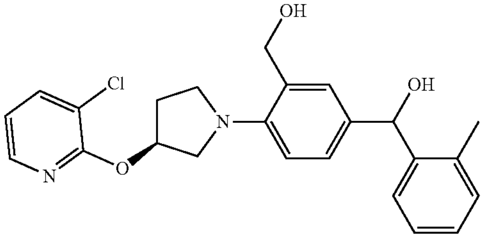

XXL-000328-069B

The title compounds were prepared in one pot by reducing the (S)-2-(3-(3-chloropyridin-2-yloxy)pyrrolidin-1-yl)-5-(2-methylbenzoyl)benzaldehyde (84 mg, 0.2 mmol)(prepared as example 168 step 1) with NaBH4 (46 mg, 1.2 mmol) in MeOH at rt for 1 h.

Compound 246: (18 mg, 21% yield), Mass spec: 423 (M+H), $t_R$=2.969 min, $^1$H-NMR (400 Hz, DMSO) δ=8.153-8.170 (m, 1H), 7.902-7.925 (m, 1H), 7.707-7.712 (m, 1H), 7.197-7.442 (m, 5H), 7.039-7.070 (m, 1H), 6.751-6.772 (d, 1H), 5.684 (br, 1H), 5.246 (t, 1H), 4.457-4.586 (m, 2H), 3.995-4.036 (m, 1H), 3.603-3.698 (m, 3H), 2.294-2.335 (m, 1H), 2.158-2.208 (m, 4H).

Compound 247: (20 mg, 23% yield), Mass spec: 425 (M+H), $t_R$=2.614 min, $^1$H-NMR (400 Hz, DMSO) δ=8.125-8.142 (m, 1H), 7.884-7.907 (m, 1H), 7.502-7.521 (m, 1H), 7.332-7.347 (s, 1H), 7.010-7.213 (m, 5H), 6.819-6.840 (d, 1H), 5.742-5.752 (m, 1H), 5.561-5.608 (m, 1H), 5.078-5.103 (t, 1H), 4.439-4.492 (m, 2H), 3.566-3.507 (m, 1H), 3.334-3.373 (m, 1H), 3.191-3.218 (m, 1H), 3.104-3.132 (m, 1H), 2.326-2.376 (m, 1H), 2.187 (s, 3H), 2.028-2.082 (m, 1H).

Example 201: (S)-(4-(3-(3-chloropyridin-2-yloxy)pyrrolidin-1-yl)-3-(hydroxymethyl)phenyl)(2-ethylphenyl)methanone & (4-((S)-3-(3-chloropyridin-2-yloxy)pyrrolidin-1-yl)-3-(hydroxymethyl)phenyl)(2-ethylphenyl)methanol (Compound 1-256 & 257)

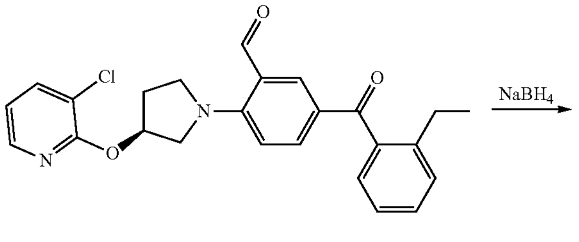

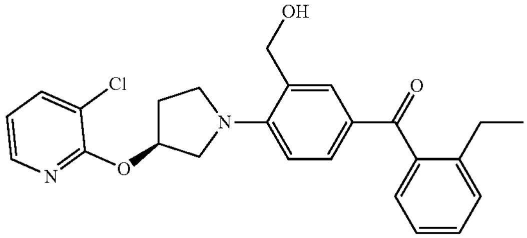

&

XXL-000328-073A

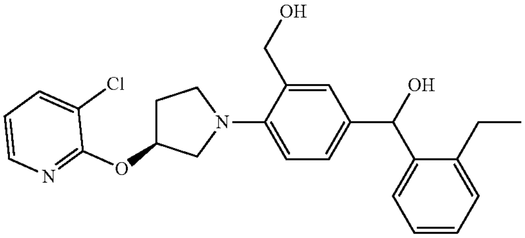

XXL-000328-073B

The title compound XXL-000328-069A & XXL-000328-069B was prepared following procedures described in example 200.

Compound 256: (31 mg, 20% yield), Mass spec: 437 (M+H), $t_R$=3.096 min, $^1$H-NMR (400 Hz, DMSO) δ=8.150-8.162 (t, 1H), 7.894-7.914 (t, 1H), 7.732-7.736 (d, 1H), 7.159-7.445 (m, 5H), 7.032-7.063 (m, 1H), 6.735-6.757 (d, 1H), 5.678 (br, 1H), 5.283-5.310 (t, 1H), 4.458-4.588 (m, 2H), 3.990-4.031 (m, 1H), 3.577-3.694 (m, 3H), 2.489-2.546 (m, 2H), 2.288-2.322 (m, 1H), 2.171-2.205 (m, 4H), 1.031-1.068 (t, 3H).

Compound 257: (37 mg, 24% yield), Mass spec: 439 (M+H), $t_R$=2.751 min, $^1$H-NMR (400 Hz, DMSO) δ=8.126-8.142 (m, 1H), 7.884-7.907 (m, 1H), 7.453-7.481 (m, 1H), 7.333-7.349 (m, 1H), 7.116-7.187 (m, 3H), 7.002-7.043 (m, 2H), 6.819-6.840 (d, 1H), 5.819-5.830 (m, 1H), 5.577-5.588 (m, 1H), 5.035-5.062 (t, 1H), 4.444-4.472 (m, 2H), 3.564-3.605 (m, 1H), 3.189-3.222 (m, 1H), 3.110-3.123 (m, 1H), 2.617-2.640 (m, 1H), 2.512-2.559 (m, 2H), 2.330-2.364 (m, 1H), 2.078-2.084 (m, 1H), 1.056-1.096 (t, 3H).

Example 202: (S)-(4-(3-(3-chloropyridin-2-yloxy) pyrrolidin-1-yl)-3-(hydroxymethyl)phenyl)(p-tolyl) methanone (Compound 1-277)

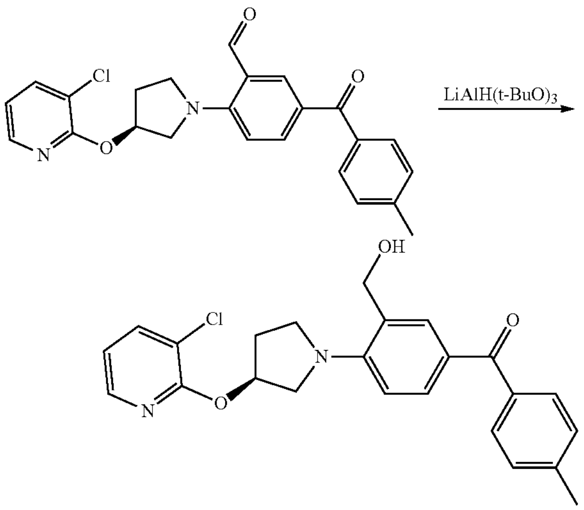

The title compound was prepared following procedures described in example 194 to give (S)-(4-(3-(3-chloropyridin-2-yloxy)pyrrolidin-1-yl)-3-(hydroxymethyl)phenyl)(p-tolyl)methanone (60 mg, 61% yield), Mass spec: 423 (M+H), $t_R$=2.954 min, $^1$H-NMR (400 Hz, DMSO) δ=8.155-8.172 (m, 1H), 7.897-7.919 (m, 1H), 7.770-7.776 (d, 1H), 7.547-7.585 (m, 3H), 7.324-7.344 (m, 2H), 7.037-7.068 (m, 1H), 6.801-6.823 (d, 1H), 5.689-5.694 (m, 1H), 5.208-5.234 (t, 1H), 4.497-4.623 (m, 2H), 3.980-4.020 (m, 1H), 3.570-3.693 (m, 3H), 2.402 (s, 3H), 2.315-2.348 (m, 1H), 2.205-2.213 (m, 1H).

Example 203: (4-((S)-3-(3-chloropyridin-2-yloxy) pyrrolidin-1-yl)-3-(hydroxymethyl)phenyl)(p-tolyl) methanol (Compound 1-287)

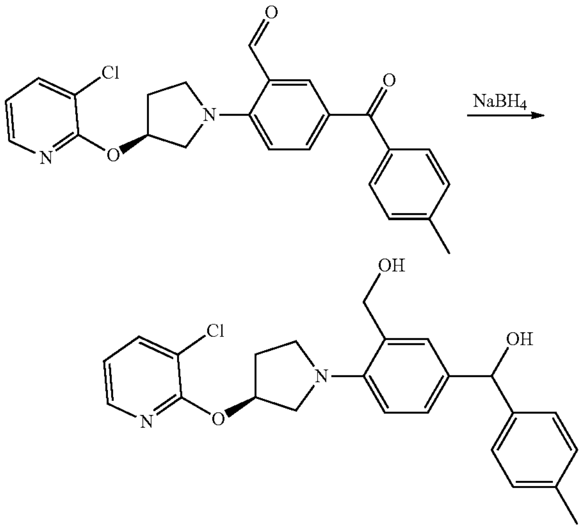

The title compound was prepared following procedures described in example 193 to give (4-((S)-3-(3-chloropyridin-2-yloxy)pyrrolidin-1-yl)-3-(hydroxymethyl)phenyl)(p-tolyl)methanol (40 mg, 50% yield), Mass spec: 421 (M+H), $t_R$=2.587 min, $^1$H-NMR (400 Hz, DMSO) δ=8.126-8.142 (m, 1H), 7.885-7.908 (m, 1H), 7.369 (s, 1H), 7.210-7.230 (m, 2H), 7.011-7.095 (m, 4H), 6.830-6.851 (d, 1H), 5.567-5.630 (m, 3H), 5.037 (t, 1H), 4.449-4.462 (m, 2H), 3.573-3.587 (m, 1H), 3.315-3.340 (m, 1H), 3.177-3.204 (m, 1H), 3.096-3.098 (m, 1H), 2.348-2.363 (m, 1H), 2.250 (s, 3H), 2.033-2.067 (m, 1H).

Example 204: (S)-(4-chlorophenyl)(4-(3-(3-chloropyridin-2-yloxy)pyrrolidin-1-yl)-3-(hydroxymethyl) phenyl)methanone (Compound 1-288)

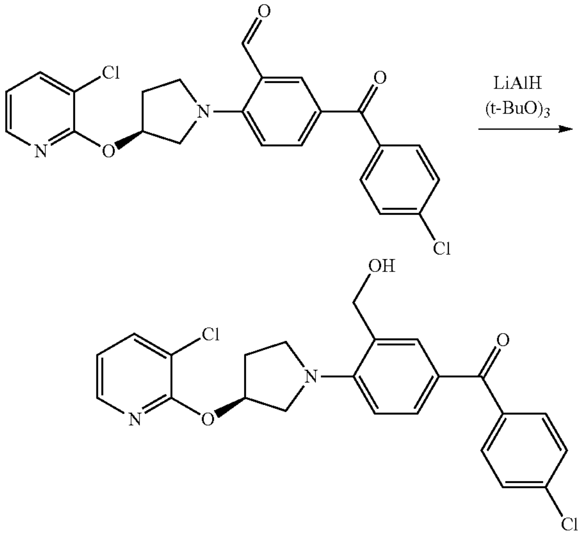

The title compound was prepared following procedures described in example 194 to give (S)-(4-chlorophenyl)(4-(3-(3-chloropyridin-2-yloxy)pyrrolidin-1-yl)-3-(hydroxymethyl)phenyl)methanone (50 mg, 50% yield), Mass spec: 443 (M+H), $t_R$=3.037 min, $^1$H-NMR (400 Hz, DMSO) δ=8.158-8.174 (m, 1H), 7.901-7.924 (m, 1H), 7.764-7.769 (d, 1H), 7.551-7.663 (m, 5H), 7.040-7.072 (m, 1H), 6.798-6.820 (d, 1H), 5.695 (br, 1H), 5.225-5.252 (t, 1H), 4.532-4.595 (m, 2H), 4.004-4.045 (m, 1H), 3.603-3.711 (m, 3H), 2.311-2.346 (m, 1H), 2.206-2.221 (m, 1H).

Example 205: (4-((S)-3-(3-chloropyridin-2-yloxy) pyrrolidin-1-yl)-3-(hydroxymethyl)phenyl)(4-(methoxymethyl)phenyl)methanol (Compound 1-290)

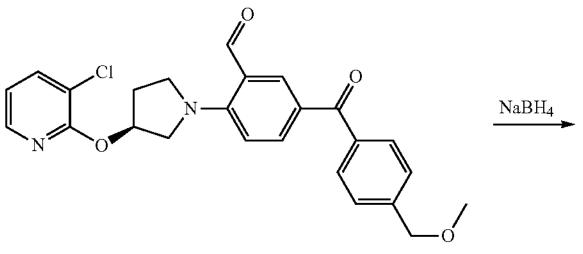

-continued

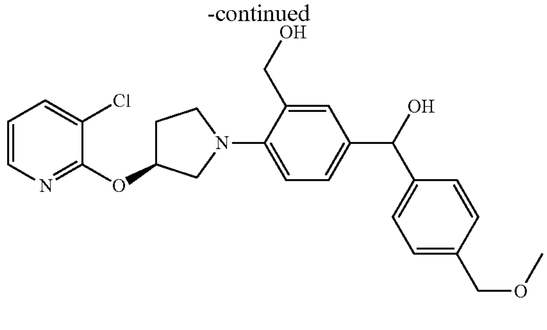

The title compound was prepared following procedures described in example 193 to give (4-((S)-3-(3-chloropyridin-2-yloxy)pyrrolidin-1-yl)-3-(hydroxymethyl)phenyl)(4-(methoxymethyl)phenyl)methanol (35 mg, 38% yield), Mass spec: 455 (M+H), $t_R$=2.320 min, $^1$H-NMR (400 Hz, DMSO) δ=8.127-8.144 (m, 1H), 7.887-7.910 (m, 1H), 7.216-7.387 (m, 3H), 7.104-7.132 (m, 2H), 7.013-7.045 (m, 2H), 6.835-6.855 (m, 1H), 5.704-5.714 (d, 1H), 5.578-5.619 (m, 2H), 5.041-5.068 (t, 1H), 4.450-4.477 (m, 2H), 4.353 (s, 2H), 3.564-3.590 (m, 1H), 3.328-3.351 (m, 1H), 3.255 (s, 3H), 3.099-3.187 (m, 2H), 2.330-2.366 (m, 1H), 2.064-2.068 (m, 1H).

Example 206: (S)-(4-(3-(3-chloropyridin-2-yloxy)pyrrolidin-1-yl)-3-(hydroxymethyl)phenyl)(4-(methoxymethyl)phenyl)methanone (Compound 1-288)

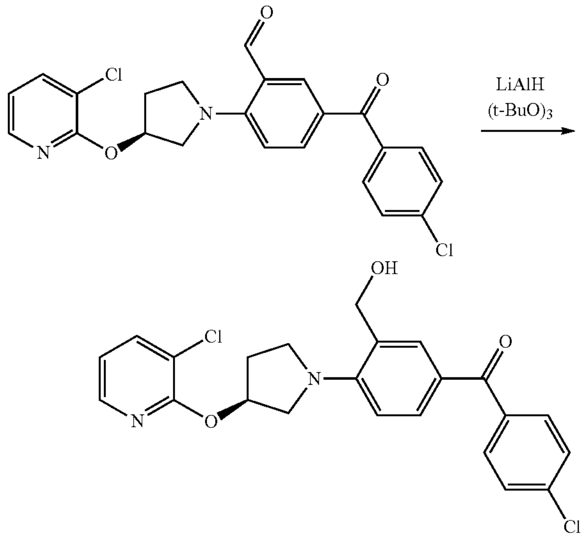

The title compound was prepared following procedures described in example 194 to (S)-(4-(3-(3-chloropyridin-2-yloxy)pyrrolidin-1-yl)-3-(hydroxymethyl)phenyl)(4-(methoxymethyl)phenyl)methanone (32 mg, 49% yield), Mass spec: 453 (M+H), $t_R$=2.746 min, $^1$H-NMR (400 Hz, DMSO) δ=8.159-8.175 (m, 1H), 7.901-7.925 (m, 1H), 7.778-7.783 (d, 1H), 7.639-7.659 (d, 2H), 7.556-7.584 (m, 1H), 7.452-7.472 (m, 2H), 7.040-7.072 (m, 1H), 6.806-6.872 (d, 1H), 5.693 (br, 1H), 5.215-5.243 (t, 1H), 4.497-4.625 (m, 4H), 3.991-4.031 (m, 1H), 3.585-3.071 (m, 3H), 3.322 (s, 3H), 2.327-2.349 (m, 1H), 2.210-2.223 (m, 1H).

Example 207: (4-((S)-3-(3-chloropyridin-2-yloxy)pyrrolidin-1-yl)-3-(hydroxymethyl)phenyl)(4-fluorophenyl)methanol (Compound 1-278)

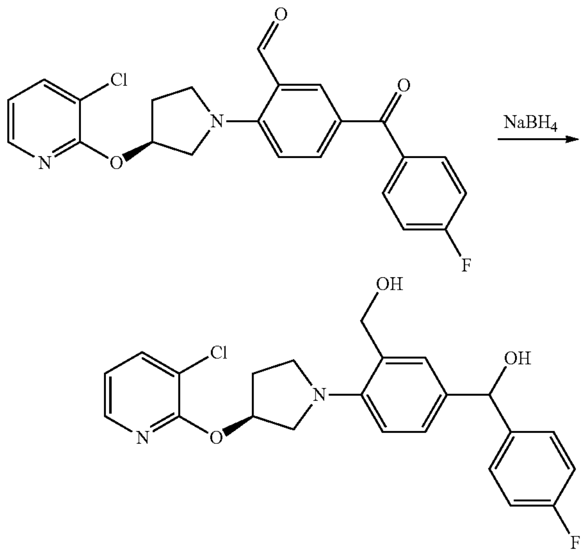

The title compound was prepared following procedures described in example 193 to give (4-((S)-3-(3-chloropyridin-2-yloxy)pyrrolidin-1-yl)-3-(hydroxymethyl)phenyl)(4-fluorophenyl)methanol (30 mg, 38% yield), Mass spec: 429 (M+H), $t_R$=2.513 min, $^1$H-NMR (400 Hz, DMSO) δ=8.127-8.143 (m, 1H), 7.883-7.907 (m, 1H), 7.352-7.387 (m, 3H), 7.084-7.128 (m, 3H), 7.011-7.043 (m, 1H), 6.841-6.862 (d, 1H), 5.754-5.764 (d, 1H), 5.627-5.637 (m, 1H), 5.582 (br, 1H), 5.035-5.062 (t, 1H), 4.459-4.485 (m, 2H), 3.561-3.615 (m, 1H), 3.341-3.380 (m, 1H), 3.101-3.222 (m, 2H), 2.331-2.382 (m, 1H), 2.039-2.074 (m, 1H).

Example 208: (S)-(4-(3-(3-chloropyridin-2-yloxy)pyrrolidin-1-yl)-3-(hydroxymethyl)phenyl)(4-fluorophenyl)methanone (Compound 1-279)

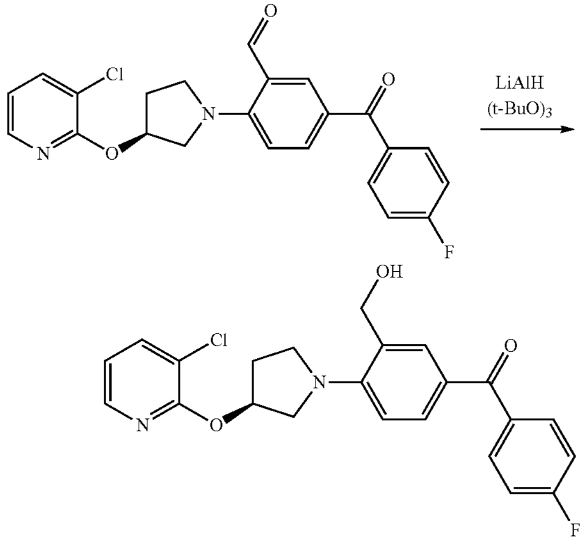

The title compound was prepared following procedures described in example 194 to (S)-(4-(3-(3-chloropyridin-2-yloxy)pyrrolidin-1-yl)-3-(hydroxymethyl)phenyl)(4-fluorophenyl)methanone (30 mg, 39% yield), Mass spec: 427 (M+H), $t_R$=2.869 min, $^1$H-NMR (400 Hz, DMSO) δ=8.159-8.174 (m, 1H), 7.901-7.920 (m, 1H), 7.722-7.774 (m, 3H), 7.548-7.574 (m, 1H), 7.337-7.381 (m, 2H), 7.040-7.071 (m, 1H), 6.805-6.827 (m, 2H), 5.695 (br, 1H), 5.221-5.248 (t, 1H), 4.502-4.630 (m, 2H), 3.997-4.038 (m, 1H), 3.577-3.707 (m, 3H), 2.315-2.349 (m, 1H), 2.210-2.219 (m, 1H).

Example 209: (2-((S)-3-(3-chloropyridin-2-yloxy) pyrrolidin-1-yl)-5-((4-fluorophenyl)(methoxy) methyl) phenyl)methanol (Compound 1-289)

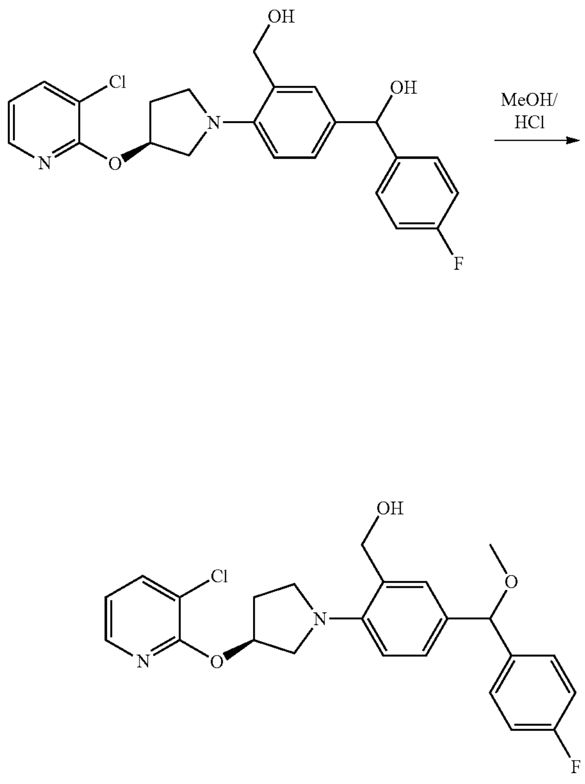

To a solution of (4-((S)-3-(3-chloropyridin-2-yloxy)pyrrolidin-1-yl)-3-(hydroxymethyl)phenyl)(4-fluorophenyl) methanol (42 mg, 0.1 mmol) in 2 mL MeOH was added 1 mL HCl/MeOH (2N), and the mixture was stirred at room temperature for 30 min, removal the solvent to left to crude product which was purified by Prep-HPLC to give (2-((S)-3-(3-chloropyridin-2-yloxy)pyrrolidin-1-yl)-5-((4-fluorophenyl)(methoxy)methyl)phenyl)methanol (20 mg, 45% yield), Mass spec: 443 (M+H), $t_R$=2.963 min, $^1$H-NMR (400 Hz, DMSO) δ=8.126-8.143 (m, 1H), 7.883-7.906 (m, 1H), 7.335-7.370 (m, 3H), 7.024-7.161 (m, 4H), 6.841-6.861 (d, 1H), 5.573-5.601 (m, 1H), 5.251 (s, 1H), 5.064-5.091 (t, 1H), 4.459-4.489 (t, 2H), 3.596-3.637 (m, 1H), 3.364-3.383 (m, 1H), 3.234-3.245 (m, 4H), 3.124-3.178 (m, 1H), 2.322-2.371 (m, 1H), 2.048-2.081 (m, 1H).

Example 210: (S)-(4-fluorophenyl)(4-(3-(3-fluoropyridin-2-yloxy)pyrrolidin-1-yl)-3-(hydroxymethyl) phenyl)methanone (Compound 1-293)

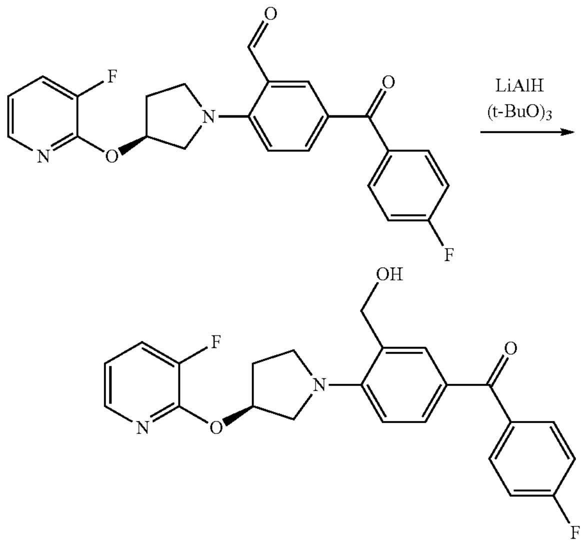

The title compound was prepared following procedures described in example 194 to give (S)-(4-fluorophenyl)(4-(3-(3-fluoropyridin-2-yloxy)pyrrolidin-1-yl)-3-(hydroxymethyl)phenyl)methanone (25 mg, 83% yield), Mass spec: 411 (M+H), $t_R$=2.682 min, $^1$H-NMR (400 Hz, DMSO) δ=8.010-8.025 (m, 1H), 7.681-7.769 (m, 4H), 7.548-7.576 (m, 1H), 7.342-7.387 (m, 2H), 7.055-7.062 (m, 1H), 6.800-6.822 (d, 1H), 5.714 (br, 1H), 5.247 (t, 1H), 4.505-4.625 (m, 2H), 4.002-4.044 (m, 1H), 33.599-3.712 (m, 3H), 2.335-2.355 (m, 1H), 2.215-2.246 (m, 1H).

Example 211: (S)-(4-(3-(3-fluoropyridin-2-yloxy) pyrrolidin-1-yl)-3-(hydroxymethyl)phenyl)(p-tolyl) methanone (Compound 1-300)

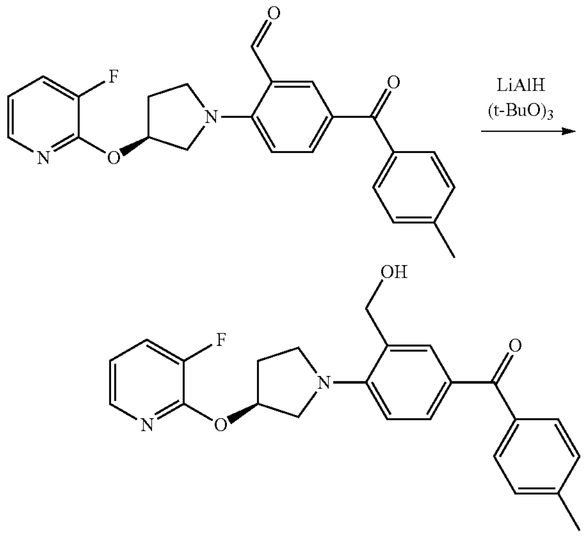

The title compound was prepared following procedures described in example 194 to give (S)-(4-(3-(3-fluoropyridin-2-yloxy)pyrrolidin-1-yl)-3-(hydroxymethyl)phenyl)(p-tolyl)methanone (20 mg, 50% yield), Mass spec: 407 (M+H), $t_R$=2.766 min, $^1$H-NMR (400 Hz, DMSO) δ=8.008-8.020 (m, 1H), 7.666-8.005 (m, 2H), 7.546-7.583 (m, 3H), 7.326-7.346 (m, 2H), 7.032-7.072 (m, 1H), 6.798-6.819 (d, 1H), 5.709 (br, 1H), 5.201-5.228 (t, 1H), 4.499-4.623 (m, 2H), 3.982-4.023 (m, 1H), 3.574-3.691 (m, 3H), 2.358 (s, 3H), 2.245-2.336 (m, 1H), 2.229-2.238 (m, 1H).

Example 212: (4-((S)-3-(3-fluoropyridin-2-yloxy)pyrrolidin-1-yl)-3-(hydroxymethyl)phenyl)(o-tolyl)methanol (Compound 1-231)

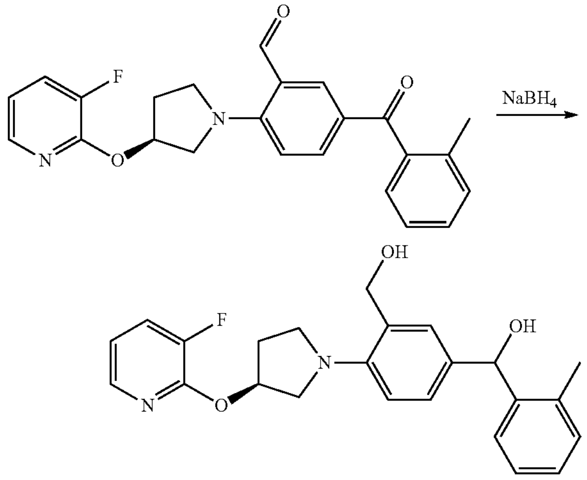

The title compound was prepared following procedures described in example 193 to give (4-((S)-3-(3-fluoropyridin-2-yloxy)pyrrolidin-1-yl)-3-(hydroxymethyl)phenyl)(o-tolyl)methanol (30 mg, 43% yield), Mass spec: 409 (M+H), $t_R$=2.456 min, $^1$H-NMR (400 Hz, DMSO) δ=7.972-7.987 (m, 1H), 7.652-7.699 (m, 1H), 7.328-7.339 (m, 1H), 7.193 (m, 1H), 7.003-7.193 (m, 5H), 6.812-6.833 (m, 1H), 5.737-5.746 (d, 1H), 5.575-5.585 (m, 2H), 5.060 (t, 1H), 4.448-4.463 (m, 2H), 3.579-3.607 (m, 1H), 3.337-3.361 (m, 1H), 3.099-3.238 (m, 2H), 2.330-2.363 (m, 1H), 2.179-2.184 (s, 3H), 2.067-2.079 (m, 1H).

Example 213: (S)-(4-(3-(3-fluoropyridin-2-yloxy)pyrrolidin-1-yl)-3-(hydroxymethyl)phenyl)(o-tolyl)methanone (Compound 1-243)

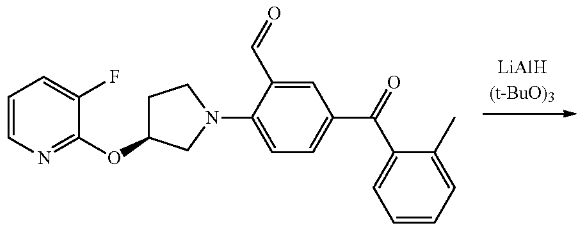

-continued

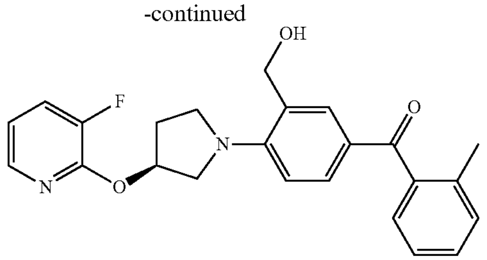

The title compound was prepared following procedures described in example 194 to give (S)-(4-(3-(3-fluoropyridin-2-yloxy)pyrrolidin-1-yl)-3-(hydroxymethyl)phenyl)(o-tolyl)methanone (20 mg, 20% yield), Mass spec: 407 (M+H), $t_R$=2.775 min, $^1$H-NMR (400 Hz, DMSO) δ=8.004-8.015 (m, 1H), 7.673-8.707 (m, 2H), 7.200-7.442 (m, 5H), 7.033-7.072 (m, 1H), 6.774-6.766 (m, 1H), 5.702 (br, 1H), 5.222-5.249 (t, 1H), 4.498-4.559 (m, 2H), 3.998-4.038 (m, 1H), 3.605-3.718 (m, 3H), 2.301-2.335 (s, 1H), 2.181-2.227 (m, 4H).

Example 214: (4-((S)-3-(3-chloropyridin-2-yloxy)pyrrolidin-1-yl)-3-(hydroxymethyl)phenyl)(m-tolyl)methanol (Compound 1-281)

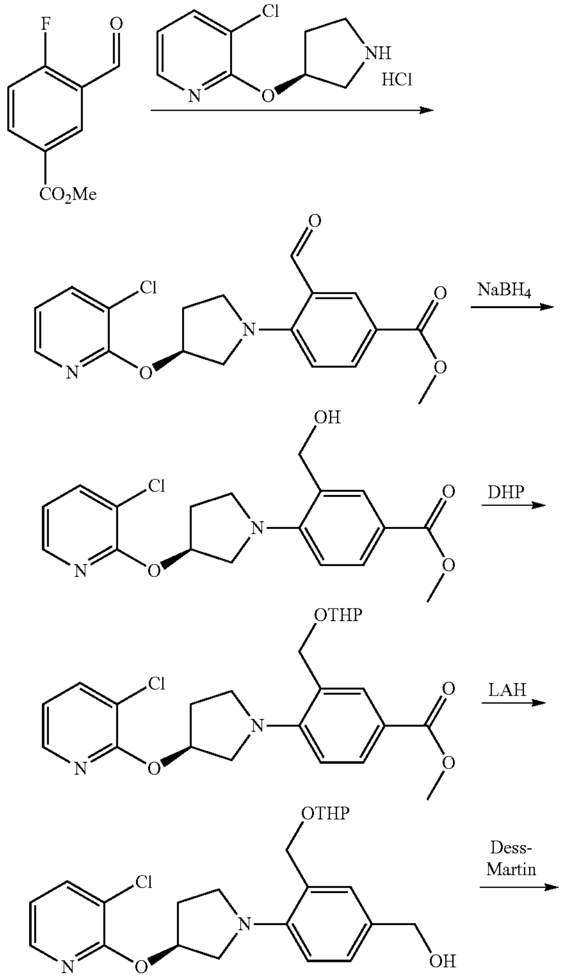

-continued

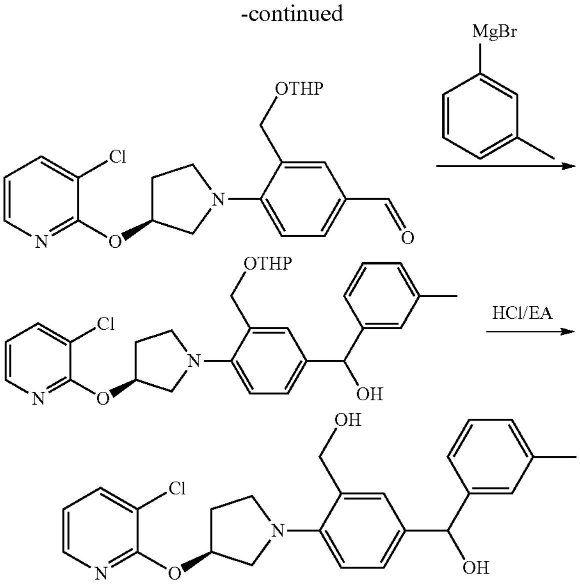

Step 1: (S)-methyl 4-(3-(3-chloropyridin-2-yloxy) pyrrolidin-1-yl)-3-formylbenzoate

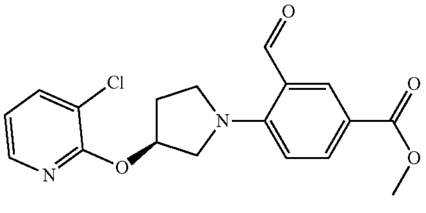 [SMILES: COC(=O)c1ccc(N2CC[C@H](Oc3ncccc3Cl)C2)c(C=O)c1]

The title compound was prepared following procedures described in example using (S)-3-chloro-2-(pyrrolidin-3-yloxy)pyridine hydrochloride (prepared as intermediate 3) and methyl 4-fluoro-3-formylbenzoate to give (S)-methyl 4-(3-(3-chloropyridin-2-yloxy)pyrrolidin-1-yl)-3-formylbenzoate (2.3 g, 74% yield), Mass spec: 361 (M+H).

Step 2: (S)-methyl 4-(3-(3-chloropyridin-2-yloxy) pyrrolidin-1-yl)-3-(hydroxymethyl)benzoate

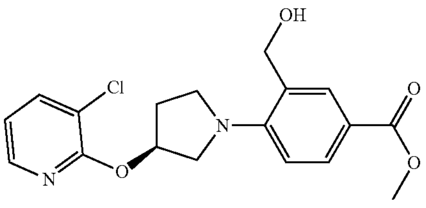 [SMILES: COC(=O)c1ccc(N2CC[C@H](Oc3ncccc3Cl)C2)c(CO)c1]

The title compound was prepared by reducing the (S)-methyl 4-(3-(3-chloropyridin-2-yloxy)pyrrolidin-1-yl)-3-formylbenzoate with NaBH4 in MeOH to give (S)-methyl 4-(3-(3-chloropyridin-2-yloxy)pyrrolidin-1-yl)-3-(hydroxymethyl)benzoate (1.5 g, quant.), Mass spec: 362 (M+H).

Step 3: methyl 4-((S)-3-(3-chloropyridin-2-yloxy) pyrrolidin-1-yl)-3-((tetrahydro-2H-pyran-2-yloxy) methyl)benzoate

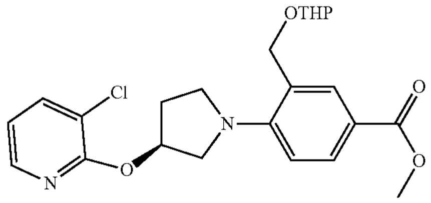

To a solution of (S)-methyl 4-(3-(3-chloropyridin-2-yloxy)pyrrolidin-1-yl)-3-(hydroxymethyl)benzoate (1 g, 2.75 mmol) in 20 ml DCM was added DHP (0.3 mL, 3.3 mmol) and PPTS (138 mg, 0.2 mmol), the mixture was stirred at rt overnight, removal the DCM to left the residue which was purified by silica gel to give methyl 4-((S)-3-(3-chloropyridin-2-yloxy)pyrrolidin-1-yl)-3-((tetrahydro-2H-pyran-2-yloxy)methyl) benzoate (1.2 g, 98% yield), Mass spec: 447 (M+H).

Step 4: (4-((S)-3-(3-chloropyridin-2-yloxy)pyrrolidin-1-yl)-3-((tetrahydro-2H-pyran-2-yloxy)methyl) phenyl)methanol

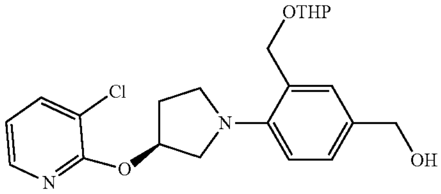

To a solution of methyl 4-((S)-3-(3-chloropyridin-2-yloxy)pyrrolidin-1-yl)-3-((tetrahydro-2H-pyran-2-yloxy) methyl)benzoate (1.3 g, 2.9 mmol) in THF was added LAH (220 mg, 5.8 mmol) at 0° C., the mixture was stirred at rt for 2 h, quenched by water, extracted with DCM, washed with water, brine, dried over Na2SO4, removal the solvent to left the crude product (1.1 g, 89% yield) which can be used directly, Mass spec: 419 (M+H).

Step 5: 4-((S)-3-(3-chloropyridin-2-yloxy)pyrrolidin-1-yl)-3-((tetrahydro-2H-pyran-2-yloxy)methyl) benzaldehyde

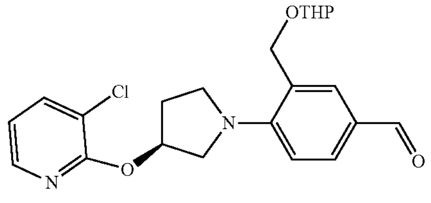

The title compound was prepared following procedures described in example 150 (step 1) to give 4-((S)-3-(3-chloropyridin-2-yloxy)pyrrolidin-1-yl)-3-((tetrahydro-2H-pyran-2-yloxy)methyl)benzaldehyde (150 mg, 50% yield), Mass spec: 417 (M+H).

Step 6: (4-((S)-3-(3-chloropyridin-2-yloxy)pyrrolidin-1-yl)-3-((tetrahydro-2H-pyran-2-yloxy)methyl) phenyl)(m-tolyl)methanol

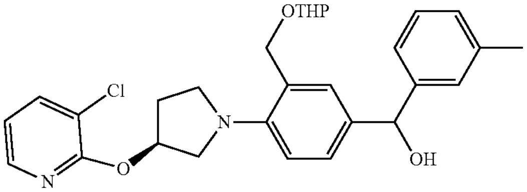

To a suspension solution of Mg (2 g, 83 mmol) and cat amount 12 in dry tTHF was added 1-bromo-3-methylbenzene (0.1 mL), the mixture was heated to reflux till to red color disappeared, before another 0.9 mL 1-bromo-3-methylbenzene was added, stirred for 10 min, then 4-((S)-3-(3-chloropyridin-2-yloxy)pyrrolidin-1-yl)-3-((tetrahydro-2H-pyran-2-yloxy)methyl) benzaldehyde (280 mg, 0.6 mmol) in THE was added and stirred for another 10 min, quenched by water, diluted with EA, washed with NH4Cl solution, brine, dried over Na2SO4, removal the solvent to left the crude product which was purified by silica gel to give (4-((S)-3-(3-chloropyridin-2-yloxy)pyrrolidin-1-yl)-3-((tetrahydro-2H-pyran-2-yloxy)methyl)phenyl)(m-tolyl)methanol (250 mg, 83% yield), Mass spec: 509 (M+H).

Step 7: (4-((S)-3-(3-chloropyridin-2-yloxy)pyrrolidin-1-yl)-3-(hydroxymethyl)phenyl)(m-tolyl)methanol

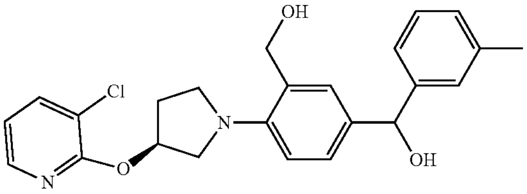

To a solution of (4-((S)-3-(3-chloropyridin-2-yloxy)pyrrolidin-1-yl)-3-((tetrahydro-2H-pyran-2-yloxy)methyl)phenyl) (o-tolyl)methanol (70 mg, 0.13 mmol) in EA was added HCl/EA, the mixture was stirred at rt for 30 min, removal the EA, the crude product was purified by Prep-HPLC to give (4-((S)-3-(3-chloropyridin-2-yloxy)pyrrolidin-1-yl)-3-(hydroxymethyl)phenyl)(m-tolyl)methanol (30 mg, 54% yield), Mass spec: 425 (M+H), $t_R$=2.530 min, H-NMR (400 Hz, DMSO) δ=8.126-8.142 (m, 1H), 7.883-7.907 (m, 1H), 7.386 (s, 1H), 7.126-7.167 (m, 4H), 6.999-7.043 (m, 2H), 6.836-6.856 (d, 1H), 5.647-5.657 (m, 1H), 5.566-5.577 (m, 2H), 5.036-5.050 (t, 1H), 4.455-4.468 (m, 2H), 3.566-3.593 (m, 1H), 3.320-3.343 (m, 1H), 3.112-3.215 (m, 2H), 2.348-2.364 (m, 1H), 2.267 (s, 3H), 2.036-2.070 (m, 1H).

Example 215: (S)-(4-(3-(3-chloropyridin-2-yloxy) pyrrolidin-1-yl)-3-(hydroxymethyl)phenyl)(m-tolyl) methanone (Compound 1-282)

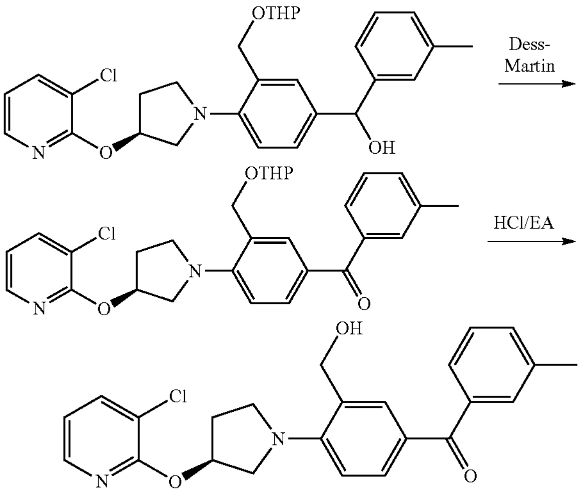

Step 1: (4-((S)-3-(3-chloropyridin-2-yloxy)pyrrolidin-1-yl)-3-((tetrahydro-2H-pyran-2-yloxy)methyl) phenyl)(m-tolyl)methanone

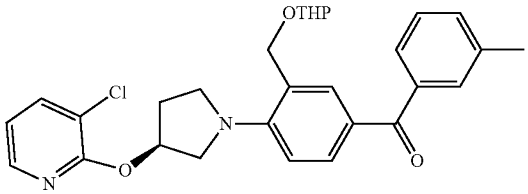

The title compound was prepared following procedures described in example 150 (step 1) to give (4-((S)-3-(3-chloropyridin-2-yloxy)pyrrolidin-1-yl)-3-((tetrahydro-2H-pyran-2-yloxy)methyl)phenyl)(m-tolyl) methadone (60 mg, 98% yield), Mass spec: 507 (M+H).

Step 2: (S)-(4-(3-(3-chloropyridin-2-yloxy)pyrrolidin-1-yl)-3-(hydroxymethyl)phenyl)(m-tolyl)methanone

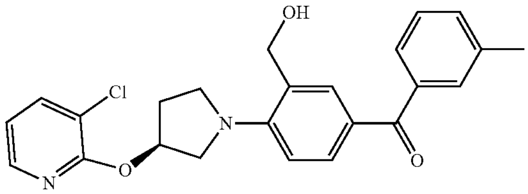 [SMILES: Cc1cccc(C(=O)c2ccc(N3CC[C@H](Oc4ncccc4Cl)C3)c(CO)c2)c1]

The title compound was prepared following procedures described in example 214 (step 7) to give (S)-(4-(3-(3-chloropyridin-2-yloxy)pyrrolidin-1-yl)-3-(hydroxymethyl) phenyl)(m-tolyl)methanone (20 mg, 42% yield), Mass spec: 423 (M+H), $t_R$=2.969 min, $^1$H-NMR (400 Hz, DMSO)

δ=8.160-8.176 (m, 1H), 7.903-7.926 (m, 1H), 7.779-7.785 (d, 1H), 7.544-7.571 (m, 1H), 7.411-7.464 (m, 4H), 7.041-7.073 (m, 1H), 6.803-6.825 (d, 1H), 5.701 (br, 1H), 5.206-5.233 (t, 1H), 4.531-4.592 (m, 2H), 3.992-4.033 (m, 1H), 3.585-3.703 (m, 3H), 2.331-2.388 (m, 4H), 2.225-2.229 (m, 1H).

Example 216: 2-(2-((S)-3-(3-chloropyridin-2-yloxy) pyrrolidin-1-yl)-5-((4-fluorophenyl)(hydroxy) methyl) phenyl)ethanol (Compound 1-296)

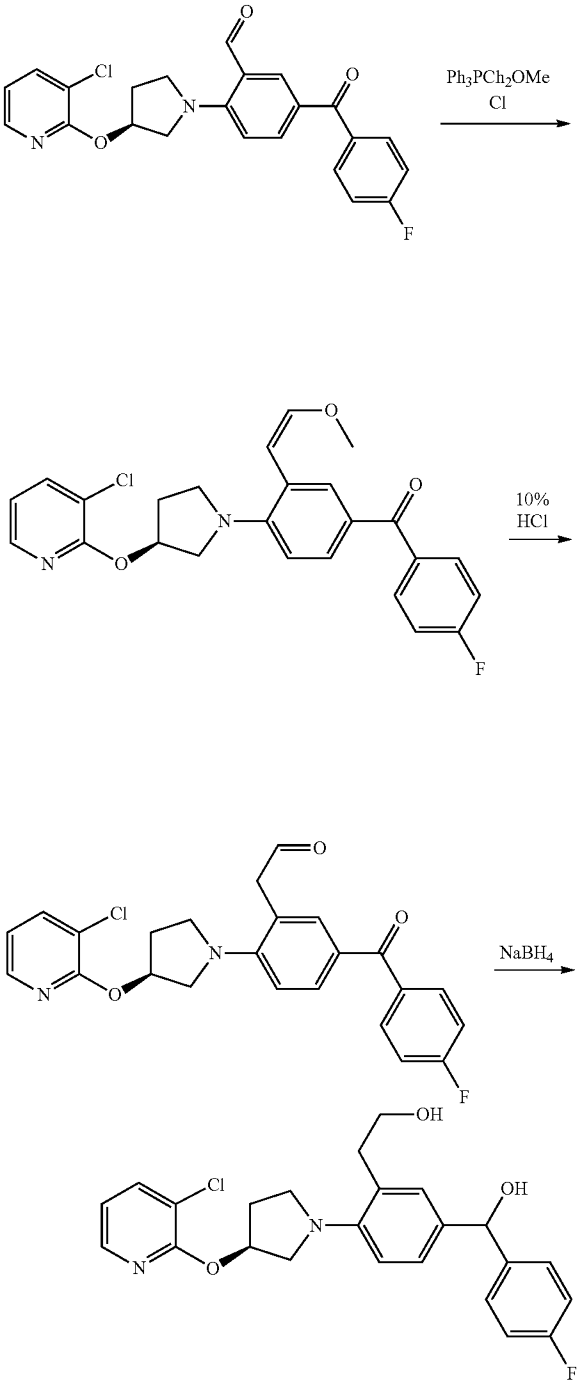

Step 1: (S)-(4-(3-(3-chloropyridin-2-yloxy)pyrrolidin-1-yl)-3-(2-methoxyvinyl)phenyl)(4-fluorophenyl)methanone

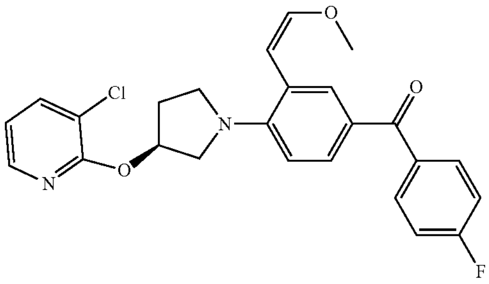 [SMILES: CO/C=C\c1cc(C(=O)c2ccc(F)cc2)ccc1N1CC[C@H](Oc2ncccc2Cl)C1]

The title compound was prepared following procedures described in example 168 (step 2) using (S)-2-(3-(3-chloropyridin-2-yloxy)pyrrolidin-1-yl)-5-(4-fluorobenzoyl)benzaldehyde (Prepared as example 168 (step 1)) to give (S)-(4-(3-(3-chloropyridin-2-yloxy)pyrrolidin-1-yl)-3-(2-methoxyvinyl)phenyl)(4-fluorophenyl)methanone (220 mg, 58% yield), Mass spec: 453 (M+H).

Step 2: (S)-2-(2-(3-(3-chloropyridin-2-yloxy)pyrrolidin-1-yl)-5-(4-fluorobenzoyl)phenyl)acetaldehyde

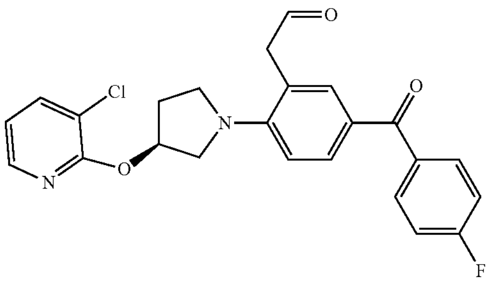 [SMILES: O=CCc1cc(C(=O)c2ccc(F)cc2)ccc1N1CC[C@H](Oc2ncccc2Cl)C1]

The title compound was prepared following procedures described in example 168 (step 3) to give (S)-2-(2-(3-(3-chloropyridin-2-yloxy)pyrrolidin-1-yl)-5-(4-fluorobenzoyl) phenyl)acetaldehyde (140 mg, 70% yield), Mass spec: 439 (M+H), Step 3: (S)-(4-(3-(3-chloropyridin-2-yloxy)pyrrolidin-1-yl)-3-(2-hydroxyethyl)phenyl)(4-fluorophenyl) methanone

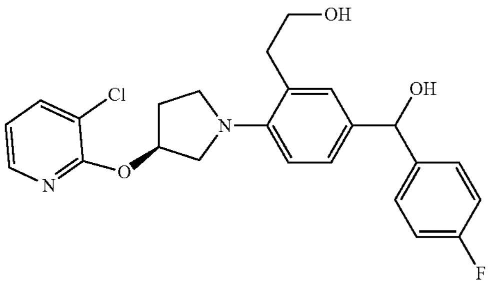 [SMILES: OCCc1cc(C(O)c2ccc(F)cc2)ccc1N1CC[C@H](Oc2ncccc2Cl)C1]

The title compound was prepared following procedures described in example 168 (step 4) to give 2-(2-((S)-3-(3-chloropyridin-2-yloxy)pyrrolidin-1-yl)-5-((4-fluorophenyl)(hydroxy)methyl) phenyl)ethanol (30 mg, 59% yield), Mass spec: 443 (M+H), $t_R$=2.307 min, $^1$H-NMR (400 Hz, DMSO) δ=8.125-8.141 (m, 1H), 7.883-7.907 (m, 1H), 7.346-7.361 (m, 2H), 7.011-7.153 (m, 5H), 6.926-6.947 (m, 1H), 5.752-5.762 (d, 1H), 5.574-5.609 (m, 2H), 4.608-4.634 (t, 1H), 3.555-3.629 (m, 3H), 3.321-3.345 (m, 1H), 3.079-3.149 (m, 2H), 2.757-2.794 (m, 2H), 2.359-2.497 (m, 1H), 2.079-2.090 (m, 1H).

Example 217: (S)-(4-(3-(3-chloropyridin-2-yloxy) pyrrolidin-1-yl)-3-(2-hydroxyethyl)phenyl)(4-fluorophenyl)methanone (Compound 1-294)

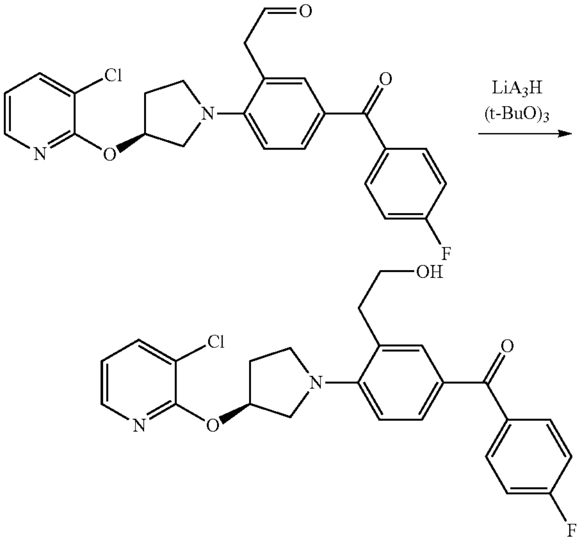

The title compound was prepared following procedures described in example 169 to give (S)-(4-(3-(3-chloropyridin-2-yloxy)pyrrolidin-1-yl)-3-(2-hydroxyethyl)phenyl)(4-fluorophenyl)methanone (70 mg, 50% yield), Mass spec: 441 (M+H), $t_R$=2.887 min, $^1$H-NMR (400 Hz, DMSO) δ=8.157-8.174 (m, 1H), 7.903-7.926 (m, 1H), 7.729 (m, 2H), 7.490-7.584 (m, 2H), 7.334-7.379 (m, 2H), 7.041-7.073 (m, 1H), 6.886-6.908 (m, 1H), 5.695 (br, 1H), 4.647-4.673 (t, 1H), 3.920-4.673 (m, 1H), 3.566-3.689 (m, 3H), 3.430-3.471 (m, 2H), 2.835-2.944 (m, 2H), 2.218-2.498 (m, 2H).

Example 218: 2-(2-((S)-3-(3-chloropyridin-2-yloxy) pyrrolidin-1-yl)-5-(hydroxy(p-tolyl)methyl) phenyl) ethanol (Compound 1-310)

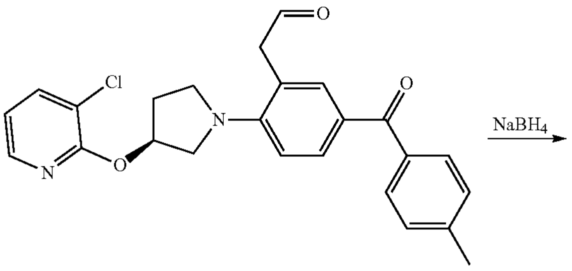

-continued

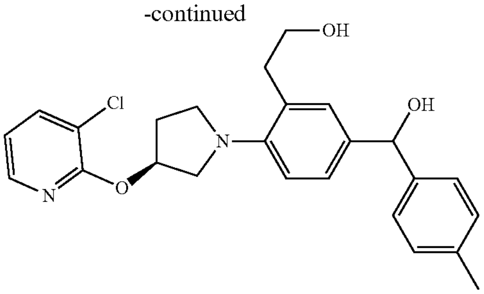

The title compound was prepared following procedures described in example 216 to give 2-(2-((S)-3-(3-chloropyridin-2-yloxy)pyrrolidin-1-yl)-5-(hydroxy(p-tolyl)methyl) phenyl)ethanol (30 mg, 60% yield), Mass spec: 439 (M+H), $t_R$=2.395 min, $^1$H-NMR (400 Hz, DMSO) δ=8.124-8.141 (m, 1H), 7.885-7.907 (m, 1H), 7.207-7.227 (m, 2H), 7.011-7.138 (m, 5H), 6.919-6.940 (m, 1H), 5.544-5.624 (m, 3H), 4.600-4.627 (t, 1H), 3.551-3.625 (m, 3H), 3.309-3.333 (m, 1H), 3.072-3.142 (m, 2H), 2.751-2.789 (m, 2H), 2.342-2.376 (m, 1H), 2.250 (s, 3H), 2.061-2.075 (m, 1H).

Example 219: (S)-(4-(3-(3-chloropyridin-2-yloxy) pyrrolidin-1-yl)-3-(2-hydroxyethyl)phenyl)(p-tolyl) methanone (Compound 1-295)

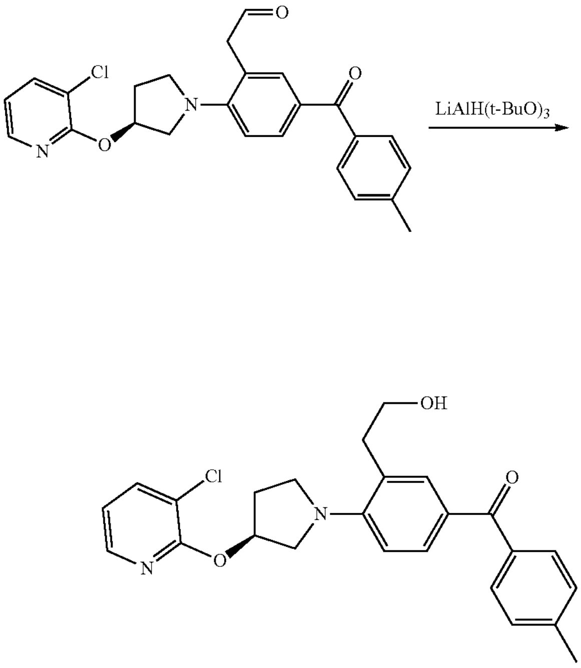 [SMILES: Cc1ccc(C(=O)c2ccc(N3CC[C@H](Oc4ncccc4Cl)C3)c(CC=O)c2)cc1 ; Cc1ccc(C(=O)c2ccc(N3CC[C@H](Oc4ncccc4Cl)C3)c(CCO)c2)cc1]

The title compound was prepared following procedures described in example 217 to give (S)-(4-(3-(3-chloropyridin-2-yloxy)pyrrolidin-1-yl)-3-(2-hydroxyethyl)phenyl)(p-tolyl)methanone (70 mg, 59% yield), Mass spec: 437 (M+H), $t_R$=2.874 min, $^1$H-NMR (400 Hz, DMSO) δ=8.158-8.175 (m, 1H), 7.905-7.928 (m, 1H), 7.571-7.592 (m, 3H), 7.489-7.516 (m, 1H), 7.326-7.346 (m, 2H), 7.041-7.073 (m, 1H), 6.885-6.907 (d, 1H), 5.684-5.689 (m, 1H), 4.654-4.681 (t, 1H), 3.921 (m, 1H), 3.637-3.660 (m, 3H), 3.418-3.447 (m, 2H), 2.836-2.937 (m, 2H), 2.315-2.403 (m, 4H), 2.151-2.194 (m, 1H).

Example 220: 2-(5-((4-chlorophenyl)(hydroxy)methyl)-2-((S)-3-(3-chloropyridin-2-yloxy)pyrrolidin-1-yl)phenyl)ethanol (Compound 1-292)

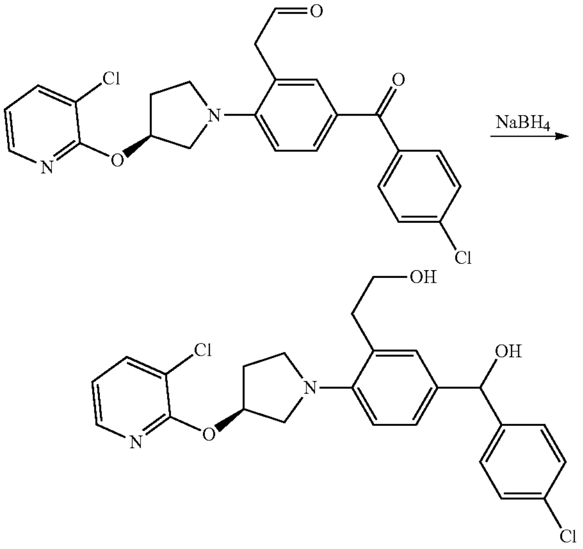

The title compound was prepared following procedures described in example 216 to give 2-(5-((4-chlorophenyl)(hydroxy)methyl)-2-((S)-3-(3-chloropyridin-2-yloxy)pyrrolidin-1-yl)phenyl)ethanol (27 mg, 71% yield), Mass spec: 459 (M+H), $t_R$=2.587 min, $^1$H-NMR (400 Hz, DMSO) δ=8.129-8.144 (m, 1H), 7.890-7.912 (m, 1H), 7.330-7.380 (m, 4H), 6.924-7.149 (m, 4H), 5.818-5.827 (m, 1H), 5.583-5.610 (m, 2H), 4.825-4.651 (t, 1H), 3.574-3.627 (m, 3H), 3.323 (m, 1H), 3.069-3.144 (m, 2H), 2.776-2.793 (m, 2H), 2.359-2.375 (m, 1H), 2.065-2.081 (m, 1H).

Example 221: (S)-(4-chlorophenyl)(4-(3-(3-chloropyridin-2-yloxy)pyrrolidin-1-yl)-3-(2-hydroxyethyl)phenyl)methanone (Compound 1-291)

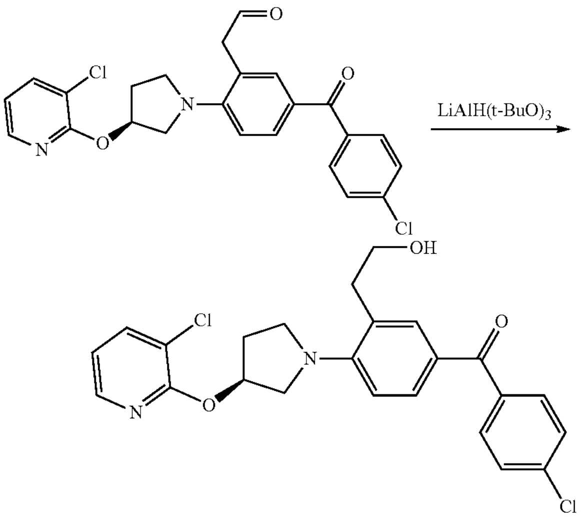

The title compound was prepared following procedures described in example 217 to give (S)-(4-chlorophenyl)(4-(3-(3-chloropyridin-2-yloxy)pyrrolidin-1-yl)-3-(2-hydroxyethyl)phenyl)methanone (38 mg, 63% yield), Mass spec: 457 (M+H), $t_R$=3.066 min, $^1$H-NMR (400 Hz, DMSO) δ=8.156-8.171 (m, 1H), 7.900-7.924 (m, 1H), 7.492-7.696 (m, 6H), 7.039-7.071 (m, 1H), 6.878-6.900 (d, 1H), 4.649-4.676 (m, 1H), 3.925-3.965 (m, 1H), 3.641-3.693 (m, 3H), 3.436-3.464 (m, 2H), 2.872-2.944 (m, 2H), 2.340-2.362 (m, 1H), 2.201-2.225 (m, 1H).

Example 222: (S)-(4-(3-(3-chloropyridin-2-yloxy)pyrrolidin-1-yl)-3-(2-hydroxyethyl)phenyl)(4-fluorophenyl)methanone (Compound 1-315)

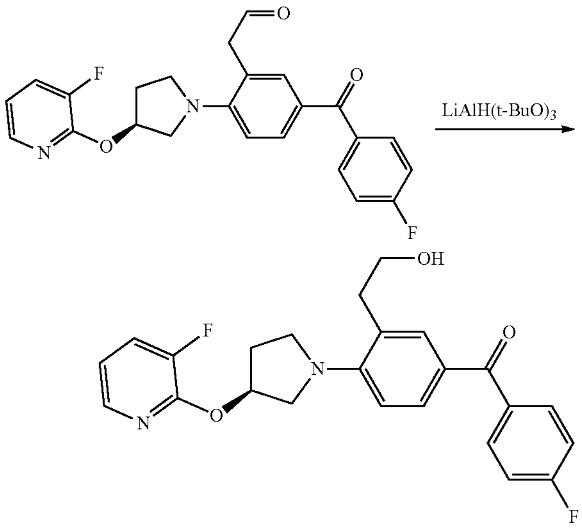

The title compound was prepared following procedures described in example 217 to give (S)-(4-(3-(3-chloropyridin-2-yloxy)pyrrolidin-1-yl)-3-(2-hydroxyethyl)phenyl)(4-fluorophenyl)methanone (40 mg, 38% yield), Mass spec: 441 (M+H), $t_R$=2.760 min, $^1$H-NMR (400 Hz, DMSO) δ=8.005-8.020 (m, 1H), 7.675-7.766 (m, 3H), 7.582-7.588 (m, 1H), 7.490-7.516 (m, 1H), 7.335-7.379 (m, 2H), 7.055 (m, 1H), 6.889-6.911 (d, 1H), 5.706 (br, 1H), 4.660-4.686 (t, 1H), 3.928-3.968 (m, 1H), 3.615-3.676 (m, 3H), 3.416-3.489 (m, 2H), 2.862-2.934 (m, 2H), 2.342-2.376 (m, 1H), 2.210-2.251 (m, 1H).

Example 223: (S)-(4-(3-(3-chloropyridin-2-yloxy)pyrrolidin-1-yl)-3-(2-hydroxyethyl)phenyl)(4-(methoxymethyl)phenyl)methanone (Compound 1-318)

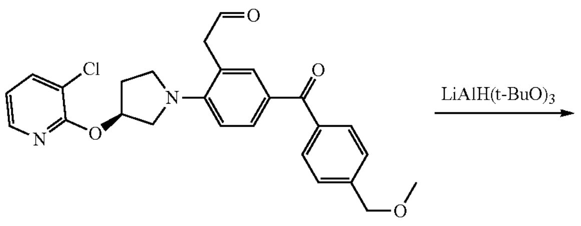

-continued

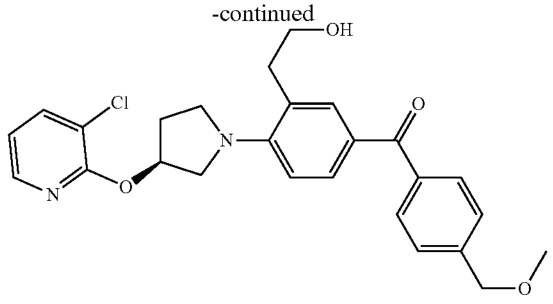

The title compound was prepared following procedures described in example 217 to give (S)-(4-(3-(3-chloropyridin-2-yloxy)pyrrolidin-1-yl)-3-(2-hydroxyethyl)phenyl)(4-(methoxymethyl)phenyl)methanone (11 mg, 27% yield), Mass spec: 467 (M+H), $t_R$=2.751 min, $^1$H-NMR (400 Hz, DMSO) δ=8.159-8.171 (m, 1H), 7.906-7.929 (m, 1H), 7.509-7.593 (m, 6H), 7.062-7.074 (m, 1H), 6.886-6.908 (d, 1H), 5.701 (br, 1H), 2.675 (t, 1H), 4.497 (s, 1H), 3.935-3.951 (m, 1H), 3.574-3.697 (m, 3H), 3.321-3.462 (m, 5H), 2.849-2.942 (m, 2H), 2.339-2.367 (m, 1H), 2.220-2.225 (m, 1H).

Example 224: (S)-(4-(3-(3-fluoropyridin-2-yloxy)pyrrolidin-1-yl)-3-(2-hydroxyethyl)phenyl)(p-tolyl)methanone (Compound 1-309)

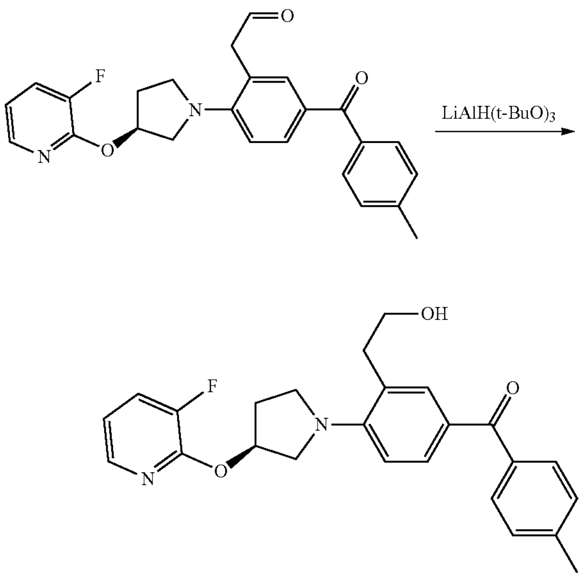

The title compound was prepared following procedures described in example 217 to give (S)-(4-(3-(3-fluoropyridin-2-yloxy)pyrrolidin-1-yl)-3-(2-hydroxyethyl)phenyl)(p-tolyl)methanone (30 mg, 39% yield), Mass spec: 421 (M+H), $t_R$=2.668 min, $^1$H-NMR (400 Hz, DMSO) δ=8.003-8.020 (m, 1H), 7.670-7.722 (m, 1H), 7.571-7.591 (m, 3H), 7.486-7.513 (m, 1H), 7.326-7.486 (d, 1H), 7.034-7.074 (m, 1H), 6.889-6.911 (d, 1H), 5.701 (br, 1H), 4.653-4.680 (t, 1H), 3.924-3.928 (m, 1H), 3.612-3.643 (m, 3H), 3.399-3.446 (m, 2H), 2.815-2.959 (m, 2H), 2.403 (s, 3H), 2.245-2.377 (m, 1H), 2.204-2.237 (m, 1H).

Example 225: (S)-(4-(3-(3-chloropyridin-2-yloxy)pyrrolidin-1-yl)-3-(2-hydroxyethyl)phenyl)(3-fluorophenyl)methanone (Compound 1-311)

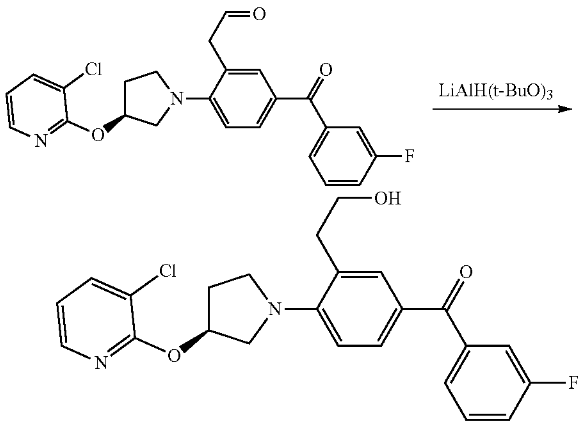

The title compound was prepared following procedures described in example 217 to give (S)-(4-(3-(3-fluoropyridin-2-yloxy)pyrrolidin-1-yl)-3-(2-hydroxyethyl)phenyl)(p-tolyl)methanone (20 mg, 20% yield), Mass spec: 441 (M+H), $t_R$=3.016 min, $^1$H-NMR (400 Hz, DMSO) δ=8.159-8.175 (m, 1H), 7.904-7.928 (m, 1H), 7.421-7.607 (m, 6H), 7.042-7.073 (m, 1H), 6.881-6.903 (d, 1H), 5.698 (br, 1H), 4.650-4.677 (t, 1H), 3.933-3.973 (m, 1H), 3.666-3.701 (m, 3H), 3.446-3.489 (m, 2H), 2.857-2.951 (m, 2H), 2.329-2.364 (m, 1H), 2.223-2.229 (m, 1H).

Example 226: 2-(2-((S)-3-(3-chloropyridin-2-yloxy)pyrrolidin-1-yl)-5-((3-fluorophenyl)(hydroxy) methyl)phenyl)ethanol (Compound 1-312)

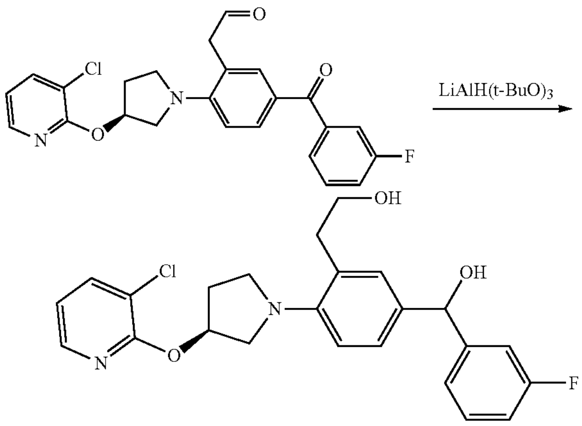

The title compound was prepared following procedures described in example 216 to give 2-(2-((S)-3-(3-chloropyridin-2-yloxy)pyrrolidin-1-yl)-5-((3-fluorophenyl)(hydroxy)methyl)phenyl)ethanol (8 mg, 8% yield), Mass spec: 443 (M+H), $t_R$=2.608 min, $^1$H-NMR (400 Hz, DMSO) δ=8.124-8.141 (m, 1H), 7.882-7.904 (m, 1H), 7.295-7.350 (m, 1H), 7.151-7.179 (m, 3H), 6.929-7.096 (m, 4H), 5.841-5.851 (d, 1H), 5.569-5.626 (m, 1H), 4.613-4.639 (t, 1H), 3.566-3.638 (m, 3H), 3.326-3.346 (m, 1H), 3.073-3.156 (m, 2H), 2.499-2.799 (m, 2H), 2.339-2.374 (m, 1H), 2.066-2.081 (m, 1H).

Example 227: (S)-(3-chlorophenyl)(3-(3-(3-chloropyridin-2-yloxy)pyrrolidin-1-yl)-4-(2-hydroxyethyl)phenyl)methanone (Compound 1-314)

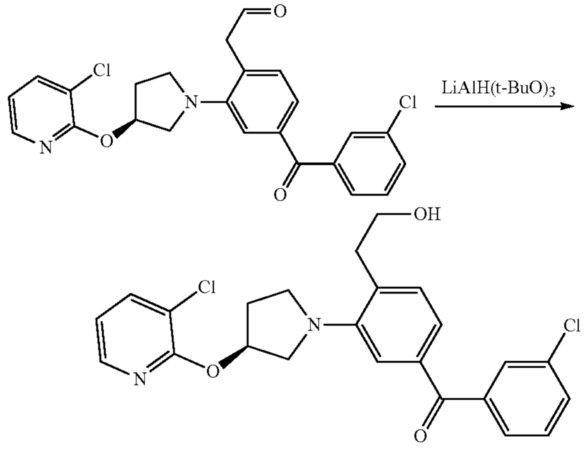

The title compound was prepared following procedures described in example 217 to give (S)-(3-chlorophenyl)(3-(3-(3-chloropyridin-2-yloxy)pyrrolidin-1-yl)-4-(2-hydroxyethyl)phenyl)methanone (18 mg, 45% yield), Mass spec: 457 (M+H), $t_R$=3.037 min, $^1$H-NMR (400 Hz, DMSO) δ=8.135-8.141 (m, 1H), 7.884-7.907 (m, 1H), 7.703-7.747 (m, 2H), 7.555-7.672 (m, 2H), 7.334-7.375 (m, 2H), 7.200-7.224 (m, 1H), 7.021-7.053 (m, 1H), 5.617-5.644 (m, 1H), 4.719 (br, 1H), 3.693-3.734 (m, 3H), 3.428-3.469 (m, 1H), 3.179-3.275 (m, 2H), 2.889-2.930 (m, 2H), 2.151-2.497 (m, 1H), 2.111-2.144 (m, 1H).

Example 228: (S)-(2-chlorophenyl)(3-(3-(3-chloropyridin-2-yloxy)pyrrolidin-1-yl)-4-(2-hydroxyethyl)phenyl)methanone (Compound 1-360)

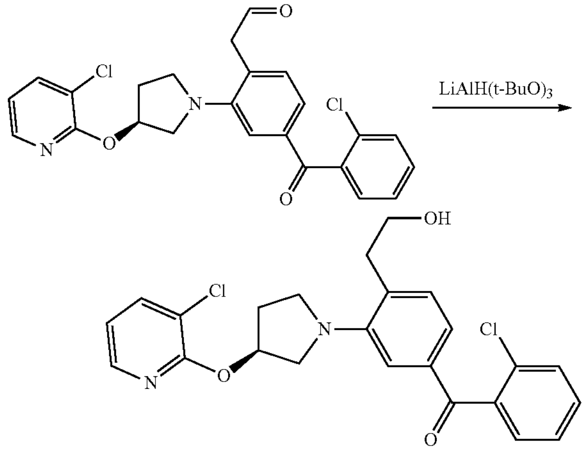

The title compound was prepared following procedures described in example 217 to give (S)-(2-chlorophenyl)(3-(3-(3-chloropyridin-2-yloxy)pyrrolidin-1-yl)-4-(2-hydroxyethyl)phenyl)methanone (41 mg, 45% yield), Mass spec: 457 (M+H), $t_R$=3.048 min, $^1$H-NMR (400 Hz, DMSO) δ=8.139-8.141 (m, 1H), 7.617-7.918 (m, 1H), 7.332-7.614 (m, 6H), 7.026-7.097 (m, 2H), 5.613-5.640 (m, 1H), 4.706-4.732 (t, 1H), 3.655-3.717 (m, 3H), 3.430-3.451 (m, 1H), 3.160-3.245 (m, 2H), 2.865-2.909 (m, 2H), 2.404-2.516 (m, 1H), 2.138-2.140 (m, 1H).

Example 229: 2-(4-((2-chlorophenyl)(hydroxy)methyl)-2-((S)-3-(3-chloropyridin-2-yloxy)pyrrolidin-1-yl)phenyl)ethanol (Compound 1-354)

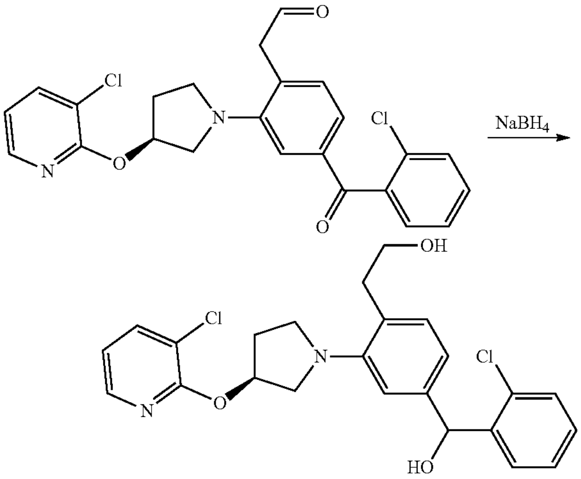

The title compound was prepared following procedures described in example 216 to give 2-(4-((2-chlorophenyl)(hydroxy)methyl)-2-((S)-3-(3-chloropyridin-2-yloxy)pyrrolidin-1-yl)phenyl)ethanol (29 mg, 28% yield), Mass spec: 459 (M+H), $t_R$=2.379 min, $^1$H-NMR (400 Hz, DMSO) δ=8.136-8.152 (m, 1H), 7.893-7.916 (m, 1H), 7.658-7.682 (m, 1H), 7.235-7.376 (m, 3H), 7.020-7.075 (m, 3H), 6.784-6.807 (m, 1H), 5.929-5.965 (m, 2H), 5.579-5.607 (br, 1H), 4.608-4.634 (t, 1H), 3.567-3.646 (m, 3H), 3.386-3.388 (m, 1H), 3.093-3.159 (m, 2H), 2.735-2.777 (m, 2H), 2.338-2.516 (m, 1H), 2.081-2.101 (m, 1H).

Example 230: (S)-(4-(3-(3-chloropyridin-2-yloxy)pyrrolidin-1-yl)-3-(hydroxymethyl)phenyl)(2-ethylphenyl)methanone (Compound 1-256)

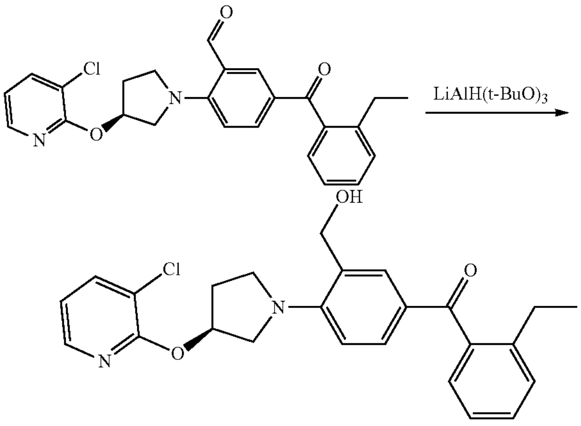

The title compound was prepared following procedures described in example 194 to give (S)-(4-(3-(3-chloropyridin-2-yloxy)pyrrolidin-1-yl)-3-(hydroxymethyl)phenyl)(2-ethylphenyl)methanone (29 mg, 28% yield), Mass spec: 437 (M+H), $t_R$=2.981 min, $^1$H-NMR (400 Hz, DMSO) δ=8.150-8.167 (m, 1H), 7.895-7.918 (m, 1H), 7.736-7.740 (m, 1H), 7.356-7.433 (m, 3H), 7.164-7.185 (m, 2H), 7.034-7.065 (m, 1H), 6.741-6.763 (m, 1H), 5.679-5.690 (br, 1H), 5.213-5.240 (t, 1H), 4.479-4.580 (m, 2H), 3.994-4.035 (m, 1H), 3.601-3.703 (m, 3H), 2.498-2.552 (m, 2H), 2.304-2.328 (m, 1H), 2.200-2.207 (m, 1H), 1.038-1.075 (m, 3H).

Example 231: (S)-5-benzoyl-2-(3-(3-chloropyridin-2-yloxy)pyrrolidin-1-yl)benzamide (Compound 1-136)

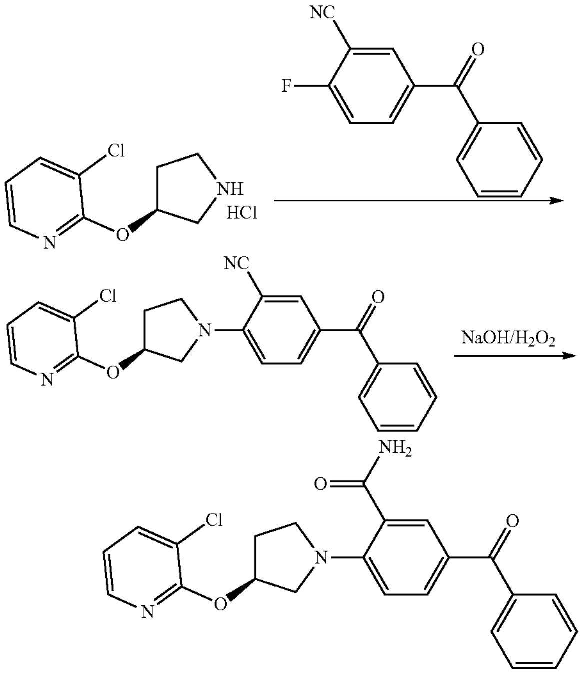

Step 1: (S)-5-benzoyl-2-(3-(3-chloropyridin-2-yloxy)pyrrolidin-1-yl)benzonitrile

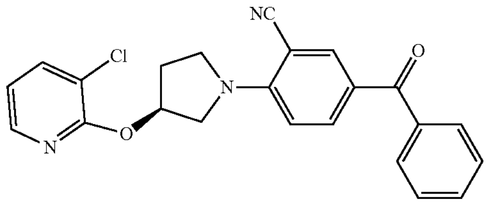 [SMILES: N#Cc1cc(C(=O)c2ccccc2)ccc1N1CC[C@H](Oc2ncccc2Cl)C1]

The title compound was prepared following procedures described in example 5 using (S)-3-chloro-2-(pyrrolidin-3-yloxy)pyridine hydrochloride (prepared as intermediate 4) and 5-benzoyl-2-fluorobenzonitrile (prepared as intermediate 8 step 4) to give (S)-5-benzoyl-2-(3-(3-chloropyridin-2-yloxy)pyrrolidin-1-yl)benzonitrile (135 mg, 33% yield), Mass spec: 404 (M+H).

Step 2: (S)-5-benzoyl-2-(3-(3-chloropyridin-2-yloxy)pyrrolidin-1-yl)benzamide

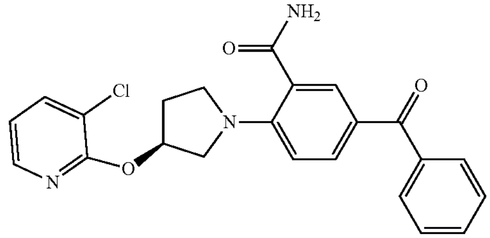 [SMILES: NC(=O)c1cc(C(=O)c2ccccc2)ccc1N1CC[C@H](Oc2ncccc2Cl)C1]

The title compound was prepared following procedures described in example 64 step 2 to give (S)-5-benzoyl-2-(3-(3-chloropyridin-2-yloxy)pyrrolidin-1-yl)benzamide (47 mg, 55% yield), Mass spec: 422 (M+H), $t_R$=2.305 min, $^1$H-NMR (400 Hz, CDCl3) δ=8.050-8.080 (m, 2H), 7.836-7.864 (m, 1H), 7.733-7.755 (m, 2H), 7.468-7.622 (m, 4H), 6.860-7.285 (m, 2H), 6.350 (br, 1H), 5.735-5.741 (br, 1H), 3.962-4.004 (m, 1H), 3.792-3.815 (m, 1H), 3.535-3.573 (m, 2H), 2.372-2.400 (m, 2H).

Example 232: (S)-5-benzyl-2-(3-(3-chloropyridin-2-yloxy)pyrrolidin-1-yl)benzamide (Compound 1-145)

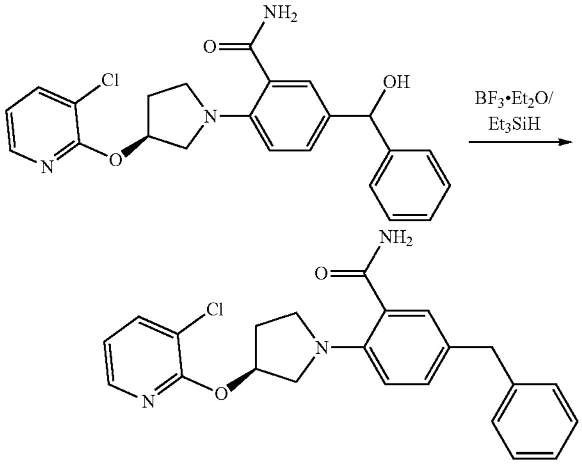

To a solution of 2-((S)-3-(3-chloropyridin-2-yloxy)pyrrolidin-1-yl)-5-(hydroxy(phenyl)methyl)benzamide (64 mg, 0.15 mmol) (prepared by reduced example 231 with NaBH4) in dry DCM/THF (5 mL/1 mL) was added Et3SiH (0.2 mL, 1.2 mmol) and BF3·Et2O (00.4 mL, 0.3 mmol), the mixture was stirred at rt for 16 h, quenched by 10% NaOH solution, separated the organic layer, dried over Na2SO4, removal the solvent to left the crude product which was purified by Prep-HPLC to give (S)-5-benzyl-2-(3-(3-chloropyridin-2-yloxy)pyrrolidin-1-yl)benzamide (42 mg, 68%), Mass spec: 408 (M+H), $t_R$=2.914 min, $^1$H-NMR (400 Hz, DMSO) δ=8.135-8.152 (m, 1H), 7.878-7.901 (m, 1H), 7.790 (s, 1H), 7.021-7.295 (m, 9H), 6.730-6.751 (d, 1H), 5.618 (br, 1H), 3.785-3.832 (m, 2H), 3.430-3.467 (m, 1H), 3.208-3.299 (m, 2H), 2.275-2.309 (m, 1H), 2.118-2.156 (m, 1H).

Example 233: 2-((S)-3-(3-chloropyridin-2-yloxy)pyrrolidin-1-yl)-5-(hydroxy(phenyl)methyl)benzamide (Compound 1-137)

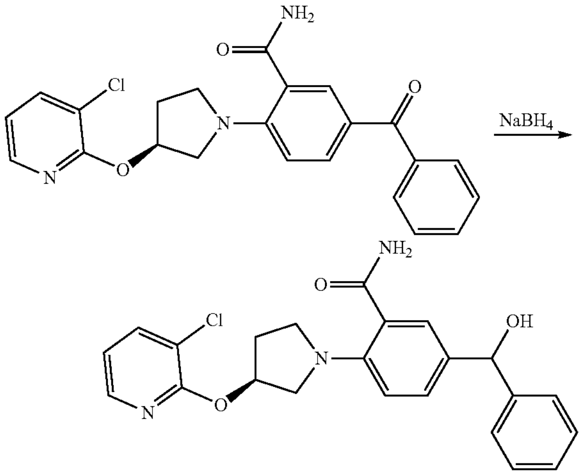

The title compound was prepared by reducing the (S)-5-benzoyl-2-(3-(3-chloropyridin-2-yloxy)pyrrolidin-1-yl)benzamide with NaBH4 to give 2-((S)-3-(3-chloropyridin-2-yloxy)pyrrolidin-1-yl)-5-(hydroxy(phenyl)methyl)benzamide (94 mg, 49% yield), Mass spec: 424 (M+H), $t_R$=2.511 min, $^1$H-NMR (400 Hz, DMSO) δ=8.105-8.121 (m, 1H), 7.846-7.869 (m, 1H), 7.724 (s, 1H), 7.143-7.342 (m, 8H), 6.990-7.021 (m, 1H), 6.699-6.720 (d, 1H), 5.684-5.698 (m, 1 h), 5.570-5.591 (m, 2H), 3.749-3.791 (m, 1H), 3.404-3.444 (m, 1H), 3.189-3.280 (m, 2H), 2.247-2.281 (m, 1H), 2.114-2.131 (m, 1H).

Example 234: (S)-5-benzyl-2-(3-(5-(trifluoromethyl)pyridin-2-yloxy)pyrrolidin-1-yl)benzamide (Compound 1-140)

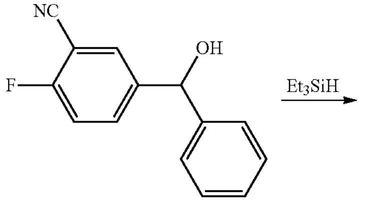

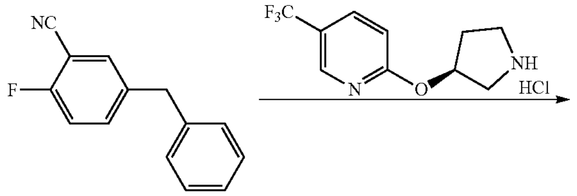

-continued

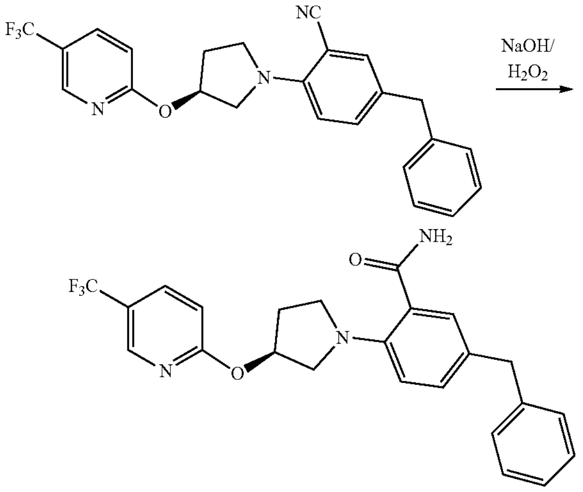

Step 1: 5-benzyl-2-fluorobenzonitrile

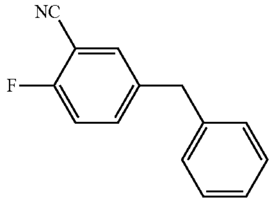 [SMILES: N#Cc1cc(Cc2ccccc2)ccc1F]

To a solution of 2-fluoro-5-(hydroxy(phenyl)methyl)benzonitrile (684 mg, 3 mmol) (prepared as intermediate 8 step 3) in 10 mL of dry DCM was added Et3SiH (3.84 mL, 24 mmol) and 0.78 mL BF3.Et2O (0.78 mL, 6 mmol), the mixture was stirred at rt for 16 h, quenched by water, separated the organic layer, dried over Na2SO4, removal the solvent to left the crude product which was purified by silica gel to give 5-benzyl-2-fluorobenzonitrile (540 mg, 85%), Mass spec: 212 (M+H).

Step 2: (S)-5-benzyl-2-(3-(5-(trifluoromethyl)pyridin-2-yloxy)pyrrolidin-1-yl)benzonitrile

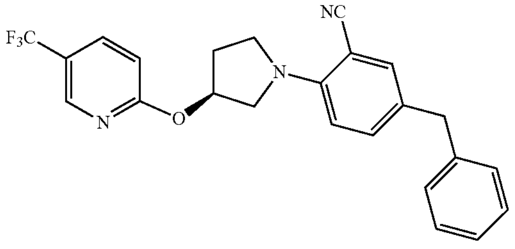 [SMILES: N#Cc1cc(Cc2ccccc2)ccc1N1CC[C@H](Oc2ccc(C(F)(F)F)cn2)C1]

The title compound was prepared following procedures described in example to give (S)-5-benzyl-2-(3-(5-(trifluoromethyl)pyridin-2-yloxy)pyrrolidin-1-yl)benzonitrile (70 mg, 13% yield), Mass spec: 424 (M+H).

Step 3: (S)-5-benzyl-2-(3-(5-(trifluoromethyl)pyridin-2-yloxy)pyrrolidin-1-yl)benzamide

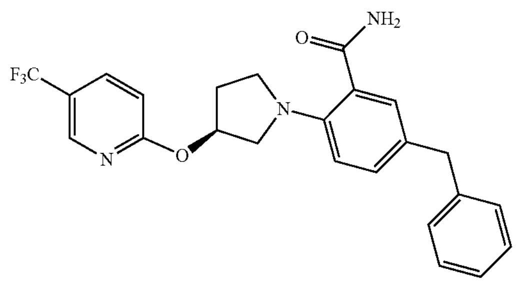 [SMILES: NC(=O)c1cc(Cc2ccccc2)ccc1N1CC[C@H](Oc2ccc(C(F)(F)F)cn2)C1]

The title compound was prepared following procedures described in example 64 step 2 to give (S)-5-benzyl-2-(3-(5-(trifluoromethyl)pyridin-2-yloxy)pyrrolidin-1-yl)benzamide (23 mg, 28% yield), Mass spec: 442 (M+H), $t_R$=2.619 min, $^1$H-NMR (400 Hz, DMSO) δ=8.608-8.610 (m, 1H), 8.048-8.075 (m, 1H), 7.770 (s, 1H), 7.091-7.295 (m, 8H), 6.987-7.008 (d, 1H), 6.716-6.738 (d, 1H), 5.641-5.647 (m, 1H), 3.831 (s, 2H), 3.761-3.779 (m, 1H), 3.452-3.470 (m, 1H), 3.236-3.293 (m, 2H), 2.289-2.343 (m, 1H), 2.133-2.177 (m, 1H).

Example 235: 5-(hydroxy(phenyl)methyl)-2-((S)-3-(5-(trifluoromethyl)pyridin-2-yloxy)pyrrolidin-1-yl)benzamide (Compound 1-146)

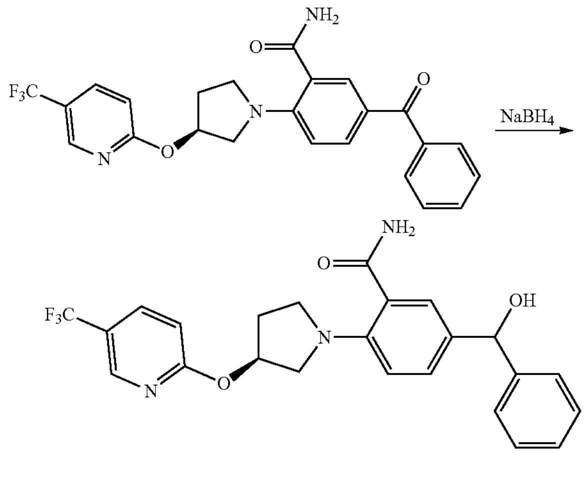

The title compound was prepared following procedures described in example 233 using (S)-5-benzoyl-2-(3-(5-(trifluoromethyl)pyridin-2-yloxy)pyrrolidin-1-yl)benzamide (prepared as example 231) to give 5-(hydroxy(phenyl)methyl)-2-((S)-3-(5-(trifluoromethyl)pyridin-2-yloxy)pyrrolidin-1-yl)benzamide (110 mg, 57% yield), Mass spec: 458 (M+H), $t_R$=2.731 min, $^1$H-NMR (400 Hz, DMSO) δ=8.607 (m, 1H), 8.042-8.069 (m, 1H), 7.744 (s, 1H), 7.182-7.368 (m, 8H), 6.981-7.003 (d, 1H), 6.710-6.731 (d, 1H), 5.726-7.736 (m, 1H), 5.644 (s, 2H), 5.595-5.605 (m, 1H), 3.755-3.795 (m, 1H), 3.427-3.491 (m, 1H), 3.234-3.306 (m, 2H), 2.272-2.340 (m, 1H), 2.144-2.177 (m, 1H).

Example 236: (S)-(2-(3-(3-chloropyridin-2-yloxy)pyrrolidin-1-yl)-5-(2-methoxyphenoxy)phenyl)methanol (Compound 1-221)

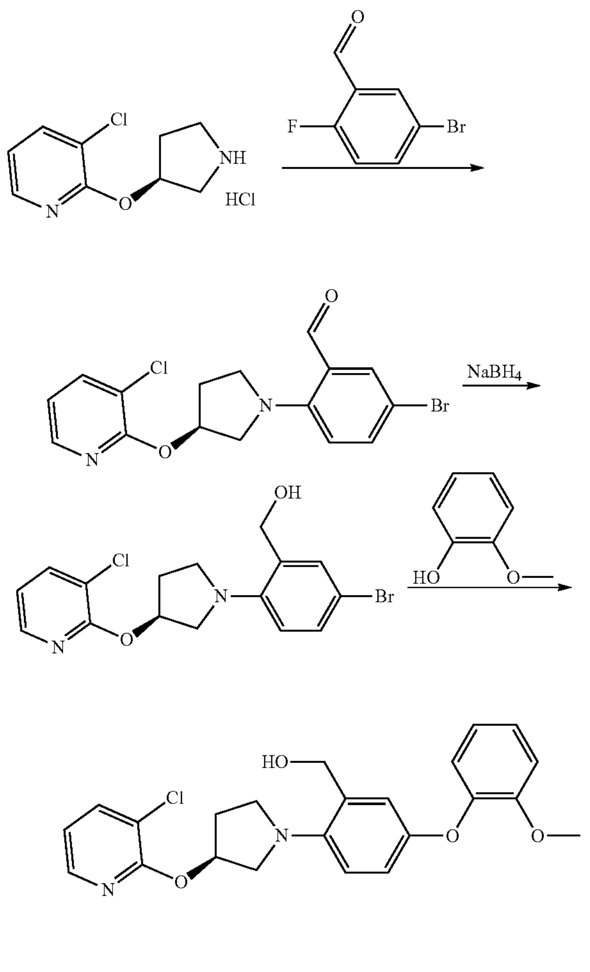

Step 1: (S)-5-bromo-2-(3-(3-chloropyridin-2-yloxy)pyrrolidin-1-yl)benzaldehyde

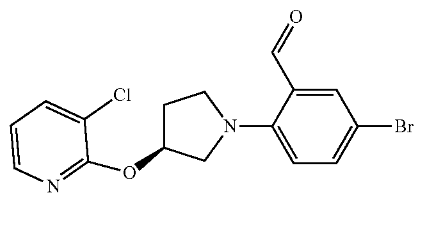 [SMILES: O=Cc1cc(Br)ccc1N1CC[C@H](Oc2ncccc2Cl)C1]

To a solution of (S)-3-chloro-2-(pyrrolidin-3-yloxy)pyridine hydrochloride (4 g, 17 mmol) (prepared as intermediate 3) in 100 mL DMF was added 5-bromo-2-fluorobenzaldehyde (2.3 g, 11.35 mmol) and K2CO3 (2.35 g, 34 mmol), the mixture was stirred at 95° C. overnight, water was added, extracted with DCM, the organic layer was washed by LiCl solution, dried over Na2SO4, removal the solvent to left the crude product which was purified by silica gel to give (S)-5-bromo-2-(3-(3-chloropyridin-2-yloxy)pyrrolidin-1-yl)benzaldehyde (2.0 g, 34% yield), Mass spec: 341 (M+H).

Step 2: (S)-(5-bromo-2-(3-(3-chloropyridin-2-yloxy)pyrrolidin-1-yl)phenyl)methanol

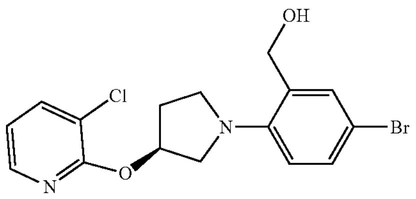 [SMILES: OCc1cc(Br)ccc1N1CC[C@H](Oc2ncccc2Cl)C1]

To a solution of (S)-5-bromo-2-(3-(3-chloropyridin-2-yloxy)pyrrolidin-1-yl)benzaldehyde (1 g, 2.62 mmol) in 30 mL MeOH was added NaBH4 (199 g, 5.23 mmol), the mixture was stirred at rt till to finished monitored by TLC, water was added, extracted with EA, the organic layer was washed by water, brine, dried over Na2SO4, removal the solvent to left the crude product which was purified by silica gel to give (S)-(5-bromo-2-(3-(3-chloropyridin-2-yloxy)pyrrolidin-1-yl)phenyl)methanol (910 mg, 91% yield), Mass spec: 383 (M+H).

Step 3: (S)-(2-(3-(3-chloropyridin-2-yloxy)pyrrolidin-1-yl)-5-(2-methoxyphenoxy)phenyl)methanol

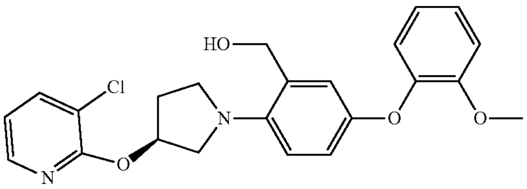 [SMILES: CCc1ccccc1Oc1ccc(N2CC[C@H](Oc3ncccc3Cl)C2)c(CO)c1]

To a solution of (S)-(5-bromo-2-(3-(3-chloropyridin-2-yloxy)pyrrolidin-1-yl)phenyl)methanol (100 mg, 0.26 mmol) in dioxane/DMF (0.8 mL/0.2 mL) was added 2-methoxyphenol (65 mg, 0.52 mmol), CuI (25 mg, 0.13 mmol), Cs2CO3 (170 mg, 0.52 mmol) and 2-(dimethylamino)acetic acid hydrochloride (18 mg, 0.13 mmol), the mixture was irradiated by microwave to 160° C. for 1 h, diluted with water, extracted by EA, washed with LiCl solution, brine, dried over Na2SO4, and removal the solvent to left the crude product which was purified by Prep-HPLC to give (S)-(2-(3-(3-chloropyridin-2-yloxy)pyrrolidin-1-yl)-5-(2-methoxyphenoxy)phenyl)methanol (30 mg, 27% yield), Mass spec: 427 (M+H), $t_R$=2.694 min, $^1$H-NMR (400 Hz, DMSO) δ=8.131-8.147 (m, 1H), 7.895-7.918 (m, 1H), 7.132-7.143 (m, 2H), 6.912-7.049 (m, 5H), 6.652-6.681 (m, 1H), 5.551-5.581 (br, 1H), 5.125-5.153 (t, 1H), 4.461-4.489 (m, 2H), 3.756 (s, 3H), 3.475-3.516 (m, 1H), 3.243-3.301 (m, 1H), 3.029-3.143 (m, 2H), 2.359-2.409 (m, 1H), 2.022-2.057 (m, 1H).

Example 237: (S)-(2-(3-(3-chloropyridin-2-yloxy)pyrrolidin-1-yl)-5-(2-ethylphenoxy)phenyl)methanol (Compound 1-222)

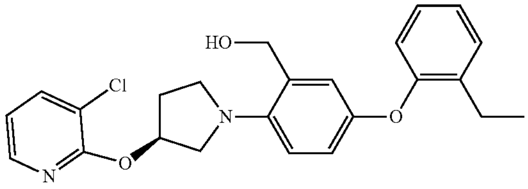

The title compound was prepared following procedures described in example 236 step 3 to give (S)-(2-(3-(3-chloropyridin-2-yloxy)pyrrolidin-1-yl)-5-(2-ethylphenoxy)phenyl)methanol (42 mg, 38% yield), Mass spec: 425 (M+H), $t_R$=2.694 min, $^1$H-NMR (400 Hz, DMSO) δ=8.128-8.144 (m, 1H), 7.893-7.916 (m, 1H), 7.283-7.304 (m, 1H), 7.143-7.181 (m, 1H), 6.956-7.139 (m, 4H), 6.718-6.776 (m, 2H), 5.556-5.586 (br, 1H), 5.161-5.188 (t, 1H), 4.466-4.496 (m, 2H), 3.496-3.537 (m, 1H), 3.262-3.320 (m, 1H), 3.045-3.157 (m, 2H), 2.572-2.629 (q, 2H), 2.374-2.499 (m, 1H), 2.040-2.062 (m, 1H), 1.135-1.173 (t, 3H).

Example 238: (S)-(5-(2-chlorophenoxy)-2-(3-(3-chloropyridin-2-yloxy)pyrrolidin-1-yl)phenyl)methanol (Compound 1-223)

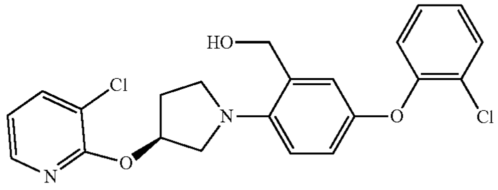 [SMILES: OCc1cc(Oc2ccccc2Cl)ccc1N1CC[C@H](Oc2ncccc2Cl)C1]

The title compound was prepared following procedures described in example 236 step 3 to give (S)-(5-(2-chlorophenoxy)-2-(3-(3-chloropyridin-2-yloxy)pyrrolidin-1-yl)phenyl)methanol (32 mg, 28% yield), Mass spec: 431 (M+H), $t_R$=3.126 min, $^1$H-NMR (400 Hz, DMSO) δ=8.138-8.151 (m, 1H), 7.903-7.923 (m, 1H), 7.556-7.575 (m, 1H), 7.293-7.331 (m, 1H), 6.942-7.165 (m, 5H), 6.803-6.831 (m, 1H), 5.590 (br, 1H), 5.202-5.207 (t, 1H), 4.448-4.505 (m, 2H), 3.538-3.579 (m, 1H), 3.301-3.341 (m, 1H), 3.071-3.188 (m, 2H), 2.363-2.414 (m, 1H), 2.050-2.082 (m, 1H).

Example 239: (S)-(2-(3-(3-chloropyridin-2-yloxy)pyrrolidin-1-yl)-5-(o-tolyloxy)phenyl)methanol (Compound 1-173)

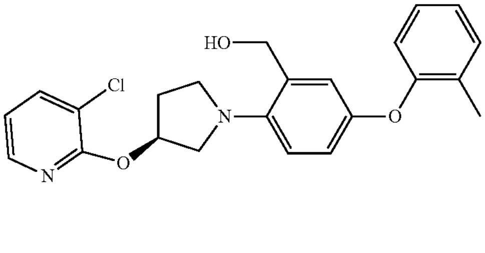 [SMILES: Cc1ccccc1Oc1ccc(N2CC[C@H](Oc3ncccc3Cl)C2)c(CO)c1]

The title compound was prepared following procedures described in example 236 step 3 to give (S)-(2-(3-(3-chloropyridin-2-yloxy)pyrrolidin-1-yl)-5-(o-tolyloxy)phenyl) methanol (1.2 g, 75% yield), Mass spec: 411 (M+H), $t_R$=3.117 min, $^1$H-NMR (400 Hz, DMSO) δ=8.110-8.122 (m, 1H), 7.872-7.891 (m, 1H), 7.251-7.268 (m, 1H), 7.119-7.157 (m, 1H), 6.934-7.022 (m, 4H), 6.695-8.772 (m, 2H), 5.551 (br, 1H), 5.098-5.123 (t, 1H), 4.450-4.478 (m, 2H), 3.474-3.516 (m, 1H), 3.242-3.280 (m, 1H), 3.042-3.141 (m, 2H), 2.335-2.386 (m, 1H), 2.178 (s, 3H), 2.009-2.042 (m, 1H).

Example 240: (S)-(2-(3-(3-chloropyridin-2-yloxy) pyrrolidin-1-yl)-5-(m-tolyloxy)phenyl)methanol (Compound 1-242)

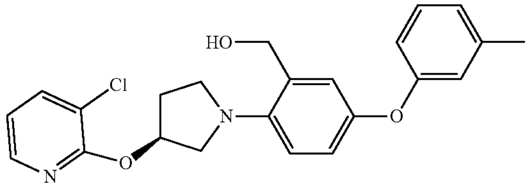 [SMILES: Cc1cccc(Oc2ccc(N3CC[C@H](Oc4ncccc4Cl)C3)c(CO)c2)c1]

The title compound was prepared following procedures described in example 236 step 3 to give (S)-(2-(3-(3-chloropyridin-2-yloxy)pyrrolidin-1-yl)-5-(m-tolyloxy)phenyl) methanol (50 mg, 46% yield), Mass spec: 411 (M+H), $t_R$=3.177 min, H-NMR (400 Hz, DMSO) δ=8.135-8.148 (m, 1H), 7.898-7.917 (m, 1H), 7.195-7.234 (m, 1H), 6.969-7.094 (m, 3H), 6.822-6.893 (m, 2H), 6.712-6.815 (m, 2H), 5.588 (br, 1H), 5.138-5.166 (t, 1H), 4.482-4.512 (m, 2H), 3.532-3.559 (m, 1H), 3.317-3.324 (m, 1H), 3.067-3.194 (m, 2H), 2.345-2.414 (m, 1H), 2.266 (s, 3H), 2.061-2.280 (m, 1H).

Example 241: (S)-(2-(3-(3-chloropyridin-2-yloxy) pyrrolidin-1-yl)-5-(p-tolyloxy)phenyl)methanol (Compound 1-250)

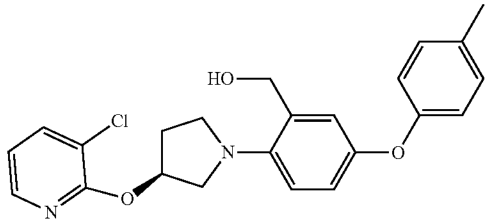 [SMILES: Cc1ccc(Oc2ccc(N3CC[C@H](Oc4ncccc4Cl)C3)c(CO)c2)cc1]

The title compound was prepared following procedures described in example 236 step 3 to give (S)-(2-(3-(3-chloropyridin-2-yloxy)pyrrolidin-1-yl)-5-(p-tolyloxy)phenyl) methanol (50 mg, 46% yield), Mass spec: 411 (M+H), $t_R$=3.186 min, H-NMR (400 Hz, DMSO) δ=8.134-8.146 (m, 1H), 7.896-7.915 (m, 1H), 7.135-7.156 (m, 2H), 6.960-7.069 (m, 3H), 6.789-6.855 (m, 3H), 5.580 (br, 1H), 5.126-5.153 (t, 1H), 4.472-4.501 (m, 2H), 3.513-3.554 (m, 1H), 3.297-3.327 (m, 1H), 3.050-3.175 (m, 2H), 2.377-2.394 (m, 1H), 2.265 (s, 3H), 2.037-2.071 (m, 1H).

Example 242: (S)-(5-(4-chlorophenoxy)-2-(3-(3-chloropyridin-2-yloxy)pyrrolidin-1-yl)phenyl)methanol (Compound 1-249)

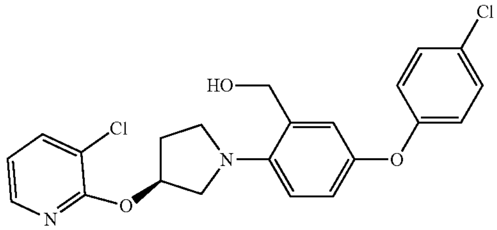 [SMILES: OCc1cc(Oc2ccc(Cl)cc2)ccc1N1CC[C@H](Oc2ncccc2Cl)C1]

The title compound was prepared following procedures described in example 236 step 3 to give (S)-(5-(4-chlorophenoxy)-2-(3-(3-chloropyridin-2-yloxy)pyrrolidin-1-yl) phenyl)methanol (40 mg, 35% yield), Mass spec: 431 (M+H), $t_R$=3.315 min, $^1$H-NMR (400 Hz, DMSO) δ=8.140-8.157 (m, 1H), 7.904-7.927 (m, 1H), 7.379-7.402 (m, 2H), 6.863-7.115 (m, 6H), 5.589 (br, 1H), 5.172-5.199 (t, 1H), 4.452-4.554 (m, 2H), 3.554-3.594 (m, 1H), 3.316-3.336 (m, 1H), 3.087-3.207 (m, 2H), 2.346-2.415 (m, 1H), 2.037-2.106 (m, 1H).

Example 243: (S)-(5-(3-chlorophenoxy)-2-(3-(3-chloropyridin-2-yloxy)pyrrolidin-1-yl)phenyl)methanol (Compound 1-248)

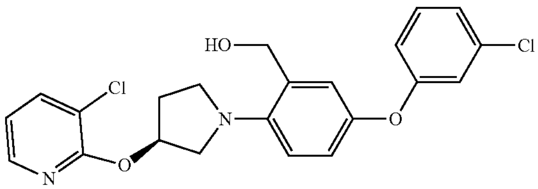 [SMILES: OCc1cc(Oc2cccc(Cl)c2)ccc1N1CC[C@H](Oc2ncccc2Cl)C1]

The title compound was prepared following procedures described in example 236 step 3 to give (S)-(5-(3-chlorophenoxy)-2-(3-(3-chloropyridin-2-yloxy)pyrrolidin-1-yl) phenyl)methanol (40 mg, 35% yield), Mass spec: 431 (M+H), $t_R$=3.316 min, $^1$H-NMR (400 Hz, DMSO) δ=8.143-8.159 (m, 1H), 7.906-7.930 (m, 1H), 7.349-7.389 (m, 1H), 6.893-7.137 (m, 7H), 5.601 (br, 1H), 5.205-5.233 (t, 1H), 4.494-4.526 (m, 2H), 3.571-3.612 (m, 1H), 3.344-3.368 (m, 1H), 3.102-3.222 (m, 2H), 2.366-2.417 (m, 1H), 2.062-2.095 (m, 1H).

Example 244: (S)-(2-(3-(3-chloropyridin-2-yloxy) pyrrolidin-1-yl)-5-(2-propylphenoxy)phenyl)methanol (Compound 1-266)

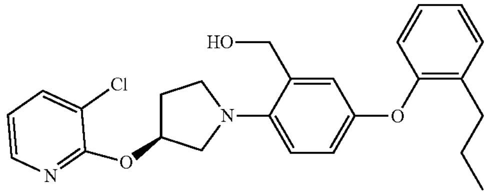 [SMILES: CCCc1ccccc1Oc1ccc(N2CC[C@H](Oc3ncccc3Cl)C2)c(CO)c1]

The title compound was prepared following procedures described in example 236 step 3 to give (S)-(2-(3-(3-chloropyridin-2-yloxy)pyrrolidin-1-yl)-5-(2-propylphenoxy)phenyl)methanol (60 mg, 52% yield), Mass spec: 439 (M+H), $t_R$=3.525 min, $^1$H-NMR (400 Hz, DMSO) δ=8.135-8.147 (m, 1H), 7.896-7.915 (m, 1H), 7.264-7.283 (m, 1H), 7.139-7.159 (m, 1H), 6.966-7.060 (m, 5H), 6.733-6.771 (m, 1H), 5.582 (br, 1H), 5.112-5.139 (t, 1H), 4.478-4.506 (m, 2H), 3.506-3.547 (m, 1H), 3.291-3.311 (m, 1H), 3.064-3.168 (m, 2H), 2.555-2.592 (q, 2H), 2.507-2.574 (m, 1H), 2.033-2.045 (m, 1H), 1.563-1.619 (m, 2H)2, 0.873-0.910 (t, 3H).

Example 245: (S)-(2-(3-(3-chloropyridin-2-yloxy)pyrrolidin-1-yl)-5-(2-fluorophenoxy)phenyl)methanol (Compound 1-270)

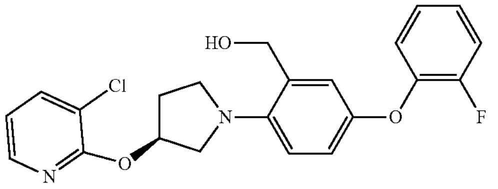 [SMILES: OCc1cc(Oc2ccccc2F)ccc1N1CC[C@H](Oc2ncccc2Cl)C1]

The title compound was prepared following procedures described in example 236 step 3 to give (S)-(2-(3-(3-chloropyridin-2-yloxy)pyrrolidin-1-yl)-5-(2-fluorophenoxy)phenyl)methanol (58 mg, 54% yield), Mass spec: 415 (M+H), $t_R$=2.922 min, $^1$H-NMR (400 Hz, DMSO) δ=8.135-8.151 (m, 1H), 7.899-7.923 (m, 1H), 7.351-7.378 (m, 1H), 6.994-7.151 (m, 6H), 6.814-6.826 (m, 1H), 5.584 (br, 1H), 5.162-5.166 (t, 1H), 4.475-4.506 (m, 2H), 3.546-3.560 (m, 1H), 3.318-3.324 (m, 1H), 3.077-3.152 (m, 2H), 2.379-2.396 (m, 1H), 2.060-2.064 (m, 1H).

Example 246: (S)-(2-(3-(3-chloropyridin-2-yloxy)pyrrolidin-1-yl)-5-(2-isopropylphenoxy)phenyl)methanol (Compound 1-271)

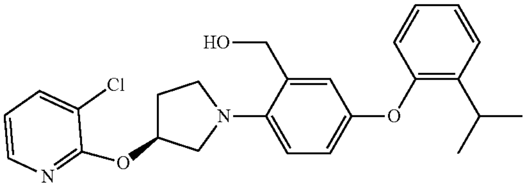 [SMILES: CC(C)c1ccccc1Oc1ccc(N2CC[C@H](Oc3ncccc3Cl)C2)c(CO)c1]

The title compound was prepared following procedures described in example 236 step 3 to give (S)-(2-(3-(3-chloropyridin-2-yloxy)pyrrolidin-1-yl)-5-(2-isopropylphenoxy)phenyl)methanol (30 mg, 17% yield), Mass spec: 439 (M+H), $t_R$=3.499 min, $^1$H-NMR (400 Hz, CD3OD) δ=8.065-8.080 (m, 1H), 7.753-7.776 (m, 1H), 7.338-7.352 (m, 1H), 7.098-7.131 (m, 4H), 6.945-6.951 (m, 1H), 6.799-6.823 (m, 2H), 5.644-5.655 (br, 1H), 4.697 (s, 2H), 3.546-3.560 (m, 1H), 3.337-3.361 (m, 1H), 2.277-3.321 (m, 1H), 3.134-3.166 (m, 1H), 2.462-2.479 (m, 1H), 2.181-2.192 (m, 1H), 1.238-1.306 (m, 6H).

Example 247: (S)-(2-(3-(3-chloropyridin-2-yloxy)pyrrolidin-1-yl)-5-phenoxyphenyl)methanol (Compound 1-168)

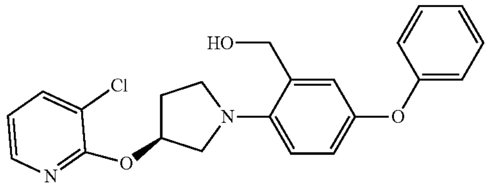 [SMILES: OCc1cc(Oc2ccccc2)ccc1N1CC[C@H](Oc2ncccc2Cl)C1]

The title compound was prepared following procedures described in example 236 step 3 to give (S)-(2-(3-(3-chloropyridin-2-yloxy)pyrrolidin-1-yl)-5-phenoxyphenyl)methanol (30 mg, 50% yield), Mass spec: 397 (M+H), $t_R$=3.015 min, $^1$H-NMR (400 Hz, DMSO) δ=8.142-8.150 (m, 1H), 7.902-7.925 (m, 1H), 7.329-7.369 (m, 2H), 6.949-7.108 (m, 6H), 6.859-6.929 (m, 1H), 5.583 (br, 1H), 5.162-5.177 (t, 1H), 4.485-4.416 (m, 2H), 3.428-3.552 (m, 1H), 3.322-3.343 (m, 1H), 3.061-3.197 (m, 2H), 2.385 (m, 1H), 2.075 (m, 1H).

Example 248: (S)-(2-(3-(5-fluoropyridin-2-yloxy)pyrrolidin-1-yl)-5-(2-methoxyphenoxy)phenyl)methanol (Compound 1-336)

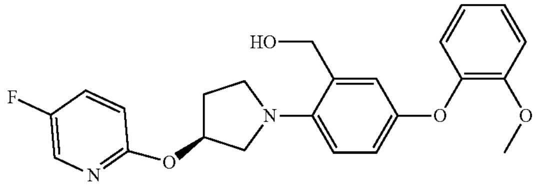 [SMILES: COc1ccccc1Oc1ccc(N2CC[C@H](Oc3ccc(F)cn3)C2)c(CO)c1]

The title compound was prepared following procedures described in example 236 to give (S)-(2-(3-(5-fluoropyridin-2-yloxy)pyrrolidin-1-yl)-5-(2-methoxyphenoxy)phenyl)methanol (30 mg, 26% yield), Mass spec: 411 (M+H), $t_R$=2.519 min, $^1$H-NMR (400 Hz, DMSO) δ=8.150-8.157 (m, 1H), 7.665-7.716 (m, 1H), 7.128-7.143 (m, 2H), 6.897-6.985 (m, 5H), 6.647-6.677 (m, 1H), 5.441-5.456 (br, 1H), 5.098-5.126 (t, 1H), 4.463 (m, 2H), 3.757 (s, 3H), 3.451-3.492 (m, 1H), 3.240-3.262 (m, 1H), 3.017-3.104 (m, 2H), 2.342-2.358 (m, 1H), 2.007-2.020 (m, 1H).

Example 249: (S)-(5-(2-methoxyphenoxy)-2-(3-(pyridin-2-yloxy)pyrrolidin-1-yl)phenyl)methanol (Compound 1-339)

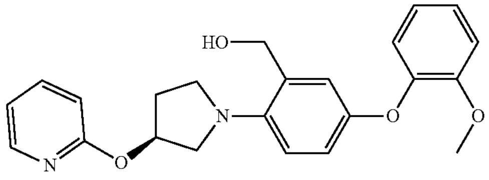 [SMILES: COc1ccccc1Oc1ccc(N2CC[C@H](Oc3ccccn3)C2)c(CO)c1]

The title compound was prepared following procedures described in example 236 to give (S)-(5-(2-methoxyphenoxy)-2-(3-(pyridin-2-yloxy)pyrrolidin-1-yl)phenyl)methanol (79 mg, 46% yield), Mass spec: 393 (M+H), $t_R$=2.280 min, $^1$H-NMR (400 Hz, DMSO) δ=8.161-8.176 (m, 1H), 7.685-7.729 (m, 1H), 7.128-7.143 (m, 2H), 6.911-6.989 (m, 5H), 6.813-6.834 (m, 1H), 6.649-6.678 (m, 1H), 5.499-5.530 (br, 1H), 5.093-5.121 (t, 1H), 4.457-4.481 (m, 2H), 3.759 (s, 3H), 3.467-3.507 (m, 1H), 3.247-3.268 (m, 1H), 3.020-3.114 (m, 2H), 2.332-2.382 (m, 1H), 2.007-2.027 (m, 1H).

Example 250: (S)-(5-(2-methoxyphenoxy)-2-(3-(3-methylpyridin-2-yloxy)pyrrolidin-1-yl)phenyl)methanol (Compound 1-340)

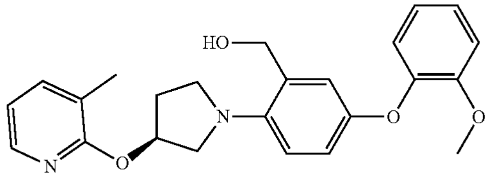 [SMILES: COc1ccccc1Oc1ccc(N2CC[C@H](Oc3ncccc3C)C2)c(CO)c1]

The title compound was prepared following procedures described in example 236 to give (S)-(5-(2-methoxyphenoxy)-2-(3-(3-methylpyridin-2-yloxy)pyrrolidin-1-yl)phenyl)methanol (40 mg, 35% yield), Mass spec: 407 (M+H), $t_R$=2.509 min, $^1$H-NMR (400 Hz, DMSO) δ=7.985-7.998 (m, 1H), 7.535-7.553 (m, 1H), 7.137-7.146 (m, 2H), 6.873-6.989 (m, 5H), 6.656-6.685 (m, 1H), 5.533-5.552 (br, 1H), 4.476-4.488 (m, 2H), 3.762 (s, 3H), 3.482-3.494 (m, 1H), 3.274-3.293 (m, 2H), 3.051-3.111 (m, 2H), 2.319-2.380 (m, 1H), 2.143 (s, 3H), 2.004-2.031 (m, 1H).

Example 251: (S)-(5-(2-ethylphenoxy)-2-(3-(3-methylpyridin-2-yloxy)pyrrolidin-1-yl)phenyl)methanol (Compound 1-268)

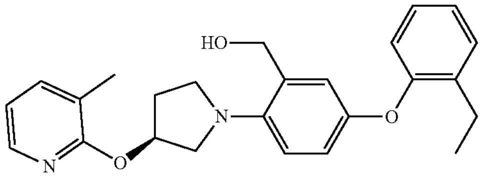 [SMILES: CCc1ccccc1Oc1ccc(N2CC[C@H](Oc3ncccc3C)C2)c(CO)c1]

The title compound was prepared following procedures described in example 236 to give (S)-(5-(2-ethylphenoxy)-2-(3-(3-methylpyridin-2-yloxy)pyrrolidin-1-yl)phenyl)methanol (1.2 g, 64% yield), Mass spec: 405 (M+H), $t_R$=3.077 min, $^1$H-NMR (400 Hz, DMSO) δ=7.985-7.995 (m, 1H), 7.529-7.547 (m, 1H), 7.289-7.307 (m, 1H), 7.141-7.165 (m, 1H), 6.781-7.077 (m, 4H), 6.723-6.760 (m, 2H), 5.532-5.548 (br, 1H), 5.131-5.158 (t, 1H), 4.480-4.507 (m, 2H), 3.485-3.526 (m, 1H), 3.290-3.312 (m, 1H), 3.062-3.129 (m, 2H), 2.582-2.638 (q, 2H), 2.344-2.361 (m, 1H), 2.138 (s, 3H), 1.998-2.029 (m, 1H), 1.142-1.180 (t, 3H).

Example 252: (S)-(5-(2-methoxyphenoxy)-2-(3-(5-methylpyridin-2-yloxy)pyrrolidin-1-yl)phenyl)methanol (Compound 1-345)

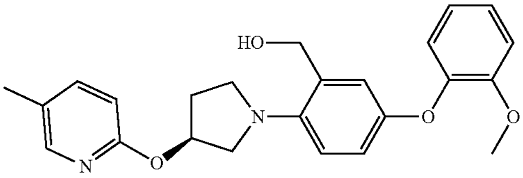 [SMILES: COc1ccccc1Oc1ccc(N2CC[C@H](Oc3ccc(C)cn3)C2)c(CO)c1]

The title compound was prepared following procedures described in example 236 to give (S)-(5-(2-methoxyphenoxy)-2-(3-(5-methylpyridin-2-yloxy)pyrrolidin-1-yl)phenyl)methanol (73 mg, 64% yield), Mass spec: 407 (M+H), $t_R$=2.442 min, $^1$H-NMR (400 Hz, DMSO) δ=7.970-7.976 (m, 1H), 7.516-7.543 (m, 1H), 7.125-7.141 (m, 2H), 6.896-6.984 (m, 4H), 6.645-6.740 (m, 2H), 5.447-5.478 (br, 1H), 5.095-5.123 (t, 1H), 4.448-4.474 (m, 2H), 3.739 (s, 3H), 3.444-3.485 (m, 1H), 3.212-3.252 (m, 1H), 3.011-3.091 (m, 2H), 2.201-2.361 (m, 1H), 2.003 (s, 3H), 1.983-1.990 (m, 1H).

Example 253: (S)-(2-(3-(3-fluoropyridin-2-yloxy)pyrrolidin-1-yl)-5-(2-methoxyphenoxy)phenyl)methanol (Compound 1-346)

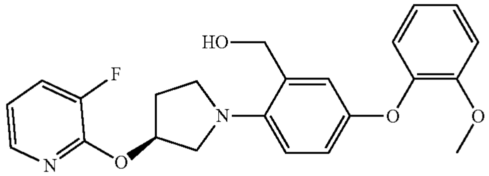

The title compound was prepared following procedures described in example 236 to give (S)-(2-(3-(3-fluoropyridin-2-yloxy)pyrrolidin-1-yl)-5-(2-methoxyphenoxy)phenyl)methanol (68 mg, 61% yield), Mass spec: 411 (M+H), $t_R$=2.500 min, $^1$H-NMR (400 Hz, DMSO) δ=7.979-7.995 (m, 1H), 7.661-7.693 (m, 1H), 7.130-7.145 (m, 2H), 6.915-7.044 (m, 5H), 6.654-6.683 (m, 1H), 5.575-5.605 (br, 1H), 5.099-5.127 (t, 1H), 4.462-4.486 (m, 2H), 3.759 (s, 3H), 3.485-3.526 (m, 1H), 3.244-3.283 (m, 1H), 3.028-3.165 (m, 2H), 2.367-2.419 (m, 1H), 2.040-2.074 (m, 1H).

Example 254: (S)-(5-(2-ethylphenoxy)-2-(3-(3-fluoropyridin-2-yloxy)pyrrolidin-1-yl)phenyl)methanol (Compound 1-267)

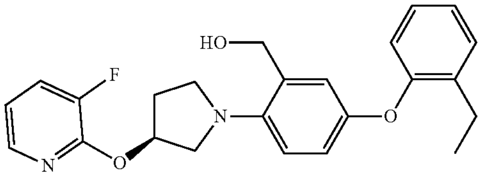

The title compound was prepared following procedures described in example 236 to give (S)-(5-(2-ethylphenoxy)-

2-(3-(3-fluoropyridin-2-yloxy)pyrrolidin-1-yl)phenyl) methanol (50 mg, 45% yield), Mass spec: 409 (M+H), $t_R$=3.058 min, $^1$H-NMR (400 Hz, DMSO) δ=7.979-7.994 (m, 1H), 7.663-7.713 (m, 1H), 7.289-7.307 (m, 1H), 6.954-7.184 (m, 5H), 6.722-6.781 (m, 2H), 5.578-5.609 (m, 1H), 5.145-5.173 (t, 1H), 4.471-4.496 (m, 2H), 3.508-3.550 (m, 1H), 3.264-3.304 (m, 1H), 3.149-3.162 (m, 1H), 3.045-3.087 (m, 1H), 2.578-2.634 (q, 2H), 2.367-2.418 (m, 1H), 2.050-2.083 (m, 1H), 1.140-1.177 (t, 3H).

Example 255: (S)-(5-(2-ethylphenoxy)-2-(3-(3-methylpyridin-2-yloxy)pyrrolidin-1-yl)phenyl) methanol (Compound 1-268)

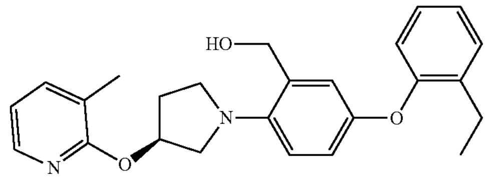 [SMILES: CCc1ccccc1Oc1ccc(N2CC[C@H](Oc3ncccc3C)C2)c(CO)c1]

The title compound was prepared following procedures described in example 236 to give (S)-(5-(2-ethylphenoxy)-2-(3-(3-methylpyridin-2-yloxy)pyrrolidin-1-yl)phenyl) methanol (40 mg, 36% yield), Mass spec: 405 (M+H), $t_R$=3.108 min, $^1$H-NMR (400 Hz, DMSO) δ=7.985-7.997 (m, 1H), 7.528-7.546 (m, 1H), 7.285-7.303 (m, 1H), 7.141-7.183 (m, 1H), 7.036-7.074 (m, 2H), 6.953-6.975 (m, 1H), 6.869-6.889 (m, 1H), 6.722-6.777 (m, 2H), 5.523-5.553 (m, 1H), 5.131-5.158 (t, 1H), 4.477-4.504 (m, 2H), 3.484-3.524 (m, 1H), 3.270-3.210 (m, 1H), 3.052-3.127 (m, 2H), 2.579-2.636 (q, 2H), 2.502-2.510 (m, 1H), 2.137 (s, 3H), 2.007-2.041 (m, 1H), 1.141-1.179 (t, 3H).

Example 256: (S)-(5-(2-fluorophenoxy)-2-(3-(3-fluoropyridin-2-yloxy)pyrrolidin-1-yl)phenyl)methanol (Compound 1-298)

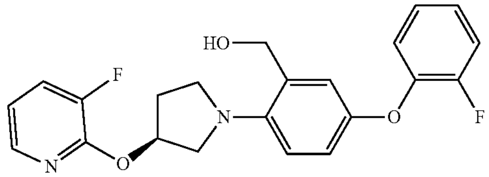 [SMILES: OCc1cc(Oc2ccccc2F)ccc1N1CC[C@H](Oc2ncccc2F)C1]

The title compound was prepared following procedures described in example 236 to give (S)-(5-(2-fluorophenoxy)-2-(3-(3-fluoropyridin-2-yloxy)pyrrolidin-1-yl)phenyl) methanol (76 mg, 38% yield), Mass spec: 399 (M+H), $t_R$=2.735 min, $^1$H-NMR (400 Hz, DMSO) δ=7.979-7.966 (m, 1H), 7.657-7.708 (m, 1H), 7.331-7.383 (m, 1H), 6.966-7.196 (m, 6H), 6.804-6.833 (m, 1H), 5.588-5.619 (m, 1H), 5.156-5.184 (t, 1H), 4.479-4.504 (m, 2H), 3.529-3.570 (m, 1H), 3.283-3.323 (m, 1H), 3.168-3.195 (m, 1H), 3.055-3.109 (m, 1H), 2.369-2.498 (m, 1H), 2.060-2.094 (m, 1H).

Example 257: (S)-(4-(2-chlorophenoxy)-2-(3-(5-(trifluoromethyl)pyridin-2-yloxy)pyrrolidin-1-yl) phenyl)methanol (Compound 1-224)

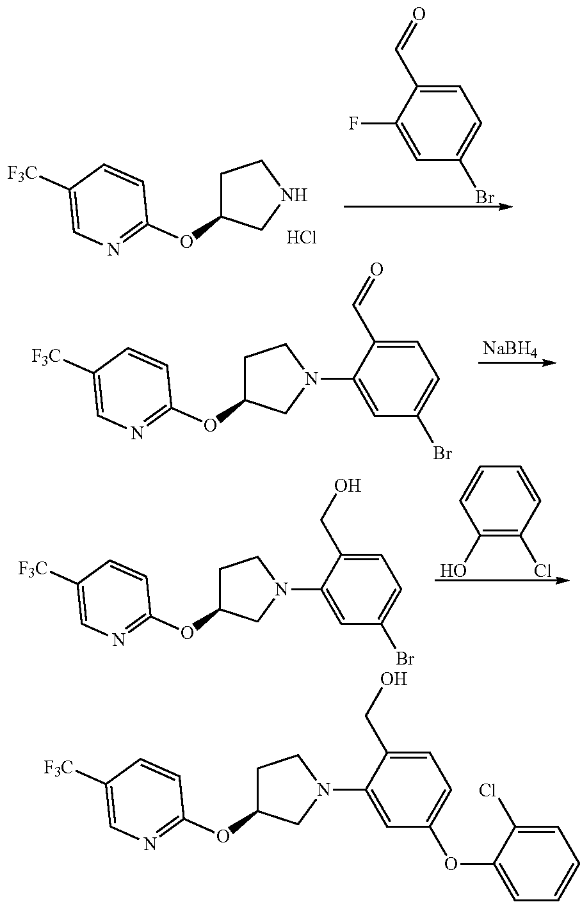

Step 1: (S)-4-bromo-2-(3-(5-(trifluoromethyl)pyridin-2-yloxy)pyrrolidin-1-yl)benzaldehyde

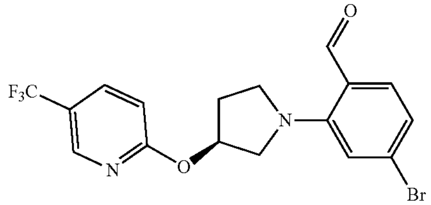 [SMILES: O=Cc1ccc(Br)cc1N1CC[C@H](Oc2ccc(C(F)(F)F)cn2)C1]

To a solution of (S)-2-(pyrrolidin-3-yloxy)-5-(trifluoromethyl)pyridine hydrochloride (2.0 g, 8.6 mmol) (prepared as intermediate 3) in 20 mL MeCN was added 4-bromo-2-fluorobenzaldehyde (2.1 g, 10.3 mmol) and DIPEA (5.7 mL, 34.5 mmol), and the mixture was heated to 90° C. for 2 h, removal the solvent, the residue was diluted with EA, washed by water, brine, dried over Na2SO4, removal the solvent to left the crude product which was purified by silica gel to give (S)-4-bromo-2-(3-(5-(trifluoromethyl)pyridin-2-yloxy)pyrrolidin-1-yl)benzaldehyde (2.4 g, 67% yield) as yellow solid, Mass spec: 415 (M+H).

Step 2: (S)-(4-bromo-2-(3-(5-(trifluoromethyl)pyridin-2-yloxy)pyrrolidin-1-yl)phenyl)methanol

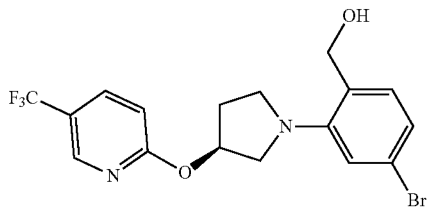 [SMILES: OCc1ccc(Br)cc1N1CC[C@H](Oc2ccc(C(F)(F)F)cn2)C1]

The title compound was prepared following procedures described in example 236 step 2 to give (S)-(4-bromo-2-(3-(5-(trifluoromethyl)pyridin-2-yloxy)pyrrolidin-1-yl)phenyl) methanol (1.4 g, quant.), Mass spec: 417 (M+H), Step 3: (S)-(4-(2-chlorophenoxy)-2-(3-(5-(trifluoromethyl)pyridin-2-yloxy)pyrrolidin-1-yl)phenyl) methanol

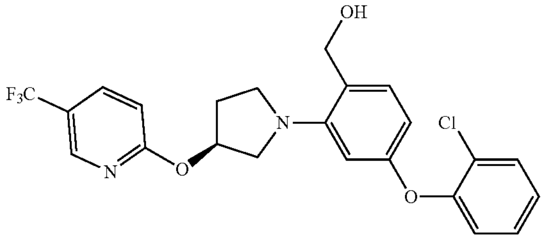 [SMILES: OCc1ccc(Oc2ccccc2Cl)cc1N1CC[C@H](Oc2ccc(C(F)(F)F)cn2)C1]

The title compound was prepared following procedures described in example 236 step 3 to give (S)-(4-(2-chlorophenoxy)-2-(3-(5-(trifluoromethyl)pyridin-2-yloxy)pyrrolidin-1-yl)phenyl) methanol (35 mg, 37.7% yield), Mass spec: 465 (M+H), $t_R$=3.294 min, $^1$H-NMR (400 Hz, DMSO) δ=8.610 (s, 1H), 8.063-8.092 (m, 1H), 7.568-7.591 (m, 1H), 7.165-7.360 (m, 3H), 7.018-7.053 (m, 2H), 6.463-6.468 (d, 1H), 6.303-6.329 (m, 1H), 5.620-5.630 (m, 1H), 5.078-5.082 (m, 1H), 4.462-4.478 (m, 2H), 3.700-3.741 (m, 1H), 3.386-3.436 (m, 2H), 3.218-3.262 (m, 1H), 2.316-2.365 (m, 1H), 2.095-2.134 (m, 1H).

Example 258: (S)-(4-(2-ethylphenoxy)-2-(3-(5-(trifluoromethyl)pyridin-2-yloxy)pyrrolidin-1-yl)phenyl) methanol (Compound 1-228)

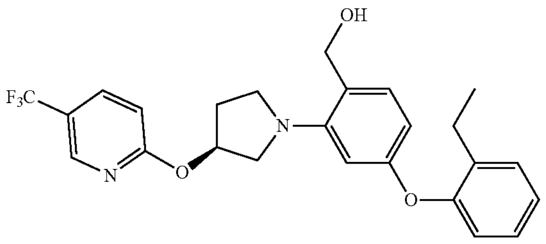 [SMILES: CCc1ccccc1Oc1ccc(CO)c(N2CC[C@H](Oc3ccc(C(F)(F)F)cn3)C2)c1]

The title compound was prepared following procedures described in example 257 step 3 to give (S)-(4-(2-ethylphenoxy)-2-(3-(5-(trifluoromethyl)pyridin-2-yloxy)pyrrolidin-1-yl)phenyl)methanol (30 mg, 27% yield), Mass spec: 459 (M+H), $t_R$=3.457 min, $^1$H-NMR (400 Hz, DMSO) δ=8.607 (s, 1H), 8.067-8.088 (m, 1H), 7.013-7.329 (m, 5H), 6.843-6.863 (m, 1H), 6.417 (s, 1H), 6.247-6.267 (d, 1H), 5.624 (br, 1H), 5.030-5.057 (t, 1H), 4.441-4.470 (m, 2H), 3.675-3.716 (m, 1H), 3.413-3.415 (m, 2H), 3.195-3.216 (m, 1H), 2.546-2.603 (m, 1H), 2.312-2.345 (m, 1H), 2.078-2.113 (m, 1H), 1.118-1.155 (t, 3H).

Example 259: (S)-(4-(o-tolyloxy)-2-(3-(5-(trifluoromethyl)pyridin-2-yloxy)pyrrolidin-1-yl)phenyl) methanol (Compound 1-230)

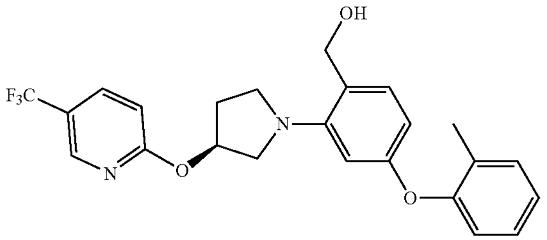 [SMILES: Cc1ccccc1Oc1ccc(CO)c(N2CC[C@H](Oc3ccc(C(F)(F)F)cn3)C2)c1]

The title compound was prepared following procedures described in example 257 step 3 to give (S)-(4-(o-tolyloxy)-2-(3-(5-(trifluoromethyl)pyridin-2-yloxy)pyrrolidin-1-yl) phenyl)methanol (60 mg, 55% yield), Mass spec: 445 (M+H), $t_R$=3.399 min, $^1$H-NMR (400 Hz, DMSO) δ=8.603 (s, 1H), 8.057-8.086 (m, 1H), 7.009-7.306 (m, 5H), 6.853-6.873 (d, 1H), 6.409-6.415 (d, 1H), 6.226-6.253 (q, 1H), 5.608-5.635 (m, 1H), 5.002-5.029 (t, 1H), 4.441-4.468 (m, 2H), 3.670-3.711 (m, 1H), 3.389-3.411 (m, 2H), 3.202-3.222 (m, 1H), 2.309-2.343 (m, 1H), 2.174 (m, 3H), 2.008-2.114 (m, 1H).

Example 260: (S)-(2-(3-(3-chloropyridin-2-yloxy) pyrrolidin-1-yl)-4-(o-tolyloxy)phenyl)methanol (Compound 1-241)

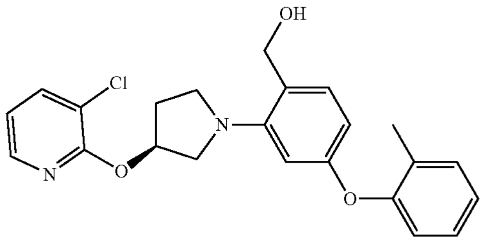 [SMILES: Cc1ccccc1Oc1ccc(CO)c(N2CC[C@H](Oc3ncccc3Cl)C2)c1]

The title compound was prepared following procedures described in example 257 to give (S)-(2-(3-(3-chloropyridin-2-yloxy)pyrrolidin-1-yl)-4-(o-tolyloxy)phenyl)methanol (30 mg, 28% yield), Mass spec: 411 (M+H), $t_R$=3.081 min, H-NMR (400 Hz, DMSO) δ=8.134-8.150 (m, 1H), 7.893-7.917 (m, 1H), 7.022-7.309 (m, 5H), 6.856-6.876 (d, 1H), 6.426-6.432 (d, 1H), 6.245-6.271 (q, 1H), 5.584-5.611 (m, 1H), 5.026-5.053 (t, 1H), 4.442-4.474 (m, 2H), 3.672-3.713 (m, 1H), 3.317-3.408 (m, 2H), 3.196-3.217 (m, 1H), 2.300-2.335 (m, 1H), 2.179 (m, 3H), 2.081-2.098 (m, 1H).

Example 261: (S)-(4-(2-chlorophenoxy)-2-(3-(3-chloropyridin-2-yloxy)pyrrolidin-1-yl)phenyl)methanol (Compound 1-232)

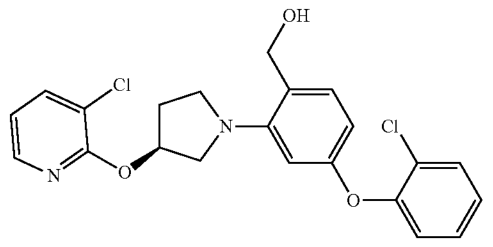 [SMILES: OCc1ccc(Oc2ccccc2Cl)cc1N1CC[C@H](Oc2ncccc2Cl)C1]

The title compound was prepared following procedures described in example 257 to give (S)-(4-(2-chlorophenoxy)-2-(3-(3-chloropyridin-2-yloxy)pyrrolidin-1-yl)phenyl) methanol (23 mg, 20% yield), Mass spec: 431 (M+H), $t_R$=3.105 min. $^1$H-NMR (400 Hz, DMSO) δ=8.135-8.152 (m, 1H), 7.894-7.918 (m, 1H), 7.566-7.590 (m, 1H), 7.288-7.358 (m, 2H), 7.161-7.204 (m, 1H), 7.023-7.055 (m, 2H), 6.480-6.487 (d, 1H), 6.320-6.346 (q, 1H), 5.593-5.619 (m, 1H), 5.069-5.089 (t, 1H), 4.432-4.518 (m, 2H), 3.696-3.737 (m, 1H), 3.370-3.450 (m, 2H), 3.202-3.254 (m, 1H), 2.278-2.354 (m, 1H), 2.075-2.116 (m, 1H).

Example 262: (S)-(2-(3-(3-chloropyridin-2-yloxy) pyrrolidin-1-yl)-4-(2-ethylphenoxy)phenyl)methanol (Compound 1-233)

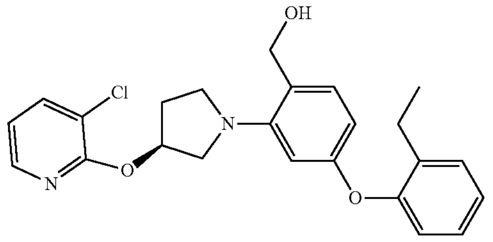 [SMILES: CCc1ccccc1Oc1ccc(CO)c(N2CC[C@H](Oc3ncccc3Cl)C2)c1]

The title compound was prepared following procedures described in example 257 to give (S)-(2-(3-(3-chloropyridin-2-yloxy)pyrrolidin-1-yl)-4-(2-ethylphenoxy)phenyl) methanol (40 mg, 36% yield), Mass spec: 425 (M+H), $t_R$=3.377 min, $^1$H-NMR (400 Hz, DMSO) δ=8.128-8.145 (m, 1H), 7.885-7.908 (m, 1H), 7.015-7.324 (m, 5H), 6.842-6.8608 (m, 1H), 6.427-6.433 (d, 1H), 6.262-6.288 (m, 1H), 5.582-5.608 (m, 1H), 5.008-5.034 (t, 1H), 4.444-4.475 (m, 2H), 3.672-3.713 (m, 1H), 3.316-3.404 (m, 2H), 3.182-3.213 (m, 1H), 2.547-2.603 (q, 2H), 2.297-2.345 (m, 1H), 2.079-2.095 (m, 1H), 1.117-1.155 (t, 3H).

Example 263: (S)-(2'-chloro-3-(3-(3-chloropyridin-2-yloxy)pyrrolidin-1-yl)biphenyl-4-yl)methanol (Compound 1-234)

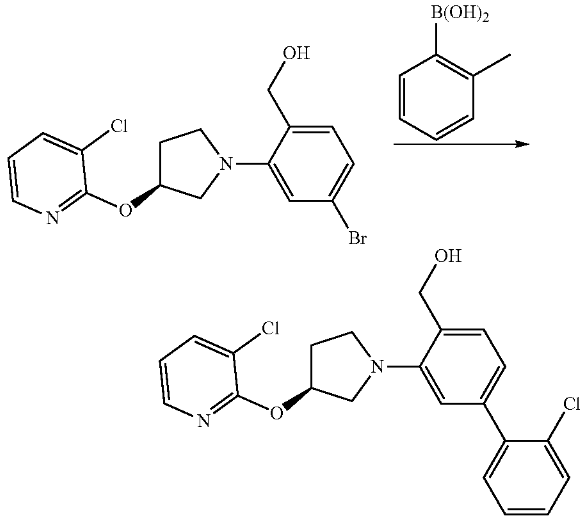

To a solution of (S)-(4-bromo-2-(3-(3-chloropyridin-2-yloxy)pyrrolidin-1-yl)phenyl)methanol (100 mg, 0.26 mol) (prepared as example 257 step 2) in 2 mL Dioxane/H2O (v:v=5:1) was added o-tolylboronic acid (61 mg, 0.39 mmol), K2CO3 (72 mg, 0.52 mmol) and Pd(dppf)Cl2 (10 mg, 10% wt), the mixture was heated to 90° C. for 2 h under N2, EA was added, washed by water, brine, dried over Na2SO4, removal the solvent to left the crude product which was purified by Prep-HPLC to give (S)-(2'-chloro-3-(3-(3-chloropyridin-2-yloxy)pyrrolidin-1-yl)biphenyl-4-yl) methanol (13.7 mg, 15% yield), Mass spec: 415 (M+H), $t_R$=3.083 min, H-NMR (400 Hz, DMSO) δ=8.135-8.147 (m, 1H), 7.885-7.904 (m, 1H), 7.363-7.535 (m, 5H), 7.030-7.049 (m, 1H), 6.892-6.948 (m, 2H), 5.609-5.622 (m, 1H), 5.141 (t, 1H), 4.505-4.605 (m, 2H), 3.681-3.695 (m, 1H), 3.420-3.461 (m, 1H), 3.321-3.345 (m, 1H), 2.234-3.266 (m, 1H), 2.331-2.414 (m, 1H), 2.080-2.113 (m, 1H).

Example 264: (S)-(3-(3-(3-chloropyridin-2-yloxy) pyrrolidin-1-yl)-2'-ethylbiphenyl-4-yl)methanol (Compound 1-229)

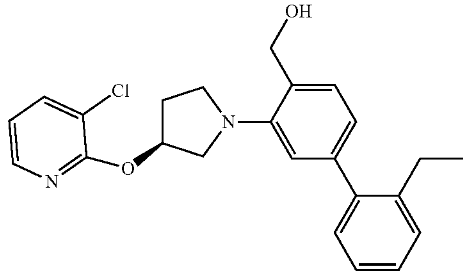 [SMILES: CCc1ccccc1-c1ccc(CO)c(N2CC[C@H](Oc3ncccc3Cl)C2)c1]

The title compound was prepared following procedures described in example 263 to give (S)-(3-(3-(3-chloropyridin-2-yloxy)pyrrolidin-1-yl)-2'-ethylbiphenyl-4-yl)methanol (30 mg, 28% yield), Mass spec: 409 (M+H), $t_R$=3.206 min, $^1$H-NMR (400 Hz, DMSO) δ=8.133-8.148 (m, 1H), 7.886-7.909 (m, 1H), 7.409-7.428 (d, 1H), 7.142-7.322 (m, 4H), 7.016-7.048 (m, 1H), 6.745-6.818 (m, 2H), 5.599-5.612 (m, 1H), 5.117-5.145 (t, 1H), 4.509-4.605 (m, 2H), 3.683-3.724 (m, 1H), 3.413-3.472 (m, 1H), 3.319-3.359 (m, 1H), 3.166-3.250 (m, 1H), 2.508-2.589 (q, 2H), 2.337-2.385 (m, 1H), 2.076-2.116 (m, 1H) 1.037-1.075 (t, 3H).

Example 265: (S)-(3-(3-(3-chloropyridin-2-yloxy) pyrrolidin-1-yl)-2'-methylbiphenyl-4-yl)methanol (Compound 1-240)

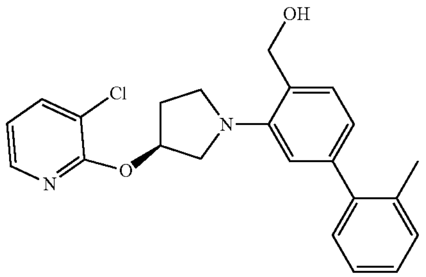 [SMILES: Cc1ccccc1-c1ccc(CO)c(N2CC[C@H](Oc3ncccc3Cl)C2)c1]

The title compound was prepared following procedures described in example 263 to give (S)-(3-(3-(3-chloropyridin-2-yloxy)pyrrolidin-1-yl)-2'-methylbiphenyl-4-yl) methanol (32 mg, 29% yield), Mass spec: 395 (M+H), $t_R$=3.193 min, $^1$H-NMR (400 Hz, DMSO) δ=8.133-8.149 (m, 1H), 7.886-8.133 (m, 1H), 7.410-7.430 (d, 1H), 7.180-7.287 (m, 4H), 7.016-7.048 (m, 1H), 6.774-6.854 (m, 2H), 5.597-5.626 (m, 1H), 5.113-5.141 (t, 1H), 4.536-4.565 (m, 2H), 3.676-3.717 (m, 1H), 3.414-3.451 (m, 1H), 3.317-3.327 (m, 1H), 3.212-3.254 (m, 1H), 2.342-2.391 (m, 1H), 2.241 (s, 3H), 2.072-2.107 (m, 1H).

Example 266: (S)-(2'-methyl-3-(3-(5-(trifluoromethyl)pyridin-2-yloxy)pyrrolidin-1-yl)biphenyl-4-yl) methanol (Compound 1-239)

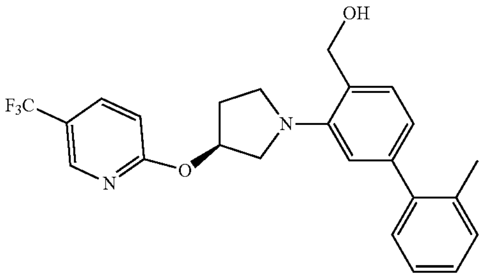 [SMILES: Cc1ccccc1-c1ccc(CO)c(N2CC[C@H](Oc3ccc(C(F)(F)F)cn3)C2)c1]

The title compound was prepared following procedures described in example 263 using (S)-(4-bromo-2-(3-(5-(trifluoromethyl)pyridin-2-yloxy)pyrrolidin-1-yl)phenyl)methanol (example 257 step 2) to give (S)-(2'-methyl-3-(3-(5-(trifluoromethyl)pyridin-2-yloxy)pyrrolidin-1-yl)biphenyl-4-yl)methanol (20 mg, 23% yield), Mass spec: 429 (M+H), $t_R$=3.254 min, H-NMR (400 Hz, DMSO) δ=8.602-8.603 (d, 1H), 8.054-8.082 (m, 1H), 7.404-7.424 (d, 1H), 7.180-7.287 (m, 4H), 7.014-7.035 (d, 1H), 6.826-6.848 (m, 1H), 6.753-6.756 (d, 1H), 5.621-5.649 (m, 1H), 5.099-5.128 (t, 1H), 4.539-4.562 (m, 2H), 3.67-3.718 (m, 1H), 3.414-3.456 (m, 1H), 3.322-3.345 (m, 1H), 3.212-3.243 (m, 1H), 2.240-2.401 (m, 1H), 2.118 (s, 3H), 2.084-2.101 (m, 1H).

Example 267: (S)-(2'-ethyl-3-(3-(5-(trifluoromethyl) pyridin-2-yloxy)pyrrolidin-1-yl)biphenyl-4-yl) methanol (Compound 1-227)

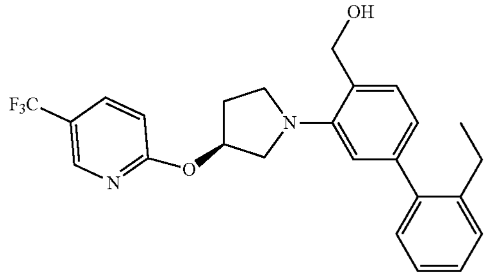 [SMILES: CCc1ccccc1-c1ccc(CO)c(N2CC[C@H](Oc3ccc(C(F)(F)F)cn3)C2)c1]

The title compound was prepared following procedures described in example 263 using (S)-(4-bromo-2-(3-(5-(trifluoromethyl)pyridin-2-yloxy)pyrrolidin-1-yl)phenyl)methanol (example 257 step 2) to give (S)-(2'-ethyl-3-(3-(5-(trifluoromethyl)pyridin-2-yloxy)pyrrolidin-1-yl)biphenyl-4-yl)methanol (53 mg, 50% yield), Mass spec: 443 (M+H), $t_R$=3.419 min, $^1$H-NMR (400 Hz, DMSO) δ=8.606 (s, 1H), 8.062-8.084 (d, 1H), 7.401-7.421 (d, 1H), 7.142-7.324 (m, 4H), 7.017-7.038 (d, 1H), 6.794-6.812 (d, 1H), 6.718 (s, 1H), 5.636 (br, 1H), 5.123-5.150 (t, 1H), 4.541-4.565 (m, 2H), 3.679-3.720 (m, 1H), 3.412-3.452 (m, 1H), 3.339-3.362 (m, 1H), 3.220-3.252 (m, 1H), 2.530-2.587 (q, 2H), 2.351-2.402 (m, 1H), 2.087-2.121 (m, 1H), 1.039-1.076 (t, 3H).

Example 268: (S)-(2'-chloro-3-(3-(5-(trifluoromethyl)pyridin-2-yloxy)pyrrolidin-1-yl)biphenyl-4-yl) methanol (Compound 1-225)

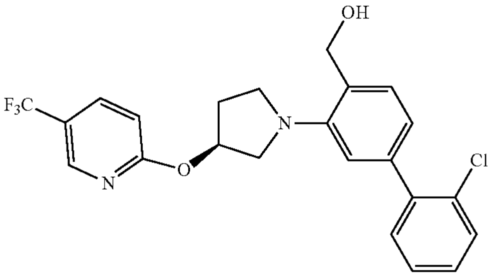 [SMILES: OCc1ccc(-c2ccccc2Cl)cc1N1CC[C@H](Oc2ccc(C(F)(F)F)cn2)C1]

The title compound was prepared following procedures described in example 263 using (S)-(4-bromo-2-(3-(5-(trifluoromethyl)pyridin-2-yloxy)pyrrolidin-1-yl)phenyl)methanol (example 257 step 2) to give (S)-(2'-chloro-3-(3-(5-(trifluoromethyl)pyridin-2-yloxy)pyrrolidin-1-yl)biphenyl-4-yl)methanol (53 mg, 50% yield), Mass spec: 449 (M+H), $t_R$=3.299 min, $^1$H-NMR (400 Hz, DMSO) δ=8.612 (s, 1H), 8.067-8.088 (d, 1H), 7.538-7.555 (m, 1H), 7.389-7.454 (m, 4H), 7.022-7.044 (d, 1H), 6.929-6.946 (d, 1H), 6.865 (s, 1H), 5.645 (br, 1H), 5.143-5.170 (t, 1H), 4.543-4.568 (m, 2H), 3.690-3.731 (m, 1H), 3.446-3.466 (m, 1H), 3.332-3.354 (m, 1H), 3.236-3.247 (m, 1H), 2.373-2.391 (m, 1H), 2.111-2.132 (m, 1H).

Example 269: (S)-(3-(3-(5-(trifluoromethyl)pyridin-2-yloxy)pyrrolidin-1-yl)biphenyl-4-yl)methanol (Compound 1-180)

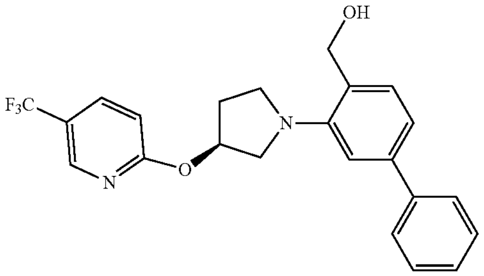 [SMILES: OCc1ccc(-c2ccccc2)cc1N1CC[C@H](Oc2ccc(C(F)(F)F)cn2)C1]

The title compound was prepared following procedures described in example 263 using (S)-(4-bromo-2-(3-(5-(trifluoromethyl)pyridin-2-yloxy)pyrrolidin-1-yl)phenyl)methanol (example 257 step 2) to give (S)-(3-(3-(5-(trifluoromethyl)pyridin-2-yloxy)pyrrolidin-1-yl)biphenyl-4-yl) methanol (100 mg, 67% yield), Mass spec: 415 (M+H), $t_R$=3.302. $^1$H-NMR (400 Hz, DMSO) δ=8.622 (s, 1H), 8.090-8.074 (m, 1H), 7.655-7.636 (m, 2H), 7.459-7.425 (m, 1H), 7.362-7.324 (m, 1H), 7.167-7.035 (m, 3H), 5.546 (s, 1H), 5.165-5.139 (m, 1H), 4.581-4.493 (m, 2H), 3.761-3.747 (m, 1H), 3.520-3.445 (m, 2H), 3.288-3.267 (m, 1H), 2.427 (m, 1H), 2.147-2.110 (m, 1H).

Example 270: (S)-(2'-ethyl-4-(3-(5-(trifluoromethyl)pyridin-2-yloxy)pyrrolidin-1-yl)biphenyl-3-yl)methanol (Compound 1-149)

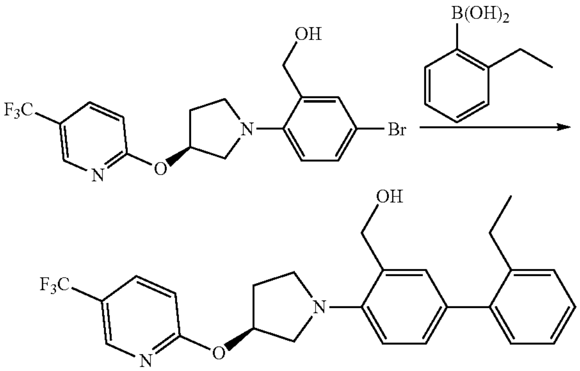

To a solution of (S)-(5-bromo-2-(3-(5-(trifluoromethyl)pyridin-2-yloxy)pyrrolidin-1-yl)phenyl)methanol (200 mg, 0.48 mol) (prepared as example 236 step 2) in 6 mL Dioxane/H2O (v:v=5:1) was added 2-ethylphenylboronic acid (84.6 mg, 0.576 mmol), K2CO3 (132.45 mg, 0.96 mmol) and Pd(dppf)Cl2 (20 mg, 10% wt), the mixture was heated to 100° C. for 1.5 h under N2, EA was added, washed by water, brine, dried over Na2SO4, removal the solvent to left the crude product which was purified by Prep-HPLC to give (S)-(2'-ethyl-4-(3-(5-(trifluoromethyl)pyridin-2-yloxy)pyrrolidin-1-yl)biphenyl-3-yl)methanol (100 mg, 47% yield), Mass spec: 443 (M+H), $t_R$=3.565 min, $^1$H-NMR (400 Hz, DMSO) δ=8.591 (s, 1H), 8.042-8.063 (m, 1H), 7.183-7.299 (m, 4H), 7.008-7.107 (m, 3H), 6.891-6.911 (m, 1H), 5.632-5.637 (m, 1H), 5.092 (br, 1H), 4.531 (m, 2H), 3.685-3.713 (m, 1H), 3.427-3.447 (m, 1H), 3.187-3.238 (m, 1H), 2.481-2.575 (q, 2H), 2.361-2.378 (m, 1H), 2.113-2.118 (m, 1H), 1.005-1.042 (t, 3H).

Example 271: (S)-(2'-fluoro-4-(3-(5-(trifluoromethyl)pyridin-2-yloxy)pyrrolidin-1-yl)biphenyl-3-yl) methanol (Compound 1-150)

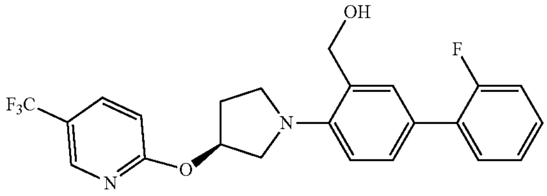 [SMILES: OCc1cc(-c2ccccc2F)ccc1N1CC[C@H](Oc2ccc(C(F)(F)F)cn2)C1]

The title compound was prepared following procedures described in example 270 to give (S)-(2'-fluoro-4-(3-(5-(trifluoromethyl)pyridin-2-yloxy)pyrrolidin-1-yl)biphenyl-3-yl)methanol (53 mg, 50% yield), Mass spec: 433 (M+H), $t_R$=3.327 min, $^1$H-NMR (400 Hz, DMSO) δ=8.598 (s, 1H), 8.042-8.070 (d, 1H), 7.545 (s, 1H), 7.221-7.473 (m, 5H), 7.010-7.032 (d, 1H), 6.910-6.931 (d, 1H), 5.633-5.646 (m, 1H), 5.103-5.131 (t, 1H), 4.521-4.511 (m, 2H), 3.715-3.755 (m, 1H), 3.355-3.481 (m, 3H), 2.338-2.387 (m, 1H), 2.100-2.134 (m, 1H).

Example 272: (S)-(2'-methoxy-4-(3-(5-(trifluoromethyl)pyridin-2-yloxy)pyrrolidin-1-yl)biphenyl-3-yl) methanol (Compound 1-151)

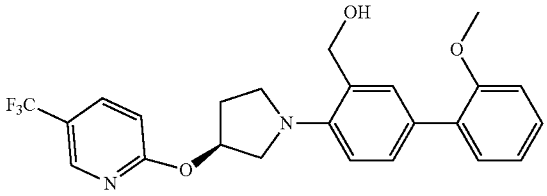 [SMILES: COc1ccccc1-c1ccc(N2CC[C@H](Oc3ccc(C(F)(F)F)cn3)C2)c(CO)c1]

The title compound was prepared following procedures described in example 270 to give (S)-(2'-methoxy-4-(3-(5-(trifluoromethyl)pyridin-2-yloxy)pyrrolidin-1-yl)biphenyl-3-yl)methanol (130 mg, 65% yield), Mass spec: 445 (M+H), $t_R$=3.338 min, $^1$H-NMR (400 Hz, DMSO) δ=8.619 (s, 1H), 8.062-8.091 (d, 1H), 7.494-7.499 (d, 1H), 7.235-7.305 (m, 3H), 6.981-7.081 (m, 3H), 6.891-6.913 (d, 1H), 5.639-5.666 (m, 1H), 5.082-5.110 (t, 1H), 4.535-4.560 (m, 2H), 3.750 (s, 1H), 3.690-3.731 (m, 1H), 3.422-3.460 (m, 1H), 3.173-3.337 (m, 2H), 2.367-2.417 (m, 1H), 2.105-2.136 (m, 1H).

Example 273: (S)-(2'-(trifluoromethyl)-4-(3-(5-(trifluoromethyl)pyridin-2-yloxy)pyrrolidin-1-yl)biphenyl-3-yl)methanol (Compound 1-152)

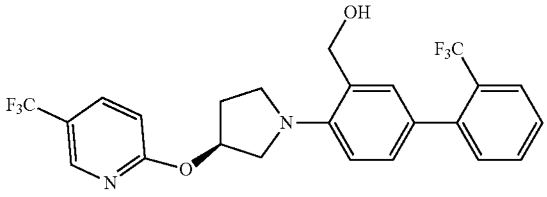 [SMILES: OCc1cc(-c2ccccc2C(F)(F)F)ccc1N1CC[C@H](Oc2ccc(C(F)(F)F)cn2)C1]

The title compound was prepared following procedures described in example 270 to give (S)-(2'-(trifluoromethyl)-4-(3-(5-(trifluoromethyl)pyridin-2-yloxy)pyrrolidin-1-yl)biphenyl-3-yl)methanol (80 mg, 46% yield), Mass spec: 483 (M+H), $t_R$=3.466 min, $^1$H-NMR (400 Hz, DMSO) δ=8.591-8.595 (t, 1H), 8.041-8.069 (m, 1H), 7.515-7.783 (m, 3H), 7.312-7.354 (m, 2H), 7.014-7.089 (m, 2H), 6.867-6.888 (d, 1H), 5.632-5.659 (m, 1H), 5.096-5.122 (t, 1H), 4.512-4.543 (m, 2H), 3.715-3.755 (m, 1H), 3.440-3.481 (m, 2H), 3.241-3.284 (m, 1H), 2.342-2.473 (m, 1H), 2.100-2.133 (m, 1H).

Example 274: (S)-(2'-(methoxymethyl)-4-(3-(5-(trifluoromethyl)pyridin-2-yloxy)pyrrolidin-1-yl)biphenyl-3-yl)methanol (Compound 1-160)

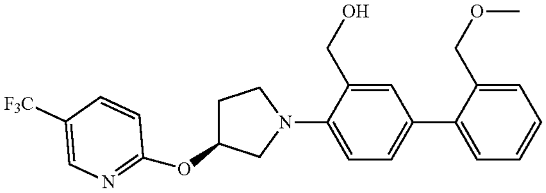 [SMILES: COCc1ccccc1-c1ccc(N2CC[C@H](Oc3ccc(C(F)(F)F)cn3)C2)c(CO)c1]

The title compound was prepared following procedures described in example 270 to give (S)-(2'-(methoxymethyl)-4-(3-(5-(trifluoromethyl)pyridin-2-yloxy)pyrrolidin-1-yl)biphenyl-3-yl)methanol (20 mg, 18% yield), Mass spec: 459 (M+H), $t_R$=3.190 min, $^1$H-NMR (400 Hz, DMSO) δ=8.622-8.628 (t, 1H), 8.073-8.100 (m, 1H), 7.160-7.485 (m, 6H), 7.039-7.061 (d, 1H), 6.910-6.931 (d, 1H), 5.667 (m, 1H), 5.110-5.137 (t, 1H), 4.543-4.570 (m, 2H), 4.315 (s, 2H), 3.746-3.761 (m, 1H), 3.399-3.480 (m, 2H), 3.277-3.346 (m, 1H), 3.263 (s, 3H), 2.342-2.473 (m, 1H), 2.100-2.133 (m, 1H).

Example 275: (S)-(2'-(trifluoromethoxy)-4-(3-(5-(trifluoromethyl)pyridin-2-yloxy)pyrrolidin-1-yl)biphenyl-3-yl)methanol (Compound 1-161)

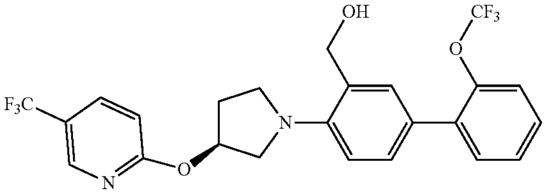 [SMILES: OCc1cc(-c2ccccc2OC(F)(F)F)ccc1N1CC[C@H](Oc2ccc(C(F)(F)F)cn2)C1]

The title compound was prepared following procedures described in example 270 to give (S)-(2'-(trifluoromethoxy)-4-(3-(5-(trifluoromethyl)pyridin-2-yloxy)pyrrolidin-1-yl)biphenyl-3-yl)methanol (80 mg, 66% yield), Mass spec: 499 (M+H), $t_R$=3.472 min, $^1$H-NMR (400 Hz, DMSO) δ=8.592 (t, 1H), 8.039-8.067 (m, 1H), 7.413-7.469 (m, 5H), 7.235-7.261 (m, 1H), 7.010-7.031 (d, 1H), 6.882-6.904 (d, 1H), 5.641 (br, 1H), 5.148-5.175 (t, 1H), 4.512-4.545 (m, 2H), 3.731-3.771 (m, 1H), 3.472-3.494 (m, 2H), 3.268-3.279 (m, 1H), 2.342-2.473 (m, 1H), 2.120-2.133 (m, 1H).

Example 276: (S)-(4-(3-(5-(trifluoromethyl)pyridin-2-yloxy)pyrrolidin-1-yl)biphenyl-3-yl)methanol (Compound 1-115)

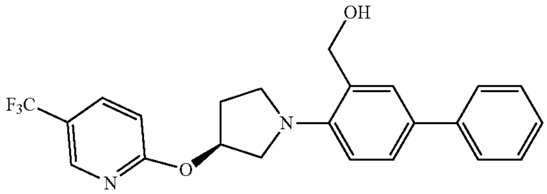 [SMILES: OCc1cc(-c2ccccc2)ccc1N1CC[C@H](Oc2ccc(C(F)(F)F)cn2)C1]

The title compound was prepared following procedures described in example 270 to give (S)-(4-(3-(5-(trifluoromethyl)pyridin-2-yloxy)pyrrolidin-1-yl)biphenyl-3-yl)methanol (1.2 g, 79% yield), Mass spec: 415 (M+H), $t_R$=2.795 min, H-NMR (400 Hz, DMSO) δ=8.590 (s, 1H), 8.033-8.060 (m, 1H), 7.560-7.656 (m, 3H), 7.235-7.440 (m, 4H), 6.906-7.024 (m, 2H), 5.621-5.647 (m, 1H), 5.109-5.137 (t, 1H), 4.535-4.563 (m, 2H), 3.689-3.730 (m, 1H), 3.420-3.462 (m, 1H), 3.208-3.260 (m, 1H), 2.337-2.387 (m, 1H), 2.088-2.129 (m, 1H).

Example 277: (S)-3'-(hydroxymethyl)-4'-(3-(5-(trifluoromethyl)pyridin-2-yloxy)pyrrolidin-1-yl)biphenyl-4-carbonitrile (Compound 1-252)

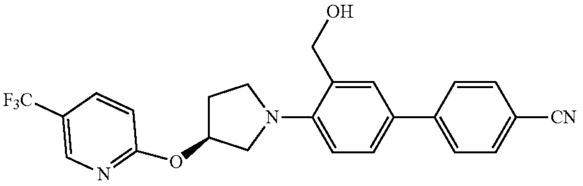 [SMILES: N#Cc1ccc(-c2ccc(N3CC[C@H](Oc4ccc(C(F)(F)F)cn4)C3)c(CO)c2)cc1]

The title compound was prepared following procedures described in example 270 to give (S)-3'-(hydroxymethyl)-4'-(3-(5-(trifluoromethyl)pyridin-2-yloxy)pyrrolidin-1-yl)biphenyl-4-carbonitrile (500 mg, 80% yield), Mass spec: 440 (M+H), $t_R$=3.534. $^1$H-NMR (400 Hz, DMSO) δ=8.504 (s, 1H), 7.964-7.942 (m, 1H), 7.814-7.756 (m, 5H), 7.577-7.550 (m, 1H), 7.063-7.042 (m, 1H), 6.976-6.953 (m, 1H), 5.745 (s, 1H), 4.796-4.725 (m, 3H), 3.849-3.820 (m, 1H), 3.622-3.331 (m, 3H), 2.466-2.265 (m, 2H).

Example 278: (S)-3'-(hydroxymethyl)-4'-(3-(5-(trifluoromethyl)pyridin-2-yloxy)pyrrolidin-1-yl)biphenyl-4-carboxamide (Compound 1-253)

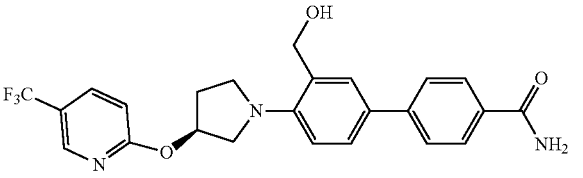 [SMILES: NC(=O)c1ccc(-c2ccc(N3CC[C@H](Oc4ccc(C(F)(F)F)cn4)C3)c(CO)c2)cc1]

The title compound was prepared following procedures described in example 6 from example 277 to give (S)-3'-(hydroxymethyl)-4'-(3-(5-(trifluoromethyl)pyridin-2-yloxy)

pyrrolidin-1-yl)biphenyl-4-carbonitrile (30 mg, 28% yield), Mass spec: 458 (M+H), $t_R$=3.832. $^1$H-NMR (400 Hz, DMSO) δ=8.509 (s, 1H), 7.970-7.927 (m, 3H), 7.765-7.715 (m, 3H), 7.569-7.548 (m, 1H), 7.085-7.064 (m, 1H), 6.984-6.963 (m, 1H), 5.741-5.721 (m, 1H), 4.941-4.768 (m, 3H), 3.813-3.786 (m, 1H), 3.595-3.303 (m, 3H), 2.496-2.447 (m, 1H), 2.248-2.232 (m, 1H).

Example 279: (S)-(4-(3-(5-(trifluoromethyl)pyridin-2-yloxy)pyrrolidin-1-yl)biphenyl-3,4'-diyl)dimethanol (Compound 1-261)

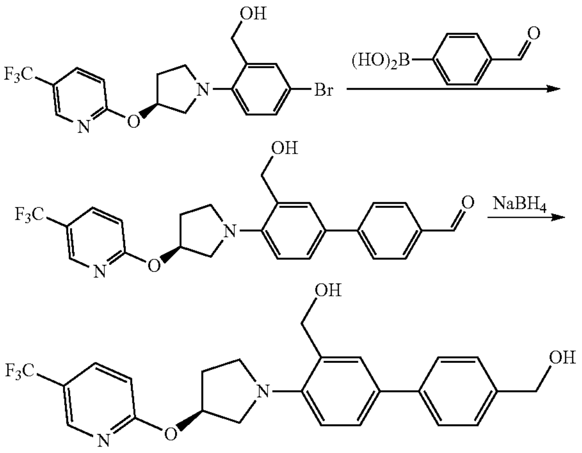

Step 1: (S)-3'-(hydroxymethyl)-4'-(3-(5-(trifluoromethyl)pyridin-2-yloxy)pyrrolidin-1-yl)biphenyl-4-carbaldehyde

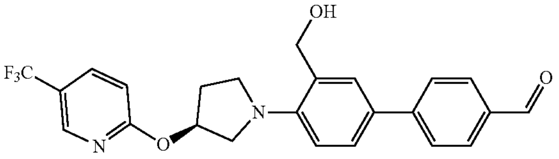 [SMILES: O=Cc1ccc(-c2ccc(N3CC[C@H](Oc4ccc(C(F)(F)F)cn4)C3)c(CO)c2)cc1]

The title compound was prepared following procedures described in example 270 to give (S)-3'-(hydroxymethyl)-4'-(3-(5-(trifluoromethyl)pyridin-2-yloxy)pyrrolidin-1-yl)biphenyl-4-carbaldehyde (200 mg, 95% yield), Mass spec: 443 (M+H).

Step 2: (S)-(4-(3-(5-(trifluoromethyl)pyridin-2-yloxy)pyrrolidin-1-yl)biphenyl-3,4'-diyl)dimethanol

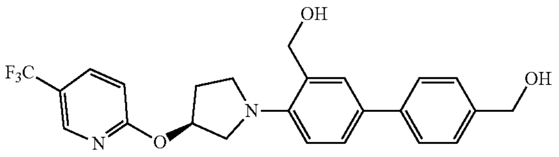 [SMILES: OCc1ccc(-c2ccc(N3CC[C@H](Oc4ccc(C(F)(F)F)cn4)C3)c(CO)c2)cc1]

To a solution of (S)-3'-(hydroxymethyl)-4'-(3-(5-(trifluoromethyl)pyridin-2-yloxy)pyrrolidin-1-yl)biphenyl-4-carbaldehyde (100 mg, 0.23 mmol) in 2 mL MeOH was added NaBH4 (22 mg, 0.58 mmol), the mixture was stirred at rt for 10 min, quenched by NH4Cl solution, diluted with EA, washed by water, brine, dried over Na2SO4, removal the solvent to left the crude product which was purified by Prep-HPLC to give (S)-(4-(3-(5-(trifluoromethyl)pyridin-2-yloxy)pyrrolidin-1-yl)biphenyl-3,4'-diyl)dimethanol (40 mg, 40% yield), Mass spec: 445 (M+H), $t_R$=2.710. $^1$H-NMR (400 Hz, DMSO) δ=8.501 (s, 1H), 7.932-7.961 (m, 1H), 7.695-7.701 (d, 1H), 7.586-7.607 (m, 2H), 7.397-7.497 (m, 3H), 7.057-7.078 (d, 1H), 6.953-6.975 (d, 1H), 5.701-5.715 (m, 1H), 4.757 (s, 2H), 4.642 (s, 2H), 3.714-3.755 (m, 1H), 3.494-3.514 (m, 1H), 3.375-3.407 (m, 1H), 3.288-3.325 (m, 1H), 2.443-2.477 (m, 1H), 2.201-2.231 (m, 1H).

Example 280: (S)-(4-(3-(5-chloropyridin-2-yloxy)pyrrolidin-1-yl)biphenyl-3-yl)methanol (Compound 1-147)

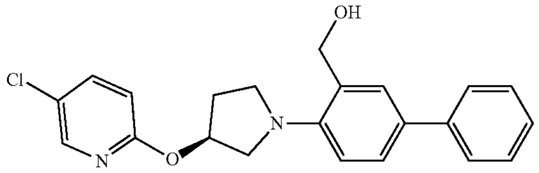 [SMILES: OCc1cc(-c2ccccc2)ccc1N1CC[C@H](Oc2ccc(Cl)cn2)C1]

The title compound was prepared following procedures described in example 270 to give (S)-(4-(3-(5-chloropyridin-2-yloxy)pyrrolidin-1-yl)biphenyl-3-yl)methanol (25 mg, 30% yield), Mass spec: 381 (M+H), $t_R$=3.009, $^1$H-NMR (400 Hz, DMSO) δ=8.240-8.247 (d, 1H), 7.803-7.833 (m, 1H), 7.589-7.677 (m, 3H), 7.409-7.447 (m, 4H), 6.890-6.948 (m, 2H), 5.540 (br, 1H), 5.159-5.187 (t, 1H), 4.552-4.581 (m, 2H), 3.689-3.716 (m, 1H), 3.417-3.472 (m, 1H), 3.244-3.376 (m, 2H), 2.331-2.365 (m, 3H), 2.091-2.117 (m, 2H).

Example 281: (S)-4'-(3-(5-chloropyridin-2-yloxy)pyrrolidin-1-yl)-3'-(hydroxymethyl)biphenyl-2-carbonitrile (Compound 1-155)

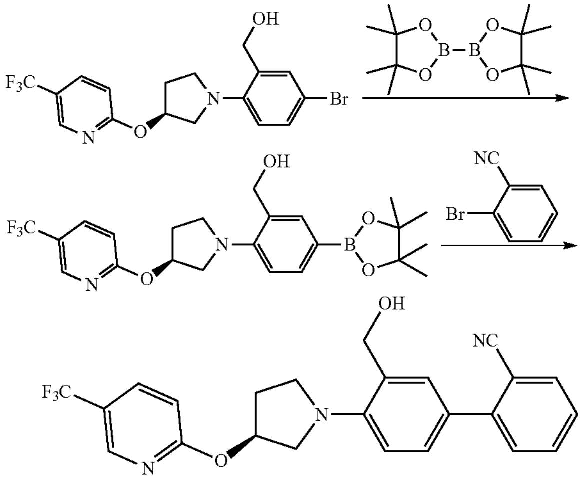

Step 1: (S)-(5-(4,4,5,5-tetramethyl-1,3,2-dioxaborolan-2-yl)-2-(3-(5-(trifluoromethyl)pyridin-2-yloxy)pyrrolidin-1-yl)phenyl)methanol

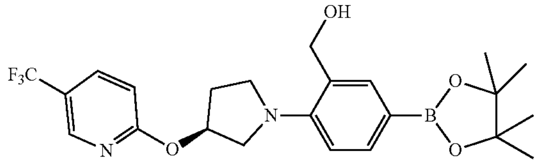 [SMILES: CC1(C)OB(c2ccc(N3CC[C@H](Oc4ccc(C(F)(F)F)cn4)C3)c(CO)c2)OC1(C)C]

To a solution of (S)-(5-bromo-2-(3-(5-(trifluoromethyl)pyridin-2-yloxy)pyrrolidin-1-yl)phenyl)methanol (100 mg, 1.24 mmol) (prepared as example 236 step 2) in 4 mL Dioxane was added 4,4,4',4',5,5,5',5'-octamethyl-2,2'-bi(1,3,2-dioxaborolane) (182 mg, 0.71 mmol). K2CO3 (70 mg, 0.79 mmol) and Pd(dppf)Cl2 (20 mg, 20% Wt.), the mixture was stirred at 110° C. for 5 h, EA was added, washed by water, brine, dried over Na2SO4, removal the solvent to left the crude product (130 mg, 116% yield) which can be used to next step directly without further purification, Mass spec: 465 (M+H).

Step 2: (S)-4'-(3-(5-chloropyridin-2-yloxy)pyrrolidin-1-yl)-3'-(hydroxymethyl)biphenyl-2-carbonitrile

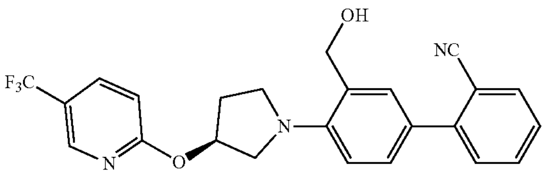 [SMILES: N#Cc1ccccc1-c1ccc(N2CC[C@H](Oc3ccc(C(F)(F)F)cn3)C2)c(CO)c1]

The title compound was prepared following procedures described in example 270 to give (S)-4'-(3-(5-chloropyridin-2-yloxy)pyrrolidin-1-yl)-3'-(hydroxymethyl)biphenyl-2-carbonitrile (20 mg, 19% yield), Mass spec: 440 (M+H), $t_R$=3.059, $^1$H-NMR (400 Hz, DMSO) δ=8.629 (s, 1H), 8.070-8.088 (q, 1H), 7.891-7.910 (m, 1H), 7.732-7.773 (m, 1H), 7.395-7.582 (m, 4H), 6.947-7.063 (m, 2H), 5.681-5.687 (m, 1H), 5.188-5.215 (t, 1H), 4.564-4.598 (m, 2H), 3.809-3.850 (m, 1H), 3.442-3.560 (m, 2H), 3.345-3.568 (m, 1H), 2.374-2.394 (m, 1H), 2.157-2.173 (m, 1H).

Example 282: (S)-1-(3'-(hydroxymethyl)-4'-(3-(5-(trifluoromethyl)pyridin-2-yloxy)pyrrolidin-1-yl)biphenyl-2-yl)ethanone (Compound 1-157)

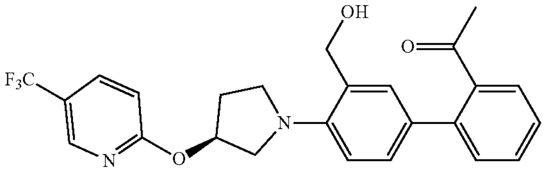

The title compound was prepared following procedures described in example 270 to give (S)-1-(3'-(hydroxymethyl)-4'-(3-(5-(trifluoromethyl)pyridin-2-yloxy)pyrrolidin-1-yl)biphenyl-2-yl)ethanone (30 mg, 31% yield), Mass spec: 457 (M+H), $t_R$=3.027, $^1$H-NMR (400 Hz, DMSO) δ=8.597 (s, 1H), 8.043-8.071 (q, 1H), 7.299-7.525 (m, 5H), 7.011-7.066 (m, 2H), 6.878-6.900 (m, 1H), 5.643 (br, 1H), 5.132-5.158 (t, 1H), 4.503-4.536 (m, 2H), 3.729 (m, 1H), 3.378-3.484 (m, 2H), 3.254-3.265 (m, 1H), 2.314-2.368 (m, 1H), 2.100-2.140 (m, 1H), 2.036 (s, 3H).

Example 283: 1-(3'-(hydroxymethyl)-4'-((S)-3-(5-(trifluoromethyl)pyridin-2-yloxy)pyrrolidin-1-yl)biphenyl-2-yl)ethanol (Compound 1-171)

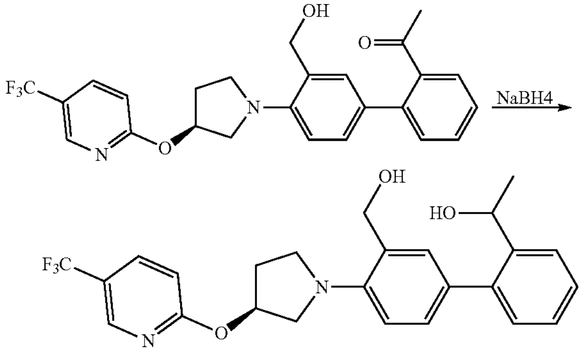

The title compound was prepared following procedures described in example 279 step 2 to give 1-(3'-(hydroxymethyl)-4'-((S)-3-(5-(trifluoromethyl)pyridin-2-yloxy)pyrrolidin-1-yl)biphenyl-2-yl)ethanol (30 mg, 30% yield), Mass spec: 457 (M+H), $t_R$=2.928, $^1$H-NMR (400 Hz, DMSO) δ=8.625 (s, 1H), 8.075-8.101 (q, 1H), 7.603-7.622 (d, 1H), 7.234-7.362 (m, 3H), 7.044-7.106 (m, 3H), 6.920-6.941 (m, 1H), 5.665-5.677 (m, 1H), 5.123-5.149 (t, 1H), 4.991-4.999 (d, 1H), 4.817-4.843 (m, 1H), 4.553 (m, 2H), 3.714-3.738 (m, 1H), 3.442-3.478 (m, 2H), 3.248-3.313 (m, 1H), 2.478-2.501 (m, 1H), 2.391-2.410 (m, 1H), 1.205-1.230 (s, 3H).

Example 284: 1-(4-((S)-3-(5-(trifluoromethyl)pyridin-2-yloxy)pyrrolidin-1-yl)biphenyl-3-yl)ethane-1,2-diol (Compound 1-148)

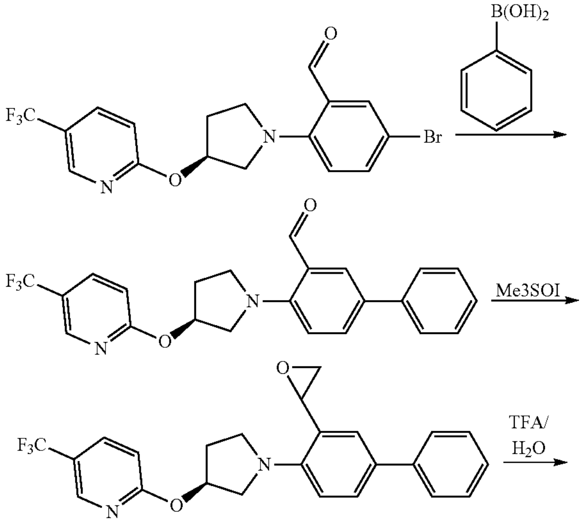

-continued

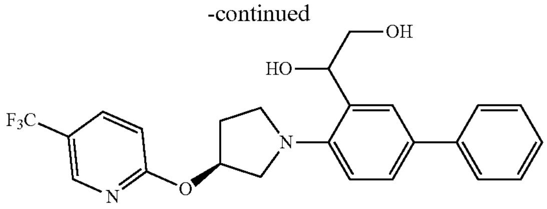

Step 1: (S)-4-(3-(5-(trifluoromethyl)pyridin-2-yloxy)pyrrolidin-1-yl)biphenyl-3-carbaldehyde

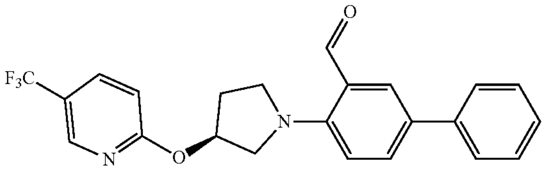 [SMILES: O=Cc1cc(-c2ccccc2)ccc1N1CC[C@H](Oc2ccc(C(F)(F)F)cn2)C1]

The title compound was prepared following procedures described in example 270 using (S)-5-bromo-2-(3-(5-(trifluoromethyl)pyridin-2-yloxy)pyrrolidin-1-yl)benzaldehyde (example 236 step 1) to give (S)-4-(3-(5-(trifluoromethyl)pyridin-2-yloxy)pyrrolidin-1-yl)biphenyl-3-carbaldehyde (900 mg, 90% yield), Mass spec: 413 (M+H).

Step 2: 2-((3S)-1-(3-(oxiran-2-yl)biphenyl-4-yl)pyrrolidin-3-yloxy)-5-(trifluoromethyl)pyridine

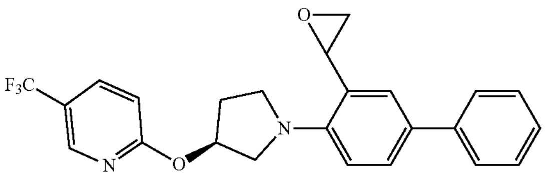 [SMILES: FC(F)(F)c1ccc(O[C@H]2CCN(c3ccc(-c4ccccc4)cc3C3CO3)C2)nc1]

To a solution of Me3SOI (321 mg, 1.45 mmol) in 3 mL DMSO was added NaH (34.9 mg, 1.45 mmol, 60% content) at 0° C., then allowed to return to rt for 30 min, before a solution of (S)-4-(3-(5-(trifluoromethyl)pyridin-2-yloxy)pyrrolidin-1-yl)biphenyl-3-carbaldehyde (300 mg, 0.727 mmol) in 1 mL DMSO was added. The mixture was stirred at rt for 2 h, EA was added, washed by water, brine, dried over Na2SO4, removal the solvent to left the crude product (240 mg) which can be used to next step directly.

Step 3: 1-(4-((S)-3-(5-(trifluoromethyl)pyridin-2-yloxy)pyrrolidin-1-yl)biphenyl-3-yl)ethane-1,2-diol

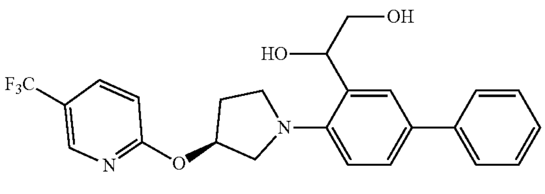 [SMILES: OCC(O)c1cc(-c2ccccc2)ccc1N1CC[C@H](Oc2ccc(C(F)(F)F)cn2)C1]

To a solution of 2-((3S)-1-(3-(oxiran-2-yl)biphenyl-4-yl)pyrrolidin-3-yloxy)-5-(trifluoromethyl)pyridine (200 mg, crude) in 4 mL DCM/H2O (v:v=1:1) was added TFA (1.5 mL) slowly, the mixture was stirred at rt for overnight, diluted with DCM, adjust the pH with naHCO3 to 7, the organic layer was washed by water, brine, dried over Na2SO4, removal the solvent to left the crude product which was purified by Prep-HPLC to give 1-(4-((S)-3-(5-(trifluoromethyl)pyridin-2-yloxy)pyrrolidin-1-yl)biphenyl-3-yl)ethane-1,2-diol (13 mg, ~14% yield), Mass spec: 445 (M+H), $t_R$=2.775, $^1$H-NMR (400 Hz, DMSO) δ=8.591 (s, 1H), 8.041-8.591 (m, 1H), 7.658-7.687 (m, 1H), 7.560-7.581 (m, 2H), 7.390-7.492 (m, 3H), 7.280-7.297 (m, 1H), 7.011-7.115 (m, 2H), 5.617-5.639 (m, 1H), 5.128-5.182 (m, 1H), 4.971-4.990 (m, 1H), 4.713-4.771 (m, 1H), 3.397-3.686 (m, 4H), 3.134-3.285 (m, 2H), 2.383-2.408 (m, 1H), 2.075-2.095 (m, 1H).

Example 285: (S)-2-hydroxy-1-(4-(3-(5-(trifluoromethyl)pyridin-2-yloxy)pyrrolidin-1-yl)biphenyl-3-yl)ethanone (Compound 1-178)

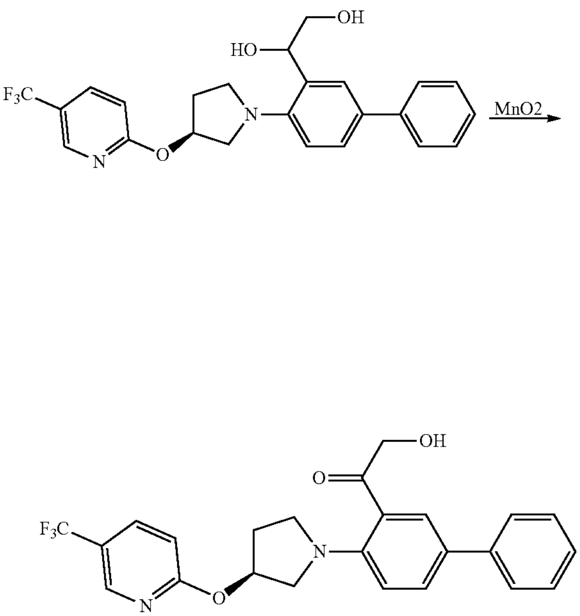

To a solution of 1-(4-((S)-3-(5-(trifluoromethyl)pyridin-2-yloxy)pyrrolidin-1-yl)biphenyl-3-yl)ethane-1,2-diol (130 mg, 0.3 mmol) in 4 mL DCM was added MnO2 (261 mg, 3 mmol), the mixture was stirred at rt for 4 h, filtered to remove the MnO2, the filtrate was concentrated to left the crude product which was purified by Prep-HPLC to give (S)-2-hydroxy-1-(4-(3-(5-(trifluoromethyl)pyridin-2-yloxy)pyrrolidin-1-yl)biphenyl-3-yl)ethanone (30 mg, 22% yield), Mass spec: 443 (M+H), $t_R$=3.318, $^1$H-NMR (400 Hz, DMSO) δ=8.654 (s, 1H), 8.130-8.151 (m, 1H), 7.578-7.613 (m, 2H), 7.392-7.498 (m, 4H), 7.256-7.293 (m, 1H), 7.129-7.151 (m, 1H), 6.796-6.869 (m, 1H), 5.456-5.505 (m, 1H), 5.279-5.287 (m, 0.5H), 5.133-5.142 (m, 0.5H), 4.846-5.002 (m, 1.5H), 4.835-4.863 (m, 0.5H), 3.958-4.000 (m, 1H), 3.728-3.813 (m, 2H), 3.403-3.420 (m, 1H), 2.579-2.652 (m, 1H), 1.985-2.056 (m, 1H).

Example 286: (S)—N-(2-hydroxyethyl)-4-(3-(5-(trifluoromethyl)pyridin-2-yloxy)pyrrolidin-1-yl) biphenyl-3-carboxamide (Compound 1-153)

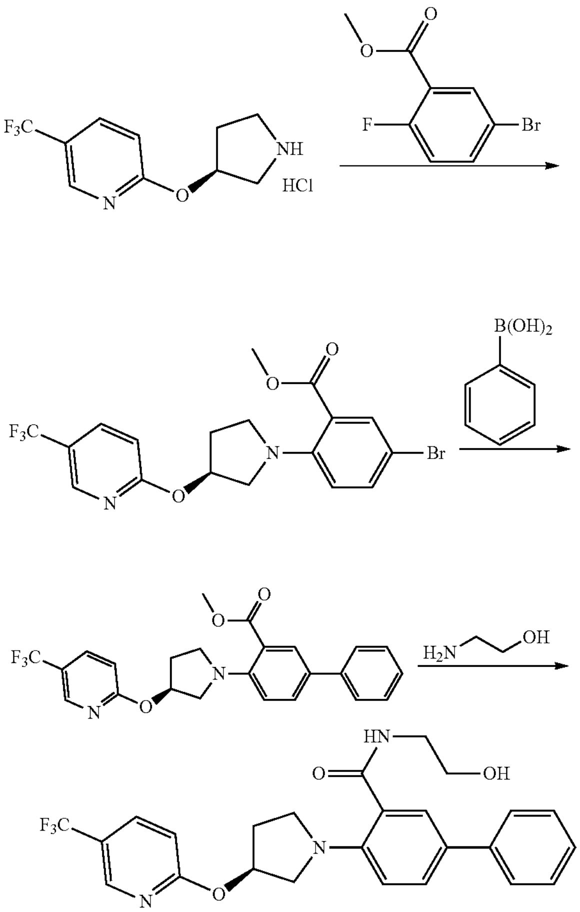

Step 1: (S)-methyl 5-bromo-2-(3-(5-(trifluoromethyl)pyridin-2-yloxy)pyrrolidin-1-yl)benzoate

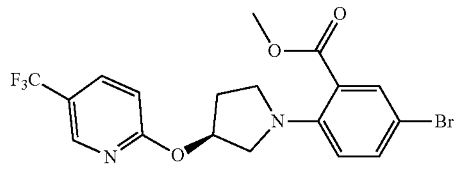 [SMILES: COC(=O)c1cc(Br)ccc1N1CC[C@H](Oc2ccc(C(F)(F)F)cn2)C1]

To a solution of (S)-2-(pyrrolidin-3-yloxy)-5-(trifluoromethyl)pyridine hydrochloride (1.98 g, 8.37 mmol) and methyl 5-bromo-2-fluorobenzoate (1.5 g, 6.44 mol) in 8 mL DMSO was added DBU at rt, the mixture was heated to 100 for 3 h, diluted with EA, washed by water, brine, dried over Na2SO4, removal the solvent to left the crude product which was purified by silica gel column to give (S)-methyl 5-bromo-2-(3-(5-(trifluoromethyl)pyridin-2-yloxy)pyrrolidin-1-yl)benzoate (800 mg, 28% yield), Mass spec: 445 (M+H).

Step 2: (S)-methyl 4-(3-(5-(trifluoromethyl)pyridin-2-yloxy)pyrrolidin-1-yl)biphenyl-3-carboxylate

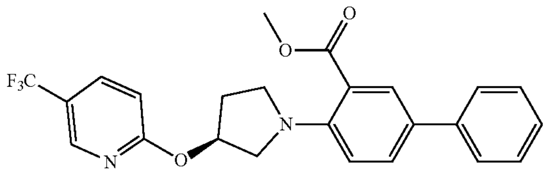 [SMILES: COC(=O)c1cc(-c2ccccc2)ccc1N1CC[C@H](Oc2ccc(C(F)(F)F)cn2)C1]

The title compound was prepared following procedures described in example 270 to give (S)-methyl 4-(3-(5-(trifluoromethyl)pyridin-2-yloxy)pyrrolidin-1-yl)biphenyl-3-carboxylate (240 mg, 69% yield), Mass spec: 443 (M+H).

Step 3: (S)—N-(2-hydroxyethyl)-4-(3-(5-(trifluoromethyl)pyridin-2-yloxy)pyrrolidin-1-yl)biphenyl-3-carboxamide

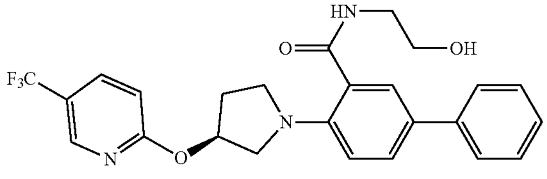 [SMILES: O=C(NCCO)c1cc(-c2ccccc2)ccc1N1CC[C@H](Oc2ccc(C(F)(F)F)cn2)C1]

To a solution of (S)-methyl 4-(3-(5-(trifluoromethyl)pyridin-2-yloxy)pyrrolidin-1-yl)biphenyl-3-carboxylate (90 mg, 0.2 mmol) was dissolved in 2-aminoethanol (1 mL), then mixture was stirred at 100° C. for overnight, 0.1 mL MeOH was added, the mixture was purified by Prep-HPLC to give (S)—N-(2-hydroxyethyl)-4-(3-(5-(trifluoromethyl)pyridin-2-yloxy)pyrrolidin-1-yl)biphenyl-3-carboxamide (40 mg, 42% yield), Mass spec: 472 (M+H), $t_R$=3.048, $^1$H-NMR (400 Hz, DMSO) δ=8.614 (s, 1H), 8.395 (m, 1H), 8.057-8.085 (m, 1H), 7.267-7.615 (m, 7H), 6.999-7.021 (d, 1H), 6.835-6.857 (d, 1H), 5.666 (br, 1H), 4.726 (br, 1H), 3.830 (m, 1H), 3.485-3.543 (m, 2H), 2.221-2.313 (m, 2H).

Example 287: (S)-2'-chloro-N-(2-hydroxyethyl)-4-(3-(5-(trifluoromethyl)pyridin-2-yloxy)pyrrolidin-1-yl)biphenyl-3-carboxamide (Compound 1-156)

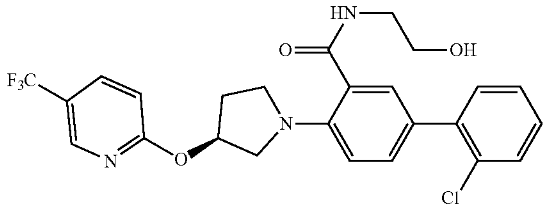 [SMILES: O=C(NCCO)c1cc(-c2ccccc2Cl)ccc1N1CC[C@H](Oc2ccc(C(F)(F)F)cn2)C1]

The title compound was prepared following procedures described in example 286 to give (S)-2'-chloro-N-(2-hydroxyethyl)-4-(3-(5-(trifluoromethyl)pyridin-2-yloxy)pyrrolidin-1-yl)biphenyl-3-carboxamide (20 mg, 25% yield), Mass spec: 506 (M+H), $t_R$=2.930, $^1$H-NMR (400 Hz, DMSO) δ=8.613-8.635 (d, 1H), 8.345-8.362 (m, 1H), 8.062-8.068 (m, 1H), 7.520-7.538 (m, 1H), 7.256-7.402 (m, 5H), 7.008-7.045 (d, 1H), 6.823-6.858 (d, 1H), 5.671 (br, 1H), 4.676-4.703 (t, 1H), 3.838-3.869 (m, 1H), 3.422-3.521 (m, 4H), 3.238-3.278 (m, 3H), 2.213-2.317 (m, 2H).

Example 288: (S)-3'-(hydroxymethyl)-4'-(3-(5-(trifluoromethyl)pyridin-2-yloxy)pyrrolidin-1-yl)biphenyl-2-carboxamide (Compound 1-159)

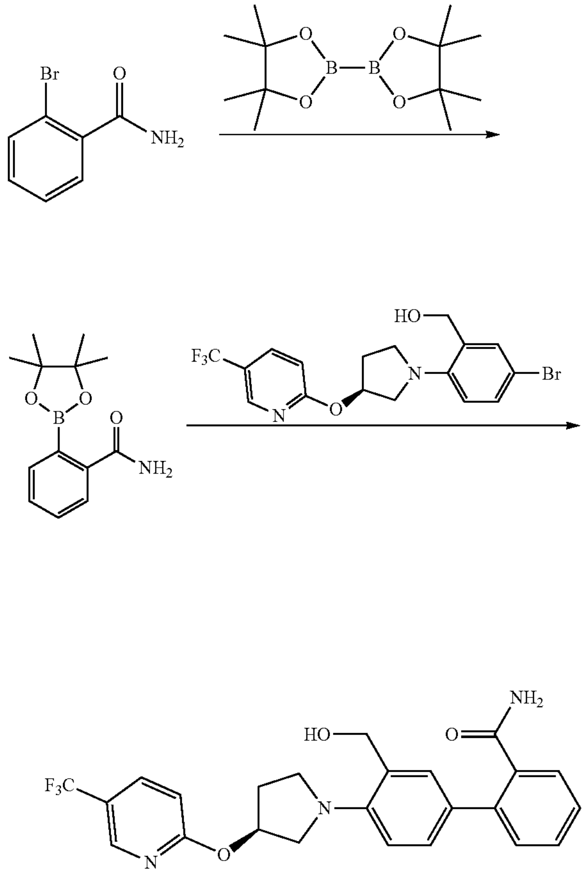

Step 1: 2-(4,4,5,5-tetramethyl-1,3,2-dioxaborolan-2-yl)benzamide

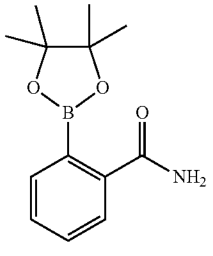 [SMILES: CC1(C)OB(c2ccccc2C(N)=O)OC1(C)C]

The title compound was prepared following procedures described in example 281 step 1 to give 2-(4,4,5,5-tetramethyl-1,3,2-dioxaborolan-2-yl)benzamide (120 mg crude), Mass spec: 248 (M+H).

Step 2: (S)-3'-(hydroxymethyl)-4'-(3-(5-(trifluoromethyl)pyridin-2-yloxy)pyrrolidin-1-yl)biphenyl-2-carboxamide

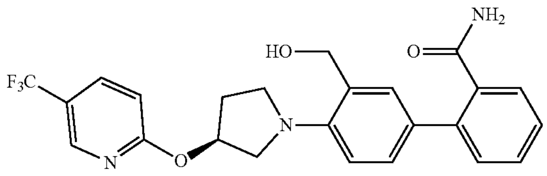 [SMILES: NC(=O)c1ccccc1-c1ccc(N2CC[C@H](Oc3ccc(C(F)(F)F)cn3)C2)c(CO)c1]

The title compound was prepared following procedures described in example 281 step 2 to give (S)-3'-(hydroxymethyl)-4'-(3-(5-(trifluoromethyl)pyridin-2-yloxy)pyrrolidin-1-yl)biphenyl-2-carboxamide (20 mg, ~18% yield), Mass spec: 458 (M+H), $t_R$=2.462, $^1$H-NMR (400 Hz, DMSO) δ=8.621 (s, 1H), 8.065-8.094 (m, 1H), 7.569 (s, 1H), 7.223-7.470 (m, 7H), 7.041-7.063 (d, 1H), 6.869-6.889 (d, 1H), 5.660 (br, 1H), 5.104 (br, 1H), 4.537 (m, 2H), 3.709-3.751 (m, 1H), 3.433-3.474 (m, 2H), 3.232-3.275 (m, 1H), 2.381-2.400 (m, 1H), 2.138-2.146 (m, 1H).

Example 289: (S)-3'-(hydroxymethyl)-N,N-dimethyl-4'-(3-(5-(trifluoromethyl)pyridin-2-yloxy)pyrrolidin-1-yl)biphenyl-2-carboxamide (Compound 1-167)

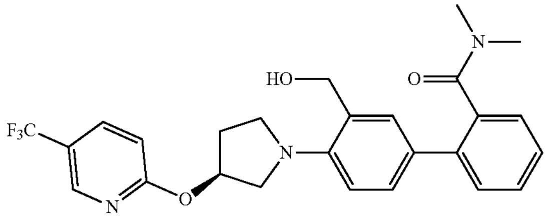 [SMILES: CN(C)C(=O)c1ccccc1-c1ccc(N2CC[C@H](Oc3ccc(C(F)(F)F)cn3)C2)c(CO)c1]

The title compound was prepared following procedures described in example 281 step 2 to give (S)-3'-(hydroxymethyl)-4'-(3-(5-(trifluoromethyl)pyridin-2-yloxy)pyrrolidin-1-yl)biphenyl-2-carboxamide (6 mg, 5% yield), Mass spec: 486 (M+H), $t_R$=2.758, $^1$H-NMR (400 Hz, CDCl3) δ=8.457 (s, 1H), 7.796-7.818 (m, 1H), 7.351-7.450 (s, 6H), 7.076-7.095 (d, 1H), 6.856-6.877 (d, 1H), 5.722 (br, 1H), 4.797-4.874 (m, 2H), 3.287-3.711 (m, 5H), 2.910 (s, 3H), 2.455-2.485 (m, 4H), 2.273 (m, 1H).

Example 290: (S)-4-(3-(5-(trifluoromethyl)pyridin-2-yloxy)pyrrolidin-1-yl)biphenyl-3-carboxylic acid (Compound 1-165)

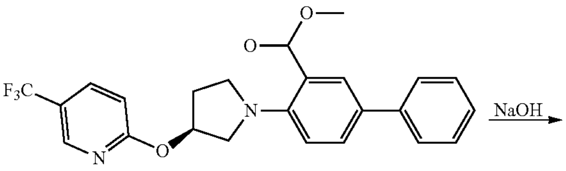

-continued

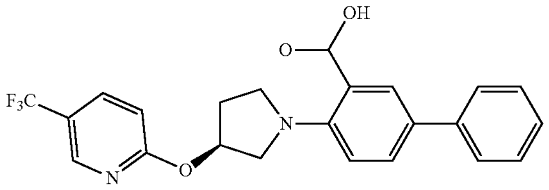

To a solution of (S)-methyl 4-(3-(5-(trifluoromethyl)pyridin-2-yloxy)pyrrolidin-1-yl)biphenyl-3-carboxylate (50 mg, 0.113 mmol) (example 285 step 2) in 2 ml MeOH/THF (v:v=1:1) was added 1 mL 30% NaOH solution, the mixture was stirred at 60° C. for 5 h, adjust the pH to 4 with 3N HCl solution, extracted with EA, washed by brine, dried over Na2SO4, removal the solvent to left the crude product which was purified by Prep-HPLC to give (S)-4-(3-(5-(trifluoromethyl)pyridin-2-yloxy)pyrrolidin-1-yl)biphenyl-3-carboxylic acid (20 mg, 41% yield), Mass spec: 429 (M+H), $t_R$=2.930, $^1$H-NMR (400 Hz, DMSO) δ=8.618 (s, 1H), 8.044-8.073 (m, 1H), 7.510-7.637 (m, 4H), 7.225-7.393 (m, 3H), 7.003-7.018 (d, 1H), 6.808-6.829 (d, 1H), 5.667 (br, 1H), 3.893-3.924 (m, 1H), 3.540-3.563 (m, 1H), 3.243-3.289 (m, 2H), 2.279-2.293 (m, 1H), 2.203-2.205 (m, 1H).

Example 291: (S)-2'-chloro-4-(3-(5-(trifluoromethyl)pyridin-2-yloxy)pyrrolidin-1-yl)biphenyl-3-carboxylic acid (Compound 1-166)

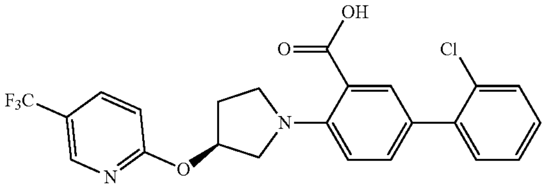 [SMILES: O=C(O)c1cc(-c2ccccc2Cl)ccc1N1CC[C@H](Oc2ccc(C(F)(F)F)cn2)C1]

The title compound was prepared following procedures described in example 290 to give (S)-2'-chloro-4-(3-(5-(trifluoromethyl)pyridin-2-yloxy)pyrrolidin-1-yl)biphenyl-3-carboxylic acid (30 mg, 62% yield), Mass spec: 463 (M+H), $t_R$=3.078, $^1$H-NMR (400 Hz, DMSO) δ=8.619 (s, 1H), 8.060-8.078 (m, 1H), 7.517-7.535 (m, 2H), 7.324-7.381 (m, 4H), 6.886-7.040 (m, 2H), 5.697 (br, 1H), 3.900-3.930 (m, 1H), 3.548-3.611 (m, 1H), 3.225-3.256 (m, 2H), 2.315-2.329 (m, 1H), 2.226-2.245 (m, 1H).

Example 292: (S)-(5-(pyridin-2-yl)-2-(3-(5-(trifluoromethyl)pyridin-2-yloxy)pyrrolidin-1-yl)phenyl)methanol (Compound 1-254)

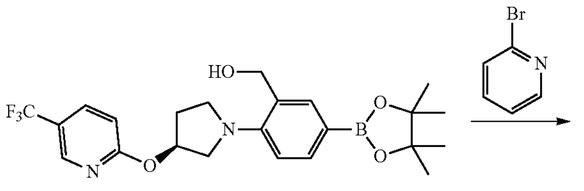

-continued

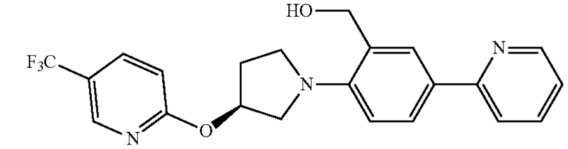

To a solution of (S)-(5-(4,4,5,5-tetramethyl-1,3,2-dioxaborolan-2-yl)-2-(3-(5-(trifluoromethyl)pyridin-2-yloxy)pyrrolidin-1-yl)phenyl)methanol (200 mg, 043 mmol) (example 281 step 1), 2-bromopyridine (74 mg, 047 mmol) in 5 mL MeCN and 1 mL H2O was added Pd(Ph3P)4 (46.2 mg, 0.04 mmol) and K2CO3 (178 mmol, 1.29 mmol), the mixture was stirred at 80° C. for 2 h under N2, diluted with EA, the organic layer was washed by water, brine, dried over Na2SO4, removal the solvent to left the crude product which was purified by Prep-HPLC to give (S)-(5-(pyridin-2-yl)-2-(3-(5-(trifluoromethyl)pyridin-2-yloxy)pyrrolidin-1-yl)phenyl) methanol (21 mg, 12% yield) as yellow solid, Mass spec: 416 (M+H), $t_R$=3.186. $^1$H-NMR (400 Hz, DMSO) δ=8.629-8.583 (m, 2H), 8.123-8.069 (m, 2H), 7.880-7.780 (m, 3H), 7.244-7.217 (m, 1H), 7.058-7.037 (m, 1H), 6.912-6.891 (m, 1H), 5.682-5.663 (m, 1H), 5.199-5.172 (m, 1H), 4.629-4.530 (m, 2H), 3.844-3.803 (m, 1H), 3.581-3.374 (m, 3H), 2.401-2.149 (m, 2H).

Example 293: (S)-(5-(3-methylpyridin-2-yl)-2-(3-(5-(trifluoromethyl)pyridin-2-yloxy)pyrrolidin-1-yl) phenyl)methanol (Compound 1-255)

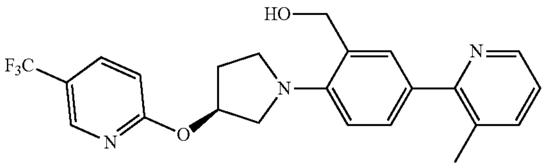 [SMILES: Cc1cccnc1-c1ccc(N2CC[C@H](Oc3ccc(C(F)(F)F)cn3)C2)c(CO)c1]

The title compound was prepared following procedures described in example 292 to give (S)-(5-(3-methylpyridin-2-yl)-2-(3-(5-(trifluoromethyl)pyridin-2-yloxy)pyrrolidin-1-yl)phenyl)methanol (20 mg, 10.8% yield), Mass spec: 430 (M+H), $t_R$=2.211. $^1$H-NMR (400 Hz, DMSO) δ=8.628-8.627 (m, 1H), 8.448-8.438 (m, 1H), 8.100-8.072 (m, 1H), 7.676-7.603 (m, 2H), 7.386-7.361 (m, 1H), 7.232-7.202 (m, 1H), 7.063-6.892 (m, 2H), 5.676 (s, 1H), 5.161-5.134 (m, 1H), 4.578-4.546 (m, 2H), 3.802-3.761 (m, 1H), 3.526-3.281 (m, 3H), 2.416-2.358 (m, 4H), 2.167-2.133 (m, 1H).

Example 294: (S)-tert-butyl (3'-(hydroxymethyl)-4'-(3-(5-(trifluoromethyl)pyridin-2-yloxy)pyrrolidin-1-yl)biphenyl-4-yl)methylcarbamate (Compound 1-269)

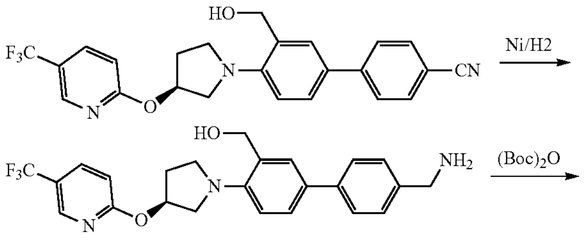

-continued

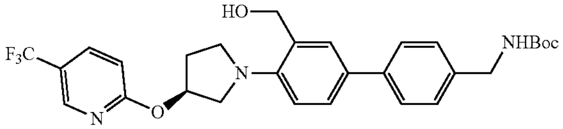

Step 1: (S)-(4'-(aminomethyl)-4-(3-(5-(trifluoromethyl)pyridin-2-yloxy)pyrrolidin-1-yl)biphenyl-3-yl) methanol

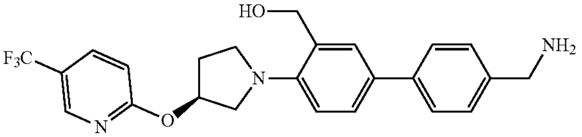 [SMILES: NCc1ccc(-c2ccc(N3CC[C@H](Oc4ccc(C(F)(F)F)cn4)C3)c(CO)c2)cc1]

To a solution of (S)-3'-(hydroxymethyl)-4'-(3-(5-(trifluoromethyl)pyridin-2-yloxy)pyrrolidin-1-yl)biphenyl-4-carbonitrile (200 mg, 0.45 mmol) (example 277) in 2 mL EtOH was added 100 mg Ni and 0.5 mL TEA, the mixture was stirred at 40° C. for overnight under H2 atmosphere, filtered, the filtrate was concentrated to give (S)-(4'-(aminomethyl)-4-(3-(5-(trifluoromethyl)pyridin-2-yloxy)pyrrolidin-1-yl)biphenyl-3-yl)methanol (crude 170 mg, 85% yield) which can be used to next step directly, Mass spec: 444 (M+H).

Step 2: (S)-tert-butyl (3'-(hydroxymethyl)-4'-(3-(5-(trifluoromethyl)pyridin-2-yloxy)pyrrolidin-1-yl) biphenyl-4-yl)methylcarbamate

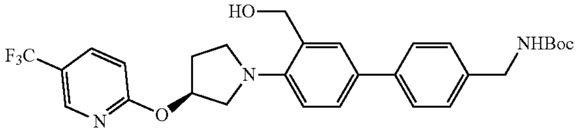 [SMILES: CC(C)(C)OC(=O)NCc1ccc(-c2ccc(N3CC[C@H](Oc4ccc(C(F)(F)F)cn4)C3)c(CO)c2)cc1]

To a solution of (S)-(4'-(aminomethyl)-4-(3-(5-(trifluoromethyl)pyridin-2-yloxy)pyrrolidin-1-yl)biphenyl-3-yl) methanol (170 mg, 0.38 mmol) in 2 ml DCM at 0° C. was added (Boc)2O (166 mg, 0.76 mmol) and TEA (0.1 mL, 0.76 mmol), the mixture was stirred at rt for 2 h, diluted with DCM, the organic layer was washed by water, brine, dried over Na2SO4, removal the solvent to left the crude product which was purified by prep-HPLC to give (S)-tert-butyl (3'-(hydroxymethyl)-4'-(3-(5-(trifluoromethyl)pyridin-2-yloxy)pyrrolidin-1-yl)biphenyl-4-yl)methylcarbamate (25 mg, 12% yield), Mass spec: 544 (M+H), $t_R$=3.223, $^1$H-NMR (400 Hz, DMSO) δ=8.494-8.500 (q, 1H), 7.937-7.953 (m, 1H), 7.682 (s, 1H), 7.557-7.577 (m, 2H), 7.465-7.487 (m, 1H), 7.314-7.335 (m, 2H), 7.056-7.077 (d, 1H), 6.953-6.975 (d, 1H), 5.702-5.717 (m, 1H), 4.754 (s, 2H), 4.265 (s, 2H), 3.711-3.752 (m, 1H), 3.493-3.552 (m, 1H), 3.373-3.401 (m, 1H), 3.268-3.325 (m, 1H), 2.445-2.495 (m, 1H), 2.214-2.226 (m, 1H), 1.436 (s, 9H).

Example 295: (S)-(5-(6-chloro-5-ethylpyrimidin-4-yloxy)-2-(3-(3-chloropyridin-2-yloxy)pyrrolidin-1-yl)phenyl)methanol (Compound 1-358)

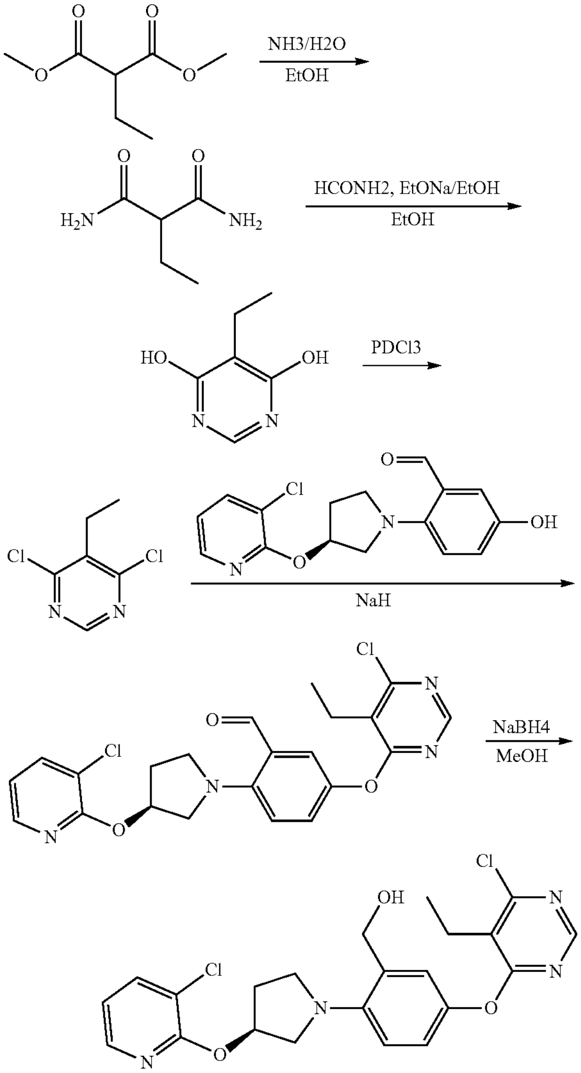

Step 1: 2-ethylmalonamide

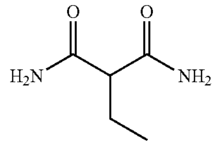

To a solution of dimethyl 2-ethylmalonate (1 g, 5.3 mmol) in EtOH (15 mL) was added NH3/H2O (15 ml) with stirring at rt. for 24 h. The mixture was concentrated, washed by water, dried over Na2SO4, removal the solvent to left the solid crude product, the solid was dried under reduced pressure to give 2-ethylmalonamide (134 mg, 16.5% yield).

Step 2: 5-ethylpyrimidine-4,6-diol

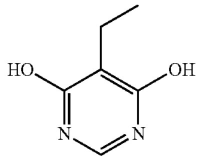

To a solution of 2-ethylmalonamide (130 mg, 1 mmol) in 3 mL EtOH was added HCONH2 (68 mg, 1.5 mmol) and EtONa in EtOH (1.3M), the mixture was refluxed for 16, concentrated to dry, water was added, HCl solution was used to adjust pH to 4, the precipitate was filtered and washed by water, dried over under reduced pressure to give 5-ethylpyrimidine-4,6-diol (30 mg, 21.4% yield), Mass spec: 141 (M+H).

Step 3: 4,6-dichloro-5-ethylpyrimidine

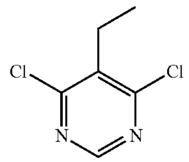

A solution of 5-ethylpyrimidine-4,6-diol (449 mg, 3.2 mmol) in POCl3 (12 mL) was heated to 125° C. for 2 h, The mixture was concentrated, the residue was diluted by DCM and washed by $NaHCO_3$ solution, dried over Na2SO4, removal the solvent to give crude 4,6-dichloro-5-ethylpyrimidine (430 mg, 76.6% yield) which can be used to next step directly, Mass spec: 177 (M+H).

Step 4: (S)-5-(6-chloro-5-ethylpyrimidin-4-yloxy)-2-(3-(3-chloropyridin-2-yloxy)pyrrolidin-1-yl)benzaldehyde

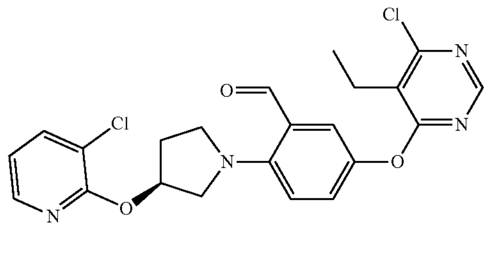 [SMILES: CCc1c(Cl)ncnc1Oc1ccc(N2CC[C@H](Oc3ncccc3Cl)C2)c(C=O)c1]

To a solution of (S)-2-(3-(3-chloropyridin-2-yloxy)pyrrolidin-1-yl)-5-hydroxybenzaldehyde (63 mg, 0.2 mmol) in 2 mL DMSO was added NaH (15 mg, 0.6 mmol) with stirring at 0° C. for 30 min, before 4,6-dichloro-5-ethylpyrimidine (71 mg, 0.4 mmol) was added, the resulting mixture was stirred at rt. for 15 min, concentrated, diluted with DCM, washed by water, dried over Na2SO4, removal the solvent to give (S)-5-(6-chloro-5-ethylpyrimidin-4-yloxy)-2-(3-(3-chloropyridin-2-yloxy)pyrrolidin-1-yl)benzaldehyde (75 mg, 83.3% yield), Mass spec: 459 (M+H).

Step 5: (S)-(5-(6-chloro-5-ethylpyrimidin-4-yloxy)-2-(3-(3-chloropyridin-2-yloxy)pyrrolidin-1-yl)phenyl)methanol

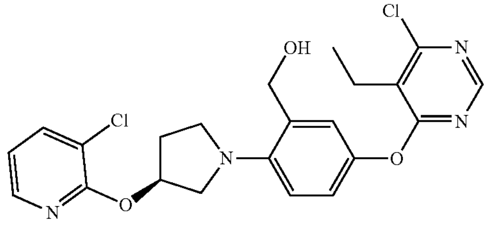 [SMILES: CCc1c(Cl)ncnc1Oc1ccc(N2CC[C@H](Oc3ncccc3Cl)C2)c(CO)c1]

To a solution of (S)-5-(6-chloro-5-ethylpyrimidin-4-yloxy)-2-(3-(3-chloropyridin-2-yloxy)pyrrolidin-1-yl)benzaldehyde (69 mg, 0.15 mmol) in 2 mL MeOH was added NaBH4 (18 mg, 0.45 mmol) with stirring at 0° C., the mixture was stirred at rt for 5 min, diluted with DCM, washed by water, dried over Na2SO4, removal the solvent to give(S)-(5-(6-chloro-5-ethylpyrimidin-4-yloxy)-2-(3-(3-chloropyridin-2-yloxy)pyrrolidin-1-yl)phenyl)methanol (25 mg, 36.2% yield). Mass spec: 461 (M+H), $t_R$=3.445 min, $^1$H-NMR (400 Hz, DMSO) δ=8.427 (s, 1H), 8.162-8.145 (m, 1H), 7.926-7.903 (m, 1H), 7.205 (s, 1H), 7.061-6.993 (m, 3H), 5.629-5.600 (m, 1H), 5.222-5.195 (m, 1H), 4.579-4.474 (m, 2H), 3.641-3.600 (m, 1H), 3.413-3.131 (m, 3H), 2.840-2.784 (m, 2H), 2.423-2.373 (m, 1H), 2.110-2.076 (m, 1H), 1.243-1.206 (m, 3H).

Example 296: (S)-(5-(6-(3-(3-chloropyridin-2-yloxy)pyrrolidin-1-yl)-5-ethylpyrimidin-4-yloxy)-2-fluorophenyl)methanol (Compound 1-359)

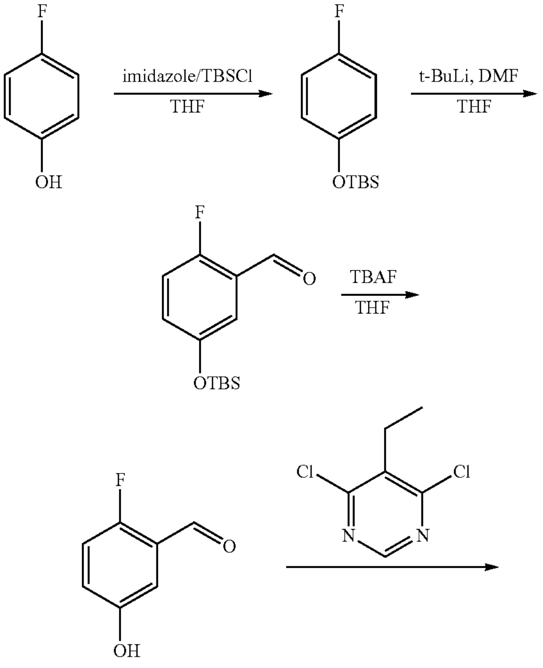

-continued

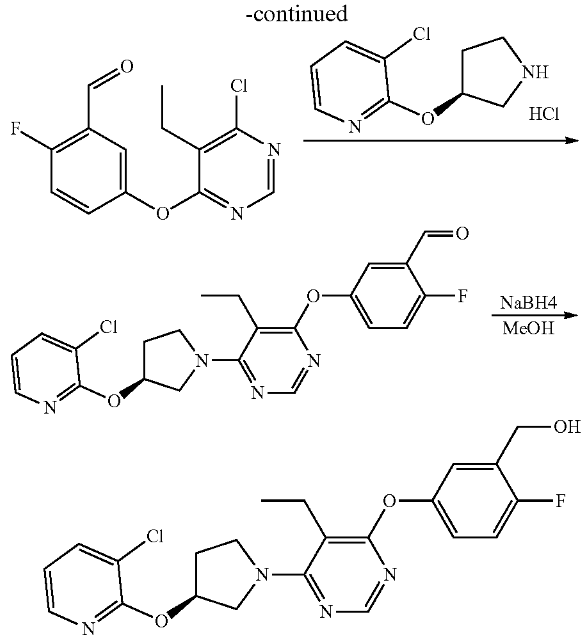

Step 1: tert-butyl(4-fluorophenoxy)dimethylsilane

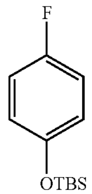

To a solution of 4-fluorophenol (2.24 g, 20 mmol) in 20 mL DMF was added imidazole (3.4 g, 50 mmol) and TBSCl (3.62 g, 24 mmol) with stirring at rt for 16 h. The mixture was diluted with DCM and washed by LiCl solution, dried over Na2SO4, removal the solvent to left the crude product which was purified by silica gel to give tert-butyl(4-fluorophenoxy)dimethylsilane (4.4 g, 97.8% yield).

Step 2: 5-(tert-butyldimethylsilyloxy)-2-fluorobenzaldehyde

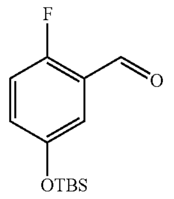 [SMILES: CC(C)(C)[Si](C)(C)Oc1ccc(F)c(C=O)c1]

To a solution of tert-butyl(4-fluorophenoxy)dimethylsilane (2.04 g, 9 mmol) in 20 mL THE was added t-BuLi (4 mL, 2.5M) with stirring at −78° C. for 30 min under N2, before DMF (731 mg) was added at this temperature. Quenched with NH4Cl solution, extracted with EA, dried over Na2SO4, removal the solvent to left the crude product which was purified by silica gel to give 5-(tert-butyldimethylsilyloxy)-2-fluorobenzaldehyde (1.5 g, 65.5% yield).

Step 3: 2-fluoro-5-hydroxybenzaldehyde

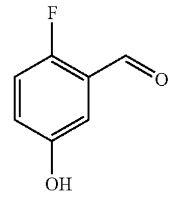

To a solution of 5-(tert-butyldimethylsilyloxy)-2-fluorobenzaldehyde (508 mg, 2 mmol) in 10 mL THE was added TBAF (2.4 mL, 2.4 mmol) with stirring at rt for 1 h. The reaction mixture was concentrated to left the crude product which was purified by silica gel to give 2-fluoro-5-hydroxybenzaldehyde (147 mg, 52.5%).

Step 4: 5-(6-chloro-5-ethylpyrimidin-4-yloxy)-2-fluorobenzaldehyde

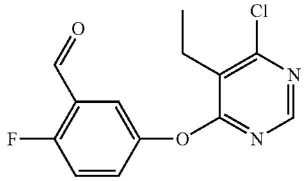 [SMILES: CCc1c(Cl)ncnc1Oc1ccc(F)c(C=O)c1]

To a solution of 2-fluoro-5-hydroxybenzaldehyde (31 mg, 0.22 mmol) and 4,6-dichloro-5-ethylpyrimidine (35 mg, 0.2 mmol) in 2 mL MeCN was added DIPEA (80 mg, 0.6 mmol), the resulting mixture was stirred at 70° C. for 16 h. removal the solvent to left the crude product which was purified by silica gel to give 5-(6-chloro-5-ethylpyrimidin-4-yloxy)-2-fluorobenzaldehyde (30 mg, 48.4% yield), Mass spec: 281 (M+H).

Step 5: (S)-5-(6-(3-(3-chloropyridin-2-yloxy)pyrrolidin-1-yl)-5-ethylpyrimidin-4-yloxy)-2-fluorobenzaldehyde

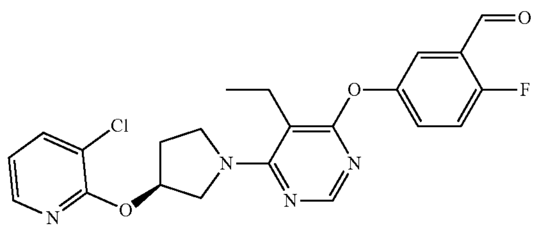 [SMILES: CCc1c(Oc2ccc(F)c(C=O)c2)ncnc1N1CC[C@H](Oc2ncccc2Cl)C1]

To a solution of (S)-3-chloro-2-(pyrrolidin-3-yloxy)pyridine hydrochloride (95 mg, 0.4 mmol) and 5-(6-chloro-5-ethylpyrimidin-4-yloxy)-2-fluorobenzaldehyde (113 mg, 0.4 mmol) in 5 mL DMF was added K2CO3 (166 mg, 1.2 mmol), the mixture was stirred at 70° C. for 8 h. diluted with DCM, washed by LiCl solution, dried over Na2SO4, removal the solvent to left the crude product which was purified by silica gel to give (S)-5-(6-(3-(3-chloropyridin-2-yloxy)pyrrolidin-1-yl)-5-ethylpyrimidin-4-yloxy)-2-fluorobenzaldehyde (70 mg, 39.3% yield), Mass spec: 443 (M+H).

Step 6: (S)-5-(6-(3-(3-chloropyridin-2-yloxy)pyrrolidin-1-yl)-5-ethylpyrimidin-4-yloxy)-2-fluorobenzaldehyde

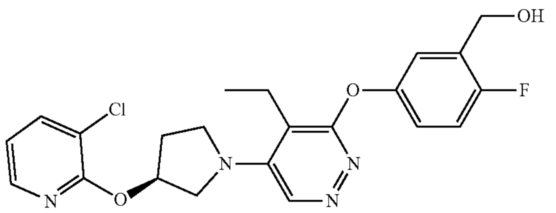 [SMILES: CCc1c(N2CC[C@H](Oc3ncccc3Cl)C2)cnnc1Oc1ccc(F)c(CO)c1]

The title compound was prepared following procedures described in Example 295 step 5 to give (S)-5-(6-(3-(3-chloropyridin-2-yloxy)pyrrolidin-1-yl)-5-ethylpyrimidin-4-yloxy)-2-fluorobenzaldehyde (33 mg, 47.1% yield), Mass spec: 445 (M+H), $t_R$=3.180 min, $^1$H-NMR (400 Hz, DMSO) δ=8.182-8.165 (m, 1H), 8.037 (s, 1H), 7.929-7.905 (m, 1H), 7.185-7.129 (m, 2H), 7.078-6.984 (m, 2H), 5.679-5.670 (m, 1H), 5.355-5.326 (m, 1H), 4.555-4.540 (m, 2H), 4.099-4.057 (m, 1H), 3.875-3.765 (m, 31H), 2.812-2.735 (m, 2H), 2.325-2.237 (m, 2H), 1.192-1.155 (m, 3H).

Example 297: (S)-2-(4-(3-(5-(trifluoromethyl)pyridin-2-yloxy)pyrrolidin-1-yl)phenyl)thiazole-4-carboxylic acid (Compound 1-184)

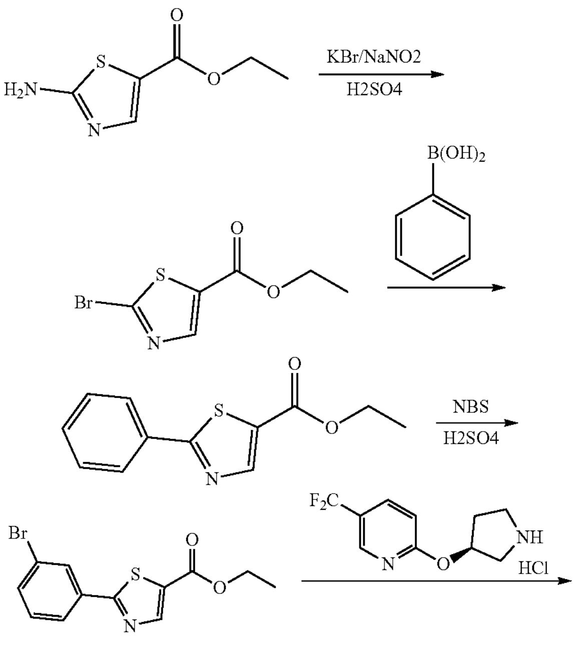

-continued

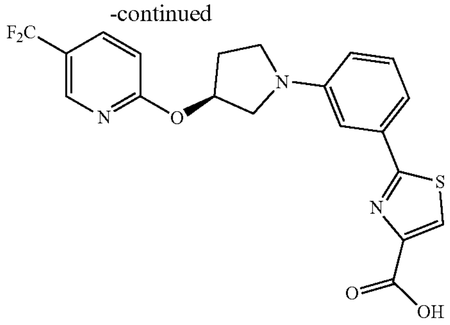

Step 1: ethyl 2-bromothiazole-5-carboxylate

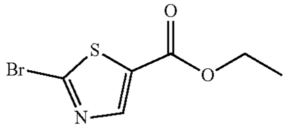

To a solution of ethyl 2-aminothiazole-5-carboxylate (3 g, 17.4 mmol) and KBr (7.25 g, 60 mmol) in 40 mL 27% H2SO4 solution was added NaNO2 (16 g, 225 mmol) in 40 mL water drop-wised during 1 h with stirring at 0° C. After finished, the mixture was kept at 0° C. for another 1 h, The resulting mixture was poured into water, extracted with EA, dried over Na2SO4, removal the solvent to left the crude product which was purified by siligel to give ethyl 2-bromothiazole-5-carboxylate (1.4 g, 34.1% yield), Mass spec: 238 (M+H).

Step 2: ethyl 2-phenylthiazole-5-carboxylate

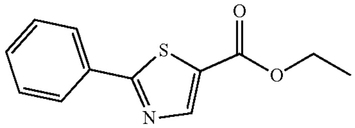 [SMILES: CCOC(=O)c1cnc(-c2ccccc2)s1]

To a solution of ethyl 2-bromothiazole-5-carboxylate (1.4 g, 5.93 mmol) and phenylboronic acid (868 mg, 7.12 mmol) in 18 ml Dioxane/H2O (v:v=5:1) was added Pd(pddf) Cl2·DCM (140 mg) and K2CO3 (2.46 g, 17.8 mmol) with stirring to 90° C. for 2 h under N2. The mixture was extracted with EA, dried over Na2SO4, removal the solvent to left the crude product which was purified by silica gel to give ethyl 2-phenylthiazole-5-carboxylate (700 mg, 54% yield), Mass spec: 234 (M+H).

Step 3: ethyl 2-(3-bromophenyl)thiazole-5-carboxylate

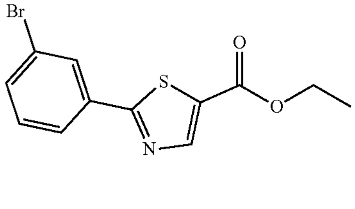 [SMILES: CCOC(=O)c1cnc(-c2cccc(Br)c2)s1]

To a solution of ethyl 2-phenylthiazole-5-carboxylate (23 mg, 0.1 mmol) in 0.5 mL con.H2SO4 was added NBS (21 mg, 0.12 mmol) with stirring at rt for 3 h. The mixture was poured into ice water, and extracted with EA, dried over Na2SO4, removal the solvent to left the crude product which was purified by silica gel to give ethyl 2-(3-bromophenyl) thiazole-5-carboxylate (28 mg, 93.3% yield), Mass spec: 232 (M+H).

Step 4: (S)-2-(4-(3-(5-(trifluoromethyl)pyridin-2-yloxy)pyrrolidin-1-yl)phenyl)thiazole-4-carboxylic acid

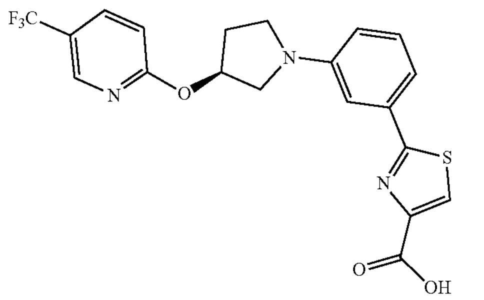 [SMILES: O=C(O)c1csc(-c2cccc(N3CC[C@H](Oc4ccc(C(F)(F)F)cn4)C3)c2)n1]

To a solution of (S)-2-(pyrrolidin-3-yloxy)-5-(trifluoromethyl)pyridine hydrochloride (46 mg, 0.2 mmol) (Intermediate 3), ethyl 2-(3-bromophenyl)thiazole-5-carboxylate (75 mg, 0.24 mmol), t-BuONa (58 mg, 0.6 mmol) and Pd$_2$(dba)$_3$ (5 mg) in 1 mL Dioxane was added x-phos (5 mg), the mixture was heated to 110° C. by microwave for 30 min, diluted with EA, washed by water, brine, removal the solvent to left the crude product which was purified by Pre-HPLC to give ((S)-2-(4-(3-(5-(trifluoromethyl)pyridin-2-yloxy)pyrrolidin-1-yl)phenyl)thiazole-4-carboxylic acid (10 mg, 11.6% yield). Mass spec: 436 (M+H), $t_R$=3.080. $^1$H-NMR (400 Hz, DMSO) δ=8.654 (s, 1H), 8.128-8.075 (m, 2H), 7.316-7.277 (m, 1H), 7.166-7.018 (m, 3H), 6.722-6.702 (m, 1H), 5.774-5.768 (m, 1H), 3.810-3.772 (m, 1H), 3.597-3.481 (m, 3H), 2.423-2.396 (m, 1H), 2.294-2.263 (m, 1H).

Example 298: 2-(3-((S)-3-(5-(trifluoromethyl)pyridin-2-yloxy)pyrrolidin-1-yl)cyclohexa-2,4-dienyl) thiazol-4-ol (Compound 1-177)

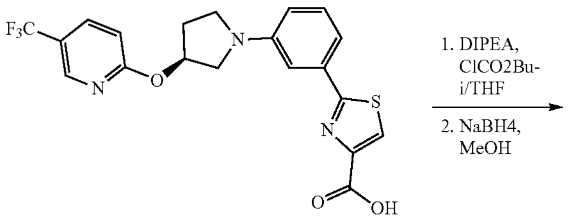

-continued

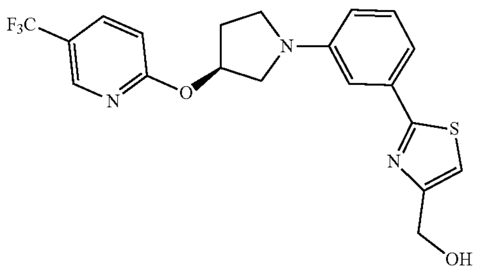

To a solution of (S)-2-(4-(3-(5-(trifluoromethyl)pyridin-2-yloxy)pyrrolidin-1-yl)phenyl)thiazole-4-carboxylic acid (Example 297)(160 mg, 0.37 mmol), ClCO2$^i$Bu (60 mg, 0.44 mmol) in 3 mL THF was added DIPEA (7 mg, 0.55 mmol) at 0° C., the mixture was stirred at rt. for 2 h, and NaBH4 (14 mg, 0.37 mmol) in MeOH (1 mL) was added dropwise at 0° C., the mixture was stirred at rt for another 2 h. The mixture was quenched by water, extracted with EA, dried over Na2SO4, removal the solvent to left crude product which was purified by Prep-HPLC to give 2-(3-((S)-3-(5-(trifluoromethyl)pyridin-2-yloxy)pyrrolidin-1-yl)cyclohexa-2,4-dienyl)thiazol-4-ol (20 mg, 12.8% yield), Mass spec: 422 (M−H), $t_R$=3.035, $^1$H-NMR (400 Hz, DMSO) δ=8.653 (s, 1H), 8.101-8.073 (m, 1H), 7.436 (m, 1H), 7.304-7.265 (m, 2H), 7.062-7.025 (m, 2H), 6.708-6.684 (m, 1H), 5.769-5.755 (s, 1H), 4.612 (s, 1H), 3.804-3.601 (m, 3H), 3.372-3.306 (m, 2H), 2.405-2.392 (m, 1H), 2.298-2.291 (m, 1H).

Example 299: (S)-ethyl 2-phenyl-5-(3-(5-(trifluoromethyl)pyridin-2-yloxy)pyrrolidin-1-yl)thiazole-4-carboxylate (Compound 1-206)

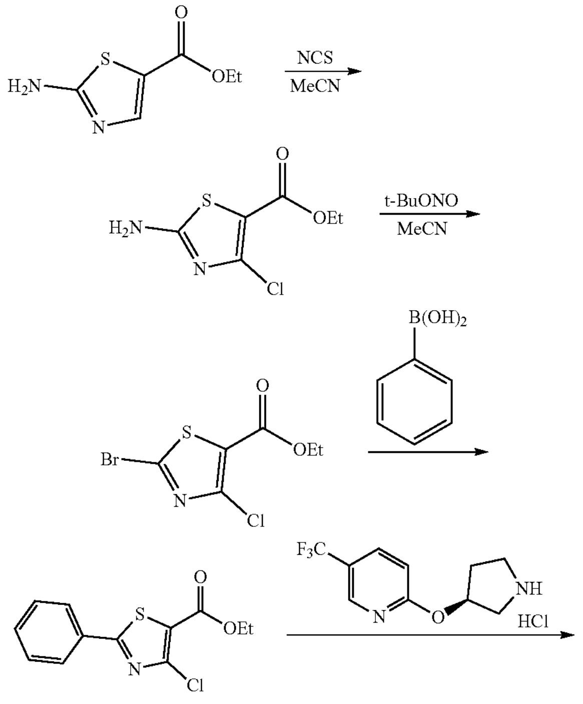

-continued

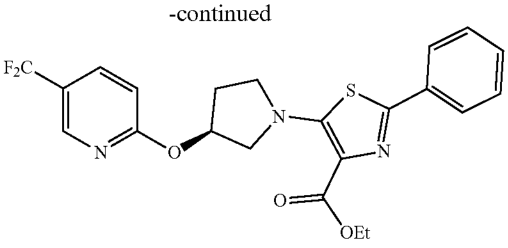

Step 1: ethyl 2-amino-4-chlorothiazole-5-carboxylate

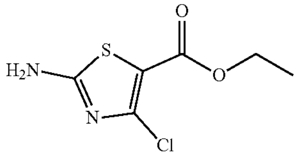

To a solution of ethyl 2-aminothiazole-5-carboxylate (3 g, 17.4 mmol) in 35 mL MeCN was added NCS (2.65 g, 19.2 mmol) with stirring at 82° C. for 5 h. The mixture was quenched by water, extracted with EA, dried over Na2SO4, removal the solvent to left the crude product which was purified by silica gel to give ethyl 2-amino-4-chlorothiazole-5-carboxylate (2.8 g, 77.8% yield), Mass spec: 207 (M+H).

Step 2: ethyl 2-bromo-4-chlorothiazole-5-carboxylate

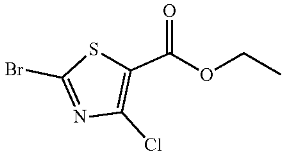

To a solution of ethyl 2-amino-4-chlorothiazole-5-carboxylate (1 g, 5 mmol) and CuBr2 (1.34 g, 6 mmol) in 35 mL MeCN was added t-BuONO (875 mg, 8.5 mmol) with stirring at 82° C. for 5 h. The mixture was quenched with water, extracted with EA, washed by brine, dried over Na2SO4, removal the solvent to left the crude product which was purified by silica gel to give ethyl 2-bromo-4-chlorothiazole-5-carboxylate (1 g, 74%), Mass spec: 270 (M+H).

Step 3: ethyl 4-chloro-2-phenylthiazole-5-carboxylate

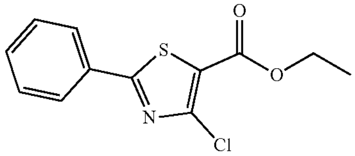 [SMILES: CCOC(=O)c1sc(-c2ccccc2)nc1Cl]

The title compound was prepared following procedures described in step 2 of example 297 to give ethyl 4-chloro-2-phenylthiazole-5-carboxylate (280 mg, 35% yield), Mass spec: 268 (M+H).

Step 4: (S)-ethyl 2-phenyl-5-(3-(5-(trifluoromethyl) pyridin-2-yloxy)pyrrolidin-1-yl)thiazole-4-carboxylate

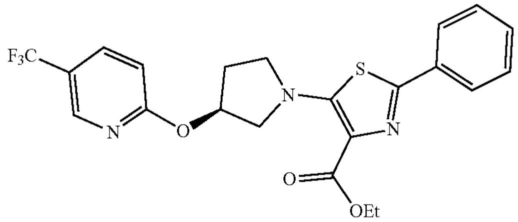 [SMILES: CCOC(=O)c1nc(-c2ccccc2)sc1N1CC[C@H](Oc2ccc(C(F)(F)F)cn2)C1]

To a solution of (S)-2-(pyrrolidin-3-yloxy)-5-(trifluoromethyl)pyridine hydrochloride (460 mg, 2 mmol) (intermediate 3) and ethyl 4-chloro-2-phenylthiazole-5-carboxylate (267 mg, 1 mmol) in 3 mL DMF was stirred at 70° C. overnight. The mixture was extracted with EA, washed by LiCl solution, brine, dried over Na2SO4, removal the solvent to left the crude product which was purified by Prep-HPLC to give (S)-ethyl 2-phenyl-5-(3-(5-(trifluoromethyl) pyridin-2-yloxy)pyrrolidin-1-yl)thiazole-4-carboxylate (250 mg, 54% yield), Mass spec: 464 (M+H), $t_R$=3.373. $^1$H-NMR (400 Hz, DMSO) δ=8.633 (s, 1H), 8.106-8.078 (m, 1H), 7.787-7.766 (m, 2H), 7.487-7.414 (m, 3H), 7.060-7.038 (m, 1H), 5.740 (s, 1H), 4.284-4.222 (m, 2H), 4.034-3.993 (m, 1H), 3.703-3.672 (m, 1H), 3.550-3.474 (m, 2H), 2.448-2.424 (m, 1H), 2.323-2.307 (m, 1H), 1.307-1.272 (m, 3H).

Example 301: (S)-2-(2-(3-(3-chloropyridin-2-yloxy) pyrrolidin-1-yl)-5-(2-isopropylphenoxy)phenyl)ethanol (Compound 1-327)

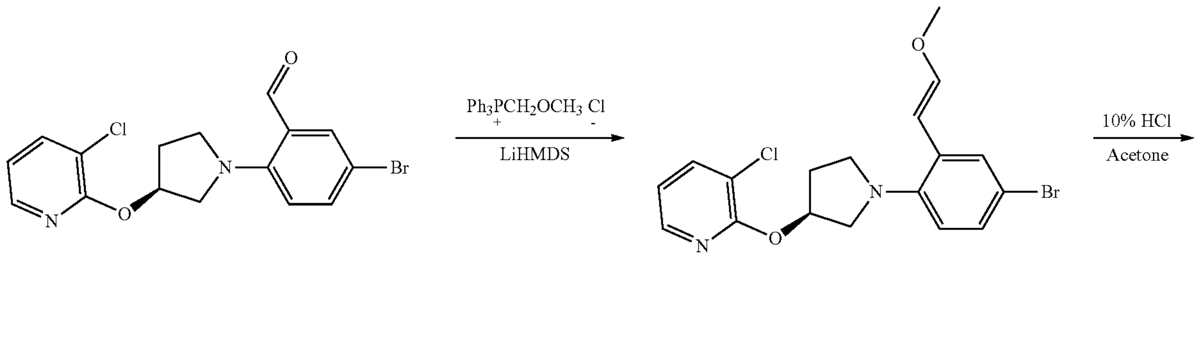

-continued

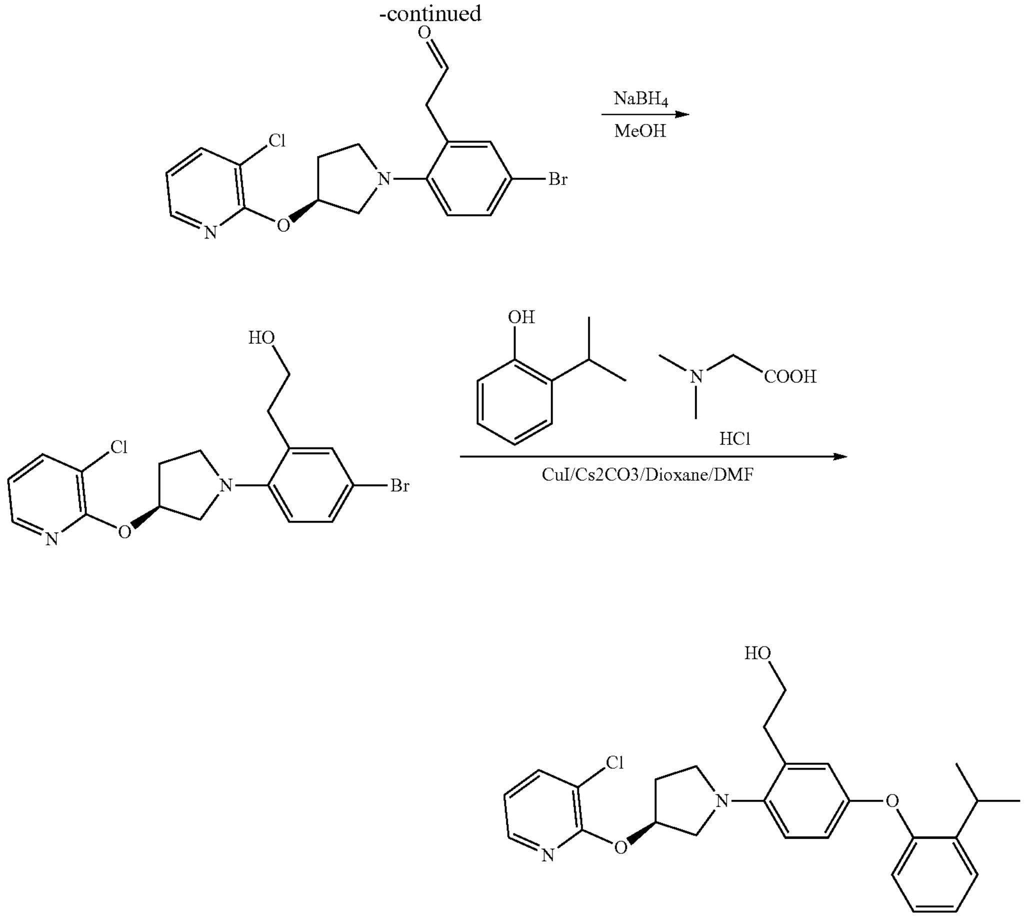

Step 1: (S, E)-2-(1-(4-bromo-2-(2-methoxyvinyl) phenyl)pyrrolidin-3-yloxy)-3-chloropyridine

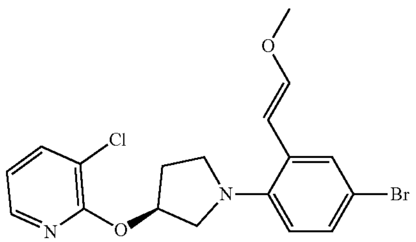 [SMILES: CO/C=C/c1cc(Br)ccc1N1CC[C@H](Oc2ncccc2Cl)C1]

To a solution of (methoxymethyl)triphenylphosphonium chloride (1.08 g, 3.14 mmol) in 14 ml THE was added LiHMDS (657 mg, 3.93 mmol) slowly at 0° C. during 20 min. the resulting solution was added To a solution of (S)-5-bromo-2-(3-(3-chloropyridin-2-yloxy)pyrrolidin-1-yl) benzaldehyde (1.0 g, 2.6 mmol, prepared as example 236 step 1) in 5 ml THE slowly at 0° C. After 5 min, the reaction was completed detected by TLC and LCMS, then the reaction was quenched by the addition of ice-water, the aqueous layer was extracted with EA, the organic layer was dried over $Na_2SO_4$, removal the solvent to left the crude product which was purified by silica gel to give (S, E)-2-(1-(4-bromo-2-(2-methoxyvinyl)phenyl)pyrrolidin-3-yloxy)-3-chloropyridine as oil (700 mg, 66% yield), Mass spec: 409 (M+1).

Step 2: (S)-2-(5-bromo-2-(3-(3-chloropyridin-2-yloxy)pyrrolidin-1-yl)phenyl)acetaldehyde

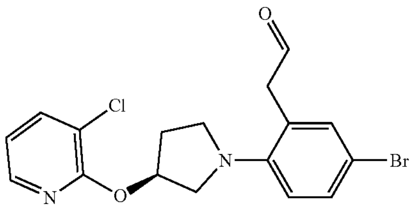 [SMILES: O=CCc1cc(Br)ccc1N1CC[C@H](Oc2ncccc2Cl)C1]

To a solution of (S, E)-2-(1-(4-bromo-2-(2-methoxyvinyl) phenyl)pyrrolidin-3-yloxy)-3-chloropyridine (200 mg, 0.49 mmol) in 6 ml acetone was added 4 ml 10% HCl, stirred at 50° C. for 2 h and the reaction was quenched by $NaHCO_3$, extracted with DCM, washed with brine, dried over $Na_2SO_4$, removal the solvent to left the crude product which was purified by silica gel to give (S)-2-(5-bromo-2-(3-(3-chloropyridin-2-yloxy)pyrrolidin-1-yl)phenyl)acetaldehyde (160 mg, 82% yield), Mass spec: 395 (M+1).

Step 3: (S)-2-(5-bromo-2-(3-(3-chloropyridin-2-yloxy)pyrrolidin-1-yl)phenyl)ethanol

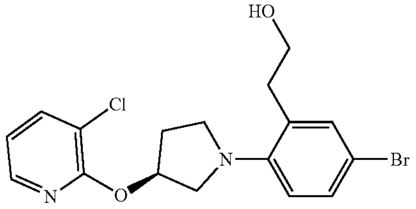 [SMILES: OCCc1cc(Br)ccc1N1CC[C@H](Oc2ncccc2Cl)C1]

To a solution of (S)-2-(5-bromo-2-(3-(3-chloropyridin-2-yloxy)pyrrolidin-1-yl)phenyl)acetaldehyde (200 mg, 0.50 mmol) in 6 ml MeOH was added $NaBH_4$ (38 mg, 1.0 mmol) at 50° C. stirred for 10 min and the mixture was quenched by water, extracted with DCM (3×15 ml), was washed with brine, dried over $Na_2SO_4$, removal the solvent to left the crude product which was purified by silica gel to give (S)-2-(5-bromo-2-(3-(3-chloropyridin-2-yloxy)pyrrolidin-1-yl)phenyl)ethanol (110 mg, 55% yield), Mass spec: 397 (M+1).

Step 4: (S)-2-(2-(3-(3-chloropyridin-2-yloxy)pyrrolidin-1-yl)-5-(2-isopropylphenoxy)phenyl)ethanol

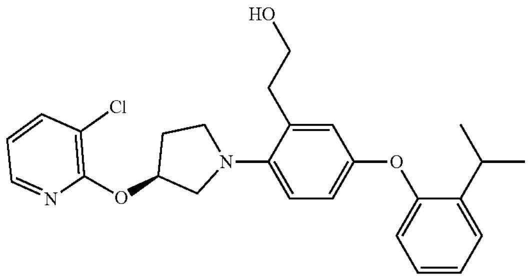 [SMILES: CC(C)c1ccccc1Oc1ccc(N2CC[C@H](Oc3ncccc3Cl)C2)c(CCO)c1]

To a solution of (S)-2-(5-bromo-2-(3-(3-chloropyridin-2-yloxy)pyrrolidin-1-yl)phenyl)ethanol (110 mg, 0.276 mmol), 2-isopropylphenol (75 mg, 0.553 mmol), CuI (26 mg, 0.138 mmol), Cs2CO3 (180 mg, 0.533 mmol) and 2-(dimethylamino)acetic acid hydrochloride (19 mg, 0.138 mmol) in 1.0 ml dioxane and 0.2 ml DMF was heated at 160° C. in microwave for 1 h. The mixture was diluted with water, extracted with EA, washed with LiCl solution, washed with brine, dried over $Na_2SO_4$, filtered, removal the solvent to left the crude product which was purified by Prep-HPLC to give (S)-2-(2-(3-(3-chloropyridin-2-yloxy)pyrrolidin-1-yl)-5-(2-isopropylphenoxy)phenyl)ethanol (45 mg, 36.3% yield), Mass spec: 453 (M+1), $t_R$=3.300 min, $^1$H-NMR (400 Hz, DMSO) δ=8.145-7.919 (d, 1H), 7.915-7.895 (m, 1H), 7.371-7.181 (d, 1H), 7.177-7.018 (m, 4H), 6.833-6.766 (m, 2H), 6.675-6.646 (m, 1H), 5.594-5.565 (s, 1H), 4.654-4.628 (m, 1H), 3.639-3.534 (m, 3H), 3.328-3.205 (m, 2H), 3.133-3.033 (m, 2H), 2.800-2.765 (m, 2H), 2.513-2.424 (m, 1H), 2.076-2.056 (s, 1H), 1.198-1.180 (d, 6H).

Example 302: (S)-2-(2-(3-(3-chloropyridin-2-yloxy)pyrrolidin-1-yl)-5-(o-tolyloxy)phenyl)ethanol (Compound 1-235)

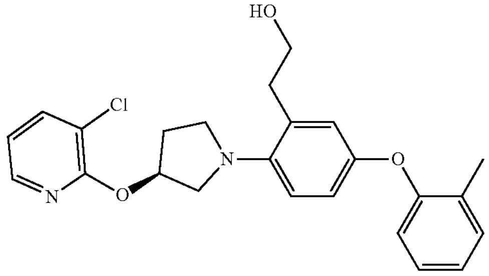 [SMILES: Cc1ccccc1Oc1ccc(N2CC[C@H](Oc3ncccc3Cl)C2)c(CCO)c1]

The title compound was prepared following procedures described in example 301 step 4 to give (S)-2-(2-(3-(3-chloropyridin-2-yloxy)pyrrolidin-1-yl)-5-(o-tolyloxy)phenyl)ethanol (24.1 mg, 24.0% yield), Mass spec: 425 (M+1), $t_R$=2.993 min, $^1$H-NMR (400 Hz, DMSO) δ=8.142-8.134 (m, 1H), 7.920-7.897 (m, 1H), 7.289-7.270 (d, 1H), 7.180-7.142 (m, 1H), 7.033-7.029 (m, 3H), 6.826-6.794 (m, 2H), 6.657-6.642 (m, 1H), 5.589-5.574 (s, 1H), 4.692-4.665 (m, 1H), 3.617-3.532 (m, 3H), 3.321-3.280 (s, 1H), 3.126-3.069 (m, 2H), 2.776-2.759 (m, 2H), 2.437-2.368 (m, 1H), 2.192 (s, 3H), 2.089-2.045 (s, 1H).

Example 303: (S)-2-(2-(3-(3-chloropyridin-2-yloxy)pyrrolidin-1-yl)-5-(2-ethylphenoxy)phenyl)ethanol (Compound 1-236)

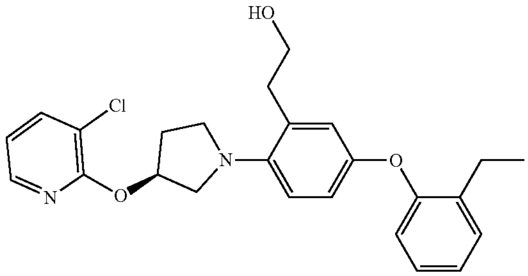 [SMILES: CCc1ccccc1Oc1ccc(N2CC[C@H](Oc3ncccc3Cl)C2)c(CCO)c1]

The title compound was prepared following procedures described in example 301 step 4 to give (S)-2-(2-(3-(3-chloropyridin-2-yloxy)pyrrolidin-1-yl)-5-(2-ethylphenoxy)phenyl)ethanol (14.9 mg, 13.5% yield), Mass spec: 439 (M+1), $t_R$=3.210 min, $^1$H-NMR (400 Hz, DMSO) δ=8.147-8.131 (d, 1H), 7.919-7.900 (d, 1H), 7.305-7.288 (d, 1H), 7.184-7.146 (m, 1H), 7.079-7.017 (m, 3H), 6.844-6.765 (m, 2H), 6.676-6.648 (m, 1H), 5.575-5.569 (s, 1H), 4.662-4.636 (m, 1H), 3.638-3.547 (m, 3H), 3.336-3.265 (m, 1H), 3.129-3.063 (m, 2H), 2.780-2.762 (m, 2H), 2.622-2.566 (m, 2H), 2.419-2.403 (m, 1H), 2.092-2.040 (s, 1H), 1.167-1.148 (m, 3H).

Example 304: (S)-2-(2-(3-(3-chloropyridin-2-yloxy)pyrrolidin-1-yl)-5-(2-methoxyphenoxy)phenyl)ethanol (Compound 1-237)

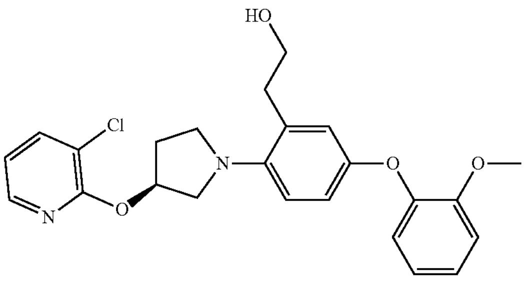

The title compound was prepared following procedures described in example 301 step 4 to give (S)-2-(2-(3-(3-chloropyridin-2-yloxy)pyrrolidin-1-yl)-5-(2-methoxyphenoxy)phenyl)ethanol (12.8 mg, 11.6% yield), Mass spec: 441 (M+1), $t_R$=2.624 min, $^1$H-NMR (400 Hz, DMSO) δ=8.143-8.128 (d, 1H), 7.915-7.892 (d, 1H), 7.137-7.131 (d, 2H), 7.045-7.013 (m, 2H), 6.922-6.915 (d, 2H), 6.791-6.783 (d, 1H), 6.584-6.570 (m, 1H), 5.576-5.562 (s, 1H), 4.635 (m, 1H), 3.752 (s, 1H), 3.600-3.525 (m, 3H), 3.280-3.241 (m, 1H), 3.084-3.032 (m, 2H), 2.787-2.751 (m, 2H), 2.399-2.365 (m, 1H), 2.043-2.030 (s, 1H).

Example 305: (S)-2-(5-(2-chlorophenoxy)-2-(3-(3-chloropyridin-2-yloxy)pyrrolidin-1-yl)phenyl)ethanol (Compound 1-238)

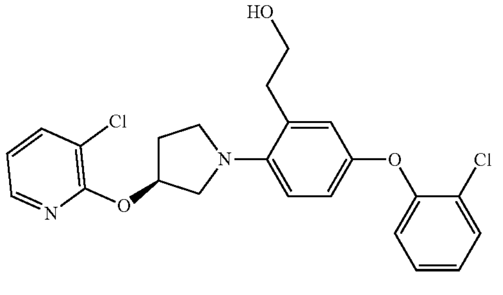 [SMILES: OCCc1cc(Oc2ccccc2Cl)ccc1N1CC[C@H](Oc2ncccc2Cl)C1]

The title compound was prepared following procedures described in example 301 step 4 to give (S)-2-(5-(2-chlorophenoxy)-2-(3-(3-chloropyridin-2-yloxy)pyrrolidin-1-yl)phenyl)ethanol (3.5 mg, 3.2% yield), Mass spec: 445 (M+1), $t_R$=3.072 min, $^1$H-NMR (400 Hz, DMSO) δ=8.086-8.070 (d, 1H), 7.784-7.701 (d, 1H), 7.491-7.471 (d, 1H), 7.278-7.081 (m, 3H), 6.970-6.939 (m, 2H), 6.886-6.880 (d, 1H), 6.785-6.756 (m, 1H), 5.661-5.630 (s, 1H), 3.826-3.778 (m, 2H), 3.646-3.605 (m, 1H), 3.406-3.365 (m, 1H), 3.237-3.134 (m, 2H), 2.973-2.932 (m, 2H), 2.498-2.463 (m, 1H), 2.200-2.167 (m, 1H).

Example 306: (S)-2-(2-(3-(3-chloropyridin-2-yloxy)pyrrolidin-1-yl)-5-(2-(methoxymethyl)phenoxy)phenyl)ethanol (Compound 1-297)

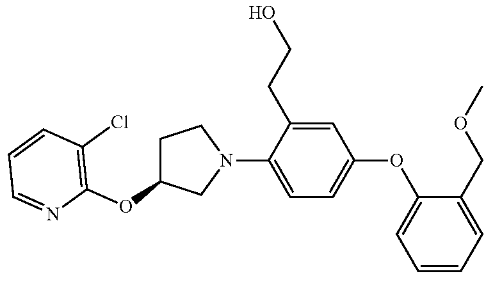 [SMILES: COCc1ccccc1Oc1ccc(N2CC[C@H](Oc3ncccc3Cl)C2)c(CCO)c1]

The title compound was prepared following procedures described in example 301 step 4 to give (S)-2-(2-(3-(3-chloropyridin-2-yloxy)pyrrolidin-1-yl)-5-(2-(methoxymethyl)phenoxy)phenyl)ethanol (8.9 mg, 6.5% yield), Mass spec: 455 (M+1), $t_R$=2.729 min, $^1$H-NMR (400 Hz, DMSO) δ=8.152-8.136 (d, 1H), 7.923-7.900 (d, 1H), 7.443-7.426 (m, 1H), 7.283-7.241 (m, 1H), 7.133-7.023 (m, 3H), 6.878-6.871 (m, 1H), 6.799-6.779 (m, 1H), 6.729-6.700 (m, 1H), 5.602-5.572 (m, 1H), 4.657-4.631 (m, 1H), 4.465 (s, 2H), 3.649-3.551 (m, 3H), 3.312-3.287 (m, 4H), 3.146-3.060 (m, 2H), 2.807-2.772 (m, 2H), 2.427-2.375 (m, 1H), 2.085-2.050 (m, 1H).

Example 307: (S)-2-(2-(3-(5-fluoropyridin-2-yloxy)pyrrolidin-1-yl)-5-(2-(methoxymethyl)phenoxy)phenyl)ethanol (Compound 1-341)

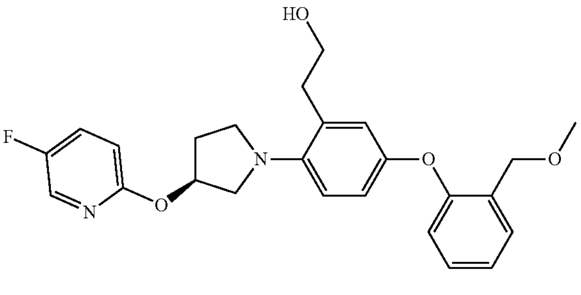 [SMILES: COCc1ccccc1Oc1ccc(N2CC[C@H](Oc3ccc(F)cn3)C2)c(CCO)c1]

The title compound was prepared following procedures described in example 301 to give (S)-2-(2-(3-(5-fluoropyridin-2-yloxy)pyrrolidin-1-yl)-5-(2-(methoxymethyl)phenoxy)phenyl)ethanol (40 mg, 35.1% yield), Mass spec: 439 (M+1), $t_R$=2.505 min, $^1$H-NMR (400 Hz, DMSO) δ=8.161-8.154 (s, 1H), 7.699 (m, 1H), 7.443-7.425 (d, 1H), 7.261 (m, 1H), 7.132-7.031 (m, 2H), 6.913-6.867 (m, 2H), 6.793-6.700 (m, 2H), 5.466 (s, 1H), 4.660 (m, 1H), 4.463 (m, 2H), 3.617-3.602 (m, 3H), 3.354-3.312 (m, 3H), 3.280 (m, 1H), 3.112-3.036 (m, 2H), 2.796-2.760 (m, 2H), 2.378-2.345 (m, 1H), 2.035 (m, 1H).

Example 308: (S)-2-(2-(3-(3-fluoropyridin-2-yloxy)pyrrolidin-1-yl)-5-(2-isopropylphenoxy)phenyl)ethanol (Compound 1-331)

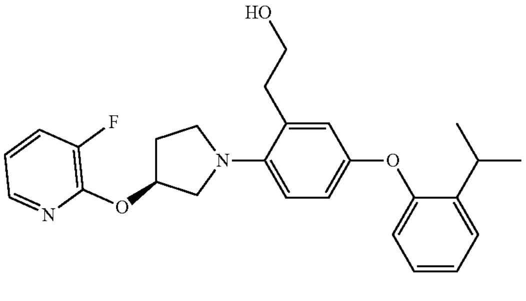

The title compound was prepared following procedures described in example 301 to give (S)-2-(2-(3-(3-fluoropyridin-2-yloxy)pyrrolidin-1-yl)-5-(2-isopropylphenoxy)phenyl)ethanol (42 mg, 37.1% yield), Mass spec: 437 (M+1), $t_R$=3.166 min $^1$H-NMR (400 Hz, DMSO) δ=7.994-7.979 (d, 1H), 7.707-7.664 (m, 1H), 7.370-7.347 (m, 1H), 7.161-7.031 (m, 4H), 6.834-6.671 (m, 3H), 5.597 (s, 1H), 4.648 (s, 1H), 3.613-3.579 (m, 3H), 3.304-3.041 (m, 4H), 2.797-2.761 (m, 2H), 2.415-2.398 (m, 1H), 2.070-2.056 (m, 1H), 1.197-1.179 (m, 6H).

Example 309: (S)-2-(2-(3-(3-fluoropyridin-2-yloxy)pyrrolidin-1-yl)-5-(2-(methoxymethyl)phenoxy)phenyl)ethanol (Compound 1-351)

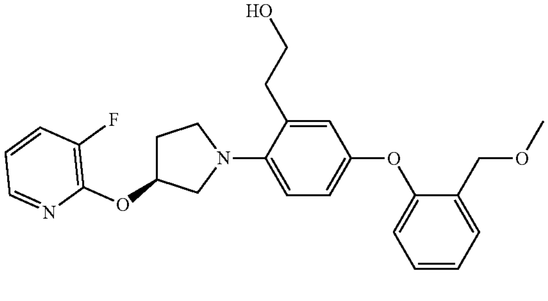 [SMILES: COCc1ccccc1Oc1ccc(N2CC[C@H](Oc3ncccc3F)C2)c(CCO)c1]

The title compound was prepared following procedures described in example 301 to give (S)-2-(2-(3-(3-fluoropyridin-2-yloxy)pyrrolidin-1-yl)-5-(2-(methoxymethyl)phenoxy)phenyl)ethanol (20.0 mg, 35.0% yield), Mass spec: 439 (M+1), $t_R$=2.553 min $^1$H-NMR (400 Hz, DMSO) δ=7.998-7.983 (d, 1H), 7.716-7.669 (m, 1H), 7.442-7.239 (m, 1H), 7.133-7.023 (m, 3H), 6.878-6.871 (d, 1H), 6.797-6.696 (m, 2H), 5.619-5.588 (s, 1H), 4.669-4.464 (m, 1H), 4.464 (s, 2H), 3.623-3.555 (m, 3H), 3.311 (s, 4H), 3.160-3.048 (m, 2H), 2.802-2.766 (m, 2H), 2.434-2.384 (m, 1H), 2.099-2.077 (m, 1H).

Example 310: (S)-2-(5-(2-(methoxymethyl)phenoxy)-2-(3-(pyridin-2-yloxy)pyrrolidin-1-yl)phenyl)ethanol (Compound 1-348)

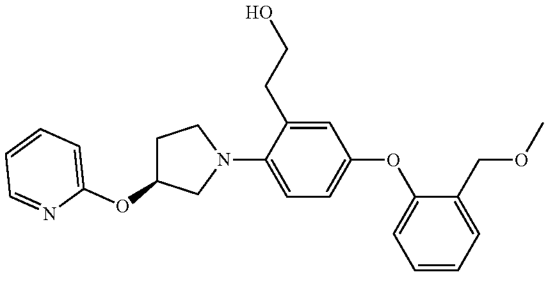 [SMILES: COCc1ccccc1Oc1ccc(N2CC[C@H](Oc3ccccn3)C2)c(CCO)c1]

The title compound was prepared following procedures described in example 301 to give (S)-2-(5-(2-(methoxymethyl)phenoxy)-2-(3-(pyridin-2-yloxy)pyrrolidin-1-yl)phenyl)ethanol (8.0 mg, 7.0% yield), Mass spec: 421 (M+1), $t_R$=2.320 min $^1$H-NMR (400 Hz, DMSO) δ=8.181-8.165 (m, 1H), 7.734-7.690 (m, 1H), 7.441-7.425 (m, 1H), 7.281-7.238 (m, 1H), 7.131-6.965 (m, 3H), 6.873-6.693 (m, 4H), 5.544-5.513 (m, 1H), 4.677-4.652 (m, 1H), 4.464 (s, 2H), 3.363-3.529 (m, 3H), 3.327-3.267 (m, 4H), 3.113-3.046 (m, 2H), 2.799-2.763 (m, 2H), 2.401-2.350 (m, 1H), 2.048-2.015 (m, 1H).

Example 311: (S)-2-(5-(2-(methoxymethyl)phenoxy)-2-(3-(5-methylpyridin-2-yloxy)pyrrolidin-1-yl)phenyl)ethanol (Compound 1-349)

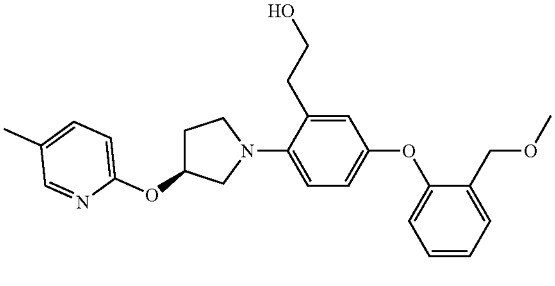

The title compound was prepared following procedures described in example 301 to give(S)-2-(5-(2-(methoxymethyl)phenoxy)-2-(3-(5-methylpyridin-2-yloxy)pyrrolidin-1-yl)phenyl)ethanol (40 mg, 23% yield), Mass spec: 435 (M+1), $t_R$=2.476 min $^1$H-NMR (400 Hz, DMSO) δ=7.796-7.787 (m, 1H), 7.549-7.522 (m, 1H), 7.433-7.421 (m, 1H), 7.275-7.237 (m, 1H), 7.130-7.093 (m, 1H), 7.046-7.024 (m, 1H), 6.869-6.862 (m, 1H), 6.791-6.690 (m, 3H), 5.495-5.464 (m, 1H), 4.673-4.647 (m, 1H), 4.463 (s, 1H), 3.628-3.510 (m, 3H), 3.291-3.269 (m, 4H), 3.093-3.04 (m, 2H), 2.793-2.758 (m, 2H), 2.380-2.329 (m, 1H), 2.205 (s, 3H), 2.024-2.011 (m, 1H).

Example 312: (S)-2-(5-(2-(methoxymethyl)phenoxy)-2-(3-(3-methylpyridin-2-yloxy)pyrrolidin-1-yl)phenyl)ethanol (Compound 1-350)

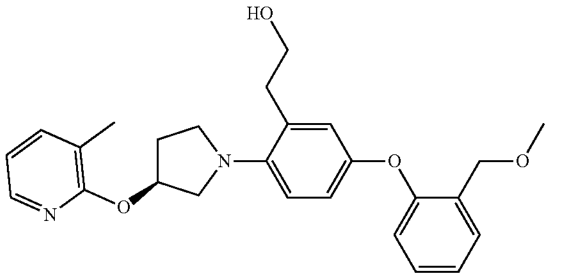

The title compound was prepared following procedures described in example 301 to give (S)-2-(5-(2-(methoxymethyl)phenoxy)-2-(3-(3-methylpyridin-2-yloxy)pyrrolidin-1-yl)phenyl)ethanol (4.8 mg, 4.2% yield), Mass spec: 435 (M+1), $t_R$=2.538 min $^1$H-NMR (400 Hz, DMSO) δ=7.996-7.984 (m, 1H), 7.550-7.534 (m, 1H), 7.440-7.423 (m, 1H), 7.276-7.239 (m, 1H), 7.130-7.04 (m, 2H), 6.903-6.69 (m, 4H), 5.553-5.536 (m, 1H), 4.657-4.631 (m, 1H), 4.464 (s, 1H), 3.647-3.520 (m, 3H), 3.343-3.311 (m, 4H), 3.114-3.053 (m, 2H), 2.808-2.775 (m, 2H), 2.392-2.341 (m, 1H), 2.149 (m, 3H), 2.056-2.022 (m, 1H).

Example 313: 2-(5-(2-(1-methoxyethyl)phenoxy)-2-((S)-3-(5-methylpyridin-2-yloxy)pyrrolidin-1-yl)phenyl)ethanol (Compound 1-355)

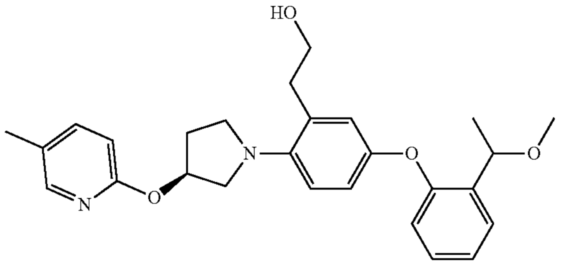

The title compound was prepared following procedures described in example 301 to give 2-(5-(2-(1-methoxyethyl)phenoxy)-2-((S)-(5-methylpyridin-2-yloxy)pyrrolidin-1-yl)phenyl)ethanol (27.0 mg, 23.3% yield), Mass spec: 449 (M+1), $t_R$=2.648 min $^1$H-NMR (400 Hz, DMSO) δ=7.979-7.973 (m, 1H), 7.547-7.521 (m, 1H), 7.429-7.405 (m, 1H), 7.260-7.217 (m, 1H), 7.170-7.133 (m, 1H), 7.050-7.029 (m, 1H), 6.858-6.851 (m, 1H), 6.796-6.692 (m, 3H), 5.492-5.461 (m, 1H), 4.681-4.634 (m, 2H), 3.622-3.504 (m, 3H), 3.285-3.246 (m, 1H), 3.149 (s, 3H), 3.088-3.014 (m, 2H), 2.791-2.755 (m, 2H), 2.379-2.328 (m, 1H), 2.204 (s, 1H), 2.022-1.988 (m, 1H), 1.333-1.317 (m, 3H).

Example 314: 2-(5-(2-(1-methoxyethyl)phenoxy)-2-((S)-3(pyridin-2-yloxy)pyrrolidin-1-yl)phenyl)ethanol (Compound 1-357)

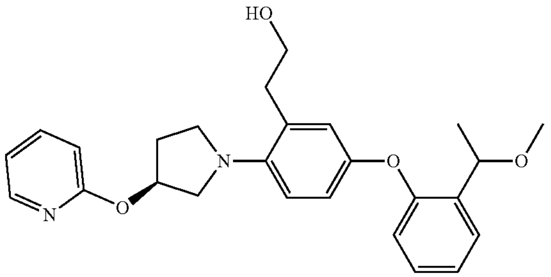 [SMILES: COC(C)c1ccccc1Oc1ccc(N2CC[C@H](Oc3ccccn3)C2)c(CCO)c1]

The title compound was prepared following procedures described in example 301 to give 2-(5-(2-(1-methoxyethyl)phenoxy)-2-((S)-3-(pyridin-2-yloxy)pyrrolidin-1-yl)phenyl)ethanol (8.0 mg, 4.5% yield), Mass spec: 435 (M+1), $t_R$=2.512 min $^1$H-NMR (400 Hz, DMSO) δ=8.175-8.166 (m, 1H), 7.731-7.689 (m, 1H), 7.429-7.410 (m, 1H), 7.261-7.133 (m, 2H), 7.060-6.962 (m, 2H), 6.861-6.695 (m, 4H), 5.540-5.526 (m, 1H), 4.671-4.650 (m, 2H), 3.611-3.550 (m, 3H), 3.151-3.041 (m, 6H), 2.796-2.761 (m, 2H), 2.399-2.348 (m, 1H), 2.045-2.026 (m, 1H), 1.333-1.317 (m, 3H).

Example 315: 2-(2-((S)-3-(5-fluoropyridin-2-yloxy)pyrrolidin-1-yl)-5-(2-(1-methoxyethyl)phenoxy)phenyl)ethanol (Compound 1-347)

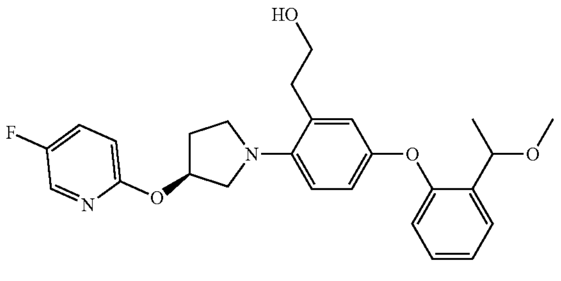 [SMILES: COC(C)c1ccccc1Oc1ccc(N2CC[C@H](Oc3ccc(F)cn3)C2)c(CCO)c1]

The title compound was prepared following procedures described in example 301 to give 2-(2-((S)-3-(5-fluoropyridin-2-yloxy)pyrrolidin-1-yl)-5-(2-(1-methoxyethyl)phenoxy)phenyl)ethanol (40.0 mg, 34.2% yield), Mass spec: 453 (M+1), $t_R$=2.707 min $^1$H-NMR (400 Hz, DMSO) δ=8.160-8.152 (m, 1H), 7.698 (m, 1H), 7.431-7.408 (m, 1H), 7.242-7.035 (m, 3H), 6.911-6.856 (m, 2H), 6.798-6.702 (m, 2H), 5.470 (s, 1H), 4.666-4.642 (m, 2H), 3.610-3.519 (m, 3H), 3.349-3.274 (m, 1H), 3.151 (s, 3H), 3.107-3.030 (m, 2H), 2.793-2.757 (m, 2H), 2.376-2.360 (m, 1H), 2.033 (m, 1H), 1.333-1.317 (m, 3H).

Example 316: (S)-2-(5-(2-fluorophenoxy)-2-(3-(3-fluoropyridin-2-yloxy)pyrrolidin-1-yl)phenyl)ethanol (Compound 1-313)

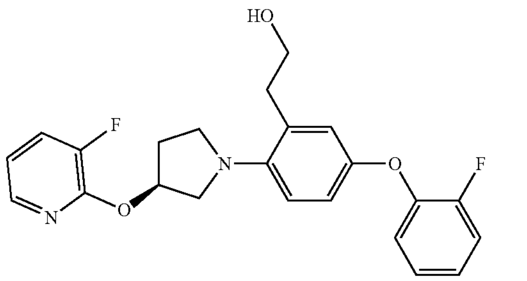 [SMILES: OCCc1cc(Oc2ccccc2F)ccc1N1CC[C@H](Oc2ncccc2F)C1]

The title compound was prepared following procedures described in example 301 to give (S)-2-(5-(2-fluorophenoxy)-2-(3-(3-fluoropyridin-2-yloxy)pyrrolidin-1-yl)phenyl)ethanol (20.0 mg, 10.0% yield), Mass spec: 413 (M+1), $t_R$=2.721 min $^1$H-NMR (400 Hz, DMSO) δ=7.997 (m, 1H), 7.694-7.686 (m, 1H), 7.356-7.347 (m, 1H), 7.183-7.158 (m, 2H), 7.063-7.027 (m, 3H), 6.920-6.912 (m, 1H), 6.756-6.726 (m, 1H), 5.620-5.598 (m, 1H), 4.657 (m, 1H), 3.640-3.570 (m, 3H), 3.302-3.284 (m, 1H), 3.162-3.038 (m, 2H), 2.790-2.772 (m, 2H), 2.453-2.384 (m, 1H), 2.105-2.079 (m, 1H).

Example 317: (S)-2-(2-(3-(3-chloropyridin-2-yloxy) pyrrolidin-1-yl)-5-(2-ethylphenylsulfonyl)phenyl) ethane (Compound 1-342)

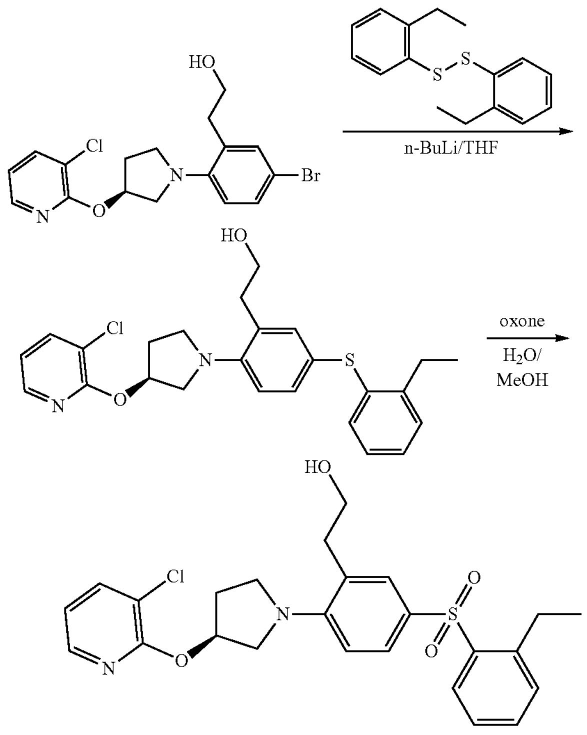

Step 1: (S)-2-(2-(3-(3-chloropyridin-2-yloxy)pyrrolidin-1-yl)-5-(2-ethylphenylthio)phenyl)ethanol

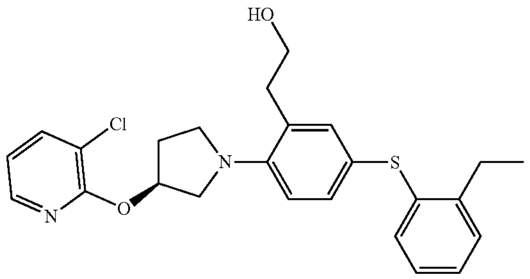 [SMILES: CCc1ccccc1Sc1ccc(N2CC[C@H](Oc3ncccc3Cl)C2)c(CCO)c1]

To a solution of (S)-2-(5-bromo-2-(3-(3-chloropyridin-2-yloxy)pyrrolidin-1-yl)phenyl)ethanol (300 mg, 0.75 mmol) in 4 ml THF was added n-BuLi (0.9 ml, 2.25 mmol) slowly at −78° C., then stirred at −78° C. for 30 min, before the solution of 1,2-bis(2-ethylphenyl)disulfane (309 mg, 1.13 mmol) in 2 ml THF was added at −78° C. After addition, the mixture was stirred at −40° C. for 3 h, then the reaction was quenched by H2O, extracted with EA, dried over Na2SO4, removal the solvent to left the crude product which was purified by silica gel to give (S)-2-(2-(3-(3-chloropyridin-2-yloxy)pyrrolidin-1-yl)-5-(2-ethylphenylthio)phenyl)ethane 150 mg, 44.1% yield), Mass spec: 455 (M+1).

Step 2: (S)-2-(2-(3-(3-chloropyridin-2-yloxy)pyrrolidin-1-yl)-5-(2-ethylphenylsulfonyl)phenyl)ethane

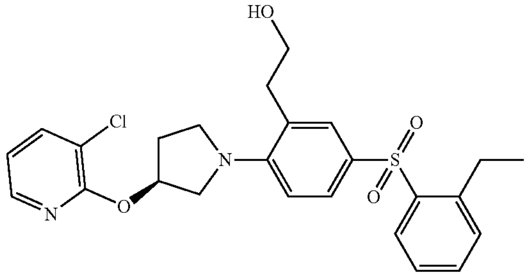 [SMILES: CCc1ccccc1S(=O)(=O)c1ccc(N2CC[C@H](Oc3ncccc3Cl)C2)c(CCO)c1]

To a solution of (S)-2-(2-(3-(3-chloropyridin-2-yloxy) pyrrolidin-1-yl)-5-(2-ethylphenylthio)phenyl)ethanol (150 mg, 0.33 mmol) in MeOH/$H_2O$ (v:v=2/1) was added oxone (405 mg, 0.66 mmol) and stirred at r.t. for overnight. The mixture was extracted with EA, washed with water, dried over $Na_2SO_4$, removal the solvent to left the crude product which was purified by Prep-HPLC to give (S)-2-(2-(3-(3-chloropyridin-2-yloxy)pyrrolidin-1-yl)-5-(2-ethylphenylsulfonyl)phenyl)ethane (20 mg, 12.5% yield), Mass spec: 487 (M+1), $t_R$=1.677 min $^1$H-NMR (400 Hz, DMSO) δ=8.497-8.483 (m, 1H), 7.762-7.725 (m, 1H), 7.589-7.592 (m, 2H), 7.461-7.377 (m, 5H), 7.277-7.256 (m, 1H), 5.853-5.836 (m, 1H), 4.249-4.230 (m, 1H), 4.151-4.122 (m, 3H), 3.876 (m, 1H), 3.630-3.620 (m, 2H), 3.475-3.309 (m, 3H), 3.155-3.100 (m, 2H), 2.921-2.865 (m, 1H), 2.251-2.152 (m, 1H), 1.293-1.250 (m, 3H).

Example 318: 3-((4-((S)-3-(3-chloropyridin-2-yloxy)pyrrolidin-1-yl)-3-(2-hydroxyethyl)phenyl)(hydroxy)methyl)benzonitrile (Compound 1-356)

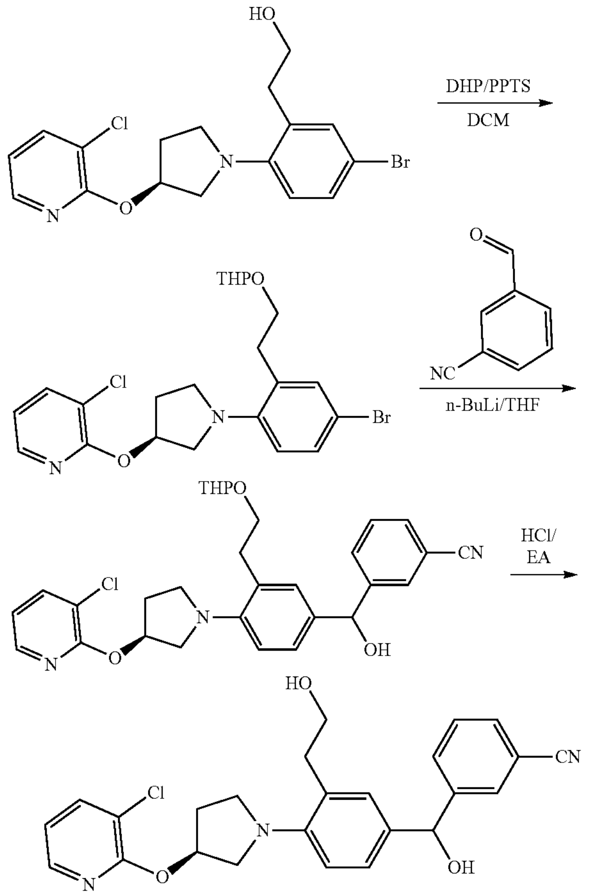

Step 1: 2-((3S)-1-(4-bromo-2-(2-(tetrahydro-2H-pyran-2-yloxy)ethyl)phenyl)pyrrolidin-3-yloxy)-3-chloropyridine

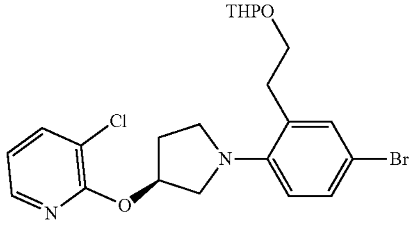

To a solution of (S)-2-(5-bromo-2-(3-(3-chloropyridin-2-yloxy)pyrrolidin-1-yl)phenyl)ethanol (1.1 g, 2.7 mmol), DHP (907 mg, 10.8 mmol) and PPTS (1.1 g, 4.05 mmol) in 5 ml DCM was stirred at rt for overnight. The reaction was completed detected by TLC, washed by water, NH4Cl solution, dried over Na2SO4, and removal the solvent to give the crude 2-((3S)-1-(4-bromo-2-(2-(tetrahydro-2H-pyran-2-yloxy)ethyl)phenyl)pyrrolidin-3-yloxy)-3-chloropyridine (670 mg, 51.9% yield) which can be used to next step directly, Mass spec: 481 (M+1).

Step 2: 3-((4-((S)-3-(3-chloropyridin-2-yloxy)pyrrolidin-1-yl)-3-(2-(tetrahydro-2H-pyran-2-yloxy)ethyl)phenyl)(hydroxy)methyl)benzonitrile

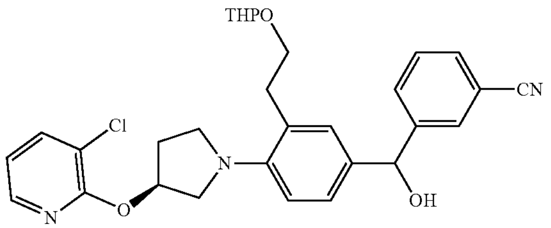

To a solution of 2-((3S)-1-(4-bromo-2-(2-(tetrahydro-2H-pyran-2-yloxy)ethyl)phenyl)pyrrolidin-3-yloxy)-3-chloropyridine (100 mg, 0.21 mmol) in 3 ml THE was added n-BuLi (0.1 ml, 0.25 mmol, 2.5M in hexane) at −78° C., and the reaction was stirred at rt for this temperature for 1 h, then 3-formylbenzonitrile (27 mg, 0.21 mmol) in 1 ml THE was added and stirred for 30 min, quenched with NH4Cl solution, extracted with EA, dried over Na2SO4, removal the solvent to left the crude product which was purified by prep-TLC to give 3-((4-((S)-3-(3-chloropyridin-2-yloxy)pyrrolidin-1-yl)-3-(2-(tetrahydro-2H-pyran-2-yloxy)ethyl)phenyl)(hydroxy)methyl)benzonitrile (35 mg, 31.5% yield), Mass spec: 534 (M+1).

Step 3: 3-((4-((S)-3-(3-chloropyridin-2-yloxy)pyrrolidin-1-yl)-3-(2-hydroxyethyl)phenyl)(hydroxy)methyl)benzonitrile

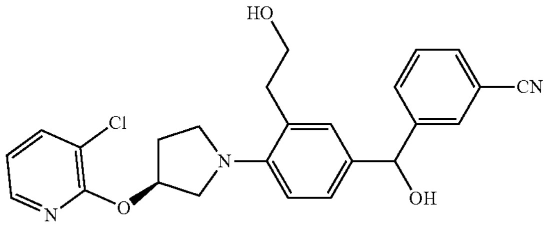 [SMILES: N#Cc1cccc(C(O)c2ccc(N3CC[C@H](Oc4ncccc4Cl)C3)c(CCO)c2)c1]

To a solution of 3-((4-((S)-3-(3-chloropyridin-2-yloxy)pyrrolidin-1-yl)-3-(2-(tetrahydro-2H-pyran-2-yloxy)ethyl)phenyl)(hydroxy)methyl)benzonitrile (20 mg, 0.045 mmol) in 1 ml EA was added 1 ml HCl/EA at 0° C., the mixture was stirred at rt and monitored by TLC. After finished, removal the solvent to left the crude product which was purified by Prep-HPLC to give 3-((4-((S)-3-(3-chloropyridin-2-yloxy)pyrrolidin-1-yl)-3-(2-hydroxyethyl)phenyl)(hydroxy)methyl)benzonitrile (5.7 mg, 28.5% yield), Mass spec: 450 (M+1), $t_R$=2.393 min $^1$H-NMR (400 Hz, DMSO) δ=8.168-8.154 (m, 1H), 7.816-7.734 (m, 2H), 7.681-7.535 (m, 2H), 7.334-7.312 (m, 1H), 7.160-7.084 (m, 2H), 6.995-6.962 (m, 1H), 6.893-6.967 (m, 1H), 6.521-6.500 (m, 1H), 6031 (s, 1H), 5.577 (s, 1H), 4.644-4.607 (m, 1H), 3.646-3.593 (m, 3H), 3.273-3.259 (m, 3H), 3.166-3.088 (m, 2H), 2.370-2.333 (m, 1H), 2.084-2.051 (m, 1H).

Example 319: (S)-2-(4-(3-(3-methylpyridin-2-yloxy)pyrrolidin-1-yl)biphenyl-3-yl)ethanol (Compound 1-193)

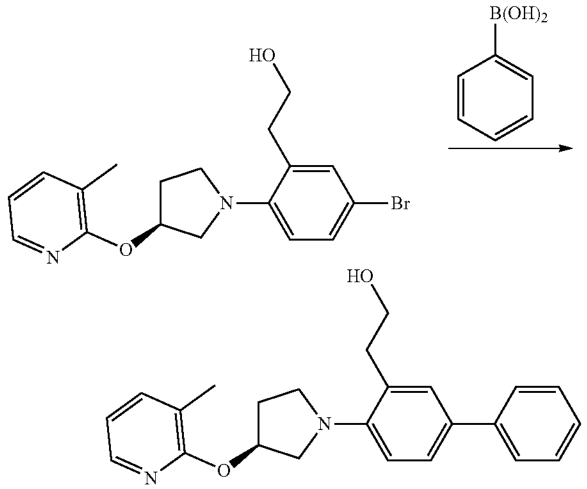

To a solution of(S)-2-(5-bromo-2-(3-(3-methylpyridin-2-yloxy)pyrrolidin-1-yl)phenyl)ethanol (90 mg, 0.24 mmol, prepared as example 301 step 3), phenylboronic acid (43.6 mg, 0.36 mmol), Pd(dppf)$Cl_2$ (13.5 mg, 15%) and $K_2CO_3$ (98.1 mg, 0.72 mmol) in 2 ml dioxane/H2O (v:v=5:1) and degassed for 2 min, then heated to 85° C. for 1 h under $N_2$. Diluted with EA, washed by water, brine, dried over Na2SO4, removal the solvent to left crude product which was purified by Prep-HPLC to give(S)-2-(4-(3-(3-methylpyridin-2-yloxy)pyrrolidin-1-yl)biphenyl-3-yl)ethanol (30 mg, 3 3.7% yield), Mass spec: 375 (M+1). $t_R$=2.861 min $^1$H-NMR (400 Hz, DMSO) δ=8.010-7.995 (m, 1H), 7.599-7.530 (m, 3H), 7.450-7.393 (m, 4H), 7.298-7.262 (m, 1H), 7.044-7.024 (m, 1H), 6.905-6.875 (m, 1H), 5.605-5.579 (m, 1H), 4.694-4.667 (m, 1H), 3.728-3.643 (m, 3H), 3.476-3.455 (m, 1H), 3.224-3.171 (m, 2H), 2.910-2.858 (m, 2H), 2.382-2.333 (m, 1H), 2.139 (s, 3H), 2.118-2.093 (m, 1H).

Example 320: (S)-2-(2'-chloro-4-(3-(3-methylpyridin-2-yloxy)pyrrolidin-1-yl)biphenyl-3-yl)ethanol (Compound 1-194)

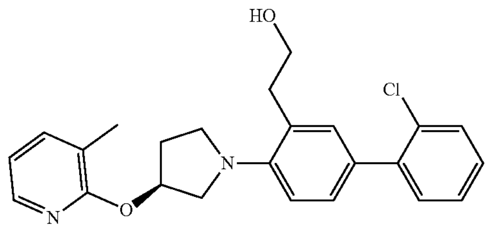

The title compound was prepared following procedures described in example 319 to give(S)-2-(2'-chloro-4-(3-(3-methylpyridin-2-yloxy)pyrrolidin-1-yl)biphenyl-3-yl)ethanol (12.7 mg, 12.9% yield), Mass spec: 409 (M+1), $t_R$=3.117 min $^1$H-NMR (400 Hz, DMSO) δ=8.012-7.995 (m, 1H), 7.552-7.511 (m, 2H), 7.391-7.312 (m, 3H), 7.234-7.184 (m, 2H), 7.027-7.007 (m, 1H), 6.908-6.877 (m, 1H), 5.613-5.585 (m, 1H), 4.684-4.657 (m, 1H), 3.732-3.620 (m, 3H), 3.502-3.481 (m, 1H), 3.245-3.164 (m, 2H), 2.891-2.834 (m, 2H), 2.384-2.335 (m, 1H), 2.143 (s, 3H), 2.117-2.101 (m, 1H).

Example 321: (S)-2-(2'-methyl-4-(3-(3-methylpyridin-2-yloxy)pyrrolidin-1-yl)biphenyl-3-yl)ethanol (Compound 1-198)

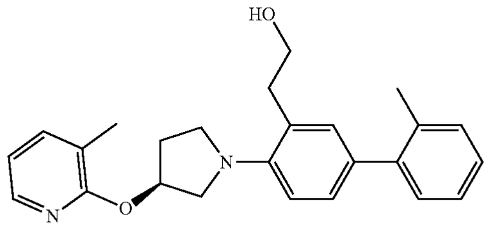 [SMILES: Cc1ccccc1-c1ccc(N2CC[C@H](Oc3ncccc3C)C2)c(CCO)c1]

The title compound was prepared following procedures described in example 319 to give (S)-2-(2'-methyl-4-(3-(3-methylpyridin-2-yloxy)pyrrolidin-1-yl)biphenyl-3-yl)ethanol (10.6 mg, 11.4% yield), Mass spec: 389 (M+1), $t_R$=2.978 min $^1$H-NMR (400 Hz, DMSO) δ=8.010-7.995 (m, 1H), 7.553-7.533 (m, 1H), 7.268-7.128 (m, 5H), 7.096-7.071 (m, 1H), 7.028-7.007 (m, 1H), 6.907-6.876 (m, 1H), 5.604-5.576 (m, 1H), 4.689-4.663 (m, 1H), 3.699-3.643 (m, 3H), 3.473-3.451 (m, 1H), 3.223-3.174 (m, 2H), 2.883-2.831 (m, 2H), 2.375-2.341 (m, 1H), 2.244 (s, 3H), 2.147 (s, 3H), 2.104 (m, 1H).

Example 322: (S)-2-(4-(3-(5-(trifluoromethyl)pyridin-2-yloxy)pyrrolidin-1-yl)biphenyl-3-yl)ethanol (Compound 1-142)

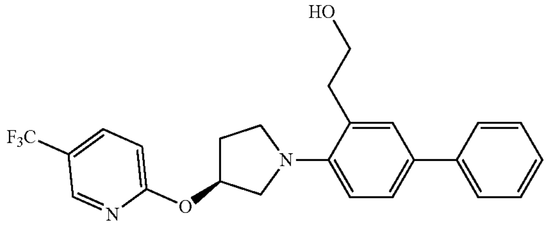 [SMILES: OCCc1cc(-c2ccccc2)ccc1N1CC[C@H](Oc2ccc(C(F)(F)F)cn2)C1]

The title compound was prepared following procedures described in example 319 to give (S)-2-(4-(3-(5-(trifluoromethyl)pyridin-2-yloxy)pyrrolidin-1-yl)biphenyl-3-yl)ethanol (42.5 mg, 22.0% yield), Mass spec: 429 (M+1), $t_R$=3.152 min, $^1$H-NMR (400 Hz, DMSO) δ=8.618 (s, 1H), 8.107-8.070 (m, 1H), 7.607-7.589 (m, 2H), 7.464-7.401 (m, 4H), 7.321-7.308 (m, 1H), 7.059-7.039 (m, 2H), 5.650 (s, 1H), 4.714 (s, 1H), 3.711-3.697 (m, 3H), 3.465-3.438 (m, 1H), 3.274-3.173 (m, 2H), 2.879 (m, 2H), 2.391-2.360 (m, 1H), 2.161-2.104 (m, 1H).

Example 324: (S)-3-(2'-methyl-4-(3-(5-(trifluoromethyl)pyridin-2-yloxy)pyrrolidin-1-yl)biphenyl-3-yl)propan-1-ol (Compound 1-176)

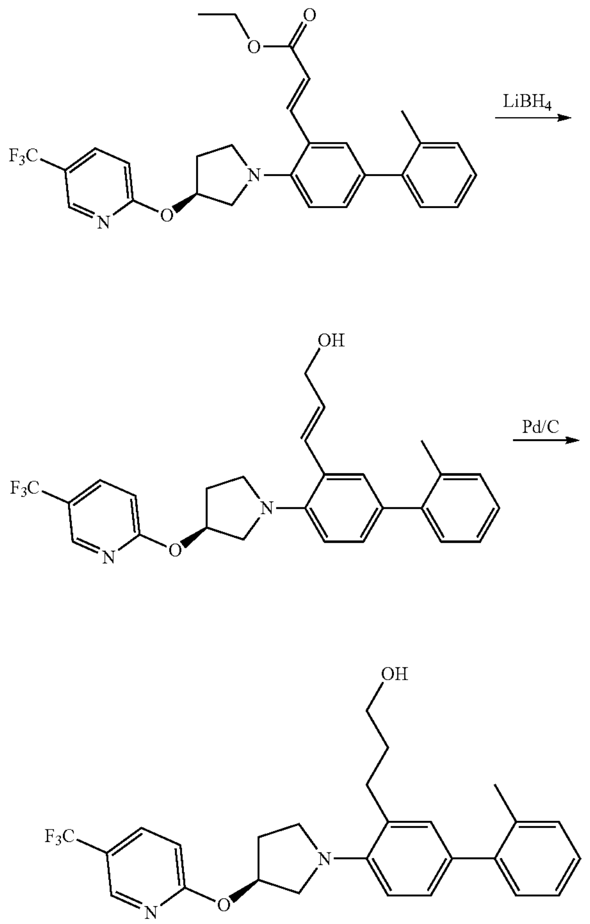

Step 1: (S, E)-3-(2'-methyl-4-(3-(5-(trifluoromethyl)pyridin-2-yloxy)pyrrolidin-1-yl)biphenyl-3-yl)prop-2-en-1-ol

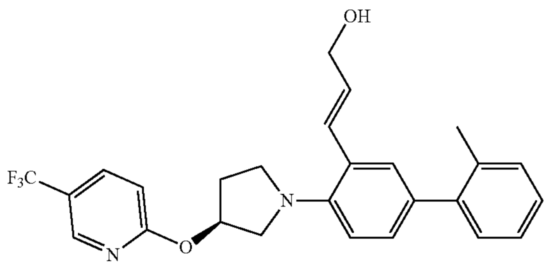 [SMILES: Cc1ccccc1-c1ccc(N2CC[C@H](Oc3ccc(C(F)(F)F)cn3)C2)c(/C=C/CO)c1]

To a solution of (S,E)-ethyl 3-(2'-methyl-4-(3-(5-(trifluoromethyl)pyridin-2-yloxy)pyrrolidin-1-yl)biphenyl-3-yl)acrylate (100 mg, 0.20 mmol, prepared as example 323 step 2) in DME was added $LiBH_4$ (8.7 mg, 0.4 mmol) and stirred at rt for overnight, LCMS detected 10% product, 14 mg $LiAH_4$ was added, stirred for another 3 h, after completed, then water was added slowly and extracted with DCM, dried over Na2SO4, removal the solvent to left crude (S, E)-3-(2'-methyl-4-(3-(5-(trifluoromethyl)pyridin-2-yloxy)pyrrolidin-1-yl)biphenyl-3-yl)prop-2-en-1-ol which was used directly (70 mg, 77.1% yield), Mass spec: 455 (M+1).

Step 2: (S)-3-(2'-methyl-4-(3-(5-(trifluoromethyl)pyridin-2-yloxy)pyrrolidin-1-yl)biphenyl-3-yl)propan-1-ol

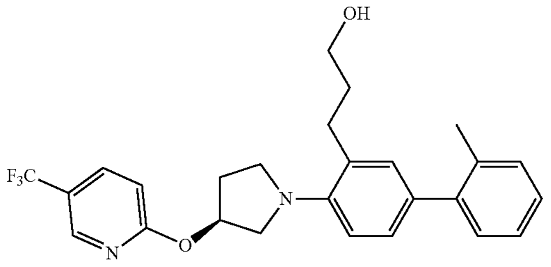

To a solution of (S, E)-3-(2'-methyl-4-(3-(5-(trifluoromethyl)pyridin-2-yloxy)pyrrolidin-1-yl)biphenyl-3-yl)prop-2-en-1-ol (80 mg, 0.18 mmol) in 2 mL MeOH was added Pd/C. the mixture was stirred at rt for 2 h under $H_2$, TLC indicated the reaction was completed, then Pd/C was filtered and the filtrate was concentrated, purified by Prep-HPLC to give the product (20.0 mg, 25.0% yield), Mass spec: 457 (M+1), $t_R$=3.592 min $^1$H-NMR (400 Hz, DMSO) δ=8.620 (s, 1H), 8.101-8.074 (m, 1H), 7.263-7.230 (m, 4H), 7.088-7.063 (m, 4H), 5.660 (s, 1H), 4.501 (m, 1H), 3.687 (m, 1H), 3.440-3.425 (m, 3H), 3.269-3.191 (m, 2H), 2.687 (m, 2H), 2.417 (m, 1H), 2.246 (m, 3H), 2.127 (m, 1H), 1.734 (m, 2H).

Example 325: (S)-3-(4-(3-(5-(trifluoromethyl)pyridin-2-yloxy)pyrrolidin-1-yl)biphenyl-3-yl)propan-1-ol (Compound 1-138)

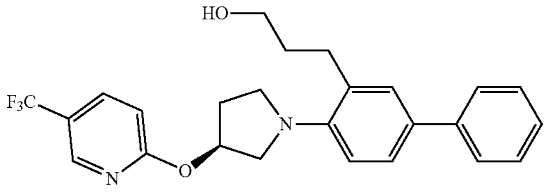 [SMILES: OCCCc1cc(-c2ccccc2)ccc1N1CC[C@H](Oc2ccc(C(F)(F)F)cn2)C1]

The title compound was prepared following procedures described in example 324 to give (S)-3-(4-(3-(5-(trifluoromethyl)pyridin-2-yloxy)pyrrolidin-1-yl)biphenyl-3-yl)propan-1-ol (12.8 mg, 25.6% yield), Mass spec: 443 (M+1), $t_R$=3.134 min $^1$H-NMR (400 Hz, DMSO) δ=8.623-8.622 (m, 1H), 8.098-8.071 (m, 1H), 7.613-7.592 (m, 2H), 7.439-7.389 (m, 4H), 7.306-7.288 (m, 1H), 7.058-7.021 (m, 2H), 5.657 (m, 1H), 4.529-4.503 (m, 1H), 3.719-3.668 (m, 1H), 3.341-3.335 (m, 3H), 3.275-3.247 (m, 2H), 2.726-2.715 (m, 2H), 2.388-2.343 (m, 1H), 2.145-2.085 (m, 1H), 1.797-1.761 (m, 2H).

Example 326: (S)-3-(4-(3-(3-(trifluoromethyl)pyridin-2-yloxy)pyrrolidin-1-yl)biphenyl-3-yl)propan-1-ol (Compound 1-170)

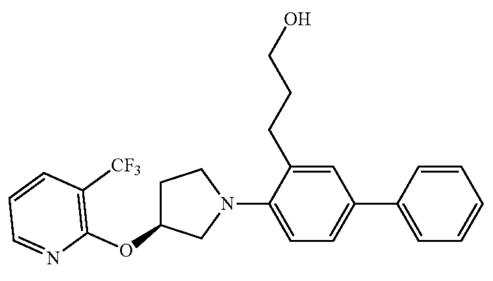 [SMILES: OCCCc1cc(-c2ccccc2)ccc1N1CC[C@H](Oc2ncccc2C(F)(F)F)C1]

The title compound was prepared following procedures described in example 324 to give (S)-3-(4-(3-(3-(trifluoromethyl)pyridin-2-yloxy)pyrrolidin-1-yl)biphenyl-3-yl)propan-1-ol (60 mg, 60% yield), Mass spec: 443 (M+1), $t_R$=3.337 min $^1$H-NMR (400 Hz, DMSO) δ=8.465-8.454 (m, 1H), 8.113-8.094 (m, 1H), 7.600-7.581 (m, 2H), 7.427-7.390 (m, 4H), 7.295-7.166 (m, 2H), 7.017-6.997 (m, 1H), 5.723 (s, 1H), 4.493-4.468 (m, 1H), 3.712-3.672 (m, 1H), 3.459-3.402 (m, 3H), 3.234-3.174 (m, 2H), 2.739-2.684 (m, 2H), 2.387-2.354 (m, 1H), 2.114-2.083 (m, 1H), 1.787-1.752 (m, 2H).

Example 327: (S)-5-(2-chlorophenoxy)-2-(3-(3-chloropyridin-2-yloxy)pyrrolidin-1-yl)benzamide (Compound 1-181)

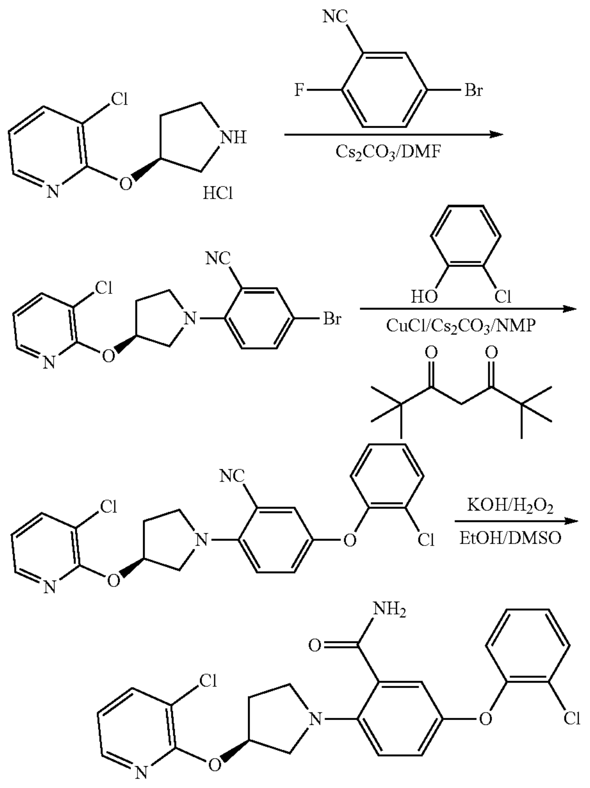

Step 1: (S)-5-bromo-2-(3-(3-chloropyridin-2-yloxy)pyrrolidin-1-yl)benzonitrile

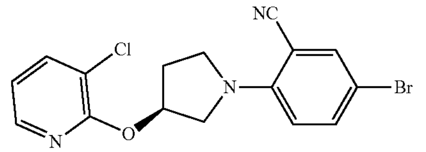 [SMILES: N#Cc1cc(Br)ccc1N1CC[C@H](Oc2ncccc2Cl)C1]

To a solution of (S)-3-chloro-2-(pyrrolidin-3-yloxy)pyridine hydrochloride (4.0 g, 17.1 mmol), 5-bromo-2-fluorobenzonitrile (4.1 g, 20.5 mmol), $Cs_2CO_3$ (16.7 g, 51.3 mmol) in 10 ml DMF was stirred at 100° C. for 3 h. then the mixture was diluted 50 ml EA and washed with 10% LiCl solution, the EA layer was dried over Na2SO4, filtered and removal the solvent to left the crude product which was purified by silica gel to give (S)-5-bromo-2-(3-(3-chloropyridin-2-yloxy)pyrrolidin-1-yl)benzonitrile as brown solid (2.8 g, 37.3%), Mass Spec: 378 (M+1).

Step 2: (S)-5-(2-chlorophenoxy)-2-(3-(3-chloropyridin-2-yloxy)pyrrolidin-1-yl)benzonitrile

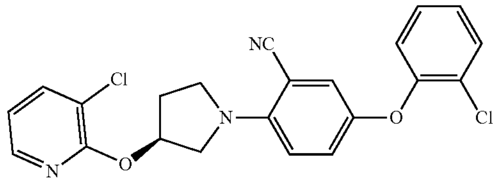 [SMILES: N#Cc1cc(Oc2ccccc2Cl)ccc1N1CC[C@H](Oc2ncccc2Cl)C1]

To a solution of (S)-5-bromo-2-(3-(3-chloropyridin-2-yloxy)pyrrolidin-1-yl)benzonitrile (1.0 g, 2.6 mmol), 2-chlorophenol (665 mg, 5.2 mmol), CuCl (129 mg, 1.3 mmol), $Cs_2CO_3$ (1.7 g, 5.2 mmol) and 2,2,6,6-tetramethylheptane-3,5-dione (239 mg, 1.3 mmol) in 3 ml NMP, and degassed with $N_2$ for 1 min, then heated at 220° C. in microwave for 30 min, the mixture was filtered and the filtrate was evaporated and purified by silica gel to give (S)-5-(2-chlorophenoxy)-2-(3-(3-chloropyridin-2-yloxy)pyrrolidin-1-yl)benzonitrile as solid (100 mg, 9.1% yield), Mass Spec: 426 (M+1).

Step 3: (S)-5-(2-chlorophenoxy)-2-(3-(3-chloropyridin-2-yloxy)pyrrolidin-1-yl)benzamide

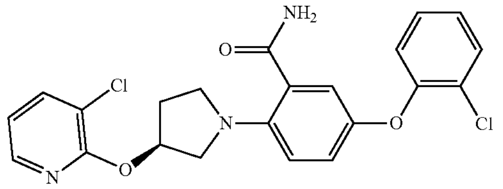 [SMILES: NC(=O)c1cc(Oc2ccccc2Cl)ccc1N1CC[C@H](Oc2ncccc2Cl)C1]

To a solution of (S)-5-(2-chlorophenoxy)-2-(3-(3-chloropyridin-2-yloxy)pyrrolidin-1-yl)benzonitrile (50 mg, 0.1 mmol) in 4 ml EtOH and 0.6 ml DMSO was added KOH at rt, then stirred at 60° C. for 5 min, then the mixture was cooled to rt and added H2O2 (0.3 ml). After stirring for 30 min at rt, the precipitate was filtered, and the solid was washed with 10 ml EtOH and 5 ml $Et_2O$, dried in vacuo to give (S)-5-(2-chlorophenoxy)-2-(3-(3-chloropyridin-2-yloxy)pyrrolidin-1-yl)benzamide as white solid (10.0 mg, 21.2% yield), Mass Spec: 444 (M+1), $t_R$=3.035 min $^1$H-NMR (400 Hz, DMSO) δ=8.161-8.145 (m, 1H), 7.987 (s, 1H), 7.920-7.897 (m, 1H), 7.575-7.552 (m, 1H), 7.425 (s, 1H), 7.314-7.295 (m, 1H), 7.158-7.139 (m, 1H), 7.065-6.898 (m, 5H), 5.642 (s, 1H), 3.805 (m, 1H), 3.506 (m, 1H), 3.336-3.249 (m, 2H), 2.362-2.308 (m, 1H), 2.179-2.165 (m, 1H).

Example 330: (S)-(2-(3-(5-methylpyridin-2-yloxy)pyrrolidin-1-yl)-5-(pyridin-2-yl)phenyl)methanol (Compound 1-220)

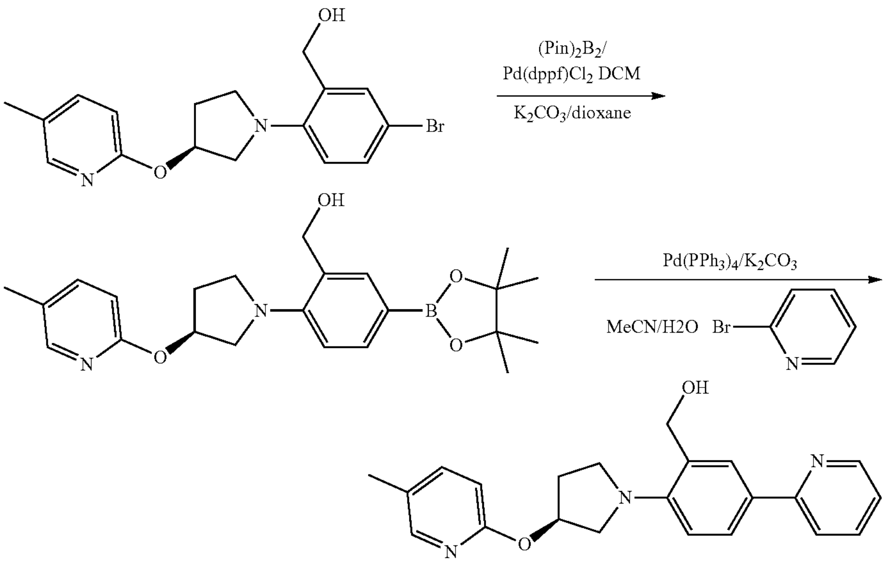

Step 1: (S)-(2-(3-(5-methylpyridin-2-yloxy)pyrrolidin-1-yl)-5-(4,4,5,5-tetramethyl-1,3,2-dioxaborolan-2-yl)phenyl)methanol

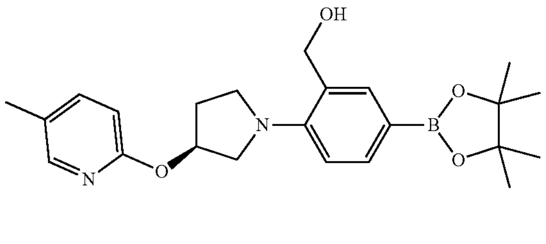

A solution of (S)-(5-bromo-2-(3-(5-methylpyridin-2-yloxy)pyrrolidin-1-yl)phenyl)methanol (700 mg, 1.93 mmol) (prepared as example 236 step 2), $(Pin)_2B2$ (983.7 mg, 3.87 mmol), $Pd(dppf)Cl_2$ DCM (157 mg, 0.193 mmol) and $K_2CO_3$ (799.0 mg, 5.79 mmol) in 10 ml Dixoane was degassed with $N_2$ for 2 min, and stirred at 90° C. for 2 h under $N_2$. The mixture was diluted with EA, washed by water, brine, dried over Na2SO4, removal the solvent to left the crude product which was purified by silica gel to give (S)-(2-(3-(5-methylpyridin-2-yloxy)pyrrolidin-1-yl)-5-(4,4,5,5-tetramethyl-1,3,2-dioxaborolan-2-yl)phenyl)methanol (200 mg, 25% yield) as oil, Mass spec: 411 (M+1).

Step 2: (S)-(2-(3-(5-methylpyridin-2-yloxy)pyrrolidin-1-yl)-5-(pyridin-2-yl)phenyl)methanol

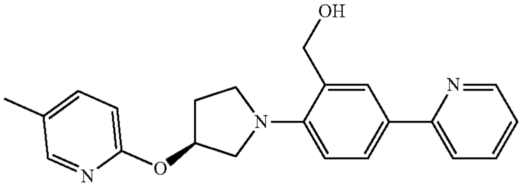 [SMILES: Cc1ccc(O[C@H]2CCN(c3ccc(-c4ccccn4)cc3CO)C2)nc1]

To a solution of (S)-(2-(3-(5-methylpyridin-2-yloxy)pyrrolidin-1-yl)-5-(4,4,5,5-tetramethyl-1,3,2-dioxaborolan-2-yl)phenyl)methanol (100 mg, 0.24 mmol), 2-bromopyridine (42.6 mg, 0.27 mmol), $Pd(PPh_3)_4$ (28 mg, 0.024 mmol) and $K_2CO_3$ (100 mg, 0.72 mmol) in 2 ml MeCN and 0.4 ml $H_2O$ was degassed for 2 min, and stirred at 80° C. for 2 h, The mixture was diluted with EA, washed by water, brine, dried over Na2SO4, removal the solvent to left the crude product which was purified by Prep-HPLC to give (S)-(2-(3-(5-methylpyridin-2-yloxy)pyrrolidin-1-yl)-5-(pyridin-2-yl)

phenyl)methanol (40 mg, 39% yield), Mass spec: 362 (M+1), $t_R$=0.819 min, $^1$H-NMR (400 Hz, DMSO) δ=8.685-8.671 (d, 1H), 8.473-8.455 (m, 1H), 8.350-8.330 (d, 1H), 8.096-7.994 (m, 3H), 7.781-7.764 (m, 1H), 7.615-7.589 (m, 1H), 6.919-6.793 (m, 2H), 5.606 (s, 1H), 4.683-4.590 (m, 2H), 4.010 (m, 1H), 3.695-3.665 (m, 3H), 2.328-2.286 (m, 1H), 2.210-2.180 (m, 4H).

Example 333: (S)-(6-(2-methoxyphenyl)-3-(3-(3-methylpyridin-2-yloxy)pyrrolidin-1-yl)pyridin-2-yl) methanol (Compound 1-186)

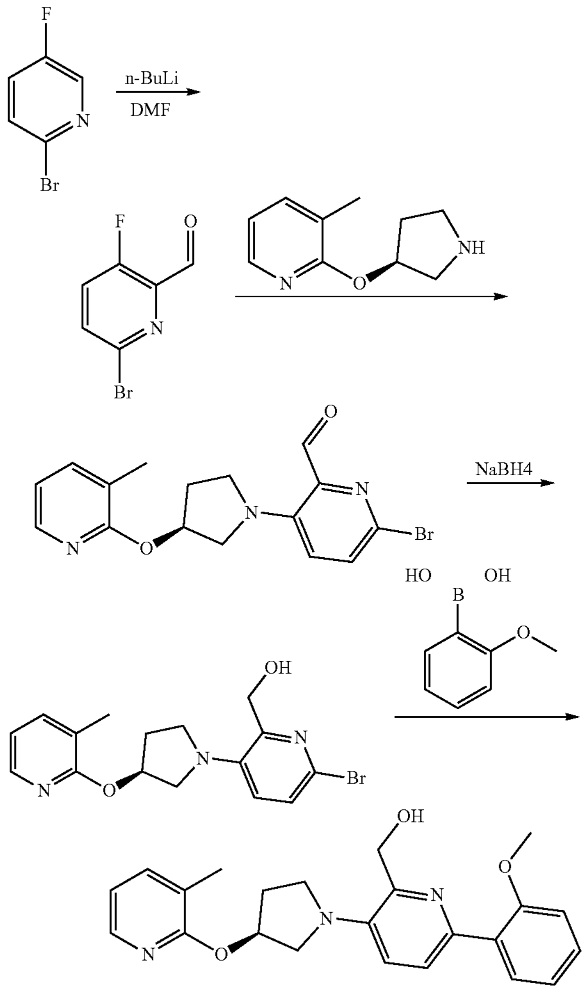

Step 1: 6-bromo-3-fluoropicolinaldehyde

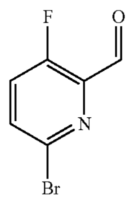

To a solution of 2-bromo-5-fluoropyridine (10 g, 56.8 mmol) was dissolved in 120 mL $Et_2O$. was added n-BuLi (27.27 ml, 2.5 M in hexane) slowly under $N_2$ at −78° C. during 20 min, the mixture was stirred at −78° C. for 30 min, before DMF (6.63 ml, 85.2 mmol) was added slowly. the reaction was monitored by TLC, after finished, quenched by water, con HCl (8 ml) was added, stirred at r.t for 30 min, diluted with EA, combined the organic layer, dried over $Na_2SO_4$, removal the solvent which was purified by silica gel to give 6-bromo-3-fluoropicolinaldehyde (3.6 g, 31.3% yield) as light-yellow solid, Mass spec: 204 (M+H).

Step 2: (S)-6-bromo-3-(3-(3-methylpyridin-2-yloxy) pyrrolidin-1-yl)picolinaldehyde

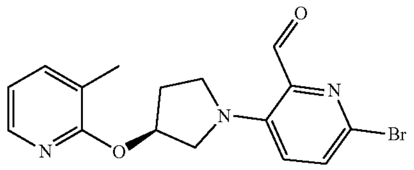 [SMILES: Cc1cccnc1O[C@H]1CCN(c2ccc(Br)nc2C=O)C1]

To a solution of 6-bromo-3-fluoropicolinaldehyde (500 mg, 2.45 mmol) in 8 mL MeCN was added DIPEA (1.26 g, 9.8 mmol) and (S)-3-methyl-2-(pyrrolidin-3-yloxy)pyridine (524 mg, 2.94 mmol) (prepared as intermediate 4) with stirring. The mixture was stirred at 80° C. for 2 h, removal the solvent to left the crude product which was purified by silica gel to give (S)-6-bromo-3-(3-(3-methylpyridin-2-yloxy)pyrrolidin-1-yl)picolinaldehyde (400 mg, 60% yield), Mass spec: 362 (M+H).

Step 3: (S)-(6-bromo-3-(3-(3-methylpyridin-2-yloxy)pyrrolidin-1-yl)pyridin-2-yl)methanol

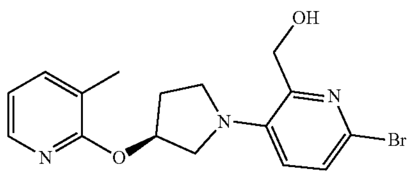 [SMILES: Cc1cccnc1O[C@H]1CCN(c2ccc(Br)nc2CO)C1]

To a solution of (S)-6-bromo-3-(3-(3-methylpyridin-2-yloxy)pyrrolidin-1-yl)picolinaldehyde (450 mg, 1.24 mmol) in 4 mL MeOH was added $NaBH_4$ (56.5 mg, 1.5 mmol) at 0° C. Then the mixture was stirred at r.t for 30 min, the reaction was quenched by $H_2O$, extracted by DCM, washed with water and brine, dried over $Na_2SO_4$, removal the solvent to left the crude product which was purified to give (S)-(6-bromo-3-(3-(3-methylpyridin-2-yloxy)pyrrolidin-1-yl)pyridin-2-yl)methanol (450 mg, quant.), Mass spec: 364 (M+H).

Step 4: S)-(6-(2-methoxyphenyl)-3-(3-(3-methylpyridin-2-yloxy)pyrrolidin-1-yl)pyridin-2-yl) methanol

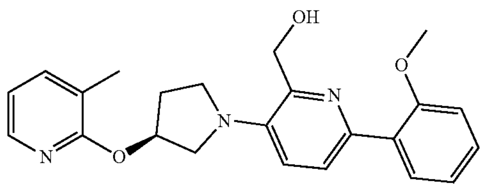 [SMILES: COc1ccccc1-c1ccc(N2CC[C@H](Oc3ncccc3C)C2)c(CO)n1]

To a solution of (S)-(6-bromo-3-(3-(3-methylpyridin-2-yloxy)pyrrolidin-1-yl)pyridin-2-yl)methanol (50 mg, 0.13 mmol) in 1.5 ml dioxane/$H_2O$ (v:v=5:1) was added 2-methoxyphenylboronic acid (25 mg, 0.164 mmol), $K_2CO_3$ (56.9 mg, 0.41 mmol) and pd(dppf)$Cl_2$ (10 mg) with stirring. Then the mixture was stirred at 90° C. under $N_2$ for 2 h, the reaction was the product was extracted by EA, washed by water and brine. Removal the solvent to left crude product which was purified by Pre-HPLC to give (S)-(6-(2-methoxyphenyl)-3-(3-(3-methylpyridin-2-yloxy)pyrrolidin-1-yl) pyridin-2-yl)methanol (20 mg, 20% yield). Mass spec: 392 (M+H), $t_R$=1.908 min, $^1$H-NMR (400 Hz, DMSO) δ=8.010-8.023 (d, 1H), 7.745-7.812 (m, 2H), 7.541-7.559 (d, 1H), 7.293-7.382 (m, 2H), 7.059-7.152 (m, 2H), 6.894-6.952 (d, 1H), 5.644 (s, 1H), 4.706-4.736 (m, 1H), 3.902-3.912 (m, 1H), 3.886 (s, 1H), 3.599-3.618 (m, 1H), 3.367-3.498 (m, 1H), 2.315-2.348 (m, 1H), 2.149-2.181 (m, 1H), 2.154 (s, 3H).

Example 334: (S)-(6-phenoxy-3-(3-(5-(trifluoromethyl)pyridin-2-yloxy)pyrrolidin-1-yl)pyridin-2-yl) methanol (Compound 1-139)

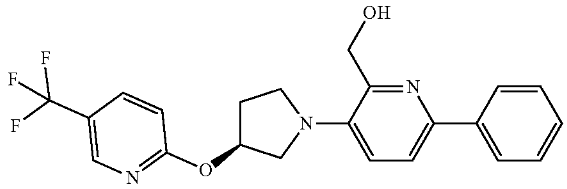 [SMILES: OCc1nc(-c2ccccc2)ccc1N1CC[C@H](Oc2ccc(C(F)(F)F)cn2)C1]

The title compound was prepared following procedures described in example 333 to (S)-(6-phenoxy-3-(3-(5-(trifluoromethyl)pyridin-2-yloxy)pyrrolidin-1-yl)pyridin-2-yl) methanol (20 mg, 50% yield), Mass spec: 432 (M+H), $t_R$=2.449 min. $^1$H-NMR (400 Hz, DMSO) δ=8.632 (s, 1H), 8.071-8.099 (m, 1H), 8.024-8.042 (d, 1H), 7.748-7.769 (d, 1H), 7.423-7.461 (m, 2H), 7.331-7.349 (m, 1H), 7.056-7.235 (d, 1H), 5.715 (m, 1H), 5.164-5.190 (m, 1H), 4.680-4.719 (m, 2H), 3.882-3.606 (m, 1H), 3.546-3.606 (m, 2H), 3.389-3.542 (m, 1H), 3.334-2.385 (m, 1H), 2.230-2.231 (m, 1H).

Example 335: (S)-(3-(3-(3-methylpyridin-2-yloxy) pyrrolidin-1-yl)-6-o-tolylpyridin-2-yl)methanol (Compound 1-179)

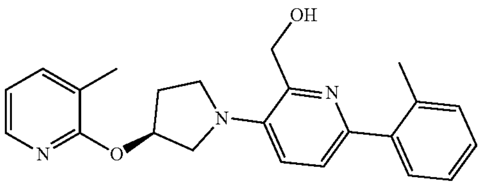 [SMILES: Cc1ccccc1-c1ccc(N2CC[C@H](Oc3ncccc3C)C2)c(CO)n1]

The title compound was prepared following procedures described in example 333 to give (S)-(3-(3-(3-methylpyridin-2-yloxy)pyrrolidin-1-yl)-6-o-tolylpyridin-2-yl)methanol (20 mg, 23% yield), Mass spec: 376 (M+H), $t_R$=2.196 min, $^1$H-NMR (400 Hz, DMSO) δ=8.011-8.027 (m, 1H), 7.546-7.564 (d, 1H), 8.024-8.042 (d, 1H), 7.748-7.769 (d, 1H), 7.423-7.461 (m, 2H), 7.331-7.349 (m, 1H), 7.056-7.235 (d, 1H), 5.715 (m, 1H), 5.164-5.190 (m, 1H), 4.680-4.719 (m, 2H), 3.882-3.606 (m, 1H), 3.546-3.606 (m, 2H), 3.389-3.542 (m, 1H), 3.334-2.385 (m, 1H), 2.230-2.231 (m, 1H).

Example 336: (S)-(6-(2-ethylphenyl)-3-(3-(3-methylpyridin-2-yloxy)pyrrolidin-1-yl)pyridin-2-yl) methanol (Compound 1-187)

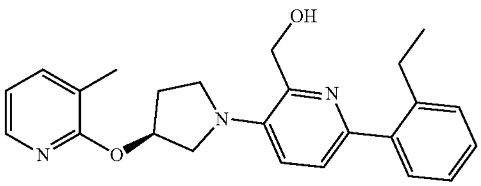 [SMILES: CCc1ccccc1-c1ccc(N2CC[C@H](Oc3ncccc3C)C2)c(CO)n1]

The title compound was prepared following procedures described in example 333 to give (S)-(6-(2-ethylphenyl)-3-(3-(3-methylpyridin-2-yloxy)pyrrolidin-1-yl)pyridin-2-yl) methanol (30 mg, 29% yield), Mass spec: 390 (M+H), $t_R$=2.436 min, $^1$H-NMR (400 Hz, DMSO) δ=8.011-8.022 (d, 1H), 7.540-7.558 (d, 1H), 7.234-7.310 (m, 6H), 6.891-6.922 (m, 1H), 5.641 (s, 1H), 5.065-5.091 (m, 1H), 4.611-4.714 (m, 2H), 3.855-3.895 (m, 1H), 3.565-3.605 (m, 1H), 3.410-3.478 (m, 2H), 2.673-2.728 (m, 2H), 2.509-2.510 (m, 1H), 2.334-2.354 (m, 1H), 2.320 (s, 3H), 1.048-1.086 (m, 3H).

Example 337: (S)-2-(6-(hydroxymethyl)-5-(3-(3-methylpyridin-2-yloxy)pyrrolidin-1-yl)pyridin-2-yl) benzonitrile (Compound 1-192)

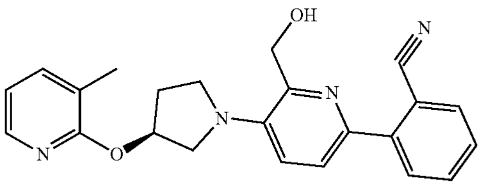 [SMILES: Cc1cccnc1O[C@H]1CCN(c2ccc(-c3ccccc3C#N)nc2CO)C1]

The title compound was prepared following procedures described in example 333 to give (S)-2-(6-(hydroxymethyl)-5-(3-(3-methylpyridin-2-yloxy)pyrrolidin-1-yl)pyridin-2-yl)benzonitri (30 mg, 30% yield), Mass spec: 387 (M+H), $t_R$=2.821 min, $^1$H-NMR (400 Hz, DMSO) δ=8.015-8.024 (m, 1H), 7.895-7.946 (m, 2H), 7.725-7.782 (m, 2H), 7.656-7.710 (m, 1H), 7.509-7.559 (m, 2H), 7.260-7.282 (d, 1H), 5.656-5.666 (m, 1H), 5.031-5.056 (m, 1H), 4.698-4.807 (m, 2H), 3.943-3.984 (m, 1H), 3.659-3.677 (m, 1H), 3.514-3.561 (m, 2H), 2.308-2.342 (m, 1H), 2.178-2.202 (m, 1H), 2.114 (s, 3H).

Example 338: (S)-(6-o-tolyl-3-(3-(5-(trifluoromethyl)pyridin-2-yloxy)pyrrolidin-1-yl)pyridin-2-yl) methanol (Compound 1-182)

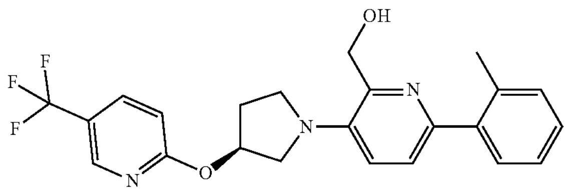 [SMILES: Cc1ccccc1-c1ccc(N2CC[C@H](Oc3ccc(C(F)(F)F)cn3)C2)c(CO)n1]

The title compound was prepared following procedures described in example 333 to give (S)-(6-o-tolyl-3-(3-(5-(trifluoromethyl)pyridin-2-yloxy)pyrrolidin-1-yl)pyridin-2-yl)methanol (28 mg, 50% yield), Mass spec: 430 (M+H), $t_R$=2.563 min, $^1$H-NMR (400 Hz, DMSO) δ=8.633 (s, 1H), 8.076-8.104 (m, 1H), 7.376-7.396 (m, 2H), 7.322-7.343 (m, 4H), 7.039-7.016 (m, 1H), 5.713 (s, 1H), 5.099-5.125 (m, 1H), 4.613-4.719 (m, 2H), 3.877-3.917 (m, 1H), 3.538-3.598 (m, 2H), 3.417-3.459 (m, 1H), 2.505-2.513 (m, 1H), 2.375 (s, 3H), 2.198-2.216 (m, 1H).

Example 339: (S)-(6-(2-methoxyphenyl)-3-(3-(5-(trifluoromethyl)pyridin-2-yloxy)pyrrolidin-1-yl) pyridin-2-yl)methanol (Compound 1-183)

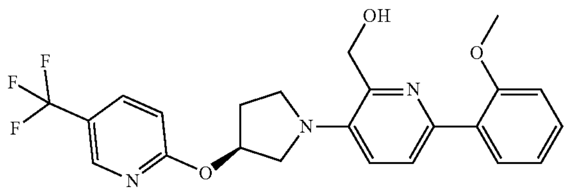

The title compound was prepared following procedures described in example 333 to give (S)-(6-(2-methoxyphenyl)-3-(3-(5-(trifluoromethyl)pyridin-2-yloxy)pyrrolidin-1-yl) pyridin-2-yl)methanol (18 mg, 23% yield), Mass spec: 446 (M+H), $t_R$=2.069 min, $^1$H-NMR (400 Hz, DMSO) δ=8.632 (s, 1H), 8.071-8.099 (m, 1H), 7.781-7.800 (m, 1H), 7.682-7.704 (m, 1H), 7.325-7.349 (m, 1H), 7.196-7.218 (m, 1H), 7.056-7.098 (m, 1H), 7.056-7.057 (m, 1H), 7.106-7.036 (m, 2H), 5.694-5.720 (m, 1H), 5.126-5.153 (m, 1H), 4.610-4.716 (m, 2H), 3.858-3.899 (m, 1H), 3.825 (s, 3H), 3.521-3.581 (m, 2H), 3.410-3.432 (m, 1H), 2.357-2.371 (m, 1H), 2.191-2.208 (m, 1H).

Example 340: (S)-(6-(2-ethylphenyl)-3-(3-(5-(trifluoromethyl)pyridin-2-yloxy)pyrrolidin-1-yl)pyridin-2-yl)methanol (Compound 1-196)

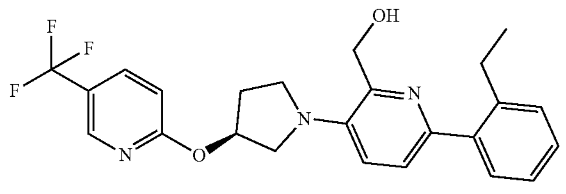 [SMILES: CCc1ccccc1-c1ccc(N2CC[C@H](Oc3ccc(C(F)(F)F)cn3)C2)c(CO)n1]

The title compound was prepared following procedures described in example 333 to give (S)-(6-(2-ethylphenyl)-3-(3-(5-(trifluoromethyl)pyridin-2-yloxy)pyrrolidin-1-yl)pyridin-2-yl)methanol (16 mg, 20% yield), Mass spec: 444 (M+H), $t_R$=2.776 min, $^1$H-NMR (400 Hz, DMSO) δ=8.622 (s, 1H), 8.066-8.094 (m, 1H), 7.229-7.307 (m, 6H), 7.033-7.055 (d, 1H), 5.697-5.722 (m, 1H), 5.068-5.094 (m, 1H), 4.607-4.713 (m, 2H), 3.871-3.912 (m, 1H), 3.530-3.594 (m, 2H), 3.372-3.445 (m, 1H), 2.668-2.724 (m, 2H), 2.361-2.395 (m, 1H), 2.193-2.218 (m, 1H), 1.044-1.081 (m, 3H).

Example 341: (S)-2-(6-(hydroxymethyl)-5-(3-(5-(trifluoromethyl)pyridin-2-yloxy)pyrrolidin-1-yl) pyridin-2-yl)benzonitrile (Compound 1-197)

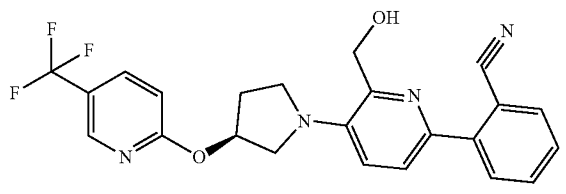 [SMILES: N#Cc1ccccc1-c1ccc(N2CC[C@H](Oc3ccc(C(F)(F)F)cn3)C2)c(CO)n1]

The title compound was prepared following procedures described in example 333 to give (S)-2-(6-(hydroxymethyl)-5-(3-(5-(trifluoromethyl)pyridin-2-yloxy)pyrrolidin-1-yl) pyridin-2-yl)benzonitrile (17 mg, 24% yield), Mass spec: 441 (M+H), $t_R$=3.084 min, $^1$H-NMR (400 Hz, DMSO) δ=8.636 (s, 1H), 8.074-8.103 (m, 1H), 7.894-7.944 (m, 2H), 7.748-7.787 (m, 2H), 7.513-7.549 (m, 1H), 7.254-7.276 (d, 1H), 3.633-3.684 (m, 2H), 3.513-3.516 (m, 1H), 2.348-2.397 (m, 1H), 2.204-2.248 (m, 1H).

Example 342: (S)-(6-(2-ethylphenyl)-3-(3-(5-methylpyridin-2-yloxy)pyrrolidin-1-yl)pyridin-2-yl) methanol (Compound 1-185)

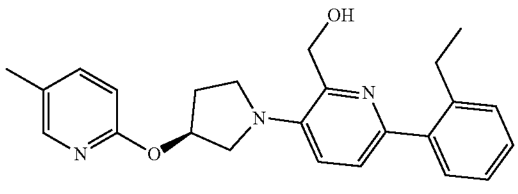 [SMILES: CCc1ccccc1-c1ccc(N2CC[C@H](Oc3ccc(C)cn3)C2)c(CO)n1]

The title compound was prepared following procedures described in example 333 to give (S)-(6-(2-ethylphenyl)-3-(3-(5-methylpyridin-2-yloxy)pyrrolidin-1-yl)pyridin-2-yl)

methanol (30 mg, 37% yield), Mass spec: 390 (M+H), $t_R$=2.388 min, $^1$H-NMR (400 Hz, DMSO) δ=8.022 (s, 1H), 7.532-7.554 (m, 1H), 7.218-7.309 (m, 6H), 6.727-6.784 (d, 1H), 5.577 (d, 1H), 5.074-5.100 (m, 1H), 4.633-4.677 (m, 2H), 3.841-3.880 (m, 1H), 3.411-3.570 (m, 3H), 2.671-2.727 (m, 2H), 2.304-2.337 (m, 1H), 2.135-2.150 (m, 1H), 1.046-1.084 (m, 3H).

Example 343: (S)-(3-(3-(5-methylpyridin-2-yloxy)pyrrolidin-1-yl)-6-o-tolylpyridin-2-yl)methanol (Compound 1-189)

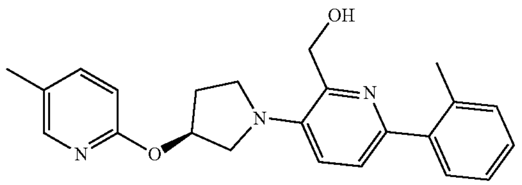 [SMILES: Cc1ccc(O[C@H]2CCN(c3ccc(-c4ccccc4C)nc3CO)C2)nc1]

The title compound was prepared following procedures described in example 333 to give (S)-(3-(3-(5-methylpyridin-2-yloxy)pyrrolidin-1-yl)-6-o-tolylpyridin-2-yl)methanol (30 mg, 37% yield), Mass spec: 376 (M+H), $t_R$=2.132 min, $^1$H-NMR (400 Hz, DMSO) δ=8.022 (s, 1H), 7.530-7.551 (d, 1H), 7.216-7.396 (m, 6H), 6.728-6.749 (d, 1H), 5.577 (d, 1H), 5.088-5.114 (m, 1H), 4.637-4.680 (m, 2H), 3.839-3.866 (m, 1H), 3.373-3.570 (m, 3H), 2.350 (s, 3H), 2.305-2.350 (m, 1H), 2.214 (s, 3H), 2.152-2.214 (m, 1H).

Example 344: (S)-2-(6-(hydroxymethyl)-5-(3-(5-methylpyridin-2-yloxy)pyrrolidin-1-yl)pyridin-2-yl)benzonitrile (Compound 1-190)

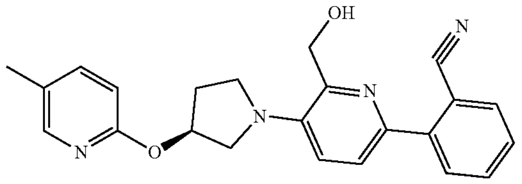 [SMILES: Cc1ccc(O[C@H]2CCN(c3ccc(-c4ccccc4C#N)nc3CO)C2)nc1]

The title compound was prepared following procedures described in example 333 to give (S)-2-(6-(hydroxymethyl)-5-(3-(5-methylpyridin-2-yloxy)pyrrolidin-1-yl)pyridin-2-yl)benzonitrile (20 mg, 22% yield), Mass spec: 387 (M+H), $t_R$=2.803 min, $^1$H-NMR (400 Hz, DMSO) δ=8.009 (s, 1H), 7.892-7.943 (m, 2H), 7.718-7.785 (m, 2H), 7.529-7.556 (m, 2H), 7.238-7.259 (d, 1H), 6.728-6.749 (d, 1H), 5.598 (s, 1H), 5.037-5.062 (m, 1H), 4.725-4.769 (m, 2H), 3.934-3.950 (m, 1H), 3.516-3.640 (m, 3H), 2.331-2.332 (m, 1H), 2.214-2.215 (m, 1H).

Example 345: (S)-(6-(2-methoxyphenyl)-3-(3-(5-methylpyridin-2-yloxy)pyrrolidin-1-yl)pyridin-2-yl)methanol (Compound 1-191)

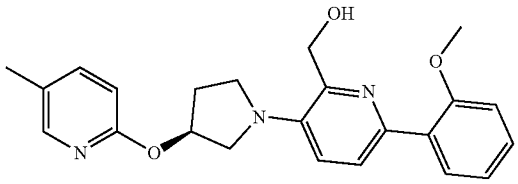 [SMILES: COc1ccccc1-c1ccc(N2CC[C@H](Oc3ccc(C)cn3)C2)c(CO)n1]

The title compound was prepared following procedures described in example 7 using (S)-(6-bromo-3-(3-(3-methylpyridin-2-yloxy)pyrrolidin-1-yl)pyridin-2-yl)methanol and 2-methoxyphenylboronic acid (20 mg, 23% yield), Mass spec: 392 (M+H), $t_R$=1.884 min, $^1$H-NMR (400 Hz, DMSO) δ=8.000 (s, 1H), 7.780-7.800 (m, 1H), 7.675-7.697 (m, 1H), 7.526-7.553 (m, 1H), 7.304-7.325 (m, 1H), 7.176-7.179 (d, 1H), 7.097-7.117 (d, 1H), 7.014-7.052 (m, 1H), 6.725-6.747 (d, 1H), 5.570 (s, 1H), 5.121-5.148 (m, 1H), 4.633-4.675 (m, 2H), 3.824-3.860 (m, 1H), 3.824 (s, 3H), 3.535-3.554 (m, 1H), 3.382-3.441 (m, 2H), 2.318-2.334 (m, 1H), 2.138-2.212 (m, 1H).

Example 346: (S)-(3-(3-(5-chloropyridin-2-yloxy)pyrrolidin-1-yl)-6-o-tolylpyridin-2-yl)methanol (Compound 1-195)

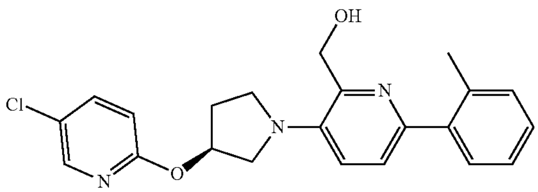 [SMILES: Cc1ccccc1-c1ccc(N2CC[C@H](Oc3ccc(Cl)cn3)C2)c(CO)n1]

The title compound was prepared following procedures described in example 333 to give (S)-(3-(3-(5-chloropyridin-2-yloxy)pyrrolidin-1-yl)-6-o-tolylpyridin-2-yl)methanol (20 mg, 30% yield), Mass spec: 396 (M+H), $t_R$=2.368 min, $^1$H-NMR (400 Hz, DMSO) 5=8.25-8.256 (d, 1H), 7.811-7.840 (m, 2H), 6.916-7.395 (m, 6H), 6.893-6.916 (d, 1H), 5.587 (s, 1H), 5.095-5.120 (m, 1H), 4.636-4.680 (m, 2H), 3.846-3.886 (m, 1H), 3.497-3.578 (m, 2H), 3.415-3.423 (m, 1H), 5.121-5.148 (m, 1H), 4.633-4.675 (m, 2H), 3.824-3.860 (m, 1H), 3.824 (s, 3H), 3.535-3.554 (m, 1H), 2.350 (s, 3H), 2.336-2.350 (m, 1H), 2.144-2.174 (m, 1H).

Example 347: (S)-(3-(3-(5-chloropyridin-2-yloxy)pyrrolidin-1-yl)-6-(2-ethylphenyl)pyridin-2-yl)methanol (Compound 1-201)

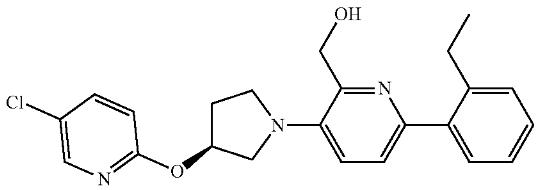 [SMILES: CCc1ccccc1-c1ccc(N2CC[C@H](Oc3ccc(Cl)cn3)C2)c(CO)n1]

The title compound was prepared following procedures described in example 333 to give (S)-(3-(3-(5-chloropyridin-2-yloxy)pyrrolidin-1-yl)-6-(2-ethylphenyl)pyridin-2-yl)methanol (20 mg, 30% yield), Mass spec: 396 (M+H), $t_R$=2.577 min, $^1$H-NMR (400 Hz, DMSO) δ=8.242-8.249 (d, 1H), 7.827-7.834 (m, 1H), 7.227-7.295 (m, 6H), 6.889-6.911 (d, 1H), 5.578-5.584 (m, 1H), 5.064-5.089 (m, 1H), 4.614-4.706 (m, 2H), 3.855-3.883 (m, 1H), 3.520-3.597 (m, 2H), 3.389-3.442 (m, 1H), 2.687-2.742 (m, 2H), 2.335-2.504 (m, 1H), 2.164-2.172 (m, 1H), 1.044-1.082 (m, 3H).

Example 348: (S)-(3-(3-(5-chloropyridin-2-yloxy)pyrrolidin-1-yl)-6-(2-methoxyphenyl)pyridin-2-yl)methanol (Compound 1-202)

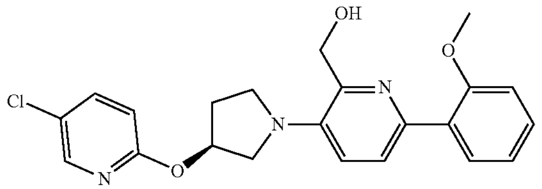 [SMILES: COc1ccccc1-c1ccc(N2CC[C@H](Oc3ccc(Cl)cn3)C2)c(CO)n1]

The title compound was prepared following procedures described in example 333 to give (S)-(3-(3-(5-chloropyridin-2-yloxy)pyrrolidin-1-yl)-6-(2-methoxyphenyl)pyridin-2-yl)methanol (20 mg, 30% yield), Mass spec: 412 (M+H), $t_R$=1.964 min, $^1$H-NMR (400 Hz, DMSO) 5=8.244-8.251 (d, 1H), 7.827-7.834 (m, 1H), 7.778-7.831 (m, 2H), 7.676-7.679 (d, 1H), 7.302-7.345 (m, 1H), 7.183-7.203 (m, 1H), 7.096-7.117 (m, 2H), 7.688-7.691 (m, 1H), 5.580 (s, 1H), 5.105-5.130 (m, 1H), 4.601-4.708 (m, 2H), 3.835 (s, 3H), 3.822-3.863 (m, 1H), 3.372-3.560 (m, 3H), 2.318-2.353 (m, 1H), 2.167-2.168 (m, 1H).

Example 349: (S)-(6-(2-ethylphenyl)-3-(3-(3-fluoropyridin-2-yloxy)pyrrolidin-1-yl)pyridin-2-yl)methanol (Compound 1-204)

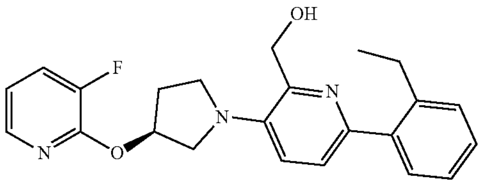 [SMILES: CCc1ccccc1-c1ccc(N2CC[C@H](Oc3ncccc3F)C2)c(CO)n1]

The title compound was prepared following procedures described in example 333 to give (S)-(6-(2-ethylphenyl)-3-(3-(3-fluoropyridin-2-yloxy)pyrrolidin-1-yl)pyridin-2-yl)methanol (24 mg, 26% yield), Mass spec: 394 (M+H), $t_R$=2.259 min, $^1$H-NMR (400 Hz, DMSO) δ=8.010-8.022 (d, 1H), 7.684-7.728 (m, 1H), 7.235-7.299 (m, 6H), 7.034-7.074 (m, 1H), 5.706 (s, 1H), 5.092-5.118 (m, 1H), 4.609-4.716 (m, 2H), 3.887-3.928 (m, 1H), 3.538-3.595 (m, 2H), 3.410-3.453 (m, 1H), 2.675-2.730 (m, 2H), 2.361-2.395 (m, 3H), 2.185-2.226 (m, 1H), 1.049-1.087 (m, 3H).

Example 350: (S)-(3-(3-(3-fluoropyridin-2-yloxy)pyrrolidin-1-yl)-6-(2-methoxyphenyl)pyridin-2-yl)methanol (Compound 1-213)

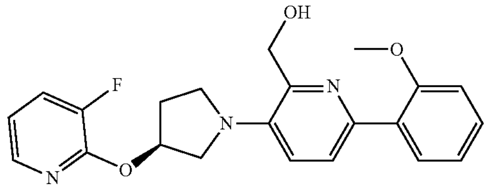 [SMILES: COc1ccccc1-c1ccc(N2CC[C@H](Oc3ncccc3F)C2)c(CO)n1]

The title compound was prepared following procedures described in example 333 to give (S)-(3-(3-(3-fluoropyridin-2-yloxy)pyrrolidin-1-yl)-6-(2-methoxyphenyl)pyridin-2-yl)methanol (65 mg, 60% yield), Mass spec: 396 (M+H), $t_R$=1.772 min, $^1$H-NMR (400 Hz, DMSO) δ=8.005-8.018 (m, 1H), 7.728-7.804 (m, 1H), 7.673-7.720 (m, 2H), 7.305-7.347 (m, 1H), 7.201-7.224 (m, 1H), 7.015-7.071 (m, 3H), 5.692-5.696 (m, 1H), 5.125-5.150 (m, 1H), 4.609-4.715 (m, 2H), 3.863-3.904 (m, 1H), 3.824 (s, 3H), 3.514-3.574 (m, 2H), 3.380-3.441 (m, 1H), 2.357-2.391 (m, 1H), 2.176-2.210 (m, 1H).

Example 351: (S)-(3-(3-(3-fluoropyridin-2-yloxy)pyrrolidin-1-yl)-6-o-tolylpyridin-2-yl)methanol (Compound 1-216)

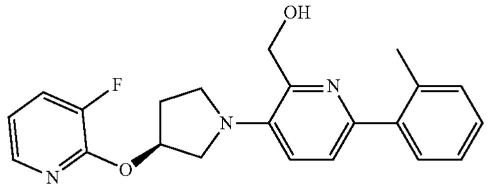 [SMILES: Cc1ccccc1-c1ccc(N2CC[C@H](Oc3ncccc3F)C2)c(CO)n1]

The title compound was prepared following procedures described in example 333 to give (S)-(3-(3-(3-fluoropyridin-2-yloxy)pyrrolidin-1-yl)-6-o-tolylpyridin-2-yl)methanol (29 mg, 31% yield), Mass spec: 380 (M+H), $t_R$=2.803 min, $^1$H-NMR (400 Hz, DMSO) δ=8.007-8.019 (d, 1H), 7.673-7.723 (m, 1H), 7.239-7.396 (m, 6H), 7.032-7.072 (m, 1H), 5.704 (s, 1H), 5.103-5.130 (m, 1H), 4.613-4.720 (m, 2H), 3.883-3.923 (m, 1H), 3.532-3.591 (m, 2H), 3.360-3.448 (m, 1H), 2.352-2.394 (m, 1H), 2.352 (s, 3H), 2.201-2.224 (m, 1H).

Example 352: (S)-2-(5-(3-(3-fluoropyridin-2-yloxy)pyrrolidin-1-yl)-6-(hydroxymethyl)pyridin-2-yl)benzonitrile (Compound 1-217)

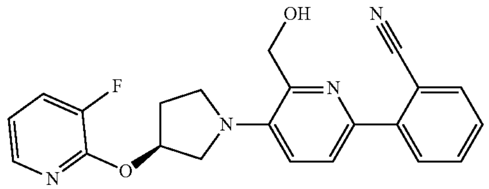 [SMILES: N#Cc1ccccc1-c1ccc(N2CC[C@H](Oc3ncccc3F)C2)c(CO)n1]

The title compound was prepared following procedures described in example 333 to give (S)-2-(5-(3-(3-fluoropyridin-2-yloxy)pyrrolidin-1-yl)-6-(hydroxymethyl)pyridin-2-yl)benzonitrile (20 mg, 21% yield), Mass spec: 391 (M+H), $t_R$=2.650 min, $^1$H-NMR (400 Hz, DMSO) 5=8.203-8.205 (d, 1H), 7.926-8.010 (m, 2H), 7.673-7.894 (m, 3H), 7.509-7.550 (m, 1H), 7.262-7.283 (d, 1H), 7.036-7.076 (m, 1H), 5.725-5.730 (m, 1H), 5.047-5.072 (m, 1H), 4.699-4.808 (m, 2H), 3.968-4.009 (m, 1H), 3.625-3.654 (m, 2H), 3.519-3.555 (m, 1H), 2.352-2.387 (m, 1H), 2.223-2.247 (m, 2H).

Example 353: (S)-2-(5-(3-(5-fluoropyridin-2-yloxy)pyrrolidin-1-yl)-6-(hydroxymethyl)pyridin-2-yl)benzonitrile (Compound 1-208)

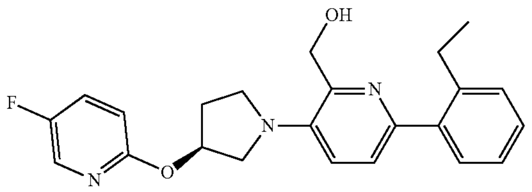

The title compound was prepared following procedures described in example 333 to give (S)-2-(5-(3-(5-fluoropyridin-2-yloxy)pyrrolidin-1-yl)-6-(hydroxymethyl)pyridin-2-yl)benzonitrile (20 mg, 20% yield), Mass spec: 394 (M+H). $t_R$=2.354 min, $^1$H-NMR (400 Hz, DMSO) δ=8.175-8.182 (d, 1H), 7.695-7.703 (m, 1H), 7.223-7.308 (m, 6H), 6.880-6.911 (m, 1H), 5.560 (m, 1H), 5.063-5.090 (m, 1H), 4.632-4.675 (m, 2H), 3.854-3.869 (m, 1H), 3.387-3.556 (m, 3H), 2.688-2.706 (m, 2H), 2.330-2.350 (m, 1H), 2.156-2.158 (m, 1H), 1.044-1.082 (m, 3H).

Example 354: (S)-(3-(3-(5-fluoropyridin-2-yloxy)pyrrolidin-1-yl)-6-o-tolylpyridin-2-yl)methanol (Compound 1-207)

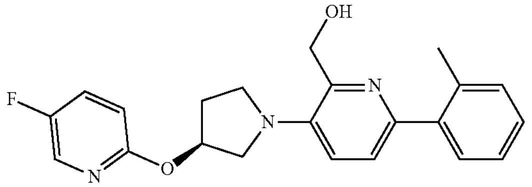 [SMILES: Cc1ccccc1-c1ccc(N2CC[C@H](Oc3ccc(F)cn3)C2)c(CO)n1]

The title compound was prepared following procedures described in example 333 to give (S)-(3-(3-(5-fluoropyridin-2-yloxy)pyrrolidin-1-yl)-6-o-tolylpyridin-2-yl)methanol (20 mg, 20% yield), Mass spec: 380 (M+H), $t_R$=2.088 min, $^1$H-NMR (400 Hz, DMSO) δ=8.175-8.183 (d, 1H), 7.674-7.725 (m, 1H), 7.220-7.391 (m, 6H), 6.879-6.911 (m, 1H), 5.553-5.560 (m, 1H), 5.080-5.106 (m, 1H), 4.635-4.678 (m, 2H), 3.838-3.879 (m, 1H), 3.419-3.573 (m, 3H), 2.329 (s, 3H), 2.347-2.370 (m, 1H), 2.155-2.157 (m, 1H).

Example 355: (S)-(3-(3-(5-fluoropyridin-2-yloxy)pyrrolidin-1-yl)-6-(2-methoxyphenyl)pyridin-2-yl)methanol (Compound 1-209)

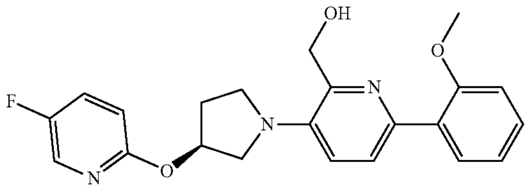 [SMILES: COc1ccccc1-c1ccc(N2CC[C@H](Oc3ccc(F)cn3)C2)c(CO)n1]

The title compound was prepared following procedures described in example 333 to give (S)-(3-(3-(5-fluoropyridin-2-yloxy)pyrrolidin-1-yl)-6-(2-methoxyphenyl)pyridin-2-yl)methanol (20 mg, 20% yield), Mass spec: 396 (M+H), $t_R$=1.738 min, $^1$H-NMR (400 Hz, DMSO) δ=8.182-8.189 (d, 1H), 7.782-7.801 (d, 1H), 7.679-7.707 (m, 2H), 7.327 (m, 1H), 7.182-7.204 (m, 1H), 7.098-7.119 (m, 1H), 7.034 (m, 1H), 6.883-6.914 (m, 1H), 5.557 (br, 1H), 5.123-5.136 (m, 1H), 4.635-4.678 (m, 2H), 3.825-3.868 (m, 1H), 3.868 (s, 3H), 3.341-3.543 (m, 3H), 2.346 (m, 1H), 2.160 (m, 1H).

Example 356: (S)-2-(5-(3-(5-fluoropyridin-2-yloxy)pyrrolidin-1-yl)-6-(hydroxymethyl)pyridin-2-yl)benzonitrile (Compound 1-210)

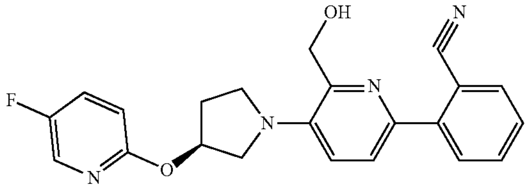 [SMILES: N#Cc1ccccc1-c1ccc(N2CC[C@H](Oc3ccc(F)cn3)C2)c(CO)n1]

The title compound was prepared following procedures described in example 333 to give (S)-2-(5-(3-(5-fluoropyridin-2-yloxy)pyrrolidin-1-yl)-6-(hydroxymethyl)pyridin-2-yl)benzonitrile (20 mg, 20% yield), Mass spec: 391 (M+H), $t_R$=2.732 min, $^1$H-NMR (400 Hz, DMSO) δ=8.184-8.192 (d, 1H), 7.892-7.943 (m, 1H), 7.686-7.782 (m, 3H), 7.509-7.547 (m, 1H), 7.241-7.509 (d, 1H), 6.883-6.915 (m, 1H), 5.582 (m, 1H), 5.046-5.072 (m, 1H), 4.726-4.772 (m, 2H), 3.928-3.968 (m, 1H), 3.376-3.645 (m, 3H), 2.340 (m, 1H), 2.198 (m, 1H).

Example 357: (S)-2-(3-(3-(5-methylpyridin-2-yloxy)pyrrolidin-1-yl)-6-o-tolylpyridin-2-yl)ethanol (Compound 1-200)

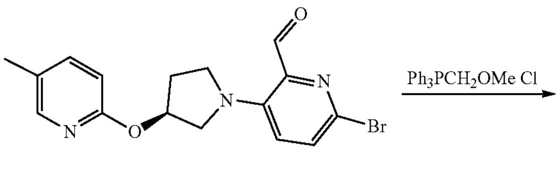

-continued

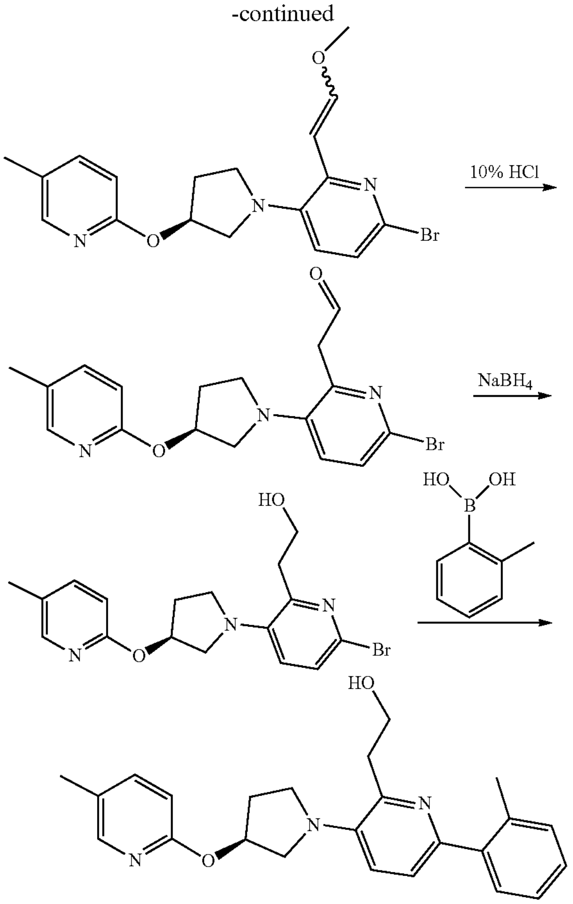

Step 1: (S)-6-bromo-2-(2-methoxyvinyl)-3-(3-(5-methylpyridin-2-yloxy)pyrrolidin-1-yl)pyridine

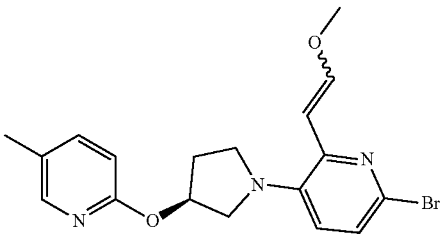 [SMILES: COC=Cc1nc(Br)ccc1N1CC[C@H](Oc2ccc(C)cn2)C1]

To a solution of (methoxymethyl)triphenylphosphonium chloride (1.28 g, 4.14 mmol) in 8 ml THE was added LDA (4.2 ml, 8.28 mmol) at 0° C. under $N_2$, the mixture was stirred at this temperature for 10 min, before It was added to (S)-6-bromo-3-(3-(5-methylpyridin-2-yloxy)pyrrolidin-1-yl)picolinaldehyde (500 mg, 1.38 mmol) (prepared as example 333 step 2) in 5 mL THE drop wise, the resulting mixture was stirred at 0° C. for 30 min, quenched by water, and diluted with EA, the organic layer was washed by water and brine, dried over $Na_2SO_4$, removal the solvent to left the crude product which was purified by silica gel to give (S)-6-bromo-2-(2-methoxyvinyl)-3-(3-(5-methylpyridin-2-yloxy)pyrrolidin-1-yl)pyridine (300 mg, 60% yield), Mass spec: 390 (M+1).

Step 2: (S)-2-(6-bromo-3-(3-(5-methylpyridin-2-yloxy)pyrrolidin-1-yl)pyridin-2-yl)acetaldehyde

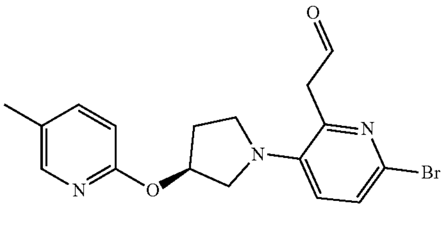 [SMILES: Cc1ccc(O[C@H]2CCN(c3ccc(Br)nc3CC=O)C2)nc1]

To a solution of (S)-6-bromo-2-(2-methoxyvinyl)-3-(3-(5-methylpyridin-2-yloxy)pyrrolidin-1-yl)pyridine (300 mg, 0.76 mmol) was dissolved in 4 mL actone was added 4 mL 10% HCl solution slowly, Then the reacting mixture was stirred at 60° C. for 3 h, the mixture was adjusted the PH to 9 with $NaHCO_3$ solution, extracted with EA, the organic layer was washed with water and brine, dried over $Na_2SO_4$, removal the solvent to left the crude (S)-2-(6-bromo-3-(3-(5-methylpyridin-2-yloxy)pyrrolidin-1-yl)pyridin-2-yl)acetaldehyde (300 mg, quant.) which can be used directly, Mass spec: 376 (M+1).

Step 3: (S)-2-(6-bromo-3-(3-(5-methylpyridin-2-yloxy)pyrrolidin-1-yl)pyridin-2-yl)ethanol

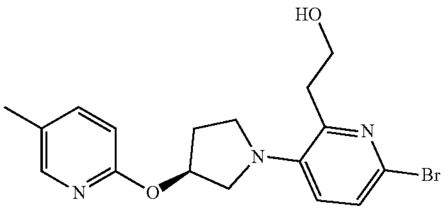 [SMILES: Cc1ccc(O[C@H]2CCN(c3ccc(Br)nc3CCO)C2)nc1]

To a solution of (S)-2-(6-bromo-3-(3-(5-methylpyridin-2-yloxy)pyrrolidin-1-yl)pyridin-2-yl)acetaldehyde (300 mg, 0.79 mmol) in 6 mL MeOH/DCM (v:v=3:1) was added $NaBH_4$ (45.2 mg, 1.2 mmol) slowly at 0° C., the mixture was stirred at r.t for 20 min. the mixture was quenched by water, and extracted with DCM, washed with water and brine, dried over $Na_2SO_4$, removal the solvent to left the crude (S)-2-(6-bromo-3-(3-(5-methylpyridin-2-yloxy)pyrrolidin-1-yl)pyridin-2-yl)ethanol (300 mg, quant.) which can be used directly, Mass spec: 378 (M+1).

Step 4: (S)-2-(3-(3-(5-methylpyridin-2-yloxy)pyrrolidin-1-yl)-6-o-tolylpyridin-2-yl)ethanol

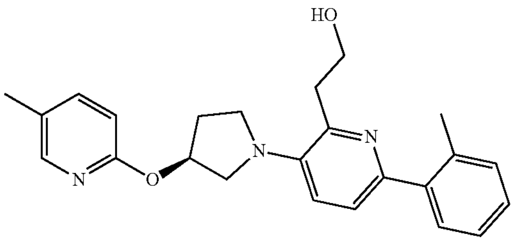 [SMILES: Cc1ccc(O[C@H]2CCN(c3ccc(-c4ccccc4C)nc3CCO)C2)nc1]

To a solution of (S)-2-(6-bromo-3-(3-(5-methylpyridin-2-yloxy)pyrrolidin-1-yl)pyridin-2-yl)ethanol (100 mg, 0.26 mmol) in 1.5 mL dioxane/$H_2O$ (v:v=5:1) was added o-tolylboronic acid (53 mg, 0.39 mmol), $K_2CO_3$ (109 mg, 0.78 mmol) and pd (dppf)$Cl_2$ (20 mg), the mixture was stirred at 90° C. under N2 for 2 h. the mixture was diluted with EA, the organic layer was washed by water and brine, dried over $Na_2SO_4$, removal the solvent to left the crude product which was purified by Pre-HPLC to give (S)-2-(3-(3-(5-methylpyridin-2-yloxy)pyrrolidin-1-yl)-6-o-tolylpyridin-2-yl) ethanol (20 mg, 20% yield). Mass spec: 390 (M+H), $^1$H-NMR (400 Hz, DMSO) δ=7.999 (s, 1H), 7.558-7.532 (m, 1H), 7.372-7.331 (m, 2H), 7.260-7.245 (m, 4H), 6.670-6.740 (m, 1H), 5.552 (s, 1H), 4.724-4.696 (m, 1H), 3.867-3.817 (m, 2H), 3.747-3.706 (m, 1H), 3.482-3.441 (m, 1H), 3.331-3.210 (m, 2H), 3.034-2.973 (m, 2H), 2.395-2.351 (m, 4H), 2.213 (m, 3H), 2.115-2.074 (m, 1H).

Example 359: (S)-2-(6-(2-ethylphenyl)-3-(3-(5-methylpyridin-2-yloxy)pyrrolidin-1-yl)pyridin-2-yl) ethanol (Compound 1-218)

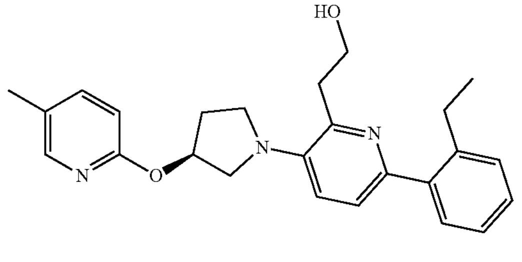 [SMILES: CCc1ccccc1-c1ccc(N2CC[C@H](Oc3ccc(C)cn3)C2)c(CCO)n1]

The title compound was prepared following procedures described in example 357 to give (S)-2-(6-(2-ethylphenyl)-3-(3-(5-methylpyridin-2-yloxy)pyrrolidin-1-yl)pyridin-2-yl)ethanol (30 mg, 30% yield), Mass spec: 403 (M+1), $t_R$=2.099 min, $^1$H-NMR (400 Hz, DMSO) δ=7.996 (s, 1H), 7.533-7.559 (m, 1H), 7.194-7.356 (m, 6H), 6.740-6.762 (m, 1H), 5.545-5.552 (m, 1H), 4.699-4.727 (m, 1H), 3.811-3.844 (m, 2H), 3.705-3.746 (m, 1H), 3.442-3.480 (m, 1H), 3.228-3.274 (m, 2H), 2.990-3.031 (m, 2H), 2.682-2.738 (m, 2H), 2.682-2.738 (m, 1H), 2.509 (s, 3H), 2.079-2.103 (m, 1H), 1.039-1.076 (m, 3H).

Example 360: (S)-(5-(3-(5-methylpyridin-2-yloxy) pyrrolidin-1-yl)-2, 2'-bipyridin-6-yl)methanol (Compound 1-244)

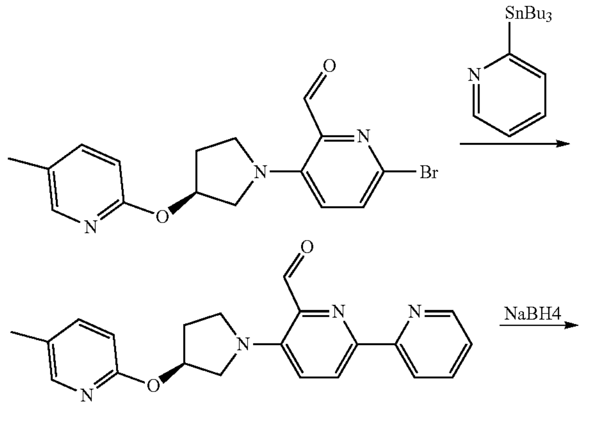

-continued

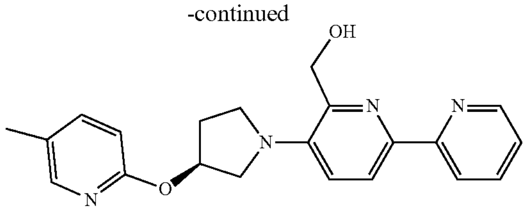

Step 1: (S)-5-(3-(5-methylpyridin-2-yloxy)pyrrolidin-1-yl)-2, 2'-bipyridine-6-carbaldehyde

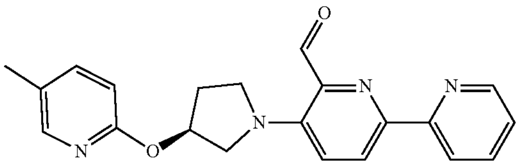 [SMILES: Cc1ccc(O[C@H]2CCN(c3ccc(-c4ccccn4)nc3C=O)C2)nc1]

To a solution of (S)-6-bromo-3-(3-(5-methylpyridin-2-yloxy)pyrrolidin-1-yl)picolinaldehyde (100 mg, 0.277 mmol) (prepared as example 333 step 2), 2-(tributylstannyl) pyridine (102 mg, 0.277 mmol), and LiCl (99 mg, 1.662) in 2 mL dixoane were added Pd($PPh_3$)$_4$ (32.3 mg, 0.028 mmol), the mixture was degassed for 2 min with N2, stirred at 100° C. overnight under N2, then added Sat. KF solution, stirred for another 1 h, extracted with EA, the organic layer was dried over $Na_2SO_4$, removal the solvent to left the crude product which was purified by Prep-TLC to give the crude (S)-5-(3-(5-methylpyridin-2-yloxy)pyrrolidin-1-yl)-2, 2'-bipyridine-6-carbaldehyde (60 mg, 60.6% yield) as brown solid, Mass spec: 361 (M+H).

Step 2

(S)-(5-(3-(5-methylpyridin-2-yloxy)pyrrolidin-1-yl)-2, 2'-bipyridin-6-yl)methanol

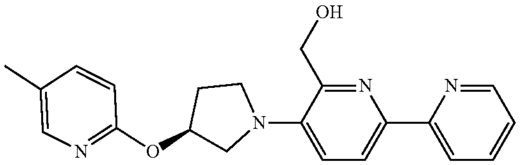 [SMILES: Cc1ccc(O[C@H]2CCN(c3ccc(-c4ccccn4)nc3CO)C2)nc1]

To a solution of S)-5-(3-(5-methylpyridin-2-yloxy)pyrrolidin-1-yl)-2, 2'-bipyridine-6-carbaldehyde (60 mg, 0.167 mmol) in 2 mL MeOH was added $NaBH_4$ at 0° C., the mixture was stirred for 5 min, and quenched with water, removal the solvent to left the residue which was purified by Pre-HPLC to give (S)-(5-(3-(5-methylpyridin-2-yloxy)pyrrolidin-1-yl)-2, 2'-bipyridin-6-yl)methanol (3.1 mg, 5% yield) as yellow solid, Mass spec: 363 (M+H), $t_R$=1.936 min, $^1$H-NMR (400 Hz, DMSO) δ=8.538-8.592 (d, 1H), 8.325-8.345 (d, 1H), 8.148-8.170 (d, 1H), 8.004-8.008 (d, 1H), 7.835-7.878 (m, 1H), 7.526-7.553 (m, 1H), 7.241-7.324 (m, 1H), 7.219-7.241 (m, 1H), 6.726-6.746 (m, 2H), 5.579-5.597 (m, 1H), 4.673-4.762 (m, 2H), 3.907-3.948 (m, 1H), 3.501-3.631 (m, 3H), 2.323-2.338 (m, 1H), 2.212 (s, 3H), 2.152-2.170 (m, 1H).

Example 361: (S)-(6-(pyrimidin-2-yl)-3-(3-(5-(trifluoromethyl)pyridin-2-yloxy)pyrrolidin-1-yl)pyridin-2-yl)methanol (Compound 1-245)

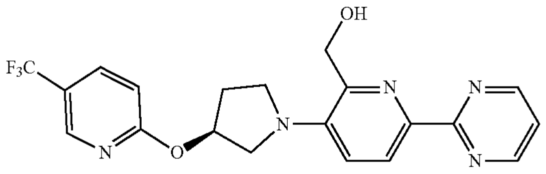 [SMILES: OCc1nc(-c2ncccn2)ccc1N1CC[C@H](Oc2ccc(C(F)(F)F)cn2)C1]

The title compound was prepared following procedures described in example 360 to give (S)-(6-(pyrimidin-2-yl)-3-(3-(5-(trifluoromethyl)pyridin-2-yloxy)pyrrolidin-1-yl) pyridin-2-yl)methanol (30 mg, 15% yield), Mass spec: 418 (M+H), $t_R$=2.338 min, $^1$H-NMR (400 Hz, DMSO) δ=8.872-8.883 (d, 1H), 8.635 (s, 1H), 8.228-8.250 (d, 1H), 8.070-8.098 (m, 1H), 7.396-7.420 (m, 1H), 7.208-7.230 (d, 1H), 7.032-7.054 (d, 1H), 5.744 (s, 1H), 5.548 (m, 1H), 4.717-4.820 (m, 2H), 4.008-4.048 (m, 1H), 3.617-3.735 (m, 3H), 2.500-2.508 (m, 1H), 2.250-2.265 (m, 1H).

Example 362: (S)-(6-phenoxy-3-(3-(5-(trifluoromethyl)pyridin-2-yloxy)pyrrolidin-1-yl)pyridin-2-yl) methanol (Compound 1-199)

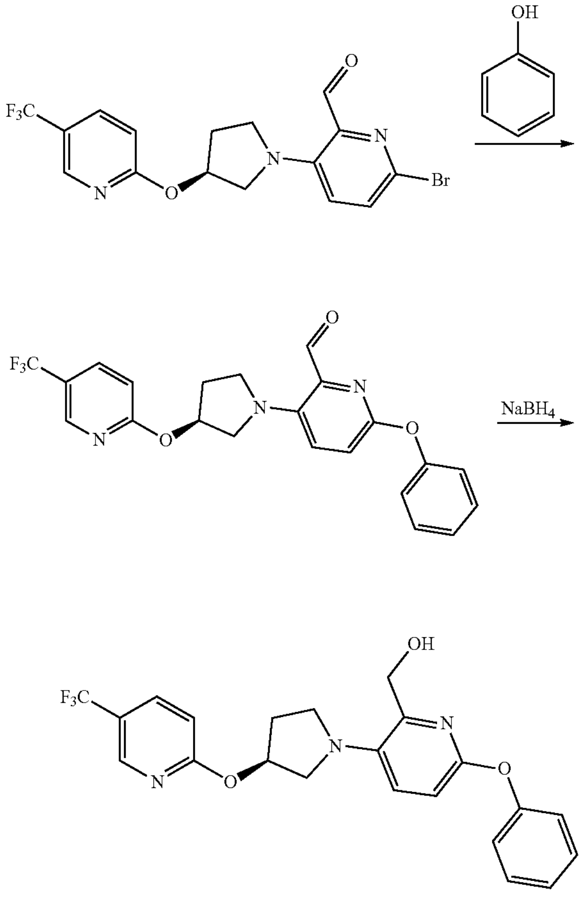

Step 1: (S)-6-phenoxy-3-(3-(5-(trifluoromethyl)pyridin-2-yloxy)pyrrolidin-1-yl)picolinaldehyde

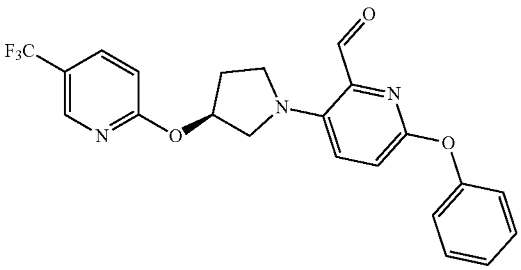 [SMILES: O=Cc1nc(Oc2ccccc2)ccc1N1CC[C@H](Oc2ccc(C(F)(F)F)cn2)C1]

The title compound was prepared following procedures described in example 236 step 3 using (S)-6-bromo-3-(3-(5-(trifluoromethyl)pyridin-2-yloxy)pyrrolidin-1-yl)picolinaldehyde (prepared as 333 step 1) and phenol to give (S)-6-phenoxy-3-(3-(5-(trifluoromethyl)pyridin-2-yloxy) pyrrolidin-1-yl)picolinaldehyde (50 mg, 58% yield), Mass spec: 430 (M+H).

Step 2: (S)-(6-phenoxy-3 (3-(5-(trifluoromethyl) pyridin-2-yloxy)pyrrolidin-1-yl)pyridin-2-yl)methanol

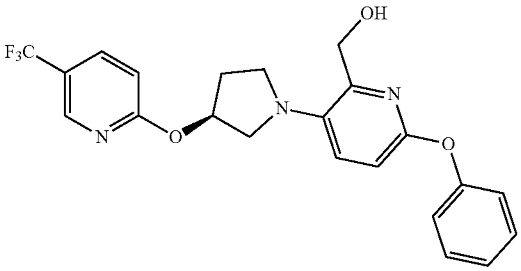 [SMILES: OCc1nc(Oc2ccccc2)ccc1N1CC[C@H](Oc2ccc(C(F)(F)F)cn2)C1]

The title compound was prepared following procedures described in example 333 step 2 to give (S)-(6-phenoxy-3 (3-(5-(trifluoromethyl)pyridin-2-yloxy)pyrrolidin-1-yl)pyridin-2-yl)methanol (25 mg, 50% yield), Mass spec: 432 (M+1), $t_R$=3.242 min, $^1$H-NMR (400 Hz, DMSO) δ=8.606 (s, 1H), 8.063-8.085 (d, 1H), 7.354-7.445 (m, 3H), 7.027-7.150 (m, 4H), 6.816-6.836 (d, 1H), 5.656 (s, 1H), 4.873-4.900 (m, 1H), 4.463-4.486 (m, 1H), 3.696-3.737 (m, 1H), 3.387-3.449 (m, 2H), 3.236-3.265 (m, 1H), 2.124-2.139 (m, 1H).

Example 363: (S)-(6-(2-methoxyphenoxy)-3-(3-(5-methylpyridin-2-yloxy)pyrrolidin-1-yl)pyridin-2-yl)methanol (Compound 1-205)

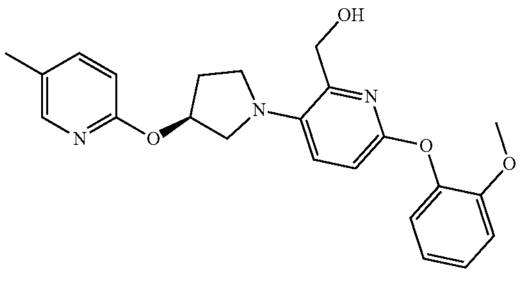 [SMILES: COc1ccccc1Oc1ccc(N2CC[C@H](Oc3ccc(C)cn3)C2)c(CO)n1]

The title compound was prepared following procedures described in example 362 to give (S)-(6-(2-methoxyphenoxy)-3-(3-(5-methylpyridin-2-yloxy)pyrrolidin-1-yl)pyridin-2-yl)methanol (30 mg, 50% yield), Mass spec: 378 (M+1), $t_R$=2.781 min, $^1$H-NMR (400 Hz, DMSO) δ=7.974-7.978 (d, 1H), 7.537-7.543 (m, 1H), 7.406-7.515 (d, 1H), 7.131-7.168 (m, 2H), 7.046-7.049 (d, 1H), 6.936-6.952 (m, 1H), 6.713-6.734 (d, 1H), 6.626-6.649 (d, 1H), 5.484-5.512 (m, 1H), 4.726-4.752 (m, 1H), 4.408-4.435 (m, 2H), 3.705 (s, 3H), 3.594-3.635 (m, 1H), 3.233-3.239 (m, 1H), 3.153-3.183 (m, 2H), 2.3172.350 (m, 1H), 2.200 (s, 3H), 2.015-2.031 (m, 3H).

Example 364: (S)-(6-(o-tolyloxy)-3-(3-(5-(trifluoromethyl)pyridin-2-yloxy)pyrrolidin-1-yl)pyridin-2-yl)methanol (Compound 1-226)

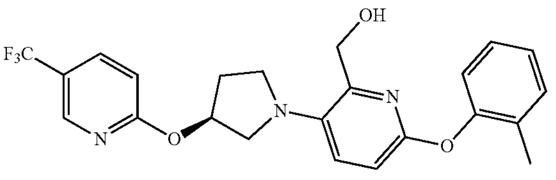 [SMILES: Cc1ccccc1Oc1ccc(N2CC[C@H](Oc3ccc(C(F)(F)F)cn3)C2)c(CO)n1]

The title compound was prepared following procedures described in example 362 to give (S)-(6-(o-tolyloxy)-3-(3-(5-(trifluoromethyl)pyridin-2-yloxy)pyrrolidin-1-yl)pyridin-2-yl)methanol (30 mg, 30% yield), Mass spec: 446 (M+1), $t_R$=3.252 min, $^1$H-NMR (400 Hz, DMSO) δ=8.604 (s, 1H), 8.061-8.089 (d, 1H), 7.418-7.440 (d, 1H), 7.283-7.302 (d, 2H), 7.175-7.194 (m, 1H), 6.939-7.108 (m, 2H), 6.919-6.939 (d, 1H), 6.702-6.724 (d, 1H), 5.637 (s, 1H), 4.827-4.854 (m, 1H), 4.432-4.455 (m, 2H), 3.654-3.695 (m, 1H), 3.319-3.414 (m, 2H), 3.192-3.234 (m, 1H), 2.356-2.406 (m, 1H), 2.140 (s, 3H), 2.086-2.140 (m, 1H).

Example 365: (S)-(6-(2-ethylphenoxy)-3-(3-(5-methylpyridin-2-yloxy)pyrrolidin-1-yl)pyridin-2-yl)methanol (Compound 1-214)

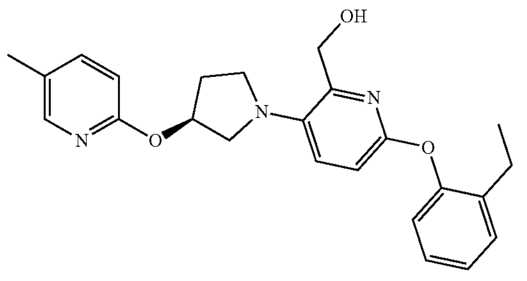 [SMILES: CCc1ccccc1Oc1ccc(N2CC[C@H](Oc3ccc(C)cn3)C2)c(CO)n1]

The title compound was prepared following procedures described in example 362 to give (S)-(6-(2-ethylphenoxy)-3-(3-(5-methylpyridin-2-yloxy)pyrrolidin-1-yl)pyridin-2-yl)methanol (20 mg, 30% yield), Mass spec: 406 (M+1), $^1$H-NMR (400 Hz, DMSO) δ=7.979 (s, 1H), 7.543-7.522 (m, 1H), 7.416-7.395 (m, 1H), 7.323-7.305 (m, 1H), 7.216-7.101 (m, 2H), 6.924-6.905 (m, 1H), 3.734-6.687 (m, 2H), 5.512-5.506 (s, 1H), 4.845-4.818 (m, 1H), 4.445-4.430 (m, 2H), 3.654-3.628 (m, 1H), 3.327-3.206 (m, 3H), 2.573-2.504 (m, 2H), 2.333-2.316 (m, 1H), 2.200 (s, 3H), 2.060-2.043 (m, 1H), 1.139-1.119 (m, 3H).

Example 366: (S)-(3-(3-(5-methylpyridin-2-yloxy)pyrrolidin-1-yl)-6-(o-tolyloxy)pyridin-2-yl)methanol (Compound 1-203)

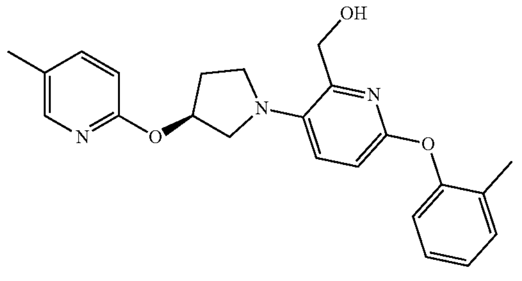

The title compound was prepared following procedures described in example 362 to give (S)-(3-(3-(5-methylpyridin-2-yloxy)pyrrolidin-1-yl)-6-(o-tolyloxy)pyridin-2-yl)methanol (30 mg, 42% yield), Mass spec: 392 (M+1), $^1$H-NMR (400 Hz, DMSO) δ=7.980-7.976 (m, 1H), 7.544-7.517 (m, 1H), 7.422-7.401 (m, 1H), 7.302-7.283 (m, 1H), 7.213-7.175 (m, 1H), 7.108-7.090, (m, 1H) 6.940-6.921 (m, 1H), 6.735-6.696 (m, 2H), 5.522-5.493 (s, 1H), 4.827-4.799 (m, 1H), 4.454-4.427 (m, 2H), 3.666-3.626 (m, 1H), 3.389-3.321 (m, 1H), 3.273-3.184 (m, 2H), 2.351-2.302 (m, 1H), 2.202-2.123 (m, 6H), 2.063-2.029 (m, 1H).

Example 367: (S)-(6-(2-ethylphenoxy)-3-(3-(5-(trifluoromethyl)pyridin-2-yloxy)pyrrolidin-1-yl)pyridin-2-yl)methanol (Compound 1-212)

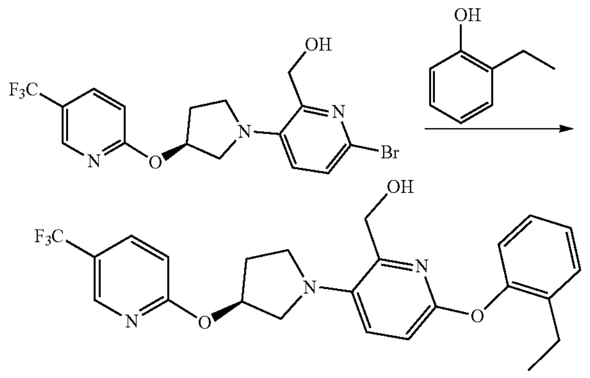

To a solution of (S)-(6-bromo-3-(3-(5-(trifluoromethyl) pyridin-2-yloxy)pyrrolidin-1-yl)pyridin-2-yl)methanol (100 mg, 0.24 mmol) ((prepared as 333 step 2) in 1.8 ml dioxane/DMF (v:v==5:1) was added $Cs_2CO_3$ (155.82 mg, 0.48 mmol) and 2-ethylphenol (58.2 mg, 0.48 mmol), CuI (22.7 mg, 0.12 mmol) and 2-(dimethylamino)acetic acid hydrochloride (16.7 mg, 0.12 mmol), the mixture was irradiated by microwave at 160° C. for 1 h, water was added, extracted with EA, the organic layer was washed with LiCl solution and brine, dried over $Na_2SO_4$, removal the solvent to left the crude product which was purified by Pre-HPLC to give (S)-(6-(2-ethylphenoxy)-3-(3-(5-(trifluoromethyl)pyridin-2-yloxy)pyrrolidin-1-yl)pyridin-2-yl)methanol (30 mg, 20% yield), Mass spec: 460 (M+H), $t_R$=3.543 min, $^1$H-NMR (400 Hz, DMSO) δ=8.603 (s, 1H), 8.061-8.088 (m, 1H), 7.416-7.4380 (d, 1H), 7.305-7.324 (d, 1H), 7.182-7.217 (m, 1H), 7.105-7.141 (m, 1H), 7.023-7.044 (d, 1H), 6.909-6.298 (d, 1H), 6.697-6.719 (d, 1H), 5.639 (m, 1H), 4.849-4.874 (m, 1H), 4.446-4.468 (m, 2H), 3.660-3.701 (m, 1H), 3.197-3.349 (m, 3H), 2.536-2.574 (m, 2H), 2.358-2.408 (m, 1H), 2.106-2.123 (m, 1H), 1.101-1.139 (m, 3H).

Example 369: (R)-2-phenyl-5-(3-(5-(trifluoromethyl)pyridin-2-yloxy)pyrrolidin-1-yl)isonicotinamide (Compound 1-99)

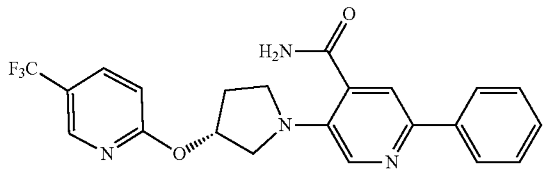 [SMILES: NC(=O)c1cc(-c2ccccc2)ncc1N1CC[C@@H](Oc2ccc(C(F)(F)F)cn2)C1]

A solution of (R)-2-phenyl-5-(3-(5-(trifluoromethyl)pyridin-2-yloxy)pyrrolidin-1-yl)isonicotinonitrile (100 mg, 0.244 mmol) (example 368 step 4) in 2 mL con H2SO4 was stirred at r.t for overnight, and the mixture was poured into ice water, adjusted the pH with 30% NaOH solution to 11, extracted with DCM, dried over $Na_2SO_4$, removal the solvent to left the crude product which was purified by silica gel to give (R)-2-phenyl-5-(3-(5-(trifluoromethyl)pyridin-2-yloxy)pyrrolidin-1-yl)isonicotinamide (50 mg, 50% yield), Mass spec: 429 (M+1), $t_R$=2.485 min, $^1$H-NMR (400 Hz, DMSO) □, 8.638 (s, 1H), 8.224 (s, 1H), 7.970-8.095 (m, 4H), 7.629-7.667 (m, 2H), 7.415-7.453 (m, 2H), 7.320-7.338 (m, 1H), 7.020-7.042 (m, 1H), 5.732 (s, 1H), 3.902-3.943 (m, 1H), 3.642-3.664 (m, 1H), 3.329-3.461 (m, 2H), 2.273-2.338 (m, 2H).

Example 370: (R)-6-phenyl-3-(3-(5-(trifluoromethyl)pyridin-2-yloxy)pyrrolidin-1-yl)picolinamide (Compound 1-98)

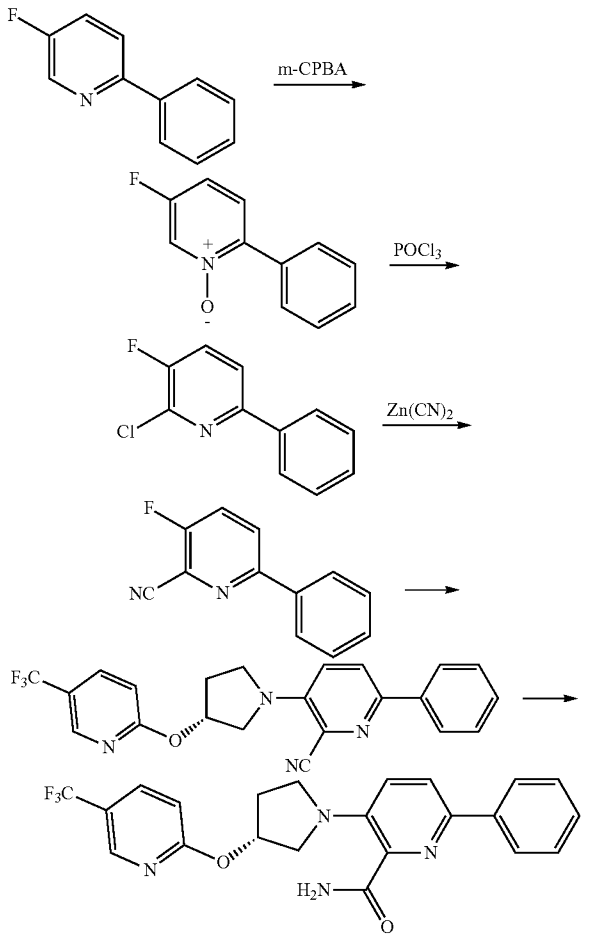

Step 1: 5-fluoro-2-phenylpyridine 1-oxide

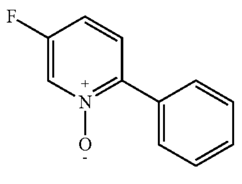

To a solution of 5-fluoro-2-phenylpyridine (100 mg, 0.57 mmol) in 5 mL DCM was added m-CPBA (200 mg, 1.15 mmol), the mixture was stirred at r.t overnight. water was added and combined the organic layer, dried over $Na_2SO_4$, removal the solvent to left the crude product which was purified by silica gel to give 5-fluoro-2-phenylpyridine 1-oxide (80 mg, 80% yield), Mass spec: 190 (M+1).

Step 2: 2-chloro-3-fluoro-6-phenylpyridine

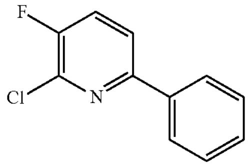 [SMILES: Fc1ccc(-c2ccccc2)nc1Cl]

To a solution of 5-fluoro-2-phenylpyridine 1-oxide (80 mg, 0.42 mmol) in 4 mL $CHCl_3$ was added $POCl_3$ (123 mg, 0.82 mmol), Then the mixture was heated to 65° C. overnight, LCMS indicated 80% yield SM, 0.25 ml $POCl_3$ was added and the mixture was heated to 75° C. for 6 h again, the mixture was cooled to r.t and ice was added, extracted with DCM, organic layer was washed with $NaHCO_3$ solution, dried over Na2SO4, removal the solvent to left the crude product which was purified by silica gel to give 2-chloro-3-fluoro-6-phenylpyridine (30 mg, 34% yield), Mass spec: 208 (M+1).

Step 3: 3-fluoro-6-phenylpicolinonitrile

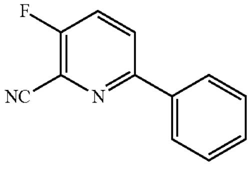 [SMILES: N#Cc1nc(-c2ccccc2)ccc1F]

The title compound was prepared following procedures described in example 368 step 3 to give 3-fluoro-6-phenylpicolinonitrile (10 mg, 50% yield), Mass spec: 199 (M+1).

Step 4: (R)-6-phenyl-3-(3-(5-(trifluoromethyl)pyridin-2-yloxy)pyrrolidin-1-yl)picolinonitrile

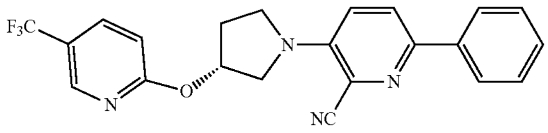 [SMILES: N#Cc1nc(-c2ccccc2)ccc1N1CC[C@@H](Oc2ccc(C(F)(F)F)cn2)C1]

The title compound was prepared following procedures described in example 368 step 4 to give (R)-6-phenyl-3-(3-(5-(trifluoromethyl)pyridin-2-yloxy)pyrrolidin-1-yl)picolinonitrile (170 mg, 85% yield) as white solid, Mass spec: 411 (M+1), $t_R$=3.335 min, $^1$H-NMR (400 Hz, DMSO) δ=8.642-8.648 (m, 1H), 8.101-8.108 (m, 1H), 8.035-8.058 (d, 1H), 7.399-7.480 (m, 4H), 7.048-7.070 (d, 1H), 5.786-5.790 (m, 1H), 4.079-4.120 (m, 1H), 3.779-3.833 (m, 3H), 2.322-2.332 (m, 2H).

Step 5: (R)-6-phenyl-3-(3-(5-(trifluoromethyl)pyridin-2-yloxy)pyrrolidin-1-yl)picolinamide

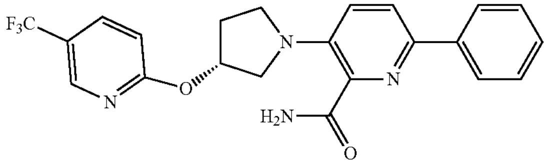 [SMILES: NC(=O)c1nc(-c2ccccc2)ccc1N1CC[C@@H](Oc2ccc(C(F)(F)F)cn2)C1]

The title compound was prepared following procedures described in example 369 to give (R)-6-phenyl-3-(3-(5-(trifluoromethyl)pyridin-2-yloxy)pyrrolidin-1-yl)picolinamide (55 mg, 80% yield) as white solid, Mass spec: 429 (M+1), $t_R$=2.852 min, $^1$H-NMR (400 Hz, DMSO) δ=8.635 (s, 1H), 8.020-8.086 (m, 3H), 7.850-7.923 (m, 2H), 7.412-7.451 (m, 3H), 7.267-7.339 (m, 2H), 7.006-7.028 (d, 1H), 5.713 (s, 1H), 3.893-3.935 (m, 1H), 3.589-3.607 (m, 1H), 3.362-3.449 (m, 2H), 2.258-2.328 (m, 2).

Example 371: (S)-(5-phenyl-3-(3-(5-(trifluoromethyl)pyridin-2-yloxy)pyrrolidin-1-yl)pyridin-2-yl)methanol (Compound 1-188)

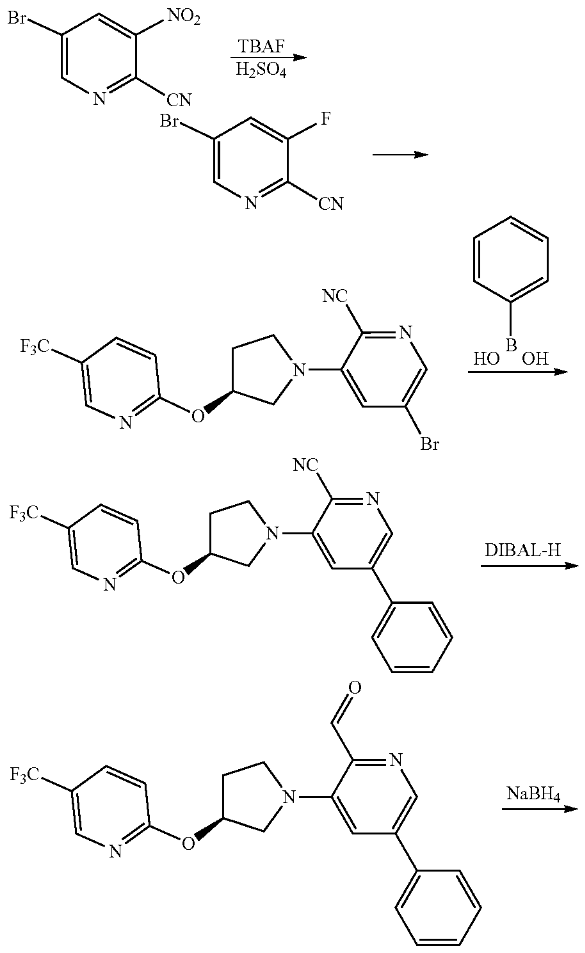

-continued

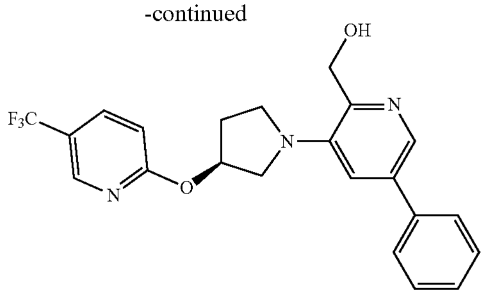

Step 1: 5-bromo-3-fluoropicolinonitrile

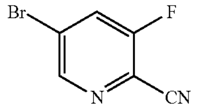

A mixture of 5-bromo-3-nitropicolinonitrile (500 mg, 2.2 mmol) in DMF was added $H_2SO_4$ (0.01 ml) and TBAF (6.6 ml) at −40° C., the mixture was stirred at −40° C. for 30 min, quenched with HCl solution (2M) at −40° C. to pH=3, The mixture was extracted with EA, washed with brine, dried over $Na_2SO_4$, removal the solvent to left the crude 5-bromo-3-fluoropicolinonitrile (500 mg, quant.) which can be used to next step directly, Mass spec: 201 (M+1)

Step 2: (S)-5-bromo-3-(3-(5-(trifluoromethyl)pyridin-2-yloxy)pyrrolidin-1-yl)picolinonitrile

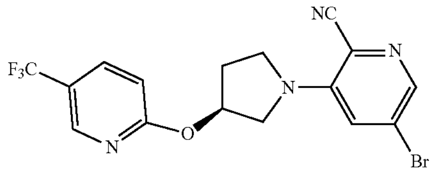 [SMILES: N#Cc1ncc(Br)cc1N1CC[C@H](Oc2ccc(C(F)(F)F)cn2)C1]

The title compound was prepared following procedures described in example 368 step 4 to give (S)-5-bromo-3-(3-(5-(trifluoromethyl)pyridin-2-yloxy)pyrrolidin-1-yl)picolinonitrile (340 mg, 80%), Mass spec: 413 (M+1).

Step 3: (S)-5-phenyl-3-(3-(5-(trifluoromethyl)pyridin-2-yloxy)pyrrolidin-1-yl)picolinonitrile

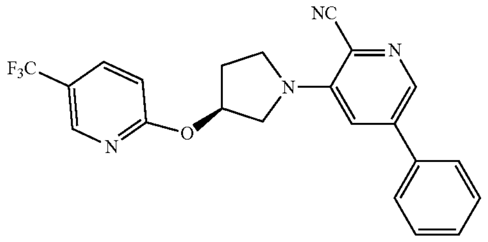 [SMILES: N#Cc1ncc(-c2ccccc2)cc1N1CC[C@H](Oc2ccc(C(F)(F)F)cn2)C1]

The title compound was prepared following procedures described in example 357 step 4 to give (S)-5-phenyl-3-(3-(5-(trifluoromethyl)pyridin-2-yloxy)pyrrolidin-1-yl)picolinonitrile (300 mg, 8% yield), Mass spec: 411 (M+1).

Step 4: (S)-5-phenyl-3-(3-(5-(trifluoromethyl)pyridin-2-yloxy)pyrrolidin-1-yl)picolinaldehyde

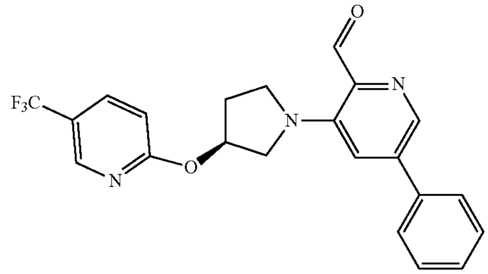 [SMILES: O=Cc1ncc(-c2ccccc2)cc1N1CC[C@H](Oc2ccc(C(F)(F)F)cn2)C1]

The title compound was prepared following procedures described in example 368 step 5 to give (S)-5-phenyl-3-(3-(5-(trifluoromethyl)pyridin-2-yloxy)pyrrolidin-1-yl)picolinaldehyde (80 mg, 26% yield), Mass spec: 414 (M+1).

Step 5: (S)-(5-phenyl-3-(3-(5-(trifluoromethyl)pyridin-2-yloxy)pyrrolidin-1-yl)pyridin-2-yl)methanol

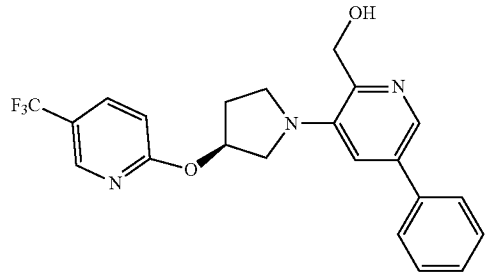

The title compound was prepared following procedures described in example 368 step 6 to give (S)-(5-phenyl-3-(3-(5-(trifluoromethyl)pyridin-2-yloxy)pyrrolidin-1-yl)pyridin-2-yl)methanol (20 mg, 25% yield), Mass spec: 416 (M+1), $t_R$=3.591 min, $^1$H-NMR (400 Hz, DMSO) δ=8.629 (s, 1H), 8.266 (s, 1H), 8.075-8.094 (m, 1H), 7.717-7.735 (m, 2H), 7.395-7.512 (m, 3H), 7.312 (s, 1H), 7.031-7.053 (d, 1H), 5.717 (m, 1H), 5.132-5.158 (m, 1H), 4.639-4.676 (m, 2H), 3.904-3.944 (m, 1H), 3.584-3.651 (m, 2H), 3.408-3.413 (m, 1H), 2.363-2.395 (m, 1H), 2.200-2.218 (m, 1H).

Example 373: (R)-5-phenyl-2-(3-(5-(trifluoromethyl)pyridin-2-yloxy)pyrrolidin-1-yl)nicotinamide (Compound 1-92)

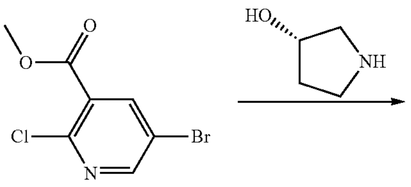

-continued

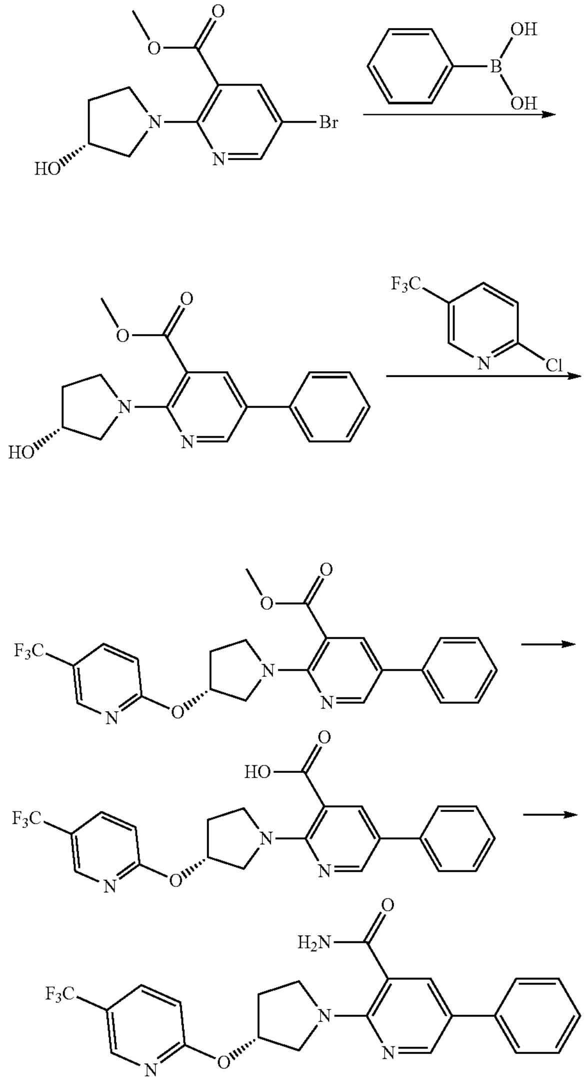

Step 1: (R)-methyl 5-bromo-2-(3-hydroxypyrrolidin-1l-yl)nicotinate

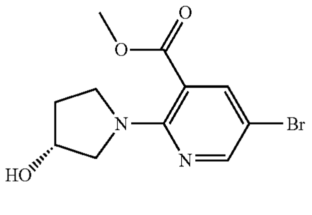 [SMILES: COC(=O)c1cc(Br)cnc1N1CC[C@@H](O)C1]

To solution of methyl 5-bromo-2-chloronicotinate (3.8 g, 15.2 mmol) and (S)-pyrrolidin-3-ol (22.4 g, 18.2 mmol) in 30 mL MeCN was added TEA (4.2 ml, 30.4 mmol), the mixture was stirred at 60° C. for 1 h, removed MeCN, the residue was diluted with EA, the organic layer was washed with water and brine, dried over $Na_2SO_4$, removal the solvent to left the crude product which was purified by silica gel to give (R)-methyl 5-bromo-2-(3-hydroxypyrrolidin-1-yl)nicotinate (4.1 g, 9% yield), Mass spec: 301 (M+1).

Step 2: (R)-methyl 2-(3-hydroxypyrrolidin-1-yl)-5-phenylnicotinate

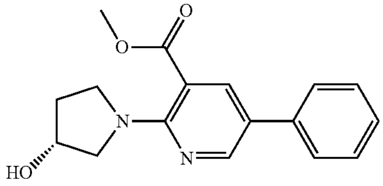 [SMILES: COC(=O)c1cc(-c2ccccc2)cnc1N1CC[C@@H](O)C1]

The title compound was prepared following procedures described in example 357 step 4 to give (R)-methyl 2-(3-hydroxypyrrolidin-1-yl)-5-phenylnicotinate (3 g, 50% yield), Mass spec: 299 (M+1).

Step 3: (R)-methyl 5-phenyl-2-(3-(5-(trifluoromethyl)pyridin-2-yloxy)pyrrolidin-1-yl)nicotinate

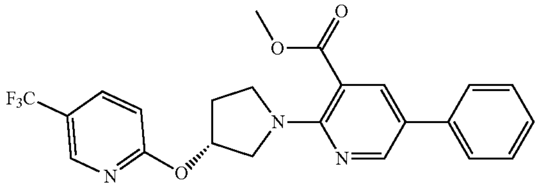 [SMILES: COC(=O)c1cc(-c2ccccc2)cnc1N1CC[C@@H](Oc2ccc(C(F)(F)F)cn2)C1]

The title compound was prepared following procedures described in intermediate 1 step 1 to give 5-phenyl-2-(3-(5-(trifluoromethyl)pyridin-2-yloxy)pyrrolidin-1-yl)nicotinate (250 mg, 80% yield), Mass spec: 444 (M+1).

Step 4: (R)-5-phenyl-2-(3-(5-(trifluoromethyl)pyridin-2-yloxy)pyrrolidin-1-yl)nicotinic acid

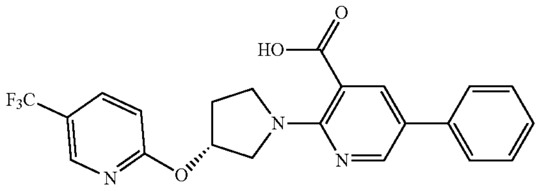 [SMILES: O=C(O)c1cc(-c2ccccc2)cnc1N1CC[C@@H](Oc2ccc(C(F)(F)F)cn2)C1]

The title compound was prepared following procedures described in intermediate 38 step 2 to give (R)-5-phenyl-2-(3-(5-(trifluoromethyl)pyridin-2-yloxy)pyrrolidin-1-yl) nicotinic acid (150 mg, 75% yield), Mass spect: 430 (M+1), $t_R$=2.658 min, $^{1}$H-NMR (400 Hz, DMSO), □□□=8.567-8.615 (m, 2H), 8.047-8.107 (m, 2H), 7.627-7.649 (m, 2H), 7.426-7.464 (m, 2H), 7.306-7.342 (m, 1H), 7.015-7.038 (d, 1H), 55.67 (m, 1H), 3.949-3.992 (m, 1H), 3.730-3.801 (m, 3H), 2.238-2.301 (m, 2H).

Step 5: (R)-5-phenyl-2-(3-(5-(trifluoromethyl)pyridin-2-yloxy)pyrrolidin-1-yl)nicotinamide

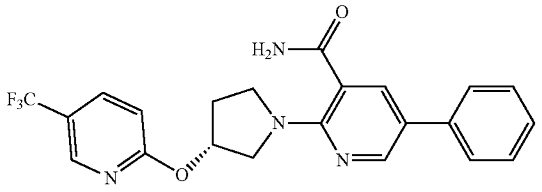 [SMILES: NC(=O)c1cc(-c2ccccc2)cnc1N1CC[C@@H](Oc2ccc(C(F)(F)F)cn2)C1]

To a solution of (R)-5-phenyl-2-(3-(5-(trifluoromethyl) pyridin-2-yloxy)pyrrolidin-1-yl)nicotinic acid (140 mg, 0.33 mmol) in 2 mL DCM was added 0.04 ml $(COCl)_2$ and one drop DMF, It was stirred at r.t for 3 h, then evaporated to dry; the residue was dissolved in 2 ml THE and NH3 in THE was added, the mixture was stirred at r.t overnight, removal the solvent to left the crude product which was purified by silica gel to give (R)-5-phenyl-2-(3-(5-(trifluoromethyl)pyridin-2-yloxy)pyrrolidin-1-yl)nicotinamide (50 mg, 36% yield), Mass spec: 429 (M+1), $t_R$=2.257 min, $^1$H-NMR (400 Hz, DMSO) □□=8.620 (s, 1H), 8.473-8.478 (d, 1H), 8.047-8.075 (m, 2H), 7.830-7.835 (d, 1H), 7.625-7.643 (d, 1H), 7.440-7.474 (m, 3H), 7.310-7.328 (m, 1H), 7.005-7.028 (d, 1H), 5.693 (s, 2H), 3.938-3.969 (m, 1H), 3.612-3.744 (m, 3H), 2.225-2.288 (m, 2H).

Example 374: (R)-2-(3-(3-chloropyridin-2-yloxy) pyrrolidin-1-yl)-5-phenylnicotinamide (Compound 1-90)

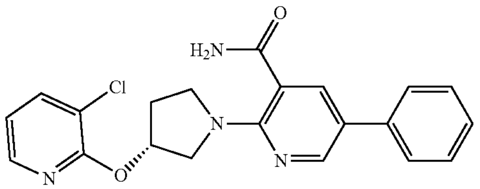 [SMILES: NC(=O)c1cc(-c2ccccc2)cnc1N1CC[C@@H](Oc2ncccc2Cl)C1]

The title compound was prepared following procedures described in example 373 to give (R)-2-(3-(3-chloropyridin-2-yloxy)pyrrolidin-1-yl)-5-phenylnicotinamide (100 mg, 50% yield), Mass spec: 395 (M+1), $t_R$=1.342 min, $^1$H-NMR (400 Hz, DMSO) □□=8.492-8.498 (d, 1H), 8.162-8.172 (m, 1H), 7.991 (s, 1H), 7.894-7.912 (m, 1H), 7.829-7.835 (m, 1H), 7.637-7.657 (d, 1H), 7.424-7.476 (m, 3H), 7.312-7.330 (m, 1H), 7.040-7.059 (m, 1H), 5.659-5.669 (m, 1H), 3.960-3.991 (m, 1H), 3.657-3.760 (m, 3H), 2.213-2.218 (m, 2H).

Example 375: (S)-tert-butyl 2-(6-(hydroxymethyl)-5-(3-(5-methylpyridin-2-yloxy)pyrrolidin-1-yl)pyridin-2-yl)benzyl (methyl)carbamate (Compound 1-258)

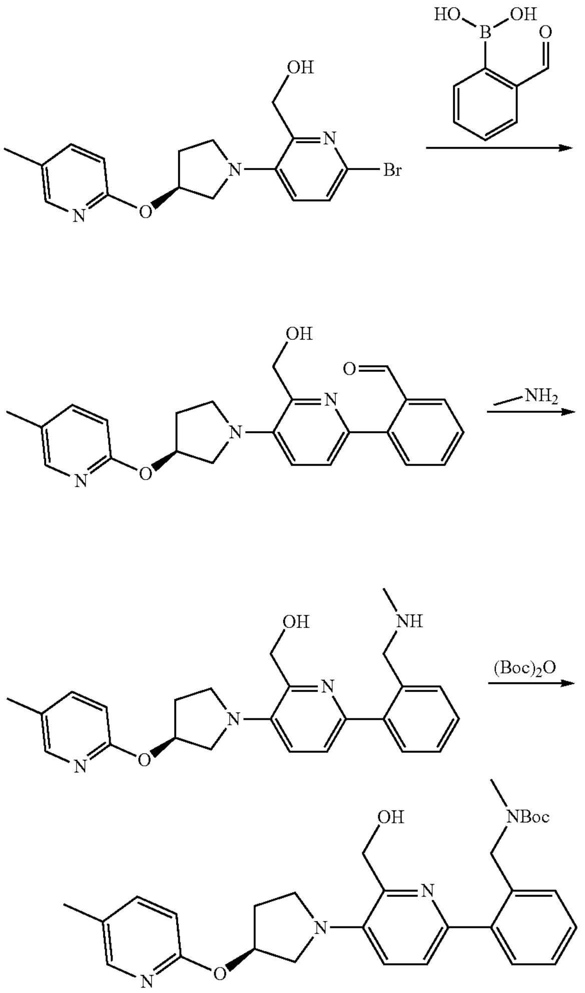

Step 1: (S)-2-(6-(hydroxymethyl)-5-(3-(5-methylpyridin-2-yloxy)pyrrolidin-1-yl)pyridin-2-yl)benzaldehyde

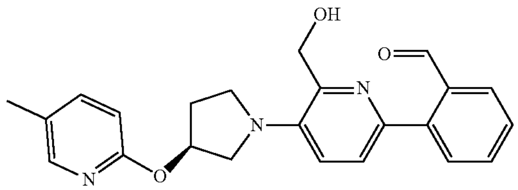 [SMILES: Cc1ccc(O[C@H]2CCN(c3ccc(-c4ccccc4C=O)nc3CO)C2)nc1]

The title compound was prepared following procedures described in example 357 step 4 to give (S)-2-(6-(hydroxymethyl)-5-(3-(5-methylpyridin-2-yloxy)pyrrolidin-1-yl)pyridin-2-yl)benzaldehyde (280 mg, 55% yield), Mass spec: 390 (M+1).

Step 2: (S)-(6-(2-((methyl amino)methyl)phenyl)-3-(3-(5-methylpyridin-2-yloxy)pyrrolidin-1-yl)pyridin-2-yl)methanol

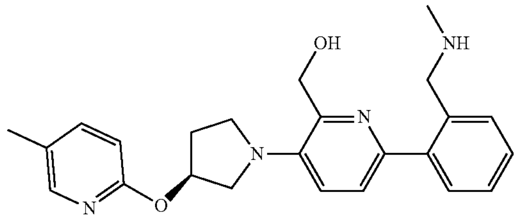 [SMILES: CNCc1ccccc1-c1ccc(N2CC[C@H](Oc3ccc(C)cn3)C2)c(CO)n1]

To a solution of (S)-2-(6-(hydroxymethyl)-5-(3-(5-methylpyridin-2-yloxy)pyrrolidin-1-yl)pyridin-2-yl)benzal (250 mg, 0.641 mmol) in 2 mL DMSO was added $MeNH_2$ (86 mg, 12.8 mmol) at r.t, the mixture was stirred at 40° C. for 2 h, then NaBH $(OAc)_3$ (204 mg, 0.96 mmol) in 1 mL DMSO was added dropwise at rt, the resulting mixture was stirred overnight at r.t, quenched by 10% citric acid solution, extracted with EA, the aqueous layer was basified by addition of a 10% $K_2CO_3$ solution to PH=10, extracted with EA, combined organic layer which was washed with brine, dried over $N_2SO_4$, removal the solvent to left the crude (S)-(6-(2-((methylamino)methyl)phenyl)-3-(3-(5-methylpyridin-2-yloxy)pyrrolidin-1-yl)pyridin-2-yl)methanol which can be used directly (180 mg, 70% yield), Mass spec: 405 (M+1).

Step 3: (S)-tert-butyl 2-(6-(hydroxymethyl)-5-(3-(5-methylpyridin-2-yloxy)pyrrolidin-1-yl)pyridin-2-yl)benzyl (methyl)carbamate

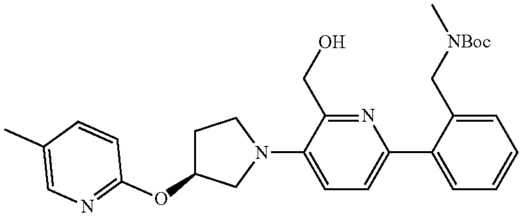 [SMILES: Cc1ccc(O[C@H]2CCN(c3ccc(-c4ccccc4CN(C)C(=O)OC(C)(C)C)nc3CO)C2)nc1]

The title compound was prepared following procedures described in example 294 step 2 to give 2-(6-(hydroxymethyl)-5-(3-(5-methylpyridin-2-yloxy)pyrrolidin-1-yl)pyridin-2-yl)benzyl (methyl)carbamate (15 mg, 8% yield), Mass spec: 505 (M+1), $t_R$=2.626 min, $^1$H-NMR (400 Hz, DMSO) δ=8.000-8.004 (m, 1H), 7.533-7.555 (m, 1H), 7.316-7.405 (m, 4H), 7.180-7.241 (m, 2H), 6.723-6.743 (d, 1H), 5.566-5.586 (m, 1H), 5.055-5.082 (m, 1H), 4.576-4.677 (m, 4H), 3.858-3.898 (m, 1H), 3.430-3.580 (m, 3H), 2.656 (s, 3H), 2.502-2.515 (m, 1H), 2.140-2.156 (m, 1H), 1.297-1.400 (m, 9H).

Example 435: (S)-(5-(3, 6-dihydro-2H-pyran-4-yl)-2-(3-(5-(trifluoromethyl)pyridin-2-yloxy)pyrrolidin-1-yl)phenyl)methanol (Compound 1-280)

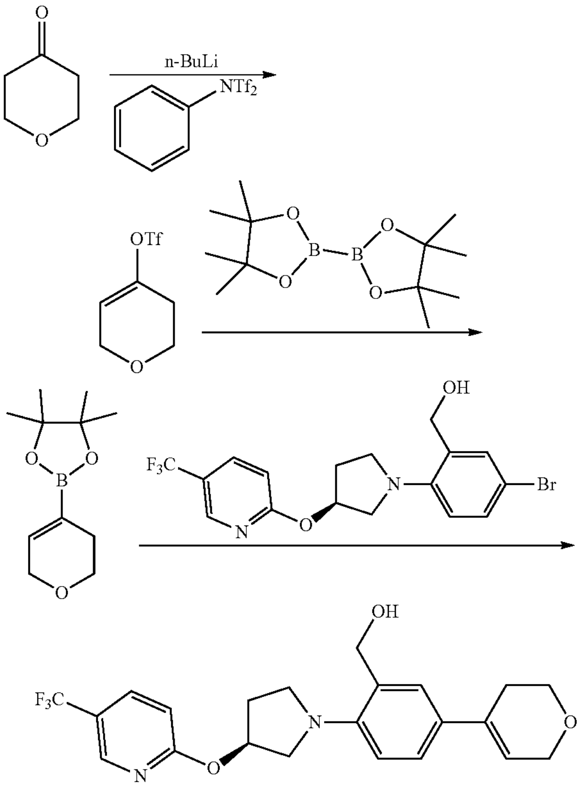

Step 1: 3, 6-dihydro-2H-pyran-4-yl trifluoromethanesulfonate

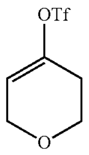 [SMILES: O=S(=O)(OC1=CCOCC1)C(F)(F)F]

To a solution of dihydro-2H-pyran-4 (3H)-one (1 g, 0.01 mol) in THE was added LDA (Prepared: To a solution of diisopropylamine (1.54 ml, 0.011 mol) in dry THE (10 ml) was added n-BuLi (4.39 ml, 2.5 Min hexane) drop-wised in ice-salt bath during 10 min under $N_2$, the mixture was stirred at this temperature for 30 min) drop-wised during 20 min at −78° C., the mixture was stirred for 3 h at this temperature, then a solution of 1,1,1-trifluoro-N-phenyl-N-(trifluoromethylsulfonyl)methanesulfonamide (3.75 g, 0.105 mol) in THE was added drop-wised, the resulting mixture was stirred at −78° C. for 2 h, then allowed to warm to rt and stirred for 18 r, removed the solvent to left the residue which was partitioned between EA and water, EA layer was washed with water, 2M NaOH solution and brine, dried over $Na_2SO_4$, removal the solvent to left the crude 3, 6-dihydro-2H-pyran-4-yl trifluoromethanesulfonate (1.1 g, 70% yield), which can be used directly.

Step 2: 2-(3,6-dihydro-2H-pyran-4-yl)-4,4,5,5-tetramethyl-1,3,2-dioxaborolane

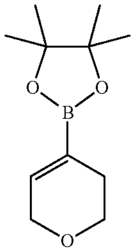

The title compound was prepared following procedures described in example 281 step 1 to give 2-(3,6-dihydro-2H-pyran-4-yl)-4,4,5,5-tetramethyl-1,3,2-dioxaborolane (100 mg, quant.) which can be used directly.

Step 3: (S)-(5-(3, 6-dihydro-2H-pyran-4-yl)-2-(3-(5-(trifluoromethyl)pyridin-2-yloxy)pyrrolidin-1-yl) phenyl)methanol

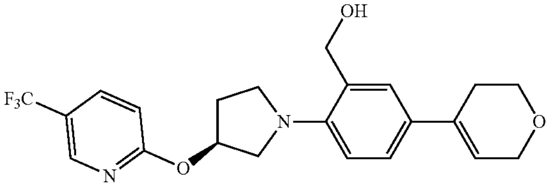 [SMILES: OCc1cc(C2=CCOCC2)ccc1N1CC[C@H](Oc2ccc(C(F)(F)F)cn2)C1]

To a solution of (S)-(5-bromo-2-(3-(5-(trifluoromethyl) pyridin-2-yloxy)pyrrolidin-1-yl)phenyl)methanol (200 mg, 0.5 mmol) in 2 ml dioxane/$H_2O$ (v:v=5:1) was added 2-(3,6-dihydro-2H-pyran-4-yl)-4,4,5,5-tetramethyl-1,3,2-dioxaborolane (100 mg), K2CO3 (276 mg, 2 mmol) and Pd $(PPh_4)_3$ (5 mg), the mixture was heated to reflux for 2 h under $N_2$, diluted with EA, the organic layer was washed by water, brine, dried over $Na_2SO_4$, removal the solvent to left the crude product which was purified by Prep-HPLC to give (S)-(5-(3, 6-dihydro-2H-pyran-4-yl)-2-(3-(5-(trifluoromethyl)pyridin-2-yloxy)pyrrolidin-1-yl)phenyl)methanol (15 mg, 7.5% yield), Mass spec: 421 (M+1), $t_R$=2.895 min, $^1$H-NMR (400 Hz, DMSO) δ=8.611 (s, 1H), 8.060-8.088 (m, 1H), 7.461-7.466 (m, 1H), 7.209-7.236 (m, 1H), 7.021-7.043 (m, 1H), 6.828-6.850 (m, 1H), 6.088 (s, 1H), 5.624-5.651 (m, 1H), 4.495-4.518 (m, 2H), 4.203-4.210 (m, 2H), 3.657-3.698 (m, 1H), 3.414-3.437 (m, 1H), 3.200-3.306 (m, 2H), 2.411 (m, 2H), 2.361-2.381 (m, 1H), 2.120-2.340 (m, 1H).

Example 436: (S)-(5-(tetrahydro-2H-pyran-4-yl)-2-(3-(5-(trifluoromethyl)pyridin-2-yloxy)pyrrolidin-1-yl)phenyl)methanol (Compound 1-276)

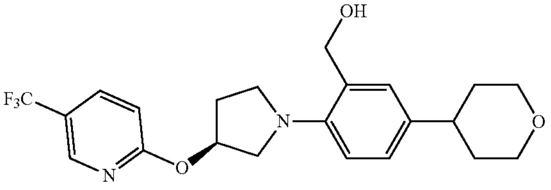 [SMILES: OCc1cc(C2CCOCC2)ccc1N1CC[C@H](Oc2ccc(C(F)(F)F)cn2)C1]

To a solution of (S)-(5-(3,6-dihydro-2H-pyran-4-yl)-2-(3-(5-(trifluoromethyl)pyridin-2-yloxy)pyrrolidin-1-yl)phenyl) methanol (20 mg, 0.047 mmol) in 2 ml MeOH was added Pd/C (5 mg), the mixture was stirred for 3 h at rt under $H_2$, filtered and the filtrate was concentrated, The residue was purified by silica gel to give (S)-(5-(tetrahydro-2H-pyran-4-yl)-2-(3-(5-(trifluoromethyl)pyridin-2-yloxy)pyrrolidin-1-yl)phenyl)methanol (5 mg, 25% yield), Mass spec: 423 (M+1), $t_R$=2.622 min, $^1$H-NMR (400 Hz, DMSO) δ=8.605 (s, 1H), 8.060-8.088 (m, 1H), 7.269-7.273 (m, 1H), 7.010-7.044 (m, 2H), 6.853-6.873 (m, 1H), 5.614 (m, 1H), 5.033 (m, 1H), 4.481-4.502 (m, 2H), 3.920-3.954 (m, 2H), 3.115-3.588 (m, 6H), 2.680 (m, 1H), 2.088 (m, 1H), 2.086 (m, 1H), 1.624-1.660 (m, 4H).

Example 437: (S)-tert-butyl 4-(3-(hydroxymethyl)-4-(3-(5-(trifluoromethyl)pyridin-2-yloxy)pyrrolidin-1-yl)phenyl)-5,6-dihydropyridine-1 (2H)-carboxylate (Compound 1-272)

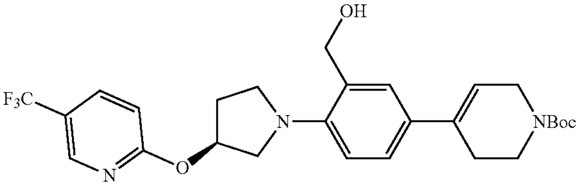 [SMILES: CC(C)(C)OC(=O)N1CC=C(c2ccc(N3CC[C@H](Oc4ccc(C(F)(F)F)cn4)C3)c(CO)c2)CC1]

The title compound was prepared following procedures described in example 435 to give (S)-tert-butyl 4-(3-(hydroxymethyl)-4-(3-(5-(trifluoromethyl)pyridin-2-yloxy) pyrrolidin-1-yl)phenyl)-5,6-dihydropyridine-1 (2H)-carboxylate (10 mg, 12.5% yield), Mass spec: 520 (M+1), $t_R$=3.292 min, $^1$H-NMR (400 Hz, DMSO) δ=8.611 (s, 1H), 8.065-8.087 (m, 1H), 7.445-7.450 (m, 1H), 7.196-7.217 (m, 1H), 7.019-7.042 (m, 1H), 6.818-6.840 (m, 1H), 5.998 (s, 2H), 5.634 (s, 1H), 5.069-5.096 (m, 1H), 4.486-4.513 (m, 2H), 3.927 (s, 2H), 3.195-3.655 (m, 6H), 2.442 (s, 2H), 2.340-2.375 (m, 1H), 2.085-2.117 (m, 1H).

Example 438: (S)-tert-butyl 4-(3-(hydroxymethyl)-4-(3-(5-(trifluoromethyl)pyridin-2-yloxy)pyrrolidin-1-yl)phenyl)piperidine-1-carboxylate (Compound 1-273)

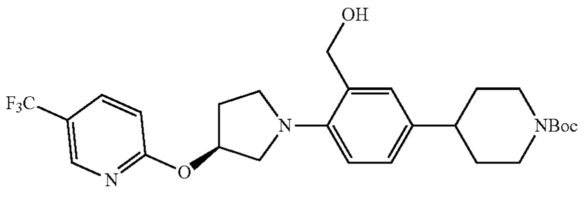 [SMILES: CC(C)(C)OC(=O)N1CCC(c2ccc(N3CC[C@H](Oc4ccc(C(F)(F)F)cn4)C3)c(CO)c2)CC1]

The title compound was prepared following procedures described in example 436 to give (S)-tert-butyl 4-(3-(hydroxymethyl)-4-(3-(5-(trifluoromethyl)pyridin-2-yloxy)pyrrolidin-1-yl)phenyl)piperidine-1-carboxylate (60 mg, 70% yield), Mass spec: 522 (M+1), $t_R$=3.355 min, $^1$H-NMR (400 Hz, DMSO) δ=8.467 (s, 1H), 7.912-7.934 (m, 1H), 7.264 (s, 1H), 6.930-7.080 (m, 3H), 5.644-5.658 (m, 1H), 4.870 (s, 2H), 4.173-4.206 (m, 2H), 3.570-3.598 (m, 1H), 3.134-3.382 (m, 3H), 2.853 (s, 2H), 2.667 (m, 1H), 2.426-2.460 (m, 1H), 2.147-2.165 (m, 1H), 1.779-1.810 (m, 1H), 1.511-1.576 (m, 2H).

Example 439: (S)-tert-butyl 4-(3-(2-hydroxyethyl)-4-(3-(5-(trifluoromethyl)pyridin-2-yloxy)pyrrolidin-1-yl)phenyl)-5,6-dihydropyridine-1 (2H)-carboxylate (Compound 1-299)

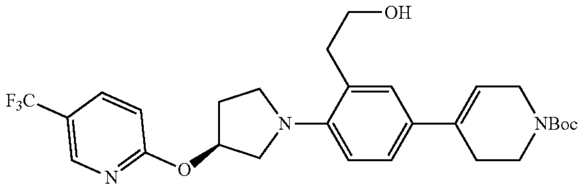 [SMILES: CC(C)(C)OC(=O)N1CC=C(c2ccc(N3CC[C@H](Oc4ccc(C(F)(F)F)cn4)C3)c(CCO)c2)CC1]

The title compound was prepared following procedures described in Example 435 step 3 using (S)-2-(5-bromo-2-(3-(5-(trifluoromethyl)pyridin-2-yloxy)pyrrolidin-1-yl)phenyl)ethanol to give 4-(3-(2-hydroxyethyl)-4-(3-(5-(trifluoromethyl)pyridin-2-yloxy)pyrrolidin-1-yl)phenyl)-5,6-dihydropyridine-1 (2H)-carboxylate (180 mg, 36% yield), Mass spec: 534 (M+1), $t_R$=3.129 min, $^1$H-NMR (400 Hz, DMSO) δ=8.612 (s, 1H), 8.065-8.093 (m, 1H), 7.227-7.232 (m, 1H), 6.922-7.159 (m, 3H), 6.010 (m, 1H), 5.617-5.647 (m, 1H), 4.648-4.674 (m, 1H), 3.571 (s, 2H), 3.136-3.627 (m, 8H), 2.789-2.806 (m, 2H), 2.366-2.406 (m, 3H), 2.114-2.366 (m, 1H).

Example 440: (S)-tert-butyl 4-(3-(2-hydroxyethyl)-4-(3-(5-(trifluoromethyl)pyridin-2-yloxy)pyrrolidin-1-yl)phenyl)piperidine-1-carboxylate (Compound 1-301)

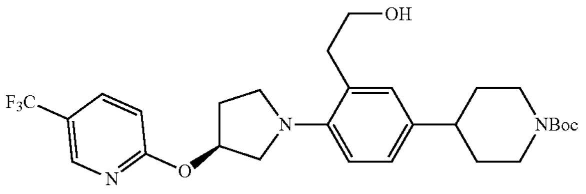 [SMILES: CC(C)(C)OC(=O)N1CCC(c2ccc(N3CC[C@H](Oc4ccc(C(F)(F)F)cn4)C3)c(CCO)c2)CC1]

The title compound was prepared following procedures described in Example 436 to give (S)-tert-butyl 4-(3-(2-hydroxyethyl)-4-(3-(5-(trifluoromethyl)pyridin-2-yloxy)pyrrolidin-1-yl)phenyl)piperidine-1-carboxylate (112 mg, 74% yield), Mass spec: 536 (M+1), $t_R$=3.161 min, $^1$H-NMR (400 Hz, DMSO) δ=8.604 (s, 1H), 8.061-8.089 (m, 1H), 6.930-7.047 (m, 4H), 5.593-5.623 (m, 1H), 3.050-3.154 (m, 2H), 2.759-2.778 (m, 3H), 2.507-2.564 (m, 1H), 2.065-2.078 (m, 1H), 1.684-1.716 (m, 2H), 1.448-1.471 (m, 3H).

Example 442: (S)-6-(1-(3-(hydroxymethyl)biphenyl-4-yl)pyrrolidin-3-yloxy)nicotinonitrile (Compound 1-143)

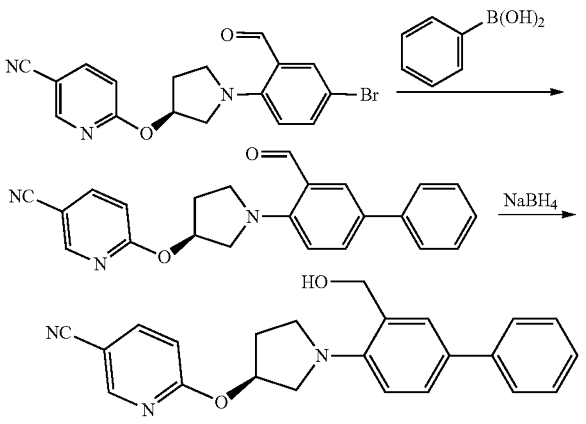

Step 1: (S)-6-(1-(3-formylbiphenyl-4-yl)pyrrolidin-3-yloxy)nicotinonitrile

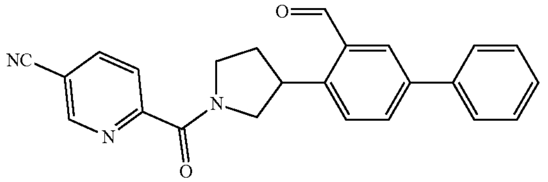 [SMILES: N#Cc1ccc(C(=O)N2CCC(c3ccc(-c4ccccc4)cc3C=O)C2)nc1]

The title compound was prepared following procedures described in Example 67 step 2 to using (S)-6-(1-(4-bromo-2-formylphenyl)pyrrolidin-3-yloxy)nicotinonitrile (prepared as example 136 step 1) give (S)-6-(1-(3-formylbiphenyl-4-yl)pyrrolidin-3-yloxy)nicotinonitrile (600 mg, 83% yield), Mass spec: 382 (M+1).

Step 2: (S)-6-(1-(3-(hydroxymethyl)biphenyl-4-yl)pyrrolidin-3-yloxy)nicotinonitrile

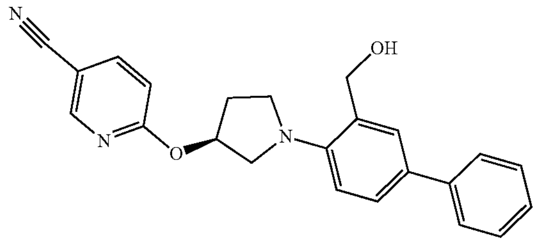 [SMILES: N#Cc1ccc(O[C@H]2CCN(c3ccc(-c4ccccc4)cc3CO)C2)nc1]

The title compound was prepared following procedures described in Example 96 step 2 to give (S)-6-(1-(3-(hydroxymethyl)biphenyl-4-yl)pyrrolidin-3-yloxy)nicotinonitrile (20 mg, 30% yield), Mass spec: 384 (M+1), $t_R$=2.873 min, $^1$H-NMR (400 Hz, DMSO) δ=8.722-8.729 (m, 1H), 8.148-8.176 (m, 1H), 7.587-7.676 (m, 3H), 7.407-7.468 (m, 3H), 7.265-7.302 (m, 1H), 6.932-7.046 (m, 2H), 5.642-5.669 (m, 1H), 5.159-5.186 (t, 1H), 4.552-4.579 (m, 2H), 3.703-3.745 (m, 1H), 3.443-3.465 (m, 1H), 3.235-3.354 (m, 2H), 2.397-2.520 (m, 1H), 2.363-2.377 (m, 1H).

Example 443: (S)-6-(1-(3-(hydroxymethyl)biphenyl-4-yl)pyrrolidin-3-yloxy)nicotinamide (Compound 1-144)

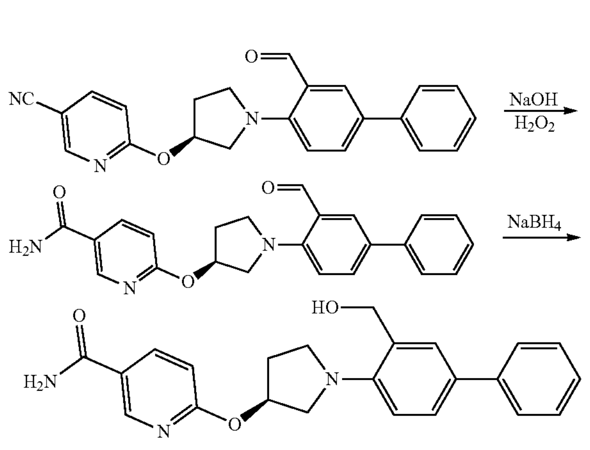

Step 1: (S)-6-(1-(3-formylbiphenyl-4-yl)pyrrolidin-3-yloxy)nicotinamide

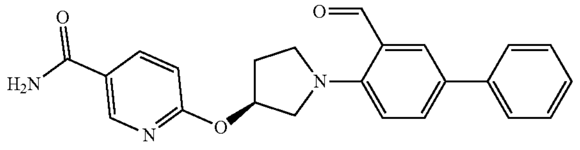 [SMILES: NC(=O)c1ccc(O[C@H]2CCN(c3ccc(-c4ccccc4)cc3C=O)C2)nc1]

The title compound was prepared following procedures described in Example 6 to give (S)-6-(1-(3-formylbiphenyl-4-yl)pyrrolidin-3-yloxy)nicotinamide (300 mg, quant.), Mass spec: 388 (M+1).

Step 2: (S)-6-(1-(3-(hydroxymethyl)biphenyl-4-yl)pyrrolidin-3-yloxy)nicotinamide

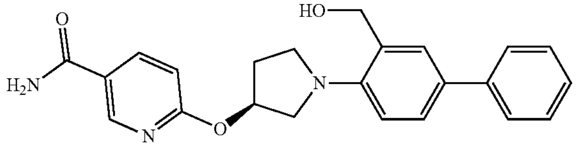 [SMILES: NC(=O)c1ccc(O[C@H]2CCN(c3ccc(-c4ccccc4)cc3CO)C2)nc1]

The title compound was prepared following procedures described in Example 96 step 2 to give (S)-6-(1-(3-(hydroxymethyl)biphenyl-4-yl)pyrrolidin-3-yloxy)nicotinamide (40 mg, 26% yield), Mass spec: 390 (M+1), $t_R$=2.394 min, $^1$H-NMR (400 Hz, DMSO) δ=8.674-8.681 (m, 1H), 8.148-8.176 (m, 1H), 7.587-7.676 (m, 3H), 7.407-7.468 (m, 1H), 7.965 (s, 1H), 7.649-7.655 (d, 1H), 7.562-7.584 (m, 2H), 7.378-7.441 (m, 4H), 7.273-7.378 (m, 1H), 6.858-6.926 (q, 2H), 5.613-5.625 (m, 1H), 5.100-5.127 (t, 1H), 4.533-4.562 (m, 2H), 3.685-3.726 (m, 1H), 3.434-3.457 (m, 1H), 3.339-3.342 (m, 1H), 3.232-3.243 (m, 2H), 2.473-2.486 (m, 1H), 2.340-2.345 (m, 1H).

Example 444: (S)-(4-(3-(5-methylpyridin-2-yloxy)pyrrolidin-1-yl)biphenyl-3-yl)methanol (Compound 1-141)

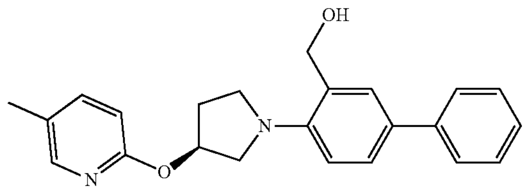 [SMILES: Cc1ccc(O[C@H]2CCN(c3ccc(-c4ccccc4)cc3CO)C2)nc1]

The title compound was prepared following procedures described in Example 124 to give (S)-(4-(3-(5-methylpyridin-2-yloxy)pyrrolidin-1-yl)biphenyl-3-yl)methanol (25 mg, 30% yield), Mass spec: 361 (M+1), $t_R$=3.077 min, $^1$H-NMR (400 Hz, DMSO) δ=7.992-7.999 (q, 1H), 7.671-7.677 (d, 1H), 7.524-7.608 (m, 3H), 7.406-7.456 (m, 3H), 7.281-7.299 (m, 1H), 6.919-6.940 (d, 1H), 6.726-6.747 (d, 1H), 5.531 (br, 1H), 5.129-5.143 (t, 1H), 4.550-4.580 (m, 2H), 3.696-3.710 (m, 1H), 3.443 (m, 1H), 3.295-3.342 (m, 2H), 2.311-2.333 (m, 1H), 2.212 (s, 3H), 2.091 (m, 1H).

Example 445: 1-(2'-chloro-4-((S)-3-(3-methylpyridin-2-yloxy)pyrrolidin-1-yl)biphenyl-3-yl)ethanol (Compound 1-172)

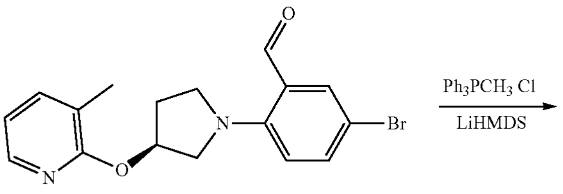

-continued

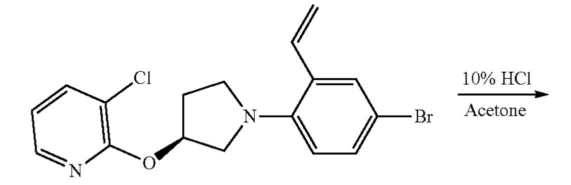

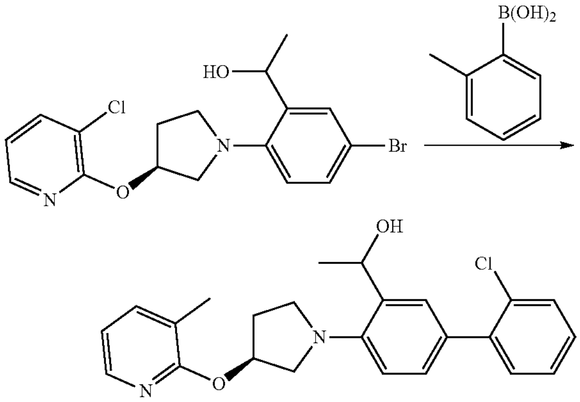

Step 1: (S)-6-(1-(4-bromo-2-vinylphenyl)pyrrolidin-3-yloxy)-5-chloropyridin-3-ide

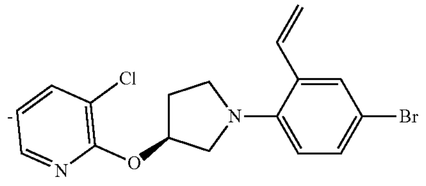 [SMILES: C=Cc1cc(Br)ccc1N1CC[C@H](Oc2nc[c-]cc2Cl)C1]

The title compound was prepared following procedures described in Example 301 step 1 to give (S)-6-(1-(4-bromo-2-vinylphenyl)pyrrolidin-3-yloxy)-5-chloropyridin-3-ide (1.7 g, 77% yield), Mass spec: 378 (M+1).

Step 2: 1-(5-bromo-2-((S)-3-(3-chloropyridin-2-yloxy)pyrrolidin-1-yl)phenyl)ethanol

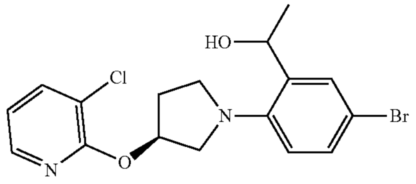 [SMILES: CC(O)c1cc(Br)ccc1N1CC[C@H](Oc2ncccc2Cl)C1]

The title compound was prepared following procedures described in Example 301 step 2 to give 1-(5-bromo-2-((S)-3-(3-chloropyridin-2-yloxy)pyrrolidin-1-yl)phenyl)ethanol (300 mg, 29% yield), Mass spec: 397 (M+1).

Step 3: 1-(2'-chloro-4-((S)-3-(3-methylpyridin-2-yloxy)pyrrolidin-1-yl)biphenyl-3-yl)ethanol

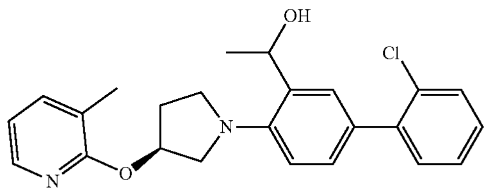 [SMILES: Cc1cccnc1O[C@H]1CCN(c2ccc(-c3ccccc3Cl)cc2C(C)O)C1]

The title compound was prepared following procedures described in Example 67 step 2 to give 1-(2'-chloro-4-((S)-3-(3-methylpyridin-2-yloxy)pyrrolidin-1-yl)biphenyl-3-yl) ethanol (17 mg, 32% yield), Mass spec: 409 (M+1), $t_R$=3.125 min, $^1$H-NMR (400 Hz, DMSO) δ=7.969-7.981 (d, 1H), 7.502-7.547 (m, 3H), 7.322-7.381 (m, 3H), 7.028-7.236 (m, 2H), 6.853-6.883 (m, 1H), 5.566 (br, 1H), 5.052-5.114 (m, 2H), 3.345-3.346 (m, 2H), 3.181-3.322 (m, 2H), 2.471-2.484 (m, 1H), 2.113-2.131 (m, 4H), 1.288-1.371 (dd, 3H).

Example 446: 1-(4-((S)-3-(3-methylpyridin-2-yloxy) pyrrolidin-1-yl)biphenyl-3-yl)ethanol (Compound 1-169)

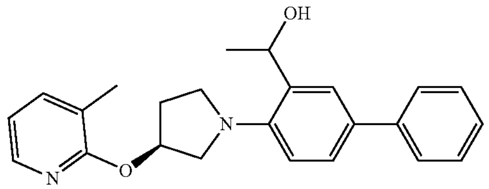 [SMILES: Cc1cccnc1O[C@H]1CCN(c2ccc(-c3ccccc3)cc2C(C)O)C1]

The title compound was prepared following procedures described in Example 445 to give 1-(4-((S)-3-(3-methylpyridin-2-yloxy)pyrrolidin-1-yl)biphenyl-3-yl)ethanol (27 mg, 55% yield), Mass spec: 375 (M+1), $t_R$=2.898 min, $^1$H-NMR (400 Hz, DMSO) δ=8.005 (d, 1H), 7.760-7.780 (d, 1H), 7.543-7.615 (m, 3H), 7.440-7.460 (m, 3H), 7.309 (m, 1H), 7.115-7.129 (m, 1H), 6.886-6.911 (m, 1H), 5.581 (br, 1H), 5.145 (m, 2H), 3.440-3.637 (m, 2H), 3.119-3.264 (m, 2H), 2.365-2.380 (m, 1H), 2.077-2.160 (m, 4H), 1.333-1.419 (dd, 3H).

Example 455: (S)-(4'-(3-(5-(trifluoromethyl)pyridin-2-yloxy)pyrrolidin-1-yl)biphenyl-2,3'-diyl)dimethanol (Compound 1-174)

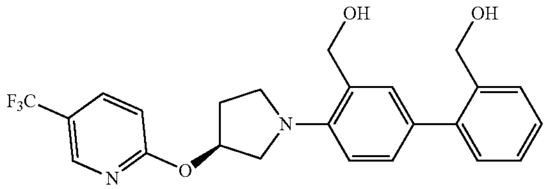 [SMILES: OCc1ccccc1-c1ccc(N2CC[C@H](Oc3ccc(C(F)(F)F)cn3)C2)c(CO)c1]

The title compound was prepared following procedures described in example 279 to give (S)-(4'-(3-(5-(trifluoromethyl)pyridin-2-yloxy)pyrrolidin-1-yl)biphenyl-2,3'-diyl)dimethanol (8 mg, 10% yield), Mass spec: 445 (M+1), $t_R$=2.845 min, $^1$H-NMR (400 Hz, DMSO) δ=8.625 (s, 1H), 8.073-8.100 (m, 1H), 7.548-7.566 (m, 1H), 7.292-7.348 (m, 3H), 7.163-7.193 (m, 2H), 7.041-7.064 (d, 1H), 6.905-6.926 (d, 1H), 5.666 (br, 1H), 5.105-5.132 (t, 2H), 4.536-4.561 (t, 2H), 4.429-4.442 (d, 2H), 3.728-3.756 (m, 1H), 3.446-3.487 (m, 2H), 3.253-3.374 (m, 1H), 2.338-2.406 (m, 1H), 2.141 (m, 1H).

Example 456: (S)-(2'-((dimethylamino)methyl)-4-(3-(5-methylpyridin-2-yloxy)pyrrolidin-1-yl)biphenyl-3-yl)methanol (Compound 1-219)

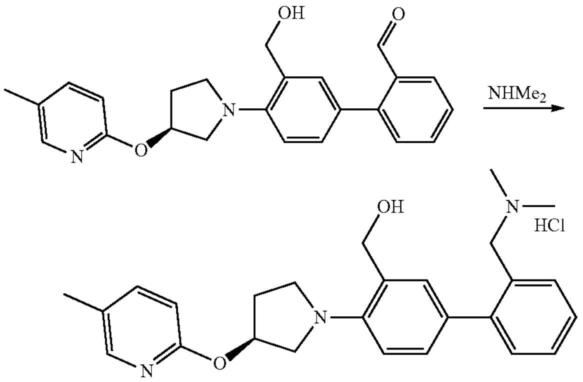

To a solution of (S)-3'-(hydroxymethyl)-4'-(3-(5-methylpyridin-2-yloxy)pyrrolidin-1-yl)biphenyl-2-carbaldehyde (150 mg, 0.387 mmol) (prepared as example 279 step 1) in 3 mL DMSO was added Me2NH HCl (62 mg, 0.77 mmol), the mixture was stirred at 40° C. for 30 min to form a cleat solution. To this reaction mixture was added a solution $NaB(OAc)_3H$ (123 mg, 0.58 mmol) in DMSO drop-wised, and stirred at rt for another 4 h, the mixture was quenched by 10% citric acid solution, the water layer was basified by 10% $K_2CO_3$ solution, extracted with EA, dried over $Na_2SO_4$, removal the solvent to left the crude product which was purified by Prep-HPLC to give (S)-(2'-((dimethylamino)methyl)-4-(3-(5-methylpyridin-2-yloxy)pyrrolidin-1-yl)biphenyl-3-yl)methanol (30 mg, 18%), Mass spec: 418 (M+1), $t_R$=1.721 min, $^1$H-NMR (400 Hz, CDCl3) δ=11.915 (br, 1H), 7.853-8.037 (m, 2H), 7.421-7.485 (m, 3H), 7.264-7.312 (m, 2 h), 7.132-7.168 (m, 2H), 6.690-6.709 (d, 1H), 5.652 (d, 1H), 4.811-4.920 (m, 2H), 4.302 (s, 2H), 3.944 (br, 1H), 3.651 (br, 1H), 3.506 (m, 2H), 2.589 (m, 7H), 2.218-2.326 (m, 4H).

Example 457: (R)-5-benzoyl-2-(3-(5-(trifluoromethyl)pyridin-2-yloxy)pyrrolidin-1-yl)benzamide (Compound 1-154)

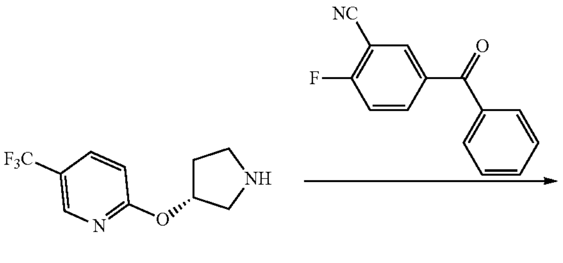

-continued

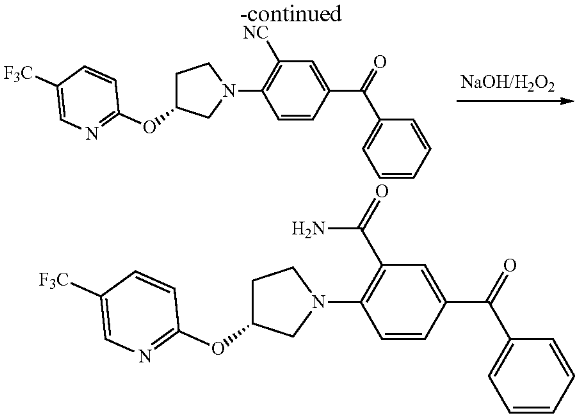

Step 1: (R)-5-benzoyl-2-(3-(5-(trifluoromethyl)pyridin-2-yloxy)pyrrolidin-1-yl)benzonitrile

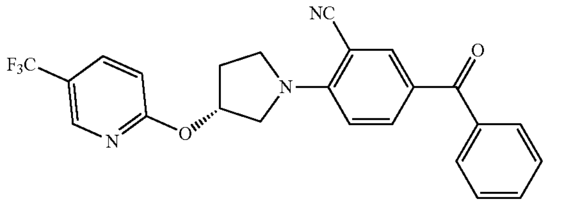 [SMILES: N#Cc1cc(C(=O)c2ccccc2)ccc1N1CC[C@@H](Oc2ccc(C(F)(F)F)cn2)C1]

To a solution of (R)-2-(pyrrolidin-3-yloxy)-5-(trifluoromethyl)pyridine (279 mg, 1.2 mmol)(intermediate 4) in 4 mL DMF was added 5-benzoyl-2-fluorobenzonitrile (226 mg, 1 mmol) (prepared as intermediate 8 step 4) and $K_2CO_3$, the mixture was stirred at 100° C. for 16 h, the mixture was diluted with EA, the organic layer was washed by LiCl solution, brine, dried over Na2SO4, removal the solvent to left th crude product which was purified by silica gel to give (R)-5-benzoyl-2-(3-(5-(trifluoromethyl)pyridin-2-yloxy)pyrrolidin-1-yl)benzonitrile (350 mg, 80% yield), Mass spec: 438 (M+1).

Step 2: (R)-5-benzoyl-2-(3-(5-(trifluoromethyl)pyridin-2-yloxy)pyrrolidin-1-yl)benzamide

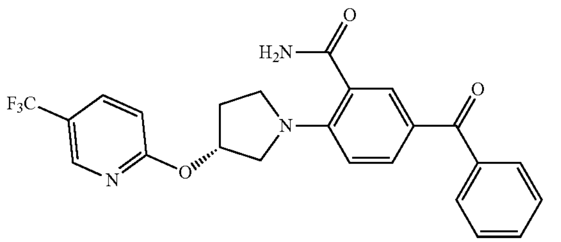 [SMILES: NC(=O)c1cc(C(=O)c2ccccc2)ccc1N1CC[C@@H](Oc2ccc(C(F)(F)F)cn2)C1]

The title compound was prepared following procedures described in example 6 to give (R)-5-benzoyl-2-(3-(5-(trifluoromethyl)pyridin-2-yloxy)pyrrolidin-1-yl)benzamide (120 mg, 78% yield), Mass spec: 456 (M+1), $t_R$=2.697 min, $^1$H-NMR (400 Hz, DMSO) δ=8.630-8.633 (d, 1H), 8.069-8.098 (q, 1H), 7.953 (s, 1H), 7.521-7.702 (m, 7H), 7.401 (s, 1H), 6.852-7.017 (d, 1H), 6.829-6.841 (d, 1H), 5.728 (br, 1H), 3.926-3.969 (m, 1H), 3.439-3.662 (m, 3H), 2.273-2.331 (m, 2H).

Example 458: (S)-5-benzoyl-2-(3-(5-(trifluoromethyl)pyridin-2-yloxy)pyrrolidin-1-yl)benzamide (Compound 1-130)

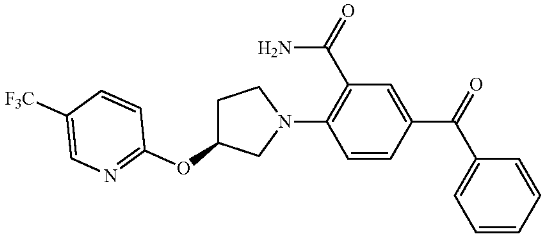 [SMILES: NC(=O)c1cc(C(=O)c2ccccc2)ccc1N1CC[C@H](Oc2ccc(C(F)(F)F)cn2)C1]

The title compound was prepared following procedures described in example 457 to give (S)-5-benzoyl-2-(3-(5-(trifluoromethyl)pyridin-2-yloxy)pyrrolidin-1-yl)benzamide (36 mg, 66% yield), Mass spec: 456 (M+1), $t_R$=2.462 min. $^1$H-NMR (400 Hz, DMSO) δ=8.635 (s, 1H), 8.071-8.099 (m, 1H), 7.947 (s, 1H), 7.522-7.697 (m, 7H), 7.399 (s, 1H), 7.019-7.040 (d, 1H), 6.831-6.854 (d, 1H), 5.727-5.734 (m, 1H), 3.927-3.970 (m, 1H), 3.440-3.664 (m, 3H), 2.276-2.336 (m, 2H).

Intermediate 300: ((2S,4S)-1-(4-phenylcyclohexa-1,5-dienyl)-4-(5-(trifluoromethyl)pyridin-2-yloxy)pyrrolidin-2-yl)methanol (Compound 1-363)

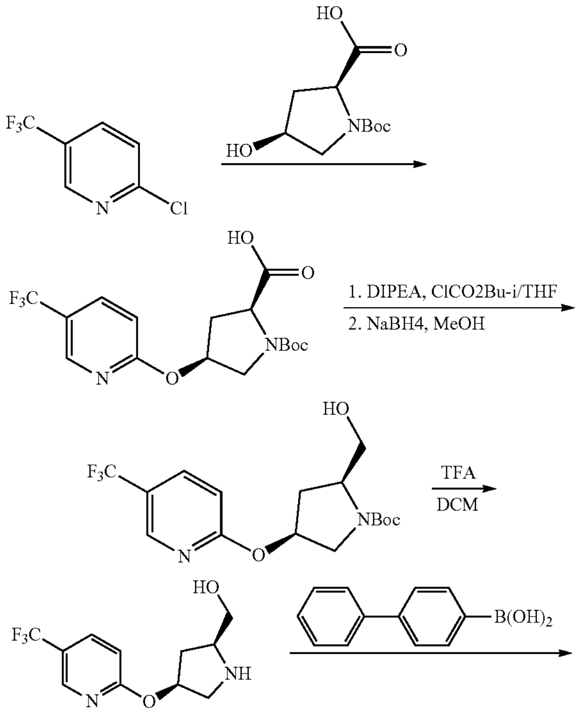

-continued

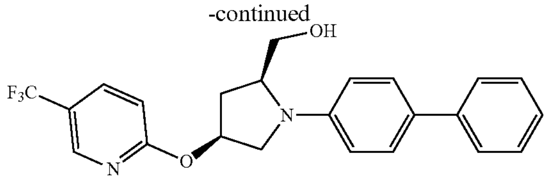

Step 1: (2S,4S)-1-(tert-butoxycarbonyl)-4-(5-(trifluoromethyl)pyridin-2-yloxy)pyrrolidine-2-carboxylic acid

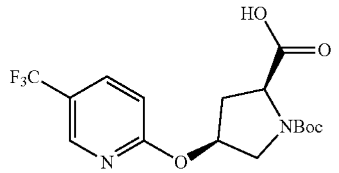 [SMILES: CC(C)(C)OC(=O)N1C[C@@H](Oc2ccc(C(F)(F)F)cn2)C[C@H]1C(=O)O]

To a solution of (2S,4S)-1-(tert-butoxycarbonyl)-4-hydroxypyrrolidine-2-carboxylic acid (4 g, 17.3 mmol) in 50 mL DMSO was added t-BuOK (4.84 g, 43.2 mmol) in 40 mL THF with stirring to rt. for 1.5 h, before 2-chloro-5-(trifluoromethyl)pyridine (3.76 g, 20.8 mmol) was added at rt, and resulting mixture was stirred for overnight. And quenched with water, extracted with EA, dried over Na2SO4, removal the solvent to left the crude product which was purified by silica gel to give (2S,4S)-1-(tert-butoxycarbonyl)-4-(5-(trifluoromethyl)pyridin-2-yloxy)pyrrolidine-2-carboxylic acid (4.3 g, 66.6% yield), Mass spec: 377 (M+H).

Step 2: (2S,4S)-tert-butyl 2-(hydroxymethyl)-4-(5-(trifluoromethyl)pyridin-2-yloxy)pyrrolidine-1-carboxylate

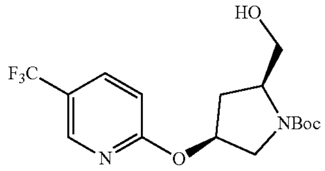 [SMILES: CC(C)(C)OC(=O)N1C[C@@H](Oc2ccc(C(F)(F)F)cn2)C[C@H]1CO]

The title compound was prepared following procedures described in Example 298 to give (2S, 4S)-tert-butyl 2-(hydroxymethyl)-4-(5-(trifluoromethyl)pyridin-2-yloxy)pyrrolidine-1-carboxylate (560 mg, 58.2% yield), Mass spec: 363 (M+H).

Step 3: ((2S, 4S)-4-(5-(trifluoromethyl)pyridin-2-yloxy)pyrrolidin-2-yl)methanol

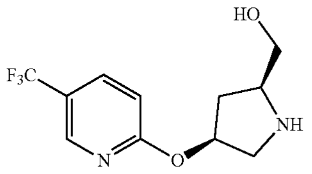 [SMILES: OC[C@@H]1C[C@H](Oc2ccc(C(F)(F)F)cn2)CN1]

To a solution of (2S, 4S)-tert-butyl 2-(hydroxymethyl)-4-(5-(trifluoromethyl)pyridin-2-yloxy)pyrrolidine-1-carboxylate (560 mg, 1.5 mmol) in 3 mL DCM was added TFA (1 mL) with stirring at 0° C. for 3 h. The mixture was extracted with EA, dried over Na2SO4, removal the solvent to left the crude product ((2S,4S)-4-(5-(trifluoromethyl)pyridin-2-yloxy)pyrrolidin-2-yl)methanol (260 mg, 64.2% yield), which can be used to next step directly, Mass spec: 263 (M+H).

Step 4: ((2S, 4S)-1-(4-phenylcyclohexa-1,5-dienyl)-4-(5-(trifluoromethyl)pyridin-2-yloxy)pyrrolidin-2-yl)methanol

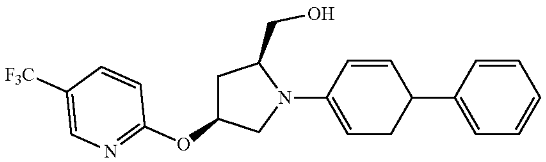

To a solution of ((2S, 4S)-4-(5-(trifluoromethyl)pyridin-2-yloxy)pyrrolidin-2-yl)methanol (160 mg, 0.61 mmol) in 5 mL DCM was added biphenyl-4-ylboronic acid (145 mg, 0.73 mmol), TEA (74 mg, 0.73 mmol), Cu(OAc)2 (133 mg, 0.73 mmol) and pyridine (49 mg, 0.61 mmol) with stirring at rt overnight. The mixture was extracted with EA, dried over Na2SO4, removal the solvent to left the crude product which was purified to give ((2S,4S)-1-(4-phenylcyclohexa-1,5-dienyl)-4-(5-(trifluoromethyl)pyridin-2-yloxy)pyrrolidin-2-yl)methanol (20 mg, 7.8%). Mass spec: 415 (M−H), $t_R$=2.229. $^1$H-NMR (400 Hz, DMSO) δ=8.608 (s, 1H), 8.092-8.064 (m, 1H), 7.628-7.597 (m, 4H), 7.455-7.409 (m, 2H), 7.330-7.295 (m, 1H), 7.054-7.000 (m, 3H), 5.522 (s, 1H), 3.966-3.946 (m, 2H), 3.715-3.688 (m, 1H), 3.337-3.252 (m, 1H), 3.031-2.991 (m, 1H), 2.153-1.931 (m, 2H).

Example 323: (S)-2-(2'-chloro-4-(3-(5-(trifluoromethyl)pyridin-2-yloxy)pyrrolidin-1-yl)biphenyl-3-yl) ethanol (Compound 1-364)

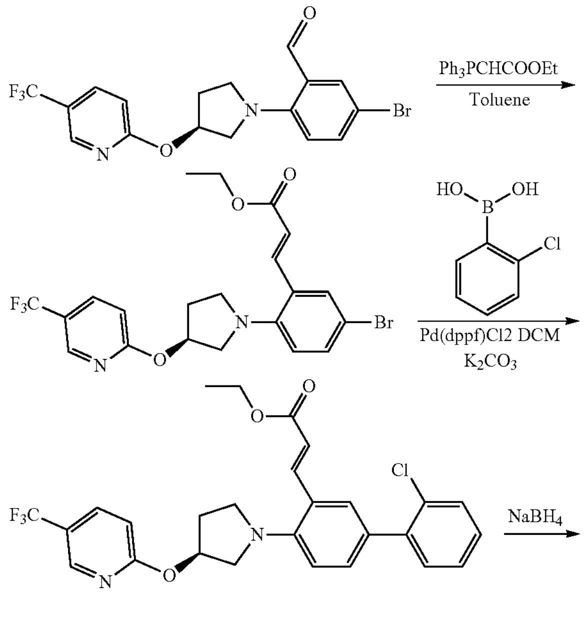

-continued

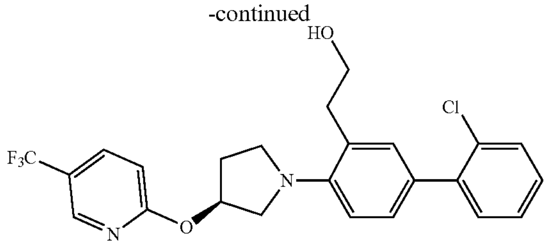

Step 1: (S, E)-ethyl 3-(5-bromo-2-(3-(5-(trifluoromethyl)pyridin-2-yloxy)pyrrolidin-1-yl)phenyl)acrylate

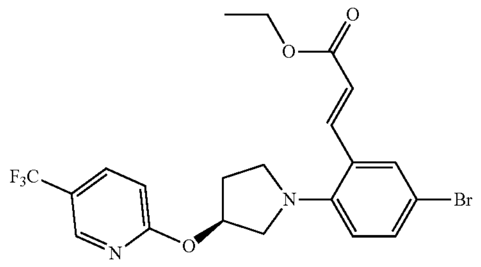 [SMILES: CCOC(=O)/C=C/c1cc(Br)ccc1N1CC[C@H](Oc2ccc(C(F)(F)F)cn2)C1]

To a solution of (S)-5-bromo-2-(3-(5-(trifluoromethyl)pyridin-2-yloxy)pyrrolidin-1-yl)benzaldehyde (1.0 g, 2.41 mmol, prepared as example 236 step) and $Ph_3PCHCO_2Et$ (1.68 g, 4.82 mmol) in 10 mL dry toluene was stirred at 110° C. overnight. The reaction was completed detected by LCMS and TLC, Diluted with EA, washed by water, brine, dried over Na2SO4, removal the solvent to left the crude product which was purified by silica gel to give (S, E)-ethyl 3-(5-bromo-2-(3-(5-(trifluoromethyl)pyridin-2-yloxy)pyrrolidin-1-yl)phenyl)acrylate as brown oil (1.05 g, 89.84% yield), Mass spec: 485 (M+1).

Step 2: (S, E)-ethyl 3-(2'-chloro-4-(3-(5-(trifluoromethyl)pyridin-2-yloxy)pyrrolidin-1-yl)biphenyl-3-yl) acrylate

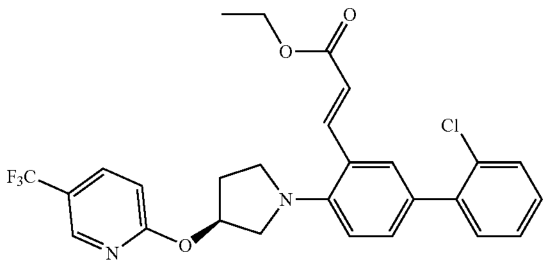 [SMILES: CCOC(=O)/C=C/c1cc(-c2ccccc2Cl)ccc1N1CC[C@H](Oc2ccc(C(F)(F)F)cn2)C1]

To a solution of (S, E)-ethyl 3-(5-bromo-2-(3-(5-(trifluoromethyl)pyridin-2-yloxy)pyrrolidin-1-yl)phenyl)acrylate (300 mg, 0.61 mmol), 2-chlorophenylboronic acid (113.8 mg, 0.73 mmol), Pd(dppf)$Cl_2$ DCM (49.7 mg, 10%) and $K_2CO_3$ (252 mg, 1.83 mmol) in 3 ml dioxane/H2O (v:v=5:1) and degassed for 2 min, then heated to 85° C. for 1 h under $N_2$. Diluted with EA, washed by water, brine, dried over Na2SO4, removal the solvent to left the crude product which was purified by silica gel to give (S, E)-ethyl 3-(2'-chloro- 4-(3-(5-(trifluoromethyl)pyridin-2-yloxy)pyrrolidin-1-yl)biphenyl-3-yl)acrylate (270 mg, 85.6% yield), Mass spec: 517 (M+1).

Step 3: (S)-2-(2'-chloro-4-(3-(5-(trifluoromethyl) pyridin-2-yloxy)pyrrolidin-1-yl)biphenyl-3-yl)ethanol

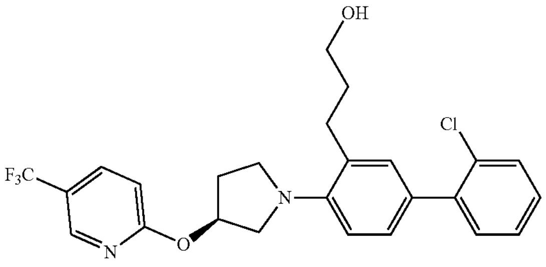 [SMILES: OCCCc1cc(-c2ccccc2Cl)ccc1N1CC[C@H](Oc2ccc(C(F)(F)F)cn2)C1]

To a solution of (S, E)-ethyl 3-(2'-chloro-4-(3-(5-(trifluoromethyl)pyridin-2-yloxy)pyrrolidin-1-yl)biphenyl-3-yl) acrylate (100 mg, 0.19 mmol) in 2 mL PEG400 was added $NaBH_4$ (380 mg, 10.0 mmol) at 60° C. for 1 h and 2 h at 75° C. the reaction was completed detected by LCMS and TLC, 5 ml water was added and acidified with 1N HCl solution, extracted with DCM, dried over Na2SO4, removal the solvent to left the crude product which was purified by Prep-HPLC to give the product (20 mg, 23.0% yield), Mass spec: 463 (M+1), $t_R$=3.152 min $^1$H-NMR (400 Hz, DMSO) δ=8.098-8.076 (m, 1H), 7.518 (m, 1H), 7.390-7.351 (m, 3H), 7.196-7.174 (m, 2H), 7.060-7.023 (m, 2H), 5.661 (m, 1H), 4.505 (m, 1H), 3.732-3.706 (m, 1H), 3.491-3.429 (m, 3H), 3.290-3.206 (m, 2H), 2.609-2.601 (m, 2H), 2.414-2.397 (m, 1H), 2.148-2.121 (m, 1H), 1.750-1.748 (m, 2H).

Example 358: (S)-2-(6-phenyl-3-(3-(5-(trifluoromethyl)pyridin-2-yloxy)pyrrolidin-1-yl)pyridin-2-yl) ethanol (Compound 1-365)

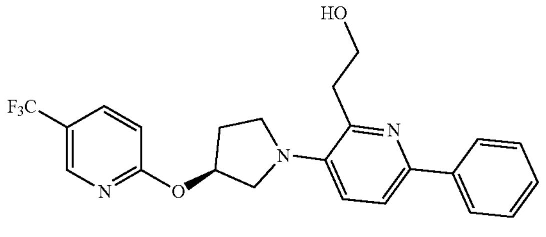 [SMILES: OCCc1nc(-c2ccccc2)ccc1N1CC[C@H](Oc2ccc(C(F)(F)F)cn2)C1]

The title compound was prepared following procedures described in example 357 to give (S)-2-(6-phenyl-3-(3-(5-(trifluoromethyl)pyridin-2-yloxy)pyrrolidin-1-yl)pyridin-2-yl)ethanol (30 mg, 30% yield), Mass spec: 428 (M+1), $t_R$=2.114 min, $^1$H-NMR (400 Hz, DMSO) δ=7.978-7.996 (d, 1H), 7.666-7.686 (d, 1H), 7.527-7.554 (m, 1H), 7.420-7.458 (m, 2H), 7.312-7.352 (m, 2H), 6.734-6.755 (d, 1H), 5.538-5.564 (m, 1H), 4.711-4.738 (m, 1H), 3.901-3.933 (m, 2H), 3.708-3.749 (m, 1H), 3.467-3.488 (m, 1H), 3.215-3.284 (m, 2H), 2.994-3.057 (m, 2H), 2.336-2.369 (m, 1H), 2.209 (s, 3H), 2.113 (m, 1H).

Example 368: (R)-(2-phenyl-5-(3-(5-(trifluoromethyl)pyridin-2-yloxy)pyrrolidin-1-yl)pyridin-4-yl) methanol (Compound 1-366)

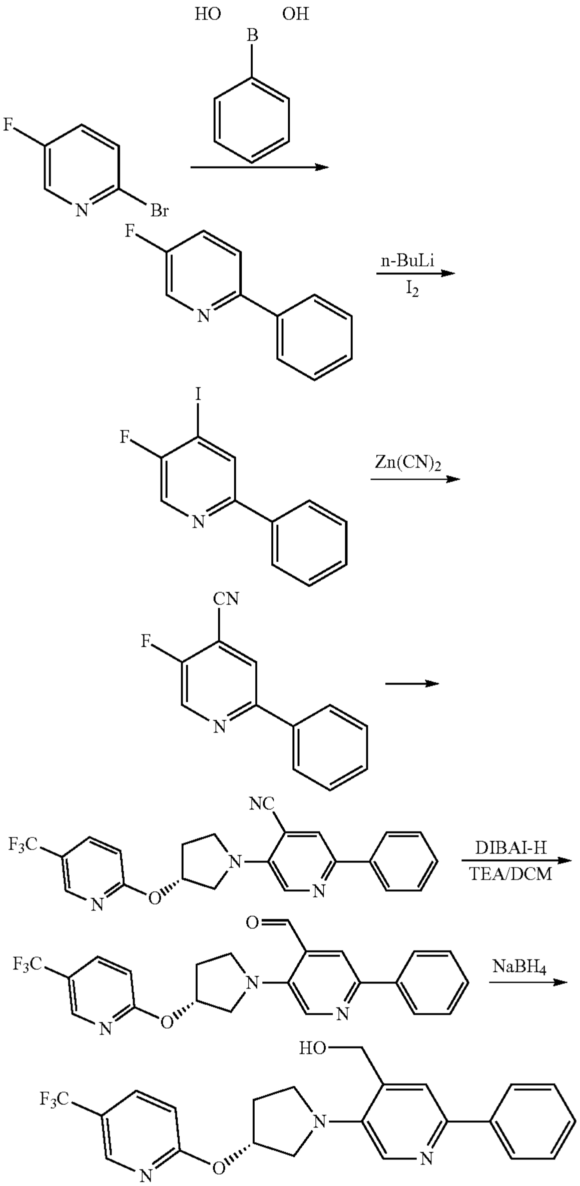

Step 1: 5-fluoro-2-phenylpyridine

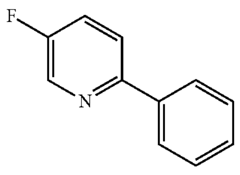 [SMILES: Fc1ccc(-c2ccccc2)nc1]

To a solution of 2-bromo-5-fluoropyridine (1.5 g, 8.523 mmol) in i-PrOH was added phenylboronic acid (1.56 g, 12.78 mmol), $K_3PO_4$ (3.62 g, 17.46 mmol), Pd $(OAc)_2$ (28.7 mg) and $H_2O$ (4 ml), the mixture was heated to 80° C. for 20 min, evaporated the i-PrOH, then diluted with DCM, washed with water and brine, dried over Na2SO4, removal the solvent to left the crude product which was purified by silica gel to give 5-fluoro-2-phenylpyridine (1.0 g, 60% yield) as white solid, Mass spec: 174 (M+1).

Step 2: 5-fluoro-4-iodo-2-phenylpyridine

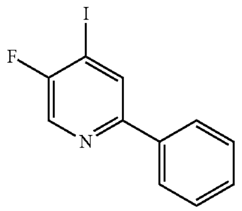 [SMILES: Fc1cnc(-c2ccccc2)cc1I]

To a solution of 5-fluoro-2-phenylpyridine (700 mg, 4.04 mmol) in 6 mL THE at −78° C. was added n-BuLi (3.79 ml, 6.06 mmol) slowly, the reacting mixture was stirred at r.t overnight, The mixture was quenched by water, extracted with EA, the organic layer was washed with $Na_2S_2O_3$ solution, brine, dried over $Na_2SO_4$, removal the solvent to left the crude product which was purified by silica gel to give 5-fluoro-4-iodo-2-phenylpyridine (800 mg, 70% yield) as yellow oil, Mass spec: 300 (M+1).

Step 3: 5-fluoro-2-phenylisonicotinonitrile

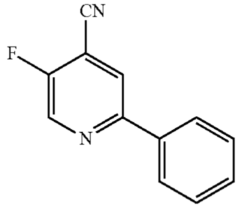 [SMILES: N#Cc1cc(-c2ccccc2)ncc1F]

To a solution of 5-fluoro-4-iodo-2-phenylpyridine (1 g, 3.34 mmol) in 7 mL DMF was added Zn $(CN)_2$ (782 mg, 6.69 mmol), dppf (182.8 mg, 0.33 mmol) and $Pd_2$ $(dba)_3$ (301.95 mg, 0.33 mmol) was stirred at 100° C. under N2 overnight, The mixture was filtered, the filtrate was exacted with DCM, washed with LiCl solution, dried over $Na_2SO_4$, removal the solvent to left the crude product which was purified by silica gel to give 5-fluoro-2-phenylisonicotinonitrile (535 mg, 50% yield), Mass spec: 199 (M+1).

Step 4: (R)-2-phenyl-5-(3-(5-(trifluoromethyl)pyridin-2-yloxy)pyrrolidin-1-yl)isonicotinonitrile

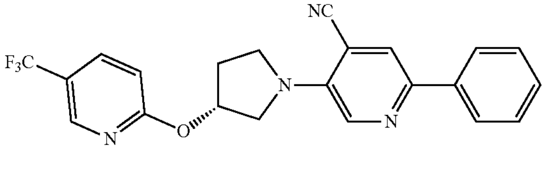 [SMILES: N#Cc1cc(-c2ccccc2)ncc1N1CC[C@@H](Oc2ccc(C(F)(F)F)cn2)C1]

To a solution of (R)-2-(pyrrolidin-3-yloxy)-5-(trifluoromethyl)pyridine (470 mg, 2.03 mmol) in 20 mL DMF was added 5-fluoro-2-phenylisonicotinonitrile (270 mg, 1.35 mmol) and $K_2CO_3$ (930 mg, 6.75 mmol), the mixture was stirred at 100° C. for 6 h, the mixture was diluted with water, extracted with DCM, washed with LiCl solution and brine, dried over $Na_2SO_4$, removal the solvent to left the crude product which was purified by silica gel to give (R)-2-phenyl-5-(3-(5-(trifluoromethyl)pyridin-2-yloxy)pyrrolidin-1-yl)isonicotinonitrile (450 mg, 100% yield) as yellow solid, Mass spec: 411 (M+1), $t_R$=3.495 min, $^1$H-NMR (400 Hz, DMSO) δ=8.654 (s, 1H), 8.393 (s, 1H), 8.093-8.116 (m, 2H), 7.329-7.366 (m, 2H), 7.329-7.461 (m, 3H), 7.058-7.079 (d, 1H), 5.806 (m, 1H), 4.128-4.169 (m, 1H), 3.848-3.890 (m, 2H), 2.336-2.383 (m, 2H).

Step 5: (R)-2-phenyl-5-(3-(5-(trifluoromethyl)pyridin-2-yloxy)pyrrolidin-1-yl)isonicotinaldehyde

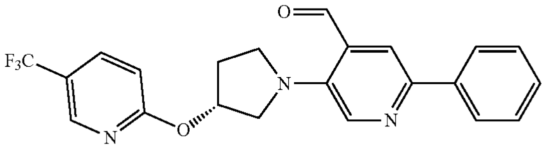 [SMILES: O=Cc1cc(-c2ccccc2)ncc1N1CC[C@@H](Oc2ccc(C(F)(F)F)cn2)C1]

To a solution of (R)-2-phenyl-5-(3-(5-(trifluoromethyl)pyridin-2-yloxy)pyrrolidin-1-yl)isonicotinonitrile (300 mg, 0.74 mmol) in 5 mL DCM at −78° C. was added TEA (0.1 ml, 0.74 mmol) and DIBAl-H (3.8 ml, 14.6 mmol), the reaction mixture was added 1 ml $H_2O$, then 2 ml HCl, and stirred at r.t for 15 min, filtered and the filtrate was extracted with DCM, removal the solvent to left the crude product which was purified by silica gel to give (R)-2-phenyl-5-(3-(5-(trifluoromethyl)pyridin-2-yloxy)pyrrolidin-1-yl)isonicotinaldehyde (80 mg, 25% yield) as yellow oil, Mass spec: 414 (M+1).

Step 6: (R)-(2-phenyl-5-(3-(5-(trifluoromethyl)pyridin-2-yloxy)pyrrolidin-1-yl)pyridin-4-yl)methanol

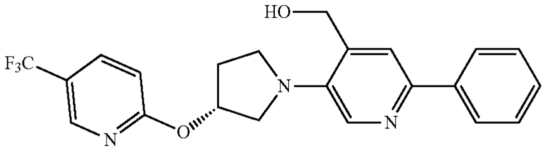 [SMILES: OCc1cc(-c2ccccc2)ncc1N1CC[C@@H](Oc2ccc(C(F)(F)F)cn2)C1]

To a solution of (R)-2-phenyl-5-(3-(5-(trifluoromethyl) pyridin-2-yloxy)pyrrolidin-1-yl)isonicotinaldehyde (85 mg, 0.205 mmol) in 3 mL MeOH at 0° C. was added $NaBH_4$ (15 mg, 0.4 mmol) slowly, the mixture was stirred at for 5 min, quenched by ice water, extracted with DCM, dried over $Na_2SO_4$, removal the solvent to left the crude product which was purified by Prep-HPLC to give (R)-(2-phenyl-5-(3-(5-(trifluoromethyl) pyridin-2-yloxy)pyrrolidin-1-yl)pyridin-4-yl)methanol (50 mg, 80% yield), Mass spec: 416 (M+1), $t_R$=2.279 min, $^1$H-NMR (400 Hz, DMSO) δ=8.630 (s, 1H), 8.177 (s, 1H), 8.074-8.100 (m, 1H), 7.969-7.988 (m, 2H), 7.897 (s, 2H), 7.430-7.468 (m, 1H), 7.339-7.357 (m, 1H), 7.040-7.062 (d, 1H), 5.700 (s, 1H), 5.417-5.445 (m, 1H), 4.579-4.621 (m, 1H), 3.823-3.849 (m, 1H), 3.581-3.600 (m, 1H), 3.409-3.450 (m, 2H), 2.509-2.510 (m, 1H), 2.183-2.185 (m, 1H).

Example 1: 3-chloro-2-(1-(2-methoxyphenyl)pyrrolidin-3-yloxy)-5-(trifluoromethyl)pyridine (Compound 1-367)

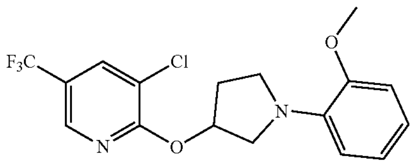 [SMILES: COc1ccccc1N1CCC(Oc2ncc(C(F)(F)F)cc2Cl)C1]

To a solution of 3-chloro-2-(pyrrolidin-3-yloxy)-5-(trifluoromethyl) pyridine trifluoroacetate salt (Intermediate 1) (400 mg, 1.05), 1-bromo-2-methoxybenzene (491 mg, 2.6 mmol), Pd2(dba)3 (288 mg, 0.316 mmol), BINAP (196 mg, 0.316 mmol), Cs2CO3 (1.71 g, 5.2 mmol) in dioxane was degassed with N2 for 10 min, then the reaction mixture was stirred at 80° C. under N2 for overnight, the solvent was removed under reduce pressure, the residue was diluted with EA, the organic layer was washed with brine, dried over Na2SO4, removal of the solvent left a dark oil which was purified by silica gel to give 3-chloro-2-(1-(2-methoxyphenyl)pyrrolidin-3-yloxy)-5-(trifluoromethyl)pyridine (90 mg, 23% yield), Mass spec: 373 (M+H), $t_R$=3.14 min, $^1$H-NMR (400 Hz, CDCl3) δ=8.34-8.35 (d, 1H), 7.850-7.855 (d, 1H), 6.83-6.94 (m, 4H), 5.69-5.72 (m, 1H), 4.04-4.09 (m, 1H), 3.87 (s, 3H), 3.52-3.55 (m, 1H), 3.39-3.44 (m, 2H), 2.41-2.45 (m, 1H), 2.28-2.30 (m, 1H).

Example 2: 3-chloro-2-(1-o-tolylpyrrolidin-3-yloxy)-5-(trifluoromethyl)pyridine (Compound 1-368)

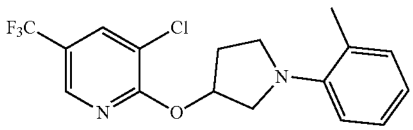 [SMILES: Cc1ccccc1N1CCC(Oc2ncc(C(F)(F)F)cc2Cl)C1]

The title compound was prepared following procedures described in example 1 using Intermediate 1 and 1-bromo-2-methylbenzene to give 3-chloro-2-(1-o-tolylpyrrolidin-3-yloxy)-5-(trifluoromethyl)pyridine (72 mg, 19% yield), Mass spec: 357 (M+H), $t_R$=3.44 min, $^1$H-NMR (400 Hz, CDCl3) δ=8.34-8.35 (q, 1H), 7.86-7.87 (d, 1H), 7.15-7.18 (m, 2H), 6.90-6.98 (m, 2H), 5.68-5.71 (m, 1H), 3.74-3.78 (q, 1H), 3.48-3.54 (m, 1H), 3.33-3.36 (m, 1H), 3.24-3.29 (m, 1H), 2.42-2.49 (m, 1H), 2.36 (s, 3H), 2.24-2.28 (m, 1H).

Example 3: 2-(1-(2-methoxyphenyl)pyrrolidin-3-yloxy)-5-(trifluoromethyl)pyridine (Compound 1-369)

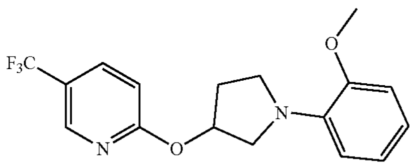 [SMILES: COc1ccccc1N1CCC(Oc2ccc(C(F)(F)F)cn2)C1]

The title compound was prepared following procedures described in example 1 using Intermediate 2 and 1-bromo-2-methoxybenzene to give 2-(1-(2-methoxyphenyl)pyrrolidin-3-yloxy)-5-(trifluoromethyl)pyridine (40 mg, 27.6% yield), Mass spec: 339 (M+H), $t_R$=2.664 min, $^1$H-NMR (400 Hz, CDCl3) δ=8.457 (s, 1H), 7.759-7.787 (m, 1H), 6.817-6.932 (m, 5H), 5.683-5.696 (m, 1H), 3.866-3.923 (m, 1H), 3.573-3.593 (m, 1H), 3.457-3.487 (m, 1H), 3.330-3.352 (m, 1H), 2.396-2.431 (m, 1H), 2.24 (m, 1H).

Example 459: (S)-(2'-ethoxy-4-(3-(5-(trifluoromethyl)pyridin-2-yloxy)pyrrolidin-1-yl)biphenyl-3-yl) methanol (Compound 1-162)

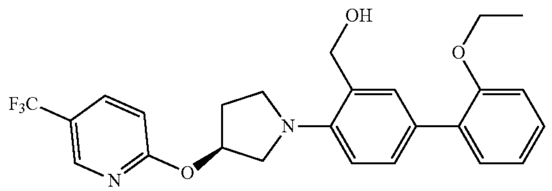 [SMILES: CCOc1ccccc1-c1ccc(N2CC[C@H](Oc3ccc(C(F)(F)F)cn3)C2)c(CO)c1]

The title compound was prepared following procedures described in example 270 to give (S)-(2'-ethoxy-4-(3-(5-(trifluoromethyl)pyridin-2-yloxy)pyrrolidin-1-yl)biphenyl-3-yl)methanol (10 mg, 8.7% yield), Mass spec: 459 (M+H), $t_R$=3.314 min, $^1$H-NMR (400 Hz, DMSO) δ=8.592 (s, 1H), 8.036-8.064 (m, 1H), 7.516 (s, 1H), 7.201-7.325 (m, 3H), 6.852-7.032 (m, 4H), 5.623 (br, 1H), 5.071 (br, 1H), 4.504-4.516 (m, 2H), 3.973-4.024 (q, 2H), 3.670-3.711 (m, 1H), 3.204-3.236 (m, 3H), 2.337-3.236 (m, 1H), 2.095-2.112 (m, 1H), 1.205-1.268 (t, 3H).

Example 460: (S)-5-fluoro-2-(3-(5-(trifluoromethyl) pyridin-2-yloxy)pyrrolidin-1-yl)benzamide (Compound 1-22)

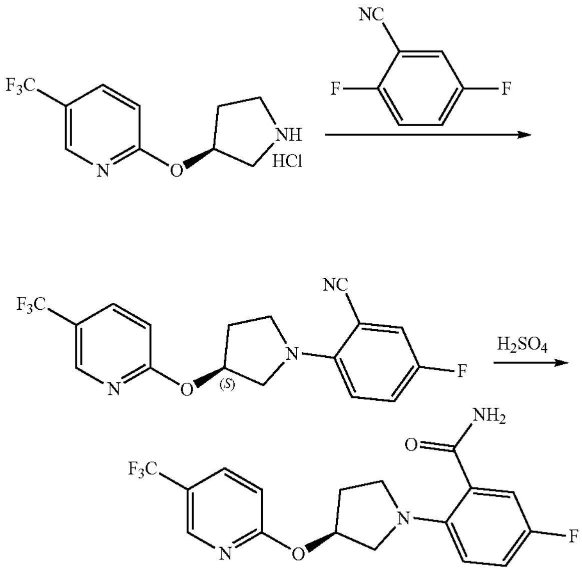

Step 1: (S)-5-fluoro-2-(3-(5-(trifluoromethyl)pyridin-2-yloxy)pyrrolidin-1-yl)benzonitrile

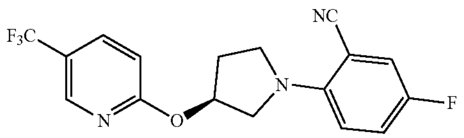 [SMILES: N#Cc1cc(F)ccc1N1CC[C@H](Oc2ccc(C(F)(F)F)cn2)C1]

The title compound was prepared following procedures described in example 5 using Intermediate 3 and 2,5-difluorobenzonitrile to give (S)-5-fluoro-2-(3-(5-(trifluoromethyl)pyridin-2-yloxy)pyrrolidin-1l-yl)benzonitrile (250 mg, 40.7% yield), Mass spec: 352 (M+H).

Step 2: (S)-5-fluoro-2-(3-(5-(trifluoromethyl)pyri din-2-yloxy)pyrrolidin-1l-yl)benzamide

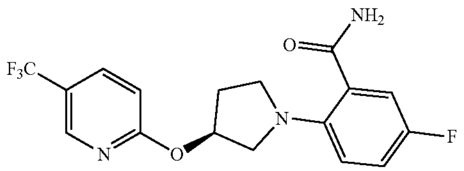 [SMILES: NC(=O)c1cc(F)ccc1N1CC[C@H](Oc2ccc(C(F)(F)F)cn2)C1]

The title compound was prepared following procedures described in Example 17 (step 3) to give (S)-5-fluoro-2-(3-(5-(trifluoromethyl)pyridin-2-yloxy)pyrrolidin-1-yl)benzamide (50 mg, 19% yield), Mass spec: 370 (M+H). $t_R$=2.585 min, $^1$H-NMR (400 Hz, DMSO) δ=8.69 (s, 1H), 8.056-8.084 (dd, 1H), 7.947 (s, 1H), 7.440 (s, 1H), 6.998-7.144 (m, 3H), 6.805-6.839 (m, 1H), 5.651 (br, 1H), 3.740-3.780 (m, 1H), 3.449-3.470 (m, 1H), 3.227-3.207 (m, 2H), 2.299-2.322 (m, 1H), 2.149-2.166 (m, 1H).

Example 461: (S)-(5-(3-methylpyridin-2-yl)-2-(3-(5-methylpyridin-2-yloxy)pyrrolidin-1-yl)phenyl) methanol (Compound 1-259)

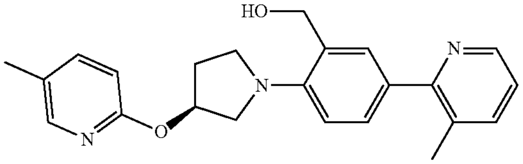 [SMILES: Cc1ccc(O[C@H]2CCN(c3ccc(-c4ncccc4C)cc3CO)C2)nc1]

The title compound was prepared following procedures described in example 293 to give (S)-(5-(3-methylpyridin-2-yl)-2-(3-(5-methylpyridin-2-yloxy)pyrrolidin-1-yl)phenyl)methanol (40 mg, 28% yield), Mass spec: 376 (M+H), $t_R$=1.843. $^1$H-NMR (400 Hz, DMSO) δ=8.446-8.436 (m, 1H), 7.997 (s, 1H), 7.672-7.527 (m, 3H), 7.378-7.356 (m, 1H), 7.230-7.199 (m, 1H), 6.895-6.874 (m, 1H), 6.752-3.731 (m, 1H), 5.539 (s, 1H), 5.156-5.128 (m, 1H), 4.569-4.536 (m, 2H), 3.763-3.724 (m, 1H), 3.497-3.457 (m, 1H), 3.333-3.290 (m, 2H), 2.357-2.309 (m, 3H), 2.211-2.067 (m, 5H).

Example 182: 3-chloro-N-(1-(2-methoxyphenyl) pyrrolidin-3-yl)-5-(trifluoromethyl)pyridin-2-amine (Compound 1-370)

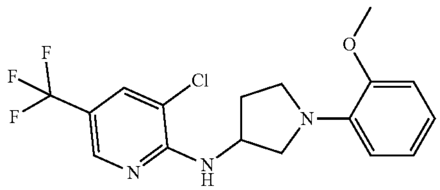 [SMILES: COc1ccccc1N1CCC(Nc2ncc(C(F)(F)F)cc2Cl)C1]

To a solution of 1-(2-methoxyphenyl)pyrrolidin-3-amine (50 mg, 0.26 mmol) and 2,3-dichloro-5-(trifluoromethyl) pyridine (214 mg, 0.78 mmol) in 4 mL THE was added Cs2CO3 (420 mg, 1.3 mmol), the mixture was heated to 100° C. for 6 min under microwave, dilute with EA, washed by water and brine, dried over Na2SO4, removal the solvent to left the crude product which was purified by Prep-HPLC to give 3-chloro-N-(1-(2-methoxyphenyl)pyrrolidin-3-yl)-5-(trifluoromethyl)pyridin-2-amine (20 mg, 13.5% yield), Mass spec: 372 (M+H), $^1$H-NMR (400 Hz, DMSO) δ=8.315-8.313 (m, 1H), 7.658-7.651 (m, 1H), 6.938-6.892 (m, 3H), 6.822-6.802 (m, 1H), 5.815-5.599 (m, 1H), 4.800-4.783 (m, 1H), 3.871 (s, 3H), 3665-3.578 (m, 2H), 3.434-3.399 (m, 1H), 3.332-3.273 (m, 1H), 2.464-2.445 (m, 1H), 1.994-1.978 (m, 1H).

Example 183: 3-chloro-N-(1-o-tolylpyrrolidin-3-yl)-5-(trifluoromethyl)pyridin-2-amine (Compound 1-371)

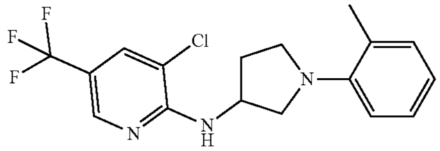 [SMILES: Cc1ccccc1N1CCC(Nc2ncc(C(F)(F)F)cc2Cl)C1]

The title compound was prepared following procedures described in example 182 to give 3-chloro-N-(1-o-tolylpyrrolidin-3-yl)-5-(trifluoromethyl)pyridin-2-amine (40 mg, 90% yield). Mass spec: 356 (M+H), $^1$H-NMR (400 Hz, DMSO) δ=8.320 (s, 1H), 7.672-7.667 (m, 1H), 7.194-7.160 (m, 2H), 6.967-6.926 (m, 2H), 5.702-5.685 (m, 1H), 4.839-4.798 (m, 1H), 3.544-3.487 (m, 2H), 3.235-3.109 (m, 2H), 2.503-2.446 m, 1H), 2.366 (s, 1H), 2.015-1.969 (m, 1H).

Example 453: (S)-4-(3-(5-(trifluoromethyl)pyridin-2-ylamino)pyrrolidin-1-yl)biphenyl-3-carboxamide (Compound 1-372)

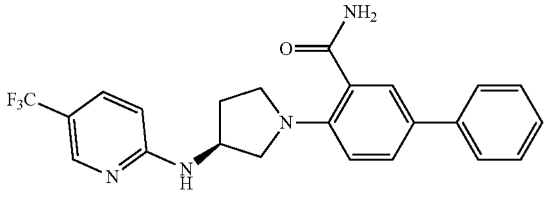 [SMILES: NC(=O)c1cc(-c2ccccc2)ccc1N1CC[C@H](Nc2ccc(C(F)(F)F)cn2)C1]

The title compound was prepared following procedures described in example 179 to give (S)-4-(3-(5-(trifluoromethyl)pyridin-2-ylamino)pyrrolidin-1-yl)biphenyl-3-carboxamide (15 mg, 30% yield), Mass spec: 427 (M+1), $t_R$=2.720 min, $^1$H-NMR (400 Hz, DMSO) δ=8.328 (s, 1H), 7.826 (s, 1H), 7.590 (s, 1H), 7.533-7.659 (m, 5H), 7.394-7.432 (m, 2H), 7.264-7.309 (m, 2H), 6.811-6.832 (d, 1H), 6.621-6.644 (d, 1H), 4.500 (br, 1H), 3.637-3.676 (m, 1H), 3.484-3.532 (m, 2H), 3.189-3.226 (m, 1H), 1.981-1.995 (m, 1H), 2.258-2.314 (m, 1H).

Example 452: (S)-4-(3-(3-chloropyridin-2-ylamino)pyrrolidin-1-yl)biphenyl-3-carboxamide (Compound 1-373)

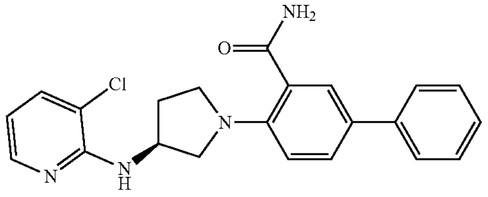 [SMILES: NC(=O)c1cc(-c2ccccc2)ccc1N1CC[C@H](Nc2ncccc2Cl)C1]

The title compound was prepared following procedures described in example 179 to give (S)-4-(3-(3-chloropyridin-2-ylamino)pyrrolidin-1-yl)biphenyl-3-carboxamide (20 mg, 19% yield), Mass spec: 393 (M+1), $t_R$=2.512 min, $^1$H-NMR (400 Hz, DMSO) δ=8.013-8.029 (m, 1H), 7.826 (s, 1H), 7.521-7.630 (m, 5H), 7.394-7.432 (m, 2H), 7.263-7.297 (m, 2H), 6.808-6.829 (d, 1H), 6.600-6.631 (m, 1H), 6.383-6.400 (d, 1H), 4.598-4.615 (m, 1H), 3.590-3.615 (m, 1H), 3.452-3.590 (m, 2H), 3.299-3.323 (m, 1H), 2.150-2.230 (m, 2H).

Example 178: (S)-5-phenyl-2-(3-(5-(trifluoromethyl)pyridin-2-ylamino)pyrrolidin-1-yl)nicotinamide (Compound 1-374)

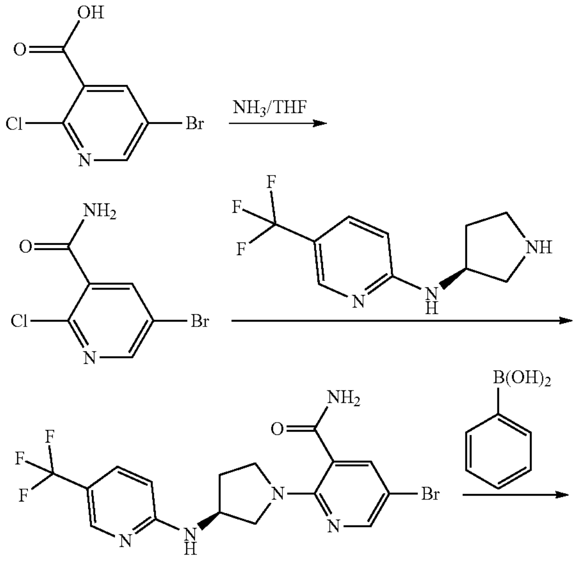

-continued

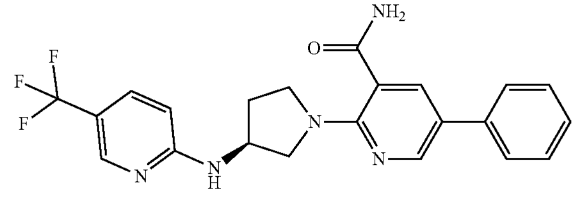

Step 1: 4: 5-bromo-2-chloronicotinamide

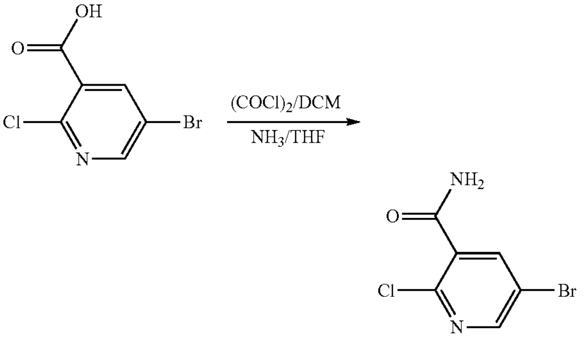

To a solution of 5-bromo-2-chloronicotinic acid (235 mg, 1 mmol) in DCM (5 ml) was added (CoCl)2 (252 mg, 2 mmol) with stirring at rt. for 2 h, and then NH3/THF was added with stirring at rt. for 12 h. The mixture was concentrated to give 5-bromo-2-chloronicotinamide (180 mg, 76.6% yield), Mass spec: 235 (M+H).

Step 2: (S)-5-bromo-2-(3-(5-(trifluoromethyl)pyridin-2-ylamino)pyrrolidin-1-yl)nicotinamide

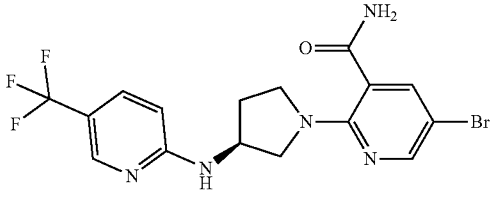 [SMILES: NC(=O)c1cc(Br)cnc1N1CC[C@H](Nc2ccc(C(F)(F)F)cn2)C1]

To a solution of (S)—N-(pyrrolidin-3-yl)-5-(trifluoromethyl)pyridin-2-amine (prepared as intermediate 7)(200 mg, 0.86 mmol) and 5-bromo-2-chloronicotinamide (201 mg, 0.86 mmol) in DMF (5 ml) was added K2CO3 (356 mg, 2.58 mmol) with stirring at 100° C. for 2 h. The mixture was extracted with EA, washed with brine, dried ($Na_2SO_4$), evaporated to give the product (S)-5-bromo-2-(3-(5-(trifluoromethyl)pyridin-2-ylamino)pyrrolidin-1-yl)nicotinamide (200 mg, 54.8% yield), Mass spec: 430 (M+H)

Step 3: (S)-5-phenyl-2-(3-(5-(trifluoromethyl)pyridin-2-ylamino)pyrrolidin-1-yl)nicotinamide

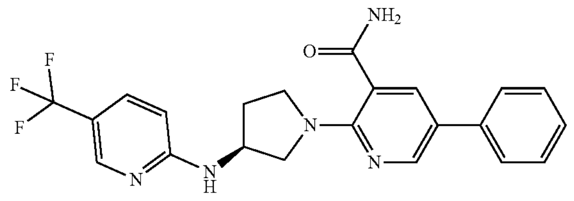 [SMILES: NC(=O)c1cc(-c2ccccc2)cnc1N1CC[C@H](Nc2ccc(C(F)(F)F)cn2)C1]

To a solution of (S)-5-bromo-2-(3-(5-(trifluoromethyl) pyridin-2-ylamino)pyrrolidin-1-yl)nicotinamide (107 mg, 0.25 mmol), phenylboronic acid (37 mg, 0.3 mmol) in Dioxane/H2O (10 mL) was added K2CO3 (138 mg, 1 mmol) and Pd(pddf)Cl2 (20 mg, 0.025) with stirring at 90° C. for 2 h. The mixture was extracted with EA, washed with brine, dried ($Na_2SO_4$), evaporated to give the product (S)-5-phenyl-2-(3-(5-(trifluoromethyl)pyridin-2-ylamino)pyrrolidin-1-yl)nicotinamide (45 mg, 42.4% yield). Mass spec: 428 (M+H), $t_R$=2.126 min, $^1$H-NMR (400 Hz, DMSO) δ=8.461-8.454 (m, 1H), 8.310 (1H), 7.889-7.806 (m, 2H), 7.641-7.593 (m, 4H), 7.434-7.395 (m, 3H), 7.300-7.262 (m, 1H), 6.621-6.598 (m, 1H), 4.480-4.454 (m, 1H), 3.778-3.668 (m, 2H), 3.581-3.555 (m, 1H), 3.352-3.276 (m, 1H), 2.244-2.475 (m, 1H), 1.961-1.930 (m, 1H).

Example 179: (S)-4-(3-(5-(trifluoromethyl)pyridin-2-ylamino)pyrrolidin-1-yl)biphenyl-3-carboxamide (Compound 1-375)

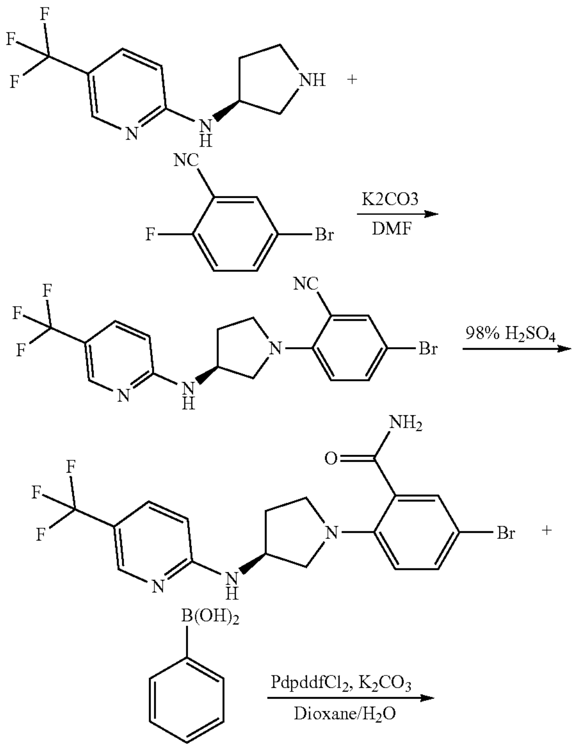

-continued

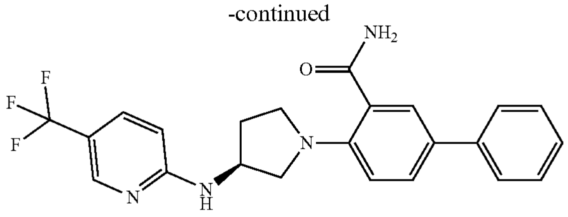

Step 1: (S)-5-bromo-2-(3-(5-(trifluoromethyl)pyridin-2-ylamino)pyrrolidin-1-yl)benzonitrile

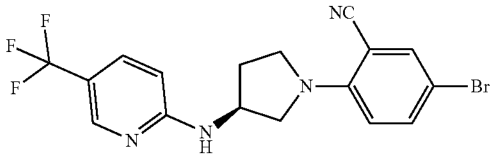 [SMILES: N#Cc1cc(Br)ccc1N1CC[C@H](Nc2ccc(C(F)(F)F)cn2)C1]

The title compound was prepared following procedures described in Step 2 of Example 178 using (S)—N-(pyrrolidin-3-yl)-5-(trifluoromethyl)pyridin-2-amine (300 mg, 1.3 mmol) and 5-bromo-2-fluorobenzonitrile (312 mg, 1.56 mmol) to give (S)-5-bromo-2-(3-(5-(trifluoromethyl)pyridin-2-ylamino)pyrrolidin-1-yl)benzonitrile (243 mg, 45.5% yield), Mass spec: 411 (M+H).

Step 2: (S)-5-bromo-2-(3-(5-(trifluoromethyl)pyridin-2-ylamino)pyrrolidin-1-yl)benzamide

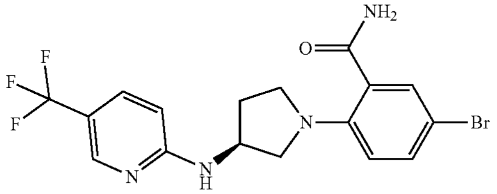 [SMILES: NC(=O)c1cc(Br)ccc1N1CC[C@H](Nc2ccc(C(F)(F)F)cn2)C1]

98% H2SO4 (4 ml) was added in 5-bromo-2-fluorobenzonitrile (243 mg, 0.6 mmol) with stirring at 90° C. for 30 min. The mixture was added 30% NaOH to adjust PH to 9 and extracted with DCM, washed with brine, dried ($Na_2SO_4$), evaporated to give the product (S)-5-bromo-2-(3-(5-(trifluoromethyl)pyridin-2-ylamino)pyrrolidin-1-yl) benzamide (250 mg, 98.8% yield), Mass spec: 429 (M+H).

Step 3: (S)-4-(3-(5-(trifluoromethyl)pyridin-2-ylamino)pyrrolidin-1-yl)biphenyl-3-carboxamide

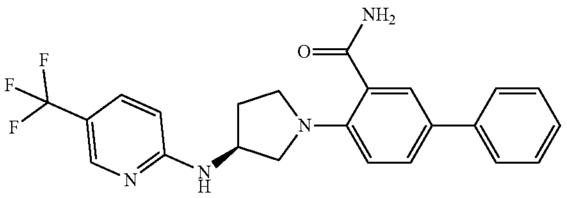 [SMILES: NC(=O)c1cc(-c2ccccc2)ccc1N1CC[C@H](Nc2ccc(C(F)(F)F)cn2)C1]

The title compound was prepared following procedures described in Step 3 of Example 178 using (S)-5-bromo-2-(3-(5-(trifluoromethyl)pyridin-2-ylamino)pyrrolidin-1-yl) benzamide (129 mg, 0.3 mmol) and phenylboronic acid (44 mg, 0.36 mmol) to (S)-4-(3-(5-(trifluoromethyl)pyridin-2-ylamino)pyrrolidin-1-yl)biphenyl-3-carboxamide (41 mg, 32.03% yield). Mass spec: 427 (M+H), $t_R$=2.633 min, $^1$H-NMR (400 Hz, DMSO) δ=8.323 (s, 1H), 7.818 (s, 1H), 7.664-7.524 (m, 6H), 7.431-7.393 (m, 2H), 7.304-7.244 (m, 2H), 6.832-6.810 (m, 1H), 6.641-6.619 (m, 1H), 4.502 (m, 1H), 3.367-3.632 (m, 1H, 3.532-3.474 (m, 2H), 3.222-3.185 (m, 1H), 2.266-2.233 (m, 1H), 1.977-1.962 (m, 1H).

Example 181: (S)-5-(pyridin-2-yl)-2-(3-(5-(trifluoromethyl)pyridin-2-ylamino)pyrrolidin-1-yl)benzamide (Compound 1-376)

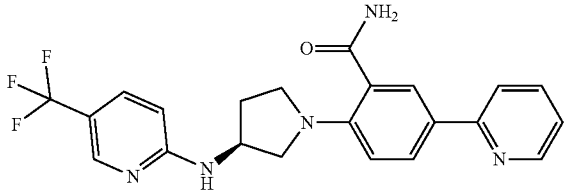

The title compound was prepared following procedures described in Example 179 to give (S)-5-(pyridin-2-yl)-2-(3-(5-(trifluoromethyl)pyridin-2-ylamino)pyrrolidin-1-yl)benzamide (100 mg, 36% yield), Mass spec: 428 (M+H), $t_R$=2.128 min. $^1$H-NMR (400 Hz, DMSO) δ=8.723 (s, 1H), 8.550-8.539 (m, 1H), 8.404-8.381 (m, 1H), 8.225-8.131 (m, 2H), 8.038-8.011 (m, 1H), 7.869-7.753 (m, 2H), 7.210-7.179 (m, 1H), 6.851-6.829 (m, 1H), 3.493-3.465 (m, 4H), 2.936-2.899 (m, 1H), 2.015-2.000 (m, 1H), 1.674-1.661 m, 1H).

Example 180: (S)-4-(3-(3-chloropyridin-2-ylamino) pyrrolidin-1-yl)biphenyl-3-carboxamide (Compound 1-377)

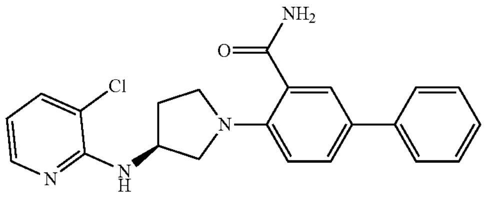 [SMILES: NC(=O)c1cc(-c2ccccc2)ccc1N1CC[C@H](Nc2ncccc2Cl)C1]

The title compound was prepared following procedures described in Intermediate 179 to give (S)-4-(3-(3-chloropyridin-2-ylamino)pyrrolidin-1-yl)biphenyl-3-carboxamide (40 mg, 40% yield). Mass spec: 427 (M+H), $t_R$=2.633 min, $^1$H-NMR (400 Hz, DMSO) δ=8.010-7.994 (m, 1H), 7.784 (s, 1H), 7.609-7.502 (m, 5H), 7.410-7.372 (m, 2H), 7.268-7.221 (m, 2H), 6.805-6.784 (m, 1H), 6.607-6.576 (m, 1H), 6.374-6.357 (m, 1H), 4.598-4.583 (m, 1H), 3.613-3.572 (m, 1H), 3.452-3.375 (m, 2H), 3.301-3.271 (m, 1H), 2.224-2.134 (m, 2H).

Example 447: (R)-5-phenyl-2-(3-(5-(trifluoromethyl)pyridin-2-ylamino)pyrrolidin-1-yl)nicotinamide (Compound 1-378)

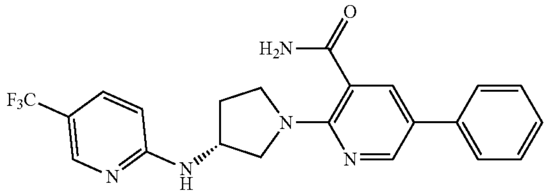 [SMILES: NC(=O)c1cc(-c2ccccc2)cnc1N1CC[C@@H](Nc2ccc(C(F)(F)F)cn2)C1]

The title compound was prepared following procedures described in example 178 to give (R)-5-phenyl-2-(3-(5-(trifluoromethyl)pyridin-2-ylamino)pyrrolidin-1-yl)nicotinamide (41 mg, 19% yield), Mass spec: 428 (M+1), $t_R$=1.908 min, $^1$H-NMR (400 Hz, CD3OD) δ=8.669 (s, 1H), 8.470-8.526 (m, 2H), 8.088-8.151 (m, 2H), 7.620-7.642 (m, 2H), 7.427-7.466 (m, 2H), 7.311-7.348 (m, 1H), 3.695-3.784 (m, 3H), 3.582-3.608 (m, 1H), 3.431-3.457 (m, 1H), 3.311-3.431 (m, 1H), 2.271-2.284 (m, 1H), 1.931-1.947 (m, 1H).

Example 454: (S)-(6-o-tolyl-3-(3-(5-(trifluoromethyl)pyridin-2-ylamino)pyrrolidin-1-yl)pyridin-2-yl)methanol (Compound 1-379)

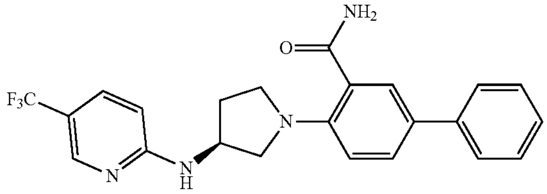 [SMILES: NC(=O)c1cc(-c2ccccc2)ccc1N1CC[C@H](Nc2ccc(C(F)(F)F)cn2)C1]

The title compound was prepared following procedures described in example 333 from (S)—N-(pyrrolidin-3-yl)-5-(trifluoromethyl)pyridin-2-amine (prepared as intermediate 7) to give (S)-(6-o-tolyl-3-(3-(5-(trifluoromethyl)pyridin-2-ylamino)pyrrolidin-1-yl)pyridin-2-yl)methanol (12 mg, 23% yield), Mass spec: 429 (M+1), $t_R$=2.151 min, $^1$H-NMR (400 Hz, DMSO) δ=8.338 (s, 1H), 7.647-7.721 (m, 2H), 7.189-7.394 (m, 6H), 6.650-6.673 (d, 1H), 5.079-5.104 (t, 1H), 4.665-4.677 (d, 2H), 4.566-4.579 (m, 1H), 3.726-3.765 (m, 1H), 3.537-3.559 (m, 1H), 3.410-3.457 (m, 1H), 3.278-3.313 (m, 1H), 2.351 (s, 3H), 2.266-2.298 (m, 1H), 1.958-1.989 (m, 1H).

Example 451: (S)-(2-(3-(3-chloropyridin-2-ylamino) pyrrolidin-1-yl)-5-(2-ethylphenoxy)phenyl)methanol (Compound 1-380)

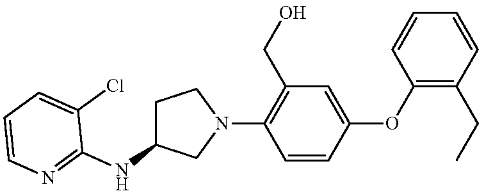 [SMILES: CCc1ccccc1Oc1ccc(N2CC[C@H](Nc3ncccc3Cl)C2)c(CO)c1]

The title compound was prepared following procedures described in example 448 to give (S)-(2-(3-(3-chloropyridin-2-ylamino)pyrrolidin-1-yl)-5-(2-ethylphenoxy)phenyl) methanol (45 mg, 40% yield), Mass spec: 424 (M+1), $t_R$=2.789 min, $^1$H-NMR (400 Hz, DMSO) δ=8.007-8.022 (m, 1H), 7.604-7.627 (dd, 1H), 7.286-7.302 (m, 1H), 7.139-7.178 (m, 3H), 6.914-6.936 (m, 1H), 6.715-6.769 (m, 2H), 6.581-6.612 (m, 1H), 6.312-6.330 (d, 1H), 5.142-5.170 (t, 1H), 4.595-4.610 (m, 1H), 4.477-4.491 (d, 2H), 3.314-3.338 (m, 1H), 3.058-3.181 (m, 3H), 2.508-2.638 (q, 2H), 2.267-2.286 (m, 1H), 1.987 (m, 1H), 1.143-1.181 (t, 3H).

Example 448: (S)-(2-(3-(3-chloropyridin-2-ylamino) pyrrolidin-1-yl)-5-phenoxyphenyl)methanol (Compound 1-381)

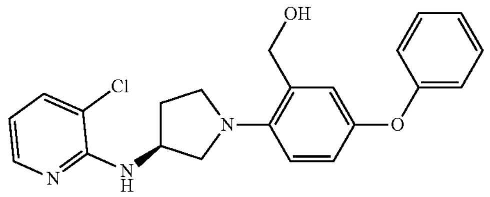 [SMILES: OCc1cc(Oc2ccccc2)ccc1N1CC[C@H](Nc2ncccc2Cl)C1]

The title compound was prepared following procedures described in example 326 from (S)-3-chloro-N-(pyrrolidin-3-yl)pyridin-2-amine (prepare as intermediate 7) to give (S)-(2-(3-(3-chloropyridin-2-ylamino)pyrrolidin-1-yl)-5-phenoxyphenyl)methanol (38 mg, 36% yield), Mass spec: 396 (M+1), $t_R$=2.498 min, $^1$H-NMR (400 Hz, DMSO) δ=8.018-8.030 (d, 1H), 7.614-7.633 (m, 1H), 7.327-7.366 (m, 2H), 7.048-7.114 (m, 2H), 6.925-6.954 (m, 3H), 6.829-6.857 (m, 1H), 6.588-6.620 (m, 1H), 6.327-6.344 (d, 1H), 5.149-5.177 (t, 1H), 4.609-4.625 (m, 1H), 4.495-4.509 (d, 2H), 3.370-3.393 (m, 1H), 3.098-3.211 (m, 3H), 2.277-2.295 (m, 1H), 1.989-2.021 (m, 1H).

Example 450: (S)-(5-(2-chlorophenoxy)-2-(3-(3-chloropyridin-2-ylamino)pyrrolidin-1-yl)phenyl) methanol (Compound 1-382)

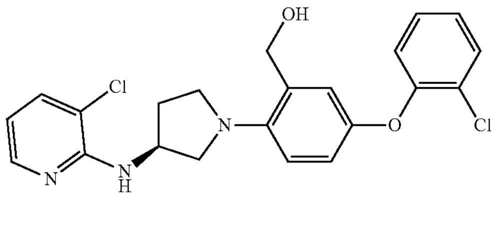 [SMILES: OCc1cc(Oc2ccccc2Cl)ccc1N1CC[C@H](Nc2ncccc2Cl)C1]

The title compound was prepared following procedures described in example 448 to give (S)-(5-(2-chlorophenoxy)-2-(3-(3-chloropyridin-2-ylamino)pyrrolidin-1-yl)phenyl) methanol (32 mg, 28% yield), Mass spec: 430 (M+1), $t_R$=2.684 min, $^1$H-NMR (400 Hz, DMSO) δ=8.014-8.026 (d, 1H), 7.554-7.632 (dd, 2H), 7.291-7.331 (m, 1H), 7.067-7.159 (m, 2H), 6.927-6.949 (d, 2H), 6.796-6.825 (m, 1H), 6.587-6.619 (m, 1H), 6.336-3.353 (d, 1H), 5.172-5.201 (t, 1H), 4.604-4.621 (m, 1H), 4.489-4.502 (d, 2H), 3.358-3.389 (m, 1H), 3.096-3.228 (m, 3H), 2.272-2.291 (m, 1H), 1.989-2.020 (m, 1H).

Example 449: (S)-(2-(3-(3-chloropyridin-2-ylamino) pyrrolidin-1-yl)-5-(o-tolyloxy)phenyl)methanol (Compound 1-383)

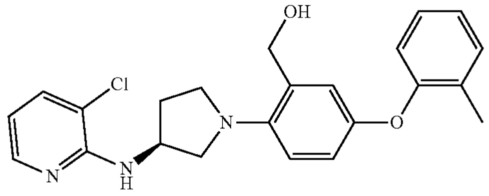 [SMILES: Cc1ccccc1Oc1ccc(N2CC[C@H](Nc3ncccc3Cl)C2)c(CO)c1]

The title compound was prepared following procedures described in example 448 to give (S)-(2-(3-(3-chloropyridin-2-ylamino)pyrrolidin-1-yl)-5-(o-tolyloxy)phenyl) methanol (36 mg, 33% yield), Mass spec: 410 (M+1), $t_R$=2.610 min, $^1$H-NMR (400 Hz, DMSO) δ=8.008-8.023 (d, 1H), 7.604-7.626 (m, 1H), 7.141-7.290 (m, 2H), 7.009-7.045 (m, 2H), 6.913-6.935 (m, 1H), 6.712-6.785 (m, 2H), 6.580-6.612 (m, 1H), 6.310-6.326 (d, 1H), 5.115-5.143 (t, 1H), 4.596-4.613 (m, 1H), 4.478-4.492 (d, 2H), 3.316-3.339 (m, 1H), 3.059-3.116 (m, 3H), 2.207-2.287 (m, 4H), 1.987 (m, 1H).

Example 174: (S)-(4-(3-(3-chloropyridin-2-ylamino) pyrrolidin-1-yl)-3-(hydroxymethyl)phenyl)(2-ethylphenyl)methanone (Compound 1-384)

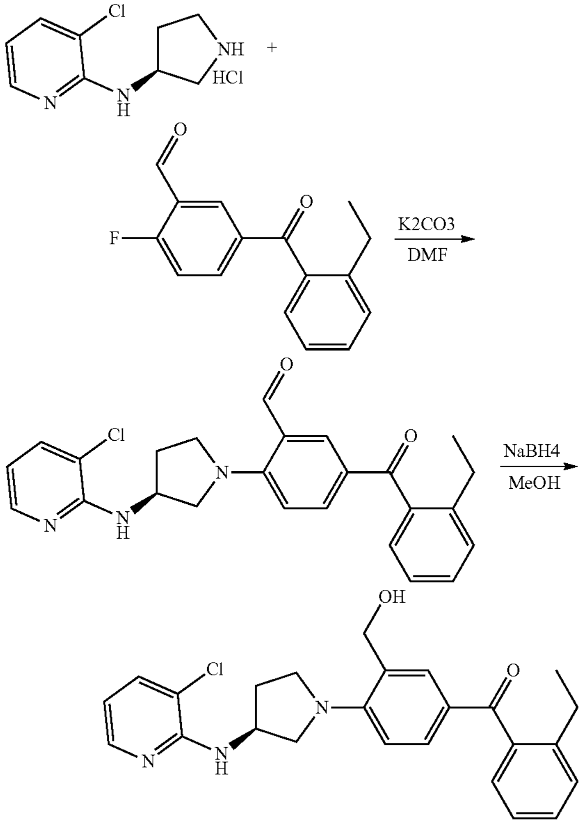

Step 1: (S)-2-(3-(3-chloropyridin-2-ylamino)pyrrolidin-1-yl)-5-(2-ethylbenzoyl)benzaldehyde

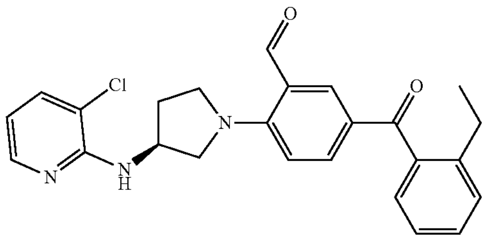 [SMILES: CCc1ccccc1C(=O)c1ccc(N2CC[C@H](Nc3ncccc3Cl)C2)c(C=O)c1]

The title compound was prepared following procedures described in step 1 of example 168 using (S)-3-chloro-N-(pyrrolidin-3-yl)pyridin-2-amine (prepared following procedures described in Intermediate 7) and 5-(2-ethylbenzoyl)-2-fluorobenzaldehyde (prepared following procedures described in Intermediate 8) to give (S)-2-(3-(3-chloropyridin-2-ylamino)pyrrolidin-1-yl)-5-(2-ethylbenzoyl)benzaldehyde (220 mg, 50% yield), Mass spec: 434 (M+H).

Step 2: (S)-(4-(3-(3-chloropyridin-2-ylamino)pyrrolidin-1-yl)-3-(hydroxymethyl)phenyl)(2-ethylphenyl)methanone

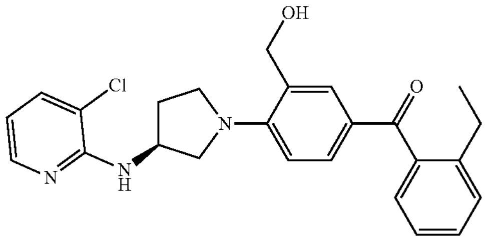 [SMILES: CCc1ccccc1C(=O)c1ccc(N2CC[C@H](Nc3ncccc3Cl)C2)c(CO)c1]

The title compound was prepared following procedures described in example 169 to give (S)-(4-(3-(3-chloropyridin-2-ylamino)pyrrolidin-1-yl)-3-(hydroxymethyl)phenyl)(2-ethylphenyl)methanone (60 mg, 80% yield), Mass spec: 436 (M+H), $^1$H-NMR (400 Hz, DMSO) δ=8.036-8.020 (m, 1H), 7.749-7.744 (m, 1H), 7.636-7.612 (m, 1H), 7.448-7.266 (m, 4H), 7.178-7.160 (m, 1H), 6.709-6.687 (m, 1H), 6.632-6.600 (m, 1H), 6.451-6.435 (m, 1H), 5.203-5.176 (m, 1H), 4.662-4.526 (m, 3H), 3.855-3.814 (m, 1H), 3.651-3.500 (m, 3H), 2.553-2.534 (m, 2H), 2.262-2.067 (m, 2H), 1.078-1.040 (m, 3H).

Example 176: 2-(2-((S)-3-(3-chloropyridin-2-ylamino)pyrrolidin-1-yl)-5-((2-ethylphenyl)(hydroxy)methyl)phenyl)ethanol (Compound 1-385)

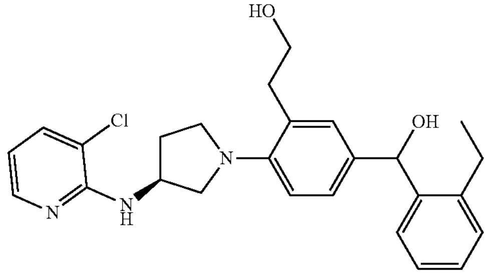 [SMILES: CCc1ccccc1C(O)c1ccc(N2CC[C@H](Nc3ncccc3Cl)C2)c(CCO)c1]

The title compound was prepared following procedures described in example 168 to give 2-(2-((S)-3-(3-chloropyridin-2-ylamino)pyrrolidin-1-yl)-5-((2-ethylphenyl)(hydroxy)methyl)phenyl)ethanol (15 mg, 20% yield). Mass spec: 452 (M+H), $^1$H-NMR (400 Hz, DMSO) δ=8.006 (m, 1H), 7.602-7.598 (m, 1H), 7.468-7.462 (m, 1H), 7.184-7.140 (m, 4H), 6.968-6.948 (m, 1H), 6.886 (m, 1H), 6.597 (m, 1H), 6.291-6.274 (m, 1H), 5.805-5.794 (m, 1H), 5.569-5.559 (m, 1H), 4.638-4.612 (m, 2H), 3.588-3.539 (m, 2H), 3.382-3.361 (m, 1H), 3.202-3.189 (m, 2H), 3.094-3.057 (m, 1H), 2.776-2.757 (m, 2H), 2.650-2.503 (m, 2H), 2.261-2.230 (m, 1H), 2.008 (m, 1H), 1.071-1.033 (m, 3H).

Example 175: (4-((S)-3-(3-chloropyridin-2-ylamino)pyrrolidin-1-yl)-3-(hydroxymethyl)phenyl)(2-ethylphenyl)methanol (Compound 1-386)

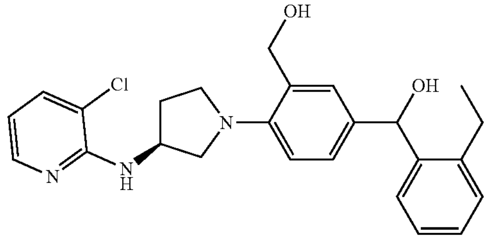 [SMILES: CCc1ccccc1C(O)c1ccc(N2CC[C@H](Nc3ncccc3Cl)C2)c(CO)c1]

The title compound was prepared following procedures described in example 168 to give (4-((S)-3-(3-chloropyridin-2-ylamino)pyrrolidin-1-yl)-3-(hydroxymethyl)phenyl)(2-ethylphenyl)methanol (15 mg, 22% yield). Mass spec: 438 (M+H), $^1$H-NMR (400 Hz, DMSO) δ=7.597 (m, 1H), 7.481-7.465 (m, 1H), 7.347-7.336 (m, 1H), 7.188-7.165 (m, 1H), 7.021-6.993 (m, 3H), 6.798-6.777 (m, 1H), 6.608 (m, 1H), 6.305-6.288 (m, 1H), 5.828-5.818 (m, 1H), 5.558-5.548 (m, 1H), 5.033-5.006 (m, 1H), 4.619-4.570 (m, 1H), 4.468-4.455 (m, 2H), 3.387-3.323 (m, 1H), 3.221-3.124 (m, 3H), 2.675-2.503 (m, 2H), 2.257-2.232 (m, 1H), 1.985-1.955 (m, 1H), 1.100-1.080 (m, 3H).

Example 177: (S)-(4-(3-(3-chloropyridin-2-ylamino)pyrrolidin-1-yl)-3-(2-hydroxyethyl)phenyl)(2-ethylphenyl)methanone (Compound 1-387)

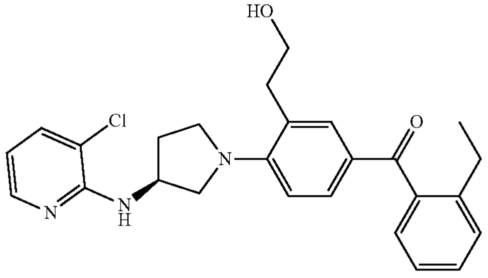 [SMILES: CCc1ccccc1C(=O)c1ccc(N2CC[C@H](Nc3ncccc3Cl)C2)c(CCO)c1]

The title compound was prepared following procedures described example 169 using (S)-3-chloro-N-(pyrrolidin-3-yl)pyridin-2-amine (prepared following procedures described in Intermediate 1) and 5-(2-ethylbenzoyl)-2-fluorobenzaldehyde (prepared following procedures described in Intermediate 2) to give (S)-(4-(3-(3-chloropyridin-2-ylamino)pyrrolidin-1-yl)-3-(2-hydroxyethyl)phenyl)(2-ethylphenyl)methanone (15 mg, 20% yield), Mass spec: 450 (M+H), $^{1}$H-NMR (400 Hz, DMSO) δ=8.024 (m, 1H), 7.533-7.263 (m, 6H), 7.185-7.163 (m, 1H), 6.786-6.764 (m, 1H), 6.459-6.442 (m, 1H), 4.672-4.629 (m, 2H), 3.734-3.710 (m, 1H), 3.572-3.448 (m, 5H), 2.887-2.863 (m, 2H), 2.551-2.497 (m, 1H), 2.260-2.229 (m, 1H), 2.112-2.100 (m, 1H), 1.074-1.036 (m, 3H).

Example 171: (S)-(4-chlorophenyl)(4-(3-(5-fluoropyridin-2-ylamino)pyrrolidin-1-yl)-3-(2-hydroxyethyl)phenyl)methanone (Compound 1-388)

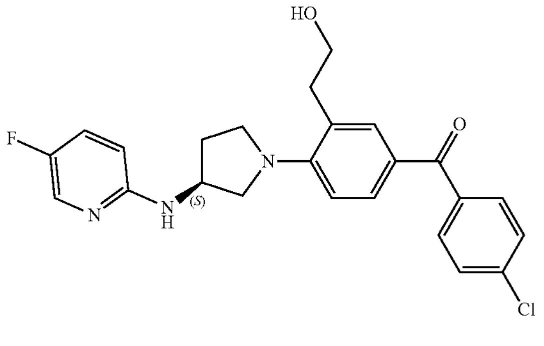

The title compound was prepared following procedures described in example 169 to give (S)-(4-chlorophenyl)(4-(3-(5-fluoropyridin-2-ylamino)pyrrolidin-1-yl)-3-(2-hydroxyethyl)phenyl)methanone (15 mg, 18.8% yield), Mass spec: 440 (M+H), $^{1}$H-NMR (400 Hz, DMSO) δ=7.970 (s, 1H), 7.963-7.350 (m, 7H), 6.865-6.810 (m, 2H), 6.559-6.527 (m, 1H), 4.684-4.658 (m, 1H), 4.398-4.385 (m, 1H), 3.778-3.738 (m, 1H), 3.618-3.569 (m, 3H), 3.479-3.459 (m, 1H), 3.347 (m, 1H), 2.893-2.516 (m, 2H), 1.955-1.941 (m, 1H), 1.238 (m, 1H).

Example 169: (S)-(2-chlorophenyl)(4-(3-(5-fluoropyridin-2-ylamino)pyrrolidin-1-yl)-3-(2-hydroxyethyl)phenyl)methanone (Compound 1-389)

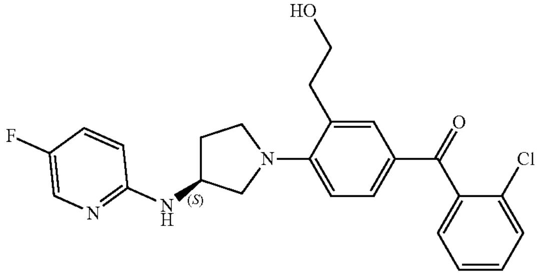

To a solution of 2-(5-((2-chlorophenyl)(hydroxy)methyl)-2-((S)-3-(5-fluoropyridin-2-ylamino)pyrrolidin-1-yl)phenyl)ethanol (90 mg, 0.2 mmol), in 2 ml THE was added LiAlH(t-BuO)3 (57.5 mg, 0.22 mmol) with stirring at r.t. for 30 min. The mixture was extracted with EA, washed with brine, dried ($Na_2SO_4$), evaporated and pre-HPLC, freeze dried to give the product (S)-(2-chlorophenyl)(4-(3-(5-fluoropyridin-2-ylamino)pyrrolidin-1-yl)-3-(2-hydroxyethyl)phenyl)methanonel (20 mg, 22.22% yield). Mass spec: 440 (M+H), $^{1}$H-NMR (400 Hz, DMSO) δ=7.964-70956 (s, 1H), 7.585-7.298 (m, 7H), 6.856-6.842 (m, 1H), 6.769-6.593 (m, 1H), 6.525 (s, 1H), 4.673-4.611 (m, 1H), 4.403-4.377 (m, 1H), 3.786-3.746 (m, 1H), 3.624-3.487 (m, 4H), 3.299 (m, 1H), 2.873-2.856 (m, 2H), 2.238-2.192 (m, 1H), 1.966 (m, 1H)

Example 168: 2-(5-((2-chlorophenyl)(hydroxy)methyl)-2-((S)-3-(5-fluoropyridin-2-ylamino)pyrrolidin-1-yl)phenyl)ethanol (Compound 1-390)

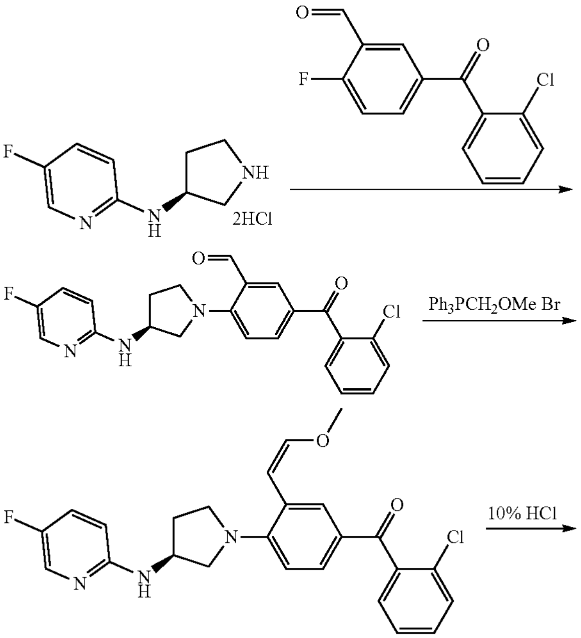

-continued

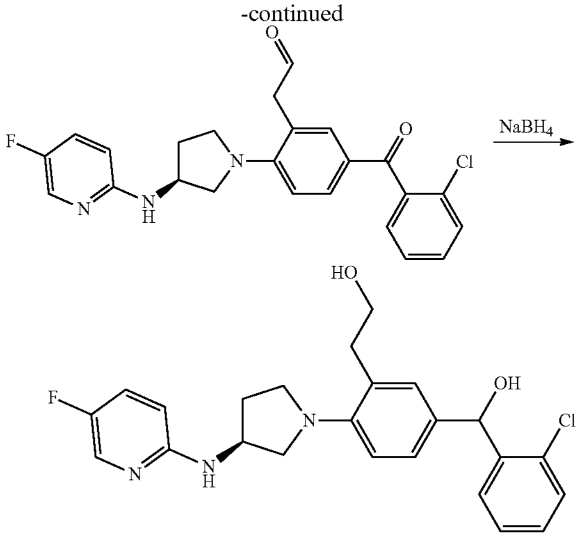

Step 1: (S)-5-(2-chlorobenzoyl)-2-(3-(5-fluoropyridin-2-ylamino)pyrrolidin-1-yl)benzaldehyde

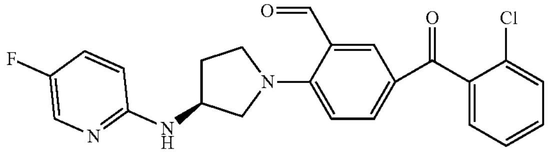 [SMILES: O=Cc1cc(C(=O)c2ccccc2Cl)ccc1N1CC[C@H](Nc2ccc(F)cn2)C1]

To a solution of (S)-5-fluoro-N-(pyrrolidin-3-yl)pyridin-2-amine (Intermediate 7) (411 mg, 1.57 mmol), 4-(2-chlorobenzoyl)-2-fluorobenzaldehyde (Intermediate 8) (556 mg, 2.2 mmol), K2CO3 (760 mg, 5.5 mmol) in DMF (10 ml) with stirring to 80° C. for 2 h. The reaction was diluted with EA (50 mL), washed with brine, and dried over $Na_2SO_4$. Concentrate to dryness, the residue was purified by silica gel to give (S)-5-(2-chlorobenzoyl)-2-(3-(5-fluoropyridin-2-ylamino)pyrrolidin-1-yl)benzaldehyde (500 mg, 60% yield) Mass spec: 424 (M+H)

Step 2: (S,Z)-(2-chlorophenyl)(4-(3-(5-fluoropyridin-2-ylamino)pyrrolidin-1-yl)-3-(2-methoxyvinyl)phenyl)methanone

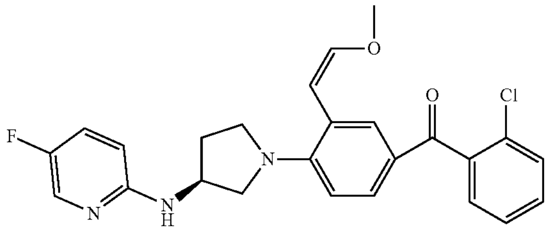 [SMILES: CO/C=C\c1cc(C(=O)c2ccccc2Cl)ccc1N1CC[C@H](Nc2ccc(F)cn2)C1]

To a solution of Ph3PCH2OMeCl (445.3 mg, 13. mmol) in THF (10 ml) was added LiHMDS (4.34 ml, 0.48 mmol) with stirring to 0° C. for 20 min, then (S)-5-(2-chlorobenzoyl)-2-(3-(5-fluoropyridin-2-ylamino)pyrrolidin-1-yl)benzaldehyde (460 mg, 1.085 mmol) in THE was added with stirring to 0° C., the reaction mixture was stirred at rt. for 2 h. The reaction was extracted, separated, dried over $Na_2SO_4$ and concentrate to give (S,Z)-(2-chlorophenyl)(4-(3-(5-fluoropyridin-2-ylamino)pyrrolidin-1-yl)-3-(2-methoxyvinyl)phenyl)methanone (210 mg, 43% yield), Mass spec: 452 (M+H)

Step 3: (S)-2-(5-(2-chlorobenzoyl)-2-(3-(5-fluoropyridin-2-ylamino)pyrrolidin-1-yl)phenyl)acetaldehyde

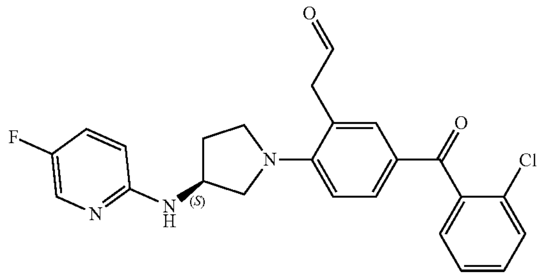

To a solution of (E)-(2-chlorophenyl)(4-(3-(5-fluoropyridin-2-ylamino)pyrrolidin-1-yl)-3-(2-methoxyvinyl)phenyl)methanone in acetone was added 10% HCL, stirred at 50° C. for 2 h. The mixture was cooled to r.t, Then adjusted pH to 9 with $NaHCO_3$ solution, extracted with EA, evaporated and give 2-(5-(2-chlorobenzoyl)-2-(3-(5-fluoropyridin-2-ylamino)pyrrolidin-1-yl)phenyl)acetaldehyde (180 mg, 88.67% yield), Mass spec: 438 (M+H)

Step 4: 2-(5-((2-chlorophenyl)(hydroxy)methyl)-2-((S)-3-(5-fluoropyridin-2-ylamino)pyrrolidin-1-yl)phenyl)ethanol

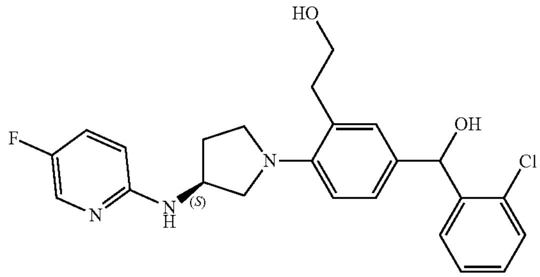

To a solution of 2-(5-((2-chlorophenyl)(hydroxy)methyl)-2-((S)-3-(5-fluoropyridin-2-ylamino)pyrrolidin-1-yl)phenyl)ethanol (90 mg, 0.2 mmol), in 2 ml THE was added $NaBH_4$ (38 mg, 1.0 mmol) at 0° C. for 30 min. The mixture was extracted with EA, washed with brine, dried ($Na_2SO_4$), evaporated and pre-HPLC, freeze dried to give the product 2-(5-((2-chlorophenyl)(hydroxy)methyl)-2-(3-(5-fluoropyridin-2-ylamino)pyrrolidin-1-yl)phenyl)ethanol (20 mg, 22.03% yield), Mass spec: 442 (M+H). $^1$H-NMR (400 Hz, DMSO) □δ=7.938-7.930 (d, 1H), 7.701-7.681 (d, 1H), 7.387-7.322 (m, 3H), 7.274-7.236 (m, 1H), 7.125-7.120 (d, 1H), 7.007-6.982 (d, 1H), 6.857-6.751 (q, 2H), 6.540-6.507 (m, 1H), 5.896-5.843 (m, 2H), 4.647-4.620 (m, 1H), 4.347-4.331 (m, 1H), 3.586-3.536 (m, 2H), 3.435-3.396 (m, 1H), 3.223-3.120 (m, 2H), 2.961-2.929 (m, 1H), 2.776-2.740 (m, 2H), 2.245-2.214 (m, 1H), 1.813-1.799 (m, 1H)

Example 170: 2-(5-((4-chlorophenyl)(hydroxy) methyl)-2-((S)-3-(5-fluoropyridin-2-ylamino)pyrrolidin-1-yl)phenyl)ethanol (Compound 1-391)

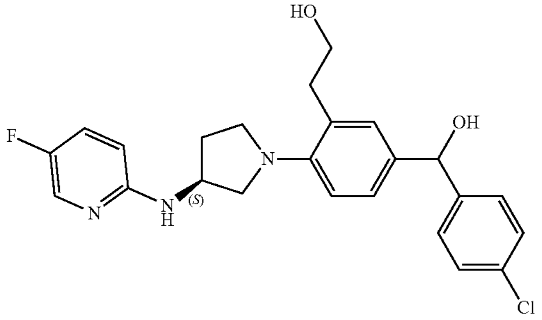

The title compound was prepared following procedures described in example 168 to give 2-(5-((4-chlorophenyl)(hydroxy)methyl)-2-((S)-3-(5-fluoropyridin-2-ylamino)pyrrolidin-1-yl)phenyl)ethanol (15 mg, 18.8% yield), Mass spec: 442 (M+H), $^{1}$H-NMR (400 Hz, DMSO) δ=7.839 (s, 1H), 7.350 (s, 5H), 7.122 (s, 1H), 7.043-7.022 (m, 1H), 6.876-6.856 (m, 1H), 6.762-6.749 (m, 1H), 6.537-6.517 (m, 1H), 5.795 (s, 1H), 5.598 (s, 1H), 4.638 (s, 1H), 4.350-4.337 (m, 1H), 3.581-3.349 (m, 3H), 3.205-3.128 (m, 2H), 2.940 (s, 1H), 2.765 (s, 2H), 2.242 (m, 1H), 1.815 (s, 1H).

Example 172: 2-(5-((3-chlorophenyl)(hydroxy) methyl)-2-((S)-3-(5-fluoropyridin-2-ylamino)pyrrolidin-1-yl)phenyl)ethanol (Compound 1-392)

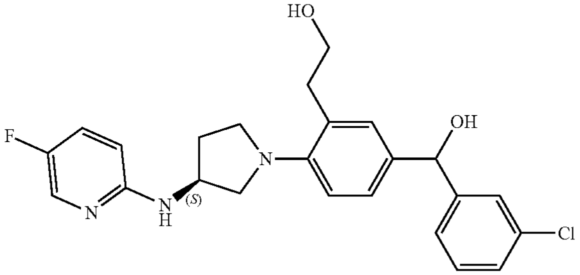

The title compound was prepared following procedures described in example 168 to give 2-(5-((4-chlorophenyl)(hydroxy)methyl)-2-((S)-3-(5-fluoropyridin-2-ylamino)pyrrolidin-1-yl)phenyl)ethanol (15 mg, 18.8% yield), Mass spec: 442 (M+H), $^{1}$H-NMR (400 Hz, DMSO) δ=7.941-7.933 (m, 1H), 7.391-7.229 (m, 5H), 7.146-7.141 (m, 1H), 7.064-7.038 (m, 1H), 6.881-6.861 (m, 1H), 6.763-6.747 (m, 1H), 6.541-6.509 (m, 1H), 5.853-5.842 (m, 1H), 5.608-5.598 (m, 1H), 4.660-4.633 (m, 1H), 4.351-4.336 (m, 1H), 3.609-3.558 (m, 2H), 3.432-3.392 (m, 1H), 3.214-3.130 (m, 2H), 2.968-2.791 (m, 1H), 2.775-2.507 (m, 2H), 2.250-2.236 (m, 1H), 1.815-1.799 (m, 1H).

Example 173: (S)-(3-chlorophenyl)(4-(3-(5-fluoropyridin-2-ylamino)pyrrolidin-1-yl)-3-(2-hydroxyethyl)phenyl)methanone (Compound 1-393)

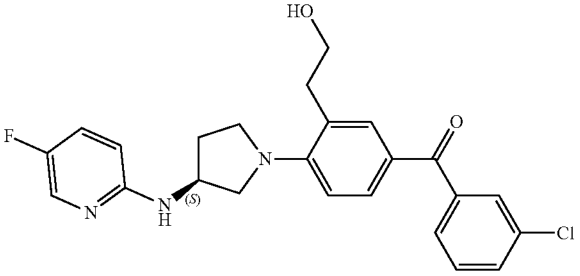

The title compound was prepared following procedures described in example 169 to give (S)-(3-chlorophenyl)(4-(3-(5-fluoropyridin-2-ylamino)pyrrolidin-1-yl)-3-(2-hydroxyethyl)phenyl)methanone (15 mg, 18.8% yield), Mass spec: 440 (M+H), $^{1}$H-NMR (400 Hz, =DMSO) δ=7.971 (s, 1H), 7.963-7.350 (m, 6H), 6.868-6.812 (m, 2H), 6.560-6.528 (m, 1H), 4.690-4.663 (m, 1H) 4.399-4.386 (m, 1H), 3.787-3.748 (m, 1H), 3.619-3.570 (m, 3H), 3.488-3.469 (m, 1H), 3.317-3.277 (m, 1H), 2.915-2.880 (m, 2H), 2.244-2.213 (m, 1H), 1.974-1.945 (m, 1H).

Example 328: (S)-(4-(3-(4-(trifluoromethyl)thiazol-2-ylamino)pyrrolidin-1-yl)biphenyl-3-yl)methanol (Compound 1-394)

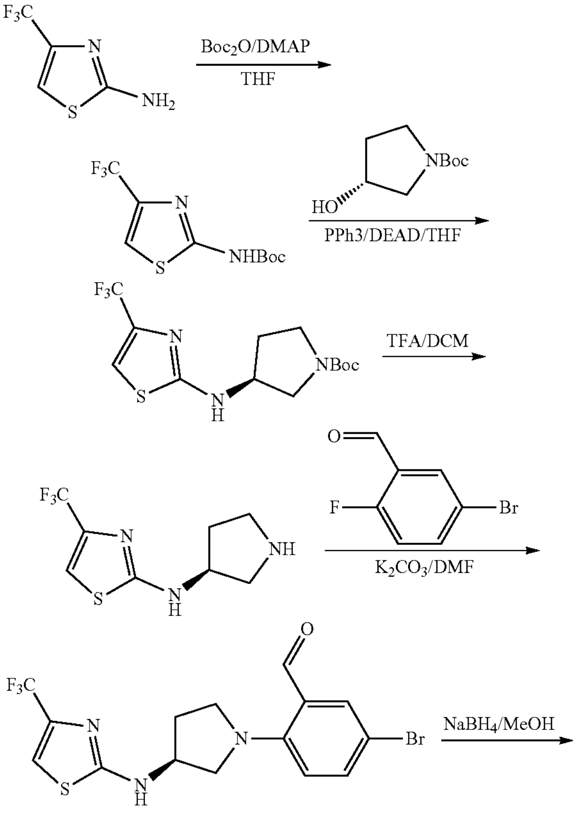

-continued

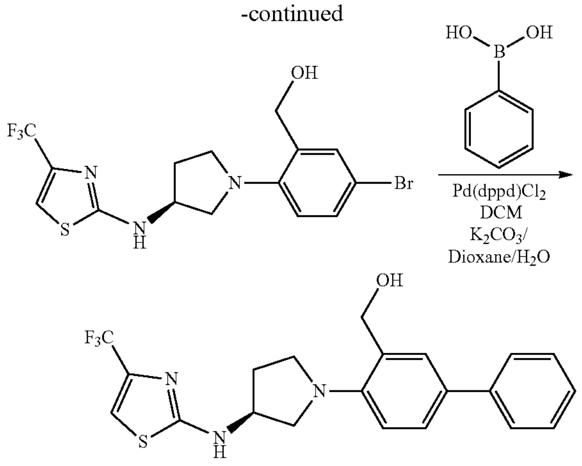

Step 1: tert-butyl 4-(trifluoromethyl)thiazol-2-ylcarbamate

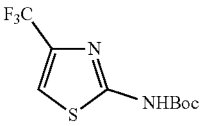 [SMILES: CC(C)(C)OC(=O)Nc1nc(C(F)(F)F)cs1]

To a solution of 4-(trifluoromethyl)thiazol-2-amine (1.0 g, 6.0 mmol) in 5 ml THE was added $Boc_2O$ (1.43 g, 6.6 mmol) and DMAP (73 mg, 0.6 mmol) at 0° C., and the mixture was stirred at 50° C. for overnight. The reaction mixture was evaporated and purified by silica gel to give tert-butyl 4-(trifluoromethyl)thiazol-2-ylcarbamate (1.3 g, 81.2% yield) as white solid, Mass spec: 213 (M+1).

Step 2: (S)-tert-butyl 3-(4-(trifluoromethyl)thiazol-2-ylamino)pyrrolidine-1-carboxylate

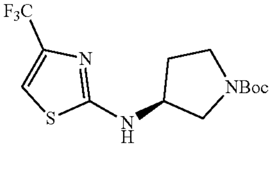 [SMILES: CC(C)(C)OC(=O)N1CC[C@H](Nc2nc(C(F)(F)F)cs2)C1]

To a solution of (R)-tert-butyl 3-hydroxypyrrolidine-1-carboxylate (140 mg, 0.75 mmol) in 5 ml THE at 0° C. was added $PPh_3$ (196.5 mg, 0.75 mmol), DEAD (130 mg, 0.75 mmol) and tert-butyl 4-(trifluoromethyl)thiazol-2-ylcarbamate (134 mg, 0.5 mmol). And the mixture was stirred at 80° C. for overnight. Diluted with EA, washed by water, brine, dried over Na2SO4, removal the solvent to left the crude product which was purified by silica gel to give (S)-tert-butyl 3-(4-(trifluoromethyl)thiazol-2-ylamino)pyrrolidine-1-carboxylate as oil (150 mg, 68.8% yield), Mass spec: 338 (M+1).

Step 3: (S)—N-(pyrrolidin-3-yl)-4-(trifluoromethyl)thiazol-2-amine

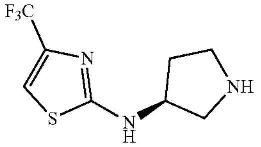 [SMILES: FC(F)(F)c1csc(N[C@H]2CCNC2)n1]

To a solution of (S)-tert-butyl 3-(4-(trifluoromethyl)thiazol-2-ylamino)pyrrolidine-1-carboxylate (150 mg, 0.34 mmol) in 3 ml DCM was added 1 ml TFA at 0° C. and stirred at rt for 6 h, adjusted the pH to 8, extracted with DCM, dried over Na2SO4, removal the solvent to left the crude (S)—N-(pyrrolidin-3-yl)-4-(trifluoromethyl)thiazol-2-amine (70 mg, 62.5% yield) which can be used to next step directly, Mass spec: 238 (M+1).

Step 4: (S)-5-bromo-2-(3-(4-(trifluoromethyl)thiazol-2-ylamino)pyrrolidin-1-yl)benzaldehyde

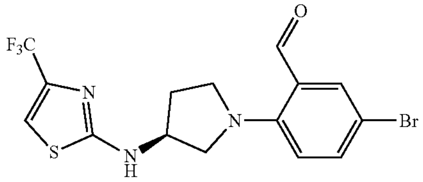 [SMILES: O=Cc1cc(Br)ccc1N1CC[C@H](Nc2nc(C(F)(F)F)cs2)C1]

The solution of (S)—N-(pyrrolidin-3-yl)-4-(trifluoromethyl)thiazol-2-amine (70 mg, 0.3 mmol), 5-bromo-2-fluorobenzaldehyde (90 mg, 0.45 mmol), $K_2CO_3$ (124.2 mg, 0.9 mmol) in 2 ml DMF was stirred at 100° C. for 2 h. the mixture was diluted with EA, washed with LiCl solution, dried over Na2SO4, removal the solvent to left the crude product which was purified by silica gel to give (S)-5-bromo-2-(3-(4-(trifluoromethyl)thiazol-2-ylamino)pyrrolidin-1-yl)benzaldehyde (70 mg, 56% yield) as oil, Mass spec: 420 (M+1.)

Step 5: (S)-(5-bromo-2-(3-(4-(trifluoromethyl)thiazol-2-ylamino)pyrrolidin-1-yl)phenyl)methanol

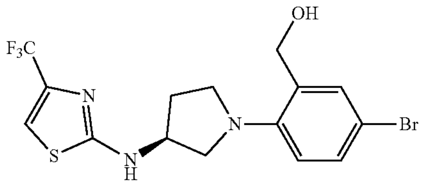 [SMILES: OCc1cc(Br)ccc1N1CC[C@H](Nc2nc(C(F)(F)F)cs2)C1]

To a solution of (S)-5-bromo-2-(3-(4-(trifluoromethyl)thiazol-2-ylamino)pyrrolidin-1-yl)benzaldehyde (70 mg, 0.167 mmol) in 2 ml MeOH was added NaBH4 (9.5 mg, 0.25 mmol) at 0° C., the mixture was stirred at rt for 15 min, and the mixture was quenched with two drops $H_2O$, evaporated the MeOH to give a residue which was dissolved in 5 ml DCM and washed with $H_2O$, the DCM layer was dried over $Na_2SO_4$, filtered and removal the solvent to give the crude (S)-(5-bromo-2-(3-(4-(trifluoromethyl)thiazol-2-ylamino)pyrrolidin-1-yl)phenyl)methanol (70 mg, 98% yield) which can be used directly, Mass spec: 422 (M+1).

Step 6: (S)-(4-(3-(4-(trifluoromethyl)thiazol-2-ylamino)pyrrolidin-1-yl)biphenyl-3-yl)methanol

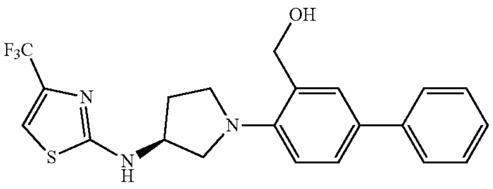 [SMILES: OCc1cc(-c2ccccc2)ccc1N1CC[C@H](Nc2nc(C(F)(F)F)cs2)C1]

A solution of S)-(5-bromo-2-(3-(4-(trifluoromethyl)thiazol-2-ylamino)pyrrolidin-1-yl)phenyl)methanol (70.0 mg, 0.17 mmol), phenylboronic acid (24.8 mg, 0.20 mmol), $Pd(dppf)Cl_2$ DCM (14 mg, 20% wt.) and $K_2CO_3$ (46.9 mg, 0.34 mmol) in 1 ml 1,4-dioxane and 0.2 ml $H_2O$ was degassed with $N_2$ for 1 min, and then stirred at 90° C. for 2 h under $N_2$. The mixture was diluted with EA, washed by water, brine, dried over Na2SO4, removal the solvent to left the crude product which was purified by Prep-HPLC to give (S)-(4-(3-(4-(trifluoromethyl)thiazol-2-ylamino)pyrrolidin-1-yl)biphenyl-3-yl)methanol (20 mg, 28% yield) as clarity oil, Mass spec: 420 (M+1), $t_R$=2.950 min, $^1$H-NMR (400 Hz, DMSO) δ=8.427-8.410 (d, 1H), 7.688-7.588 (m, 3H), 7.457-7.383 (m, 4H), 7.299-7.262 (m, 1H), 6.921-6.900 (d, 1H), 5.193-5.165 (m, 1H), 4.582-4.568 (m, 2H), 4.330-4.318 (s, 1H), 3.584-3.544 (m, 1H), 3.433-3.381 (m, 1H), 3.249-3.166 (m, 2H), 2.302-2.271 (m, 1H), 1.944-1.913 (m, 1H).

Example 329: (S)-(4-(3-(4-(trifluoromethyl)thiazol-2-yloxy)pyrrolidin-1-yl)biphenyl-3-yl)methanol (Compound 1-395)

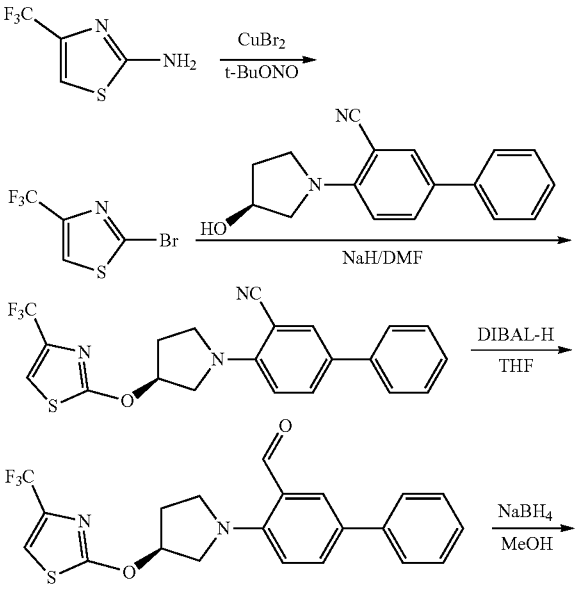

-continued

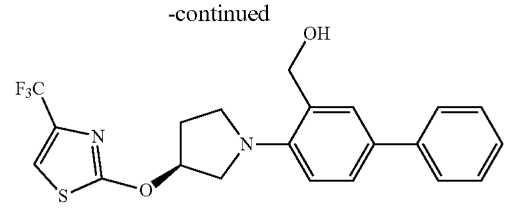

Step 1: 2-bromo-4-(trifluoromethyl)thiazole

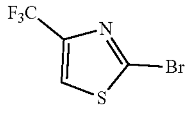

To a solution of 4-(trifluoromethyl)thiazol-2-amine (840 mg, 5 mmol) in 20 mL MeCN was added t-BuONO (670 mg, 6.5 mmol) at 0° C., CuBr2 (1.34 g, 6 mmol) in turn, the mixture was allowed to heated to 70° C. for 3 h, evaporated the MeCN, the residue was diluted with EA, the organic layer was washed by water, 1H HCl solution, and brine, dried over $Na_2SO_4$, removal the solvent to left the crude product which was purified by silica gel to give 2-bromo-4-(trifluoromethyl)thiazole (600 mg, 43% yield) as light yellow liquid, Mass spec: 232 (M+1).

Step 2: (S)-4-(3-(4-(trifluoromethyl)thiazol-2-yloxy)pyrrolidin-1-yl)biphenyl-3-carbonitrile

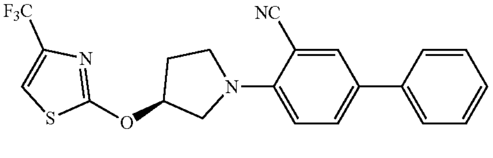 [SMILES: N#Cc1cc(-c2ccccc2)ccc1N1CC[C@H](Oc2nc(C(F)(F)F)cs2)C1]

To a solution of (S)-4-(3-hydroxypyrrolidin-1-yl)biphenyl-3-carbonitrile ( ) in 5 mL DMF at 0° C. was added NaH (120 mg, 3 mmol, 60%), the mixture was stirred at this temperature for 30 min, before 2-bromo-4-(trifluoromethyl)thiazole (230 mg, 1 mmol) was added, the reaction was stirred for another 1 h at rt, diluted with EA, washed by LiCl solution, brine, dried over Na2SO4, removal the solvent to left crude product which was purified by silica gel to give (S)-4-(3-(4-(trifluoromethyl)thiazol-2-yloxy)pyrrolidin-1-yl)biphenyl-3-carbonitrile (95 mg, 23% yield), Mass spec: 416 (M+1).

Step 3: (S)-4-(3-(4-(trifluoromethyl)thiazol-2-yloxy)pyrrolidin-1-yl)biphenyl-3-carbaldehyde

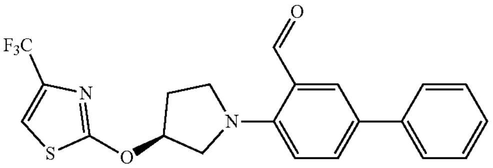 [SMILES: O=Cc1cc(-c2ccccc2)ccc1N1CC[C@H](Oc2nc(C(F)(F)F)cs2)C1]

The title compound was prepared following procedures described in intermediate step 5 to give (S)-4-(3-(4-(trifluoromethyl)thiazol-2-yloxy)pyrrolidin-1-yl)biphenyl-3-carbaldehyde (80 mg, 70% yield), Mass spec: 419 (M+H)

Step 4: (S)-(4-(3-(4-(trifluoromethyl)thiazol-2-yloxy)pyrrolidin-1-yl)biphenyl-3-yl)methanol

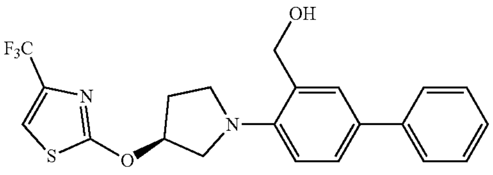 [SMILES: OCc1cc(-c2ccccc2)ccc1N1CC[C@H](Oc2nc(C(F)(F)F)cs2)C1]

The title compound was prepared following procedures described in example 328 step 5 to give (S)-(4-(3-(4-(trifluoromethyl)thiazol-2-yloxy)pyrrolidin-1-yl)biphenyl-3-yl) methanol (20 mg, 21% yield), Mass spec: 421 (M+H), $t_R$=3.006 min $^1$H-NMR (400 Hz, DMSO) □=7.825-7.827 (d, 1H), 7.705-7.711 (d, 1H), 7.583-7.601 (m, 2H), 7.365-7.469 (m, 3H), 7.249-7.296 (m, 1H), 6.986-7.007 (m, 1H), 5.506 (br, 1H), 3.782-3.859 (m, 2H), 3.607-3.636 (m, 2H), 3.329-3.334 (m, 1H), 3.150-3.202 (m, 1H), 2.313-2.363 (m, 1H), 2.102-2.136 (m, 1H).

Example 372: (S)-(6-phenyl-3-(3-(4-(trifluoromethyl)thiazol-2-yloxy)pyrrolidin-1-yl)pyridin-2-yl) methanol (Compound 1-396)

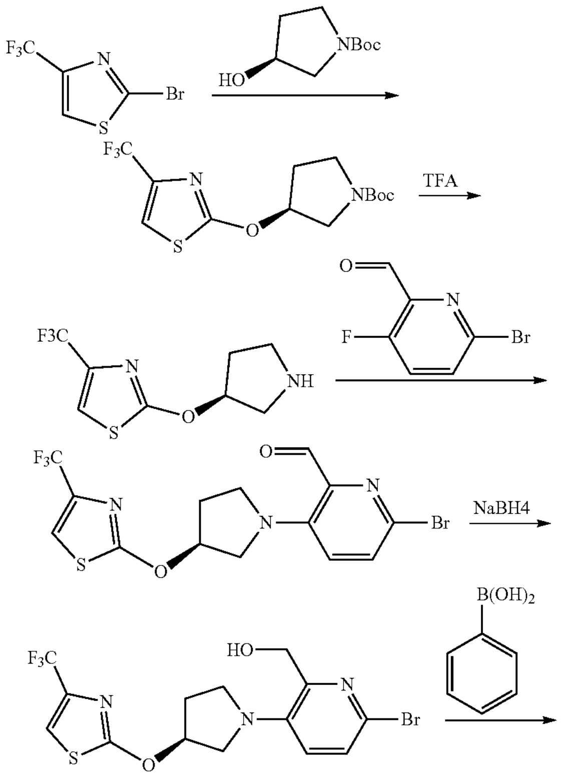

-continued

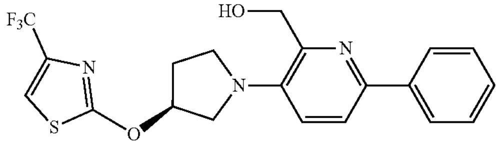

Step 1: (S)-tert-butyl 3-(4-(trifluoromethyl)thiazol-2-yloxy)pyrrolidine-1-carboxylate

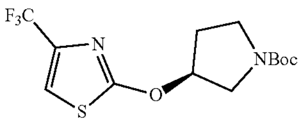 [SMILES: CC(C)(C)OC(=O)N1CC[C@H](Oc2nc(C(F)(F)F)cs2)C1]

To a solution of (S)-tert-butyl 3-hydroxypyrrolidine-1-carboxylate (321 mg, 1.2 mmol) in 5 ml DMF was added NaH (96 mg, 2.4 mmol) at 0° C., the mixture was stirred at this temperature for 30 min, before 2-bromo-4-(trifluoromethyl)thiazole (201 mg, 1.0 mmol) (example 329 step 1) was added, stirred at r.t for another 1.5 h, the mixture was extracted with EA, washed with LiCl solution, dried over $Na_2SO_4$, removal the solvent to left the crude product which was purified by silica gel to give crude (S)-tert-butyl 3-(4-(trifluoromethyl)thiazol-2-yloxy)pyrrolidine-1-carboxylate (300 mg, 88% yield yield), Mass spec: 339 (M+1).

Step 2: (S)-2-(pyrrolidin-3-yloxy)-4-(trifluoromethyl)thiazole

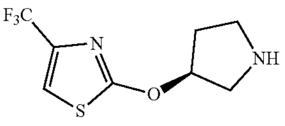 [SMILES: FC(F)(F)c1csc(O[C@H]2CCNC2)n1]

The title compound was prepared following procedures described in Intermediate 2 step 2 to give crude (S)-2-(pyrrolidin-3-yloxy)-4-(trifluoromethyl)thiazole (300 mg, quant), Mass spec: 239 (M+1).

Step 3: (S)-6-bromo-3-(3-(4-(trifluoromethyl)thiazol-2-yloxy)pyrrolidin-1-yl)picolinaldehyde

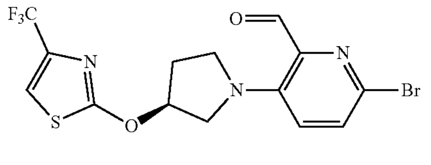 [SMILES: O=Cc1nc(Br)ccc1N1CC[C@H](Oc2nc(C(F)(F)F)cs2)C1]

The title compound was prepared following procedures described in example to give (S)-6-bromo-3-(3-(4-(trifluoromethyl)thiazol-2-yloxy)pyrrolidin-1-yl)picolinaldehyde (40 mg, 13% yield). Mass spec: 423 (M+1).

Step 4: (S)-(6-bromo-3-(3-(4-(trifluoromethyl)thiazol-2-yloxy)pyrrolidin-1-yl)pyridin-2-yl)methanol

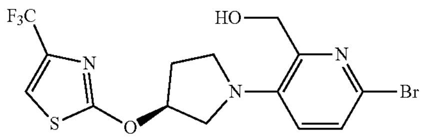 [SMILES: OCc1nc(Br)ccc1N1CC[C@H](Oc2nc(C(F)(F)F)cs2)C1]

The title compound was prepared following procedures described in example 368 step 6 to give (S)-(6-bromo-3-(3-(4-(trifluoromethyl)thiazol-2-yloxy)pyrrolidin-1-yl)pyridin-2-yl)methanol (40 mg, quant.), Mass spec: 426 (M+1).

Step 5: (S)-(6-phenyl-3-(3-(4-(trifluoromethyl)thiazol-2-yloxy)pyrrolidin-1-yl)pyridin-2-yl)methanol

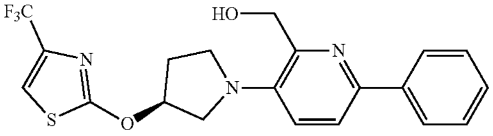 [SMILES: OCc1nc(-c2ccccc2)ccc1N1CC[C@H](Oc2nc(C(F)(F)F)cs2)C1]

The title compound was prepared following procedures described in example 357 step 4 to give (S)-(6-phenyl-3-(3-(4-(trifluoromethyl)thiazol-2-yloxy)pyrrolidin-1-yl)pyridin-2-yl)methanol (10 mg, 20% yield), Mass spec: 422 (M+1), $t_R$=2.827 min, $^1$H-NMR (400 Hz, DMSO) δ=8.024-8.043 (d, 2H), 7.878 (s, 1H), 7.750-7.771 (d, 1H), 7.421-7.459 (m, 2H), 7.312-7.349 (m, 1H), 7.247-7.268 (d, 1H), 5.631 (m, 1H), 5.163-5.189 (m, 1H), 4.655-4.732 (m, 2H), 3.845-3.887 (m, 1H), 3.581-3.670 (m, 2H), 3.398-3.434 (m, 1H), 2.298-2.366 (m, 2H).

Example 462: (S)-(4-(3-(6-(trifluoromethyl)pyridazin-3-yloxy)pyrrolidin-1-yl)biphenyl-3-yl)methanol (Compound 1-397)

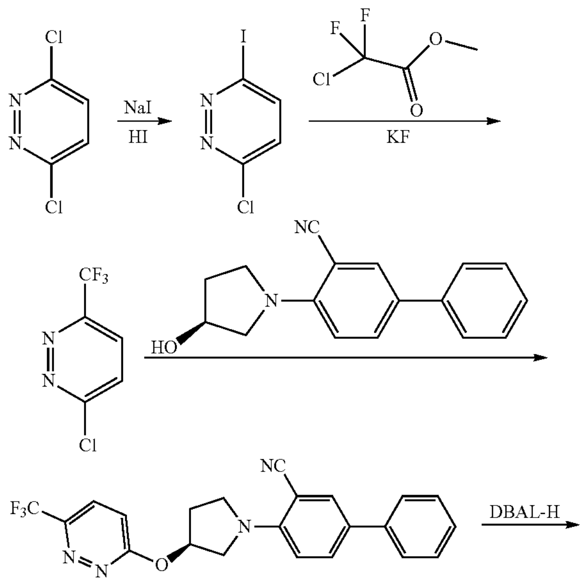

-continued

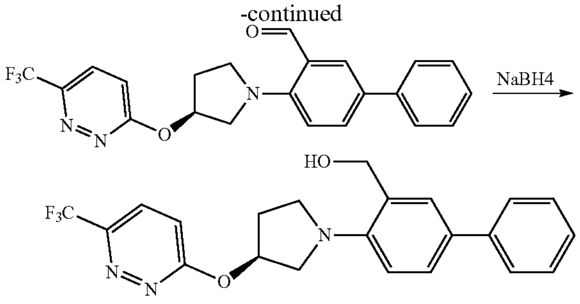

Step 1: 3-chloro-6-iodopyridazine

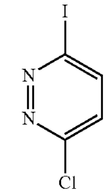

To a solution of 3,6-dichloropyridazine (2.5 g, 16.8 mmol) in 10 mL HI (55.58%) was added NaI (3.87 g, 22.5 mmol), the mixture was heated to 44° C. under $N_2$ overnight, the mixture was cooled to r.t and quenched with NaOH to PH>12, Then stirred for another 10 min, and extracted with DCM, the organic layer was washed, dried over $Na_2SO_4$, removal the solvent to left the crude 3-chloro-6-iodopyridazine (4.1 g, 60% content), Mass spec: 241 (M+1).

Step 2: 3-chloro-6-(trifluoromethyl)pyridazine

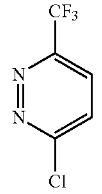 [SMILES: FC(F)(F)c1ccc(Cl)nn1]

To a solution of 3-chloro-6-iodopyridazine (500 mg, 2.08 mmol) in 5 mL DMF was added methyl 2-chloro-2,2-difluoroacetate (601 mg, 4.16 mmol), KF (241 mg, 4.16 mmol), CuI (594 mg, 3.12 mmol, the mixture was heated to 115° C. for 6 h, the mixture was cooled to rt and used directly without workup. (Boiling point of product was low), got (400 mg, 80% yield), Mass spec: 183 (M+1).

Step 3: (S)-4-(3-(6-(trifluoromethyl)pyridazin-3-yloxy)pyrrolidin-1-yl)biphenyl-3-carbonitrile

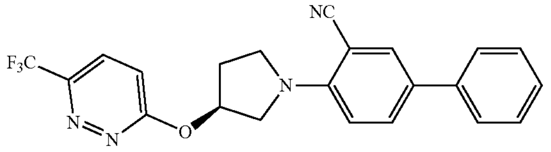 [SMILES: N#Cc1cc(-c2ccccc2)ccc1N1CC[C@H](Oc2ccc(C(F)(F)F)nn2)C1]

To a solution of (S)-4-(3-hydroxypyrrolidin-1-yl)biphenyl-3-carbonitrile (100 mg, 0.378 mmol) in 10 mL DMF was added NaH ( )27.24 mg, 1.13 mmol), The mixture was stirred for 1.5 h, the crude solution of 3-chloro-6-(trifluoromethyl)pyridazine (82.87 mg, 0.454 mmol) in DMF was added, the mixture was stirred overnight, water was added and extracted with EA, the EA layer was washed with LiCl solution, dried over $Na_2SO_4$, removal the solvent to left the crude product which was purified by silica gel to give (S)-4-(3-(6-(trifluoromethyl)pyridazin-3-yloxy)pyrrolidin-1-yl)biphenyl-3-carbonitrile (30 mg, 45% yield), Mass spec: 411 (M+1).

Step 4: (S)-4-(3-(6-(trifluoromethyl)pyridazin-3-yloxy)pyrrolidin-1-yl)biphenyl-3-carbaldehyde

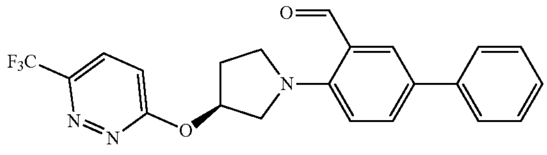 [SMILES: O=Cc1cc(-c2ccccc2)ccc1N1CC[C@H](Oc2ccc(C(F)(F)F)nn2)C1]

The title compound was prepared following procedures described in example 96 step 1 to give (S)-4-(3-(6-(trifluoromethyl)pyridazin-3-yloxy)pyrrolidin-1-yl)biphenyl-3-carbaldehyde (20 mg, 40% yield), Mass spec: 414 (M+1).

Step 5: (S)-(4-(3-(6-(trifluoromethyl)pyridazin-3-yloxy)pyrrolidin-1-yl)biphenyl-3-yl)methanol

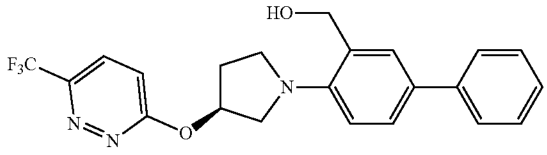 [SMILES: OCc1cc(-c2ccccc2)ccc1N1CC[C@H](Oc2ccc(C(F)(F)F)nn2)C1]

The title compound was prepared following procedures described in example 96 step 2 to give (S)-(4-(3-(6-(trifluoromethyl)pyridazin-3-yloxy)pyrrolidin-1-yl)biphenyl-3-yl) methanol (2.6 mg, 10% yield), Mass spec: 416 (M+1), $t_R$=2.862 min, $^1$H-NMR (400 Hz, DMSO) δ=8.147-8.170 (d, 1H), 7.682-7.687 (d, 1H), 7.287-7.614 (m, 7H), 6.960-6.982 (d, 1H), 5.873 (m, 1H), 5.167 (m, 1H), 4.584 (m, 2H), 3.766-3.813 (m, 1H), 3.450-3.515 (m, 2H), 3.264-3.304 (m, 1H), 2.430-2.500 (m, 1H), 2.202-2.222 (m, 1H).

Section B: Synthesis of the Example

Example 130: (3-(2-(hydroxymethyl)-4-(2-isopropylphenoxy)phenyl)pyrrolidin-1-yl)(6-methylpyridin-2-yl)methanone (Compound 2-19)

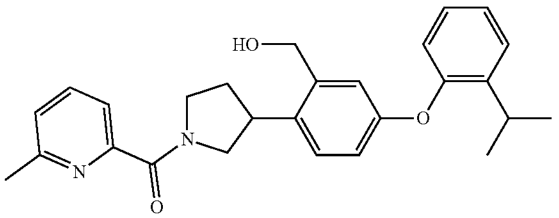 [SMILES: Cc1cccc(C(=O)N2CCC(c3ccc(Oc4ccccc4C(C)C)cc3CO)C2)n1]

To a solution of 3-(4-(2-isopropylphenoxy)-2-((tetrahydro-2H-pyran-2-yloxy)methyl)phenyl)pyrrolidine (Intermediate 6) (80 mg, 0.20 mmol) in 2 ml THE was added 6-methylpicolinic acid (26.4 mg, 0.2 mmol), HATU (114 mg, 0.30 mmol), DIPEA (51.6 mg, 0.4 mmol). the mixture was stirred at 40° C. for 2 h. the mixture was diluted with EA (10 mL), washed with H2O, the organic layer was dried (Na2SO4), evaporated to give the crude compound (3-(2-(hydroxymethyl)-4-(2-isopropylphenoxy)phenyl)pyrrolidin-1-yl)(6-methylpyridin-2-yl)methanone (110 mg), which dissolved in EA/HCl 2 mL at ° C., stirred at r.t. for 30 min, the mixture was evaporated directly, and purified by Prep-HPLC to give (3-(2-(hydroxymethyl)-4-(2-isopropylphenoxy)phenyl)pyrrolidin-1-yl)(6-methylpyridin-2-yl)methanone (37.0 mg, 43% yield), Mass spec: 431 (M+1). $t_R$=2.872 min, $^1$H-NMR (400 Hz, DMSO) δ=7.860-7.848 (m, 1H), 7.573-7.555 (m, 1H), 7.409-7.326 (q, 3H), 7.209-7.165 (q, 2H), 6.997-6.750 (q, 3H), 4.589-4.506 (m, 2H), 3.961-3.932 (m, 1H), 3.789-3.724 (m, 1H), 3.582-3.145 (m, 3H), 2.512-2.486 (m, 3H), 2.181 (s, 1H), 2.028-2.026 (m, 1H), 1.196-1.163 (m, 6H).

Example 131: (6-chloropyridin-2-yl)(3-(2-(hydroxymethyl)-4-(2-isopropylphenoxy)phenyl)pyrrolidin-1-yl)methanone (Compound 2-20)

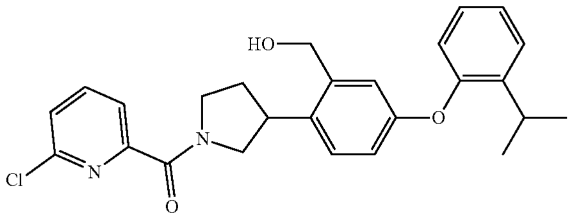 [SMILES: CC(C)c1ccccc1Oc1ccc(C2CCN(C(=O)c3cccc(Cl)n3)C2)c(CO)c1]

The title compound was prepared following procedures described in example 130 to give (6-chloropyridin-2-yl)(3-(2-(hydroxymethyl)-4-(2-isopropylphenoxy)phenyl)pyrrolidin-1-yl)methanone (13.4 mg, 18% yield), Mass spec: 451 (M+1), $t_R$=3.115 min, $^1$H-NMR (400 Hz, DMSO) δ=8.025-7.982 (m, 1H), 7.783-7.760 (m, 1H), 7.655-7.622 (q, 1H), 7.412-7.319 (q, 2H), 7.214-7.153 (q, 2H), 6.997-6.949 (m, 1H), 6.878-6.837 (m, 1H), 6.771-6.763 (m, 1H), 5.230-5.203 (m, 1H), 4.593-4.517 (m, 2H), 3.961-3.949 (m, 1H), 3.789-3.735 (m, 1.5H), 3.608-3.525 (m, 2H), 3.427-3.404 (m, 0.5H), 3.203-3.134 (m, 1H), 2.206-2.192 (m, 1H), 2.045-2.021 (m, 1H), 1.184-1.167 (m, 6H).

Example 132: (3-(2-(hydroxymethyl)-4-(2-isopropylphenoxy)phenyl)pyrrolidin-1-yl)(5-(trifluoromethyl)pyridin-2-yl)methanone (Compound 2-21)

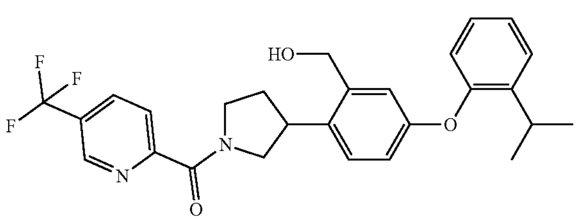 [SMILES: CC(C)c1ccccc1Oc1ccc(C2CCN(C(=O)c3ccc(C(F)(F)F)cn3)C2)c(CO)c1]

The title compound was prepared following procedures described in example 130 to give (3-(2-(hydroxymethyl)-4-(2-isopropylphenoxy)phenyl)pyrrolidin-1-yl)(5-(trifluoromethyl)pyridin-2-yl)methanone (31.2 mg, 47.6% yield), Mass spec: 485 (M+1), $t_R$=3.115 min, $^1$H-NMR (400 Hz, DMSO) δ=8.025-7.982 (m, 1H), 7.783-7.760 (m, 1H), 7.655-7.622 (q, 1H), 7.412-7.319 (q, 2H), 7.214-7.153 (q, 2H), 6.997-6.949 (m, 1H), 6.878-6.837 (m, 1H), 6.771-6.763 (m, 1H), 5.230-5.203 (m, 1H), 4.593-4.517 (m, 2H), 3.961-3.949 (m, 1H), 3.789-3.735 (m, 1.5H), 3.608-3.525 (m, 2H), 3.427-3.404 (m, 0.5H), 3.203-3.134 (m, 1H), 2.206-2.192 (m, 1H), 2.045-2.021 (m, 1H), 1.184-1.167 (m, 6H).

Example 133: (3-(2-(hydroxymethyl)-4-(2-isopropylphenoxy)phenyl)pyrrolidin-1-yl)(pyridin-2-yl)methanone (Compound 2-13)

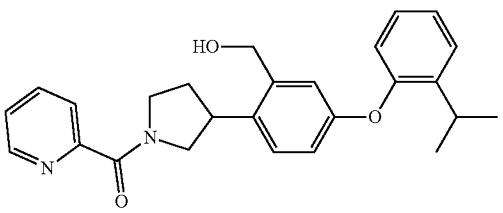 [SMILES: CC(C)c1ccccc1Oc1ccc(C2CCN(C(=O)c3ccccn3)C2)c(CO)c1]

The title compound was prepared following procedures described in example 130 to give (3-(2-(hydroxymethyl)-4-(2-isopropylphenoxy)phenyl)pyrrolidin-1-yl)(pyridin-2-yl)methanone (9.4 mg, 18% yield), Mass spec: 417 (M+1), $t_R$=2.783 min, $^1$H-NMR (400 Hz, DMSO) δ=8.629-8.566 (m, 1H), 7.952-7.928 (m, 1H), 7.778-7.742 (m, 1H), 7.497-7.480 (m, 1H), 7.413-7.379 (m, 2H), 7.354-7.317 (m, 2H), 7.214-7.152 (m, 2H), 7.000-6.938 (m, 1H), 6.879-6.826 (m, 1H), 6.771-6.742 (m, 1H), 5.218-5.118 (m, 1H), 4.598-4.497 (m, 1H), 3.977-3.955 (m, 1H), 3.816-3.787 (m, 1H), 3.606-3.565 (m, 1H), 3.448-3.375 (m, 1H), 3.188-3.167 (m, 1H), 2.195-2.177 (m, 1H), 2.059-2.003 (m, 1H), 1.198-1.168 (m, 6H).

Example 134: (5-fluoropyridin-2-yl)(3-(2-(hydroxymethyl)-4-(2-isopropylphenoxy)phenyl)pyrrolidin-1-yl)methanone (Compound 2-16)

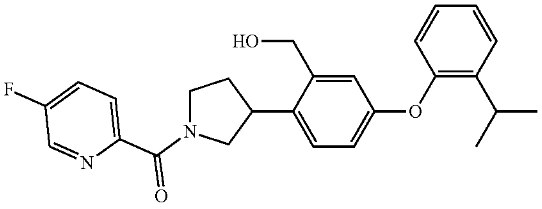 [SMILES: CC(C)c1ccccc1Oc1ccc(C2CCN(C(=O)c3ccc(F)cn3)C2)c(CO)c1]

The title compound was prepared following procedures described in example 130 to give (5-fluoropyridin-2-yl)(3-(2-(hydroxymethyl)-4-(2-isopropylphenoxy)phenyl)pyrrolidin-1-yl)methanone (20.8 mg, 16% yield), Mass spec: 435 (M+1), $t_R$=2.934 min, $^1$H-NMR (400 Hz, DMSO) δ=8.629-8.572 (m, 1H), 7.893-7.872 (m, 2H), 7.387-7.332 (m, 2H), 7.184-7.179 (m, 2H), 6.948-6.763 (q, 3H), 5.211-5.134 (q, 1H), 4.582-4.500 (q, 2H), 4.009-3.951 (m, 1H), 3.832-3.753 (m, 1.5H), 3.560-3.587 (m, 2H), 3.449-3.396 (m, 1H), 3.205-3.152 (m, 1H), 2.192-2.174 (m, 1H), 2.061-1.997 (m, 1H), 1.198-1.169 (m, 6H).

Example 135: (5-chloropyridin-2-yl)(3-(2-(hydroxymethyl)-4-(2-isopropylphenoxy)phenyl)pyrrolidin-1-yl)methanone (Compound 2-17)

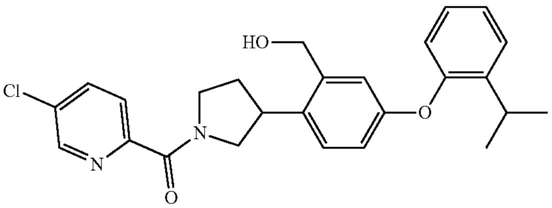 [SMILES: CC(C)c1ccccc1Oc1ccc(C2CCN(C(=O)c3ccc(Cl)cn3)C2)c(CO)c1]

The title compound was prepared following procedures described in example 130 to give (5-chloropyridin-2-yl)(3-(2-(hydroxymethyl)-4-(2-isopropylphenoxy)phenyl)pyrrolidin-1-yl)methanone (22.8 mg, 31.5% yield), Mass spec: 451 (M+1), $t_R$=3.088 min, $^1$H-NMR (400 Hz, DMSO) δ=8.690-8.633 (m, 1H), 8.082-8.053 (m, 1H), 7.830-7.800 (m, 1H), 7.386-7.309 (m, 2H), 7.184-7.158 (m, 2H), 6.999-6.763 (q, 3H), 5.212-5.132 (q, 2H), 4.582-4.500 (q, 2H), 3.986-3.933 (m, 1H), 3.806-3.747 (m, 1.5H), 3.619-3.573 (m, 2H), 3.446-3.416 (m, 0.5H), 3.205-3.152 (m, 1H), 2.186-2.173 (m, 1H), 2.043-1.997 (m, 1H), 1.197-1.169 (m, 6H).

Example 136: (3-(2-(hydroxymethyl)-4-(2-isopropylphenoxy)phenyl)pyrrolidin-1-yl)(3-methylpyridin-2-yl)methanone (Compound 2-18)

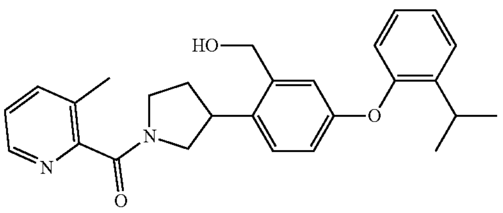 [SMILES: Cc1cccnc1C(=O)N1CCC(c2ccc(Oc3ccccc3C(C)C)cc2CO)C1]

The title compound was prepared following procedures described in example 130 to give (3-(2-(hydroxymethyl)-4-(2-isopropylphenoxy)phenyl)pyrrolidin-1-yl)(3-methylpyridin-2-yl)methanone (23.8 mg, 16% yield), Mass spec: 431 (M+1), $t_R$=2.742 min, $^1$H-NMR (400 Hz, DMSO) δ=8.415-8.374 (m, 1H), 7.752-7.700 (m, 1H), 7.394-7.282 (m, 3H), 7.189-7.148 (m, 2H), 6.999-6.797 (q, 3H), 5.218-5.125 (q, 1H), 4.579-4.472 (q, 2H), 3.979-3.756 (q, 1H), 3.601-3.540 (m, 1.5H), 3.477-3.443 (m, 1H), 3.306-3.286 (m, 1H), 3.152-3.132 (m, 1.5H), 2.291-2.268 (m, 3H), 2.179-2.149 (m, 1H), 2.068-1.951 (m, 1H), 1.199-1.156 (m, 6H).

Example 137: (3-chloropyridin-2-yl)(3-(2-(hydroxymethyl)-4-(2-isopropylphenoxy)phenyl)pyrrolidin-1-yl)methanone (Compound 2-12)

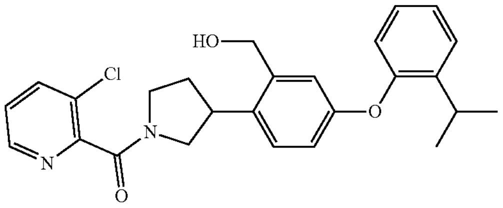 [SMILES: CC(C)c1ccccc1Oc1ccc(C2CCN(C(=O)c3ncccc3Cl)C2)c(CO)c1]

The title compound was prepared following procedures described in example 130 to give (3-chloropyridin-2-yl)(3-(2-(hydroxymethyl)-4-(2-isopropylphenoxy)phenyl)pyrrolidin-1-yl)methanone (13.2 mg, 18.3% yield), Mass spec: 451 (M+1), $t_R$=2.846 min, $^1$H-NMR (400 Hz, DMSO) δ=8.591-8.541 (m, 1H), 8.099-8.041 (m, 1H), 7.556-7.486 (m, 1H), 7.416-7.150 (m, 4H), 6.992-6.725 (q, 3H), 5.221-5.135 (q, 1H), 4.587-4.478 (q, 2H), 3.984-3.773 (q, 1H), 3.619-3.582 (m, 1.5H), 3.484-3.417 (m, 1H), 3.292-3.273 (m, 1H), 3.185-3.107 (m, 1.5H), 2.248-2.204 (m, 1H), 2.076-1.971 (m, 1H), 1.197-1.155 (m, 6H).

Example 153: 2-(1-(3-chloropicolinoyl)pyrrolidin-3-yl)-5-(2-isopropylphenoxy)benzoic acid (Compound 2-25)

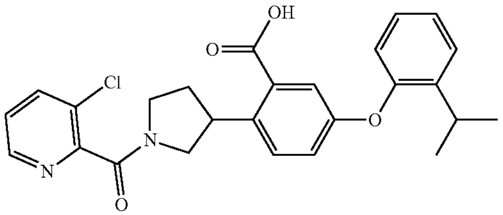 [SMILES: CC(C)c1ccccc1Oc1ccc(C2CCN(C(=O)c3ncccc3Cl)C2)c(C(=O)O)c1]

The title compound was prepared following procedures described in example 150 step 2 using example 8 to give 2-(1-(3-chloropicolinoyl)pyrrolidin-3-yl)-5-(2-isopropylphenoxy)benzoic acid (29.3 mg, 12.0% yield), Mass spec: 465 (M+1), $t_R$=2.717 min, $^1$H-NMR (400 Hz, DMS 0) δ=8.589-8.537 (m, 1H), 8.009-8.036 (m, 1H), 7.543-7.386 (m, 3H), 7.231-7.058 (m, 4H), 6.639-6.884 (m, 1H), 4.009-3.968 (m, 1.5H), 3.776-3.456 (m, 2H), 3.254 (m, 1H), 30125-3.105 (m, 1.5H), 2.269-2.080 (m, 2H), 1.182-1.139 (m, 6H).

Example 154: 2-(1-(3-chloropicolinoyl)pyrrolidin-3-yl)-5-(2-isopropylphenoxy)benzamide (Compound 2-26)

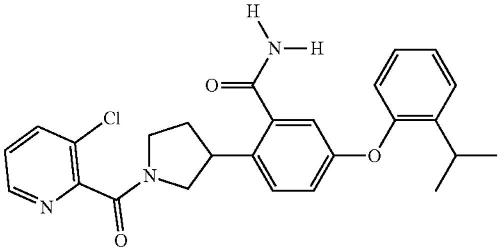 [SMILES: CC(C)c1ccccc1Oc1ccc(C2CCN(C(=O)c3ncccc3F)C2)c(C(N)=O)c1]

The title compound was prepared following procedures described in example 150 step 3 using example 153 to give 2-(1-(3-chloropicolinoyl)pyrrolidin-3-yl)-5-(2-isopropylphenoxy)benzamide (5.7 mg, 7.1% yield), Mass spec: 464 (M+1), $t_R$=2.429 min, $^1$H-NMR (400 Hz, DMSO) δ=8.590-8.540 (m, 1H), 8.098-8.042 (m, 1H), 7.928 (s, 1H), 7.822 (s, 1H), 7.555-7.396 (m, 4H), 7.247-7.183 (m, 2H), 6.935-6.821 (m, 3H), 3.999-3.970 (m, 0.5H), 3.796-3.377 (m, 3.5H), 3.294-3.080 (m, 2H), 2.229-1.996 (m, 2H), 1.202-1.157 (m, 6H).

Example 157: 2-(1-(3-fluoropicolinoyl)pyrrolidin-3-yl)-5-(2-isopropylphenoxy)benzamide (Compound 2-46)

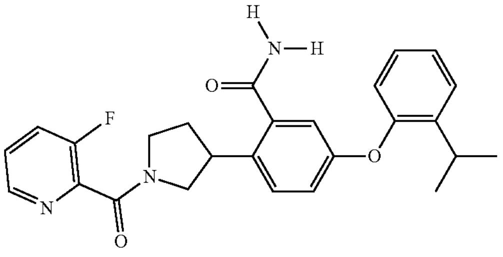

The title compound was prepared following procedures described in example 154 to give 2-(1-(3-fluoropicolinoyl)pyrrolidin-3-yl)-5-(2-isopropylphenoxy)benzamide (10.4 mg, 17.4% yield), Mass spec: 448 (M+1), $t_R$=3.299 min, $^1$H-NMR (400 Hz, DMSO) δ=8.488-8.441 (m, 1H), 7.912-7.835 (m, 2H), 7.579-7.415 (m, 4H), 7.223-7.201 (m, 2H), 6.894-6.819 (m, 3H), 4.003-3.973 (m, 0.6H), 3.838-3.466 (m, 4H), 3.355-3.135 (m, 1.4H), 2.195-2.111 (m, 2H), 1.197-1.155 (m, 6H).

Example 158: 2-(1-(5-chloropicolinoyl)pyrrolidin-3-yl)-5-(2-isopropylphenoxy)benzamide (Compound 2-32)

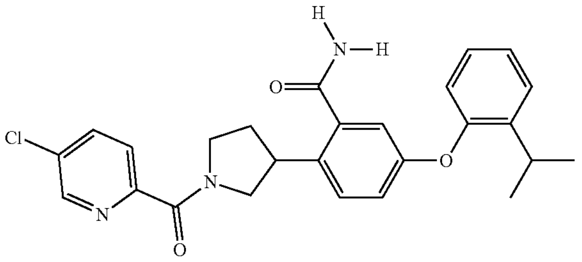 [SMILES: CC(C)c1ccccc1Oc1ccc(C2CCN(C(=O)c3ccc(Cl)cn3)C2)c(C(N)=O)c1]

The title compound was prepared following procedures described in example 154 to give 2-(1-(5-chloropicolinoyl) pyrrolidin-3-yl)-5-(2-isopropylphenoxy)benzamide (27.5 mg, 13.7% yield), Mass spec: 464 (M+1), $t_R$=2.951 min, $^1$H-NMR (400 Hz, DMSO) δ=8.684-8.636 (m, 1H), 8.099-8.057 (m, 1H), 7.918 (s, 1H), 7.841-7.796 (m, 2H), 7.513-7.405 (m, 3H), 7.244-7.194 (m, 2H), 6.931-6.842 (m, 3H), 4.014-3.964 (m, 1H), 3.839-3.544 (m, 4H), 3.193-3.140 (m, 1H), 2.194-2.081 (m, 2H), 1.199-1.170 (m, 6H).

Example 159: 5-(2-isopropylphenoxy)-2-(1-picolinoylpyrrolidin-3-yl)benzamide (Compound 2-31)

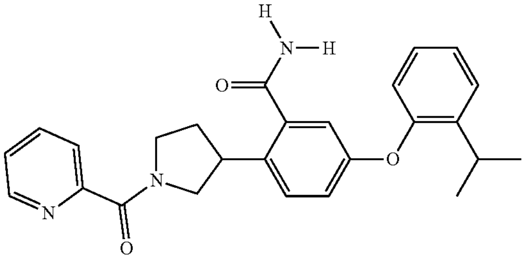 [SMILES: CC(C)c1ccccc1Oc1ccc(C2CCN(C(=O)c3ccccn3)C2)c(C(N)=O)c1]

The title compound was prepared following procedures described in example 154 to give 5-(2-isopropylphenoxy)-2-(1-picolinoylpyrrolidin-3-yl)benzamide (14.5 mg, 14.3% yield), Mass spec: 430 (M+1), $t_R$=2.788 min, $^1$H-NMR (400 Hz, DMSO) δ=8.581-8.570 (m, 1H), 7.949-7.912 (m, 1.4H), 7.848 (s, 0.6H), 7.770-7.739 (m, 1H), 7.524-7.405 (m, 4H), 7.245-7.189 (m, 2H), 6.934-6.838 (m, 3H), 3.988-3.967 (m, 1H), 3.811-3.420 (m, 4H), 3.180-3.157 (m, 1H), 2.173-2.056 (m, 2H), 1.200-1.170 (m, 6H).

Example 160: 5-(2-isopropylphenoxy)-2-(1-(6-methylpicolinoyl)pyrrolidin-3-yl)benzamide (Compound 2-33)

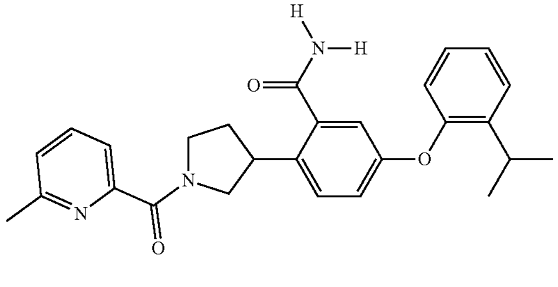 [SMILES: Cc1cccc(C(=O)N2CCC(c3ccc(Oc4ccccc4C(C)C)cc3C(N)=O)C2)n1]

The title compound was prepared following procedures described in example 154 to give 5-(2-isopropylphenoxy)-2-(1-(6-methylpicolinoyl)pyrrolidin-3-yl)benzamide (15.7 mg, 16.1% yield), Mass spec: 444 (M+1), $t_R$=2.757 min, $^1$H-NMR (400 Hz, DMSO) δ=8.581-8.570 (m, 1H), 7.949-7.912 (m, 1.4H), 7.848 (s, 0.6H), 7.770-7.739 (m, 1H), 7.524-7.405 (m, 4H), 70245-7.189 (m, 2H), 6.934-6.838 (m, 3H), 3.988-3.967 (m, 1H), 3.811-3.420 (m, 4H), 3.180-3.157 (m, 1H), 2.173-2.056 (m, 2H), 1.200-1.170 (m, 6H).

Example 161: 2-(1-(3-chloropicolinoyl)pyrrolidin-3-yl)-5-(2-ethylphenoxy)benzamide (Compound 2-37)

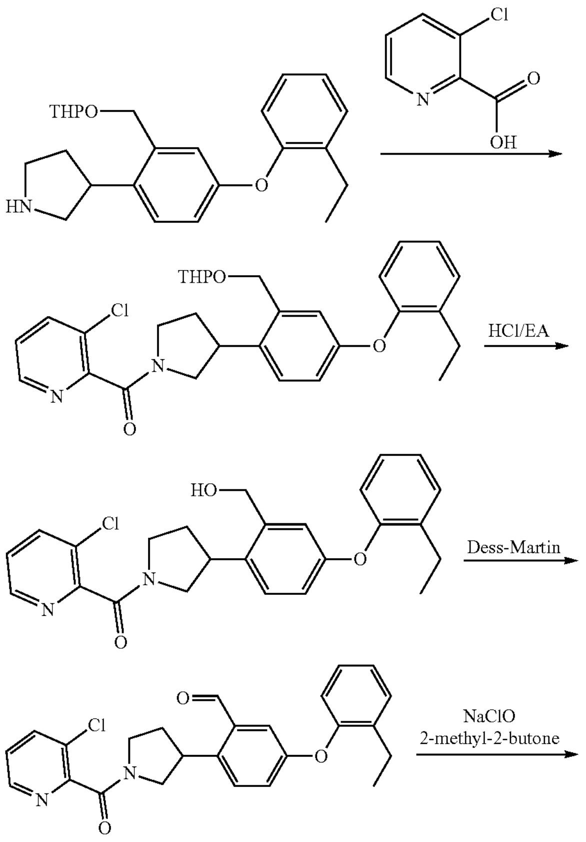

-continued

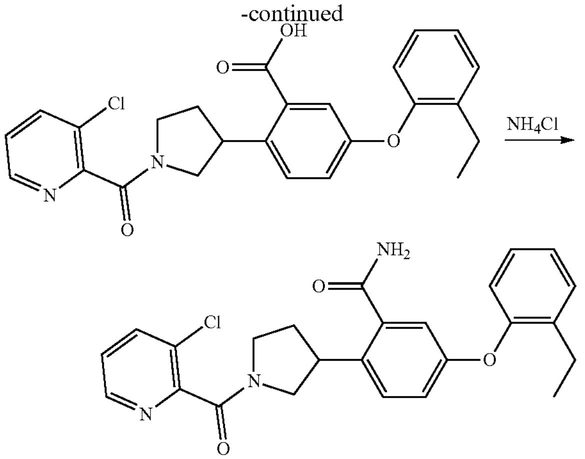

Step 1: (3-chloropyridin-2-yl)(3-(4-(2-ethylphenoxy)-2-((tetrahydro-2H-pyran-2-yloxy)methyl)phenyl)pyrrolidin-1-yl)methanone

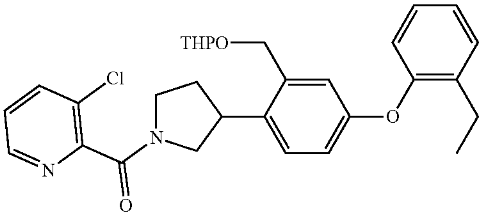

To a solution of 3-(4-(2-ethylphenoxy)-2-((tetrahydro-2H-pyran-2-yloxy)methyl)phenyl)pyrrolidine (150 mg, 0.39 mmol) (prepared as intermediate 6) and 3-chloropicolinic acid (67 mg, 0.43 mmol) in 4 mL THE was added HATU (177 mg, 0.468 mmol) and DIPEA (0.15 mL, 0.78 mmol), the mixture was stirred at 40° C. for 2 h, EA was added, and washed by water, brine, dried over Na2SO4, removal the solvent to left the crude (3-chloropyridin-2-yl)(3-(4-(2-ethylphenoxy)-2-((tetrahydro-2H-pyran-2-yloxy)methyl)phenyl) pyrrolidin-1-yl)methanone (130 mg, 64%), Mass spec: 521 (M+1).

Step 2: (3-chloropyridin-2-yl)(3-(4-(2-ethylphenoxy)-2-(hydroxymethyl)phenyl)pyrrolidin-1-yl) methanone

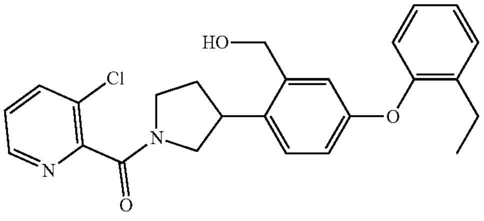

A solution of (3-chloropyridin-2-yl)(3-(4-(2-ethylphenoxy)-2-((tetrahydro-2H-pyran-2-yloxy)methyl)phenyl) pyrrolidin-1-yl)methanone (150 mg, 0.288 mmol) in HCl/MeOH (2N, 2 mL) was stirred at rt for 2 h, removal the MeOH to left the crude (3-chloropyridin-2-yl)(3-(4-(2-ethylphenoxy)-2-(hydroxymethyl)phenyl)pyrrolidin-1-yl) methanone (150 mg, 118%) which can be used directly, Mass spec: 437 (M+1).

Step 3: 2-(1-(3-chloropicolinoyl)pyrrolidin-3-yl)-5-(2-ethylphenoxy)benzaldehyde

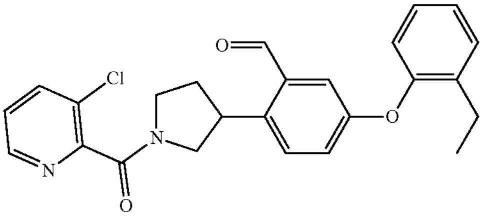 [SMILES: CCc1ccccc1Oc1ccc(C2CCN(C(=O)c3ncccc3Cl)C2)c(C=O)c1]

The title compound was prepared following procedures described in example 150 (step 1) to give crude 2-(1-(3-chloropicolinoyl)pyrrolidin-3-yl)-5-(2-ethylphenoxy)benzaldehyde (130 mg, 87% yield), Mass spec: 435 (M+1), Step 4: 2-(1-(3-chloropicolinoyl)pyrrolidin-3-yl)-5-(2-ethylphenoxy)benzoic acid

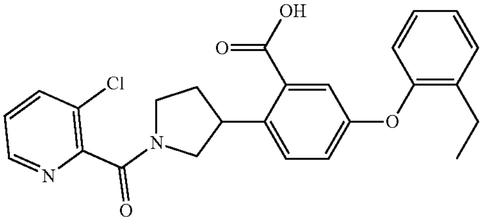 [SMILES: CCc1ccccc1Oc1ccc(C2CCN(C(=O)c3ncccc3Cl)C2)c(C(=O)O)c1]

The title compound was prepared following procedures described in example 150 (step 2) to give crude 2-(1-(3-chloropicolinoyl)pyrrolidin-3-yl)-5-(2-ethylphenoxy)benzoic acid (110 mg, 81% yield), Mass spec: 451 (M+1).

Step 5: 2-(1-(3-chloropicolinoyl)pyrrolidin-3-yl)-5-(2-ethylphenoxy)benzamide

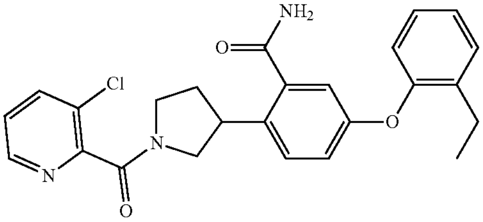

The title compound was prepared following procedures described in example 150 (step 3) to give 2-(1-(3-chloropicolinoyl)pyrrolidin-3-yl)-5-(2-ethylphenoxy)benzamide (30 mg, 34% yield), Mass spec: 450 (M+1), $t_R$=2.479 min, $^1$H-NMR (400 Hz, DMSO) δ=8.541-8.589 (m, 1H), 8.041-8.098 (m, 1H), 7.818-7.922 (m, 1H), 7.253-7.555 (m, 4H), 6.950-7.211 (m, 2H), 6.807-6.930 (m, 3H), 3.970-4.019 (m, 1H), 3.731-3.790 (m, 1.5H), 3.377-3.498 (m, 1.5H), 3.107-3.183 (m, 1H), 2.510-2.596 (m, 2H), 1.981-2.256 (m, 2H), 1.108-1.176 (m, 3H).

Example 162: 5-(2-ethylphenoxy)-2-(1-picolinoylpyrrolidin-3-yl)benzamide (Compound 2-38)

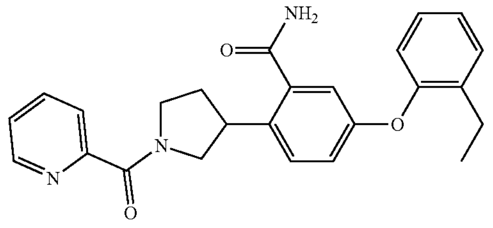 [SMILES: CCc1ccccc1Oc1ccc(C2CCN(C(=O)c3ccccn3)C2)c(C(N)=O)c1]

The title compound was prepared following procedures described in example 161 to give 5-(2-ethylphenoxy)-2-(1-picolinoylpyrrolidin-3-yl)benzamide (60 mg, 30% yield), Mass spec: 416 (M+1), $t_R$=2.422 min, $^1$H-NMR (400 Hz, DMSO) δ=8.582-8.626 (m, 1H), 7.772-7.931 (m, 3H), 7.370-7.514 (m, 4H), 7.171-7.222 (m, 2H), 6.823-6.922 (m, 3H), 3.988 (m, 1H), 3.762-3.812 (m, 1H), 3.574-3.625 (m, 2.5H), 3.392-3.410 (m, 0.5H), 2.505-2.596 (m, 2H), 2.080-2.172 (m, 2H), 1.123-1.175 (m, 3H).

Example 163: 2-(1-(5-chloropicolinoyl)pyrrolidin-3-yl)-5-(2-ethylphenoxy)benzamide (Compound 2-39)

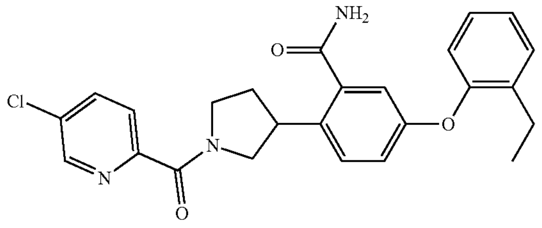 [SMILES: CCc1ccccc1Oc1ccc(C2CCN(C(=O)c3ccc(Cl)cn3)C2)c(C(N)=O)c1]

The title compound was prepared following procedures described in example 161 to give 2-(1-(5-chloropicolinoyl)pyrrolidin-3-yl)-5-(2-ethylphenoxy)benzamide (80 mg, 42% yield), Mass spec: 450 (M+1), $t_R$=2.722 min, $^1$H-NMR (400 Hz, DMSO) δ=8.644-8.686 (m, 1H), 8.080-8.083 (m, 1H), 7.827-7.915 (m, 2H), 7.354-7.514 (m, 3H), 7.166-7.244 (m, 2H), 6.826-6.922 (m, 3H), 3.988 (m, 1H), 3.785-3.850 (m, 1H), 3.357-3.681 (m, 2.5H), 3.347-3.408 (m, 0.5H), 2.505-2.594 (m, 2H), 2.093-2.178 (m, 2H), 1.123-1.173 (m, 3H).

Example 164: 5-(2-ethylphenoxy)-2-(1-(6-methylpicolinoyl)pyrrolidin-3-yl)benzamide (Compound 2-40)

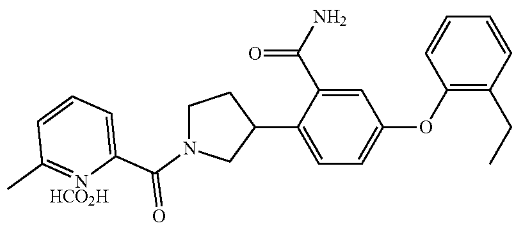

The title compound was prepared following procedures described in example 161 to give 5-(2-ethylphenoxy)-2-(1-(6-methylpicolinoyl)pyrrolidin-3-yl)benzamide (27 mg, 37% yield), Mass spec: 430 (M+1), $t_R$=2.483 min, $^1$H-NMR (400 Hz, DMSO) δ=8.171 (s, 0.2H), 7.781-7.915 (m, 2H), 7.330-7.528 (m, 5H), 7.164-7.256 (m, 2H), 6.819-6.950 (m, 3H), 3.948-3.991 (m, 1H), 3.641-3.788 (m, 3H), 3.527-3.577 (m, 1H), 2.609-2.696 (m, 2H), 2.470-2.506 (m, 3H), 2.089-2.184 (m, 2H), 1.122-1.178 (m, 3H).

Example 187: (3-chloropyridin-2-yl)(3-(4-(2-ethylphenoxy)-2-(hydroxymethyl)phenyl)pyrrolidin-1-yl)methanone (Compound 2-83)

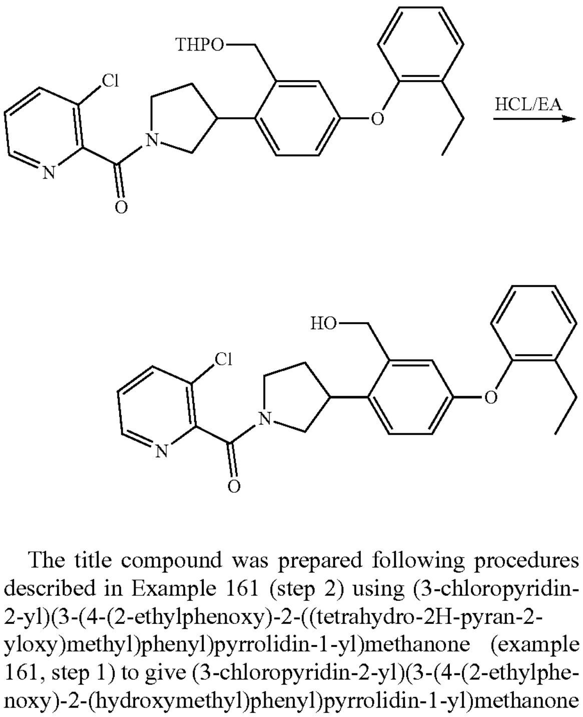

The title compound was prepared following procedures described in Example 161 (step 2) using (3-chloropyridin-2-yl)(3-(4-(2-ethylphenoxy)-2-((tetrahydro-2H-pyran-2-yloxy)methyl)phenyl)pyrrolidin-1-yl)methanone (example 161, step 1) to give (3-chloropyridin-2-yl)(3-(4-(2-ethylphenoxy)-2-(hydroxymethyl)phenyl)pyrrolidin-1-yl)methanone (20 mg, 10% yield), Mass spec: 437 (M+H), $t_R$=2.583 min, $^1$H-NMR (400 Hz, DMSO) δ=8.072-8.566 (m, 1H), 7.530-8.051 (m, 1H), 7.459-7.517 (m, 1H), 7.093-7.326 (m, 4H), 6.712-6.959 (m, 3H), 5.095-5.205 (br, 1H), 4.457-4.550 (m, 2H), 3.911-3.960 (m, 1H), 3.530-3.596 (m, 2H), 3.392-3.411 (m, 1H), 3.060-3.310 (m, 1H), 2.480-2.586 (m, 2H), 1.997-2.212 (m, 2H), 1.107-1.144 (m, 3H).

Example 188: (3-chloropyridin-2-yl)(3-(2-(hydroxymethyl)-4-(o-tolyloxy)phenyl)pyrrolidin-1-yl) methanone (Compound 2-84)

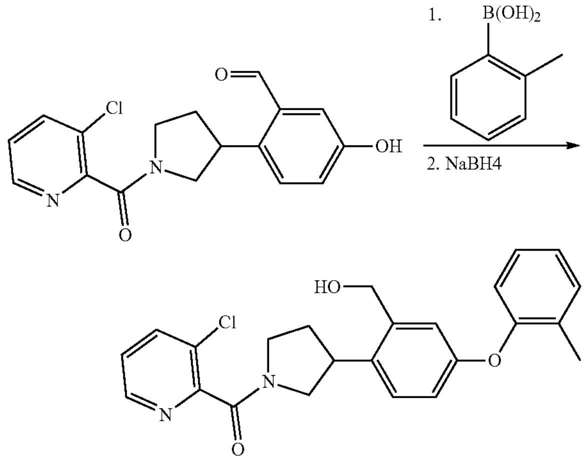

A solution of 2-(1-(3-chloropicolinoyl)pyrrolidin-3-yl)-5-hydroxybenzaldehyde (220 mg, 0.66 mmol), o-tolylboronic acid (450 mg, 3.3 mmol), Cu(OAc)2 (600 mg, 3.3 mmol) and TEA (333 mg, 3.3 mmol) in 10 mL DCM was stirred at 30° C. for 20 h, the mixture was filtered to give the intermediate 2-(1-(3-chloropicolinoyl)pyrrolidin-3-yl)-5-(o-tolyloxy)benzaldehyde as brown oil, which was dissolved in 10 ml DCM and 10 drops MeOH at 0° C. was add NaBH4 (50 mg, 1.3 mmol), and stirred for 45 min, treated with 10 mL water, extracted with DCM, dried over Na2SO4, removal the solvent to left the crude product which was purified by prep-HPLC to give (3-chloropyridin-2-yl)(3-(2-(hydroxymethyl)-4-(o-tolyloxy)phenyl)pyrrolidin-1-yl) methanone (20 mg, 10% yield), Mass spec: 423 (M+H), $t_R$=2.428 min, $^1$H-NMR (400 Hz, DMSO) δ=8.554-8.591 (d, 1H), 8.043-8.102 (m, 1H), 7.299-7.556 (m, 1H), 7.075-7.536 (m, 4H), 6.772-6.490 (m, 3H), 5.127-5.226 (br, 1H), 4.471-4.580 (m, 2H), 3.935-3.984 (m, 1H), 3.559-3.781 (m, 2H), 3.437-3.465 (m, 1H), 3.255-3.315 (m, 1H), 2.503-2.518 (m, 4H), 2.150-2.241 (m, 1H).

Example 331: (S)-(2-(3-(5-methylpyridin-2-yloxy) pyrrolidin-1-yl)-5-(pyridin-2-yl)phenyl)methanol (Compound 2-85)

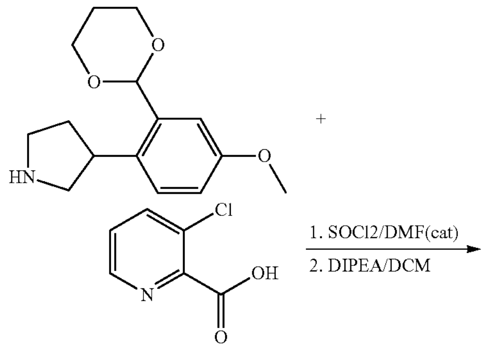

-continued

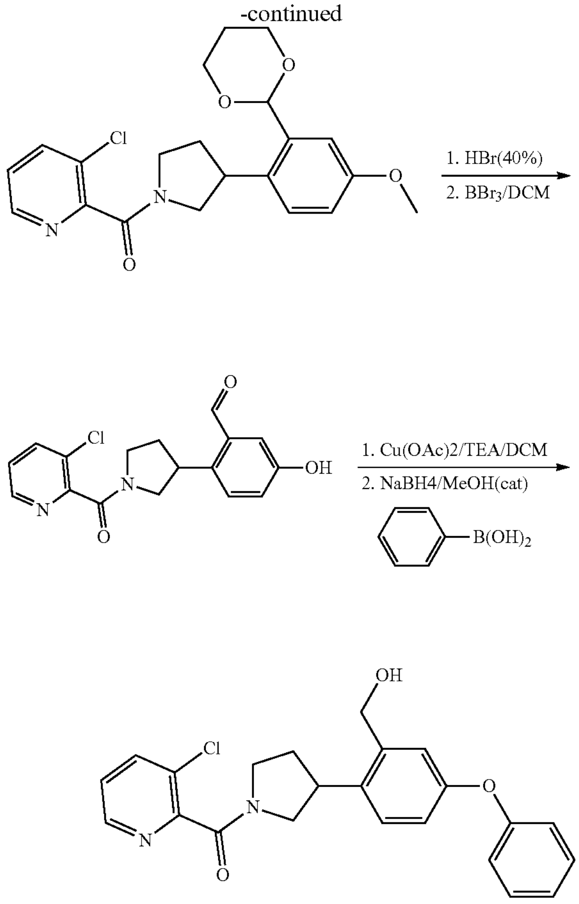

Step 1: (3-(2-(1,3-dioxan-2-yl)-4-methoxyphenyl) pyrrolidin-1-yl)(3-chloropyridin-2-yl)methanone

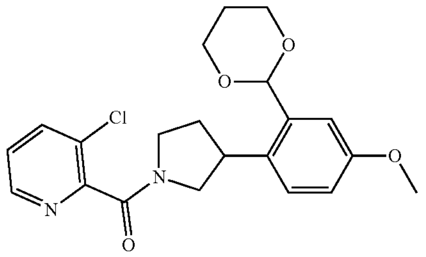 [SMILES: COc1ccc(C2CCN(C(=O)c3ncccc3Cl)C2)c(C2OCCCO2)c1]

To a solution of 3-(2-(1,3-dioxan-2-yl)-4-methoxyphenyl) pyrrolidine (500 mg, 1.9 mmol, Intermediate 5) dissolved in 5 ml DCM was added 3-chloropicolinoyl chloride (3-chloropicolinic acid (596.6 mg, 3.8 mmol) in 5 ml $SOCl_2$ was refluxed for 1.5 h, the SOCl2 was concentrated to give 3-chloropicolinoyl chloride) and DIPEA (0.67 ml, 3.8 mmol) at 0° C., monitored with TLC, after finished, the mixture was diluted with EA, washed by washed by water, brine, dried over Na2SO4, removal the solvent to left the crude product which was purified by silica gel to give (3-(2-(1,3-dioxan-2-yl)-4-methoxyphenyl)pyrrolidin-1-yl) (3-chloropyridin-2-yl)methanone (600 mg, 78.6% yield) as oil, Mass spec: 403 (M+1).

Step 2: 2-(1-(3-chloropicolinoyl)pyrrolidin-3-yl)-5-hydroxybenzaldehyde

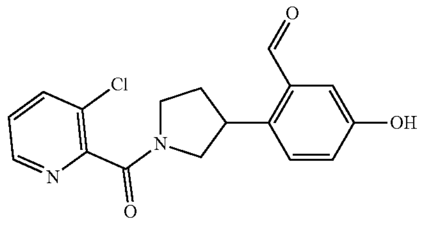 [SMILES: O=Cc1cc(O)ccc1C1CCN(C(=O)c2ncccc2Cl)C1]

To a solution of (3-(2-(1,3-dioxan-2-yl)-4-methoxyphenyl)pyrrolidin-1-yl)(3-chloropyridin-2-yl)methanone (500 mg, 1.24 mmol) in 5 ml HBr solution and stirred at rt for 1.5 h. the mixture was diluted with water, extracted with DCM, dried over Na2SO4 and removal the DCM to give the intermediate 2-(1-(3-chloropicolinoyl)pyrrolidin-3-yl)-5-methoxybenzaldehyde, which dissolved in 5 ml anhydrous DCM at −78° C. was added BBr3 slowly and stirred at rt for 30 min, cooled to 0° C. and quenched by ice-water, extracted with DCM, dried over Na2SO4 and removal the solvent to left the crude product which was purified by silica gel to give 2-(1-(3-chloropicolinoyl)pyrrolidin-3-yl)-5-hydroxybenzaldehyde (200 mg, 50% yield) as solid, Mass spec: 331 (M+1).

Step 3: (3-chloropyridin-2-yl)(3-(2-(hydroxymethyl)-4-phenoxyphenyl)pyrrolidin-1-yl)methanone

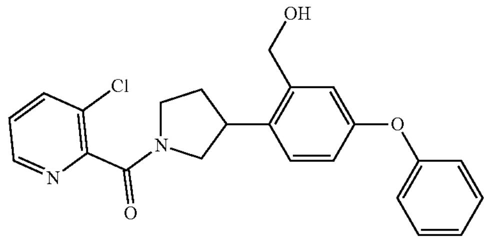 [SMILES: O=C(c1ncccc1Cl)N1CCC(c2ccc(Oc3ccccc3)cc2CO)C1]

A solution of 2-(1-(3-chloropicolinoyl)pyrrolidin-3-yl)-5-hydroxybenzaldehyde (220 mg, 0.66 mmol), phenylboronic acid (402 mg, 3.3 mmol), $Cu(OAc)_2$ (600 mg, 3.3 mmol), TEA (0.46 ml, 3.3 mmol) in 10 ml DCM was stirred at 30° C. for 20 h. the mixture was filtered and the filtrate was evaporated to left the crude product which was purified by silica gel to give the intermediate 2-(1-(3-chloropicolinoyl)pyrrolidin-3-yl)-5-phenoxybenzaldehyde, which was dissolved in 10 ml DCM was added 10 drops MeOH, $NaBH_4$ (50 mg, 1.32 mmol) was added at 0° C., then stirred at rt for 45 min, treated with 10 ml $H_2O$, extracted with DCM, dried over Na2SO4 and removal the solvent to left the crude product which was purified by Prep-HPLC to give (3-chloropyridin-2-yl)(3-(2-(hydroxymethyl)-4-phenoxyphenyl)pyrrolidin-1-yl)methanone (70.0 mg, 26% yield) as solid, Mass spec: 409 (M+1). $t_R$=2.282 min, $^1$H-NMR (400 Hz, DMSO) δ=8.556-8.546 (m, 1H), 8.068-8.044 (m, 1H), 7.558-7.510 (m, 1H), 7.399-7.323 (m, 3H), 7.143-7.122 (m, 1H), 7.064-6.886 (m, 4H), 5.245-5.161 (m, 1H), 4.587-4.496 (m, 2H), 3.976-3.810 (m, 1H), 3.760-3.661 (m, 1H), 3.612-3.456 (m, 1H), 3.300-3.268 (m, 1H), 3.152-3.104 (m, 1H), 2.274-2.250 (m, 1H), 2.071-2.018 (m, 1H).

Example 376: (3-chloropyridin-2-yl)(3-(4-(hydroxy(p-tolyl)methyl)-2-(hydroxymethyl)phenyl)pyrrolidin-1-yl)methanone (Compound 2-6)

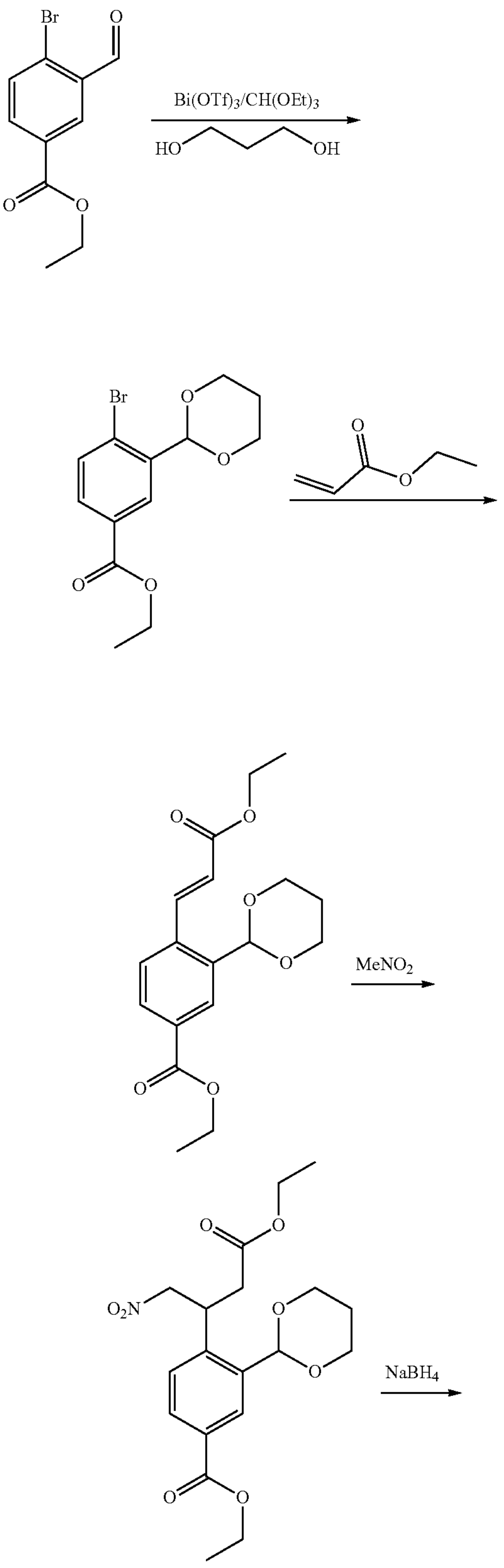

-continued

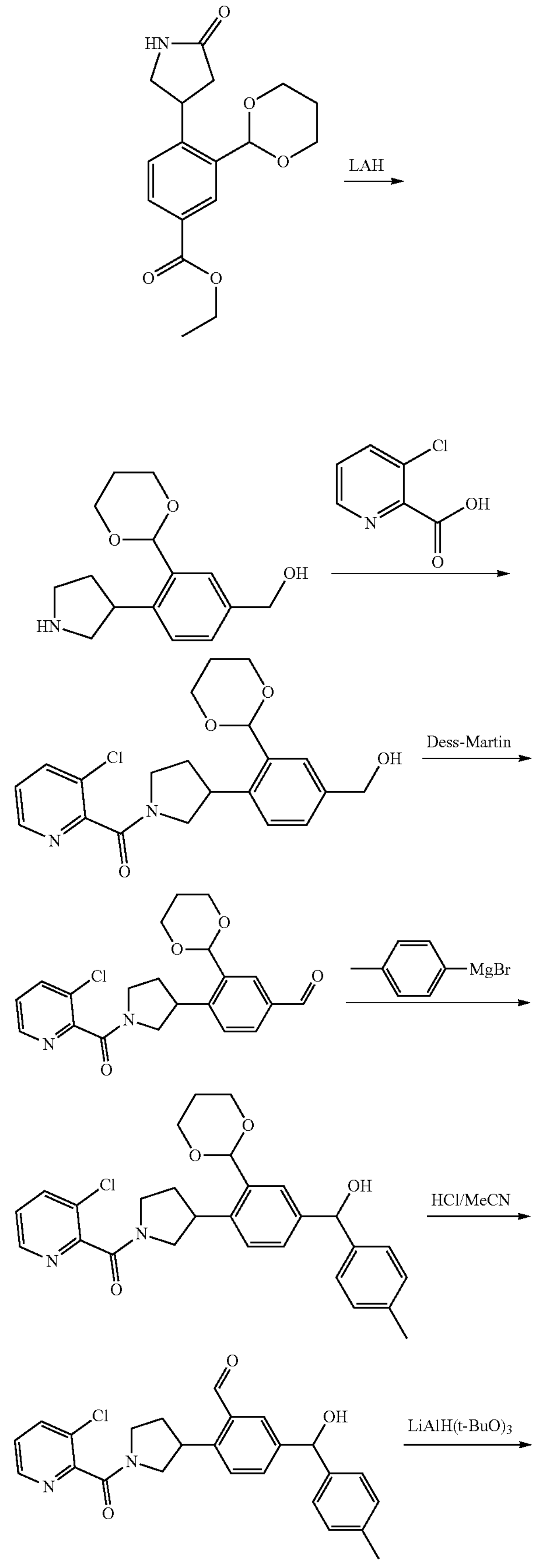

-continued

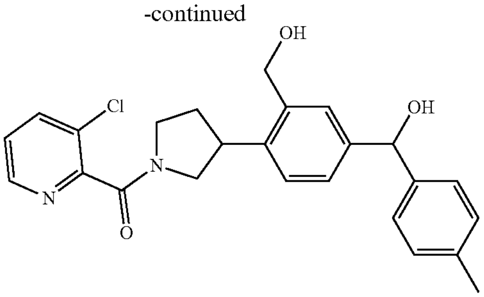

Step 1: ethyl 4-bromo-3-(1,3-dioxan-2-yl)benzoate

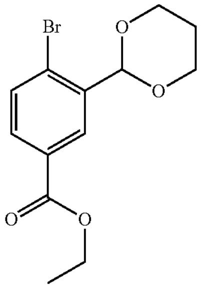 [SMILES: CCOC(=O)c1ccc(Br)c(C2OCCCO2)c1]

The title compound was prepared following procedures described in Intermediate 5 step 2 to give ethyl 4-bromo-3-(1,3-dioxan-2-yl)benzoate (320 mg, 63% yield).

Step 2: (E)-ethyl 3-(1,3-dioxan-2-yl)-4-(3-ethoxy-3-oxoprop-1-enyl)benzoate

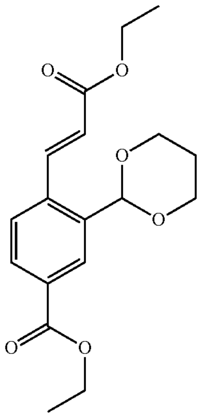 [SMILES: CCOC(=O)/C=C/c1ccc(C(=O)OCC)cc1C1OCCCO1]

The title compound was prepared following procedures described in Intermediate 5 step 3 to give (E)-ethyl 3-(1,3-dioxan-2-yl)-4-(3-ethoxy-3-oxoprop-1-enyl)benzoate (200 mg, 62.5% yield).

Step 3: ethyl 3-(1,3-dioxan-2-yl)-4-(4-ethoxy-1-nitro-4-oxobutan-2-yl)benzoate

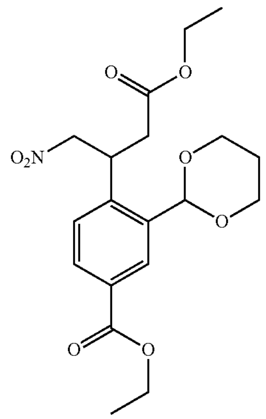 [SMILES: CCOC(=O)CC(C[N+](=O)[O-])c1ccc(C(=O)OCC)cc1C1OCCCO1]

The title compound was prepared following procedures described in Intermediate 5 step 4 to give ethyl 3-(1,3-dioxan-2-yl)-4-(4-ethoxy-1-nitro-4-oxobutan-2-yl)benzoate (110 mg, 90% yield), Mass spec: 396 (M+1).

Step 4: ethyl 3-(1,3-dioxan-2-yl)-4-(5-oxopyrrolidin-3-yl)benzoate

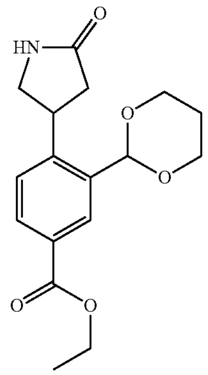 [SMILES: CCOC(=O)c1ccc(C2CNC(=O)C2)c(C2OCCCO2)c1]

The title compound was prepared following procedures described in Intermediate 5 step 5 to give ethyl 3-(1,3-dioxan-2-yl)-4-(5-oxopyrrolidin-3-yl)benzoate (3.5 g, 50% yield), Mass spec: 320 (M+1).

Step 5: (3-(1,3-dioxan-2-yl)-4-(pyrrolidin-3-yl)phenyl)methanol (LHP-000387-009)

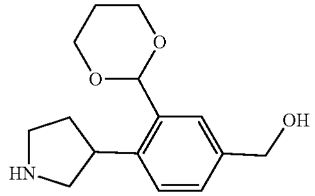 [SMILES: OCc1ccc(C2CCNC2)c(C2OCCCO2)c1]

The title compound was prepared following procedures described in Intermediate 5 step 6 to give (3-(1,3-dioxan-2-yl)-4-(pyrrolidin-3-yl)phenyl)methanol (1 g, 66% yield), Mass spec: 264 (M+1).

Step 6: (3-(2-(1,3-dioxan-2-yl)-4-(hydroxymethyl)phenyl)pyrrolidin-1-yl)(3-chloropyridin-2-yl)methanone

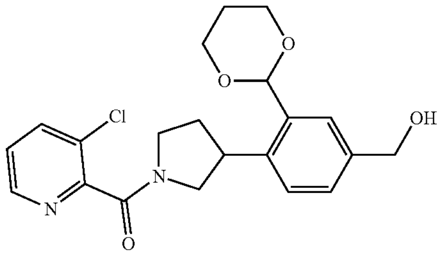 [SMILES: O=C(c1ncccc1Cl)N1CCC(c2ccc(CO)cc2C2OCCCO2)C1]

The title compound was prepared following procedures described in example 130 to give to give (3-(2-(1,3-dioxan-2-yl)-4-(hydroxymethyl)phenyl)pyrrolidin-1-yl)(3-chloropyridin-2-yl)methanone (15 mg, 50% yield), Mass spec: 403 (M+1).

Step 7: 4-(1-(3-chloropicolinoyl)pyrrolidin-3-yl)-3-(1,3-dioxan-2-yl)benzaldehyde

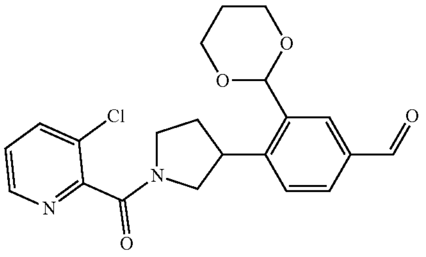 [SMILES: O=Cc1ccc(C2CCN(C(=O)c3ncccc3Cl)C2)c(C2OCCCO2)c1]

The title compound was prepared following procedures described in example 130 to give to give 4-(1-(3-chloropicolinoyl)pyrrolidin-3-yl)-3-(1,3-dioxan-2-yl)benzaldehyde (120 mg, 85% yield), Mass spec: 401 (M+1).

Step 8: (3-(2-(1,3-dioxan-2-yl)-4-(hydroxy(p-tolyl)methyl)phenyl)pyrrolidin-1-yl)(3-chloropyridin-2-yl)methanone

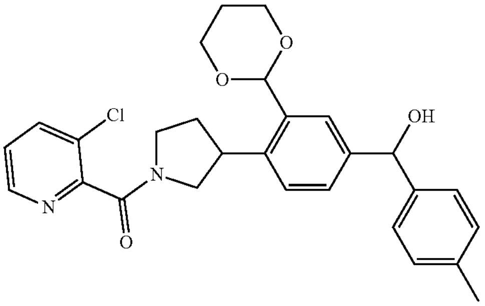 [SMILES: Cc1ccc(C(O)c2ccc(C3CCN(C(=O)c4ncccc4Cl)C3)c(C3OCCCO3)c2)cc1]

To a solution of 4-(1-(3-chloropicolinoyl)pyrrolidin-3-yl)-3-(1,3-dioxan-2-yl)benzaldehyde (200 mg, 0.5 mmol) in 3 mL THE was added p-tolylmagnesium bromide (0.5 ml, 2M in THF) slowly at 0° C., After stirred for 10 min at this temperature, quenched with saturated $NH_4Cl$ solution and extracted with DCM, the organic layer was separated, dried over $Na_2SO_4$, removal the solvent to left the crude (3-(2-(1,3-dioxan-2-yl)-4-(hydroxy(p-tolyl)methyl)phenyl)pyrrolidin-1-yl)(3-chloropyridin-2-yl)methanone (230 mg, 80% yield) which can be used directly, Mass spec: 493 (M+1).

Step 9: 2-(1-(3-chloropicolinoyl)pyrrolidin-3-yl)-5-(hydroxy(p-tolyl)methyl)benzaldehyde

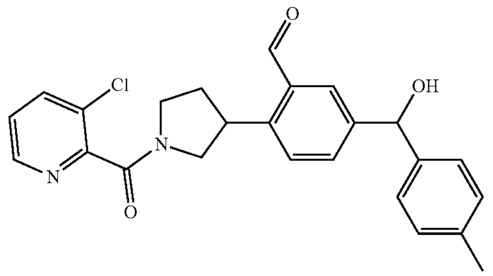 [SMILES: Cc1ccc(C(O)c2ccc(C3CCN(C(=O)c4ncccc4Cl)C3)c(C=O)c2)cc1]

To a solution of (3-(2-(1,3-dioxan-2-yl)-4-(hydroxy (p-tolyl)methyl)phenyl)pyrrolidin-1-yl)(3-chloropyridin-2-yl)methanone (230 mg, 0.42 mmol) in 1.5 mL MeCN was added 1.5 ml of 3N HCl, The resulting mixture was stirred at r.t for 10 min, After that, saturated $NaHCO_3$ solution and DCM was added for extract, the organic layer was separated, dried over $Na_2SO_4$, removal the solvent to left the crude 2-(1-(3-chloropicolinoyl)pyrrolidin-3-yl)-5-(hydroxy(p-tolyl)methyl)benzaldehyde (180 mg, 78% yield) which can be used directly, Mass spec: 435 (M+1).

Step 10: (3-chloropyridin-2-yl)(3-(4-(hydroxy(p-tolyl)methyl)-2-(hydroxymethyl)phenyl)pyrrolidin-1-yl)methanone

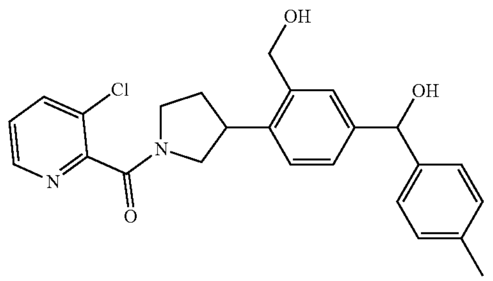 [SMILES: Cc1ccc(C(O)c2ccc(C3CCN(C(=O)c4ncccc4Cl)C3)c(CO)c2)cc1]

To a solution of 2-(1-(3-chloropicolinoyl)pyrrolidin-3-yl)-5-(hydroxy(p-tolyl)methyl)benzaldehyde (180 mg, 0.25 mmol) in 3 mL THE was added LiAlH $(t\text{-}BuO)_3$ (97 mg, 0.4 mmol), the resulting mixture was stirred at 0° C. for 15 min, After that, saturated $NaHCO_3$ solution and DCM was added for extracted, the organic layer was separated, dried over Na2SO4, removal the solvent to left the crude product which was purified by Pre-HPLC to give (3-chloropyridin-2-yl)(3-(4-(hydroxy(p-tolyl)methyl)-2-(hydroxymethyl)phenyl)pyrrolidin-1-yl)methanone (85 mg, 47% yield), Mass spec: 437 (M+1), $t_R$=1.765 min, $^1$H-NMR (400 Hz, DMSO) δ=8.079-8.080 (m, 1H), 8.027-8.077 (m, 1H), 7.482-7.553 (m, 1H), 7.066-7.298 (m, 7H), 5.736-5.780 (m, 1H), 5.588-5.637 (m, 1H), 5.050-5.170 (m, 1H), 4.460-4.571 (m, 2H), 3.243-3.969 (m, 5H), 2.512 (s, 3H), 1.971-2.169 (m, 2H).

Example 377: (4-(1-(3-chloropicolinoyl)pyrrolidin-3-yl)-3-(hydroxymethyl)phenyl)(p-tolyl)methanone (Compound 2-1)

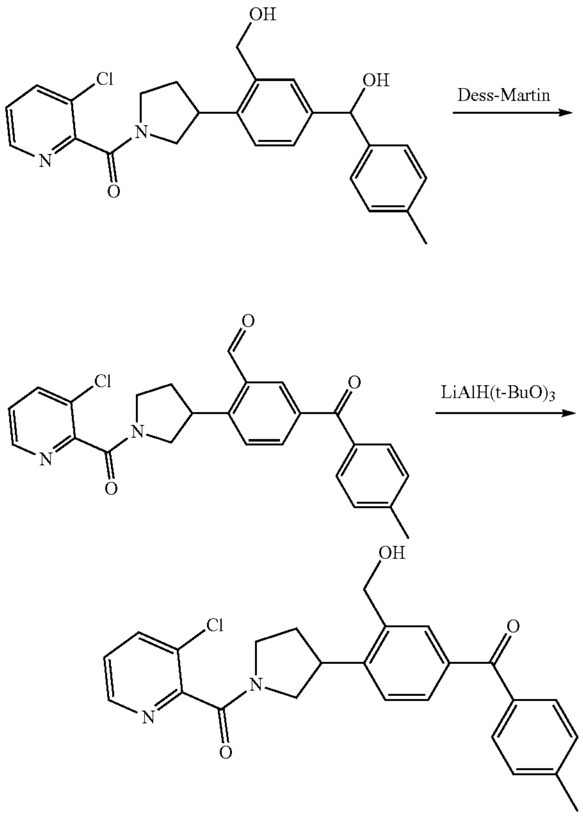

Step 1: (3-(2-(1, 3-dioxan-2-yl)-4-(hydroxymethyl) phenyl)pyrrolidin-1-yl)(3-chloropyridin-2-yl)methanone

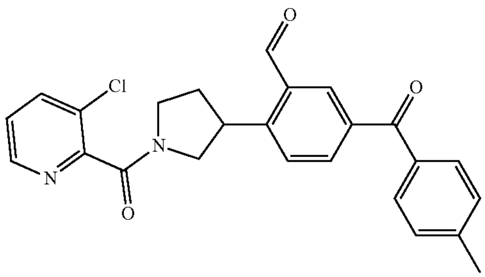 [SMILES: Cc1ccc(C(=O)c2ccc(C3CCN(C(=O)c4ncccc4Cl)C3)c(C=O)c2)cc1]

The title compound was prepared following procedures described in example 130 to give to give 3-dioxan-2-yl)-4-(hydroxymethyl)phenyl)pyrrolidin-1-yl)(3-chloropyridin-2-yl)methanone (33 mg, 70% yield), Mass spec: 433 (M+1).

Step 2: (4-(1-(3-chloropicolinoyl)pyrrolidin-3-yl)-3-(hydroxymethyl)phenyl)(p-tolyl)methanone

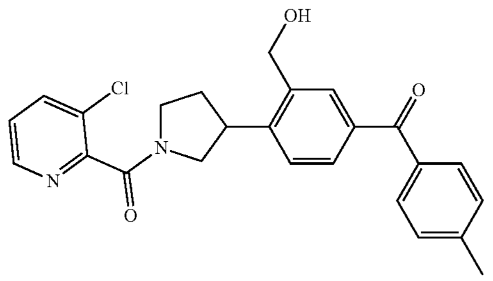 [SMILES: Cc1ccc(C(=O)c2ccc(C3CCN(C(=O)c4ncccc4Cl)C3)c(CO)c2)cc1]

The title compound was prepared following procedures described in 376 step 10 to give (4-(1-(3-chloropicolinoyl) pyrrolidin-3-yl)-3-(hydroxymethyl)phenyl)(p-tolyl)methanone (18 mg, 54% yield), Mass spec: 435 (M+1), $t_R$=2.224 min, $^1$H-NMR (400 Hz, DMSO) δ=8.551-8.594 (m, 1H), 8.053-8.113 (m, 1H), 7.354-7.723 (m, 8H), 5.254-5.365 (m, 1H), 4.600-4.705 (m, 2H), 3.197-4.016 (m, 5H), 2.411-2.425 (m, 3H), 2.081-2.274 (m, 1H), 2.050-2.2.102 (m, 1H).

Example 378: (3-(4-((2-chlorophenyl)(hydroxy)methyl)-2-(hydroxymethyl)phenyl)pyrrolidin-1-yl)(3-chloropyridin-2-yl)methanone (Compound 2-11)

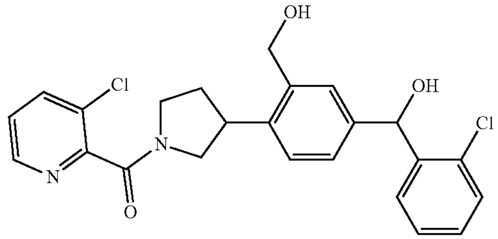 [SMILES: O=C(c1ncccc1Cl)N1CCC(c2ccc(C(O)c3ccccc3Cl)cc2CO)C1]

The title compound was prepared following procedures described in Example 376 to give (3-(4-((2-chlorophenyl)(hydroxy)methyl)-2-(hydroxymethyl)phenyl)pyrrolidin-1-yl)(3-chloropyridin-2-yl)methanone (40 mg, 44% yield), Mass spec: 457 (M+1), $t_R$=2.019 min, $^1$H-NMR (400 Hz, DMSO) δ=8.080-8.097 (m, 1H), 8.045-8.049 (m, 1H), 7.206-7.533 (m, 8H), 5.944-6.035 (m, 2H), 5.079-5.189 (m, 1H), 4.460-4.573 (m, 2H), 2.081-3.954 (m, 5H), 2.081-2.512 (m, 2H).

Example 379: (3-(4-(2-chlorobenzoyl)-2-(hydroxymethyl)phenyl)pyrrolidin-1-yl)(3-chloropyridin-2-yl)methanone (Compound 2-14)

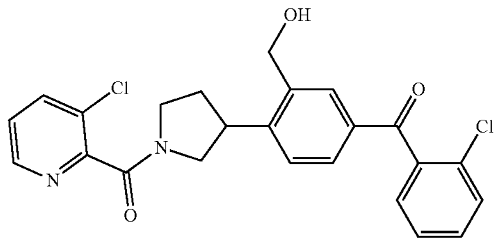 [SMILES: O=C(c1ccc(C2CCN(C(=O)c3ncccc3Cl)C2)c(CO)c1)c1ccccc1Cl]

The title compound was prepared following procedures described in Example 377 to give (3-(4-(2-chlorobenzoyl)-2-(hydroxymethyl)phenyl)pyrrolidin-1-yl)(3-chloropyridin-2-yl)methanone (45 mg, 41% yield), Mass spec: 455 (M+1), $t_R$=2.293 min, $^1$H-NMR (400 Hz, DMSO) δ=8.539-8.547 (m, 1H), 8.038-8.103 (m, 1H), 7.771-8.038 (d, 1H), 7.438-7.641 (m, 7H), 5.270-5.380 (m, 1H), 4.575-4.680 (m, 2H), 3.221-3.787 (m, 5H), 2.097-2.271 (m, 1H), 2.027-2.086 (m, 1H).

Example 380: (4-(1-(3-chloropicolinoyl)pyrrolidin-3-yl)-3-(hydroxymethyl)phenyl)(2-ethylphenyl)methanone (Compound 2-15)

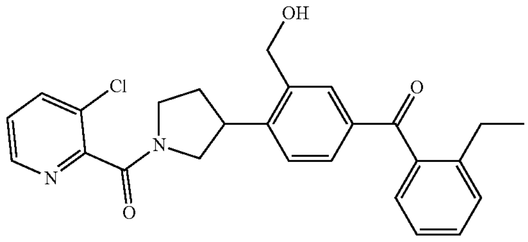 [SMILES: CCc1ccccc1C(=O)c1ccc(C2CCN(C(=O)c3ncccc3Cl)C2)c(CO)c1]

The title compound was prepared following procedures described in Example 377 to give (4-(1-(3-chloropicolinoyl) pyrrolidin-3-yl)-3-(hydroxymethyl)phenyl)(2-ethylphenyl) methanone (44 mg, 53% yield), Mass spec: 449 (M+1), $t_R$=2.485 min, $^1$H-NMR (400 Hz, DMSO) δ=8.079-8.080 (m, 1H), 8.027-8.077 (m, 1H), 7.766-7.830 (d, 1H), 7.205-7.590 (m, 7H), 5.241-5.351 (m, 1H), 4.030-4.677 (m, 2H), 3.290-4.030 (m, 5H), 2.532-2.600 (m, 2H), 2.106-2.287 (m, 1H), 2.203-2.219 (m, 1H), 1.082-1.101 (m, 3H).

Example 381: (3-chloropyridin-2-yl)(3-(4-((2-fluorophenyl)(hydroxy)methyl)-2-(hydroxymethyl)phenyl)pyrrolidin-1-yl)methanone (Compound 2-5)

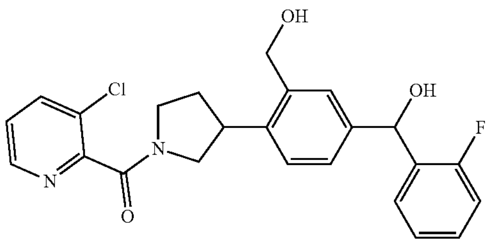 [SMILES: O=C(c1ncccc1Cl)N1CCC(c2ccc(C(O)c3ccccc3F)cc2CO)C1]

The title compound was prepared following procedures described in Example 376 to give (3-chloropyridin-2-yl)(3-(4-((2-fluorophenyl)(hydroxy)methyl)-2-(hydroxymethyl) phenyl)pyrrolidin-1-yl)methanone (11 mg, 31% yield), Mass spec: 441 (M+1), $t_R$=1.590 min, $^1$H-NMR (400 Hz, DMSO) δ=8.527-8.538 (m, 1H), 8.025-8.079 (m, 1H), 7.065-7.575 (m, 8H), 5.884-5.981 (m, 2H), 5.070-5.186 (m, 1H), 4.467-4.575 (m, 2H), 3.263-3.763 (m, 5H), 2.188-2.2.503 (m, 1H), 2.081-2.226 (m, 1H).

Example 382: (3-chloropyridin-2-yl)(3-(4-((4-fluorophenyl)(hydroxy)methyl)-2-(hydroxymethyl)phenyl)pyrrolidin-1-yl)methanone (Compound 2-4)

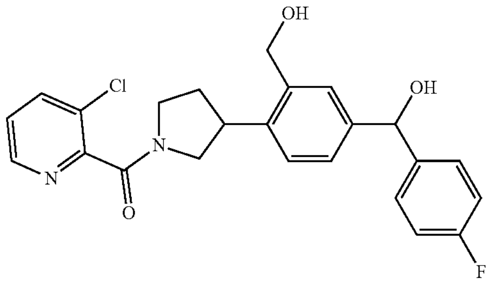 [SMILES: O=C(c1ncccc1Cl)N1CCC(c2ccc(C(O)c3ccc(F)cc3)cc2CO)C1]

The title compound was prepared following procedures described in Example 376 to give (3-chloropyridin-2-yl)(3-(4-((4-fluorophenyl)(hydroxy)methyl)-2-(hydroxymethyl)phenyl)pyrrolidin-1-yl)methanone (40 mg, 70% yield), Mass spec: 441 (M+1), $t_R$=1.655 min, $^1$H-NMR (400 Hz, DMSO) 5=8.582-8.593 (m, 1H), 8.031-8.099 (m, 1H), 7.249-7.522 (m, 8H), 5.866-5.909 (m, 1H), 5.648-5.697 (m, 1H), 4.468-4.578 (m, 2H), 3.922-3.952 (m, 0.5H), 3.263-3.574 (m, 4.5H), 2.173-2.504 (m, 1H), 1.969-2.203 (m, 1H).

Example 383: (4-(1-(3-chloropicolinoyl)pyrrolidin-3-yl)-3-(hydroxymethyl)phenyl)(4-fluorophenyl)methanone (Compound 2-10)

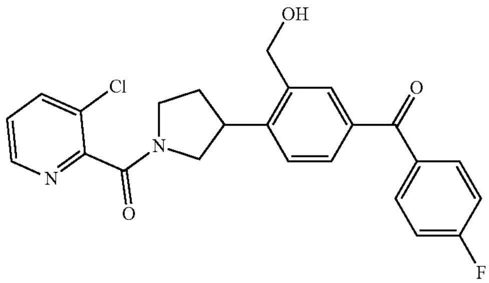 [SMILES: O=C(c1ccc(F)cc1)c1ccc(C2CCN(C(=O)c3ncccc3Cl)C2)c(CO)c1]

The title compound was prepared following procedures described in Example 377 to give (4-(1-(3-chloropicolinoyl)pyrrolidin-3-yl)-3-(hydroxymethyl)phenyl)(4-fluorophenyl)methanone (15 mg, 50% yield), Mass spec: 439 (M+1), $t_R$=2.253 min, $^1$H-NMR (400 Hz, DMSO) δ=8.549-8.603 (m, 1H), 8.051-8.111 (m, 1H), 7.365-7.836 (m, 8H), 5.285-5.383 (m, 1H), 4.606-4.710 (m, 2H), 3.199-4.048 (m, 5H), 2.306-2.304 (m, 1H), 2.060-2.125 (m, 1H).

Example 384: (3-chloropyridin-2-yl)(3-(4-(hydroxy(m-tolyl)methyl)-2-(hydroxymethyl)phenyl)pyrrolidin-1-yl)methanone (Compound 2-2)

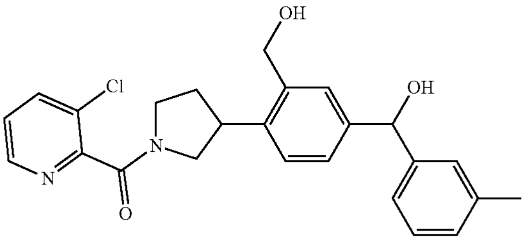 [SMILES: Cc1cccc(C(O)c2ccc(C3CCN(C(=O)c4ncccc4Cl)C3)c(CO)c2)c1]

The title compound was prepared following procedures described in Example 376 to give (3-chloropyridin-2-yl)(3-(4-(hydroxy(m-tolyl)methyl)-2-(hydroxymethyl)phenyl)pyrrolidin-1-yl)methanone (30 mg, 50% yield), Mass spec: 437 (M+1), $t_R$=2.020 min, $^1$H-NMR (400 Hz, DMSO) δ=8.525-8.592 (m, 1H), 8.025-8.080 (m, 1H), 6.998-7.502 (m, 8H), 5.755-5.789 (m, 1H), 5.584-5.633 (m, 1H), 5.063-5.157 (m, 1H), 4.463-4.560 (m, 2H), 3.092-3.757 (m, 5H), 2.254-2.277 (d, 3H), 2.010-2.040 (m, 2H).

Example 385: (4-(1-(3-chloropicolinoyl)pyrrolidin-3-yl)-3-(hydroxymethyl)phenyl)(m-tolyl)methanone (Compound 2-9)

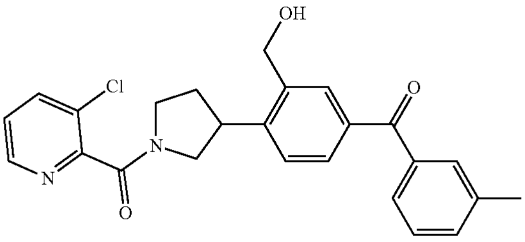 [SMILES: Cc1cccc(C(=O)c2ccc(C3CCN(C(=O)c4ncccc4Cl)C3)c(CO)c2)c1]

The title compound was prepared following procedures described in Example 377 to give (4-(1-(3-chloropicolinoyl)pyrrolidin-3-yl)-3-(hydroxymethyl)phenyl)(m-tolyl)methanone (15 mg, 71% yield), Mass spec: 435 (M+1), $t_R$=2.010, $^1$H-NMR (400 Hz, DMSO) δ=8.550-8.603 (m, 1H), 8.051-8.112 (m, 1H), 7.434-7.643 (m, 8H), 5.270-5.355 (m, 2H), 3.220-4.046 (m, 5H), 2.274-2.385 (m, 3H), 2.104-2.134 (m, 1H), 1.969-2.030 (m, 1H).

Example 386: (3-chloropyridin-2-yl)(3-(2'-cyclopropyl-3-(hydroxymethyl)biphenyl-4-yl)pyrrolidin-1-yl)methanone (Compound 2-55)

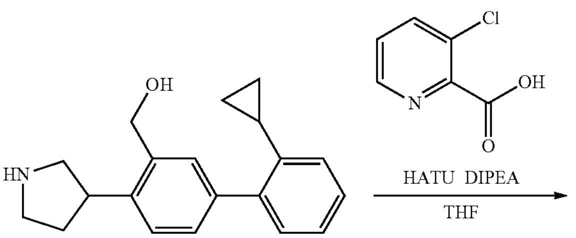

-continued

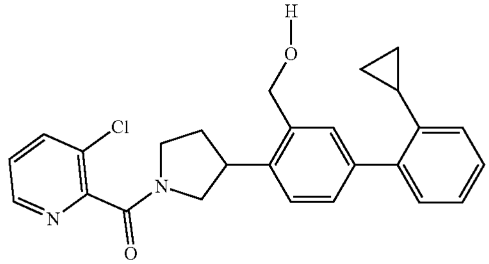

To a solution of (2'-cyclopropyl-4-(pyrrolidin-3-yl)biphenyl-3-yl)methanol (80 mg, 0.051 mmol) (Intermediate 10) in THE was added 3-chloropicolinic acid (25 mg, 0.085 mmol), HATU (30 mg, 0.085 mL) and DIPEA (100 mg, 0.085 mmol), the mixture was stirred at 45° C. for 1 h, water was added, extracted with EA, The organic phase washed with water and brine, dried over $Na_2SO_4$, removal the solvent to left the crude product which was purified by Pre-HPLC to give 3-chloropyridin-2-yl)(3-(2'-cyclopropyl-3-(hydroxymethyl)biphenyl-4-yl)pyrrolidin-1-yl)methanone (15 mg, 12.8% yield), $t_R$=2.746 min, $^1$H-NMR (400 Hz, DMSO) δ=8.597 (dd, 1H), 8.050-8.112 (m, 1H), 6.928-7.523 (m, 8H), 5.216 (br, 1H), 4.582-4.674 (m, 2H), 3.193-4.018 (m, 5H), 2.289-2.318 (m, 1H), 2.074-2.171 (m, 1H), 1.809-1.854 (m, 1H), 0.807-0.817 (m, 2H), 0.702-0.710 (m, 2H).

Example 387: 5-chloropyridin-2-yl)(3-(2'-cyclopropyl-3-(hydroxymethyl)biphenyl-4-yl)pyrrolidin-1-yl) methanone (Compound 2-56)

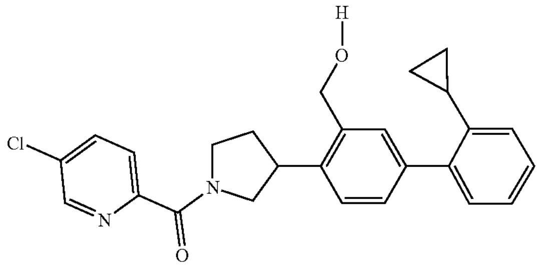 [SMILES: O=C(c1ccc(Cl)cn1)N1CCC(c2ccc(-c3ccccc3C3CC3)cc2CO)C1]

The title compound was prepared following procedures described in example 386 to give 5-chloropyridin-2-yl)(3-(2'-cyclopropyl-3-(hydroxymethyl)biphenyl-4-yl)pyrrolidin-1-yl)methanone (10 mg, 27% yield), Mass spec: 433 (M+H), $t_R$=30.005 min, $^1$H-NMR (400 Hz, DMSO) δ=8.650 (dd, 1H), 8.085 (t, d, 1H), 7.822-7.852 (m, 1H), 6.918-7.470 (m, 1H), 5.187 (br, 1H), 4.601-4.680 (m, 2H), 3.486-4.054 (m, 5H), 2.234-2.252 (m, 1H), 2.113-2.158 (m, 1H), 1.826-1.877 (m, 1H), 0.833-0.865 (m, 2H), 0.687-0.702 (m, 2H).

Example 388: (6-chloropyridin-2-yl)(3-(2'-cyclopropyl-3-(hydroxymethyl)biphenyl-4-yl)pyrrolidin-1-yl) methanone (Compound 2-57)

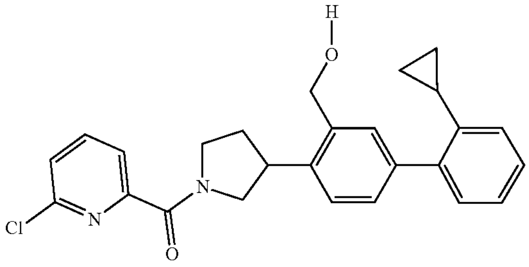 [SMILES: O=C(c1cccc(Cl)n1)N1CCC(c2ccc(-c3ccccc3C3CC3)cc2CO)C1]

The title compound was prepared following procedures described in example 386 to give (6-chloropyridin-2-yl)(3-(2'-cyclopropyl-3-(hydroxymethyl)biphenyl-4-yl)pyrrolidin-1-yl)methanone (15 mg, 40.6% yield), Mass spec: 433 (M+H), $t_R$=2.966 min, $^1$H-NMR (400 Hz, DMSO) δ=8.015-8.041 (m, 1H), 7.086 (d, 1H), 7.631-7.652 (m, 1H), 7.169-7.499 (m, 6H), 6.934 (t, 1H), 5.148 (br, 1H), 4.607-4.684 (m, 2H), 3.347-4.071 (m, 5H), 2.248-2.309 (m, 1H), 2.088-2.166 (m, 1H), 1.822-1.845 (m, 1H), 0.832-0.868 (m, 2H), 0.680-0.708 (m, 2H).

Example 389: (4-chloropyridin-2-yl)(3-(2'-cyclopropyl-3-(hydroxymethyl)biphenyl-4-yl)pyrrolidin-1-yl) methanone (Compound 2-60)

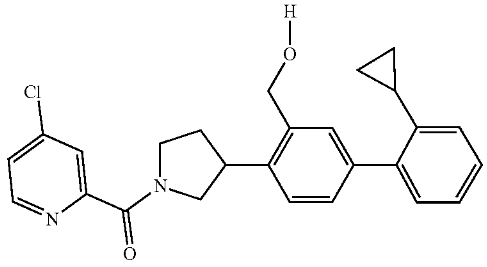 [SMILES: O=C(c1cc(Cl)ccn1)N1CCC(c2ccc(-c3ccccc3C3CC3)cc2CO)C1]

The title compound was prepared following procedures described in example 386 to give (4-chloropyridin-2-yl)(3-(2'-cyclopropyl-3-(hydroxymethyl)biphenyl-4-yl)pyrrolidin-1-yl)methanone (10.5 mg, 35.7% yield), Mass spec: 433 (M+H), $t_R$=2.966 min, $^1$H-NMR (400 Hz, DMSO) δ=8.622 (dd, 1H), 7.863 (s, 1H), 7.652-7.704 (m, 1H), 7.145-7.472 (m, 6H), 6.935 (t, 1H), 5.125-5.240 (m, 1H), 4.604-4.680 (m, 2H), 3.517-4.057 (m, 5H), 2.252-2.287 (m, 1H), 2.907-2.157 (m, 1H), 1.808-1.916 (m, 1H), 0.784-0.900 (m, 2H), 0.668-0.743 (m, 2H).

Example 390: (3-(2'-cyclopropyl-3-(hydroxymethyl) biphenyl-4-yl)pyrrolidin-1-yl)(5-(trifluoromethyl) pyridin-2-yl)methanone (Compound 2-58)

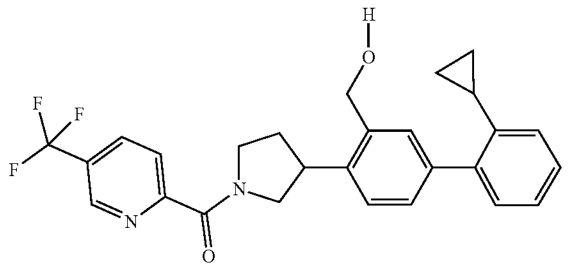 [SMILES: O=C(c1ccc(C(F)(F)F)cn1)N1CCC(c2ccc(-c3ccccc3C3CC3)cc2CO)C1]

The title compound was prepared following procedures described in example 386 to give (3-(2'-cyclopropyl-3-(hydroxymethyl)biphenyl-4-yl)pyrrolidin-1-yl)(5-(trifluoromethyl)pyridin-2-yl)methanone (15 mg, 37.7% yield), Mass spec: 467 (M+H), $t_R$=3.107 min, $^1$H-NMR (400 Hz, DMSO) δ=9.005 (d, 1H), 8.361 (t, 1H), 7.981 (d, 1H), 6.951-7.479 (m, 6H), 6.934 (t, 1H), 5.118 (br, 1H), 4.601-4.686 (m, 2H), 3.509-4.064 (m, 5H), 2.264 (s, 1H), 2.132-2.159 (m, 1H), 1.820-1.859 (m, 1H), 0.824-0.872 (m, 2H), 0.682-0.692 (m, 2H).

Example 391: (3-(2'-cyclopropyl-3-(hydroxymethyl) biphenyl-4-yl)pyrrolidin-1-yl)(5-fluoropyridin-2-yl) methanone (Compound 2-72)

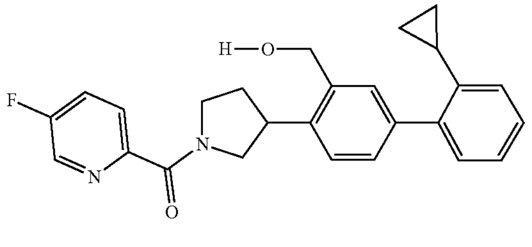 [SMILES: O=C(c1ccc(F)cn1)N1CCC(c2ccc(-c3ccccc3C3CC3)cc2CO)C1]

The title compound was prepared following procedures described in example 386 to give (3-(2'-cyclopropyl-3-(hydroxymethyl)biphenyl-4-yl)pyrrolidin-1-yl)(5-fluoropyridin-2-yl)methanone (9 mg, 7.5% yield), Mass spec: 417 (M+H), $t_R$=2.799 min, $^1$H-NMR (400 Hz, DMSO) δ=8.651-8.589 (m, 1H), 7.943-7.867 (m, 2H), 7.478-7.146 (m, 6H), 7.695-6.921 (m, 1H), 4.685-4.605 (m, 3H), 4.065-3.491 (m, 5H), 2.268-2.103 (m, 2H), 1.845-1.831 (m, 1H), 0.870-0.690 (m, 4H).

Example 392: (3-(2'-ethyl-3-(hydroxymethyl)biphenyl-4-yl)pyrrolidin-1-yl)(5-methoxypyridin-2-yl) methanone (Compound 2-74)

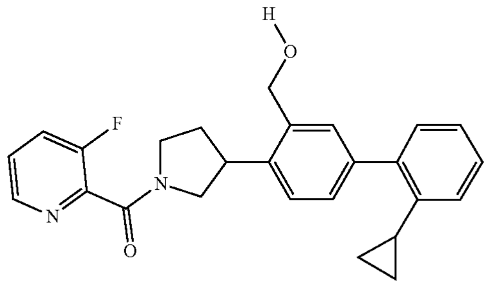 [SMILES: O=C(c1ncccc1F)N1CCC(c2ccc(-c3ccccc3C3CC3)cc2CO)C1]

The title compound was prepared following procedures described in example 386 to give (3-(2'-ethyl-3-(hydroxymethyl)biphenyl-4-yl)pyrrolidin-1-yl)(5-methoxypyridin-2-yl)methanone (12 mg, 31% yield), Mass spec: 417 (M+H), $t_R$=2.761 min, $^1$H-NMR (400 Hz, DMSO) δ=8.503-8.450 (m, 1H), 7.912-7.871 (m, 1H), 7.592-7.144 (m, 7H), 6.952-6.911 (m, 1H), 5.176 (s, 1H), 4.680-4.590 (m, 2H), 4.064-3.433 (m, 5H), 2.316-2.094 (m, 3H), 0.870-0.815 (m, 2H), 0.709-0.673 (m, 2H).

Example 393: (3-(2'-cyclopropyl-3-(hydroxymethyl) biphenyl-4-yl)pyrrolidin-1-yl)(4-methoxypyridin-2-yl)methanone (Compound 2-75)

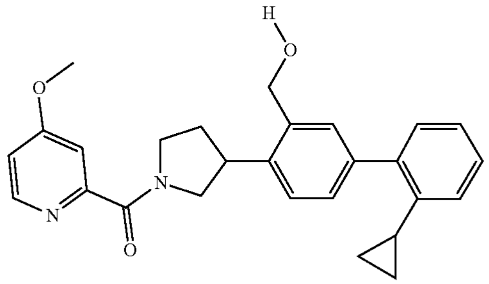 [SMILES: COc1ccnc(C(=O)N2CCC(c3ccc(-c4ccccc4C4CC4)cc3CO)C2)c1]

The title compound was prepared following procedures described in example 386 to give (3-(2'-cyclopropyl-3-(hydroxymethyl)biphenyl-4-yl)pyrrolidin-1-yl)(4-methoxypyridin-2-yl)methanone (15 mg, 50% yield), Mass spec: 429 (M+H), $t_R$ 2.623 min, $^1$H-NMR (400 Hz, DMSO) δ=8.477-8.412 (m, 1H), 7.465-7.160 (m, 8H), 6.934 (m, 1H), 4.679-4.600 (m, 3H), 4.024-3.410 (m, 8H), 2.247-2.091 (m, 2H), 1.838 (m, 1H), 0.867-0.829 (m, 2H), 0.706-0.681 (m, 2H).

Example 394: (3-(2'-cyclopropyl-3-(hydroxymethyl)biphenyl-4-yl)pyrrolidin-1-yl)(5-methoxypyridin-2-yl)methanone (Compound 2-76)

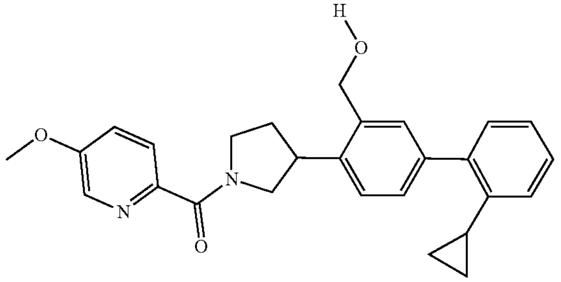 [SMILES: COc1ccc(C(=O)N2CCC(c3ccc(-c4ccccc4C4CC4)cc3CO)C2)nc1]

The title compound was prepared following procedures described in example 386 to give 3-(2'-cyclopropyl-3-(hydroxymethyl)biphenyl-4-yl)pyrrolidin-1-yl)(5-methoxypyridin-2-yl)methanone (8 mg, 20% yield), Mass spec: 429 (M+H), $t_R$=3.766 min, $^1$H-NMR (400 Hz, DMSO) δ=8.323-8.271 (m, 1H), 7.832 (m, 1H), 7.517-7.169 (m, 7H), 6.938 (m, 1H), 5.120 (s, 1H), 4.682-4.607 (m, 2H), 4.118-3.364 (m, 8H), 2.241 (s, 1H), 2.118 (m, 1H), 1.824 (m, 1H), 0.865-0.837 (m, 2H), 0.700-0.689 (m, 2H).

Example 405: (3-(2'-ethoxy-3-(hydroxymethyl)biphenyl-4-yl)pyrrolidin-1-yl)(5-fluoropyridin-2-yl)methanone (Compound 2-59)

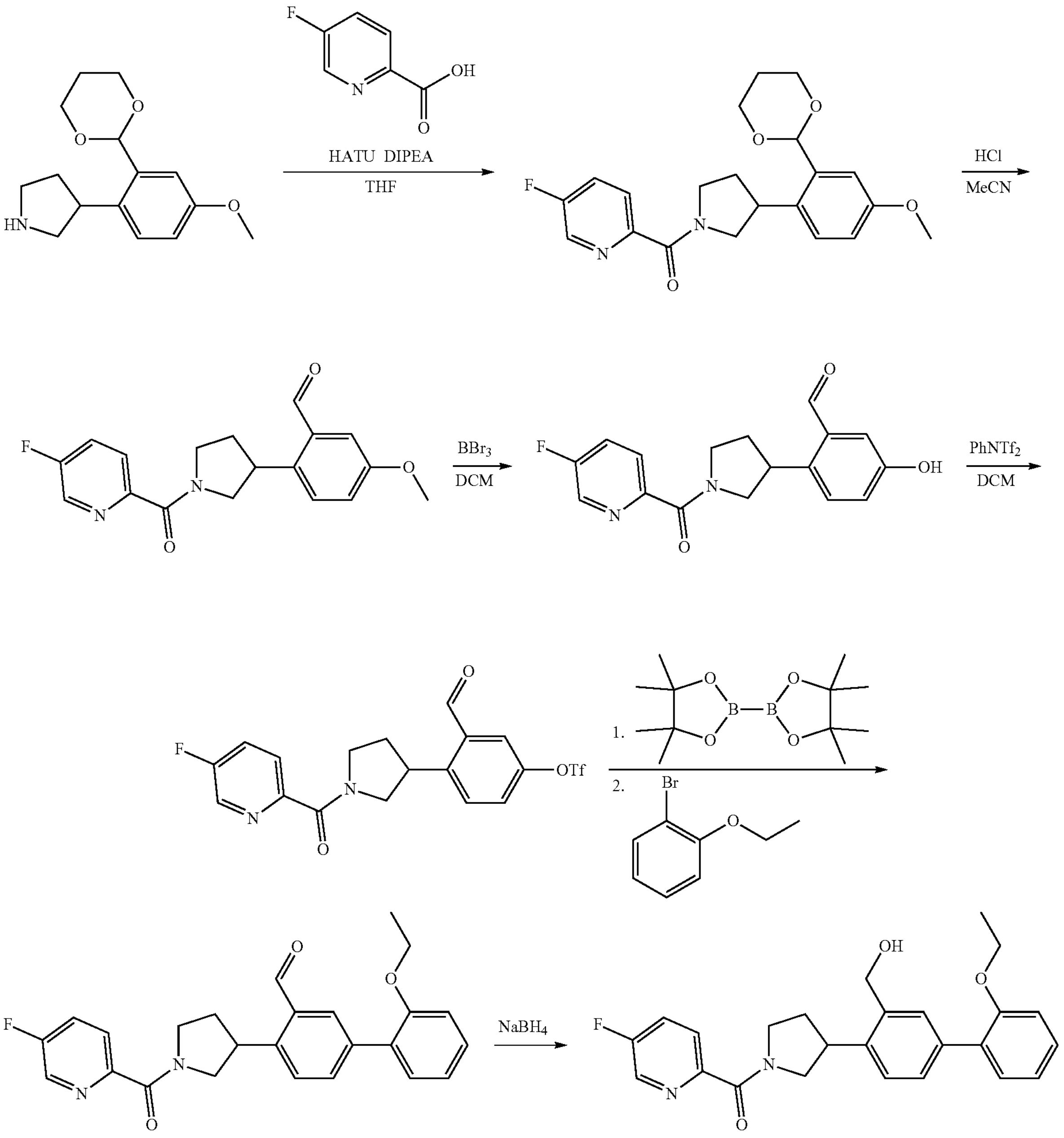

Step 1: (3-(2-(1,3-dioxan-2-yl)-4-methoxyphenyl)pyrrolidin-1-yl)(5-fluoropyridin-2-yl)methanone

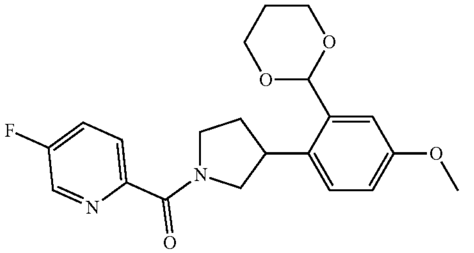 [SMILES: COc1ccc(C2CCN(C(=O)c3ccc(F)cn3)C2)c(C2OCCCO2)c1]

To a solution of 3-(2-(1,3-dioxan-2-yl)-4-methoxyphenyl)pyrrolidine (3 g, 11 mmol) in 20 mL THE was added 5-fluoropicolinic acid (1.76 g, 12.5 mmol), HATU (5.01 g, 13.2 mmol) and DIPEA (2.8 g, 22 mmol), The mixture was stirred at 45° C. for 30 min, when reaction completed, EA was added, The combined organic phase was washed with water, brine, dried over $Na_2SO_4$, removal the solvent to left crude product which was purified by silica gel to give (3-(2-(1,3-dioxan-2-yl)-4-methoxyphenyl)pyrrolidin-1-yl)(5-fluoropyridin-2-yl)methanone (3.8 g, 84.4% yield), Mass spec: 387 (M+H).

Step 2: 2-(1-(5-fluoropicolinoyl)pyrrolidin-3-yl)-5-methoxybenzaldehyde

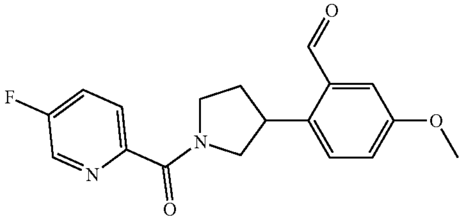 [SMILES: COc1ccc(C2CCN(C(=O)c3ccc(F)cn3)C2)c(C=O)c1]

To a solution of (3-(2-(1,3-dioxan-2-yl)-4-methoxyphenyl)pyrrolidin-1-yl)(5-fluoropyridin-2-yl)methanone (3.8 g, 9.8 mmol) in MeCN (20 mL) was added HCl (3N) (20 mL) dropwise, when added completed, the mixture was stirred at rt for 1 h, the mixture was extracted with EA, the organic phase was washed by water and brine, dried over Na2SO4, removal the solvent to left crude (3.2 g), which can be used for next step without any purification.

Step 3: 2-(1-(5-fluoropicolinoyl)pyrrolidin-3-yl)-5-hydroxybenzaldehyde

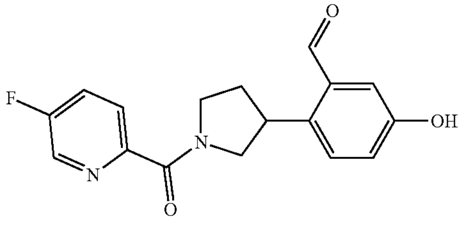

To a solution of 2-(1-(5-fluoropicolinoyl)pyrrolidin-3-yl)-5-methoxybenzaldehyde (3.2 g, 10 mmol) in DCM at 0° C. was added $BBr_3$ (7.4 g, 30 mmo) drop-wised, when added completed, the mixture was stirred at rt for 2 h, the mixture was poured into ice-water, extracted with DCM/MeOH (10/1), dried over $Na_2SO_4$, removal the solvent to left crude product which was purified by silica gel to give 2-(1-(5-fluoropicolinoyl)pyrrolidin-3-yl)-5-hydroxybenzaldehyde (1.06 g, 34.6% yield), Mass spec: 315 (M+H).

Step 4: 4-(1-(5-fluoropicolinoyl)pyrrolidin-3-yl)-3-formylphenyl trifluoromethanesulfonate

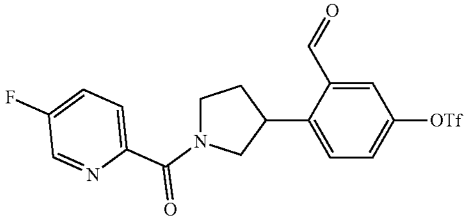 [SMILES: O=Cc1cc(OS(=O)(=O)C(F)(F)F)ccc1C1CCN(C(=O)c2ccc(F)cn2)C1]

To a solution of 2-(1-(5-fluoropicolinoyl)pyrrolidin-3-yl)-5-hydroxybenzaldehyde (1 g, 3.17 mmol) in 20 mL DCM was added $PhNTf_2$ (1.35 g, 3.8 mmol) and DIPEA (8.17 mg, 6.34 mmol), The mixture was stirred at rt for 2 h. DCM was added, washed with water, brine, dried over $Na_2SO_4$, removal the solvent to left crude product which was purified by silica gel to give 4-(1-(5-fluoropicolinoyl)pyrrolidin-3-yl)-3-formylphenyl trifluoromethanesulfonate (1.3 g). Mass spec: 447 (M+H).

Step 5: 2'-ethoxy-4-(1-(5-fluoropicolinoyl)pyrrolidin-3-yl)biphenyl-3-carbaldehyde

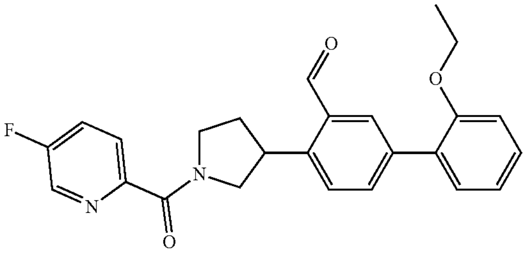

To a solution of 4-(1-(5-fluoropicolinoyl)pyrrolidin-3-yl)-3-formylphenyl trifluoromethanesulfonate (110 mg, 0.25 mmol) in 3 mL Dioxane was added 4,4,4',4',5,5,5',5'-octamethyl-2,2'-bi(1,3,2-dioxaborolane) (125 mg, 0.5 mmol), AcOK (49 mg, 0.5 mmol) and Pd (dppf)$Cl_2$ (11 mg), the mixture was degassed with $N_2$, and heated to 100° C. for 2 h under $N_2$; At this time, $K_2CO_3$ (69 mg, 0.5 mmol), $H_2O$ (1 mL) and Pd(dppf)$Cl_2$ (11 mg) were added, and mixture was stirred at 90° C. for another 2 h, the mixture was diluted with EA, the organic layer was washed by water, brine, dried over $Na_2SO_4$, removal the solvent to give crude product which was purified by prep-TLC to give 2'-ethoxy-4-(1-(5-fluoropicolinoyl)pyrrolidin-3-yl)biphenyl-3-carbaldehyde (60 mg, 57% yield), Mass spec: 419 (M+H).

Step 6: (3-(2'-ethoxy-3-(hydroxymethyl)biphenyl-4-yl)pyrrolidin-1-yl)(5-fluoropyridin-2-yl)methanone

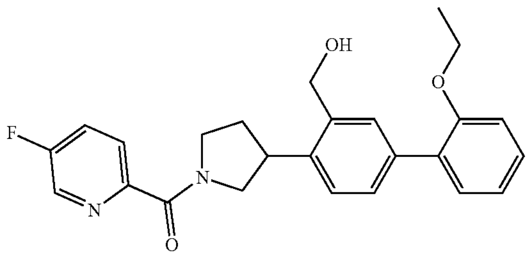 [SMILES: CCOc1ccccc1-c1ccc(C2CCN(C(=O)c3ccc(F)cn3)C2)c(CO)c1]

To a solution of 2'-ethoxy-4-(1-(5-fluoropicolinoyl)pyrrolidin-3-yl)biphenyl-3-carbaldehyde (50 mg, 0.12 mmol) in MeOH was added $NaBH_4$ (18 mg, 0.48 mmol), and stirred at rt, after finished, water was added, exacted with EA, dried over $Na_2SO_4$, removal the solvent to left the crude product which was purified by prep-HPLC to give (3-(2'-ethoxy-3-(hydroxymethyl)biphenyl-4-yl)pyrrolidin-1-yl)(5-fluoropyridin-2-yl)methanone (9.7 mg, 19% yield), Mass spec: 421 (M+H), $t_R$=2.706 min, $^1$H-NMR (400 Hz, DMSO) δ=8.583-8.647 (m, 1H), 7.861-7.937 (m, 6H), 7.265-7.541 (m, 5H), 6.991-7.107 (m, 2H), 5.037-5.194 (m, 1H), 4.580-4.658 (m, 2H), 3.993-4.087 (m, 3H), 3.613-3.879 (m, 4H), 2.240 (br, 1H), 2.081-2.119 (m, 1H), 1.257-1.304 (m, 3H).

Example 406: (5-fluoropyridin-2-yl)(3-(3-(hydroxymethyl)-2'-isopropylbiphenyl-4-yl)pyrrolidin-1-yl)methanone (Compound 2-29)

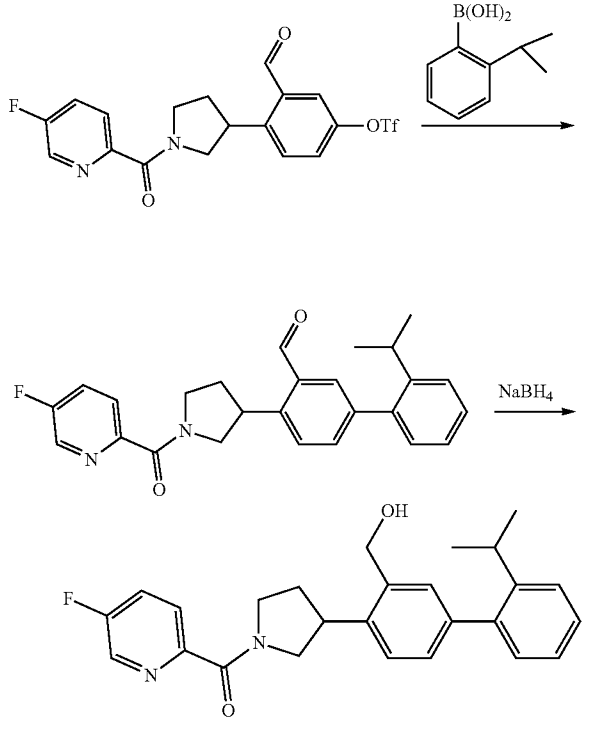

Step 1: 4-(1-(5-fluoropicolinoyl)pyrrolidin-3-yl)-2'-isopropylbiphenyl-3-carbaldehyde

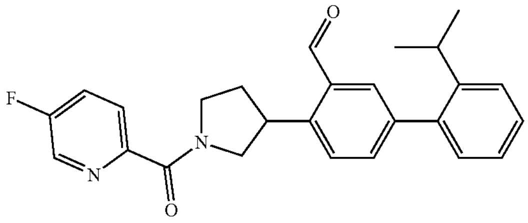 [SMILES: CC(C)c1ccccc1-c1ccc(C2CCN(C(=O)c3ccc(F)cn3)C2)c(C=O)c1]

To a solution of 4-(1-(5-fluoropicolinoyl)pyrrolidin-3-yl)-3-formylphenyl trifluoromethanesulfonate (15 g, 47 mmol), 2-isopropylphenylboronic acid (9.4 g, 57 mmol) in 240 ml Dixoane/H2O (v:v=5:1) was added $PdCl_2$(dppf) (1.95 g) and K2CO3 (13 g, 94 mmol), the mixture was heated to 90° C. under $N_2$, monitored by TLC, after finished, water was added, and extracted by EA, dried over $Na_2SO_4$, removal the solvent to left the crude product which was purified by silica gel to give 4-(1-(5-fluoropicolinoyl)pyrrolidin-3-yl)-2'-isopropylbiphenyl-3-carbaldehyde (6.5 g, 32% yield), Mass spec: 417 (M+H).

Step 2: (5-fluoropyridin-2-yl)(3-(3-(hydroxymethyl)-2'-isopropylbiphenyl-4-yl)pyrrolidin-1-yl)methanone

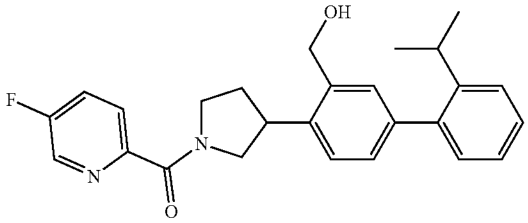 [SMILES: CC(C)c1ccccc1-c1ccc(C2CCN(C(=O)c3ccc(F)cn3)C2)c(CO)c1]

The title compound was prepared following procedures described in example 405 step 6 to give (5-fluoropyridin-2-yl)(3-(3-(hydroxymethyl)-2'-isopropylbiphenyl-4-yl)pyrrolidin-1-yl)methanone (5.2 g, 80% yield), Mass spec: 419 (M+H).

And chiral separated by SFC to give peak1 and peak2, Mass spec: 419 (M+H), $t_R$=2.953 min (CJJ-000411-033-peak1) and $t_R$=2.955 min (CJJ-000411-033-peak2), $^1$H-NMR (400 Hz, DMSO)

Peak1: δ=8.585-8.640 (m, 1H), 7.857-7.933 (m, 2H), 7.080-7.451 (m, 7H), 5.200 (m, 1H), 4.591-4.671 (m, 2H), 4.018-4.060 (m, 1H), 3.484-3.851 (m, 4H), 2.966-3.033 (m, 1H), 2.241-2.256 (m, 1H), 2.094-2.117 (m, 1H), 1.121-1.137 (m, 6H).

Peak2: δ=8.585-8.641 (m, 1H), 7.857-7.911 (m, 2H), 7.079-7.451 (m, 7H), 5.200 (m, 1H), 4.591-4.670 (m, 2H), 4.051-4.670 (m, 1H), 3.498-3.877 (m, 4H), 2.983-3.000 (m, 1H), 2.241-2.251 (m, 1H), 2.094-2.125 (m, 1H), 1.104-1.135 (m, 6H).

Example 407: (4-chloropyridin-2-yl)(3-(3-(hydroxymethyl)-2'-isopropylbiphenyl-4-yl)pyrrolidin-1-yl)methanone (Compound 2-49)

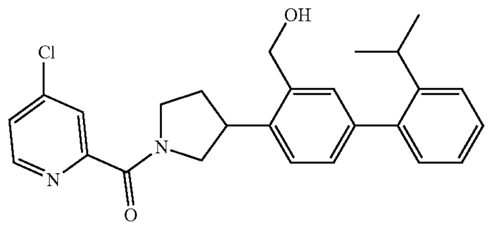 [SMILES: CC(C)c1ccccc1-c1ccc(C2CCN(C(=O)c3cc(Cl)ccn3)C2)c(CO)c1]

The title compound was prepared following procedures described in example 386 to give (4-chloropyridin-2-yl)(3-(3-(hydroxymethyl)-2'-isopropylbiphenyl-4-yl)pyrrolidin-1-yl)methanone (20 mg, 25% yield), Mass spec: 435 (M+1). $t_R$=2.975 min, $^1$H-NMR (400 Hz, DMSO) δ=8.577-8.640 (m, 1H), 7.870 (s, 1H), 7.666-7.697 (m, 1H), 7.088-7.460 (m, 7H), 4.598-4.678 (m, 2H), 4.031-4.042 (m, 1H), 3.676-3.839 (m, 5H), 2.991-3.008 (m, 1H), 2.261-2.456 (m, 1H), 2.122-2.124 (m, 1H), 1.111-1.144 (m, 6H).

Example 408: (5-fluoropyridin-2-yl)(3-(3-(hydroxymethyl)-2'-(methoxymethyl)biphenyl-4-yl)pyrrolidin-1-yl)methanone (Compound 2-61)

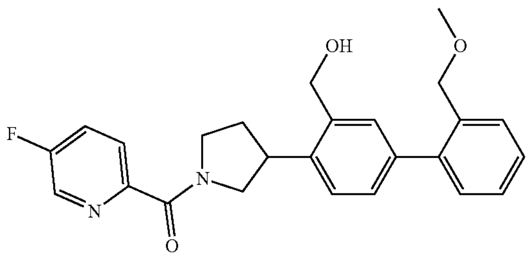 [SMILES: COCc1ccccc1-c1ccc(C2CCN(C(=O)c3ccc(F)cn3)C2)c(CO)c1]

The title compound was prepared following procedures described in example 405 to give (5-fluoropyridin-2-yl)(3-(3-(hydroxymethyl)-2'-(methoxymethyl)biphenyl-4-yl)pyrrolidin-1-yl)methanone (10 mg, 7% yield), Mass spec: 421 (M+H), $t_R$=2.460 min, $^1$H-NMR (400 Hz, DMSO) δ=8.589-8.648 (m, 1H), 7.893-7.918 (m, 2H), 7.274-7.498 (m, 7H), 5.134-5.214 (dt, 1H), 4.594-4.675 (m, 2H), 4.303-4.321 (m, 2H), 4.029-4.061 (m, 1H), 3.517-3.861 (m, 4H), 3.250-3.262 (m, 3H), 2.262 (m, 1H), 2.131 (m, 1H).

Example 409: (5-chloropyridin-2-yl)(3-(3-(hydroxymethyl)-2'-(methoxymethyl)biphenyl-4-yl)pyrrolidin-1-yl)methanone (Compound 2-65)

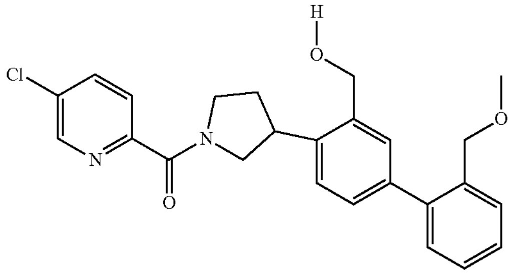 [SMILES: COCc1ccccc1-c1ccc(C2CCN(C(=O)c3ccc(Cl)cn3)C2)c(CO)c1]

The title compound was prepared following procedures described in example 405 to give product (12 mg, 30% yield), Mass spec: 437 (M+H), $t_R$=2.608. $^1$H-NMR (400 Hz, DMSO) δ=8.708-8.650 (m, 1H), 8.117-8.065 (m, 1H), 7.853-7.822 (m, 7H), 4.409-4.597 (m, 3H), 4.318-4.299 (m, 2H), 4.053-4.007 (m, 1H), 3.881-3.346 (m, 3H), 2.257-2.080 (m, 2H).

Example 410: (3-(2'-ethyl-3-(hydroxymethyl)-4'-methylbiphenyl-4-yl)pyrrolidin-1-yl)(5-fluoropyridin-2-yl)methanone (Compound 2-62)

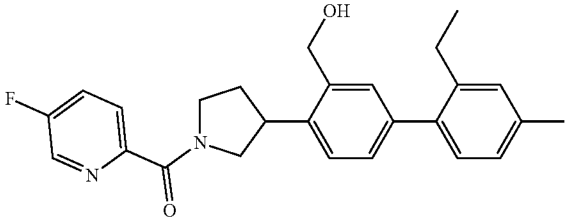 [SMILES: CCc1cc(C)ccc1-c1ccc(C2CCN(C(=O)c3ccc(F)cn3)C2)c(CO)c1]

The title compound was prepared following procedures described in Example 405 to give (3-(2'-ethyl-3-(hydroxymethyl)-4'-methylbiphenyl-4-yl)pyrrolidin-1-yl)(5-fluoropyridin-2-yl)methanone (16 mg, 11% yield), Mass spec: 419 (M+H). $t_R$=2.963 min, $^1$H-NMR (400 Hz, DMSO) δ=8.589-8.647 (m, 1H), 7.892-7.910 (m, 2H), 7.418-7.439 (1H), 7.136-7.253 (m, 3H), 7.020-7.045 (m, 2H), 5.127 (m, 1H), 4.579-4.660 (m, 2H), 3.793-3.880 (m, 1H), 3.517-3.793 (m, 4H), 2.513-2.545 (m, 2H), 2.331 (s, 1H), 2.248-2.324 (m, 1H), 2.082-2.124 (m, 1H), 1.018-1.072 (m, 3H).

Example 411: (5-chloropyridin-2-yl)(3-(2'-ethyl-3-(hydroxymethyl)-4'-methylbiphenyl-4-yl)pyrrolidin-1-yl)methanone (Compound 2-66)

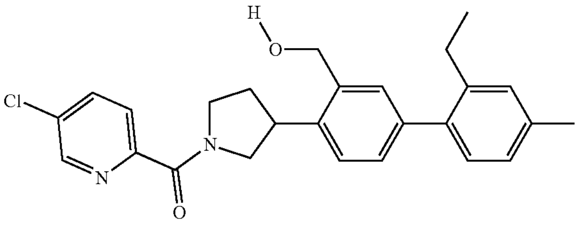 [SMILES: CCc1cc(C)ccc1-c1ccc(C2CCN(C(=O)c3ccc(Cl)cn3)C2)c(CO)c1]

The title compound was prepared following procedures described in example 405 to give (5-chloropyridin-2-yl)(3-(2'-ethyl-3-(hydroxymethyl)-4'-methylbiphenyl-4-yl)pyrrolidin-1-yl)methanone (5 mg, 12.5% yield), Mass spec: 435 (M+H), $t_R$=3.108 min, $^1$H-NMR (400 Hz, DMSO) δ=8.706-8.650 (m, 1H), 8.116-8.063 (m, 1H), 7.850-7.822 (m, 1H), 7.435-7.001 (m, 6H), 4.665-4.587 (m, 3H), 4.052-3.479 (m, 5H), 2.564-2.546 (m, 2H), 2.331-2.091 (m, 5H), 1.244-1.018 (m, 3H).

Example 412: (5-chloropyridin-2-yl)(3-(2'-ethyl-3-(hydroxymethyl)-3'-methylbiphenyl-4-yl)pyrrolidin-1-yl)methanone (Compound 2-67)

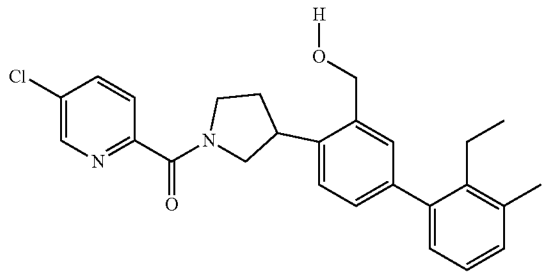 [SMILES: CCc1c(C)cccc1-c1ccc(C2CCN(C(=O)c3ccc(Cl)cn3)C2)c(CO)c1]

The title compound was prepared following procedures described in example 405 to give (5-chloropyridin-2-yl)(3-(2'-ethyl-3-(hydroxymethyl)-3'-methylbiphenyl-4-yl)pyrrolidin-1-yl)methanone (10 mg, 7% yield), Mass spec: 435 (M+H), $t_R$=3.050 min, $^1$H-NMR (400 Hz, DMSO) δ=8.705-8.653 (m, 1H), 8.090-8.064 (m, 1H), 7.851-7.824 (m, 1H), 7.439-7.397 (m, 1H), 7.297-7.108 (m, 4H), 6.931-6.913 (m, 1H), 5.137 (m, 1H), 4.666-4.586 (m, 2H), 4.054 (m, 1H), 3.690-3.536 (m, 4H), 2.510 (m, 2H), 2.361-2.353 (m, 3H), 2.260 (s, 1H), 2.132 (m, 1H), 0.979-0.924 (m, 3H).

Example 413: (5-chloropyridin-2-yl)(3-(2'-ethoxy-3-(hydroxymethyl)biphenyl-4-yl)pyrrolidin-1-yl)methanone (Compound 2-69)

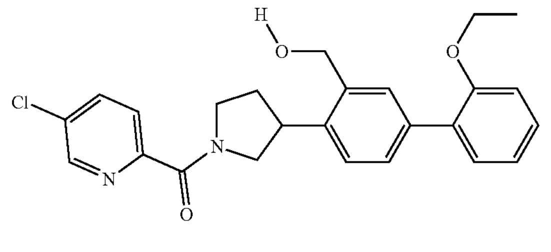 [SMILES: CCOc1ccccc1-c1ccc(C2CCN(C(=O)c3ccc(Cl)cn3)C2)c(CO)c1]

The title compound was prepared following procedures described in example 405 to give (5-chloropyridin-2-yl)(3-(2'-ethoxy-3-(hydroxymethyl)biphenyl-4-yl)pyrrolidin-1-yl)methanone (3 mg, 5% yield), Mass spec: 437 (M+H), $t_R$=2.792. $^1$H-NMR (400 Hz, DMSO) δ=8.707-8.644 (m, 1H), 8.117-8.063 (m, 1H), 7.851-7.819 (m, 1H), 7.538-6.989 (m, 7H), 5.170-5.073 (m, 1H), 4.662-4.570 (m, 2H), 4.085-4.023 (m, 3H), 3.850-3.627 (m, 4H), 2.230-2.094 (m, 2H), 1.303-1.225 (m, 3H).

Example 414: (3-(4'-fluoro-2'-(1-hydroxyethyl)-3-(hydroxymethyl)biphenyl-4-yl)pyrrolidin-1-yl)(5-fluoropyridin-2-yl)methanone (Compound 2-70)

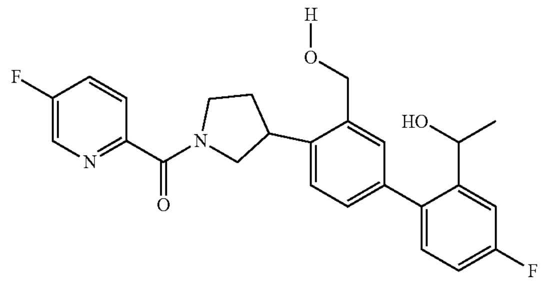 [SMILES: CC(O)c1cc(F)ccc1-c1ccc(C2CCN(C(=O)c3ccc(F)cn3)C2)c(CO)c1]

The title compound was prepared following procedures described in Example 405 to give (3-(4'-fluoro-2'-(1-hydroxyethyl)-3-(hydroxymethyl)biphenyl-4-yl)pyrrolidin-1-yl)(5-fluoropyridin-2-yl)methanone (6 mg, 10% yield), Mass spec: 439 (M+H), $t_R$=2.270. $^1$H-NMR (400 Hz, DMSO) δ=8.647-8.592 (m, 1H), 7.925-7.864 (m, 2H), 7.467-7.105 (m, 6H), 4.773-4.594 (m, 4H), 4.062-3.483 (m, 6H), 2.253-2.120 (m, 2H), 1.202-1.170 (m, 3H).

Example 415: (5-chloropyridin-2-yl)(3-(4'-fluoro-2'-(1-hydroxyethyl)-3-(hydroxymethyl)biphenyl-4-yl)pyrrolidin-1-yl)methanone (Compound 2-71)

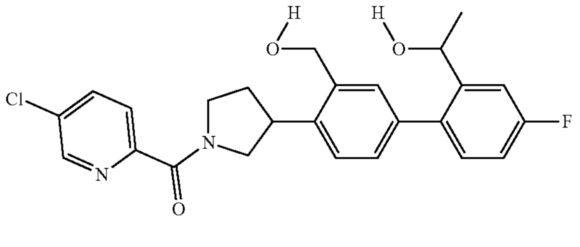 [SMILES: CC(O)c1cc(F)ccc1-c1ccc(C2CCN(C(=O)c3ccc(Cl)cn3)C2)c(CO)c1]

The title compound was prepared following procedures described in Example 405 to give (5-chloropyridin-2-yl)(3-(4'-fluoro-2'-(1-hydroxyethyl)-3-(hydroxymethyl)biphenyl-4-yl)pyrrolidin-1-yl)methanone (2.5 mg, 5% yield), Mass spec: 455 (M+H), $t_R$=2.428. $^1$H-NMR (400 Hz, DMSO) δ=8.706-8.655 (m, 1H), 8.120-8.067 (m, 1H), 7.854-7.821 (m, 1H), 7.466-7.106 (m, 6H), 4.773-4.595 (m, 4H), 4.057-4.018 (m, 1H), 3.853-3.512 (m, 5H), 2.255-2.115 (m, 2H), 1.208-1.171 (m, 3H).

Example 416: (3-(4-(3-ethylpyrazin-2-yl)-2-(hydroxymethyl)phenyl)pyrrolidin-1-yl)(5-fluoropyridin-2-yl)methanone (Compound 2-68)

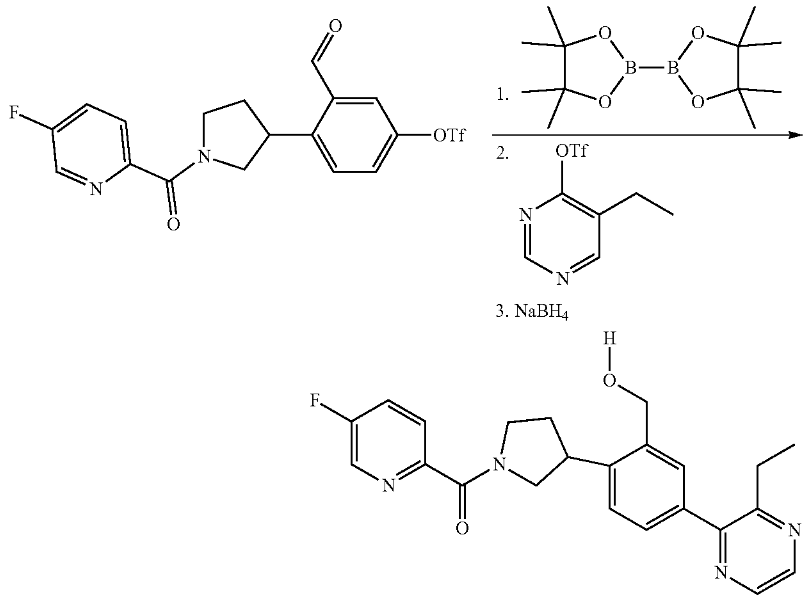

The title compound was prepared following procedures described in Example 405 step 5 and step 6 to give (10 mg, 33.3% yield), Mass spec: 407 (M+H), $t_R$=1.943. $^1$H-NMR (400 Hz, DMSO) δ=8.650-8.552 (m, 3H), 7.913-7.872 (m, 2H), 7.617-7.498 (m, 3H), 5.285-5.208 (m, 1H), 4.704-4.629 (m, 2H), 4.074 (m, 1H), 3.828-3.528 (m, 4H), 2.884-2.827 (m, 2H), 2.270-2.135 (m, 2H), 1.226-1.175 (m, 3H).

Example 417: (3-(2'-ethyl-3-(hydroxymethyl)biphenyl-4-yl)pyrrolidin-1-yl)(5-fluoropyridin-2-yl) methanone (Compound 2-28)

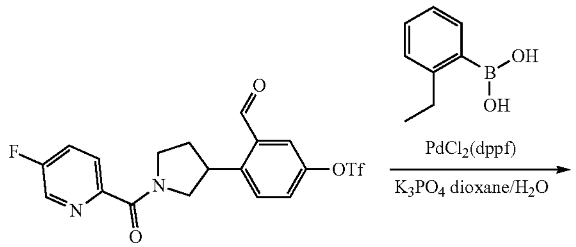

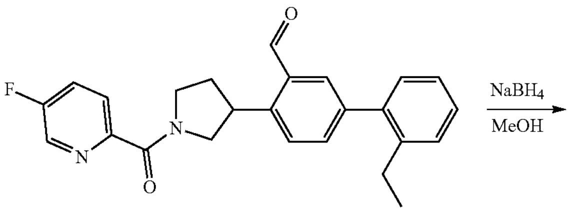

-continued

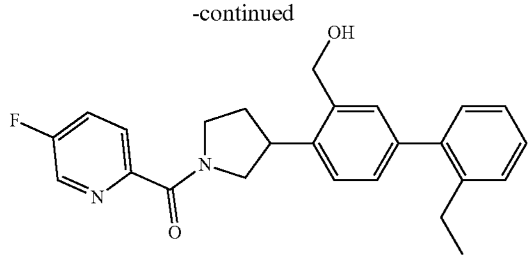

Step 1: 2'-ethyl-4-(1-(5-fluoropicolinoyl)pyrrolidin-3-yl)biphenyl-3-carbaldehyde

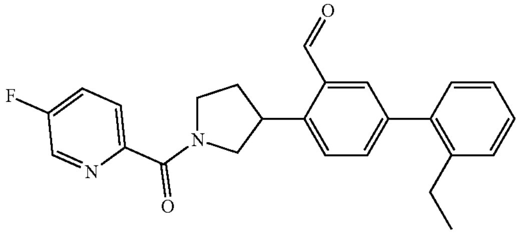 [SMILES: CCc1ccccc1-c1ccc(C2CCN(C(=O)c3ccc(F)cn3)C2)c(C=O)c1]

To a solution of 4-(1-(5-fluoropicolinoyl)pyrrolidin-3-yl)-3-formylphenyl trifluoromethanesulfonate (210 mg, 0.47 mmol) in 5 mL dioxane/$H_2O$ (v:v=4:1) was added 2-ethylphenylboronic acid (85 mg, 0.57 mmol), $K_3PO_4$ (300 mg, 1.41 mmol) and Pd(dppf)$Cl_2$ (39 mg, 0.047 mmol), the mixture was stirred at 90° C. for 2 h under $N_2$, after reaction completed, extracted with EA, the organic phase was washed by water, brine, dried over Na2SO4, removal the solvent to left the crude product which was purified by Pre-HPLC to give the product 2'-ethyl-4-(1-(5-fluoropicolinoyl)pyrrolidin-3-yl)biphenyl-3-carbaldehyde (100 mg, 52.9% yield), Mass spec: 403 (M+H).

Step 2: 3-(2'-ethyl-3-(hydroxymethyl)biphenyl-4-yl) pyrrolidin-1-yl)(5-fluoropyridin-2-yl)methanone

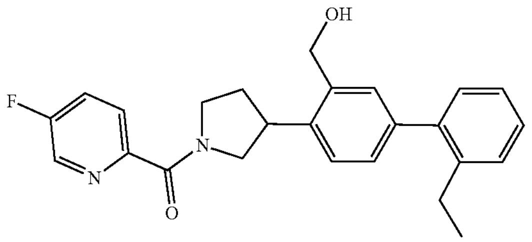 [SMILES: CCc1ccccc1-c1ccc(C2CCN(C(=O)c3ccc(F)cn3)C2)c(CO)c1]

A solution of 2'-ethyl-4-(1-(5-fluoropicolinoyl)pyrrolidin-3-yl)biphenyl-3-carbaldehyde (26 mg, 0.065 mmol) in MeOH (1 mL) was added $NaBH_4$ (8 mg, 0.2 mmol), the mixture was stirred at rt for 15 min, the mixture was quenched by several drops water, filtrated, the filtrate was purified by Pre-HPCL to give 3-(2'-ethyl-3-(hydroxymethyl)biphenyl-4-yl)pyrrolidin-1-yl)(5-fluoropyridin-2-yl)methanone (8 mg, 30% yield), Mass spec: 405 (M+H), $t_R$=2.762 min, $^1$H-NMR (400 Hz, DMSO) δ=7.648-8.592 (d, 1H), 7.864-7.940 (m, 2H), 7.437 (t, 1H), 7.198-7.458 (m, 5H), 7.139 (t, 1H), 5.175 (br, 1H), 4.599-4.679 (m, 2H), 3.513-3.406 (m, 5H), 2.612 (m, 2H), 2.257 (s, 1H), 2.121 (s, 1H), 1.029-1.083 (m, 3H).

Example 418: (3-(2'-ethyl-3-(hydroxymethyl)biphenyl-4-yl)pyrrolidin-1-yl)(pyridin-2-yl)methanone (Compound 2-27)

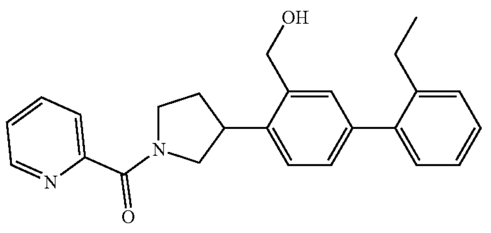 [SMILES: CCc1ccccc1-c1ccc(C2CCN(C(=O)c3ccccn3)C2)c(CO)c1]

The title compound was prepared following procedures described in example 417 using 5-methylpicolinic acid to give (3-(2'-ethyl-3-(hydroxymethyl)biphenyl-4-yl)pyrrolidin-1-yl)(pyridin-2-yl)methanone (32 mg, 29% yield), Mass spec: 387 (M+H), $t_R$=2.612 min, $^1$H-NMR (400 Hz, DMSO) δ=8.652-8.715 (m, 1H), 7.943-7.986 (m, 1H), 7.765-7.842 (m, 1H), 7.417-7.539 (m, 2H), 7.116-7.335 (m, 6H), 5.124-5.239 (dt, 1H), 4.584-4.687 (m, 2H), 4.007-4.049 (m, 1H), 3.540-3.868 (m, 4H), 2.504-2.579 (m, 2H), 2.238-2.276 (m, 1H), 2.110-2.210 (m, 1H), 1.094-1.123 (m, 3H).

Example 419: (3-(2'-ethyl-3-(hydroxymethyl)biphenyl-4-yl)pyrrolidin-1-yl)(5-(trifluoromethyl) pyridin-2-yl)methanone (Compound 2-47)

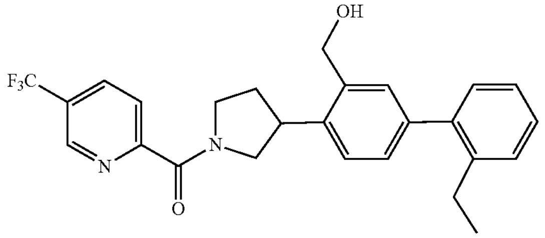 [SMILES: CCc1ccccc1-c1ccc(C2CCN(C(=O)c3ccc(C(F)(F)F)cn3)C2)c(CO)c1]

The title compound was prepared following procedures described in example 386 using intermediate 9 and 5-(trifluoromethyl)picolinic acid to give (3-(2'-ethyl-3-(hydroxymethyl)biphenyl-4-yl)pyrrolidin-1-yl)(5-(trifluoromethyl)pyridin-2-yl)methanone (20 mg, 16.8% yield), Mass spec: 455 (M+H), $t_R$=3.016 min, $^1$H-NMR (400 Hz, DMSO) δ=9.013 (d, 2H), 8.378 (t, 1H), 7.981 (d, 1H), 7.444 (t, 1H), 7.215-7.338 (m, 6H), 5.120 (br, 1H), 4.595-4.678 (m, 2H), 3.486-3.405 (m, 5H), 2.513-2.563 (q, d, 2H), 2.505 (s, 1H), 2.106 (s, 1H), 1.061 (t, d, 3H).

Example 420: (4-chloropyridin-2-yl)(3-(2'-ethyl-3-(hydroxymethyl)biphenyl-4-yl)pyrrolidin-1-yl) methanone (Compound 2-48)

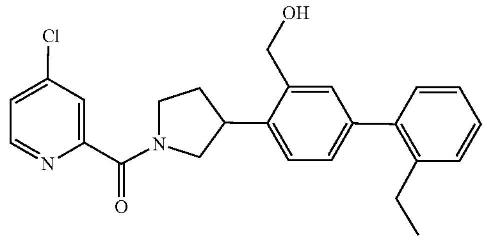 [SMILES: CCc1ccccc1-c1ccc(C2CCN(C(=O)c3cc(Cl)ccn3)C2)c(CO)c1]

The title compound was prepared following procedures described in example 386 to give (4-chloropyridin-2-yl)(3-(2'-ethyl-3-(hydroxymethyl)biphenyl-4-yl)pyrrolidin-1-yl) Methanone (18 mg, 16.3% yield), Mass spec: 421 (M+H), $t_R$=2.854 min, $^1$H-NMR (400 Hz, DMSO) δ=8.573-8.624 (d, d, 1H), 7.868 (s, 1H), 7.661-7.674 (m, 1H), 7.437 (t, 3H), 7.136-7.332 (m, 6H), 5.137 (br, 1H), 4.598-4.676 (m, 2H) 7.438-4.029 (m, 5H), 5.556-2.581 (q, d, 2H), 2.252 (s, 1H), 2.095 (s, 1H), 1.064 (t, d, 3H).

Example 421: (5-chloropyridin-2-yl)(3-(2'-ethyl-3-(hydroxymethyl)biphenyl-4-yl)pyrrolidin-1-yl) methanone (Compound 2-51)

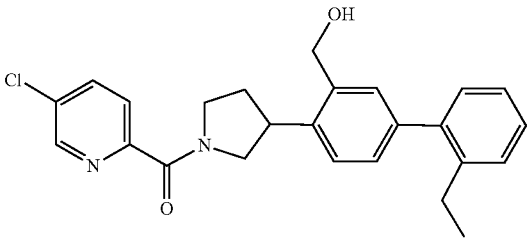 [SMILES: CCc1ccccc1-c1ccc(C2CCN(C(=O)c3ccc(Cl)cn3)C2)c(CO)c1]

The title compound was prepared following procedures described in example 386 to give (5-chloropyridin-2-yl)(3-(2'-ethyl-3-(hydroxymethyl)biphenyl-4-yl)pyrrolidin-1-yl) methanone (15 mg, 13.6% yield), Mass spec: 421 (M+H), $t_R$=2.919 min, $^1$H-NMR (400 Hz, DMSO) δ=8.659 (d, 1H), 8.094 (t, 1H), 7.436 (t, 1H), 7.137-7.331 (m, 6H), 5.141 (br, 1H), 4.597-4.676 (m, 2H), 3.348-4.067 (m, 5H), 2.557 (q, d, 2H), 2.265 (s, 1H), 2.140 (s, 1H), 1.064 (t, d, 3H).

Example 422: (3-chloropyridin-2-yl)(3-(2'-ethyl-3-(hydroxymethyl)biphenyl-4-yl)pyrrolidin-1-yl) methanone (Compound 2-52)

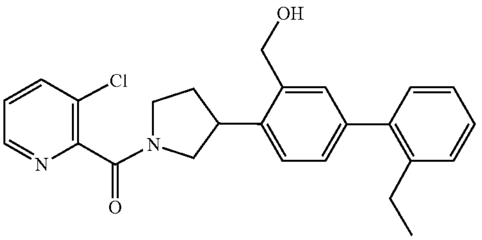

The title compound was prepared following procedures described in example 386 to give (3-chloropyridin-2-yl)(3-(2'-ethyl-3-(hydroxymethyl)biphenyl-4-yl)pyrrolidin-1-yl) methanone (15 mg, 13.4% yield), Mass spec: 421 (M+H), $t_R$=2.661 min, $^1$H-NMR (400 Hz, DMSO) δ=8.569 (d, d, 1H), 8.050-8.095 (m, 1H), 7.110-7.534 (m, 7H), 7.617 (br, 1H), 4.576-4.669 (m, 2H), 3.196-4.050 (m, 5H), 2.561 (q, d, 2H), 1.027 (t, d, 3H).

Example 423: (6-chloropyridin-2-yl)(3-(2'-ethyl-3-(hydroxymethyl)biphenyl-4-yl)pyrrolidin-1-yl) methanone (Compound 2-53)

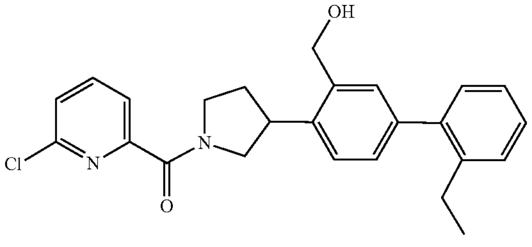 [SMILES: CCc1ccccc1-c1ccc(C2CCN(C(=O)c3cccc(Cl)n3)C2)c(CO)c1]

The title compound was prepared following procedures described in example 386 to give (6-chloropyridin-2-yl)(3-(2'-ethyl-3-(hydroxymethyl)biphenyl-4-yl)pyrrolidin-1-yl) methanone (15 mg, 12.6% yield), Mass spec: 421 (M+H), $t_R$=2.911 min, $^1$H-NMR (400 Hz, DMSO) δ=8.016 (t, d, 1H), 7.806 (d, 1H), 7.634-7.654 (m, 1H), 7.450 (t, 1H), 7.146-7.332 (m, 6H), 5.163 (br, 1H), 4.605-4.679 (m, 2H), 3.348-4.028 (m, 5H), 2.562 (q, d, 2H), 2.263 (s, 1H), 2.112 (s, 1H), 1.050 (t, d, 3H).

Example 424: (3-(2'-ethyl-3-(hydroxymethyl)biphenyl-4-yl)pyrrolidin-1-yl)(3-fluoropyridin-2-yl) methanone (Compound 2-54)

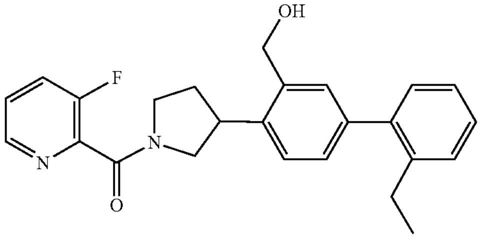 [SMILES: CCc1ccccc1-c1ccc(C2CCN(C(=O)c3ncccc3F)C2)c(CO)c1]

The title compound was prepared following procedures described in example 386 to give (3-(2'-ethyl-3-(hydroxymethyl)biphenyl-4-yl)pyrrolidin-1-yl)(3-fluoropyridin-2-yl) methanone (15 mg, 8.6% yield), Mass spec: 405 (M+H), $t_R$=2.598 min, $^1$H-NMR (400 Hz, DMSO) δ=8.462 (d, 1H), 7.874-7.914 (m, 1H), 7.102-7.595 (m, 8H), 5.152 (br, 1H), 4.587-4.677 (m, 2H), 3.352-4.024 (m, 5H), 2.511-2.583 (q, d, 2H), 2.304 (s, 1H), 2.085 (s, 1H), 1.051 (t, d, 3H).

Example 426: (3-(2'-ethyl-3-(hydroxymethyl)biphenyl-4-yl)pyrrolidin-1-yl)(5-methylpyridin-2-yl) methanone (Compound 2-50)

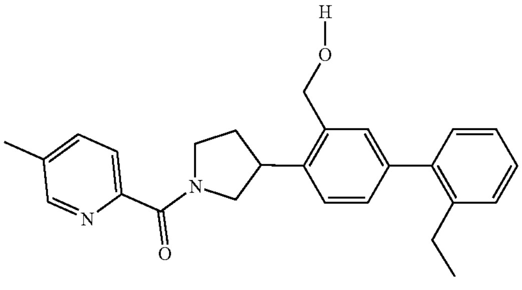 [SMILES: CCc1ccccc1-c1ccc(C2CCN(C(=O)c3ccc(C)cn3)C2)c(CO)c1]

The title compound was prepared following procedures described in example 386 to give (3-(2'-ethyl-3-(hydroxymethyl)biphenyl-4-yl)pyrrolidin-1-yl)(5-methylpyridin-2-yl) methanone (10 mg, 7.0% yield), Mass spec: 401 (M+H), $t_R$=2.716 min, $^1$H-NMR (400 Hz, DMSO) δ=8.425 (d, 1H), 7.697-7.763 (m, 2H), 7.432 (t, 1H), 7.119-7.331 (m, 6H), 5.778 (br, 1H), 4.594-4.676 (m, 2H), 3.477-3.811 (m, 5H), 2.513-2.580 (q, d, 2H), 2.249 (s, 1H), 2.092 (s, 1H), 1.065 (t, d, 3H).

Example 427: (3-(2'-ethyl-3-(hydroxymethyl)biphenyl-4-yl)pyrrolidin-1-yl)(3-fluoropyridin-2-yl) methanone (Compound 2-54)

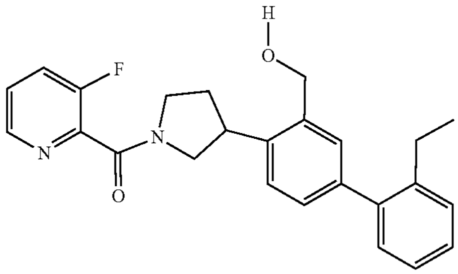 [SMILES: CCc1ccccc1-c1ccc(C2CCN(C(=O)c3ncccc3F)C2)c(CO)c1]

The title compound was prepared following procedures described in example 386 to give (3-(2'-ethyl-3-(hydroxymethyl)biphenyl-4-yl)pyrrolidin-1-yl)(3-fluoropyridin-2-yl) methanone (20 mg, 20% yield), Mass spec: 406 (M+H), $t_R$=2.612 min, $^1$H-NMR (400 Hz, DMSO) δ=8.462-8.451 (m, 1H), 7.870 (m, 1H), 7.431-7.402 (m, 2H), 7.331-7.096 (m, 6H), 5.145-4.583 (m, 3H), 4.037-3.356 (m, 5H), 2.580-2.537 (m, 2H), 2.290-2.092 (m, 2), 1.082-1.010 (m, 3H).

Example 428: (3-(2'-ethyl-3-(hydroxymethyl)biphenyl-4-yl)pyrrolidin-1-yl)(5-methoxypyridin-2-yl) methanone (Compound 2-73)

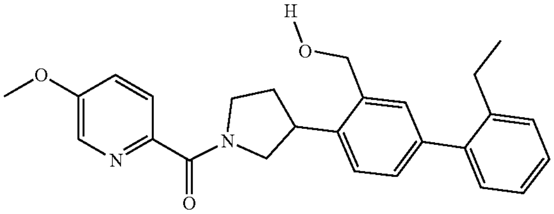 [SMILES: CCc1ccccc1-c1ccc(C2CCN(C(=O)c3ccc(OC)cn3)C2)c(CO)c1]

The title compound was prepared following procedures described in example 386 to give (3-(2'-ethyl-3-(hydroxymethyl)biphenyl-4-yl)pyrrolidin-1-yl)(5-methoxypyridin-2-yl)methanone (29 mg, 45% yield), Mass spec: 417 (M+H), $t_R$=2.761 min, $^1$H-NMR (400 Hz, DMSO) δ=8.358-8.280 (m, 1H), 7.853-7.832 (m, 1H), 7.518-7.142 (m, 8H), 5.213-5.120 (m, 1H), 4.673-4.598 (m, 2H), 3.904-3.871 (m, 7H), 2.580-2.542 (m, 2H), 2.509-2.505 (m, 2), 1.082-1.031 (m, 3H).

Example 429: 2'-ethyl-4-(1-(5-fluoropicolinoyl) pyrrolidin-3-yl)biphenyl-3-carboxamide (Compound 2-34)

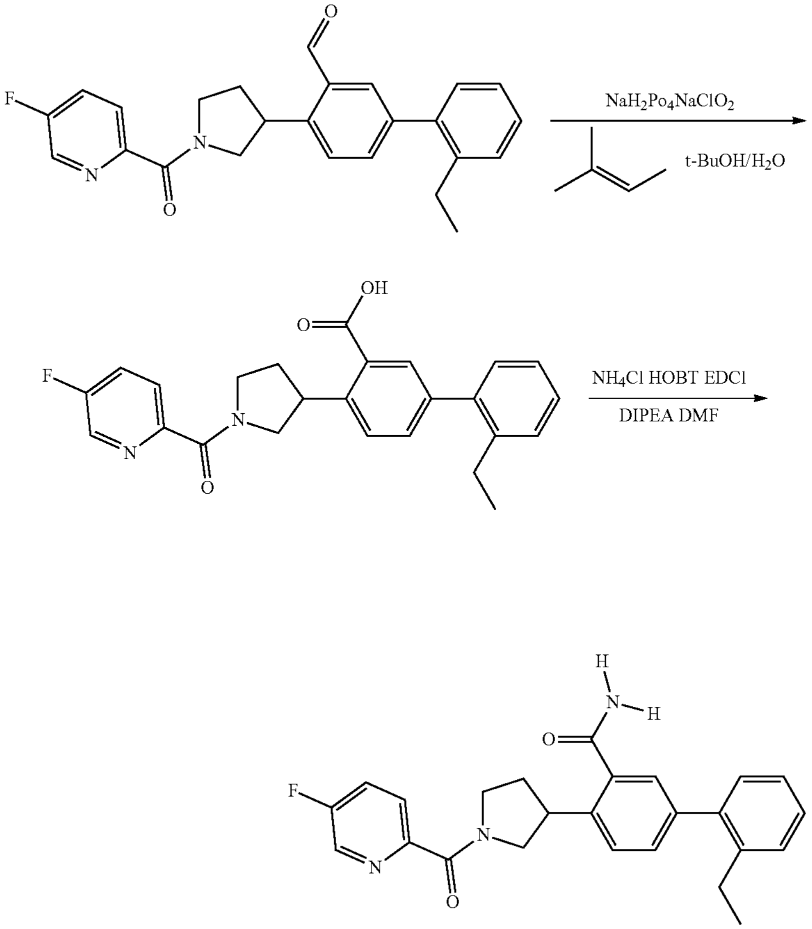

Step 1: 2'-ethyl-4-(1-(5-fluoropicolinoyl)pyrrolidin-3-yl)biphenyl-3-carboxylic acid

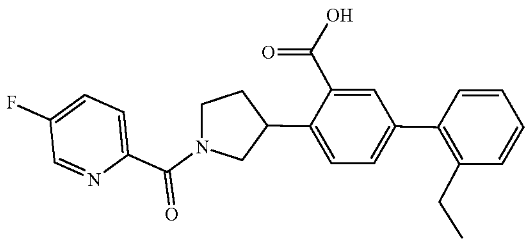 [SMILES: CCc1ccccc1-c1ccc(C2CCN(C(=O)c3ccc(F)cn3)C2)c(C(=O)O)c1]

To a solution of 2'-ethyl-4-(1-(5-fluoropicolinoyl)pyrrolidin-3-yl)biphenyl-3-carbaldehyde (70 mg, 0.17 mmol) (Example 417 step 1) in 2.4 mL t-BUOH/$H_2O$ (v:v=5:1) was added $NaH_2PO_4$ (27 mg, 0.17 mmol), $NaClO_2$ (53 mg, 0.578 mmol) and 2-methyl-2-butene (54 mg, 0.765 mmol), the mixture was stirred at rt for 2 h, adjusted the pH to 4 with 1N HCl solution, then extracted with EA, the organic layer was washed by water and brine, dried over Na2SO4, removal the solvent to left the crude 2'-ethyl-4-(1-(5-fluoropicolinoyl)pyrrolidin-3-yl)biphenyl-3-carboxylic acid (50 mg. 69% yield), which can be used to next step directly, Mass spec: 420 (M+H).

Step 2: 2'-ethyl-4-(1-(5-fluoropicolinoyl)pyrrolidin-3-yl)biphenyl-3-carboxamide

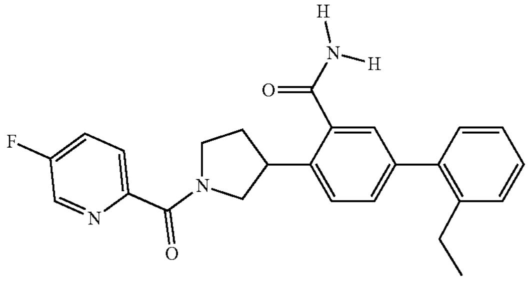 [SMILES: CCc1ccccc1-c1ccc(C2CCN(C(=O)c3ccc(F)cn3)C2)c(C(N)=O)c1]

To a solution of 2'-ethyl-4-(1-(5-fluoropicolinoyl)pyrrolidin-3-yl)biphenyl-3-carboxylic acid (50 mg. 0.12 mmol) in 2 ml DMF was added $NH_4Cl$ (13.4 mg, 0.18 mmol), HOBt (29 mg, 0.16 mmol), EDCI (41 mg, 0.16 mmol) and DIPEA (0.089 mL, 0.36 mmol), the mixture was stirred at rt overnight, the mixture was diluted with EA, and the organic layer was washed with water and brine, dried over $Na_2SO_4$, removal the solvent to left the crude product which was purified by Pre-HPLC to give 2'-ethyl-4-(1-(5-fluoropicolinoyl)pyrrolidin-3-yl)biphenyl-3-carboxamide (20 mg, 40.2% yield), Mass spec: 418 (M+H), $t_R$=2.516 min, $^1$H-NMR (400 Hz, DMSO) δ=8.642 (d, 1H), 7.882-7.953 (m, 3H), 7.238-7.518 (m, 8H), 3.462-4.093 (m, 4.5H), 2.970-3.013 (m, 0.5H), 2.582 (q, 2H), 2.114-2.242 (m, 2H), 1.070 (m, 3H).

Example 430: (3-(4-(5-ethylpyrimidin-4-yloxy)-2-(hydroxymethyl)phenyl)pyrrolidin-1-yl)(5-fluoropyridin-2-yl)methanone (Compound 2-24)

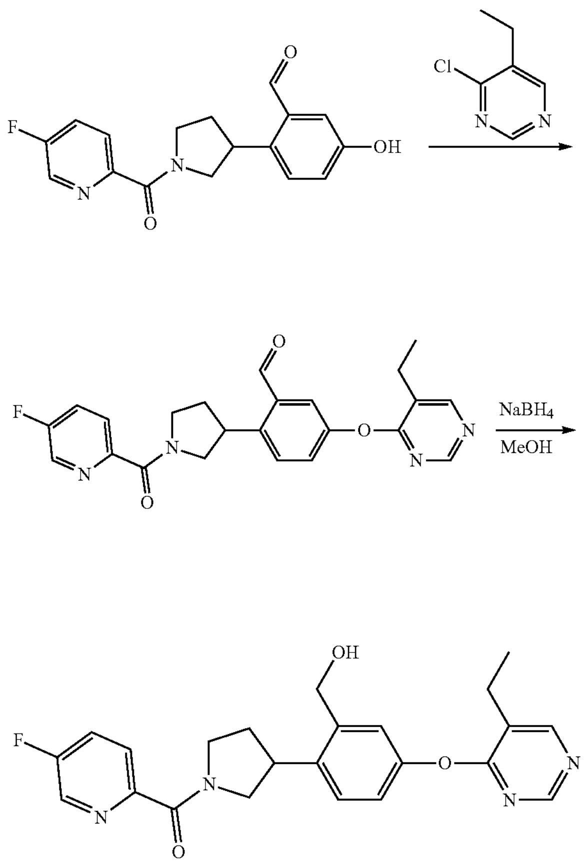

Step 1: 5-(5-ethylpyrimidin-4-yloxy)-2-(1-(5-fluoropicolinoyl)pyrrolidin-3-yl)benzaldehyde

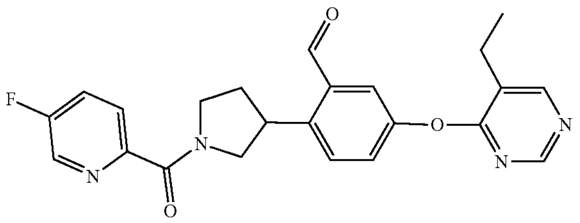 [SMILES: CCc1cncnc1Oc1ccc(C2CCN(C(=O)c3ccc(F)cn3)C2)c(C=O)c1]

To a solution of 2-(1-(5-fluoropicolinoyl)pyrrolidin-3-yl)-5-hydroxybenzaldehyde (40 mg, 0.12 mmol) (example 405 step 3) in 2 mL DMF was added $K_2CO_3$ (50 mg, 0.36 mmol) and 4-chloro-5-ethylpyrimidine (17 mg, 0.24 mmol), the mixture was stirred at 50° C. overnight. EA was added, the organic layer was washed by water and brine, dried over $Na_2SO_4$, removal the solvent to left crude product which was purified by Prep-TCL to give 5-(5-ethylpyrimidin-4-yloxy)-2-(1-(5-fluoropicolinoyl)pyrrolidin-3-yl)benzaldehyde (30 mg, 56% yield), Mass spec: 421 (M+H).

Step 2: (3-(4-(5-ethylpyrimidin-4-yloxy)-2-(hydroxymethyl)phenyl)pyrrolidin-1-yl)(5-fluoropyridin-2-yl)methanone

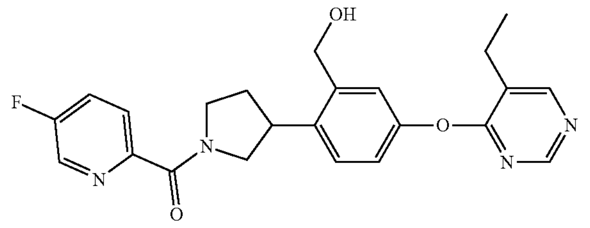 [SMILES: CCc1cncnc1Oc1ccc(C2CCN(C(=O)c3ccc(F)cn3)C2)c(CO)c1]

To a solution of 5-(5-ethylpyrimidin-4-yloxy)-2-(1-(5-fluoropicolinoyl)pyrrolidin-3-yl)benzaldehyde (30 mg, 0.07 mmol) in 2 mL MeOH was added $NaBH_4$ (27 mg, 0.7 mmol), the mixture was stirred at rt for 15 min, water was added, the mixture was extracted with EA, the organic phase washed by water and brine, dried over Na2SO4, removal the solvent to left crude product which was purified by Prep-HPLC to give (3-(4-(5-ethylpyrimidin-4-yloxy)-2-(hydroxymethyl)phenyl)pyrrolidin-1-yl)(5-fluoropyridin-2-yl) methanone (14 mg, 46% yield), Mass spec: 423 (M+H), $t_R$=2.117 min, $^1$H-NMR (400 Hz, DMSO) δ=8.551-8.644 (m, 3H), 7.840-7.936 (m, 2H), 7.413-7.463 (m, 1H), 7.069-7.212 (m, 2H), 5.254 (Br, 1H), 5.473-4.686 (m, 2H), 3.484-4.061 (m, 5H), 2.681-2.748 (m, 2H), 2.035-2.238 (m, 2H), 1.251-1.298 (m, 3H).

Example 431: (3-(4-(4-chloro-3-ethylpyridin-2-yloxy)-2-(hydroxymethyl)phenyl)pyrrolidin-1-yl)(5-fluoropyridin-2-yl)methanone (Compound 2-43)

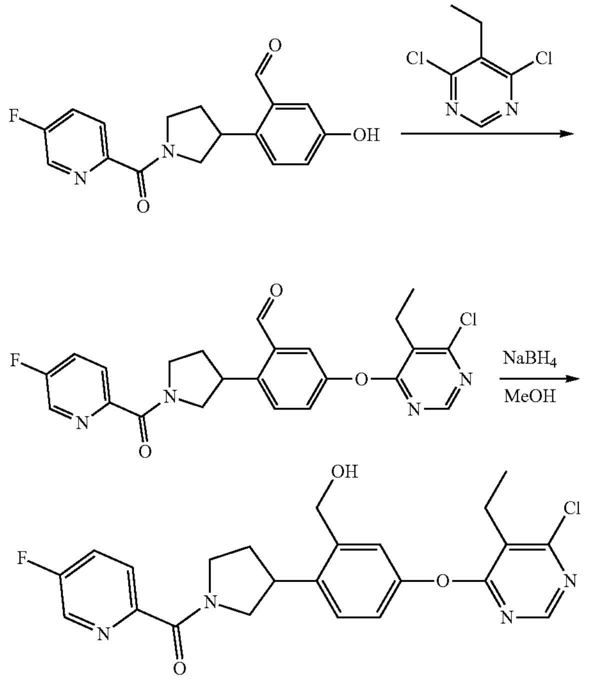

Step 1: 5-(5-ethylpyrimidin-4-yloxy)-2-(1-(5-fluoropicolinoyl)pyrrolidin-3-yl)benzaldehyde

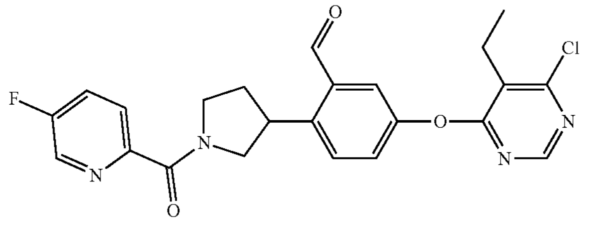 [SMILES: CCc1c(Cl)ncnc1Oc1ccc(C2CCN(C(=O)c3ccc(F)cn3)C2)c(C=O)c1]

To a solution of 2-(1-(5-fluoropicolinoyl)pyrrolidin-3-yl)-5-hydroxybenzaldehyde (100 mg, 0.318 mmol) (example 405 step 3) in 2 mL DMSO at 0° C. was added NaH (38 mg, 0.954 mmol), The mixture was stirred at 0° C. for 30 min, before 4,6-dichloro-5-ethylpyrimidine (111.3 mg, 0.382 mmol) was added, then stirred at rt for another 15 min, quenched by water, extracted with DCM, the organic phase was washed with water, brine, dried over $Na_2SO_4$, removal the solvent to left crude 5-(5-ethylpyrimidin-4-yloxy)-2-(1-(5-fluoropicolinoyl)pyrrolidin-3-yl)benzaldehyde (120 mg, 90.2%) which can be used directly, Mass spec: 421.

Step 2: (3-(4-(4-chloro-3-ethylpyridin-2-yloxy)-2-(hydroxymethyl)phenyl)pyrrolidin-1-yl)(5-fluoropyridin-2-yl)methanone

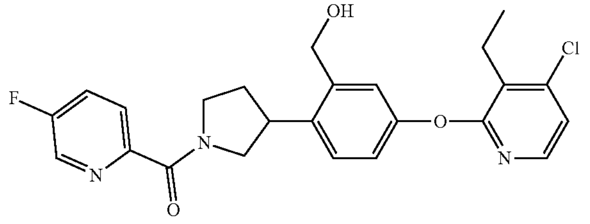 [SMILES: CCc1c(Cl)ccnc1Oc1ccc(C2CCN(C(=O)c3ccc(F)cn3)C2)c(CO)c1]

The title compound was prepared following procedures described in example 430 step 2 to give (3-(4-(4-chloro-3-ethylpyridin-2-yloxy)-2-(hydroxymethyl)phenyl)pyrrolidin-1-yl)(5-fluoropyridin-2-yl)methanone (10 mg, 8.3% yield), Mass spec: 456 (M+H), $t_R$=3.339 min, $^1$H-NMR (400 Hz, DMSO) δ=8.596 (d, 1H), 8.440 (d, 1H), 7.841-7.935 (m, 2H), 7.100-7.476 (m, 3H), 5.317 (br, 1H), 4.574-4.654 (m, 2H), 3.286-4.059 (m, 5H), 2.788-2.835 (m, 2H), 1.997-2.300 (m, 2H), 1.164-1.255 (m, 3H).

Example 432: (3-(4-(3-ethylpyridin-2-yloxy)-2-(hydroxymethyl)phenyl)pyrrolidin-1-yl)(5-fluoropyridin-2-yl)methanone (Compound 2-44)

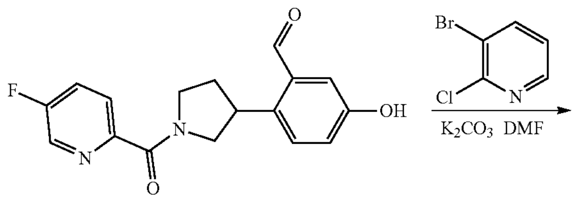

-continued

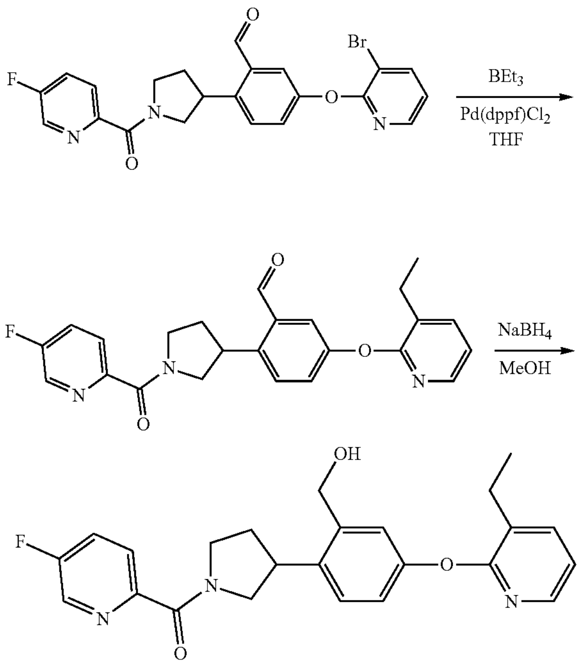

Step 1: 5-(3-bromopyridin-2-yloxy)-2-(1-(5-fluoropicolinoyl)pyrrolidin-3-yl)benzaldehyde

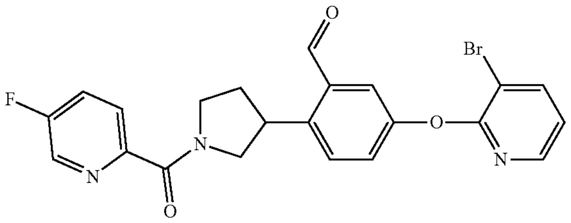 [SMILES: O=Cc1cc(Oc2ncccc2Br)ccc1C1CCN(C(=O)c2ccc(F)cn2)C1]

The title compound was prepared following procedures described in example 430 step 1 to give 5-(3-bromopyridin-2-yloxy)-2-(1-(5-fluoropicolinoyl)pyrrolidin-3-yl)benzaldehyde (85 mg, 70% yield), Mass spec: 470 (M+H).

Step 2: 5-(3-ethylpyridin-2-yloxy)-2-(1-(5-fluoropicolinoyl)pyrrolidin-3-yl)benzaldehyde

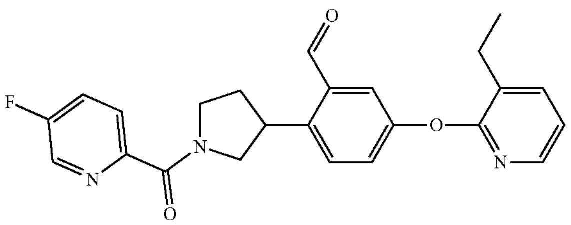 [SMILES: CCc1cccnc1Oc1ccc(C2CCN(C(=O)c3ccc(F)cn3)C2)c(C=O)c1]

To a solution of 5-(3-bromopyridin-2-yloxy)-2-(1-(5-fluoropicolinoyl)pyrrolidin-3-yl)benzaldehyde (80 mg, 0.17 mmol) in THE was added $BEt_3$ (0.5 mL, 0.51 mmol, 1M in THF) and Pd(dppf)$Cl_2$ (5 mg, 0.017 mmol), The mixture was stirred at 80° C. for 2 h under N2. When reaction completed, concentrated to give a crude, which was purified by silica gel to give 5-(3-ethylpyridin-2-yloxy)-2-(1-(5-fluoropicolinoyl)pyrrolidin-3-yl)benzaldehyde (40 mg, 56.1% yield), Mass spec: 420 (M+H).

Step 3: (3-(4-(3-ethylpyridin-2-yloxy)-2-(hydroxymethyl)phenyl)pyrrolidin-1-yl)(5-fluoropyridin-2-yl)methanone

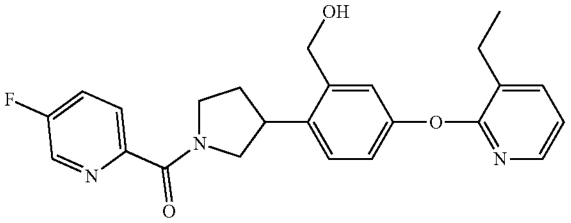 [SMILES: CCc1cccnc1Oc1ccc(C2CCN(C(=O)c3ccc(F)cn3)C2)c(CO)c1]

The title compound was prepared following procedures described in example 430 step 2 to give (3-(4-(3-ethylpyridin-2-yloxy)-2-(hydroxymethyl)phenyl)pyrrolidin-1-yl)(5-fluoropyridin-2-yl)methanone (10 mg, 24.9% yield), Mass spec: 422 (M+H), $t_R$=2.486 min, $^{1}$H-NMR (400 Hz, DMSO) δ=8.621 (d, 1H), 7.838-73942 (m, 3H), 7.708 (d, 1H), 7.380 (t, 1H), 7.063-7.109 (m, 2H), 6.975 (t, 1H), 5.157-5.261 (m, 1H), 4.541-4.621 (m, 2H), 3.442-4.044 (m, 5H), 2.663-2.711 (m, 2H), 2.223 (br, 1H), 2.087 (br, 1H), 1.213-1.259 (m, 3H).

Example 433: (3-(2'-ethyl-3-(hydroxymethyl)-3'-methylbiphenyl-4-yl)pyrrolidin-1-yl)(5-fluoropyridin-2-yl)methanone (Compound 2-64)

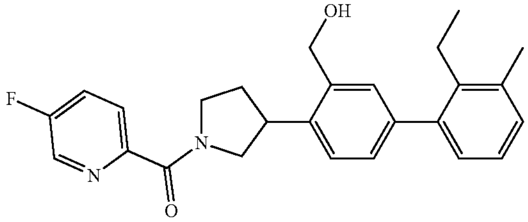 [SMILES: CCc1c(C)cccc1-c1ccc(C2CCN(C(=O)c3ccc(F)cn3)C2)c(CO)c1]

The title compound was prepared following procedures described in Example 405 to give (3-(2'-ethyl-3-(hydroxymethyl)-3'-methylbiphenyl-4-yl)pyrrolidin-1-yl)(5-fluoropyridin-2-yl)methanone (5.1 mg, 55.4% yield), Mass spec: 419 (M+H), $t_R$=2.889 min, 1H-NMR (400 Hz, DMSO) δ=8.646-8.594 (m, 1H), 7.892-7.841 (m, 2H), 7.442-7.397 (m, 1H), 7.294-7.107 (m, 4H), 6.959-6.914 (m, 1H), 5.211-5.132 (d, 1H), 4.666-4.588 (d, 2H), 4.055-4.003 (m, 1H), 3.883-3.603 (m, 3H), 3.537-3.486 (m, 1H), 2.508 (s, 2H), 2.360-2.353 (d, 3H), 2.257 (s, 1H), 2.176-2.072 (m, 1H), 0.979-0.924 (m, 3H).

Example 434: (3-(2'-ethyl-3-(hydroxymethyl)biphenyl-4-yl)pyrrolidin-1-yl)(4-methoxypyridin-2-yl) methanone (Compound 2-63)

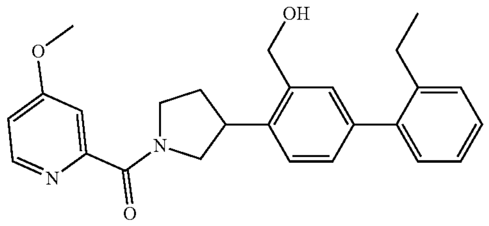 [SMILES: CCc1ccccc1-c1ccc(C2CCN(C(=O)c3cc(OC)ccn3)C2)c(CO)c1]

The title compound was prepared following procedures described in Example 405 to give (3-(2'-ethyl-3-(hydroxymethyl)biphenyl-4-yl)pyrrolidin-1-yl)(4-methoxypyridin-2-yl)methanone (110 mg, 80% yield), Mass spec: 417 (M+H), $t_R$=2.566 min, 1H-NMR (400 Hz, DMSO) δ=8.484-8.394 (m, 1H), 7.330-7.059 (m, 8H), 5.133 (s, 1H), 4.706-4.556 (m, 2H), 4.041-3.993 (m, 1H), 3.893-3.786 (m, 4H), 3.710-3.641 (m, 2H), 3.571-3.467 (m, 1H), 2.556-2.536 (m, 2H), 2.254 (d, 1H), 2.162-2.059 (m, 1H), 1.081-1.025 (m, 3H).

Example 441: (3-chloropyridin-2-yl)(3-(4-(5-ethylpyrimidin-4-yloxy)-2-(hydroxymethyl)phenyl) pyrrolidin-1-yl)methanone (Compound 2-22)

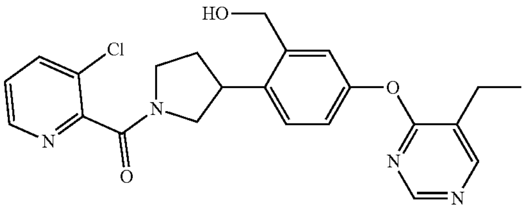 [SMILES: CCc1cncnc1Oc1ccc(C2CCN(C(=O)c3ncccc3Cl)C2)c(CO)c1]

The title compound was prepared following procedures described in Example 430 to give (3-chloropyridin-2-yl)(3-(4-(5-ethylpyrimidin-4-yloxy)-2-(hydroxymethyl)phenyl) pyrrolidin-1-yl)methanone (24 mg, 21% yield), Mass spec: 439 (M+1), $t_R$=1.995 min, $^1$H-NMR (400 Hz, DMSO) δ=8.551-8.644 (m, 3H), 8.048-8.051 (m, 1H), 7.493-7.564 (m, 1H), 7.379-7.441 (m, 1H), 7.050-7.205 (m, 2H), 4.648-5.318 (m, 1H), 4.541-4.643 (m, 2H), 3.391-4.025 (m, 3.5H), 3.147-3.340 (m, 1.5H), 2.512-2.745 (m, 2H), 1.301-2.225 (m, 2H), 1.251-1.298 (m, 3H).

Example 332: (S)-(2-(3-(5-methylpyridin-2-yloxy) pyrrolidin-1-yl)-5-(pyridin-2-yl)phenyl)methanol (Compound 2-86)

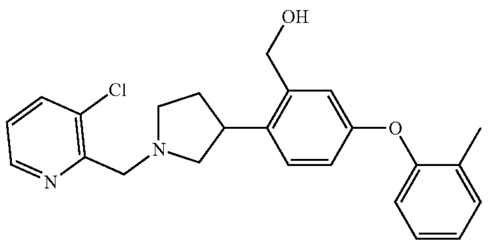 [SMILES: Cc1ccccc1Oc1ccc(C2CCN(Cc3ncccc3Cl)C2)c(CO)c1]

To a solution of (3-chloropyridin-2-yl)(3-(2-(hydroxymethyl)-4-(o-tolyloxy)phenyl)pyrrolidin-1-yl)methanone (80.0 mg, 0.19 mmol, example 330) in 5 ml THE at 0° C. was added DIBAL-H (1.26 ml, 1.9 mmol, 1.5 M in Tol), after 1 h, the mixture was diluted with EA and 1N HCl solution, dried over Na2SO4, removal the solvent to left the crude product which was purified by Prep-HPLC to give (S)-(2-(3-(5-methylpyridin-2-yloxy)pyrrolidin-1-yl)-5-(pyridin-2-yl)phenyl)methanol (1.2 mg, 1.5% yield) as white solid, Mass spec: 409 (M+H), $t_R$=1.856 min, $^1$H-NMR (400 Hz, DMSO) δ=8.534-8.520 (m, 1H), 7.924-7.900 (m, 1H), 7.441-7.370 (m, 2H), 7.291-7.273 (m, 1H), 7.203-7.164 (m, 1H), 7.101-7.063 (m, 1H), 6.918-6.861 (m, 2H), 6.812-6.783 (m, 1H), 4.651-4.595 (m, 4H), 4.210 (s, 2H), 3.773-3.732 (m, 1H), 3.144-3.102 (d, 2H), 2.883 (m, 1H), 2.396-2.372 (m, 1H), 2.214 (s, 3H), 1.993-1.960 (m, 1H).

Example 141: (5-(2-isopropylphenoxy)-2-(1-(pyridin-2-ylmethyl)pyrrolidin-3-yl)phenyl)methanol (Compound 2-87)

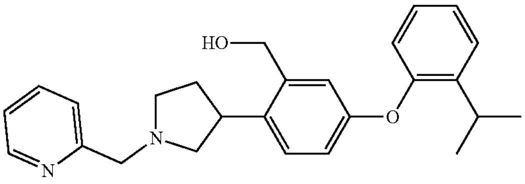 [SMILES: CC(C)c1ccccc1Oc1ccc(C2CCN(Cc3ccccn3)C2)c(CO)c1]

To a solution of 3-(4-(2-isopropylphenoxy)-2-((tetrahydro-2H-pyran-2-yloxy)methyl)phenyl)pyrrolidine (Intermediate 6) (39 mg, 0.1 mmol) in 2 ml DCM was added 2-(bromomethyl)-5-methylpyridine hydrobromide (50 mg, 0.12 mmol), DIPEA (26 mg, 0.2 mmol) at 0° C. The mixture was stirred and returned to r.t. naturally and monitored the process by TLC. After finished, 10 ml DCM was added, washed with $H_2O$, NaCl solution, dried, evaporated to give the crude intermediate, and the following procedure was the same as the example 1 to give (5-(2-isopropylphenoxy)-2-(1-(pyridin-2-ylmethyl)pyrrolidin-3-yl)phenyl)methanol as white solid (8.1 mg, 20% yield), Mass spec: 417 (M+1). $t_R$=2.065 min, $^1$H-NMR (400 Hz, DMSO) δ=8.486-8.476 (d, 1H), 7.781-7.746 (m, 1H), 7.476-7.457 (m, 1H), 7.388-7.367 (q, 2H), 7.266-7.121 (q, 3H), 6.920-6.915 (m, 1H), 6.833-6.757 (q, 2H), 5.126 (s, 1H), 4.503 (m, 2H), 3.808-3.707 (m, 2H), 3.513-3.456 (m, 1H), 3.224-3.173 (m, 1H), 2.900-2.657 (m, 3H), 2.560-2.508 (m, 1H), 2.253-2.231 (m, 1H), 2.253-2.231 (m, 1H), 1.237-1.175 (m, 6H).

Example 149: 1-((3-chloropyridin-2-yl)methyl)-4-(2-(hydroxymethyl)-4-(2-isopropylphenoxy)phenyl) pyrrolidin-2-one (Compound 2-88)

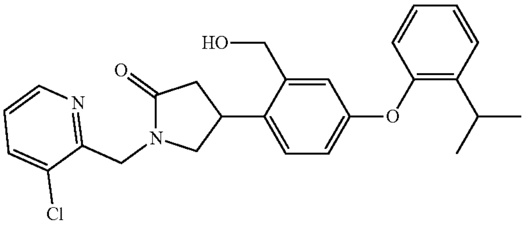 [SMILES: CC(C)c1ccccc1Oc1ccc(C2CC(=O)N(Cc3ncccc3Cl)C2)c(CO)c1]

The title compound was prepared following procedures described in example 148 to give 1-((3-chloropyridin-2-yl)methyl)-4-(2-(hydroxymethyl)-4-(2-isopropylphenoxy)phenyl)pyrrolidin-2-one (2.5 mg, 2.9% yield), Mass spec: 451 (M+1), $t_R$=2.769 min, $^{1}$H-NMR (400 Hz, DMSO) δ=8.532-8.518 (m, 1H), 7.956-7.933 (m, 1H), 7.405-7.371 (m, 3H), 7.203-7.153 (m, 2H), 6.945-6.939 (m, 1H), 6.848-6.782 (m, 2H), 5.148 (m, 1H), 4.741-4.620 (q, 2H), 4.513 (s, 2H), 3.793-3.726 (m, 2H), 3.193-3.158 (m, 2H), 2.795-2.731 (m, 1H), 2.400-2.341 (m, 1H), 1.189-1.170 (d, 6H).

Example 143: (5-(2-isopropylphenoxy)-2-(1-((3-methylpyridin-2-yl)methyl)pyrrolidin-3-yl)phenyl)methanol hydrochloride (Compound 2-89)

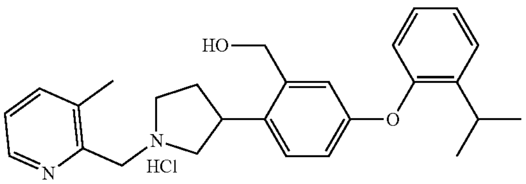 [SMILES: Cc1cccnc1CN1CCC(c2ccc(Oc3ccccc3C(C)C)cc2CO)C1 ; Cl]

To a solution of 3-methylpicolinaldehyde (33.7 mg, 0.27 mmol) in 2 ml DCM was added 3-(4-(2-isopropylphenoxy)-2-((tetrahydro-2H-pyran-2-yloxy)methyl)phenyl)pyrrolidine (Intermediate 6) (100 mg, 0.25 mmol) and AcOH (3 drops). The mixture was stirred at r.t. for 30 min, then $NaBH_3CN$ (25 mg, 0.40 mmol) was added slowly, and stirred at r.t. for 2 h. after the reaction was completed, the mixture was diluted with 10 ml DCM, washed with water (3×5 ml), the organic layer was dried, evaporated to get the crude intermediate, and the following procedure was the same as the example 1 to give (5-(2-isopropylphenoxy)-2-(1-((3-methylpyridin-2-yl)methyl)pyrrolidin-3-yl)phenyl)methanol hydrochloride as white solid (18.5 mg, 17.8% yield), Mass spec: 417 (M+1), $t_R$=2.132 min, $^{1}$H-NMR (400 Hz, DMSO) δ=8.473-8.429 (m, 1H), 7.819 (s, 1H), 7.404-7.381 (m, 3H), 7.201-7.152 (m, 2H), 6.956-6.950 (m, 1H), 6.845-6.776 (m, 2H), 5.181 (m, 1H), 4.524 (s, 2H), 4.219 (s, 2H), 3.688 (s, 1H), 3.193-3.142 (m, 4H), 2.860 (s, 1H), 2.371-2.285 (m, 4H), 1.912 (s, 1H), 1.188-1.117 (d, 6H).

Example 142: (5-(2-isopropylphenoxy)-2-(1-((5-methylpyridin-2-yl)methyl)pyrrolidin-3-yl)phenyl)methanol hydrochloride (Compound 2-90)

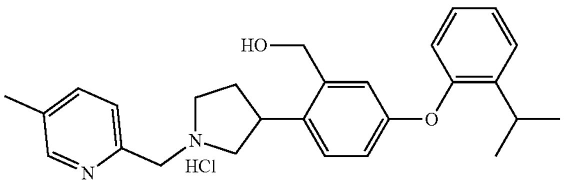 [SMILES: Cc1ccc(CN2CCC(c3ccc(Oc4ccccc4C(C)C)cc3CO)C2)nc1 ; Cl]

The title compound was prepared following procedures described in example 141 to give (5-(2-isopropylphenoxy)-2-(1-((5-methylpyridin-2-yl)methyl)pyrrolidin-3-yl)phenyl)methanol hydrochloride (8.7 mg, 13.9% yield), Mass spec: 417 (M+1), $t_R$=1.130 min, $^{1}$H-NMR (400 Hz, DMSO) δ=10.842 (s, 1H), 8.505 (s, 1H), 7.742-7.722 (m, 1H), 7.502-7.393 (m, 3H), 7.231-7.154 (q, 2H), 6.944-6.812 (q, 3H), 5.253-5.227 (m, 1H), 4.5565-4.499 (m, 4H), 3.780-3.658 (m, 1H), 3.538-3.144 (q, 4H), 0.338 (s, 4H), 2.124-2.079 (m, 1H), 1.187-1.168 (m, 6H).

Example 144: (2-(1-((5-chloropyridin-2-yl)methyl)pyrrolidin-3-yl)-5-(2-isopropylphenoxy)phenyl)methanol (Compound 2-91)

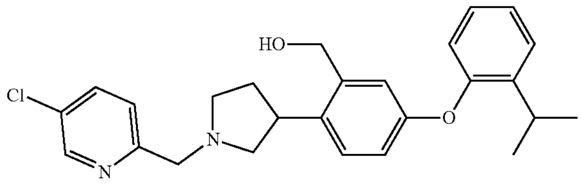 [SMILES: CC(C)c1ccccc1Oc1ccc(C2CCN(Cc3ccc(Cl)cn3)C2)c(CO)c1]

The title compound was prepared following procedures described in example 141 to give (2-(1-((5-chloropyridin-2-yl)methyl)pyrrolidin-3-yl)-5-(2-isopropylphenoxy)phenyl)methanol (25.6 mg, 23.2% yield), Mass spec: 437 (M+1), $t_R$=2.018 min, $^{1}$H-NMR (400 Hz, DMSO) δ=8.536-8.530 (d, 1H), 7.910-7.882 (m, 1H), 7.524-7.504 (d, 1H), 7.391-7.357 (m, 2H), 7.193-7.139 (m, 2H), 6.920-6.914 (d, 1H), 6.834-6.753 (m, 2H), 5.134 (m, 1H), 4.507-4.494 (m, 2H), 3.811-3.718 (m, 2H), 3.516-3.475 (m, 1H), 3.222-3.170 (m, 1H), 2.904-2.862 (m, 1H), 2.784-2657 (m, 2H), 2.563-2.512 (m, 1H), 2.252-2.211 (m, 1H), 1.733-1.685 (m, 1H), 1.191-1.173 (d, 6H).

Example 145: (2-(1-((3-chloropyridin-2-yl)methyl)pyrrolidin-3-yl)-5-(2-isopropylphenoxy)phenyl)methanol hydrochloride (Compound 2-92)

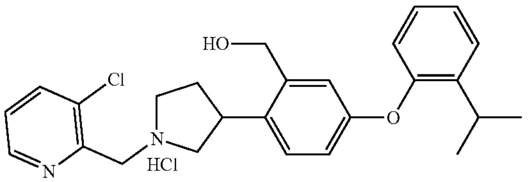

The title compound was prepared following procedures described in example 141 to give (2-(1-((3-chloropyridin-2-yl)methyl)pyrrolidin-3-yl)-5-(2-isopropylphenoxy)phenyl)methanol hydrochloride (10.6 mg, 9.7% yield), Mass spec: 437 (M+1), $t_R$=2.051 min, $^{1}$H-NMR (400 Hz, DMSO) δ=10.743-10.624 (s, 1H), 8.638-8.629 (d, 1H), 8.097-8.081 (m, 1H), 7.553-7.395 (m, 3H), 7.232-7.157 (m, 2H), 6.955 (m, 1H), 6.858-6.839 (m, 2H), 5.279 (m, 1H), 4.875 (s, 1H), 4.539 (s, 1H), 3.920-3.542 (m, 3H), 3.183-3.148 (m, 1H), 2.359 (m, 1H), 2.188-2.131 (m, 1H), 1.189-1.171 (d, 6H).

Example 148: 4-(2-(hydroxymethyl)-4-(2-isopropylphenoxy)phenyl)-1-(pyridin-2-ylmethyl)pyrrolidin-2-one (Compound 2-93)

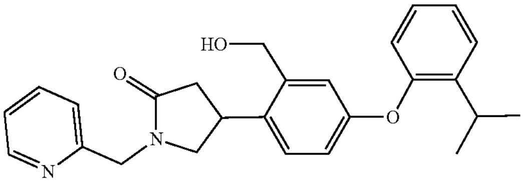 [SMILES: CC(C)c1ccccc1Oc1ccc(C2CC(=O)N(Cc3ccccn3)C2)c(CO)c1]

To a solution of 4-(4-(2-isopropylphenoxy)-2-((tetrahydro-2H-pyran-2-yloxy)methyl)phenyl)pyrrolidin-2-one Intermediate 6 step 8 (80 mg, 0.2 mmol) in 2 ml DMF was added NaH 60%(16 mg, 0.4 mmol) at ° C., the mixture was stirred for 30 min at ° C. before 2-(bromomethyl)pyridine hydrobromide (60 mg, 0.24 mmol). the reaction mixture was stirred and monitored by TLC. After the completion of the reaction, 10 ml EA was added, washed with LiCl solution, NaCl solution, dried, evaporated to give a residue, which dissolved in EA 2 ml, and 2 ml EA/HCl solution was added at ° C., and stirred at r.t. for 1 h, then the mixture was evaporated and purified by Prep-HPLC to give 4-(2-(hydroxymethyl)-4-(2-isopropylphenoxy)phenyl)-1-(pyridin-2-ylmethyl)pyrrolidin-2-one as white solid (16.0 mg, 19.2% yield), Mass spec: 417 (M+1), $t_R$=2.512 min, $^1$H-NMR (400 Hz, DMSO) δ=8.540-8.521 (m, 1H), 7.797-7.754 (m, 1H), 7.405-7.382 (m, 1H), 7.326-7.281 (m, 3H), 7.204-7.155 (m, 2H), 6.943-6.936 (m, 1H), 6.843-6.820 (m, 1H), 6.777-6.749 (m, 1H), 5.196-5.169 (m, 1H), 4.533-4.498 (m, 4H), 3.732-3.689 (m, 2H), 3.289-3.274 (m, 1H), 3.185-3.151 (m, 1H), 0.765-2.723 (m, 1H), 2.451-2.390 (m, 1H), 1.185-1.167 (d, 6H).

Example 147: (5-(2-isopropylphenoxy)-2-(1-((6-methylpyridin-2-yl)methyl)pyrrolidin-3-yl)phenyl) methanol hydrochloride (Compound 2-94)

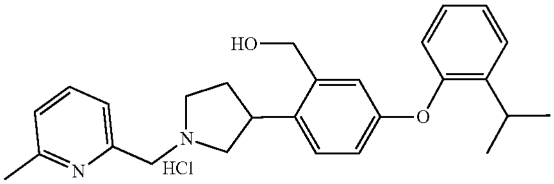 [SMILES: Cc1cccc(CN2CCC(c3ccc(Oc4ccccc4C(C)C)cc3CO)C2)n1 ; Cl]

The title compound was prepared following procedures described in example 141 to give (5-(2-isopropylphenoxy)-2-(1-((6-methylpyridin-2-yl)methyl)pyrrolidin-3-yl)phenyl) methanol hydrochloride (11.2 mg, 10.0% yield), Mass spec: 437 (M+1), $t_R$=2.078 min, $^1$H-NMR (400 Hz, DMSO) δ=11.153 (s, 1H), 7.935-7.896 (d, 1H), 7.585-7.565 (m, 1H), 7.483-7.395 (m, 3H), 7.227-7.152 (m, 2H), 6.945-6.939 (m, 1H), 6.854-6.803 (m, 2H), 4.642 (s, 2H), 4.512 (s, 2H), 3.795-3.712 (m, 5H), 3.434-3.404 (m, 1H), 3.191-3.122 (s, 1H), 2.573 (s, 3H), 2.348-2.334 (m, 1H), 2.133-2.079 (m, 1H), 1.182-1.165 (d, 6H).

Example 146: (2-(1-((6-chloropyridin-2-yl)methyl) pyrrolidin-3-yl)-5-(2-isopropylphenoxy)phenyl) methanol hydrochloride (Compound 2-96)

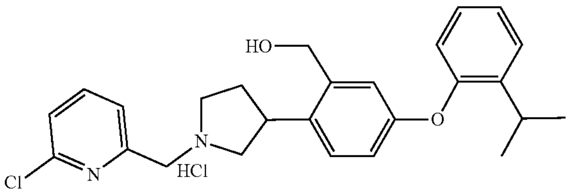 [SMILES: CC(C)c1ccccc1Oc1ccc(C2CCN(Cc3cccc(Cl)n3)C2)c(CO)c1 ; Cl]

The title compound was prepared following procedures described in example 141 to give (2-(1-((6-chloropyridin-2-yl)methyl)pyrrolidin-3-yl)-5-(2-isopropylphenoxy)phenyl)methanol hydrochloride (8.7 mg, 8.0% yield), Mass spec: 437 (M+1), $t_R$=2.348 min, $^1$H-NMR (400 Hz, DMSO) δ=10.833-10.629 (m, 1H), 7.990 (d, 1H), 7.619-7.600 (m, 2H), 7.417-7.394 (m, 2H), 7.216-7.170 (m, 2H), 6.945-6.939 (m, 1H), 6.855-6.824 (m, 2H), 5.241 (m, 1H), 4.645-4.513 (m, 4H), 3.193-3.632 (m, 4H), 3.177-3.143 (m, 2H), 2.338 (m, 1H), 2.107-2.050 (m, 1H), 1.186-1.169 (d, 6H).

Example 151: 5-(2-isopropylphenoxy)-2-(1-((6-methylpyridin-2-yl)methyl)-5-oxopyrrolidin-3-yl) benzamide (Compound 2-97)

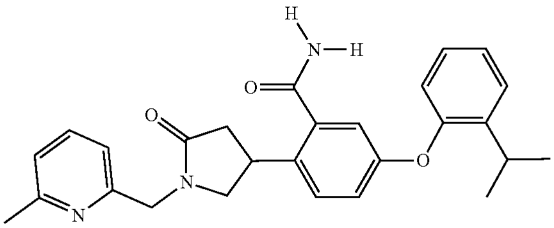 [SMILES: Cc1cccc(CN2CC(c3ccc(Oc4ccccc4C(C)C)cc3C(N)=O)CC2=O)n1]

The title compound was prepared following procedures described in example 150 to give 5-(2-isopropylphenoxy)-2-(1-((6-methylpyridin-2-yl)methyl)-5-oxopyrrolidin-3-yl) benzamide (14.9 mg, 17.2% yield), Mass spec: 444 (M+1), $t_R$=2.168 min, $^1$H-NMR (400 Hz, DMSO) δ=7.874 (s, 1H), 7.671-7.632 (m, 1H), 7.497-7.409 (m, 3H), 7.235-7.050 (m, 1H), 6.896-6.871 (m, 3H), 4.528-4.422 (m, 2H), 3.888-3.849 (m, 1H), 3.712-3.668 (m, 1H), 3.309 (m, 1H), 3.181-3.146 (m, 1H), 2.769-2.705 (m, 1H), 2.510-2.442 (m, 4H), 1.190-1.172 (m, 6H).

Example 165: 5-(2-ethylphenoxy)-2-(1-((6-methylpyridin-2-yl)methyl)-5-oxopyrrolidin-3-yl)benzamide (Compound 2-98)

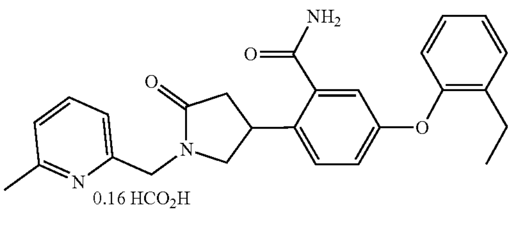 [SMILES: CCc1ccccc1Oc1ccc(C2CC(=O)N(Cc3cccc(C)n3)C2)c(C(N)=O)c1]

The title compound was prepared following procedures described in example 150 to give 5-(2-ethylphenoxy)-2-(1-((6-methylpyridin-2-yl)methyl)-5-oxopyrrolidin-3-yl)benzamide (20 mg, 20% yield), Mass spec: 430 (M+1), $t_R$=2.027 min, $^1$H-NMR (400 Hz, DMSO) δ=8.172 (s, 0.16H), 7.864 (s, 1H), 7.633-7.671 (t, 1H), 7.352-7.484 (m, 3H), 7.049-6.912 (m, 4H), 4.422-4.526 (m, 2H), 3.851-3.889 (m, 1H), 3.667-3.711 (m, 1H), 3.307-3.310 (m, 2H), 2.703-2.767 (m, 1H), 2.543-2.600 (m, 2H), 2.442 (s, 3H), 1.124-1.162 (m, 3H).

Example 150: 5-(2-isopropylphenoxy)-2-(5-oxo-1-(pyridin-2-ylmethyl)pyrrolidin-3-yl)benzamide (Compound 2-99)

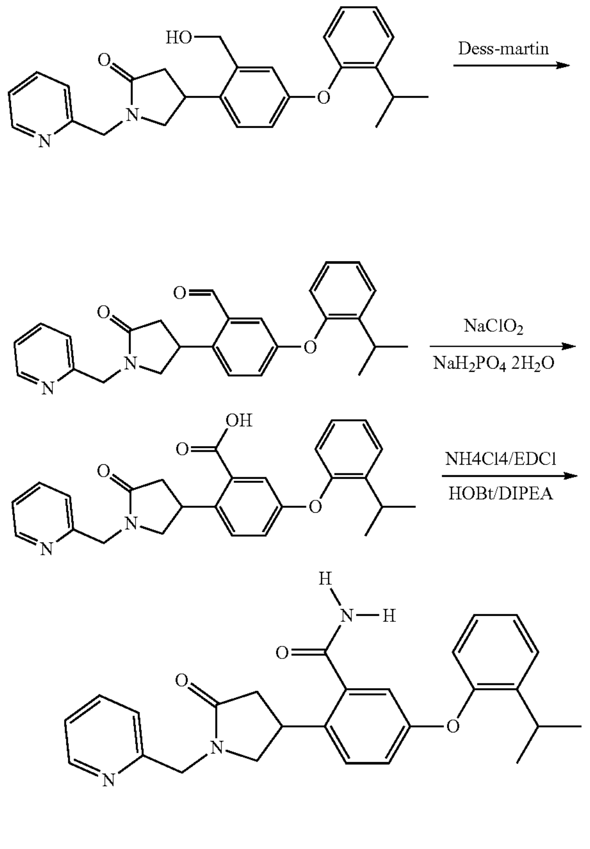

Step 1:5-(2-isopropylphenoxy)-2-(5-oxo-1-(pyridin-2-ylmethyl)pyrrolidin-3-yl)benzaldehyde

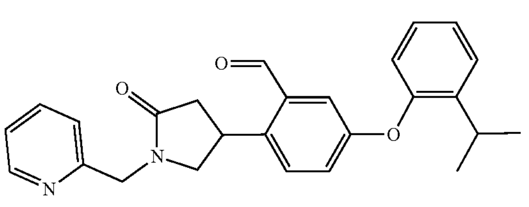 [SMILES: CC(C)c1ccccc1Oc1ccc(C2CC(=O)N(Cc3ccccn3)C2)c(C=O)c1]

To a solution of 4-(2-(hydroxymethyl)-4-(2-isopropylphenoxy)phenyl)-1-(pyridin-2-ylmethyl)pyrrolidin-2-one Example 148 (120 mg, 0.29 mmol), in 10 ml DCM was added Dess-Martin (183 mg, 0.43 mmol) and stirred at r.t. for 30 min, then extracted with DCM (3×10 ml), and NaOH solution (1.5 ml), brine (2×10 ml), dried, concentrated to give the product 5-(2-isopropylphenoxy)-2-(5-oxo-1-(pyridin-2-ylmethyl)pyrrolidin-3-yl)benzaldehyde (100 mg 80% yield), Mass spec: 415 (M+1).

Step 2: 5-(2-isopropylphenoxy)-2-(5-oxo-1-(pyridin-2-ylmethyl)pyrrolidin-3-yl)benzoic acid

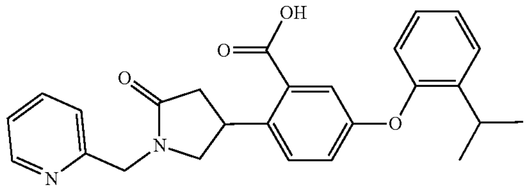 [SMILES: CC(C)c1ccccc1Oc1ccc(C2CC(=O)N(Cc3ccccn3)C2)c(C(=O)O)c1]

To a solution of 5-(2-isopropylphenoxy)-2-(5-oxo-1-(pyridin-2-ylmethyl)pyrrolidin-3-yl)benzaldehyde (100 mg, 0.24 mmol) in BuOH/H2O 10 ml (v:v=1:1) was added NaOCl2 (74 mg, 082 mmol), NaH2PO4 2H2O (37 mg, 0.24 mmol), 2-methylbut-2-ene (126 mg, 1.8 mmol), and stirred at r.t. for 2 h, the mixture was extracted with EA/H2O, the EA layer was dried (Na2SO4), filtered and evaporated to give 5-(2-isopropylphenoxy)-2-(5-oxo-1-(pyridin-2-ylmethyl)pyrrolidin-3-yl)benzoic acid (90 mg, 87.3% yield), Mass spec: 431 (M+1).

Step 3: 5-(2-isopropylphenoxy)-2-(5-oxo-1-(pyridin-2-ylmethyl)pyrrolidin-3-yl)benzamide

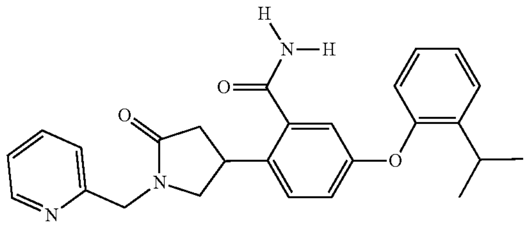 [SMILES: CC(C)c1ccccc1Oc1ccc(C2CC(=O)N(Cc3ccccn3)C2)c(C(N)=O)c1]

To a solution of 5-(2-isopropylphenoxy)-2-(5-oxo-1-(pyridin-2-ylmethyl)pyrrolidin-3-yl)benzoic acid (90 mg, 0.21 mmol), NH4Cl (23 mg, 0.42 mmol), EDCI (60 mg, 0.32 mmol), HOBt (43.2 mg, 0.32 mmol), DIPEA (54 mg, 0.42 mmol) in 10 ml DMF was stirred at r.t. for overnight. The reaction mixture was extracted with DCM (50 ml), washed with LiCl solution, dried, filtered and concentrated and purified by Prep-HPLC to give 5-(2-isopropylphenoxy)-2-(5-oxo-1-(pyridin-2-ylmethyl)pyrrolidin-3-yl)benzamide as white solid (11.8 mg, 13.1% yield), Mass spec: 430 (M+1), $t_R$=2.322 min, $^1$H-NMR (400 Hz, DMSO) δ=8.536-8.525 (m, 1H), 7.870-7.754 (m, 2H), 7.490-7.407 (m, 4H), 7.309-7.189 (m, 3H), 4.522 (s, 1H), 3.872 (m, 1H), 3.712-3.667 (m, 1H), 3.304 (m, 1H), 3.180-3.146 (m, 1H), 2.758-2.694 (m, 1H), 1.189-1.173 (m, 6H).

Example 166: 5-(2-ethylphenoxy)-2-(5-oxo-1-(pyridin-2-ylmethyl)pyrrolidin-3-yl)benzamide (Compound 2-100)

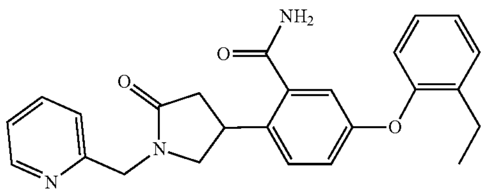 [SMILES: CCc1ccccc1Oc1ccc(C2CC(=O)N(Cc3ccccn3)C2)c(C(N)=O)c1]

The title compound was prepared following procedures described in example 150 to give 5-(2-ethylphenoxy)-2-(5-oxo-1-(pyridin-2-ylmethyl)pyrrolidin-3-yl)benzamide (135 mg, 49.5% yield), Mass spec: 416 (M+1), $t_R$=3.112 min, $^1$H-NMR (400 Hz, DMSO) δ=8.525-8.537 (d, 1H), 7.869 (s, 1H), 7.756-7.799 (t, 1H), 7.145-7.489 (m, 7H), 6.850-6.911 (m, 3H), 4.524 (s, 2H), 3.854-3.892 (m, 1H), 3.667-3.712 (m, 1H), 3.302-3.327 (m, 2H), 2.694-2.759 (m, 1H), 2.536-2.599 (m, 2H), 1.125-1.162 (t, 3H).

Example 167: 2-(1-((5-chloropyridin-2-yl)methyl)-5-oxopyrrolidin-3-yl)-5-(2-ethylphenoxy)benzamide (Compound 2-101)

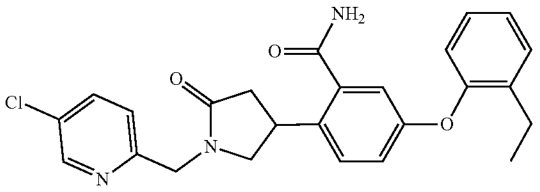 [SMILES: CCc1ccccc1Oc1ccc(C2CC(=O)N(Cc3ccc(Cl)cn3)C2)c(C(N)=O)c1]

The title compound was prepared following procedures described in example 150 to give 2-(1-((5-chloropyridin-2-yl)methyl)-5-oxopyrrolidin-3-yl)-5-(2-ethylphenoxy)benzamide (4.1 mg, 4% yield), Mass spec: 450 (M+1), $t_R$=3.403 min, $^1$H-NMR (400 Hz, DMSO) δ=8.584-8.591 (d, 1H), 7.873-7.926 (m, 1H), 7.347-7.491 (m, 4H), 7.162-7.244 (m, 2H), 6.850-6.926 (m, 3H), 4.526 (s, 2H), 3.795-3.801 (m, 1H), 3.680-3.704 (m, 1H), 3.295-3.327 (m, 2H), 2.685-2.709 (m, 1H), 2.561-2.580 (m, 2H), 1.124-1.162 (t, 3H).

Example 152: 2-(1-((5-chloropyridin-2-yl)methyl)-5-oxopyrrolidin-3-yl)-5-(2-isopropylphenoxy)benzamide (Compound 2-102)

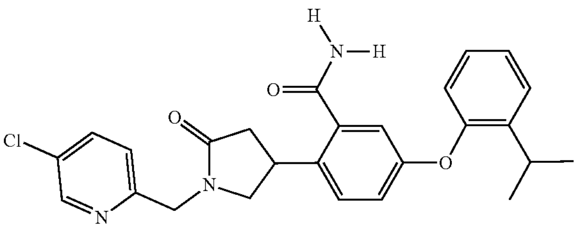 [SMILES: CC(C)c1ccccc1Oc1ccc(C2CC(=O)N(Cc3ccc(Cl)cn3)C2)c(C(N)=O)c1]

The title compound was prepared following procedures described in example 150 to give 2-(1-((5-chloropyridin-2-yl)methyl)-5-oxopyrrolidin-3-yl)-5-(2-isopropylphenoxy) benzamide (5.1 mg, 5.8% yield), Mass spec: 464 (M+1), $t_R$=2.660 min, $^1$H-NMR (400 Hz, DMSO) δ=8.587-8.581 (m, 1H), 7.922-7.878 (m, 2H), 7.495 (s, 1H), 7.428-7.344 (m, 4H), 7.234-7.189 (m, 2.5H), 6.908-6.866 (m, 3H), 4.525 (s, 2H), 3.884-3.845 (m, 1H), 3.704-3.660 (m, 1H), 3.336-3.295 (m, 1H), 3.177-3.142 (m, 1H), 2.751-2.687 (m, 1H), 2.514-2.465 (m, 1H), 1.238-1.170 (m, 6H).

Example 156: 5-(2-isopropylphenoxy)-2-(1-(pyrazine-2-carbonyl)pyrrolidin-3-yl)benzamide (Compound 2-103)

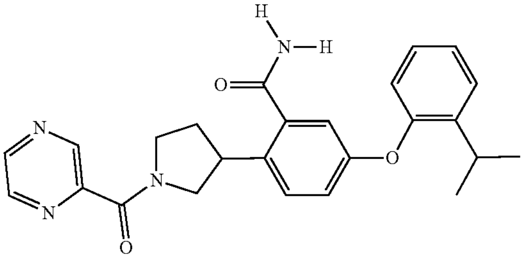 [SMILES: CC(C)c1ccccc1Oc1ccc(C2CCN(C(=O)c3cnccn3)C2)c(C(N)=O)c1]

The title compound was prepared following procedures described in example 154 to give 5-(2-isopropylphenoxy)-2-(1-(pyrazine-2-carbonyl)pyrrolidin-3-yl)benzamide (9.9 mg, 16.4% yield), Mass spec: 431 (M+1), $t_R$=2.465 min, $^1$H-NMR (400 Hz, DMS O) δ=8.990 (s, 1H), 80986-8.657 (m, 2H), 7.926-7.846 (m, 1H), 7.524-7.407 (m, 3H), 7.246-7.189 (m, 2H), 6.934-6.846 (m, 3H), 4.029-4.007 (m, 1H), 3.851-3.412 (m, 4H), 3.177-3.156 (m, 1H), 2.208-2.105 (m, 2H), 1.200-1.170 (m, 6H).

Example 397: (3-(2'-cyclopropyl-3-(hydroxymethyl)biphenyl-4-yl)pyrrolidin-1-yl)(3-methylpyrazin-2-yl)methanone (Compound 2-104)

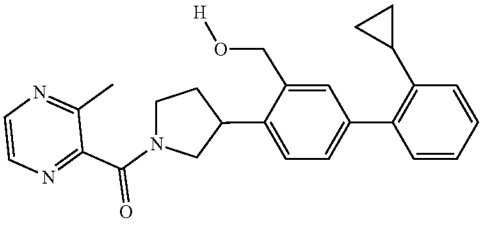 [SMILES: Cc1nccnc1C(=O)N1CCC(c2ccc(-c3ccccc3C3CC3)cc2CO)C1]

The title compound was prepared following procedures described in example 386 to give 3-(2'-cyclopropyl-3-(hydroxymethyl)biphenyl-4-yl)pyrrolidin-1-yl)(3-methylpyrazin-2-yl)methanone (15 mg, 33.3% yield), Mass spec: 414 (M+H), $t_R$=2.594 min, $^1$H-NMR (400 Hz, DMSO) δ=8.547-8.380 (m, 2H), 7.369-7.051 (m, 6H), 6.840 (m, 1H), 4.589-4.494 (m, 3H), 3.949-3.419 (m, 5H), 2.462-2.418 (m, 3H), 2.254-2.022 (m, 2H), 1.744-1.707 (m, 1H), 0.777-0.719 (m, 2H), 0.619-0.582 (m, 2H).

Example 396: (3-(2'-cyclopropyl-3-(hydroxymethyl) biphenyl-4-yl)pyrrolidin-1-yl)(pyrazin-2-yl)methanone (Compound 2-105)

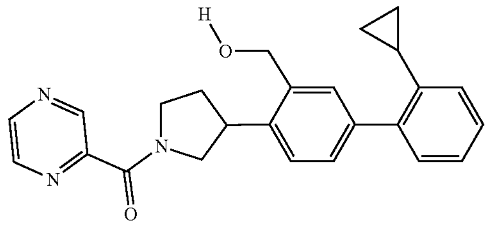 [SMILES: O=C(c1cnccn1)N1CCC(c2ccc(-c3ccccc3C3CC3)cc2CO)C1]

The title compound was prepared following procedures described in example 386 to give (10 mg, 25% yield), Mass spec: 400 (M+H), $t_R$=2.528 min, $^1$H-NMR (400 Hz, DMSO) δ=8.920 (s, 1H), 8.705-8.576 (m 2H), 7.393-7.052 (m, 6H), 6.858-6.825 (m, 1H), 4.593-4.513 (m, 3H), 3.991-3.972 (m, 1H), 3.792-3.417 (m, 4H), 2.187-2.402 (m, 1H), 2.049 (m, 1H), 1.766-1.733 (m, 1H), 0.776-0.728 (m, 2H), 0.615-0.590 (m, 2H).

Example 402: (3-(2'-cyclopropyl-3-(hydroxymethyl) biphenyl-4-yl)pyrrolidin-1-yl)(5-methylpyrazin-2-yl) methanone (Compound 2-106)

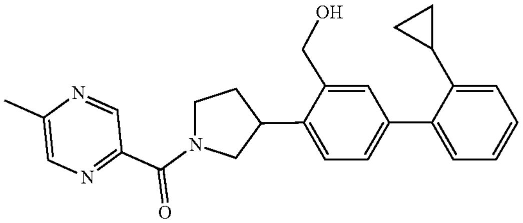 [SMILES: Cc1cnc(C(=O)N2CCC(c3ccc(-c4ccccc4C4CC4)cc3CO)C2)cn1]

The title compound was prepared following procedures described in example 399 to give (3-(2'-cyclopropyl-3-(hydroxymethyl)biphenyl-4-yl)pyrrolidin-1-yl)(5-methylpyrazin-2-yl)methanone (18 mg, 43.5% yield), Mass spec: 414 (M+H), $t_R$=2.692 min, $^1$H-NMR (400 Hz, DMSO) δ=8.792 (s, 1H), 8.518-8.454 (d, 1H), 7.345-7.257 (m, 2H), 7.164-7.054 (m, 4H), 6.856-6.825 (m, 1H), 5.095-5.043 (s, 1H), 4.580-4.476 (m, 2H), 4.018-3.914 (m, 1H), 3.827-3.799 (m, 1H), 3.701-3.556 (m, 2H), 3.426-3.405 (m, 1H), 2.490-2.453 (d, 3H), 2.167-2.094 (m, 1H), 2.020-1.904 (m, 1H), 1.825-1.701 (m, 1H), 0.805-0.738 (m, 2H), 0.592-0.554 (m, 2H).

Example 395: (3-(2'-cyclopropyl-3-(hydroxymethyl) biphenyl-4-yl)pyrrolidin-1-yl)(pyrimidin-4-yl) methanone (Compound 2-110)

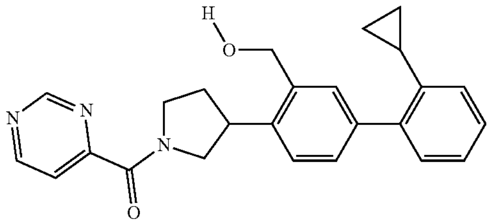 [SMILES: O=C(c1ccncn1)N1CCC(c2ccc(-c3ccccc3C3CC3)cc2CO)C1]

The title compound was prepared following procedures described in example 386 to give (3-(2'-cyclopropyl-3-(hydroxymethyl)biphenyl-4-yl)pyrrolidin-1-yl)(pyrimidin-4-yl)methanone (10 mg, 25% yield), Mass spec: 400 (M+H), $t_R$=2.585 min, $^1$H-NMR (400 Hz, DMSO) δ=9.307-9.247 (m, 1H), 9.024-8.983 (m, 1H), 7.829-7.813 (m, 1H), 7.470-7.152 (m, 6H), 6.927 (m, 1H), 4.673-4.598 (m, 3H), 4.039-4.013 (m, 1H), 3.829-3.351 (m, 4H), 2.272-1.815 (m, 3H), 0.860-0.820 (m, 2H), 0.699-0.673 (m, 2H).

Example 398: (3-(2'-cyclopropyl-3-(hydroxymethyl) biphenyl-4-yl)pyrrolidin-1-yl)(thiazol-4-yl)methanone (Compound 2-111)

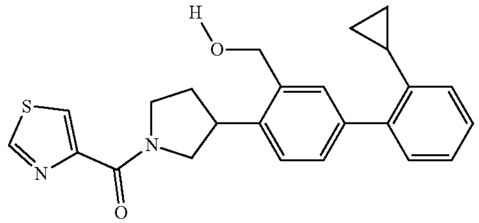 [SMILES: O=C(c1cscn1)N1CCC(c2ccc(-c3ccccc3C3CC3)cc2CO)C1]

The title compound was prepared following procedures described in example 386 to give (3-(2'-cyclopropyl-3-(hydroxymethyl)biphenyl-4-yl)pyrrolidin-1-yl)(thiazol-4-yl)methanone (10 mg, 25% yield), Mass spec: 405 (M+H), $t_R$=2.714 min, $^1$H-NMR (400 Hz, DMSO) δ=9.041-9.113 (d, 1H), 8.224-8.227 (d, 1H), 7.331-7.386 (m, 2H), 7.063-7.248 (m, 4H), 6.829-6.848 (d, 1H), 4.495-4.622 (m, 2H), 4.150-4.165 (m, 0.5H), 3.396-3.926 (m, 4.5), 2.240-2.248 (m, 1H), 2.028-2.129 (m, 1H), 1.733-1.747 (m, 1H), 0.752-0.771 (m, 2H), 0.597-0.610 (m, 2H).

Example 400: (3-(2'-cyclopropyl-3-(hydroxymethyl) biphenyl-4-yl)pyrrolidin-1-yl)(1H-pyrazol-3-yl) methanone (Compound 2-112)

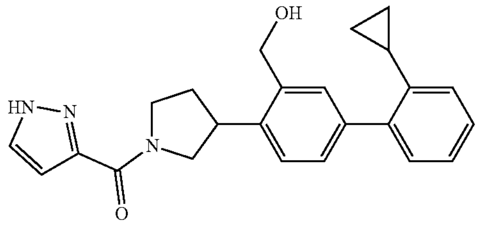 [SMILES: O=C(c1cc[nH]n1)N1CCC(c2ccc(-c3ccccc3C3CC3)cc2CO)C1]

The title compound was prepared following procedures described in example 399 to give (3-(2'-cyclopropyl-3-(hydroxymethyl)biphenyl-4-yl)pyrrolidin-1-yl)(1H-pyrazol-3-yl)methanone (10 mg, 25% yield), Mass spec: 388 (M+H), $t_R$=2.480 min, $^1$H-NMR (400 Hz, DMSO) δ=13.102-13.072 (d, 1H), 7.077-7.653 (s, 1H), 7.370-7.344 (m, 2H), 7.227-7.097 (m, 4H), 6.850-6.831 (d, 1H), 6.595 (s, 1H), 5.097 (s, 1H), 4.586-4.511 (m, 2H), 4.290-4.030 (d, 1H), 3.925-3.818 (m, 1H), 3.723-3.607 (m, 2H), 3.503-3.403 (m, 1H), 2.243-2.184 (m, 1H), 2.086-1.991 (m, 1H), 1.904-1.825 (m, 1H), 0.725 (d, 4H), 0.598 (d, 4H).

Example 63: (R)-2-(1-(5-(trifluoromethyl)pyridin-2-yl)pyrrolidin-3-yloxy)benzamide (Compound 2-113)

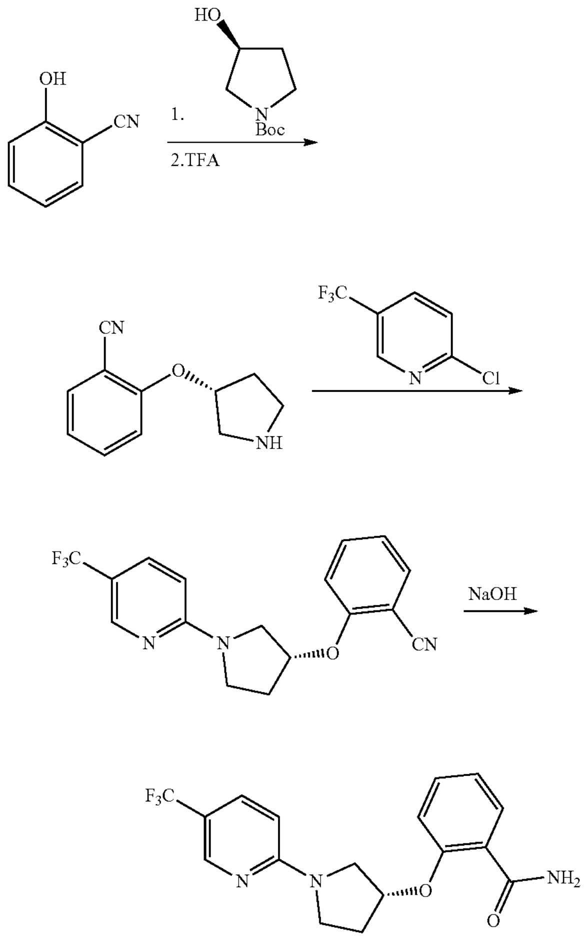

Step 1: (R)-2-(pyrrolidin-3-yloxy)benzonitrile

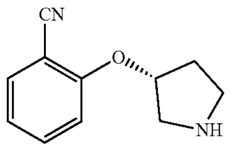 [SMILES: N#Cc1ccccc1O[C@@H]1CCNC1]

To a solution of (S)-tert-butyl 3-hydroxypyrrolidine-1-carboxylate (187 mg, 1 mmol) and 2-hydroxybenzonitrile (119 mg, 1 mmol) in THE was added DEAD (348 mg, 2 mmol) and PPh3 (524 mg, 2 mmol), the mixture was stirred ar rt for overnight, remove the THF to left the residue which was stirred in TFA/DCM (9 mL/3 mL) at rt for 1 h, remove the DCM, 3N HCl (2 mL) was added and stirred for 30 min, extracted with ether, the water layer was adjusted the pH to 12 with KOH solid, extracted with DCM, (20 mL×2), dried over Na2SO4, removal the solvent to left the crude product (80 mg, 42.5% yield) which can be used to next step directly. Mass spec: 189 (M+H).

Step 2: (R)-2-(1-(5-(trifluoromethyl)pyridin-2-yl)pyrrolidin-3-yloxy)benzonitrile

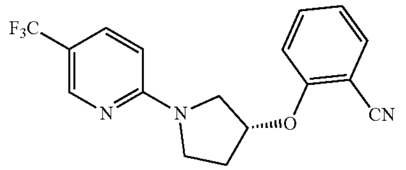 [SMILES: N#Cc1ccccc1O[C@@H]1CCN(c2ccc(C(F)(F)F)cn2)C1]

To a solution of (R)-2-(pyrrolidin-3-yloxy)benzonitrile (80 mg, 0.42 mmol) in DMSO was added 2-chloro-5-(trifluoromethyl)pyridine (84 mg, 0.47 mmol) and K2CO3 (87 mg, 0.63 mmol). The mixture was stirred at 100° C. for 3 h, EA was added, washed with water, brine, dried over Na2SO4, removal the solvent to left the crude product which was purified by silica gel to give (R)-2-(1-(5-(trifluoromethyl)pyridin-2-yl)pyrrolidin-3-yloxy)benzonitrile (90 mg, 64% yield), Mass spec: 334 (M+H).

Step 3: (R)-2-(1-(5-(trifluoromethyl)pyridin-2-yl)pyrrolidin-3-yloxy)benzamide

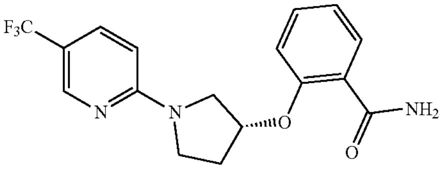 [SMILES: NC(=O)c1ccccc1O[C@@H]1CCN(c2ccc(C(F)(F)F)cn2)C1]

The title compound was prepared following procedures described in example 6 with EtOH at 60° C. for 5 h to give (R)-2-(1-(5-(trifluoromethyl)pyridin-2-yl)pyrrolidin-3-yloxy)benzamide (30 mg, 35% yield), Mass spec: 352 (M+H), $t_R$=2.079 min, $^1$H-NMR (400 Hz, DMSO) δ=8.391 (s, 1H), 7.741-7.793 (m, 2H), 7.415-7.509 (m, 3H), 7.234-7.256 (d, 1H), 7.041-7.079 (s, 1H), 6.626-6.649 (d, 1H), 5.352 (s, 1H), 3.797-3.805 (m, 1H), 3.654 (m, 1H), 3.540-3.562 (m, 1H), 2.335-2.342 (m, 2H).

Example 64: (S)-2-(1-(5-(trifluoromethyl)pyridin-2-yl)pyrrolidin-3-yloxy)benzamide (Compound 2-114)

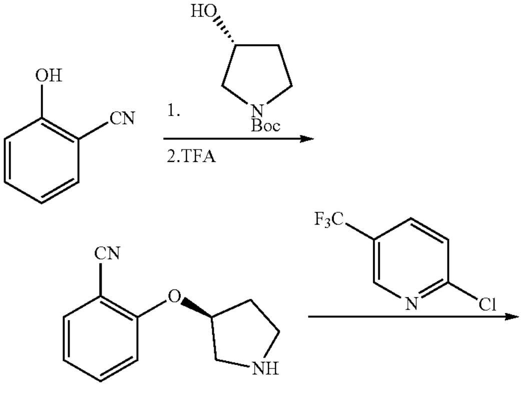

-continued

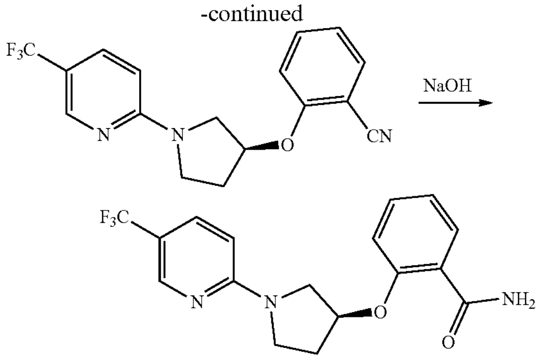

Step 1: (S)-2-(pyrrolidin-3-yloxy)benzonitrile

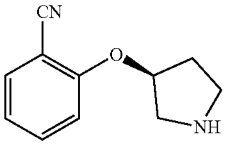 [SMILES: N#Cc1ccccc1O[C@H]1CCNC1]

The title compound was prepared following procedures described in example 63 (step 1) to give (S)-2-(pyrrolidin-3-yloxy)benzonitrile (94 mg, 50% yield), Mass spec: 189 (M+H).

Step 2: (S)-2-(1-(5-(trifluoromethyl)pyridin-2-yl)pyrrolidin-3-yloxy)benzonitrile

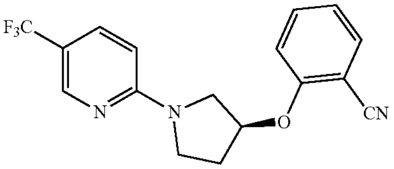 [SMILES: N#Cc1ccccc1O[C@H]1CCN(c2ccc(C(F)(F)F)cn2)C1]

The title compound was prepared following procedures described in example 63 (step 2) to give (S)-2-(1-(5-(trifluoromethyl)pyridin-2-yl)pyrrolidin-3-yloxy)benzonitrile (95 mg, 60% yield), Mass spec: 334 (M+H).

Step 3: (S)-2-(1-(5-(trifluoromethyl)pyridin-2-yl)pyrrolidin-3-yloxy)benzamide

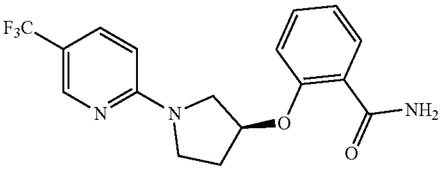 [SMILES: NC(=O)c1ccccc1O[C@H]1CCN(c2ccc(C(F)(F)F)cn2)C1]

The title compound was prepared following procedures described in example 63 (step 3) to give (S)-2-(1-(5-(trifluoromethyl)pyridin-2-yl)pyrrolidin-3-yloxy)benzamide (40 mg, 42% yield), Mass spec: 352 (M+H), $t_R$=2.095 min, $^1$H-NMR (400 Hz, DMSO) δ=8.393 (s, 1H), 7.743-7.791 (m, 2H), 7.414-7.510 (m, 3H), 7.235-7.256 (d, 1H), 7.043-7.078 (s, 1H), 6.628-6.650 (d, 1H), 5.354 (s, 1H), 3.797-3.805 (m, 1H), 3.691-3.704 (m, 1H), 3.541-3.565 (m, 1H), 2.336 (br, 2H).

Example 425: 3-(2'-ethyl-3-(hydroxymethyl)biphenyl-4-yl)pyrrolidin-1-yl)(1-methylpiperidin-4-yl)methanone (Compound 2-115)

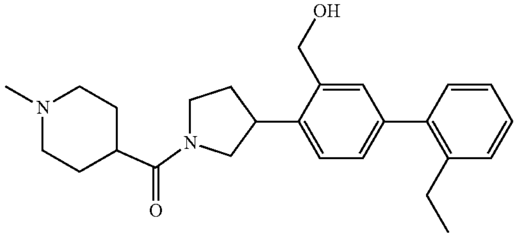 [SMILES: CCc1ccccc1-c1ccc(C2CCN(C(=O)C3CCN(C)CC3)C2)c(CO)c1]

The title compound was prepared following procedures described in example 386 to give 3-(2'-ethyl-3-(hydroxymethyl)biphenyl-4-yl)pyrrolidin-1-yl)(1-methylpiperidin-4-yl)methanone (1.4 mg, 1.6% yield), Mass spec: 407 (M+H), $t_R$=1.842 min, $^1$H-NMR (400 Hz, DMSO) δ=9.987 (s, 1H), 7.125-7.439 (m, 7H), 4.630-4.667 (m, 2H), 3.609-4.017 (m, 5H), 3.271-3.293 (m, 3H), 2.926-2.964 (m, 2H), 2.547-2.762 (m, 4H), 2.565 (q, d, 2H), 1.841-2.337 (m, 5H), 1.306 (t, d, 3H).

Example 463: Compound 2-125

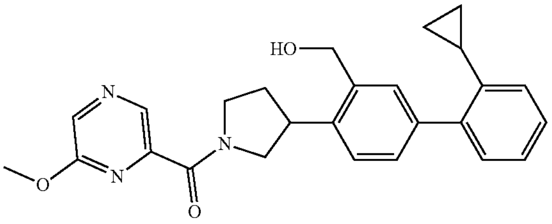 [SMILES: COc1cncc(C(=O)N2CCC(c3ccc(-c4ccccc4C4CC4)cc3CO)C2)n1]

The title compound was prepared following procedures described in Example 386.

Example 464: Compound 2-126

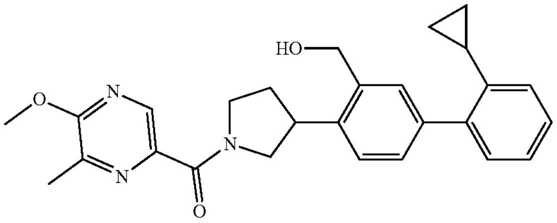 [SMILES: COc1ncc(C(=O)N2CCC(c3ccc(-c4ccccc4C4CC4)cc3CO)C2)nc1C]

The title compound was prepared following procedures described herein e.g. in Example 386.

Example 465: Compound 2-127

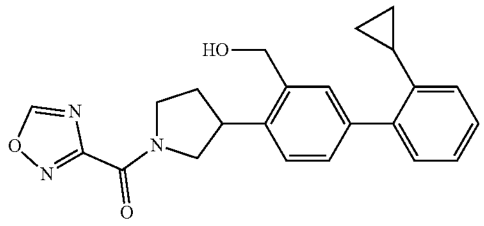 [SMILES: O=C(c1ncon1)N1CCC(c2ccc(-c3ccccc3C3CC3)cc2CO)C1]

The title compound was prepared following procedures described herein e.g. in Example 386.

Example 466: Compound 2-128

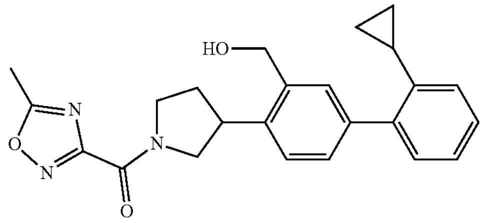 [SMILES: Cc1nc(C(=O)N2CCC(c3ccc(-c4ccccc4C4CC4)cc3CO)C2)no1]

The title compound was prepared following procedures described herein e.g. in Example 386.

Example 467: Compound 2-129

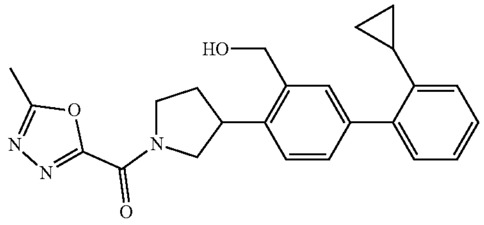

The title compound was prepared following procedures described herein e.g. in Example 386.

Example 468: Compound 2-130

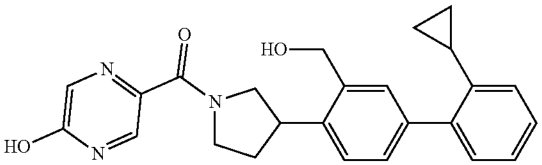

The title compound was prepared following procedures described herein e.g. in Example 386.

Example 469: Compound 2-131

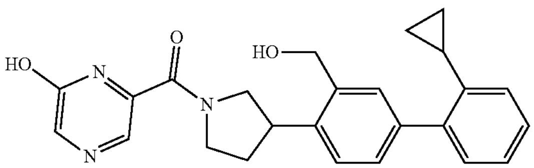

The title compound was prepared following procedures described herein e.g. in Example 386.

Example 470: Compound 2-132

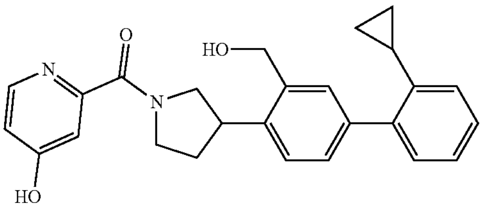 [SMILES: O=C(c1cc(O)ccn1)N1CCC(c2ccc(-c3ccccc3C3CC3)cc2CO)C1]

The title compound was prepared following procedures described herein e.g. in Example 386.

Example 471: Compound 2-133

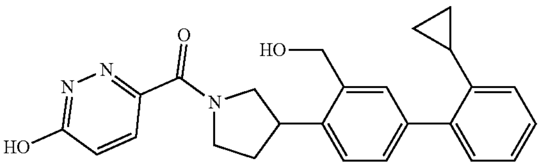 [SMILES: O=C(c1ccc(O)nn1)N1CCC(c2ccc(-c3ccccc3C3CC3)cc2CO)C1]

The title compound was prepared following procedures described herein e.g. in Example 386.

Example 472: Compound 2-134

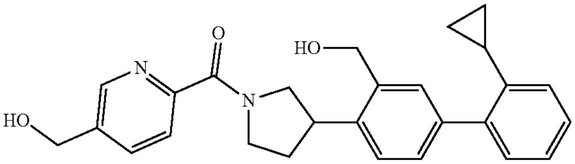 [SMILES: O=C(c1ccc(CO)cn1)N1CCC(c2ccc(-c3ccccc3C3CC3)cc2CO)C1]

The title compound was prepared following procedures described herein e.g. in Example 386.

Example 473: Compound 2-135

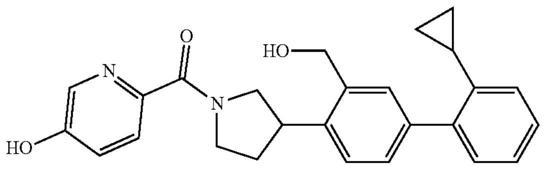 [SMILES: O=C(c1ccc(O)cn1)N1CCC(c2ccc(-c3ccccc3C3CC3)cc2CO)C1]

The title compound was prepared following procedures described herein e.g. in Example 386.

Example 474: Compound 2-136

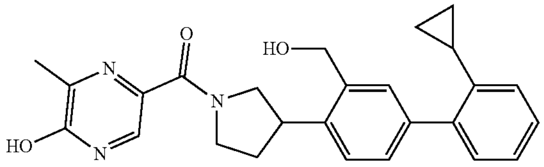 [SMILES: Cc1nc(C(=O)N2CCC(c3ccc(-c4ccccc4C4CC4)cc3CO)C2)cnc1O]

The title compound was prepared following procedures described herein e.g. in Example 386.

Example 475: Compound 2-137

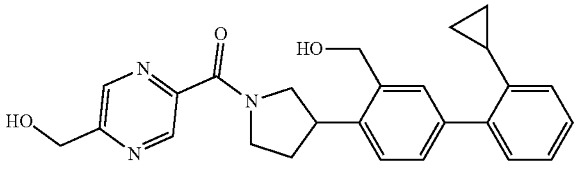 [SMILES: O=C(c1cnc(CO)cn1)N1CCC(c2ccc(-c3ccccc3C3CC3)cc2CO)C1]

The title compound was prepared following procedures described herein e.g. in Example 386.

Example 476: Compound 2-138

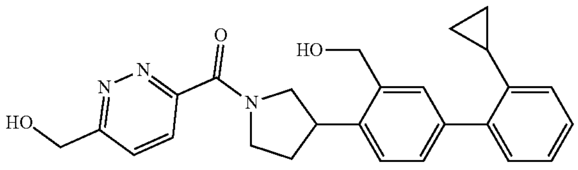 [SMILES: O=C(c1ccc(CO)nn1)N1CCC(c2ccc(-c3ccccc3C3CC3)cc2CO)C1]

The title compound was prepared following procedures described herein e.g. in Example 386.

Example 477: Compound 2-139

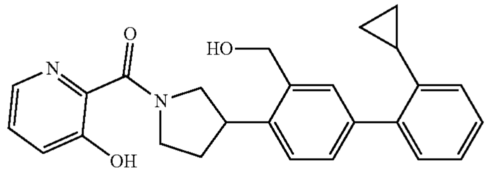 [SMILES: O=C(c1ncccc1O)N1CCC(c2ccc(-c3ccccc3C3CC3)cc2CO)C1]

The title compound was prepared following procedures described herein e.g. in Example 386.

Example 478: Compound 2-140

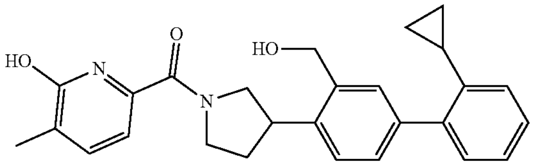 [SMILES: Cc1ccc(C(=O)N2CCC(c3ccc(-c4ccccc4C4CC4)cc3CO)C2)nc1O]

The title compound was prepared following procedures described herein e.g. in Example 386.

Example 479: Compound 2-141

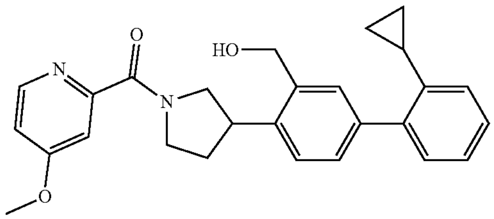 [SMILES: COc1ccnc(C(=O)N2CCC(c3ccc(-c4ccccc4C4CC4)cc3CO)C2)c1]

The title compound was prepared following procedures described herein e.g. in Example 386.

Example 480: Compound 2-142

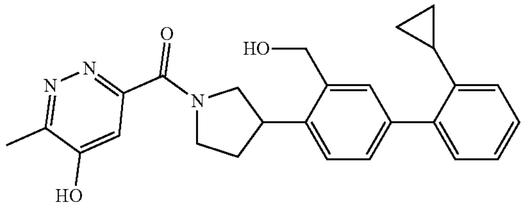 [SMILES: Cc1nnc(C(=O)N2CCC(c3ccc(-c4ccccc4C4CC4)cc3CO)C2)cc1O]

The title compound was prepared following procedures described herein e.g. in Example 386.

Example 481: Compound 2-143

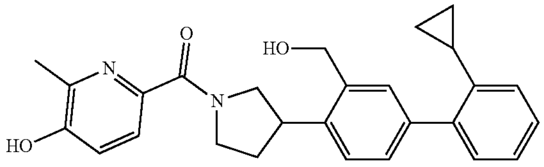 [SMILES: Cc1nc(C(=O)N2CCC(c3ccc(-c4ccccc4C4CC4)cc3CO)C2)ccc1O]

The title compound was prepared following procedures described herein e.g. in Example 386.

Example 482: Compound 2-144

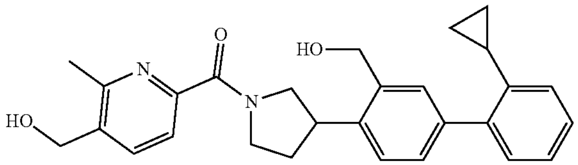 [SMILES: Cc1nc(C(=O)N2CCC(c3ccc(-c4ccccc4C4CC4)cc3CO)C2)ccc1CO]

The title compound was prepared following procedures described herein e.g. in Example 386.

Example 483: Compound 2-145

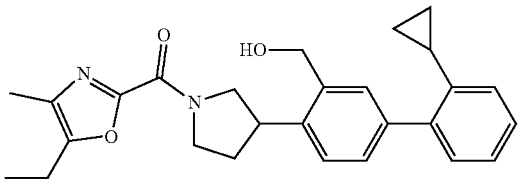 [SMILES: CCc1oc(C(=O)N2CCC(c3ccc(-c4ccccc4C4CC4)cc3CO)C2)nc1C]

The title compound was prepared following procedures described herein e.g. in Example 386.

Example 484: Compound 2-146

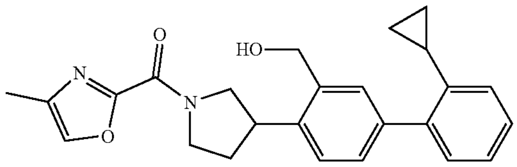 [SMILES: Cc1coc(C(=O)N2CCC(c3ccc(-c4ccccc4C4CC4)cc3CO)C2)n1]

The title compound was prepared following procedures described herein e.g. in Example 386.

Example 485: Compound 2-147

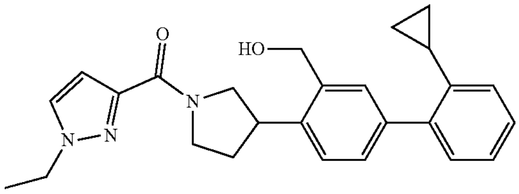

The title compound was prepared following procedures described herein e.g. in Example 386.

Example 486: Compound 2-148

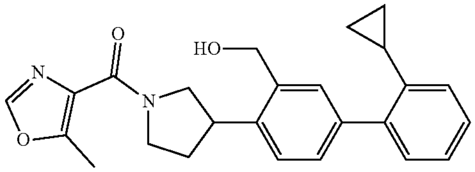 [SMILES: Cc1ocnc1C(=O)N1CCC(c2ccc(-c3ccccc3C3CC3)cc2CO)C1]

The title compound was prepared following procedures described herein e.g. in Example 386.

Example 487: Compound 2-149

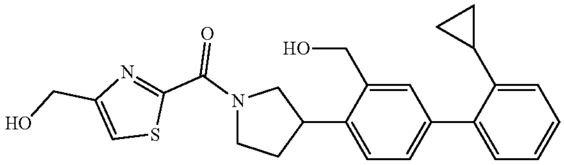 [SMILES: O=C(c1nc(CO)cs1)N1CCC(c2ccc(-c3ccccc3C3CC3)cc2CO)C1]

The title compound was prepared following procedures described herein e.g. in Example 386.

Example 488: Compound 2-150

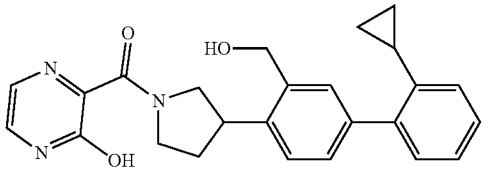

The title compound was prepared following procedures described herein e.g. in Example 386.

Example 489: Compound 2-151

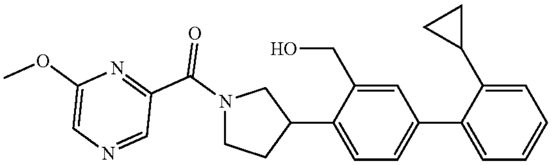 [SMILES: COc1cncc(C(=O)N2CCC(c3ccc(-c4ccccc4C4CC4)cc3CO)C2)n1]

The title compound was prepared following procedures described herein e.g. in Example 386.

Example 490: Compound 2-152

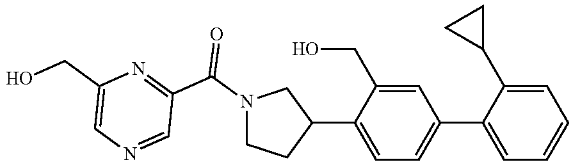 [SMILES: O=C(c1cncc(CO)n1)N1CCC(c2ccc(-c3ccccc3C3CC3)cc2CO)C1]

The title compound was prepared following procedures described herein e.g. in Example 386.

Example 491: Compound 2-153

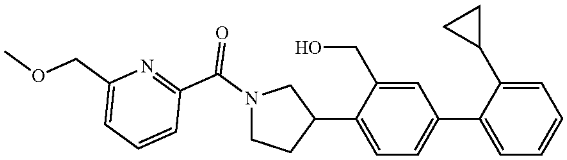 [SMILES: COCc1cccc(C(=O)N2CCC(c3ccc(-c4ccccc4C4CC4)cc3CO)C2)n1]

The title compound was prepared following procedures described herein e.g. in Example 386.

Example 492: Compound 2-154

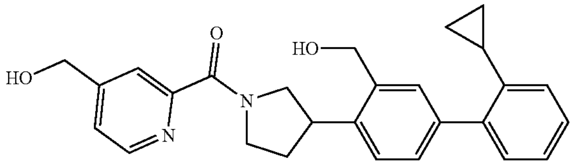 [SMILES: O=C(c1cc(CO)ccn1)N1CCC(c2ccc(-c3ccccc3C3CC3)cc2CO)C1]

The title compound was prepared following procedures described herein e.g. in Example 386.

Example 493: Compound 2-155

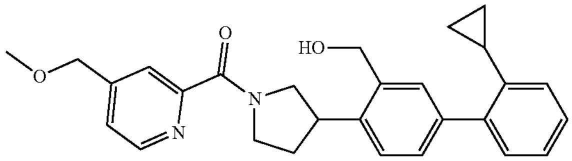 [SMILES: COCc1ccnc(C(=O)N2CCC(c3ccc(-c4ccccc4C4CC4)cc3CO)C2)c1]

The title compound was prepared following procedures described herein e.g. in Example 386.

Example 494: Compound 2-156

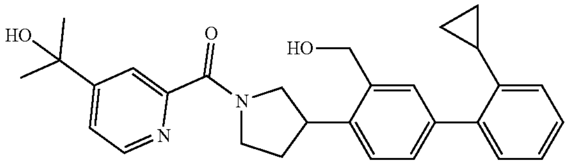 [SMILES: CC(C)(O)c1ccnc(C(=O)N2CCC(c3ccc(-c4ccccc4C4CC4)cc3CO)C2)c1]

The title compound was prepared following procedures described herein e.g. in Example 386.

Example 495: Compound 2-157

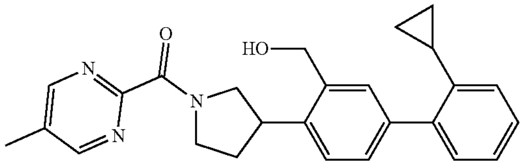

The title compound was prepared following procedures described herein e.g. in Example 386.

Example 496: Compound 2-158

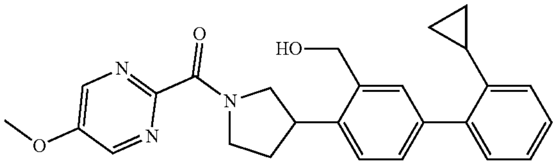 [SMILES: COc1cnc(C(=O)N2CCC(c3ccc(-c4ccccc4C4CC4)cc3CO)C2)nc1]

The title compound was prepared following procedures described herein e.g. in Example 386.

Example 497: Compound 2-159

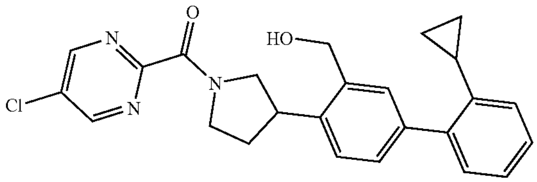 [SMILES: O=C(c1ncc(Cl)cn1)N1CCC(c2ccc(-c3ccccc3C3CC3)cc2CO)C1]

The title compound was prepared following procedures described herein e.g. in Example 386.

Example 498: Compound 2-160

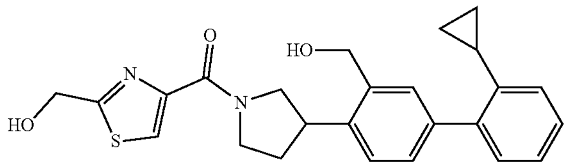 [SMILES: O=C(c1csc(CO)n1)N1CCC(c2ccc(-c3ccccc3C3CC3)cc2CO)C1]

The title compound was prepared following procedures described herein e.g. in Example 386.

Example 499: Compound 2-161

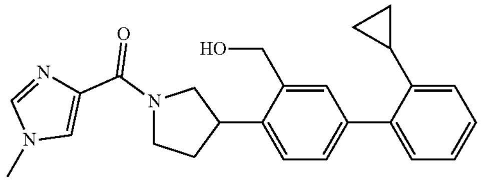 [SMILES: Cn1cnc(C(=O)N2CCC(c3ccc(-c4ccccc4C4CC4)cc3CO)C2)c1]

The title compound was prepared following procedures described herein e.g. in Example 386.

Example 500: Compound 2-162

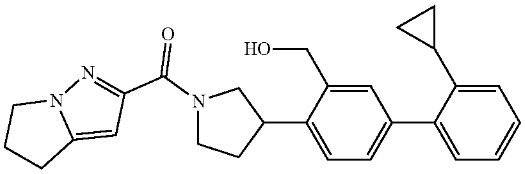 [SMILES: O=C(c1cc2n(n1)CCC2)N1CCC(c2ccc(-c3ccccc3C3CC3)cc2CO)C1]

The title compound was prepared following procedures described herein e.g. in Example 386.

Example 501: Compound 2-163

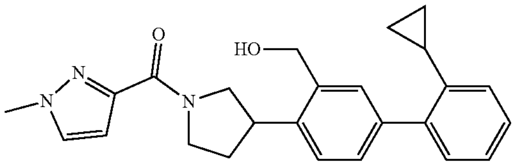 [SMILES: Cn1ccc(C(=O)N2CCC(c3ccc(-c4ccccc4C4CC4)cc3CO)C2)n1]

The title compound was prepared following procedures described herein e.g. in Example 386.

Example 502: Compound 2-164

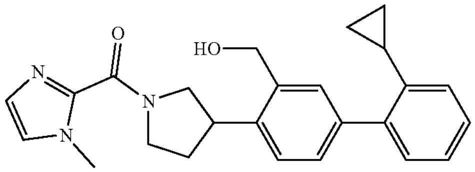 [SMILES: Cn1ccnc1C(=O)N1CCC(c2ccc(-c3ccccc3C3CC3)cc2CO)C1]

The title compound was prepared following procedures described herein e.g. in Example 386.

Example 503: Compound 2-165

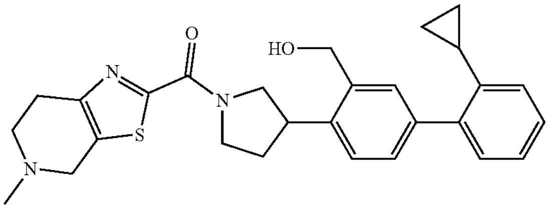 [SMILES: CN1CCc2nc(C(=O)N3CCC(c4ccc(-c5ccccc5C5CC5)cc4CO)C3)sc2C1]

The title compound was prepared following procedures described herein e.g. in Example 386.

Example 504: Compound 2-166

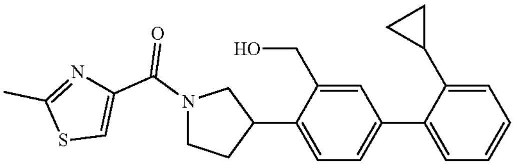 [SMILES: Cc1nc(C(=O)N2CCC(c3ccc(-c4ccccc4C4CC4)cc3CO)C2)cs1]

The title compound was prepared following procedures described herein e.g. in Example 386.

Example 505: Compound 2-167

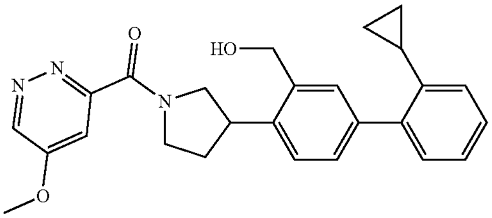

The title compound was prepared following procedures described herein e.g. in Example 386.

Example 506: Compound 2-168

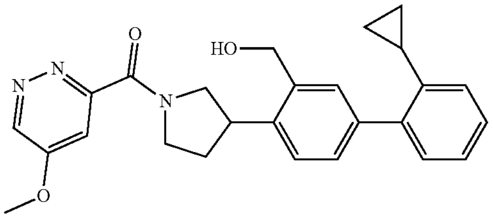 [SMILES: COc1cnnc(C(=O)N2CCC(c3ccc(-c4ccccc4C4CC4)cc3CO)C2)c1]

The title compound was prepared following procedures described herein e.g. in Example 386.

Example 507: Compound 2-170

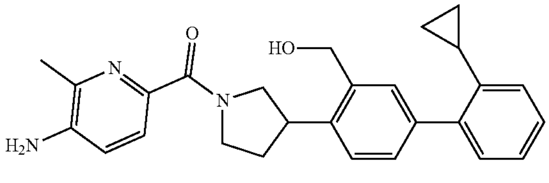 [SMILES: Cc1nc(C(=O)N2CCC(c3ccc(-c4ccccc4C4CC4)cc3CO)C2)ccc1N]

The title compound was prepared following procedures described in Example 386 to form compound 2-170-S followed by hydrogenation to provide compound 2-170.

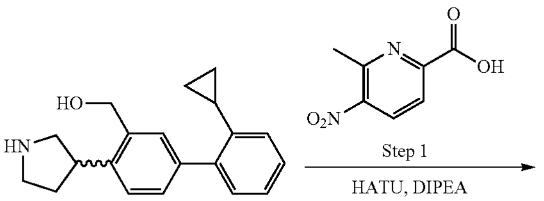

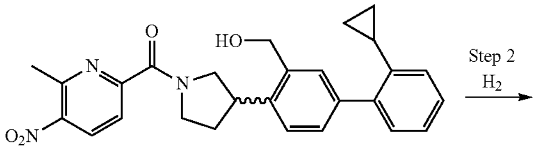

2-170-S

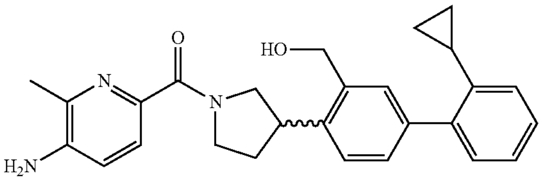

2-170

Example 509: Compound 2-171

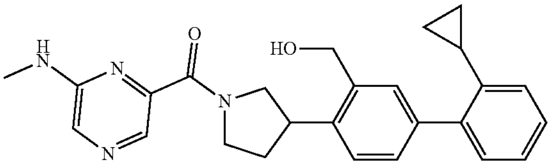 [SMILES: CNc1cncc(C(=O)N2CCC(c3ccc(-c4ccccc4C4CC4)cc3CO)C2)n1]

The title compound was prepared according to the following protocol:

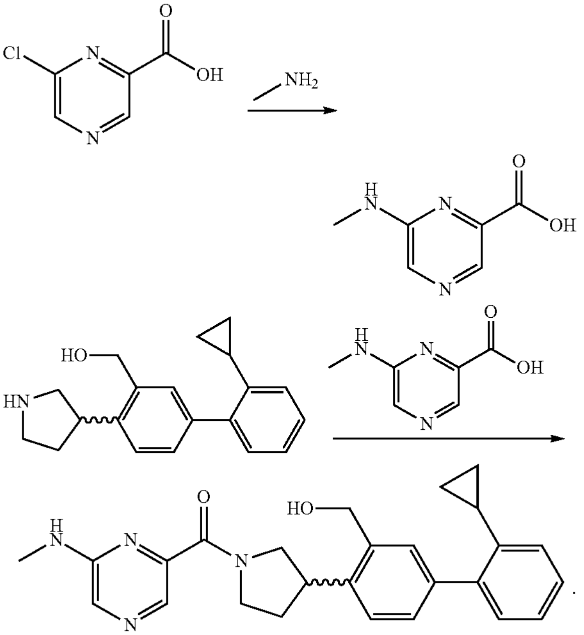

Example 507: Compound 2-169

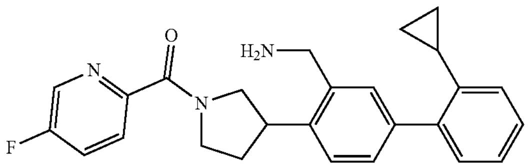 [SMILES: NCc1cc(-c2ccccc2C2CC2)ccc1C1CCN(C(=O)c2ccc(F)cn2)C1]

The title compound was prepared according to the following protocol:

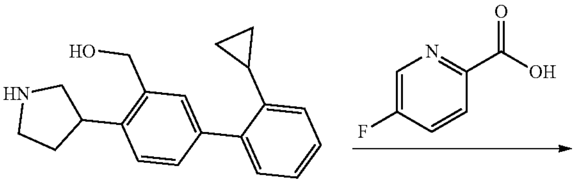

-continued
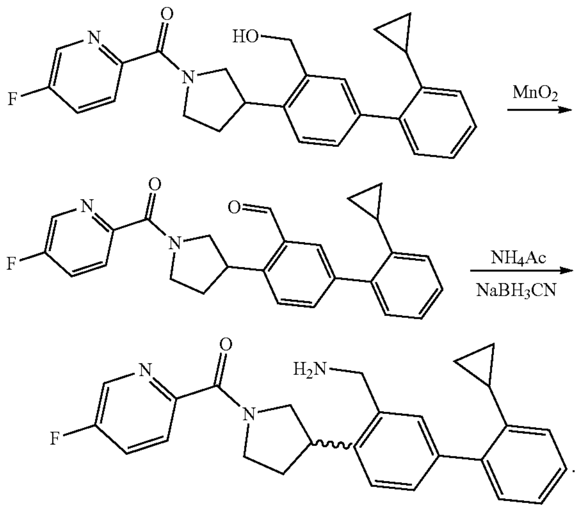
Example 510: Compound 2-172
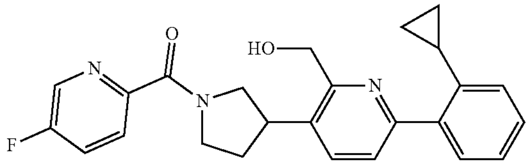 [SMILES: O=C(c1ccc(F)cn1)N1CCC(c2ccc(-c3ccccc3C3CC3)nc2CO)C1]
The title compound was prepared according to the following procedure:
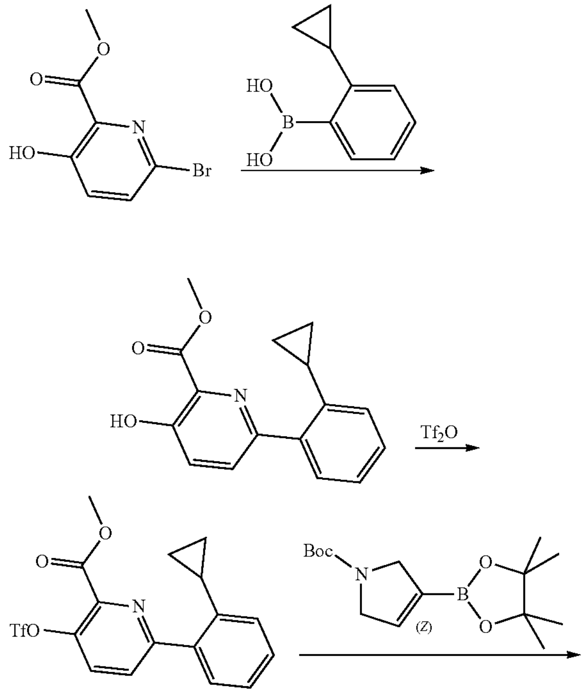
-continued
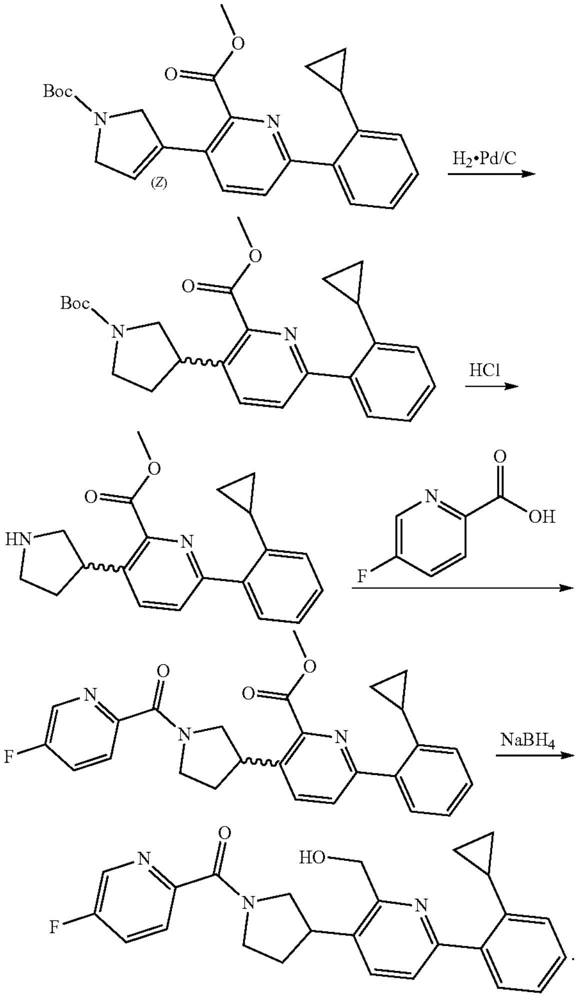
Example 512: Compound 2-174
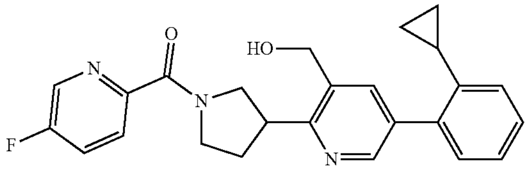 [SMILES: O=C(c1ccc(F)cn1)N1CCC(c2ncc(-c3ccccc3C3CC3)cc2CO)C1]
The title compound was prepared according to the following procedure:
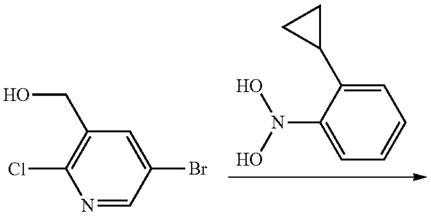

-continued
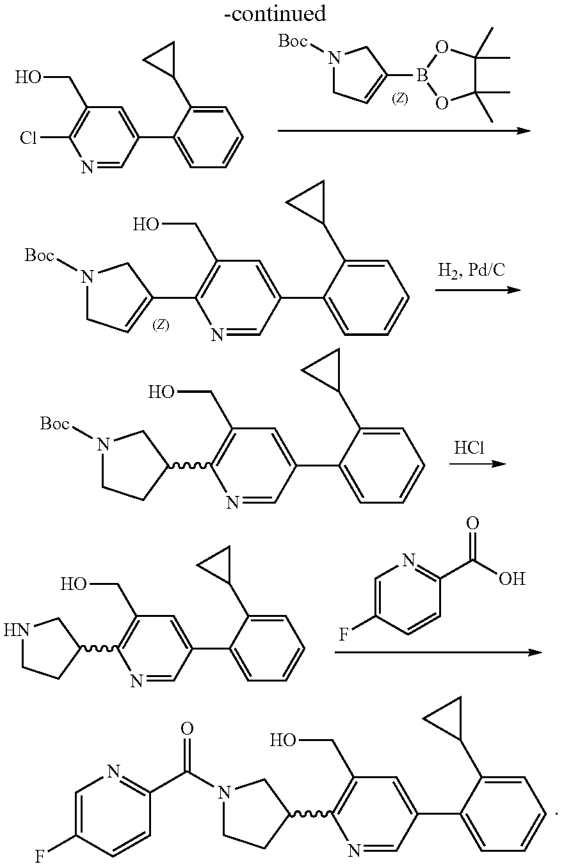
Example 515: Compound 2-177
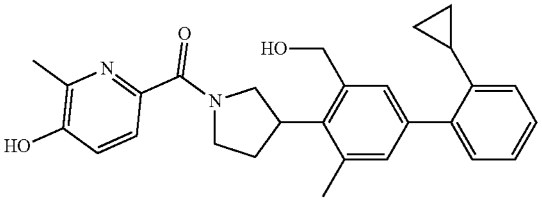 [SMILES: Cc1cc(-c2ccccc2C2CC2)cc(CO)c1C1CCN(C(=O)c2ccc(O)c(C)n2)C1]
The title compound was prepared according to the following procedure:
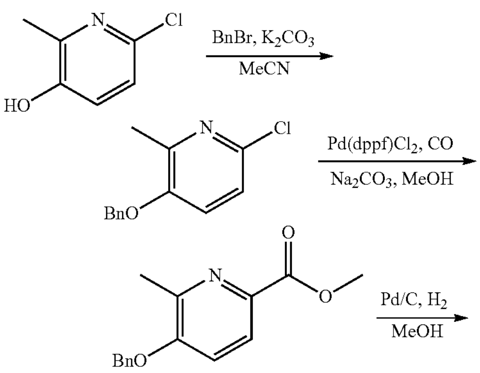
-continued
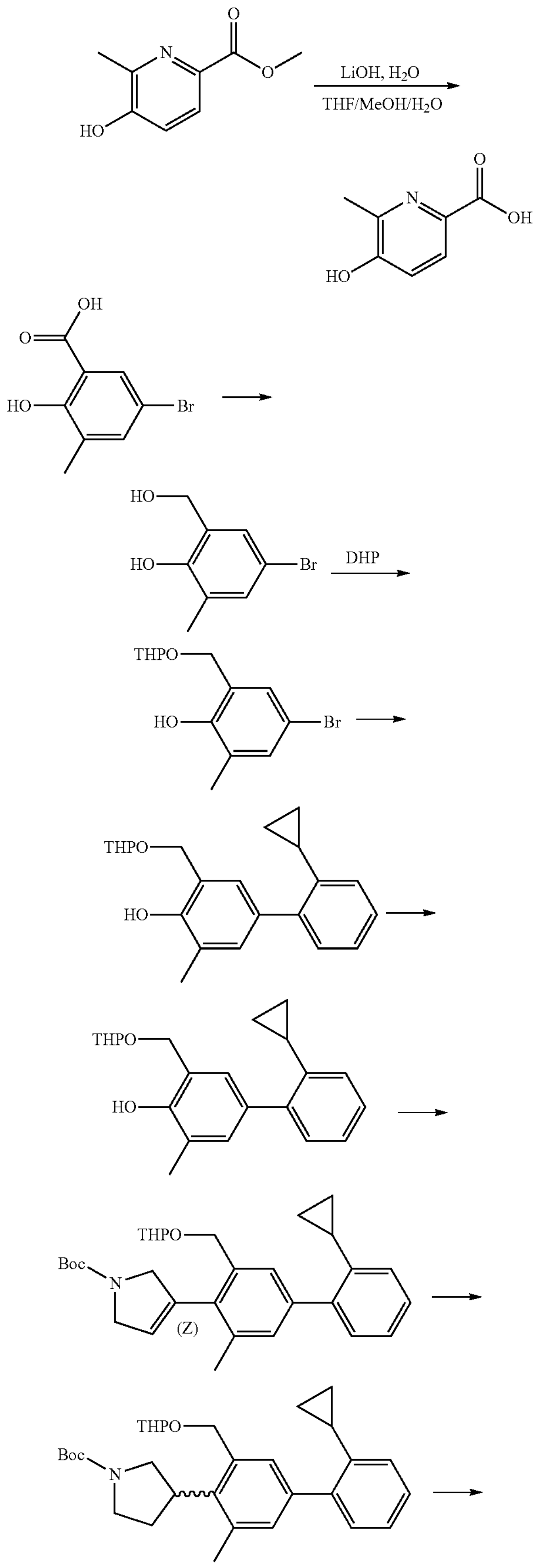

-continued
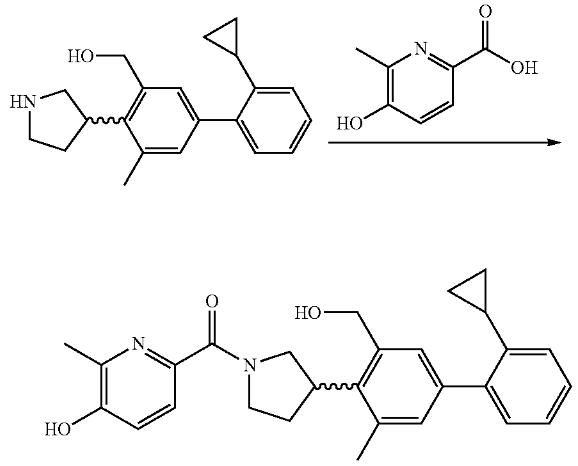
Example 518: Compound 2-180
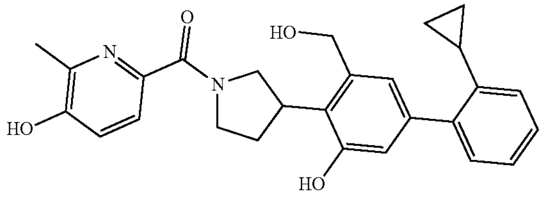 [SMILES: Cc1nc(C(=O)N2CCC(c3c(O)cc(-c4ccccc4C4CC4)cc3CO)C2)ccc1O]
The title compound was prepared according to the following procedure:
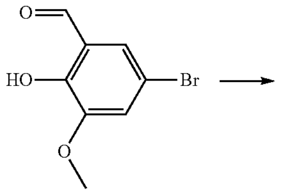
5034-74-2
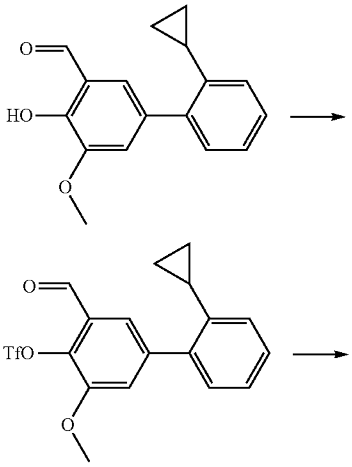
-continued
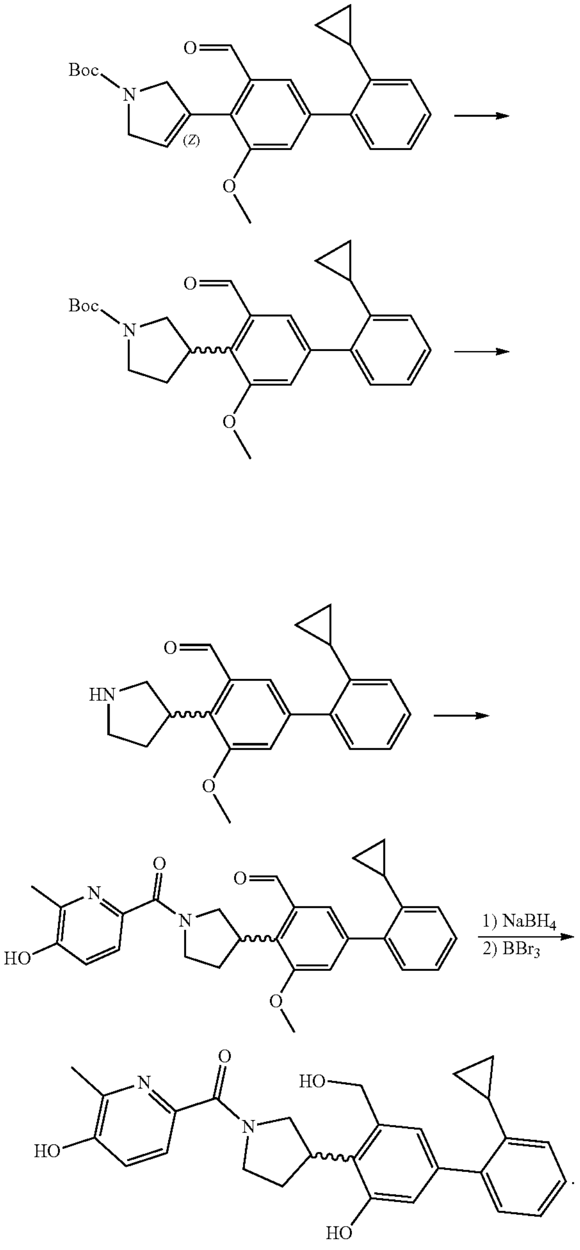
Example 521: Compound 2-183
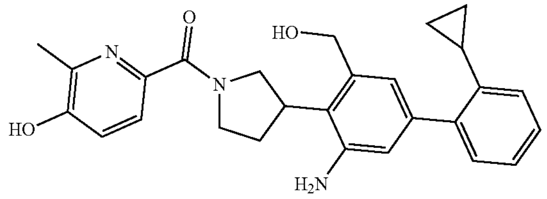

The title compound was prepared according to the following procedure:
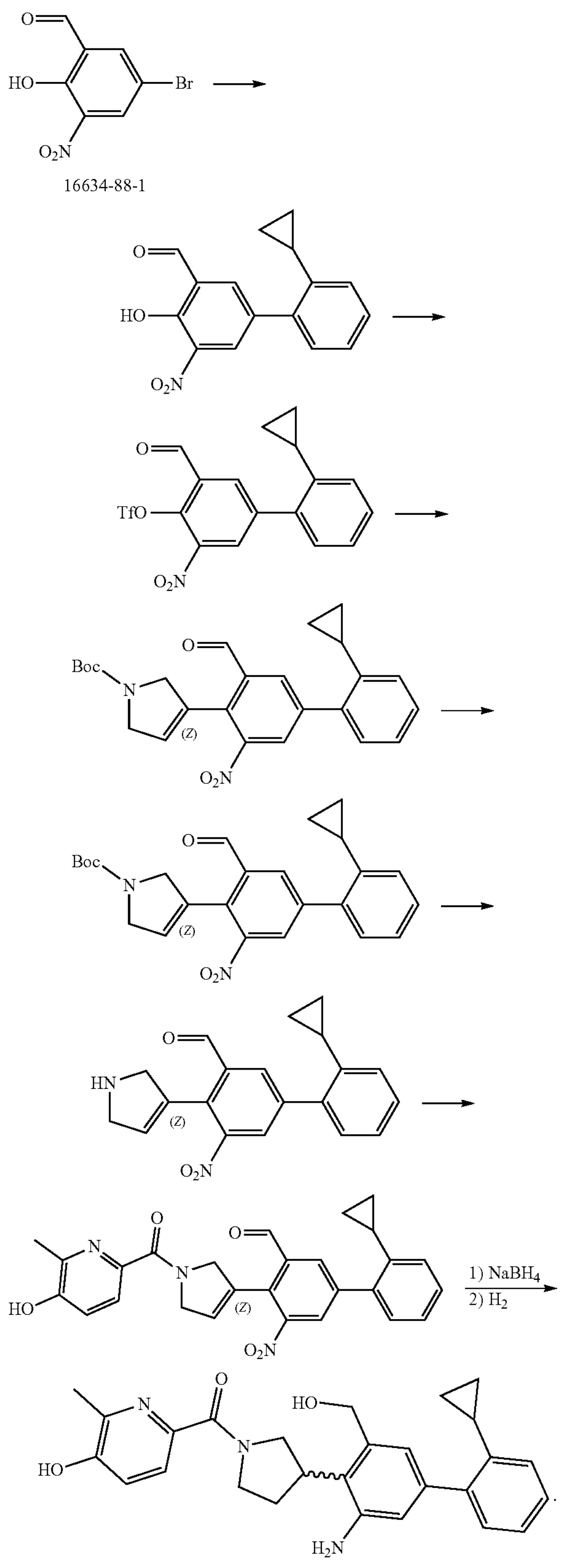
Example 511 Compound 2-173
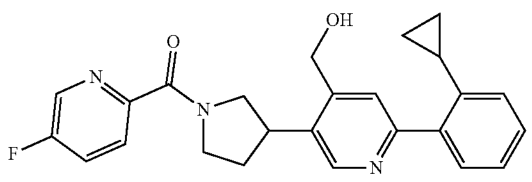 [SMILES: O=C(c1ccc(F)cn1)N1CCC(c2cnc(-c3ccccc3C3CC3)cc2CO)C1]
The title compound was prepared according to the following procedure:
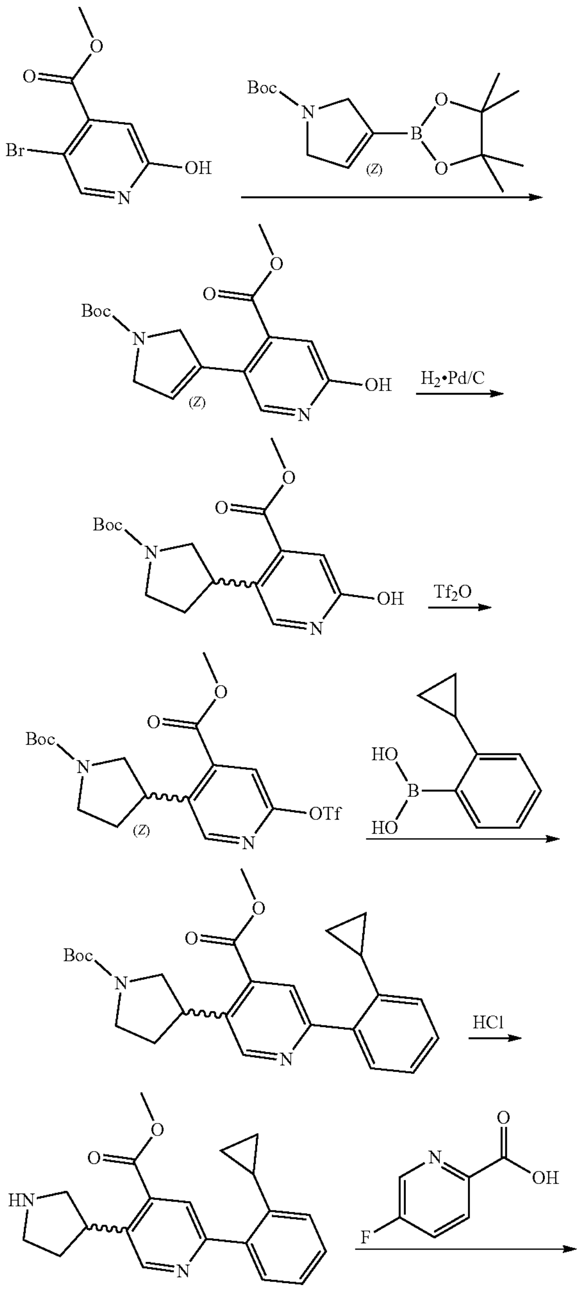

-continued
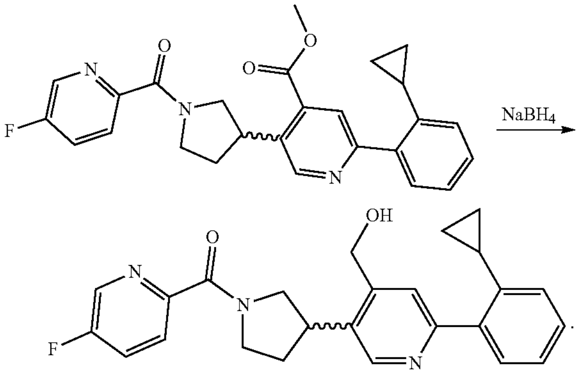
Example 513: Compound 2-175
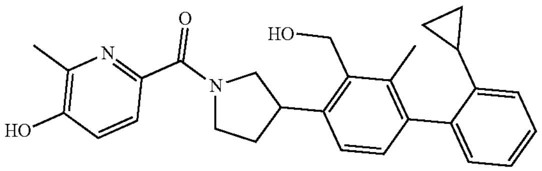 [SMILES: Cc1nc(C(=O)N2CCC(c3ccc(-c4ccccc4C4CC4)c(C)c3CO)C2)ccc1O]
The title compound was prepared according to the following procedure:
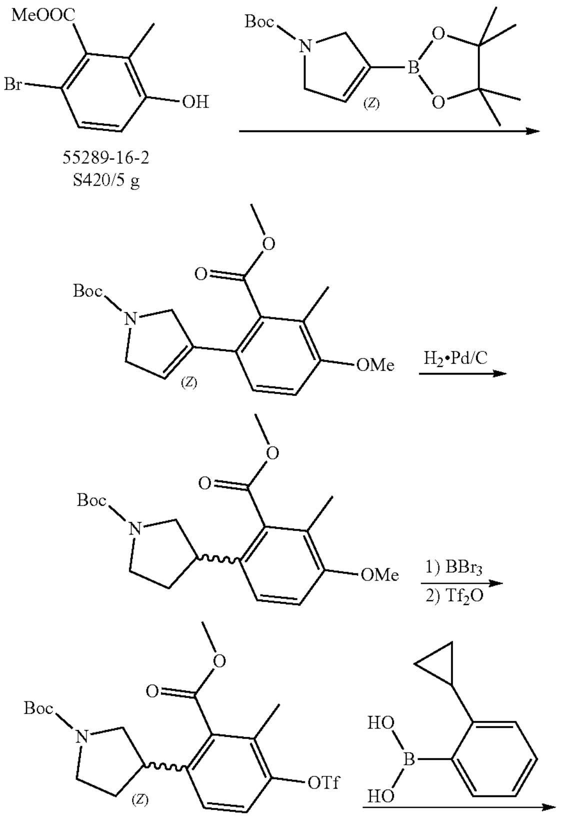
-continued
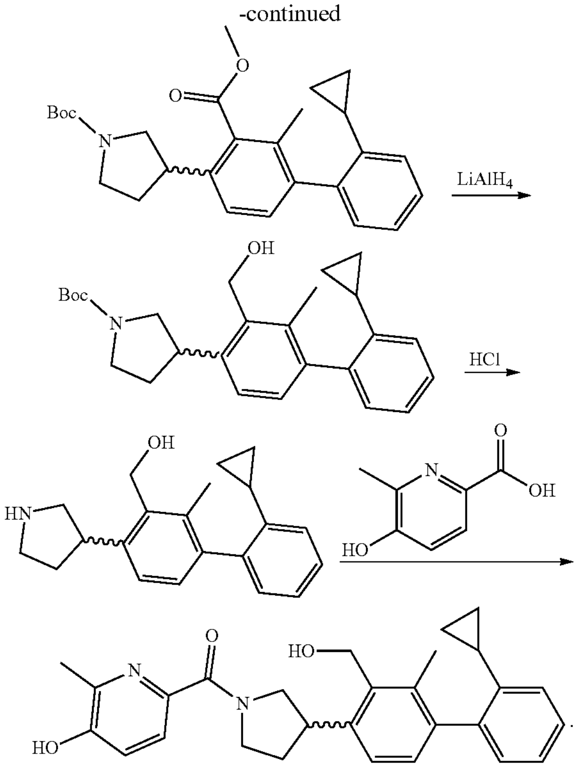
Example 514: Compound 2-176
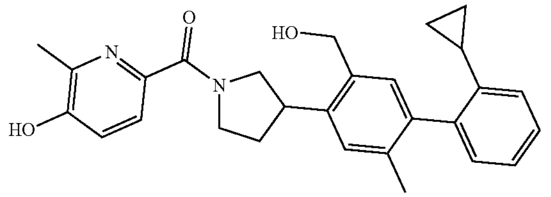 [SMILES: Cc1cc(C2CCN(C(=O)c3ccc(O)c(C)n3)C2)c(CO)cc1-c1ccccc1C1CC1]
The title compound was prepared according to the following procedure:
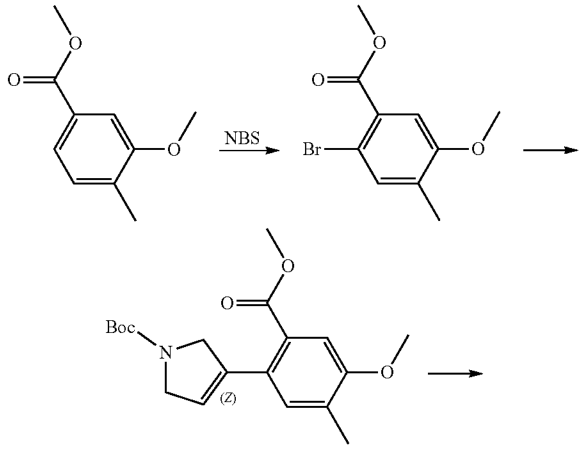

-continued
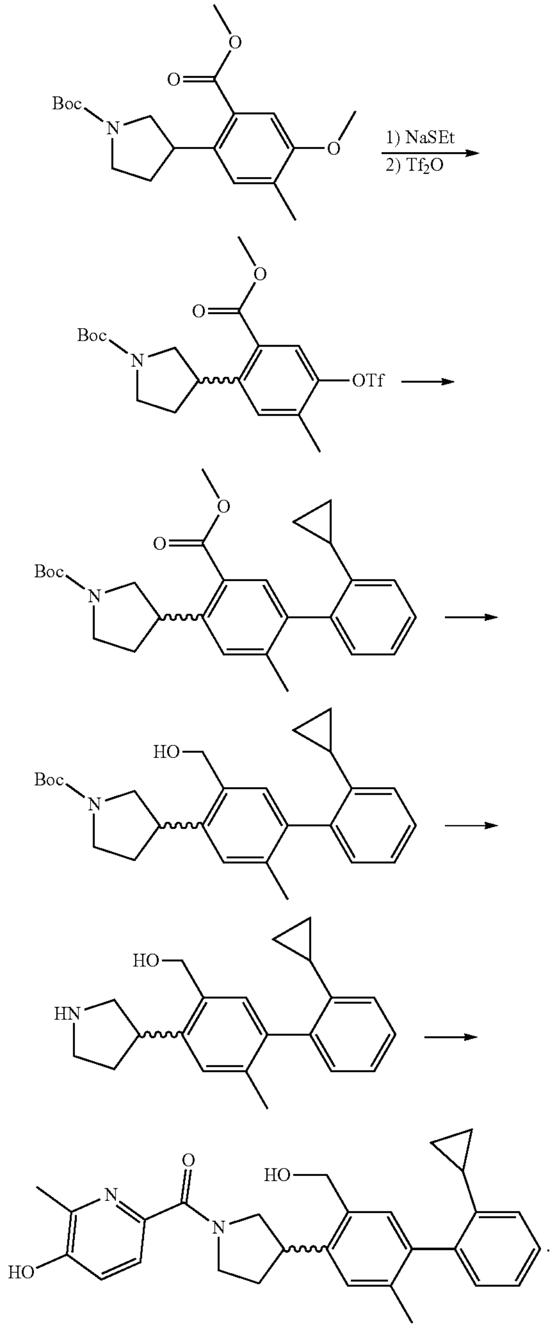
Example 516: Compound 2-178
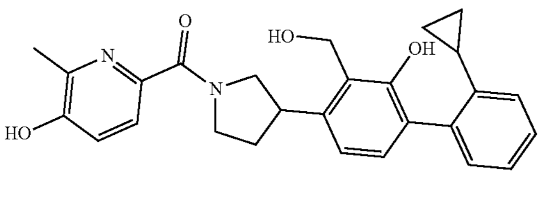 [SMILES: Cc1nc(C(=O)N2CCC(c3ccc(-c4ccccc4C4CC4)c(O)c3CO)C2)ccc1O]
The title compound was prepared according to the following procedure:
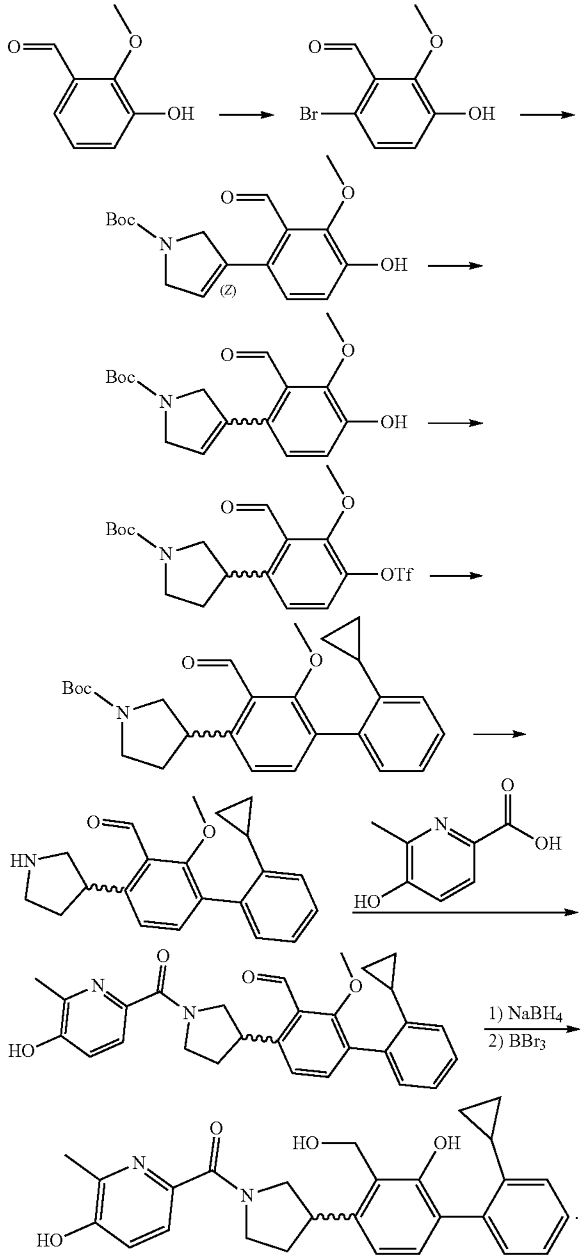
Example 517: Compound 2-179
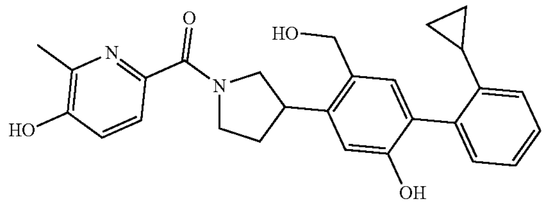 [SMILES: Cc1nc(C(=O)N2CCC(c3cc(O)c(-c4ccccc4C4CC4)cc3CO)C2)ccc1O]

The title compound was prepared according to the following procedure:
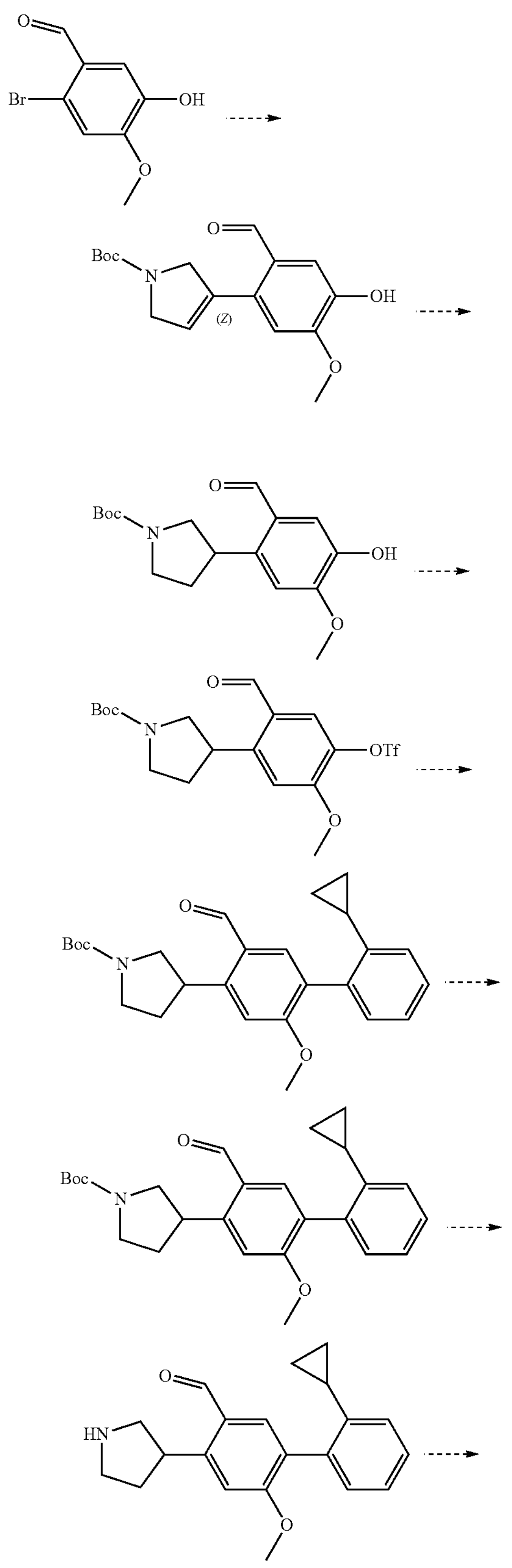
-continued
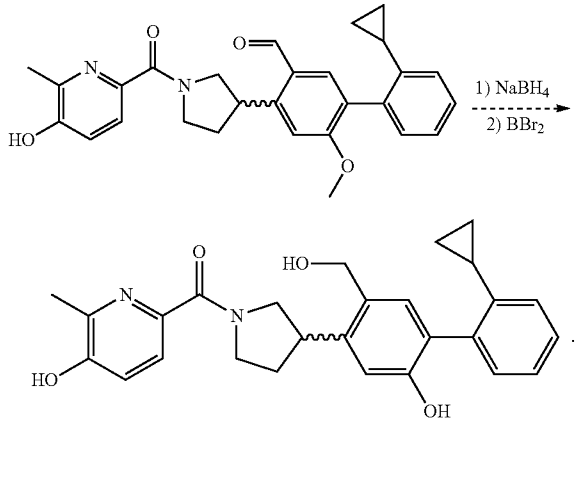
Example 519: Compound 2-181
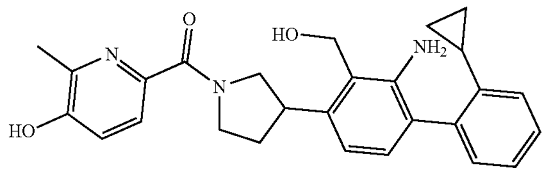 [SMILES: Cc1nc(C(=O)N2CCC(c3ccc(-c4ccccc4C4CC4)c(N)c3CO)C2)ccc1O]
The title compound was prepared according to the following procedure:
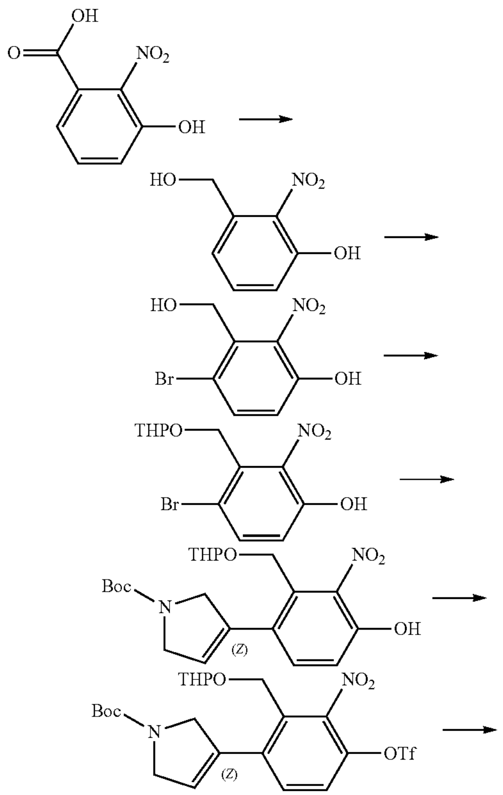

-continued

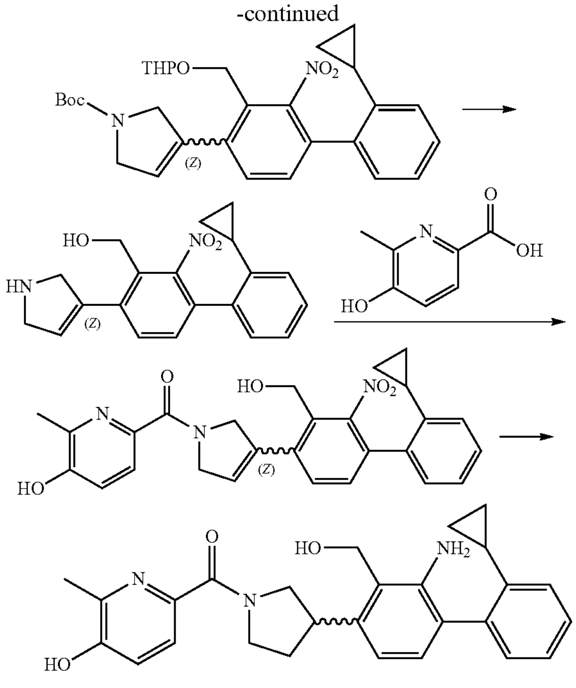

Example 520: Compound 2-182

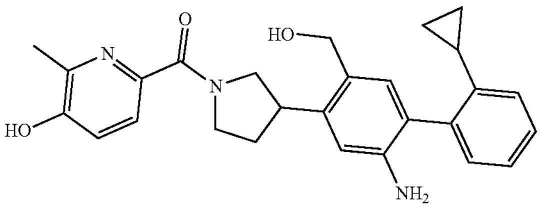 [SMILES: Cc1nc(C(=O)N2CCC(c3cc(N)c(-c4ccccc4C4CC4)cc3CO)C2)ccc1O]

The title compound was prepared according to the following procedure:

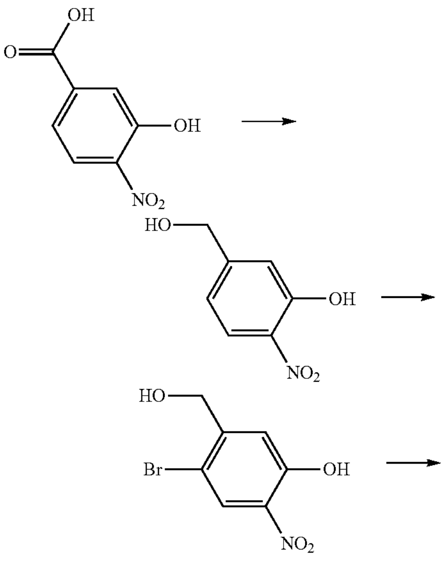

-continued

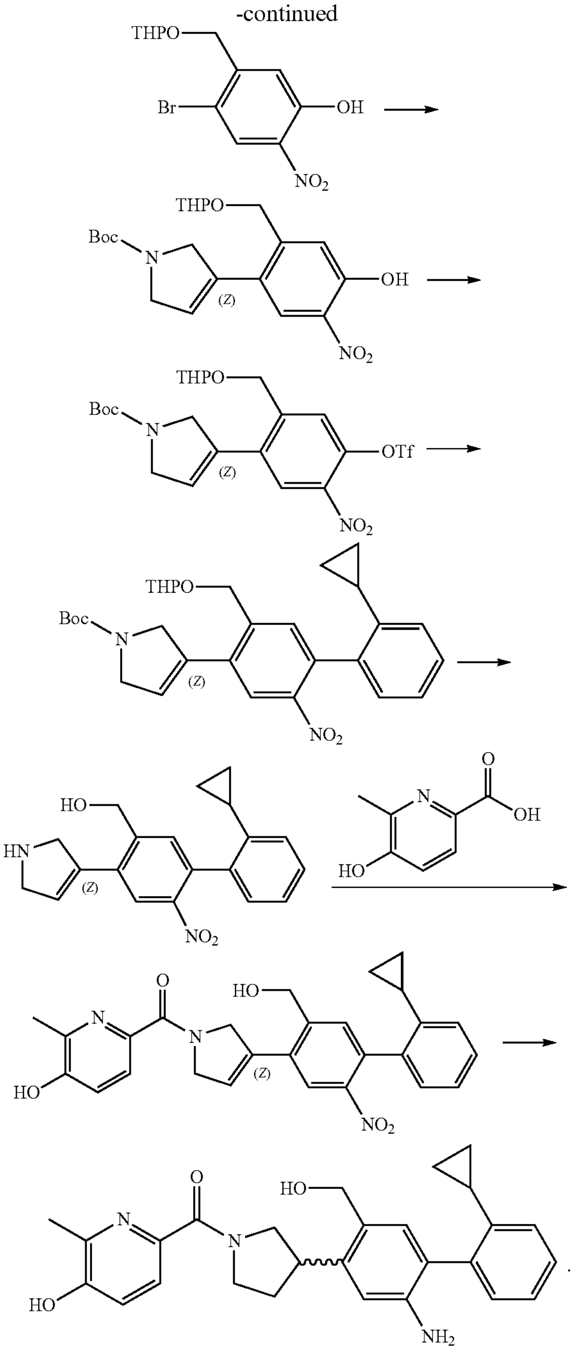

Example 3 Pre-Clinical Evaluation of PK of KM-001 via IV and Topical routes of Administration and assessment of Systemic-to-Skin Penetration and in minipig Model Study Objectives:

To evaluate the dermal irritation potential of KM-001 using topical formulations (ointment) at different KM-001 active concentrations (compared to placebo treatment). To sample blood to determine systemic bioavailability of topically applied KM-001 (in different active concentrations).

To evaluate the IV toxicity of KM-001 and its Pharmacokinetics (PK) at different active concentration. To sample blood for bioavailability following KM-001 IV application (in different active concentrations).

Animal Care:

Animal handling was compliant with guidelines of the National Institute of Health (NIH). Animals were inspected daily for any signs of morbidity or mortality.

Study Design:

On day 0, each animal received a prophylactic loading dose of antibiotic: Pen & Strep inj. susp. (1 ml/10 kg, IM) and Cefzoline HCl (30 mg/kg, IV) and Marbofloxicine (2 mg/kg, slow IV), administered prior to the cannulation procedure. Following induction of anesthesia, animals were placed in dorsal recumbency and the hair covering the animals' treated sites were carefully clipped using an electric clipper. The skin around incision or puncture sites was surgically prepared using Septal Scrub (Chlorhexidine). Two (2) animals participated in this study and were allocated to two groups: Both animals underwent cannulation in the jugular vein in favor of blood sampling during the three days of the experiment. Group 1: The first animal was anesthetized and placed on its abdomen. Eight application areas were drawn on the animal's back. Each area size was 2.5 cm by 2.5 cm. Six areas were applied with the tested substance KM-001 in different concentrations (two with 1%, two with 0.3% and two with 0.1%). In the remaining two areas, placebo was applied. Group 2: The KM-001 Substance was injected IV (bolus) to the marginal ear vein. The animal underwent the procedure during two consecutive days in the morning of each day. On the first day the dose was 0.5 mg/kg, and on the second day 8 mg/kg. After applying the test substance, on day 0, blood samples were taken from the animal at different time points:

For Topical Application:

Day 0—Time 0 (baseline), 60 min, 180 min, 6 h and 24 h. Day 1—6 h and 24 h post application.

For IV Administration:

Blood samples (BS) for PK analysis were drawn at the following time points: Baseline (time 0), 5 min post injection (PI), 30 min PI, 1 h PI, 2 h PI, 6 h PI and. 24 h PI. Blood samples for chemistry and CBC evaluation were withdrawn and sent to an analytical laboratory prior to each application and 6-8 hours following application.

Results:

Draize Test:

Skin evaluation was performed twice during each procedure day (3 hours post application and 6-8 hours post application) for group 1 animal. Tested sites were assessed, and observations were recorded for erythema and edema using a modified Draize scoring system, according to the table 6 below:

TABLE 6

Modified Draize scoring system

| Score | Erythema | Edema |
|---|---|---|
| 0 | No erythema | No edema |
| 1 | Very slight erythema | Very slight edema |
| 2 | Well-defined erythema | Slight edema with raised margin |
| 3 | Moderate to severe erythema | Moderate edema with raised margin ~1 mm |
| 4 | Sever erythema with slight eschar formation | Sever edema with raised margin ~1 mm and extending beyond the area of exposure |

The two pigs tested for two days were scored in each day as "0" or both Draize test components, Erythema and Edema: In other words, no erythema and no edema were observed. None of the pigs showed signs of irritation when treated with KM-001 ointments at all strengths.

Clinical Observations:

Animals were observed individually by the technical staff at least twice daily on regular working days and once daily on weekend, throughout the study period No abnormal clinical signs were observed during the study.

PK Profile:

PK blood samples were collected using tubes containing K2-EDTA as an anticoagulant. Samples were processed for plasma by centrifugation at 2900 g for 10 minutes, at approximately 4° C. Each plasma sample was equally divided into two samples and transferred into pre-chilled polypropylene tubes on dry ice and then quickly frozen over dry ice and kept at −70±10° C. until LC-MS/MS analysis.

Noncompartmental toxicokinetic analysis was performed for KM-001 using Phoenix WinNonlin version 8.0 [Pharsight Corporation, Mountain View, CA, USA]. The IV bolus model was chosen for intravenous administration. Predefined, selected toxicokinetic parameters were estimated from the pig plasma concentration versus time curve.

For the toxicokinetic evaluation, rounded concentration values were used and values below the limit of quantification were set to zero. The toxicokinetic parameters were calculated based on nominal sampling times. All values were rounded to 3 significant digits.

In none of the samples from topically treated pig, KM-001 was detected. Thus, there was no skin to systemic exposure observed with KM-001.

In IV administered of an additional pig receiving KM-001, exposure KM-001 was measured after both administrations:

Apartment maximum concentration (tmax) was at 5 minutes post-dose.

Following intravenous administration at t=0, the plasma concentration-time profile decreased up to 24 h. At dose of 0.5 mg/kg (Day 0), concentration measured at 24 h post-dose was below limit of quantification (LLOQ: 0.300 ng/mL) whereas for a dose of 8 mg/kg (Day 1) there was still KM-001 measurable at 24 h post-dose (61.6 ng/mL)

Exposure based on AUC increased roughly in a dose-proportional manner. Half-time ranged between 3.1 h and 9.5 h, however accuracy of this parameter was low as the regression coefficient was approximately of 0.7. Estimation of the Toxicokinetics (TK) parameters are given in the table below.

TABLE 7

| Estimation of the TK parameters of a male pig. | | | | | | | |
|---|---|---|---|---|---|---|---|
| Dose (mg/kg) | Day | $C_0$ (ng/mL) | $T_{max}$ (h) | $C_{max}$ (ng/mL) | $C_{max}$/dose (kg * ng/mL/mg) | $AUC_{0\text{-}24\,h}$ (h * ng/mL) | $AUC_{0\text{-}t}$ (h * ng/mL) |
| 0.50 | 0 | 552 | 0.0833 | 418 | 836 | 399 | 275 |
| 8.00 | 1 | 2710 | 0.0833 | 2190 | 274 | 3620 | 3620 |

| $AUC_{0\text{-}t}$/dose (h * kg * ng/mL/mg) | $AUC_{0\text{-}\infty}$ (h * ng/mL) | $AUC_{0\text{-}\infty}$/dose (h * kg * ng/mL/mg) | $t_{1/2}$ (h) | Vz/F (mL/kg) | CL/F (mL/h/kg) |
|---|---|---|---|---|---|
| 550 | 337 | 674 | 3.13 | 6690 | 1480 |
| 452 | 4460 | 558 | 9.50 | 24600 | 1790 |

KM-001, when administered intravenously, reaches Tmax at 0.83 h and exhibits near linear dose proportionality when assessed in minipig's plasma.

Example 4: KM-001 Bacterial Mutation Assay (*S. typhimurium* and *E. coli*)

Introduction

Reverse mutation assays employ bacterial strains which are already mutant at a locus whose phenotypic effects are easily detected. The *Salmonella* tester strains have mutations causing dependence on a particular amino acid (histidine) for growth. The ability of test items to cause reverse mutations (reversions) to histidine-independence can easily be measured. The *E. coli* tester strains of the WP2 series are similarly mutant at the tryptophan locus.

Since many chemicals only demonstrate mutagenic activity after metabolism to reactive forms, in order to detect these promutagens the test is performed in the presence and absence of a rat liver metabolising system.

Study Design:

Solutions of the KM-001, were prepared immediately before use in DMSO. Solutions were prepared on a weight/volume basis without correction for the displacement due to the volume of KM-001. Concentrations were expressed in terms of material as received. All test item solutions were used within 1 hour and 10 minutes from the initial preparation.

KM-001 was examined for the ability to induce gene mutations in tester strains of *Salmonella typhimurium* and *Escherichia coli*, as measured by reversion of auxotrophic strains to prototrophy. The five tester strains TA1535, TA1537, TA98, TA100 and WP2 uvrA were used. Experiments were performed both in the absence and presence of metabolic activation, using liver S9 fraction from rats pretreated with phenobarbital and 5,6-benzoflavone. The KM-001 was used as a solution in dimethylsulfoxide (DMSO).

KM-001 was assayed in the toxicity test at a maximum concentration of 5000 μg/plate and at four lower concentrations spaced at approximately half-log intervals: 1580, 500, 158 and 50.0 μg/plate. No toxicity or relevant increases in revertant numbers were observed with any tester strain, at any dose level, in the absence or presence of S9 metabolism. On the basis of the results obtained in this toxicity test, in the Main Assay, using the plate incorporation method, KM-001 was assayed with all tester strains at the following dose levels: 1000, 500, 250, 125 and 62.5 μg/plate.

Main Assay was performed including negative and positive controls in the absence and presence of an S9 metabolising system. Three replicate plates were used at each test point. In addition, plates were prepared to check the sterility of the test item solutions and the S9 mix and dilutions of the bacterial cultures were plated on nutrient agar plates to establish the number of bacteria in the cultures.

The experiment was performed using a plate-incorporation method. The components of the assay (the tester strain bacteria, the test item and S9 mix or phosphate buffer) were added to molten overlay agar and vortexed. The mixture was then poured onto the surface of a minimal medium agar plate and allowed to solidify prior to incubation.

The prepared plates were inverted and incubated for approximately 72 hours at 37° C. After this period of incubation, plates were immediately scored by counting the number of revertant colonies on each plate.

Results:

Toxicity Test

KM-001 was assayed in the toxicity test at a maximum dose level of 5000 μg/plate and at four lower concentrations spaced at approximately half-log intervals: 1580, 500, 158 and 50.0 μg/plate.

Main Assay standard error of the mean for each test point, together with a statistical analysis are presented in Table 8.

TABLE 8

| Bacterial Mutation Assay | | | | | |
|---|---|---|---|---|---|
| | | Without metabolic activation | | With metabolic activation | |
| Strain | Dose level (μg/pl) | Mean of Plate counts | S.E. | Mean of Plate counts | S.E. |
| TA1535 | untreated | 17 | 0.9 | 16 | 1 |
| TA1535 | 1000 | 15 | 0.9 | 16 | 1.2 |
| TA1537 | untreated | 16 | 1.5 | 21 | 1 |
| TA1537 | 1000 | 19 | 0.3 | 17 | 0.9 |

TABLE 8-continued

| Bacterial Mutation Assay | | | | | |
|---|---|---|---|---|---|
| | | Without metabolic activation | | With metabolic activation | |
| Strain | Dose level (μg/pl) | Mean of Plate counts | S.E. | Mean of Plate counts | S.E. |
| WP2 uvrA | untreated | 28 | 0.3 | 38 | 2.1 |
| WP2 uvrA | 1000 | 30 | 2.4 | 35 | 2.4 |
| TA98 | untreated | 29 | 1.3 | 33 | 2.2 |
| TA98 | 1000 | 32 | 0.3 | 42 | 0.3 |
| TA100 | untreated | 125 | 6.2 | 132 | 2.9 |
| TA100 | 1000 | 129 | 5.2 | 147 | 6.1 |

KM-001 was assayed at 1000, 500, 250, 125 and 62.5 μg/plate with all tester strains, both in the absence and presence of S9 metabolic activation. No toxicity or relevant increases in revertant numbers were observed with any tester strain at any dose level, in the absence or presence of S9 metabolism. The sterility of the S9 mix and of KM-001 was confirmed by the absence of colonies on additional agar plates spread separately with these solutions. Marked increases in revertant numbers were obtained in these tests following treatment with the positive control items, indicating that the assay system was functioning correctly. Since a clear negative result was obtained, no further experiment was undertaken.

Evaluation

Results show that mean plate counts for untreated and positive control plates fell within the normal range based on historical control data.

Conclusion:

It is concluded that the KM-001 does not induce reverse mutation in *Salmonella typhimurium* or *Escherichia coli* in the absence or presence of S9 metabolism, under the reported experimental conditions.

Example 5: The Effect of KM001 Treatment on Keratinocyte Involucrin mRNA Expression in TRPV3 Mutant Transfected Cells 250K nHEK cells were seeded in 10 cm2 plates and settle for 5 days in medium contend 0.1 mM Ca+2. After 5 days cells were transfected with plasmid contend TRPV3 mutant for 24 h in medium contend 0.3 mM Ca+2 and KM001 was added in 4 different concentrations 0.1, 0.25, 0.5, and 1 μM 24 h post-transfection.

Total RNA was extracted from the cells by using innuPREP RNA Mini Kit (cat. #845-KS-2040050). cDNA was performed using qPCRBIO High-quality cDNA synthesis Kit (cat. #PB30.11-10).

Involucrin expression levels were measured by QPCR using qPCRBIO Fast qPCR SyGreen Blue Mix, Hi-ROX (cat. #PB20.16-20). With the following primers: Forward 5'-CTGCCTCAGCCTTACTGTGA-3' (SEQ ID NO: 2), Revers 5'-GGAGGAGGAACAGTCTTGAGG-3' (SEQ ID NO: 3). Involucrin expression levels were normalized to HPRT expression levels in each sample. HPRT expression levels were measured using the following primers: Forward 5'-CATTATGCTGAGGATTTGGAAAG-3' (SEQ ID NO: 4), Revers 5'-CTTGAGCACACAGAGGGCTACA-3' (SEQ ID NO: 5).

FIG. 1 shows the results of Involucrin mRNA expression. As can be seen in this figure, nHEK transfected cells with TRPV3 mutant (T) showed elevated levels of Involucrin mRNA expression compared to non-transfected cells. In addition, treatment with 0.1, 0.25, 0.5 μM KM-001 showed reduce expression of involucrin, 1 μM KM-001 did not affect involucrin expression.

Treatment with KM-001 at concentrations between 100 to 500 nM reduced the expression of mRNA of terminal differentiation markers in keratinocytes expressing mutant form of TRPV3, thus normalizing abnormalities in keratinocytes differentiation pattern.

Example 6: 7-Day Preliminary Dermal Tolerance/Toxicity Study in Minipigs

The purpose of this preliminary dose range finding study is to investigate the tolerance/toxicity of KM-001 Ointment, 0.1% w/w, 0.3% w/w and 1% w/w in minipigs after twice daily dermal administrations, in order to select dose levels for subsequent studies. The kinetic profile is also to be evaluated.

KM-001 has been administered by direct dermal application.

Animal Care:

A total of 18 Gottingen minipigs (9 males and 9 females) approximately 4-5 months old and weighing 9-11 kg, were ordered from Ellegaard Göttingen Minipigs (Dalmose, Denmark). Each animal was given a detailed physical examination by a veterinarian at the end of the quarantine period. An acclimatization period of approximately 3 weeks was carried out before the start of experimental procedure.

The animals were housed in a limited access animal facility. Animal room controls were set to maintain temperature and relative humidity at 22° C.±2° C. and 55%±15%, respectively.

Study Design:

On the day of allocation (about 7 days prior to treatment) all animals were weighed and allocated to groups as detailed in Table 9 below.

TABLE 9 study details

| Group No | Treatment | Test item concentration (%, w/w) | Dose mass (g/animal/day | Approximate dose level (mg/kg/day)* | Minipig numbers M (even) | Minipig numbers F (odd) |
|---|---|---|---|---|---|---|
| 1 | Control (placebo) | 0 | 6 × 2 | 0 | 2, 4 | 1, 3 |
| 2 | KM-001 | 0.1 | 6 × 2 | 0.9 | 6, 8 | 5, 7 |
| 3 | KM-001 | 0.3 | 6 × 2 | 2.7 | 10, 12 | 9, 11 |
| 4 | KM-001 | 1 | 6 × 2 | 9 | 14, 16 | 13, 15 |

*In terms of active ingredient (calculated on a mean body weight of 14 kg)

A 6 g aliquot of each formulation have been administered and spread evenly over the skin of the prepared site by gentle massage, over an area of approximately 20×25 cm (which represents approximately 10% of the body surface) in animals of the relevant group. An area of approximately 20×5 cm of the prepared skin, posterior to the treated areas, was remained untreated and acted as a control. Approximately 6 hours later, the treated site was cleaned by washing with a piece surgical gauze soaked with warm water, removing any residual test item. The treatment then was repeated in the same manner. Each day, prior to the first administration, the treatment sites were cleaned by washing with surgical gauze soaked with lukewarm water.

All animals were dosed twice a day, for 7 days up until the day before necropsy. Throughout the study, all animals were checked twice a day. Samples of urine and bone marrow were obtained at necropsy. A complete necropsy was performed in all cases. All clinical signs have been recorded for individual animals. Once before commencement of treatment and daily during treatment, each animal was observed and any clinical signs were recorded. Observations have been performed at the same time interval each day.

Each day, prior to each application of the test and control items, the treatment site of all animals was examined. Irritation of the site, when compared to adjacent untreated skin, was assigned a numerical value according to Table 6 above.

Blood samples of at least 2 mL each were collected at the following time points: pre-dose, 15, 30 minutes, 1, 2, 6 and 24 hours after treatment on Day 1 and 7 of treatment. Controls have been bled at 1 time point only. Samples were transferred into tubes containing K2EDTA anticoagulant and kept on ice until centrifuge. Samples were centrifuged in refrigerated conditions (approximately +4° C.), the plasma and were divided in two aliquots and frozen at −80° C. Analysis of the samples was carried out by the Analytical Chemistry Department of ERBC, according to the validated analytical method (ERBC Study No. A4005).

Results:

Haematology: No relevant changes were observed. eticulocytosis was observed in one female dosed with the test Item 2. Compared with the pre-test data, the increment was 3.4 fold. This finding was not considered treatment-related due to the lack of dose-dependence. Coagulation: No changes were recorded. Clinical Chemistry: No changes were recorded. Urinalyses: No changes were recorded. Terminal body weight and organ weights: No relevant changes were observed in terminal body weight and organ weights of treated animals of both sexes, when compared to the controls. Any organ weight changes were within the range of occasionally observed and expected spontaneous changes in Göttingen minipig of the same age and considered unrelated to treatment. Macroscopic observations: No systemic or local treatment-related changes were noted following gross pathology examination in animals of both sexes euthanized after the last treatment. Locally, at the site of administration, cutaneous red colour was observed in all males of low and mid dose groups, in all control females and in one animal of each of the female low, mid and high dose groups. These changes were considered related to the administration procedure and not to the test item since there was no corresponding microscopic observations and no dose relationship and since it was observed in control animals. Any other macroscopic observations were within the range of occasionally observed and expected spontaneous changes in Gottingen minipig of the same age and considered incidental and unrelated to treatment. Microscopic observations: The skin treated with KM-001 Ointment, 0.1% w/w, 0.3% w/w and 1% w/w did not show any treatment-related changes, when compared with the correspondent untreated site of the same animal or when compared with the control animals treated with placebo. Any microscopic observations were within the range of occasionally observed and expected spontaneous changes in Göttingen minipig of the same age and considered incidental and unrelated to treatment.

SUMMARY

No relevant changes were observed in terminal body weight and organ weights of treated animals of both sexes, when compared to the controls. No systemic or local treatment-related changes were noted following gross pathology examination in animals of both sexes euthanized after the last treatment. The skin treated with KM-001 Ointment, 0.1% w/w, 0.3% w/w and 1% w/w did not show any treatment-related changes, when compared with the correspondent untreated site of the same animal or when compared with the control animals treated with placebo.

Example 7: Topical Pharmacokinetics and Skin Irritation of KM-001

The aims of the study were to evaluate the dermal irritation potential of KM-001 using topical application of KM-001 (1 gr per area) for 3 days repeated dosing, and to assess blood samples for PK evaluation for bioavailability following KM-001 using topical administration at two KM-001 active concentrations.

Animal Care:

Animal handling was compliant with guidelines of the National Institute of Health (NIH). Animals were housed in a closed Swine Facility for the whole period of the study in designated cages. Animals were provided with a commercial swine diet twice a day. Meals were served using a designated cup, pre-measured to contain ~100 gr of the food per animal per meal. Water was available ad libitum to all animals, supplied to each cage via stainless steel sipper-tubes. Animals were housed under standard conditions, under a 12 hours light/dark cycle. The pigs' environment was controlled by a HVAC system (heating, ventilation, and air conditioning) at a temperature range of 16-27° C. and a relative humidity of 30-70% with adequate fresh air.

Study Design:

On day −2 the animal was anesthetized according to the anesthesia protocol underwent cannulation in the jugular vein in favor of blood sampling during the three days of the experiment.

On day 0, 1 and 2, each one of the animal received repeated dosing (No occlusion). The tested sites and (KM-001 ointment 1%) remains w ere washed ~6 hour post implantation. Each day blood samples were drawn from the animal at different times for pharmacokinetic evaluation were collected. Draize score was performed on daily basis up to 6 hr post application (two time points: 2 h pa and 6 h pa) Clinical signs will be performed daily. Irritation; (erythema, edema). Erythema and edema were assessed using a modified Draize scoring system as detailed in Table 6 above. Placebo vs. 2 treatment groups of ointment (0.3% and 1.0%) were applied onto three large application sites for topical route as follows:

After administration of the test substance, blood was taken from the animal at different time points. Day 0: baseline (time 0), 30 min post application (pa), 2 h pa, 6 h pa, 24 h pa. Day 1: • No blood samples were drawn. Day 2: Baseline (time 0), 2 h pa.

PK blood samples were transferred into pre-chilled commercial polyethylene microcentrifuge tubes containing K2-EDTA as an anticoagulant. Samples were processed for plasma by centrifugation at 2900 g for about 10 minutes, approximately 4° C. Each plasma sample was equally divided into two samples and transferred into polypropylene tubes pre-chilled on dry ice and then quickly frozen over dry ice and will be kept at −70±10° C. until LC-MS/MS analysis. Samples of plasma, skin and CSF were analyzed.

Results:

Animals were observed daily throughout the study period. No abnormal clinical signs were observed during the study.

Draize Test Evaluation Results:

No edema/erythema were observed. All tests indicated score "0".

All porcine plasma samples were measured below the limit of quantification for KM-001 (0.300 ng/mL) therefore no pharmacokinetic evaluation was performed for the tested pigs.

Example 8: Anti-Pruritic Activity of KM-001 in a Murine Model of Acetone-Ether-Water-Induced Pruritus The aims of the study to evaluate the efficacy of the test article KM-001 in an AEW induced pruritus model in male C57BL/6J mice. A total of 72 male C57BL/6J mice were used in this study. The right cheek of all animals were shaved 1 day before the start of the experiment. The shaved cheek area was treated twice daily with either an acetone/ether/water (AEW) mixture or water for 5 days. Animals were randomized into 6 groups based on body weight on day 4. On day 5, body weight was recorded in the morning. Test compound KM-001-P1 (0.1 mg/kg), KM-001-P1 (0.01 mg/kg), was administered orally to 20 mice 30 minutes before video recording. Behavior of 8 mice was video recorded. The amount of time spent scratching and the number of bouts during the 20 minutes were recorded by an observer blinded to treatment group. Another 12 mice per treatment group were used for evaluation of compound exposure. Blood and skin samples were collected at 0, 0.5, 1 and 1.5 hour post dosing.

The TRPA1 inhibitor HC-030031 (4 mg/mice) served as the positive control for this study and was subcutaneously administered 5 minutes before recording the AEW evoked itch behavior. Immediately after AEW, the mice were placed in the cages and behavior was recorded for 90 min using a video camera.

Animal Care:

C57BL/6J mice (6-7 weeks old), male, were purchased from Jiangsu Gem Pharmatech, Co., Ltd. Animals were acclimatized for 1 week prior to the experiment. All the in vivo experimental procedures were approved by the institutional animal care and use committee (IACUC) at HDB. Euthanasia procedures was performed using carbon dioxide inhalation and all efforts were made to minimize animal suffering. The AUF number for this study at HDB is 170. Animals were housed (5 per cage) with bedding under controlled temperature (20-25° C.), noise, humidity (40-70%), and lighting (12 h light and 12 h dark) conditions. All animals had free access to purified water and standard certified rodent chow (Beijing Keaoxieli Feed Co., Ltd.).

Study Design:

At the beginning of the study, 8 mice were randomized to group 1 (naïve group). Other animals were treated with AEW and randomized into groups 2, 3, 4, 5 and 6 on day 4 based on body weight before compound treatment. Group information was as below in Table 10.

TABLE 10

Group and Dose Design

| Group | # of Animals | Compound Treatment | Dosing Route | Dosing Time before AEW |
|---|---|---|---|---|
| 1 | 8 | 4% DMSO/10% Solutol/86% WFI (Vehicle1) | PO | −30 min |
| 2 | 8 | 4% DMSO/10% Solutol/86% WFI (Vehicle1) | PO | −30 min |
| 3 | 12 (8 for study, 12 for PK analysis) | KM-001-P1, 0.1 mg/kg | PO | −30 min |
| 4 | 12 (8 for study, 12 for PK analysis) | KM-001-P1, 0.01 mg/kg | PO | −30 min |
| 5 | 10 | 12.5% DMSO/87.5% PBS (Vehicle2) | SC | −5 min |
| 6 | 10 | HC-030031, 4 mg/mouse (positive control) | SC | −5 min |

Day Days 1-3: AEW treated twice (at least 3-4 hours apart), acetone-alcohol (AE) 30 s, Water 30 s. Day 4-5: AEW treated twice (at least 3-4 hours apart), AE 15 s, Water 30 s. Day 5: Compound dosing, video record, plasma and skin sample collection.

The general condition (appearance, activity and spontaneous activity) of all animals was monitored daily by the attending veterinarian. Immediately after AEW application, behavior of the mice was recorded for 60 min using a video camera under unmanned conditions to assess spontaneous scratching. Videos were manually scored for time spent spontaneously scratching the affected cheek for 20 minutes (between 10 to 30 min).

Scratching is defined as an episode in which a mouse lifted its paw and scratched continuously for any length of time, until the paw returned to the floor. Only scratches of the affected cheek with their hind paws were counted. Other scratching behaviors were disregarded. Behavioral scoring was performed by an observer blinded to the experimental condition. Scratch time (s) and Scratch bouts per 20 min were be generated for analysis.

Results:

Scratching Reaction

Following five days of twice daily application of AEW or water, mice were administrated KM-001-P1 0.1 mpk (Group 3), KM-001-P1 0.01 mpk (Group 4), HC-030031 4 mg/mouse (Group 6), 4% DMSO/10% Solutol/86% WFI (vehicle1, Group 1 and Group 2) or 12.5% DMSO/87.5% PBS (vehicle 2, Group 5). KM-001-P1 and vehicle1 were administrated 30 minutes before video recording. Positive control HC-030031 and vehicle 2 were administrated 5 minutes before video recording.

Figure 2A:
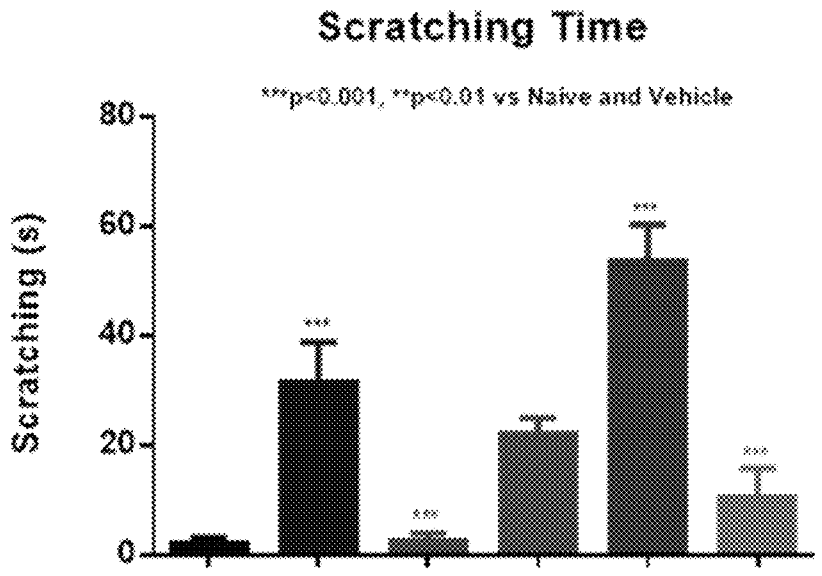
FIGS. 2A and 2B are bar graphs showing scratching time and scratching bouts, respectfully.
Figure 2B:
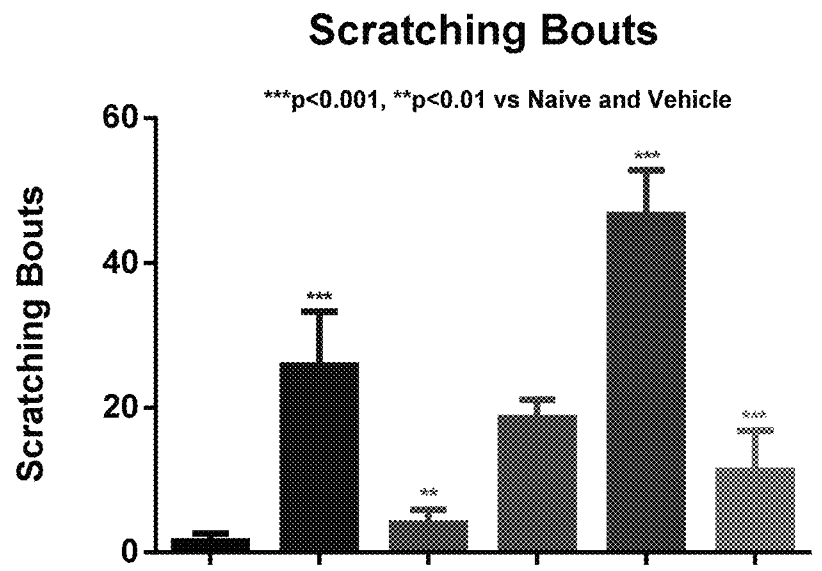

The number of scratches of the affected cheek with their hind paws was counted (scratching time and scratching bouts). Scratching behavior was counted between 10-30 min. As shown in FIGS. 2A and 2B, AEW treated mice group had a significant increase of scratching time and scratching bouts as compared with naive control mice and KM-001-P1 treatment at 0.1 mpk dose level significantly decreased scratching time and bouts. KM-001-P1 treatment at 0.01 mpk treatment trended to decrease scratching time and scratching bouts. Vehicle 2 treated mice group also had a significant increase of scratching time and scratching bouts as compared with naive control mice, HC-030031 treatment significantly decreased scratching time and scratching bouts.

FIG. 2A shows the scratching time. Group2 (G2) Vehicle1 versus Group1 Naïve. P=0.0001, Group3 (G3) KM-001-P1 0.1 mpk versus Group2 Vehicle1. P=0.0002, Group4 (G4) KM-001-P1 0.01 mpk versus Group2 Vehicle1. P=0.2124, Group5 (G5) Vehicle2 versus Group1 Naive. P=0.0001, Group6 (G6) HC-030031 versus Group5 Vehicle2. P=0.0005

FIG. 2B shows scratching bouts. Group2 Vehicle1 versus Group1 Naïve. P=0.0002, Group3 KM-001-P1 0.1 mpk versus Group2 Vehicle1. P=0.0016, Group4 KM-001-PI 0.01 mpk versus Group2 Vehicle1. P=0.4288, Group5 Vehicle2 versus Group1 Naive. P=0.0001, Group6 HC-030031 versus Group5 Vehicle2. P=0.0005.

Pharmacokinetics of KM-001 was evaluated in plasma and skin samples after oral compound administration in C57BL/6J mice. Plasma and skin samples were collected at 0, 0.5, 1 and 1.5 hour post dosing. 0.1 mpk KM-001 reached its peak concentration in plasma at 0.5 hr post dosing. Maximum concentrations observed were 1.34 ng/ml in plasma. However, KM-001 was undetectable.

Figure 3:
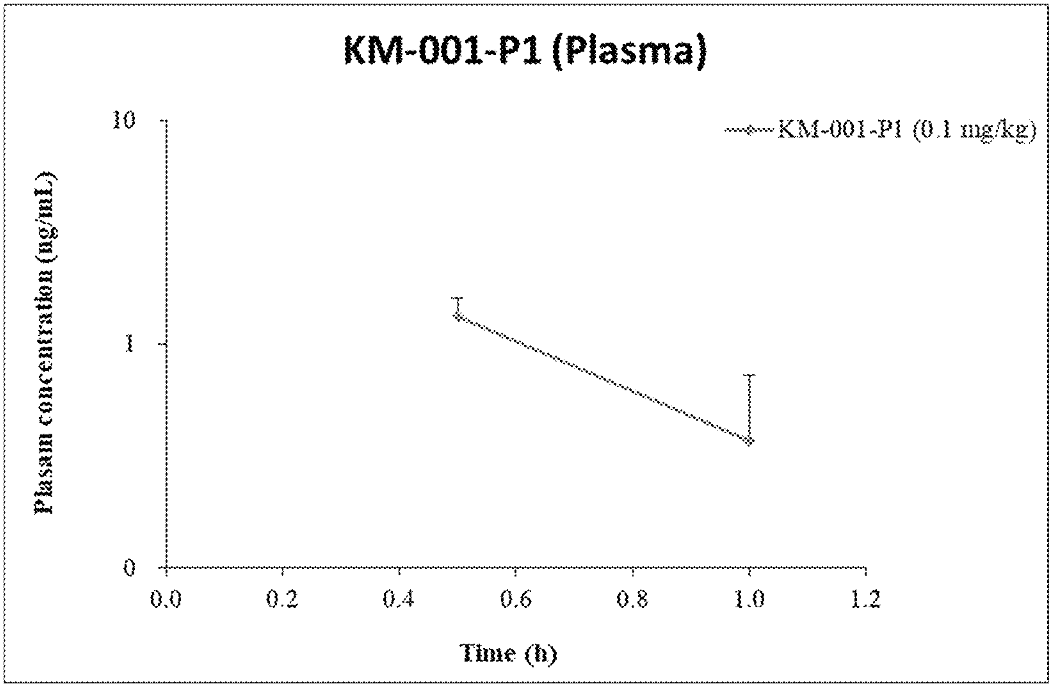
FIG. 3 is a graph showing plasma concentration (ng/ml) of KM-001-P1 after PO administration.

FIG. 3 shows plasma concentration (ng/ml) of KM-001-P1 after PO administration to male C57BL/6J mice.

AEW application twice a day for 5 days significantly increased spontaneous scratching time and number of bouts in C57 BL/6J mice.

KM-001-P1 (0.1 mpk) concentration in plasma peaked at about 0.5 hr post compound dosing and reached 1.34 ng/ml. Treatment with KM-001-P1 (0.1 mg/kg) significantly decreased the scratching time and scratching bouts ($P<0.001$ in scratching time and $P<0.01$ scratching bouts). Treatment with KM-001-P1 (0.1 mg/kg) trended to decrease scratching time and scratching bouts. The positive control HC-030031 (4 mg/mouse) significantly decreased scratching time and scratching bouts ($P<0.001$, $P<0.001$).

Results from this study indicated that administration of KM-001-P1 (0.1 mpk) have a robust anti-pruritic effect on AEW-induced dry skin pruritus model in mice.

Example 9: KM-001: Bioavailability Study in Rats by Intravenous, Oral and Dermal Routes The bioanalytical method in rat plasma for the determination of KM-001 was validated using a liquid chromatographic system coupled with a tandem mass spectrometric detector (LC-MS/MS). Deuterated KM-001 was used as internal standard (ISTD).

Stock and working solution stability test indicated that KM-001 and ISTD solutions were stable for up to 54 days at +4° C. The results for validation are summarized below: Selectivity was assessed in blank rat plasma from six different animals and no interfering peaks were found at the KM-001 and ISTD retention times. No effect in hyperlipidemic and hemolyzed plasma was observed. Linearity was assessed in the range from 0.3025 ng/mL to 10000 ng/mL in rat plasma. Accuracy and precision were tested at 0.7663 ng/mL (QCL), 4000 ng/mL (QCM) and 8000 ng/mL (QCH). LLOQ accuracy and precision were tested at 0.3025 ng/mL. No dilution effect (10-fold) with blank rat plasma was observed when assessed at 71430 ng/mL (10-fold). The stability study in rat plasma indicated that KM-001 was stable at low (QCL) and high (QCH) concentrations in the following storage conditions:

Plasma samples of approximately 100 μL (2 aliquots) were obtained from blood samples collected at Pre-dose, 30 minutes, 1, 3, 6 and 24 hours from the start of treatment from animals treated by intravenous bolus (Group 1), dermal (Group 2) and oral route (Group 3). Plasma samples were stored at −80° C. until analysis. Bioanalysis was conducted following a validated method.

Figure 4:
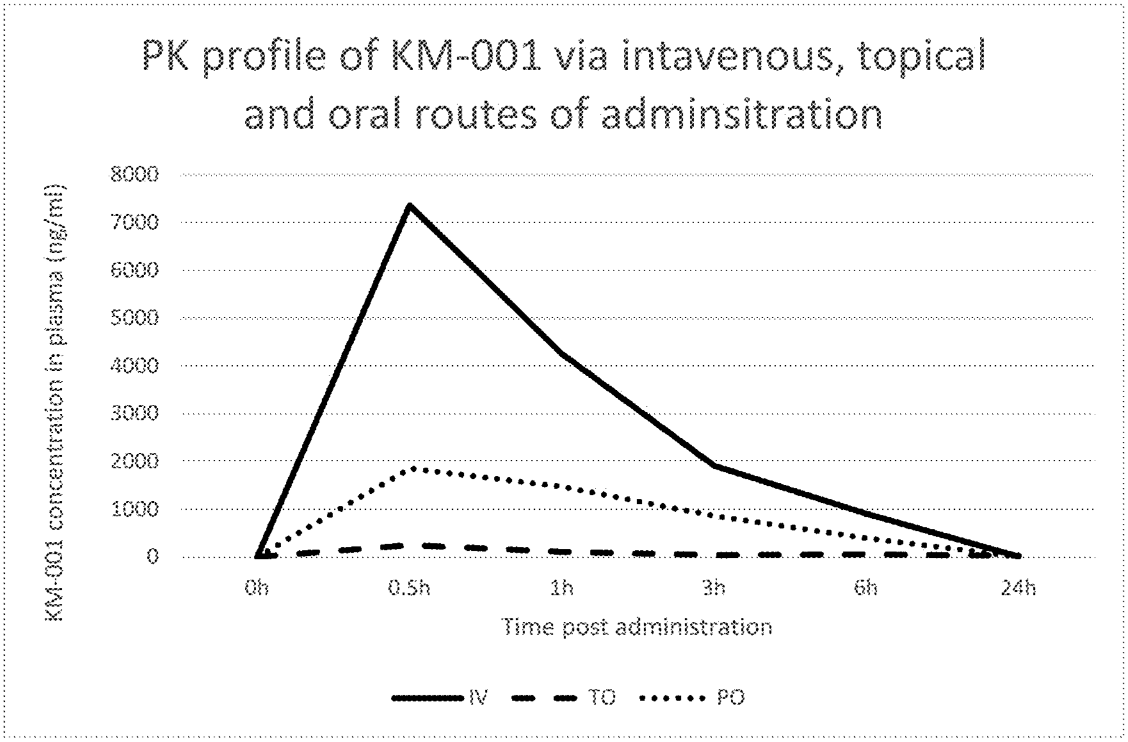
FIG. 4 is a graph showing bioavailability studies of KM-001.

Results of bioanalysis are presented in FIG. 4. Samples indicated as BLOQ were found to be below the validated limit of quantification (0.3025 ng/mL).

Example 10: The Effect of KM-001 Treatment on Protein Markers of Differentiation in Cultured Human Keratinocytes The aim of the experiment was to characterize differentiation profile of cultured human keratinocytes following treatment with KM-001

Study Design:

250K nHEK cells were seeded in 10 cm2 plates and were incubated for 5 days in medium containing 0.1 mM Ca+2. To induce cellular differentiation, 5 days following the seeding, the growth medium was changed to a medium containing 1.2 mM Ca+2, and the keratinocytes cultures were incubated overnight. Thereafter, KM-001 in 4 different concentrations (100, 250, 500, and 1000 nM) was added to the cells for 24 h incubation.

Protein Extraction from the Cells:

nHEK cells were rinsed once with cold DPBS, detached from the growth surface by applying TripLE, and were centrifuged at 1100 rpm for 5 min. Immediately before use, 10 μL/ml of Halt Protease Inhibitor Cocktail and 10 μL/ml of EDTA 0.5M were added directly to the cell lysis buffer (RIPA buffer). 250 μl cold lysis buffer was added to each sample and the samples were put on ice for 15 min. After 15 min, samples were centrifuged at ~14,000×g for 15 min to remove pelleted cell debris.

Protein concentrations were measured by Pierce™ BCA Protein Assay Kit based on manufacturer instructions.

To measure filaggrin and involucrin levels Western Blot (WB) analysis was performed:

25 μg of protein from each sample mixed with sample buffer and was loaded and incubated at 75° C. for 10 min. Samples were then loaded to the SDS/PAGE gel and were run at 220V for 45 min. Proteins from the gel were transferred to nitrocellulose membrane using Gel Transfer System Trans-Blot Turbo.

BSA 5% blocker solution was added to the membrane for 60 min in RT under gentle shaking. Primary antibody was added overnight under refrigerator conditions and gentle shaking. Following the above steps, the membrane was washed 3 times with TBST×1 for 5 min. Secondary antibody was added for 60 min incubation and rinsed 3 times with TBST×1 for 5 min each. and dried in Whatman paper. The membrane, then was exposed to ECL solution development according to manufacturer's instructions.

Figure 5A:
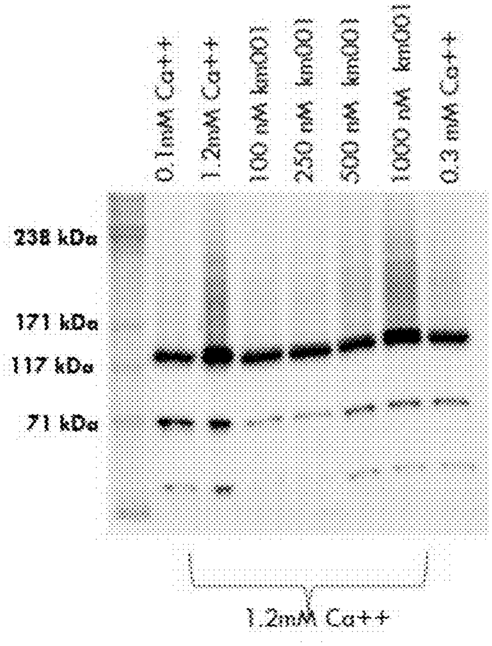
FIGS. 5A and 5B are SDS-PAGE images showing effect of various concentrations of KM001 on involucrin and filaggrin, respectively.
Figure 5B:
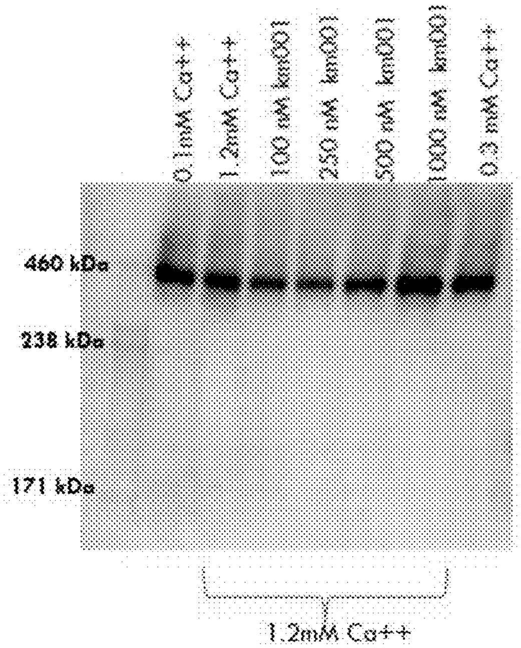

FIGS. 5A and 5B show the effect of various concentrations of KM001 on involucrin and filaggrin, respectively.

As can be seen in these figures, treatment of cultured human keratinocytes with KM-001 at concentration of 100 nM, 250 nM and 500 nM KM-001 lead to decrease in the expression of involucrin and filaggrin, whereas higher concentration of KM-001 does not affect the proteins levels.

Example 11: Determine the Effect of KM-001 on Locomotor Activity in C57 Mice

The aim of the study is to evaluate the effect of KM-001 on locomotor activity in CD-1 mice.

Animal Care:

Animals were randomly assigned to cages containing corncob bedding material. Room temperature was maintained within the range 65-82° F. and relative humidity within the range 30-80%. The room was illuminated with fluorescent lighting on a daily 12-hour light/dark cycle. Animals were checked a minimum of once a day. Cages were changed and cleaned a minimum of twice weekly. All animals had free access to dry mouse food. Municipal tap water was freely available.

Study Design:

KM-001 was prepared as solutions of 0.3 1.0 & 3.0 mg/mL in 10% Solutol HS-15, 90% WFI. For each dose concentration, KM-001 was weighed into a 20 mL glass vial. Solutol was added and the compound vortexed, then placed briefly in a 50° C. water bath until dissolution occurred. Each solution was brought to its final volume by addition of water for injection (WFI).

The spontaneous locomotor activity of each animal was recorded by using the infrared equipped open field activity monitoring system (Model: Opto-M3) purchased from Columbus Instruments, Columbus, OH. The system consists of 12 activity monitoring chambers and 2 interface boxes. Each chamber has low level and high level infrared emitters and detectors surrounding the chamber to form a grid. Beam spacing is 1 inch and beam diameter is 0.125 inch. As animals cross the grid, the beam breaks are recorded to represent the animal's locomotor activity. Low level infrared beam breaks represent horizontal activity.

Animals were removed from their home cage and numbered on the tail. Body weight was measured and recorded in grams. Animals were then randomly assigned to different treatment groups. Animals were placed into activity chambers, one per chamber, and acclimated for 30 minutes. At the end of the 30-minute acclimation period, animals were removed from activity chambers and orally administered 10 mL/kg vehicle or KM-001. Another group of mice received 3 mg/kg D-Amphetamine SC. Immediately following dosing, animals were returned to the chamber they were acclimated in for activity recording. Each animal's horizontal locomotor activity was recorded for 90 minutes. Recording software was set at 1-minute intervals. Treatment groups were assigned to different recording channels.

Animals were randomly assigned to each dosing group, as shown in the table bellow:

TABLE 11

Details on groups for testing

| Group | Species | Compound | Dose (mg/kg) | Route | Vehicle | End-point |
|---|---|---|---|---|---|---|
| #1 | ♂ CD-1 mice | Vehicle | n/a | PO | 10% Solutol, 90% WFI | Horizontal activity for 90 minutes post dose |
| #2 | | KM-001 | 3 | PO | 10% Solutol, 90% WFI | |
| #3 | | KM-001 | 10 | PO | | |
| #4 | | KM-001 | 30 | PO | | |
| #5 | | D-Amph | 3 | SC | 0.9% NaCl | |

Body weights were taken and recorded during the morning of the day of testing.

Compounds were orally administered using a 1 cc syringe (BD, Franklin Lakes, NJ) with a 20G 1½" disposable gavage needle (Popper & Sons, New Hyde Park, NY). Subcutaneous (SC) drug administration was accomplished using a 1 cc syringe and 25G needle (BD). All dose volumes were administered at 10 mL/kg At the end of locomotor activity recording, all animals were humanely euthanized by CO2 inhalation. Blood was collected via cardiac puncture and placed into microtainers containing EDTA (B-D). Blood was centrifuged at 8,000 rpm for 6 minutes and plasma stored in separate Eppendorf tubes. Plasma was stored at −80° C. for subsequent analysis by LC/MS/MS.

Data for horizontal activity were presented as the mean±SEM, and comparison between vehicle and KM-001 groups was performed using a One-way ANOVA. A probability of $p<0.05$ was considered significant. A comparison between vehicle and positive control was performed using a 1-tailed Student's t-test.

Results:

Locomotor Activity of CD-1 Mice Administered KM-001:

Groups of eight 7 week old male CD-1 mice were acclimated to the locomotor activity chambers for 30 minutes prior to dosing. Animals were dosed orally with 10 mL/kg 10% solutol, 90% WFI, 0.9% NaCl or 3, 10 or 30 mg/kg KM-001. Control animals were administered 3 mg/kg subcutaneous D-Amphetamine. Horizontal locomotor activity was recorded for 90 minutes. One animal was removed from the D-Amphetamine dose group due to a mis-injection. Male CD-1 mice dosed with 3 10 or 30 mg/kg KM-001 showed no significant increase in locomotion as compared to vehicle control (One-way ANOVA $p=0.38$). The positive control, 3 mg/kg D-Amphetamine SC significantly increased horizontal activity ($p<0.005$).

Figure 6:
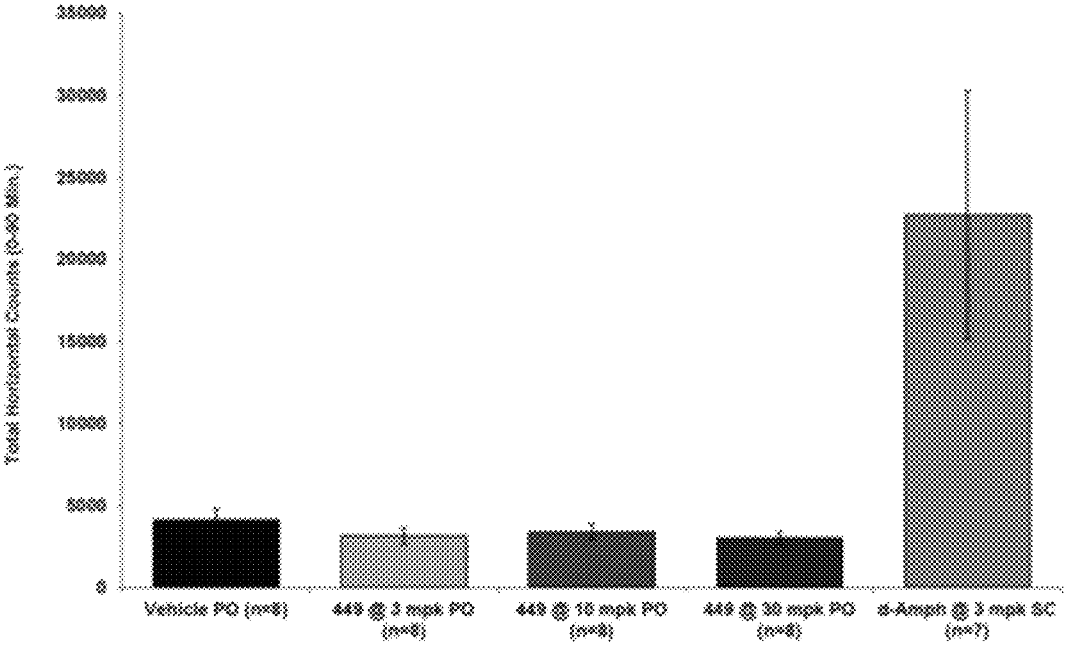
FIG. 6 is a bar graph showing the effect of KM-001 on total horizontal counts.

FIG. 6 shows the effect of KM-001 on locomotor activity in male CD-1 mice. One way ANOVA KM-001 groups versus 10% Solutol; $p=0.38$ l-tailed ttest d-Amphetamine vs vehicle ***$p=0.002$ Dose solution analysis confirmed that dose concentrations were at least 95% of the target doses. Actual doses administered were 3, 9.6 and 29 mg/kg. Plasma levels in CD-1 mice administered 3, 10 & 30 mg/kg were determined to be 19.1±5.8, 56.9±12.8 and 180±35, respectively.

TABLE 12

Dose Solution & Plasma Levels of KM-001 in CD-1 mice

| Compound | Target dose PO (actual mg/kg) | Plasma levels at sac (ng/ml) |
|---|---|---|
| KM-001 | 3 (3) | 19.1 ± 5.8 |
| | 10 (9.6) | 56.9 ± 12.8 |
| | 30 (29) | 180 ± 35 |

Conclusions:

In CD-1 mice, no increases in horizontal locomotor activity were observed following a single oral dose of 3, 10 or 30 mg/kg KM-001 (One way ANOVA vs. vehicle, $p>0.05$). The positive control, 3 mg/kg D-Amphetamine dosed subcutaneously, significantly increased activity compared to vehicle ($p<0.005$).

Example 12: Effect of KM-001 on Organotypic 3D Skin Culture of Harlequin Ichthyosis

Introduction

Harlequin ichthyosis (HI), is a severe skin disorder, caused by loss of function mutations in the gene of the lipid transporter ATP Binding Cassette A12 (ABCA12), is poorly understood and to date no satisfactory treatment has been developed.

For this study, the inventors used HI an engineered CRISPR-Cas9 ABCA12 KO equivalent (3D model) recapitulated the HI skin phenotype. HI 3D model exhibits loss of barrier function as well as disruption in skin differentiation and structure that is part of underlying pathology of HI 3D. KM-001 in various concentrations was used test to the it's effect on the HI phenotype by restoring the lipid barrier and skin differentiation in the HI 3D model.

Figure 7A:
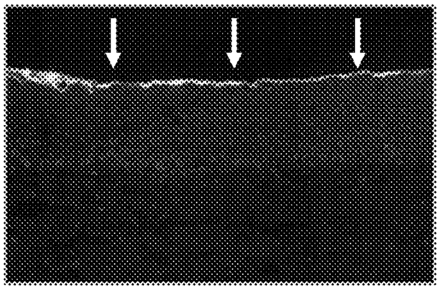
FIGS. 7A-7J are images showing the effect of KM-001 on skin structure and keratin 10 expression.
Figure 7B:
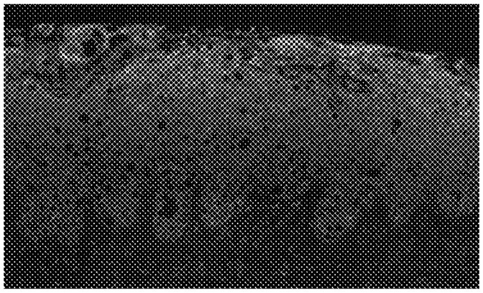

FIG. 7A shows normal barrier depicted by Lucifer yellow staining (IF) (marked by arrows) on CRISPR control 3D culture, while FIG. 7B shows disrupted skin structure and no barrier, Lucifer yellow staining (arrows) was not confined to outer.

Figure 7C:
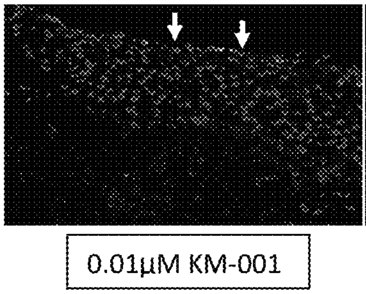
Figure 7D:
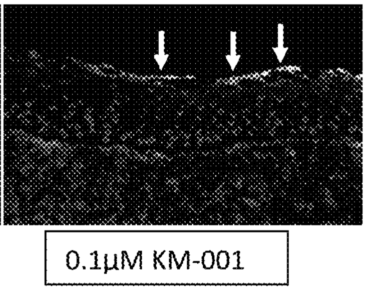
Figure 7E:
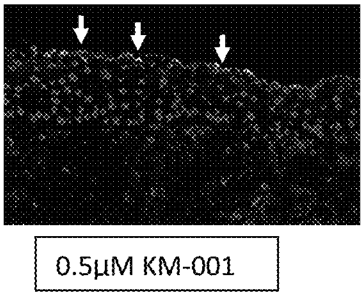

Selective inhibition by KM-001 restores skin structure as well as barrier function (lucifer yellow marked by arrows) in a dose dependent manner (FIG. 7C-7E).

Figure 7F:
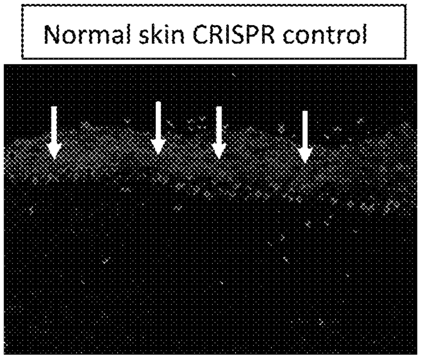
Figure 7G:
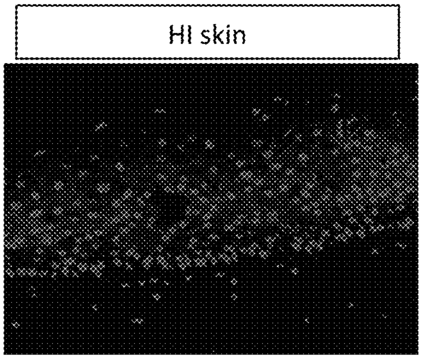
Figure 7H:
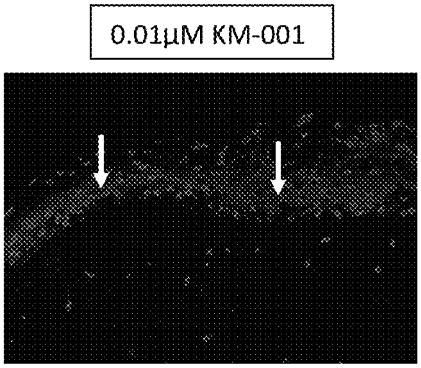
Figure 7I:
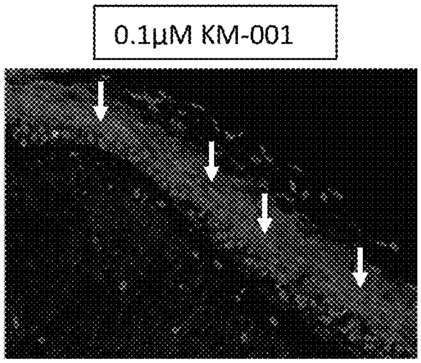
Figure 7J:
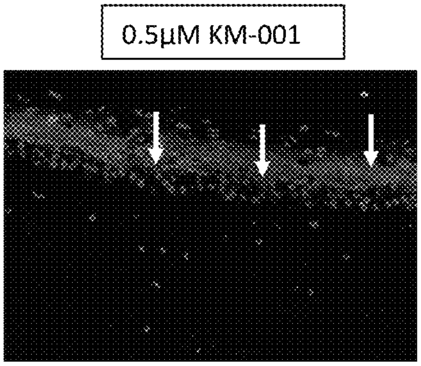

Keratin 10 staining by IF was performed on the 3D normal and HI skin organotypic cultures. Keratin-10 (red staining marked by arrow) is a marker for Spinous skin differentiation (FIG. 7F) that is reduced and disrupted in HI (FIG. 7G) KM-001 normalizes Keratin 10 expression in a dose dependent manner (FIGS. 7H-7J).

In summary, treatment of HI 3D skin with KM-001 also normalizes Involucrin and Transglutaminase expression dose dependently.

KM-001 treatment doesn't change structure and function of normal skin thus, it is safe as well as effective.

Example 13: Pre-Clinical Evaluation of Bioavailability of iv and Po Administration and PK Sampling of KM-023 in Swine Model Study Objectives:

To evaluate the dermal irritation potential of KM-023 using PO and IV at different escalating KM-0023 active concentrations. To assess PK profile of escalating doses of KM-023 administered via PO and IV routes. Animal care was carried out as described above. Animals were observed daily throughout the study period. No abnormal clinical signs were observed during the study.

PK samples were obtained in the following time points:

On Day 0 and Day 1—time 0, 5 min post injection, 30 min post injection, 1 h post injection, 2 h post injection, 6 h post injection, 24 h post injection (on the following day)

On Day 2, 5 min post injection, 30 min post injection, 1 h post injection, 2 h post injection, 6 h post injection PK blood samples were collected using tubes containing K2-EDTA as an anticoagulant. Samples were processed for plasma by centrifugation at 2900 g for 10 minutes, at approximately 4° C. Each plasma sample was equally divided into two samples and transferred into pre-chilled polypropylene tubes on dry ice and then quickly frozen over dry ice and kept at −70±10° C. until LC-MS/MS analysis.

Plasma samples for PK analysis have been send to Swiss BioQuant AG, Switzerland for further processing.

Results:

Methodology used for the detection of KM-023 in minipigs plasma is described in above. In both animals dosed with test item, exposure to KM-023 was detected.

Oral Dosing

Following oral administration of KM-023, maximum concentration (tmax) was observed between 5- and 30-minutes post-dose. The plasma concentration-time profile decreased after Cmax.

TABLE 13

PK data for KM-0023 after oral administration

| Day | Dosing (mg/kg) | $T_{max}$ (h) | $C_{max}$ (ng/mL) | $C_{max}$/dose (kg * ng) (mg/kg) | $AUC_{0\text{-}24\,h}$ (h * ng/mL) | $AUC_{0\text{-}t}$ (h * ng/mL) | $AUC_{0\text{-}t}$/dose (h * kg * ng/mL/mg) | $AUC_{0\text{-}\infty}$ (h * ng/mL) | $AUC_{0\text{-}\infty}$/dose (h * kg * ng/mL/mg) | $t_{1/2}$ (h) |
|---|---|---|---|---|---|---|---|---|---|---|
| 0 | 1 | 0.0830 | 1.26 | 1.26 | 0.442 | | 0.442 | 0.596 | | |
| 1 | 5 | 0.5 | 1.18 | 0.236 | 1.31 | | 0.262 | 2.01 | | |
| 2 | 10 | 0.083 | 23.0 | 2.30 | 23.2 | 31.2 | 2.32 | 23.2 | 3.12 | 4.04 |

Intravenous Dosing

Following intravenous administration of KM-023, apparent maximum concentration (tmax) was at 5 minutes post-dose. The plasma concentration-time profile decreased up to 24 h.

At intravenous doses of 1 and 5 mg/kg, KM-023 concentrations at 24 h post-dose were still measurable (above 0.300 ng/mL).

Half-time ranged between 3.3 h and 4.2 h (regression coefficient of about 0.9).

In the case of intravenous administration, exposure based on AUC increased dose-proportionality with doses between 1 and 10 mg/kg Regardless of the individual variability, bioavailability of the KM-023 formulation ranged between 0.2 to 0.8%.

TABLE 14

| PK data KM-0023 in female after intravenous administration | | | | | | | |
|---|---|---|---|---|---|---|---|
| Day | Dosing (mg/kg) | $C_0$ (ng/mL) | $T_{max}$ (h) | $C_{max}$ (ng/mL) | $C_{max}$/dose (ng/mL)/(mg/kg) | $AUC_{0-8\ h}$ (h * ng/mL) | $AUC_{0-t}$/dose (h * ng/mL)/(mg/kg) |
| 0 | 1 | 422 | 0.0830 | 343 | 343 | 314 | 314 |
| 1 | 5 | 2340 | 0.0830 | 1780 | 356 | 1300 | 260 |
| 2 | 10 | 6880 | 0.0830 | 4990 | 499 | 2800 | 280 |

| Day | Dosing (mg/kg) | $AUC_{0-h}$ (h * ng/mL) | $AUC_{0-t}$/dose (h * ng/mL)/(mg/kg) | $t_{1/2}$ (h) | Vz/F (mL/kg) | CL/F (mL/h/kg) |
|---|---|---|---|---|---|---|
| 0 | 1 | 320 | 320 | 4.23 | 19100 | 3130 |
| 1 | 5 | 1300 | 261 | 3.3 | 18200 | 3830 |
| 2 | 10 | 2910 | 291 | | | 3440 |

Both, intravenous and oral administrations of KM-023 to minipig result in dose dependent blood exposure of the compound. Tmax for both peaks at the same time, at 0.83 h. Bioavailability of the oral KM-023 formulation ranged between 0.2 to 0.8%.

Example 14: MTD Toxicity Test of KM-023 Compounds in Mice

The aim of the study is to evaluate the MTD of KM-023 Compounds in male Balb/c mice, in oral administration once a day in 5 dose levels.

Animal Care:

Animal handling was performed according to guidelines of the National Institute of Health (NIH) and the Association for Assessment and Accreditation of Laboratory Animal Care (AAALAC). Animals were housed in polyethylene cages (3/cage) measuring 35×30×15 cm, with stainless steel top grill facilitating pelleted food and drinking water in plastic bottle; bedding: steam sterilized clean paddy husk are used and bedding material is changed along with the cage at least twice a week. Animals were provided ad libitum a commercial rodent diet, sterilized. Animals had free access to acidified autoclaved drinking water obtained from the municipality supply. Animals were housed in IVC cages in dedicated HVAC (Heat, Ventilation, Air, Conditioning) animal facility at temperature from 22±2° C. and RH (Relative Humidity) of 55±15%. Temperature and humidity are monitored continuously. The facility has no exposure to outside light, and it is maintained on automatic alternating cycles of 12 hours of light and 12 hours of dark. Animals were inspected upon arrival; all animals were found healthy and were admitted to the facility and acclimatized for the study. Animals were inspected daily; no signs of morbidity or mortality were observed. This study was performed under the approval by "The Israel Board for Animal Experiments", in compliance with "The Israel Animal Welfare Act" and Ethics Committee No. IL-19-10-435/

Study Design:

Animals were allocated randomly into the study groups. Following routes of administration were employed Oral (test article) and Subcutaneous (control article).

At the beginning of the study, 3 mice were weight before compound treatment. Group of 3 mice received an increasing dose of KM-023 every 24 hours 1 mg/kg, 10 mg/kg, 30 mg/kg, 100 mg/kg, 500 mg/kg once daily, in a volume of 0.2 ml, administered orally. The mice were weighed daily before treatment.

No abnormal findings were found in their weight.

At the end of the experiment, the mice were sacrificed with CO2.

Results:

During all days of the experiment, the animals was observed to assess their overall condition.

No abnormalities or external side effects observed in live animals.

TABLE 15

| changes in Body weight | | | | | | | |
|---|---|---|---|---|---|---|---|
| mouse | Day 0 weight | Day 1 weight | Day 2 weight | Day 3 weight | Day 4 weight | Day 5 weight | Day 6 weight |
| 1 | 27.9 | 27.3 | 28.1 | 27.9 | 28.1 | 28.1 | 28.1 |
| 2 | 27.5 | 27.5 | 27.5 | 27.7 | 27.6 | 27.6 | 27.5 |
| 3 | 28.2 | 28.3 | 28.6 | 28.3 | 28.1 | 28.2 | 28.3 |
| Ave. | 27.8666 | 27.7 | 28.0666 | 27.9666 | 27.9333 | 27.96667 | 27.96667 |
| STDEV | 0.35118 | 0.5291 | 0.55075 | 0.30550 | 0.28867 | 0.321455 | 0.416333 |

Body Weight Data Presented as Mean and SEM:

During all experimental days, the animals were weighed and monitored daily for clinical signs, no abnormal or toxic findings were found. The highest dose in this study, 500 mg/kg, was determined as the Maximal Feasible Dose (MFD), since there were no AEs observed at this dose, and higher dosage presents a challenge for administration in mice via oral gavage, either due to poor solubility of the compound or the amount restrictions for acute administration in mice.

Example 15: PK Test of KM-023 Compound in Rat Plasma, Skin and Csf

The aim of the study was to determine the pharmacokinetic profile of KM-023 compound in male SD rat, administered orally in rat plasma, skin and Cerebrospinal fluid (CSF). The rats per group for either skin or CSF sample collection contains 9 rats.

This chosen model is suitable for the evaluation of drug pharmacokinetic profile.

Animal Care:

Animal handling was performed according to guidelines of the National Institute of Health (NIH) and the Association for Assessment and Accreditation of Laboratory Animal Care (AAALAC). Animals were provided ad libitum a commercial rodent diet, sterilized. Animals had free access to acidified autoclaved drinking water obtained from the municipality supply. The food arrives from the vendor with a certificate of analysis.

Study Design:

Animals were allocated randomly into the following treatment groups. Route of administration: Oral at doses of 20 and 60 mg/kg.

Group 1: Control—2 untreated, naïve animals for the collection of blood, skin, and CSF at the point of euthanasia.

Group 2: 6 animals treated with 20 mg/kg KM-023—200 ul blood collection at times 5 min, 15 min, 30 min, 1 h, 3 h and 8 h. The same 3 rats were allocated to each alternating time point of bleeding.

Group 3: 6 animals treated with 60 mg/kg KM-023—200 ul blood collection at times 5 min, 15 min, 30 min, 1 h, 3 h and 8 h. The same 3 rats were allocated to each alternating time point of bleeding.

Group 4: 9 animals treated with 20 mg/kg KM-023—skin biopsies and CSF sampling at times 15 min, 1 h, and 8 h.

Group 5: 9 animals treated with 60 mg/kg KM-023—skin biopsies and CSF sampling at times 15 min, 1 h, and 8 h.

Samples of plasma, skin and CSF were sent to Swiss BioQuant AG, Reinach, Switzerland for further analysis.

Results:

Pharmacokinetic Evaluation

Noncompartmental pharmacokinetic analysis was performed for KM-023 using Phoenix WinNonlin version 8.0 [Pharsight Corporation, Mountain View, CA, USA]. The extravascular model was used for oral dosing. Sparse sampling option was used for plasma concentration.

The following pharmacokinetic parameters were estimated from the plasma, skin and CSF concentration versus time curve:

tmax Time to reach the maximum plasma concentration read directly from the individual plasma concentration-time curve.

Cmax Maximum plasma concentration read directly from the individual plasma concentration-time curve.

Cmax/doseCmax corrected for dose.

AUC0-t Area under the plasma concentration-time curve from time point zero to last measurable concentration. AUC0-t was calculated according to the "linear up log down" trapezoidal rule.

AUC0-8 h Area under the plasma concentration-time curve from time point zero to time point 8 h after dosing. AUC0-8 h was calculated according to the "linear up log down" trapezoidal rule.

AUC0-8 h/dose AUC0-8 h corrected for dose

For the pharmacokinetic evaluation, rounded concentration values were used and values below the limit of quantification were set to zero. The pharmacokinetic parameters were calculated based on nominal sampling times. All values were rounded to 3 significant digits.

Descriptive Statistics of Concentration-Time Profiles

Figure 8A:
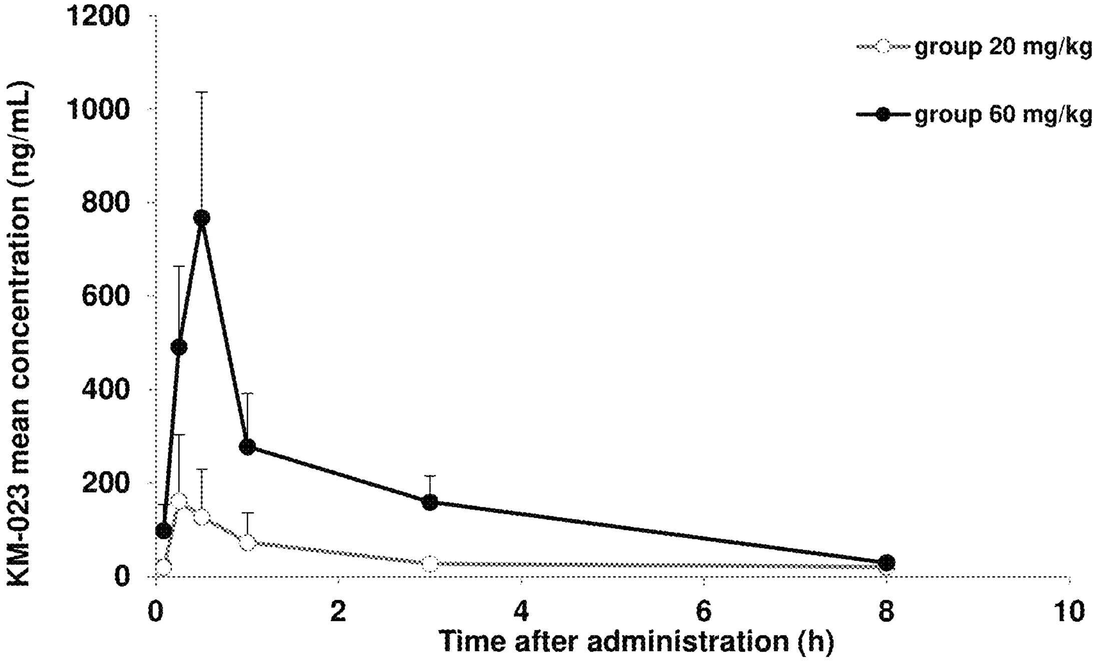
FIGS. 8A and 8B are bar graphs showing mean KM-023 plasma concentration-time profiles in rats in linear and semi-logarithmic scales, respectively.
Figure 8B:
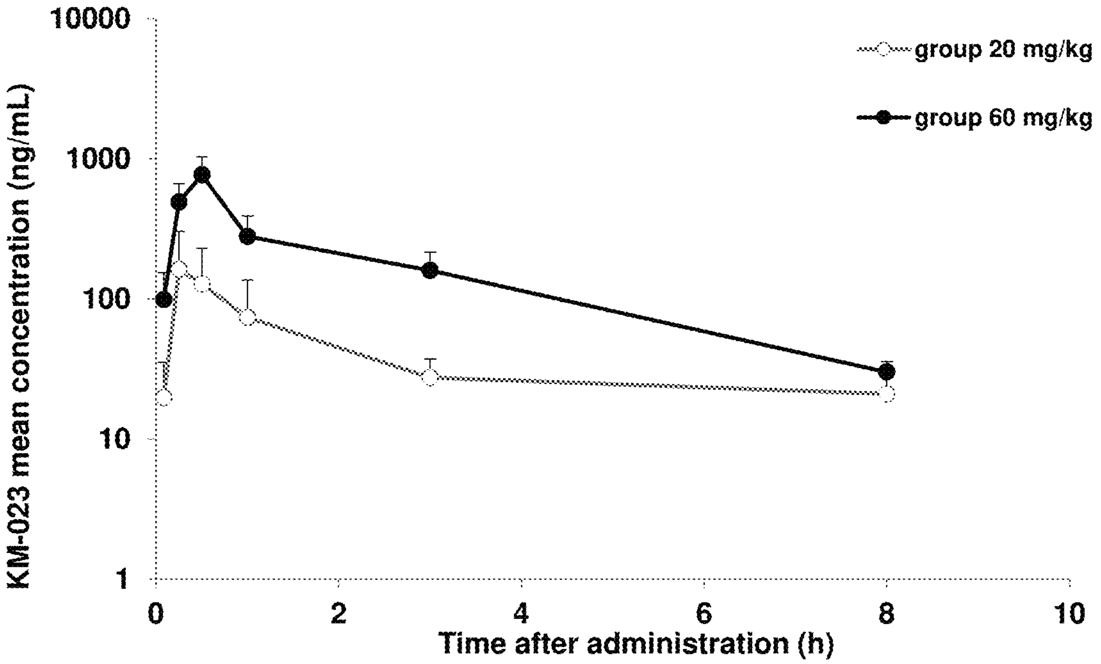

FIGS. 8A and 8B show comparative mean (n=3) KM-023 plasma concentration-time profiles in rats (linear and semi-logarithmic scales).

Oral administration of KM-023 in rats manifests acceptable systemic absorption, as can be seen by the obtained levels in plasma, and almost linear dose dependent manner.

TABLE 16

Individual skin concentrations and descriptive statistics (n = 3) of KM-023 in rats

| | | Time (h) | | |
|---|---|---|---|---|
| Dose | | 0.250 | 1.00 | 8.00 |
| (mg/kg) | skin | Concentration (ng/g) | | |
| 20 | | 72.8 | 55.8 | 8.55 |
| | | 53.0 | 58.6 | 11.3 |
| | | 56.5 | 82.3 | 12.1 |
| | Mean | 60.8 | 65.5 | 10.6 |
| | SD | 10.5 | 14.5 | 1.85 |
| | CV % | 17.3 | 22.2 | 17.4 |
| 60 | | 103 | 130 | 23.2 |
| | | 177 | 211 | 9.90 |
| | | 291 | 185 | 8.98 |
| | Mean | 190 | 175 | 14.0 |
| | SD | 94.6 | 41.2 | 7.93 |
| | CV % | 49.7 | 23.5 | 56.6 |

TABLE 17

Individual CSF concentrations and descriptive statistics (n = 3) of KM-023 in rats.

| | | Time (h) | | |
|---|---|---|---|---|
| Dose | | 0.250 | 1.00 | 8.00 |
| (mg/kg) | CSF | Concentration(ng/mL) | | |
| 20 | | 1.90 | 1.84 | 0.00 |
| | | 0.00 | 0.640 | 0.00 |
| | | 2.34 | 1.07 | 0.00 |
| | Mean | 1.41 | 1.18 | 0.00 |
| | SD | 1.24 | 0.608 | 0.00 |
| | CV % | 88.0 | 51.4 | |
| 60 | | 1.78 | 10.5 | 0.00 |
| | | 0.00 | 2.26 | 0.00 |
| | | 18.7 | 0.792 | 0.00 |
| | Mean | 6.83 | 4.52 | 0.00 |
| | SD | 10.3 | 5.23 | 0.00 |
| | CV % | 151.2 | 115.8 | |

Toxicokinetic Variables

TABLE 18

| Pharmacokinetic variables of KM-023 in rat plasma | | | | | | | |
|---|---|---|---|---|---|---|---|
| Dose (mg/kg) | $T_{max}$ (h) | $C_{max}$ (ng/mL) | SE of $C_{max}$ (ng/mL | $C_{max}$/dose (kg * ng) (mL/mg) | $AUC_{0\text{-}8\ h}$ (h * ng/mL) | SE of $AUC_{0\text{-}8\ h}$ (h * ng/mL) | $AUC_{0\text{-}8\ h}$/dose (h * kg * ng/mL/mg) |
| 20 | 0.250 | 162 | 81.7 | 8.10 | 326 | 59.6 | 16.3 |
| 60 | 0.500 | 768 | 155 | 12.8 | 1390 | 189 | 23.1 |

TABLE 19

| Pharmacokinetic variables of KM-023 in skin and CSF plasma | | | | | | | |
|---|---|---|---|---|---|---|---|
| Dose (mg/kg) | matrix | $t_{max}$ | $C_{max}$ (ng/mL) | $C_{max}$/dose (kg * ng/ mL/mg) | AUClast (h * ng/mL) | $AUC_{0\text{-}8\ h}$ (h * ng/mL) | $AUC_{0\text{-}8\ h}$/dose (h * kg * ng/mL/mg) |
| 20 | CSF | 0.250 | 1.41 | 0.0705 | 1.14 | 5.27 | 0.264 |
| | skin | 1.00 | 65.5 | 3.28 | 266 | 266 | 13.3 |
| 60 | CSF | 0.250 | 6.83 | 0.114 | 5.05 | 20.9 | 0.348 |
| | skin | 0.250 | 190 | 3.17 | 607 | 607 | 10.1 |

TABLE 20

| Summary of KM-023 exposure in divers matrices from rat | | | | | |
|---|---|---|---|---|---|
| Dose | | $C_{max}$ | $AUC_{0\text{-}8\ h}$ | Ratio organ/plasma | |
| (mg/kg) | matrix | (ng/mL) | (h * ng/mL) | $C_{max}$ | $AUC_{0\text{-}8\ h}$ |
| 20 | plasma | 162 | 326 | | |
| | CSF | 1.41 | 5.27 | 0.00870 | 0.0162 |
| | skin | 65.5 | 266 | 0.404 | 0.816 |
| 60 | plasma | 768 | 1390 | | |
| | CSF | 6.83 | 20.9 | 0.00889 | 0.0150 |
| | skin | 190 | 607 | 0.247 | 0.437 |

As can be see, all rats from control group animals were free of KM-023. However, all animals dosed with test item, were exposed to KM-023.

A sparse sampling design was chosen for profiling the exposure in rat. The standard error of exposure (SE of AUC0-8h) in plasma showed that the variability was moderate with a relative coefficient of variability ranging from 13.6% to 18.3%.

Following oral administration of 20 and 60 mg/kg of KM-023, maximum concentration (tmax) in plasma was observed 15 min and 30 min post-dose, respectively.

Following oral administration of 20 and 60 mg/kg of KM-023, maximum concentration (tmax) in CSF was observed 15 min post-dose.

Following oral administration of 20 and 60 mg/kg of KM-023, maximum concentration (tmax) in skin was observed 15 min to 1-hour post-dose.

The concentration time profiles showed a moderate decline of KM-023 mean concentrations after reaching of tmax up to 8 h post-dose.

Based on plasma exposure, estimation based on calculated AUC0-8 h does not reflect the complete exposure to KM-023 as the mean concentrations at 8 h post-dose represented 3.9% to 13.0% of the Cmax concentration.

The exposure to KM-023 as based on AUC0-8 h in plasma increased with dose increasing from 20 to 60 mg/kg, in a roughly more than dose proportional manner.

Concentrations were measured in plasma were higher than in skin and in CSF.

Exposure ratio skin/plasma of AUC0-8 h ranged from 0.437 to 0.816, which indicated that KM-023 distributed well in skin after an oral administration.

Exposure ratio CSF/plasma of AUC0-8 h ranged from 0.0150 to 0.0162, which indicated that KM-023 did not distribute well in CSF after an oral administration. This suggests that when given orally, KM-023 reaches plasma and skin, it does not cross BBB and thus does not enter CNS.

Example 16: Efficacy of KM-001 DS-Nh Mouse Model

Introduction:

Olmsted syndrome is a combination of hyperkeratotic lesions and palmoplantar keratoderma severe enough to result in spontaneous digit amputation. De novo gain-of-function mutations in the thermosensitive cation channel TRPV3, most frequently Gly573Ser, was identified as causative in OS patients. The 573 residue is also mutated in two autosomal dominant rodent models of OS, DS-Nh mice which develop hyperkeratosis.

The physiological relevance of TRPV3 expression in the skin was highlighted when the hairless DS-Nh mouse strain was linked to a gain-of-function mutation in the TRPV3 gene caused by a Gly573Ser mutation in keratinocytes. This mutation led to not only hairlessness but also to the development of spontaneous dermatitis and pruritus, increased *Staphylococcus aureus* colonization, higher IgE and IL-4 levels, increased CD4+ T-cell infiltration, and hyperkeratosis in the affected mice, hinting at the potentially complex role of TRPV3 in cutaneous pathophysiology.

Study Design:

Mice were identified by left ear punch. Each cage will be also given a specific identification code. On Day −30, −23, −20, −14, −9, −2, 0, 3, 7, 10, 14, erythema and edema of the mice face have been scored on the right and left sides according to criteria in table 21 (Dermatitis scoring criteria).

TABLE 21

| Dermatitis scoring criteria | | |
|---|---|---|
| Item | Score | Remarks |
| Facial Bleeding Inflammation Erythema Score by Erythema only, inflammation as a remark | 0: No facial bleeding and erythema<br>1: Locally facial Bleeding, and erythema (not diffused)<br>2: Sporadic facial Bleeding, and erythema (less than half of whole face)<br>3: Overall facial Bleeding, and erythema (more than half of whole face) | Score by Erythema only, add inflammation as a remark in a separate column |
| Periorbital edema | 0: No edema<br>1: Slightly edema (barely identifiable)<br>2: Significant edema (1 mm or more)<br>3: Eyelid ptosis | Score by edema, add all other phenotypes as remarks |

Tacrolimus 0.1% (positive control), KM-001 topical vehicle, KM-001 1% and 0.3% were applied in the amount of 25 microg of ointment per cheek on one side/mouse.

The viability, clinical signs and behavior were monitored daily. Body weight was recorded daily. Mice were observed for significant clinical signs of toxicity, moribundity and mortality. Mice were monitored just and 7 hours after administration. Animals in all groups were sacrificed at Day 14 by exsanguination through abdominal vena cava under isoflurane.

For skin samples, the skin at the inflammation site from both cheeks of the face were collected. For histological analyses, the skin was fixed in 4% paraformaldehyde for 24 hours. After fixation, these specimens were processed to paraffin embedding for H&E staining, MT staining and immunohistochemistry and toluidine blue staining.

Results:

Skin sections taken from facial treated area of each mouse are fixed in paraffin and stained with Hematoxylin & Eosin. Representative pictures are presented. DS-Nh mouse skin presents thick epidermis and high level of inflammation in the dermis.

Figure 9A:
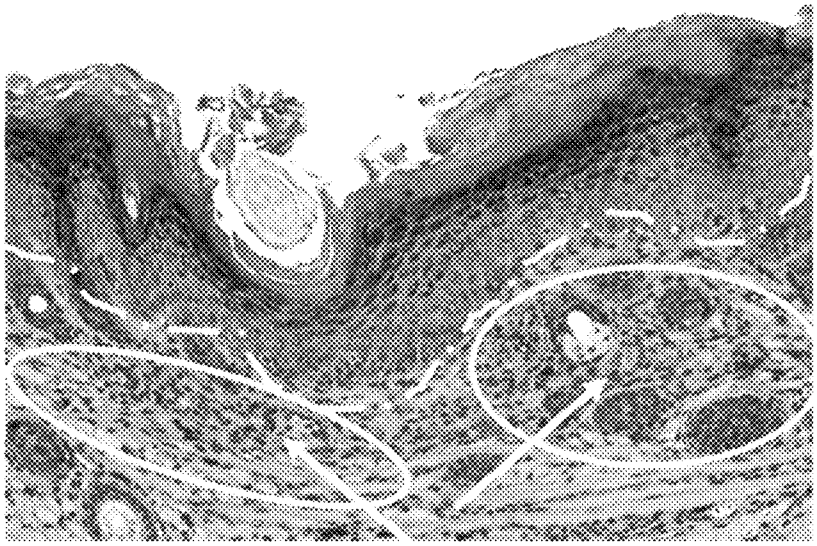
FIG. 9A to 9F are images showing the effect of KM-001 in DS-Nh mouse model.
Figure 9B:
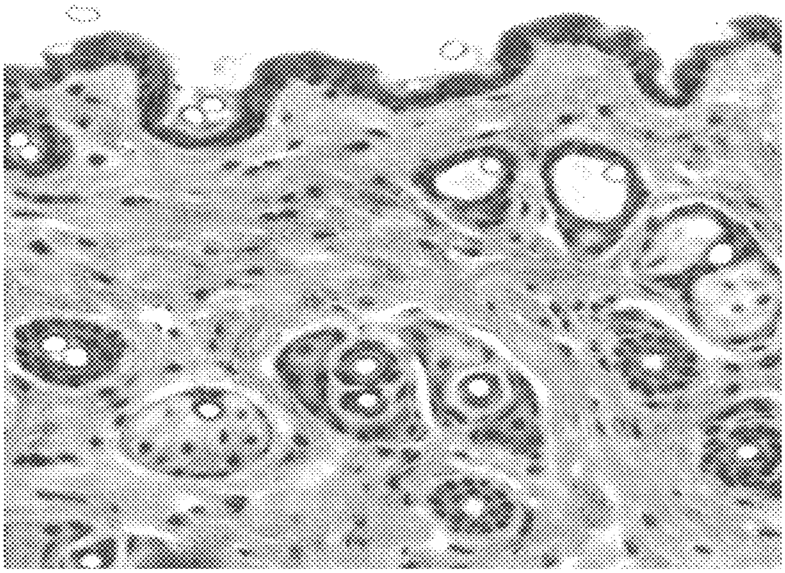
Figure 9C:
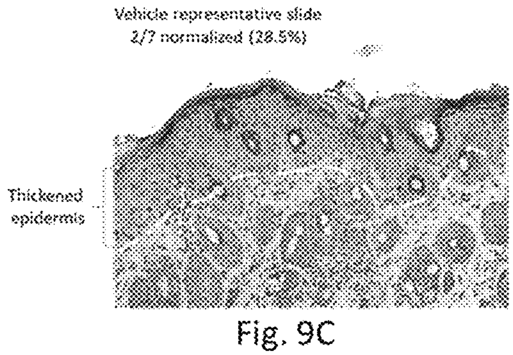
Figure 9D:
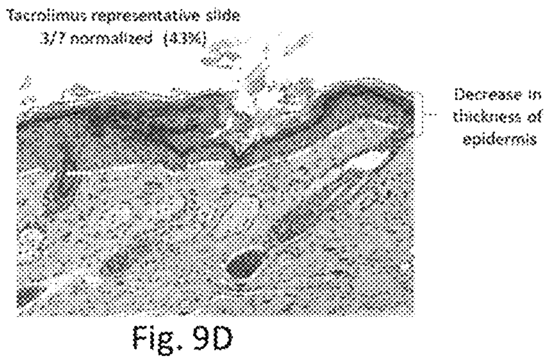
Figure 9E:
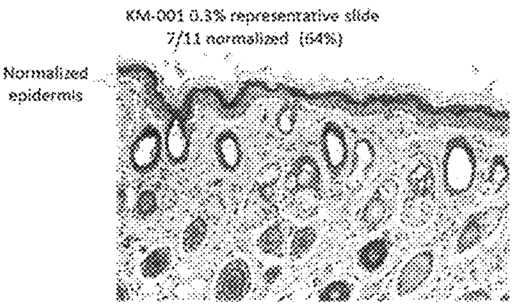
Figure 9F:
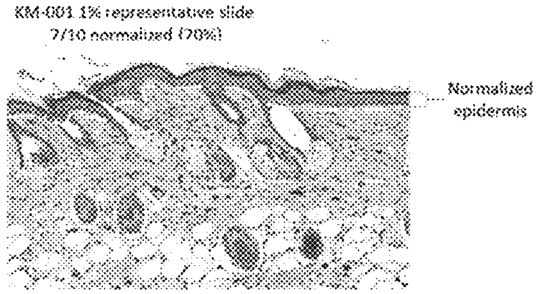

DS-Nh mouse untreated skin exhibits thickened epidermis and massive inflammation (FIG. 9A). Normal mouse skin exhibits normal epidermis and no inflammation as shown in FIG. 9B.

KM-001 normalizes epidermis differentiation and reduces inflammation in DS-Nh TRPV3 mutation genetic model.

Positive control (Tacrolimus) only slightly improved skin pathology associated with Ds-Nh phenotype. (FIG. 9C-9F)

Both strengths of KM-001 ointments demonstrated superiority in normalization of skin morphology and integrity over the vehicle as well as over the positive control. These results show potential therapeutic applicability in utilizing KM-001 for treating keratodermas, such as Olmsted syndrome.

Example 17: Efficacy Study of KM-023 in SLIGRL-NH2 (SEQ ID NO: 1) Itching Mouse Model The aim of this study is to evaluate the efficacy of anti-itching activity of KM-023 in SLIGRL-NH2 (SEQ ID NO: 1) mouse itching model.

Proteinase-activated receptors (PAR) are a group of G-protein coupled receptors which are activated by cleavage of their terminal sequence by serine proteinases. The anatomical location of PAR2 in the sensory system, along with its activation by proteinases, suggests that PAR2 might be involved in itch. Thus, the administration of the murine PAR2 agonist peptide, SLIGRL-NH2 (SEQ ID NO: 1), is an known and acceptable model to assess anti-pruritic compounds in mice.

Mouse is considered as a suitable model for evaluating efficacy and pharmacodynamics of new drugs.

32 mice in good health status and corresponding to the specifications details above were included in the in vivo phase.

The animals were weighed before treatment. Induction of itching was performed on animals by intradermal administration of SLIGRL-NH2 (SEQ ID NO: 1) peptide in neck (volume about 20 μL).

TABLE 22

| Administration dosages | | | | |
|---|---|---|---|---|
| Group | Number of animals | Drug con. (mg/mL) | Volume to be administered (mL/kg) | Dose (mg/kg)/Time before induction |
| 1/Control group Saline | 10 | 0 | 10 | 0/−30 min |
| 2/Test group 1 KM-023 | 11 | 1 | 10 | 10/−30 min |
| 3/Test group 3 KM-023 | 11 | 10 | 10 | 100/−30 min |

Oral route was performed by oral gavage using plastic probe 30 min before induction with SLIGRL-NH2 (SEQ ID NO: 1) peptide.

All treatment details were recorded in the raw data files and final report including dosage calculations, dose administered, date and time of administration.

Animals were placed in plexiglass red walls observation devices (for simultaneous observations of 4 mice). Red walls permitted observations of animals by the operator without the possibility for animals to see the operator. Animals were placed in observation cages before induction for 20 to 30 minutes.

Intradermal injections of SLIGRL (SEQ ID NO: 1) was performed on vigil animals in shaved neck and video recording was initiated immediately after injection for a duration of 30 minutes.

Manual image analysis was performed on recorded movies.

Scratching/itching bouts were counted on 6 time periods of 5 minutes (total of 30 min for each mouse).

Figure 10A:
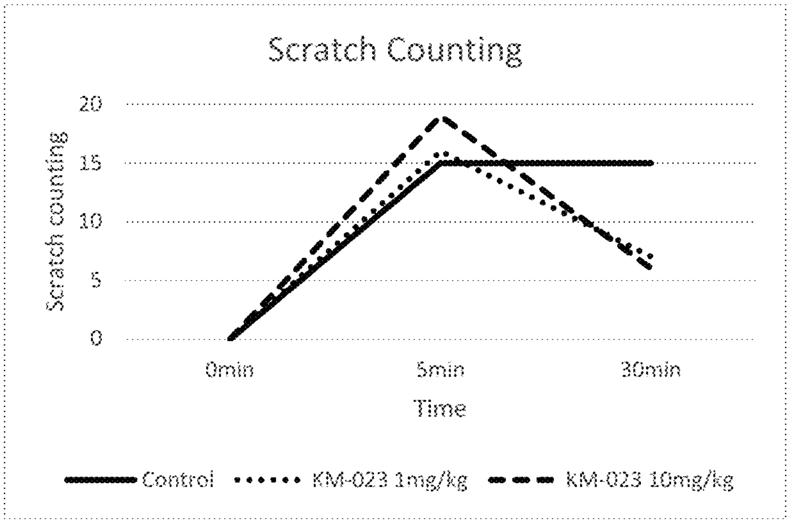
FIGS. 10A and 10B are graphs showing the effect of KM-0023 in SLIGRL-$NH_2$ (SEQ ID NO: 1) itching mouse model.

Results:

As can be seen in FIG. 10A, in animals treated by oral administration of KM-023, the induction with SLIGRL (SEQ ID NO: 1) occurred 30 minutes post-treatment.

Figure 10B:
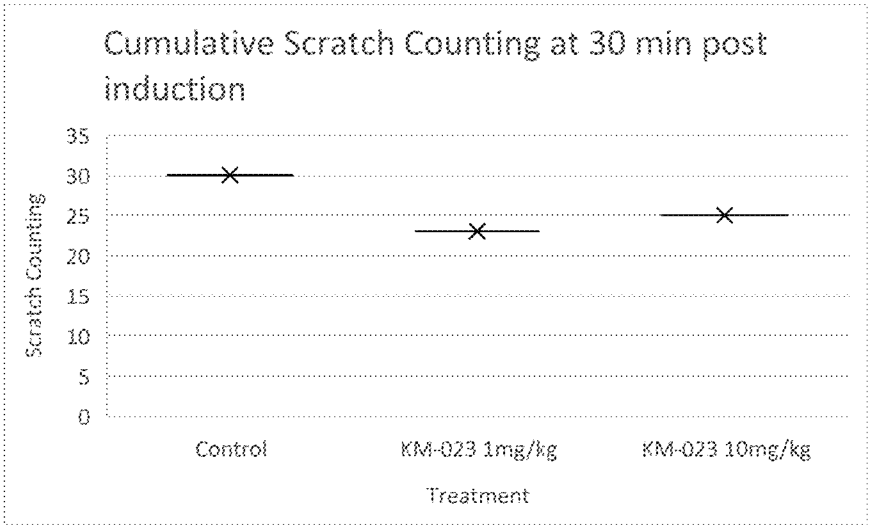

The scratches were counted at predefined time intervals of 5 minutes post induction and 30 minutes post induction. The results shown in FIG. 10B represent the scratch counting at predefined time intervals and as the sum of the scratches for all time points per each treatment group. Time 0 represent the time point prior to SLIGRL (SEQ ID NO: 1) induction The results show that administration of vehicle (control) did not affect SLIGRL (SEQ ID NO: 1) induced increase in scratch behaviour in mice. Pre-treatment with either dose of oral KM-023 decrease the number of scratches observed 30 minutes post induction by 56.25% in KM-023 1 mg/kg group and by 68.8% in KM-023 10 mg/kg group. Pretreatment with KM-023 has shown to counteract SLIGRL (SEQ ID NO: 1) induced behaviour in mice and KM023 manifest anti-pruritic activity in mice.

Example 18: Efficacy Study of KM-001 SLIGRL-NH2 Itching Mouse Model

The aim of this study is to evaluate the efficacy of anti-itching activity of KM001 in SLIGRL-NH2 (SEQ ID NO: 1) mouse itching model.

Proteinase-activated receptors (PAR) are a group of G-protein coupled receptors which are activated by cleavage of their terminal sequence by serine proteinases. The anatomical location of PAR2 in the sensory system, along with its activation by proteinases, suggests that PAR2 might be involved in itch. Thus, the administration of the murine PAR2 agonist peptide, SLIGRL-NH2 (SEQ ID NO: 1), is a known and acceptable model to assess anti-pruritic compounds in mice.

Mouse is a suitable model for evaluating efficacy and pharmacodynamics of new drugs. There is a substantial amount of historical data available in literature for comparison purposes. There is no suitable in vitro model to study pharmacodynamics of new drugs.

52 mice in good health status and corresponding to the specifications details above are included in the in vivo phase.

Oral route is performed by oral gavage using plastic probe 30 min before induction with SLIGRL-NH2 (SEQ ID NO: 1) peptide.

The following administration dosages is performed for the topical route:

TABLE 23

Administration dosages

| Group | Number of animals | Formulation ID | Drug con. (mg/mL) | Volume to be administered (mL/kg) | Dose (mg/kg)/Time before induction |
|---|---|---|---|---|---|
| 4/Control group | 10 | Topical excipient | 0 | 50 (0.05 mL) | 0/−1 h |
| 5/Test group 3 | 10 | KM-001 at 1% | 10 (1%) | 50 (0.05 mL) | 25/−1 h |

For topical route, animals are administered 1 h before induction with SLIGRL-NH2 (SEQ ID NO: 1) peptide. 50 µL (0.05 mL) is deposited on shaved neck.

All treatment details are recorded in the raw data files and final report including dosage calculations, dose administered, date and time of administration.

Animals are placed in plexiglass red walls observation devices (for simultaneous observations of 4 mice). Red walls permit observations of animals by the operator without the possibility for animals to see the operator. Animals are placed in observation cages before induction for 20 to 30 minutes.

Intradermal injections of SLIGRL (SEQ ID NO: 1) is performed on vigil animals in shaved neck and video recording is initiated immediately after injection for a duration of 30 minutes.

Manual image analysis is performed on recorded movies.

Scratching/itching bouts are counted on 6 time periods of 5 minutes (total of 30 min for each mouse).

For animals injected with SLIGRL (SEQ ID NO: 1), on euthanized animals, neck skin is collected and is snap frozen and placed afterwards at −80° C. for further histological analysis.

The invention claimed is:

1. A compound of formula (XXXII):

(XXXII)

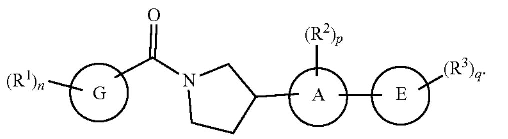

or a pharmaceutically acceptable salt, racemate, or stereoisomer thereof, wherein;

G is pyridinyl pyrazinyl, or thiazolyl;

A is

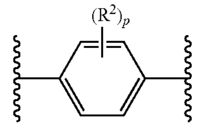

or

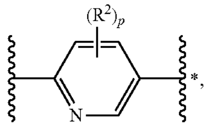

wherein* is bond to E or pyrrolidinyl ring of formula XXXII);

E is phenyl or pyrazinyl;

each $R^1$ is independently cyano, nitro, hydroxy, halo, $C_1$-$C_3$ haloalkyl, $C_1$-$C_3$ haloalkoxy, $C_1$-$C_6$ alkyl, $C_1$-$C_6$ alkoxy, ether, aryl, —$N(R^a)(R^b)$, —C(O) $R^c$, —$CO_2R^c$, —$C(O)N(R^a)(R^b)$, —$SO_2N(R^a)(R^b)$, or —$SOR^c$, or two $R^1$ groups together form a ring system;

each $R^2$ and $R^3$ is independently cyano, nitro, hydroxy, halo, $C_1$-$C_3$ haloalkyl, $C_1$-$C_3$ haloalkoxy, $C_1$-$C_6$ alkyl, hydroxyalkyl, $C_3$-$C_8$ cycloalkyl, $C_1$-$C_6$ alkoxy, aryl, —$N(R^a)(R^b)$, —$C(O)R^c$, —$CH_2R^c$, —$CO_2R^c$, —$C(O)N(R^a)(R^b)$, —$SO_2N(R^a)(R^b)$, or —$SOR^c$; each $R^a$ and $R^b$ is independently H, hydroxyl, —$OR^c$, $C_1$-$C_6$ alkyl, —$C(O)R^c$, or —$C(O)OR^c$; each $R^c$ is independently H, $C_1$-$C_6$ alkyl, or aryl;

n is 0, 1, or 2; p is 1, or 2; and q is 0, 1, or 2.

2. The compound of claim 1, wherein A is

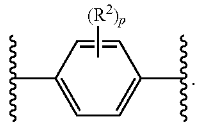

3. The compound of claim 1, wherein E is phenyl.

4. The compound of claim 1, wherein G is pyridinyl, or pyrazinyl.

5. The compound of claim 1, wherein n is 1 or 2 and each $R^1$ is independently halo, $C_1$-$C_6$ alkyl, $C_1$-$C_6$ alkoxy, hydroxy, $C_1$-$C_3$ haloalkyl, cyano, ether, —$N(R^a)(R^b)$, or —$C(O)R^c$, each $R^a$ and $R^b$ is independently H, or $C_1$-$C_6$ alkyl; and each $R^c$ is independently H or $C_1$-$C_6$ alkyl.

6. The compound of claim 5, wherein each $R^1$ is fluorine, chlorine, methyl, methoxy, hydroxy, methyl amine, —$CH_2OCH_3$, or —$CF_3$.

7. The compound of claim 1, wherein each $R^2$ is independently cyano, nitro, hydroxy, hydroxyalkyl, —$NH_2$, halo, aryl, —$N(R^a)(R^b)$, —C(O)OH, —$CH_2R^c$, —$CO_2R^c$, or —$C(O)N(R^a)(R^b)$.

8. The compound of claim 7, wherein each $R^2$ is independently hydroxyalkyl or halo.

9. The compound of claim 7, wherein each $R^2$ is independently —$CH_2OH$ or fluorine.

10. The compound of claim 1, wherein q is 1 or 2 and each $R^3$ is independently halo, $C_1$-$C_6$ alkyl, $C_1$-$C_6$ alkoxy, or $C_3$-$C_8$ cycloalkyl.

11. The compound of claim 10, wherein each $R^3$ is independently fluorine, cyclopropyl, methyl, ethyl, or propyl.

12. A compound of formula (XXXIII)

(XXXIII)

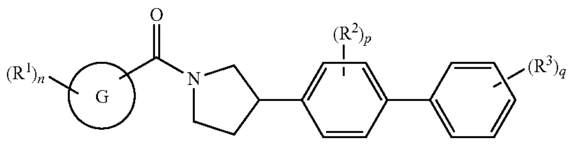

or a pharmaceutically acceptable salt, racemate, or stereoisomer thereof, wherein:

G is pyridinyl, pyrazinyl, or thiazolyl;

each $R^1$ is independently cyano, nitro, hydroxy, halo, $C_1$-$C_3$ haloalkyl, $C_1$-$C_3$ haloalkoxy, $C_1$-$C_6$ alkyl, hydroxyalkyl, $C_1$-$C_6$ alkoxy, aryl, —$N(R^a)(R^b)$, —$C(O)R^c$, —$COR^c$, —$C(O)N(R^a)(R^b)$, —$SO_2N(R^a)(R^b)$, or —$SOR^c$, or two $R^1$ groups together form a ring system;

each $R^2$ and $R^3$ is independently cyano, nitro, hydroxy, halo, $C_1$-$C_3$ haloalkyl, $C_1$-$C_3$ haloalkoxy, $C_1$-$C_6$ alkyl, hydroxyalkyl, $C_3$-$C_8$ cycloalkyl, $C_1$-$C_6$ alkoxy, aryl, —$N(R^a)(R^b)$, —$C(O)R^c$, —$CH_2R^c$, —$CO_2R^c$, —$C(O)N(R^2)(R^b)$, —$SO_2N(R^a)(R^b)$, or —$SOR^c$; each $R^a$ and $R^b$ is independently H, hydroxyl, —$OR^c$, $C_1$-$C_6$ alkyl, —$C(O)R^c$, or —$C(O)OR^c$; each $R^c$ is independently H, $C_1$-$C_6$ alkyl, or aryl;

n is 0, 1, or 2; p is 1, or 2; and q is 0, 1, or 2.

13. The compound of claim 12, wherein G is

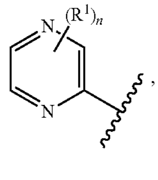

, or

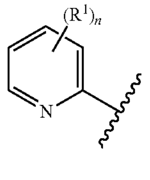

.

14. The compound of claim 12, wherein n is 1 or 2 and each $R^1$ is independently halo, $C_1$-$C_6$ alkyl, $C_1$-$C_6$ alkoxy, hydroxy, $C_1$-$C_3$ haloalkyl, cyano, ether, —$N(R^a)(R^b)$, or —$C(O)R^c$, each $R^a$ and $R^b$ is independently H, or $C_1$-$C_6$ alkyl; and each $R^c$ is independently H or $C_1$-$C_6$ alkyl.

15. The compound of claim 14, wherein each $R^1$ is independently fluorine, chlorine, methyl, methoxy, hydroxy, methyl amine, —$CH_2OCH_3$, or —$CF_3$.

16. The compound of claim 12, wherein each $R^2$ is independently cyano, nitro, hydroxy, hydroxyalkyl, —$NH_2$, halo, aryl, —$N(R^a)(R^b)$, —C(O)OH, —$CH_2R^c$, —$CO_2R^c$, or —$C(O)N(R^a)(R^b)$.

17. The compound of claim 16, wherein each $R^2$ is independently hydroxyalkyl or halo.

18. The compound of claim 15, wherein each $R^2$ is independently —$CH_2OH$ or fluorine.

19. The compound of claim 12, wherein q is 1 or 2 and each $R^3$ is independently halo, $C_1$-$C_6$ alkyl, $C_1$-$C_6$ alkoxy, or $C_3$-$C_8$ cycloalkyl.

20. The compound of claim 19, wherein each $R^3$ is independently fluorine, cyclopropyl, methyl, ethyl, or propyl.

21. A compound of formula (XXXXIII)

(XXXXIII)

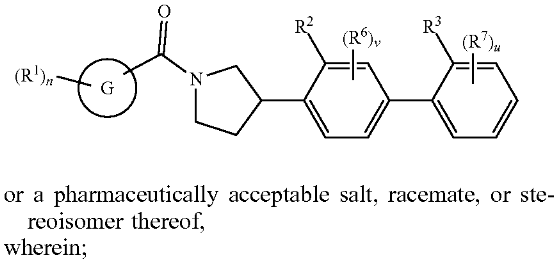

or a pharmaceutically acceptable salt, racemate, or stereoisomer thereof, wherein;

G is pyridinyl, pyrazinyl, or thiazolyl;

each $R^1$ is independently halo, $C_1$-$C_6$ alkyl, $C_1$-$C_6$ alkoxy, hydroxy, $C_1$-$C_3$ haloalkyl, cyano, ether, —$N(R^a)(R^b)$, or —$C(O)R^c$; each $R^a$ and $R^b$ is independently H, or $C_1$-$C_6$ alkyl, each $R^2$ and $R^6$ is independently cyano, nitro, hydroxy, hydroxyalkyl, —$NH_2$, halo, aryl, —$N(R^a)(R^b)$, —C(O)OH, —$CH_2R^c$, —$CO_2R^c$, or —$C(O)N(R^a)(R^b)$;

each $R^c$ is H, $C_1$-$C_6$ alkyl, aryl, —$OR^a$, or —$N(R^a)(R^a)$;

each $R^3$ and $R^7$ is independently halo, $C_1$-$C_6$ alkyl, $C_1$-$C_6$ alkoxy, or $C_3$-$C_6$ cycloalkyl;

n is 0, 1, or 2; u is 0, 1, or 2; and vis 0, 1, or 2.

22. The compound of claim 21, which is a compound of formula (XXXV) or (XXXVI):

(XXXV)

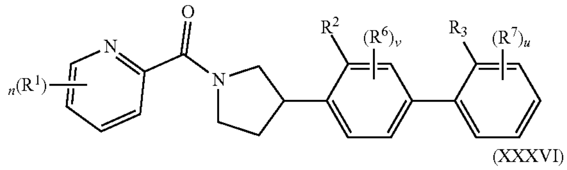

(XXXVI)

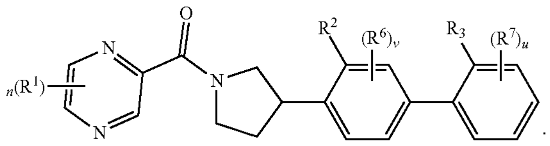

.

23. The compound of claim 21, wherein n is 1 or 2 and each $R^1$ is independently halo, $C_1$-$C_6$ alkyl, $C_1$-$C_6$ alkoxy, hydroxy, $C_1$-$C_3$ haloalkyl, or —$N(R^a)(R^b)$; each $R^a$ and $R^b$ is independently H, or $C_1$-$C_6$ alkyl; and each Re is independently H or $C_1$-$C_6$ alkyl.

24. The compound of claim 21, wherein n is 1 or 2 and each $R^1$ is independently fluorine, chlorine, methyl, methoxy, hydroxy, methyl amine, —$CH_2OCH_3$, or —$CF_3$.

25. The compound of claim 21, wherein (i) n is 1 or 2 and each $R^1$ is independently fluorine, chlorine, methyl, methoxy, hydroxy, methyl amine, or —$CF_3$, (ii) n is 2 and each $R^1$ is independently fluorine, chlorine, methyl, methoxy, hydroxy, methyl amine, or —$CF_3$, (iii) n is 2 and each $R^1$ is independently methyl or hydroxy, (iv) n is 1 and $R^1$ is fluorine, or (v) n is 2 and one $R^1$ is methyl and the other $R^1$ is hydroxy.

26. The compound of claim 21, wherein $R^2$ is cyano, nitro, hydroxy, hydroxyalkyl, —$NH_2$, halo, aryl, —$N(R^a)(R^b)$, —C(O)OH, —$CH_2R^c$, —$CO_2R^c$, or —$C(O)N(R^a)(R^b)$.

27. The compound of claim 21, wherein $R^2$ is hydroxyalkyl or halo.

28. The compound of claim 21, wherein (i) $R^2$ is —$CH_2OH$, (ii) $R^2$ is fluorine, (iii) v is 1, $R^2$ is hydroxyalkyl, and $R^6$ is halo, or (iv) v is 1, $R^2$ is —$CH_2OH$, and $R^6$ is fluorine.

29. The compound of claim 21, wherein $R^3$ is halo, $C_1$-$C_6$ alkyl, $C_1$-$C_6$ alkoxy, or $C_3$-$C_8$ cycloalkyl.

30. The compound of claim 21, wherein $R^3$ is fluorine, cyclopropyl, methyl, ethyl or propyl.

31. The compound of claim 21, wherein (i) $R^3$ is halo, $C_1$-$C_6$ alkyl, $C_1$-$C_6$ alkoxy, or $C_3$-$C_8$ cycloalkyl, (ii) u is 1, $R^3$ is halo, $C_1$-$C_6$ alkyl, $C_1$-$C_6$ alkoxy, or $C_3$-$C_8$ cycloalkyl, and $R^7$ is halo, or (iii) u is 1, $R^3$ is cyclopropyl, methyl, ethyl, or propyl, and $R^7$ is fluorine.

32. The compound of claim 1, comprising at least 70% chirally pure enantiomer.

33. A composition comprising a therapeutically effective amount of at least one compound of claim 1 or a pharmaceutically acceptable salt, racemate, or stereoisomer thereof.

34. A method for inhibiting TRPV3 activity in a cell, the method comprises contacting the cell with an effective amount of i) at least one compound of claim 1 or a pharmaceutically acceptable salt, racemate, or stereoisomer thereof, or ii) a pharmaceutical composition comprising at least one compound of claim 1 or a pharmaceutically acceptable salt, racemate, or stereoisomer thereof and a pharmaceutically acceptable carrier.

35. A method for treating, inhibiting, reducing, protecting or delaying the onset of a skin disorder in a subject in need thereof, the method comprises administering to the subject i) a therapeutically effective amount of at least one compound of claim 1 or a pharmaceutically acceptable salt, racemate, or stereoisomer thereof, or ii) a composition comprising a therapeutically effective amount of at least one compound of claim 1 or a pharmaceutically acceptable salt, racemate, or stereoisomer thereof.

36. The method according to claim 35, wherein the subject has the skin disorder.

37. The method of claim 35, wherein the skin disorder is at least one keratoderma.

38. The method of claim 37, wherein the at least one keratoderma is Olmsted Syndrome.

39. The method of claim 35, wherein the skin disorder is ichthyosis.

40. The method of claim 39, wherein the ichthyosis is Harlequin Ichtyosis.

41. The method of claim 35, wherein the skin disorder comprises pachyonychia congenita.

42. The method of claim 37, wherein the at least one keratoderma is punctate palmoplantar keratoderma.

43. The method of claim 37, wherein the at least one keratoderma is Mal de Meleda.

44. The compound of claim 1, having a structure selected from:

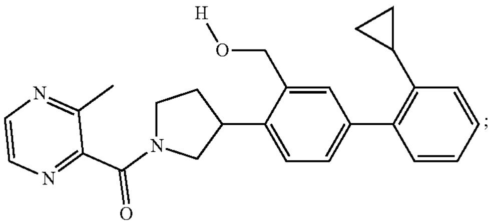
;

-continued

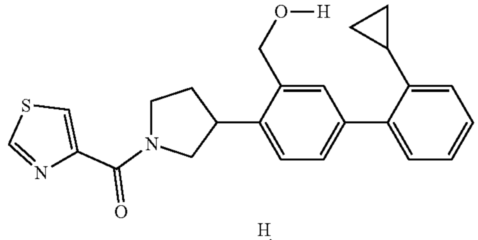
;

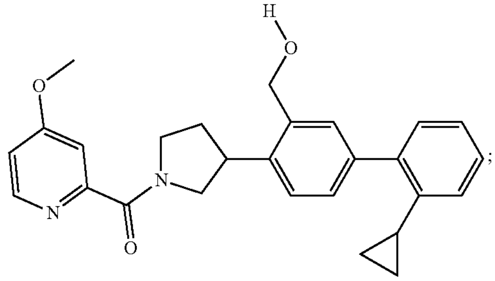
;

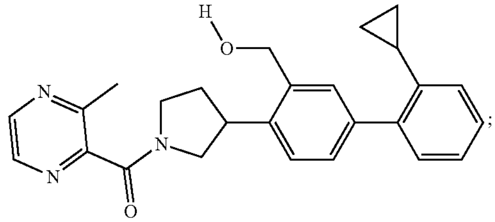
;

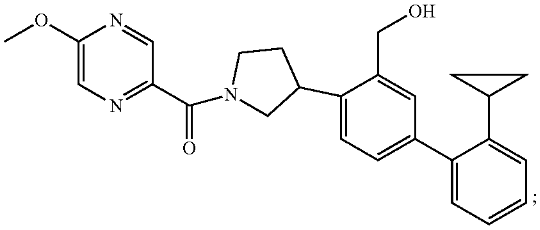
;

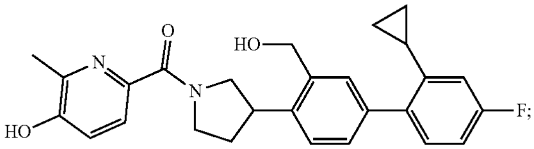
; and

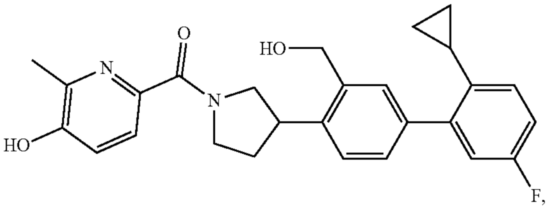
, or a pharmaceutically acceptable salt, racemate, or stereoisomer thereof.

* * * * *

SEQUENCE LISTING

```
Sequence total quantity: 5
SEQ ID NO: 1           moltype = AA  length = 6
FEATURE                Location/Qualifiers
source                 1..6
                       mol_type = protein
                       organism = synthetic construct
SITE                   6
                       note = C terminus is amidated
SEQUENCE: 1
SLIGRL                                                             6

SEQ ID NO: 2           moltype = DNA  length = 20
FEATURE                Location/Qualifiers
source                 1..20
                       mol_type = other DNA
                       organism = synthetic construct
SEQUENCE: 2
ctgcctcagc cttactgtga                                              20

SEQ ID NO: 3           moltype = DNA  length = 21
FEATURE                Location/Qualifiers
source                 1..21
                       mol_type = other DNA
```

-continued

```
                        organism = synthetic construct
SEQUENCE: 3
ggaggaggaa cagtcttgag g                                        21

SEQ ID NO: 4            moltype = DNA  length = 23
FEATURE                 Location/Qualifiers
source                  1..23
                        mol_type = other DNA
                        organism = synthetic construct
SEQUENCE: 4
cattatgctg aggatttgga aag                                      23

SEQ ID NO: 5            moltype = DNA  length = 22
FEATURE                 Location/Qualifiers
source                  1..22
                        mol_type = other DNA
                        organism = synthetic construct
SEQUENCE: 5
cttgagcaca cagagggcta ca                                       22
```